United States Patent
Vu et al.

(10) Patent No.: US 11,807,644 B2
(45) Date of Patent: Nov. 7, 2023

(54) METHODS AND COMPOUNDS FOR RESTORING MUTANT P53 FUNCTION

(71) Applicant: PMV Pharmaceuticals, Inc., Cranbury, NJ (US)

(72) Inventors: Binh Vu, North Caldwell, NJ (US); Romyr Dominique, East Brunswick, NJ (US); Hongju Li, Edison, NJ (US); Bruce Fahr, East Windsor, NJ (US); Andrew Good, Wallingford, CT (US)

(73) Assignee: PMV PHARMACEUTICALS, INC., Princeton, NJ (US)

( * ) Notice: Subject to any disclaimer, the term of this patent is extended or adjusted under 35 U.S.C. 154(b) by 27 days.

(21) Appl. No.: 17/317,423

(22) Filed: May 11, 2021

(65) Prior Publication Data

US 2023/0002403 A1    Jan. 5, 2023

Related U.S. Application Data

(60) Provisional application No. 63/023,601, filed on May 12, 2020.

(51) Int. Cl.

| | |
|---|---|
| *C07D 491/107* | (2006.01) |
| *C07D 413/14* | (2006.01) |
| *C07D 417/14* | (2006.01) |
| *C07D 471/04* | (2006.01) |
| *C07D 495/04* | (2006.01) |
| *C07D 498/18* | (2006.01) |

(52) U.S. Cl.
CPC ....... *C07D 491/107* (2013.01); *C07D 413/14* (2013.01); *C07D 417/14* (2013.01); *C07D 471/04* (2013.01); *C07D 495/04* (2013.01); *C07D 498/18* (2013.01)

(58) Field of Classification Search
None
See application file for complete search history.

(56) References Cited

U.S. PATENT DOCUMENTS

| | | |
|---|---|---|
| 6,518,273 B1 | 2/2003 | Chapman et al. |
| 6,747,052 B2 | 6/2004 | Cai et al. |
| 2009/0186922 A1 | 7/2009 | Alisi et al. |
| 2017/0240525 A1 | 8/2017 | Vu et al. |
| 2019/0284135 A1 | 9/2019 | Bonafoux et al. |

OTHER PUBLICATIONS

Database Registry Chemical Abstracts Service, Columbus, Ohio, Accession No. RN 1610707-41-9, Entered STN: Jun. 16, 2014.*
Database Registry Chemical Abstracts Service, Columbus, Ohio, Accession No. RN 1511000-46-6, Entered STN: Jan. 5, 2014.*
Database Registry Chemical Abstracts Service, Columbus, Ohio, Accession No. RN 1400286-50-1, Entered STN: Oct. 10, 2012.*
Database Registry Chemical Abstracts Service, Columbus, Ohio, Accession No. RN 1336929-69-1, Entered STN: Oct. 17, 2011.*
International Search Report and Written Opinion issued in PCT/US2021/031838 dated Sep. 14, 2021.

* cited by examiner

*Primary Examiner* — Samantha L Shterengarts
(74) *Attorney, Agent, or Firm* — Wilson Sonsini Goodrich & Rosati

(57) ABSTRACT

Mutations in oncogenes and tumor suppressors contribute to the development and progression of cancer. The present disclosure describes compounds and methods to recover wild-type function to p53 mutants. The compounds of the present disclosure can bind to mutant p53 and restore the ability of the p53 mutant to bind DNA and activate downstream effectors involved in tumor suppression. The disclosed compounds can be used to reduce the progression of cancers that contain a p53 mutation.

21 Claims, 20 Drawing Sheets

Specification includes a Sequence Listing.

METHODS AND COMPOUNDS FOR RESTORING MUTANT P53 FUNCTION

CROSS REFERENCE

This application claims the benefit of U.S. Provisional Application No. 63/023,601, filed May 12, 2020, which is incorporated herein by reference.

SEQUENCE LISTING

The instant application contains a Sequence Listing, which has been submitted electronically in ASCII format and is hereby incorporated by reference in its entirety. Said ASCII copy, created on May 10, 2021, is named 44727706201SL_1.txt and is 2,540 bytes in size.

BACKGROUND

Cancer, an uncontrolled proliferation of cells, is a multifactorial disease characterized by tumor formation, growth, and in some instances, metastasis. Cells carrying an activated oncogene, damaged genome, or other cancer-promoting alterations can be prevented from replicating through an elaborate tumor suppression network. A central component of this tumor suppression network is p53, one of the most potent tumor suppressors in the cell. Both the wild type and mutant conformations of p53 are implicated in the progression of cancer.

INCORPORATION BY REFERENCE

Each patent, publication, and non-patent literature cited in the application is hereby incorporated by reference in its entirety as if each was incorporated by reference individually.

SUMMARY OF THE INVENTION

In some embodiments, provided herein is a compound comprising: an indole group, wherein the indole group comprises: a) a haloalkyl group at a 1-position of the indole group; b) a first substituent at a 2-position of the indole group, wherein the first substituent is a cyclic group; and c) a second substituent, wherein the second substituent is substituted with at least halo-; or a pharmaceutically-acceptable salt thereof.

In some embodiments, provided herein is a compound comprising an indole group, wherein the indole group comprises: a) a substituted or unsubstituted non-cyclic group at a 3-position of the indole group; and b) a substituted or unsubstituted cyclic group at a 2-position of the indole group, wherein the compound increases a stability of a biologically active conformation of a p53 mutant relative to a stability of a biologically-active conformation of the p53 mutant in an absence of the compound, or a pharmaceutically-acceptable salt thereof.

In some embodiments, provided herein is a compound of the formula:

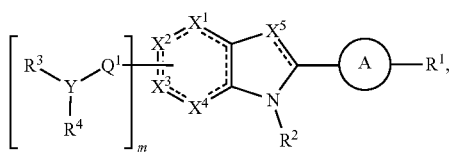

wherein:
each ═══ is independently a single bond or a double bond;
$X^1$ is $CR^5$, $CR^5R^6$, N, $NR^5$, O, S, C═O, C═S, or a carbon atom connected to $Q^1$;
$X^2$ is $CR^7$, $CR^7R^8$, N, $NR^7$, O, S, C═O, C═S, or a carbon atom connected to $Q^1$;
$X^3$ is $CR^9$, $CR^9R^{10}$, N, $NR^9$, O, S, C═O, C═S, or a carbon atom connected to $Q^1$;
$X^4$ is $CR^{11}$, $CR^{11}R^{12}$, N, $NR^9$, O, S, C═O, C═S, or a carbon atom connected to $Q^1$;
$X^5$ is $CR^{13}$, N, or $NR^{13}$;
wherein at least one of $X^1$, $X^2$, $X^3$, and $X^4$ is a carbon atom connected to $Q^1$;
A is a substituted or unsubstituted ring;
$Q^1$ is C═O, C═S, C═$CR^{14}R^{15}$, C═$NR^{14}$, alkylene, alkenylene, or alkynylene, each of which is independently substituted or unsubstituted, or a bond;
m is 1, 2, 3, or 4;
Y is N, O, or absent;
$R^1$ is $-C(O)R^{16}$, $-C(O)OR^{16}$, $-C(O)NR^{16}R^{17}$, $-OR^{16}$, $-SR^{16}$, $-NR^{16}R^{17}$, $-NR^{16}C(O)R^{16}$, $-OC(O)R^{16}$, $-SiR^{16}R^{17}R^{18}$, alkyl, alkenyl, alkynyl, alkoxy, aryl, heteroaryl, heterocyclyl, or halo, each of which is independently substituted or unsubstituted, or hydrogen;
each $R^3$ and $R^4$ is independently $-C(O)R^{19}$, $-C(O)OR^{19}$, $-C(O)NR^{19}R^{20}$, $-SOR^{19}$, $-SO_2R^{19}$, alkyl, alkenyl, alkynyl, aryl, heteroaryl, or heterocyclyl, each of which is independently substituted or unsubstituted, or hydrogen, or $R^3$ and $R^4$ together with the nitrogen atom to which $R^3$ and $R^4$ are bound form a ring, wherein the ring is substituted or unsubstituted, or R is absent;
each $R^2$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ is independently $-C(O)R^{21}$, $-C(O)OR^{21}$, $-C(O)NR^{21}R^{22}$, $-OR^{21}$, $-SR^{21}$, $-NR^{21}R^{22}$, $-NR^{21}C(O)R^{22}$, $-OC(O)R^{21}$, alkyl, alkenyl, alkynyl, aryl, heteroaryl, or heterocyclyl, each of which is independently substituted or unsubstituted, or hydrogen or halogen;
each $R^{19}$ and $R^{20}$ is $-C(O)R^{23}$, $-C(O)OR^{23}$, $-C(O)NR^{23}R^{24}$, $-OR^{23}$—$SR^{23}$, $-NR^{23}R^{24}$, $NR^{23}C(O)R^{24}$, $-OC(O)R^{23}$, alkyl, alkenyl, alkynyl, aryl, heteroaryl, or heterocyclyl, each of which is independently substituted or unsubstituted, or hydrogen or halogen;
each $R^{21}$ and $R^{22}$ is independently alkyl, alkenyl, alkynyl, aryl, heteroaryl, or heterocyclyl, each of which is independently substituted or unsubstituted, or hydrogen; and
each $R^{23}$ and $R^{24}$ is independently alkyl, alkenyl, alkynyl, aryl, heteroaryl, or heterocyclyl, each of which is independently substituted or unsubstituted, or hydrogen, or a pharmaceutically-acceptable salt thereof In some embodiments, provided herein is a compound of the formula:

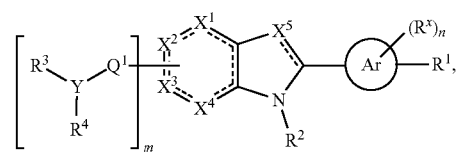

wherein:
each ====== is independently a single bond or a double bond;
$X^1$ is $CR^5$, $CR^5R^6$, N, $NR^5$, O, S, C=O, C=S, or a carbon atom connected to $Q^1$;
$X^2$ is $CR^7$, $CR^7R^8$, N, $NR^7$, O, S, C=O, C=S, or a carbon atom connected to $Q^1$;
$X^3$ is $CR^9$, $CR^9R^{10}$, N, $NR^9$, O, S, C=O, C=S, or a carbon atom connected to $Q^1$;
$X^4$ is $CR^{11}$, $CR^{11}R^{12}$, N, $NR^{11}$, O, S, C=O, C=S, or a carbon atom connected to $Q^1$;
$X^5$ is $CR^{13}$, N, or $NR^{13}$;
wherein at least one of $X^1$, $X^2$, $X^3$, and $X^4$ is a carbon atom connected to $Q^1$;
Ar is unsubstituted or substituted aryl;
$Q^1$ is C=O, C=S, C=$CR^{14}R^{15}$, C=$NR^{14}$, alkylene, alkenylene, or alkynylene, each of which is independently substituted or unsubstituted, or a bond;
m is 1, 2, 3, or 4;
n is 0, 1, 2, 3, or 4;
Y is N, O, or absent;
each $R^x$ and $R^1$ is independently $C(O)R^{16}$, —$C(O)OR^{16}$, —$C(O)NR^{16}R^{17}$, —$OR^{16}$, —$SR^{16}$, —$NR^{16}R^{17}$, —$NR^{16}C(O)R^{16}$, —$OC(O)R^{16}$, —$SiR^{16}R^{17}R^{18}$, alkyl, alkenyl, alkynyl, alkoxy, aryl, heteroaryl, or heterocyclyl, each of which is independently substituted or unsubstituted; cyano, halo, or hydrogen; or $R^1$ and $R^x$ together with Ar form a fused ring;
each $R^3$ and $R^4$ is independently —$C(O)R^{19}$, —$C(O)OR^{19}$, —$C(O)NR^{19}R^{20}$, —$SOR^{19}$, —$SO_2R^{19}$, alkyl, alkenyl, alkynyl, aryl, heteroaryl, or heterocyclyl, each of which is independently substituted or unsubstituted, or hydrogen, or $R^3$ and $R^4$ together with the nitrogen atom to which $R^3$ and $R^4$ are bound form a ring, wherein the ring is substituted or unsubstituted, or $R^3$ is absent;
each $R^2$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ is independently —$C(O)R^{21}$, —$C(O)OR^{21}$, —$C(O)NR^{21}R^{22}$, —$OR^{21}$, —$SR^{21}$, —$NR^{21}R^{22}$, —$NR^{21}C(O)R^{22}$, —$OC(O)R^{21}$, alkyl, alkenyl, alkynyl, aryl, heteroaryl, or heterocyclyl, each of which is independently substituted or unsubstituted, or hydrogen or halogen;
each $R^{19}$ and $R^{20}$ is —$C(O)R^{23}$, —$C(O)OR^{23}$, —$C(O)NR^{23}R^{24}$, —$OR^{23}$, —$SR^{23}$, —$NR^{23}R^{24}$, —$NR^{23}C(O)R^{24}$, —$OC(O)R^{23}$, alkyl, alkenyl, alkynyl, aryl, heteroaryl, or heterocyclyl, each of which is independently substituted or unsubstituted, or hydrogen or halogen;
each $R^{21}$ and $R^{22}$ is independently alkyl, alkenyl, alkynyl, aryl, heteroaryl, or heterocyclyl, each of which is independently substituted or unsubstituted, or hydrogen; and
each $R^{23}$ and $R^{24}$ is independently alkyl, alkenyl, alkynyl, aryl, heteroaryl, or heterocyclyl, each of which is independently substituted or unsubstituted, or hydrogen, or a pharmaceutically-acceptable salt thereof.

In some embodiments, provided herein is a method of inducing apoptosis in a cell, the method comprising contacting the cell with a therapeutically-effective amount of a compound of the formula:

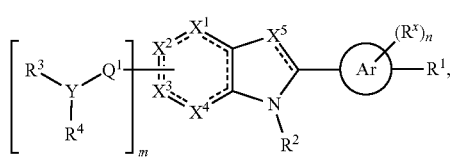

wherein:
each ====== is independently a single bond or a double bond;
$X^1$ is $CR^5$, $CR^5R^6$, N, $NR^5$, O, S, C=O, C=S, or a carbon atom connected to $Q^1$;
$X^2$ is $CR^7$, $CR^7R^8$, N, $NR^7$, O, S, C=O, C=S, or a carbon atom connected to $Q^1$;
$X^3$ is $CR^9$, $CR^9R^{10}$, N, $NR^9$, O, S, C=O, C=S, or a carbon atom connected to $Q^1$;
$X^4$ is $CR^{11}$, $CR^{11}R^{12}$, N, $NR^{11}$, O, S, C=O, C=S, or a carbon atom connected to $Q^1$;
$X^5$ is $CR^{13}$, N, or $NR^{13}$;
wherein at least one of $X^1$, $X^2$, $X^3$, and $X^4$ is a carbon atom connected to $Q^1$;
Ar is unsubstituted or substituted aryl;
$Q^1$ is C=O, C=S, C=$CR^{14}R^{15}$, C=$NR^{14}$, alkylene, alkenylene, or alkynylene, each of which is independently substituted or unsubstituted, or a bond;
m is 1, 2, 3, or 4;
n is 0, 1, 2, 3, or 4;
Y is N, O, or absent;
each $R^x$ and $R^1$ is independently $C(O)R^{16}$, —$C(O)OR^{16}$, —$C(O)NR^{16}R^{17}$, —$OR^{16}$, —$SR^{16}$, —$NR^{16}RD$, —$NR^{16}C(O)R^{16}$, —$OC(O)R^{16}$, —$SiR^{16}R^{17}R^{18}$, alkyl, alkenyl, alkynyl, alkoxy, aryl, heteroaryl, or heterocyclyl, each of which is independently substituted or unsubstituted; cyano, halo, or hydrogen; or $R^1$ and $R^x$ together with Ar form a fused ring;
each $R^3$ and $R^4$ is independently —$C(O)R^{19}$, —$C(O)OR^{19}$, —$C(O)NR^{19}R^{20}$, —$SOR^{19}$, —$SO_2R^{19}$, alkyl, alkenyl, alkynyl, aryl, heteroaryl, or heterocyclyl, each of which is independently substituted or unsubstituted, or hydrogen, or $R^3$ and $R^4$ together with the nitrogen atom to which $R^3$ and $R^4$ are bound form a ring, wherein the ring is substituted or unsubstituted, or $R^3$ is absent;
each $R^2$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ is independently —$C(O)R^{21}$, —$C(O)OR^{21}$, —$C(O)NR^{21}R^{22}$, —$OR^{21}$, —$SR^{21}$, —$NR^{21}R^{22}$, —$NR^{21}C(O)R^{22}$, —$OC(O)R^{21}$, alkyl, alkenyl, alkynyl, aryl, heteroaryl, or heterocyclyl, each of which is independently substituted or unsubstituted, or hydrogen or halogen;
each $R^{19}$ and $R^{20}$ is —$C(O)R^{23}$, —$C(O)OR^{23}$, —$C(O)NR^{23}R^{24}$, —$OR^{23}$, —$SR^{23}$, —$NR^{23}R^{24}$, —$NR^{23}C(O)R^{24}$, —$OC(O)R^{23}$, alkyl, alkenyl, alkynyl, aryl, heteroaryl, or heterocyclyl, each of which is independently substituted or unsubstituted, or hydrogen or halogen;
each $R^{21}$ and $R^{22}$ is independently alkyl, alkenyl, alkynyl, aryl, heteroaryl, or heterocyclyl, each of which is independently substituted or unsubstituted, or hydrogen; and
each $R^{23}$ and $R^{24}$ is independently alkyl, alkenyl, alkynyl, aryl, heteroaryl, or heterocyclyl, each of which is independently substituted or unsubstituted, or hydrogen, or a pharmaceutically-acceptable salt thereof.

In some embodiments, provided herein is a method of treating a cancer, the method comprising administering to a subject in need thereof a therapeutically-effective amount of a compound, wherein the compound is of the formula:

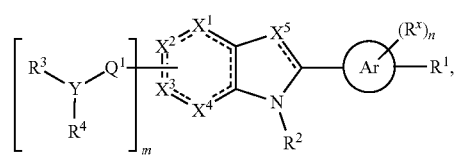

wherein:
  each ------- is independently a single bond or a double bond;
  $X^1$ is $CR^5$, $CR^5R^6$, N, $NR^5$, O, S, C=O, C=S, or a carbon atom connected to $Q^1$;
  $X^2$ is $CR^7$, $CR^7R^8$, N, $NR^7$, O, S, C=O, C=S, or a carbon atom connected to $Q^1$;
  $X^3$ is $CR^9$, $CR^9R^{10}$, N, $NR^9$, O, S, C=O, C=S, or a carbon atom connected to $Q^1$;
  $X^4$ is $CR^{11}$, $CR^{11}R^{12}$, N, $NR^{11}$, O, S, C=O, C=S, or a carbon atom connected to $Q^1$;
  $X^5$ is $CR^{13}$, N, or $NR^{13}$;
wherein at least one of $X^1$, $X^2$, $X^3$, and $X^4$ is a carbon atom connected to $Q^1$;
  Ar is unsubstituted or substituted aryl;
  $Q^1$ is C=O, C=S, C=$CR^{14}R^{15}$, C=$NR^{14}$, alkylene, alkenylene, or alkynylene, each of which is independently substituted or unsubstituted, or a bond;
  m is 1, 2, 3, or 4;
  n is 0, 1, 2, 3, or 4;
  Y is N, O, or absent;
  each $R^x$ and $R^1$ is independently $C(O)R^{16}$, —$C(O)OR^{16}$, —$C(O)NR^{16}R^{17}$, —$OR^{16}$, —$SR^{16}$, —$NR^{16}R^{17}$, —$NR^{16}C(O)R^{16}$, —$OC(O)R^{16}$, —$SiR^{16}R^{17}R^{18}$, alkyl, alkenyl, alkynyl, alkoxy, aryl, heteroaryl, or heterocyclyl, each of which is independently substituted or unsubstituted; cyano, halo, or hydrogen; or $R^1$ and $R^x$ together with Ar form a fused ring;
  each $R^3$ and $R^4$ is independently —$C(O)R^{19}$, —$C(O)OR^{19}$, —$C(O)NR^{19}R^{20}$, —$SOR^{19}$, —$SO_2R^{19}$, alkyl, alkenyl, alkynyl, aryl, heteroaryl, or heterocyclyl, each of which is independently substituted or unsubstituted, or hydrogen, or $R^3$ and $R^4$ together with the nitrogen atom to which $R^3$ and $R^4$ are bound form a ring, wherein the ring is substituted or unsubstituted, or $R^3$ is absent;
  each $R^2$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ is independently —$C(O)R^{21}$, —$C(O)OR^{21}$, —$C(O)NR^{21}R^{22}$, —$OR^{21}$, —$SR^{21}$, —$NR^{21}R^{22}$, —$NR^{21}C(O)R^{22}$, —$OC(O)R^{21}$, alkyl, alkenyl, alkynyl, aryl, heteroaryl, or heterocyclyl, each of which is independently substituted or unsubstituted, or hydrogen or halogen;
  each $R^{19}$ and $R^{20}$ is —$C(O)R^{23}$, —$C(O)OR^{23}$, —$C(O)NR^{23}R^{24}$, —$OR^{23}$, —$SR^{23}$, —$NR^{23}R^{24}$, —$NR^{23}C(O)R^{24}$, —$OC(O)R^{23}$, alkyl, alkenyl, alkynyl, aryl, heteroaryl, or heterocyclyl, each of which is independently substituted or unsubstituted, or hydrogen or halogen;
  each $R^{21}$ and $R^{22}$ is independently alkyl, alkenyl, alkynyl, aryl, heteroaryl, or heterocyclyl, each of which is independently substituted or unsubstituted, or hydrogen; and
  each $R^{23}$ and $R^{24}$ is independently alkyl, alkenyl, alkynyl, aryl, heteroaryl, or heterocyclyl,
    each of which is independently substituted or unsubstituted, or hydrogen, or a pharmaceutically-acceptable salt thereof.

In some embodiments, disclosed herein is a compound of the formula:

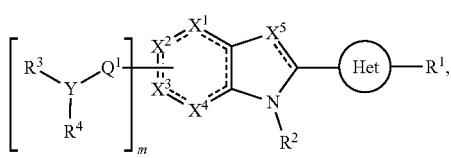

wherein:
  each ------- is independently a single bond or a double bond;
  $X^1$ is $CR^5$, $CR^5R^6$, N, $NR^5$, O, S, C=O, C=S, or a carbon atom connected to $Q^1$;
  $X^2$ is $CR^7$, $CR^7R^8$, N, $NR^7$, O, S, C=O, C=S, or a carbon atom connected to $Q^1$;
  $X^3$ is $CR^9$, $CR^9R^{10}$, N, $NR^9$, O, S, C=O, C=S, or a carbon atom connected to $Q^1$;
  $X^4$ is $CR^{11}$, $CR^{11}R^{12}$, N, $NR^{11}$, O, S, C=O, C=S, or a carbon atom connected to $Q^1$;
  $X^5$ is $CR^{13}$, N, or $NR^{13}$;
wherein at least one of $X^1$, $X^2$, $X^3$, and $X^4$ is a carbon atom connected to $Q^1$;
  Het is substituted or unsubstituted heteroaryl;
  $Q^1$ is C=O, C=S, C=$CR^{14}R^{15}$, C=$NR^{14}$, alkylene, alkenylene, or alkynylene, each of which is independently substituted or unsubstituted, or a bond;
  m is 1, 2, 3, or 4;
  Y is N, O, or absent;
  $R^1$ is —$C(O)R^{16}$, —$C(O)OR^{16}$, —$C(O)NR^{16}R^{17}$, —$OR^{16}$, —$SR^{16}$, —$NR^{16}R^{17}$, —$NR^{16}C(O)R^{16}$, $OC(O)R^{16}$, —$SiR^{16}R^{17}R^{18}$, alkyl, alkenyl, alkynyl, alkoxy, aryl, heteroaryl, heterocyclyl, or halo, each of which is independently substituted or unsubstituted, or hydrogen;
  each $R^3$ and $R^4$ is independently —$C(O)R^{19}$, —$C(O)OR^{19}$, —$C(O)NR^{19}R^{20}$, —$SOR^{19}$, —$SO_2R^{19}$, alkyl, alkenyl, alkynyl, aryl, heteroaryl, or heterocyclyl, each of which is independently substituted or unsubstituted, or hydrogen, or $R^3$ and $R^4$ together with the nitrogen atom to which $R^3$ and $R^4$ are bound form a ring, wherein the ring is substituted or unsubstituted, or R is absent;
  each $R^2$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ is independently —$C(O)R^{21}$, —$C(O)OR^{21}$, —$C(O)NR^{21}R^{22}$, —$OR^{21}$, —$SR^{21}$, —$NR^{21}R^{22}$, —$NR^{21}C(O)R^{22}$, —$OC(O)R^{21}$, alkyl, alkenyl, alkynyl, aryl, heteroaryl, or heterocyclyl, each of which is independently substituted or unsubstituted, or hydrogen or halogen;
  each $R^{19}$ and $R^{20}$ is —$C(O)R^{23}$, —$C(O)OR^{23}$, —$C(O)NR^{23}R^{21}$, —$OR^{23}$, —$SR^{23}$, —$NR^{23}R^{24}$, —$NR^{23}C(O)R^{24}$, —$OC(O)R^{23}$, alkyl, alkenyl, alkynyl, aryl, heteroaryl, or heterocyclyl, each of which is independently substituted or unsubstituted, or hydrogen or halogen;
  each $R^{21}$ and $R^{22}$ is independently alkyl, alkenyl, alkynyl, aryl, heteroaryl, or heterocyclyl, each of which is independently substituted or unsubstituted, or hydrogen; and
  each $R^{23}$ and $R^{24}$ is independently alkyl, alkenyl, alkynyl, aryl, heteroaryl, or heterocyclyl, each of which is independently substituted or unsubstituted, or hydrogen, or a pharmaceutically-acceptable salt thereof.

In some embodiments, described herein is a method of inducing apoptosis in a cell, the method comprising contacting the cell with a therapeutically-effective amount of a compound of the formula:

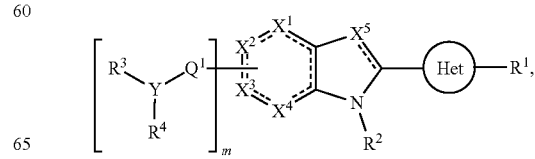

wherein:
- each ═══ is independently a single bond or a double bond;
- $X^1$ is $CR^5$, $CR^5R^6$, N, $NR^5$, O, S, C═O, C═S, or a carbon atom connected to $Q^1$;
- $X^2$ is $CR^7$, $CR^7R^8$, N, $NR^7$, O, S, C═O, C═S, or a carbon atom connected to $Q^1$;
- $X^3$ is $CR^9$, $CR^9R^{10}$, N, $NR^9$, O, S, C═O, C═S, or a carbon atom connected to $Q^1$;
- $X^4$ is $CR^{11}$, $CR^{11}R^{12}$, N, $NR^{11}$, O, S, C═O, C═S, or a carbon atom connected to $Q^1$;
- $X^5$ is $CR^{13}$, N, or $NR^{13}$;

wherein at least one of $X^1$, $X^2$, $X^3$, and $X^4$ is a carbon atom connected to $Q^1$;

- Het is substituted or unsubstituted heteroaryl;
- $Q^1$ is C═O, C═S, C═$CR^{14}R^{15}$, C═$NR^{14}$, alkylene, alkenylene, or alkynylene, each of which is independently substituted or unsubstituted, or a bond;
- m is 1, 2, 3, or 4;
- Y is N, O, or absent;
- $R^1$ is —C(O)$R^{16}$, —C(O)O$R^{16}$, —C(O)N$R^{16}R^{17}$, —O$R^{16}$, —S$R^{16}$, —N$R^{16}R^{17}$, —N$R^{16}$C(O)$R^{16}$, OC(O)$R^{16}$, —Si$R^{16}R^{17}R^{18}$, alkyl, alkenyl, alkynyl, alkoxy, aryl, heteroaryl, heterocyclyl, or halo, each of which is independently substituted or unsubstituted, or hydrogen;
- each $R^3$ and $R^4$ is independently —C(O)$R^{19}$, —C(O)O$R^{19}$, —C(O)N$R^{19}R^{20}$, —SO$R^{19}$, —SO$_2R^{19}$, alkyl, alkenyl, alkynyl, aryl, heteroaryl, or heterocyclyl, each of which is independently substituted or unsubstituted, or hydrogen, or $R^3$ and $R^4$ together with the nitrogen atom to which $R^3$ and $R^4$ are bound form a ring, wherein the ring is substituted or unsubstituted, or R is absent;
- each $R^2$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ is independently —C(O)$R^{21}$, —C(O)O$R^{21}$, —C(O)N$R^{21}R^{22}$, —O$R^{21}$, —S$R^{21}$, —N$R^{21}R^{22}$, —N$R^{21}$C(O)$R^{22}$, —OC(O)$R^{21}$, alkyl, alkenyl, alkynyl, aryl, heteroaryl, or heterocyclyl, each of which is independently substituted or unsubstituted, or hydrogen or halogen;
- each $R^{19}$ and $R^{20}$ is —C(O)$R^{23}$, —C(O)O$R^{23}$, —C(O)N$R^{23}R^{24}$, —O$R^{21}$, —S$R^{23}$, —N$R^{23}R^{24}$, —N$R^{23}$C(O)$R^{24}$, —OC(O)$R^{13}$, alkyl, alkenyl, alkynyl, aryl, heteroaryl, or heterocyclyl, each of which is independently substituted or unsubstituted, or hydrogen or halogen;
- each $R^{21}$ and $R^{22}$ is independently alkyl, alkenyl, alkynyl, aryl, heteroaryl, or heterocyclyl, each of which is independently substituted or unsubstituted, or hydrogen; and
- each $R^{23}$ and $R^{24}$ is independently alkyl, alkenyl, alkynyl, aryl, heteroaryl, or heterocyclyl, each of which is independently substituted or unsubstituted, or hydrogen, or a pharmaceutically-acceptable salt thereof.

In some embodiments, disclosed herein is a method of treating a cancer, the method comprising administering to a subject in need thereof a therapeutically-effective amount of a compound, wherein the compound is of the formula:

$$\left[ R^3\underset{R^4}{\overset{}{Y}}-Q^1-\underset{X^3}{\overset{X^2}{\underset{X^4}{\overline{\phantom{XX}}}}}\overset{X^1}{\underset{}{\phantom{X}}}\overset{X^5}{\underset{N}{\phantom{X}}}-\text{Het}-R^1\right]_m, R^2$$

wherein:
- each ═══ is independently a single bond or a double bond;
- $X^1$ is $CR^5$, $CR^5R$, N, $NR^5$, O, S, C═O, C═S, or a carbon atom connected to $Q^1$;
- $X^2$ is $CR^7$, $CR^7R^8$, N, $NR^7$, O, S, C═O, C═S, or a carbon atom connected to $Q^1$;
- $X^3$ is $CR^9$, $CR^9R^{10}$, N, $NR^9$, O, S, C═O, C═S, or a carbon atom connected to $Q^1$;
- $X^4$ is $CR^{11}$, $CR^{11}R^{12}$, N, $NR^{11}$, O, S, C═O, C═S, or a carbon atom connected to $Q^1$;
- $X^5$ is $CR^{13}$, N, or $NR^{13}$;

wherein at least one of $X^1$, $X^2$, $X^3$, and $X^4$ is a carbon atom connected to $Q^1$;

- Het is substituted or unsubstituted heteroaryl;
- $Q^1$ is C═O, C═S, C═$CR^{14}R^{15}$, C═$NR^{14}$, alkylene, alkenylene, or alkynylene, each of which is independently substituted or unsubstituted, or a bond;
- m is 1, 2, 3, or 4;
- Y is N, O, or absent;
- $R^1$ is —C(O)$R^{16}$, —C(O)O$R^{16}$, —C(O)N$R^{16}R^{17}$, —O$R^{16}$, —S$R^{16}$, —N$R^{16}R^{17}$, —N$R^{16}$C(O)$R^{16}$, OC(O)$R^{16}$, —Si$R^{16}R^{17}R^{18}$, alkyl, alkenyl, alkynyl, alkoxy, aryl, heteroaryl, heterocyclyl, or halo, each of which is independently substituted or unsubstituted, or hydrogen;
- each $R^3$ and $R^4$ is independently —C(O)$R^{19}$, —C(O)O$R^{19}$, —C(O)N$R^{19}R^{20}$, —SO$R^{19}$, —SO$_2R^{19}$, alkyl, alkenyl, alkynyl, aryl, heteroaryl, or heterocyclyl, each of which is independently substituted or unsubstituted, or hydrogen, or $R^3$ and $R^4$ together with the nitrogen atom to which $R^3$ and $R^4$ are bound form a ring, wherein the ring is substituted or unsubstituted, or $R^3$ is absent;
- each $R^2$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ is independently —C(O)$R^{21}$, —C(O)O$R^{21}$, —C(O)N$R^{21}R^{22}$, —O$R^{21}$, —S$R^{21}$, —N$R^{21}R^{22}$, —N$R^{21}$C(O)$R^{22}$, —OC(O)$R^{21}$, alkyl, alkenyl, alkynyl, aryl, heteroaryl, or heterocyclyl, each of which is independently substituted or unsubstituted, or hydrogen or halogen;
- each $R^{19}$ and $R^{20}$ is —C(O)$R^{23}$, —C(O)O$R^{23}$, —C(O)N$R^{23}R^{24}$, —O$R^{21}$, —S$R^{23}$, —N$R^{23}R^{24}$, —N$R^{23}$C(O)$R^{24}$, —OC(O)$R^{23}$, alkyl, alkenyl, alkynyl, aryl, heteroaryl, or heterocyclyl, each of which is independently substituted or unsubstituted, or hydrogen or halogen;
- each $R^2$ and $R^{22}$ is independently alkyl, alkenyl, alkynyl, aryl, heteroaryl, or heterocyclyl, each of which is independently substituted or unsubstituted, or hydrogen; and
- each $R^{23}$ and $R^{24}$ is independently alkyl, alkenyl, alkynyl, aryl, heteroaryl, or heterocyclyl, each of which is independently substituted or unsubstituted, or hydrogen, or a pharmaceutically-acceptable salt thereof.

In some embodiments, disclosed herein is a method of inducing apoptosis in a cell, the method comprising contacting the cell with a therapeutically-effective amount of a compound of the disclosure that binds a p53 mutant, wherein the compound increases the ability of the p53 mutant to bind DNA, wherein the cell expresses the p53 mutant.

In some embodiments, disclosed herein is a method of treating a cancer, the method comprising administering to a subject in need thereof a therapeutically-effective amount of a compound of the disclosure.

DETAILED DESCRIPTION

Figure 1:
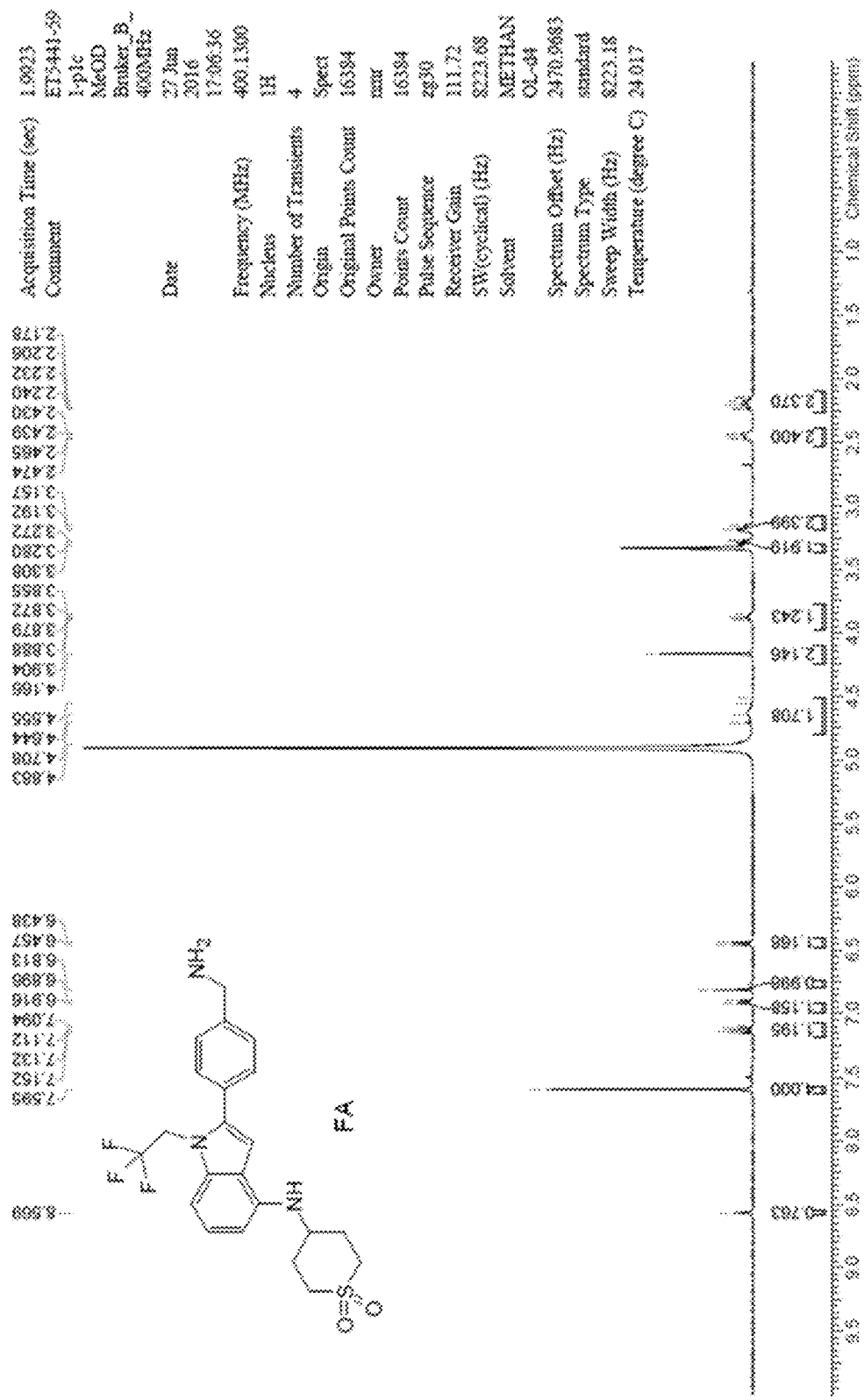
FIG. 1 shows a $^1$H NMR spectrum of 4-((2-(4-(aminomethyl)phenyl)-1-(2,2,2-trifluoroethyl)-1H-indol-4-yl)amino) tetrahydro-2H-thiopyran 1,1-dioxide.
Figure 2:
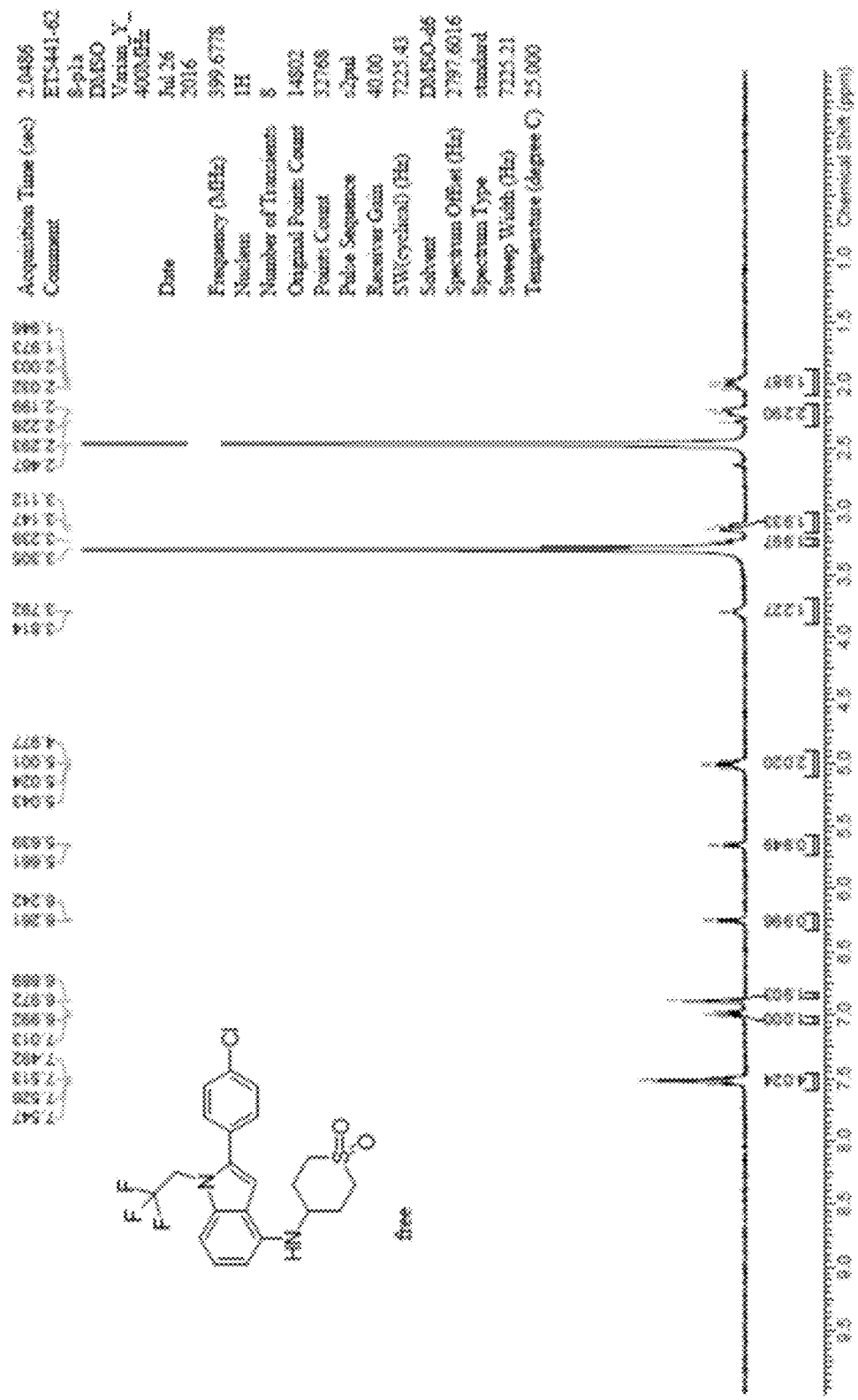
FIG. 2 shows a $^1$H NMR spectrum of 4-((2-(4-chlorophenyl)-1-(2,2,2-trifluoroethyl)-1H-indol-4-yl)amino)tetrahydro-2H-thiopyran 1,1-dioxide.
Figure 3:
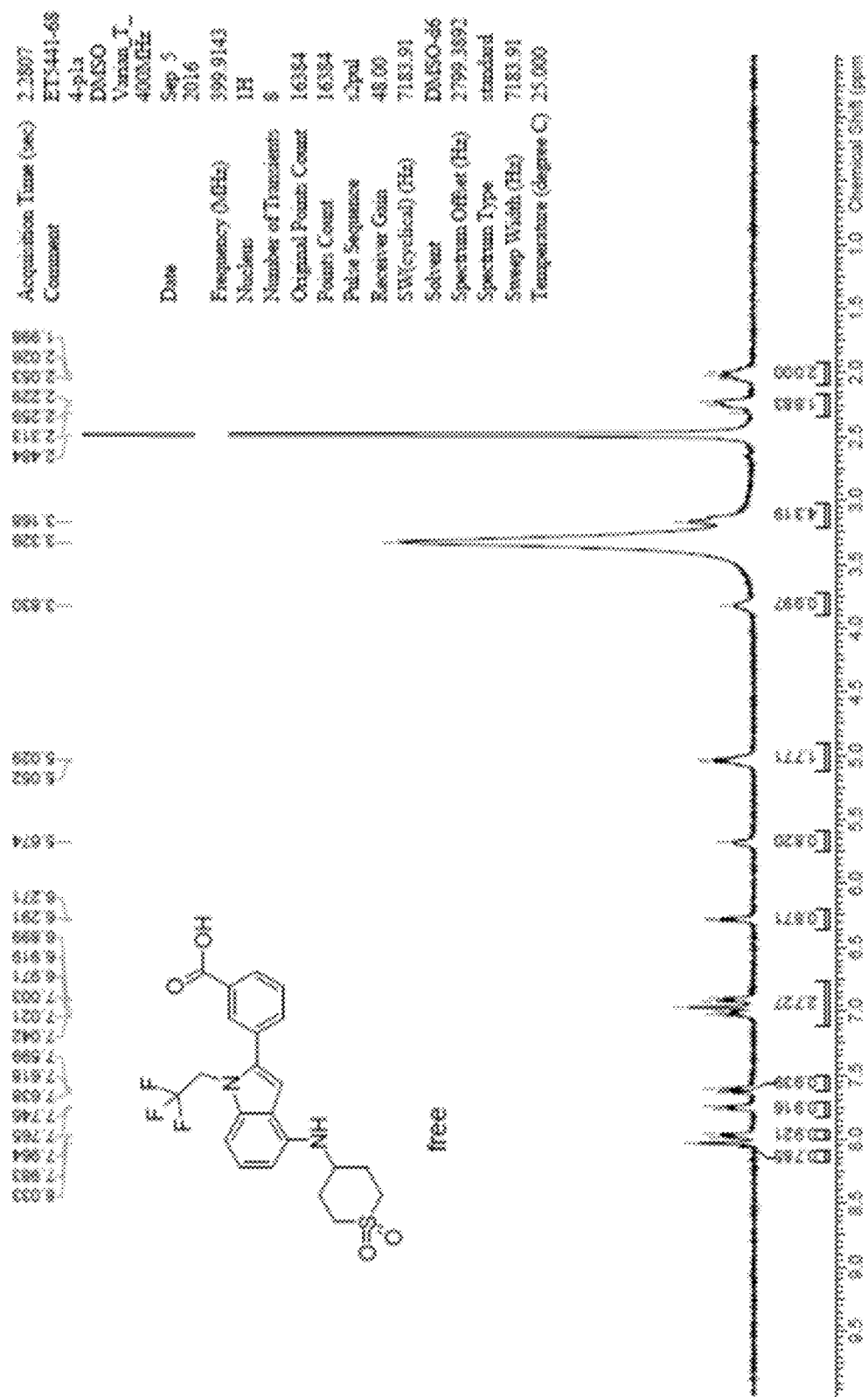
FIG. 3 shows a $^1$H NMR spectrum of 3-(4-((1,1-dioxidotetrahydro-2H-thiopyran-4-yl)amino)-1-(2,2,2-trifluoroethyl)-1H-indol-2-yl)benzoic acid.
Figure 4:
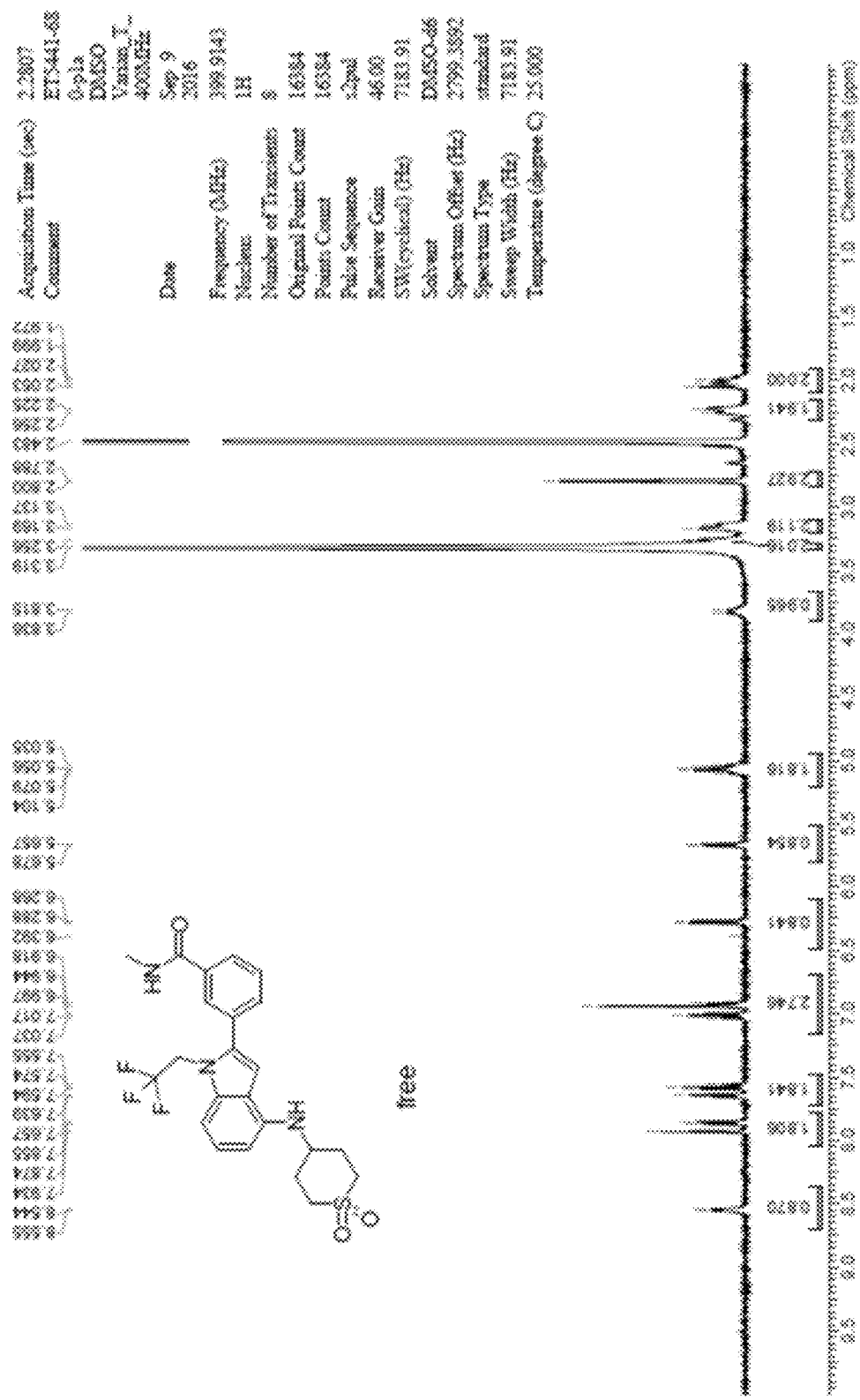
FIG. 4 shows a $^1$H NMR spectrum of 3-(4-((1,1-dioxidotetrahydro-2H-thiopyran-4-yl)amino)-1-(2,2,2-trifluoroethyl)-1H-indol-2-yl)-N-methylbenzamide.
Figure 5:
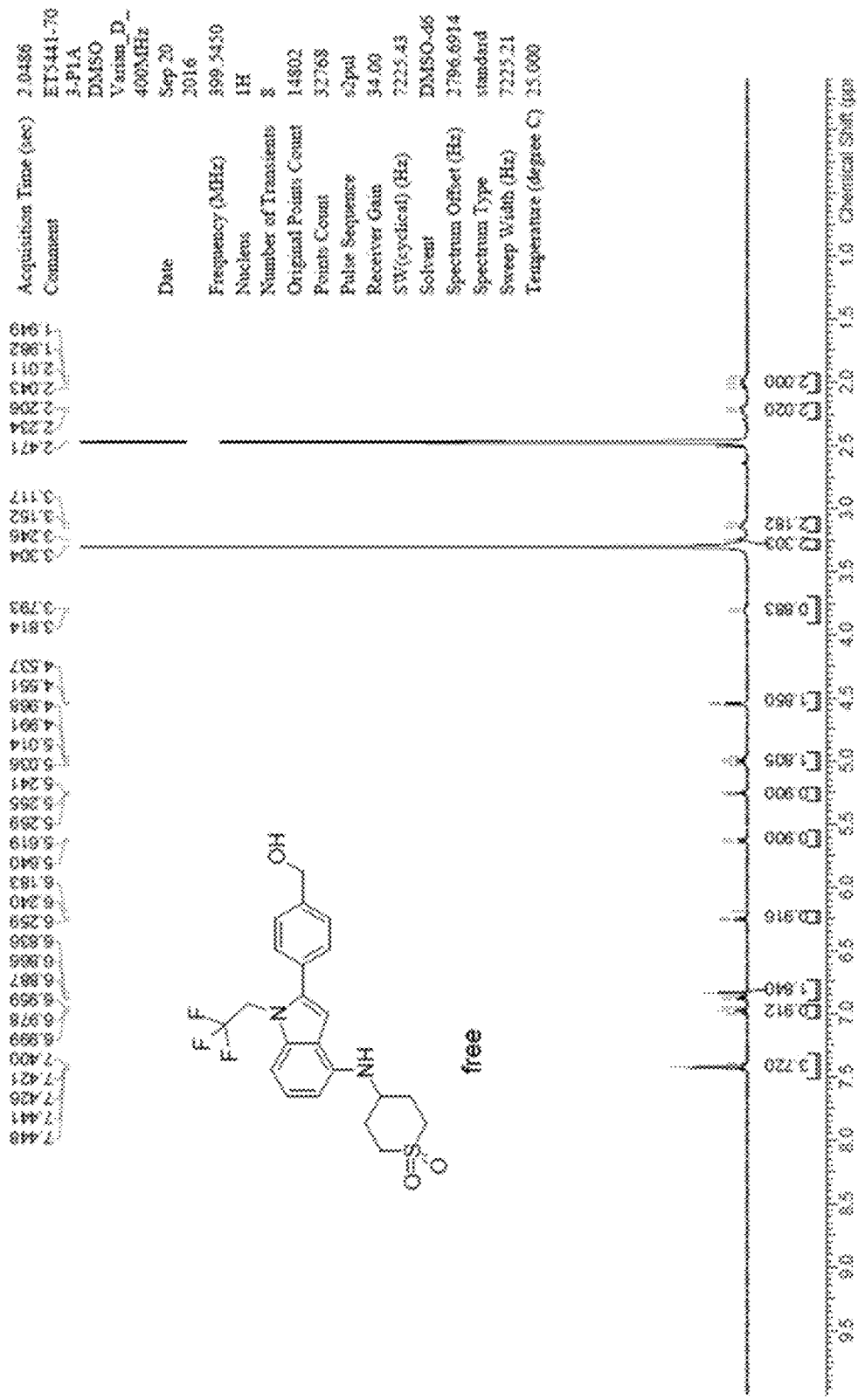
FIG. 5 shows a $^1$H NMR spectrum of 4-((2-(4-(hydroxymethyl)phenyl)-1-(2,2,2-trifluoroethyl)-1H-indol-4-yl)amino)tetrahydro-2H-thiopyran 1,1-dioxide.
Figure 6:
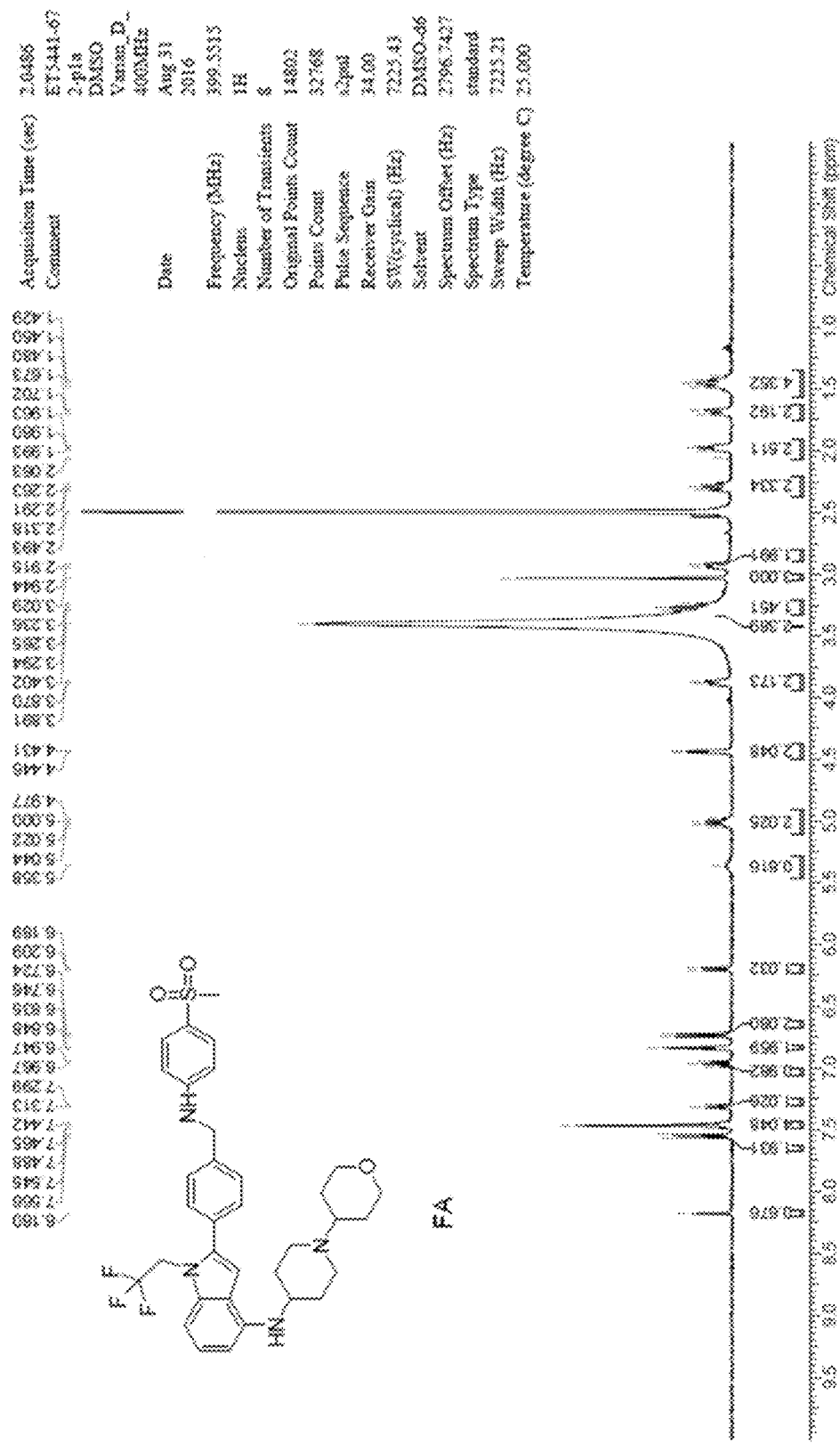
FIG. 6 shows a $^1$H NMR spectrum of 2-(4-(((4-(methylsulfonyl)phenyl)amino)methyl)phenyl)-N-(1-(tetrahydro-2H-pyran-4-yl)piperidin-4-yl)-1-(2,2,2-trifluoroethyl)-1H-indol-4-amine.
Figure 7:
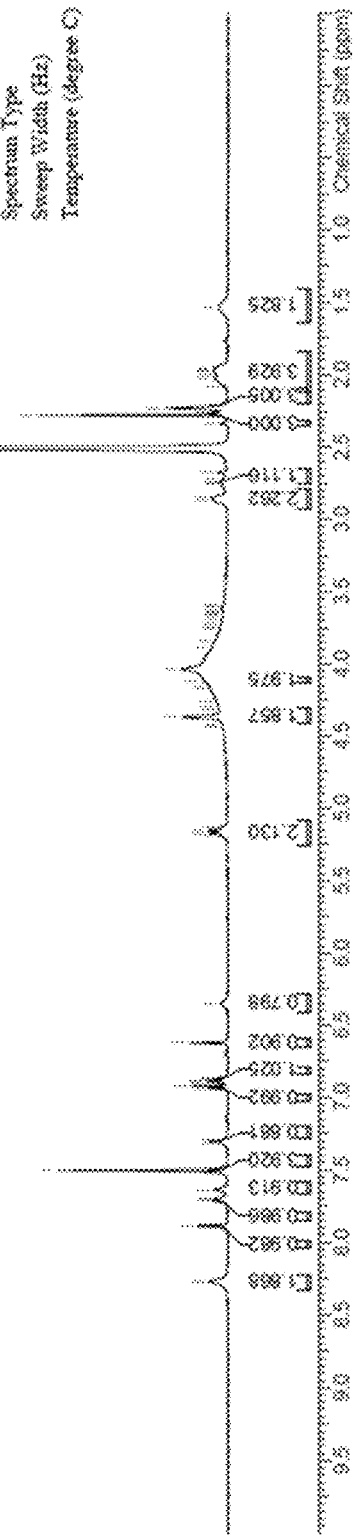
FIG. 7 shows a $^1$H NMR spectrum of 6-methyl-N-(4-(5-(((1-methylpiperidin-4-yl)amino)methyl)-1-(2,2,2-trifluoroethyl)-1H-indol-2-yl)benzyl)pyridin-3-amine.
Figure 8:
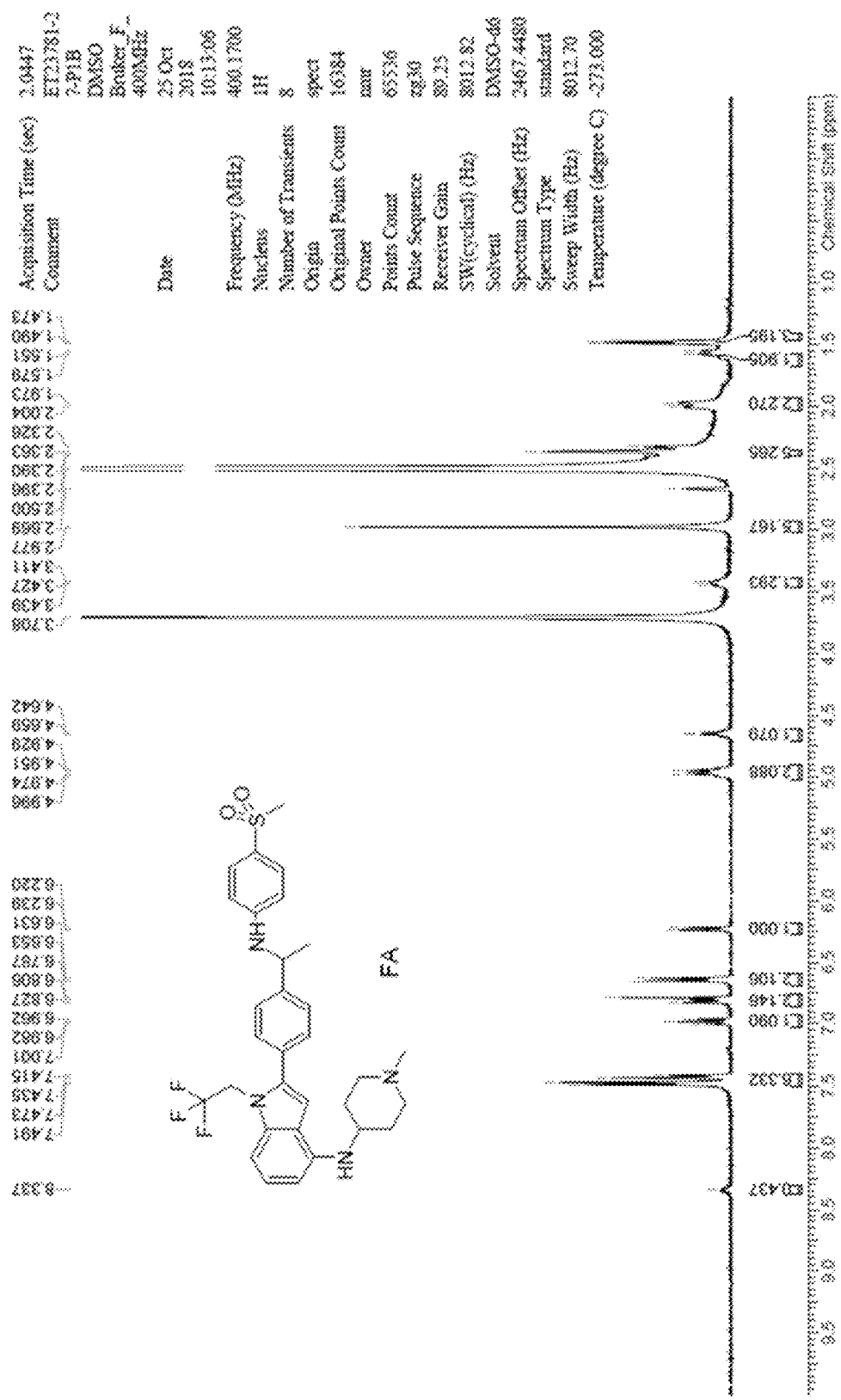
FIG. 8 shows a $^1$H NMR spectrum of N-(1-methylpiperidin-4-yl)-2-(4-(1-((6-(methylsulfonyl)pyridin-3-yl)amino)ethyl)phenyl)-1-(2,2,2-trifluoroethyl)-1H-indol-4-amine.
Figure 9:
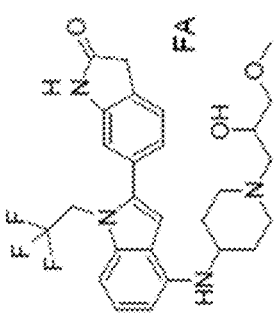
FIG. 9 shows a $^1$H NMR spectrum of 6-(4-((1-(2-hydroxy-3-methoxypropyl)piperidin-4-yl)amino)-1-(2,2,2-trifluoroethyl)-1H-indol-2-yl)indolin-2-one.
Figure 9:
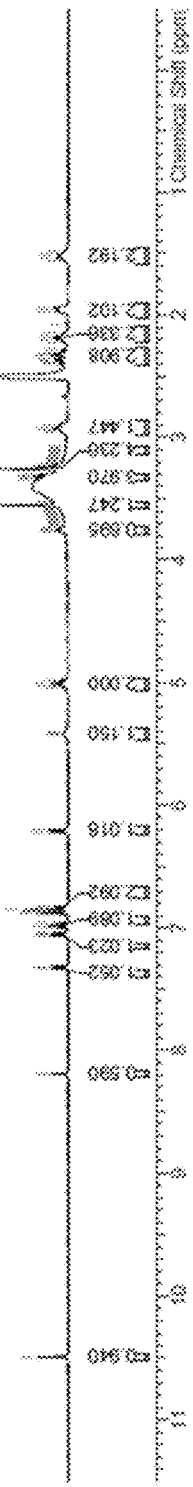
Figure 10:
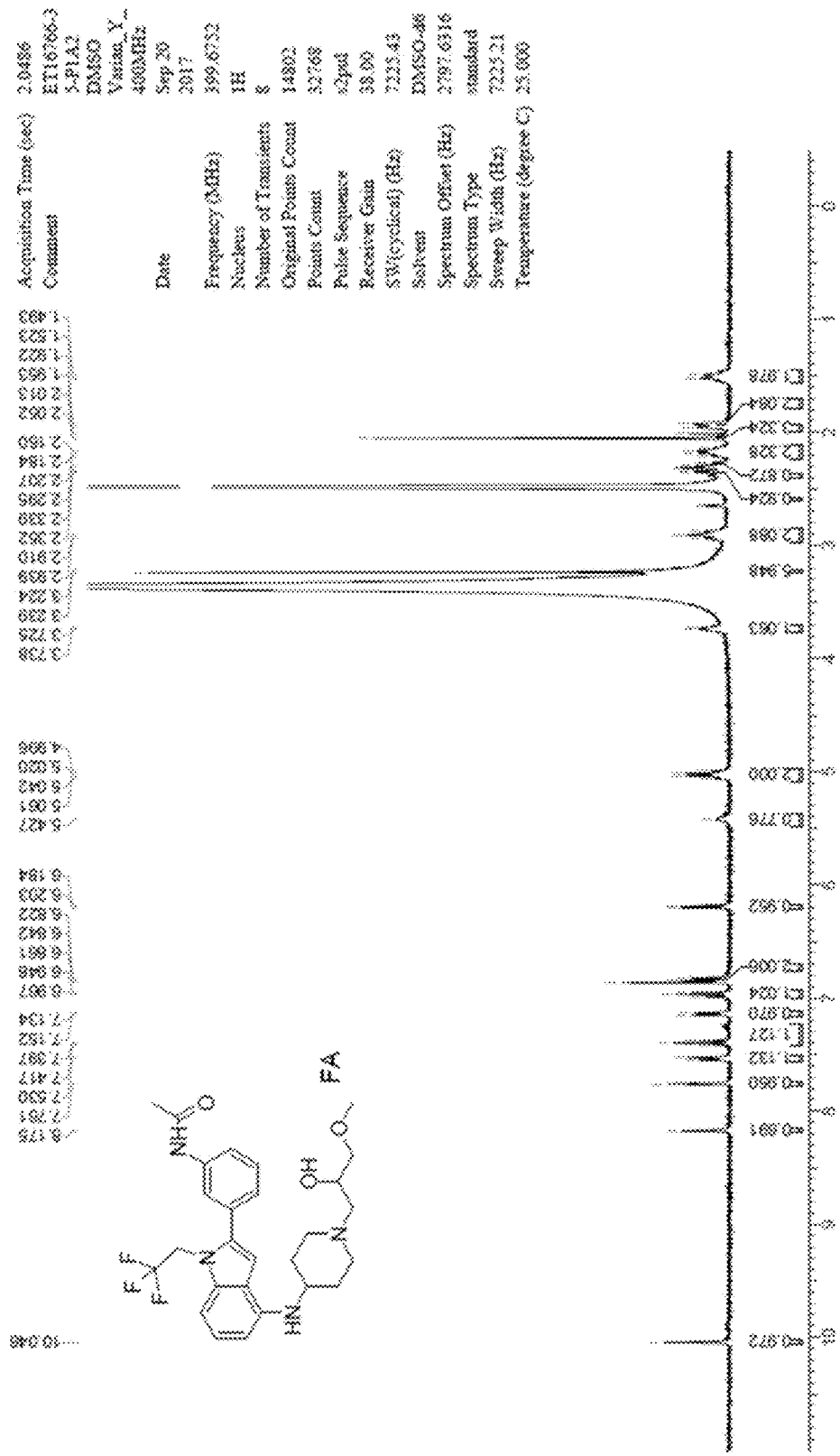
FIG. 10 shows a $^1$H NMR spectrum of N-(3-(4-((1-(2-hydroxy-3-methoxypropyl)piperidin-4-yl)amino)-1-(2,2,2-trifluoroethyl)-1H-indol-2-yl)phenyl)acetamide.
Figure 11:
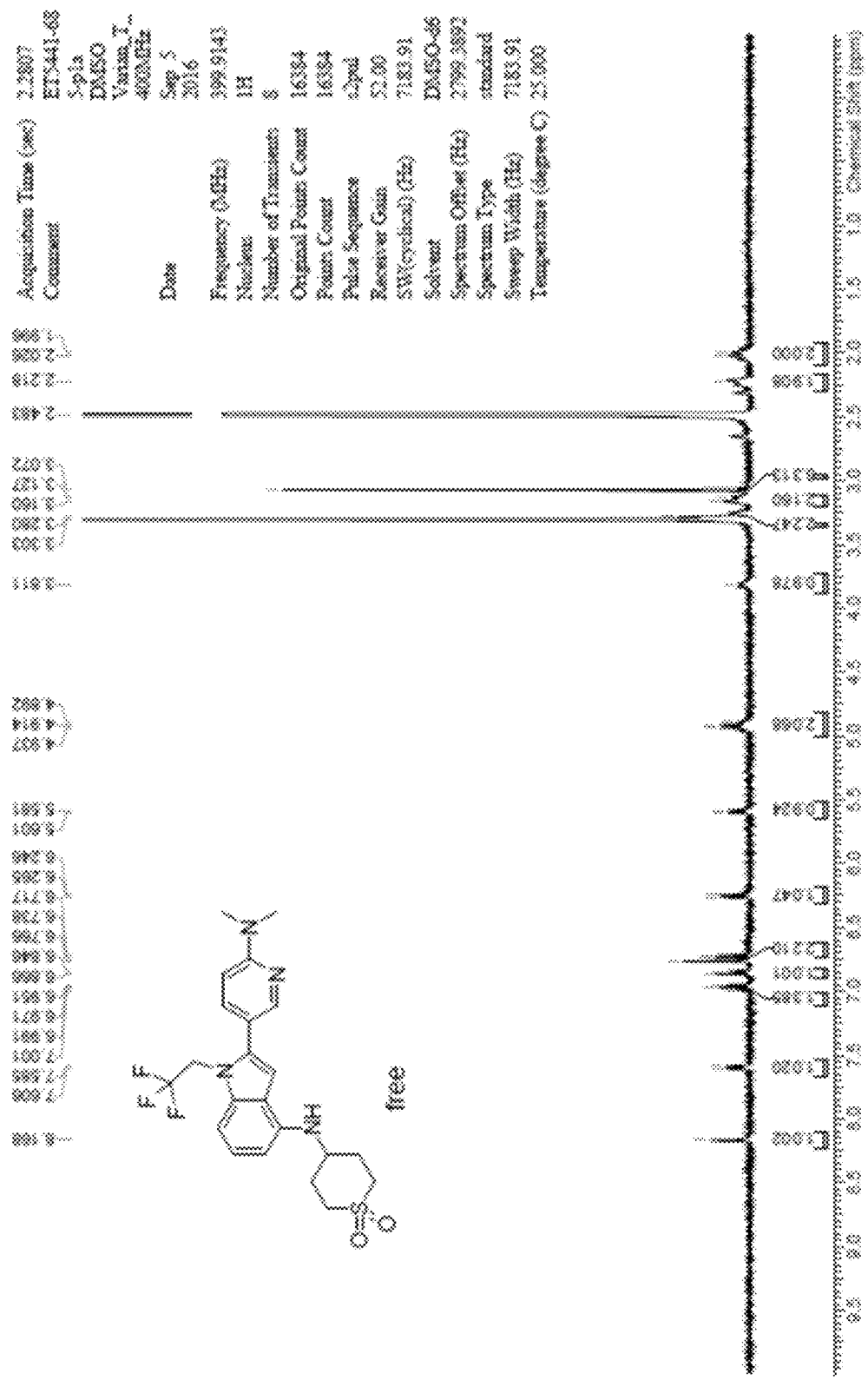
FIG. 11 shows a $^1$H NMR spectrum of 4-((2-(6-(dimethylamino)pyridin-3-yl)-1-(2,2,2-trifluoroethyl)-1H-indol-4-yl)amino)tetrahydro-2H-thiopyran 1,1-dioxide.
Figure 12:
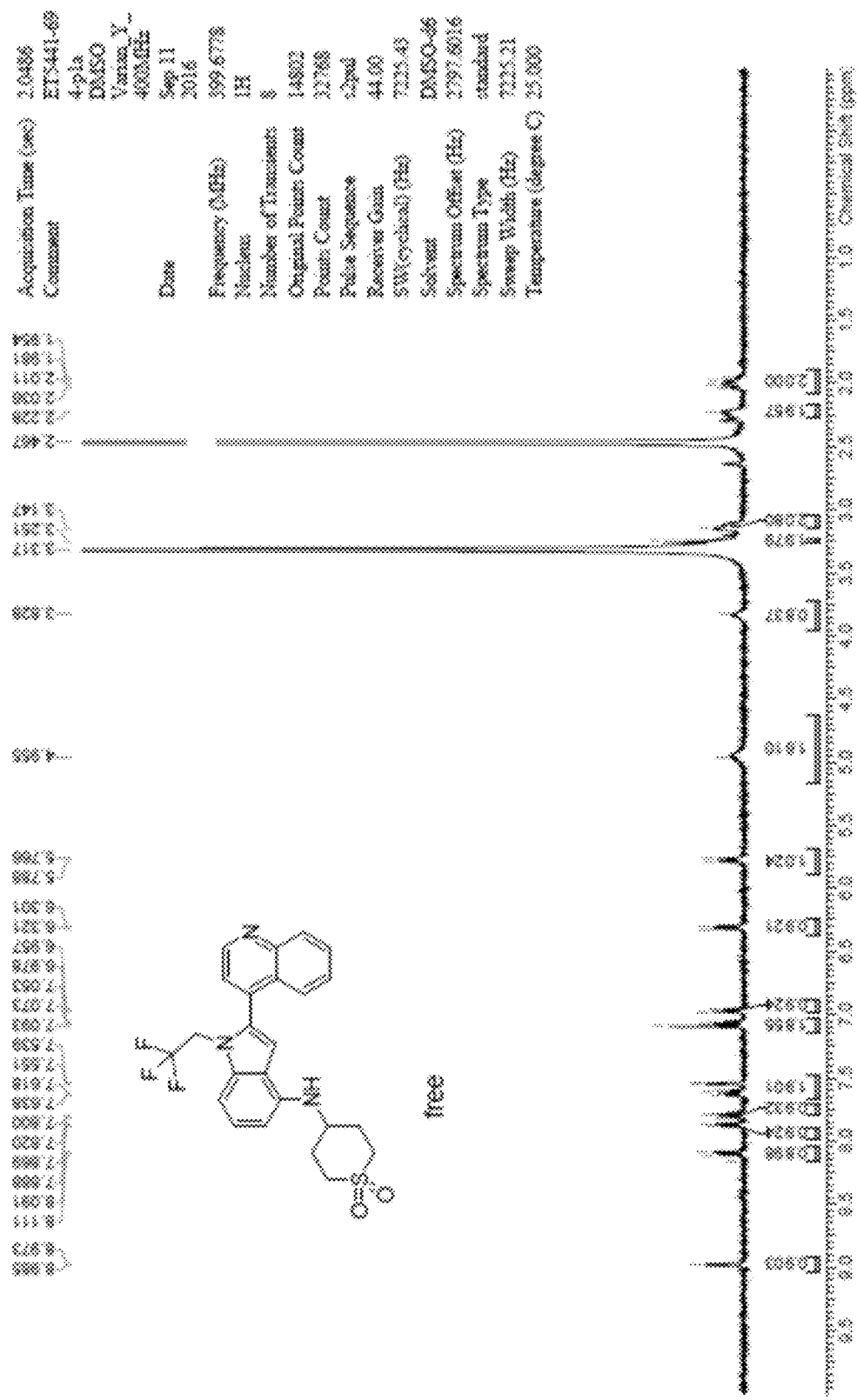
FIG. 12 shows a $^1$H NMR spectrum of 4-((2-(quinolin-4-yl)-1-(2,2,2-trifluoroethyl)-1H-indol-4-yl)amino)tetrahydro-2H-thiopyran 1,1-dioxide.
Figure 13:
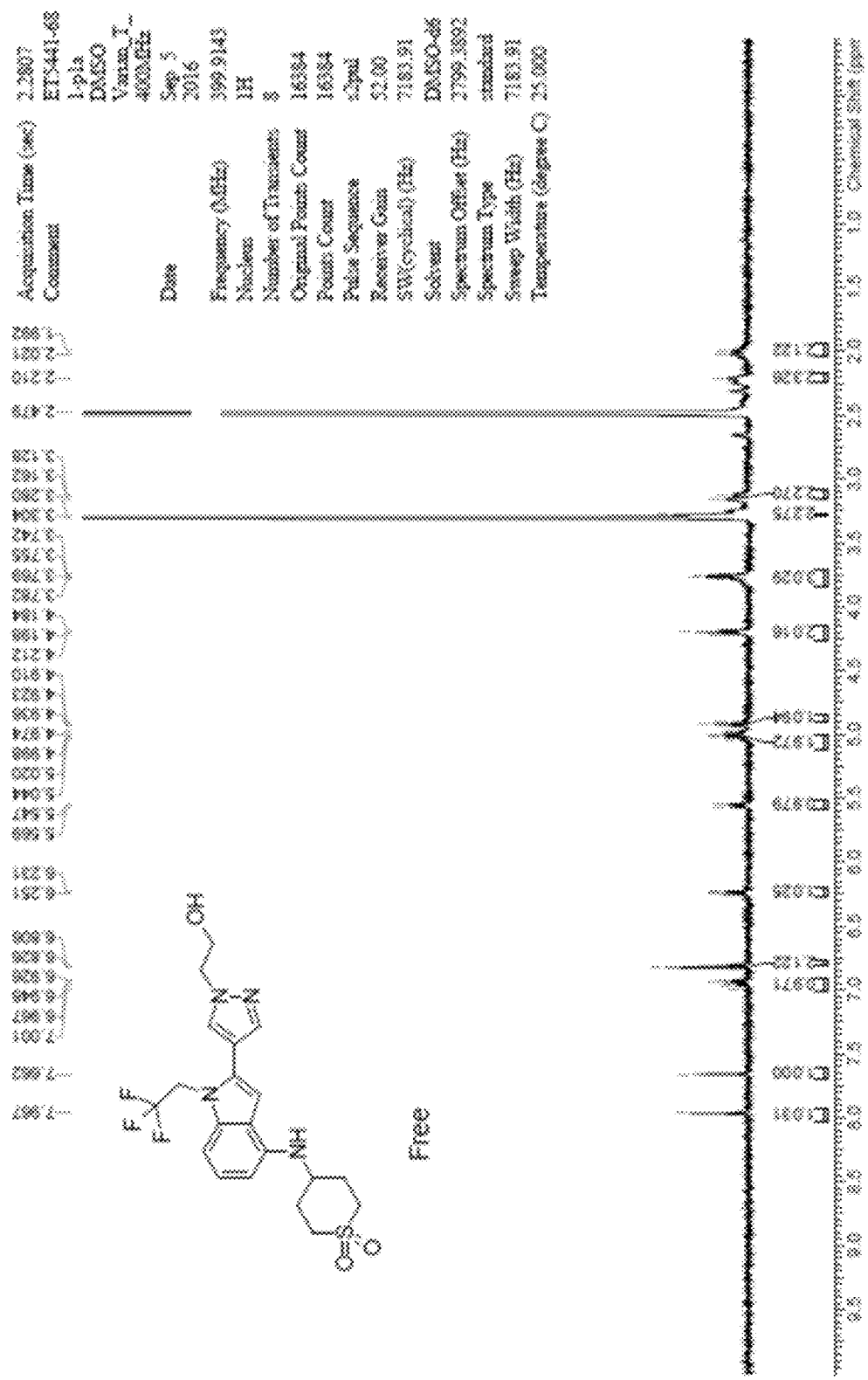
FIG. 13 shows a $^1$H NMR spectrum of 4-((2-(1-(2-hydroxyethyl)-1H-pyrazol-4-yl)-1-(2,2,2-trifluoroethyl)-1H-indol-4-yl)amino)tetrahydro-2H-thiopyran 1,1-dioxide.
Figure 14:
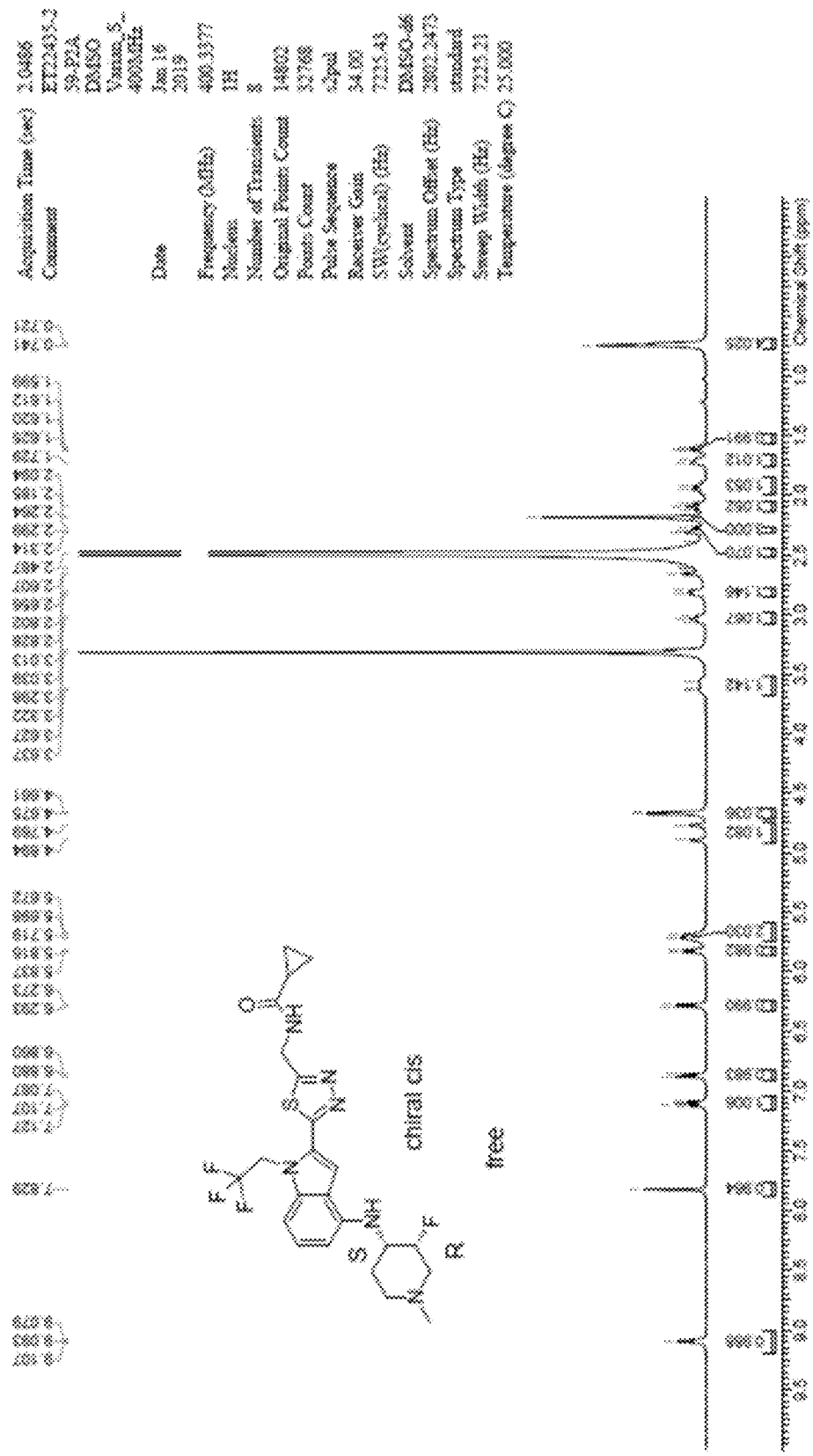
FIG. 14 shows a $^1$H NMR spectrum of N-((3R,4S)-3-fluoro-1-methylpiperidin-4-yl)-2-(5-((prop-1-en-2-ylamino)methyl)-1,3,4-thiadiazol-2-yl)-1-(2,2,2-trifluoroethyl)-1H-indol-4-amine.
Figure 15:
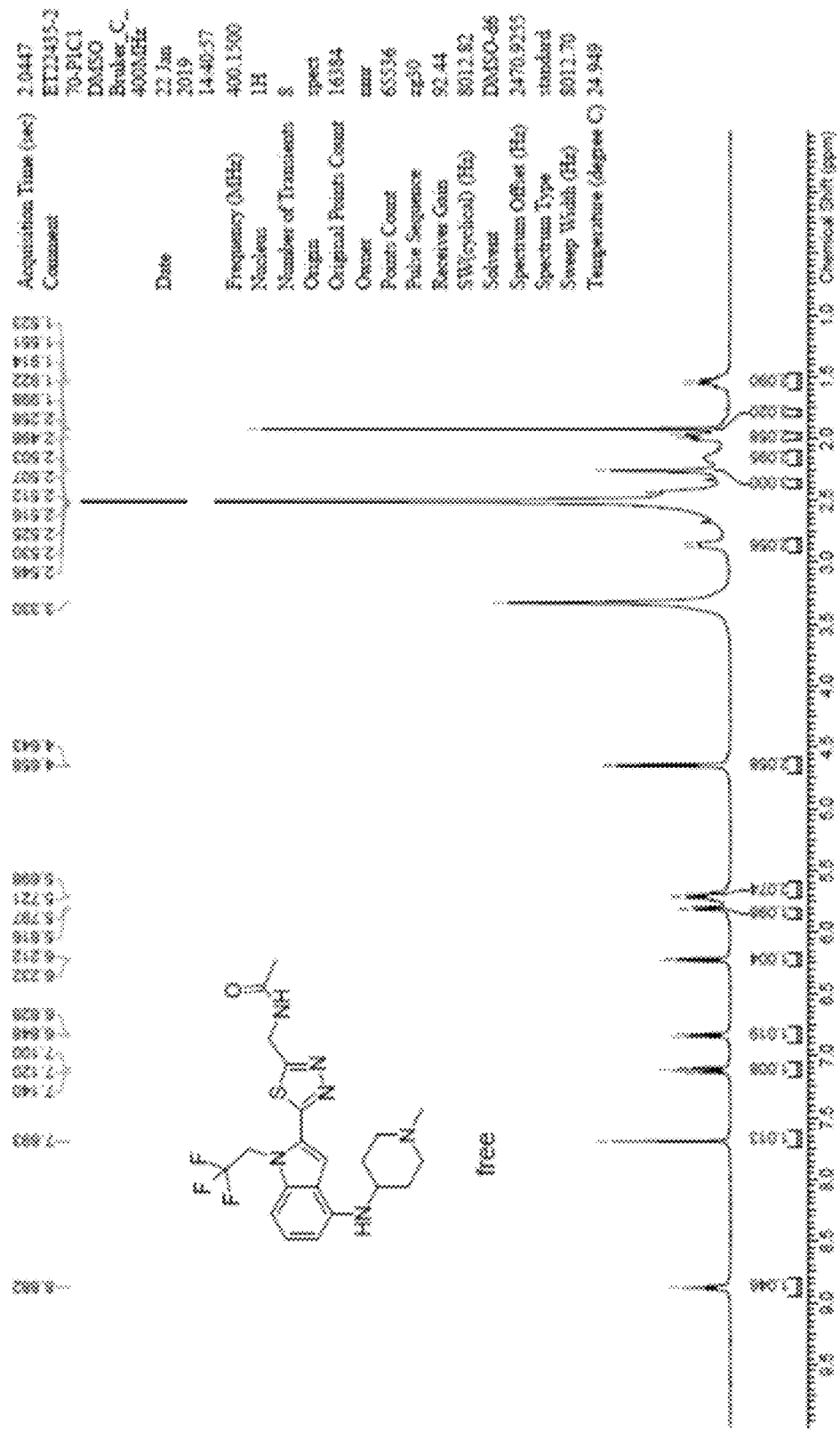
FIG. 15 shows a $^1$H NMR spectrum of N-((5-(4-(((3R,4S)-3-fluoro-1-methylpiperidin-4-yl)amino)-1-(2,2,2-trifluoroethyl)-1H-indol-2-yl)-1,3,4-thiadiazol-2-yl)methyl)acetamide.
Figure 16:
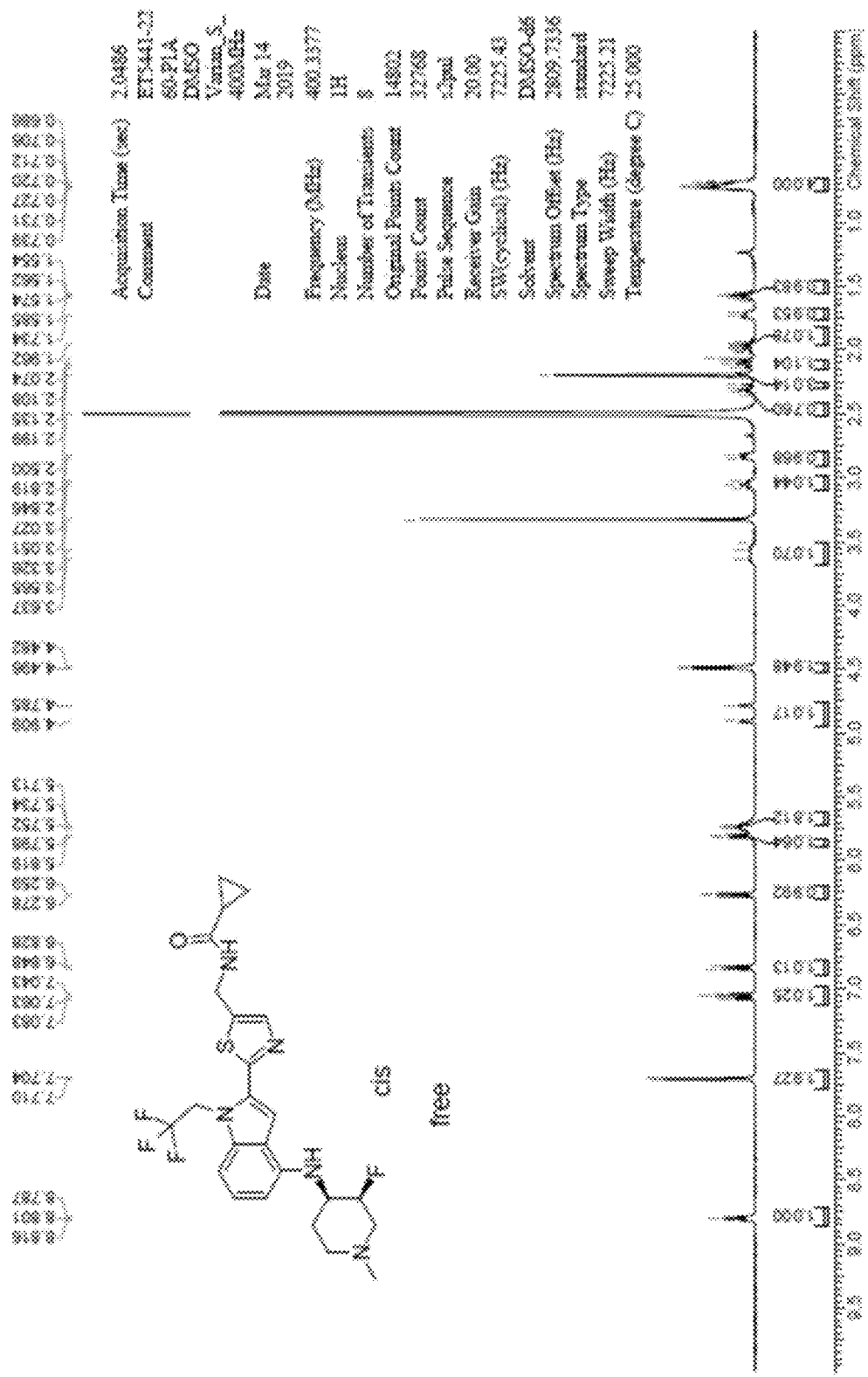
FIG. 16 shows a $^1$H NMR spectrum of N-((2-(4-(((3S,4R)-3-fluoro-1-methylpiperidin-4-yl)amino)-1-(2,2,2-trifluoroethyl)-1H-indol-2-yl)thiazol-5-yl)methyl)cyclopropanecarboxamide.
Figure 17:
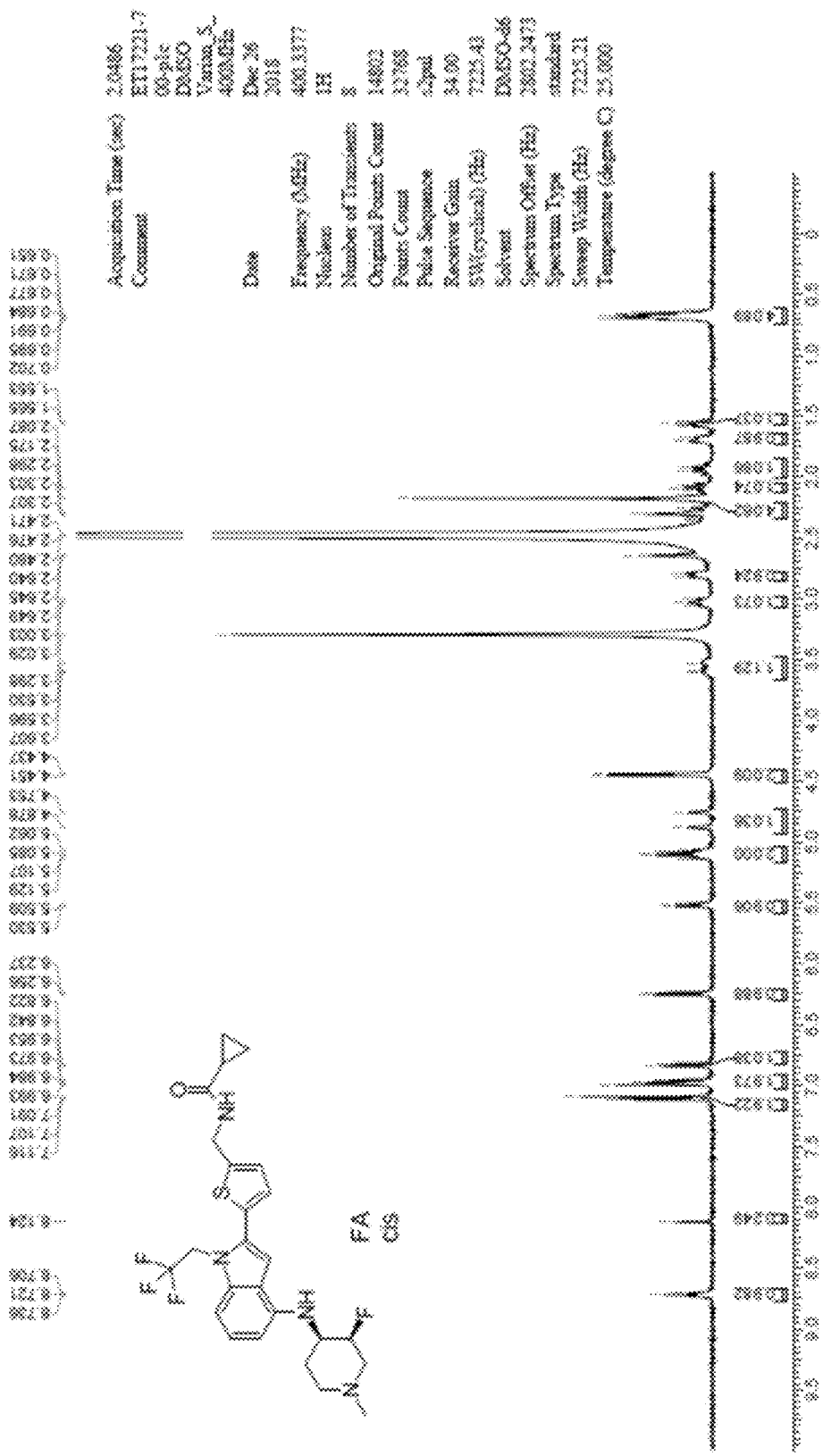
FIG. 17 shows a $^1$H NMR spectrum of N-((5-(4-(((3S,4R)-3-fluoro-1-methylpiperidin-4-yl)amino)-1-(2,2,2-trifluoroethyl)-1H-indol-2-yl)thiophen-2-yl)methyl)cyclopropanecarboxamide.
Figure 18:
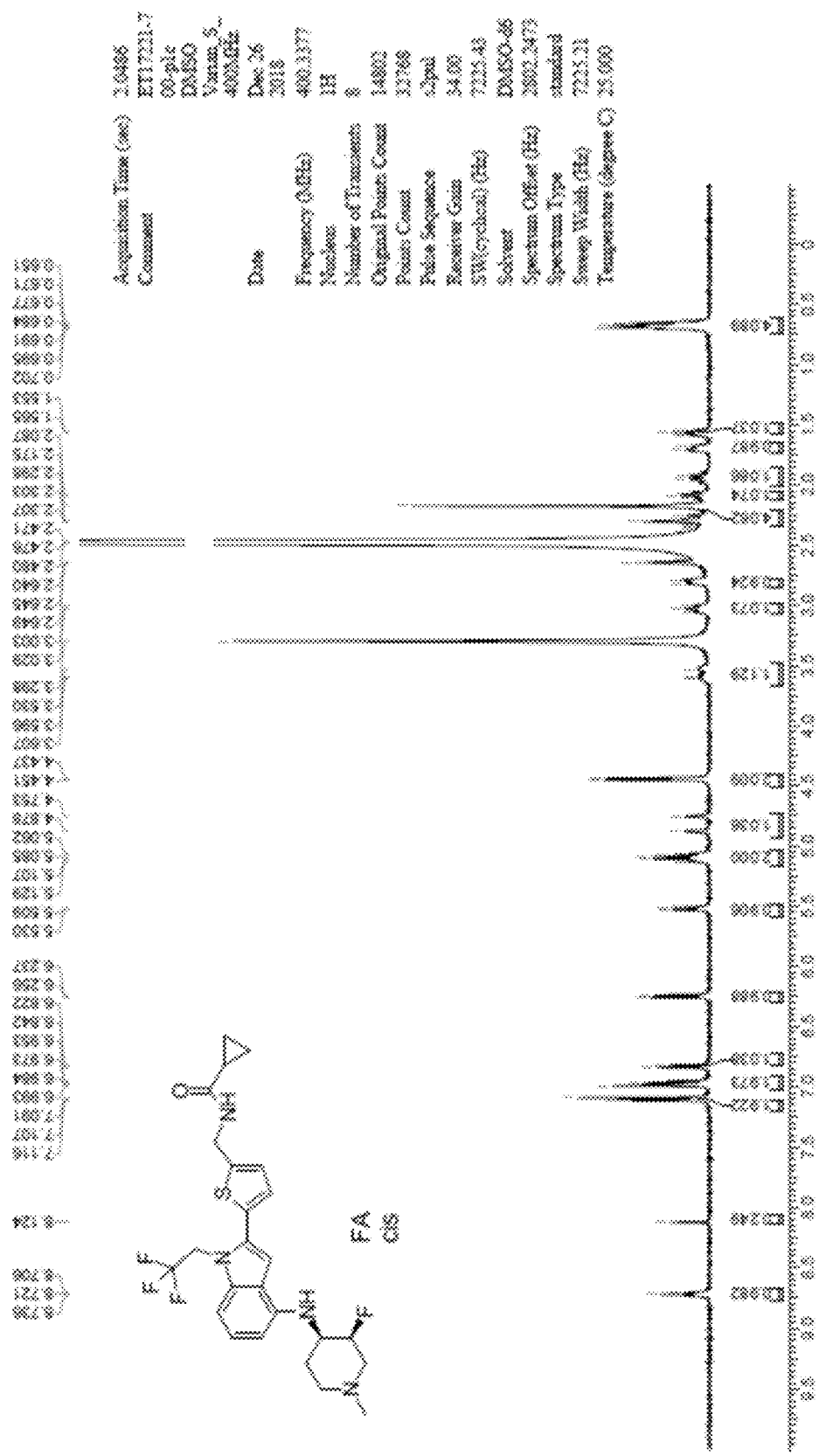
FIG. 18 shows a $^1$H NMR spectrum of N-((5-(4-(((3S,4R)-3-fluoro-1-methylpiperidin-4-yl)amino)-1-(2,2,2-trifluoroethyl)-1H-indol-2-yl)thiophen-2-yl)methyl)cyclopropanecarboxamide.
Figure 19:
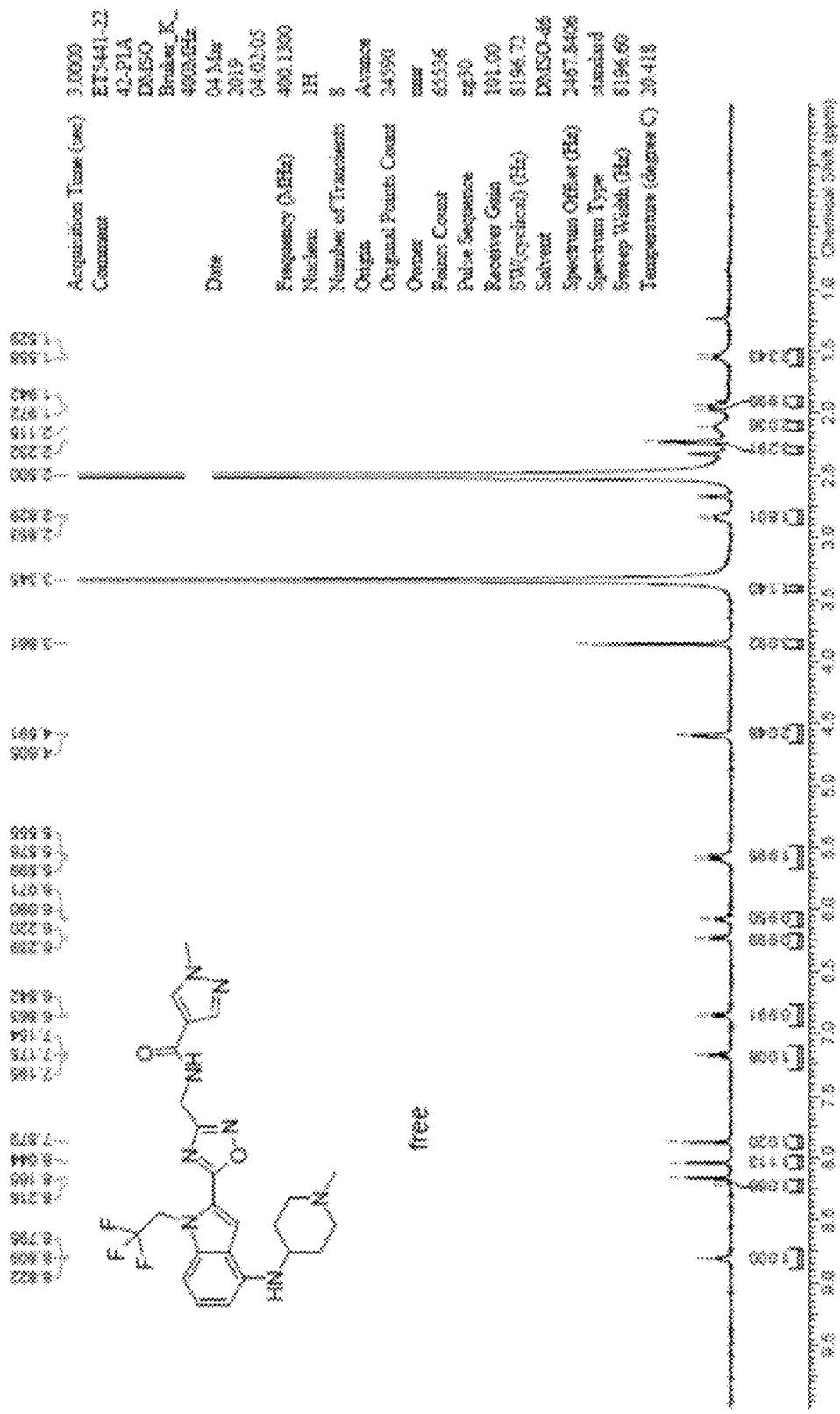
FIG. 19 shows a $^1$H NMR spectrum of 1-methyl-N-((5-(4-((1-methylpiperidin-4-yl)amino)-1-(2,2,2-trifluoroethyl)-1H-indol-2-yl)-1,2,4-oxadiazol-3-yl)methyl)-1H-pyrazole-4-carboxamide.
Figure 20:
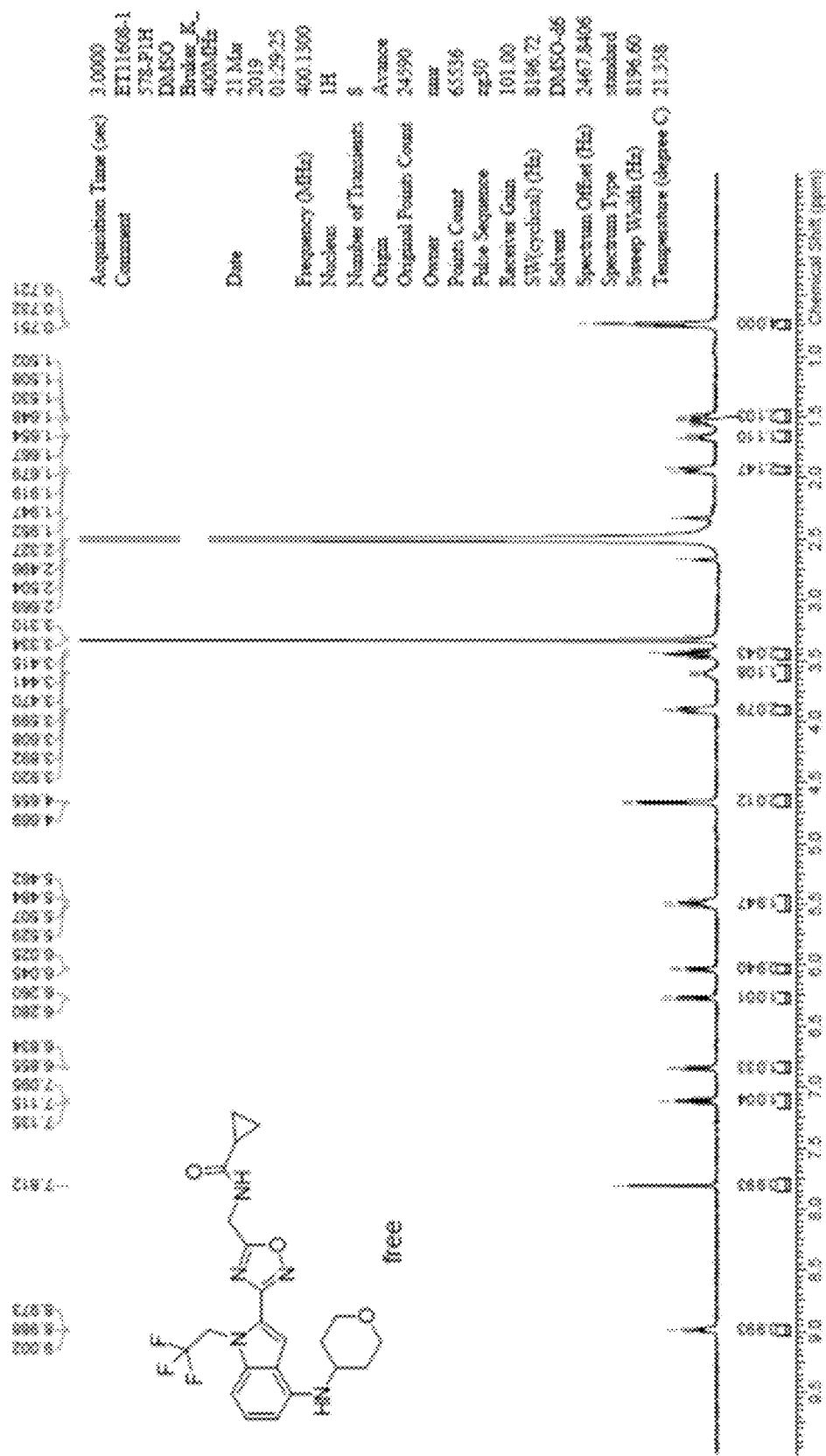
FIG. 20 shows a $^1$H NMR spectrum of N-((3-(4-((tetrahydro-2H-pyran-4-yl)amino)-1-(2,2,2-trifluoroethyl)-1H-indol-2-yl)-1,2,4-oxadiazol-5-yl)methyl)cyclopropanecarboxamide.

The present disclosure provides compounds and methods for restoring wild-type function to mutant p53. The compounds of the present disclosure can bind to mutant p53 and restore the ability of the p53 mutant to bind DNA. The restoration of activity of the p53 mutant can allow for the activation of downstream effectors of p53 leading to inhibition of cancer progression. The disclosure further provides methods of treatment of a cancerous lesion or a tumor harboring a p53 mutation.

Cancer is a collection of related diseases characterized by uncontrolled proliferation of cells with the potential to metastasize throughout the body. Cancer can be classified into five broad categories including, for example: carcinomas, which can arise from cells that cover internal and external parts of the body such as the lung, breast, and colon; sarcomas, which can arise from cells that are located in bone, cartilage, fat, connective tissue, muscle, and other supportive tissues; lymphomas, which can arise in the lymph nodes and immune system tissues; leukemia, which can arise in the bone marrow and accumulate in the bloodstream; and adenomas, which can arise in the thyroid, the pituitary gland, the adrenal gland, and other glandular tissues.

Although different cancers can develop in virtually any of the body's tissues, and contain unique features, the basic processes that cause cancer can be similar in all forms of the disease. Cancer begins when a cell breaks free from the normal restraints on cell division and begins to grow and divide out of control. Genetic mutations in the cell can preclude the ability of the cell to repair damaged DNA or initiate apoptosis and can result in uncontrolled growth and division of cells.

The ability of tumor cell populations to multiply is determined not only by the rate of cell proliferation but also by the rate of cell attrition. Programmed cell death, or apoptosis, represents a major mechanism of cellular attrition. Cancer cells can evade apoptosis through a variety of strategies, for example, through the suppression of p53 function, thereby suppressing expression of pro-apoptotic proteins.

Oncogenes and tumor suppressor genes can regulate the proliferation of cells. Genetic mutations can affect oncogenes and tumor suppressors, potentially activating or suppressing activity abnormally, further facilitating uncontrolled cell division. Whereas oncogenes assist in cellular growth, tumor suppressor genes slow cell division by repairing damaged DNA and activating apoptosis. Cellular oncogenes that can be mutated in cancer include, for example, Cdk1, Cdk2, Cdk3, Cdk4, Cdk6, EGFR, PDGFR, VEGF, HER2, Raf kinase, K-Ras, and myc. Tumor suppressor genes that can be mutated in cancer include, for example, BRCA1, BRCA2, cyclin-dependent kinase inhibitor 1C, Retinoblastoma protein (pRb), PTEN, p16, p27, p53, and p73.

Tumor Suppressor p53.

The tumor suppressor protein p53 is a 393 amino acid transcription factor that can regulate cell growth in response to cellular stresses including, for example, UV radiation, hypoxia, oncogene activation, and DNA damage. p53 has various mechanisms for inhibiting the progression of cancer including, for example, initiation of apoptosis, maintenance of genomic stability, cell cycle arrest, induction of senescence, and inhibition of angiogenesis. Due to the critical role of p53 in tumor suppression, p53 is inactivated in almost all cancers either by direct mutation or through perturbation of associated signaling pathways involved in tumor suppression. Homozygous loss of the p53 gene occurs in almost all types of cancer, including carcinomas of the breast, colon, and lung. The presence of certain p53 mutations in several types of human cancer can correlate with less favorable patient prognosis.

In the absence of stress signals, p53 levels are maintained at low levels via the interaction of p53 with Mdm2, an E3 ubiquitin ligase. In an unstressed cell, Mdm2 can target p53 for degradation by the proteasome. Under stress conditions, the interaction between Mdm2 and p53 is disrupted, and p53 accumulates. The critical event leading to the activation of p53 is phosphorylation of the N-terminal domain of p53 by protein kinases, thereby transducing upstream stress signals. The phosphorylation of p53 leads to a conformational change, which can promote DNA binding by p53 and allow transcription of downstream effectors. The activation of p53 can induce, for example, the intrinsic apoptotic pathway, the extrinsic apoptotic pathway, cell cycle arrest, senescence, and DNA repair. p53 can activate proteins involved in the above pathways including, for example, Fas/Apo1, KILLER/DR5, Bax, Puma, Noxa, Bid, caspase-3, caspase-6, caspase-7, caspase-8, caspase-9, and p21 (WAF1). Additionally, p53 can repress the transcription of a variety of genes including, for example, c-MYC, Cyclin B, VEGF, RAD51, and hTERT.

Each chain of the p53 tetramer is composed of several functional domains including the transactivation domain (amino acids 1-100), the DNA-binding domain (amino acids 101-306), and the tetramerization domain (amino acids 307-355), which are highly mobile and largely unstructured. Most p53 cancer mutations are located in the DNA-binding core domain of the protein, which contains a central β-sandwich of anti-parallel, β-sheets that serves as a basic scaffold for the DNA-binding surface. The DNA-binding surface is composed of two β-turn loops, L2 and L3, which are stabilized by a zinc ion, for example, at Arg175 and Arg248, and a loop-sheet-helix motif. Altogether, these structural elements form an extended DNA-binding surface that is rich in positively-charged amino acids and makes specific contact with various p53 response elements.

Due to the prevalence of p53 mutations in virtually every type of cancer, the reactivation of wild type p53 function in a cancerous cell can be an effective therapy. Mutations in p53 located in the DNA-binding domain of the protein or periphery of the DNA-binding surface result in aberrant protein folding required for DNA recognition and binding. Mutations in p53 can occur, for example, at amino acids Val143, His168, Arg175, Tyr220, Gly245, Arg248, Arg249, Phe270, Arg273, and Arg282. p53 mutations that can abrogate the activity of p53 include, for example, R175H, Y220C, G245S, R248Q, R248W, R273H, and R282H. These p53 mutations can either distort the structure of the DNA-binding site or thermodynamically destabilize the folded protein at body temperature. Wild-type function of p53 mutants can be recovered by binding of the p53 mutant to a compound that can shift the folding-unfolding equilibrium towards the folded state, thereby reducing the rate of unfolding and destabilization.

Non-limiting examples of amino acids include: alanine (A, Ala); arginine (R, Arg); asparagine (N, Asn); aspartic acid (D, Asp); cysteine (C, Cys); glutamic acid (E, Glu); glutamine (Q, Gln); glycine (G, Gly); histidine (H, His); isoleucine (I, Ile); leucine (L, Leu); lysine (K, Lys); methionine (M, Met); phenylalanine (F, Phe); proline (P, Pro); serine (S, Ser); threonine (T, Thr); tryptophan (W, Trp); tyrosine (Y, Tyr); and valine (V, Val).

Mechanism of Compounds of the Disclosure.

The compounds of the present disclosure can selectively bind to a p53 mutant and can recover wild-type activity of the p53 mutant including, for example, DNA binding function and activation of downstream targets involved in tumor suppression. In some embodiments, a compound of the disclosure selectively binds to the p53 Y220C mutant. The Y220C mutant is a temperature sensitive mutant, which binds to DNA at lower temperature and is denatured at body temperature. A compound of the disclosure can stabilize the Y220C mutant to reduce the likelihood of denaturation of the protein at body temperature.

Located in the periphery of the p53 β-sandwich connecting β-strands S7 and S8, the aromatic ring of Y220 is an integral part of the hydrophobic core of the β-sandwich. The Y220C mutation can be highly destabilizing, due to the formation of an internal surface cavity. A compound of the disclosure can bind to and occupy this surface crevice to stabilize the β-sandwich, thereby restoring wild-type p53 DNA-binding activity.

To determine the ability of a compound of the disclosure to bind and stabilize mutant p53, assays can be employed to detect, for example, a conformational change in the p53 mutant or activation of wild-type p53 targets. Conformational changes in p53 can be measured by, for example, differential scanning fluorimetry (DSF), isothermal titration calorimetry (ITC), nuclear magnetic resonance spectrometry (NMR), or X-ray crystallography. Additionally, antibodies specific for the wild type of mutant conformation of p53 can be used to detect a conformational change via, for example, immunoprecipitation (IP), immunofluorescence (IF), or immunoblotting.

Methods used to detect the ability of the p53 mutant to bind DNA can include, for example, DNA affinity immunoblotting, modified enzyme-linked immunosorbent assay (ELISA), electrophoretic mobility shift assay (EMSA), fluorescence resonance energy transfer (FRET), homogeneous time-resolved fluorescence (HTRF), and a chromatin immunoprecipitation (ChIP) assay.

To determine whether a compound described herein is able to reactivate the transcriptional activity of p53, the activation of downstream targets in the p53 signaling cascade can be measured. Activation of p53 effector proteins can be detected by, for example, immunohistochemistry (IHC-P), reverse transcription polymerase chain reaction (RT-PCR), and western blotting. The activation of p53 can also be measured by the induction of apoptosis via the caspase cascade and using methods including, for example, Annexin V staining, TUNEL assays, pro-caspase and caspase levels, and cytochrome c levels. Another consequence of p53 activation is senescence, which can be measured using methods such as β-galactosidase staining.

A p53 mutant that can be used to determine the effectiveness of a compound of the disclosure to increase the DNA binding ability of a p53 mutant is a p53 truncation mutant, which contains only amino acids 94-312, encompassing the DNA-binding domain of p53. For example, the sequence of the p53 Y220C mutant used for testing compound efficacy can be:

```
                                          (SEQ ID NO. 1)
SSSVPSQ KTYQGSYGFR LGFLHSGTAK SVTCTYSPAL

NKMFCQLAKT CPVQLWVDST PPPGTRVRAM AIYKQSQHMT

EVVRRCPHHE RCSDSDGLAP PQHLIRVEGN LRVEYLDDRN

TFRHSVVVPC EPPEVGSDCT TIHYNYMCNS SCMGGMNRRP
```

-continued

ILTIITLEDS SGNLLGRNSF EVHVCACPGR DRRTEEENLR

KKGEPHHELP PGSTKRALSN NT

A compound of the disclosure can increase the ability of a p53 mutant to bind DNA by at least or up to about 0.1%, at least or up to about 0.2%, at least or up to about 0.3%, at least or up to about 0.4%, at least or up to about 0.5%, at least or up to about 0.6%, at least or up to about 0.7%, at least or up to about 0.8%, at least or up to about 0.9%, at least or up to about 1%, at least or up to about 2%, at least or up to about 3%, at least or up to about 4%, at least or up to about 5%, at least or up to about 6%, at least or up to about 7%, at least or up to about 8%, at least or up to about 9%, at least or up to about 10%, at least or up to about 11%, at least or up to about 12%, at least or up to about 13%, at least or up to about 14%, at least or up to about 15%, at least or up to about 16%, at least or up to about 17%, at least or up to about 18%, at least or up to about 19%, at least or up to about 20%, at least or up to about 21%, at least or up to about 22%, at least or up to about 23%, at least or up to about 24%, at least or up to about 25%, at least or up to about 26%, at least or up to about 27%, at least or up to about 28%, at least or up to about 29%, at least or up to about 30%, at least or up to about 31%, at least or up to about 32%, at least or up to about 33%, at least or up to about 34%, at least or up to about 35%, at least or up to about 36%, at least or up to about 37%, at least or up to about 38%, at least or up to about 39%, at least or up to about 40%, at least or up to about 41%, at least or up to about 42%, at least or up to about 43%, at least or up to about 44%, at least or up to about 45%, at least or up to about 46%, at least or up to about 47%, at least or up to about 48%, at least or up to about 49%, at least or up to about 50%, at least or up to about 51%, at least or up to about 52%, at least or up to about 53%, at least or up to about 54%, at least or up to about 55%, at least or up to about 56%, at least or up to about 57%, at least or up to about 58%, at least or up to about 59%, at least or up to about 60%, at least or up to about 61%, at least or up to about 62%, at least or up to about 63%, at least or up to about 64%, at least or up to about 65%, at least or up to about 66%, at least or up to about 67%, at least or up to about 68%, at least or up to about 69%, at least or up to about 70%, at least or up to about 71%, at least or up to about 72%, at least or up to about 73%, at least or up to about 74%, at least or up to about 75%, at least or up to about 76%, at least or up to about 77%, at least or up to about 78%, at least or up to about 79%, at least or up to about 80%, at least or up to about 81%, at least or up to about 82%, at least or up to about 83%, at least or up to about 84%, at least or up to about 85%, at least or up to about 86%, at least or up to about 87%, at least or up to about 88%, at least or up to about 89%, at least or up to about 90%, at least or up to about 91%, at least or up to about 92%, at least or up to about 93%, at least or up to about 94%, at least or up to about 95%, at least or up to about 96%, at least or up to about 97%, at least or up to about 98%, at least or up to about 99%, at least or up to about 100%, at least or up to about 125%, at least or up to about 150%, at least or up to about 175%, at least or up to about 200%, at least or up to about 225%, or at least or up to about 250% as compared to the ability of the p53 mutant to bind DNA in the absence of a compound of the disclosure.

A compound described herein can increase the activity of the p53 mutant that is, for example, at least or up to about 2-fold, at least or up to about 3-fold, at least or up to about 4-fold, at least or up to about 5-fold, at least or up to about 6-fold, at least or up to about 7-fold, at least or up to about 8-fold, at least or up to about 9-fold, at least or up to about 10-fold, at least or up to about 11-fold, at least or up to about 12-fold, at least or up to about 13-fold, at least or up to about 14-fold, at least or up to about 15-fold, at least or up to about 16-fold, at least or up to about 17-fold, at least or up to about 18-fold, at least or up to about 19-fold, at least or up to about 20-fold, at least or up to about 25-fold, at least or up to about 30-fold, at least or up to about 35-fold, at least or up to about 40-fold, at least or up to about 45-fold, at least or up to about 50-fold, at least or up to about 55-fold, at least or up to about 60-fold, at least or up to about 65-fold, at least or up to about 70-fold, at least or up to about 75-fold, at least or up to about 80-fold, at least or up to about 85-fold, at least or up to about 90-fold, at least or up to about 95-fold, at least or up to about 100-fold, at least or up to about 110-fold, at least or up to about 120-fold, at least or up to about 130-fold, at least or up to about 140-fold, at least or up to about 150-fold, at least or up to about 160-fold, at least or up to about 170-fold, at least or up to about 180-fold, at least or up to about 190-fold, at least or up to about 200-fold, at least or up to about 250-fold, at least or up to about 300-fold, at least or up to about 350-fold, at least or up to about 400-fold, at least or up to about 450-fold, at least or up to about 500-fold, at least or up to about 550-fold, at least or up to about 600-fold, at least or up to about 650-fold, at least or up to about 700-fold, at least or up to about 750-fold, at least or up to about 800-fold, at least or up to about 850-fold, at least or up to about 900-fold, at least or up to about 950-fold, at least or up to about 1,000-fold, at least or up to about 1,500-fold, at least or up to about 2,000-fold, at least or up to about 3,000-fold, at least or up to about 4,000-fold, at least or up to about 5,000-fold, at least or up to about 6,000-fold, at least or up to about 7,000-fold, at least or up to about 8,000-fold, at least or up to about 9,000-fold, or at least or up to about 10,000-fold greater than the activity of the p53 mutant in the absence of the compound.

A compound of the disclosure can be used, for example, to induce apoptosis, cell cycle arrest, or senescence in a cell. In some embodiments, the cell is a cancer cell. In some embodiments, the cell carries a mutation in p53.

Compounds of the Disclosure.

In some embodiments, the disclosure provides a compound comprising: an indole group, wherein the indole group comprises: a) a haloalkyl group at a 1-position of the indole group; b) a first substituent at a 2-position of the indole group, wherein the first substituent is a cyclic group; and c) a second substituent, wherein the second substituent is substituted with at least halo-; or a pharmaceutically-acceptable salt thereof.

In some embodiments, the cyclic group is aryl, heteroaryl, or heterocyclyl, each of which is substituted or unsubstituted. In some embodiments, the cyclic group is unsubstituted aryl. In some embodiments, the cyclic group is substituted aryl. In some embodiments, the cyclic group is substituted phenyl. In some embodiments, the cyclic group is substituted or unsubstituted heteroaryl. In some embodiments, the heteroaryl is an aromatic 5-membered or 6-membered monocyclic ring. In some embodiments, the heteroaryl is thiazolyl, thiadiazolyl, pyrazolyl, thiophenyl, or oxadiazolyl. In some embodiments, the heteroaryl is pyridinyl or pyrimidinyl.

In some embodiments, the second substituent is at a 4-position of the indole group. In some embodiments, the second substituent is a second cyclic group that is substituted or unsubstituted. In some embodiments, the second cyclic group is heterocyclyl. In some embodiments, the heterocyclyl is piperidinyl. In some embodiments, the heterocyclyl is tetrahydropyranyl. In some embodiments, the heterocyclyl is substituted with fluoro-. In some embodiments, the heterocyclyl is substituted with chloro-. In some embodiments, the haloalkyl group is trifluoroethyl.

In some embodiments, the disclosure provides a compound, the compound comprising an indole group, wherein the indole group comprises: a) a substituted or unsubstituted non-cyclic group at a 3-position of the indole group; and b) a substituted or unsubstituted cyclic group at a 2-position of the indole group, wherein the compound increases a stability of a biologically-active conformation of a p53 mutant relative to a stability of a biologically-active conformation of the p53 mutant in an absence of the compound, or a pharmaceutically-acceptable salt thereof.

In some embodiments, the non-cyclic group is hydrogen. In some embodiments, the non-cyclic group is halo-. In some embodiments, the cyclic group is aryl, heteroaryl, heterocyclyl, or cycloalkylene, each of which is substituted or unsubstituted. In some embodiments, the cyclic group is aryl or heteroaryl, each of which is substituted or unsubstituted. In some embodiments, the cyclic group is substituted aryl. In some embodiments, the cyclic group is substituted phenyl. In some embodiments, the cyclic group is phenyl substituted with alkyl, cycloalkyl, alkoxy, an amine group, a carboxyl group, a carboxylic acid group, a carbamide group, or an amide group, each of which is substituted or unsubstituted; cyano, halo-, or hydrogen.

In some embodiments, the cyclic group is substituted heteroaryl. In some embodiments, the cyclic group is an aromatic 5-membered, 6-membered, 7-membered, or 8-membered monocyclic ring system comprising 1, 2, or 3 heteroatoms as ring members, wherein each heteroatom is independently selected from O, N, or S. In some embodiments, the cyclic group is pyridinyl, pyrimidinyl, thiadiazolyl, thiazolyl, pyrazolyl, thiophenyl, or oxadiazolyl, In some embodiments, the cyclic group is 1,3,5-thiadiazol-2-yl. In some embodiments, the cyclic group is 1,3,4-oxadiazol-2-yl or 1,2,4-oxadiazol-2-yl. In some embodiments, the cyclic group is pyridinyl.

In some embodiments, the indole group further comprises a substituent at a 4-position of the indole group. In some embodiments, the substituent is an amino group that is substituted or unsubstituted. In some embodiments, the amino group is substituted with a second cyclic group. In some embodiments, the second cyclic group is a heterocyclyl group substituted with at least halo-. In some embodiments, the heterocyclyl group is substituted with at least fluoro-. In some embodiments, the heterocyclyl group is substituted with at least chloro-. In some embodiments, the heterocyclyl group is piperidinyl. In some embodiments, the heterocyclyl group is tetrahydropyranyl.

Non-limiting examples of compounds of the disclosure include compounds of any of the following formulae:

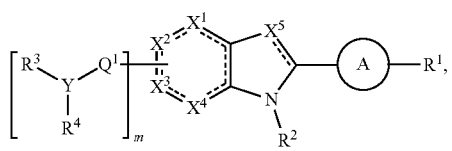

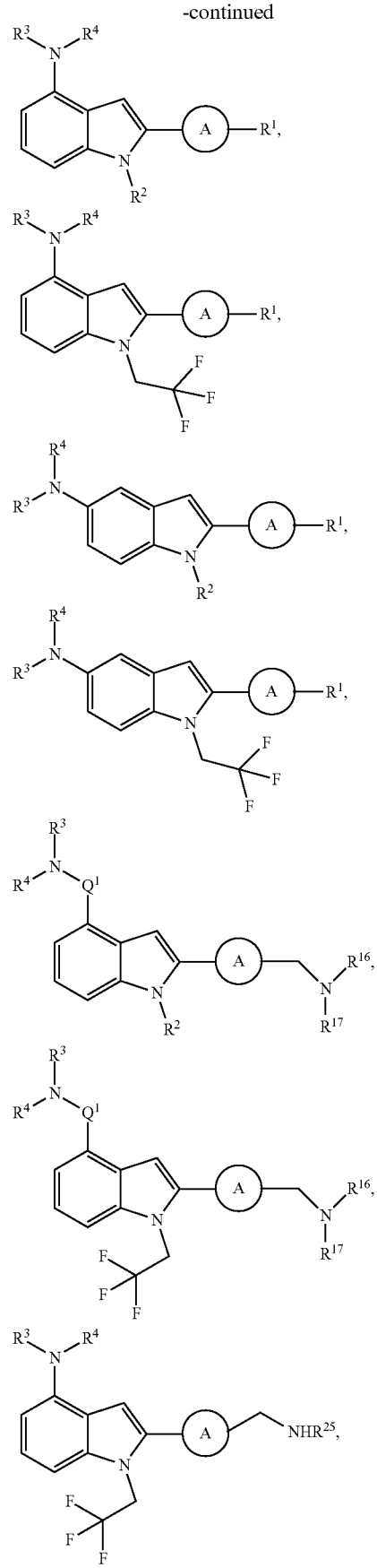

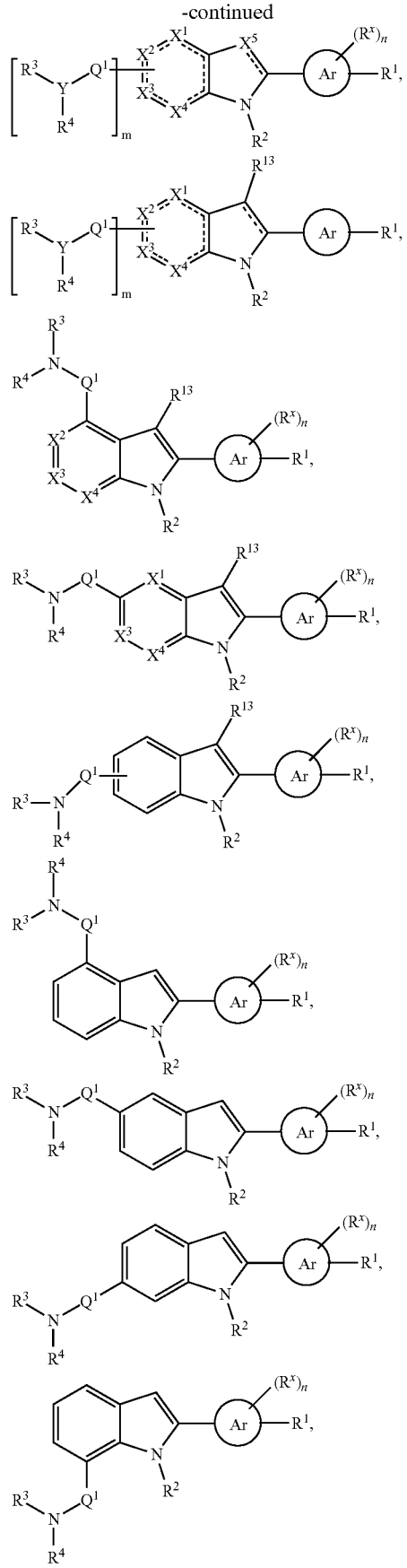
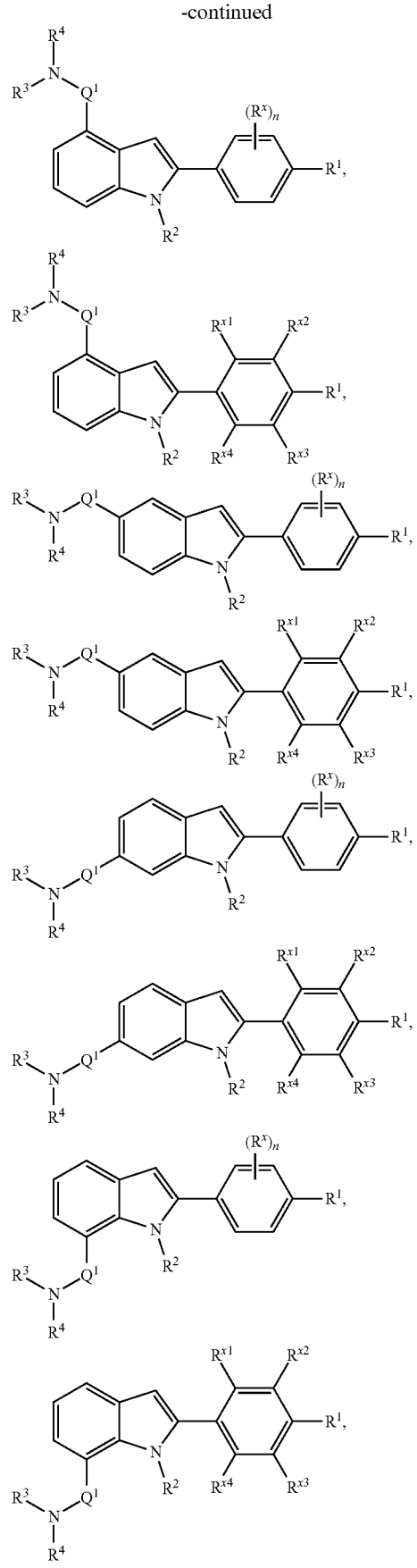

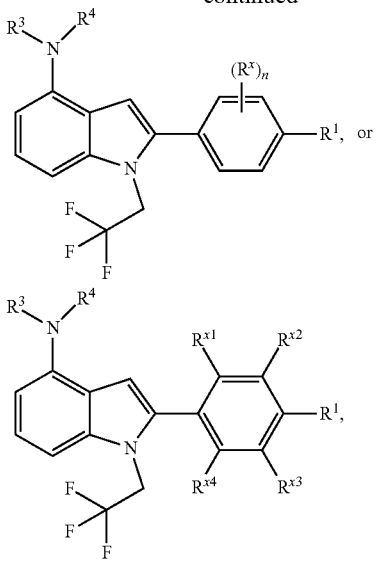

or a pharmaceutically-acceptable salt thereof.

In some embodiments, the disclosure provides a compound of the formula:

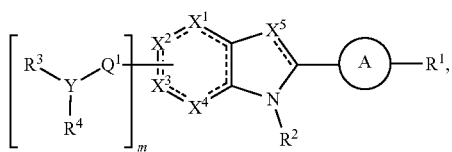

wherein:
each ------- is independently a single bond or a double bond;
$X^1$ is $CR^5$, $CR^5R^6$, $N$, $NR^5$, $O$, $S$, $C=O$, $C=S$, or a carbon atom connected to $Q^1$;
$X^2$ is $CR^7$, $CR^7RR$, $N$, $NR^7$, $O$, $S$, $C=O$, $C=S$, or a carbon atom connected to $Q^1$;
$X^3$ is $CR^9$, $CR^9R^{10}$, $N$, $NR^9$, $O$, $S$, $C=O$, $C=S$, or a carbon atom connected to $Q^1$;
$X^4$ is $CR^{11}$, $CR^{11}R^{12}$, $N$, $NR^{11}$, $O$, $S$, $C=O$, $C=S$, or a carbon atom connected to $Q^1$;
$X^5$ is $CR^{13}$, $N$, or $NR^{13}$;
wherein at least one of $X^1$, $X^2$, $X^3$, and $X^4$ is a carbon atom connected to $Q^1$;
A is a substituted or unsubstituted ring;
$Q^1$ is $C=O$, $C=S$, $C=CR^{14}R^{15}$, $C=NR^{14}$, alkylene, alkenylene, or alkynylene, each of which is independently substituted or unsubstituted, or a bond;
m is 1, 2, 3, or 4;
Y is N, O, or absent;
$R^1$ is $-C(O)R^{16}$, $-C(O)OR^{16}$, $-C(O)NR^{16}R^{17}$, $-OR^{16}$, $-SR^{16}$, $-NR^{16}R^{17}$, $-NR^{16}C(O)R^1$, $-OC(O)R^{16}$, $-SiR^{16}R^{17}R^{18}$, alkyl, alkenyl, alkynyl, alkoxy, aryl, heteroaryl, heterocyclyl, or halo, each of which is independently substituted or unsubstituted, or hydrogen;
each $R^3$ and $R^4$ is independently $-C(O)R^{19}$, $-C(O)R^9$, $-C(O)NR^{19}R^{20}$, $-SOR^{19}$, $-SO_2R^{19}$, alkyl, alkenyl, alkynyl, aryl, heteroaryl, or heterocyclyl, each of which is independently substituted or unsubstituted, or hydrogen, or $R^3$ and $R^4$ together with the nitrogen atom to which $R^3$ and $R^4$ are bound form a ring, wherein the ring is substituted or unsubstituted, or $R^3$ is absent;
each $R^2$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ is independently $-C(O)R^{21}$, $-C(O)OR^{21}$, $-C(O)NR^{21}R^{22}$, $-OR^{21}$, $-SR^{21}$, $-NR^{21}R^{22}$, $-NR^{21}C(O)R^{22}$, $-OC(O)R^{21}$, alkyl, alkenyl, alkynyl, aryl, heteroaryl, or heterocyclyl, each of which is independently substituted or unsubstituted, or hydrogen or halogen;
each $R^{19}$ and $R^{20}$ is $-C(O)R^{23}$, $-C(O)OR^{23}$, $-C(O)NR^{23}R^{24}$, $-OR^{23}$, $-SR^{23}$, $-NR^{23}R^{24}$, $-NR^{23}C(O)R^{24}$, $-OC(O)R^{23}$, alkyl, alkenyl, alkynyl, aryl, heteroaryl, or heterocyclyl, each of which is independently substituted or unsubstituted, or hydrogen or halogen;
each $R^{21}$ and $R^{22}$ is independently alkyl, alkenyl, alkynyl, aryl, heteroaryl, or heterocyclyl, each of which is independently substituted or unsubstituted, or hydrogen; and
each $R^{23}$ and $R^{24}$ is independently alkyl, alkenyl, alkynyl, aryl, heteroaryl, or heterocyclyl, each of which is independently substituted or unsubstituted, or hydrogen,
or a pharmaceutically-acceptable salt thereof.

In some embodiments, A is substituted or unsubstituted aryl, heteroaryl, heterocyclyl, cycloalkylene. In some embodiments, A is a 6-carbon monocyclic or 10-carbon bicyclic aromatic ring system wherein 0, 1, 2, 3, or 4 atoms of each ring are optionally substituted. In some embodiments, A is naphthyl. In some embodiments, A is indazolyl.

In some embodiments, A is substituted aryl. In some embodiments, A is substituted phenyl. In some embodiments, A is phenyl substituted with alkyl, cycloalkyl, alkoxy, an amine group, a carboxyl group, a carboxylic acid group, a carbamide group, or an amide group, each of which is substituted or unsubstituted; cyano, halogen, or hydrogen. In some embodiments, A is phenyl substituted with alkyl, wherein alkyl is substituted. In some embodiments, A is phenyl substituted with alkyl, wherein alkyl is substituted with an amino group that is substituted or unsubstituted. In some embodiments, A is phenyl substituted with an amine group that is substituted or unsubstituted. In some embodiments, A is phenyl substituted with a carboxyl group that is substituted or unsubstituted. In some embodiments, A is phenyl substituted with cyano. In some embodiments, A is phenyl substituted with halo-.

In some embodiments, A is substituted or unsubstituted heterocyclyl. In some embodiments, A is substituted heterocyclyl.

In some embodiments, A is an aromatic 5-membered, 6-membered, 7-membered, or 8-membered monocyclic ring system comprising 1, 2, or 3 heteroatoms as ring members, wherein each heteroatom is independently selected from O, N, or S. In some embodiments, A is an aromatic 8-membered, 9-membered, 10-membered, 11-membered, or 12-membered bicyclic ring system comprising 1, 2, 3, 4, 5, or 6 heteroatoms, wherein each heteroatom is independently selected from O, N, or S. In some embodiments, A is an aromatic 5-membered, 6-membered, 7-membered, or 8-membered monocyclic ring system comprising 1, 2, or 3 heteroatoms, and the aromatic 5-membered, 6-membered, 7-membered, or 8-membered monocyclic ring system is substituted. In some embodiments, A is an 8-membered, 9-membered, 10-membered, 11-membered, or 12-membered bicyclic ring system having 1, 2, 3, 4, 5, or 6 heteroatoms, and the 8-membered, 9-membered, 10-membered, 11-membered, or 12-membered bicyclic ring system is substituted.

In some embodiments, A is pyridinyl, pyrimidinyl, thiadiazolyl, thiazolyl, pyrazolyl, thiophenyl, or oxadiazolyl, each of which is independently substituted or unsubstituted. In some embodiments, A is 1,3,5-thiadiazol-2-yl. In some embodiments, A is 1,3,4-oxadiazol-2-yl or 1,2,4-oxadiazol-2-yl. In some embodiments, A is 1,3,4-oxadiazol-2-yl.

In some embodiments, m is 1. In some embodiments, m is 2. In some embodiments, $Q^1$ is alkylene, alkenylene, or alkynylene, each of which is independently substituted or unsubstituted, or a bond. In some embodiments, $Q^1$ is a bond. In some embodiments, Y is N.

In some embodiments, $R^2$ is hydrogen. In some embodiments, $R^2$ is substituted or unsubstituted alkyl. In some embodiments, $R^2$ is trifluoroethyl. In some embodiments, $R^2$ is cycloalkyl.

In some embodiments, $R^1$ is —C(O)$R^{16}$, —C(O)O$R^{16}$, —C(O)N$R^{16}R^{17}$, —O$R^{16}$, —N$R^{16}R^{17}$, —N$R^{16}$C(O)$R^{16}$, —OC(O)$R^{16}$, alkyl, alkoxy, aryl, heteroaryl, or heterocyclyl, each of which is independently substituted or unsubstituted; cyano, halo, or halogen. In some embodiments, $R^1$ is —N$R^{16}R^{17}$. In some embodiments, $R^1$ is substituted alkyl.

In some embodiments, each $R^3$ and $R^4$ is independently aryl, heteroaryl, or heterocyclyl, each of which is independently substituted or unsubstituted; or hydrogen. In some embodiments, $R^3$ is hydrogen, and $R^4$ is heterocyclyl substituted at least with halo-. In some embodiments, $R^4$ is heterocyclyl substituted with fluoro. In some embodiments, $R^4$ is heterocyclyl substituted with chloro.

In some embodiments, $R^{13}$ is alkyl, alkenyl, hydrogen, or halogen. In some embodiments, $R^{13}$ is hydrogen.

In some embodiments, the compound has the formula:

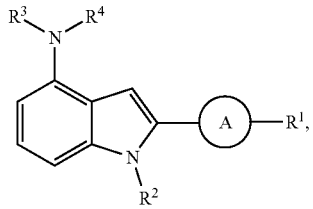

or a pharmaceutically-acceptable salt thereof, wherein the variable are as defined above.

In some embodiments, the compound has the formula:

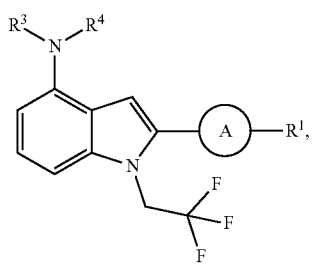

or a pharmaceutically-acceptable salt thereof, wherein the variables are as defined above.

In some embodiments, the compound has the formula:

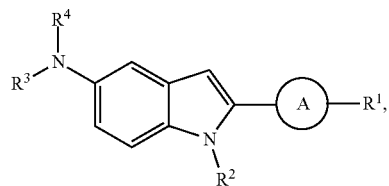

or a pharmaceutically-acceptable salt thereof, wherein the variables are as defined above.

In some embodiments, the compound has the formula:

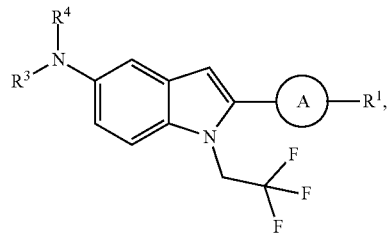

or a pharmaceutically-acceptable salt thereof, wherein the variables are as defined above.

In some embodiments, the disclosure provides a compound of the formula:

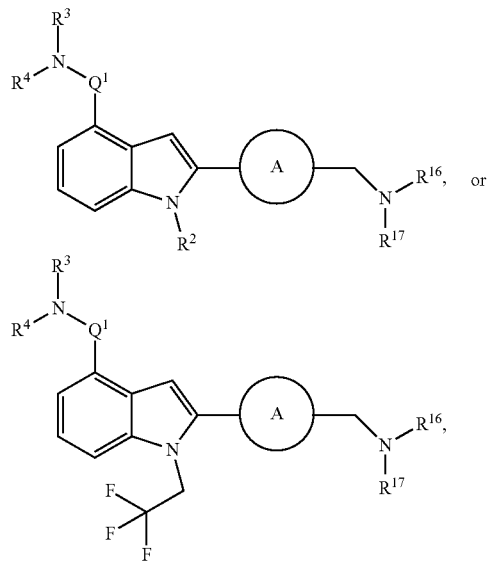

or a pharmaceutically-acceptable salt thereof, wherein the variables are as defined above.

In some embodiments, $Q^1$ is C=O, C=S, C=C$R^{14}R^{15}$, C=N$R^{14}$, alkylene, alkenylene, or alkynylene, each of which is independently substituted or unsubstituted, or a bond. In some embodiments, $Q^1$ is alkylene, alkenylene, or alkynylene. In some embodiments, $Q^1$ is C-alkylene. In some embodiments, each $R^{16}$ and $R^{17}$ is independently alkyl, alkenyl, aryl, heteroaryl, heterocyclyl, or hydrogen. In some embodiments, $Q^1$ is a bond.

In some embodiments, $R^3$ is H, and $R^4$ is —C(O)$R^{19}$, —C(O)O$R^{19}$, —C(O)N$R^{19}R^{20}$, —SO$R^{19}$, —SO$_2R^{19}$, alkyl, alkenyl, alkynyl, aryl, heteroaryl, or heterocyclyl, each of which is independently substituted or unsubstituted; or hydrogen. In some embodiments, $R^3$ is H, and $R^4$ is alkyl, alkenyl, alkynyl, aryl, heteroaryl, or heterocyclyl, each of which is independently substituted or unsubstituted, or hydrogen. In some embodiments, $R^4$ is heterocyclyl. In some embodiments, $R^4$ is piperidinyl, piperazinyl, tetahydropyranyl, morpholinyl, or pyrrolidinyl, each of which is independently substituted or unsubstituted.

In some embodiments, $R^4$ is a ring that is:

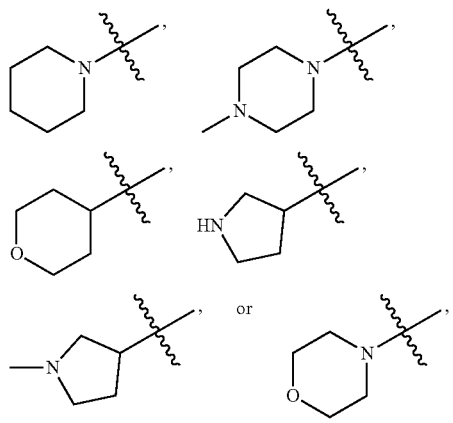

wherein the ring is substituted or unsubstituted. In some embodiments, $R^3$ is H, and $R^4$ is a ring that is

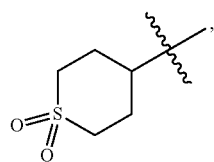 [SMILES: *C1CCS(=O)(=O)CC1]

wherein the ring is substituted or unsubstituted. In some embodiments, $R^3$ is H, and $R^4$ is a ring that is

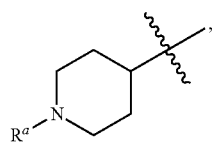

wherein the ring is substituted or unsubstituted. In some embodiments, $R^a$ is alkylene. In some embodiments, $R^a$ is methyl. In some embodiments, $R^3$ is H, and $R^4$ is a ring that is

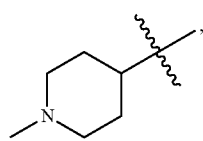 [SMILES: *C1CCN(C)CC1]

wherein the ring is substituted or unsubstituted. In some embodiments, $R^3$ is H, and $R^4$ is a ring that is

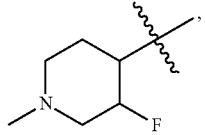 [SMILES: *C1CCN(C)CC1F]

wherein the ring is substituted or unsubstituted.

In some embodiments, each $R^{16}$ and $R^{17}$ is independently alkyl, cycloalkyl, aryl, heteroaryl, heterocyclyl, alkoxy, carboxyl group, amino group, acyl group, acyloxy group, or an amide group, any of which is unsubstituted or substituted, or hydrogen. In some embodiments, $R^{16}$ is hydrogen, and $R^{17}$ is a substituted carboxyl group.

In some embodiments, the compound is of the formula:

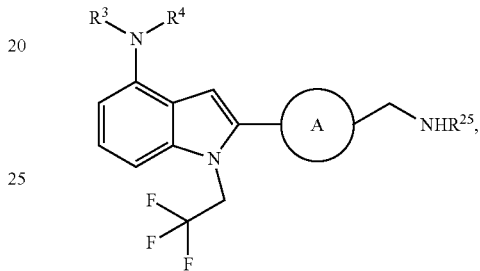

wherein $R^{25}$ is —C(O)$R^{16}$, —C(O)N$R^{16}R^{17}$ ?, alkyl, alkenyl, alkynyl, aryl, heteroaryl, or heterocyclyl, each of which is independently substituted or unsubstituted, or hydrogen. In some embodiments, $R^{25}$ is aryl that is substituted or unsubstituted. In some embodiments, $R^{25}$ is substituted phenyl. In some embodiments, $R^{25}$ is —C(O)$R^{16}$, wherein $R^{16}$ is alkyl, aryl, heteroaryl, or heterocyclyl. In some embodiments, $R^{25}$ is —C(O)$R^{16}$, wherein $R^{16}$ is substituted phenyl.

In some embodiments, the disclosure provides a compound of the formula:

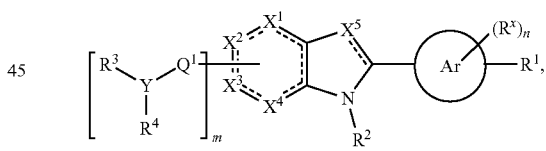

wherein:
each ------- is independently a single bond or a double bond;
$X^1$ is $CR^5$, $CR^5R^6$, N, NR, O, S, C=O, C=S, or a carbon atom connected to $Q^1$;
$X^2$ is $CR^7$, $CR^7R^8$, N, N$R^7$, O, S, C=O, C=S, or a carbon atom connected to $Q^1$;
$X^3$ is $CR^9$, $CR^9R^{10}$, N, N$R^9$, O, S, C=O, C=S, or a carbon atom connected to $Q^1$;
$X^4$ is $CR^{11}$, $CR^{11}R^{12}$, N, N$R^{11}$, O, S, C=O, C=S, or a carbon atom connected to $Q^1$;
$X^5$ is $CR^{13}$, N. or N$R^3$;
wherein at least one of $X^1$, $X^2$, $X^3$, and $X^4$ is a carbon atom connected to $Q^1$;
Ar is unsubstituted or substituted aryl;
$Q^1$ is C=O, C=S, C=$CR^{14}R^{15}$, C=N$R^{14}$, alkylene, alkenylene, or alkynylene, each of which is independently substituted or unsubstituted, or a bond;

m is 1, 2, 3, or 4;
n is 0, 1, 2, 3, or 4;
Y is N, O, or absent;
each $R^x$ and $R^1$ is independently $C(O)R^{16}$, —$C(O)OR^{16}$, —$C(O)NR^{16}R^{17}$, —$OR^{16}$, —$SR^{16}$, —$NR^{16}R^{17}$, —$NR^{16}C(O)R^{16}$, —$OC(O)R^{16}$, —$SiR^{16}R^{17}R^{18}$, alkyl, alkenyl, alkynyl, alkoxy, aryl, heteroaryl, or heterocyclyl, each of which is independently substituted or unsubstituted; cyano, halo, or hydrogen; or $R^1$ and $R^x$ together with Ar form a fused ring;
each $R^3$ and $R^4$ is independently —$C(O)R^{19}$, —$C(O)OR^{19}$, —$C(O)NR^{19}R^{20}$, —$SOR^{19}$, —$SO_2R^{19}$, alkyl, alkenyl, alkynyl, aryl, heteroaryl, or heterocyclyl, each of which is independently substituted or unsubstituted, or hydrogen, or $R^3$ and $R^4$ together with the nitrogen atom to which $R^3$ and $R^4$ are bound form a ring, wherein the ring is substituted or unsubstituted, or $R^3$ is absent;
each $R^2$, R, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ is independently —$C(O)R^{21}$, —$C(O)OR^{21}$, —$C(O)NR^{21}R^{22}$, —$OR^{21}$, —$SR^{21}$, —$NR^{21}R^{22}$, —$NR^{21}C(O)R^{22}$, —$OC(O)R^{21}$, alkyl, alkenyl, alkynyl, aryl, heteroaryl, or heterocyclyl, each of which is independently substituted or unsubstituted, or hydrogen or halogen;
each $R^{19}$ and $R^{20}$ is —$C(O)R^{23}$, —$C(O)OR^{23}$, —$C(O)NR^{23}R^{24}$, —$OR^{23}$, —$SR^{23}$, —$NR^{23}R^{24}$, —$NR^{23}C(O)R^{24}$, —$OC(O)R^{23}$, alkyl, alkenyl, alkynyl, aryl, heteroaryl, or heterocyclyl, each of which is independently substituted or unsubstituted, or hydrogen or halogen;
each $R^{21}$ and $R^{22}$ is independently alkyl, alkenyl, alkynyl, aryl, heteroaryl, or heterocyclyl, each of which is independently substituted or unsubstituted, or hydrogen; and
each $R^{23}$ and $R^{24}$ is independently alkyl, alkenyl, alkynyl, aryl, heteroaryl, or heterocyclyl, each of which is independently substituted or unsubstituted, or hydrogen,
or a pharmaceutically-acceptable salt thereof.

The pattern of dashed bonds can be chosen to provide an aromatic system, for example, an indole, an indolene, a pyrrolopyridine, a pyrrolopyrimidine, or a pyrrolopyrazine. In some embodiments, $X^1$ is $CR^5$, $CR^5R^6$, or a carbon atom connected to $Q^1$. In some embodiments, $X^2$ is $CR^7$, $CR^7R$, or a carbon atom connected to $Q^1$. In some embodiments, $X^3$ is $CR^9$, $CR^9R^{10}$, or a carbon atom connected to $Q^1$. In some embodiments, $X^4$ is $CR^{11}$, $CR^{11}R^{12}$, or a carbon atom connected to $Q^1$. In some embodiments, $X^5$ is $CR^{13}$, N, or $NR^{13}$. In some embodiments, $X^1$ is a carbon atom connected to $Q^1$. In some embodiments, $X^2$ is a carbon atom connected to $Q^1$. In some embodiments, $X^3$ is a carbon atom connected to $Q^1$. In some embodiments, $X^4$ is a carbon atom connected to $Q^1$. In some embodiments, $X^5$ is N.

In some embodiments, Ar is a 6-carbon monocyclic or 10-carbon bicyclic aromatic ring system wherein 0, 1, 2, 3, or 4 atoms of each ring are optionally substituted. In some embodiments, Ar is phenyl. In some embodiments, Ar is naphthyl. In some embodiments, Ar is indazolyl.

$R^1$ can be —$C(O)R^{16}$, —$C(O)OR^{16}$, —$C(O)NR^{16}R^{17}$, —$OR^{16}$, —$SR^{16}$, —$NR^{16}R^{17}$, —$NR^{16}C(O)R^{16}$, —$OC(O)R^{16}$, —$SiR^{16}R^{17}R^{18}$, alkyl, alkenyl, alkynyl, alkoxy, aryl, heteroaryl, or heterocyclyl, each of which is independently substituted or unsubstituted, or hydrogen. In some embodiments, $R^1$ is alkyl, alkylene, alkoxy, —$NR^{21}R^{22}$, or aryl, each of which is independently substituted or unsubstituted; halo or hydrogen. In some embodiments, $R^1$ is methyl, cyclohexyl, methylene, methoxy, or benzyl. In some embodiments, $R^1$ is fluoro or chloro. In some embodiments, $R^1$ is phenyl. In some embodiments, $R^1$ is hydrogen.

In some embodiments, $R^1$ is a substituted alkyl. $R^1$ can be substituted by one or more substituents selected from a hydroxyl group, sulfhydryl group, halogen, amino group, nitro group, nitroso group, cyano group, azido group, sulfoxide group, sulfone group, sulfonamide group, carboxyl group, carboxaldehyde group, imine group, alkyl group, halo-alkyl group, cyclic alkyl group, alkenyl group, halo-alkenyl group, alkynyl group, halo-alkynyl group, alkoxy group, aryl group, aryloxy group, aralkyl group, arylalkoxy group, heterocyclyl group, acyl group, acyloxy group, carbamate group, amide group, urethane group, and ester group.

In some embodiments, $R^1$ is alkyl substituted with an amine group. In some embodiments, $R^1$ is methyl substituted with $NR^{16}R^{17}$. In some embodiments, $R^1$ is alkyl substituted with —$C(O)NR^{16}R^{17}$. In some embodiments, $R^1$ is methyl substituted with —$C(O)NR^{16}R^{17}$. In some embodiments, $R^1$ is alkyl substituted with —$C(O)OR^{16}$. In some embodiments, $R^1$ is methyl substituted with COOH. In some embodiments, $R^1$ is methyl substituted with $NR^{16}R^{17}$, wherein $R^{16}$ is hydrogen, and $R^{17}$ is a carboxyl group substituted with heteroaryl. In some embodiments, $R^1$ is methyl substituted with $NR^{16}R^{17}$, wherein $R^{16}$ is hydrogen, and $R^{17}$ is a carboxyl group substituted with a 5-membered heteroaryl ring that is substituted.

In some embodiments, m is 1, 2, 3, or 4. In some embodiments, m is 1. In some embodiments, $X^3$ is carbon atom connected to $Q^1$, and m is 1. In some embodiments, n is 1, 2, or 3. In some embodiments, n is 1. In some embodiments, n is 2. In some embodiments, n is 0.

In some embodiments, $Q^1$ is C=O, C=S, C=$CR^{14}R^{15}$, C=$NR^{14}$, alkylene, alkenylene, or alkynylene, each of which is independently substituted or unsubstituted, or a bond. In some embodiments, $Q^1$ is alkylene, alkenylene, or alkynylene. In some embodiments, $Q^1$ is a bond. In some embodiments, $Q^1$ is $C_1$-alkylene.

In some embodiments, $R^2$ is hydrogen or alkyl. In some embodiments, $R^{13}$ is alkyl, alkenyl, hydrogen, or halogen. In some embodiments, $R^2$ is alkyl, and $R^{13}$ is alkyl. In some embodiments, $R^2$ is hydrogen, and $R^{13}$ is alkyl. In some embodiments, $R^2$ is methyl, ethyl, propyl, iso-propyl, butyl, or tert-butyl. In some embodiments, $R^3$ is methyl, ethyl, propyl, iso-propyl, butyl or tert-butyl. In some embodiments, $R^2$ is hydrogen, and $R^3$ is hydrogen. In some embodiments, $R^2$ is trifluoroethyl, and $R^{13}$ is hydrogen.

In some embodiments, $R^3$ is —$C(O)R^{19}$, —$C(O)OR^{19}$, alkyl, alkenyl, alkynyl, aryl, heteroaryl, or heterocyclyl, each of which is independently substituted or unsubstituted, or hydrogen, and $R^4$ is —$C(O)R^{19}$, —$C(O)OR^{19}$, alkyl, alkenyl, alkynyl, aryl, heteroaryl, or heterocyclyl, each of which is independently substituted or unsubstituted, or hydrogen.

In some embodiments, $R^3$ is H, and $R^4$ is —$C(O)R^{19}$, —$C(O)OR^{19}$, —$C(O)NR^{19}R^{20}$, —$SOR^{19}$, —$SO_2R^{19}$, alkyl, alkenyl, alkynyl, aryl, heteroaryl, or heterocyclyl, each of which is independently substituted or unsubstituted; or hydrogen. In some embodiments, $R^3$ is H, and $R^4$ is alkyl, alkenyl, alkynyl, aryl, heteroaryl, or heterocyclyl, each of which is independently substituted or unsubstituted, or hydrogen. In some embodiments, $R^4$ is heterocyclyl. In some embodiments, $R^4$ is piperidinyl, piperazinyl, tetahydropyranyl, morpholinyl, or pyrrolidinyl, each of which is independently substituted or unsubstituted.

In some embodiments, $R^4$ is a ring that is:

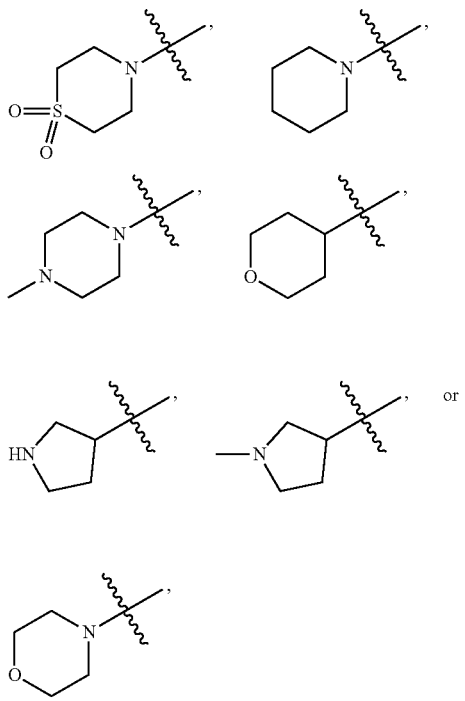

wherein the ring is substituted or unsubstituted. In some embodiments, $R^3$ is H, and $R^4$ is a ring that is

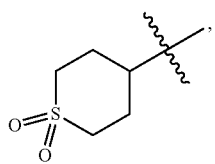 [SMILES: *C1CCS(=O)(=O)CC1]

wherein the ring is substituted or unsubstituted. In some embodiments, $R^3$ is H, and $R^4$ is a ring that is

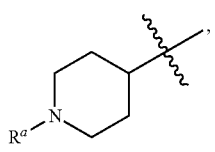

wherein the ring is substituted or unsubstituted. In some embodiments, $R^a$ is alkylene. In some embodiments, $R^a$ is methyl. In some embodiments, $R^3$ is H, and $R^4$ is a ring that is

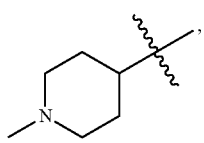 [SMILES: *C1CCN(C)CC1]

wherein the ring is substituted or unsubstituted. In some embodiments, $R^3$ is H, and $R^4$ is a ring that is

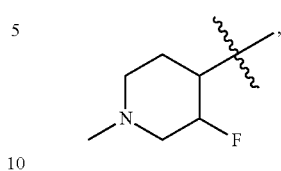

wherein the ring is substituted or unsubstituted. In some embodiments, $R^3$ is H, and $R^4$ is a ring that is

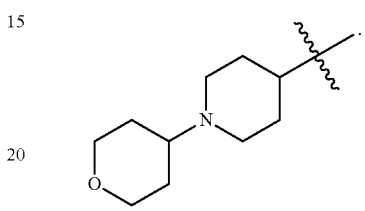

In some embodiments, the disclosure provides a compound of the formula:

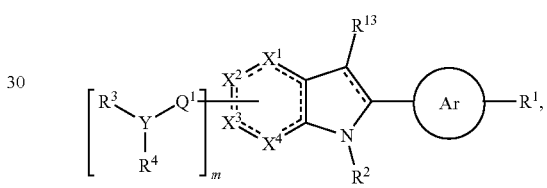

wherein the variables are as defined above.

In some embodiments, the disclosure provides a compound of the formula:

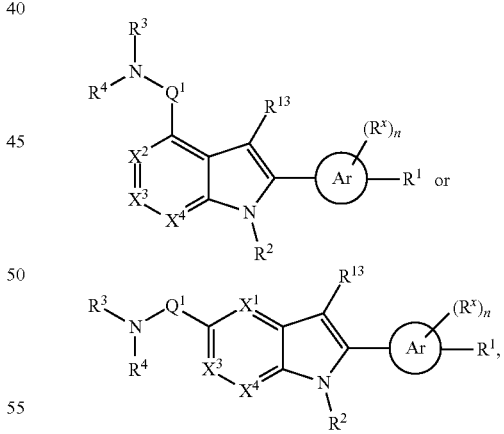

wherein:
$X^1$ is $CR^5$, $CR^5R^6$, N, $NR^5$, O, S, C=O, C=S, or a carbon atom connected to $Q^1$;
$X^2$ is $CR^7$, $CR^7R^8$, N, $NR^7$, O, S, C=O, C=S, or a carbon atom connected to $Q^1$;
$X^3$ is $CR^9$, $CR^9R^{10}$, N, $NR^9$, O, S, C=O, C=S, or a carbon atom connected to $Q^1$;
$X^4$ is $CR^{11}$, $CR^{11}R^{12}$, N, $NR^{11}$, O, S, C=O, C=S, or a carbon atom connected to $Q^1$;
Ar is unsubstituted or substituted aryl;

$Q^1$ is C=O, C=S, C=CR$^{14}$R$^{15}$, C=NR$^{14}$, alkylene, alkenylene, or alkynylene, each of which is independently substituted or unsubstituted, or a bond;

n is 0, 1, 2, 3, or 4;

each $R^x$ and $R^1$ is independently C(O)R$^{16}$, —C(O)OR$^{16}$, —C(O)NR$^{16}$R$^{17}$, —OR$^{16}$, —SR$^{16}$, —NR$^{16}$R$^{17}$, —NR$^{16}$C(O)R$^{16}$, —OC(O)R$^{16}$, —SiR$^{16}$R$^{17}$R$^{18}$, alkyl, alkenyl, alkynyl, alkoxy, aryl, heteroaryl, or heterocyclyl, each of which is independently substituted or unsubstituted; cyano, halo, or hydrogen; or $R^1$ and $R^x$ together with Ar form a fused ring;

each $R^3$ and $R^4$ is independently —C(O)R$^{19}$, —C(O)OR$^{19}$, —C(O)NR$^{19}$R$^{20}$, —SOR$^{19}$, —SO$_2$R$^9$, alkyl, alkenyl, alkynyl, aryl, heteroaryl, or heterocyclyl, each of which is independently substituted or unsubstituted, or hydrogen, or $R^3$ and $R^4$ together with the nitrogen atom to which $R^3$ and $R^4$ are bound form a ring, wherein the ring is substituted or unsubstituted, or $R^3$ is absent;

each $R^2$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ is independently —C(O)R$^{21}$, —C(O)OR$^{21}$, —C(O)NR$^{21}$R$^{22}$, —OR$^{21}$, —SR$^{21}$, —NR$^{21}$R$^{22}$, —NR$^{21}$C(O)R$^{22}$, —OC(O)R$^{21}$, alkyl, alkenyl, alkynyl, aryl, heteroaryl, or heterocyclyl, each of which is independently substituted or unsubstituted, or hydrogen or halogen;

each $R^{19}$ and $R^{20}$ is —C(O)R$^{21}$, —C(O)OR$^{23}$, —C(O)NR$^{23}$R$^{24}$, —OR$^{23}$, —SR$^{23}$, —NR$^{23}$R$^{24}$, —NR$^{23}$C(O)R$^{24}$, —OC(O)R$^{23}$, alkyl, alkenyl, alkynyl, aryl, heteroaryl, or heterocyclyl, each of which is independently substituted or unsubstituted, or hydrogen or halogen;

each $R^{21}$ and $R^{22}$ is independently alkyl, alkenyl, alkynyl, aryl, heteroaryl, or heterocyclyl, each of which is independently substituted or unsubstituted, or hydrogen; and each $R^{23}$ and $R^{24}$ is independently alkyl, alkenyl, alkynyl, aryl, heteroaryl, or heterocyclyl, each of which is independently substituted or unsubstituted, or hydrogen, or a pharmaceutically-acceptable salt thereof.

In some embodiments, the compound is of the formula:

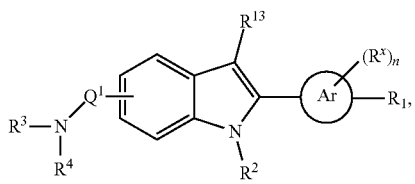

wherein the variables are as defined above.

In some embodiments, Ar is a 6-carbon monocyclic or 10-carbon bicyclic aromatic ring system wherein 0, 1, 2, 3, or 4 atoms of each ring are optionally substituted. In some embodiments, Ar is phenyl. In some embodiments, Ar is naphthyl. In some embodiments, Ar is indazolyl.

In some embodiments, $R^1$ is a substituted alkyl. $R^1$ can be substituted by one or more substituents selected from a hydroxyl group, sulfhydryl group, halogen, amino group, nitro group, nitroso group, cyano group, azido group, sulfoxide group, sulfone group, sulfonamide group, carboxyl group, carboxaldehyde group, imine group, alkyl group, halo-alkyl group, cyclic alkyl group, alkenyl group, halo-alkenyl group, alkynyl group, halo-alkynyl group, alkoxy group, aryl group, aryloxy group, aralkyl group, arylalkoxy group, heterocyclyl group, acyl group, acyloxy group, carbamate group, amide group, urethane group, and ester group.

In some embodiments, $R^1$ is alkyl substituted with an amine group. In some embodiments, $R^1$ is methyl substituted with NR$^{16}$R$^{17}$. In some embodiments, $R^1$ is alkyl substituted with —C(O)NR$^{16}$R$^{17}$. In some embodiments, $R^1$ is methyl substituted with —C(O)NR$^{16}$R$^{17}$. In some embodiments, $R^1$ is alkyl substituted with —C(O)OR$^{16}$. In some embodiments, $R^1$ is methyl substituted with COOH. In some embodiments, $R^1$ is methyl substituted with NR$^{16}$R$^{17}$, wherein $R^{16}$ is hydrogen, and $R^{17}$ is a carboxyl group substituted with heteroaryl. In some embodiments, $R^1$ is methyl substituted with NR$^{16}$R$^{17}$, wherein $R^{16}$ is hydrogen, and $R^{17}$ is a carboxyl group substituted with a 5-membered heteroaryl ring that is substituted.

In some embodiments, $Q^1$ is C=O, C=S, C=CR$^{14}$R$^{15}$, C=NR$^{14}$, alkylene, alkenylene, or alkynylene, each of which is independently substituted or unsubstituted, or a bond. In some embodiments, $Q^1$ is alkylene, alkenylene, or alkynylene. In some embodiments, $Q^1$ is a bond. In some embodiments, $Q^1$ is C$_1$-alkylene.

In some embodiments, $R^2$ is hydrogen or alkyl. In some embodiments, $R^{13}$ is alkyl, alkenyl, hydrogen, or halogen. In some embodiments, $R^2$ is alkyl, and $R^{13}$ is alkyl. In some embodiments, $R^2$ is hydrogen, and $R^{13}$ is alkyl. In some embodiments, $R^2$ is methyl, ethyl, propyl, iso-propyl, butyl, or tert-butyl. In some embodiments, $R^3$ is methyl, ethyl, propyl, iso-propyl, butyl or tert-butyl. In some embodiments, $R^2$ is hydrogen, and $R^{13}$ is hydrogen. In some embodiments, $R^2$ is trifluoroethyl, and $R^{13}$ is hydrogen.

In some embodiments, $R^3$ is —C(O)R$^{19}$, —C(O)OR$^{19}$, alkyl, alkenyl, alkynyl, aryl, heteroaryl, or heterocyclyl, each of which is independently substituted or unsubstituted, or hydrogen, and $R^4$ is —C(O)R$^{19}$, —C(O)OR$^{19}$, alkyl, alkenyl, alkynyl, aryl, heteroaryl, or heterocyclyl, each of which is independently substituted or unsubstituted, or hydrogen.

In some embodiments, $R^3$ is H, and $R^4$ is —C(O)R$^{19}$, —C(O)OR$^{19}$, —C(O)NR$^{19}$R$^{20}$, —SOR$^{19}$, —SO$_2$R$^{19}$, alkyl, alkenyl, alkynyl, aryl, heteroaryl, or heterocyclyl, each of which is independently substituted or unsubstituted; or hydrogen. In some embodiments, $R^3$ is H, and $R^4$ is alkyl, alkenyl, alkynyl, aryl, heteroaryl, or heterocyclyl, each of which is independently substituted or unsubstituted, or hydrogen. In some embodiments, $R^4$ is heterocyclyl. In some embodiments, $R^4$ is piperidinyl, piperazinyl, tetahydropyranyl, morpholinyl, or pyrrolidinyl, each of which is independently substituted or unsubstituted.

In some embodiments, $R^4$ is a ring that is:

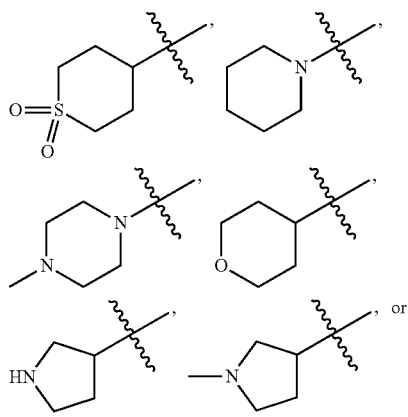

-continued

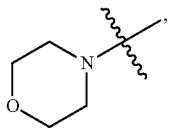

wherein the ring is substituted or unsubstituted. In some embodiments, $R^3$ is H, and $R^4$ is a ring that is

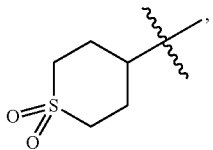

wherein the ring is substituted or unsubstituted. In some embodiments, $R^3$ is H, and $R^4$ is a ring that is

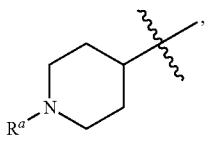

wherein the ring is substituted or unsubstituted. In some embodiments, $R^a$ is alkylene. In some embodiments, $R^a$ is methyl. In some embodiments, $R^3$ is H, and $R^4$ is a ring that is

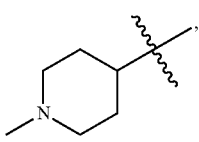

wherein the ring is substituted or unsubstituted. In some embodiments, $R^3$ is H, and $R^4$ is a ring that is

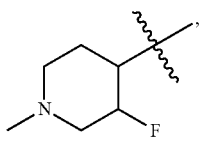 [SMILES: *C1CCN(C)CC1F]

wherein the ring is substituted or unsubstituted. In some embodiments, $R^3$ is H, and $R^4$ is a ring that is

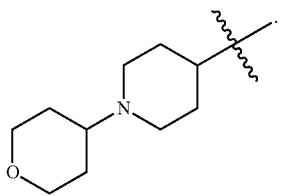 [SMILES: *C1CCN(C2CCOCC2)CC1]

In some embodiments, the disclosure provides a compound of the formula:

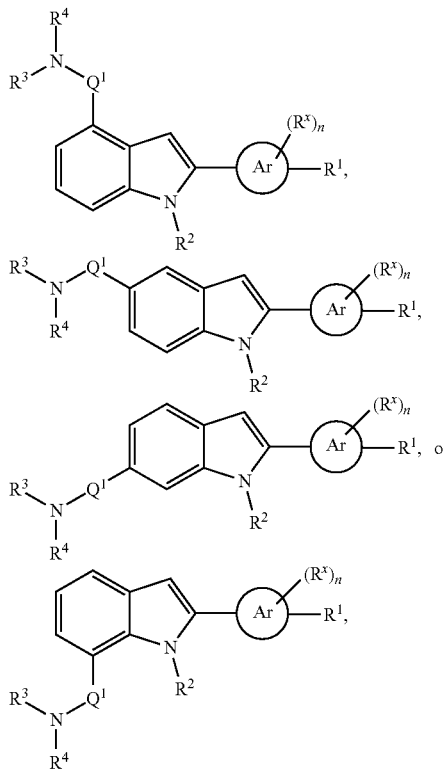

or a pharmaceutically-acceptable salt thereof, wherein the variables are as defined above.

In some embodiments, the disclosure provides a compound of the formula:

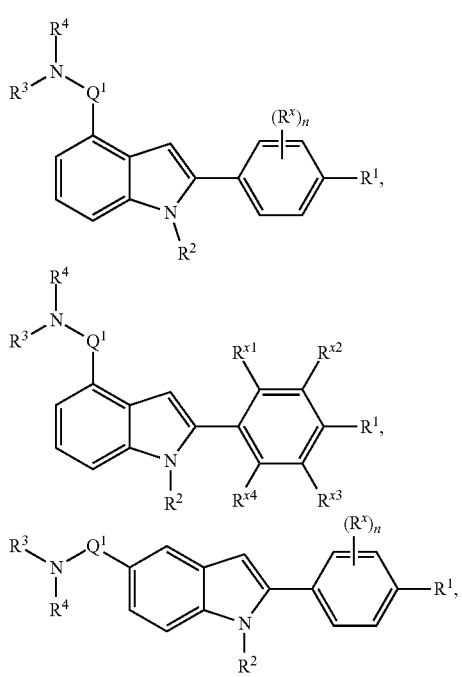

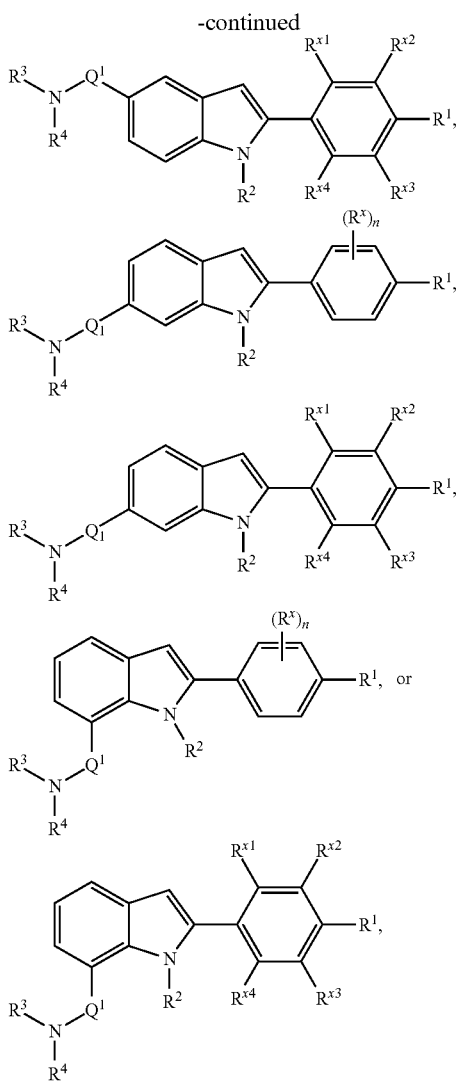

wherein:
Q$^1$ is C═O, C═S, C═CR$^{14}$R$^{15}$, C═NR$^4$, alkylene, alkenylene, or alkynylene, each of which is independently substituted or unsubstituted, or a bond;
each R$^1$, R$^x$, R$^{x1}$, R$^{x2}$, R$^{x3}$, and R$^{x4}$ is independently —C(O)R$^{16}$, —C(O)OR$^{16}$, —C(O)NR$^{16}$R$^{17}$, —OR$^{16}$, —SR$^{16}$, —NR$^{16}$R$^{17}$, —NR$^{16}$C(O)R$^{16}$, —OC(O)R$^{16}$, —SiR$^{16}$R$^{17}$R$^{18}$, alkyl, alkenyl, alkynyl, alkoxy, aryl, heteroaryl, or heterocyclyl, each of which is independently substituted or unsubstituted; cyano, halo, or hydrogen; or R$^1$ and R$^X$ together with Ar form a fused ring;
each R$^3$ and R$^4$ is independently —C(O)R$^{19}$, —C(O)OR$^{19}$, —C(O)NR$^{19}$R$^{20}$, —SOR$^{19}$, —SO$_2$R$^{19}$, alkyl, alkenyl, alkynyl, aryl, heteroaryl, or heterocyclyl, each of which is independently substituted or unsubstituted, or hydrogen, or R$^3$ and R$^4$ together with the nitrogen atom to which R$^3$ and R$^4$ are bound form a ring, wherein the ring is substituted or unsubstituted, or R is absent;
n is 0, 1, 2, 3, or 4;
each R$^2$, R$^{14}$, R$^{15}$, R$^{16}$, R$^{17}$, and R$^{18}$ is independently —C(O)R$^{21}$, —C(O)OR$^{21}$, —C(O)NR$^{21}$R$^{22}$, —OR$^{21}$, —SR$^{21}$, —NR$^{21}$R$^{22}$, —NR$^{21}$C(O)R$^{22}$, —OC(O)R$^{21}$, alkyl, alkenyl, alkynyl, aryl, heteroaryl, or heterocyclyl, each of which is independently substituted or unsubstituted, or hydrogen or halogen;
each R$^{19}$ and R$^{20}$ is —C(O)R$^{23}$, —C(O)OR$^{23}$, —C(O)NR$^{23}$R$^{24}$, —OR$^2$, —SR$^{23}$, —NR$^{23}$R$^{24}$, —NR$^{23}$C(O)R$^{24}$, —OC(O)R$^{23}$, alkyl, alkenyl, alkynyl, aryl, heteroaryl, or heterocyclyl, each of which is independently substituted or unsubstituted, or hydrogen or halogen;
each R$^{21}$ and R$^{22}$ is independently alkyl, alkenyl, alkynyl, aryl, heteroaryl, or heterocyclyl, each of which is independently substituted or unsubstituted, or hydrogen; and
each R$^{23}$ and R$^{24}$ is independently alkyl, alkenyl, alkynyl, aryl, heteroaryl, or heterocyclyl, each of which is independently substituted or unsubstituted, or hydrogen,
or a pharmaceutically-acceptable salt thereof.

In some embodiments, R$^1$ is a substituted alkyl. R$^1$ can be substituted by one or more substituents selected from a hydroxyl group, sulfhydryl group, halogen, amino group, nitro group, nitroso group, cyano group, azido group, sulfoxide group, sulfone group, sulfonamide group, carboxyl group, carboxaldehyde group, imine group, alkyl group, halo-alkyl group, cyclic alkyl group, alkenyl group, halo-alkenyl group, alkynyl group, halo-alkynyl group, alkoxy group, aryl group, aryloxy group, aralkyl group, arylalkoxy group, heterocyclyl group, acyl group, acyloxy group, carbamate group, amide group, urethane group, and ester group.

In some embodiments, R$^1$ is alkyl substituted with an amine group. In some embodiments, R$^1$ is methyl substituted with NR$^{16}$R$^{17}$. In some embodiments, R$^1$ is methyl substituted with NR$^{16}$R$^{17}$, wherein R$^{16}$ is hydrogen, and R$^{17}$ is alkyl, aryl, heteroaryl, an amino group, a carboxyl group, or an ester group, any of which is substituted or unsubstituted. In some embodiments, R$^1$ is methyl substituted with NR$^{16}$R$^{17}$, wherein R$^{16}$ is hydrogen, and R$^{17}$ is substituted or unsubstituted alkyl, aryl, or heteroaryl. In some embodiments, R$^1$ is methyl substituted with NR$^{16}$R$^{17}$, wherein R$^{16}$ is hydrogen, and R$^{17}$ is substituted or unsubstituted phenyl. In some embodiments, R$^1$ is methyl substituted with NR$^{16}$R$^{17}$, wherein R$^{16}$ is hydrogen, and R$^{17}$ is substituted or unsubstituted pyridinyl. In some embodiments, R$^1$ is methyl substituted with NR$^{16}$R$^{17}$, wherein R$^{16}$ is hydrogen, and R$^{17}$ is a carboxyl group substituted with heteroaryl. In some embodiments, R$^1$ is methyl substituted with NR$^{16}$R$^{17}$, wherein R$^{16}$ is hydrogen, and R$^{17}$ is a carboxyl group substituted with a 5-membered heteroaryl ring that is substituted.

In some embodiments, R$^1$ is —C(O)NR$^{16}$R$^{17}$. In some embodiments, R$^1$ is —C(O)NR$^{16}$R$^{17}$, wherein R$^{16}$ and R$^{17}$ are hydrogen. In some embodiments, R$^1$ is —C(O)NR$^{16}$R$^{17}$, wherein R$^{16}$ is hydrogen, and R$^{17}$ alkyl. In some embodiments, R$^1$ is —C(O)NR$^{16}$R$^{17}$, wherein R$^{16}$ is hydrogen, and R$^{17}$ methyl. In some embodiments, R$^1$ is —C(O)OR$^{16}$. In some embodiments, R$^1$ is —C(O)OH. In some embodiments, R$^1$ is methyl. In some embodiments, R$^1$ is halogen. In some embodiments, R$^1$ is chloro or fluoro.

In some embodiments, n is 0, 1, 2, or 3. In some embodiments, n is 1. In some embodiments, n is 2. In some embodiments, n is 0.

In some embodiments, Q$^1$ is C═O, C═S, C═CR$^{14}$R$^{15}$, C═NR$^{14}$, alkylene, alkenylene, or alkynylene, each of which is independently substituted or unsubstituted, or a bond. In some embodiments, Q$^1$ is alkylene, alkenylene, or alkynylene. In some embodiments, Q$^1$ is a bond. In some embodiments, Q$^1$ is C$_1$-alkylene.

In some embodiments, $R^2$ is hydrogen or alkyl. In some embodiments, $R^{13}$ is alkyl, alkenyl, hydrogen, or halogen. In some embodiments, $R^2$ is alkyl, and $R^{13}$ is alkyl. In some embodiments, $R^2$ is hydrogen, and $R^{13}$ is alkyl. In some embodiments, $R^2$ is methyl, ethyl, propyl, iso-propyl, butyl, or tert-butyl. In some embodiments, $R^3$ is methyl, ethyl, propyl, iso-propyl, butyl or tert-butyl. In some embodiments, $R^2$ is hydrogen, and $R^{13}$ is hydrogen. In some embodiments, $R^2$ is trifluoroethyl, and $R^{13}$ is hydrogen.

In some embodiments, $R^3$ is —C(O)$R^{19}$, —C(O)O$R^{19}$, alkyl, alkenyl, alkynyl, aryl, heteroaryl, or heterocyclyl, each of which is independently substituted or unsubstituted, or hydrogen, and $R^4$ is —C(O)$R^{19}$, —C(O)O$R^{19}$, alkyl, alkenyl, alkynyl, aryl, heteroaryl, or heterocyclyl, each of which is independently substituted or unsubstituted, or hydrogen.

In some embodiments, $R^3$ is H, and $R^4$ is —C(O)$R^{19}$, —C(O)O$R^{19}$, —C(O)N$R^{19}R^{20}$, —SO$R^{19}$, —SO$_2R^{19}$, alkyl, alkenyl, alkynyl, aryl, heteroaryl, or heterocyclyl, each of which is independently substituted or unsubstituted; or hydrogen. In some embodiments, $R^3$ is H, and $R^4$ is alkyl, alkenyl, alkynyl, aryl, heteroaryl, or heterocyclyl, each of which is independently substituted or unsubstituted, or hydrogen. In some embodiments, $R^4$ is heterocyclyl. In some embodiments, $R^4$ is piperidinyl, piperazinyl, tetahydropyranyl, morpholinyl, or pyrrolidinyl, each of which is independently substituted or unsubstituted.

In some embodiments, $R^4$ is a ring that is:

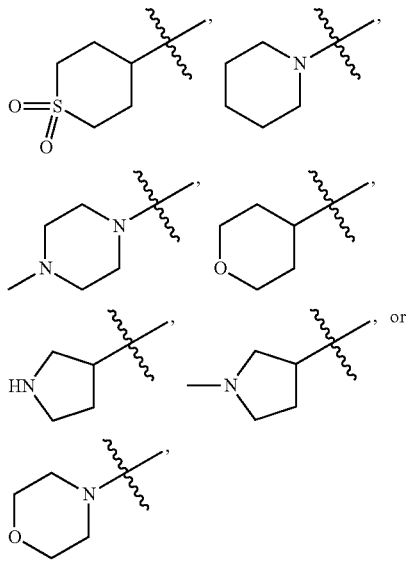

wherein the ring is substituted or unsubstituted. In some embodiments, $R^3$ is H, and $R^4$ is a ring that is

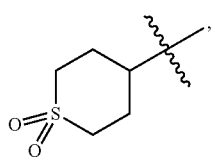

wherein the ring is substituted or unsubstituted. In some embodiments, $R^3$ is H, and $R^4$ is a ring that is

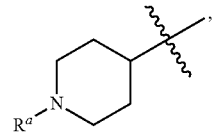

wherein the ring is substituted or unsubstituted. In some embodiments, $R^a$ is alkylene. In some embodiments, $R^a$ is methyl. In some embodiments, $R^3$ is H, and $R^4$ is a ring that is

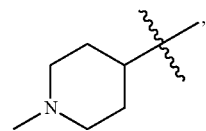 [SMILES: *C1CCN(C)CC1]

wherein the ring is substituted or unsubstituted. In some embodiments, $R^3$ is H, and $R^4$ is a ring that is

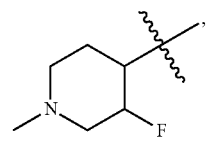 [SMILES: *C1CCN(C)CC1F]

wherein the ring is substituted or unsubstituted. In some embodiments, $R^3$ is H, and $R^4$ is a ring that is

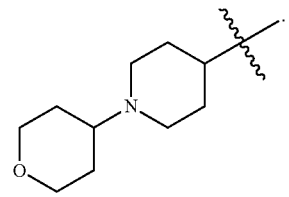 [SMILES: *C1CCN(C2CCOCC2)CC1]

In some embodiments, the disclosure provides a compound of the formula:

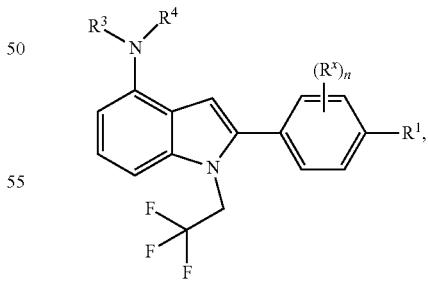

or a pharmaceutically-acceptable salt thereof, wherein the variables are as defined above.

In some embodiments, $R^1$ is a substituted alkyl. $R^1$ can be substituted by one or more substituents selected from a hydroxyl group, sulfhydryl group, halogen, amino group, nitro group, nitroso group, cyano group, azido group, sulfoxide group, sulfone group, sulfonamide group, carboxyl group, carboxaldehyde group, imine group, alkyl group, halo-alkyl group, cyclic alkyl group, alkenyl group, haloalkenyl group, alkynyl group, halo-alkynyl group, alkoxy group, aryl group, aryloxy group, aralkyl group, arylalkoxy group, heterocyclyl group, acyl group, acyloxy group, carbamate group, amide group, urethane group, and ester group.

In some embodiments, $R^1$ is alkyl substituted with an amine group. In some embodiments, $R^1$ is methyl substituted with $NR^{16}R^{17}$. In some embodiments, $R^1$ is methyl substituted with $NR^{16}R^{17}$, wherein $R^{16}$ is hydrogen, and $R^7$ is alkyl, aryl, heteroaryl, an amino group, a carboxyl group, or an ester group, any of which is substituted or unsubstituted. In some embodiments, $R^1$ is methyl substituted with $NR^{16}R^{17}$, wherein $R^{16}$ is hydrogen, and $R^{17}$ is substituted or unsubstituted alkyl, aryl, or heteroaryl. In some embodiments, $R^1$ is methyl substituted with $NR^{16}R^{17}$, wherein $R^{16}$ is hydrogen, and $R^{17}$ is substituted or unsubstituted phenyl. In some embodiments, $R^1$ is methyl substituted with $NR^{16}R^{17}$, wherein $R^{16}$ is hydrogen, and $R^{17}$ is substituted or unsubstituted pyridinyl. In some embodiments, $R^1$ is methyl substituted with $NR^{16}R^{17}$, wherein $R^{16}$ is hydrogen, and $R^{17}$ is a carboxyl group substituted with heteroaryl. In some embodiments, $R^1$ is methyl substituted with $NR^{16}R^{17}$, wherein $R^{16}$ is hydrogen, and $R^{17}$ is a carboxyl group substituted with a 5-membered heteroaryl ring that is substituted.

In some embodiments, $R^1$ is —C(O)$NR^{16}R^{17}$. In some embodiments, $R^1$ is —C(O)$NR^{16}R^{17}$, wherein $R^{16}$ and $R^7$ are hydrogen. In some embodiments, $R^1$ is —C(O)$NR^{16}R^{17}$ ?, wherein $R^{16}$ is hydrogen, and $R^{17}$ alkyl. In some embodiments, $R^1$ is —C(O)$NR^{16}R^{17}$ ?, wherein $R^{16}$ is hydrogen, and $R^{17}$ methyl. In some embodiments, $R^1$ is —C(O)$OR^{16}$. In some embodiments, $R^1$ is —C(O)OH. In some embodiments, $R^1$ is methyl. In some embodiments, $R^1$ is halogen. In some embodiments, $R^1$ is chloro or fluoro.

In some embodiments, n is 1, 2, or 3. In some embodiments, n is 1. In some embodiments, n is 2. In some embodiments, n is 0.

In some embodiments, $R^3$ is —C(O)$R^{19}$, —C(O)$OR^{19}$, alkyl, alkenyl, alkynyl, aryl, heteroaryl, or heterocyclyl, each of which is independently substituted or unsubstituted, or hydrogen, and $R^4$ is —C(O)$R^{19}$, —C(O)$OR^{19}$, alkyl, alkenyl, alkynyl, aryl, heteroaryl, or heterocyclyl, each of which is independently substituted or unsubstituted, or hydrogen.

In some embodiments, $R^3$ is H, and $R^4$ is —C(O)$R^{19}$, —C(O)$OR^{19}$, —C(O)$NR^{19}R^{20}$, —SO$R^{19}$, —SO$_2R^{19}$, alkyl, alkenyl, alkynyl, aryl, heteroaryl, or heterocyclyl, each of which is independently substituted or unsubstituted; or hydrogen. In some embodiments, $R^3$ is H, and $R^4$ is alkyl, alkenyl, alkynyl, aryl, heteroaryl, or heterocyclyl, each of which is independently substituted or unsubstituted, or hydrogen. In some embodiments, $R^4$ is heterocyclyl. In some embodiments, $R^4$ is piperidinyl, piperazinyl, tetahydropyranyl, morpholinyl, or pyrrolidinyl, each of which is independently substituted or unsubstituted.

In some embodiments, $R^3$ is H, and $R^4$ is a ring that is:

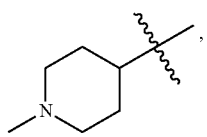

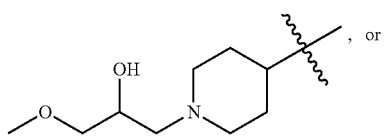

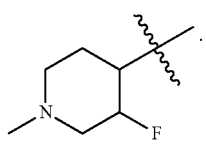

In some embodiments, $R^3$ is H, and $R^4$ is a ring that is

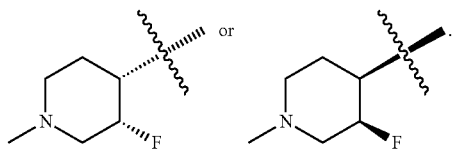

In some embodiments, $R^3$ is H, and $R^4$ is a ring that is

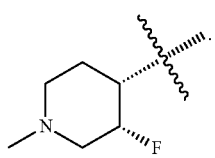

Non-limiting examples of compounds of the disclosure include compounds of any of the following formulae:

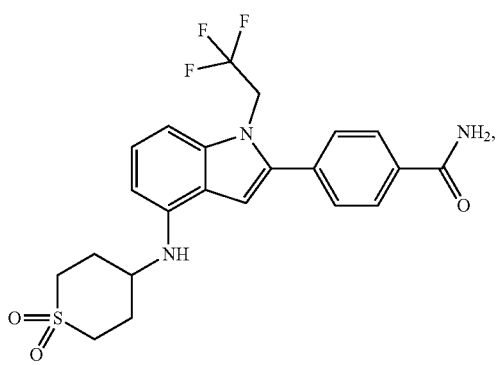

39
-continued
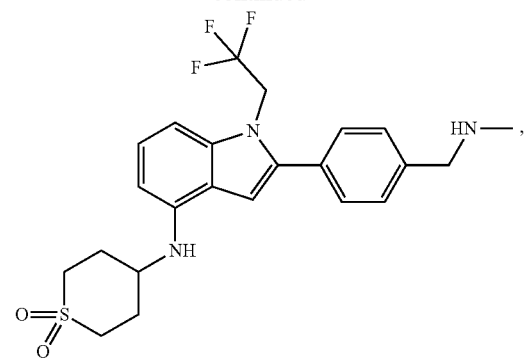
40
-continued
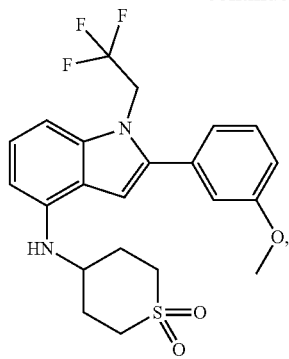
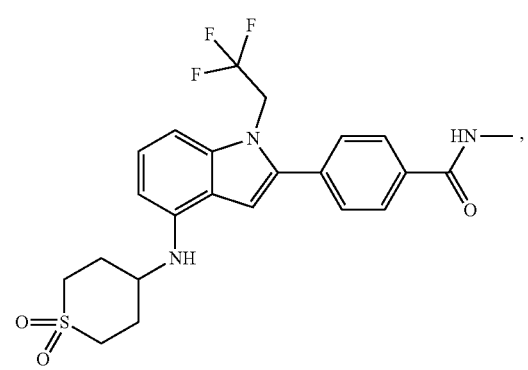
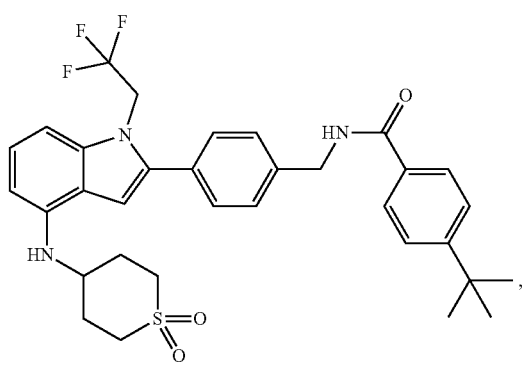
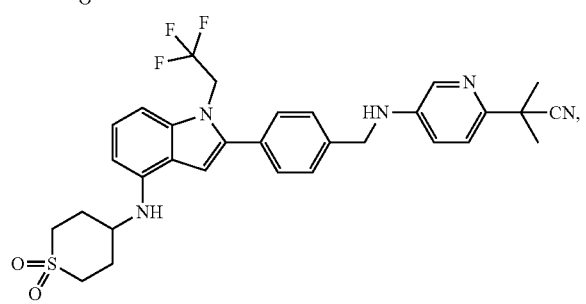
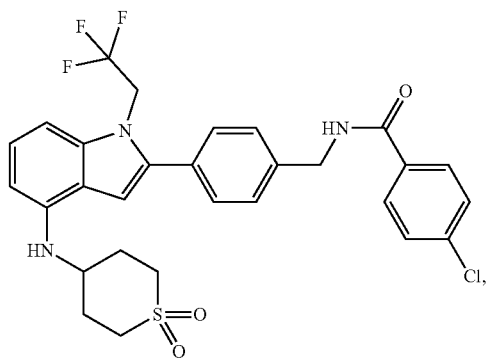
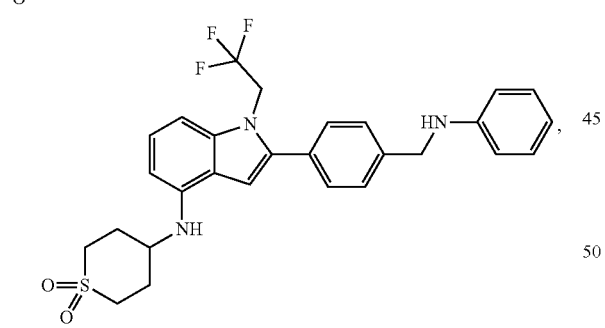
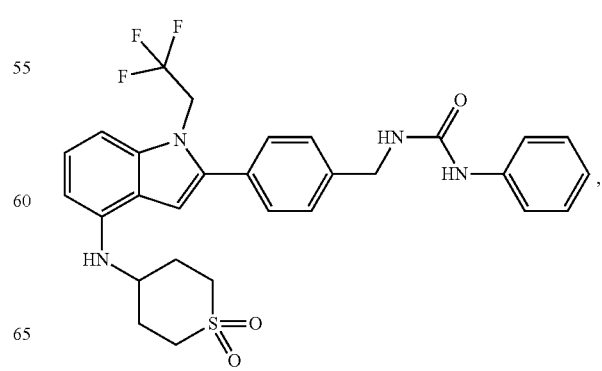

41
-continued

42
-continued

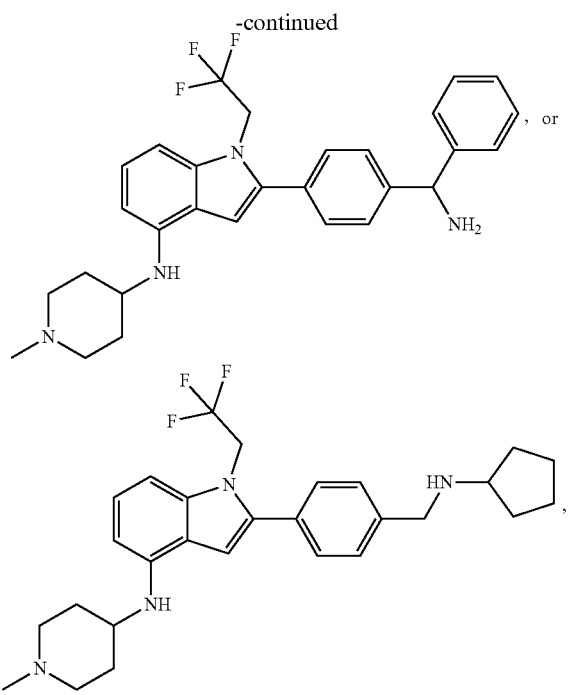

, or or a pharmaceutically-acceptable salt thereof.

In some embodiments, the disclosure provides a compound of the formula:

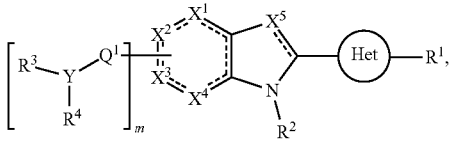

wherein:
each ------- is independently a single bond or a double bond;
$X^1$ is $CR^5$, $CR^5R^6$, N, $NR^5$, O, S, C=O, C=S, or a carbon atom connected to $Q^1$;
$X^2$ is $CR^7$, $CR^7R^8$, N, $NR^7$, O, S, C=O, C=S, or a carbon atom connected to $Q^1$;
$X^3$ is $CR^9$, $CR^9R^{10}$, N. $NR^9$, 0, S, C=O, C=S, or a carbon atom connected to $Q^1$;
$X^4$ is $CR^{11}$, $CR^{11}R^{12}$, N, $NR^{11}$, O, S, C=O, C=S, or a carbon atom connected to $Q^1$;
$X^5$ is $CR^{13}$, N, or $NR^{13}$;
wherein at least one of $X^1$, $X^2$, $X^3$, and $X^4$ is a carbon atom connected to $Q^1$;
Het is substituted or unsubstituted heteroaryl;
$Q^1$ is C=O, C=S, C=$CR^{14}R^{15}$, C=$NR^{14}$, alkylene, alkenylene, or alkynylene, each of which is independently substituted or unsubstituted, or a bond;
m is 1, 2, 3, or 4;
Y is N, O, or absent;
$R^1$ is —C(O)$R^{16}$, —C(O)O$R^{16}$, —C(O)N$R^{16}R^{17}$, —O$R^{16}$, —S$R^{16}$, —N$R^{16}R^{17}$, —N$R^{16}$C(O)$R^{16}$, —OC(O)$R^{16}$, —Si$R^{16}R^{17}R^{18}$, alkyl, alkenyl, alkynyl, alkoxy, aryl, heteroaryl, heterocyclyl, or halo, each of which is independently substituted or unsubstituted, or hydrogen;
each R and $R^4$ is independently —C(O)$R^{19}$, —C(O)O$R^{19}$, —C(O)N$R^{19}R^{20}$, —SO$R^{19}$, —SO$_2R^{19}$, alkyl, alkenyl, alkynyl, aryl, heteroaryl, or heterocyclyl, each of which is independently substituted or unsubstituted, or hydrogen, or $R^3$ and $R^4$ together with the nitrogen atom to which $R^3$ and $R^4$ are bound form a ring, wherein the ring is substituted or unsubstituted, or $R^3$ is absent;
each $R^2$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ is independently —C(O)$R^1$, —C(O)O$R^{21}$, —C(O)N$R^{21}R^{22}$, —O$R^{21}$, —S$R^{21}$, —N$R^{21}R^{22}$, —N$R^{21}$C(O)$R^{22}$, —OC(O)$R^{21}$, alkyl, alkenyl, alkynyl, aryl, heteroaryl, or heterocyclyl, each of which is independently substituted or unsubstituted, or hydrogen or halogen;
each $R^{19}$ and $R^{20}$ is —C(O)$R^{23}$, —C(O)O$R^{23}$, —C(O)N$R^{23}R^{24}$, —O$R^{23}$, —S$R^{23}$, —N$R^{23}R^{24}$, —N$R^{23}$C(O)$R^{24}$, —OC(O)$R^{23}$, alkyl, alkenyl, alkynyl, aryl, heteroaryl, or heterocyclyl, each of which is independently substituted or unsubstituted, or hydrogen or halogen;
each $R^{21}$ and $R^{22}$ is independently alkyl, alkenyl, alkynyl, aryl, heteroaryl, or heterocyclyl, each of which is independently substituted or unsubstituted, or hydrogen; and
each $R^{23}$ and $R^{24}$ is independently alkyl, alkenyl, alkynyl, aryl, heteroaryl, or heterocyclyl, each of which is independently substituted or unsubstituted, or hydrogen,
or a pharmaceutically-acceptable salt thereof.

The pattern of dashed bonds can be chosen to provide an aromatic system, for example, an indole, an indolene, a pyrrolopyridine, a pyrrolopyrimidine, or a pyrrolopyrazine. In some embodiments, $X^1$ is $CR^5$, $CR^5R^6$, or a carbon atom connected to $Q^1$. In some embodiments, $X^2$ is $CR^7$, $CR^7R^8$, or a carbon atom connected to $Q^1$. In some embodiments, $X^3$ is $CR^9$, $CR^9R^{10}$, or a carbon atom connected to $Q^1$. In some embodiments, $X^4$ is $CR^{11}$, $CR^{11}R^{12}$, or a carbon atom connected to $Q^1$. In some embodiments, $X^5$ is $CR^{13}$, N, or $NR^{13}$. In some embodiments, $X^1$ is a carbon atom connected to $Q^1$. In some embodiments, $X^2$ is a carbon atom connected to $Q^1$. In some embodiments, $X^3$ is a carbon atom connected to $Q^1$. In some embodiments, $X^4$ is a carbon atom connected to $Q^1$. In some embodiments, $X^5$ is N.

In some embodiments, Het is an aromatic 5-membered, 6-membered, 7-membered, or 8-membered monocyclic ring system comprising 1, 2, or 3 heteroatoms as ring members, wherein each heteroatom is independently selected from O, N, or S. In some embodiments, Het is an aromatic 8-membered, 9-membered, 10-membered, 11-membered, or 12-membered bicyclic ring system comprising 1, 2, 3, 4, 5, or 6 heteroatoms, wherein each heteroatom is independently selected from O, N, or S. In some embodiments, Het is an aromatic 5-membered, 6-membered, 7-membered, or 8-membered monocyclic ring system comprising 1, 2, or 3 heteroatoms, and the aromatic 5-membered, 6-membered, 7-membered, or 8-membered monocyclic ring system is substituted. In some embodiments, Het is an 8-membered, 9-membered, 10-membered, 11-membered, or 12-membered bicyclic ring system having 1, 2, 3, 4, 5, or 6 heteroatoms, and the 8-membered, 9-membered, 10-membered, 11-membered, or 12-membered bicyclic ring system is substituted.

In some embodiments, Het is pyridinyl, pyrimidinyl, thiadiazolyl, thiazolyl, pyrazolyl, thiophenyl, or oxadiazolyl, each of which is independently substituted or unsubstituted. In some embodiments, Het is 1,3,5-thiadiazol-2-yl. In some embodiments, Het is 1,3,4-oxadiazol-2-yl or 1,2,4-oxadiazol-2-yl. In some embodiments, Het is 1,3,4-oxadiazol-2-yl. In some embodiments, Het is 1,2,4-oxadiazol-2-yl.

In some embodiments, $R^1$ is —C(O)R$^{16}$, —C(O)OR$^{16}$, —C(O)NR$^{16}$R$^{17}$, —OR$^{16}$, —SR$^{16}$, —NR$^{16}$R$^{17}$, —NR$^{16}$C(O)R$^{16}$, —OC(O)R$^{16}$, —SiR$^{16}$R$^{17}$R$^{18}$, alkyl, alkenyl, alkynyl, alkoxy, aryl, heteroaryl, or heterocyclyl, each of which is independently substituted or unsubstituted, or hydrogen. In some embodiments, $R^1$ is alkyl, alkylene, alkoxy, —NR$^{21}$R$^{22}$, or aryl, each of which is independently substituted or unsubstituted; halo or hydrogen. In some embodiments, $R^1$ is methyl, cyclohexyl, methylene, methoxy, or benzyl, each of which is substituted or unsubstituted. In some embodiments, $R^1$ is fluoro or chloro. In some embodiments, $R^1$ is phenyl. In some embodiments, $R^1$ is hydrogen.

In some embodiments, $R^1$ is a substituted alkyl or alkylene that is substituted or unsubstituted. $R^1$ can be substituted by one or more substituents selected from a hydroxyl group, sulfhydryl group, halogen, amino group, nitro group, nitroso group, cyano group, azido group, sulfoxide group, sulfone group, sulfonamide group, carboxyl group, carboxaldehyde group, imine group, alkyl group, halo-alkyl group, cyclic alkyl group, alkenyl group, halo-alkenyl group, alkynyl group, halo-alkynyl group, alkoxy group, aryl group, aryloxy group, aralkyl group, arylalkoxy group, heterocyclyl group, acyl group, acyloxy group, carbamate group, amide group, urethane group, and ester group.

In some embodiments, $R^1$ is substituted alkyl. In some embodiments, $R^1$ is alkyl substituted with NR$^{16}$R$^{17}$. In some embodiments, $R^1$ is methyl substituted with NR$^{16}$R$^{17}$, wherein each R$^{16}$ and R$^{17}$ is independently alkyl, cycloalkyl, aryl, heteroaryl, heterocyclyl, alkoxy, carboxyl group, amino group, acyl group, acyloxy group, or an amide group, any of which is unsubstituted or substituted, or hydrogen. In some embodiments, $R^1$ is methyl substituted with NR$^{16}$R$^{17}$, wherein R$^{16}$ is hydrogen, and R$^{17}$ is a substituted carboxyl group. In some embodiments, $R^1$ is methyl substituted with NR$^{16}$R$^{17}$, wherein R$^{16}$ is hydrogen, and R$^{17}$ is a carboxyl group substituted with heteroaryl. In some embodiments, $R^1$ is methyl substituted with NR$^{16}$R$^{17}$, wherein R$^{16}$ is hydrogen, and R$^{17}$ is a carboxyl group substituted with a 5-membered heteroaryl ring that is substituted.

In some embodiments, m is 1, 2, 3, or 4. In some embodiments, m is 1. In some embodiments, $X^1$ is carbon atom connected to $Q^1$, and m is 1. In some embodiments, $X^2$ is carbon atom connected to $Q^1$, and m is 1.

In some embodiments, $Q^1$ is C=O, C=S, C=CR$^{14}$R$^{15}$, C=NR$^{14}$, alkylene, alkenylene, or alkynylene, each of which is independently substituted or unsubstituted, or a bond. In some embodiments, $Q^1$ is alkylene, alkenylene, or alkynylene. In some embodiments, $Q^1$ is C-alkylene. In some embodiments, each R$^{16}$ and R$^{17}$ is independently alkyl, alkenyl, aryl, heteroaryl, heterocyclyl, or hydrogen. In some embodiments, $Q^1$ is a bond.

In some embodiments, $Q^1$ is C-alkylene, R$^{16}$ is aryl, and R$^7$ is alkyl. In some embodiments, $Q^1$ is C$_2$ alkylene, R$^{16}$ is aryl, and R$^{17}$ is hydrogen. In some embodiments, $Q^1$ is C-alkylene, R$^{16}$ is heteroaryl, and R$^{17}$ is alkyl. In some embodiments, $Q^1$ is C$_1$-alkylene, R$^{16}$ is heteroaryl, and R$^{17}$ is hydrogen. In some embodiments, $Q^1$ is C$_1$-alkylene, R$^{16}$ is substituted heteroaryl, and R$^{17}$ is hydrogen. In some embodiments, $Q^1$ is C$_1$-alkylene, R$^{16}$ is substituted alkyl, and R$^7$ is hydrogen. In some embodiments, R$^{17}$ is aryl, heteroaryl, or heterocyclyl, each of which is independently substituted or unsubstituted with halogen, alkyl, or hydroxyl. In some embodiments, R$^{16}$ is hydrogen, and R$^{17}$ is aryl or heteroaryl, substituted or unsubstituted with halogen or alkyl. In some embodiments, R$^{16}$ is alkyl, and R$^{17}$ is heteroaryl substituted with halogen or alkyl. In some embodiments, R$^{17}$ is aryl, heteroaryl, or heterocyclyl, each of which is independently substituted or unsubstituted with alkyl. In some embodiments, R$^{17}$ is aryl or heteroaryl, each of which is independently substituted with alkyl, wherein the alkyl is optionally substituted with fluorine, chlorine, bromine, iodine, or cyano.

In some embodiments, $R^2$ is hydrogen or alkyl. In some embodiments, $R^2$ is substituted alkyl. In some embodiments, $R^2$ is trifluoroethyl. In some embodiments, $R^3$ is alkyl, alkenyl, hydrogen, or halogen. In some embodiments, R$^{13}$ is methyl, ethyl, propyl, iso-propyl, butyl or tert-butyl. In some embodiments, $R^2$ is trifluoroethyl, and R$^{13}$ is hydrogen.

In some embodiments, $R^3$ is —C(O)R$^{19}$, —C(O)OR$^{19}$, alkyl, alkenyl, alkynyl, aryl, heteroaryl, or heterocyclyl, each of which is independently substituted or unsubstituted, or hydrogen; and $R^4$ is —C(O)R$^{19}$, —C(O)OR$^{19}$, alkyl, alkenyl, alkynyl, aryl, heteroaryl, or heterocyclyl, each of which is independently substituted or unsubstituted, or hydrogen.

In some embodiments, $R^3$ is H, and $R^4$ is —C(O)R$^{19}$, —C(O)OR$^{19}$, —C(O)NR$^{19}$R$^{20}$, —SOR$^9$, —SO$_2$R$^9$, alkyl, alkenyl, alkynyl, aryl, heteroaryl, or heterocyclyl, each of which is independently substituted or unsubstituted; or hydrogen. In some embodiments, $R^3$ is H, and $R^4$ is alkyl, alkenyl, alkynyl, aryl, heteroaryl, or heterocyclyl, each of which is independently substituted or unsubstituted, or hydrogen. In some embodiments, $R^4$ is heterocyclyl. In some embodiments, $R^4$ is piperidinyl, piperazinyl, tetahydropyranyl, morpholinyl, or pyrrolidinyl, each of which is independently substituted or unsubstituted.

In some embodiments, $R^4$ is a ring that is:

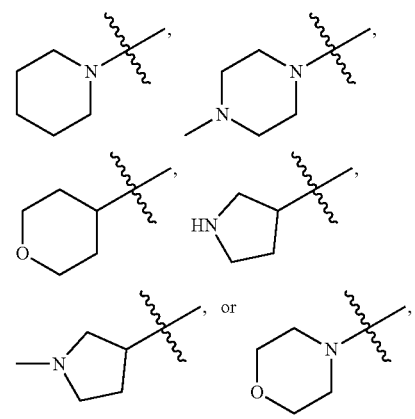

wherein the ring is substituted or unsubstituted. In some embodiments, $R^3$ is H, and $R^4$ is a ring that is

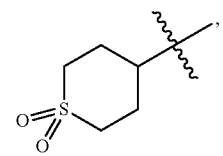 [SMILES: *C1CCS(=O)(=O)CC1]

wherein the ring is substituted or unsubstituted. In some embodiments, $R^3$ is H, and $R^4$ is a ring that is

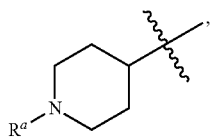

wherein the ring is substituted or unsubstituted. In some embodiments, $R^a$ is alkylene. In some embodiments, $R^a$ is methyl. In some embodiments, $R^3$ is H, and $R^4$ is a ring that is

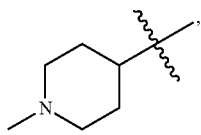 [SMILES: *C1CCN(C)CC1]

wherein the ring is substituted or unsubstituted. In some embodiments, $R^3$ is H, and $R^4$ is a ring that is

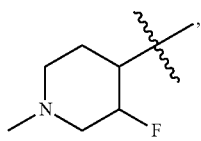 [SMILES: *C1CCN(C)CC1F]

wherein the ring is substituted or unsubstituted.

In some embodiments, $R^3$ and $R^4$ together with the nitrogen atom to which $R^3$ and $R^4$ are bound form a ring, wherein the ring is substituted or unsubstituted. In some embodiments, $R^3$ and $R^4$ together with the nitrogen atom to which $R^3$ and $R^4$ are bound form a substituted heterocycle. In some embodiments, $R^3$ and $R^4$ together with the nitrogen atom to which $R^3$ and $R^4$ are bound form a heterocycle substituted with a hydroxyl group, halogen, amino group, or alkyl group. In some embodiments, $R^3$ and $R^4$ together with the nitrogen atom to which $R^3$ and $R^4$ are bound form a heterocycle, wherein the heterocycle is substituted by a substituted or unsubstituted heterocycle.

In some embodiments, the disclosure provides a compound of the formula:

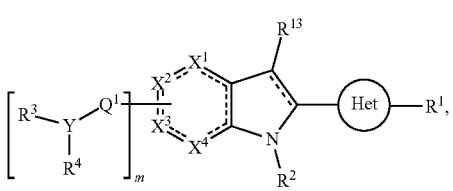

or a pharmaceutically-acceptable salt thereof, wherein the variables are as defined above.

In some embodiments, the disclosure provides a compound of the formula:

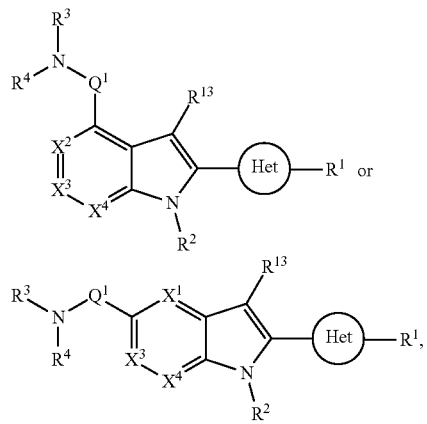

or a pharmaceutically-acceptable salt thereof, wherein the variables are as defined above.

In some embodiments, the compound is of the formula:

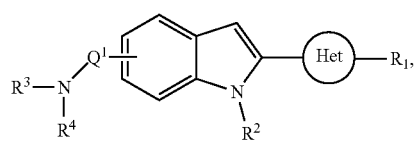

or a pharmaceutically-acceptable salt thereof, wherein the variables are as defined above.

In some embodiments, the disclosure provides a compound of the formula:

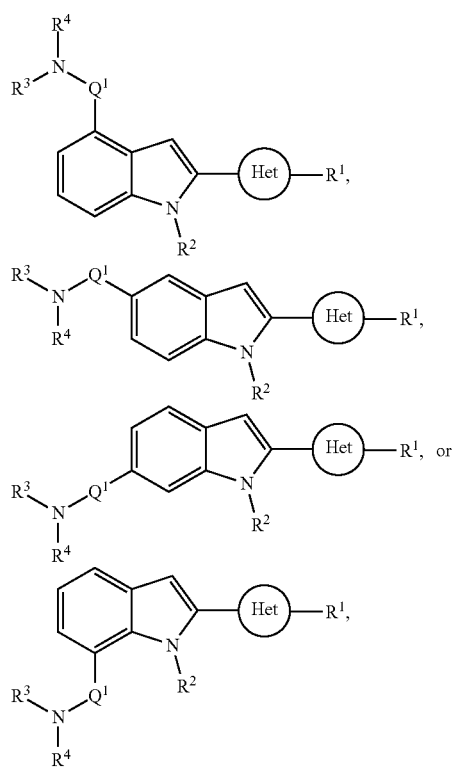

or a pharmaceutically-acceptable salt thereof, wherein the variables are as defined above.

In some embodiments, $R^1$ is —C(O)$R^{16}$, —C(O)O$R^{16}$, —C(O)N$R^{16}R^{17}$, —O$R^{16}$, —S$R^{16}$, —N$R^{16}R^{17}$, —N$R^{16}$C(O)$R^{16}$, —OC(O)$R^{16}$, —Si$R^{16}R^{17}R^{18}$, alkyl, alkenyl, alkynyl, alkoxy, aryl, heteroaryl, or heterocyclyl, each of which is independently substituted or unsubstituted, or hydrogen. In some embodiments, $R^1$ is alkyl, alkylene, alkoxy, —N$R^{71}R^{22}$, or aryl, each of which is independently substituted or unsubstituted; halo or hydrogen.

In some embodiments, $R^1$ is substituted alkyl. In some embodiments, $R^1$ is alkyl substituted with N$R^{16}R^{17}$. In some embodiments, $R^1$ is methyl substituted with N$R^{16}R^{17}$, wherein each $R^{16}$ and $R^{17}$ is independently alkyl, cycloalkyl, aryl, heteroaryl, heterocyclyl, alkoxy, carboxyl group, amino group, acyl group, acyloxy group, or an amide group, any of which is unsubstituted or substituted, or hydrogen. In some embodiments, $R^1$ is methyl substituted with N$R^{16}R^{17}$, wherein $R^{16}$ is hydrogen, and $R^{17}$ is a substituted carboxyl group. In some embodiments, $R^1$ is methyl substituted with N$R^{16}R^{17}$, wherein $R^{16}$ is hydrogen, and $R^{17}$ is a carboxyl group substituted with heteroaryl. In some embodiments, $R^1$ is methyl substituted with N$R^{16}R^{17}$, wherein $R^{16}$ is hydrogen, and $R^{17}$ is a carboxyl group substituted with a 5-membered heteroaryl ring that is substituted.

In some embodiments, $R^2$ is hydrogen or alkyl. In some embodiments, $R^2$ is substituted alkyl. In some embodiments, $R^2$ is trifluoroethyl.

In some embodiments, $Q^1$ is C=O, C=S, C=C$R^{14}R^{15}$, C=N$R^{14}$, alkylene, alkenylene, or alkynylene, each of which is independently substituted or unsubstituted, or a bond. In some embodiments, $Q^1$ is alkylene, alkenylene, or alkynylene. In some embodiments, $Q^1$ is $C_1$-alkylene. In some embodiments, each $R^{16}$ and $R^{17}$ is independently alkyl, alkenyl, aryl, heteroaryl, heterocyclyl, or hydrogen. In some embodiments, $Q^1$ is a bond.

In some embodiments, $R^3$ is H, and $R^4$ is —C(O)$R^{19}$, —C(O)O$R^{19}$, —C(O)N$R^{19}R^{20}$, —SO$R^{19}$, —SO$_2R^{19}$, alkyl, alkenyl, alkynyl, aryl, heteroaryl, or heterocyclyl, each of which is independently substituted or unsubstituted; or hydrogen. In some embodiments, R is H, and $R^4$ is alkyl, alkenyl, alkynyl, aryl, heteroaryl, or heterocyclyl, each of which is independently substituted or unsubstituted, or hydrogen. In some embodiments, $R^4$ is heterocyclyl. In some embodiments, $R^4$ is piperidinyl, piperazinyl, tetahydropyranyl, morpholinyl, or pyrrolidinyl, each of which is independently substituted or unsubstituted.

In some embodiments, $R^4$ is a ring that is:

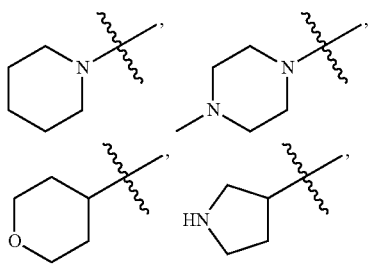

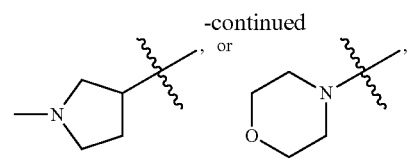

wherein the ring is substituted or unsubstituted. In some embodiments, $R^3$ is H, and $R^4$ is a ring that is

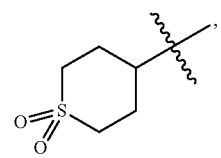 [SMILES: *C1CCS(=O)(=O)CC1]

wherein the ring is substituted or unsubstituted. In some embodiments, $R^3$ is H, and $R^4$ is a ring that is

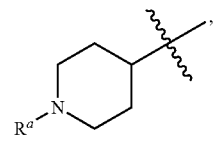

wherein the ring is substituted or unsubstituted. In some embodiments, $R^a$ is alkylene. In some embodiments, $R^a$ is methyl. In some embodiments, $R^3$ is H, and $R^4$ is a ring that is

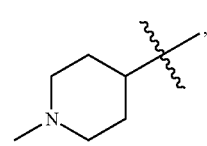 [SMILES: *C1CCN(C)CC1]

wherein the ring is substituted or unsubstituted. In some embodiments, $R^3$ is H, and $R^4$ is a ring that is

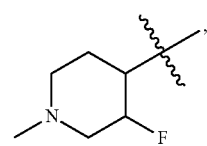 [SMILES: *C1CCN(C)CC1F]

wherein the ring is substituted or unsubstituted.

In some embodiments, the disclosure provides a compound of the formula:

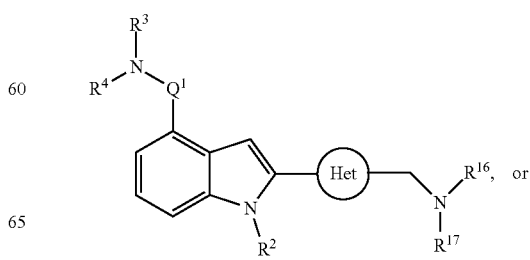

-continued

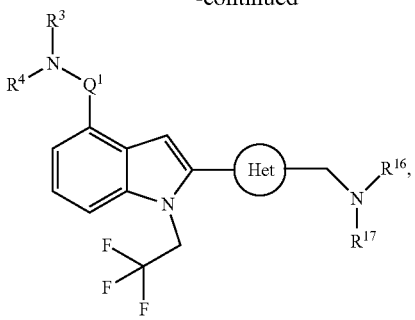

or a pharmaceutically-acceptable salt thereof, wherein the variables are as defined above.

In some embodiments, $Q^1$ is C=O, C=S, C=CR$^{14}$R$^{15}$, C=NRi$^4$, alkylene, alkenylene, or alkynylene, each of which is independently substituted or unsubstituted, or a bond. In some embodiments, $Q^1$ is alkylene, alkenylene, or alkynylene. In some embodiments, $Q^1$ is C-alkylene. In some embodiments, each $R^{16}$ and $R^{17}$ is independently alkyl, alkenyl, aryl, heteroaryl, heterocyclyl, or hydrogen. In some embodiments, $Q^1$ is a bond.

In some embodiments, $R^3$ is H, and $R^4$ is —C(O)R$^{19}$, —C(O)OR$^{19}$, —C(O)NR$^{19}$R$^{20}$, —SOR$^{19}$, —SO$_2$R$^{19}$, alkyl, alkenyl, alkynyl, aryl, heteroaryl, or heterocyclyl, each of which is independently substituted or unsubstituted; or hydrogen. In some embodiments, $R^3$ is H, and $R^4$ is alkyl, alkenyl, alkynyl, aryl, heteroaryl, or heterocyclyl, each of which is independently substituted or unsubstituted, or hydrogen. In some embodiments, $R^4$ is heterocyclyl. In some embodiments, $R^4$ is piperidinyl, piperazinyl, tetahydropyranyl, morpholinyl, or pyrrolidinyl, each of which is independently substituted or unsubstituted.

In some embodiments, $R^4$ is a ring that is:

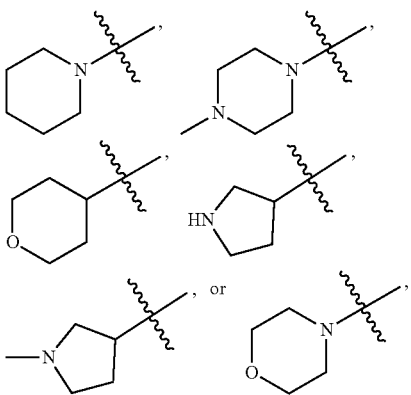

wherein the ring is substituted or unsubstituted. In some embodiments, $R^3$ is H, and $R^4$ is a ring that is

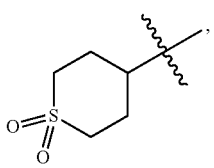 [SMILES: *C1CCS(=O)(=O)CC1]

wherein the ring is substituted or unsubstituted. In some embodiments, $R^3$ is H, and $R^4$ is a ring that is

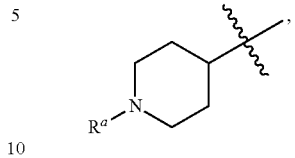

wherein the ring is substituted or unsubstituted. In some embodiments, $R^a$ is alkylene. In some embodiments, $R^a$ is methyl. In some embodiments, $R^3$ is H, and $R^4$ is a ring that is

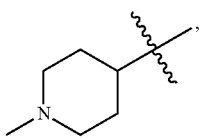 [SMILES: *C1CCN(C)CC1]

wherein the ring is substituted or unsubstituted. In some embodiments, $R^3$ is H, and $R^4$ is a ring that is

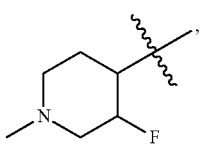

wherein the ring is substituted or unsubstituted.

In some embodiments, each $R^{16}$ and $R^{17}$ is independently alkyl, cycloalkyl, aryl, heteroaryl, heterocyclyl, alkoxy, carboxyl group, amino group, acyl group, acyloxy group, or an amide group, any of which is unsubstituted or substituted, or hydrogen. In some embodiments, $R^{16}$ is hydrogen, and $R^{17}$ is a substituted carboxyl group.

In some embodiments, the compound is of the formula:

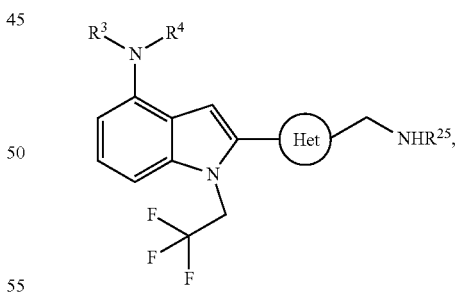

wherein $R^{25}$ is —C(O)R$^{16}$, —C(O)NR$^{16}$R$^{17}$, alkyl, alkenyl, alkynyl, aryl, heteroaryl, or heterocyclyl, each of which is independently substituted or unsubstituted, or hydrogen. In some embodiments, $R^{25}$ is aryl that is substituted or unsubstituted. In some embodiments, $R^{25}$ is substituted phenyl. In some embodiments, $R^{25}$ is —C(O)R$^{16}$, wherein $R^{16}$ is alkyl, aryl, heteroaryl, or heterocyclyl. In some embodiments, $R^{21}$ is —C(O)R$^{16}$, wherein $R^{16}$ is substituted phenyl; or a pharmaceutically-acceptable salt thereof.

In some embodiments, the compound is of the formula:

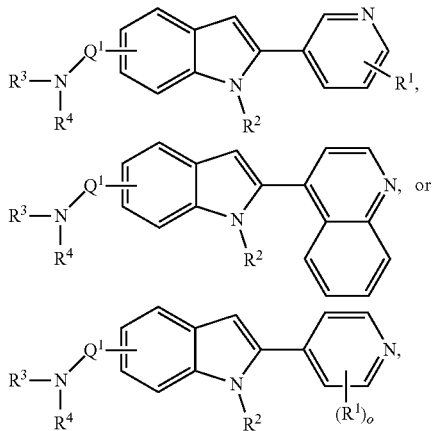

wherein:
- $Q^1$ is C=O, C=S, C=CR$^{14}$R$^{15}$, C=NR$^{14}$, alkylene, alkenylene, or alkynylene, each of which is independently substituted or unsubstituted, or a bond;
- $R^1$ is —C(O)R$^{16}$, —C(O)OR$^{16}$, —C(O)NR$^6$R$^{17}$, —OR$^6$, —SR$^{16}$, —NR$^{16}$R$^{17}$, —NR$^{16}$C(O)R$^{16}$, —OC(O)R$^{16}$, —SiR$^{16}$R$^{17}$R$^{18}$, alkyl, alkenyl, alkynyl, alkoxy, aryl, heteroaryl, heterocyclyl, or halo, each of which is independently substituted or unsubstituted, or hydrogen;
- each $R^3$ and $R^4$ is independently —C(O)R$^{19}$, —C(O)OR$^{19}$, —C(O)NR$^{19}$R$^{20}$, —SOR$^{19}$, —SO$_2$R$^{19}$, alkyl, alkenyl, alkynyl, aryl, heteroaryl, or heterocyclyl, each of which is independently substituted or unsubstituted, or hydrogen, or $R^3$ and $R^4$ together with the nitrogen atom to which $R^3$ and $R^4$ are bound form a ring, wherein the ring is substituted or unsubstituted, or $R^3$ is absent;
- each $R^2$, $R^{14}$, $R^{15}$, $R^{16}$, $R^{17}$, and $R^{18}$ is independently —C(O)R$^{21}$, —C(O)OR$^{21}$, —C(O)NR$^{21}$R$^{22}$, —OR$^{21}$, —SR$^{21}$, —NR$^{21}$R$^{22}$, —NR$^{21}$C(O)R$^{21}$, —OC(O)R$^{21}$, alkyl, alkenyl, alkynyl, aryl, heteroaryl, or heterocyclyl, each of which is independently substituted or unsubstituted, or hydrogen or halogen;
- each $R^{19}$ and $R^{20}$ is —C(O)R$^{23}$, —C(O)OR$^{23}$, —C(O)NR$^{23}$R$^{24}$, —OR$^{23}$, —SR$^{23}$, —NR$^{21}$R$^{24}$, —NR$^{23}$C(O)R$^{24}$, —OC(O)R$^{23}$, alkyl, alkenyl, alkynyl, aryl, heteroaryl, or heterocyclyl, each of which is independently substituted or unsubstituted, or hydrogen or halogen;
- each $R^{21}$ and $R^{22}$ is independently alkyl, alkenyl, alkynyl, aryl, heteroaryl, or heterocyclyl, each of which is independently substituted or unsubstituted, or hydrogen; and
- each $R^{23}$ and $R^{24}$ is independently alkyl, alkenyl, alkynyl, aryl, heteroaryl, or heterocyclyl, each of which is independently substituted or unsubstituted, or hydrogen, or a pharmaceutically-acceptable salt thereof.

the variables are as defined above, and wherein o is 1, 2, 3, or 4.

In some embodiments, the compound is of the formula:

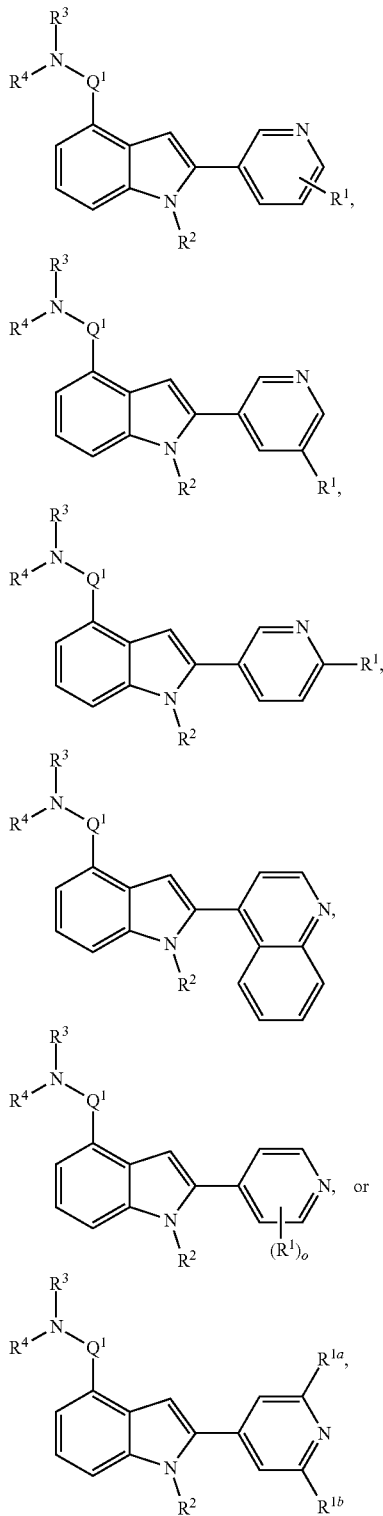

wherein:
- $Q^1$ is C=O, C=S, C=CR$^{14}$R$^{15}$, C=NR$^{14}$, alkylene, alkenylene, or alkynylene, each of which is independently substituted or unsubstituted, or a bond;
- each $R^1$, $R^{1a}$, and $R^{1b}$ is independently —C(O)R$^{16}$, —C(O)OR$^{16}$, —C(O)NR$^{16}$R$^{17}$, —OR$^{16}$, —SR$^{16}$, —NR$^{16}$R$^{17}$, —NR$^{16}$C(O)R$^{16}$, —OC(O)R$^{16}$, —SiR$^{16}$R$^{17}$R$^{18}$, alkyl, alkenyl, alkynyl, alkoxy, aryl, heteroaryl, heterocyclyl, or halo, each of which is independently substituted or unsubstituted, or hydrogen;

each R$^3$ and R$^4$ is independently —C(O)R$^{19}$, —C(O)OR$^{19}$, —C(O)NR$^{19}$R$^{20}$, —SOR$^{19}$, —SO$_2$R$^{19}$, alkyl, alkenyl, alkynyl, aryl, heteroaryl, or heterocyclyl, each of which is independently substituted or unsubstituted, or hydrogen, or R$^3$ and R$^4$ together with the nitrogen atom to which R$^3$ and R$^4$ are bound form a ring, wherein the ring is substituted or unsubstituted, or R$^3$ is absent;

o is 0, 1, 2, 3, or 4;

each R$^2$, R$^{14}$, R$^{15}$, R$^{16}$, R$^{17}$, and R$^{18}$ is independently —C(O)R$^{21}$, —C(O)OR$^{21}$, —C(O)NR$^{21}$R$^{22}$, —OR$^{21}$, —SR$^{21}$, —NR$^{21}$R$^{22}$, —NR$^{21}$C(O)R$^{22}$, —OC(O)R$^{21}$, alkyl, alkenyl, alkynyl, aryl, heteroaryl, or heterocyclyl, each of which is independently substituted or unsubstituted, or hydrogen or halogen;

each R$^{19}$ and R$^{20}$ is —C(O)R$^{23}$, —C(O)OR$^{23}$, —C(O)NR$^{23}$R$^{24}$, —OR$^{23}$, —SR$^2$, —NR$^{23}$R$^{24}$, —NR$^{23}$C(O)R$^{24}$, —OC(O)R$^{23}$, alkyl, alkenyl, alkynyl, aryl, heteroaryl, or heterocyclyl, each of which is independently substituted or unsubstituted, or hydrogen or halogen;

each R$^{21}$ and R$^{22}$ is independently alkyl, alkenyl, alkynyl, aryl, heteroaryl, or heterocyclyl, each of which is independently substituted or unsubstituted, or hydrogen; and each R$^{23}$ and R$^{24}$ is independently alkyl, alkenyl, alkynyl, aryl, heteroaryl, or heterocyclyl, each of which is independently substituted or unsubstituted, or hydrogen, or a pharmaceutically-acceptable salt thereof.

In some embodiments, each R$^{1a}$ and R$^{1b}$ is independently alkyl, alkoxy, aryl, heteroaryl, heterocyclyl, or NR$^{16}$R$^{17}$. In some embodiments, R$^{1a}$ is unsubstituted phenyl, and R$^{1b}$ is amino.

In some embodiments, the compound is of the formula:

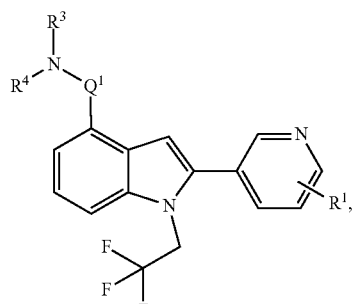

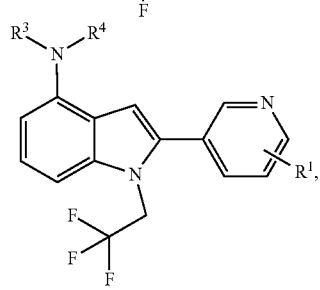

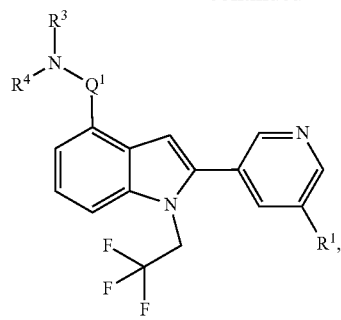

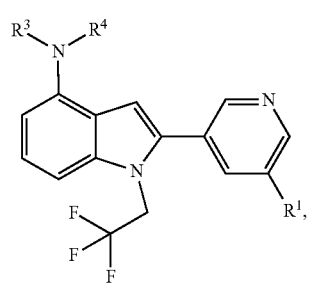

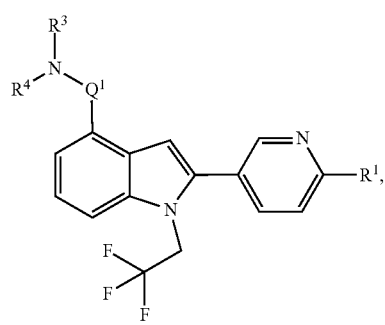

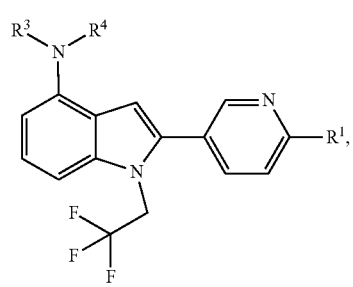

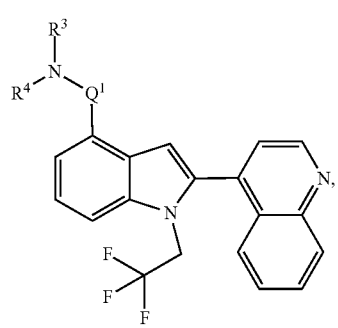

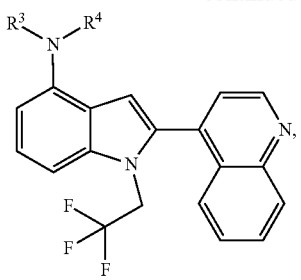
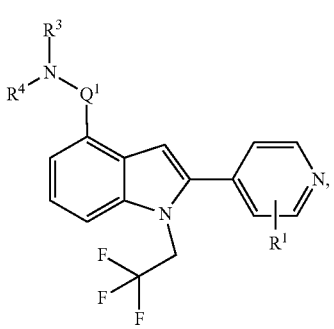
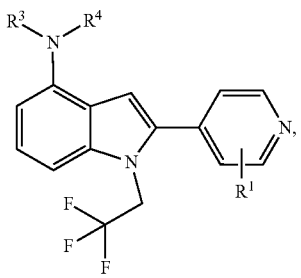
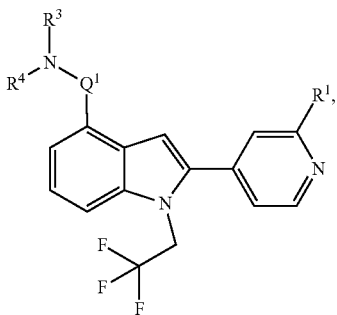
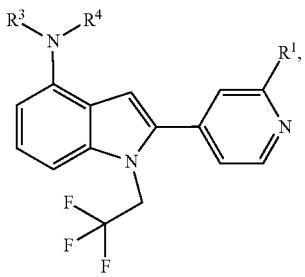

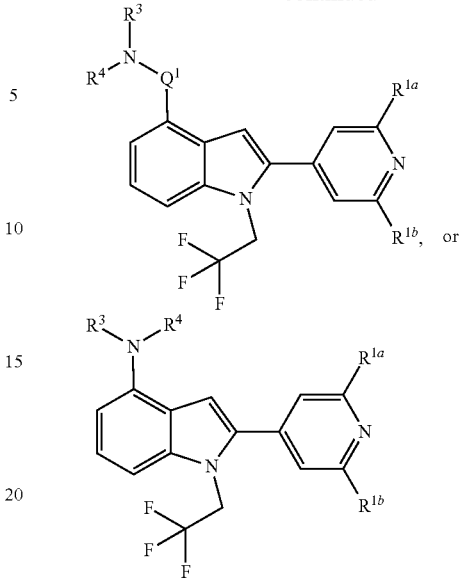

or a pharmaceutically-acceptable salt thereof, wherein the variables are as defined above.

In some embodiments, $R^1$ is —C(O)NR$^{16}$R$^{17}$, alkyl, alkenyl, alkynyl, alkoxy, aryl, heteroaryl, heterocyclyl, or halo, each of which is independently substituted or unsubstituted, or hydrogen. In some embodiments, $R^1$ is alkyl, alkoxy, aryl, or halo. In some embodiments, $R^1$ is methoxy, methyl, or phenyl. In some embodiments, each $R^{1a}$ and $R^{1b}$ is independently alkyl, alkoxy, aryl, heteroaryl, heterocyclyl, or NR$^{16}$R$^{17}$. In some embodiments, $R^{1a}$ is unsubstituted phenyl, and $R^{1b}$ is amino.

In some embodiments, $Q^1$ is C=O, C=S, C=CR$^4$R$^{15}$, C=NR$^{14}$, alkylene, alkenylene, or alkynylene, each of which is independently substituted or unsubstituted, or a bond. In some embodiments, $Q^1$ is alkylene, alkenylene, or alkynylene. In some embodiments, $Q^1$ is C$_1$-alkylene. In some embodiments, each $R^{16}$ and $R^{17}$ is independently alkyl, alkenyl, aryl, heteroaryl, heterocyclyl, or hydrogen. In some embodiments, $Q^1$ is a bond.

In some embodiments, $R^3$ is H, and $R^4$ is —C(O)R$^{19}$, —C(O)OR$^{19}$, —C(O)NR$^{19}$R$^{20}$, —SOR$^{19}$, —SO$_2$R$^{19}$, alkyl, alkenyl, alkynyl, aryl, heteroaryl, or heterocyclyl, each of which is independently substituted or unsubstituted; or hydrogen. In some embodiments, $R^3$ is H, and $R^4$ is alkyl, alkenyl, alkynyl, aryl, heteroaryl, or heterocyclyl, each of which is independently substituted or unsubstituted, or hydrogen. In some embodiments, $R^4$ is heterocyclyl. In some embodiments, $R^4$ is piperidinyl, piperazinyl, tetahydropyranyl, morpholinyl, or pyrrolidinyl, each of which is independently substituted or unsubstituted.

In some embodiments, $R^4$ is a ring that is:

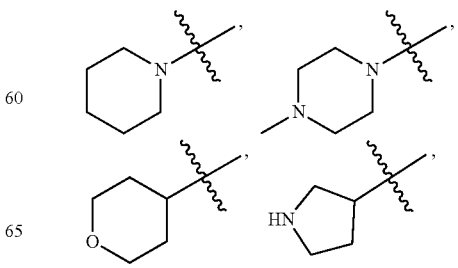

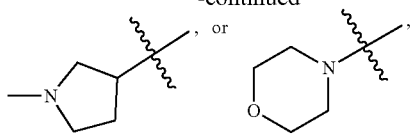

wherein the ring is substituted or unsubstituted. In some embodiments, $R^3$ is H, and $R^4$ is a ring that is

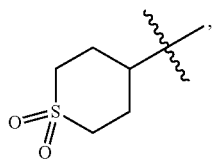 [SMILES: *C1CCS(=O)(=O)CC1]

wherein the ring is substituted or unsubstituted. In some embodiments, $R^3$ is H, and $R^4$ is a ring that is

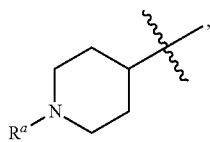

wherein the ring is substituted or unsubstituted. In some embodiments, $R^a$ is alkylene. In some embodiments, $R^a$ is methyl. In some embodiments, $R^3$ is H, and $R^4$ is a ring that is

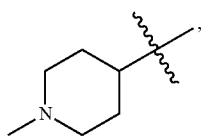 [SMILES: *C1CCN(C)CC1]

wherein the ring is substituted or unsubstituted. In some embodiments, $R^3$ is H, and $R^4$ is a ring that is

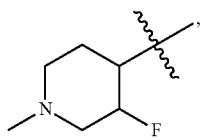 [SMILES: *C1CCN(C)CC1F]

wherein the ring is substituted or unsubstituted.

In some embodiments, each $R^{16}$ and $R^{17}$ is independently alkyl, cycloalkyl, aryl, heteroaryl, heterocyclyl, alkoxy, carboxyl group, amino group, acyl group, acyloxy group, or an amide group, any of which is unsubstituted or substituted, or hydrogen. In some embodiments, $R^{16}$ is hydrogen, and $R^{17}$ is a substituted carboxyl group.

In some embodiments, the compound is of the formula:

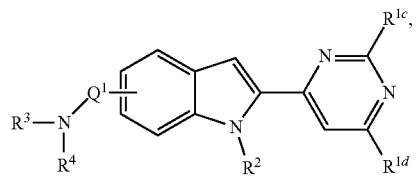

wherein:
$Q^1$ is C=O, C=S, C=CR$^{14}$R$^{15}$, C=NR$^{14}$, alkylene, alkenylene, or alkynylene, each of which is independently substituted or unsubstituted, or a bond;
each $R^{1c}$ and $R^{1d}$ is independently —C(O)R$^{16}$, —C(O)OR$^{16}$, —C(O)NR$^{16}$R$^{17}$, —OR$^{16}$, —SR$^{16}$, —NR$^{16}$R$^{17}$, —NR$^{16}$C(O)R$^{16}$, —OC(O)R$^{16}$, —SiR$^{16}$R$^{17}$R$^{18}$, alkyl, alkenyl, alkynyl, alkoxy, aryl, heteroaryl, heterocyclyl, or halo, each of which is independently substituted or unsubstituted, or hydrogen;
each $R^3$ and $R^4$ is independently —C(O)R$^{19}$, —C(O)OR$^{19}$, —C(O)NR$^{19}$R$^{20}$, —SOR$^{19}$, —SO$_2$R$^{19}$, alkyl, alkenyl, alkynyl, aryl, heteroaryl, or heterocyclyl, each of which is independently substituted or unsubstituted, or hydrogen, or $R^3$ and $R^4$ together with the nitrogen atom to which $R^3$ and $R^4$ are bound form a ring, wherein the ring is substituted or unsubstituted, or $R^3$ is absent;
each $R^2$, $R^{14}$, $R^{15}$, $R^{16}$, $R^{17}$, and $R^{18}$ is independently —C(O)R$^{21}$, —C(O)OR$^{21}$, —C(O)NR$^{21}$R$^{22}$, —OR$^{21}$, —SR$^{21}$, —NR$^{21}$R$^{22}$, —NR$^{21}$C(O)R$^{22}$, —OC(O)R$^{21}$, alkyl, alkenyl, alkynyl, aryl, heteroaryl, or heterocyclyl, each of which is independently substituted or unsubstituted, or hydrogen or halogen;
each $R^{19}$ and $R^{20}$ is —C(O)R$^{23}$, —C(O)OR$^{23}$, —C(O)NR$^{23}$R$^{24}$, —OR$^2$, —SR$^{23}$, —NR$^{23}$R$^{24}$, —NR$^{23}$C(O)R$^{24}$, —OC(O)R$^{73}$, alkyl, alkenyl, alkynyl, aryl, heteroaryl, or heterocyclyl, each of which is independently substituted or unsubstituted, or hydrogen or halogen;
each $R^{21}$ and $R^{22}$ is independently alkyl, alkenyl, alkynyl, aryl, heteroaryl, or heterocyclyl, each of which is independently substituted or unsubstituted, or hydrogen; and
each $R^{23}$ and $R^{24}$ is independently alkyl, alkenyl, alkynyl, aryl, heteroaryl, or heterocyclyl, each of which is independently substituted or unsubstituted, or hydrogen,
or a pharmaceutically-acceptable salt thereof.
In some embodiments, each $R^{1c}$ and $R^{1d}$ is independently —OR$^{16}$, —NR$^{16}$R$^{17}$, —NR$^{16}$C(O)R$^{16}$, alkyl, alkenyl, alkynyl, alkoxy, aryl, heteroaryl, or heterocyclyl, each of which is independently substituted or unsubstituted, or hydrogen.
In some embodiments, the compound is of the formula:

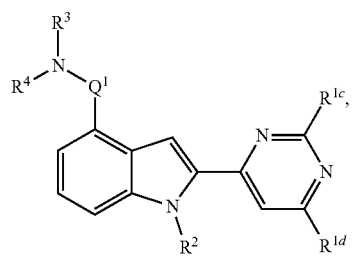

-continued

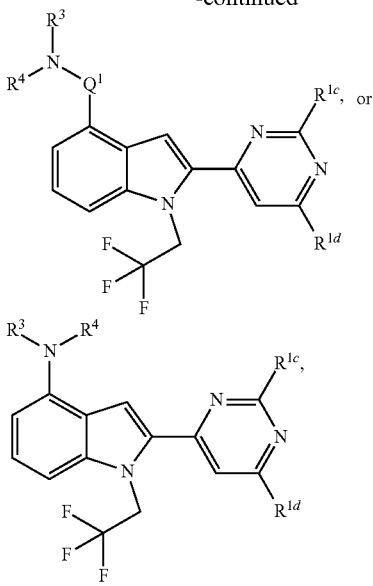

or a pharmaceutically-acceptable salt thereof, wherein the variables are as defined above.

In some embodiments, each $R^{1c}$ and $R^{1d}$ is independently $C(O)R^{16}$, $-C(O)OR^{16}$, $-C(O)NR^{16}R^{17}$, $-OR^6$, $-SR^{16}$, $-NR^{16}R^{17}$, $-NR^{16}C(O)R^{16}$, $-OC(O)R^{16}$, $-SiR^{16}R^{17}R^{18}$, alkyl, alkenyl, alkynyl, alkoxy, aryl, heteroaryl, heterocyclyl, or halo, each of which is independently substituted or unsubstituted, or hydrogen. In some embodiments, $R^{1c}$ is amino, and $R^{1d}$ is phenyl. In some embodiments, $R^{1c}$ is amino, and $R^{1d}$ is cycloalkenyl.

In some embodiments, the compound is of the formula:

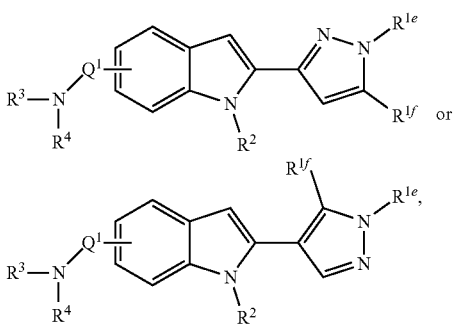

wherein:

$Q^1$ is C=O, C=S, $C=CR^{14}R^{15}$, $C=NR^4$, alkylene, alkenylene, or alkynylene, each of which is independently substituted or unsubstituted, or a bond;

each $R^{1e}$ and $R^{1f}$ is independently $-C(O)R^{16}$, $-C(O)OR^{16}$, $-C(O)NR^{16}R^{17}$, $-OR^{16}$, $-SR^{16}$, $-NR^{16}R^{17}$, $-NR^{16}C(O)R^{16}$, $-OC(O)R^{16}$, $-SiR^{16}R^{17}R^{18}$, alkyl, alkenyl, alkynyl, alkoxy, aryl, heteroaryl, heterocyclyl, or halo, each of which is independently substituted or unsubstituted, or hydrogen;

each $R^3$ and $R^4$ is independently $-C(O)R^{19}$, $-C(O)OR^{19}$, $-C(O)NR^{19}R^{20}$, $-SOR^9$, $-SO_2R^{19}$, alkyl, alkenyl, alkynyl, aryl, heteroaryl, or heterocyclyl, each of which is independently substituted or unsubstituted, or hydrogen, or $R^3$ and $R^4$ together with the nitrogen atom to which $R^3$ and $R^4$ are bound form a ring, wherein the ring is substituted or unsubstituted, or R is absent;

each $R^2$, $R^{14}$, $R^{15}$, $R^{16}$, $R^{17}$, and $R^{18}$ is independently $-C(O)R^{21}$, $-C(O)OR^{21}$, $-C(O)NR^{21}R^{22}$, $-OR^{21}$, $-SR^{21}$, $-NR^{21}R^{22}$, $-NR^{21}C(O)R^{22}$, $-OC(O)R^{23}$, alkyl, alkenyl, alkynyl, aryl, heteroaryl, or heterocyclyl, each of which is independently substituted or unsubstituted, or hydrogen or halogen;

each $R^{19}$ and $R^{20}$ is $-C(O)R^{23}$, $-C(O)OR^{23}$, $-C(O)NR^{23}R^{24}$, $-OR^{21}$, $-SR^2$, $-NR^{23}R^{24}$, $-NR^{23}C(O)R^{24}$, $-OC(O)R^{23}$, alkyl, alkenyl, alkynyl, aryl, heteroaryl, or heterocyclyl, each of which is independently substituted or unsubstituted, or hydrogen or halogen;

each $R^{21}$ and $R^{22}$ is independently alkyl, alkenyl, alkynyl, aryl, heteroaryl, or heterocyclyl, each of which is independently substituted or unsubstituted, or hydrogen; and each $R^{23}$ and $R^{24}$ is independently alkyl, alkenyl, alkynyl, aryl, heteroaryl, or heterocyclyl, each of which is independently substituted or unsubstituted, or hydrogen, or a pharmaceutically-acceptable salt thereof.

In some embodiments, the compound is of the formula:

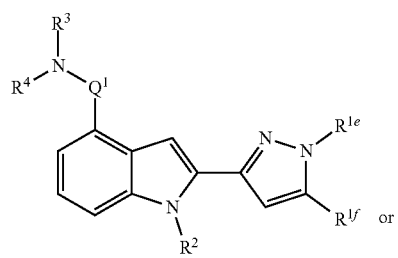

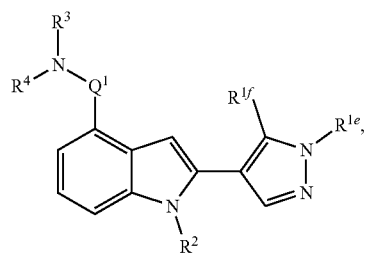

or a pharmaceutically-acceptable salt thereof, wherein the variables are as defined above.

In some embodiments, the compound is of the formula:

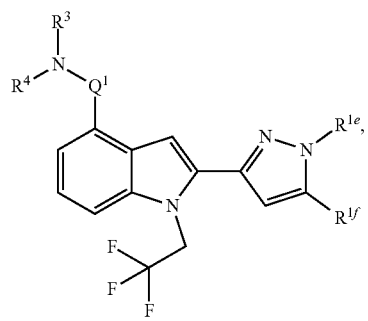

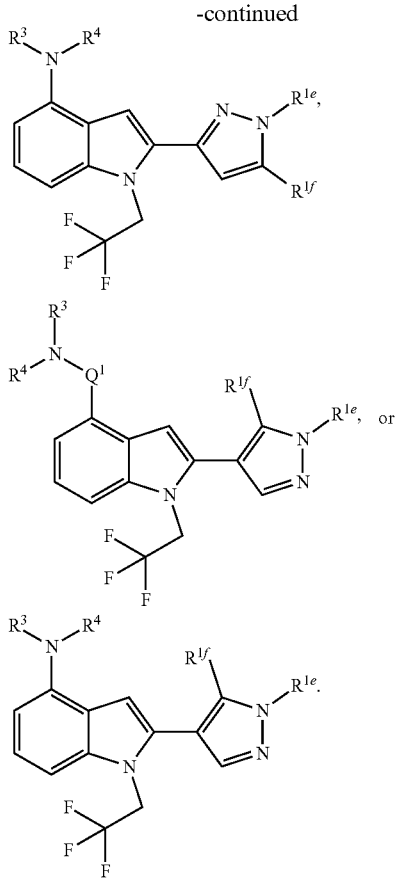

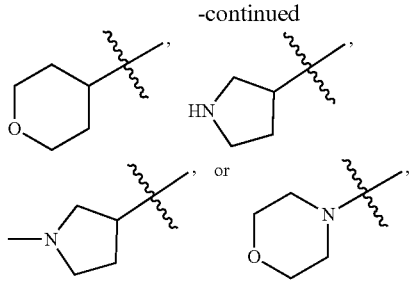

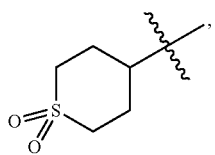 [SMILES: *C1CCS(=O)(=O)CC1]

or a pharmaceutically-acceptable salt thereof, wherein the variables are as defined above.

In some embodiments, $Q^1$ is C=O, C=S, C=CR$^{14}$R$^{15}$, C=NR$^{14}$, alkylene, alkenylene, or alkynylene, each of which is independently substituted or unsubstituted, or a bond. In some embodiments, $Q^1$ is alkylene, alkenylene, or alkynylene. In some embodiments, $Q^1$ is $C_1$-alkylene. In some embodiments, each R$^{16}$ and R$^{17}$ is independently alkyl, alkenyl, aryl, heteroaryl, heterocyclyl, or hydrogen. In some embodiments, $Q^1$ is a bond.

In some embodiments, R$^3$ is H, and R$^4$ is —C(O)R$^{19}$, —C(O)OR$^{19}$, —C(O)NR$^{19}$R$^{20}$, —SOR$^{19}$, —SO$_2$R$^{19}$, alkyl, alkenyl, alkynyl, aryl, heteroaryl, or heterocyclyl, each of which is independently substituted or unsubstituted; or hydrogen. In some embodiments, R$^3$ is H, and R$^4$ is alkyl, alkenyl, alkynyl, aryl, heteroaryl, or heterocyclyl, each of which is independently substituted or unsubstituted, or hydrogen. In some embodiments, R$^4$ is heterocyclyl. In some embodiments, R$^4$ is piperidinyl, piperazinyl, tetahydropyranyl, morpholinyl, or pyrrolidinyl, each of which is independently substituted or unsubstituted.

In some embodiments, R$^4$ is a ring that is:

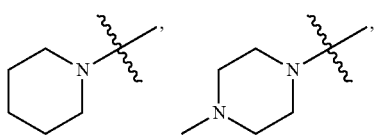

wherein the ring is substituted or unsubstituted. In some embodiments, R$^3$ is H, and R$^4$ is a ring that is

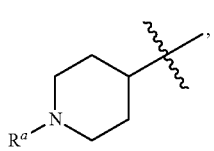

wherein the ring is substituted or unsubstituted. In some embodiments, R$^3$ is H, and R$^4$ is a ring that is

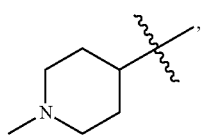 [SMILES: *C1CCN(C)CC1]

wherein the ring is substituted or unsubstituted. In some embodiments, R$^a$ is alkylene. In some embodiments, R$^a$ is methyl. In some embodiments, R$^3$ is H, and R$^4$ is a ring that is

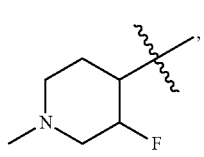 [SMILES: *C1CCN(C)CC1F]

wherein the ring is substituted or unsubstituted. In some embodiments, R$^3$ is H, and R$^4$ is a ring that is wherein the ring is substituted or unsubstituted.

In some embodiments, each R$^{1e}$ and R$^{1f}$ is independently alkyl, NR$^{16}$R$^{17}$, aryl, heteroaryl, or heterocyclyl, each of which is independently substituted or unsubstituted, or hydrogen. In some embodiments, R$^{1e}$ is substituted alkyl, and R$^{1f}$ is hydrogen. In some embodiments, R$^{1e}$ is hydrogen, and R$^{1f}$ is NR$^{16}$R$^{17}$, wherein each R$^{16}$ and R$^{17}$ is independently alkyl, alkenyl, aryl, heteroaryl, or heterocyclyl, each of which is independently substituted or unsubstituted, or hydrogen. In some embodiments, R$^{1e}$ is hydrogen, and R$^{1f}$ is NR[16]R[17], wherein R[16] is hydrogen, and R[17] is alkyl. In some embodiments, R[1e] is hydrogen, and R[1f] is NR[16]R[17], wherein R[16] is hydrogen, and R[17] is phenyl. In some embodiments, R[1e] is hydrogen, and R[1f] is amino.

In some embodiments, the compound is of the formula:

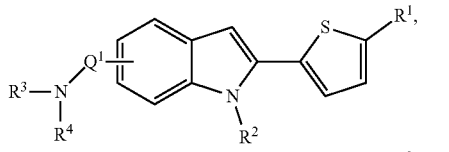

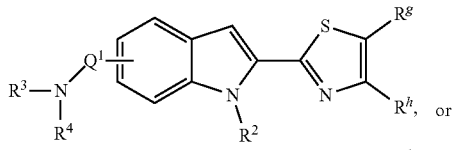

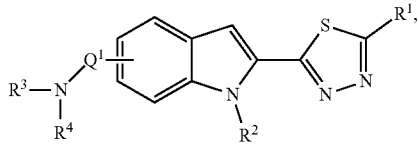

wherein:

- $Q^1$ is C=O, C=S, C=CR[14]R[15], C=NR[14], alkylene, alkenylene, or alkynylene, each of which is independently substituted or unsubstituted, or a bond;
- each $R^1$, $R^{1g}$, and $R^{1h}$ is independently —C(O)R[16], —C(O)OR[16], —C(O)NR[16]R[17], —OR[16], —SR[16], —NR[16]R[16], —NR[16]C(O)R[16], —OC(O)R[16], —SiR[16]R[17]R[18], alkyl, alkenyl, alkynyl, alkoxy, aryl, heteroaryl, heterocyclyl, or halo, each of which is independently substituted or unsubstituted, or hydrogen;
- each $R^3$ and $R^4$ is independently —C(O)R[19], —C(O)OR[19], —C(O)NR[19]R[20], —SOR[19], —SO$_2$R[19], alkyl, alkenyl, alkynyl, aryl, heteroaryl, or heterocyclyl, each of which is independently substituted or unsubstituted, or hydrogen, or $R^3$ and $R^4$ together with the nitrogen atom to which $R^3$ and $R^4$ are bound form a ring, wherein the ring is substituted or unsubstituted, or $R^3$ is absent;
- each $R^2$, $R^{14}$, $R^{15}$, $R^{16}$, $R^{17}$, and $R^{18}$ is independently —C(O)R[21], —C(O)OR[21], —C(O)NR[21]R[22], —OR[21], —SR[21], —NR[21]R[22], —NR[21]C(O)R[22], —OC(O)R[22], alkyl, alkenyl, alkynyl, aryl, heteroaryl, or heterocyclyl, each of which is independently substituted or unsubstituted, or hydrogen or halogen;
- each $R^{19}$ and $R^{20}$ is —C(O)R[23], —C(O)OR[23], —C(O)NR[23]R[24], —OR[23], —SR[23], —NR[23]R[24], —NR[23]C(O)R[24], —OC(O)R[13], alkyl, alkenyl, alkynyl, aryl, heteroaryl, or heterocyclyl, each of which is independently substituted or unsubstituted, or hydrogen or halogen;
- each $R^2$ and $R^{22}$ is independently alkyl, alkenyl, alkynyl, aryl, heteroaryl, or heterocyclyl, each of which is independently substituted or unsubstituted, or hydrogen; and
- each $R^{23}$ and $R^{24}$ is independently alkyl, alkenyl, alkynyl, aryl, heteroaryl, or heterocyclyl, each of which is independently substituted or unsubstituted, or hydrogen, or a pharmaceutically-acceptable salt thereof.

In some embodiments, the compound is of the formula:

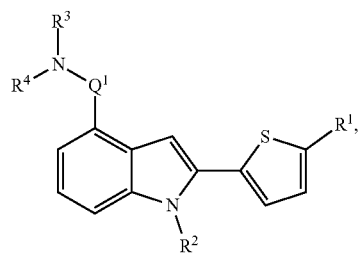

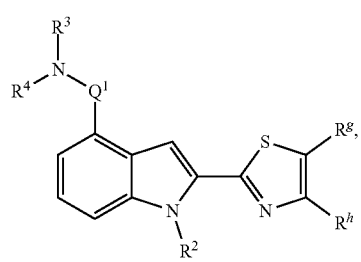

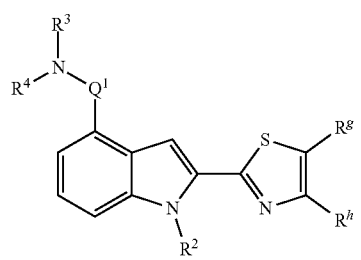

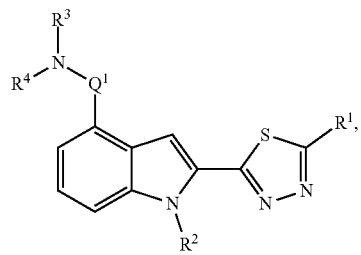

or a pharmaceutically-acceptable salt thereof, wherein the variables are as defined above.

In some embodiments, the compound is of the formula:

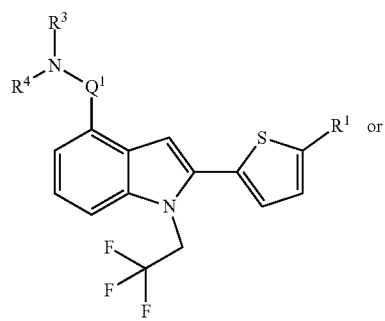

-continued

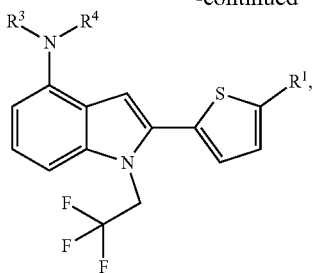

or a pharmaceutically-acceptable salt thereof, wherein the variables are as defined above.

In some embodiments, $Q^1$ is C=O, C=S, C=CR$^{14}$R$^{15}$, C=NR$^{14}$, alkylene, alkenylene, or alkynylene, each of which is independently substituted or unsubstituted, or a bond. In some embodiments, $Q^1$ is alkylene, alkenylene, or alkynylene. In some embodiments, $Q^1$ is $C_1$-alkylene. In some embodiments, each R$^{16}$ and R$^{17}$ is independently alkyl, alkenyl, aryl, heteroaryl, heterocyclyl, or hydrogen. In some embodiments, $Q^1$ is a bond.

In some embodiments, R$^3$ is H, and R$^4$ is —C(O)R$^{19}$, —C(O)OR$^{19}$, —C(O)NR$^{19}$R$^{21}$, —SOR$^{19}$, —SO$_2$R$^{19}$, alkyl, alkenyl, alkynyl, aryl, heteroaryl, or heterocyclyl, each of which is independently substituted or unsubstituted; or hydrogen. In some embodiments, R$^3$ is H, and R$^4$ is alkyl, alkenyl, alkynyl, aryl, heteroaryl, or heterocyclyl, each of which is independently substituted or unsubstituted, or hydrogen. In some embodiments, R$^4$ is heterocyclyl. In some embodiments, R$^4$ is piperidinyl, piperazinyl, tetahydropyranyl, morpholinyl, or pyrrolidinyl, each of which is independently substituted or unsubstituted.

In some embodiments, R$^4$ is a ring that is:

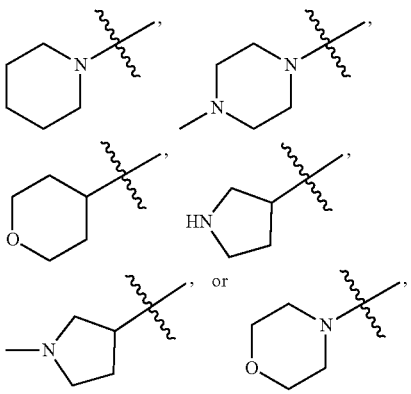

wherein the ring is substituted or unsubstituted. In some embodiments, R$^3$ is H, and R$^4$ is a ring that is

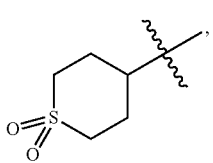

wherein the ring is substituted or unsubstituted. In some embodiments, R$^3$ is H, and R$^4$ is a ring that is

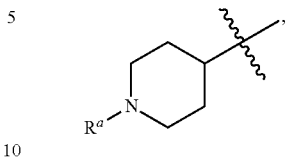

wherein the ring is substituted or unsubstituted. In some embodiments, R$^a$ is alkylene. In some embodiments, R$^a$ is methyl. In some embodiments, R$^3$ is H, and R$^4$ is a ring that is

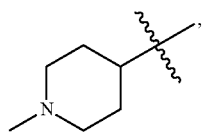

wherein the ring is substituted or unsubstituted. In some embodiments, R$^3$ is H, and R$^4$ is a ring that is

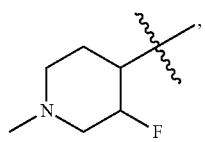 [SMILES: *C1CCN(C)CC1F]

wherein the ring is substituted or unsubstituted.

In some embodiments, R$^1$ is —C(O)R$^{16}$, —C(O)OR$^{16}$, —C(O)NR$^{16}$R$^{17}$, —OR$^{16}$, —SR$^{16}$, —NR$^{16}$R$^{17}$, —NR$^{16}$C(O)R$^{16}$, —OC(O)R$^{16}$, —SiR$^{16}$R$^{17}$R$^{18}$, alkyl, alkenyl, alkynyl, alkoxy, aryl, heteroaryl, heterocyclyl, or halo, each of which is independently substituted or unsubstituted, or hydrogen. In some embodiments, R$^1$ is substituted alkyl. In some embodiments, R$^1$ is alkyl substituted with NR$^{16}$R$^{17}$, wherein each R$^{16}$ and R$^{17}$ is independently alkyl, cycloalkyl, aryl, heteroaryl, heterocyclyl, alkoxy, carboxyl group, amino group, acyl group, acyloxy group, or an amide group, any of which is unsubstituted or substituted, or hydrogen. In some embodiments, R$^{16}$ is hydrogen, and R$^{17}$ is a substituted carboxyl group. In some embodiments, R$^{16}$ is hydrogen, and R$^{17}$ is carboxyl substituted with alkyl or aryl. In some embodiments, R$^{16}$ is hydrogen, and R$^{17}$ is carboxyl substituted with cycloalkyl or phenyl. In some embodiments, R$^{16}$ and R$^{17}$ are hydrogen.

In some embodiments, the compound is of the formula:

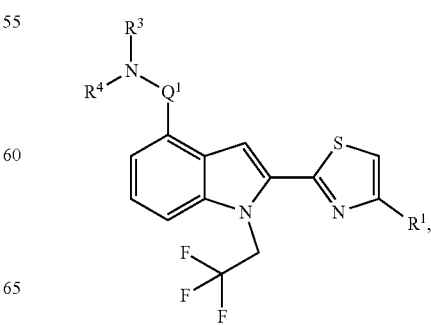

-continued

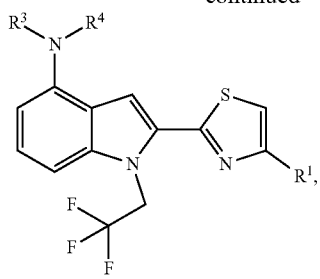

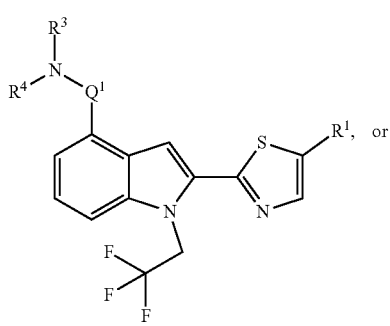

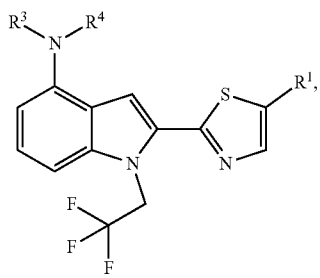

or a pharmaceutically-acceptable salt thereof, wherein the variables are as defined above.

In some embodiments, $R^1$ is —C(O)R$^{16}$, —C(O)OR$^{16}$, —C(O)NR$^{16}$R$^{17}$, —OR$^{16}$, —SR$^{16}$, —NR$^{16}$R$^{17}$, —NR$^{16}$C(O)R$^{16}$, —OC(O)R$^{16}$, —SiR$^{16}$R$^{17}$R$^{18}$, alkyl, alkenyl, alkynyl, alkoxy, aryl, heteroaryl, heterocyclyl, or halo, each of which is independently substituted or unsubstituted, or hydrogen. In some embodiments, $R^1$ is substituted alkyl. In some embodiments, $R^1$ is alkyl substituted with NR$^{16}$R$^{17}$, wherein each R$^{16}$ and R$^{17}$ is independently alkyl, cycloalkyl, aryl, heteroaryl, heterocyclyl, alkoxy, carboxyl group, amino group, acyl group, acyloxy group, or an amide group, any of which is unsubstituted or substituted, or hydrogen. In some embodiments, R$^{16}$ is hydrogen, and R$^{17}$ is a substituted carboxyl group. In some embodiments, R$^{16}$ is hydrogen, and R$^{17}$ is carboxyl substituted with alkyl or aryl. In some embodiments, R$^{16}$ is hydrogen, and R$^{17}$ is carboxyl substituted with cycloalkyl or phenyl. In some embodiments, R$^{16}$ and R$^{17}$ are hydrogen.

In some embodiments, the compounds if of the formula:

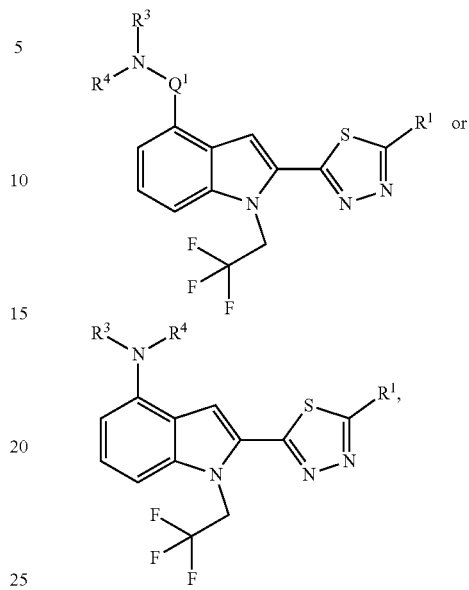

or a pharmaceutically-acceptable salt thereof wherein the variables are as defined above.

In some embodiments, $Q^1$ is C=O C=S, C=CR$^{14}$R$^{15}$, C=NR$^{14}$, alkylene, alkenylene, or alkynylene, each of which is independently substituted or unsubstituted, or a bond. In some embodiments, $Q^1$ is alkylene, alkenylene, or alkynylene. In some embodiments, $Q^1$ is C$^1$-alkylene. In some embodiments, each R$^{16}$ and R$^{17}$ is independently alkyl, alkenyl, aryl, heteroaryl, heterocyclyl, or hydrogen. In some embodiments, $Q^1$ is a bond.

In some embodiments, $R^3$ is H, and $R^4$ is —C(O)R$^{19}$, —C(O)OR$^{19}$, —C(O)NR$^{19}$R$^{20}$, —SOR$^{19}$, —SO$_2$R$^{19}$, alkyl, alkenyl, alkynyl, aryl, heteroaryl, or heterocyclyl, each of which is independently substituted or unsubstituted; or hydrogen. In some embodiments, $R^3$ is H, and $R^4$ is alkyl, alkenyl, alkynyl, aryl, heteroaryl, or heterocyclyl, each of which is independently substituted or unsubstituted, or hydrogen. In some embodiments, $R^4$ is heterocyclyl. In some embodiments, $R^4$ is piperidinyl, piperazinyl, tetahydropyranyl, morpholinyl, or pyrrolidinyl, each of which is independently substituted or unsubstituted.

In some embodiments, $R^4$ is a ring that is:

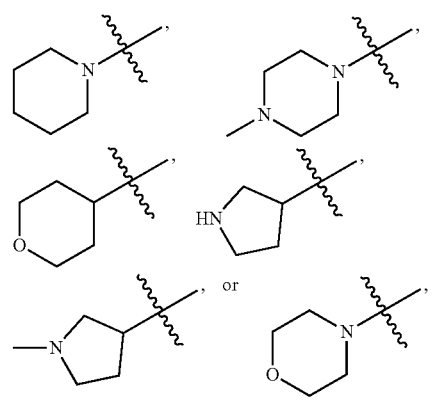

wherein the ring is substituted or unsubstituted. In some embodiments, $R^3$ is H, and $R^4$ is a ring that is

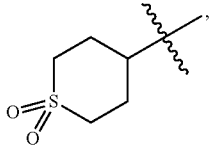

wherein the ring is substituted or unsubstituted. In some embodiments, $R^3$ is H, and $R^4$ is a ring that is

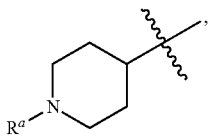

wherein the ring is substituted or unsubstituted. In some embodiments, $R^a$ is alkylene. In some embodiments, $R^a$ is methyl. In some embodiments, $R^3$ is H, and $R^4$ is a ring that is

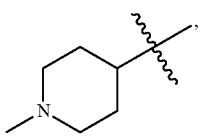 [SMILES: *C1CCN(C)CC1]

wherein the ring is substituted or unsubstituted. In some embodiments, $R^3$ is H, and $R^4$ is a ring that is

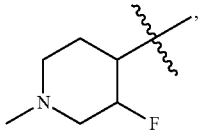 [SMILES: *C1CCN(C)CC1F]

wherein the ring is substituted or unsubstituted.

In some embodiments, $R^1$ is —C(O)$R^{16}$, —C(O)O$R^{16}$, —C(O)N$R^{16}R^{17}$, —O$R^{16}$, —S$R^{16}$, —N$R^{16}R^{17}$, —N$R^{16}$C(O)$R^{16}$, —OC(O)$R^{16}$, —Si$R^{16}R^{17}R^{18}$, alkyl, alkenyl, alkynyl, alkoxy, aryl, heteroaryl, heterocyclyl, or halo, each of which is independently substituted or unsubstituted, or hydrogen. In some embodiments, $R^1$ is substituted alkyl. In some embodiments, $R^1$ is alkyl substituted with N$R^{16}R^{17}$, wherein each $R^{16}$ and $R^{17}$ is independently alkyl, cycloalkyl, aryl, heteroaryl, heterocyclyl, alkoxy, carboxyl group, amino group, acyl group, acyloxy group, or an amide group, any of which is unsubstituted or substituted, or hydrogen. In some embodiments, $R^{16}$ is hydrogen, and $R^{17}$ is aryl, heteroaryl, carboxyl, or hydrogen. In some embodiments, $R^{16}$ is hydrogen, and $R^{17}$ is carboxyl substituted with aryl, heteroaryl, cycloalkyl, or alkyl. In some embodiments, $R^{16}$ and $R^{17}$ are hydrogen.

In some embodiments, the compound is of the formula:

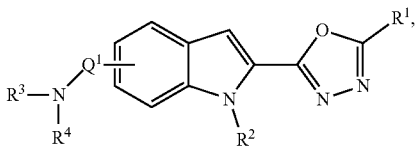

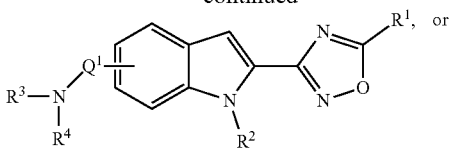

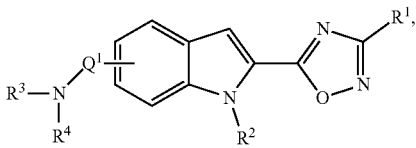

wherein:

$Q^1$ is C=O, C=S, C=C$R^{14}R^{15}$, C=N$R^{14}$, alkylene, alkenylene, or alkynylene, each of which is independently substituted or unsubstituted, or a bond;

$R^1$ is —C(O)$R^{16}$, —C(O)O$R^{16}$, —C(O)N$R^{16}R^{17}$, —O$R^{16}$, —S$R^{16}$, —N$R^{16}R^{17}$, —N$R^{16}$C(O)$R^{16}$, —OC(O)$R^{16}$, —Si$R^{16}R^{17}R^{18}$, alkyl, alkenyl, alkynyl, alkoxy, aryl, heteroaryl, heterocyclyl, or halo, each of which is independently substituted or unsubstituted, or hydrogen;

each $R^3$ and $R^4$ is independently —C(O)$R^{19}$, —C(O)O$R^{19}$, —C(O)N$R^{19}R^{20}$, —SO$R^{19}$, —SO$_2R^{19}$, alkyl, alkenyl, alkynyl, aryl, heteroaryl, or heterocyclyl, each of which is independently substituted or unsubstituted, or hydrogen, or $R^3$ and $R^4$ together with the nitrogen atom to which $R^3$ and $R^4$ are bound form a ring, wherein the ring is substituted or unsubstituted, or $R^3$ is absent;

each $R^2$, $R^{14}$, $R^{15}$, $R^{16}$, $R^{17}$, and $R^{18}$ is independently —C(O)$R^{21}$, —C(O)O$R^{21}$, —C(O)N$R^{21}R^{22}$, —O$R^{21}$, —S$R^{21}$, —N$R^{21}R^{22}$, —N$R^{2}$C(O)$R^{22}$, —OC(O)$R^{21}$, alkyl, alkenyl, alkynyl, aryl, heteroaryl, or heterocyclyl, each of which is independently substituted or unsubstituted, or hydrogen or halogen;

each $R^{19}$ and $R^{20}$ is —C(O)$R^{23}$, —C(O)O$R^{23}$, —C(O)N$R^{23}R^{24}$, —O$R^{23}$, —S$R^{23}$, —N$R^{21}R^{24}$, —N$R^{23}$C(O)$R^{24}$, —OC(O)$R^{23}$, alkyl, alkenyl, alkynyl, aryl, heteroaryl, or heterocyclyl, each of which is independently substituted or unsubstituted, or hydrogen or halogen;

each $R^{21}$ and $R^{22}$ is independently alkyl, alkenyl, alkynyl, aryl, heteroaryl, or heterocyclyl, each of which is independently substituted or unsubstituted, or hydrogen; and each $R^{23}$ and $R^{24}$ is independently alkyl, alkenyl, alkynyl, aryl, heteroaryl, or heterocyclyl, each of which is independently substituted or unsubstituted, or hydrogen, or a pharmaceutically-acceptable salt thereof.

In some embodiments, the compound is of the formula:

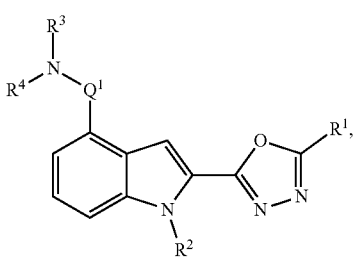

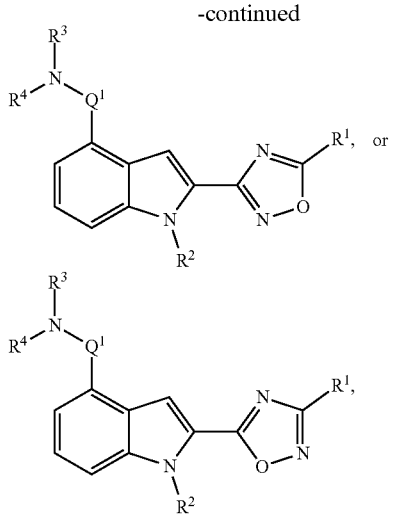
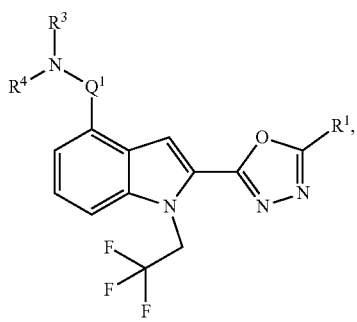
or a pharmaceutically-acceptable salt thereof, wherein the variables are as defined above.
In some embodiments, the compound is of the formula:
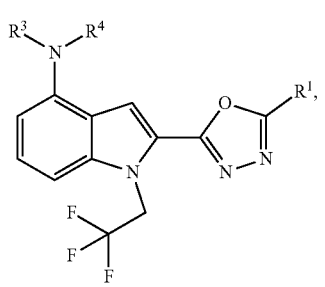
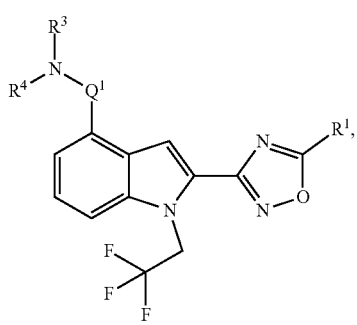
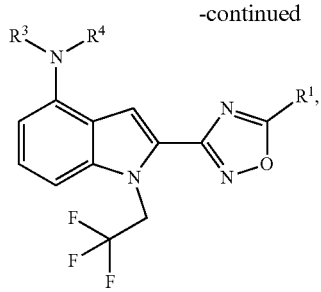
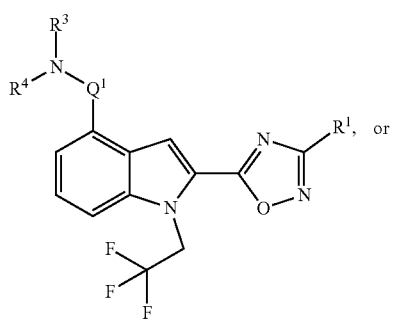
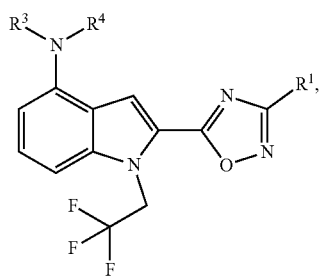
or a pharmaceutically-acceptable salt thereof, wherein the variables are as defined above.
In some embodiments, the compound is of the formula:
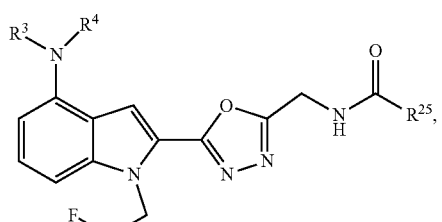
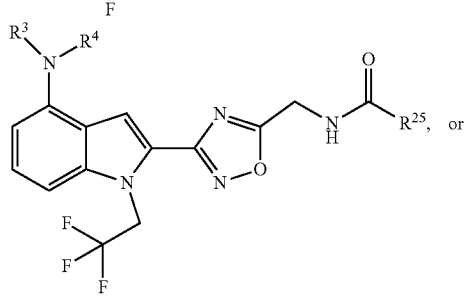

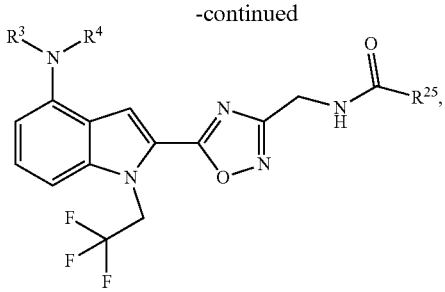

wherein:
- Q¹ is C=O, C=S, C=CR¹⁴R¹⁵, C=NR¹⁴, alkylene, alkenylene, or alkynylene, each of which is independently substituted or unsubstituted, or a bond;
- each RC and Rid is independently —C(O)R¹⁶, —C(O)OR¹⁶, —C(O)NR⁶R⁷, —OR¹⁶, —SR^M, —NR¹⁶R¹⁷ ?, —NR¹⁶C(O)R¹⁶, —OC(O)R¹⁶, —SiR¹⁶R¹⁷R¹⁸, alkyl, alkenyl, alkynyl, alkoxy, aryl, heteroaryl, heterocyclyl, or halo, each of which is independently substituted or unsubstituted, or hydrogen;
- each R³ and R⁴ is independently —C(O)R¹⁹, —C(O)OR¹⁹, —C(O)NR¹⁹R²⁰, —SOR¹⁹, —SO₂R¹⁹, alkyl, alkenyl, alkynyl, aryl, heteroaryl, or heterocyclyl, each of which is independently substituted or unsubstituted, or hydrogen, or R³ and R⁴ together with the nitrogen atom to which R³ and R⁴ are bound form a ring, wherein the ring is substituted or unsubstituted, or R³ is absent;
- each R¹⁴, R¹⁵, R¹⁶, R¹⁷, and R¹⁸ is independently —C(O)R²¹, —C(O)OR²¹, —C(O)NR²¹R²², —OR²¹, —SR²¹, —NR²¹R²², —NR²¹C(O)R²², —OC(O)R²¹, alkyl, alkenyl, alkynyl, aryl, heteroaryl, or heterocyclyl, each of which is independently substituted or unsubstituted, or hydrogen or halogen;
- each R¹⁹ and R²⁰ is —C(O)R²³, —C(O)OR²³, —C(O)NR²³R²⁴, —OR²³, —SR²³, —NR²¹R²⁴, —NR²³C(O)R²⁴, —OC(O)R²³, alkyl, alkenyl, alkynyl, aryl, heteroaryl, or heterocyclyl, each of which is independently substituted or unsubstituted, or hydrogen or halogen;
- each R²¹ and R²² is independently alkyl, alkenyl, alkynyl, aryl, heteroaryl, or heterocyclyl, each of which is independently substituted or unsubstituted, or hydrogen; and
- each R²³ and R²⁴ is independently alkyl, alkenyl, alkynyl, aryl, heteroaryl, or heterocyclyl, each of which is independently substituted or unsubstituted, or hydrogen,
- R²⁵ is alkyl, alkenyl, alkynyl, aryl, heteroaryl, or heterocyclyl, each of which is independently substituted or unsubstituted, or hydrogen;

or a pharmaceutically-acceptable salt thereof.

In some embodiments, R²⁵ is heterocyclyl, cycloalkyl, aryl, each of which is substituted or unsubstituted. In some embodiments, R²⁵ is phenyl or cyclopropyl, each of which is substituted or unsubstituted. In some embodiments, R⁷⁵ is substituted cyclopropyl. In some embodiments, R²⁵ is heteroaryl or heterocyclyl, each of which is substituted or unsubstituted. In some embodiments, R²⁵ is thiophenyl, indolenyl, or pyrrolyl, each of which is substituted or unsubstituted.

Non-limiting examples of compounds of the disclosure include compounds of any of the following formulae:

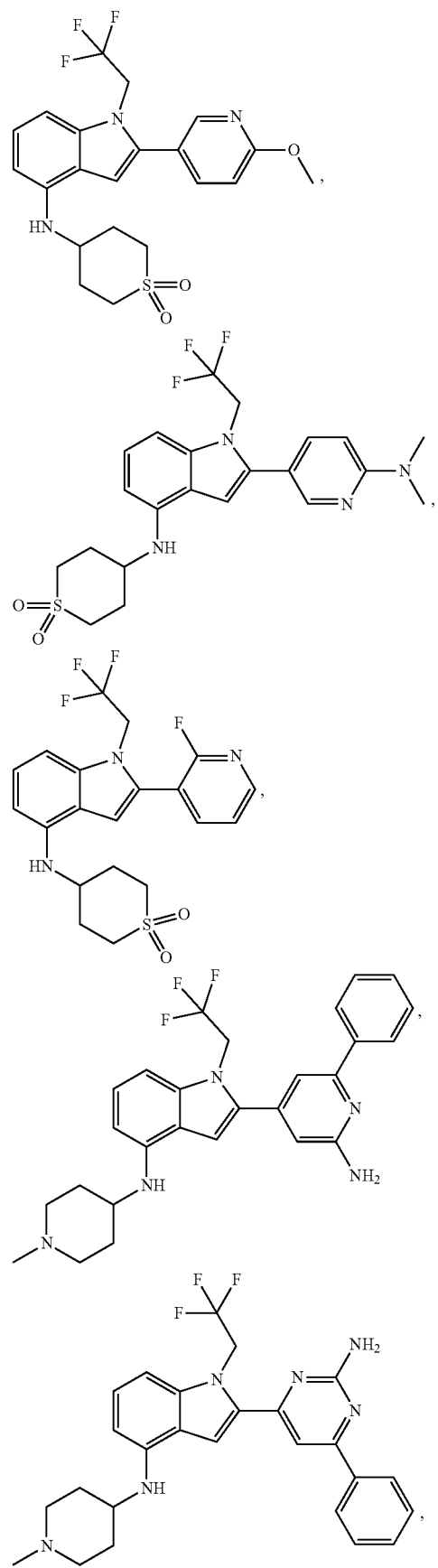

77
-continued
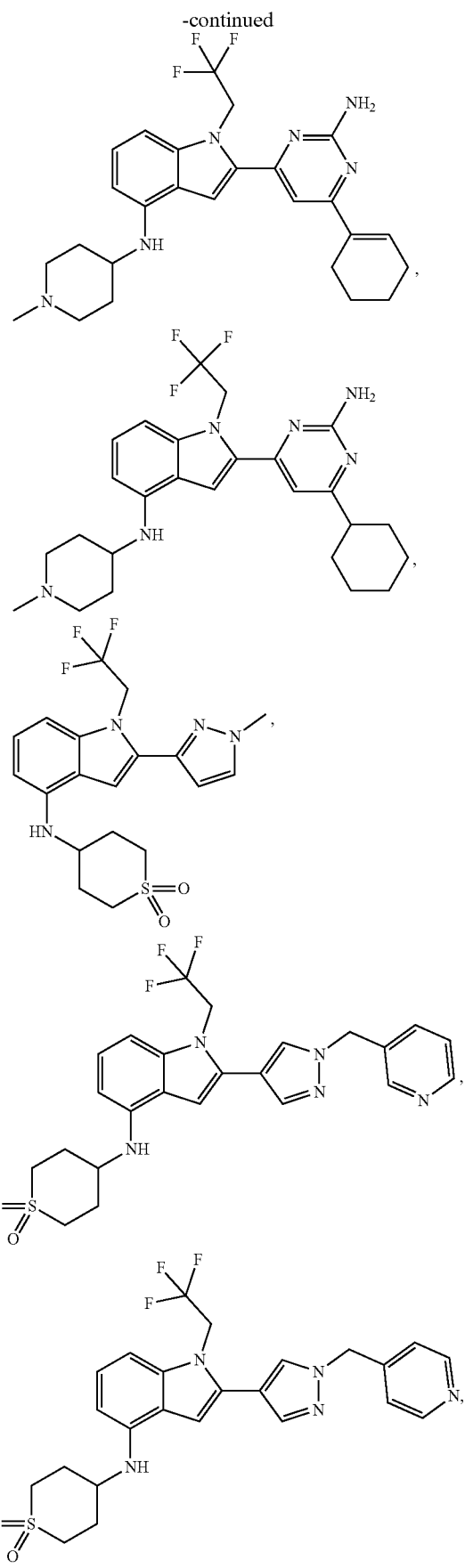
78
-continued
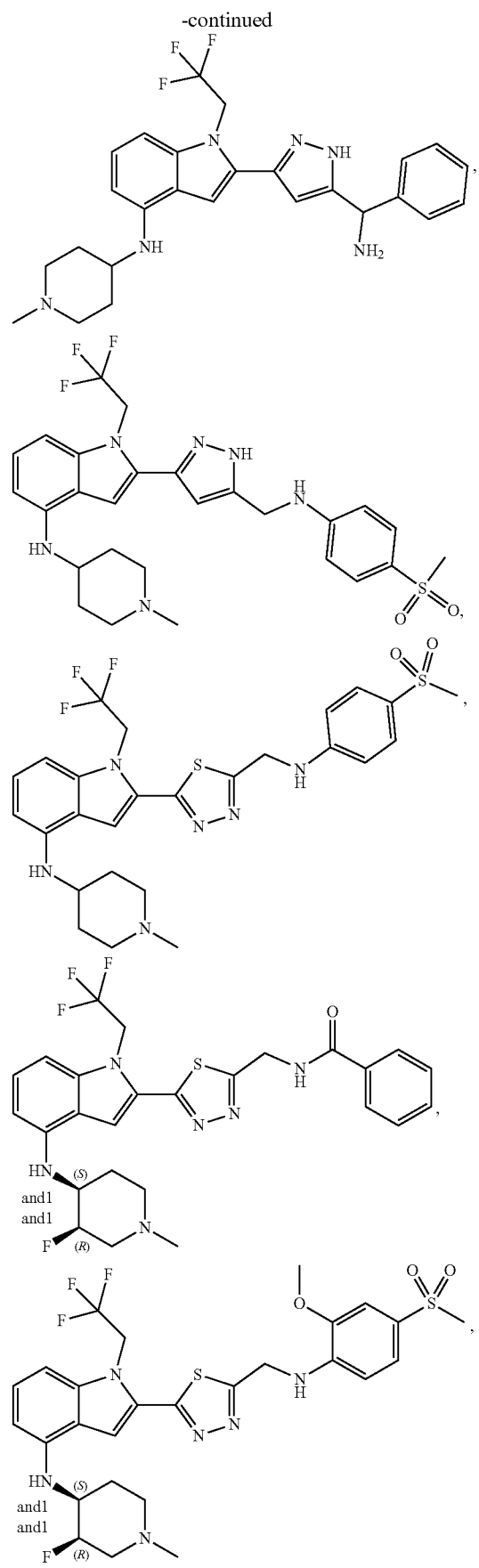

-continued
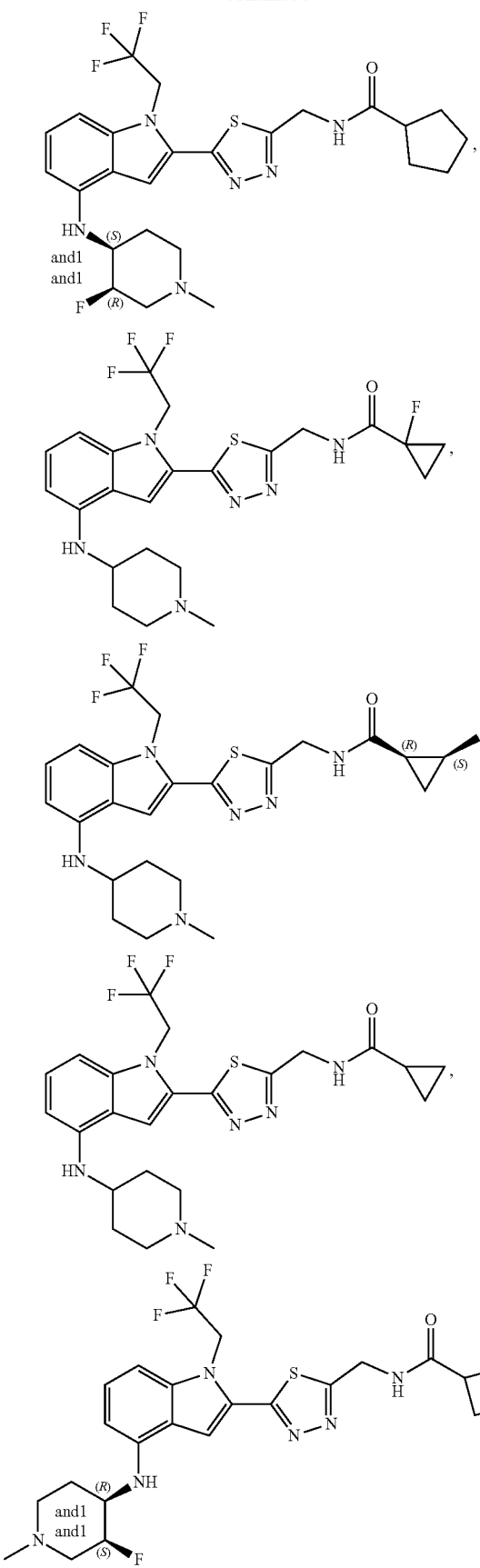
-continued
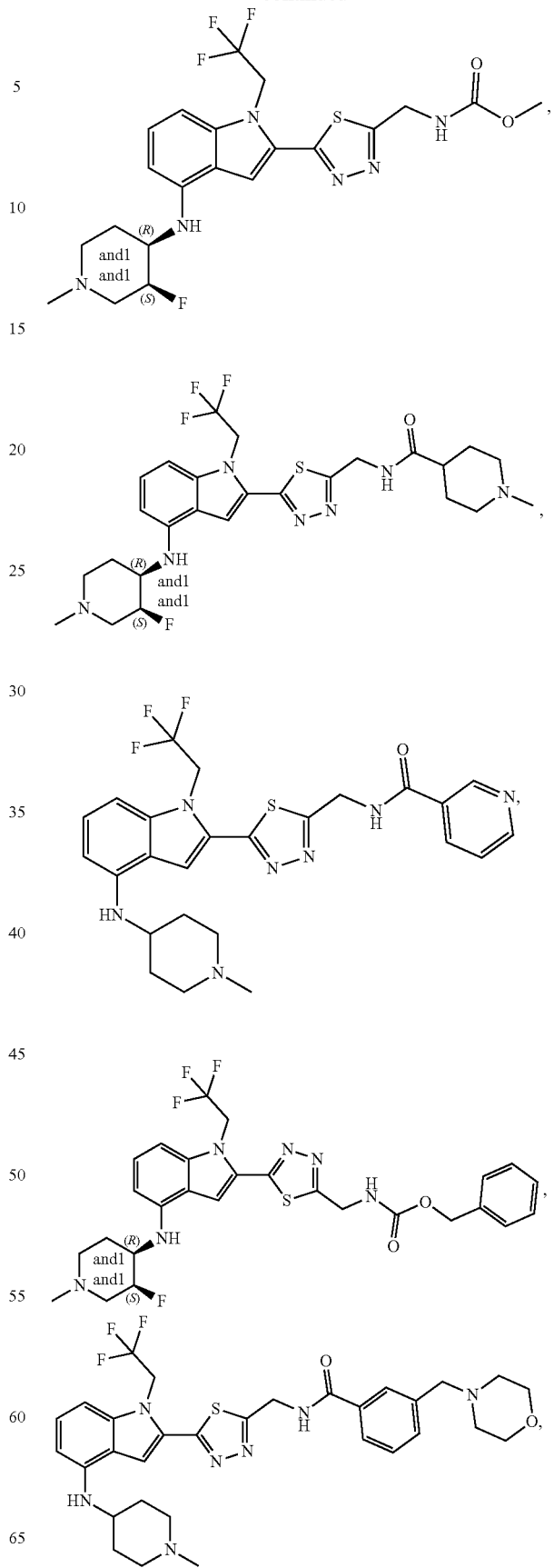

-continued

83
-continued
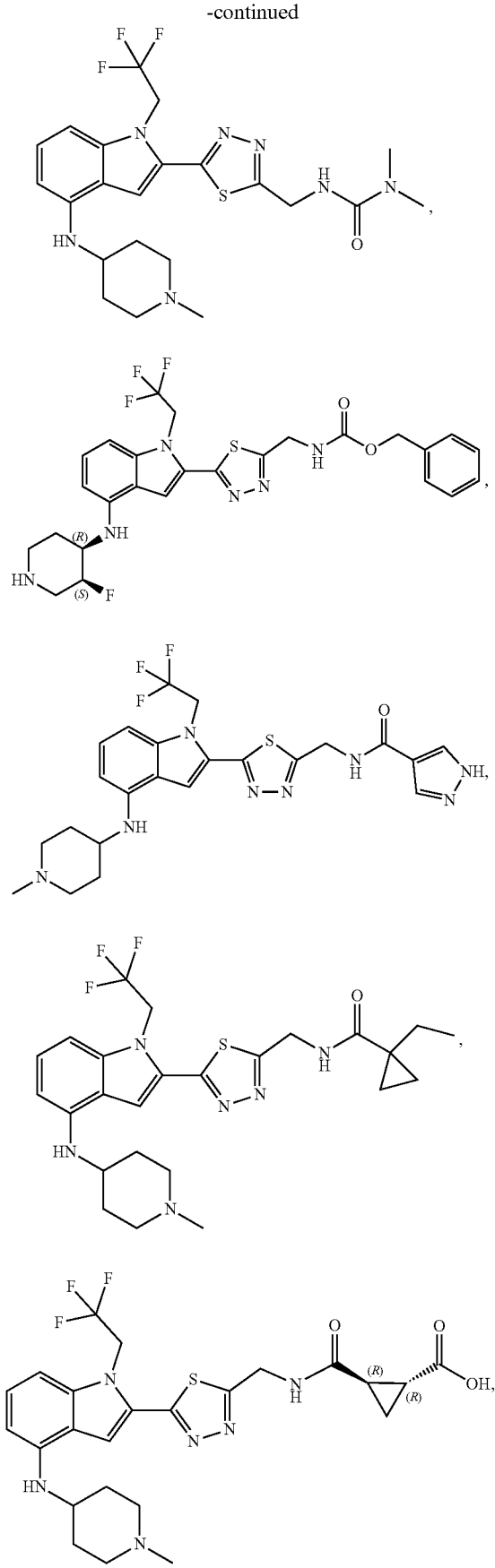
84
-continued
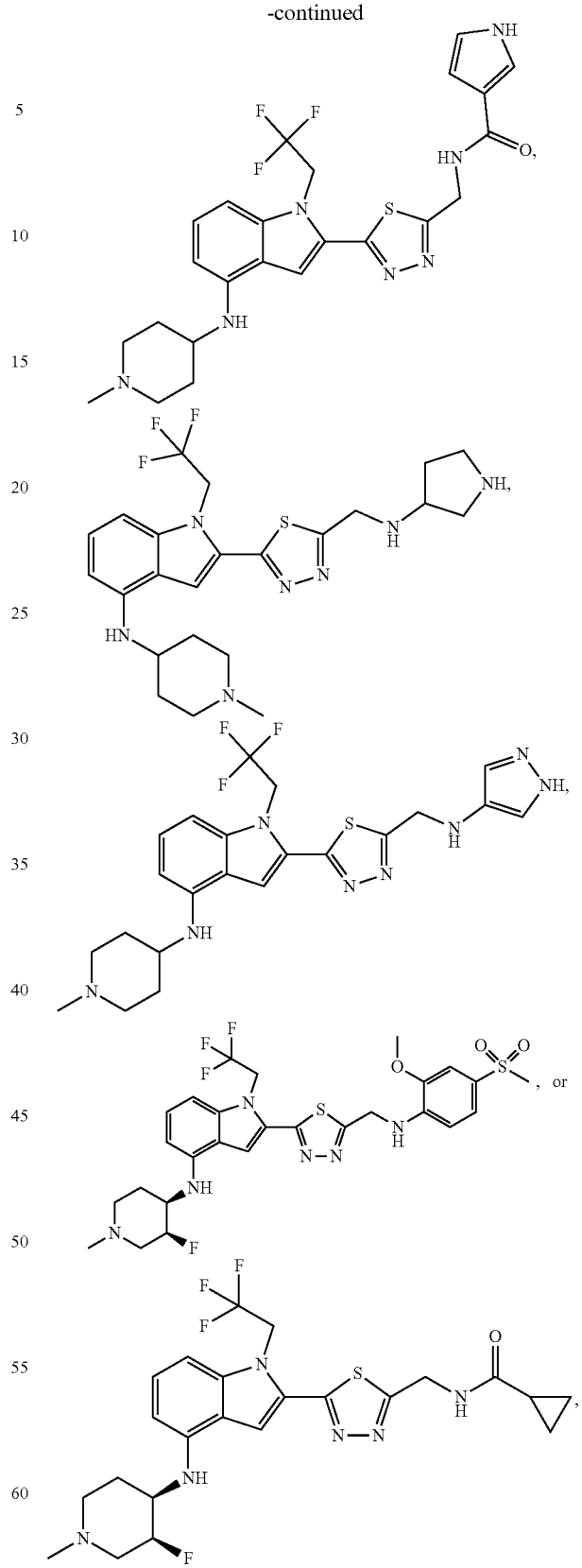
or a pharmaceutically-acceptable salt thereof.
Non-limiting examples of compounds of the disclosure include compounds of any of the following formulae:

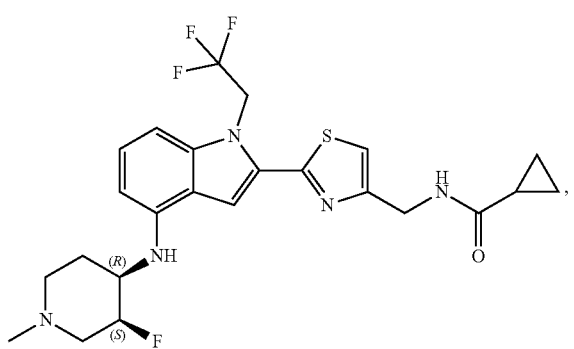
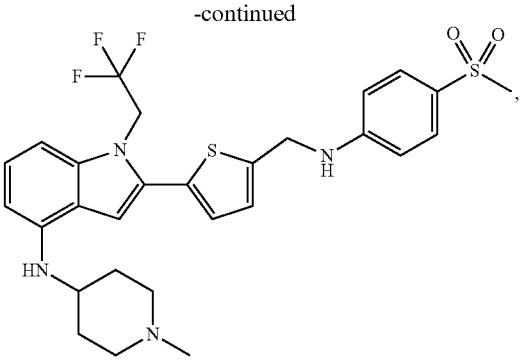
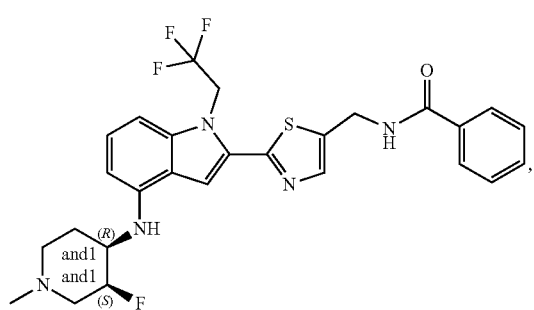
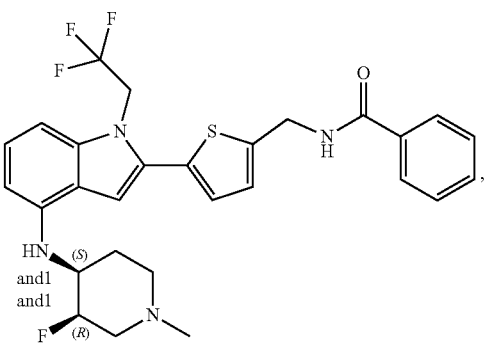
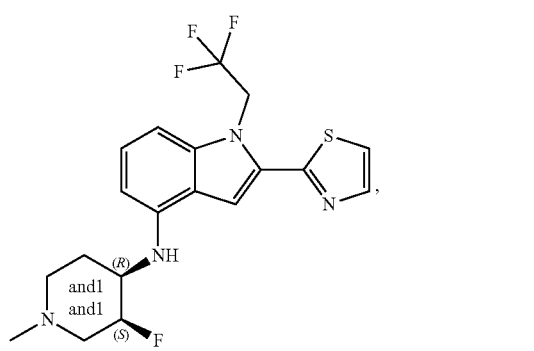
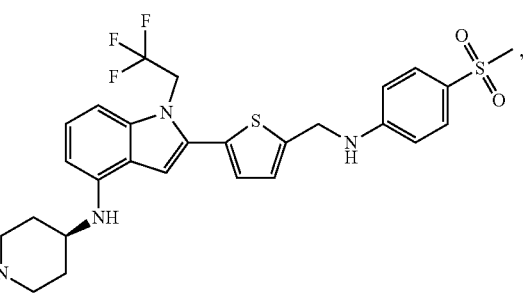
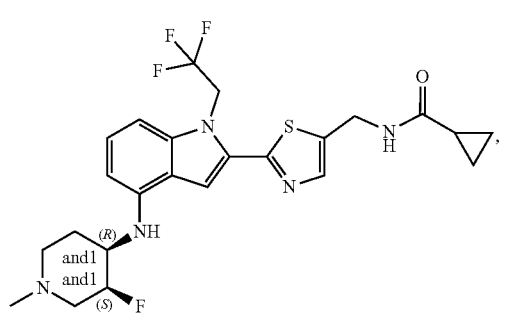
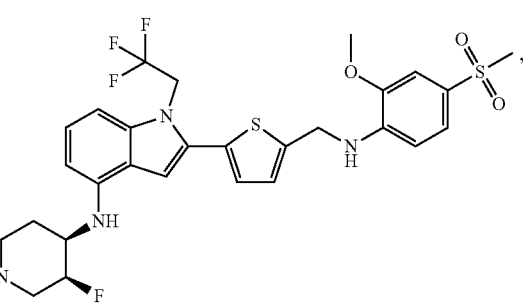
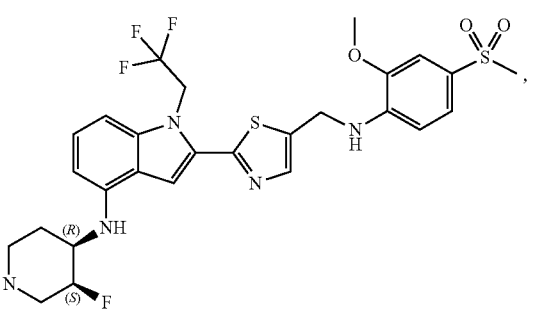
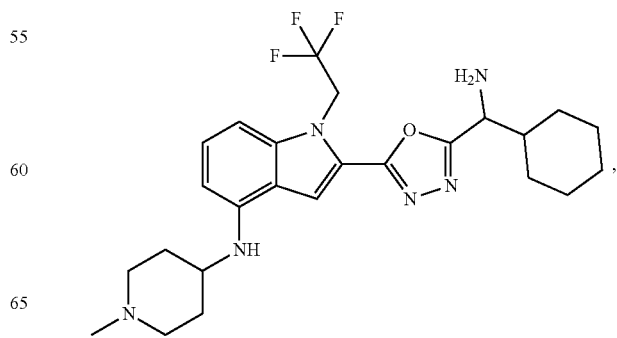

87
-continued
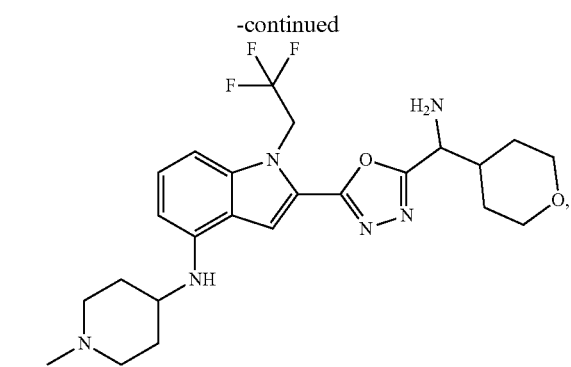
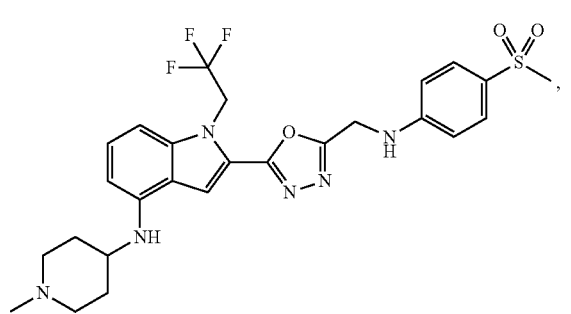
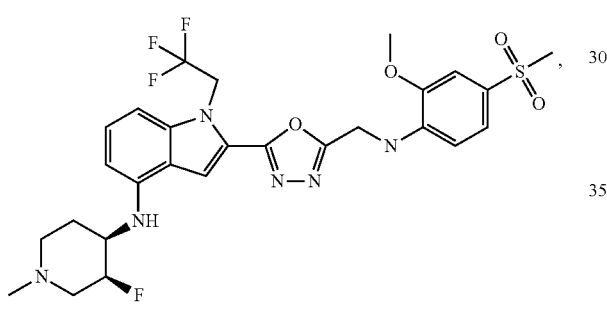
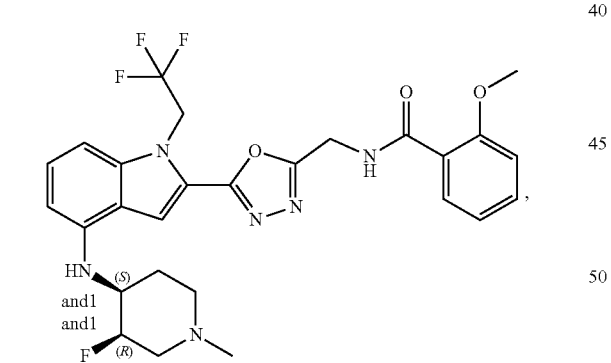
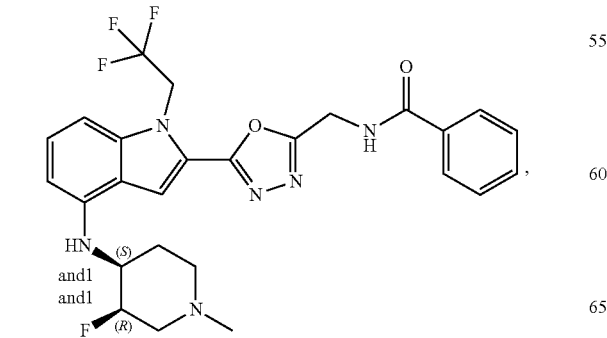
88
-continued
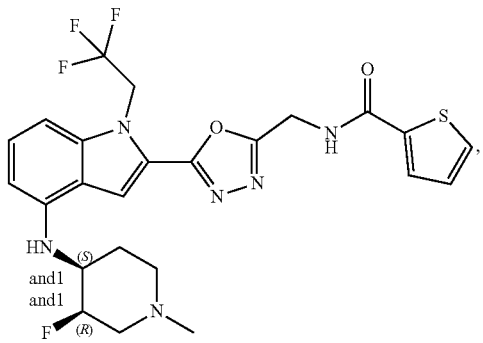
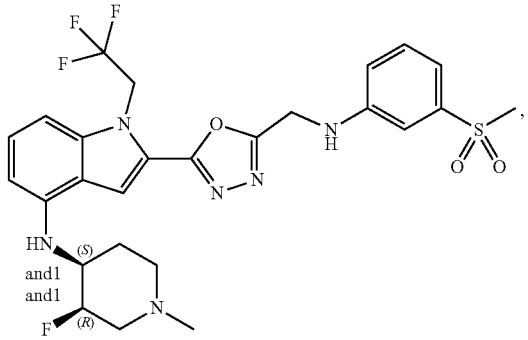
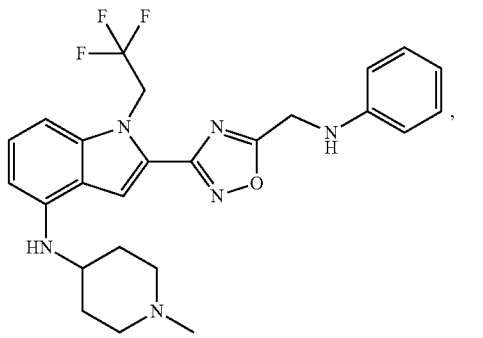
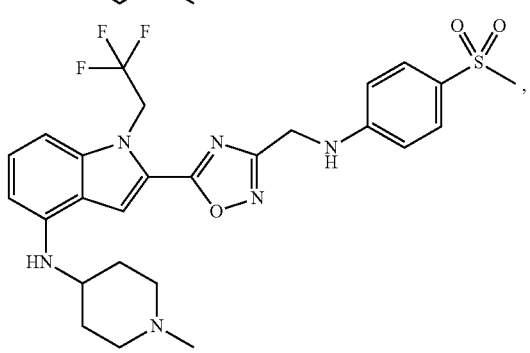
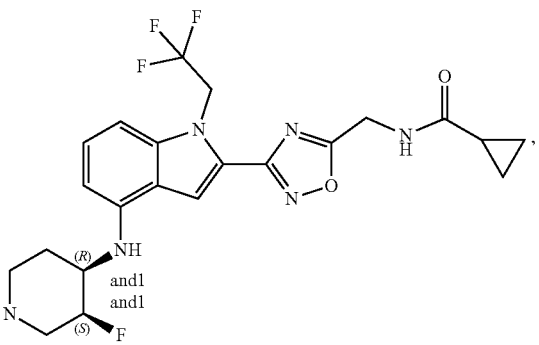

89
-continued
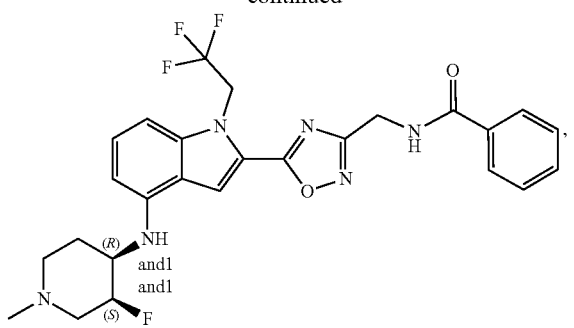
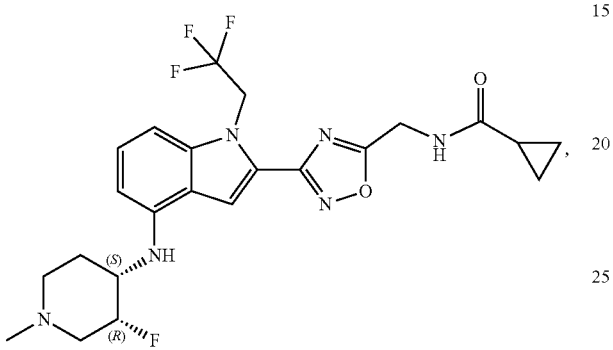
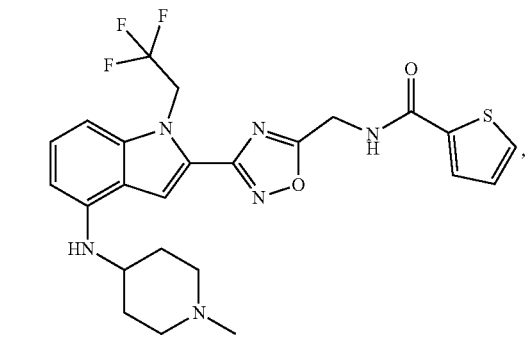
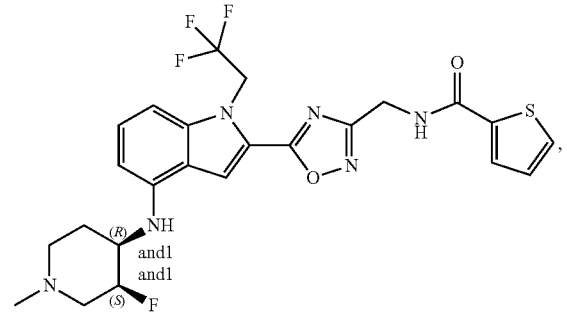
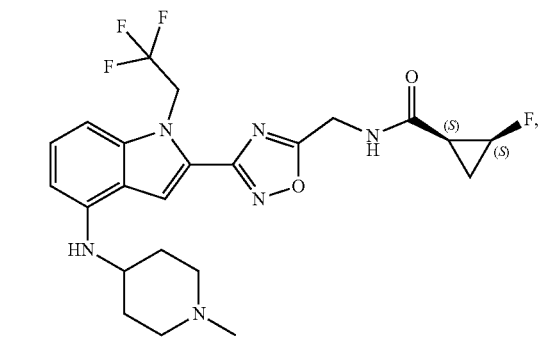
90
-continued
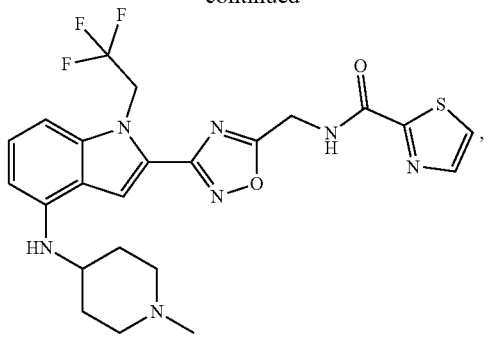
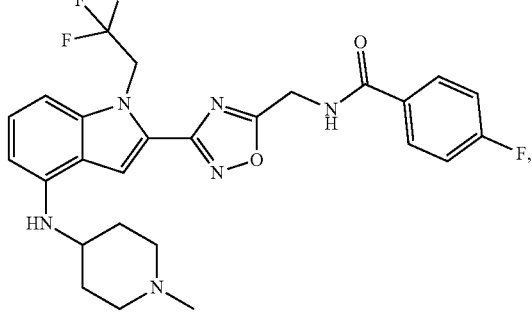
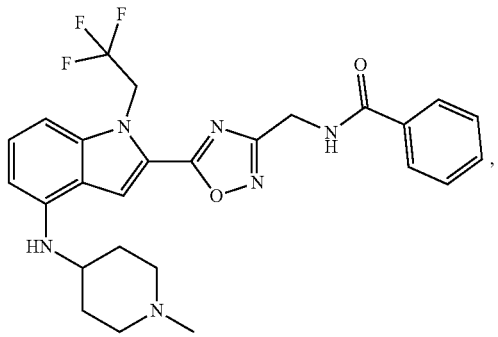
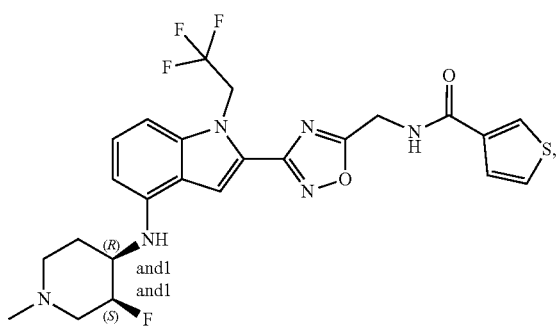
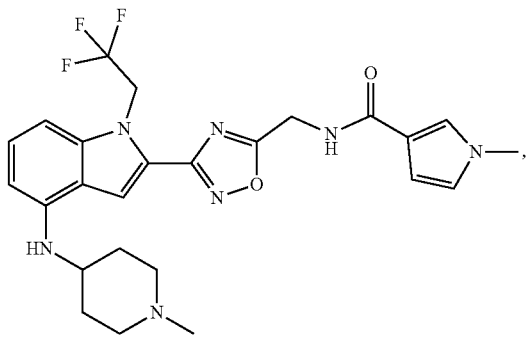

91
-continued
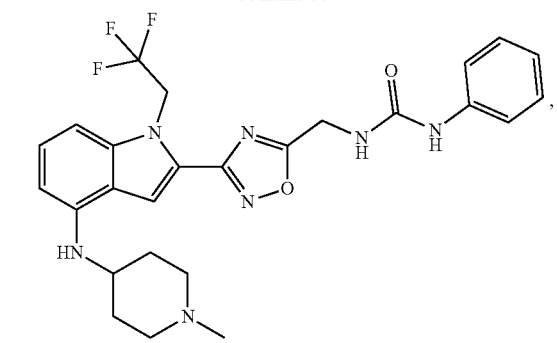
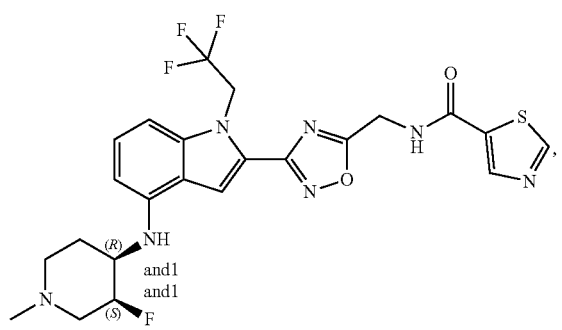
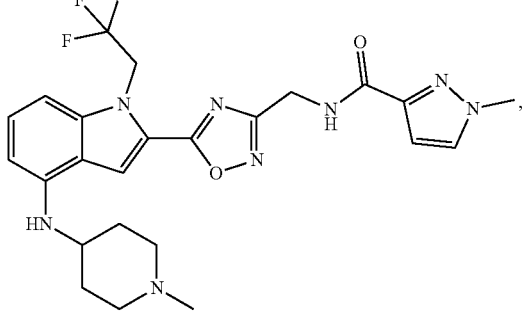
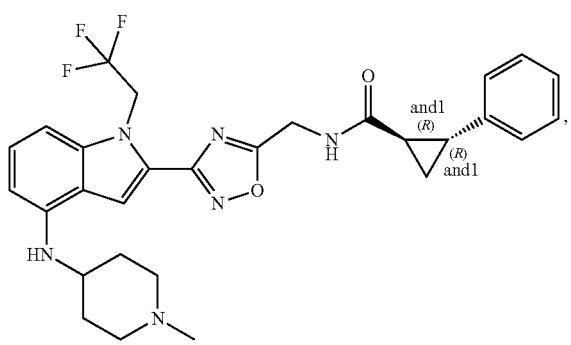
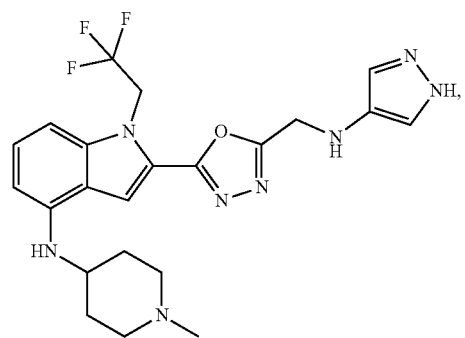
92
-continued
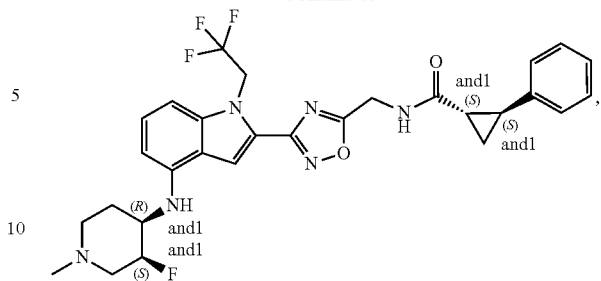
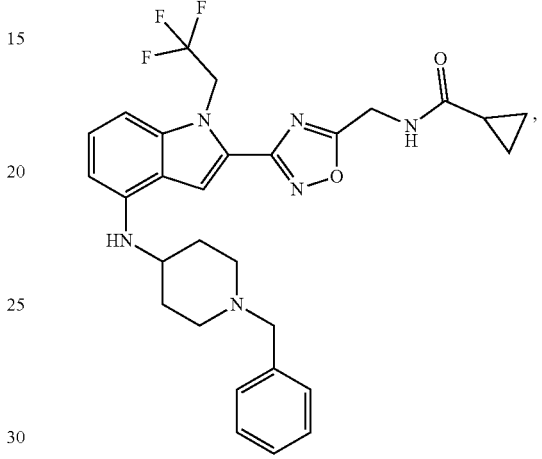
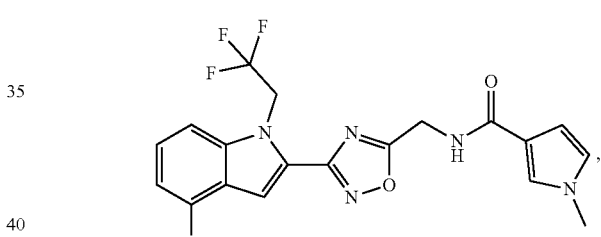
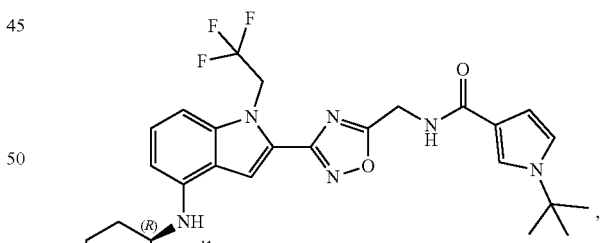
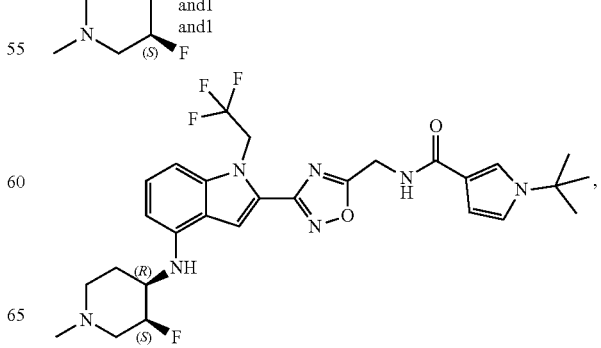

93
-continued
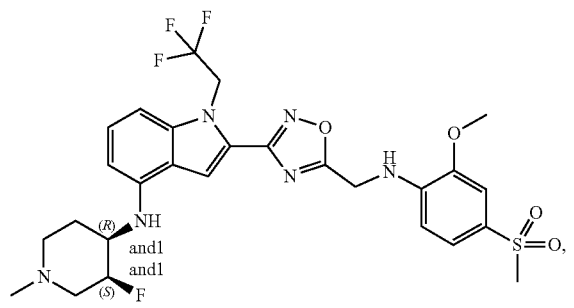
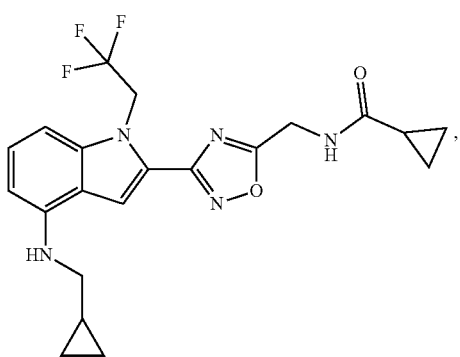
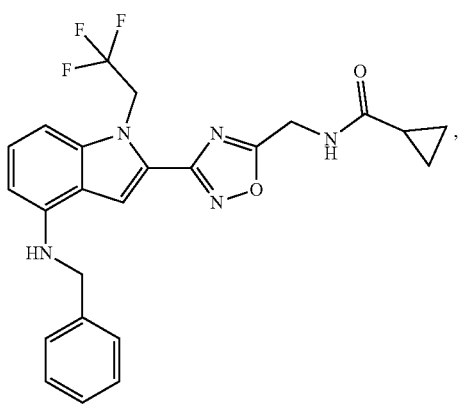
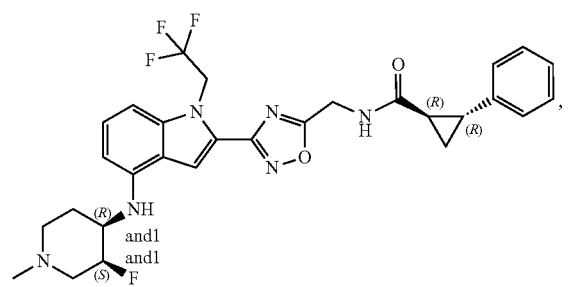
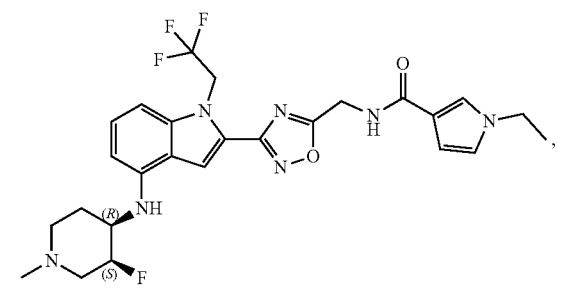
94
-continued
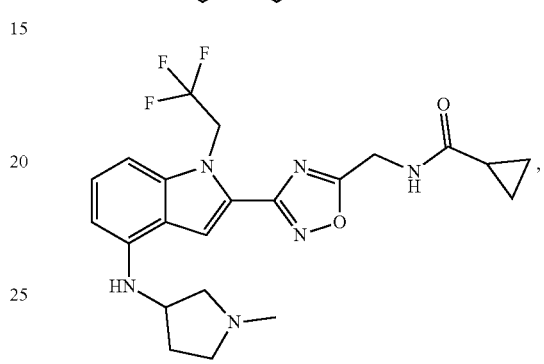
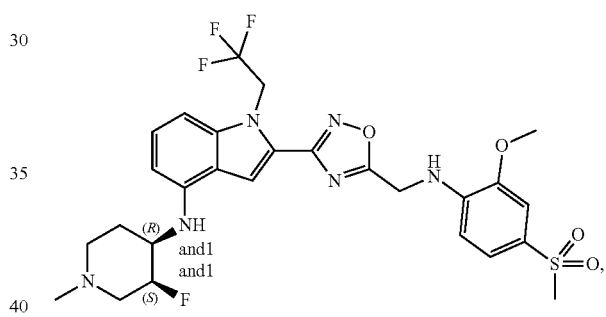
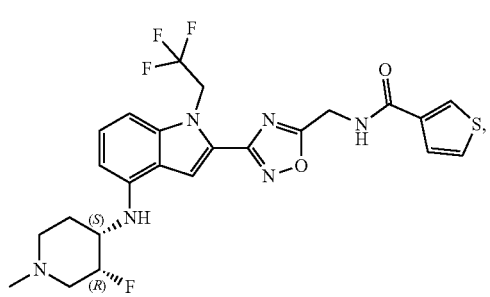
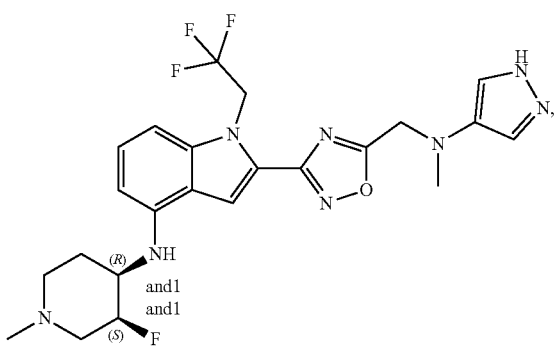

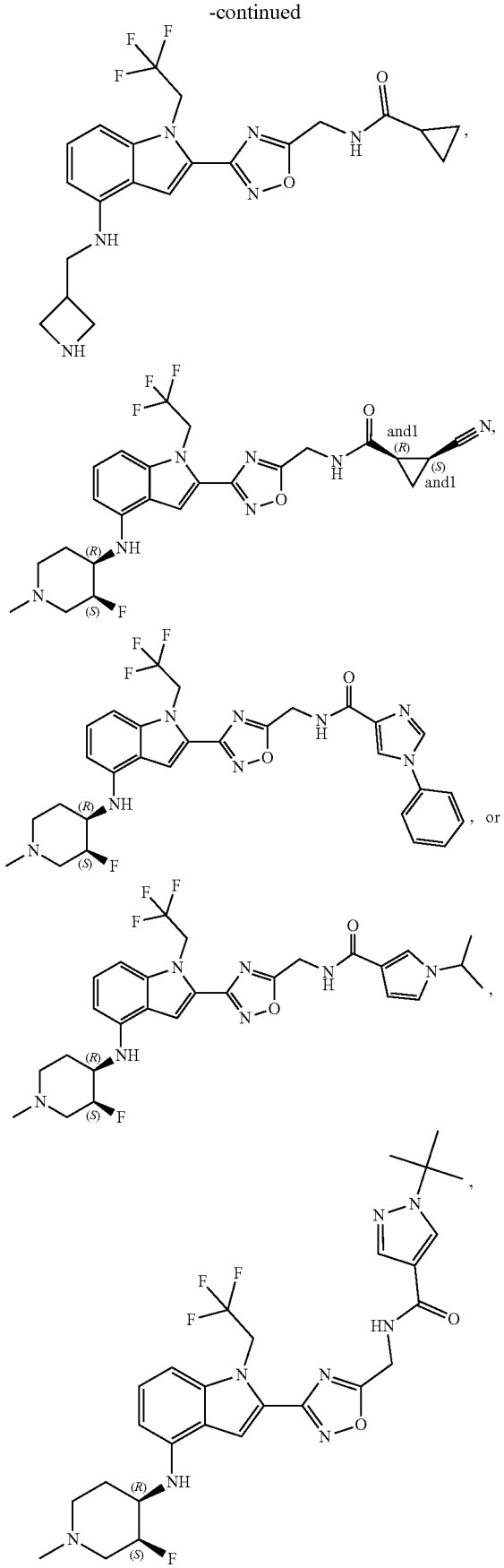

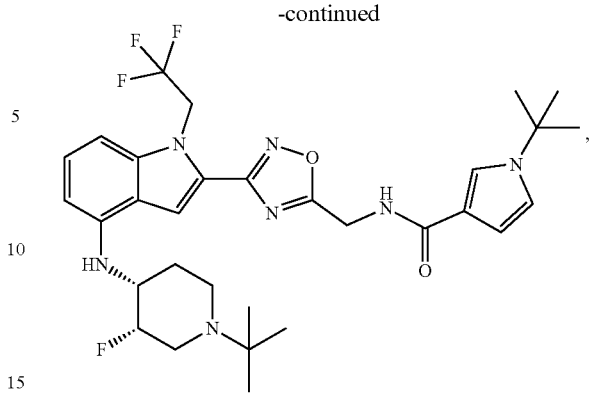

or a pharmaceutically-acceptable salt thereof.

Compounds herein can include all stereoisomers, enantiomers, diastereomers, mixtures, racemates, atropisomers, and tautomers thereof.

Non-limiting examples of optional substituents include a hydroxyl group, sulfhydryl group, halogen, amino group, nitro group, nitroso group, cyano group, azido group, sulfoxide group, sulfone group, sulfonamide group, carboxyl group, carboxaldehyde group, imine group, alkyl group, halo-alkyl group, alkenyl group, halo-alkenyl group, alkynyl group, halo-alkynyl group, alkoxy group, aryl group, aryloxy group, aralkyl group, arylalkoxy group, heterocyclyl group, acyl group, acyloxy group, carbamate group, amide group, ureido group, epoxy group, and ester group.

Non-limiting examples of alkyl and alkylene groups include straight, branched, and cyclic alkyl and alkylene groups. An alkyl or alkylene group can be, for example, a $C_1$, $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ group that is substituted or unsubstituted.

Non-limiting examples of straight alkyl groups include methyl, ethyl, propyl, butyl, pentyl, hexyl, heptyl, octyl, nonyl, and decyl.

Branched alkyl groups include any straight alkyl group substituted with any number of alkyl groups. Non-limiting examples of branched alkyl groups include isopropyl, isobutyl, sec-butyl, and t-butyl.

Non-limiting examples of substituted alkyl groups includes hydroxymethyl, chloromethyl, trifluoromethyl, trifluoroethyl, aminomethyl, 1-chloroethyl, 2-hydroxyethyl, 1,2-difluoroethyl, and 3-carboxypropyl.

Non-limiting examples of cyclic alkyl groups include cyclopropyl, cyclobutyl, cyclopentyl, cyclohexyl, cycloheptlyl, and cyclooctyl groups. Cyclic alkyl groups also include fused-, bridged-, and spiro-bicycles and higher fused-, bridged-, and spiro-systems. A cyclic alkyl group can be substituted with any number of straight, branched, or cyclic alkyl groups. Non-limiting examples of cyclic alkyl groups include cyclopropyl, 2-methyl-cycloprop-1-yl, cycloprop-2-en-1-yl, cyclobutyl, 2,3-dihydroxycyclobut-1-yl, cyclobut-2-en-1-yl, cyclopentyl, cyclopent-2-en-1-yl, cyclopenta-2,4-dien-1-yl, cyclohexyl, cyclohex-2-en-1-yl, cycloheptyl, cyclooctanyl, 2,5-dimethylcyclopent-1-yl, 3,5-dichlorocyclohex-1-yl, 4-hydroxycyclohex-1-yl, 3,3,5-trimethylcyclohex-1-yl, octahydropentalenyl, octahydro-1H-indenyl, 3a,4,5,6,7,7a-hexahydro-3H-inden-4-yl, decahydroazulenyl, bicyclo-[2.1.1]hexanyl, bicyclo[2.2.1]heptanyl, bicyclo

[3.1.1]heptanyl, 1,3-dimethyl[2.2.1]heptan-2-yl, bicyclo[2.2.2]octanyl, and bicyclo[3.3.3]undecanyl.

Non-limiting examples of alkenyl and alkenylene groups include straight, branched, and cyclic alkenyl groups. The olefin or olefins of an alkenyl group can be, for example, E, Z, cis, trans, terminal, or exo-methylene. An alkenyl or alkenylene group can be, for example, a $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C_{50}$ group that is substituted or unsubstituted. Non-limiting examples of alkenyl and alkenylene groups include ethenyl, prop-1-en-1-yl, isopropenyl, but-1-en-4-yl; 2-chloroethenyl, 4-hydroxybuten-1-yl, 7-hydroxy-7-methyloct-4-en-2-yl, and 7-hydroxy-7-methyloct-3,5-dien-2-yl.

Non-limiting examples of alkynyl or alkynylene groups include straight, branched, and cyclic alkynyl groups. The triple bond of an alkylnyl or alkynylene group can be internal or terminal. An alkylnyl or alkynylene group can be, for example, a $C_2$, $C_3$, $C_4$, $C_5$, $C_6$, $C_7$, $C_8$, $C_9$, $C_{10}$, $C_{11}$, $C_{12}$, $C_{13}$, $C_{14}$, $C_{15}$, $C_{16}$, $C_{17}$, $C_{18}$, $C_{19}$, $C_{20}$, $C_{21}$, $C_{22}$, $C_{23}$, $C_{24}$, $C_{25}$, $C_{26}$, $C_{27}$, $C_{28}$, $C_{29}$, $C_{30}$, $C_{31}$, $C_{32}$, $C_{33}$, $C_{34}$, $C_{35}$, $C_{36}$, $C_{37}$, $C_{38}$, $C_{39}$, $C_{40}$, $C_{41}$, $C_{42}$, $C_{43}$, $C_{44}$, $C_{45}$, $C_{46}$, $C_{47}$, $C_{48}$, $C_{49}$, or $C^{50}$ group that is substituted or unsubstituted. Non-limiting examples of alkynyl or alkynylene groups include ethynyl, prop-2-yn-1-yl, prop-1-yn-1-yl, and 2-methyl-hex-4-yn-1-yl; 5-hydroxy-5-methylhex-3-yn-1-yl, 6-hydroxy-6-methylhept-3-yn-2-yl, and 5-hydroxy-5-ethylhept-3-yn-1-yl.

A halo-alkyl group can be any alkyl group substituted with any number of halogen atoms, for example, fluorine, chlorine, bromine, and iodine atoms. A halo-alkenyl group can be any alkenyl group substituted with any number of halogen atoms. A halo-alkynyl group can be any alkynyl group substituted with any number of halogen atoms.

An alkoxy group can be, for example, an oxygen atom substituted with any alkyl, alkenyl, or alkynyl group. An ether or an ether group comprises an alkoxy group. Non-limiting examples of alkoxy groups include methoxy, ethoxy, propoxy, isopropoxy, and isobutoxy.

An aryl group can be heterocyclic or non-heterocyclic. An aryl group can be monocyclic or polycyclic. An aryl group can be substituted with any number of substituents described herein, for example, hydrocarbyl groups, alkyl groups, alkoxy groups, and halogen atoms. Non-limiting examples of aryl groups include phenyl, toluyl, naphthyl, pyrrolyl, pyridyl, imidazolyl, thiophenyl, and furyl. Non-limiting examples of substituted aryl groups include 3,4-dimethylphenyl, 4-tert-butylphenyl, 4-cyclopropylphenyl, 4-diethylaminophenyl, 4-(trifluoromethyl)phenyl, 4-(difluoromethoxy)-phenyl, 4-(trifluoromethoxy)phenyl, 3-chlorophenyl, 4-chlorophenyl, 3,4-dichlorophenyl, 2-fluorophenyl. 2-chlorophenyl, 2-iodophenyl, 3-iodophenyl, 4-iodophenyl, 2-methylphenyl, 3-fluorophenyl, 3-methylphenyl, 3-methoxyphenyl, 4-fluorophenyl, 4-methylphenyl, 4-methoxyphenyl, 2,3-difluorophenyl, 3,4-difluorophenyl, 3,5-difluorophenyl, 2,3-dichlorophenyl, 3,4-dichlorophenyl, 3,5-dichlorophenyl, 2-hydroxyphenyl, 3-hydroxyphenyl, 4-hydroxyphenyl, 2-methoxyphenyl, 3-methoxyphenyl, 4-methoxyphenyl, 2,3-dimethoxyphenyl, 3,4-dimethoxyphenyl, 3,5-dimethoxyphenyl, 2,4-difluorophenyl, 2,5-difluorophenyl, 2,6-difluorophenyl, 2,3,4-trifluorophenyl, 2,3,5-trifluorophenyl, 2,3,6-trifluorophenyl, 2,4,5-trifluorophenyl, 2,4,6-trifluorophenyl, 2,4-dichlorophenyl, 2,5-dichlorophenyl, 2,6-dichlorophenyl, 3,4-dichlorophenyl, 2,3,4-trichlorophenyl, 2,3,5-trichlorophenyl, 2,3,6-trichlorophenyl, 2,4,5-trichlorophenyl, 3,4,5-trichlorophenyl, 2,4,6-trichlorophenyl, 2,3-dimethylphenyl, 2,4-dimethylphenyl, 2,5-dimethylphenyl, 2,6-dimethylphenyl, 2,3,4-trimethylphenyl, 2,3,5-trimethylphenyl, 2,3,6-trimethylphenyl, 2,4,5-trimethylphenyl, 2,4,6-trimethylphenyl, 2-ethylphenyl, 3-ethylphenyl, 4-ethylphenyl, 2,3-diethylphenyl, 2,4-diethylphenyl, 2,5-diethylphenyl, 2,6-diethylphenyl, 3,4-diethylphenyl, 2,3,4-triethylphenyl, 2,3,5-triethylphenyl, 2,3,6-triethylphenyl, 2,4,5-triethylphenyl, 2,4,6-triethylphenyl, 2-isopropylphenyl, 3-isopropylphenyl, and 4-isopropylphenyl.

Non-limiting examples of substituted aryl groups include 2-aminophenyl, 2-(N-methylamino)phenyl, 2-(N,N-dimethylamino)phenyl, 2-(N-ethylamino)phenyl, 2-(N,N-diethylamino)phenyl, 3-aminophenyl, 3-(N-methylamino)phenyl, 3-(N,N-dimethylamino)phenyl, 3-(N-ethylamino)phenyl, 3-(N,N-diethylamino)phenyl, 4-aminophenyl, 4-(N-methylamino)phenyl, 4-(N,N-dimethylamino)phenyl, 4-(N-ethylamino)phenyl, and 4-(N,N-diethylamino)phenyl.

A heterocycle can be any ring containing a ring atom that is not carbon, for example, N, O, S, P, Si, B, or any other heteroatom. A heterocycle can be substituted with any number of substituents, for example, alkyl groups and halogen atoms. A heterocycle can be aromatic (heteroaryl) or non-aromatic. Non-limiting examples of heterocycles include pyrrole, pyrrolidine, pyridine, piperidine, succinamide, maleimide, morpholine, imidazole, thiophene, furan, tetrahydrofuran, pyran, and tetrahydropyran.

Non-limiting examples of heterocycles include: heterocyclic units having a single ring containing one or more heteroatoms, non-limiting examples of which include, diazirinyl, aziridinyl, azetidinyl, pyrazolidinyl, imidazolidinyl, oxazolidinyl, isoxazolinyl, thiazolidinyl, isothiazolinyl, oxathiazolidinonyl, oxazolidinonyl, hydantoinyl, tetrahydrofuranyl, pyrrolidinyl, morpholinyl, piperazinyl, piperidinyl, dihydropyranyl, tetrahydropyranyl, piperidin-2-onyl, 2,3,4,5-tetrahydro-1H-azepinyl, 2,3-dihydro-1H-indole, and 1,2,3,4-tetrahydroquinoline; and ii) heterocyclic units having 2 or more rings one of which is a heterocyclic ring, non-limiting examples of which include hexahydro-1H-pyrrolizinyl, 3a,4,5,6,7,7a-hexahydro-1H-benzo[d]imidazolyl, 3a,4,5,6,7,7a-hexahydro-1H-indolyl, 1,2,3,4-tetrahydroquinolinyl, and decahydro-1H-cycloocta[b]pyrrolyl.

Non-limiting examples of heteroaryl include: i) heteroaryl rings containing a single ring, non-limiting examples of which include, 1,2,3,4-tetrazolyl, [1,2,3]triazolyl, [1,2,4]triazolyl, triazinyl, thiazolyl, 1H-imidazolyl, oxazolyl, isoxazolyl, isothiazolyl, furanyl, thiophenyl, pyrimidinyl, 2-phenylpyrimidinyl, pyridinyl, 3-methylpyridinyl, and 4-dimethylaminopyridinyl; and ii) heteroaryl rings containing 2 or more fused rings one of which is a heteroaryl ring, non-limiting examples of which include: 7H-purinyl, 9H-purinyl, 6-amino-9H-purinyl, 5H-pyrrolo[3,2-d]pyrimidinyl, 7H-pyrrolo[2,3-d]pyrimidinyl, pyrido[2,3-d]pyrimidinyl, 4,5,6,7-tetrahydro-1-H-indolyl, quinoxalinyl, quinazolinyl, quinolinyl, 8-hydroxy-quinolinyl, and isoquinolinyl.

Any compound herein can be purified. A compound herein can be least 1% pure, at least 2% pure, at least 3% pure, at least 4% pure, at least 5% pure, at least 6% pure, at least 7% pure, at least 8% pure, at least 9% pure, at least 10% pure, at least 11% pure, at least 12% pure, at least 13% pure, at least 14% pure, at least 15% pure, at least 16% pure, at least 17% pure, at least 18% pure, at least 19% pure, at least 20% pure, at least 21% pure, at least 22% pure, at least 23% pure, at least 24% pure, at least 25% pure, at least 26% pure, at least 27% pure, at least 28% pure, at least 29% pure, at least 30% pure, at least 31% pure, at least 32% pure, at least 33% pure, at least 34% pure, at least 35% pure, at least 36% pure, at least 37% pure, at least 38% pure, at least 39% pure, at least 40% pure, at least 41% pure, at least 42% pure, at least 43% pure, at least 44% pure, at least 45% pure, at least 46% pure, at least 47% pure, at least 48% pure, at least 49% pure, at least 50% pure, at least 51% pure, at least 52% pure, at least 53% pure, at least 54% pure, at least 55% pure, at least 56% pure, at least 57% pure, at least 58% pure, at least 59% pure, at least 60% pure, at least 61% pure, at least 62% pure, at least 63% pure, at least 64% pure, at least 65% pure, at least 66% pure, at least 67% pure, at least 68% pure, at least 69% pure, at least 70% pure, at least 71% pure, at least 72% pure, at least 73% pure, at least 74% pure, at least 75% pure, at least 76% pure, at least 77% pure, at least 78% pure, at least 79% pure, at least 80% pure, at least 81% pure, at least 82% pure, at least 83% pure, at least 84% pure, at least 85% pure, at least 86% pure, at least 87% pure, at least 88% pure, at least 89% pure, at least 90% pure, at least 91% pure, at least 92% pure, at least 93% pure, at least 94% pure, at least 95% pure, at least 96% pure, at least 97% pure, at least 98% pure, at least 99% pure, at least 99.1% pure, at least 99.2% pure, at least 99.3% pure, at least 99.4% pure, at least 99.5% pure, at least 99.6% pure, at least 99.7% pure, at least 99.8% pure, or at least 99.9% pure.

In some embodiments, compounds of the disclosure can be used to treat cancer in a subject. A compound of the disclosure can, for example, slow the proliferation of cancer cell lines, or kill cancer cells. Non-limiting examples of cancer that can be treated by a compound of the disclosure include: acute lymphoblastic leukemia, acute myeloid leukemia, adrenocortical carcinoma, AIDS-related cancers, AIDS-related lymphoma, anal cancer, appendix cancer, astrocytomas, basal cell carcinoma, bile duct cancer, bladder cancer, bone cancers, brain tumors, such as cerebellar astrocytoma, cerebral astrocytoma/malignant glioma, ependymoma, medulloblastoma, supratentorial primitive neuroectodermal tumors, visual pathway and hypothalamic glioma, breast cancer, bronchial adenomas, Burkitt lymphoma, carcinoma of unknown primary origin, central nervous system lymphoma, cerebellar astrocytoma, cervical cancer, childhood cancers, chronic lymphocytic leukemia, chronic myelogenous leukemia, chronic myeloproliferative disorders, colon cancer, cutaneous T-cell lymphoma, desmoplastic small round cell tumor, endometrial cancer, ependymoma, esophageal cancer, Ewing's sarcoma, germ cell tumors, gallbladder cancer, gastric cancer, gastrointestinal carcinoid tumor, gastrointestinal stromal tumor, gliomas, hairy cell leukemia, head and neck cancer, heart cancer, hepatocellular (liver) cancer, Hodgkin lymphoma, Hypopharyngeal cancer, intraocular melanoma, islet cell carcinoma, Kaposi sarcoma, kidney cancer, laryngeal cancer, lip and oral cavity cancer, liposarcoma, liver cancer, lung cancers, such as non-small cell and small cell lung cancer, lymphomas, leukemias, macroglobulinemia, malignant fibrous histiocytoma of bone/osteosarcoma, medulloblastoma, melanomas, mesothelioma, metastatic squamous neck cancer with occult primary, mouth cancer, multiple endocrine neoplasia syndrome, myelodysplastic syndromes, myeloid leukemia, nasal cavity and paranasal sinus cancer, nasopharyngeal carcinoma, neuroblastoma, non-Hodgkin lymphoma, non-small cell lung cancer, oral cancer, oropharyngeal cancer, osteosarcoma/malignant fibrous histiocytoma of bone, ovarian cancer, ovarian epithelial cancer, ovarian germ cell tumor, pancreatic cancer, pancreatic cancer islet cell, paranasal sinus and nasal cavity cancer, parathyroid cancer, penile cancer, pharyngeal cancer, pheochromocytoma, pineal astrocytoma, pineal germinoma, pituitary adenoma, pleuropulmonary blastoma, plasma cell neoplasia, primary central nervous system lymphoma, prostate cancer, rectal cancer, renal cell carcinoma, renal pelvis and ureter transitional cell cancer, retinoblastoma, rhabdomyosarcoma, salivary gland cancer, sarcomas, skin cancers, skin carcinoma merkel cell, small intestine cancer, soft tissue sarcoma, squamous cell carcinoma, stomach cancer, T-cell lymphoma, throat cancer, thymoma, thymic carcinoma, thyroid cancer, trophoblastic tumor (gestational), cancers of unknown primary site, urethral cancer, uterine sarcoma, vaginal cancer, vulvar cancer, Waldenström macroglobulinemia, and Wilms tumor.

In some embodiments, the compounds of the disclosure show non-lethal toxicity.

Pharmaceutically-Acceptable Salts.

The disclosure provides the use of pharmaceutically-acceptable salts of any therapeutic compound described herein. Pharmaceutically-acceptable salts include, for example, acid-addition salts and base-addition salts. The acid that is added to the compound to form an acid-addition salt can be an organic acid or an inorganic acid. A base that is added to the compound to form a base-addition salt can be an organic base or an inorganic base. In some embodiments, a pharmaceutically-acceptable salt is a metal salt. In some embodiments, a pharmaceutically-acceptable salt is an ammonium salt.

Metal salts can arise from the addition of an inorganic base to a compound of the disclosure. The inorganic base consists of a metal cation paired with a basic counterion, such as, for example, hydroxide, carbonate, bicarbonate, or phosphate. The metal can be an alkali metal, alkaline earth metal, transition metal, or main group metal. In some embodiments, the metal is lithium, sodium, potassium, cesium, cerium, magnesium, manganese, iron, calcium, strontium, cobalt, titanium, aluminum, copper, cadmium, or zinc.

In some embodiments, a metal salt is a lithium salt, a sodium salt, a potassium salt, a cesium salt, a cerium salt, a magnesium salt, a manganese salt, an iron salt, a calcium salt, a strontium salt, a cobalt salt, a titanium salt, an aluminum salt, a copper salt, a cadmium salt, or a zinc salt.

Ammonium salts can arise from the addition of ammonia or an organic amine to a compound of the disclosure. In some embodiments, the organic amine is triethyl amine, diisopropyl amine, ethanol amine, diethanol amine, triethanol amine, morpholine, N-methylmorpholine, piperidine, N-methylpiperidine, N-ethylpiperidine, dibenzylamine, piperazine, pyridine, pyrrazole, pipyrrazole, imidazole, pyrazine, or pipyrazine.

In some embodiments, an ammonium salt is a triethyl amine salt, a diisopropyl amine salt, an ethanol amine salt, a diethanol amine salt, a triethanol amine salt, a morpholine salt, an N-methylmorpholine salt, a piperidine salt, an N-methylpiperidine salt, an N-ethylpiperidine salt, a dibenzylamine salt, a piperazine salt, a pyridine salt, a pyrrazole salt, a pipyrrazole salt, an imidazole salt, a pyrazine salt, or a pipyrazine salt.

Acid addition salts can arise from the addition of an acid to a compound of the disclosure. In some embodiments, the acid is organic. In some embodiments, the acid is inorganic. In some embodiments, the acid is hydrochloric acid, hydrobromic acid, hydroiodic acid, nitric acid, nitrous acid, sulfuric acid, sulfurous acid, a phosphoric acid, isonicotinic acid, lactic acid, salicylic acid, tartaric acid, ascorbic acid, gentisinic acid, gluconic acid, glucaronic acid, saccaric acid, formic acid, benzoic acid, glutamic acid, pantothenic acid, acetic acid, propionic acid, butyric acid, fumaric acid, succinic acid, methanesulfonic acid, ethanesulfonic acid, benzenesulfonic acid, p-toluenesulfonic acid, citric acid, oxalic acid, or maleic acid.

In some embodiments, the salt is a hydrochloride salt, a hydrobromide salt, a hydroiodide salt, a nitrate salt, a nitrite salt, a sulfate salt, a sulfite salt, a phosphate salt, isonicotinate salt, a lactate salt, a salicylate salt, a tartrate salt, an ascorbate salt, a gentisinate salt, a gluconate salt, a glucaronate salt, a saccarate salt, a formate salt, a benzoate salt, a glutamate salt, a pantothenate salt, an acetate salt, a propionate salt, a butyrate salt, a fumarate salt, a succinate salt, a methanesulfonate (mesylate) salt, an ethanesulfonate salt, a benzenesulfonate salt, a p-toluenesulfonate salt, a citrate salt, an oxalate salt, or a maleate salt.

Pharmaceutical Compositions of the Disclosure.

A pharmaceutical composition of the disclosure can be used, for example, before, during, or after treatment of a subject with, for example, another pharmaceutical agent.

Subjects can be, for example, elderly adults, adults, adolescents, pre-adolescents, children, toddlers, infants, neonates, and non-human animals. In some embodiments, a subject is a patient.

A pharmaceutical composition of the disclosure can be a combination of any pharmaceutical compounds described herein with other chemical components, such as carriers, stabilizers, diluents, dispersing agents, suspending agents, thickening agents, and/or excipients. The pharmaceutical composition facilitates administration of the compound to an organism. Pharmaceutical compositions can be administered in therapeutically-effective amounts as pharmaceutical compositions by various forms and routes including, for example, intravenous, subcutaneous, intramuscular, oral, parenteral, ophthalmic, subcutaneous, transdermal, nasal, vaginal, and topical administration.

A pharmaceutical composition can be administered in a local manner, for example, via injection of the compound directly into an organ, optionally in a depot or sustained release formulation or implant. Pharmaceutical compositions can be provided in the form of a rapid release formulation, in the form of an extended release formulation, or in the form of an intermediate release formulation. A rapid release form can provide an immediate release. An extended release formulation can provide a controlled release or a sustained delayed release.

For oral administration, pharmaceutical compositions can be formulated by combining the active compounds with pharmaceutically-acceptable carriers or excipients. Such carriers can be used to formulate liquids, gels, syrups, elixirs, slurries, or suspensions, for oral ingestion by a subject. Non-limiting examples of solvents used in an oral dissolvable formulation can include water, ethanol, isopropanol, saline, physiological saline, DMSO, dimethylformamide, potassium phosphate buffer, phosphate buffer saline (PBS), sodium phosphate buffer, 4-2-hydroxyethyl-1-piperazineethanesulfonic acid buffer (HEPES), 3-(N-morpholino)propanesulfonic acid buffer (MOPS), piperazine-N,N'-bis(2-ethanesulfonic acid) buffer (PIPES), and saline sodium citrate buffer (SSC). Non-limiting examples of co-solvents used in an oral dissolvable formulation can include sucrose, urea, cremaphor, DMSO, and potassium phosphate buffer.

Pharmaceutical preparations can be formulated for intravenous administration. The pharmaceutical compositions can be in a form suitable for parenteral injection as a sterile suspension, solution or emulsion in oily or aqueous vehicles, and can contain formulatory agents such as suspending, stabilizing and/or dispersing agents. Pharmaceutical formulations for parenteral administration include aqueous solutions of the active compounds in water-soluble form. Suspensions of the active compounds can be prepared as oily injection suspensions. Suitable lipophilic solvents or vehicles include fatty oils such as sesame oil, or synthetic fatty acid esters, such as ethyl oleate or triglycerides, or liposomes. The suspension can also contain suitable stabilizers or agents which increase the solubility of the compounds to allow for the preparation of highly concentrated solutions. Alternatively, the active ingredient can be in powder form for constitution with a suitable vehicle, e.g., sterile pyrogen-free water, before use.

The active compounds can be administered topically and can be formulated into a variety of topically administrable compositions, such as solutions, suspensions, lotions, gels, pastes, medicated sticks, balms, creams, and ointments. Such pharmaceutical compositions can contain solubilizers, stabilizers, tonicity enhancing agents, buffers and preservatives.

The compounds of the disclosure can be applied topically to the skin, or a body cavity, for example, oral, vaginal, bladder, cranial, spinal, thoracic, or pelvic cavity of a subject. The compounds of the disclosure can be applied to an accessible body cavity.

The compounds can also be formulated in rectal compositions such as enemas, rectal gels, rectal foams, rectal aerosols, suppositories, jelly suppositories, or retention enemas, containing conventional suppository bases such as cocoa butter or other glycerides, as well as synthetic polymers such as polyvinylpyrrolidone, and PEG. In suppository forms of the compositions, a low-melting wax such as a mixture of fatty acid glycerides, optionally in combination with cocoa butter, can be melted.

In practicing the methods of treatment or use provided herein, therapeutically-effective amounts of the compounds described herein are administered in pharmaceutical compositions to a subject having a disease or condition to be treated. In some embodiments, the subject is a mammal such as a human. A therapeutically-effective amount can vary widely depending on the severity of the disease, the age and relative health of the subject, the potency of the compounds used, and other factors. The compounds can be used singly or in combination with one or more therapeutic agents as components of mixtures.

Pharmaceutical compositions can be formulated using one or more physiologically-acceptable carriers comprising excipients and auxiliaries, which facilitate processing of the active compounds into preparations that can be used pharmaceutically. Formulations can be modified depending upon the route of administration chosen. Pharmaceutical compositions comprising a compound described herein can be manufactured, for example, by mixing, dissolving, emulsifying, encapsulating, entrapping, or compression processes.

The pharmaceutical compositions can include at least one pharmaceutically-acceptable carrier, diluent, or excipient and compounds described herein as free-base or pharmaceutically-acceptable salt form. Pharmaceutical compositions can contain solubilizers, stabilizers, tonicity enhancing agents, buffers and preservatives.

Methods for the preparation of compositions comprising the compounds described herein include formulating the compounds with one or more inert, pharmaceutically-acceptable excipients or carriers to form a solid, semi-solid, or liquid composition. Solid compositions include, for example, powders, tablets, dispersible granules, capsules, and cachets. Liquid compositions include, for example, solutions in which a compound is dissolved, emulsions comprising a compound, or a solution containing liposomes, micelles, or nanoparticles comprising a compound as disclosed herein. Semi-solid compositions include, for example, gels, suspensions and creams. The compositions can be in liquid solutions or suspensions, solid forms suitable for solution or suspension in a liquid prior to use, or as emulsions. These compositions can also contain minor amounts of nontoxic, auxiliary substances, such as wetting or emulsifying agents, pH buffering agents, and other pharmaceutically-acceptable additives.

Non-limiting examples of dosage forms suitable for use in the disclosure include liquid, powder, gel, nanosuspension, nanoparticle, microgel, aqueous or oily suspensions, emulsion, and any combination thereof.

Non-limiting examples of pharmaceutically-acceptable excipients suitable for use in the disclosure include binding agents, disintegrating agents, anti-adherents, anti-static agents, surfactants, anti-oxidants, coating agents, coloring agents, plasticizers, preservatives, suspending agents, emulsifying agents, anti-microbial agents, spheronization agents, and any combination thereof.

A composition of the disclosure can be, for example, an immediate release form or a controlled release formulation. An immediate release formulation can be formulated to allow the compounds to act rapidly. Non-limiting examples of immediate release formulations include readily dissolvable formulations. A controlled release formulation can be a pharmaceutical formulation that has been adapted such that release rates and release profiles of the active agent can be matched to physiological and chronotherapeutic requirements or, alternatively, has been formulated to effect release of an active agent at a programmed rate. Non-limiting examples of controlled release formulations include granules, delayed release granules, hydrogels (e.g., of synthetic or natural origin), other gelling agents (e.g., gel-forming dietary fibers), matrix-based formulations (e.g., formulations comprising a polymeric material having at least one active ingredient dispersed through), granules within a matrix, polymeric mixtures, and granular masses.

In some, a controlled release formulation is a delayed release form. A delayed release form can be formulated to delay a compound's action for an extended period of time. A delayed release form can be formulated to delay the release of an effective dose of one or more compounds, for example, for about 4, about 8, about 12, about 16, or about 24 hours.

A controlled release formulation can be a sustained release form. A sustained release form can be formulated to sustain, for example, the compound's action over an extended period of time. A sustained release form can be formulated to provide an effective dose of any compound described herein (e.g., provide a physiologically-effective blood profile) over about 4, about 8, about 12, about 16 or about 24 hours.

Non-limiting examples of pharmaceutically-acceptable excipients can be found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pennsylvania 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams and Wilkins 1999), each of which is incorporated by reference in its entirety.

Multiple therapeutic agents can be administered in any order or simultaneously. In some embodiments, a compound of the disclosure is administered in combination with, before, or after treatment with another therapeutic agent. If simultaneously, the multiple therapeutic agents can be provided in a single, unified form, or in multiple forms, for example, as multiple separate pills. The agents can be packed together or separately, in a single package or in a plurality of packages. One or all of the therapeutic agents can be given in multiple doses. If not simultaneous, the timing between the multiple doses can vary to as much as about a month.

Therapeutic agents described herein can be administered before, during, or after the occurrence of a disease or condition, and the timing of administering the composition containing a therapeutic agent can vary. For example, the compositions can be used as a prophylactic and can be administered continuously to subjects with a propensity to conditions or diseases in order to lessen a likelihood of the occurrence of the disease or condition. The compositions can be administered to a subject during or as soon as possible after the onset of the symptoms. The administration of the therapeutic agents can be initiated within the first 48 hours of the onset of the symptoms, within the first 24 hours of the onset of the symptoms, within the first 6 hours of the onset of the symptoms, or within 3 hours of the onset of the symptoms. The initial administration can be via any route practical, such as by any route described herein using any formulation described herein.

A compound can be administered as soon as is practical after the onset of a disease or condition is detected or suspected, and for a length of time necessary for the treatment of the disease, such as, for example, from about 1 month to about 3 months. In some embodiments, the length of time a compound can be administered can be about 1 day, about 2 days, about 3 days, about 4 days, about 5 days, about 6 days, about 1 week, about 2 weeks, about 3 weeks, about 4 weeks, about 1 month, about 5 weeks, about 6 weeks, about 7 weeks, about 8 weeks, about 2 months, about 9 weeks, about 10 weeks, about 11 weeks, about 12 weeks, about 3 months, about 13 weeks, about 14 weeks, about 15 weeks, about 16 weeks, about 4 months, about 17 weeks, about 18 weeks, about 19 weeks, about 20 weeks, about 5 months, about 21 weeks, about 22 weeks, about 23 weeks, about 24 weeks, about 6 months, about 7 months, about 8 months, about 9 months, about 10 months, about 11 months, about 1 year, about 13 months, about 14 months, about 15 months, about 16 months, about 17 months, about 18 months, about 19 months, about 20 months, about 21 months, about 22 months about 23 months, about 2 years, about 2.5 years, about 3 years, about 3.5 years, about 4 years, about 4.5 years, about 5 years, about 6 years, about 7 years, about 8 years, about 9 years, or about 10 years. The length of treatment can vary for each subject.

Pharmaceutical compositions described herein can be in unit dosage forms suitable for single administration of precise dosages. In unit dosage form, the formulation is divided into unit doses containing appropriate quantities of one or more compounds. The unit dosage can be in the form of a package containing discrete quantities of the formulation. Non-limiting examples are packaged injectables, vials, or ampoules. Aqueous suspension compositions can be packaged in single-dose non-reclosable containers. Multiple-dose reclosable containers can be used, for example, in combination with or without a preservative. Formulations for injection can be presented in unit dosage form, for example, in ampoules, or in multi-dose containers with a preservative.

Pharmaceutical compositions provided herein, can be administered in conjunction with other therapies, for example, chemotherapy, radiation, surgery, anti-inflammatory agents, and selected vitamins. The other agents can be administered prior to, after, or concomitantly with the pharmaceutical compositions.

Depending on the intended mode of administration, the pharmaceutical compositions can be in the form of solid, semi-solid or liquid dosage forms, such as, for example, tablets, suppositories, pills, capsules, powders, liquids, suspensions, lotions, creams, or gels, for example, in unit dosage form suitable for single administration of a precise dosage.

For solid compositions, nontoxic solid carriers include, for example, pharmaceutical grades of mannitol, lactose, starch, magnesium stearate, sodium saccharin, talc, cellulose, glucose, sucrose, and magnesium carbonate.

Non-limiting examples of pharmaceutically active agents suitable for combination with compositions of the disclosure include anti-infectives, i.e., aminoglycosides, antiviral agents, antimicrobials, anticholinergics/antispasmotics, antidiabetic agents, antihypertensive agents, antineoplastics, cardiovascular agents, central nervous system agents, coagulation modifiers, hormones, immunologic agents, immunosuppressive agents, and ophthalmic preparations.

Compounds can be delivered via liposomal technology. The use of liposomes as drug carriers can increase the therapeutic index of the compounds. Liposomes are composed of natural phospholipids and can contain mixed lipid chains with surfactant properties (e.g., egg phosphatidylethanolamine). A liposome design can employ surface ligands for attaching to unhealthy tissue. Non-limiting examples of liposomes include the multilamellar vesicle (MLV), the small unilamellar vesicle (SUV), and the large unilamellar vesicle (LUV). Liposomal physicochemical properties can be modulated to optimize penetration through biological barriers and retention at the site of administration, and to reduce a likelihood of developing premature degradation and toxicity to non-target tissues. Optimal liposomal properties depend on the administration route: large-sized liposomes show good retention upon local injection, small-sized liposomes are better suited to achieve passive targeting. PEGylation reduces the uptake of the liposomes by the liver and spleen, and increases the circulation time, resulting in increased localization at the inflamed site due to the enhanced permeability and retention (EPR) effect. Additionally, liposomal surfaces can be modified to achieve selective delivery of the encapsulated drug to specific target cells. Non-limiting examples of targeting ligands include monoclonal antibodies, vitamins, peptides, and polysaccharides specific for receptors concentrated on the surface of cells associated with the disease.

Non-limiting examples of dosage forms suitable for use in the disclosure include liquid, elixir, nanosuspension, aqueous or oily suspensions, drops, syrups, and any combination thereof. Non-limiting examples of pharmaceutically-acceptable excipients suitable for use in the disclosure include granulating agents, binding agents, lubricating agents, disintegrating agents, sweetening agents, glidants, anti-adherents, anti-static agents, surfactants, anti-oxidants, gums, coating agents, coloring agents, flavoring agents, coating agents, plasticizers, preservatives, suspending agents, emulsifying agents, plant cellulosic material and spheronization agents, and any combination thereof.

Compositions of the disclosure can be packaged as a kit. In some embodiments, a kit includes written instructions on the administration/use of the composition. The written material can be, for example, a label. The written material can suggest conditions methods of administration. The instructions provide the subject and the supervising physician with the best guidance for achieving the optimal clinical outcome from the administration of the therapy. The written material can be a label. In some embodiments, the label can be approved by a regulatory agency, for example the U.S. Food and Drug Administration (FDA), the European Medicines Agency (EMA), or other regulatory agencies.

Dosing.

Pharmaceutical compositions described herein can be in unit dosage forms suitable for single administration of precise dosages. In unit dosage form, the formulation is divided into unit doses containing appropriate quantities of one or more compounds. The unit dosage can be in the form of a package containing discrete quantities of the formulation. Non-limiting examples are liquids in vials or ampoules. Aqueous suspension compositions can be packaged in single-dose non-reclosable containers. Multiple-dose reclosable containers can be used, for example, in combination with a preservative. Formulations for parenteral injection can be presented in unit dosage form, for example, in ampoules, or in multi-dose containers with a preservative.

A compound described herein can be present in a composition in a range of from about 1 mg to about 2000 mg; from about 100 mg to about 2000 mg; from about 10 mg to about 2000 mg; from about 5 mg to about 1000 mg, from about 10 mg to about 500 mg, from about 50 mg to about 250 mg, from about 100 mg to about 200 mg, from about 1 mg to about 50 mg, from about 50 mg to about 100 mg, from about 100 mg to about 150 mg, from about 150 mg to about 200 mg, from about 200 mg to about 250 mg, from about 250 mg to about 300 mg, from about 300 mg to about 350 mg, from about 350 mg to about 400 mg, from about 400 mg to about 450 mg, from about 450 mg to about 500 mg, from about 500 mg to about 550 mg, from about 550 mg to about 600 mg, from about 600 mg to about 650 mg, from about 650 mg to about 700 mg, from about 700 mg to about 750 mg, from about 750 mg to about 800 mg, from about 800 mg to about 850 mg, from about 850 mg to about 900 mg, from about 900 mg to about 950 mg, or from about 950 mg to about 1000 mg.

A compound described herein can be present in a composition in an amount of about 1 mg, about 2 mg, about 3 mg, about 4 mg, about 5 mg, about 10 mg, about 15 mg, about 20 mg, about 25 mg, about 30 mg, about 35 mg, about 40 mg, about 45 mg, about 50 mg, about 55 mg, about 60 mg, about 65 mg, about 70 mg, about 75 mg, about 80 mg, about 85 mg, about 90 mg, about 95 mg, about 100 mg, about 125 mg, about 150 mg, about 175 mg, about 200 mg, about 250 mg, about 300 mg, about 350 mg, about 400 mg, about 450 mg, about 500 mg, about 550 mg, about 600 mg, about 650 mg, about 700 mg, about 750 mg, about 800 mg, about 850 mg, about 900 mg, about 950 mg, about 1000 mg, about 1050 mg, about 1100 mg, about 1150 mg, about 1200 mg, about 1250 mg, about 1300 mg, about 1350 mg, about 1400 mg, about 1450 mg, about 1500 mg, about 1550 mg, about 1600 mg, about 1650 mg, about 1700 mg, about 1750 mg, about 1800 mg, about 1850 mg, about 1900 mg, about 1950 mg, or about 2000 mg.

In some embodiments, a dose can be expressed in terms of an amount of the drug divided by the mass of the subject, for example, milligrams of drug per kilograms of subject body mass. In some embodiments, a compound is administered in an amount ranging from about 5 mg/kg to about 50 mg/kg, 250 mg/kg to about 2000 mg/kg, about 10 mg/kg to about 800 mg/kg, about 50 mg/kg to about 400 mg/kg, about 100 mg/kg to about 300 mg/kg, or about 150 mg/kg to about 200 mg/kg.

EXAMPLES

Example 1: Synthesis of compounds with 4-((1-(2,2,2-trifluoroethyl)-1H-indol-4-yl)amino)tetrahydro-2H-thiopyran 1,1-dioxide core

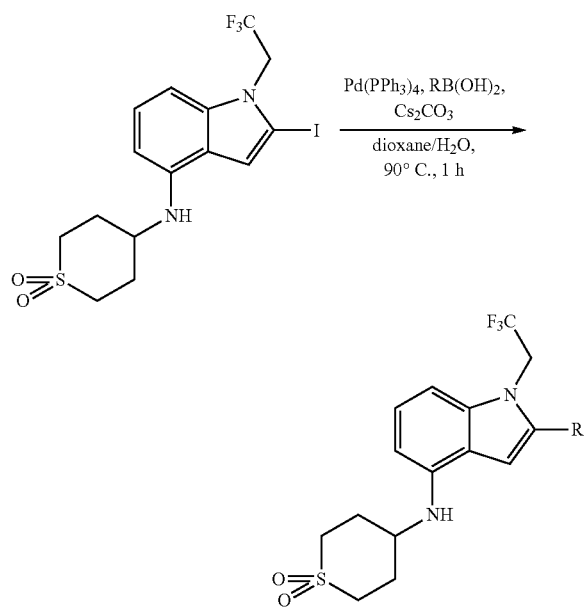

A solution of 4-((2-iodo-1-(2,2,2-trifluoroethyl)-1H-indol-4-yl)amino)tetrahydro-2H-thiopyran 1,1-dioxide (50 mg, 105.87 μmol, 1 eq) was prepared in a mixture of dioxane (1.2 mL) and H$_2$O (300 μL). RB(OH)$_2$ (2 eq), Cs$_2$CO$_3$ (103.48 mg, 317.61 μmol, 3 eq), and Pd(PPh$_3$)$_4$(24.47 mg, 21.17 μmol, 0.2 eq) were added to the solution under a nitrogen atmosphere. The resulting reaction mixture was stirred at 100° C. for 1 hr. LC-MS analysis was used to monitor completion of the reaction. The reaction mixture was poured into a saturated EDTA solution (5 mL), stirred for 2 hours, and extracted twice with dichloromethane (5 mL). The organic phase was washed with water (5 mL) and brine (5 mL), dried with sodium sulfate, and concentrated in vacuo. The resulting residue was purified using preparatory HPLC to afford the desired R-substituted product.

Synthesis of 4-{4-[(1,1-dioxo-1λ$^6$-thian-4-yl)amino]-1-(2,2,2-trifluoroethyl)-1H-indol-2-yl}benzamide (Compound LA): To a solution of 4-((2-iodo-1-(2,2,2-trifluoroethyl)-1H-indol-4-yl)amino)tetrahydro-2H-thiopyran 1,1-dioxide (40 mg, 84.70 μmol, 1 eq) in dioxane (1.60 mL) and H$_2$O (400 μL) were added (4-carbamoylphenyl)boronic acid (27.94 mg, 169.40 μmol, 2 eq), Cs$_2$CO$_3$ (82.79 mg, 254.10 μmol, 3 eq), and Pd(PPh$_3$)$_4$(9.79 mg, 8.47 μmol, 0.10 eq). The resulting mixture was stirred at 100° C. for 1 hr under a nitrogen atmosphere. The mixture was poured into a saturated EDTA solution (5 mL) and stirred for 2 hr. The mixture was then extracted with DCM (5 mL×2), and the organic phase was washed with water (5 mL) and brine (5 mL), dried with anhydrous sodium sulfate, filtered, and concentrated in vacuo. The crude residue was purified by prep-HPLC to afford 4-{4-[(1,1-dioxo-1λ$^6$-thian4-yl)amino]-1-(2,2,2-trifluoroethyl)-1H-indol-2-yl}benzamide (Compound 1A) (18.60 mg, 39.16 μmol, 46.23% yield) as a yellow solid. LC-MS (ES$^+$, m/z): 466.2.

Additional compounds: 4-{4-[(1,1-dioxo-1λ$^6$-thian-4-yl)amino]-1-(2,2,2-trifluoroethyl)-1H-indol-2-yl}-N-methylbenzamide (Compound 5A), 23.8% yield, LC-MS (ES', m/z): 496.2; 3-{4-[(1,1-dioxo-1λ$^6$-thian-4-yl)amino]-1-(2,2,2-trifluoroethyl)-1H-indol-2-yl}benzonitrile (Compound 10A), 32.5% yield, LC-MS (ES$^+$ m/z): 448.0; 4-{[2-(2-fluoro-4-methylphenyl)-1-(2,2,2-trifluoroethyl)-1H-indol-4-yl]amino}-1λ$^6$-thiane-1,1-dione (Compound 11A), 31% yield, LC-MS (ES$^+$, m/z): 455.2; 4-{[2-(3-chlorophenyl)-1-(2,2,2-trifluoroethyl)-1H-indol-4-yl]amino}-1λ$^6$-thiane-1,1-dione (Compound 12A), 34.5% yield, LC-MS (ES$^+$, m/z): 457.1; 4-{[2-(3-methoxyphenyl)-1-(2,2,2-trifluoroethyl)-1H-indol-4-yl]amino}-1λ$^6$-thiane-1,1-dione (Compound 13A), 24.9% yield, LC-MS (ES$^+$, m/z): 453.2; 4-{[2-(4-chlorophenyl)-1-(2,2,2-trifluoroethyl)-1H-indol-4-yl]amino}-1λ$^6$-thiane-1,1-dione (Compound 14A), 51.8% yield, LC-MS (ES$^+$, m/z): 457.1; 3-{4-[(1,1-dioxo-1λ$^6$-thian-4-yl)amino]-1-(2,2,2-trifluoroethyl)-1H-indol-2-yl}benzoic acid (Compound 20A), 14.7% yield, LC-MS (ES$^+$, m/z): 467.2; 4-{4-[(1,1-dioxo-1λ$^6$-thian-4-yl)amino]-1-(2,2,2-trifluoroethyl)-1H-indol-2-yl}benzoic acid (Compound 23AB), 8.3% yield, LC-MS (ES$^+$, m/z): 467.2; 4-({2-[3-(dimethylamino)phenyl]-1-(2,2,2-trifluoroethyl)-1H-indol-4-yl}amino)-1λ$^6$-thiane-1,1-dione (Compound 21A), 17.6% yield, LC-MS (ES$^+$, m/z): 466.2; 3-{4-[(1,1-dioxo-1λ$^6$-thian-4-yl)amino]-1-(2,2,2-trifluoroethyl)-1H-indol-2-yl}-N-methylbenzamide (Compound 22A), 18.1% yield, LC-MS (ES$^+$, m/z): 480.2; 4-[(2-{4-[(morpholin-4-yl)methyl]phenyl}-1-(2,2,2-trifluoroethyl)-1H-indol-4-yl)amino]-1λ$^6$-thiane-1,1-dione (Compound 24A), 18.9% yield, LC-MS (ES$^+$, m/z): 522.3; 1-(4-{4-[(1,1-dioxo-1λ$^6$-thian-4-yl)amino]-1-(2,2,2-trifluoroethyl)-1H-indol-2-yl}phenyl)cyclopropane-1-carbonitrile (Compound 26A), 26.8% yield, LC-MS (ES$^+$, m/z): 488.1; 4-({2-[4-(hydroxymethyl)phenyl]-1-(2,2,2-trifluoroethyl)-1H-indol-4-yl}amino)-1λ$^6$-thiane-1,1-dione (Compound 27A), 9.1% yield, LC-MS (ES$^+$, m/z): 453.2.

Example 2: Synthesis of 4-({2-[4-(aminomethyl)phenyl]-1-(2,2,2-trifluoroethyl)-1H-indol-4-yl}amino)-1λ$^6$-thiane-1,1-dione (Compound 2A) and 4-[(2-{4-[(methylamino)methyl]phenyl}-1-(2,2,2-trifluoroethyl)-1H-indol-4-yl)amino]-1λ$^6$-thiane-1,1-dione (Compound 3A)

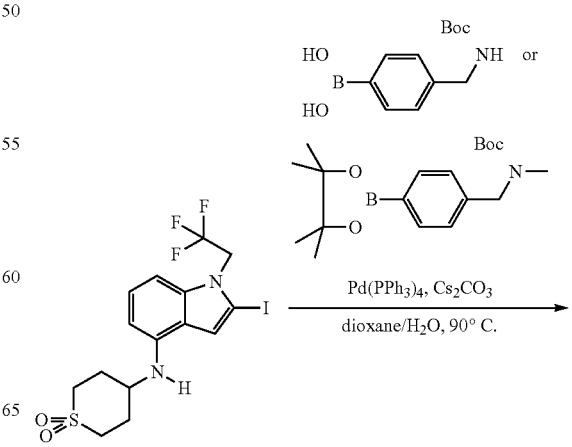

109

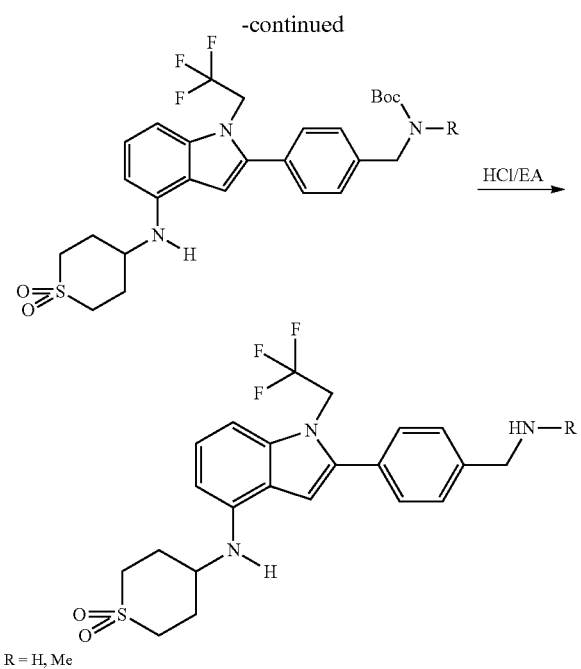

R = H, Me

110

To a solution of 4-((2-iodo-1-(2,2,2-trifluoroethyl)-1H-indol-4-yl)amino)tetrahydro-2H-thiopyran 1,1-dioxide (200 mg, 423.5 μmol, 1 eq) in dioxane (2.40 mL) and H$_2$O (600 μL) were added (4-(((tert-butoxycarbonyl)amino)methyl)phenyl)boronic acid or tert-butyl methyl(4-(4,4,5,5-tetramethyl-1,3,2-dioxaborolan-2-yl)benzyl)carbamate (212.67 mg, 847 μmol, 2 eq), Cs$_2$CO$_3$ (413.95 mg, 1.27 mmol, 3 eq), and Pd(PPh$_3$)$_4$(97.88 mg, 84.70 μmol, 0.20 eq). The resulting mixture was stirred at 100° C. for 1 hr under a nitrogen atmosphere. The mixture was poured into saturated EDTA (5 mL) and stirred for 2 hr. The mixture was then extracted with DCM (5 mL×2), and the organic phase was washed with water (5 mL) and brine (5 mL), dried with anhydrous sodium sulfate, filtered, and concentrated in vacuo. The crude residue was purified by prep-HPLC to afford the desired product. 4-({2-[4-(aminomethyl)phenyl]-1-(2,2,2-trifluoroethyl)-1H-indol-4-yl}amino)-1λ$^6$-thiane-1,1-dione (Compound 2A), 42.5% yield, LC-MS (ES$^+$, m/z): 452.2; 4-[(2-{4-[(methylamino)methyl]phenyl}-1-(2,2,2-trifluoroethyl)-1H-indol-4-yl)amino]-1λ$^6$-thiane-1,1-dione (Compound 3A), 36.2% yield, LC-MS (ES$^+$, m/z): 466.2.

Example 3: Synthesis of compounds with a 4-((2-(4-(aminomethyl)phenyl)-1-(2,2,2-trifluoroethyl)-1H-indol-4-yl)amino)tetrahydro-2H-thiopyran 1,1-dioxide core

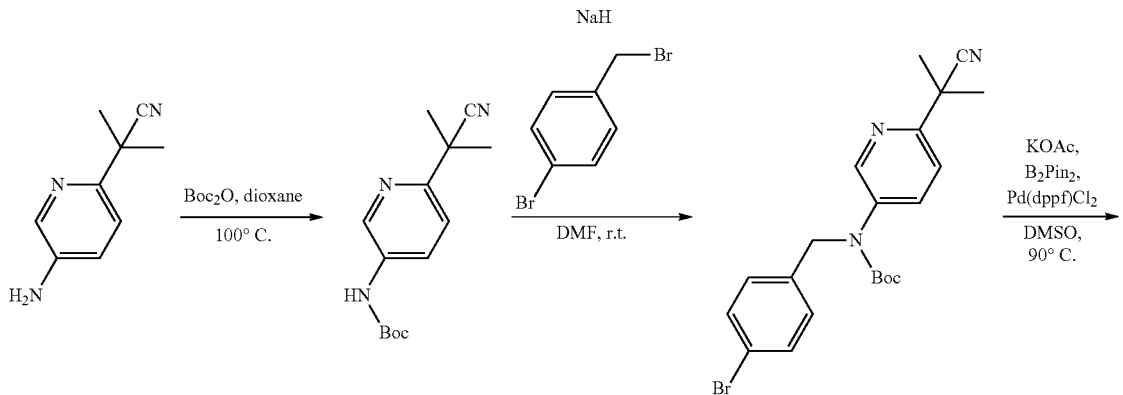

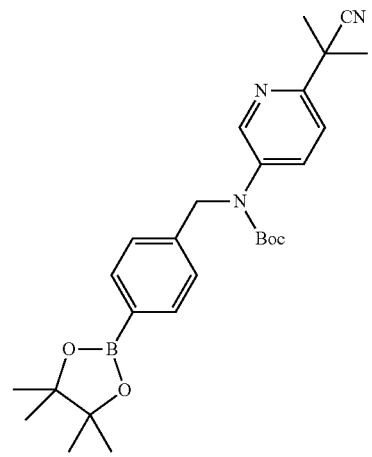

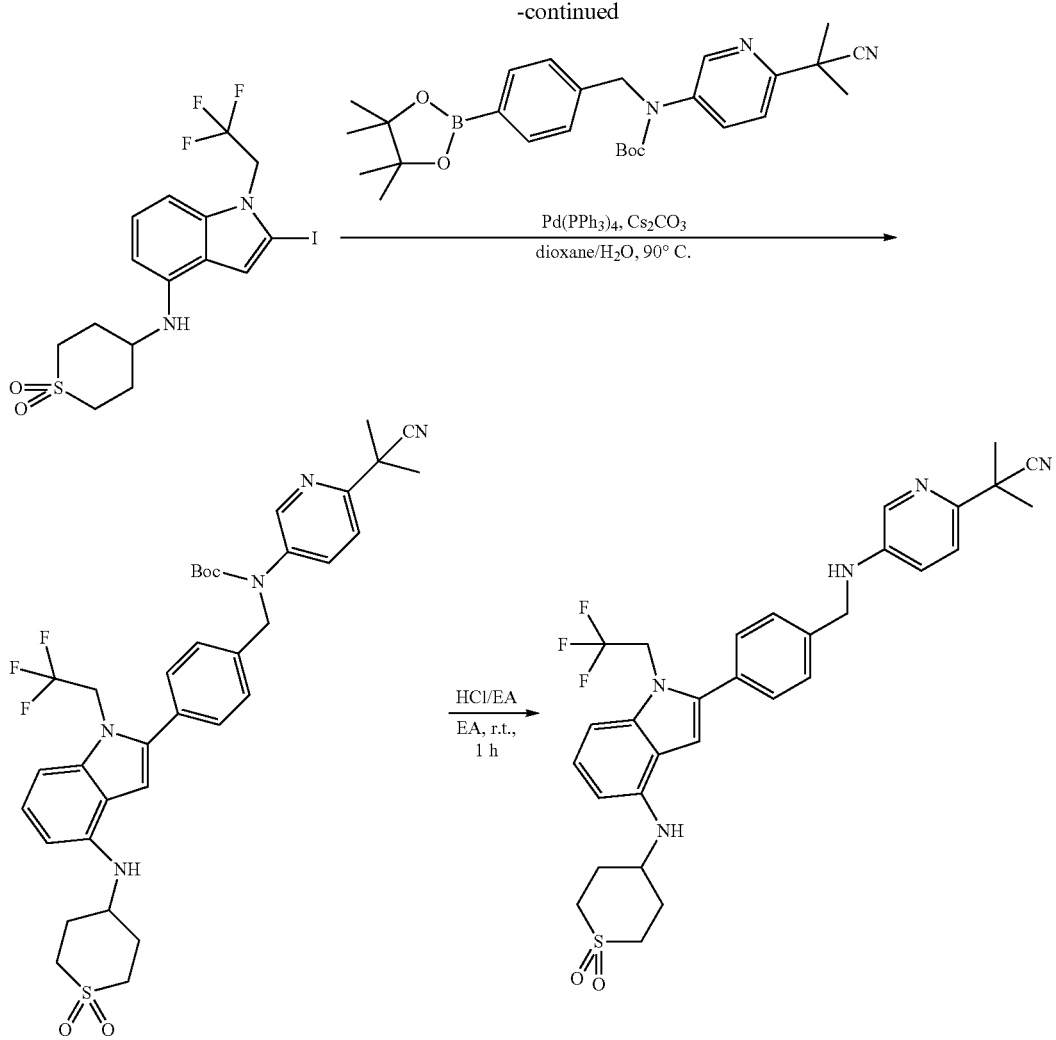

To a solution of 2-(5-aminopyridin-2-yl)-2-methylpropanenitrile (999.44 mg, 6.20 mmol, 1 eq) in dioxane (10 mL) was added Boc$_2$O (4.06 g, 18.60 mmol, 4.27 mL, 3 eq). The reaction was stirred at 100° C. for 12 hr under N$_2$. Water was added, and the reaction mixture was extracted with DCM (10 mL×2), and the organic phase was washed with water (10 mL) and brine (10 mL), dried with sodium sulfate, filtered, and concentrated in vacuo. The crude residue was purified by column chromatography (PE:EA=10:1) to afford tert-butyl (6-(2-cyanopropan-2-yl)pyridin-3-yl)carbamate (1.50 g, 5.74 mmol, 92.58% yield). LC-MS (ES$^+$, m/z): 262.2.

To a solution of tert-butyl (6-(2-cyanopropan-2-yl)pyridin-3-yl)carbamate (1.50 g, 5.74 mmol, 1 eq) in DMF (15 mL) was added NaH (688.81 mg, 17.22 mmol, 60% purity, 3 eq). The reaction was stirred for 0.5 hr, and 1-bromo-4-(bromomethyl)benzene (1.43 g, 5.74 mmol, 1 eq) was added. The reaction was stirred for another 1.5 hr under N$_2$. The mixture was poured into a saturated NH$_4$Cl solution (15 mL) and extracted with DCM (15 mL×2). The organic phase was washed with water (15 mL) and brine (15 mL), dried with anhydrous sodium sulfate, filtered, and concentrated in vacuo. The residue was purified by column chromatography (PE:EA=10:1) to afford tert-butyl (4-bromobenzyl)(6-(2-cyanopropan-2-yl)pyridin-3-yl)carbamate (1.50 g, 3.49 mmol, 60.73% yield).

To a solution of tert-butyl (4-bromobenzyl)(6-(2-cyanopropan-2-yl)pyridin-3-yl)carbamate (498.63 mg, 1.51 mmol, 1 eq) in DMSO (5 mL) were added KOAc (474.21 mg, 4.83 mmol, 3.20 eq), B$_2$Pin$_2$(766.90 mg, 3.02 mmol, 2 eq), and Pd(dppf)Cl$_2$(36.99 mg, 45.30 μmol, 0.03 eq). The reaction was stirred at 90° C. 2 hr under N$_2$. The reaction was poured into 2M EDTA and stirred. The reaction mixture was extracted with DCM (15 mL×2), and the organic phase was washed with water (15 mL) and brine (15 mL), dried with anhydrous sodium sulfate, filtered, and concentrated in vacuo. The crude residue was purified by column chromatography (PE:EA=10:1) to afford tert-butyl (6-(2-cyanopropan-2-yl)pyridin-3-yl)(4-(4,4,5,5-tetramethyl-1,3,2-dioxaborolan-2-yl)benzyl)carbamate (300 mg, 795.14 μmol, 52.66% yield). LC-MS (ES$^+$, m/z): 478.4.

To a solution of 4-((2-iodo-1-(2,2,2-trifluoroethyl)-1H-indol-4-yl)amino)tetrahydro-2H-thiopyran 1,1-dioxide (100 mg, 211.75 μmol, 1 eq) in dioxane (1.20 mL) and H$_2$O (300 μL) were added tert-butyl (6-(2-cyanopropan-2-yl)pyridin-3-yl)(4-(4,4,5,5-tetramethyl-1,3,2-dioxaborolan-2-yl)benzyl)carbamate (202.18 mg, 423.50 μmol, 2 eq), Cs$_2$CO$_3$ (206.98 mg, 635.25 μmol, 3 eq), and Pd(PPh$_3$)$_4$(24.47 mg, 21.18 μmol, 0.10 eq). The reaction was stirred at 100° C. for 1 hr under N$_2$. The mixture was poured into a saturated EDTA solution (5 mL) and stirred for 2 hr. The mixture was then extracted with DCM (5 mL×2). The organic phase was washed with water (5 mL) and brine (5 mL), dried with anhydrous sodium sulfate, filtered, and concentrated in vacuo. The crude residue was purified by prep-TLC (PE: EA=1:1) to afford tert-butyl (6-(2-cyanopropan-2-yl)pyridin-3-yl)(4-(4-((1,1-dioxidotetrahydro-2H-thiopyran-4-yl) amino)-1-(2,2,2-trifluoroethyl)-1H-indol-2-yl)benzyl) carbamate (100 mg, 143.72 μmol, 67.87% yield). LC-MS (ES+, m/z): 696.3.

A solution of tert-butyl (6-(2-cyanopropan-2-yl)pyridin-3-yl)(4-(4-((1,1-dioxidotetrahydro-2H-thiopyran-4-yl) amino)-1-(2,2,2-trifluoroethyl)-1H-indol-2-yl)benzyl)carbamate (100 mg, 143.72 μmol, 1 eq) was prepared in HCl/EA (4 M, 10 mL, 278.32 eq) and stirred at 25° C. for 1 hr under $N_2$. The solvent was removed in vacuo to give the crude product. The crude residue was purified by prep-HPLC to afford the desired product. 2-(5-{[(4-{4-[(1,1-dioxo-1λ⁶-thian-4-yl)amino]-1-(2,2,2-trifluoroethyl)-1H-indol-2-yl}phenyl)methyl]amino}pyridine-2-yl)-2-methylpropanenitrile (Compound 7A): 37.35% yield. LC-MS (ES+, m/z): 596.1.

Additional compounds: The method described above was used to synthesize 4-{[2-(4-{[(4-methanesulfonylphenyl) amino]methyl}phenyl)-1-(2,2,2-trifluoroethyl)-1H-indol-4-yl]amino}-1λ⁶-thiane-, 1-dione (Compound 8A): 33.03% yield. LC-MS (ES+, m/z): 606.0; and 4-[(2-{4-[(phenylamino)methyl]phenyl}-1-(2,2,2-trifluoroethyl)-1H-indol-4-yl)amino]-1λ⁶-thiane-1,1-dione (Compound 9A): 27.66% yield. LC-MS (ES+, m/z): 528.2.

Example 4: Synthesis of compounds with a 2-(4-(aminomethyl)phenyl)-N-(1-(tetrahydro-2H-pyran-4-yl)piperidin-4-yl)-1-(2,2,2-trifluoroethyl)-1H-indol-4-amine core Route 1

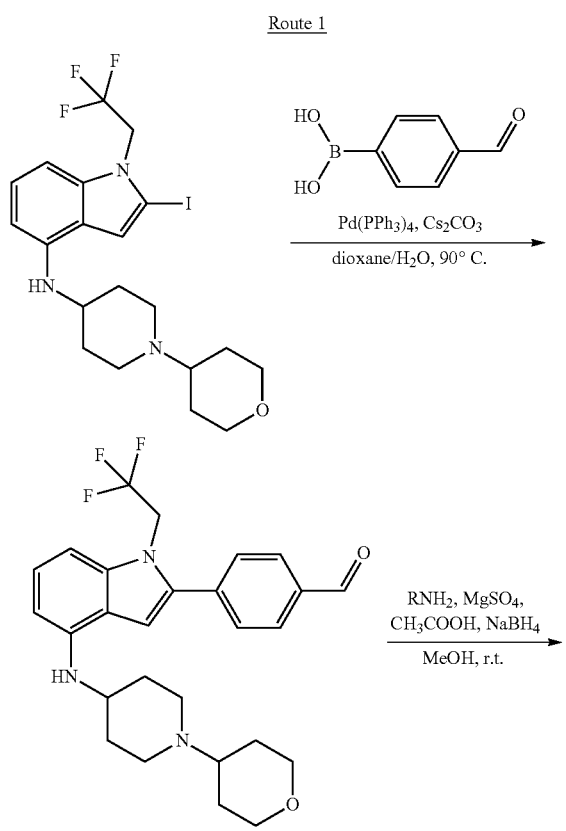

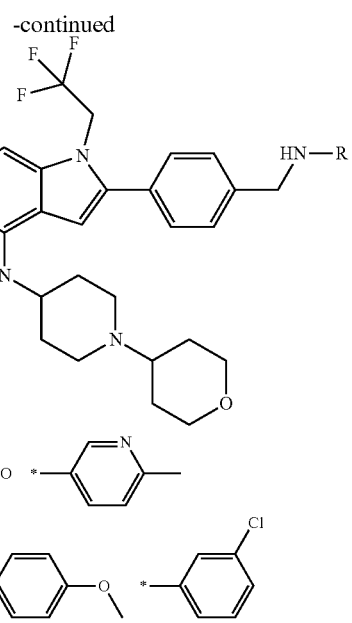

Route 1: To a solution of 2-iodo-N-(1-(tetrahydro-2H-pyran-4-yl)piperidin-4-yl)-1-(2,2,2-trifluoroethyl)-1H-indol-4-amine (100 mg, 167.54 μmol, 1 eq) in dioxane (2.40 mL) and $H_2O$ (600 μL) were added (4-formylphenyl)boronic acid (50.24 mg, 335.09 μmol, 2 eq), $Cs_2CO_3$ (163.77 mg, 502.63 μmol, 3 eq), and $Pd(PPh_3)_4$ (38.72 mg, 33.51 μmol, 0.20 eq). The reaction was stirred at 90° C. for 2 hr. The mixture was poured into a saturated EDTA solution (5 mL) and stirred for 2 hr. The mixture was then extracted with DCM (5 mL×2), and the organic phase was washed with water (5 mL) and brine (5 mL), dried with anhydrous sodium sulfate, filtered, and concentrated in vacuo. The crude residue was purified by column chromatography (DCM:methanol=10:1) to afford 4-(4-((1-(tetrahydro-2H-pyran-4-yl)piperidin-4-yl)amino)-1-(2,2,2-trifluoroethyl)-1H-indol-2-yl)benzaldehyde (50 mg, 102.98 μmol, 61.46% yield). LC-MS (ES+, m/z): 486.4.

To a solution of 4-(4-((1-(tetrahydro-2H-pyran-4-yl)piperidin-4-yl)amino)-1-(2,2,2-trifluoroethyl)-1H-indol-2-yl) benzaldehyde (40 mg, 82.38 μmol, 1 eq) in methanol (2 mL) were added $RNH_2$ (3-chloroaniline; 10.51 mg, 82.38 μmol, 8.76 μL, 1 eq) and $MgSO_4$ (49.58 mg, 411.90 μmol, 5 eq). The reaction was stirred at 80° C. for 1.5 hr. Then, $CH_3COOH$ (4.95 mg, 82.38 μmol, 4.71 μL, 1 eq) and $NaBH_4$ (15.58 mg, 411.90 μmol, 5 eq) were added, and the mixture was stirred further at 25° C. for 0.5 hr. The mixture was poured into 2M NaOH and extracted with DCM (5 mL×2). The organic phase was washed with water (5 mL) and brine (5 mL), dried with anhydrous sodium sulfate, filtered, and concentrated in vacuo. The crude residue was purified by prep-HPLC to afford the R-substituted 2-(4-(aminomethyl)phenyl)-N-(1-(tetrahydro-2H-pyran-4-yl)piperidin-4-yl)-1-(2,2,2-trifluoroethyl)-1H-indol-4-amine product. 2-(4-(((3-chlorophenyl)amino)methyl)phenyl)-N-(1-(tetrahydro-2H-pyran-4-yl)piperidin-4-yl)-1-(2,2,2-trifluoroethyl)-1H-indol-4-amine (Compound 12A) (13.50 mg, 22.52 μmol, 27.33% yield). LC-MS (ES+, m/z): 597.0.

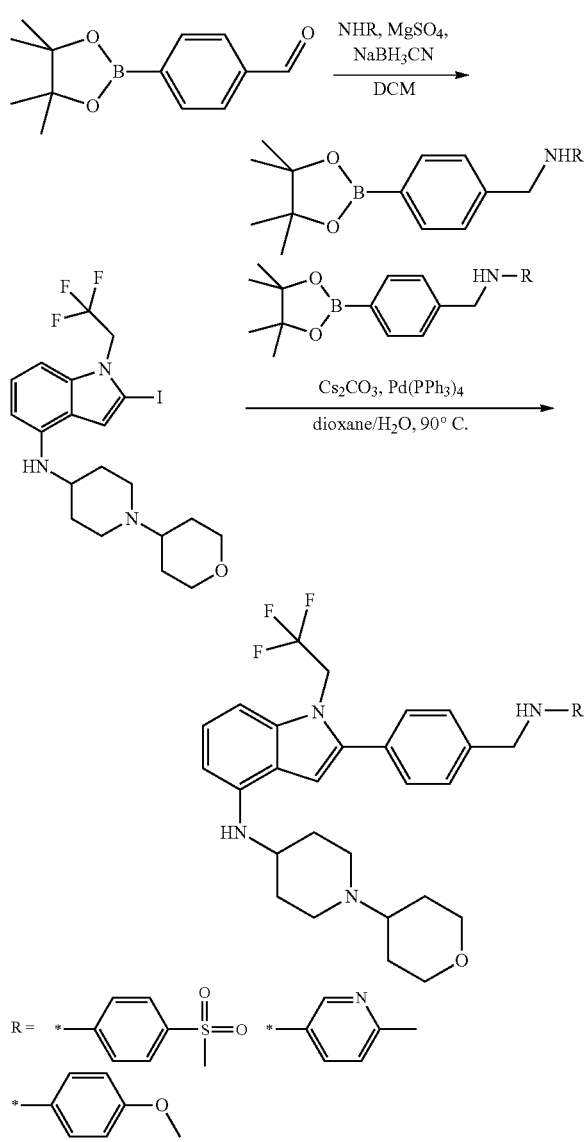

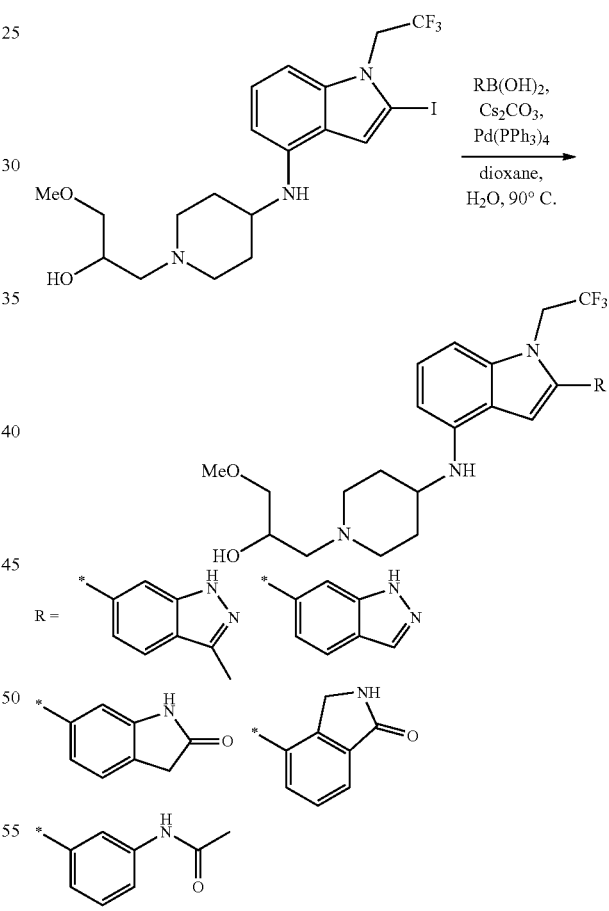

Route 2: To a solution of 4-(4,4,5,5-tetramethyl-1,3,2-dioxaborolan-2-yl)benzaldehyde (1 eq) in DCM were added NHR, MgSO$_4$ (5 eq), and NaBH$_3$CN (5 eq). The reaction was stirred at 25° C. for 2 hr under N$_2$. Water was added, and the reaction mixture was extracted with DCM (5 mL×2). The organic phase was washed with water (5 mL) and brine (5 mL), dried with anhydrous sodium sulfate, filtered, and concentrated in vacuo. The residue was purified by column chromatography or prep-TLC (DCM:methanol=20:1) to afford the desired R-substituted 4,4,5,5-tetramethyl-2-(p-tolyl)-1,3,2-dioxaborolane product.

To a solution of 2-iodo-N-(1-(tetrahydro-2H-pyran-4-yl)piperidin-4-yl)-1-(2,2,2-trifluoroethyl)-1H-indol-4-amine (1 eq) and N—(R-substituted)-1-(4-(4,4,5,5-tetramethyl-1,3,2-dioxaborolan-2-yl)phenyl)methanamine (2 eq) in dioxane (1.20 mL) and H$_2$O (300 μL) were added Cs$_2$CO$_3$ (96.34 mg, 295.68 μmol, 3 eq) and Pd(PPh$_3$)$_4$(22.78 mg, 19.71 μmol, 0.20 eq). The reaction was stirred at 90° C. for 2 hr under N$_2$. The mixture was poured into a saturated EDTA solution (10 mL) and stirred for 2 hr. The mixture was then extracted with DCM (10 mL×2), and the organic phase was washed with water (10 mL) and brine (10 mL), dried with anhydrous sodium sulfate, filtered, and concentrated in vacuo. The crude residue was purified by prep-HPLC to afford the desired R-substituted 2-(4-(aminomethyl)phenyl)-N-(1-(tetrahydro-2H-pyran-4-yl)piperidin-4-yl)-1-(2,2,2-trifluoroethyl)-1H-indol-4-amine product.

2-(4-{[(4-methanesulfonylphenyl)amino]methyl}phenyl)-N-[1-(oxan-4-yl)piperidin-4-yl]-1-(2,2,2-trifluoroethyl)-1H-indol-4-amine (Compound 30A), LC-MS (ES$^+$, m/z): 641.4; 2-(4-{[(6-methylpyridin-3-yl)amino]methyl}phenyl)-N-[1-(oxan-4-yl)piperidin-4-yl]-1-(2,2,2-trifluoroethyl)-1H-indol-4-amine (Compound 31A), LC-MS (ES$^+$, m/z): 578.4; 2-(4-{[(4-methoxyphenyl)amino]methyl}phenyl)-N-1λ$^6$-(oxan-4-yl)piperidin-4-yl]-1-(2,2,2-trifluoroethyl)-1H-indol-4-amine (Compound 33A), LC-MS (ES$^+$, m/z): 593.4.

Example 5: Synthesis of compounds with a 1-methoxy-3-(4-((2-phenyl-1-(2,2,2-trifluoroethyl)-1H-indol-4-yl)amino)piperidin-1-yl)propan-2-ol core To a solution of 1-(4-((2-iodo-1-(2,2,2-trifluoroethyl)-1H-indol-4-yl)amino)piperidin-1-yl)-3-methoxypropan-2-ol (1 eq) in dioxane (20 mL) and H$_2$O (5 mL) were added an R-substituted boric acid or R-substituted boric acid ester (2 eq), Cs$_2$CO$_3$ (1 eq), and Pd(PPh$_3$)$_4$(1 eq). The reaction was stirred at 90° C. for 2 hr. Saturated EDTA solution (20 mL) and EA (30 mL) were added to the reaction, and the resulting mixture was stirred for 1 hr. The aqueous phase was extracted with EA (10 mL×3), dried with anhydrous Na₂SO₄, filtered, and concentrated in vacuo. The residue was purified by prep-TLC (DCM:methanol=10:1) to give a residue. The residue was re-purified by prep-HPLC to afford the desired R-substituted 1-methoxy-3-(4-((1-(2,2,2-trifluoroethyl)-1H-indol-4-yl)amino)piperidin-1-yl)propan-2-ol product as yellow solid.

1-methoxy-3-(4-{[2-(3-methyl-2H-indazol-6-yl)-1-(2,2,2-trifluoroethyl)-1H-indol-4-yl]amino}piperidin-1-yl)propan-2-ol (Compound 47A), LC-MS (ES⁺, m/z): 516.2; 1-(4-{[2-(2H-indazol-6-yl)-1-(2,2,2-trifluoroethyl)-1H-indol-4-yl]amino}piperidin-1-yl)-3-methoxypropan-2-ol (Compound 48A), LC-MS (ES⁺, m/z): 502.2; and 4-{[1-(2-hydroxy-3-methoxypropyl)piperidin-4-yl]amino}-1-(2,2,2-trifluoroethyl)-2',3'-dihydro-1H, 1'H-[2,6'-biindol]-2'-one (Compound 49A), LC-MS (ES⁺, m/z): 517.2.

Example 6: Synthesis of compounds with a 2-(4-(aminomethyl)phenyl)-N-(1-methylpiperidin-4-yl)-1-(2,2,2-trifluoroethyl)-1H-indol-4-amine core

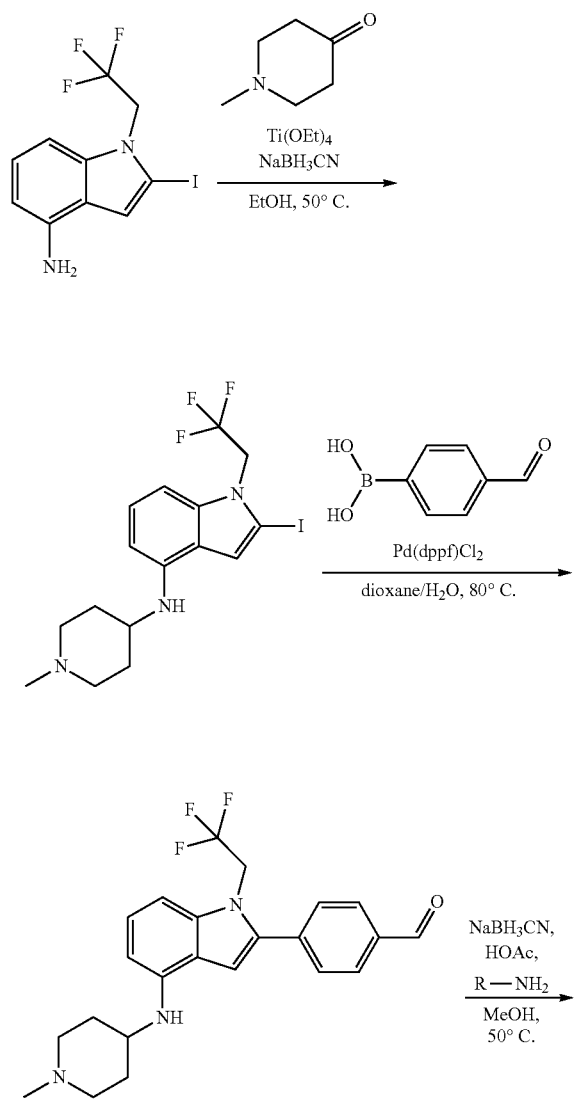

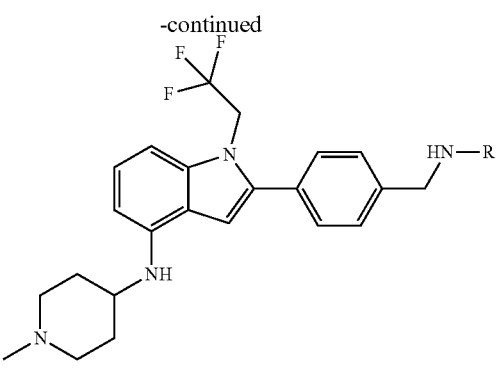

To a solution of 2-iodo-1-(2,2,2-trifluoroethyl)-1H-indol-4-amine (12 g, 1 eq) in ethanol (120 mL) were added 1-methylpiperidin-4-one (3 eq) and Ti(OEt)₄ (3 eq). The mixture was stirred for 1 hr at 50° C., and NaBH₃CN (5 eq) was added. The resulting mixture was stirred for 0.5 hr at 50° C. The residue was quenched with a saturated solution of NaHCO₃ (200 mL), and the mixture was extracted with EA (100 mL×3). The combined organic phase was washed with brine (100 mL×2), dried with anhydrous Na₂SO₄, filtered, and concentrated in vacuo. The residue was purified by column chromatography to afford 2-iodo-N-(1-methylpiperidin-4-yl)-1-(2,2,2-trifluoroethyl)-1H-indol-4-amine.

To a solution of 2-iodo-N-(1-methylpiperidin-4-yl)-1-(2,2,2-trifluoroethyl)-1H-indol-4-amine (200 mg, 1 eq) and (4-formylphenyl)boronic acid (2 eq) in dioxane (1.6 mL) and H₂O (0.4 mL) were added Na₂CO₃ (3 eq) and Pd(dppf)Cl₂ (0.1 eq). The mixture was stirred at 80° C. for 0.5 hr. The residue was poured into 2M EDTA (50 mL), and the resulting mixture was stirred for 60 min. The aqueous phase was extracted with EA (30 mL×3). The combined organic phase was washed with brine (30 mL×3), dried with anhydrous Na₂SO₄, filtered, and concentrated in vacuo. The residue was purified by prep-TLC to afford 4-(4-((1-methylpiperidin-4-yl)amino)-1-(2,2,2-trifluoroethyl)-1H-indol-2-yl)benzaldehyde.

To a solution of 4-(4-((1-methylpiperidin-4-yl)amino)-1-(2,2,2-trifluoroethyl)-1H-indol-2-yl)benzaldehyde (50 mg, 1 eq) in methanol (3 mL) were added R—NH₂ (2 eq) and AcOH (10 eq). The mixture was stirred at 50° C. for 1 hr. NaBH₃CN (5 eq) was then added, and the resulting reaction mixture was stirred at 50° C. for 15 min. The residue was poured into saturated aqueous NaHCO₃ (100 mL), and the aqueous phase was extracted with EA (100 mL×3). The combined organic phase was washed with brine (100 mL×3), dried with anhydrous Na₂SO₄, filtered, and concentrated in vacuo. The crude residue was purified by prep-HPLC to afford the desired R-substituted 2-(4-(aminomethyl)phenyl)-N-(1-methylpiperidin-4-yl)-1-(2,2,2-trifluoroethyl)-1H-indol-4-amine product.

2-(4-{[(4-methanesulfonylphenyl)amino]methyl}phenyl)-N-[1-(oxan-4-yl)piperidin-4-yl]-1-(2,2,2-trifluoroethyl)-1H-indol-4-amine (Compound 35A), 5.3% yield, LC-MS (ES⁺, m/z): 522.2; 2-{4-[(cyclopentylamino)methyl]phenyl}-N-(1-methylpiperidin-4-yl)-1-(2,2,2-trifluoroethyl)-1H-indol-4-amine (Compound 40A), LC-MS (ES⁺, m/z): 485.4; 2-(4-{1-1λ⁶-methanesulfonylphenyl)amino]ethyl}phenyl)-N-(1-methylpiperidin-4-yl)-1-(2,2,2-trifluoroethyl)-1H-indol-4-amine (Compound 41A), 2.25% yield, LC-MS (ES⁺, m/z): 585.4.

Example 7: Synthesis of compounds with a 2-(4-(aminomethyl)phenyl)-N-((3R,4S)-3-fluoro-1-methylpiperidin-4-yl)-1-(2,2,2-trifluoroethyl)-1H-indol-4-amine core

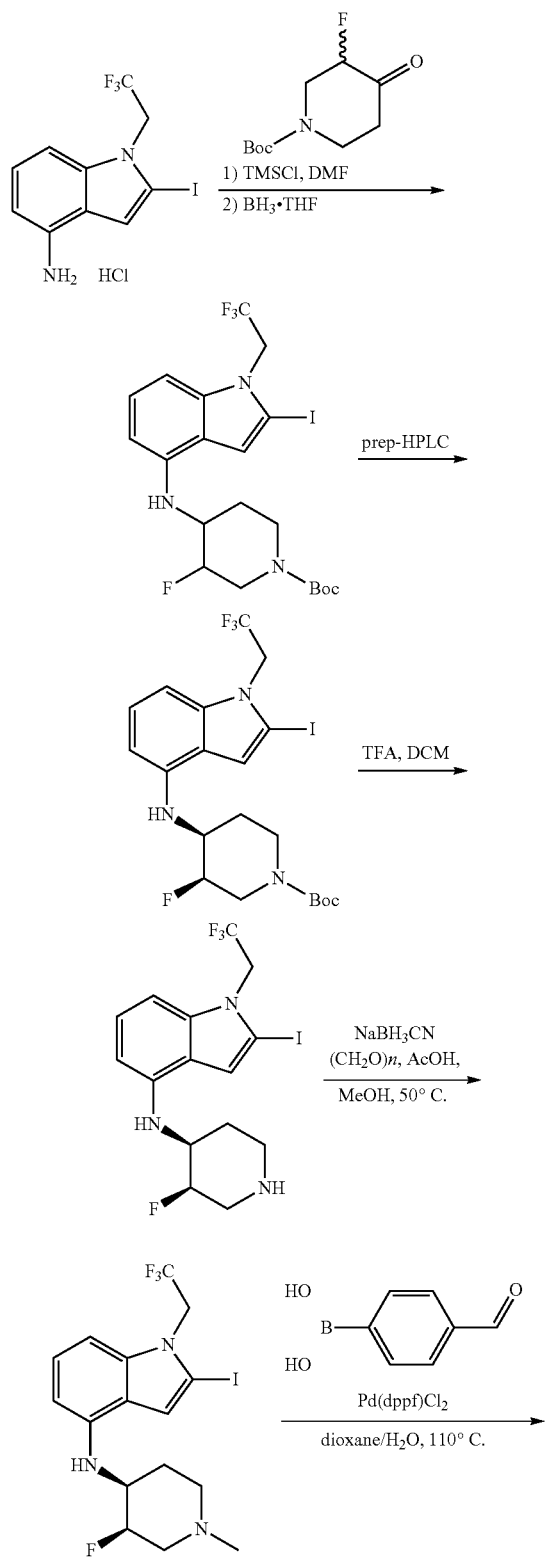

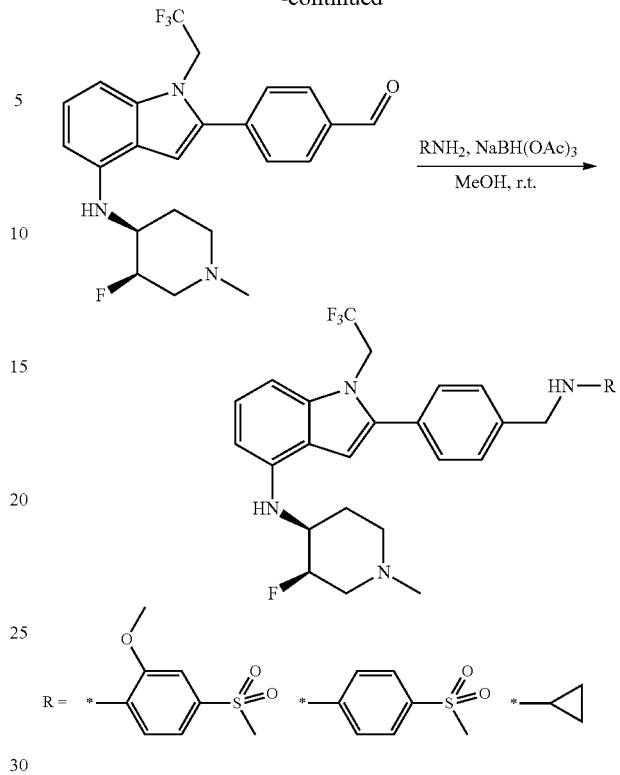

To a solution of 2-iodo-1-(2,2,2-trifluoroethyl)-1H-indol-4-amine hydrochloride (10 g, 29.40 mmol, 1 eq) and tert-butyl 3-fluoro-4-oxopiperidine-1-carboxylate (31.93 g, 147 mmol, 5 eq) in DMF (100 mL) was added TMSCl (15.97 g, 147 mmol, 18.66 mL, 5 eq) at 0° C. The reaction was stirred for 1 hr, and BH₃-THF (1 M, 294 mL, 10 eq) was added. The reaction was stirred further at 0° C. for 2 hr. The mixture was quenched with Na₂CO₃ (10 mL). The mixture was extracted with DCM (10 mL×2), and the organic phase was washed with water (10 mL) and brine (10 mL), dried with anhydrous sodium sulfate, filtered, and concentrated in vacuo. The crude residue was purified by prep-HPLC to afford tert-butyl (3R,4S)-3-fluoro-4-((2-iodo-1-(2,2,2-trifluoroethyl)-1H-indol-4-yl)amino)piperidine-1-carboxylate.

To a solution of tert-butyl (3R,4S)-3-fluoro-4-((2-iodo-1-(2,2,2-trifluoroethyl)-1H-indol-4-yl)amino)piperidine-1-carboxylate (1 eq) in DCM was added TFA (12.19 eq). The reaction was stirred at 25° C. for 1 hr. The mixture was quenched with a saturated solution of Na₂CO₃ (20 mL) and extracted with DCM (10 mL×2). The organic phase was washed with water (10 mL) and brine (10 mL), dried with anhydrous sodium sulfate, filtered, and concentrated in vacuo to afford N-((3R,4S)-3-fluoropiperidin-4-yl)-2-iodo-1-(2,2,2-trifluoroethyl)-1H-indol-4-amine.

To a solution of N-((3R,4S)-3-fluoropiperidin-4-yl)-2-iodo-1-(2,2,2-trifluoroethyl)-1H-indol-4-amine (800 mg, 1.81 mmol, 1 eq) and paraformaldehyde (108.89 mg, 3.63 mmol, 99.90 µL, 2 eq) in methanol (10 mL) were added NaBH₃CN (569.71 mg. 9.07 mmol, 5 eq) and AcOH (108.88 ug, 1.81 µmol, 1.04e-1 µL, 0.001 eq). The reaction was stirred at 50° C. for 0.5 hr. The mixture was extracted with DCM (10 mL×2), and the organic phase was washed with water (10 mL) and brine (10 mL), dried with anhydrous sodium sulfate, filtered, and concentrated in vacuo. The crude residue was purified by column chromatography to afford N-((3R,4S)-3-fluoro-1-methylpiperidin-4-yl)-2-iodo-1-(2,2,2-trifluoroethyl)-1H-indol-4-amine.

To a solution of N-((3R,4S)-3-fluoro-1-methylpiperidin-4-yl)-2-iodo-1-(2,2,2-trifluoroethyl)-1H-indol-4-amine (1 eq) in dioxane and H₂O were added (4-formylphenyl)boronic acid (2 eq), Na₂CO₃ (3 eq), and Pd(dppf)Cl₂ (0.05 eq). The reaction was stirred at 110° C. for 0.5 hr. The mixture was poured into 2M EDTA and stirred for 2 hr. The mixture was extracted with DCM (×2), and the organic phase was washed with water and brine, dried with anhydrous sodium sulfate, filtered, and concentrated in vacuo. The crude residue was purified by column chromatography (PE/EA=1:1) to afford 4-(4-(((3R,4S)-3-fluoro-1-methylpiperidin-4-yl)amino)-1-(2,2,2-trifluoroethyl)-1H-indol-2-yl)benzaldehyde.

To a solution of 4-(4-(((3R,4S)-3-fluoro-1-methylpiperidin-4-yl)amino)-1-(2,2,2-trifluoroethyl)-1H-indol-2-yl)benzaldehyde (1 eq) and R—NH₂ (2 eq) in methanol was added AcOH (75.79 eq). The reaction was stirred for 0.5 hr, and NaBH₃CN (5 eq) was added. The mixture was stirred further at 50° C. for 1 hr. The mixture was extracted with DCM (10 mL×2), and the organic phase was washed with water (10 mL) and brine (10 mL), dried with anhydrous sodium sulfate, filtered, and concentrated in vacuo. The crude residue was purified by prep-HPLC to afford the desired R-substituted 2-(4-(aminomethyl)phenyl)-N-((3R,4S)-3-fluoro-1-methylpiperidin-4-yl)-1-(2,2,2-trifluoroethyl)-1H-indol-4-amine product.

(+/−)-2-{4-[(cyclopropylamino)methyl]phenyl}-N-[(3R,4S)-3-fluoro-1-methylpiperidin-4-yl]-1-(2,2,2-trifluoroethyl)-1H-indol-4-amine (Compound 41A), 11% yield, LC-MS (ES⁺, m/z): 475.3; (+/−)-N-[(3R,4S)-3-fluoro-1-methylpiperidin-4-yl]-2-(4-{[(4-methanesulfonyl-2-methoxyphenyl)amino]methyl}phenyl)-1-(2,2,2-trifluoroethyl)-1H-indol-4-amine (Compound 43A), 8% yield, LC-MS (ES⁺, m/z): 619.2; N-[(3R,4S)-3-fluoro-1-methylpiperidin-4-yl]-2-(4-{[(4-methanesulfonylphenyl)amino]methyl}phenyl)-1-(2,2,2-trifluoroethyl)-1H-indol-4-amine (Compound 44A), 11.8% yield, LC-MS (ES⁺, m/z): 589.2; (+/−)-N-{[4-(4-{[(3R,4S)-3-fluoro-1-methylpiperidin-4-yl]amino}-1-(2,2,2-trifluoroethyl)-1H-indol-2-yl)phenyl]methyl}benzamide (Compound 45A), 73.8% yield, LC-MS (ES⁻, m/z): 589.2; 539.2; (+/−)-N-{[4-(4-{[(3R,4S)-3-fluoro-1-methylpiperidin-4-yl]amino}-1-(2,2,2-trifluoroethyl)-1H-indol-2-yl)phenyl]methyl}cyclopropanecarboxamide (Compound 46A), 7.92% yield, LC-MS (ES⁺, m/z): 503.2.

TABLE 1 shows compounds with a 2-phenyl-1-(2,2,2-trifluoroethyl)-1H-indole core.

TABLE 1

| Compound No. | Structure | IUPAC | LC-MS (ES⁺, m/z) |
|---|---|---|---|
| 1A | 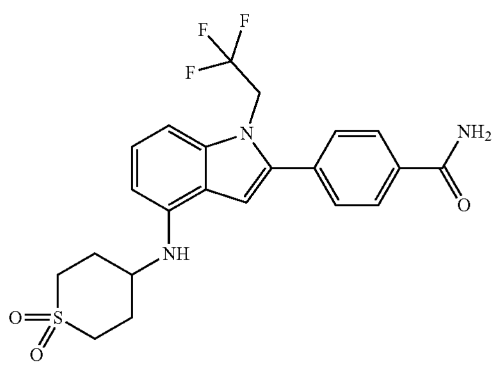 [SMILES: NC(=O)c1ccc(-c2cc3c(NC4CCS(=O)(=O)CC4)cccc3n2CC(F)(F)F)cc1] | 4-{4-[(1,1-dioxo-1λ⁶-thian-4-yl)amino]-1-(2,2,2-trifluoroethyl)-1H-indol-2-yl}benzamide | 466.2 |
| 2A | 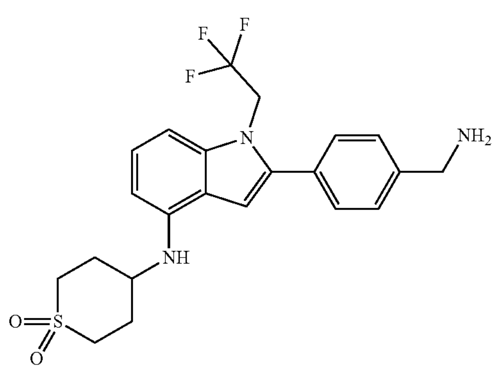 [SMILES: NCc1ccc(-c2cc3c(NC4CCS(=O)(=O)CC4)cccc3n2CC(F)(F)F)cc1] | 4-({2-[4-(aminomethyl)phenyl]-1-(2,2,2-trifluoroethyl)-1H-indol-4-yl}amino)-1λ⁶-thiane-1,1-dione | 452.2 |

TABLE 1-continued

| Compound No. | Structure | IUPAC | LC-MS (ES+, m/z) |
| --- | --- | --- | --- |
| 3A | 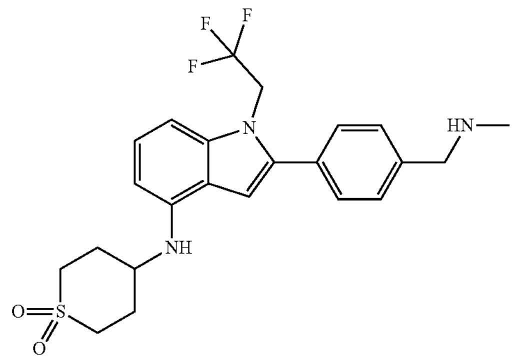 [SMILES: CNCc1ccc(-c2cc3c(NC4CCS(=O)(=O)CC4)cccc3n2CC(F)(F)F)cc1] | 4-[(2-{4-[(methylamino)methyl]phenyl}-1-(2,2,2-trifluoroethyl)-1H-indol-4-yl)amino]-1λ⁶-thiane-1,1-dione | 466.2 |
| 4A | 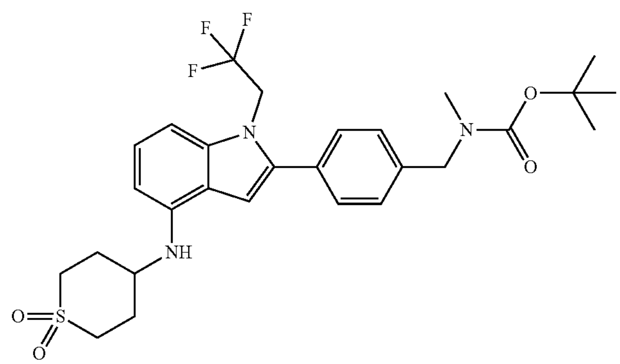 [SMILES: CN(Cc1ccc(-c2cc3c(NC4CCS(=O)(=O)CC4)cccc3n2CC(F)(F)F)cc1)C(=O)OC(C)(C)C] | tert-butyl N-[(4-{4-[(1,1-dioxo-1λ⁶-thian-4-yl)amino]-1-(2,2,2-trifluoroethyl)-1H-indol-2-yl}phenyl)methyl]-N-methylcarbamate | 566.3 |
| 5A | 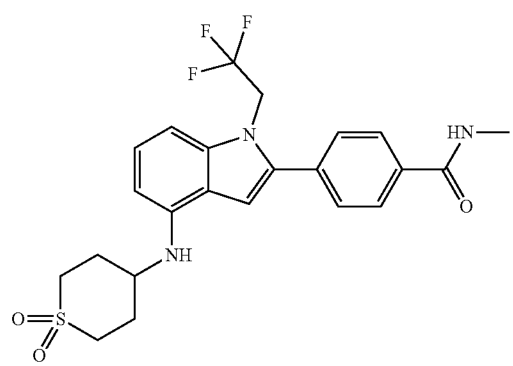 [SMILES: CNC(=O)c1ccc(-c2cc3c(NC4CCS(=O)(=O)CC4)cccc3n2CC(F)(F)F)cc1] | 4-{4-[(1,1-dioxo-1λ⁶-thian-4-yl)amino]-1-(2,2,2-trifluoroethyl)-1H-indol-2-yl}-N-methylbenzamide | 480.2 |
| 6A | 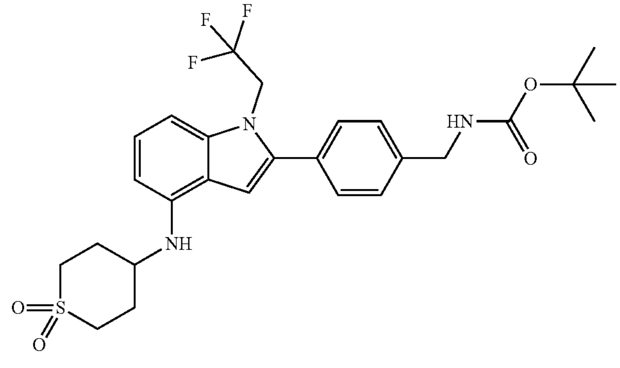 [SMILES: CC(C)(C)OC(=O)NCc1ccc(-c2cc3c(NC4CCS(=O)(=O)CC4)cccc3n2CC(F)(F)F)cc1] | tert-butyl N-[(4-{4-[(1,1-dioxo-1λ⁶-thian-4-yl)amino]-1-(2,2,2-trifluoroethyl)-1H-indol-2-yl}phenyl)methyl]carbamate | 552.3 |

TABLE 1-continued

| Compound No. | Structure | IUPAC | LC-MS (ES+, m/z) |
|---|---|---|---|
| 7A | 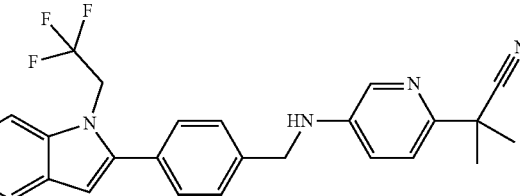 | 2-(5-{[(4-{4-[(1,1-dioxo-1λ6-thian-4-yl)amino]-1-(2,2,2-trifluoroethyl)-1H-indol-2-yl}phenyl)methyl]amino}pyridin-2-yl)-2-methylpropanenitrile | 596.1 |
| 8A | 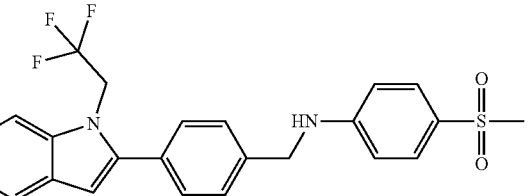 | 4-{[2-(4-{[(4-methanesulfonylphenyl)amino]methyl}phenyl)-1-(2,2,2-trifluoroethyl)-1H-indol-4-yl]amino}-1λ6-thiane-1,1-dione | 606.0 |
| 9A | 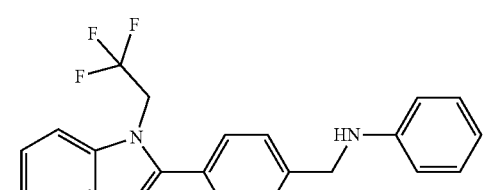 | 4-[(2-{4-[(phenylamino)methyl]phenyl}-1-(2,2,2-trifluoroethyl)-1H-indol-4-yl)amino]-1λ6-thiane-1,1-dione | 528.2 |
| 10A | 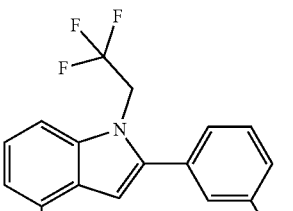 | 3-{4-[(1,1-dioxo-1λ6-thian-4-yl)amino]-1-(2,2,2-trifluoroethyl)-1H-indol-2-yl}benzonitrile | 448.0 |

TABLE 1-continued

| Compound No. | Structure | IUPAC | LC-MS (ES+, m/z) |
|---|---|---|---|
| 11A | 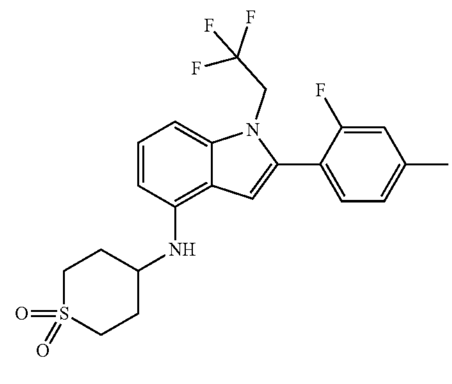 [SMILES: Cc1ccc(-c2cc3c(NC4CCS(=O)(=O)CC4)cccc3n2CC(F)(F)F)c(F)c1] | 4-{[2-(2-fluoro-4-methylphenyl)-1-(2,2,2-trifluoroethyl)-1H-indol-4-yl]amino}-1$\lambda^6$-thiane-1,1-dione | 455.2 |
| 12A | 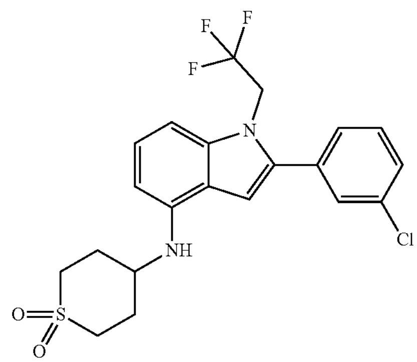 [SMILES: O=S1(=O)CCC(Nc2cccc3c2cc(-c2cccc(Cl)c2)n3CC(F)(F)F)CC1] | 4-{[2-(3-chlorophenyl)-1-(2,2,2-trifluoroethyl)-1H-indol-4-yl]amino}-1$\lambda^6$-thiane-1,1-dione | 457.1 |
| 13A | 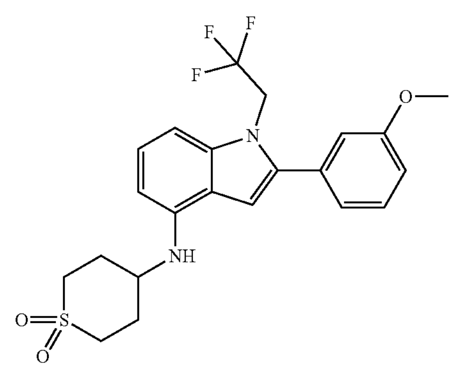 [SMILES: COc1cccc(-c2cc3c(NC4CCS(=O)(=O)CC4)cccc3n2CC(F)(F)F)c1] | 4-{[2-(3-methoxyphenyl)-1-(2,2,2-trifluoroethyl)-1H-indol-4-yl]amino}-1$\lambda^6$-thiane-1,1-dione | 453.2 |
| 14A | 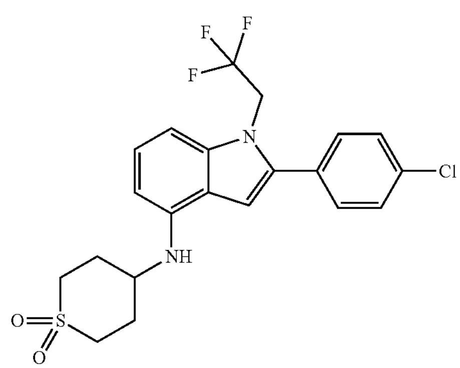 [SMILES: O=S1(=O)CCC(Nc2cccc3c2cc(-c2ccc(Cl)cc2)n3CC(F)(F)F)CC1] | 4-{[2-(4-chlorophenyl)-1-(2,2,2-trifluoroethyl)-1H-indol-4-yl]amino}-1$\lambda^6$-thiane-1,1-dione | 457.1 |

TABLE 1-continued

| Compound No. | Structure | IUPAC | LC-MS (ES+, m/z) |
|---|---|---|---|
| 15A | 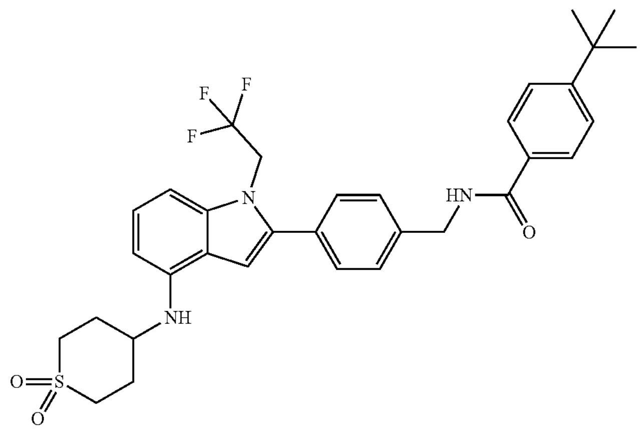 [SMILES: CC(C)(C)c1ccc(C(=O)NCc2ccc(-c3cc4c(NC5CCS(=O)(=O)CC5)cccc4n3CC(F)(F)F)cc2)cc1] | 4-tert-butyl-N-[(4-{4-[(1,1-dioxo-1λ6-thian-4-yl)amino]-1-(2,2,2-trifluoroethyl)-1H-indol-2-yl}phenyl)methyl]benzamide | 612.2 |
| 16A | 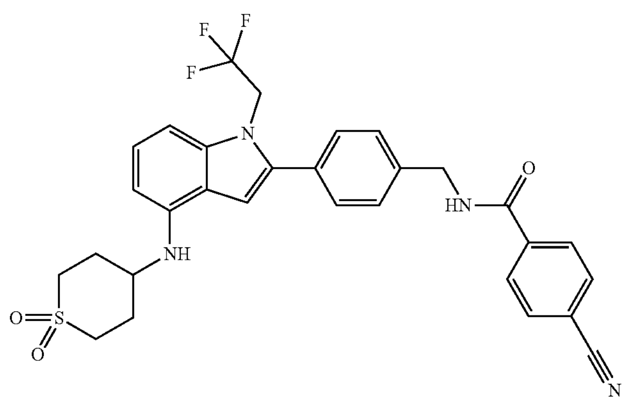 [SMILES: N#Cc1ccc(C(=O)NCc2ccc(-c3cc4c(NC5CCS(=O)(=O)CC5)cccc4n3CC(F)(F)F)cc2)cc1] | 4-cyano-N-[(4-{4-[(1,1-dioxo-1λ6-thian-4-yl)amino]-1-(2,2,2-trifluoroethyl)-1H-indol-2-yl}phenyl)methyl]benzamide | 581.3 |
| 17A | 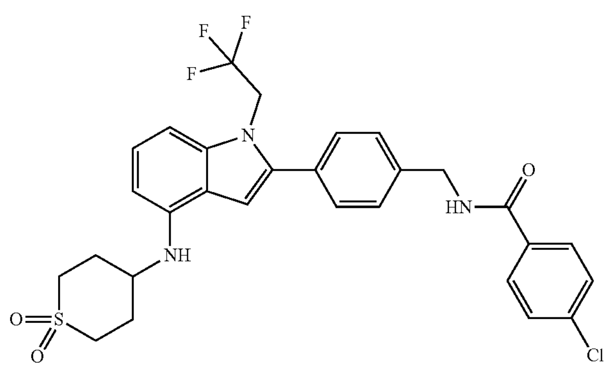 [SMILES: O=C(NCc1ccc(-c2cc3c(NC4CCS(=O)(=O)CC4)cccc3n2CC(F)(F)F)cc1)c1ccc(Cl)cc1] | 4-chloro-N-[(4-{4-[(1,1-dioxo-1λ6-thian-4-yl)amino]-1-(2,2,2-trifluoroethyl)-1H-indol-2-yl}phenyl)methyl]benzamide | 590.3 |
| 18A | 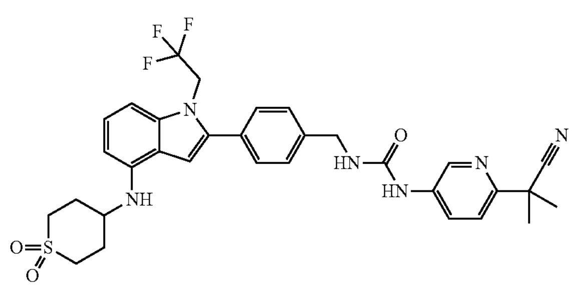 [SMILES: CC(C)(C#N)c1ccc(NC(=O)NCc2ccc(-c3cc4c(NC5CCS(=O)(=O)CC5)cccc4n3CC(F)(F)F)cc2)cn1] | 3-[6-(1-cyano-1-methylethyl)pyridin-3-yl]-1-[(4-{4-[(1,1-dioxo-1λ6-thian-4-yl)amino]-1-(2,2,2-trifluoroethyl)-1H-indol-2-yl}phenyl)methyl]urea | 639.3 |

TABLE 1-continued
| Compound No. | Structure | IUPAC | LC-MS (ES+, m/z) |
|---|---|---|---|
| 19A | 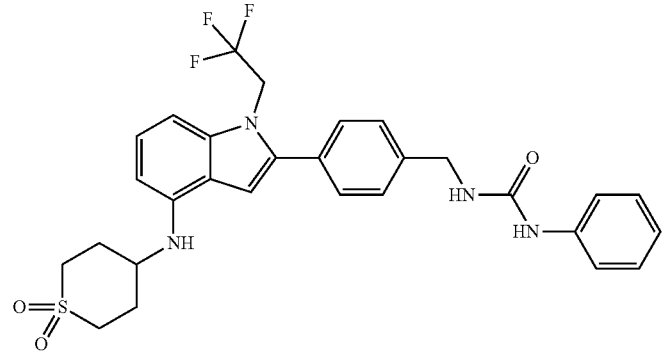 [SMILES: O=C(NCc1ccc(-c2cc3c(NC4CCS(=O)(=O)CC4)cccc3n2CC(F)(F)F)cc1)Nc1ccccc1] | 3-[(4-{4-[(1,1-dioxo-1λ6-thian-4-yl)amino]-1-(2,2,2-trifluoroethyl)-1H-indol-2-yl}phenyl)methyl]-1-phenylurea | 571.3 |
| 20A | 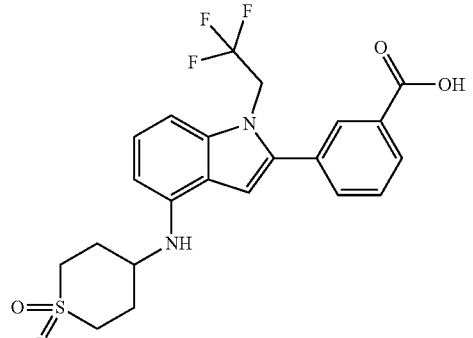 | 3-{4-[(1,1-dioxo-1λ6-thian-4-yl)amino]-1-(2,2,2-trifluoroethyl)-1H-indol-2-yl}benzoic acid | 467.2 |
| 21A | 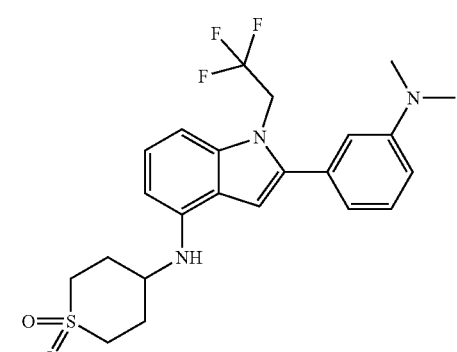 | 4-({2-[3-(dimethylamino)phenyl]-1-(2,2,2-trifluoroethyl)-1H-indol-4-yl}amino)-1λ6-thiane-1,1-dione | 466.2 |
| 22A | 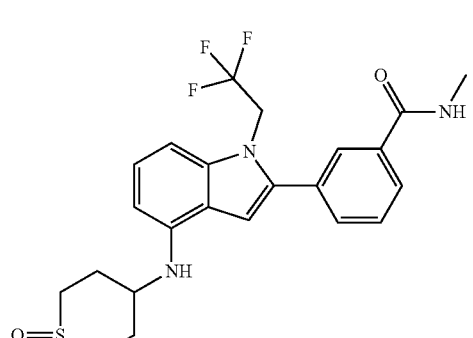 | 3-{4-[(1,1-dioxo-1λ6-thian-4-yl)amino]-1-(2,2,2-trifluoroethyl)-1H-indol-2-yl}-N-methylbenzamide | 480.2 |

TABLE 1-continued

| Compound No. | Structure | IUPAC | LC-MS (ES+, m/z) |
|---|---|---|---|
| 23A | 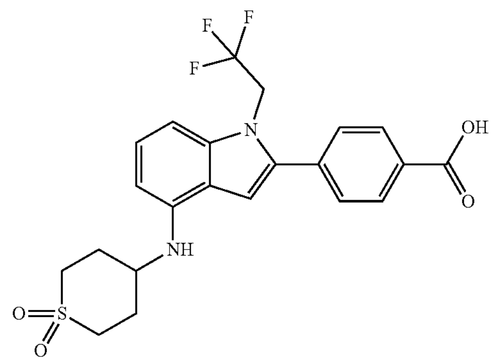 [SMILES: O=C(O)c1ccc(-c2cc3c(NC4CCS(=O)(=O)CC4)cccc3n2CC(F)(F)F)cc1] | 4-{4-[(1,1-dioxo-1λ6-thian-4-yl)amino]-1-(2,2,2-trifluoroethyl)-1H-indol-2-yl}benzoic acid | 467.2 |
| 24A | 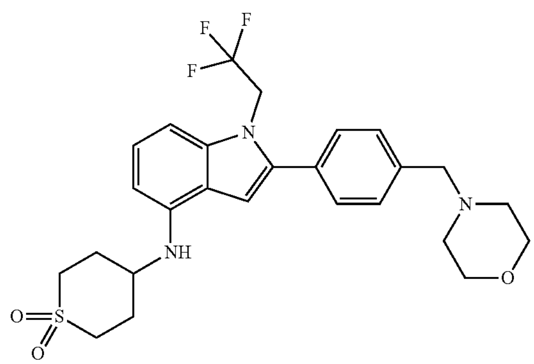 [SMILES: O=S1(=O)CCC(Nc2cccc3c2cc(-c2ccc(CN4CCOCC4)cc2)n3CC(F)(F)F)CC1] | 4-[(2-{4-[(morpholin-4-yl)methyl]phenyl}-1-(2,2,2-trifluoroethyl)-1H-indol-4-yl)amino]-1λ6-thiane-1,1-dione | 522.3 |
| 25A | 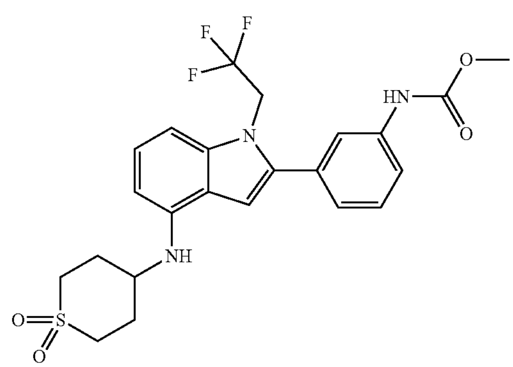 [SMILES: COC(=O)Nc1cccc(-c2cc3c(NC4CCS(=O)(=O)CC4)cccc3n2CC(F)(F)F)c1] | methyl N-(3-{4-[(1,1-dioxo-1λ6-thian-4-yl)amino]-1-(2,2,2-trifluoroethyl)-1H-indol-2-yl}phenyl)carbamate | 496.2 |
| 26A | 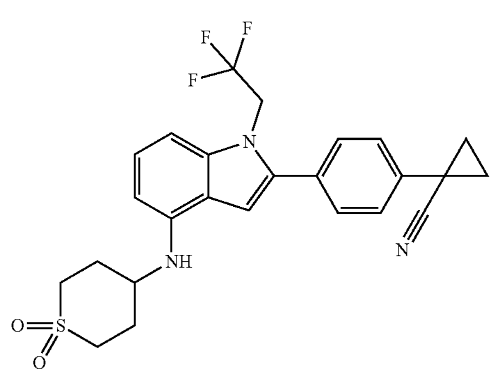 [SMILES: N#CC1(c2ccc(-c3cc4c(NC5CCS(=O)(=O)CC5)cccc4n3CC(F)(F)F)cc2)CC1] | 1-(4-{4-[(1,1-dioxo-1λ6-thian-4-yl)amino]-1-(2,2,2-trifluoroethyl)-1H-indol-2-yl}phenyl)cyclopropane-1-carbonitrile | 488.1 |

TABLE 1-continued

| Compound No. | Structure | IUPAC | LC-MS (ES+, m/z) |
|---|---|---|---|
| 27A | 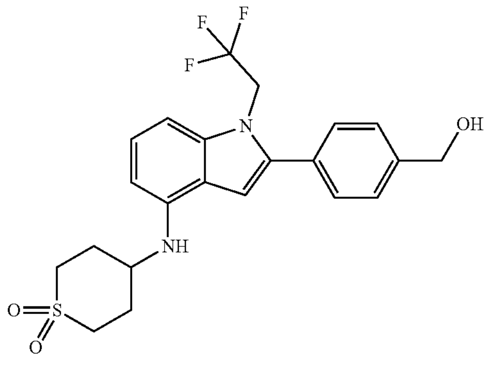 [SMILES: O=S1(=O)CCC(Nc2cccc3c2cc(-c2ccc(CO)cc2)n3CC(F)(F)F)CC1] | 4-({2-[4-(hydroxymethyl)phenyl]-1-(2,2,2-trifluoroethyl)-1H-indol-4-yl}amino)-1λ$^6$-thiane-1,1-dione | 453.2 |
| 28A | 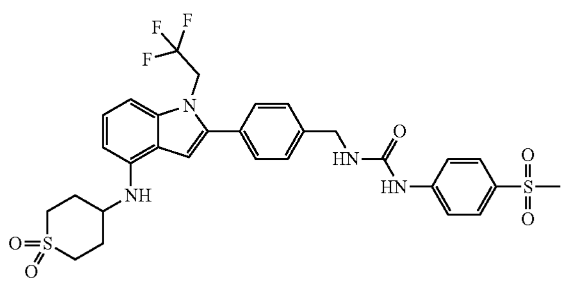 [SMILES: CS(=O)(=O)c1ccc(NC(=O)NCc2ccc(-c3cc4c(NC5CCS(=O)(=O)CC5)cccc4n3CC(F)(F)F)cc2)cc1] | 1-[(4-{4-[(1,1-dioxo-1λ$^6$-thian-4-yl)amino]-1-(2,2,2-trifluoroethyl)-1H-indol-2-yl}phenyl)methyl]-3-(4-methanesulfonylphenyl)urea | 649.1 |
| 29A | 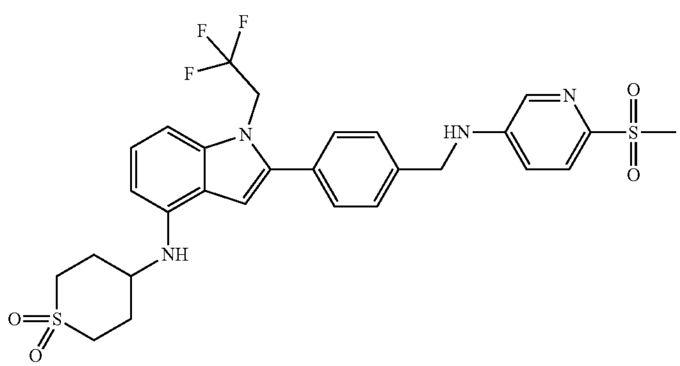 [SMILES: CS(=O)(=O)c1ccc(NCc2ccc(-c3cc4c(NC5CCS(=O)(=O)CC5)cccc4n3CC(F)(F)F)cc2)cn1] | 4-{[2-(4-{[(6-methanesulfonylpyridin-3-yl)amino]methyl}phenyl)-1-(2,2,2-trifluoroethyl)-1H-indol-4-yl]amino}-1λ$^6$-thiane-1,1-dione | 607.2 |
| 30A | 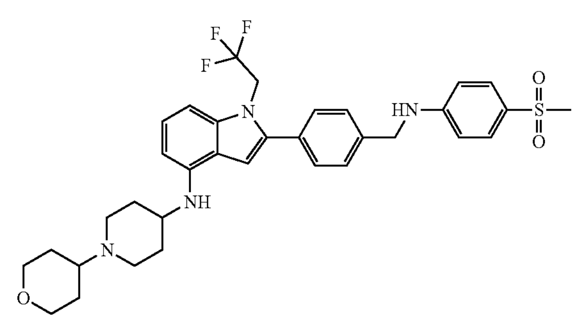 [SMILES: CS(=O)(=O)c1ccc(NCc2ccc(-c3cc4c(NC5CCN(C6CCOCC6)CC5)cccc4n3CC(F)(F)F)cc2)cc1] | 2-(4-{[(4-methanesulfonylphenyl)amino]methyl}phenyl)-N-[1-(oxan-4-yl)piperidin-4-yl]-1-(2,2,2-trifluoroethyl)-1H-indol-4-amine | 641.4 |

TABLE 1-continued

| Compound No. | Structure | IUPAC | LC-MS (ES+, m/z) |
| --- | --- | --- | --- |
| 31A | 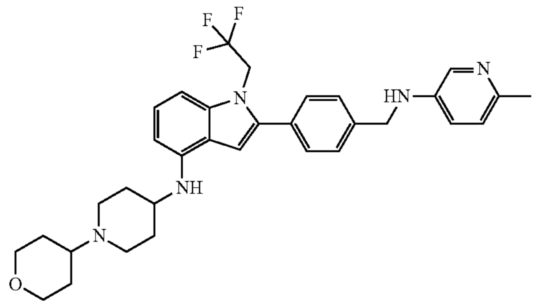 [SMILES: Cc1ccc(NCc2ccc(-c3cc4c(NC5CCN(C6CCOCC6)CC5)cccc4n3CC(F)(F)F)cc2)cn1] | 2-(4-{[(6-methylpyridin-3-yl)amino]methyl}phenyl)-N-[1-(oxan-4-yl)piperidin-4-yl]-1-(2,2,2-trifluoroethyl)-1H-indol-4-amine | 578.4 |
| 32A | 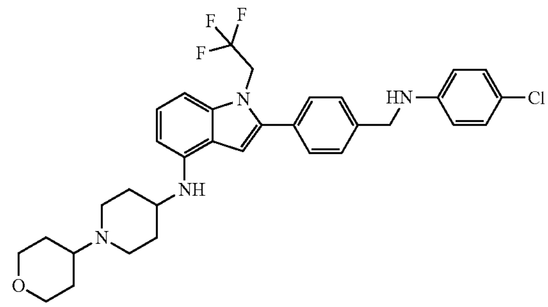 [SMILES: FC(F)(F)Cn1c(-c2ccc(CNc3ccc(Cl)cc3)cc2)cc2c(NC3CCN(C4CCOCC4)CC3)cccc21] | 2-(4-{[(4-chlorophenyl)amino]methyl}phenyl)-N-[1-(oxan-4-yl)piperidin-4-yl]-1-(2,2,2-trifluoroethyl)-1H-indol-4-amine | 597.3 |
| 33A | 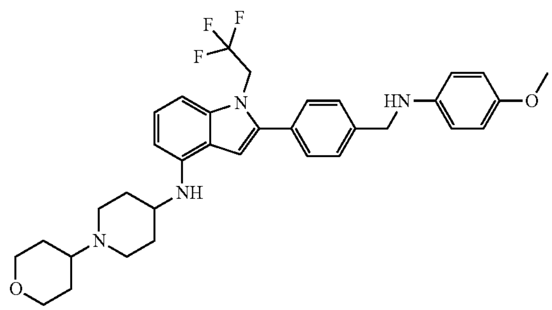 [SMILES: COc1ccc(NCc2ccc(-c3cc4c(NC5CCN(C6CCOCC6)CC5)cccc4n3CC(F)(F)F)cc2)cc1] | 2-(4-{[(4-methoxyphenyl)amino]methyl}phenyl)-N-[1-(oxan-4-yl)piperidin-4-yl]-1-(2,2,2-trifluoroethyl)-1H-indol-4-amine | 593.4 |
| 34A | 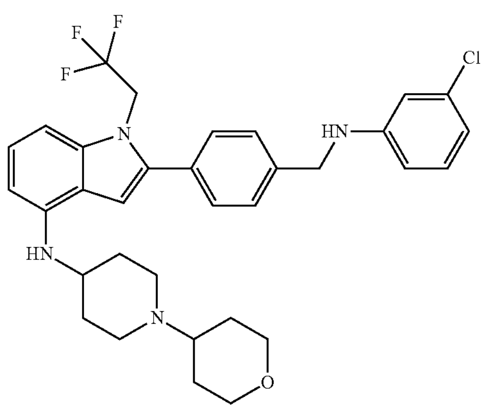 [SMILES: FC(F)(F)Cn1c(-c2ccc(CNc3cccc(Cl)c3)cc2)cc2c(NC3CCN(C4CCOCC4)CC3)cccc21] | 2-(4-{[(3-chlorophenyl)amino]methyl}phenyl)-N-[1-(oxan-4-yl)piperidin-4-yl]-1-(2,2,2-trifluoroethyl)-1H-indol-4-amine | 597.0 |
| 35A | 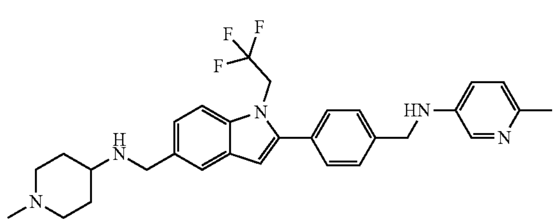 | 6-methyl-N-{[4-(5-{[(1-methylpiperidin-4-yl)amino]methyl}-1-(2,2,2-trifluoroethyl)-1H-indol-2-yl)phenyl]methyl}pyridin-3-amine | 522.2 |

TABLE 1-continued

| Compound No. | Structure | IUPAC | LC-MS (ES+, m/z) |
|---|---|---|---|
| 36A | 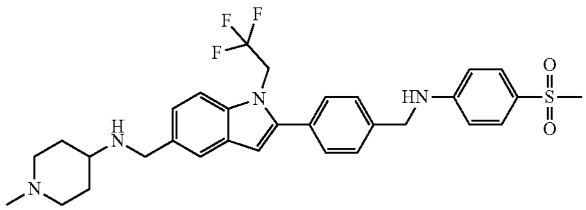 | N-{[2-(4-{[(4-methanesulfonyl-phenyl)amino]meth-yl}phenyl)-1-(2,2,2-trifluoroethyl)-1H-indol-5-yl]methyl}-1-methylpiperidin-4-amine | 585.2 |
| 37A | 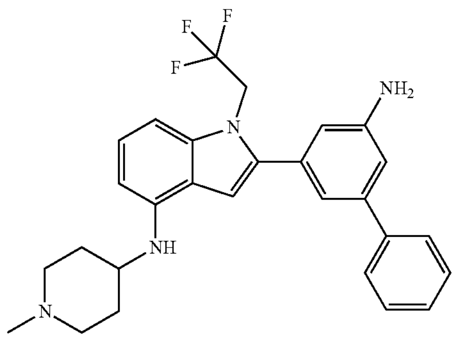 [SMILES: CN1CCC(Nc2cccc3c2cc(-c2cc(N)cc(-c4ccccc4)c2)n3CC(F)(F)F)CC1] | 2-(5-amino-[1,1'-biphenyl]-3-yl)-N-(1-methylpiperidin-4-yl)-1-(2,2,2-trifluoroethyl)-1H-indol-4-amine | 479.3 |
| 38A | 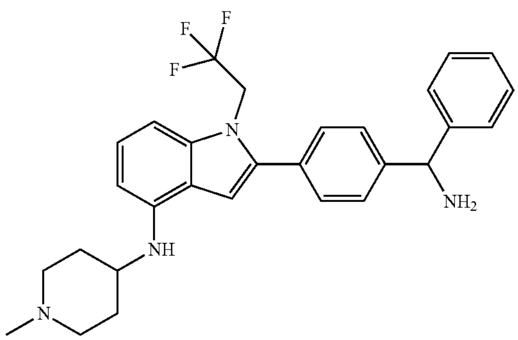 [SMILES: CN1CCC(Nc2cccc3c2cc(-c2ccc(C(N)c4ccccc4)cc2)n3CC(F)(F)F)CC1] | 2-{4-[amino(phenyl)methyl]phenyl}-N-(1-methylpiperidin-4-yl)-1-(2,2,2-trifluoroethyl)-1H-indol-4-amine | 493.3 |
| 39A | 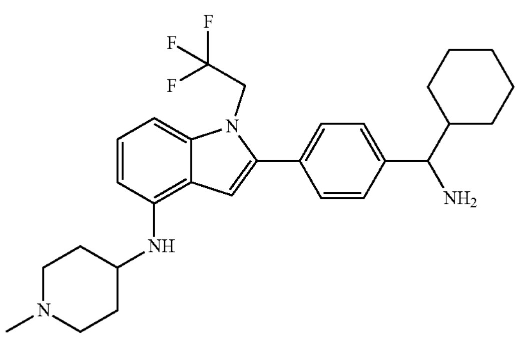 [SMILES: CN1CCC(Nc2cccc3c2cc(-c2ccc(C(N)C4CCCCC4)cc2)n3CC(F)(F)F)CC1] | 2-(4-(amino(cyclohexyl)meth-yl)phenyl)-N-(1-methylpiperidin-4-yl)-1-(2,2,2-trifluoroethyl)-1H-indol-4-amine | 499.3 |
| 40A | 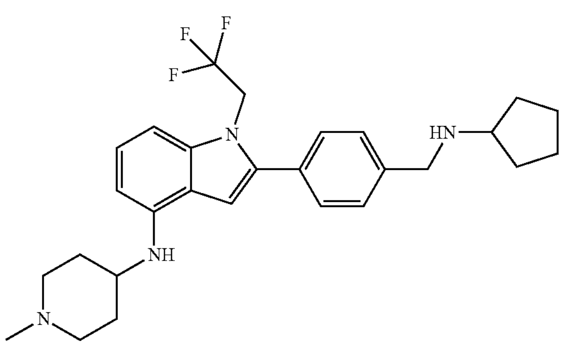 [SMILES: CN1CCC(Nc2cccc3c2cc(-c2ccc(CNC4CCCC4)cc2)n3CC(F)(F)F)CC1] | 2-{4-[(cyclopentylamino)meth-yl]phenyl}-N-(1-methylpiperidin-4-yl)-1-(2,2,2-trifluoroethyl)-1H-indol-4-amine | 485.4 |

TABLE 1-continued

| Compound No. | Structure | IUPAC | LC-MS (ES+, m/z) |
|---|---|---|---|
| 41A | 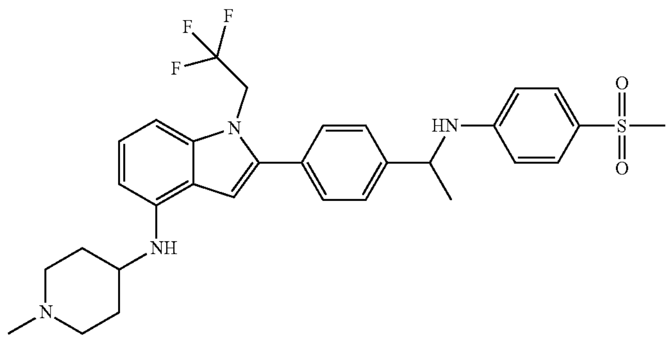 | 2-(4-{1-[(4-methanesulfonyl-phenyl)amino]ethyl}phenyl)-N-(1-methylpiperidin-4-yl)-1-(2,2,2-trifluoroethyl)-1H-indol-4-amine | 585.4 |
| 42A | 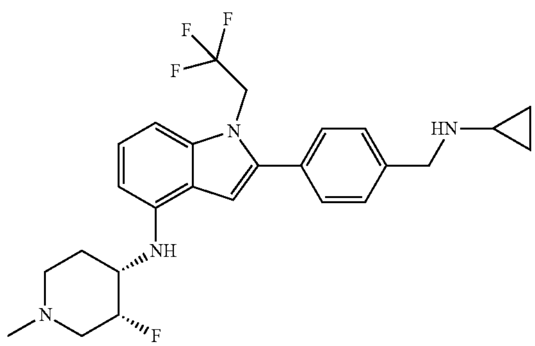 [SMILES: CN1CC[C@H](Nc2cccc3c2cc(-c2ccc(CNC4CC4)cc2)n3CC(F)(F)F)[C@H](F)C1] | (+/−)-2-{4-[(cyclopropyl-amino)methyl]phenyl}-N-[(3R,4S)-3-fluoro-1-methylpiperidin-4-yl]-1-(2,2,2-trifluoroethyl)-1H-indol-4-amine | 475.3 |
| 43A | 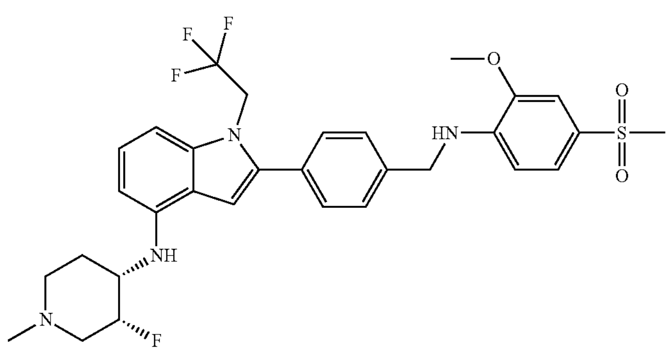 | (+/−)-N-[(3R,4S)-3-fluoro-1-methylpiperidin-4-yl]-2-(4-{[(4-methanesulfonyl-2-methoxyphenyl)amino]meth-yl}phenyl)-1-(2,2,2-trifluoroethyl)-1H-indol-4-amine | 619.2 |
| 44A | 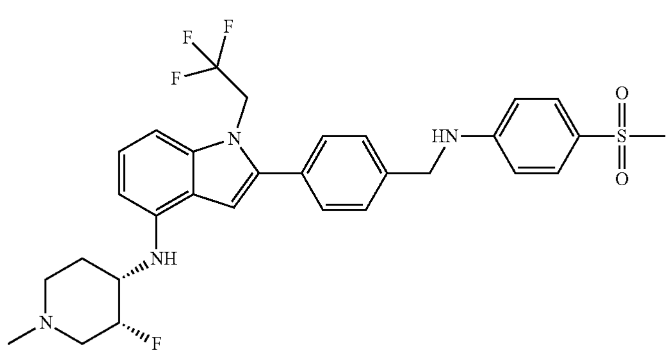 | N-[(3R,4S)-3-fluoro-1-methylpiperidin-4-yl]-2-(4-{[(4-methanesulfonyl-phenyl)amino]meth-yl}phenyl)-1-(2,2,2-trifluoroethyl)-1H-indol-4-amine | 589.2 |

TABLE 1-continued

| Compound No. | Structure | IUPAC | LC-MS (ES+, m/z) |
| --- | --- | --- | --- |
| 45A | 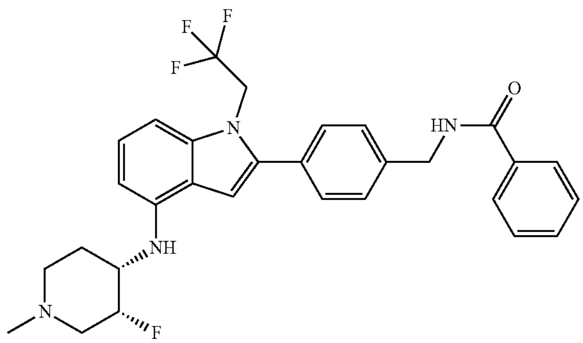 [SMILES: CN1CC[C@H](Nc2cccc3c2cc(-c2ccc(CNC(=O)c4ccccc4)cc2)n3CC(F)(F)F)[C@H](F)C1] | (+/−)-N-{[4-(4-{[(3R,4S)-3-fluoro-1-methylpiperidin-4-yl]amino}-1-(2,2,2-trifluoroethyl)-1H-indol-2-yl)phenyl]methyl}benzamide | 539.2 |
| 46A | 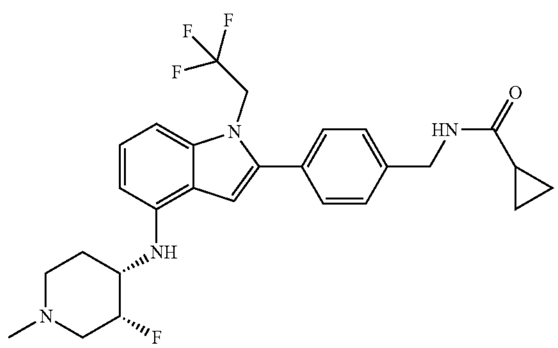 [SMILES: CN1CC[C@H](Nc2cccc3c2cc(-c2ccc(CNC(=O)C4CC4)cc2)n3CC(F)(F)F)[C@H](F)C1] | (+/−)-N-{[4-(4-{[(3R,4S)-3-fluoro-1-methylpiperidin-4-yl]amino}-1-(2,2,2-trifluoroethyl)-1H-indol-2-yl)phenyl]methyl}cyclopropane-carboxamide | 503.2 |
| 47A | 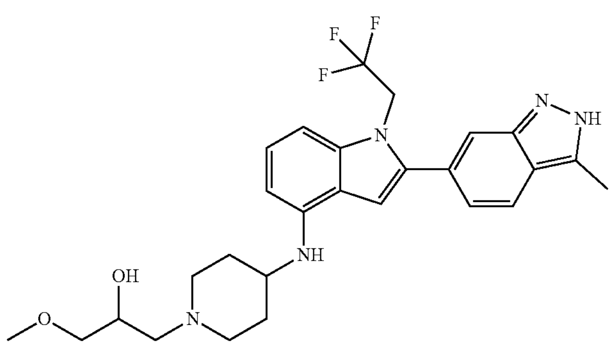 | 1-methoxy-3-(4-{[2-(3-methyl-2H-indazol-6-yl)-1-(2,2,2-trifluoroethyl)-1H-indol-4-yl]amino}piperidin-1-yl)propan-2-ol | 516.2 |
| 48A | 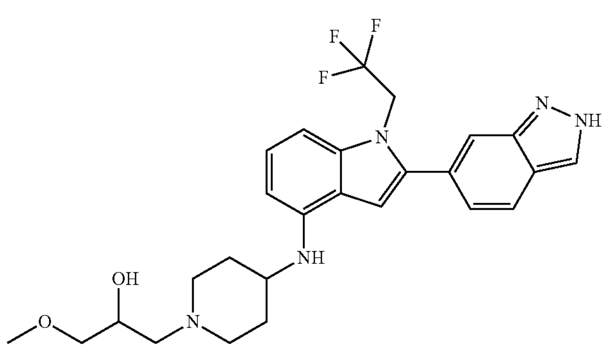 [SMILES: COCC(O)CN1CCC(Nc2cccc3c2cc(-c2ccc4c[nH]nc4c2)n3CC(F)(F)F)CC1] | 1-(4-{[2-(2H-indazol-6-yl)-1-(2,2,2-trifluoroethyl)-1H-indol-4-yl]amino}piperidin-1-yl)-3-methoxypropan-2-ol | 502.2 |

TABLE 1-continued

| Compound No. | Structure | IUPAC | LC-MS (ES+, m/z) |
|---|---|---|---|
| 49A | 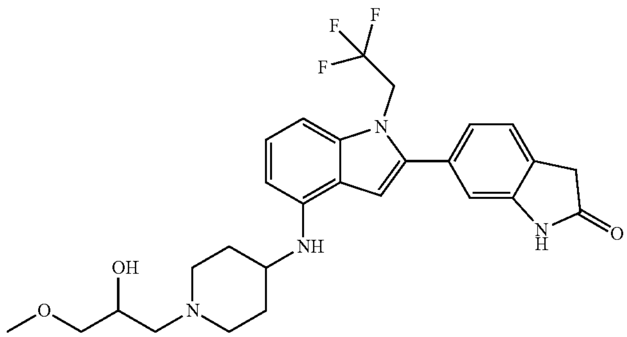 [SMILES: COCC(O)CN1CCC(Nc2cccc3c2cc(-c2ccc4c(c2)NC(=O)C4)n3CC(F)(F)F)CC1] | 4-{[1-(2-hydroxy-3-methoxypropyl)piperidin-4-yl]amino}-1-(2,2,2-trifluoroethyl)-2',3'-dihydro-1H,1'H-[2,6'-biindol]-2'-one | 517.2 |
| 50A | 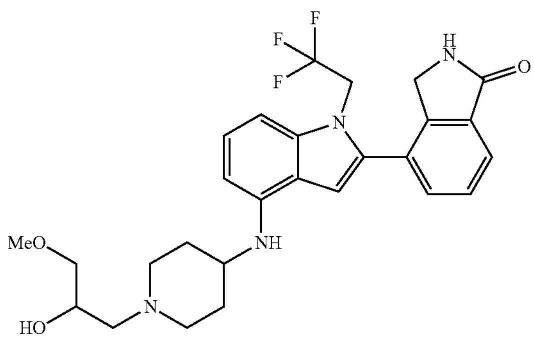 [SMILES: COCC(O)CN1CCC(Nc2cccc3c2cc(-c2cccc4c2CNC4=O)n3CC(F)(F)F)CC1] | 4-(4-((1-(2-hydroxy-3-methoxypropyl)piperidin-4-yl)amino)-1-(2,2,2-trifluoroethyl)-1H-indol-2-yl)isoindolin-1-one | |
| 51A | 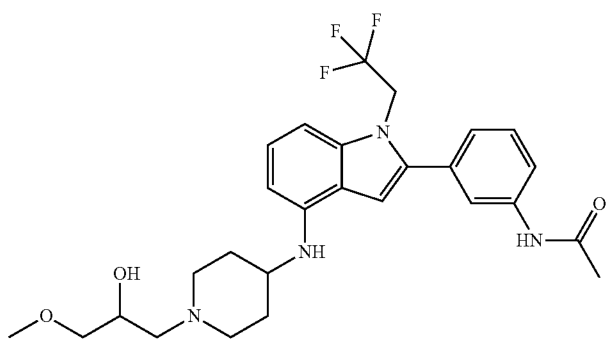 [SMILES: COCC(O)CN1CCC(Nc2cccc3c2cc(-c2cccc(NC(C)=O)c2)n3CC(F)(F)F)CC1] | N-[3-(4-{[1-(2-hydroxy-3-methoxypropyl)piperidin-4-yl]amino}-1-(2,2,2-trifluoroethyl)-1H-indol-2-yl)phenyl]acetamide | 519.2 |

Example 8: Preparation of (+/−)-N-((3S,4R)-3-fluoro-1-methylpiperidin-4-yl)-2-iodo-1-(2,2,2-trifluoroethyl)-1H-indol-4-amine; (+/−)-N-((3R,4R)-3-fluoro-1-methylpiperidin-4-yl)-2-iodo-1-(2,2,2-trifluoroethyl)-1H-indol-4-amine; and 2-iodo-N-(1-methylpiperidin-4-yl)-1-(2,2,2-trifluoroethyl)-1H-indol-4-amine

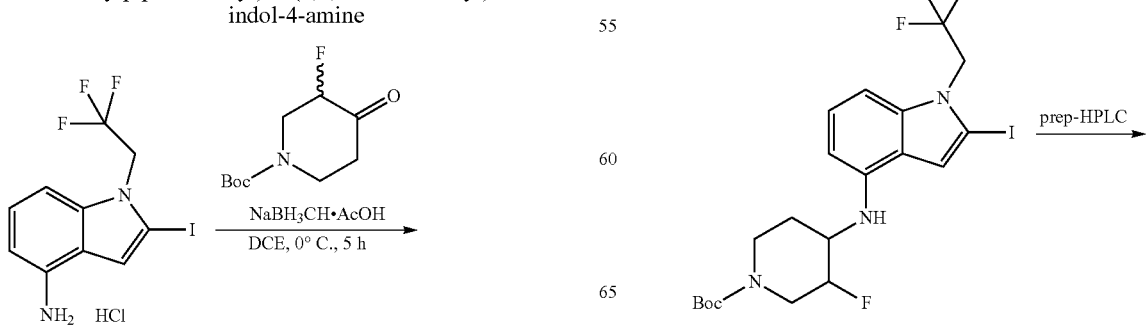

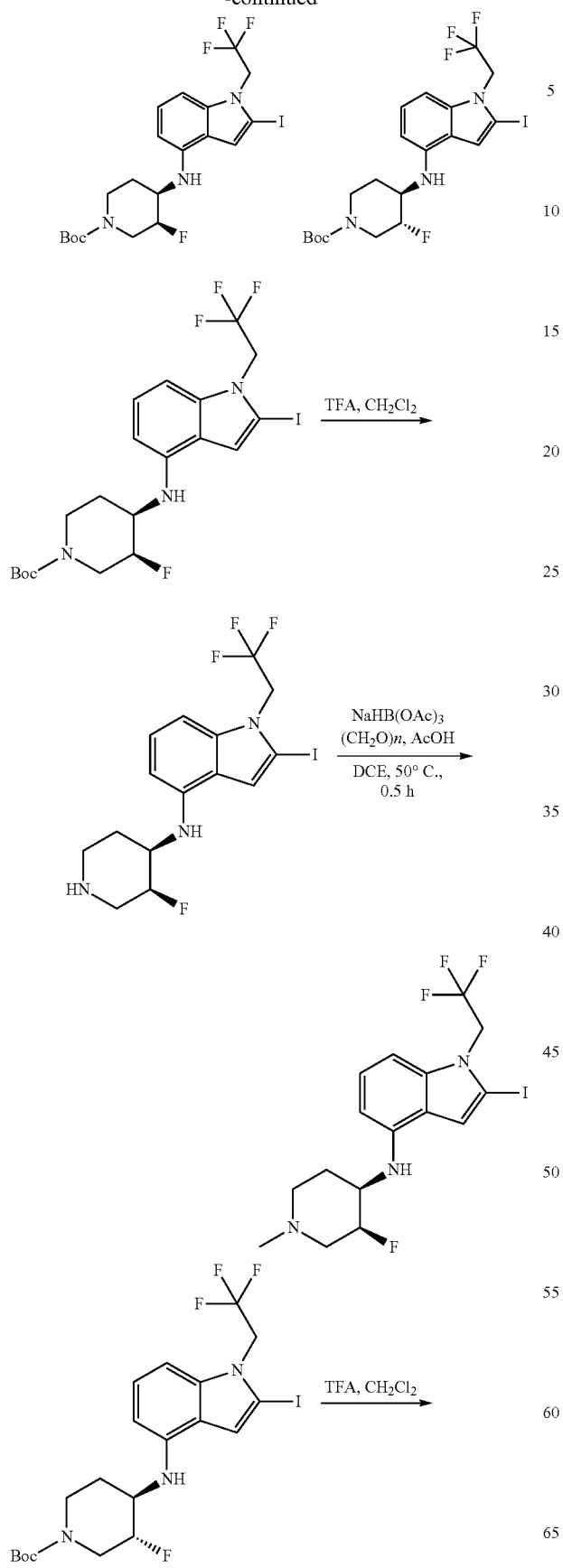

To a solution of 2-iodo-1-(2,2,2-trifluoroethyl)-1H-indol-4-amine (2 g, 5.88 mmol, 1 eq) and tert-butyl-3-fluoro-4-oxopiperidine-1-carboxylate (6.39 g, 29.40 mmol, 5 eq) in a mixture of 1,2-dichloroethane (20 mL) and acetic acid (60 mL) was added Sodium triacetoxyborohydride (6.23 g, 29.40 mmol, 5 eq) at 0° C. The reaction was heated to 50° C. and stirred for 5 hr. The residue was poured into saturated aqueous sodium carbonate to adjust the pH of the mixture to 7-8. The aqueous phase was extracted with EA (500 mL×3). The combined organic phase was washed with brine (500 mL×3), dried with anhydrous sodium sulfate, filtered, and concentrated in vacuo. The crude product was purified by preparative-HPLC (basic conditions) to afford the (+/−)-(3S,4R)-Boc intermediate (9.5 g, 17.55 mmol, 59.7% yield) as a light yellow solid. LC-MS (M+H)=542.0. The (3R,4R)-isomer was also obtained from the HPLC separation.

To a solution of the above (+/−)-(3S,4R)-Boc intermediate (7 g, 12.93 mmol, 1 eq) in DCM (500 mL) was added TFA (17.97 g, 157.57 mmol, 11.67 mL, 12.19 eq). The mixture was stirred at 25° C. for 1 hr. The mixture was quenched by adding aqueous saturated sodium carbonate (500 mL), and the mixture was extracted with DCM (500 mL×2). The organic phase was washed with brine (500 mL), dried with anhydrous sodium sulfate, filtered, and concentrated in vacuo to afford the desired (3S,4R)-deprotected piperidine compound (4 g, crude). LC-MS (M+H$^+$)=441.9.

To a solution of the above (3S,4R)-deprotected piperidine compound (1 g, 2.27 mmol, 1 eq) and paraformaldehyde (340.27 mg, 11.33 mmol, 312.2 μL, 5 eq) in MeOH (10 mL) were added sodium cyanoborohydride (712.14 mg, 11.33 mmol, 5 eq) and acetic acid (136.10 ug, 2.27 μmol, 0.13 μL, 0.001 eq). The mixture was stirred at 50° C. for 30 min. The mixture was extracted with DCM (100 mL×2). The organic phase was washed with brine (100 mL), dried over anhydrous sodium sulfate, filtered, and concentrated in vacuo to afford (+/−)-N-((3S,4R)-3-fluoro-1-methylpiperidin-4-yl)-2-iodo-1-(2,2,2-trifluoroethyl)-1H-indol-4-amine (0.8 g, crude). LC-MS (M+H$^+$)=456.0.

149

(+/−)-N-((3R,4R)-3-fluoro-1-methylpiperidin-4-yl)-2-iodo-1-(2,2,2-trifluoroethyl)-1H-indol-4-amine was obtained using a sequence identical to that above with the (3R,4R)-isomer.

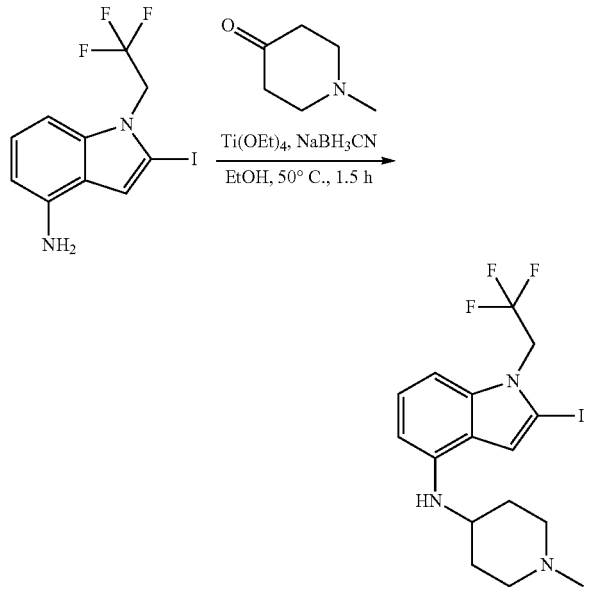

To a solution of 2-iodo-1-(2,2,2-trifluoroethyl)-1H-indol-4-amine (12 g, 35.29 mmol, 1 eq) in ethanol (120 mL) were added N-methyl-4-piperidone (11.98 g, 105.86 mmol, 12.31 mL, 3 eq) and titanium ethoxide (24.15 g, 105.86 mmol, 21.95 mL, 3 eq). The mixture was stirred for 1 hr at 50° C. Then, sodium cyanoborohydride (11.09 g, 176.43 mmol, 5 eq) was added. The mixture was stirred for 0.5 hr at 50° C. The reaction was quenched by adding a saturated aqueous sodium bicarbonate solution (200 mL). The mixture was extracted with EA (100 mL×3). The combined organic phase was washed with brine (100 mL×2), dried with anhydrous sodium sulfate, filtered, and concentrated in vacuo. The crude residue was purified by column chromatography (PE:EA=1:0 to 1:1, then DCM:MeOH=10:1 to 20:1) to provide 2-iodo-N-(1-methylpiperidin-4-yl)-1-(2,2,2-trifluoroethyl)-1H-indol-4-amine (12.5 g, 26.30 mmol, 74.5% yield) as a red-brown solid. LC-MS (ES+, m/z)=438.1.

Example 9: General Procedure for Synthesis of Compounds 1B, 2B, 31B, 41B, 811, 14B, 1511, 16B, and 17B

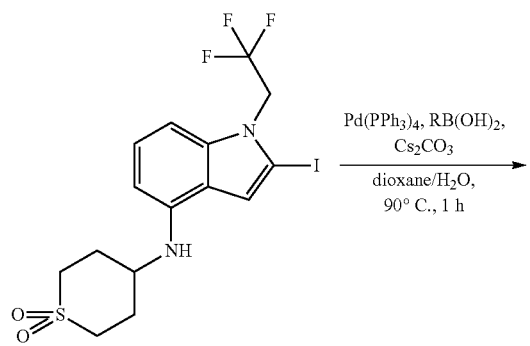

150

-continued

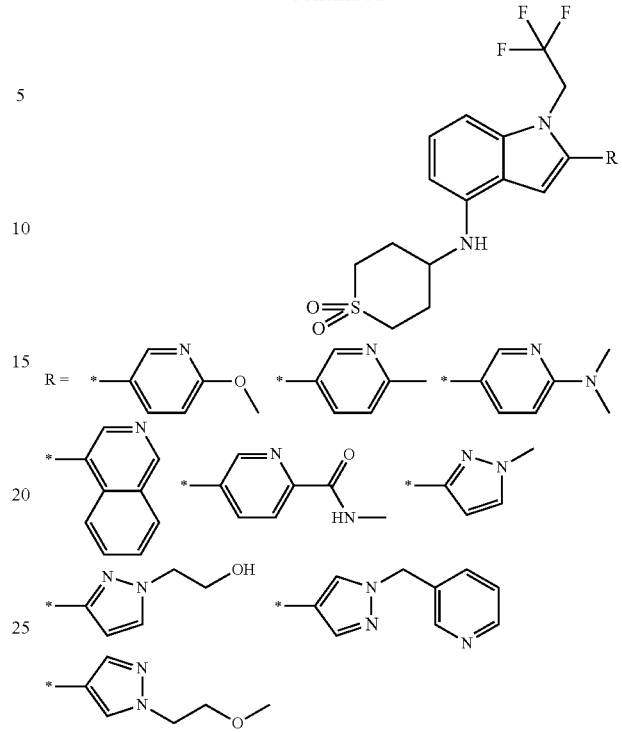

A solution of 4-((2-iodo-1-(2,2,2-trifluoroethyl)-1H-indol-4-yl)amino)tetrahydro-2H-thiopyran-1,1-dioxide (50 mg, 105.87 µmol, 1 eq) was prepared in a mixture of dioxane (1.2 mL) and H$_2$O (300 µL). RB(OH)$_2$, Cs$_2$CO$_3$ (103.48 mg, 317.61 µmol, 3 eq), and Pd(PPh$_3$)$_4$ (24.47 mg, 21.17 µmol, 0.2 eq) were added to the solution under a nitrogen atmosphere. The resulting reaction mixture was stirred at 100° C. for 1 hr under a nitrogen atmosphere. LC-MS analysis was used to monitor reaction completion. The reaction mixture was poured into aqueous 2.0 M EDTA (5 mL), stirred for 2 hr, and extracted twice with DCM (5 mL). The organic phase was washed with water (5 mL) and brine (5 mL), dried with sodium sulfate, filtered, and concentrated in vacuo. The crude residue was purified using preparatory-HPLC to afford the desired R-substituted 4-((1-(2,2,2-trifluoroethyl)-1H-indol-4-yl)amino)tetrahydro-2H-thiopyran-1,1-dioxide compounds.

4-((2-(6-methoxypyridin-3-yl)-1-(2,2,2-trifluoroethyl)-1H-indol-4-yl)amino)tetrahydro-2H-thiopyran-1,1-dioxide (Compound 1B), 34.1% yield, LC-MS (ES+, m/z): 454.2; 4-((2-(6-methylpyridin-3-yl)-1-(2,2,2-trifluoroethyl)-1H-indol-4-yl)amino)tetrahydro-2H-thiopyran-1,1-dioxide (Compound 213), 39.1% yield, LC-MS (ES+, m/z): 438.2; 4-((2-(6-(dimethylamino)pyridin-3-yl)-1-(2,2,2-trifluoroethyl)-1H-indol-4-yl)amino)tetrahydro-2H-thiopyran-1,1-dioxide (Compound 3B), 28.1% yield, LC-MS (ES+, m/z): 467.1; 4-((2-(quinolin-4-yl)-1-(2,2,2-trifluoroethyl)-1H-indol-4-yl)amino)tetrahydro-2H-thiopyran-1,1-dioxide (Compound 4B), 30.5% yield, LC-MS (ES+, m/z): 474.3; 5-(4-((1,1-dioxidotetrahydro-2H-thiopyran-4-yl)amino)-1-(2,2,2-trifluoroethyl)-1H-indol-2-yl)-N-methylpicolinamide (Compound 8B), 21.0% yield, LC-MS (ES+, m/z): 481.2; 4-{[2-(1-methyl-1H-pyrazol-3-yl)-1-(2,2,2-trifluoroethyl)-1H-indol-4-yl]amino}-1λ$^6$-thiane-1,1-dione (Compound 14B), 36.6% yield, LC-MS (ES+, m/z): 427.2; 4-({2-[1-(2-hydroxyethyl)-1H-pyrazol-4-yl]-1-(2,2,2-trifluoroethyl)-1H-indol-4-yl}amino)-1λ$^6$-thiane-1,1-dione (Compound 15B), 22.3% yield, LC-MS (ES+, m/z): 456.9; 4-[(2-{1-[(pyridin-3-yl)methyl]-1H-pyrazol-4-yl}-1-(2,2,2-trifluoroethyl)-1H-indol-4-yl)amino]-1λ⁶-thiane-1,1-dione (Compound 16B), 37.7% yield, LC-MS (ES+, m/z): 504.3; 4-((2-(1-(2-methoxyethyl)-1H-pyrazol-4-yl)-1-(2,2,2-trifluoroethyl)-1H-indol-4-yl)amino)tetrahydro-2H-thiopyran 1,1-dioxide (Compound 171B), 19.0% yield, LC-MS (ES+, m/z): 471.2.

Example 10: Synthesis of Compound 7B

To a solution of 4,6-dichloropyridin-2-anine (1 g, 6.13 mmol, 1 eq) and phenylboronic acid (1.12 g, 9.20 mmol, 1.5 eq) in a mixture of dioxane (20 mL) and water (10 mL) were added cesium carbonate (6 g, 18.40 mmol, 3 eq) and dichloropalladium bis(triphenylphosphine) (861.20 mg, 1.23 mmol, 0.2 eq). The mixture was stirred at 70° C. for 1 hr. The mixture was extracted with DCM (10 mL×2). The organic phase was washed with water (10 mL) and brine (10 mL), dried with anhydrous sodium sulfate, filtered, and concentrated in vacuo. The crude residue was purified by column chromatography (silica gel, PE:EA=10:1) to afford the intermediate, 4-chloro-6-phenylpyridin-2-amine, in 57% yield.

To 4-chloro-6-phenylpyridin-2-amine (200 mg, 977.3 µmol, 1 eq) in dioxane (2 mL) were added bis(pinacolato)diboron (496.32 mg, 1.95 mmol, 2 eq), potassium acetate (287.72 mg, 2.93 mmol, 3 eq), tricyclohexylphosphine (20.55 mg, 73.3 µmol, 23.8 µL, 0.075 eq), and tris(dibenzylideneacetone) dipalladium (44.74 mg, 48.86 µmol, 0.05 eq). The resulting reaction mixture was stirred at 120° C. for 0.5 hr, and the mixture was extracted with DCM (10 mL×2). The organic phase was washed with water (10 mL) and brine (10 mL), dried over anhydrous sodium sulfate, filtered, and concentrated in vacuo to provide 6-phenyl-4-(4,4,5,5-tetramethyl-1,3,2-dioxaborolan-2-yl)pyridin-2-amine.
LC-MS (M+H+)=297.3.

To a solution of 6-phenyl-4-(4,4,5,5-tetramethyl-1,3,2-dioxaborolan-2-yl)pyridin-2-amine (50 mg, 114.4 µmol, 1 eq) and 2-iodo-N-(1-methylpiperidin-4-yl)-1-(2,2,2-trifluoroethyl)-1H-indol-4-amine (36.71 mg, 171.53 µmol, 1.5 eq) in dioxane (2 mL) were added water (0.5 mL), sodium carbonate (36.36 mg, 343.06 µmol, 3 eq), and dichloropalladium bis(triphenylphosphine) (4.18 mg, 5.72 µmol, 0.05 eq). The mixture was stirred at 50° C. for 1 hr. The mixture was poured into 2M EDTA (10 mL) and stirred for 2 hr, then was extracted with DCM (10 mL×2). The organic phase was washed with water (10 mL) and brine (10 mL), dried with anhydrous sodium sulfate, filtered, and concentrated in vacuo. The residue was purified by preparative-HPLC under formic acid conditions to provide the desired product 2-(2-amino-6-phenylpyridin-4-yl)-N-(1-methylpiperidin-4-yl)-1-(2,2,2-trifluoroethyl)-1H-indol-4-amine.

Example 11: 1-tert-butyl-N-{[6-(4-{[(3S,4R)-3-fluoro-1-methylpiperidin-4-yl]amino}-1-(2,2,2-trifluoroethyl)-1H-indol-2-yl)pyridin-3-yl]methyl}-1H-pyrazole-4-carboxamide (Compound 285B)

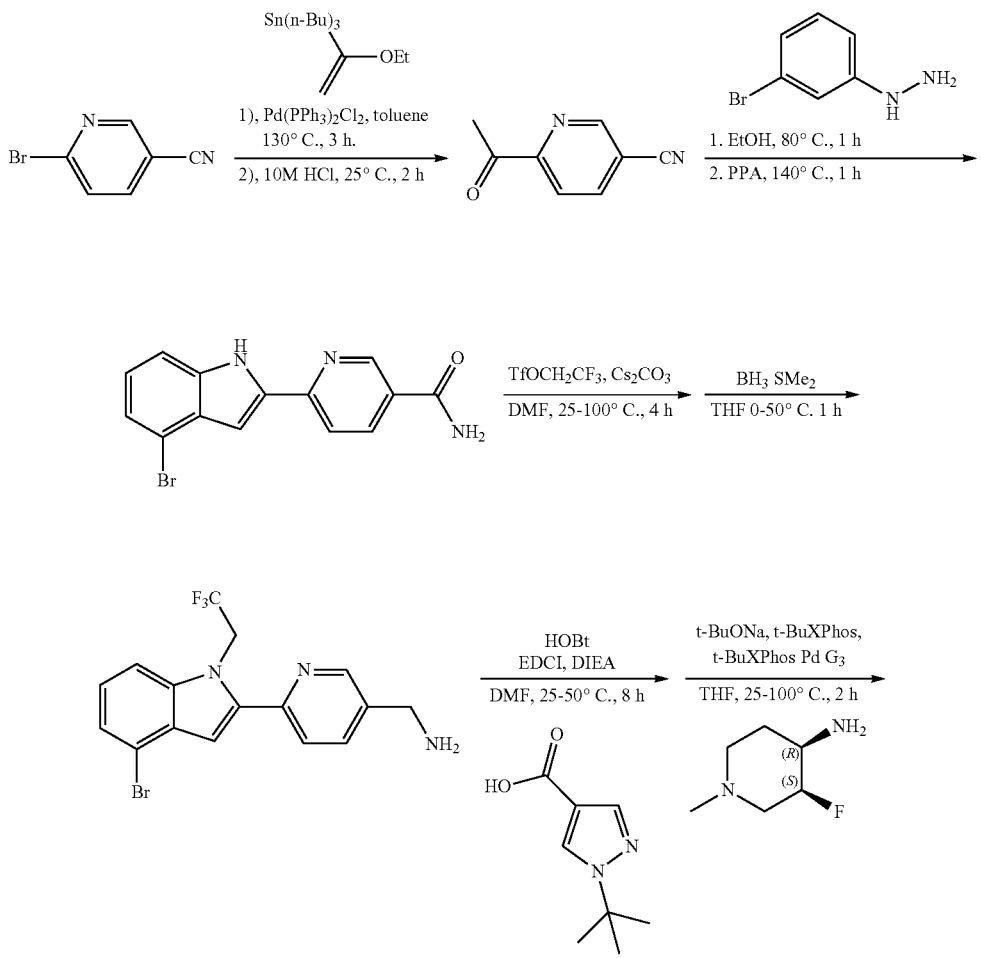

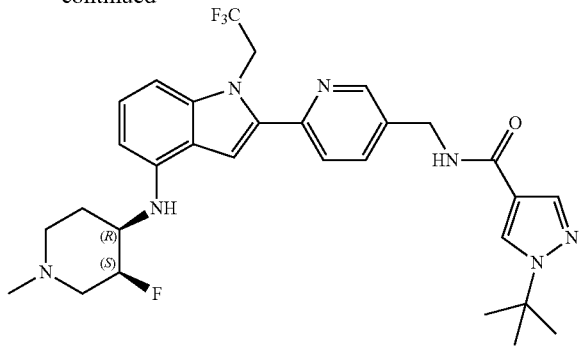

To a mixture of methyl tributyl(1-ethoxyvinyl)stannane (342 mmol, 115 mL, 1.25 eq) and 6-bromopyridine-3-carbonitrile (50 g, 273 mmol, 1 eq) in toluene (500 mL) was added Pd(PPh$_3$)$_2$Cl$_2$ (19.18 g, 27.32 mmol, 0.1 eq) in one portion at 25° C. under nitrogen. The mixture was stirred at 130° C. for 3 h. The reaction mixture was poured into sat. EDTA (100 mL) and stirred for 60 min. The aqueous phase was extracted with EA (3×100 mL). 10 M HCl (100 mL) was added, and the reaction stirred for 2 h, then sat. sodium carbonate was added to adjust the pH of the solution to 7~8. The aqueous phase was extracted with EA (3×100 mL). The combined organic phase was washed with brine (3×100 mL), dried over anhydrous sodium sulfate, filtered, and concentrated in vacuo. The crude product was triturated with methanol at 25° C. for 30 min. The residue was purified by column chromatography (SiO$_2$, PE:EA=4:1 to 1:1) to provide 6-acetylpyridine-3-carbonitrile as a white solid (36 g, 246 mmol, 90.2% yield). LC-MS (ES$^+$, m/z): 147.0 [(M+H)+].

A mixture of 6-acetylpyridine-3-carbonitrile (10 g, 68 mmol, 1 eq), (3-bromophenyl)hydrazine hydrochloride (15.3 g, 68 mmol, 1 eq) in ethanol (100 mL) was degassed and purged with nitrogen 3 times, then the mixture was stirred at 80° C. for 1 h under nitrogen atmosphere. The mixture was evaporated to afford the crude product 6-[(E)-N-(3-bromoanilino)-C-methyl-carbonimidoyl]pyridine-3-carbonitrile as a red solid (20 g, crude). LC-MS (ES$^+$, m/z): 316.9 [(M+H)+].

A mixture of 6-[(E)-N-(3-bromoanilino)-C-methyl-carbonimidoyl]pyridine-3-carbonitrile (20 g, 63.5 mmol, 1 eq), PPA (63.5 mmol, 10 mL, 1 eq) was degassed and purged with nitrogen 3 times, and the mixture was stirred at 140° C. for 1 h under nitrogen atmosphere. The reaction mixture was poured into water (100 mL), then the mixture was adjusted to pH-9 with sat. sodium bicarbonate. The aqueous layer was extracted with EA (4×100 mL). The combined organic layers were washed with brine (1×200 mL), dried over anhydrous sodium sulfate, filtered, and concentrated in vacuo to give a residue. The residue was purified by prep-HPLC (column: Phenomenex luna C18 250 mm×100 mm×10 um; mobile phase: [water (0.225% FA)-ACN]; B %: 30%-60%, 24 min) to provide 6-(4-bromo-1H-indol-2-yl)pyridine-3-carboxamide as a light yellow solid (1 g, 5.0% yield). LC-MS (ES$^+$, m/z): 317.9 [(M+H)+].

To a mixture of 6-(4-bromo-1H-indol-2-yl)pyridine-3-carboxamide (1 g, 3.16 mmol, 1 eq), 2,2,2-trifluoroethyl trifluoromethanesulfonate (881 mg, 3.80 mmol, 1.2 eq) in DMF (10 mL) was added cesium carbonate (721.4 mg, 2.21 mmol, 0.7 eq) in one portion at 0° C. under nitrogen, then the reaction was heated to 100° C. and stirred for 4 h. The residue was poured into water (30 mL). The aqueous phase was extracted with EA (3×20 mL). The combined organic phase was washed with brine (1×30 mL), dried over anhydrous sodium sulfate, filtered, and concentrated in vacuo. The residue was purified by prep-HPLC (column: Phenomenex luna C18 (250×70 mm, 15 um); mobile phase: [water (0.225% FA)-ACN]; B %: 27%-57%, 30 min) to provide 6-[4-bromo-1-(2,2,2-trifluoroethyl)indol-2-yl]pyridine-3-carboxamide as a yellow solid (400 mg, 1 mmol, 31.8% yield). LC-MS (ES$^+$, m/z): 400.0 [(M+H)+]. $^1$H NMR (400 MHz, DMSO-d6) δ=9.12 (d, J=1.9 Hz, 1H), 8.33 (dd, J=2.1, 8.3 Hz, 1H), 8.23 (t, J=8.4 Hz, 2H), 7.80 (d, J=8.3 Hz, 1H), 7.69 (br s, 1H), 7.41 (d, J=7.5 Hz, 1H), 7.31-7.29 (m, 1H), 7.28-7.23 (m, 1H), 6.05 (q, J=8.3 Hz, 2H), 4.02 (q, J=7.1 Hz, 1H), 1.99 (s, 1H), 1.17 (t, J=7.1 Hz, 1H).

To a mixture of 6-[4-bromo-1-(2,2,2-trifluoroethyl)indol-2-yl]pyridine-3-carboxamide (400 mg, 1 mmol, 1 eq) in THF (8 mL) was added borane-dimethyl sulfide complex (10 M, 40 mL, 398 eq) in one portion at 0° C. under nitrogen, then the mixture was heated to 50° C. and stirred for 1 h. The reaction mixture was poured slowly into methanol (15 mL), and concentrated in vacuo to provide [6-[4-bromo-1-(2,2,2-trifluoroethyl)indol-2-yl]-3-pyridyl]methanamine as a yellow solid (300 mg, crude). LC-MS (ES$^+$, m/z): 386.0 [(M+H)$^+$].

[6-[4-bromo-1-(2,2,2-trifluoroethyl)indol-2-yl]-3-pyridyl] methanamine (270 mg, 703 μmol, 1 eq) and 1-tert-butylpyrazole-4-carboxylic acid (130 mg, 774 μmol, 1.1 eq) in DMF (3 mL) were coupled under conditions A. The residue was purified by prep-TLC (SiO$_2$, DCM:methanol=10:1) to provide the desired product 1-tert-butyl-N-{[6-(4-{[(3S,4R)-3-fluoro-1-methylpiperidin-4-yl]amino}-1-(2,2,2-trifluoroethyl)-1H-indol-2-yl)pyridin-3-yl]methyl}-1H-pyrazole-4-carboxamide as a yellow solid (120 mg, 28.4% yield). LC-MS (ESN, m/z): 535.9 [(M+H)]. $^1$H NMR (400 MHz, DMSO-d6) δ=8.68 (br t, J=5.7 Hz, 1H), 8.62 (d, J=1.6 Hz, 1H), 8.31 (s, 1H), 8.06 (d, J=8.2 Hz, 1H), 7.95 (s, 1H), 7.91 (s, 1H), 7.83 (dd, J=2.1, 8.3 Hz, 1H), 7.77 (d, J=8.3 Hz, 1H), 7.38 (d, J=7.6 Hz, 1H), 7.22 (t, J=8.0 Hz, 1H), 7.10 (s, 1H), 6.02 (br d, J=8.9 Hz, 2H), 4.51 (d, J=5.7 Hz, 2H), 1.53 (s, 9H).

TABLE 2 shows a list of compounds prepared with a 2-(pyridine-3-yl)-1H-indole core.

TABLE 2

| Compound No. | Structure | IUPAC | LC-MS (ES+, m/z) |
|---|---|---|---|
| 1B | 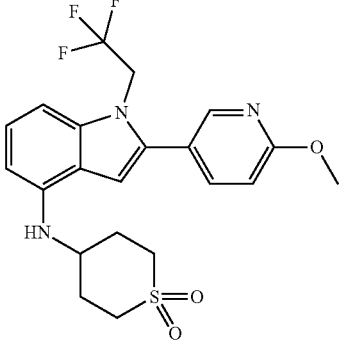 | 4-((2-(6-methoxypyridin-3-yl)-1-(2,2,2-trifluoroethyl)-1H-indol-4-yl)amino)tetrahydro-2H-thiopyran 1,1-dioxide | 454.2 |
| 2B | 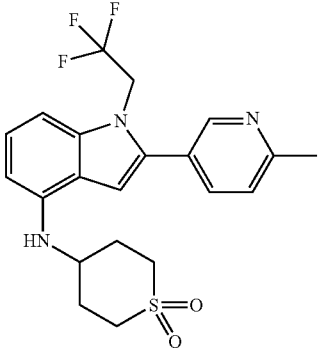 [SMILES: Cc1ccc(-c2cc3c(NC4CCS(=O)(=O)CC4)cccc3n2CC(F)(F)F)cn1] | 4-((2-(6-methylpyridin-3-yl)-1-(2,2,2-trifluoroethyl)-1H-indol-4-yl)amino)tetrahydro-2H-thiopyran 1,1-dioxide | 438.2 |
| 3B | 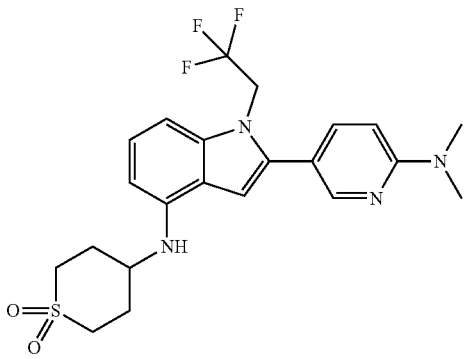 [SMILES: CN(C)c1ccc(-c2cc3c(NC4CCS(=O)(=O)CC4)cccc3n2CC(F)(F)F)cn1] | 4-((2-(6-(dimethylamino)pyridin-3-yl)-1-(2,2,2-trifluoroethyl)-1H-indol-4-yl)amino)tetrahydro-2H-thiopyran 1,1-dioxide | 467.1 |
| 4B | 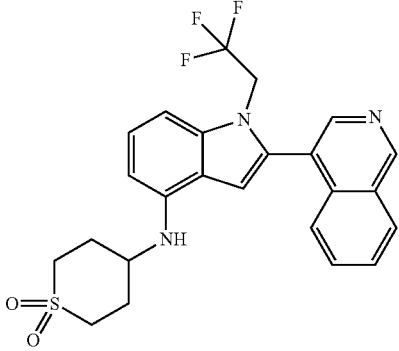 [SMILES: O=S1(=O)CCC(Nc2cccc3c2cc(-c2cncc4ccccc24)n3CC(F)(F)F)CC1] | 4-((2-(quinolin-4-yl)-1-(2,2,2-trifluoroethyl)-1H-indol-4-yl)amino)tetrahydro-2H-thiopyran 1,1-dioxide | 474.3 |

TABLE 2-continued

| Compound No. | Structure | IUPAC | LC-MS (ES+, m/z) |
| --- | --- | --- | --- |
| 5B | 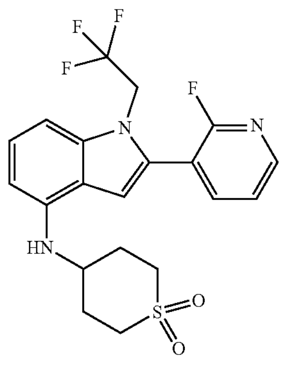 [SMILES: O=S1(=O)CCC(Nc2cccc3c2cc(-c2cccnc2F)n3CC(F)(F)F)CC1] | 4-((2-(2-fluoropyridin-3-yl)-1-(2,2,2-trifluoroethyl)-1H-indol-4-yl)amino)tetrahydro-2H-thiopyran 1,1-dioxide | 442.2 |
| 6B | 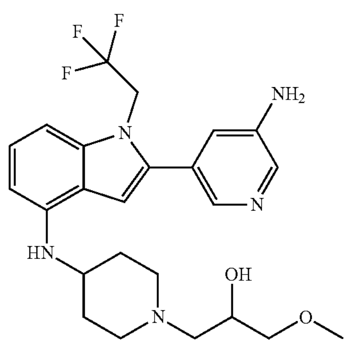 [SMILES: COCC(O)CN1CCC(Nc2cccc3c2cc(-c2cncc(N)c2)n3CC(F)(F)F)CC1] | 1-(4-((2-(5-aminopyridin-3-yl)-1-(2,2,2-trifluoroethyl)-1H-indol-4-yl)amino)piperidin-1-yl)-3-methoxypropan-2-ol | 478.1 |
| 7B | 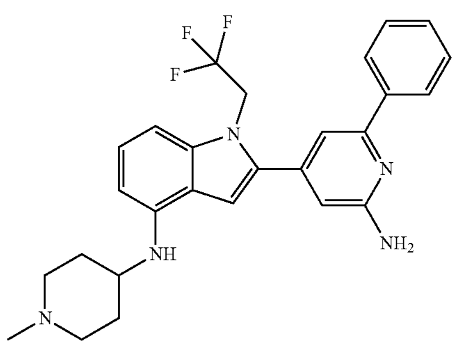 [SMILES: CN1CCC(Nc2cccc3c2cc(-c2cc(N)nc(-c4ccccc4)c2)n3CC(F)(F)F)CC1] | 2-(2-amino-6-phenylpyridin-4-yl)-N-(1-methylpiperidin-4-yl)-1-(2,2,2-trifluoroethyl)-1H-indol-4-amine | 480.1 |
| 8B | 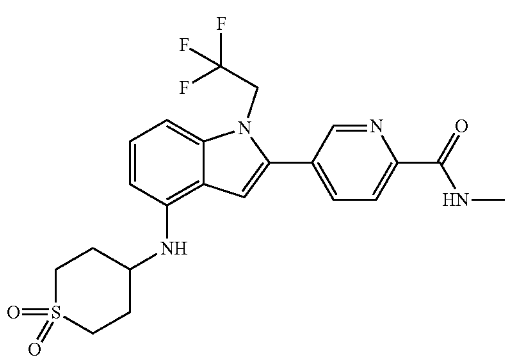 [SMILES: CNC(=O)c1ccc(-c2cc3c(NC4CCS(=O)(=O)CC4)cccc3n2CC(F)(F)F)cn1] | 5-(4-((1,1-dioxidotetrahydro-2H-thiopyran-4-yl)amino)-1-(2,2,2-trifluoroethyl)-1H-indol-2-yl)-N-methylpicolinamide | 481.2 |

TABLE 2-continued

| Compound No. | Structure | IUPAC | LC-MS (ES+, m/z) |
|---|---|---|---|
| 285B | 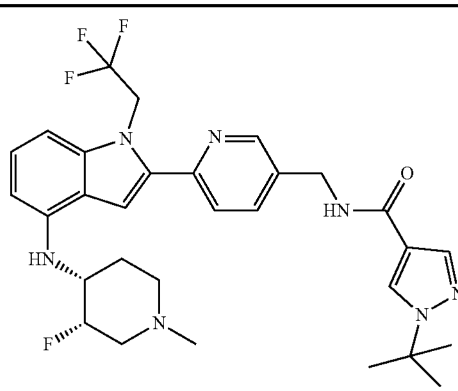 | 1-tert-butyl-N-{[6-(4-{[(3S,4R)-3-fluoro-1-methylpiperidin-4-yl]amino}-1-(2,2,2-trifluoroethyl)-1H-indol-2-yl)pyridin-3-yl]methyl}-1H-pyrazole-4-carboxamide | 586.2 |

Example 12: Synthesis of Compounds 9B, 11B, 12B, and 13B

Compound 11B: To a solution of 4,6-dichloropyridin-2-amine (2 g, 12.20 mmol, 1 eq) and cyclohex-1-en-1-ylboronic acid (1.38 g, 10.98 mmol, 0.9 eq) in a mixture of dioxane (10 mL) an d water (5 mL) were added cesium carbonate (11.92 g, 36.59 mmol, 3 eq) and dichloropalladium bis(triphenylphosphine) (428.01 mg, 609.78 µMol, 0.05 eq). The mixture was stirred at 70° C. for 1 hr. The mixture was poured into 50 mL of water and extracted with DCM (10 mL×2). The organic phase was washed with water (10 mL) and brine (10 mL) dried over anhydrous sodium sulfate, filtered, and concentrated in vacuo. The residue was purified by column chromatography (SiO$_2$, PE:EA=10:1) to afford 4-chloro-6-(cyclohex-1-en-1-yl)pyrimidin-2-amine (1.3 g, 6.20 mmol, 50.84% yield) as a yellow solid.

4-chloro-6-(cyclohex-1-en-1-yl)pyrimidin-2-amine was treated with acetic anhydride (5 eq) in toluene (2 mL) and stirred at 120° C. for 1 hr. The mixture was extracted with DCM (10 mL×2). The organic phase was washed with water (10 mL) and brine (10 mL), dried over anhydrous sodium sulfate, filtered, and concentrated in vacuo to afford N-acetyl-N-(4-chloro-6-(cyclohex-1-en-1-yl)pyrimidin-2-yl)acetamide. LC-MS (M+H)+=252.2.

Compounds 9B, 12B, and 13B: N-acetyl-N-(4-chloro-6-(cyclohex-1-en-1-yl)pyrimidin-2-yl)acetamide (1 eq) was treated with 2-iodo-N-(1-methylpiperidin-4-yl)-1-(2,2,2-trifluoroethyl)-1H-indol-4-amine (1.5 eq), potassium carbonate (2 eq), Pd(dppf)Cl$_2$(0.1 eq), and bis(pinacolato) diboron (1.5 eq), in DMA (2 mL) and water (0.5 mL). The reaction was heated to 140° C. and stirred for 0.1 hr to provide the monoacetyl intermediate, N-(4-(cyclohex-1-en-1-yl)-6-(4-((1-methylpiperidin-4-yl)amino)-1-(2,2,2-trifluoroethyl)-1H-indol-2-yl)pyrimidin-2-yl)acetamide, in 42% yield after purification by preparative-TLC. LC-MS (ES+, m/z)=527.2.

To a solution of N-(4-(cyclohex-1-en-1-yl)-6-(4-((1-methylpiperidin-4-yl)amino)-1-(2,2,2-trifluoroethyl)-1H-indol-2-yl)pyrimidin-2-yl)acetamide (1 eq) in THF (I mL) was added palladium on carbon (1 eq). The reaction was stirred at 25° C. for 0.5 hr under 15 psi of hydrogen gas. The mixture was filtered and poured into 2M aqueous EDTA (10 mL) and stirred for 2 hr. The mixture was extracted with DCM (10 mL×2). The organic phase was washed with water (10 mL) and brine (10 mL), dried over anhydrous sodium sulfate, filtered, and concentrated in vacuo. The residue was purified by TLC to provide N-(4-cyclohexyl-6-(4-((1-methylpiperidin-4-yl)amino)-1-(2,2,2-trifluoroethyl)-1H-indol-2-yl)pyrimidin-2-yl)acetamide in 66% yield.

To a solution of N-(4-cyclohexyl-6-(4-((1-methylpiperidin-4-yl)amino)-1-(2,2,2-trifluoroethyl)-1H-indol-2-yl)pyrimidin-2-yl)acetamide (1 eq) in MeOH (1 mL) were added water (1 mL) and sodium hydroxide (3 eq). The reaction was stirred at 25° C. for 1 hr. The mixture was extracted with DCM (10 mL×2). The organic phase was washed with water (10 mL) and brine (10 mL), dried over anhydrous sodium sulfate, filtered, and concentrated in vacuo. The residue was purified by preparative-HPLC under formic acid conditions to provide the desired compound 2-(2-amino-6-cyclohexylpyrimidin-4-yl)-N-(1-methylpiperidin-4-yl)-1-(2,2,2-trifluoroethyl)-1H-indol-4-amine in 16% yield. LC-MS (M+H+)=487.4.

2-(2-Amino-6-phenylpyrimidin-4-yl)-N-(1-methylpiperidin-4-yl)-1-(2,2,2-trifluoroethyl)-1H-indol-4-amine (Compound 9B), 10% yield, LC-MS (ES+, m/z): 481.3; 2-(2-(methylamino)pyrimidin-4-yl)-N-(1-methylpiperidin-4-yl)-1-(2,2,2-trifluoroethyl)-1H-indol-4-amine (Compound 12B), 4% yield, LC-MS (ES+, m/z): 419.3; 2-(2-aminopyrimidin-4-yl)-N-(1-methylpiperidin-4-yl)-1-(2,2,2-trifluoroethyl)-1H-indol-4-amine (Compound 13B), 4% yield, LC-MS (ES+, m/z): 405.1.

TABLE 3 shows a list of compounds prepared with a 2-(pyrimidin-4-yl)-1H-indole core.

TABLE 3

| Compound No. | Structure | IUPAC | LC-MS (ES⁺, m/z) |
|---|---|---|---|
| 9B | 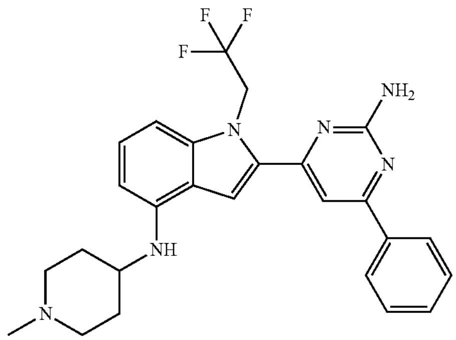 [SMILES: CN1CCC(Nc2cccc3c2cc(-c2cc(-c4ccccc4)nc(N)n2)n3CC(F)(F)F)CC1] | 2-(2-amino-6-phenylpyrimidin-4-yl)-N-(1-methylpiperidin-4-yl)-1-(2,2,2-trifluoroethyl)-1H-indol-4-amine | 481.3 |
| 10B | 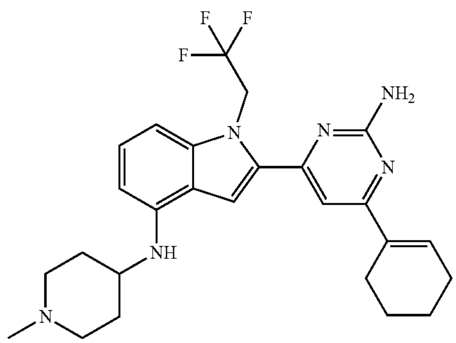 [SMILES: CN1CCC(Nc2cccc3c2cc(-c2cc(C4=CCCCC4)nc(N)n2)n3CC(F)(F)F)CC1] | 2-(2-amino-6-(cyclohex-1-en-1-yl)pyrimidin-4-yl)-N-(1-methylpiperidin-4-yl)-1-(2,2,2-trifluoroethyl)-1H-indol-4-amine | 485.2 |
| 11B | 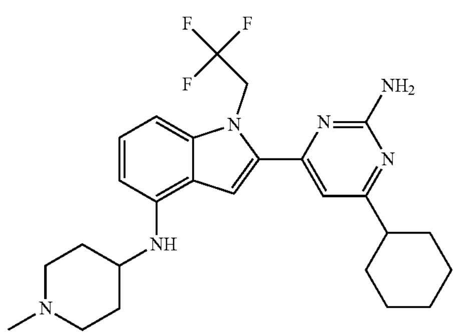 [SMILES: CN1CCC(Nc2cccc3c2cc(-c2cc(C4CCCCC4)nc(N)n2)n3CC(F)(F)F)CC1] | 2-(2-amino-6-cyclohexylpyrimidin-4-yl)-N-(1-methylpiperidin-4-yl)-1-(2,2,2-trifluoroethyl)-1H-indol-4-amine | 487.4 |
| 12B | 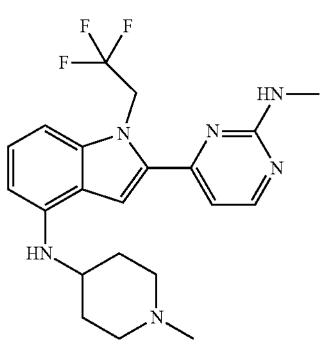 [SMILES: CNc1nccc(-c2cc3c(NC4CCN(C)CC4)cccc3n2CC(F)(F)F)n1] | 2-(2-(methylamino)pyrimidin-4-yl)-N-(1-methylpiperidin-4-yl)-1-(2,2,2-trifluoroethyl)-1H-indol-4-amine | 419.3 |

TABLE 3-continued

| Compound No. | Structure | IUPAC | LC-MS (ES+, m/z) |
|---|---|---|---|
| 13B | 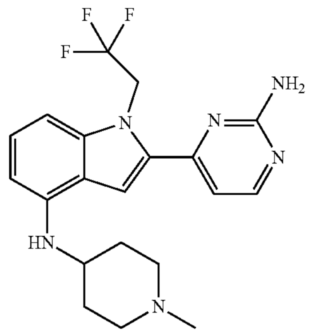 [SMILES: CN1CCC(Nc2cccc3c2cc(-c2ccnc(N)n2)n3CC(F)(F)F)CC1] | 2-(2-aminopyrimidin-4-yl)-N-(1-methylpiperidin-4-yl)-1-(2,2,2-trifluoroethyl)-1H-indol-4-amine | 405.1 |

Example 13: Synthesis of Compound 21B

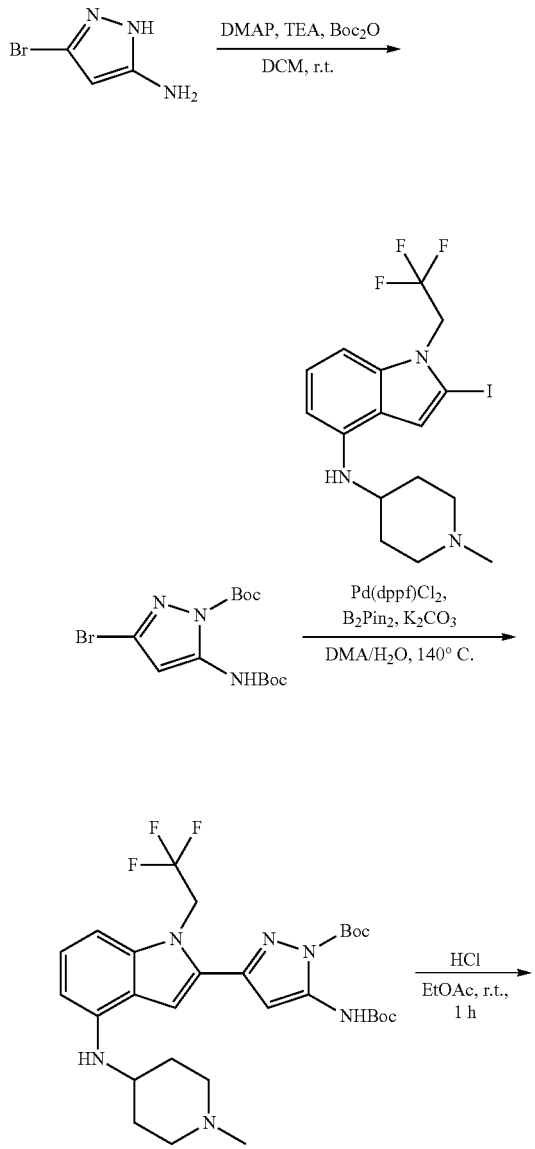

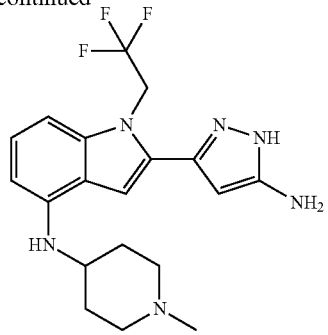

Preparation of tert-butyl 3-bromo-5-((tert-butoxycarbonyl)amino)-1H-pyrazole-1-carboxylate: To a solution of 3-bromo-1H-pyrazol-5-amine (800 mg, 4.94 mmol, 1 eq) and (Boc)$_2$O (2.16 g, 9.88 mmol, 2.27 mL, 2 eq) in DCM (10 mL) were added DMAP (60.3 mg, 493.9 μmol, 0.1 eq) and TEA (999.5 mg, 9.88 mmol, 1.37 mL, 2 eq). The mixture was stirred at 20° C. for 1 hr. TLC analysis showed one major new spot with lower polarity than that of the starting material. The reaction mixture was diluted with water (60 mL) and extracted with EA (20 mL×3). The combined organic layer was washed with brine (10 mL×3), dried over anhydrous sodium sulfate, filtered, and concentrated in vacuo. The residue was purified by column chromatography (SiO$_2$, PE:EA=5:1) to afford tert-butyl 3-bromo-5-((tert-butoxycarbonyl)amino)-1H-pyrazole-1-carboxylate (1 g, 2.76 mmol, 55.90% yield) as a white solid.

Preparation of tert-butyl 5-((tert-butoxycarbonyl)amino)-3-(4-((1-methylpiperidin-4-yl)amino)-1-(2,2,2-trifluoroethyl)-1H-indol-2-yl)-1H-pyrazole-1-carboxylate: To a mixture of 2-iodo-N-(1-methylpiperidin-4-yl)-1-(2,2,2-trifluoroethyl)-1H-indol-4-amine (531.1 mg, 1.21 mmol, 1.1 eq), bis(pinacolato)diboron (420.6 mg, 1.66 mmol, 1.5 eq) and tert-butyl 3-bromo-5-((tert-butoxycarbonyl)amino)-1H-pyrazole-1-carboxylate (400 mg, 1.10 mmol, 1 eq) in a mixture of DMA (2 mL) and H$_2$O (0.5 mL) were added potassium carbonate (305.3 mg, 2.21 mmol, 2 eq) and Pd(dppf)Cl$_2$ (808 mg, 1.10 mmol, 1 eq). The mixture was heated and stirred at 140° C. for 5 min. LC-MS analysis showed several new peaks. The reaction mixture was diluted with H$_2$O (60 mL) and extracted with EA (20 mL×3). The combined organic layer was washed with brine (10 mL×3), dried over anhydrous sodium sulfate, filtered, and concentrated in vacuo. The residue was purified by preparative- TLC (SiO$_2$, DCM:MeOH=10:1) to afford tert-butyl 5-((tert-butoxycarbonyl)amino)-3-(4-((1-methylpiperidin-4-yl)amino)-1-(2,2,2-trifluoroethyl)-1H-indol-2-yl)-1H-pyrazole-1-carboxylate (50 mg, 84.37 μmol, 7.64% yield) as a black-brown solid.

2-(5-amino-1H-pyrazol-3-yl)-N-(1-methylpiperidin-4-yl)-1-(2,2,2-trifluoroethyl)-1H-indol-4-amine: To a solution of tert-butyl 5-((tert-butoxycarbonyl)amino)-3-(4-((1-methylpiperidin-4-yl)amino)-1-(2,2,2-trifluoroethyl)-1H-indol-2-yl)-1H-pyrazole-1-carboxylate (50 mg, 84.4 μmol, 1 eq) in EA (5 mL) was added HCl (12 M, 7.0 μL, 1 eq). The mixture was stirred at 25° C. for 1 hr. LC-MS analysis detected that ~60% of the desired compound had formed. The reaction mixture was filtered, and concentrated in vacuo. The crude residue was purified by preparative-TLC (SiO$_2$, DCM:MeOH=20:1) to afford 2-(5-amino-1H-pyrazol-3-yl)-N-(1-methylpiperidin-4-yl)-1-(2,2,2-trifluoroethyl)-1H-indol-4-amine (Compound 21B) (5.6 mg, 13.41 μmol, 15.90% yield) as a white solid. LC-MS (ES$^+$, m/z): 393.2.

Example 14: Synthesis of Compound 23B

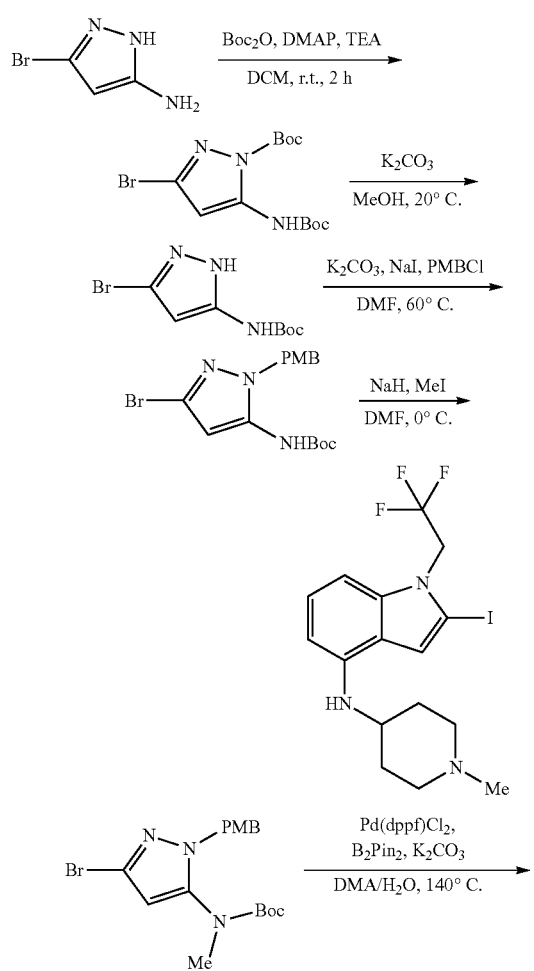

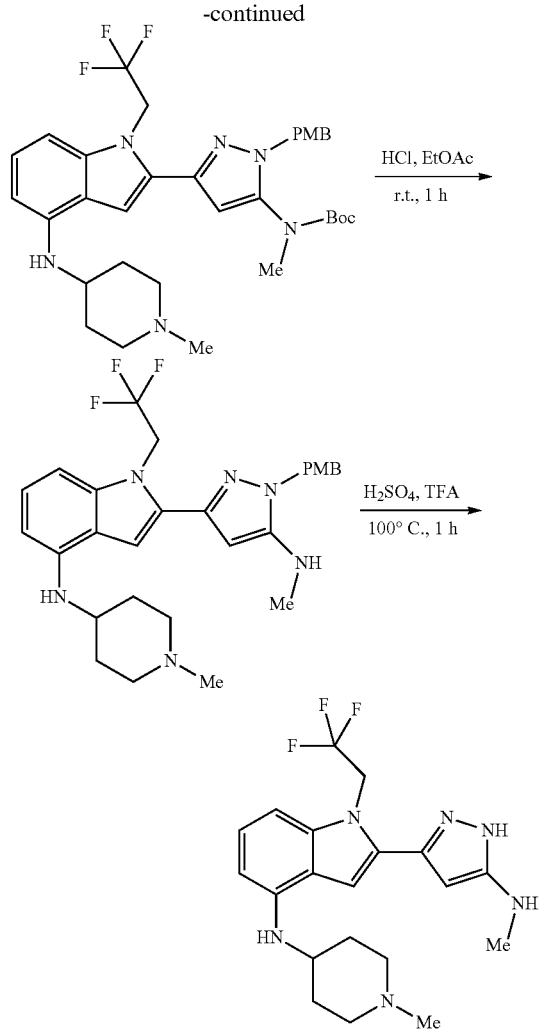

Preparation of tert-butyl 3-bromo-5-((tert-butoxycarbonyl)amino)-1H-pyrazole-1-carboxylate: To a solution of 3-bromo-1H-pyrazol-5-amine (5 g, 30.87 mmol, 1 eq) and (Boc)$_2$O (13.47 g, 61.73 mmol, 14.18 mL, 2 eq) in DCM (20 mL) were added DMAP (377.1 mg, 3.09 mmol, 0.1 eq) and TEA (6.25 g, 61.73 mmol, 8.59 mL, 2 eq). The mixture was stirred at 20° C. for 2 hr. TLC analysis indicated one major new spot with lower polarity than that of the starting material. The reaction mixture was diluted with water (60 mL) and extracted with EA (20 mL×3). The combined organic layer was washed with brine (10 mL×3), dried over anhydrous sodium sulfate, filtered, and concentrated in vacuo. The residue was purified by column chromatography (SiO$_2$, PE/EA=5:1) to afford tert-butyl 3-bromo-5-((tert-butoxycarbonyl)amino)-1H-pyrazole-1-carboxylate (10 g, 27.61 mmol, 89.44% yield) as a white solid.

Preparation of tert-butyl (3-bromo-1H-pyrazol-5-yl)carbamate: To a solution of tert-butyl 3-bromo-5-((tert-butoxycarbonyl)amino)-1H-pyrazole-1-carboxylate (10 g, 27.61 mmol, 1 eq) in MeOH (20 mL) was added potassium carbonate (19.08 g, 138.04 mmol, 5 eq). The mixture was stirred at 20° C. for 1 hr. TLC analysis (PE:EA=3:1, R$_f$=0.2) indicated that ~80% of the starting material remained, and one major new spot with polarity lower than that of the starting material was detected. The reaction mixture was diluted with water (60 mL) and extracted with EA (20 mL×3). The combined organic layer was washed with brine (20 mL×3), dried over anhydrous sodium sulfate filtered, and concentrated in vacuo to afford tert-butyl (3-bromo-1H-pyrazol-5-yl)carbamate (7 g, crude) as a white solid.

Preparation of tert-butyl (3-bromo-1-(4-methoxybenzyl)-1H-pyrazol-5-yl)carbamate: To a solution of tert-butyl (3-bromo-1H-pyrazol-5-yl)carbamate (7 g, 26.71 mmol, 1 eq) in DMF (20 mL) were added potassium carbonate (11.07 g, 80.12 mmol, 3 eq), sodium iodide (8.01 g, 53.41 mmol, 2 eq), and 4-methoxybenzyl chloride (4.18 g, 26.71 mmol, 3.64 mL, 1 eq). The mixture was stirred at 60° C. for 1 hr. The reaction mixture was diluted with water (80 mL) and extracted with EA (20 mL×3). The combined organic layer was washed with brine (20 mL×3), dried over anhydrous sodium sulfate, filtered, and concentrated in vacuo. The crude residue was purified by column chromatography (SiO$_2$, PE:EA=5:1) to afford tert-butyl (3-bromo-1-(4-methoxybenzyl)-1H-pyrazol-5-yl)carbamate (4.2 g, 10.99 mmol, 41.14% yield) as a white solid. LC-MS (ES$^+$, m/z): 383.9.

Preparation of tert-butyl (3-bromo-1-(4-methoxybenzyl)-1H-pyrazol-5-yl)(methyl)carbamate: To a solution of tert-butyl (3-bromo-1-(4-methoxybenzyl)-1H-pyrazol-5-yl)carbamate (4.2 g, 10.99 mmol, 1 eq) in DMF (1 mL) were added sodium hydride (659.3 mg, 16.5 mmol, 60% purity, 1.5 eq) and iodomethane (2.34 g, 16.5 mmol, 1.03 mL, 1.5 eq). The mixture was stirred at 0° C. for 1 hr. LC-MS analysis showed several new peaks, and ~70% of the desired compound was detected. The reaction mixture was diluted with water (60 mL) and extracted with EA (20 mL×3). The combined organic layer was washed with brine (20 mL×3), dried over anhydrous sodium sulfate, filtered, and concentrated in vacuo. The residue was purified by column chromatography (SiO$_2$, PE:EA=5:1) to afford tert-butyl (3-bromo-1-(4-methoxybenzyl)-1H-pyrazol-5-yl)(methyl) carbamate (4 g, 10.09 mmol, 91.87% yield) as a white oil. LC-MS (ES$^+$, m/z): 396.0.

Preparation of tert-butyl (1-(4-methoxybenzyl)-3-(4-((1-methylpiperidin-4-yl)amino)-1-(2,2,2-trifluoroethyl)-1H-indol-2-yl)-1H-pyrazol-5-yl)(methyl)carbamate: To a solution of 2-iodo-N-(1-methylpiperidin-4-yl)-1-(2,2,2-trifluoroethyl)-1H-indol-4-amine (242.74 mg, 555.17 μmol, 1.1 eq), bis(pinacolato)diboron (192.2 mg, 757.0 μmol, 1.5 eq), and tert-butyl (3-bromo-1-(4-methoxybenzyl)-1H-pyrazol-5-yl)(methyl)carbamate (200 mg, 504.7 μmol, 1 eq) in a mixture of DMA (2 mL) and water (0.5 mL) were added potassium carbonate (139.5 mg, 1.01 mmol, 2 eq) and Pd(dppf)Cl$_2$ (369.3 mg, 504.7 μmol, 1 eq). The mixture was stirred at 140° C. for 5 min. The reaction mixture was diluted with water (60 mL) and extracted with EA (20 mL×3). The combined organic layer was washed with brine (20 mL×3), dried over anhydrous sodium sulfate, filtered, and concentrated in vacuo. The residue was purified by column chromatography (SiO$_2$, DCM:MeOH=10:1) to afford tert-butyl (1-(4-methoxybenzyl)-3-(4-((1-methylpiperidin-4-yl)amino)-1-(2,2,2-trifluoroethyl)-1H-indol-2-yl)-1H-pyrazol-5-yl)(methyl)carbamate (80 mg, 127.65 μmol, 25.29% yield) as a black-brown solid. LC-MS (ES$^+$, m/z): 627.3.

Preparation of 2-(1-(4-methoxybenzyl)-5-(methylamino)-1H-pyrazol-3-yl)-N-(1-methylpiperidin-4-yl)-1-(2,2,2-trifluoroethyl)-1H-indol-4-amine: To a solution of tert-butyl (1-(4-methoxybenzyl)-3-(4-((1-methylpiperidin-4-yl)amino)-1-(2,2,2-trifluoroethyl)-1H-indol-2-yl)-1H-pyrazol-5-yl)(methyl)carbamate (80 mg, 127.65 mol, 1 eq) in EA (2 mL) was added 4N HCl in EA. The mixture was stirred at 25° C. for 1 hr. LC-MS analysis showed several new peaks, and ~90% of the desired compound was detected. The reaction mixture was filtered, and concentrated in vacuo to afford 2-(1-(4-methoxybenzyl)-5-(methylamino)-1H-pyrazol-3-yl)-N-(1-methylpiperidin-4-yl)-1-(2,2,2-trifluoroethyl)-1H-indol-4-amine (60 mg, crude) as a black-brown solid. LC-MS (ES$^+$, m/z): 527.1.

Preparation of 2-(5-(methylamino)-1H-pyrazol-3-yl)-N-(1-methylpiperidin-4-yl)-1-(2,2,2-trifluoroethyl)-1H-indol-4-amine: To a solution of 2-(1-(4-methoxybenzyl)-5-(methylamino)-1H-pyrazol-3-yl)-N-(1-methylpiperidin-4-yl)-1-(2,2,2-trifluoroethyl)-1H-indol-4-amine (60 mg, 113.94 μmol, 1 eq) in DCM were added sulfuric acid (11.2 mg, 113.9 μmol, 2.11 μL, 1 eq) and TFA (13 mg, 113.9 μmol, 8.4 μL, 1 eq). The mixture was stirred at 100° C. for 1 hr. The reaction mixture was diluted with water (60 mL) and extracted with EA (20 mL×3). The combined organic layers were washed with brine (20 mL×3), dried over anhydrous sodium sulfate, filtered, and concentrated in vacuo. The residue was purified by preparative-TLC (DCM:MeOOH=10:1) to afford 2-(5-(methylamino)-1H-pyrazol-3-yl)-N-(1-methylpiperidin-4-yl)-1-(2,2,2-trifluoroethyl)-1H-indol-4-amine (Compound 23B) (6.5 mg, 16.0 μmol, 14.04% yield) as a white solid. LC-MS (ES$^+$, m/z): 407.1.

Example 15: Synthesis of Compound 22B

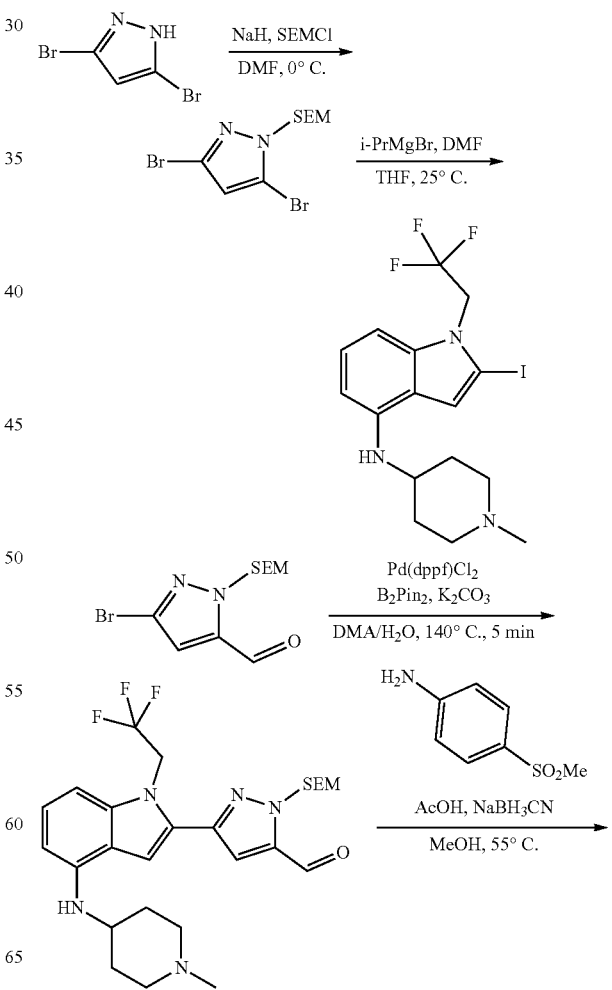

-continued

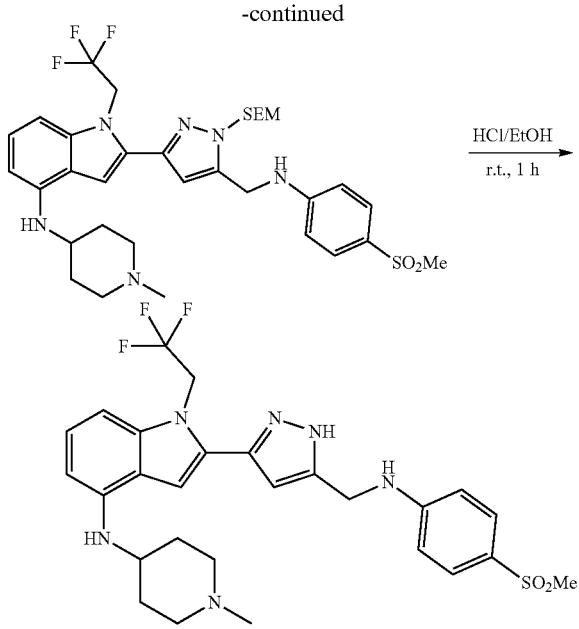

Preparation of 3,5-dibromo-1-((2-(trimethylsilyl)ethoxy)methyl)-1H-pyrazole: To a solution of 3,5-dibromo-1H-pyrazole in DMF (20 mL) was added sodium hydride (slow addition, 708.3 mg, 17.7 mmol, 60% purity, 2 eq) at 0° C. The reaction mixture was stirred at 0° C. for 0.5 hr, and SEMCI (1.92 g, 11.5 mmol, 2.04 mL, 1.3 eq) was added dropwise at 0° C. The resulting mixture was stirred at 0° C. for 2 hr. and one new spot was detected. The reaction mixture was quenched with aqueous saturated ammonium chloride (35 mL) and extracted with EA (50 mL×3). The combined organic layers were washed with brine (30 mL×3), dried over anhydrous sodium sulfate, filtered, and concentrated in vacuo. The crude residue was purified by column chromatography (SiO$_2$, PE:EA=1:0 to 0:1) to afford 3,5-dibromo-1-((2-(trimethylsilyl)ethoxy)methyl)-1H-pyrazole (3.1 g, 6.53 mmol, 73.73% yield) as a colorless oil.

Preparation of 3-bromo-1-((2-(trimethylsilyl)ethoxy)methyl)-1H-pyrazole-5-carbaldehyde: To a solution 3,5-dibromo-1-((2-(trimethylsilyl)ethoxy)methyl)-1H-pyrazole in THF (3 mL) was added isopropylmagnesium bromide (2 M, 1.68 mL, 2 eq). The mixture was stirred at 25° C. for 1 hr. DMF (369 mg, 5.05 mmol, 390 µL, 3 eq) was added to the reaction, and the mixture was stirred further at 25° C. for 1 hr. The reaction mixture was diluted with water (20 mL) and extracted with EA (30 mL×3). The combined organic layers were washed with brine (15 mL×3), dried over anhydrous sodium sulfate, filtered, and concentrated in vacuo. The residue was purified by preparative-TLC (SiO$_2$, PE:EA=5:1) to afford 3-bromo-1-((2-(trimethylsilyl)ethoxy)methyl)-1H-pyrazole-5-carbaldehyde (0.4 g, 1.18 mmol, 70% yield) as a colorless oil.

Preparation of 3-(4-((1-methylpiperidin-4-yl)amino)-1-(2,2,2-trifluoroethyl)-1H-indol-2-yl)-1-((2-(trimethylsilyl)ethoxy)methyl)-1H-pyrazole-5-carbaldehyde: To a solution of 3-bromo-1-((2-(trimethylsilyl)ethoxy)methyl)-1H-pyrazole-5-carbaldehyde and 2-iodo-N-(1-methylpiperidin-4-yl)-1-(2,2,2-trifluoroethyl)-1H-indol-4-amine (374.4 mg, 1.47 mmol, 1.5 eq) in a mixture of DMA (2 mL) and H$_2$O (0.5 mL) were added bis(pinacolato)diboron (374.4 mg, 1.47 mmol, 1.5 eq), potassium carbonate (271.7 mg, 1.97 mmol, 2 eq) and Pd(dppf)Cl$_2$ (719.1 mg, 982.8 µmol, 1 eq). The mixture was stirred at 140° C. for 5 min. The reaction mixture was diluted with water (20 mL) and extracted with EA (20 mL×3). The combined organic layer was washed with brine (15 mL×3), dried over anhydrous sodium sulfate, filtered, and concentrated in vacuo. The residue was purified by preparative-TLC (SiO$_2$, EA:TEA:MeOH=20:1:1) to afford 3-(4-((1-methylpiperidin-4-yl)amino)-1-(2,2,2-trifluoroethyl)-1H-indol-2-yl)-1-((2-(trimethylsilyl)ethoxy)methyl)-1H-pyrazole-5-carbaldehyde (0.03 g, 47.60 µmol, 70% yield) as a yellow oil.

Preparation of N-(1-methylpiperidin-4-yl)-2-(5-(((4-(methylsulfonyl)phenyl)amino)methyl)-1-((2-(trimethylsilyl)ethoxy)methyl)-1H-pyrazol-3-yl)-1-(2,2,2-trifluoroethyl)-1H-indol-4-amine: To a solution of 3-(4-((1-methylpiperidin-4-yl)amino)-1-(2,2,2-trifluoroethyl)-1H-indol-2-yl)-1-((2-(trimethylsilyl)ethoxy)methyl)-1H-pyrazole-5-carbaldehyde and 4-(methylsulfonyl)aniline in MeOH (3 mL) was added acetic acid (5.6 mg, 93.3 mol, 5.34 µL, 1 eq) at 55° C. The mixture was stirred, and sodium cyanoborohydride (29.3 mg, 466.7 µmol, 5 eq) was added at 55° C. The resulting mixture was stirred further at 55° C. for 1 hr. The reaction mixture was diluted with water (10 mL) and extracted with EA (20 mL×3). The combined organic layers were washed with brine (10 mL×3), dried over anhydrous sodium sulfate, filtered, and concentrated in vacuo. The residue was purified by preparative-TLC (SiO$_2$, EA:TEA:MeOH=20:1: 1) to afford N-(1-methylpiperidin-4-yl)-2-(5-(((4-(methylsulfonyl)phenyl)amino)methyl)-1-((2-(trimethylsilyl)ethoxy)methyl)-1H-pyrazol-3-yl)-1-(2,2,2-trifluoroethyl)-1H-indol-4-amine (0.055 g, 67.7 mol, 72.5% yield) as a white solid.

Preparation of N-(1-methylpiperidin-4-yl)-2-(5-(((4-(methylsulfonyl)phenyl)amino)methyl)-1H-pyrazol-3-yl)-1-(2,2,2-trifluoroethyl)-1H-indol-4-amine: A solution of N-(1-methylpiperidin-4-yl)-2-(5-(((4-(methylsulfonyl)phenyl)amino)methyl)-1-((2-(trimethylsilyl)ethoxy)methyl)-1H-pyrazol-3-yl)-1-(2,2,2-trifluoroethyl)-1H-indol-4-amine and hydrochloric acid (12 M, 36.2 µL, 5 eq) were prepared in ethanol (1 mL). The mixture was stirred at 20° C. for 1 hr. The reaction mixture was quenched by adding aqueous saturated sodium bicarbonate. The pH of the mixture was adjusted to 7-8, and the reaction mixture was diluted with water (10 mL) and extracted with EA (30 mL×3). The combined organic layer was washed with brine (15 mL×3), dried over anhydrous sodium sulfate, filtered, and concentrated in vacuo. The crude residue was purified by preparative-HPLC to afford N-(1-methylpiperidin-4-yl)-2-(5-(((4-(methylsulfonyl)phenyl)amino)methyl)-1H-pyrazol-3-yl)-1-(2,2,2-trifluoroethyl)-1H-indol-4-amine (Compound 22B) as a yellow solid in 24.7% yield. LC-MS (ES$^-$, m/z): 561.3.

Example 16: Synthesis of Compound 19B

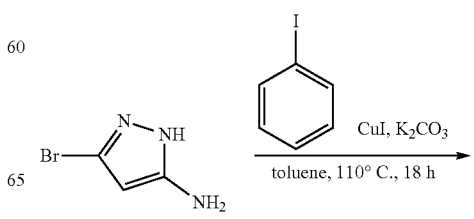

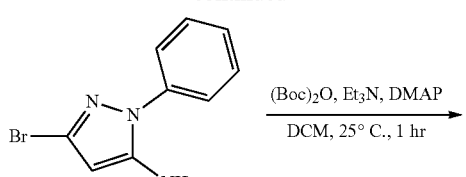

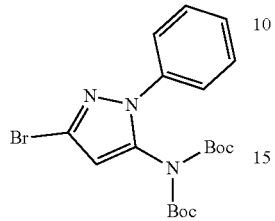

Preparation of 3-bromo-1-phenyl-1H-pyrazol-5-amine: To a solution of 3-bromo-1H-pyrazol-5-amine (1.75 g, 1.1 eq) in toluene (5 mL) were added copper(I) iodide (93.4 mg, 0.05 eq), iodobenzene (2 g, 1 eq), and potassium carbonate (2.85 g, 2.1 eq). The mixture was stirred at 110° C. for 1 hr. Aqueous saturated EDTA (20 mL) was added to the mixture, and the mixture was stirred for 1 hr. The reaction mixture was diluted with water (10 mL) and extracted with EA (20 mL). The combined organic layer was washed with brine (10 mL), dried over anhydrous sodium sulfate, filtered, and concentrated in vacuo. The crude residue was purified by column chromatography (SiO$_2$, PE:EA=1:0 to 5:1) to afford 3-bromo-1-phenyl-1H-pyrazol-5-amine as a brown solid in 40.7% yield.

Preparation of 3-bromo-1-phenyl-1H-pyrazol-5-di(tert-butoxycarbonyl)-amine: To a solution of 3-bromo-1-phenyl-1H-pyrazol-5-amine (300 mg, 1 eq), TEA (191.3 mg, 1.5 eq), and DMAP (7.70 mg, 0.05 eq) in DCM (5 mL) was added Boc$_2$O (825 mg, 3 eq). The mixture was stirred at 25° C. for 1 hr. The reaction mixture was diluted with H$_2$O (10 mL) and extracted with EA (20 mL). The combined organic layer was washed with brine (10 mL), dried over anhydrous sodium sulfate, filtered, and concentrated in vacuo. The residue was purified by preparative-TLC (PE:EA=5:1) to afford 3-bromo-1-phenyl-1H-pyrazol-5-di(tert-butoxycarbonyl)-amine as a white solid in 86.9% yield.

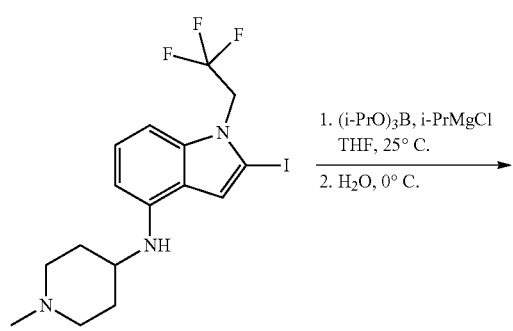

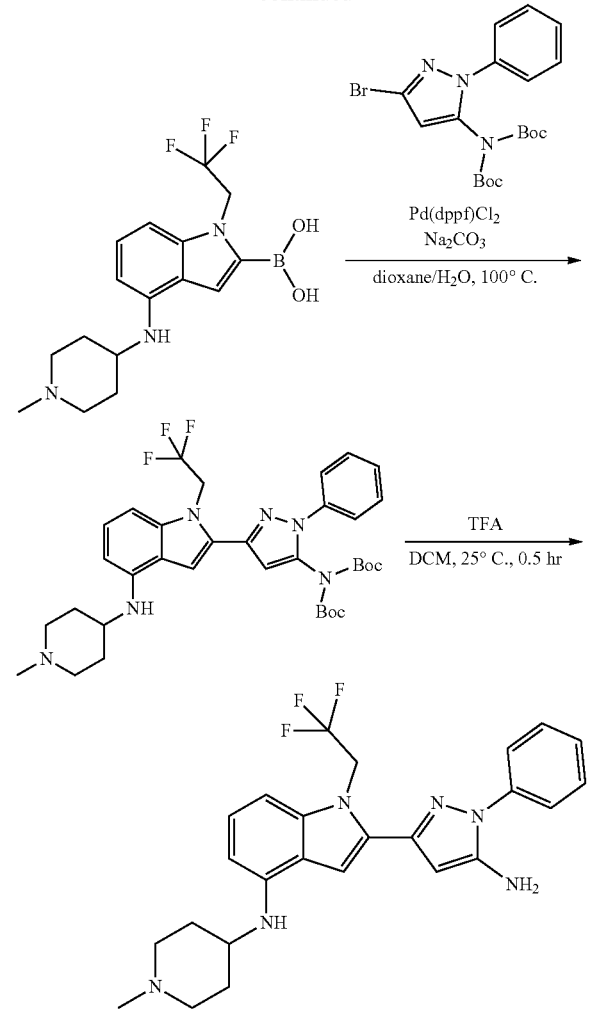

Preparation of (4-((1-methylpiperidin-4-yl)amino)-1-(2,2,2-trifluoroethyl)-1H-indol-2-yl)boronic acid: To a mixture of 2-iodo-N-(1-methylpiperidin-4-yl)-1-(2,2,2-trifluoroethyl)-1H-indol-4-amine (0.6 g, 1.37 mmol, 1 eq) and triisopropyl borate (387.1 mg, 2.06 mmol, 473.25 μL, 1.5 eq) in THF (5 mL) was added isopropyl magnesium chloride (2 M, 3.4 mL, 5 eq) in one portion at 25° C. under nitrogen.

The mixture was stirred at 25° C. for 1 hr. The residue was poured into ice water (w/w=1/1) (30 mL), and the resulting mixture was stirred for 5 min. The aqueous phase was extracted with EA (10 mL×3). The combined organic phase was washed with brine (10 mL×3), dried with anhydrous sodium sulfate, filtered, and concentrated in vacuo. The crude product was purified by preparative-TLC (DCM:MeOH=10:1) to afford (4-((1-methylpiperidin-4-yl)amino)-1-(2,2,2-trifluoroethyl)-1H-indol-2-yl)boronic acid as a yellow solid in 18.5% yield. LC-MS (ES$^+$, m/z): 356.1.

Preparation of 2-(5-(di(tert-butoxycarbonyl)amino)-1-phenyl-1H-pyrazol-3-yl)-N-(1-methylpiperidin-4-yl)-1-(2,2,2-trifluoroethyl)-1H-indol-4-amine: To a solution of (4-((1-methylpiperidin-4-yl)amino)-1-(2,2,2-trifluoroethyl)-1H-indol-2-yl)boronic acid (80 mg, 225.25 μmol, 1 eq) in a mixture of water (0.5 mL) and dioxane (2 mL) were added 3-bromo-1-phenyl-1H-pyrazol-5-di(tert-butoxycarbonyl)-amine (118.48 mg, 1.2 eq), sodium carbonate (47.75 mg, 2 eq), and Pd(dppf)Cl$_2$ (16.48 mg, 0.1 eq) under N$_2$. The mixture was stirred at 100° C. for 10 min. 2M aqueous EDTA (20 mL) was added to the mixture, and the resulting mixture was stirred further for 1 hr. The reaction mixture was diluted with water (10 mL) and extracted with EA (20 mL). The combined organic layer was washed with brine (10 mL), dried over anhydrous sodium sulfate, filtered, and concentrated in vacuo. The crude residue was purified by preparative-TLC (SiO$_2$, DCM:MeOH=10:1) to afford 2-(5-(di(tert-butoxycarbonyl)amino)-1-phenyl-1H-pyrazol-3-yl)-N-(1-methylpiperidin-4-yl)-1-(2,2,2-trifluoroethyl)-1H-indol-4-amine as a white solid in 13.28% yield. LC-MS (ES$^+$, m/z): 669.4.

Preparation of 2-(5-amino-1-phenyl-1H-pyrazol-3-yl)-N-(1-methylpiperidin-4-yl)-1-(2,2,2-trifluoroethyl)-1H-indol-4-amine: A mixture of 2-(5-(di(tert-butoxycarbonyl)amino)-1-phenyl-1H-pyrazol-3-yl)-N-(1-methylpiperidin-4-yl)-1-(2,2,2-trifluoroethyl)-1H-indol-4-amine (20 mg, 29.9 µmol, 1 eq) in DCM (1 mL) was added TFA (1 mL). The mixture was degassed and purged with nitrogen (×3), and the mixture was stirred at 25° C. for 30 min under nitrogen. The reaction mixture was poured into saturated aqueous sodium bicarbonate (10 mL), diluted with water (10 mL), and extracted with EA (10 mL). The combined organic layers were washed with brine (10 mL), dried over anhydrous sodium sulfate, filtered, and concentrated in vacuo. The crude residue was purified by preparative-TLC (SiO$_2$, DCM:MeOH=10:1) to afford 2-(5-amino-1-phenyl-1H-pyrazol-3-yl)-N-(1-methylpiperidin-4-yl)-1-(2,2,2-trifluoroethyl)-1H-indol-4-amine (Compound 19B) as a white solid. LC-MS (ES$^+$, m/z): 469.2.

Example 17: Alternative Method of Synthesizing Compound 19B

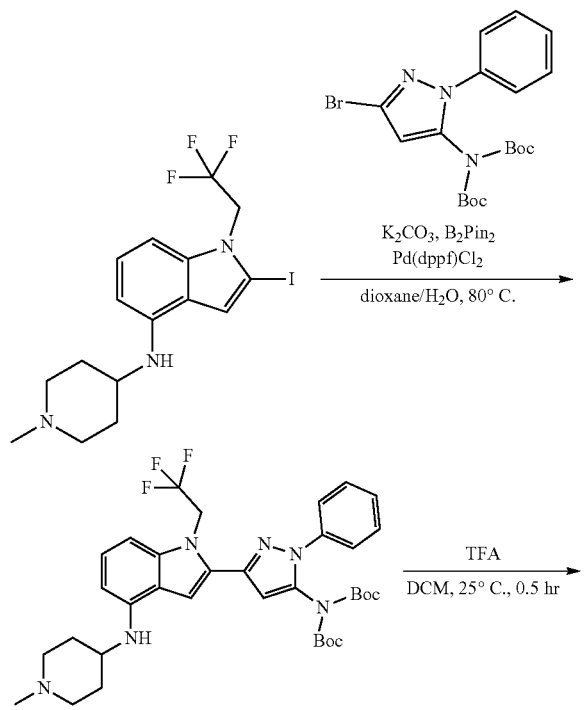

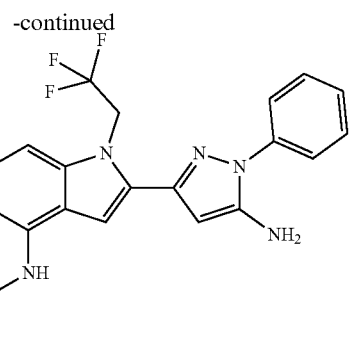

Preparation of 2-(5-(di(tert-butoxycarbonyl)amino)-1-phenyl-1H-pyrazol-3-yl)-N-(1-methylpiperidin-4-yl)-1-(2,2,2-trifluoroethyl)-1H-indol-4-amine: A solution of 2-iodo-N-(1-methylpiperidin-4-yl)-1-(2,2,2-trifluoroethyl)-1H-indol-4-amine (100 mg, 228.71 µmol, 1 eq), 3-bromo-N,N-di(tert-butoxycarbonyl)-1-phenyl-1H-pyrazol-5-amine (100.3 mg, 228.7 µmol, 1 eq), bis(pinacoloto)diboron (87.1 mg, 343.1 µmol, 1.5 eq), and potassium carbonate (63.2 mg. 457.4 µmol, 2 eq) was prepared in a mixture of dioxane (2 mL) and water (0.5 mL). The solution was degassed and purged with nitrogen 3 times. Pd(dppf)Cl$_2$ (33.5 mg, 45.7 µmol, 0.2 eq) was then added to the mixture and stirred 80° C. for 2 hr under nitrogen. 2M aqueous EDTA (20 mL) was added to the mixture, and the resulting mixture was stirred for 1 hr. The mixture was diluted with water (10 mL) and extracted with EA (20 mL). The combined organic layer was washed with brine (10 mL), dried over anhydrous sodium sulfate, filtered, and concentrated in vacuo. The residue was purified by preparative-TLC (SiO$_2$, DCM:MeOH=10:1) to afford 2-(5-(di(tert-butoxycarbonyl)amino)-1-phenyl-1H-pyrazol-3-yl)-N-(1-methylpiperidin-4-yl)-1-(2,2,2-trifluoroethyl)-1H-indol-4-amine as a white solid in 14.4% yield. LC-MS (ES$^+$, m/z): 669.3.

Preparation of 2-(5-amino-1-phenyl-1H-pyrazol-3-yl)-N-(1-methylpiperidin-4-yl)-1-(2,2,2-trifluoroethyl)-1H-indol-4-amine: To a mixture of 2-(5-(di(tert-butoxycarbonyl)amino)-1-phenyl-1H-pyrazol-3-yl)-N-(1-methylpiperidin-4-yl)-1-(2,2,2-trifluoroethyl)-1H-indol-4-amine (20 mg, 29.91 µmol, 1 eq) in DCM (1 mL) was added TFA (1 mL). The mixture was degassed and purged with nitrogen 3 times and stirred at 25° C. for 30 min under nitrogen. The reaction mixture was poured into saturated aqueous sodium bicarbonate (10 mL), diluted with water (10 mL), and extracted with EA (10 mL). The combined organic layer was washed with brine (10 mL), dried over anhydrous sodium sulfate, filtered, and concentrated in vacuo. The crude residue was purified by preparative-TLC (SiO$_2$, DCM:MeOH=10:1) to afford 2-(5-amino-1-phenyl-1H-pyrazol-3-yl)-N-(1-methylpiperidin-4-yl)-1-(2,2,2-trifluoroethyl)-1H-indol-4-amine (Compound 19B) as a white solid. LC-MS (ES$^+$, m/z): 469.2.

Example 18: Synthesis of Compound 20B

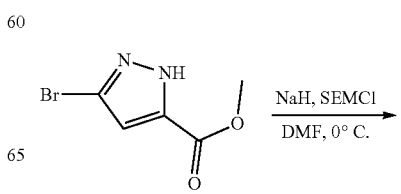

-continued

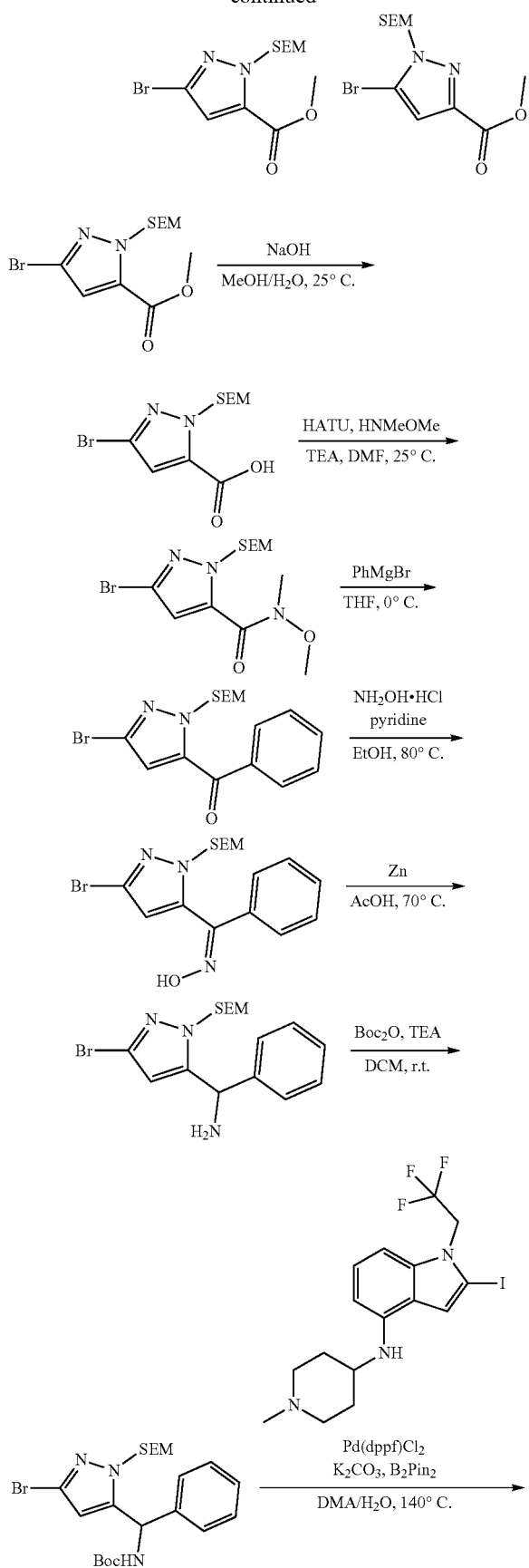

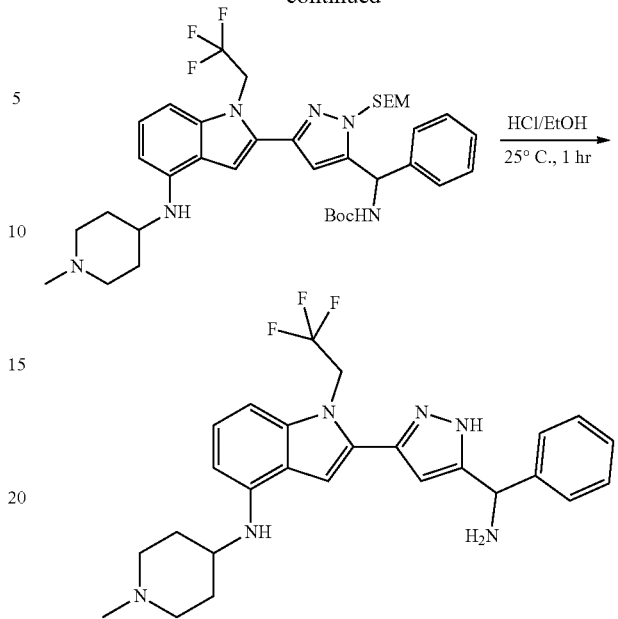

Preparation of methyl 3-bromo-1-((2-(trimethylsilyl)ethoxy)methyl)-1H-pyrazole-5-carboxylate: To a mixture of methyl 3-bromo-1H-pyrazole-5-carboxylate (4.5 g, 21.95 mmol, 1 eq) and SEMCl (7.32 g, 43.90 mmol, 7.77 mL, 2 eq) in DMF (30 mL) was added sodium hydride (1.76 g, 43.90 mmol, 60% purity, 2 eq) in one portion at 0° C. under $N_2$. The mixture was stirred at 0° C. for 0.5 hr. The residue was poured into a solution of 2M aqueous $NH_4Cl$:water (w/w=1/1) (50 mL) and stirred for 5 min. The aqueous phase was extracted with EA (20 mL×3). The combined organic phase was washed with brine (20 mL×3), dried with anhydrous sodium sulfate, filtered, and concentrated in vacuo. The residue was purified by silica gel chromatography (PE:EA=10:1 to 5:1) to afford methyl 5-bromo-1-((2-(trimethylsilyl)ethoxy)methyl)-1H-pyrazole-3-carboxylate (2 g, 5.97 mmol, 27.18% yield) as a yellow oil and methyl 3-bromo-1-((2-(trimethylsilyl)ethoxy)methyl)-1H-pyrazole-5-carboxylate (6 g, 17.90 mmol, 81.53% yield) as a yellow oil.

Preparation of 3-bromo-1-((2-(trimethylsilyl)ethoxy)methyl)-1H-pyrazole-5-carboxylic acid: To a mixture of methyl 3-bromo-1-((2-(trimethylsilyl)ethoxy)methyl)-1H-pyrazole-5-carboxylate (6 g, 17.90 mmol, 1 eq) in a mixture of MeOH (50 mL) and water (10 mL) was added sodium hydroxide (1.43 g, 35.79 mmol, 2 eq) in one portion at 25° C. under nitrogen. The mixture was stirred at 25° C. for 1 hr. The residue was poured into ice water (w/w=1/1) (300 mL) and stirred for 5 min. Then, the pH of the residue was adjusted to 3 using 2M aqueous HCl. The aqueous phase was extracted with EA (100 mL×3). The combined organic phase was washed with brine (100 mL×3), dried with anhydrous sodium sulfate, filtered, and concentrated in vacuo to afford 3-bromo-1-((2-(trimethylsilyl)ethoxy)methyl)-1H-pyrazole-5-carboxylic acid (5.7 g, crude) as a yellow oil.

Preparation of 3-bromo-N-methoxy-N-methyl-1-((2-(trimethylsilyl)ethoxy)methyl)-1H-pyrazole-5-carboxamide: To a mixture of 3-bromo-1-((2-(trimethylsilyl)ethoxy)methyl)-1H-pyrazole-5-carboxylic acid (0.33 g, 1.03 mmol, 1 eq) in DMF (5 mL) were added HATU (585.9 mg, 1.54 mmol, 1.5 eq) and TEA (312 mg, 3.08 mmol, 429 μL, 3 eq) each in one portion at 25° C. under nitrogen. The mixture was stirred at 25° C. for 5 min, and N,O-dimethylhydroxylamine hydrochloride (200.41 mg, 2.05 mmol, 2 eq) was added. The reaction mixture was stirred for 55 min. The residue was poured into ice water (w/w=1/1) (30 mL), and the mixture was stirred for 5 min. The aqueous phase was extracted with EA (10 mL×3). The combined organic phase was washed with brine (10 mL×3), dried with anhydrous sodium sulfate, filtered, and concentrated in vacuo. The crude product was purified by preparative-TLC (PE:EA=1:1) to afford 3-bromo-N-methoxy-N-methyl-1-((2-(trimethylsilyl)ethoxy)methyl)-1H-pyrazole-5-carboxamide (0.15 g, 411.7 μmol, 40.1% yield) as a yellow oil.

Preparation of (3-bromo-1-((2-(trimethylsilyl)ethoxy)methyl)-1H-pyrazol-5-yl)(phenyl)methanone: To a mixture of 3-bromo-N-methoxy-N-methyl-1-((2-(trimethylsilyl)ethoxy)methyl)-1H-pyrazole-5-carboxamide (0.15 g, 411.7 μmol, 1 eq) in THF (1 mL) was added phenyl magnesium bromide (3 M, 165 μL, 1.2 eq) in one portion at −20° C. under nitrogen. The mixture was stirred at −20° C. for 1 hr. The residue was poured into ice water (w/w=1/1) (30 mL), and the mixture was stirred for 5 min. The aqueous phase was extracted with EA (10 mL×3). The combined organic phase was washed with brine (10 mL×3), dried with anhydrous sodium sulfate, filtered, and concentrated in vacuo. The crude product was purified by preparative-TLC (PE:EA=5:1) to afford (3-bromo-1-((2-(trimethylsilyl)ethoxy)methyl)-1H-pyrazol-5-yl)(phenyl)methanone (0.1 g, 262.23 μmol, 63.69% yield) as a yellow oil. LC-MS (ES⁻, m/z): 381.4

Preparation of (3-bromo-1-((2-(trimethylsilyl)ethoxy)methyl)-1H-pyrazol-5-yl)(phenyl)methanone oxime: To a mixture of (3-bromo-1-((2-(trimethylsilyl)ethoxy)methyl)-1H-pyrazol-5-yl)(phenyl)methanone (4 g, 10.5 mmol, 1 eq) in ethanol (40 mL) were added hydroxylamine hydrochloride (1.46 g, 21 mmol, 2 eq) and pyridine (1.66 g, 20.98 mmol, 1.69 mL, 2 eq) in one portion at 80° C. under nitrogen. The mixture was stirred at 80° C. for 2 hr. The mixture was concentrated in vacuo to afford the crude product. The residue was purified by silica gel chromatography (PE:EA=10:1 to 5:1) to afford (3-bromo-1-((2-(trimethylsilyl)ethoxy)methyl)-1H-pyrazol-5-yl)(phenyl)methanone oxime (4.1 g, 10.34 mmol, 98.6% yield) as a yellow oil. LC-MS (ES⁺, m/z): 396.1.

Preparation of (3-bromo-1-((2-(trimethylsilyl)ethoxy)methyl)-1H-pyrazol-5-yl)(phenyl)methanamine: To a solution of (3-bromo-1-((2-(trimethylsilyl)ethoxy)methyl)-1H-pyrazol-5-yl)(phenyl)methanone oxime (0.1 g, 252.3 μmol, 1 eq) in acetic acid (1 mL) was added zinc powder (82.5 mg, 1.26 mmol, 5 eq) in one portion at 70° C. under nitrogen. The mixture was stirred at 70° C. for 1 hr. The residue was poured into 2 M aqueous sodium carbonate (50 mL) and stirred for 5 min. The aqueous phase was extracted with EA (20 mL×3). The combined organic phase was washed with brine (20 mL×3), dried with anhydrous sodium sulfate, filtered, and concentrated in vacuo. The crude product was purified by preparative-TLC (PE:EA=1:1) to afford (3-bromo-1-((2-(trimethylsilyl)ethoxy)methyl)-1H-pyrazol-5-yl)(phenyl)methanamine (0.05 g, 130.8 μmol, 51.8% yield) as a yellow oil. LC-MS (ES⁺, m/z): 382.1.

Preparation of tert-butyl ((3-bromo-1-((2-(trimethylsilyl)ethoxy)methyl)-1H-pyrazol-5-yl)(phenyl)methyl)carbamate: To a mixture of (3-bromo-1-((2-(trimethylsilyl)ethoxy)methyl)-1H-pyrazol-5-yl)(phenyl)methanamine (0.8 g, 2.09 mmol, 1 eq) and Boc₂O (547.9 mg, 2.51 mmol, 577 μL, 1.2 eq) in DCM (10 mL) was added TEA (1.06 g, 10.5 mmol, 1.46 mL, 5 eq) in one portion at 25° C. under nitrogen. The mixture was stirred at 25° C. for 2 hr. The residue was poured into ice water (w/w=1/1) (50 mL) and stirred for 5 min. The aqueous phase was extracted with DCM (20 mL×3). The combined organic phase was washed with brine (20 mL×3), dried with anhydrous sodium sulfate, filtered, and concentrated in vacuo. The crude product was purified by preparative-TLC (PE:EA=5:1) to afford tert-butyl ((3-bromo-1-((2-(trimethylsilyl)ethoxy)methyl)-11H-pyrazol-5-yl)(phenyl)methyl)carbamate (0.4 g, 829.0 μmol, 39.63% yield) as a yellow oil. LC-MS (ES⁺, m/z): 484.1.

Preparation of tert-butyl ((3-(4-((1-methylpiperidin-4-yl)amino)-1-(2,2,2-trifluoroethyl)-1H-indol-2-yl)-1-((2-(trimethylsilyl)ethoxy)methyl)-1H-pyrazol-5-yl)(phenyl)methyl)carbamate: To a mixture of 2-iodo-N-(1-methylpiperidin-4-yl)-1-(2,2,2-trifluoroethyl)-1H-indol-4-amine (0.2 g, 457.41 μmol, 1 eq), tert-butyl ((3-bromo-1-((2-(trimethylsilyl)ethoxy)methyl)-1H-pyrazol-5-yl)(phenyl)methyl)carbamate (220.70 mg, 457.41 μmol, 1 eq), and bis(pinacolato)diboron (174.2 mg, 686.1 μmol, 1.5 eq) in a mixture of DMA (1 mL) and water (0.25 mL) were added potassium carbonate (126.4 mg, 914.8 μmol, 2 eq) and Pd(dppf)Cl₂ (33.5 mg, 45.7 μmol, 0.10 eq) in one portion at room temperature under nitrogen. The mixture was heated and stirred at 140° C. for 5 min. The residue was poured into 2M aqueous EDTA (50 mL) and stirred for 5 min. The aqueous phase was extracted with EA (20 mL×3). The combined organic phase was washed with brine (20 mL×3), dried with anhydrous sodium sulfate, filtered, and concentrated in vacuo. The crude product was purified by preparative-TLC (DCM:MeOH=20:1) to afford tert-butyl ((3-(4-((1-methylpiperidin-4-yl)amino)-1-(2,2,2-trifluoroethyl)-1H-indol-2-yl)-1-((2-(trimethylsilyl)ethoxy)methyl)-1H-pyrazol-5-yl)(phenyl)methyl)carbamate (0.043 g, 60.3 μmol, 13.2% yield) as a yellow oil.

Preparation of 2-(5-(amino(phenyl)methyl)-1H-pyrazol-3-yl)-N-(1-methylpiperidin-4-yl)-1-(2,2,2-trifluoroethyl)-1H-indol-4-amine: To a mixture of tert-butyl ((3-(4-((1-methylpiperidin-4-yl)amino)-1-(2,2,2-trifluoroethyl)-1H-indol-2-yl)-1-((2-(trimethylsilyl)ethoxy)methyl)-1H-pyrazol-5-yl)(phenyl)methyl)carbamate (0.043 g, 60.3 μmol, 1 eq) in ethanol (0.5 mL) was added HCl (12 M, 4.30 mL, 855 eq) in one portion at 25° C. under nitrogen. The mixture was stirred at 25° C. for 1 hr. The residue was poured into 2 M aqueous sodium carbonate (50 mL) and stirred for 5 min. The aqueous phase was extracted with EA (20 mL×3). The combined organic phase was washed with brine (20 mL×3), dried with anhydrous sodium sulfate, filtered, and concentrated in vacuo. The crude product was purified by preparative-HPLC to afford Compound 20B, 2-(5-(amino(phenyl)methyl)-1H-pyrazol-3-yl)-N-(1-methylpiperidin-4-yl)-1-(2,2,2-trifluoroethyl)-1H-indol-4-amine, (8.7 mg, 17.7 μmol, 29% yield) as a yellow solid. LC-MS (ES⁺, m/z): 483.2.

TABLE 4 shows a list of compounds prepared with a 2-(1H-pyrazol-3-yl)-1H-indole core.

TABLE 4

| Compound No. | Structure | IUPAC | LC-MS (ES⁺, m/z) |
|---|---|---|---|
| 14B | 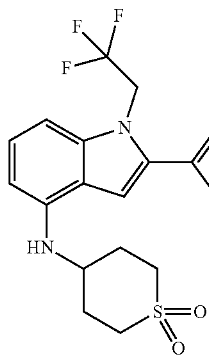 | 4-{[2-(1-methyl-1H-pyrazol-3-yl)-1-(2,2,2-trifluoroethyl)-1H-indol-4-yl]amino}-1λ⁶-thiane-1,1-dione | 427.2 |
| 15B | 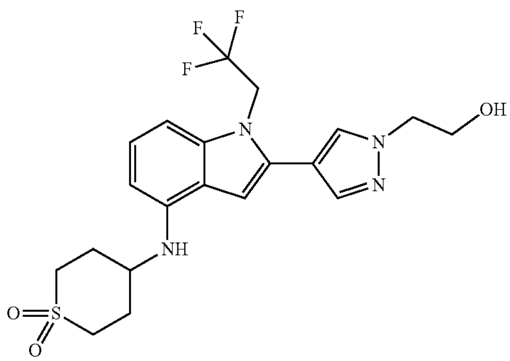 [SMILES: O=S1(=O)CCC(Nc2cccc3c2cc(-c2cnn(CCO)c2)n3CC(F)(F)F)CC1] | 4-({2-[1-(2-hydroxyethyl)-1H-pyrazol-4-yl]-1-(2,2,2-trifluoroethyl)-1H-indol-4-yl}amino)-1λ⁶-thiane-1,1-dione | 456.9 |
| 16B | 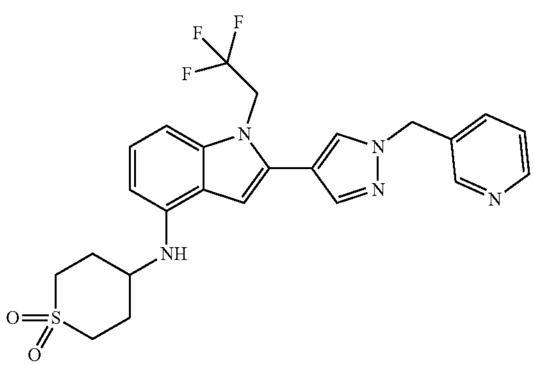 [SMILES: O=S1(=O)CCC(Nc2cccc3c2cc(-c2cnn(Cc4cccnc4)c2)n3CC(F)(F)F)CC1] | 4-[(2-{1-[(pyridin-3-yl)methyl]-1H-pyrazol-4-yl}-1-(2,2,2-trifluoroethyl)-1H-indol-4-yl)amino]-1λ⁶-thiane-1,1-dione | 504.3 |
| 17B | 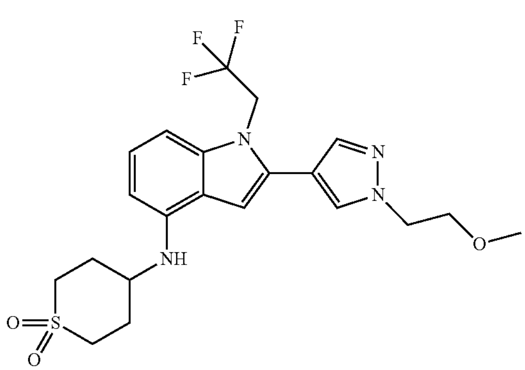 [SMILES: COCCn1cc(-c2cc3c(NC4CCS(=O)(=O)CC4)cccc3n2CC(F)(F)F)cn1] | 4-((2-(1-(2-methoxyethyl)-1H-pyrazol-4-yl)-1-(2,2,2-trifluoroethyl)-1H-indol-4-yl)amino)tetrahydro-2H-thiopyran 1,1-dioxide | 471.2 |

TABLE 4-continued

| Compound No. | Structure | IUPAC | LC-MS (ES+, m/z) |
|---|---|---|---|
| 18B | 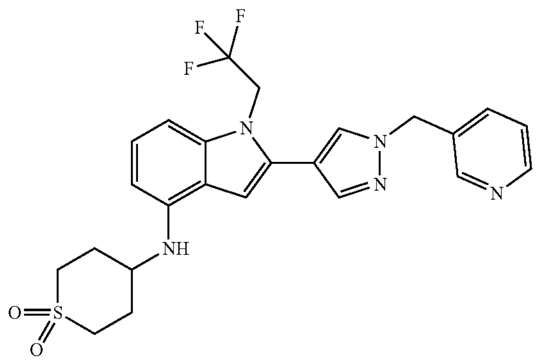 [SMILES: O=S1(=O)CCC(Nc2cccc3c2cc(-c2cnn(Cc4cccnc4)c2)n3CC(F)(F)F)CC1] | 4-[(2-{1-[(pyridin-4-yl)methyl]-1H-pyrazol-4-yl}-1-(2,2,2-trifluoroethyl)-1H-indol-4-yl)amino]-1λ⁶-thiane-1,1-dione | 504.2 |
| 19B | 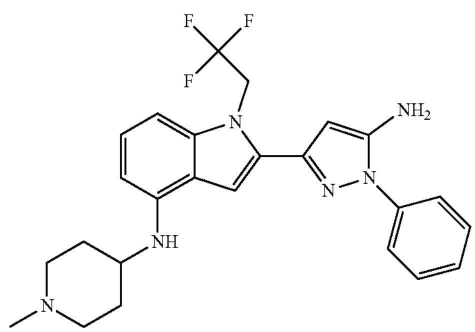 [SMILES: CN1CCC(Nc2cccc3c2cc(-c2cc(N)n(-c4ccccc4)n2)n3CC(F)(F)F)CC1] | 2-(5-amino-1-phenyl-1H-pyrazol-3-yl)-N-(1-methylpiperidin-4-yl)-1-(2,2,2-trifluoroethyl)-1H-indol-4-amine | 483.2 |
| 20B | 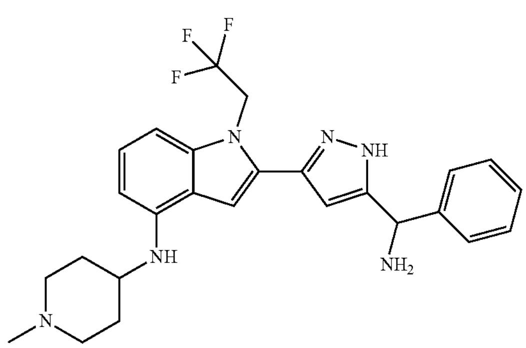 [SMILES: CN1CCC(Nc2cccc3c2cc(-c2cc(C(N)c4ccccc4)[nH]n2)n3CC(F)(F)F)CC1] | 2-{5-[amino(phenyl)methyl]-1H-pyrazol-3-yl}-N-(1-methylpiperidin-4-yl)-1-(2,2,2-trifluoroethyl)-1H-indol-4-amine | 483.2 |
| 21B | 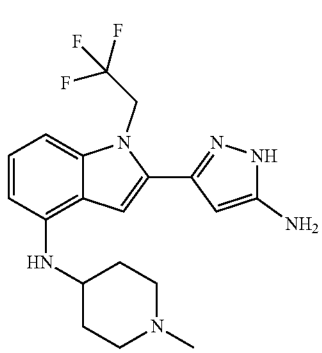 [SMILES: CN1CCC(Nc2cccc3c2cc(-c2cc(N)[nH]n2)n3CC(F)(F)F)CC1] | 2-(5-amino-1H-pyrazol-3-yl)-N-(1-methylpiperidin-4-yl)-1-(2,2,2-trifluoroethyl)-1H-indol-4-amine | 393.2 |

TABLE 4-continued
| Compound No. | Structure | IUPAC | LC-MS (ES+, m/z) |
|---|---|---|---|
| 22B | 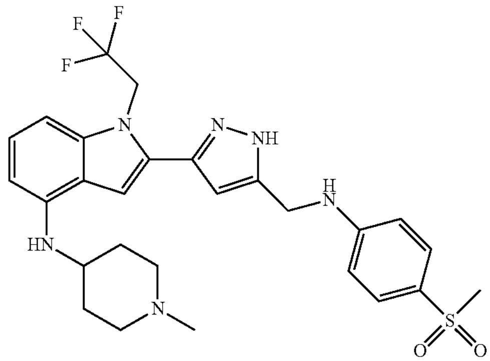 [SMILES: CN1CCC(Nc2cccc3c2cc(-c2cc(CNc4ccc(S(C)(=O)=O)cc4)[nH]n2)n3CC(F)(F)F)CC1] | 2-(5-{[(4-methanesulfonyl-phenyl)amino]meth-yl}-1H-pyrazol-3-yl)-N-(1-methylpiperidin-4-yl)-1-(2,2,2-trifluoroethyl)-1H-indol-4-amine | 561.3 |
| 23B | 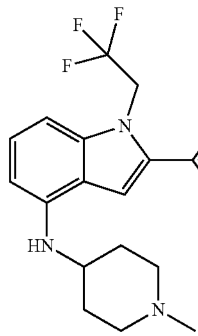 | 2-[5-(methylamino)-1H-pyrazol-3-yl]-N-(1-methylpiperidin-4-yl)-1-(2,2,2-trifluoroethyl)-1H-indol-4-amine | 407.1 |
Example 19: Synthesis of Compounds 30B, 31B, 32B, 33B, 34B, and 35B
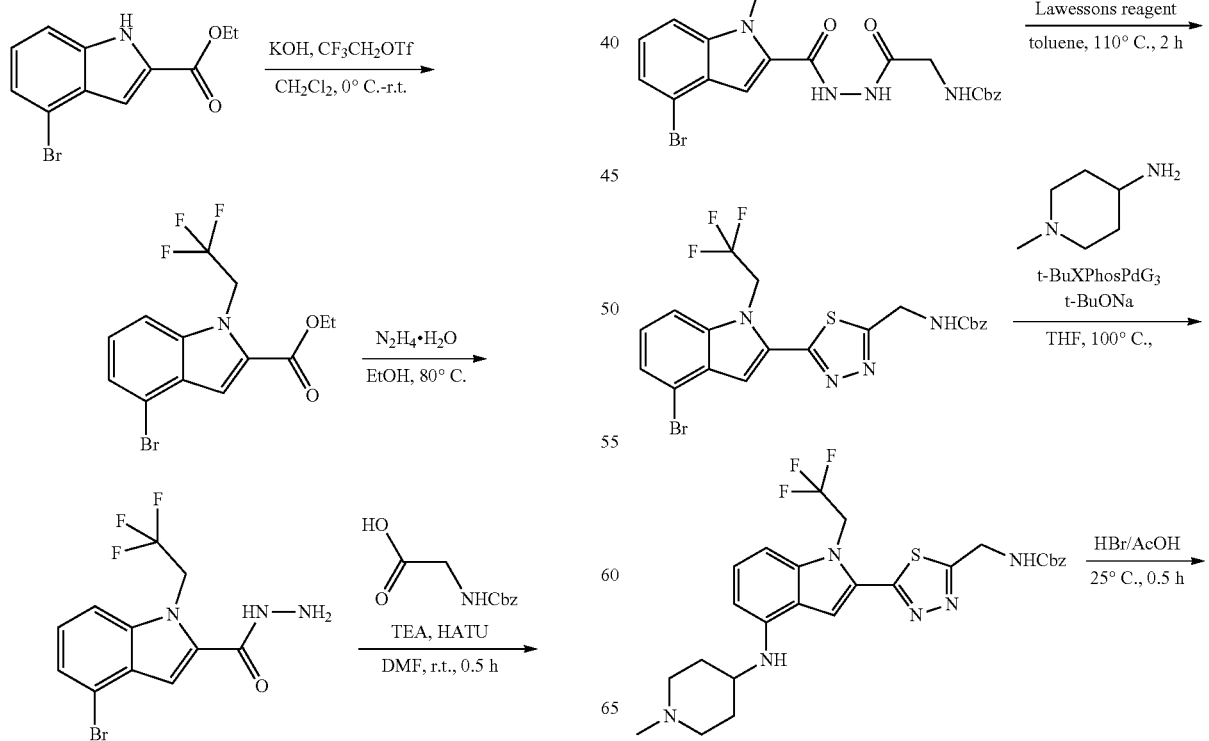

-continued

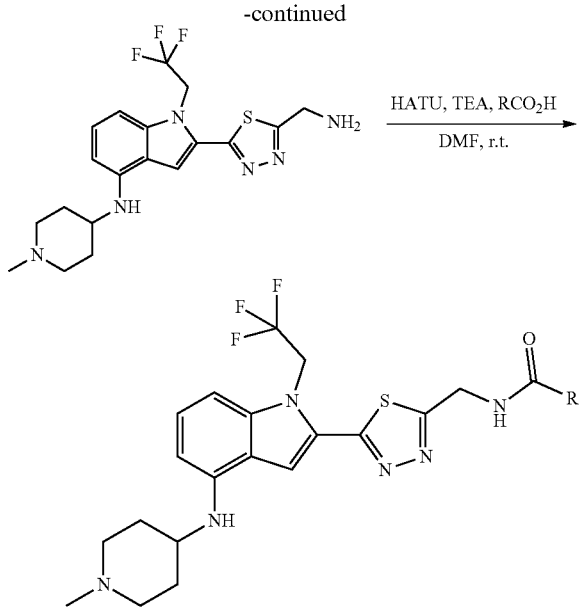

Preparation of ethyl 4-bromo-1-(2,2,2-trifluoroethyl)-1H-indole-2-carboxylate: To a solution of ethyl 4-bromo-1H-indole-2-carboxylate (10 g, 37.30 mmol, 1 eq) in DCM (100 mL) was added TBAI (2.76 g, 7.46 mmol, 0.2 eq) and potassium hydroxide (6.28 g, 111.90 mmol, 3 eq) at 25° C. The mixture was stirred at 25° C. for 10 min, and CF$_3$CH$_2$OTf (17.31 g, 74.60 mmol, 2 eq) was added to the reaction. The mixture was stirred at 25° C. for 50 min. The residue was poured into ice-water (w/w=1/1) (500 mL) and stirred for 5 min. The aqueous phase was extracted with EA (150 mL×3). The combined organic phase was washed with brine (150 mL×3), dried with anhydrous sodium sulfate, filtered, and concentrated in vacuum. To afford the desired product (26 g, crude) as a yellow solid. LC-MS (ES$^+$, m/z): 351.9.

Preparation of 4-bromo-1-(2,2,2-trifluoroethyl)-1H-indole-2-carbohydrazide: To a solution of ethyl 4-bromo-1-(2,2,2-trifluoroethyl)-1H-indole-2-carboxylate (26 g, 74.26 mmol, 1 eq) in ethanol (150 mL) was added hydrazine hydrate (154.50 g, 3.09 mol, 150 mL, 41.56 eq). The resulting mixture was stirred at 80° C. for 1 hr, and TLC analysis was used to confirm completion of the reaction. The reaction was poured into water (1000 mL), and the resulting white precipitate was filtered and dried under a vacuum to afford 4-bromo-1-(2,2,2-trifluoroethyl)-1H-indole-2-carbohydrazide (23.4 g, crude) as a white solid.

Preparation of benzyl (2-(2-(4-bromo-1-(2,2,2-trifluoroethyl)-1H-indole-2-carbonyl)hydrazinyl)-2-oxoethyl)carbamate: To a solution of ((benzyloxy)carbonyl)glycine (3.11 g, 14.88 mmol, 1 eq) in DMF (100 mL) were added TEA (7.53 g, 74.38 mmol, 10.35 mL, 5 eq) and HATU (11.31 g, 29.75 mmol, 2 eq). 4-bromo-1-(2,2,2-trifluoroethyl)-1H-indole-2-carbohydrazide (5 g, 14.9 mmol, 1 eq) was added to the mixture, and the reaction mixture was stirred at 25° C. for 0.5 hr. TLC analysis was used to confirm completion of the reaction. The reaction mixture was poured into water (500 mL) and extracted with EA (150 mL×3). The combined organic phase was washed with brine (100 mL), dried with anhydrous sodium sulfate, filtered, and concentrated in vacuo. DCM was added to the residue, and the resulting white precipitate was filtered and dried under a vacuum to afford benzyl (2-(2-(4-bromo-1-(2,2,2-trifluoroethyl)-1H-indole-2-carbonyl)hydrazinyl)-2-oxoethyl)carbamate (14 g, 26.55 mmol, 59.5% yield) as a white solid. LC-MS (ES$^+$, m/z): 529.1.

Preparation of benzyl ((5-(4-bromo-1-(2,2,2-trifluoroethyl)-1H-indol-2-yl)-1,3,4-thiadiazol-2-yl)methyl)carbamate: To a solution of benzyl (2-(2-(4-bromo-1-(2,2,2-trifluoroethyl)-1H-indole-2-carbonyl)hydrazinyl)-2-oxoethyl)carbamate (5 g, 9.48 mmol, 1 eq) in toluene (50 mL) was added Lawesson's reagent (7.67 g, 18.96 mmol, 2 eq). The reaction mixture was stirred at 110° C. for 2 hr, and LC-MS analysis was used to confirm completion of the reaction. The reaction mixture was poured into water (250 mL) and extracted with EA (80 mL×3). The combined organic phase was washed with a 1M aqueous copper(II) sulfate solution (50 mL), dried with anhydrous sodium sulfate, filtered, and concentrated in vacuo. The crude residue was purified by column chromatography (SiO$_2$, PE:EA=10:1 to 4:1) to afford benzyl ((5-(4-bromo-1-(2,2,2-trifluoroethyl)-1H-indol-2-yl)-1,3,4-thiadiazol-2-yl)methyl)carbamate (10.2 g, 19.4 mmol, 77.1% yield) as a white solid. LC-MS (ES$^+$, m/z): 525.0.

Preparation of benzyl ((5-(4-((1-methylpiperidin-4-yl)amino)-1-(2,2,2-trifluoroethyl)-1H-indol-2-yl)-1,3,4-thiadiazol-2-yl)methyl)carbamate: To a mixture of benzyl ((5-(4-bromo-1-(2,2,2-trifluoroethyl)-1H-indol-2-yl)-1,3,4-thiadiazol-2-yl)methyl)carbamate (1 g, 1.90 mmol, 1 eq) and 1-methylpiperidin-4-amine (1.09 g, 9.52 mmol, 5 eq) in THF (10 mL) were added t-BuONa (2 M, 1.90 mL, 2 eq) and t-BuXPhos Palladium Generation 3 (300 mg, 377.66 µmol, 0.2 eq) under a nitrogen atmosphere. The mixture was stirred at 100° C. for 60 min, and LC-MS analysis was used to confirm completion of the reaction. The residue was poured into a 2 M aqueous EDTA solution (50 mL) and stirred for 60 min. The aqueous phase was extracted with EA (30 mL×2). The combined organic phase was washed with brine (20 mL×3), dried with anhydrous sodium sulfate, filtered, and concentrated in vacuo. The residue was purified by silica gel chromatography (silica gel, DCM:MeOH=40:1 to 10:1) to afford benzyl ((5-(4-((1-methylpiperidin-4-yl)amino)-1-(2,2,2-trifluoroethyl)-1H-indol-2-yl)-1,3,4-thiadiazol-2-yl)methyl)carbamate (0.81 g, 1.45 mmol, 76.17% yield) as a yellow solid. LC-MS (ES$^+$, m/z): 559.2.

Preparation of 2-(5-(aminomethyl)-1,3,4-thiadiazol-2-yl)-N-(1-methylpiperidin-4-yl)-1-(2,2,2-trifluoroethyl)-1H-indol-4-amine: Benzyl ((5-(4-((1-methylpiperidin-4-yl)amino)-1-(2,2,2-trifluoroethyl)-1H-indol-2-yl)-1,3,4-thiadiazol-2-yl)methyl)carbamate (0.7 g, 1.26 mmol, 1 eq) was treated with hydrogen bromide in acetic acid (14.90 g, 55.25 mmol, 10 mL, 30%, 43.77 eq) at 25° C. under a nitrogen atmosphere. The mixture was stirred at 25° C. for 30 min, and LC-MS analysis was used to confirm completion of the reaction. The residue was poured into 2M aqueous sodium carbonate (50 mL) and stirred for 5 min. The aqueous phase was extracted with EA (20 mL×3). The combined organic phase was washed with brine (20 mL×3), dried with anhydrous sodium sulfate, and filtered. Then, 10 mL of 4 M HCl in EA was added to the residue, and the mixture was concentrated in vacuo to afford 2-(5-(aminomethyl)-1,3,4-thiadiazol-2-yl)-N-(1-methylpiperidin-4-yl)-1-(2,2,2-trifluoroethyl)-1H-indol-4-amine (0.55 g, crude, HCl) as a yellow solid. LC-MS (ES$^+$, m/z): 425.1.

Preparation of Compounds 30B, 31B, 32B, 33B, 34B, and 35B: To a mixture of RCOOH (0.8 eq) in DMF were added TEA (3 eq) and HATU (1.5 eq) in one portion at 25° C. under a nitrogen atmosphere. The mixture was stirred at 25° C. for 5 min, and 2-(5-(aminomethyl)-1,3,4-thiadiazol-2-yl)-N-(1-methylpiperidin-4-yl)-1-(2,2,2-trifluoroethyl)-1H-indol-4- amine (1 eq, HCl) was added to the reaction. The resulting reaction mixture was stirred at 25° C. for 5 min. LC-MS analysis was used to confirm completion of the reaction. The residue was poured into ice water (w/w=1/1) (50 mL), and the mixture was stirred for 5 min. The aqueous phase was extracted with EA (20 mL×3). The combined organic phase was washed with brine (30 mL×2), dried with anhydrous sodium sulfate, filtered, and concentrated in vacuo. The crude product was purified using preparative-TLC DCM:MeOH=4:1 to afford Compounds 30B, 31C, 32C, 33C, 34C, and 35C. -(+/−)-N-{[5-(4-{[(3R,4S)-3-fluoro-1-methylpiperidin-4-yl]amino}-1-(2,2,2-trifluoroethyl)-1H-indol-2-yl)-1,3,4-thiadiazol-2-yl]methyl}thiophene-2-carboxamide (Compound 30B), LC-MS (ES+, m/z): 553.1; 1-fluoro-N-[(5-{4-[(1-methylpiperidin-4-yl)amino]-1-(2,2,2-trifluoroethyl)-1H-indol-2-yl}-1,3,4-thiadiazol-2-yl)methyl]cyclopropane-1-carboxamide (Compound 31B), LC-MS (ES−, m/z): 511.1; 2,2-difluoro-N-[(5-{4-[(1-methylpiperidin-4-yl)amino]-1-(2,2,2-trifluoroethyl)-1H-indol-2-yl}-1,3,4-thiadiazol-2-yl)methyl]cyclopropane-1-carboxamide (Compound 32B), LC-MS (ES−, m/z): 529.1; (1R,2S)-2-methyl-N-[(5-{4-[(1-methylpiperidin-4-yl)amino]-1-(2,2,2-trifluoroethyl)-1H-indol-2-yl}-1,3,4-thiadiazol-2-yl)methyl]cyclopropane-1-carboxamide (Compound 33B), LC-MS (ES+, m/z): 507.1; (1R,2R)-2-methyl-N-[(5-{4-[(1-methylpiperidin-4-yl)amino]-1-(2,2,2-trifluoroethyl)-1H-indol-2-yl}-1,3,4-thiadiazol-2-yl)methyl]cyclopropane-1-carboxamide (Compound 34B), LC-MS (ES+, m/z): 507.2; N-[(5-{4-[(1-methylpiperidin-4-yl)amino]-1-(2,2,2-trifluoroethyl)-1H-indol-2-yl}-1,3,4-thiadiazol-2-yl)methyl]cyclopropanecarboxamide (Compound 35B), LC-MS (ES+, m/z): 493.2.

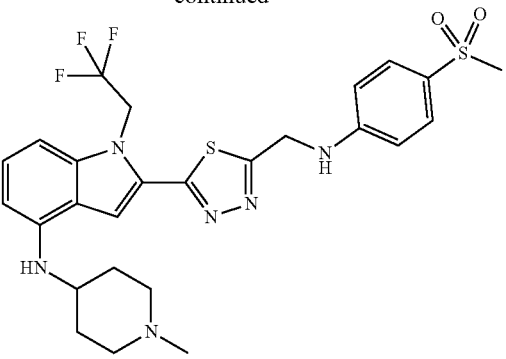

Procedure for synthesis of N-(1-methylpiperidin-4-yl)-2-(5-(((4-(methylsulfonyl)phenyl)amino)methyl)-1,3,4-thiadiazol-2-yl)-1-(2,2,2-trifluoroethyl)-1H-indol-4-amine: To a mixture of 4-((1-methylpiperidin-4-yl)amino)-1-(2,2,2-trifluoroethyl)-1H-indole-2-carbohydrazide (100 mg, 270.7 μmol, 1 eq) and (4-(methylsulfonyl)phenyl)glycine (62.1 mg, 270.7 μmol, 1 eq) in DMF (1 mL) were added HATU (205.9 mg, 541.4 μmol, 2 eq) and TEA (137 mg, 1.35 mmol, 188 μL, 5 eq) each in one portion at 20° C. under a nitrogen atmosphere. The mixture was stirred at 20° C. for 30 min, and LC-MS analysis was used to confirm completion of the reaction. The residue was poured into ice water (w/w=1/1) (30 mL), and the aqueous phase was extracted with EA (10 mL×3). The combined organic phase was washed with brine (10 mL×3), dried with anhydrous sodium sulfate, filtered, and concentrated in vacuo. The crude product was purified using preparative-TLC (SiO2, DCM:MeOH=8:1) to afford compound 4-((1-methylpiperidin-4-yl)amino)-N'-((4-(methylsulfonyl)phenyl)glycyl)-1-(2,2,2-trifluoroethyl)-1H-indole-2-carbohydrazide in 25.5% yield. LC-MS (ES+, m/z): 581.3.

Preparation of N-(1-methylpiperidin-4-yl)-2-(5-(((4-(methylsulfonyl)phenyl)amino)methyl)-1,3,4-thiadiazol-2-yl)-1-(2,2,2-trifluoroethyl)-1H-indol-4-amine: To a mixture of 4-((1-methylpiperidin-4-yl)amino)-N'-((4-(methylsulfonyl)phenyl)glycyl)-1-(2,2,2-trifluoroethyl)-1H-indole-2-carbohydrazide (30 mg, 51.67 μmol, 1 eq) in toluene (1 mL) was added Lawesson's Reagent (41.8 mg, 103.3 μmol, 2 eq) in one portion at 110° C. under a nitrogen atmosphere. The mixture was stirred at 130° C. for 4 hr. The reaction mixture was concentrated in vacuo, and purified using preparative-HPLC to afford N-(1-methylpiperidin-4-yl)-2-(5-(((4-(methylsulfonyl)phenyl)amino)methyl)-1,3,4-thiadiazol-2-yl)-1-(2,2,2-trifluoroethyl)-H-indol-4-amine (Compound 24B). LC-MS (ES+, m/z): 579.1.

Example 20: Synthesis of Compounds 41B, 42B, 45B, 46B, 49B, 57B, 58B, 59B, 60B, 63B, 64B, 65B, 66B, and 67B

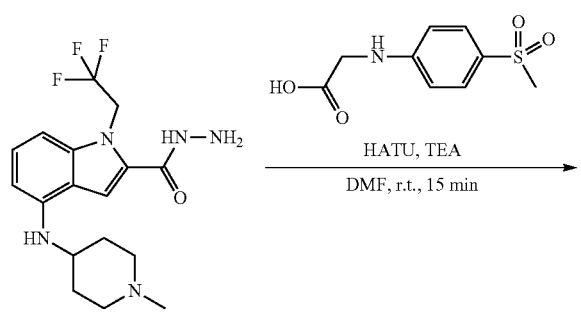

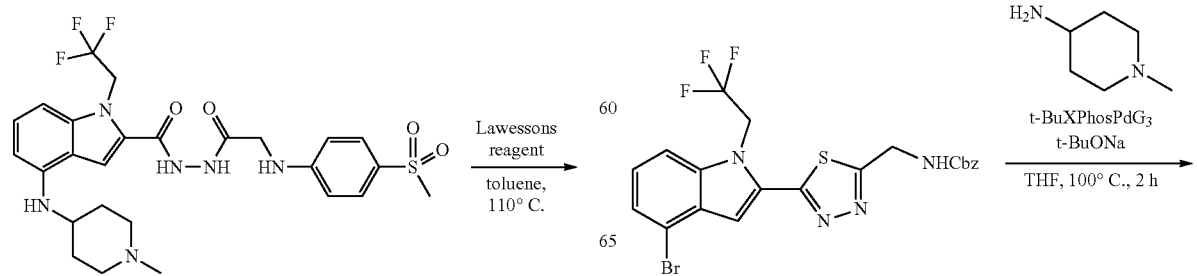

-continued

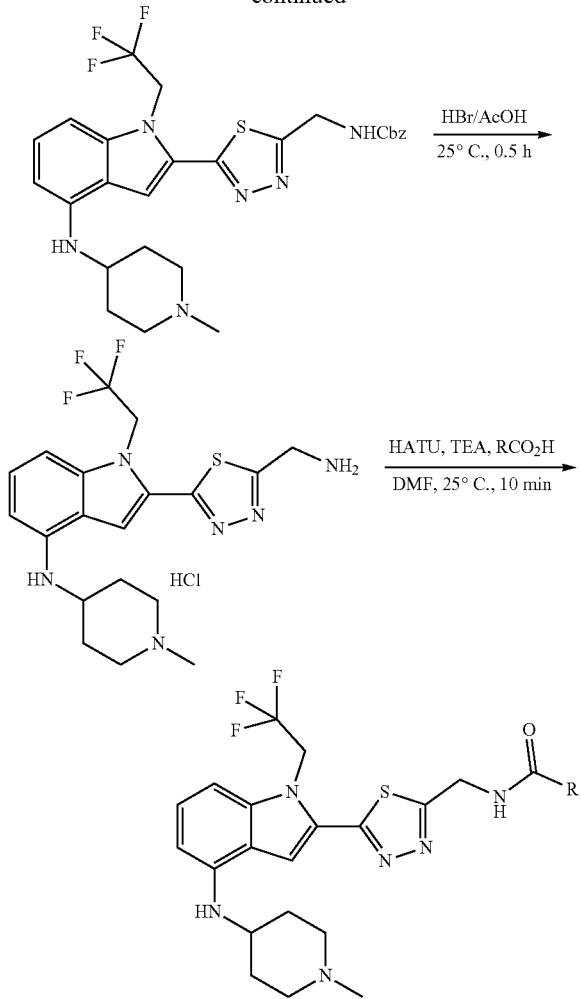

Preparation of benzyl ((5-(4-((1-methylpiperidin-4-yl) amino)-1-(2,2,2-trifluoroethyl)-1H-indol-2-yl)-1,3,4-thiadiazol-2-yl)methyl)carbamate: To a mixture of benzyl ((5-(4-bromo-1-(2,2,2-trifluoroethyl)-1H-indol-2-yl)-1,3,4-thiadiazol-2-yl)methyl)carbamate (1.3 g, 2.47 mmol, 1 eq) and 1-methylpiperidin-4-amine (1.41 g, 12.37 mmol, 5 eq) in THF (13 mL) were added t-BuONa (2 M, 2.47 mL, 2 eq) and t-BuXPhos Palladium Generation 3 (196.6 mg, 247.5 μmol, 0.1 eq). The reaction mixture was heated and stirred at 100° C. for 1 hr, and TLC analysis was used to confirm completion of the reaction. The reaction mixture was poured into a 2M aqueous EDTA solution (100 mL) and stirred for 2 hr, then extracted with EA (50 mL×3). The combined organic phase was washed with brine (30 mL), dried with anhydrous sodium sulfate, filtered, and concentrated in vacuo. The residue was purified by column chromatography ($SiO_2$, PE:EA=1:1 to DCM:MeOH=10:1) to give benzyl ((5-(4-((1-methylpiperidin-4-yl)amino)-1-(2,2,2-trifluoroethyl)-1H-indol-2-yl)-1,3,4-thiadiazol-2-yl)methyl)carbamate (1.8 g, 3.22 mmol, 65.11% yield) as a brown solid.

Preparation of 2-(5-(aminomethyl)-1,3,4-thiadiazol-2-yl)-N-(1-methylpiperidin-4-yl)-1-(2,2,2-trifluoroethyl)-1H-indol-4-amine hydrogen chloride: A solution of benzyl ((5-(4-((1-methylpiperidin-4-yl)amino)-1-(2,2,2-trifluoroethyl)-1H-indol-2-yl)-1,3,4-thiadiazol-2-yl)methyl)carbamate (0.9 g, 1.61 mmol, 1 eq) in HBr (18.50 g, 75.44 mmol, 12.41 mL, 33% purity, 46.82 eq) was stirred at 25° C. for 0.5 hr under a nitrogen atmosphere. TLC analysis was used to confirm completion of the reaction. The reaction mixture was poured into MTBE (200 mL), and the yellow precipitate was filtered out. The resulting solution was concentrated in vacuo. The crude residue was purified by preparative-HPLC to give 2-(5-(aminomethyl)-1,3,4-thiadiazol-2-yl)-N-(1-methylpiperidin-4-yl)-1-(2,2,2-trifluoroethyl)-1H-indol-4-amine hydrobromide (725.1 mg, 1.58 mmol, 49.0% yield, HCl) as a yellow solid. LC-MS ($ES^+$, m/z): 425.2.

General procedure for preparation of Compounds 41B, 42B, 45B, 46B, 49B, 57B, 58B, 59B, 60B, 63B, 64B, 65B, 66B, and 67B: To a mixture of $RCO_2H$ (1 eq) in DMF were added TEA (5 eq) and HATU (2 eq) in one portion at 25° C. under a nitrogen atmosphere. The mixture was stirred at 25° C. for 5 min, and 2-(5-(aminomethyl)-1,3,4-thiadiazol-2-yl)-N-(1-methylpiperidin-4-yl)-1-(2,2,2-trifluoroethyl)-1H-indol-4-amine hydrobromide was added to the reaction at 25° C. with stirring further for 5 min. The residue was poured into ice water (w/w=1/1) (50 mL), and the resulting mixture was stirred for 5 min. The aqueous phase was extracted with EA (20 mL×3). The combined organic phase was washed with brine (30 mL), dried with anhydrous sodium sulfate, filtered, and concentrated in vacuo. The crude product was purified by preparative-TLC (DCM:MeOH=4:1) or preparative-HPLC to afford the desired product.

N-[(5-{4-[(1-methylpiperidin-4-yl)amino]-1-(2,2,2-trifluoroethyl)-1H-indol-2-yl}-1,3,4-thiadiazol-2-yl)methyl]pyridine-2-carboxamide (Compound 411B) in 18.8% yield, LC-MS ($ES^+$, m/z): 530.2; N-[(5-{4-[(1-methylpiperidin-4-yl)amino]-1-(2,2,2-trifluoroethyl)-1H-indol-2-yl}-1,3,4-thiadiazol-2-yl)methyl]pyridine-3-carboxamide (Compound 42B) in 18.9% yield, LC-MS ($ES^+$, m/z): 530.3; N-[(5-{4-[(1-methylpiperidin-4-yl)amino]-1-(2,2,2-trifluoroethyl)-1H-indol-2-yl}-1,3,4-thiadiazol-2-yl)methyl]-4-[(morpholin-4-yl)methyl]benzamide (Compound 45B) in 15.4% yield, LC-MS ($ES^+$, m/z): 628.3; N-[(5-{4-[(1-methylpiperidin-4-yl)amino]-1-(2,2,2-trifluoroethyl)-LH-indol-2-yl}-1,3,4-thiadiazol-2-yl)methyl]-3-[(morpholin-4-yl)methyl]benzamide (Compound 46B) in 15.7% yield, LC-MS ($ES^+$, m/z): 628.3; N-[(5-{4-[(1-methylpiperidin-4-yl)amino]-1-(2,2,2-trifluoroethyl)-1H-indol-2-yl}-1,3,4-thiadiazol-2-yl)methyl]pyridine-4-carboxamide (Compound 49B) in 25.3% yield, LC-MS ($ES^+$, m/z): 530.2; 2-methyl-N-[(5-{4-[(1-methylpiperidin-4-yl)amino]-1-(2,2,2-trifluoroethyl)-1H-indol-2-yl}-1,3,4-thiadiazol-2-yl)methyl]propanamide (Compound 57B) in 26.2% yield, LC-MS ($ES^+$, m/z): 495.2; N-[(5-{4-[(1-methylpiperidin-4-yl)amino]-1-(2,2,2-trifluoroethyl)-1H-indol-2-yl}-1,3,4-thiadiazol-2-yl)methyl]acetamide (Compound 58B) in 29.9% yield, LC-MS ($ES^+$, m/z): 467.1; N-[(5-{4-[(1-methylpiperidin-4-yl)amino]-1-(2,2,2-trifluoroethyl)-1H-indol-2-yl}-1,3,4-thiadiazol-2-yl)methyl]-2-phenylacetamide (Compound 59B) in 24.5% yield, LC-MS ($ES^+$, m/z): 543.3; 2-methoxy-N-[(5-{4-[(1-methylpiperidin-4-yl)amino]-1-(2,2,2-trifluoroethyl)-1H-indol-2-yl}-1,3,4-thiadiazol-2-yl)methyl]acetamide (Compound 60B) in 27.1% yield, LC-MS ($ES^+$, m/z): 497.1; 4-methoxy-N-[(5-{4-[(1-methylpiperidin-4-yl)amino]-1-(2,2,2-trifluoroethyl)-1H-indol-2-yl}-1,3,4-thiadiazol-2-yl)methyl]benzamide (Compound 63B) in 17.5% yield, LC-MS ($ES^+$, m/z): 559.2; 3-methoxy-N-[(5-{4-[(1-methylpiperidin-4-yl)amino]-1-(2,2,2-trifluoroethyl)-1H-indol-2-yl}-1,3,4-thiadiazol-2-yl)methyl]benzamide (Compound 64B) in 22.7% yield, LC-MS ($ES^+$, m/z): 559.2; N-[(5-{4-[(1-methylpiperidin-4-yl)amino]-1-(2,2,2-trifluoroethyl)-1H-indol-2-yl}-1,3,4-thiadiazol-2-yl)methyl]butanamide (Compound 65B) in 22.3% yield, LC-MS ($ES^+$, m/z): 495.2; 2-methoxy-N-[(5-{4-[(1-methylpiperidin-4-yl)

amino]-1-(2,2,2-trifluoroethyl)-1H-indol-2-yl}-1,3,4-thiadiazol-2-yl)methyl]benzamide (Compound 66B) in 17.7% yield, LC-MS (ES+, m/z): 559.2.

Example 21: Synthesis of 4-{[(5-{4-[(1-methylpiperidin-4-yl)amino]-1-(2,2,2-trifluoroethyl)-1H-indol-2-yl}-1,3,4-thiadiazol-2-yl)methyl]carbamoyl}benzoic acid (Compound 54B)

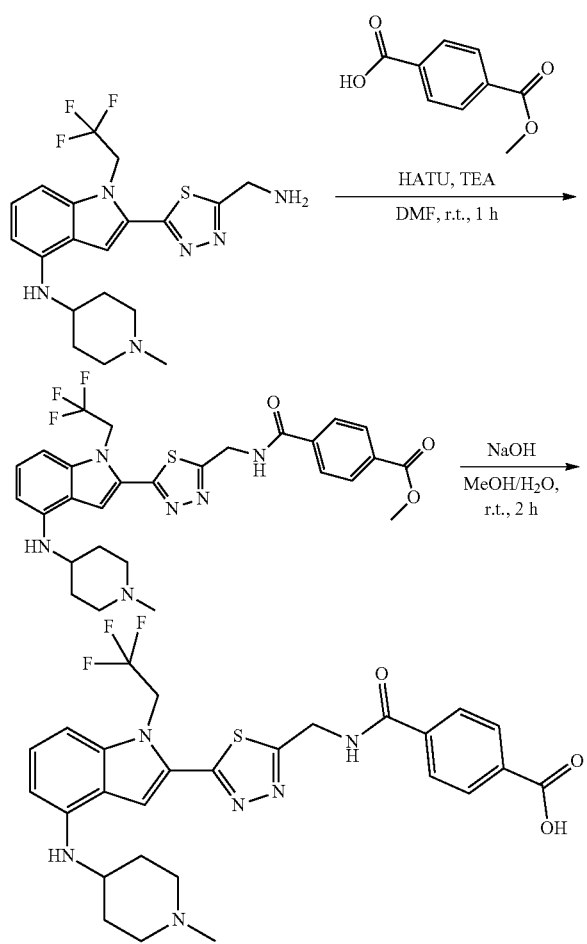

Procedure for preparation of methyl 4-(((5-(4-((1-methylpiperidin-4-yl)amino)-1-(2,2,2-trifluoroethyl)-1H-indol-2-yl)-1,3,4-thiadiazol-2-yl)methyl)carbamoyl)benzoate: To a mixture of 4-(methoxycarbonyl)benzoic acid (18.5 mg, 102.5 μmol, 1 eq) in DMF (1 mL) were added TEA (31.1 mg, 307.5 μmol, 42.8 μL, 3 eq) and HATU (58.5 mg, 153.8 mol, 1.5 eq) in one portion at 25° C. under a nitrogen atmosphere. The mixture was stirred at 25° C. for 5 min, and 2-(5-(aminomethyl)-1,3,4-thiadiazol-2-yl)-N-(1-methylpiperidin-4-yl)-1-(2,2,2-trifluoroethyl)-1H-indol-4-amine (0.05 g, 102.5 μmol, HCl) was added at 25° C. The mixture was stirred for 10 min, and LC-MS analysis was used to confirm completion of the reaction. The residue was poured into ice water (w/w=1/1) (50 mL) and stirred for 5 min. The aqueous phase was extracted with EA (20 mL×3). The combined organic phase was washed with brine (20 mL×3), dried with anhydrous sodium sulfate, filtered, and concentrated in vacuo. The crude product was purified using preparative-TLC to afford methyl 4-(((5-(4-((1-methylpiperidin-4-yl)amino)-1-(2,2,2-trifluoroethyl)-1H-indol-2-yl)-1,3,4-thiadiazol-2-yl)methyl)carbamoyl)benzoate (5 mg, 8.52 μmol, 8.3% yield) as a yellow solid. LC-MS (ES+, m/z): 587.3.

Preparation of 4-{[(5-{4-[(1-methylpiperidin-4-yl)amino]-1-(2,2,2-trifluoroethyl)-1H-indol-2-yl}-1,3,4-thiadiazol-2-yl)methyl]carbamoyl}benzoic acid: To a solution of methyl 4-(((5-(4-((1-methylpiperidin-4-yl)amino)-1-(2,2,2-trifluoroethyl)-1H-indol-2-yl)-1,3,4-thiadiazol-2-yl)methyl)carbamoyl)benzoate (0.05 g, 85.23 μmol, 1 eq) in a mixture of MeOH (0.5 mL) and water (0.1 mL) was added sodium hydroxide (6.82 mg, 170.47 μmol, 2 eq) in one portion at 25° C. under a nitrogen atmosphere. The mixture was stirred at 25° C. for 1 hr. The solvent was removed, and the resulting crude residue was purified using preparative-HPLC to afford 4-{[(5-{$^4$-[(1-methylpiperidin-4-yl)amino]-1-(2,2,2-trifluoroethyl)-1H-indol-2-yl}-1,3,4-thiadiazol-2-yl)methyl]carbamoyl}benzoic acid (Compound 54B) (5.4 mg, 9.11 μmol, 10.69% yield) as a yellow solid. LC-MS (ES+, m/z): 573.1.

Example 22: Synthesis of N-[(5-{4-[(1-methylpiperidin-4-yl)amino]-1-(2,2,2-trifluoroethyl)-1H-indol-2-yl}-1,3,4-thiadiazol-2-yl)methyl]-1H-indazole-5-carboxamide (Compound 55B)

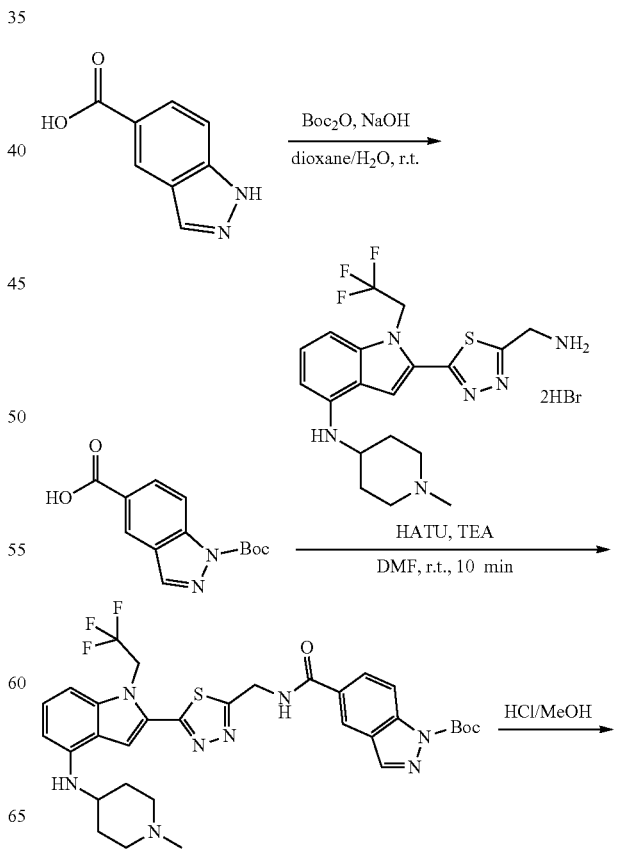

-continued

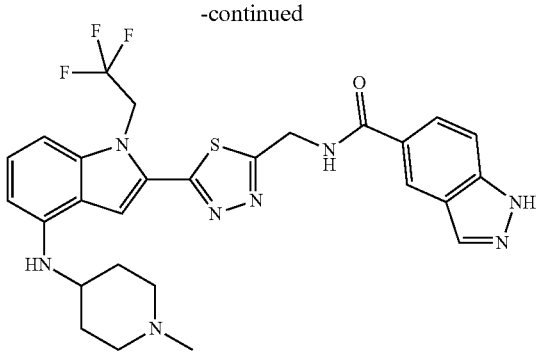

Preparation of 1-(tert-butoxycarbonyl)-1H-indazole-5-carboxylic acid: To a mixture of 1H-indazole-5-carboxylic acid (0.8 g, 4.93 mmol, 1 eq) and Boc₂O (1.29 g, 5.92 mmol, 1.36 mL, 1.2 eq) in dioxane (22 mL) and water (8 mL) was added sodium hydroxide (236.8 mg, 5.92 mmol, 1.2 eq) in one portion at 25° C. under a nitrogen atmosphere. The mixture was stirred at 25° C. for 12 hr, and LC-MS analysis was used to confirm completion of the reaction. The residue was poured into 2M aqueous ammonium chloride (30 mL) and stirred for 5 min. The aqueous phase was adjusted to pH=4 using 1M aqueous HCl and extracted with EA (20 mL×3). The combined organic phase was washed with brine (20 mL×3), dried with anhydrous sodium sulfate, filtered, and concentrated in vacuo. The crude product was purified by preparative-TLC to afford 1-(tert-butoxycarbonyl)-1H-indazole-5-carboxylic acid (0.2 g, 762.60 µmol, 15.46% yield) as a white solid. LC-MS (ES⁺, m/z): 547.2.

Preparation of tert-butyl 5-(((5-(4-((1-methylpiperidin-4-yl)amino)-1-(2,2,2-trifluoroethyl)-1H-indol-2-yl)-1,3,4-thiadiazol-2-yl)methyl)carbamoyl)-1H-indazole-1-carboxylate: To a solution of 1-(tert-butoxycarbonyl)-1H-indazole-5-carboxylic acid (33.8 mg, 128.9 µmol, 1 eq) in DMF (2 mL) were added TEA (39 mg, 387 µmol, 53.8 µL, 3 eq) and HATU (73.54 mg, 193.41 µmol, 1.5 eq) in one portion at 25° C. under a nitrogen atmosphere. The mixture was stirred at 25° C. for 5 min, and 2-(5-(aminomethyl)-1,3,4-thiadiazol-2-yl)-N-(1-methylpiperidin-4-yl)-1-(2,2,2-trifluoroethyl)-1H-indol-4-amine (0.08 g, 128.9 µmol, 1 eq, 2HBr) was added at 25° C. The resulting mixture was stirred for an additional 5 min, and LC-MS analysis was used to confirm completion of the reaction. The residue was poured into ice water (w/w=1/1) (50 mL) and stirred for 5 min. The aqueous phase was extracted with EA (20 mL×3). The combined organic phase was washed with brine (20 mL×3), dried with anhydrous sodium sulfate, filtered, and concentrated in vacuo. The crude product was purified using preparative-TLC to afford tert-butyl 5-(((5-(4-((1-methylpiperidin-4-yl)amino)-1-(2,2,2-trifluoroethyl)-1H-indol-2-yl)-1,3,4-thiadiazol-2-yl)methyl)carbamoyl)-1H-indazole-1-carboxylate (0.05 g, 72.5 µmol, 56.3% yield) as a yellow solid. LC-MS (ES⁺, m/z): 669.3.

Preparation of N-[(5-{4-[(1-methylpiperidin-4-yl)amino]-1-(2,2,2-trifluoroethyl)-1H-indol-2-yl}-1,3,4-thiadiazol-2-yl)methyl]-1H-indazole-5-carboxamide: Tert-butyl 5-(((5-(4-((1-methylpiperidin-4-yl)amino)-1-(2,2,2-trifluoroethyl)-1H-indol-2-yl)-1,3,4-thiadiazol-2-yl)methyl)carbamoyl)-1H-indazole-1-carboxylate (0.05 g, 72.53 µmol, 1 eq) was added to a mixture of 4N HCl in EA (20 mL) in one portion at 25° C. under a nitrogen atmosphere. The mixture was stirred at 25° C. for 10 min, and TLC analysis was used to confirm completion of the reaction. The residue was poured into 2 M aqueous sodium carbonate (100 mL) and stirred for 5 min. The aqueous phase was extracted with EA (30 mL×2). The combined organic phase was washed with brine (20 mL×3), dried with anhydrous sodium sulfate, filtered, and concentrated in vacuo. The crude product was purified by preparative-TLC (DCM:MeOH=10:1) to afford N-[(5-{4-[(1-methylpiperidin-4-yl)amino]-1-(2,2,2-trifluoroethyl)-1H-indol-2-yl}-1,3,4-thiadiazol-2-yl)methyl]-1H-indazole-5-carboxamide (Compound 55B) (20.4 mg, 35.6 µmol, 49.0% yield) as a yellow solid. LC-MS (ES⁺, m/z): 569.2.

Example 23: Synthesis of 3-methyl-1-[(5-{4-[(1-methylpiperidin-4-yl)amino]-1-(2,2,2-trifluoroethyl)-1H-indol-2-yl}-1,3,4-thiadiazol-2-yl)methyl]urea (Compound 56B)

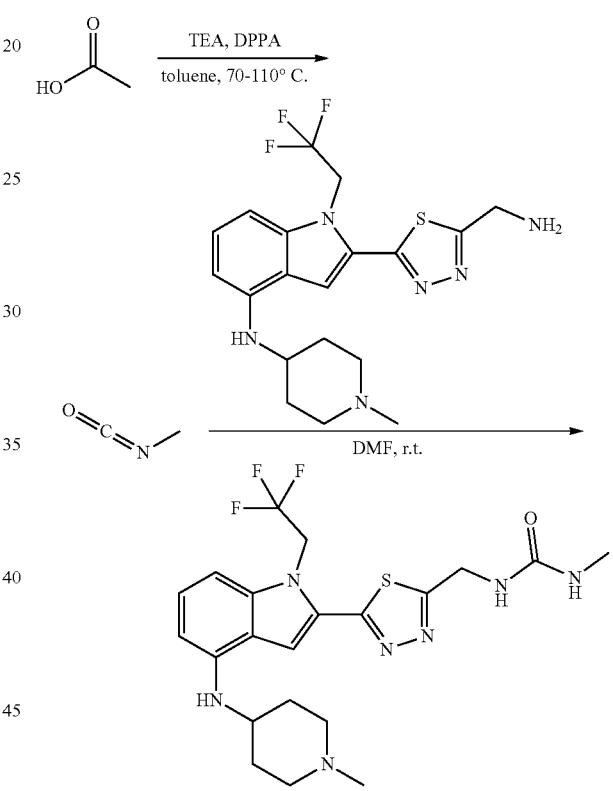

Preparation of isocyanomethane: To a solution of acetic acid (2 g, 33.30 mmol, 1.90 mL, 1 eq) in toluene (15 mL) was added TEA (3.37 g, 33.30 mmol, 4.64 mL, 1 eq) in one portion at 70° C. under a nitrogen atmosphere. The mixture was stirred at 70° C. for 30 min, and diphenyl phosphoryl azide (DPPA) (11.92 g, 43.3 mmol, 9.38 mL, 1.3 eq) was added dropwise at 70° C. The resulting mixture was heated to 110° C. and stirred for 2 hr. An aliquot of the solution was quenched with benzylamine, and TLC analysis was used to confirm completion of the reaction. The reaction was then distilled to afford ~5 mL of isocyanatomethane in toluene as a colorless oil.

Preparation of 3-methyl-1-[(5-{4-[(1-methylpiperidin-4-yl)amino]-1-(2,2,2-trifluoroethyl)-1H-indol-2-yl}-1,3,4-thiadiazol-2-yl)methyl]urea: To a mixture of 2-(5-(aminomethyl)-1,3,4-thiadiazol-2-yl)-N-(1-methylpiperidin-4-yl)-1-(2,2,2-trifluoroethyl)-1H-indol-4-amine (0.08 g, 178.10 µmol, 1 eq) in DMF (1.5 mL) was added TEA (54.1 mg, 534.3 μmol, 74.4 μL, 3 eq) in one portion at 25° C. under a nitrogen atmosphere. The mixture was stirred at 25° C. for 5 min, and isocyanatomethane (101.6 mg, 178.1 μmol, 1 eq) was added at 25° C. The resulting reaction mixture was stirred for 25 min, and LC-MS analysis was used to confirm completion of the reaction. The residue was poured into ice water (w/w=1/1) (50 mL) and was stirred for 5 min. The aqueous phase was extracted with EA (20 mL×3). The combined organic phase was washed with brine (20 mL×3), dried with anhydrous sodium sulfate, filtered, and concentrated in vacuo. The residue was purified by preparative-TLC to afford 3-methyl-1-[(5-{4-[(1-methylpiperidin-4-yl)amino]-1-(2,2,2-trifluoroethyl)-1H-indol-2-yl}-1,3,4-thiadiazol-2-yl)methyl]urea (Compound 56B) (20.1 mg, 40.07 μmol, 22.50% yield) as a yellow solid. LC-MS (ES⁻, m/z): 482.2.

Example 24: Synthesis of 3,3-dimethyl-1-[(5-{4-[(1-methylpiperidin-4-yl)amino]-1-(2,2,2-trifluoroethyl)-1H-indol-2-yl}-1,3,4-thiadiazol-2-yl)methyl]urea (Compound 68B)

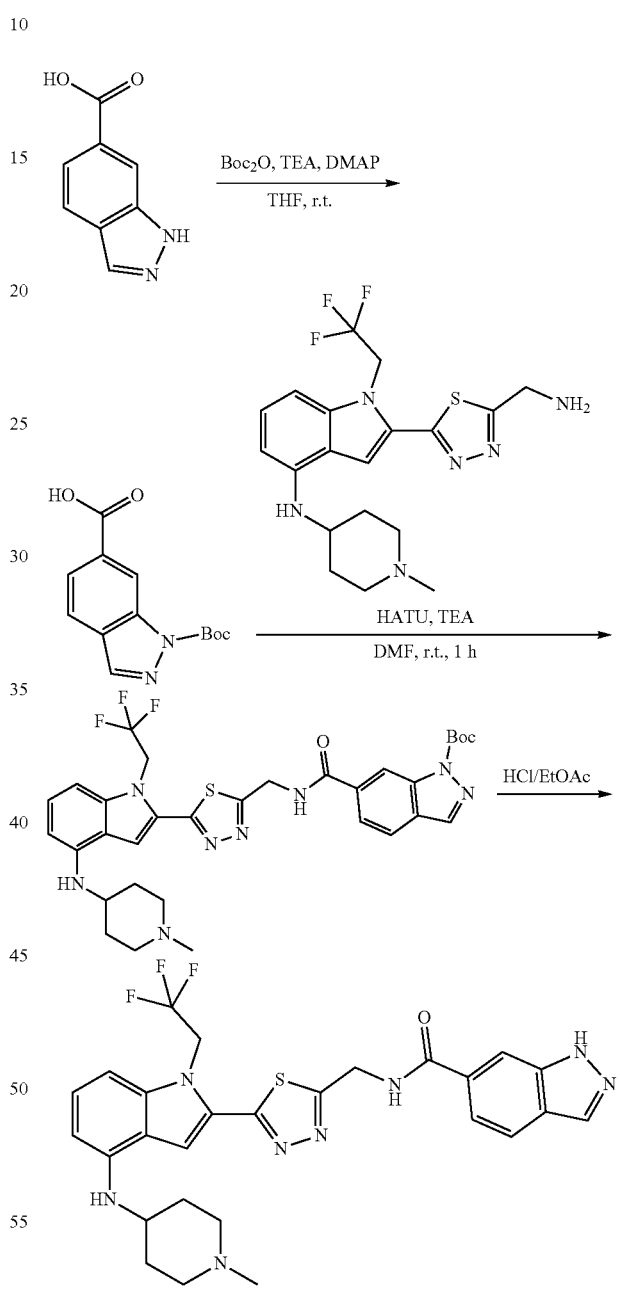

To a mixture of 2-(5-(aminomethyl)-1,3,4-thiadiazol-2-yl)-N-(1-methylpiperidin-4-yl)-1-(2,2,2-trifluoroethyl)-1H-indol-4-amine (80 mg, 173.56 μmol, 1 eq, HCl) and dimethylcarbamic chloride (16.8 mg, 156.2 μmol, 14.4 KL, 0.9 eq) in DCM (1 mL) was added TEA (52.7 mg, 520.7 μmol, 72.5 μL, 3 eq) in one portion under a nitrogen atmosphere. The mixture was heated and stirred at 50° C. for 2 hr, and LC-MS analysis was used to confirm completion of the reaction. The residue was poured into ice water (w/w=1/1) (50 mL). The aqueous phase was extracted with EA (20 mL×3). The combined organic phase was washed with brine (20 mL×3), dried with anhydrous sodium sulfate, filtered, and concentrated in vacuo. The crude product was purified by preparative-HPLC to afford 3,3-dimethyl-1-[(5-{4-[(1-methylpiperidin-4-yl)amino]-1-(2,2,2-trifluoroethyl)-1H-indol-2-yl}-1,3,4-thiadiazol-2-yl)methyl]urea (Compound 68B) (20.9 mg, 41.88 μmol, 24.13% yield) as a yellow solid. LC-MS (ES⁻, m/z): 496.2.

Example 25: Synthesis of N-[(5-{4-[(1-methylpiperidin-4-yl)amino]-1-(2,2,2-trifluoroethyl)-1H-indol-2-yl}-1,3,4-thiadiazol-2-yl)methyl]-1H-indazole-6-carboxamide (Compound 69B)

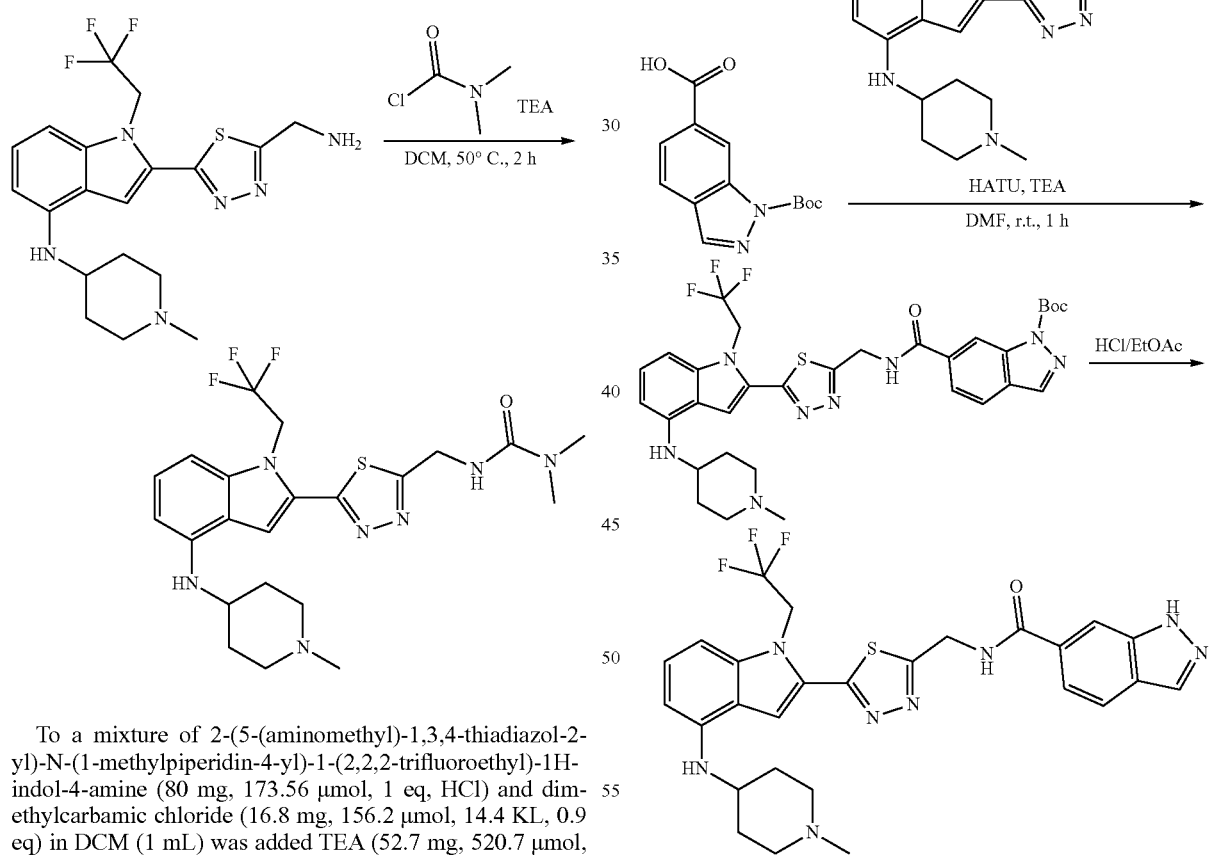

Preparation of 1-(tert-butoxycarbonyl)-1H-indazole-6-carboxylic acid: To a mixture of 1H-indazole-6-carboxylic acid (0.3 g, 1.85 mmol, 1 eq) and Boc₂O (605.7 mg, 2.78 mmol, 1.5 eq) in THF (6 mL) were added TEA (561.7 mg, 5.55 mmol, 772.6 μL, 3 eq) and DMAP (22.6 mg, 185.0 μmol, 0.1 eq) in one portion at 25° C. under a nitrogen atmosphere. The mixture was stirred at 25° C. for 2 hr. The residue was poured into ice water (w/w=1/1) (60 mL) and stirred for 5 min. The aqueous phase was extracted with EA (20 mL×3). The combined organic phase was washed with brine (20 mL×3), dried with anhydrous sodium sulfate, filtered, and concentrated in vacuo. The crude product was purified by preparative-TLC (PE:EA=1:1) to give 1-(tert-butoxycarbonyl)-1H-indazole-6-carboxylic acid (0.16 g, 610.1 μmol, 33.0% yield) as a white solid.

Preparation of tert-butyl 6-(((5-(4-((1-methylpiperidin-4-yl)amino)-1-(2,2,2-trifluoroethyl)-1H-indol-2-yl)-1,3,4-thiadiazol-2-yl)methyl)carbamoyl)-1H-indazole-1-carboxylate: To a solution of 1-(tert-butoxycarbonyl)-1H-indazole-6-carboxylic acid (45.5 mg, 173.6 μmol, 19.8 μL, 1 eq) in DMF (2 mL) were added HATU (99 mg, 260.3 μmol, 1.5 eq), TEA (87.8 mg, 867.8 μmol, 120.8 μL, 5 eq), and 2-(5-(aminomethyl)-1,3,4-thiadiazol-2-yl)-N-(1-methylpiperidin-4-yl)-1-(2,2,2-trifluoroethyl)-1H-indol-4-amine (80 mg, 173.6 μmol, 1 eq, HCl). The mixture was stirred at 20° C. for 1 hr. The reaction mixture was diluted with water (50 mL) and extracted with EA (20 mL×3). The combined organic layer was washed with brine (20 mL×3), dried over sodium sulfate, filtered, and concentrated in vacuo. The crude residue was purified by preparative-TLC (SiO₂, DCM:MeOH=5:1) to give tert-butyl 6-(((5-(4-((1-methylpiperidin-4-yl)amino)-1-(2,2,2-trifluoroethyl)-1H-indol-2-yl)-1,3,4-thiadiazol-2-yl)methyl)carbamoyl)-1H-indazole-1-carboxylate (100 mg, 149.5 μmol, 86.2% yield) as a yellow solid. LC-MS (ES⁺, m/z): 669.0.

Preparation of N-[(5-{4-[(1-methylpiperidin-4-yl)amino]-1-(2,2,2-trifluoroethyl)-1H-indol-2-yl}-1,3,4-thiadiazol-2-yl)methyl]-1H-indazole-6-carboxamide: A solution of tert-butyl 6-(((5-(4-((1-methylpiperidin-4-yl)amino)-1-(2,2,2-trifluoroethyl)-1H-indol-2-yl)-1,3,4-thiadiazol-2-yl)methyl)carbamoyl)-1H-indazole-1-carboxylate (100 mg, 149.54 μmol, 1 eq) in 1M HCl in EA (20 mL, 133.75 eq) was stirred at 25° C. for 1 hr. The reaction mixture was diluted with water (50 mL) and extracted with EA (20 mL×3). The combined organic layers were washed with brine (20 mL×3), dried over sodium sulfate, filtered, and concentrated in vacuo. The crude residue was purified by preparative-TLC (SiO₂, DCM:MeOH=4:1) to give N-[(5-{4-[(1-methylpiperidin-4-yl)amino]-1-(2,2,2-trifluoroethyl)-1H-indol-2-yl}-1,3,4-thiadiazol-2-yl)methyl]-1H-indazole-6-carboxamide (Compound 69B) (23.3 mg, 41.0 μmol, 27.4% yield) as a yellow solid. LC-MS (ES⁺, m/z): 569.3.

Example 26: Synthesis of 2-(5-{[(4-methanesulfonylphenyl)amino]methyl}-1,3,4-thiadiazol-2-yl)-N-(1-methylpiperidin-4-yl)-1-(2,2,2-trifluoroethyl)-1H-indol-4-amine (Compound 24B)

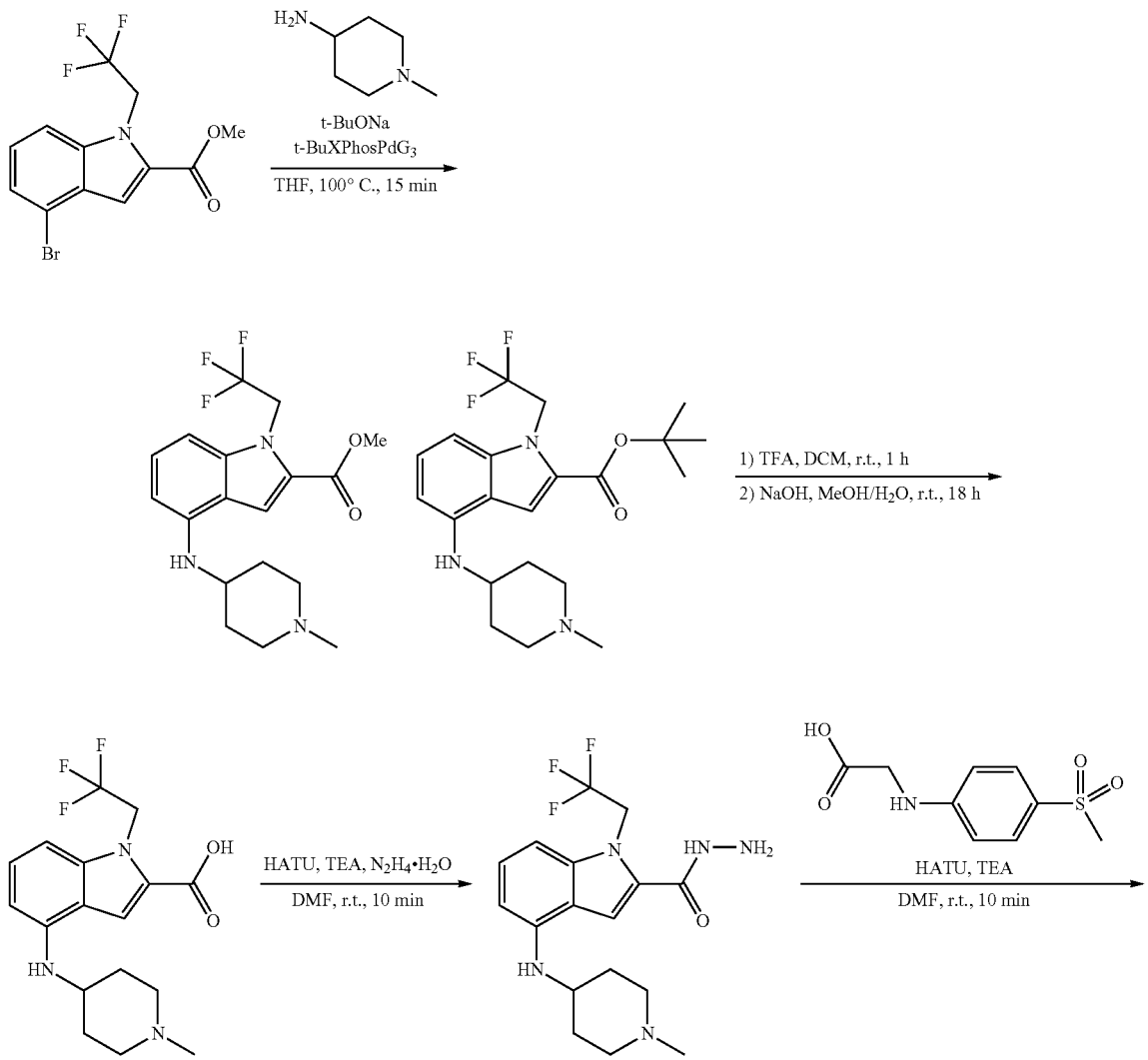

-continued

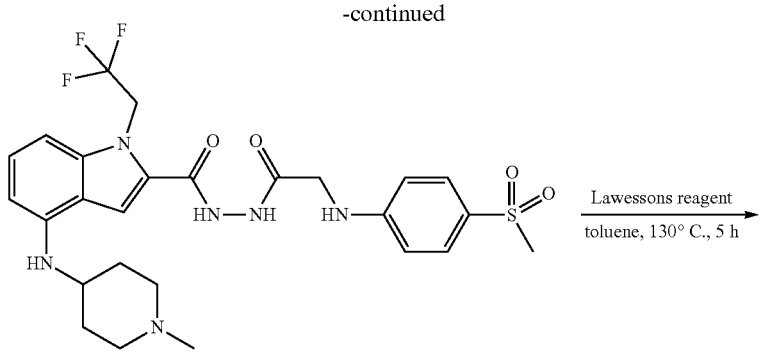

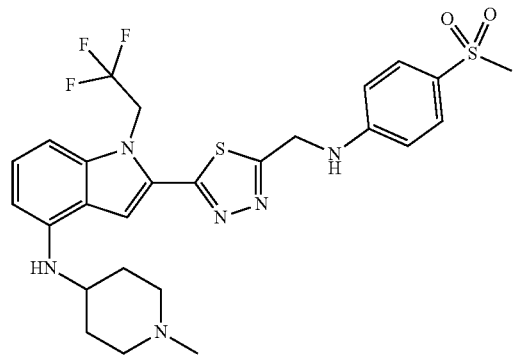 [SMILES: CN1CCC(Nc2cccc3c2cc(-c2nnc(CNc4ccc(S(C)(=O)=O)cc4)s2)n3CC(F)(F)F)CC1]

Preparation of methyl 4-((1-methylpiperidin-4-yl)amino)-1-(2,2,2-trifluoroethyl)-1H-indole-2-carboxylate and tert-butyl 4-((1-methylpiperidin-4-yl)amino)-1-(2,2,2-trifluoroethyl)-1H-indole-2-carboxylate: To a mixture of methyl 4-bromo-1-(2,2,2-trifluoroethyl)-1H-indole-2-carboxylate (2 g, 5.95 mmol, 1 eq) and 1-methylpiperidin-4-amine (1.36 g, 11.90 mmol, 2 eq) in THF (20 mL) were added t-BuXPhos Palladium Generation 3 (472.7 mg, 595.1 μmol, 0.1 eq) and t-BuONa (2 M, 5.95 mL, 2 eq) under nitrogen. The mixture was heated and stirred at 100° C. for 15 min. The residue was poured into an aqueous 2M EDTA solution (150 mL) and stirred for 1 hr. Then the aqueous phase was extracted with EA (100 mL×3). The combined organic phase was washed with brine (100 mL×3), dried with anhydrous sodium sulfate, filtered, and concentrated in vacuo. The residue was purified by column chromatography to afford methyl 4-((1-methylpiperidin-4-yl)amino)-1-(2,2,2-trifluoroethyl)-1H-indole-2-carboxylate and tert-butyl 4-((1-methylpiperidin-4-yl)amino)-1-(2,2,2-trifluoroethyl)-1H-indole-2-carboxylate.

Preparation of 4-((1-methylpiperidin-4-yl)amino)-1-(2,2,2-trifluoroethyl)-1H-indole-2-carboxylic acid: To a solution of methyl 4-((1-methylpiperidin-4-yl)amino)-1-(2,2,2-trifluoroethyl)-1H-indole-2-carboxylate (1 g, 2.71 mmol, 1 eq) and tert-butyl 4-((1-methylpiperidin-4-yl)amino)-1-(2,2,2-trifluoroethyl)-1H-indole-2-carboxylate (1.11 g, 2.71 mmol, 1 eq) in DCM (10 mL) was added TFA (15.40 g, 135.1 mmol, 10 mL, 49.9 eq). The mixture was stirred at 20° C. for 1 hr. The mixture was concentrated in vacuo, and sodium hydroxide (2 g, 50 mmol, 18.47 eq), MeOH (20 mL), and water (2 mL) were added to the crude residue. The resulting mixture was stirred at 20° C. for 18 hr. The reaction was filtered, concentrated in vacuo, and purified by preparative-HPLC to afford 4-((1-methylpiperidin-4-yl)amino)-1-(2,2,2-trifluoroethyl)-1H-indole-2-carboxylic acid. LC-MS (ES+, m/z): 356.1.

Preparation of 4-((1-methylpiperidin-4-yl)amino)-1-(2,2,2-trifluoroethyl)-1H-indole-2-carbohydrazide: To a solution of 4, ((I-methylpiperidin-4-yl)amino)-1-(2,2,2-trifluoroethyl)-1H-indole-2-carboxylic acid (1 g, 2.81 mmol, 1 eq) in DMF (20 mL) were added HATU (2.14 g, 5.63 mmol, 2 eq) and TEA (1.42 g, 14.1 mmol, 1.96 mL, 5 eq). The mixture was stirred at 20° C. for 5 min, and hydrazine hydrate (287.50 mg, 5.63 mmol, 279.12 μL, 2 eq) was added. The mixture was stirred at 20° C. for 5 min. The residue was poured into water (150 mL), and the aqueous phase was extracted with EA (100 mL×3). The combined organic phase was washed with brine (100 mL×3), dried with anhydrous sodium sulfate, filtered, and concentrated in vacuo to afford 4-((1-methylpiperidin-4-yl)amino)-1-(2,2,2-trifluoroethyl)-1H-indole-2-carbohydrazide.

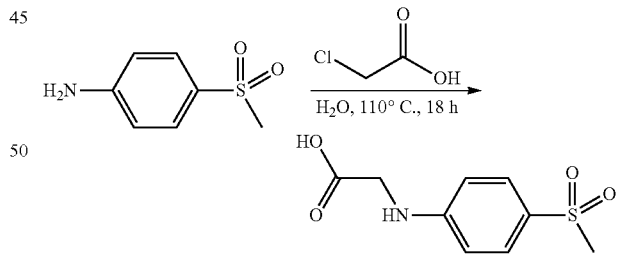

Preparation of (4-(methylsulfonyl)phenyl)glycine: To a solution of 4-(methylsulfonyl)aniline (10 g, 58.41 mmol, 1 eq) in water (100 mL) was added 2-chloroacetic acid (11.04 g, 116.8 mmol, 13.14 mL, 2 eq). The mixture was stirred at 110° C. for 18 hr. The reaction mixture was poured into a 6 M aqueous sodium hydroxide solution (500 mL) and extracted with EA (300 mL×3). The combined aqueous phase was acidified at 0° C. to pH=2 with 4 M aqueous HCl. The resulting precipitate was filtered and washed with water to give (4-(methylsulfonyl)phenyl)glycine in 55.3% yield.

Preparation of 4-((1-methylpiperidin-4-yl)amino)-N'-((4-(methylsulfonyl)phenyl)glycyl)-1-(2,2,2-trifluoroethyl)-1H- indole-2-carbohydrazide: To a solution of (4-(methylsulfonyl)phenyl)glycine (1.74 g, 7.58 mmol, 2 eq) in DMF (20 mL) were added HATU (2.88 g, 7.58 mmol, 2 eq) and TEA (1.92 g, 18.95 mmol, 2.64 mL, 5 eq). The mixture was stirred at 20° C. for 5 min, and 4-((1-methylpiperidin-4-yl)amino)-1-(2,2,2-trifluoroethyl)-1H-indole-2-carbohydrazide (1.4 g, 3.79 mmol, 1 eq) was added. The resulting mixture was stirred at 20° C. for 5 min. The residue was poured into water (150 mL), and the aqueous phase was extracted with EA (100 mL×3). The combined organic phase was washed with brine (100 mL×3), dried with anhydrous sodium sulfate, filtered, and concentrated in vacuo. The residue was purified by preparative-HPLC to afford 4-((1-methylpiperidin-4-yl)amino)-N'-((4-(methylsulfonyl)phenyl)glycyl)-1-(2,2,2-trifluoroethyl)-1H-indole-2-carbohydrazide in 13.6% yield. LC-MS (ES+, m/z): 581.3.

Preparation of 2-(5-{[(4-methanesulfonylphenyl)amino]methyl}-1,3,4-thiadiazol-2-yl)-N-(1-methylpiperidin-4-yl)-1-(2,2,2-trifluoroethyl)-1H-indol-4-amine: To a solution of 4-((1-methylpiperidin-4-yl)amino)-N'-((4-(methylsulfonyl)phenyl)glycyl)-1-(2,2,2-trifluoroethyl)-1H-indole-2-carbohydrazide (200 mg, 344.46 μmol, 1 eq) in toluene (5 mL) was added Lawesson's Reagent (278.64 mg, 688.92 μmol, 2 eq). The mixture was stirred at 130° C. for 5 hr. The residue was poured into water (50 mL), and the aqueous phase was extracted with EA (30 mL×3). The combined organic phase was washed with brine (30 mL×3), dried with anhydrous sodium sulfate, filtered, and concentrated in vacuo. The residue was purified by preparative-HPLC to afford 2-(5-{[(4-methanesulfonylphenyl)amino]methyl}-1,3,4-thiadiazol-2-yl)-N-(1-methylpiperidin-4-yl)-1-(2,2,2-trifluoroethyl)-1H-indol-4-amine (Compound 24B) in 9.69% yield. LC-MS (ES+, m/z): 579.2.

Example 27: Synthesis of 1-ethyl-N-[(5-{4-[(1-methylpiperidin-4-yl)amino]-1-(2,2,2-trifluoroethyl)-1H-indol-2-yl}-1,3,4-thiadiazol-2-yl)methyl]cyclopropane-1-carboxamide (Compound 74B)

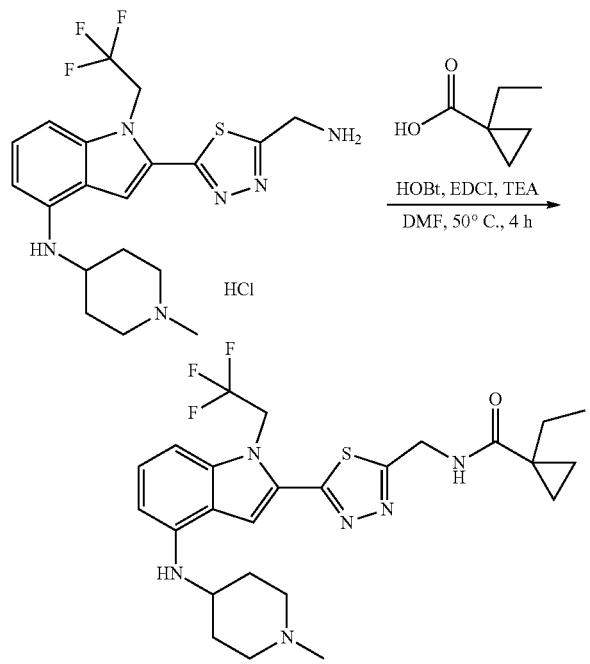

To a solution of 2-(5-(aminomethyl)-1,3,4-thiadiazol-2-yl)-N-(1-methylpiperidin-4-yl)-1-(2,2,2-trifluoroethyl)-1H-indol-4-amine (100 mg, 235.6 μmol, 1 eq, HCl) in DMF (2 mL) were added hydroxybenzotriazole (HOBt) (63.7 mg, 471 μmol, 2 eq), 1-ethyl-3-(3-dimethylaminopropyl)carbodiimide (EDCI) (90.3 mg, 472 μmol, 2 eq), TEA (23.8 mg, 236 μmol, 32.8 μL, 1 eq), and 1-ethylcyclopropane-1-carboxylic acid (26.9 mg, 235.6 μmol, 1 eq). The mixture was stirred at 50° C. for 4 hr. The residue was poured into water (50 mL), and the aqueous phase was extracted with EA (30 mL×3). The combined organic phase was washed with brine (30 mL×3), dried with anhydrous sodium sulfate, filtered, and concentrated in vacuo. The residue was purified by preparative-TLC (SiO₂, DCM:MeOH=4:1) and preparative-HPLC to afford 1-ethyl-N-[(5-{4-[(1-methylpiperidin-4-yl)amino]-1-(2,2,2-trifluoroethyl)-1H-indol-2-yl}-1,3,4-thiadiazol-2-yl)methyl]cyclopropane-1-carboxamide (Compound 74B). LC-MS (ES+, m/z): 521.2.

Example 28: Synthesis of methyl (1R,2R)-2-{[(5-{4-[(1-methylpiperidin-4-yl)amino]-1-(2,2,2-trifluoroethyl)-1H-indol-2-yl}-1,3,4-thiadiazol-2-yl)methyl]carbamoyl}cyclopropane-1-carboxylate (Compound 75B) and (1R,2R)-2-{1[(5-{4-[(1-methylpiperidin-4-yl)amino]-1-(2,2,2-trifluoroethyl)-1H-indol-2-yl}-1,3,4-thiadiazol-2-yl)methyl]carbamoyl}cyclopropane-1-carboxylic acid (Compound 76B)

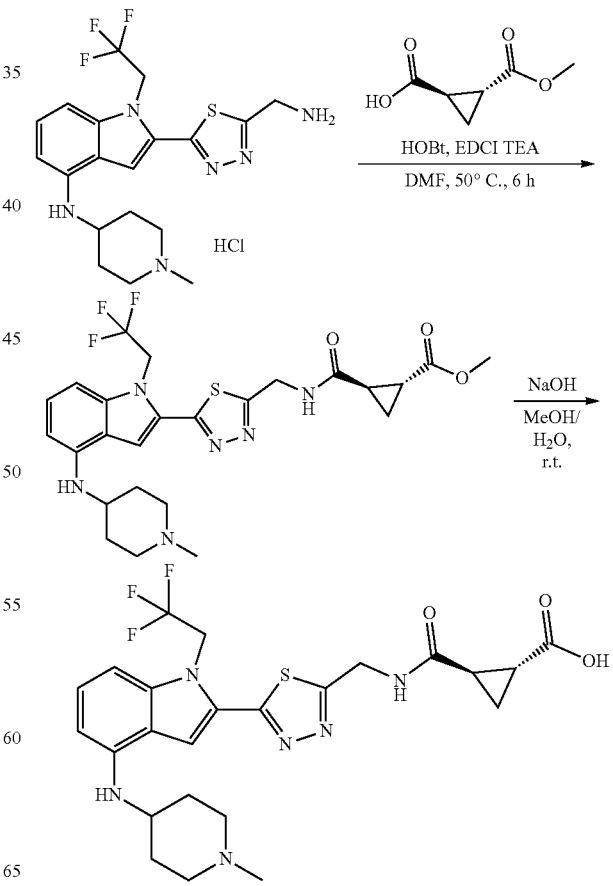

Preparation of (1R,2R)-2-{[(5-{4-[(1-methylpiperidin-4-yl)amino]-1-(2,2,2-trifluoroethyl)-1H-indol-2-yl}-1,3,4-thiadiazol-2-yl)methyl]carbamoyl}cyclopropane-1-carboxylic acid: To a solution of 2-(5-(aminomethyl)-1,3,4-thiadiazol-2-yl)-N-(1-methylpiperidin-4-yl)-1-(2,2,2-trifluoroethyl)-1H-indol-4-amine hydrogen chloride (150 mg, 353.4 µmol, 1 eq) in DMF (2 mL) were added HOBt (95.5 mg, 706.74 µmol, 2 eq), EDCI (135.5 mg, 706.7 µmol, 2 eq), TEA (179 mg, 1.77 mmol, 246 µL, 5 eq), and (1R,2R)-2-(methoxycarbonyl)cyclopropane-1-carboxylic acid (50.9 mg, 353.4 µmol, 1 eq). The mixture was stirred at 50° C. for 6 hr. The residue was poured into water (50 mL), and the aqueous phase was extracted with EA (30 mL×3). The combined organic phase was washed with brine (30 mL×3), dried with anhydrous sodium sulfate, filtered, and concentrated in vacuo. The residue was purified by preparative-TLC (SiO₂, DCM:MeOH=4:1) and preparative-HPLC to afford (1R,2R)-2-{[(5-{4-[(1-methylpiperidin-4-yl)amino]-1-(2,2,2-trifluoroethyl)-1H-indol-2-yl}-1,3,4-thiadiazol-2-yl)methyl]carbamoyl}cyclopropane-1-carboxylic acid (Compound 76BC) in 12.2% yield. LC-MS (ES⁻, m/z): 551.2.

Preparation of (1R,2R)-2-{[(5-{4-[(1-methylpiperidin-4-yl)amino]-1-(2,2,2-trifluoroethyl)-1H-indol-2-yl}-1,3,4-thiadiazol-2-yl)methyl]carbamoyl}cyclopropane-1-carboxylate: To a solution of (1R,2R)-2-{[(5-{4-[(1-methylpiperidin-4-yl)amino]-1-(2,2,2-trifluoroethyl)-1H-indol-2-yl}-1,3,4-thiadiazol-2-yl)methyl]carbamoyl}cyclopropane-1-carboxylic acid (1 eq) in water and MeOH was added sodium hydroxide (2 eq). The mixture was stirred at 20° C. until the reaction was complete as monitored using TLC analysis. The residue was dissolved in MeOH and purified using preparative-HPLC to give product (1R,2R)-2-{[(5-{4-[(1-methylpiperidin-4-yl)amino]-1-(2,2,2-trifluoroethyl)-1H-indol-2-yl}-1,3,4-thiadiazol-2-yl)methyl]carbamoyl}cyclopropane-1-carboxylate (Compound 7513) in 31.8% yield. LC-MS (ES⁺, m/z): 537.1.

Example 29: Synthesis of N-((3S,4S)-3-fluoro-1-methylpiperidin-4-yl)-2-(5-(((2-methoxy-4-(methylsulfonyl)phenyl)amino)methyl)-1,3,4-thiadiazol-2-yl)-1-(2,2,2-trifluoroethyl)-1H-indol-4-amine (Compound 88B)

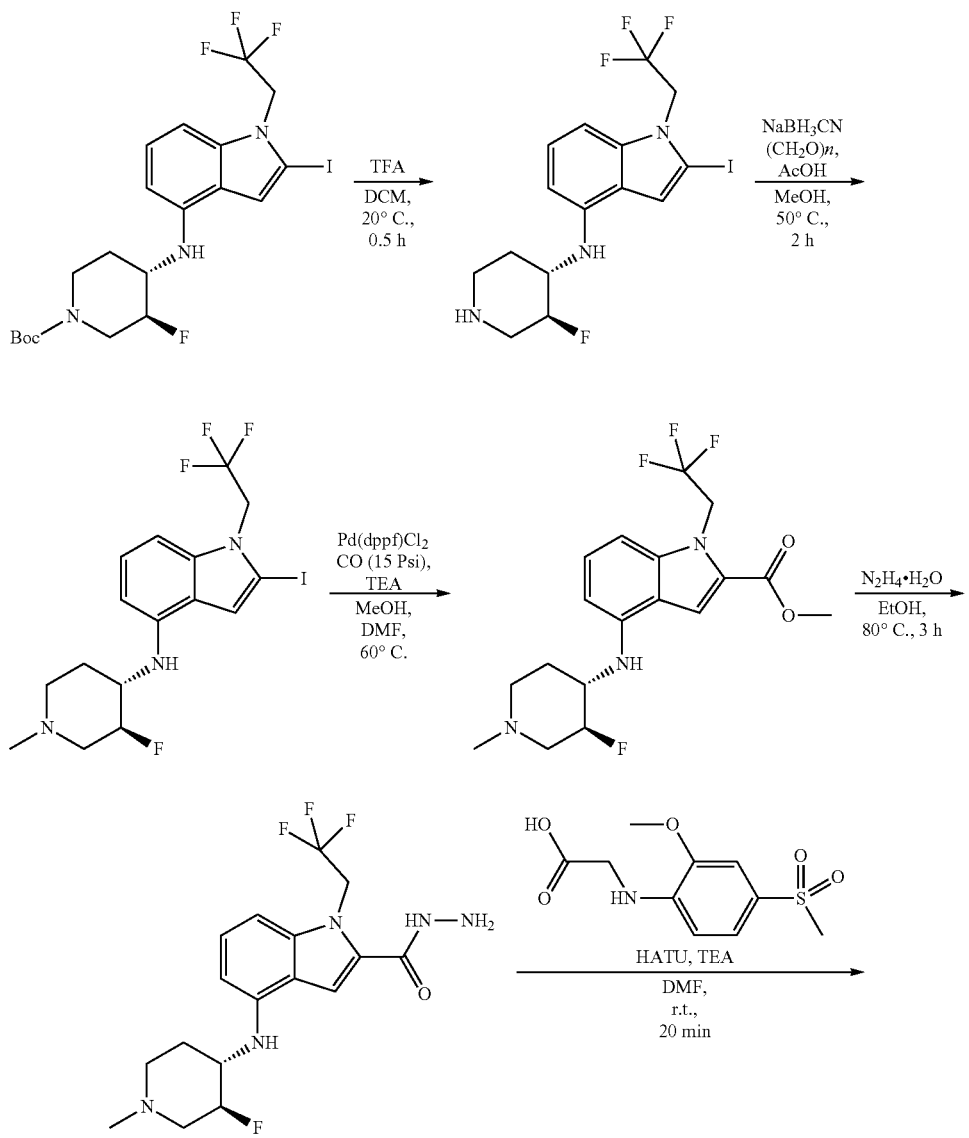

-continued

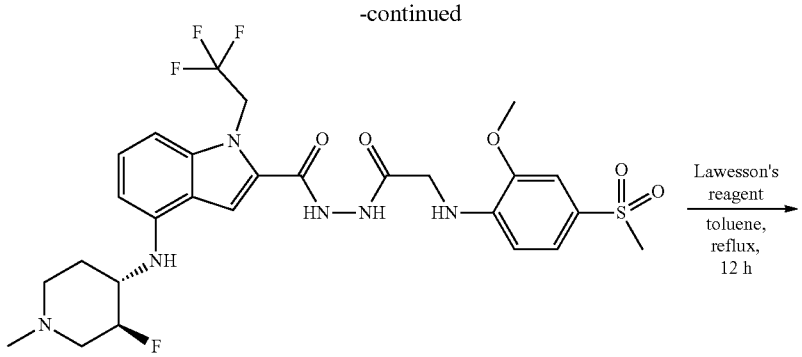

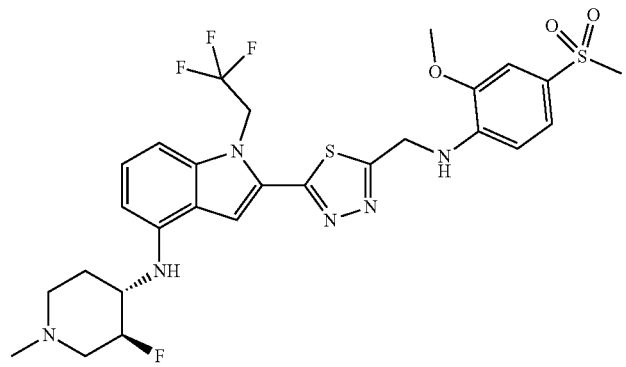

Preparation of N-((3S,4S)-3-fluoropiperidin-4-yl)-2-iodo-1-(2,2,2-trifluoroethyl)-1H-indol-4-amine: To a mixture of tert-butyl-(3S,4S)-3-fluoro-4-((2-iodo-1-(2,2,2-trifluoroethyl)-1H-indol-4-yl)amino)piperidine-1-carboxylate (10 g, 18.5 mmol, 1 eq) in DCM (30 mL) was added TFA (7.70 g, 67.5 mmol, 5 mL, 3.66 eq) in one portion at 20° C. for 30 min. Completion of the reaction was monitored using TLC. The resulting residue was poured into saturated aqueous sodium carbonate to adjust the pH of the residue to 7-8. The aqueous phase was extracted with DCM (200 mL×3). The combined organic phase was washed with brine (200 mL×3), dried with anhydrous sodium sulfate, filtered, and concentrated in vacuo. The concentrated residue was washed with DCM (30 mL) and PE (60 mL) to afford N-((3S,4S)-3-fluoropiperidin-4-yl)-2-iodo-1-(2,2,2-trifluoroethyl)-1H-indol-4-amine.

Preparation of N-((3S,4S)-3-fluoro-1-methylpiperidin-4-yl)-2-iodo-1-(2,2,2-trifluoroethyl)-1H-indol-4-amine: To a mixture of N-((3S,4S)-3-fluoropiperidin-4-yl)-2-iodo-1-(2,2,2-trifluoroethyl)-1H-indol-4-amine (5 g, 11.33 mmol, 1 eq) and paraformaldehyde (1.70 g, 56.7 mmol, 1.56 mL, 5 eq) in MeOH (80 mL) were added sodium cyanoborohydride (3.56 g, 56.7 mmol, 5 eq) and acetic acid (2.10 g, 35 mmol, 2 mL, 3.09 eq) in one portion at 50° C. under a nitrogen atmosphere. The mixture was stirred at 50° C. for 2 hr. Completion of the reaction was confirmed using LC-MS analysis. The reaction residue was poured into ice water (w/w=1/1) (200 mL). The aqueous phase was extracted with EA (100 mL×3). The combined organic phase was washed with brine (100 mL×3), dried with anhydrous sodium sulfate, filtered, and concentrated in vacuo. The residue was purified by silica gel chromatography to afford N-((3S,4S)-3-fluoro-1-methylpiperidin-4-yl)-2-iodo-1-(2,2,2-trifluoroethyl)-1H-indol-4-amine in 58.2% yield. LC-MS (ES$^+$, m/z): 456.0.

Preparation of methyl 4-(((3S,4S)-3-fluoro-1-methylpiperidin-4-yl)amino)-1-(2,2,2-trifluoroethyl)-1H-indole-2-carboxylate: To a solution of N-((3S,4S)-3-fluoro-1-methylpiperidin-4-yl)-2-iodo-1-(2,2,2-trifluoroethyl)-1H-indol-4-amine (3 g, 6.59 mmol, 1 eq) in DMF (20 mL) and MeOH (10 mL) were added Pd(dppf)Cl$_2$ (1.45 g, 1.98 mmol, 0.3 eq) and TEA (3.33 g, 33 mmol, 4.59 mL, 5 eq) at 60° C. under a nitrogen atmosphere. The mixture was stirred at 60° C. under 15 psi carbon monoxide for 2 hr. Completion of the reaction was confirmed using LC-MS analysis. The residue was poured into a 2M aqueous EDTA solution (100 mL) and stirred for 60 min. The aqueous phase was extracted with EA (50 mL×3). The combined organic phase was washed with brine (50 mL×3), dried with anhydrous sodium sulfate, filtered, and concentrated in vacuo. The residue was washed with EA (20 mL) and PE (60 mL) to afford methyl 4-(((3S, 4S)-3-fluoro-1-methylpiperidin-4-yl)amino)-1-(2,2,2-trifluoroethyl)-1H-indole-2-carboxylate in 78.4% yield. LC-MS (ES$^+$, m/z): 388.1.

Preparation of 4-(((3S,4S)-3-fluoro-1-methylpiperidin-4-yl)amino)-1-(2,2,2-trifluoroethyl)-1H-indole-2-carbohydrazide: To a solution of methyl 4-(((3S,4S)-3-fluoro-1-methylpiperidin-4-yl)amino)-1-(2,2,2-trifluoroethyl)-1H-indole-2-carboxylate (2 g, 5.16 mmol, 1 eq) in ethanol (15 mL) was added hydrazine hydrate (10.51 g, 205.8 mmol, 10.20 mL, 98% purity, 39.9 eq) in one portion under a nitrogen atmosphere. The mixture was heated and stirred at 80° C. for 3 hr. Completion of the reaction was confirmed using TLC. The residue was poured into ice water (w/w=1/1) (200 mL), and the aqueous phase was extracted with EA (100 mL×3). The combined organic phase was washed with brine (100 mL×3), dried with anhydrous sodium sulfate, filtered, and concentrated in vacuo. The crude residue was purified by silica gel chromatography to afford 4-(((3S,4S)-3-fluoro-1-methylpiperidin-4-yl)amino)-1-(2,2,2-trifluoroethyl)-1H-indole-2-carbohydrazide in 51.6% yield. LC-MS (ES$^+$, m/z): 388.2.

Preparation of 4-(((3S,4S)-3-fluoro-1-methylpiperidin-4-yl)amino)-N'-((2-methoxy-4-(methylsulfonyl)phenyl)

glycyl)-1-(2,2,2-trifluoroethyl)-1H-indole-2-carbohydrazide: To a mixture of (2-methoxy-4-(methylsulfonyl)phenyl) glycine (796.5 mg, 3.07 mmol, 2 eq) in DMF (10 mL) were added HATU (1.17 g, 3.07 mmol, 2 eq) and TEA (777.1 mg, 7.68 mmol, 1.07 mL, 5 eq) in one portion at 20° C. under a nitrogen atmosphere. The resulting reaction mixture was stirred at 20° C. for 5 min. 4-(((3S,4S)-3-fluoro-1-methylpiperidin-4-yl)amino)-1-(2,2,2-trifluoroethyl)-1H-indole-2-carbohydrazide (0.7 g, 1.54 mmol, 1 eq) was added, and the mixture was stirred at 20° C. for 15 min. The residue was poured into ice water (w/w=1/1) (80 mL), and the aqueous phase was extracted with EA (30 mL×3). The combined organic phase was washed with brine (30 mL×3), dried with anhydrous sodium sulfate, filtered, and concentrated in vacuo. The residue was purified by silica gel chromatography to afford 4-(((3S,4S)-3-fluoro-1-methylpiperidin-4-yl)amino)-N'-((2-methoxy-4-(methylsulfonyl)phenyl)glycyl)-1-(2,2,2-trifluoroethyl)-1H-indole-2-carbohydrazide in 41.1% yield.

Preparation of N-((3S,4S)-3-fluoro-1-methylpiperidin-4-yl)-2-(5-(((2-methoxy-4-(methylsulfonyl)phenyl)amino)methyl)-1,3,4-thiadiazol-2-yl)-1-(2,2,2-trifluoroethyl)-1H-indol-4-amine: To a solution of 4-(((3S,4S)-3-fluoro-1-methylpiperidin-4-yl)amino)-N'-((2-methoxy-4-(methylsulfonyl)phenyl)glycyl)-1-(2,2,2-trifluoroethyl)-1H-indole-2-carbohydrazide (1 eq) in toluene (4 mL) was added Lawesson's Reagent (772.1 mg, 1.91 mmol, 4 eq) in one portion under a nitrogen atmosphere. The mixture was heated and stirred at 130° C. for 12 hr, and completion of the reaction was confirmed using LC-MS analysis. The residue was poured into ice water (w/w=1/1) (50 mL) and stirred for 20 min. The aqueous phase was extracted with EA (20 mL×3). The combined organic phase was washed with brine (20 mL×3), dried with anhydrous sodium sulfate, filtered, and concentrated in vacuo. The crude residue was purified by preparative-HPLC to afford N-((3S,4S)-3-fluoro-1-methylpiperidin-4-yl)-2-(5-(((2-methoxy-4-(methylsulfonyl)phenyl)amino)methyl)-1,3,4-thiadiazol-2-yl)-1-(2,2,2-trifluoroethyl)-1H-indol-4-amine (Compound 88B). LC-MS (ES+, m/z): 627.2

Example 30: Synthesis of N-((5-(4-(((3S,4R)-3-fluoro-1-methylpiperidin-4-yl)amino)-1-(2,2,2-trifluoroethyl)-1H-indol-2-yl)-1,3,4-thiadiazol-2-yl)methyl)cyclopentanecarboxamide (Compound 83B)

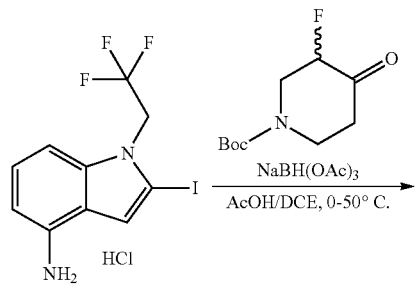

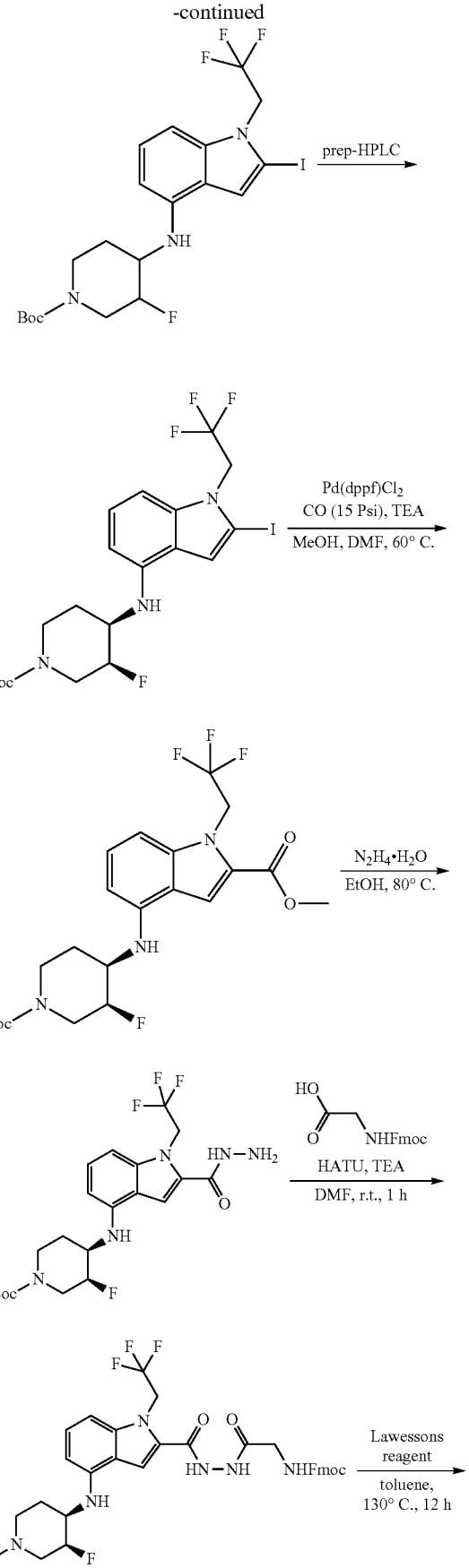

-continued

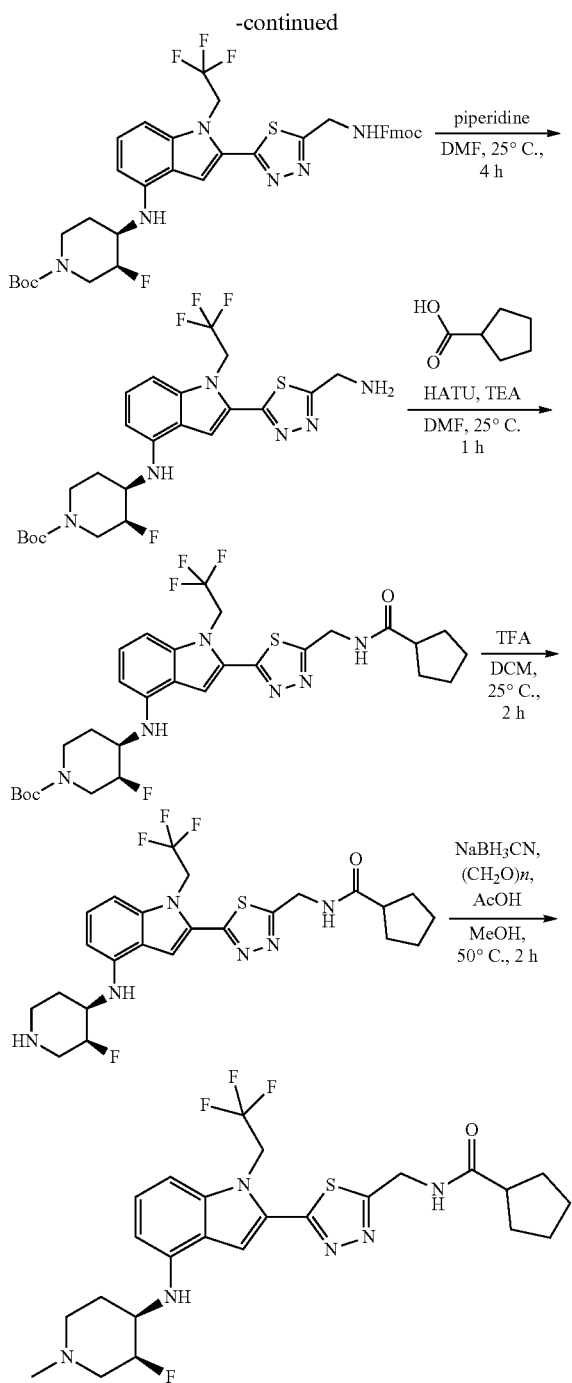

Preparation of (+/−) tert-butyl (3S,4R)-3-fluoro-4-((2-iodo-1-(2,2,2-trifluoroethyl)-1H-indol-4-yl)amino)piperidine-1-carboxylate: To a solution of 2-iodo-1-(2,2,2-trifluoroethyl)-1H-indol-4-amine (5 g, 14.70 mmol, 1 eq, HCl) and tert-butyl 3-fluoro-4-oxopiperidine-1-carboxylate (15.97 g, 73.51 mmol, 5 eq) in DCE (50 mL) and acetic acid (150 mL) was added sodium triacetoxyborohydride (15.58 g, 73.51 mmol, 5 eq) at 0° C. The reaction mixture was then heated to 50° C. and stirred at 50° C. for 4 hr. Completion of the reaction was confirmed using LC-MS analysis. The reaction mixture was poured into a saturated aqueous sodium carbonate solution (150 mL) and extracted with EA (100 mL×3). The combined organic phase was washed with brine (50 mL), dried with anhydrous sodium sulfate, filtered, and concentrated in vacuo. The crude residue was purified by preparative-HPLC to afford (+/−) tert-butyl (3S,4R)-3-fluoro-4-((2-iodo-1-(2,2,2-trifluoroethyl)-1H-indol-4-yl)amino)piperidine-1-carboxylate (6.26 g, 11.47 mmol, 79.8% yield) as a light yellow solid. LC-MS (ES$^+$, m/z): 542.0.

Preparation of (+/−) methyl 4-(((3S,4R)-1-(tert-butoxycarbonyl)-3-fluoropiperidin-4-yl)amino)-1-(2,2,2-trifluoroethyl)-1H-indole-2-carboxylate: To a solution of tert-butyl (3S,4R)-3-fluoro-4-((2-iodo-1-(2,2,2-trifluoroethyl)-1H-indol-4-yl)amino)piperidine-1-carboxylate (5 g, 9.24 mmol, 1 eq) in MeOH (50 mL) and DMF (100 mL) were added TEA (1.87 g, 18.47 mmol, 2.57 mL, 2 eq) and Pd(dppf)Cl$_2$ (2.26 g, 2.77 mmol, 0.3 eq). The reaction mixture was degassed with carbon monoxide 3 times, and the resulting mixture was stirred at 60° C. for 2 hr under a carbon monoxide atmosphere. Completion of the reaction was confirmed using LC-MS analysis. The mixture was poured into a 2M aqueous EDTA solution (1000 mL) and stirred for 2 h, then extracted with EA (500 mL×3). The combined organic phase was washed with brine (200 mL), dried with anhydrous sodium sulfate, filtered, and concentrated in vacuo. The crude residue was purified by column chromatography (SiO$_2$, PE:EA=5:1 to 2:1) and preparative-HPLC to afford (+/−) methyl 4-(((3S,4R)-1-(tert-butoxycarbonyl)-3-fluoropiperidin-4-yl)amino)-1-(2,2,2-trifluoroethyl)-1H-indole-2-carboxylate (6.2 g, 13.1 mmol, 71.2% yield) as a light yellow solid. LC-MS (ES$^+$, m/z): 474.1.

Preparation of (+/−) tert-butyl (3S,4R)-3-fluoro-4-((2-(hydrazinecarbonyl)-1-(2,2,2-trifluoroethyl)-1H-indol-4-yl)amino)piperidine-1-carboxylate: To a solution of methyl 4-(((3S,4R)-1-(tert-butoxycarbonyl)-3-fluoropiperidin-4-yl)amino)-1-(2,2,2-trifluoroethyl)-1H-indole-2-carboxylate (2.6 g, 5.49 mmol, 1 eq) in EtOH (10 mL) was added hydrazine hydrate (10.30 g, 205.8 mmol, 10 mL, 37.5 eq). The reaction mixture was heated and stirred at 80° C. for 1 h, and completion of the reaction was confirmed using TLC analysis. The reaction was poured into water (60 mL), extracted with EA (30 mL×3). The combined organic phase was washed with brine (20 mL), dried with anhydrous sodium sulfate, filtered, and concentrated in vacuo to afford (+/−) tert-butyl (3S,4R)-3-fluoro-4-((2-(hydrazinecarbonyl)-1-(2,2,2-trifluoroethyl)-1H-indol-4-yl)amino)piperidine-1-carboxylate (2.4 g, crude) as a white solid. LC-MS (ES$^+$, m/z): 474.3.

Preparation of (+/−) tert-butyl (3S,4R)-4-((2-(2-(((((9H-fluoren-9-yl)methoxy)carbonyl)glycyl)hydrazine-1-carbonyl)-1-(2,2,2-trifluoroethyl)-1H-indol-4-yl)amino)-3-fluoropiperidine-1-carboxylate: To a solution of (((9H-fluoren-9-yl)methoxy)carbonyl)glycine (1.57 g, 5.28 mmol, 1 eq) in DMF (75 mL) were added TEA (2.67 g, 26.40 mmol, 3.67 mL, 5 eq) and HATU (4.02 g, 10.56 mmol, 2 eq). Tert-butyl (3S,4R)-3-fluoro-4-((2-(hydrazinecarbonyl)-1-(2,2,2-trifluoroethyl)-1H-indol-4-yl)amino)piperidine-1-carboxylate (2.5 g, 5.28 mmol, 1 eq) was then added to the mixture, and the resulting reaction mixture was stirred at 25° C. for 1 hr. Completion of the reaction was confirmed using TLC analysis. The reaction mixture was poured into water (200 mL) and extracted with EA (80 mL×3). The combined organic phase was washed with brine (50 mL), dried with anhydrous sodium sulfate, filtered, and concentrated in vacuo. The crude residue was purified by column chromatography (SiO$_2$, PE:EA=5:1 to 1:1) to afford (+/−) tert-butyl (3S,4R)-4-((2-(2-(((((9H-fluoren-9-yl)methoxy)carbonyl)glycyl)hydrazine-1-carbonyl)-1-(2,2,2-trifluoroethyl)-1H-indol-4-yl)amino)-3-fluoropiperidine-1-carboxylate (4.6 g, 6.11 mmol, 57.87% yield) as a light yellow solid. LC-MS (ES$^+$, m/z): 753.2.

Preparation of (+/−) tert-butyl (3S,4R)-4-((2-(5-(((((9H-fluoren-9-yl)methoxy)carbonyl)amino)methyl)-1,3,4-thiadiazol-2-yl)-1-(2,2,2-trifluoroethyl)-1H-indol-4-yl)amino)-3-fluoropiperidine-1-carboxylate: To a solution of tert-butyl (3S,4R)-4-((2-(2-(((((9H-fluoren-9-yl)methoxy)carbonyl)

glycyl)hydrazine-1-carbonyl)-1-(2,2,2-trifluoroethyl)-1H-indol-4-yl)amino)-3-fluoropiperidine-1-carboxylate (2.1 g, 2.79 mmol, 1 eq) in toluene (44 mL) was added Lawesson's Reagent (2.26 g, 5.58 mmol, 2 eq). The mixture was stirred at 80° C. for 40 min, and completion of the reaction was confirmed using TLC analysis. The reaction mixture was poured into water (200 mL) and extracted with EA (80 mL×3). The combined organic phase was washed with brine (50 mL), dried with anhydrous sodium sulfate, filtered, and concentrated in vacuo. The crude residue was purified by column chromatography (SiO$_2$, PE:EA=5:1 to 1:1, R$_f$=0.39) to afford (+/−) tert-butyl (3S,4R)-4-((2-(5-(((((9H-fluoren-9-yl)methoxy)carbonyl)amino)methyl)-1,3,4-thiadiazol-2-yl)-1-(2,2,2-trifluoroethyl)-1H-indol-4-yl)amino)-3-fluoropiperidine-1-carboxylate (800 mg, 1.07 mmol, 38.2% yield) as a light yellow solid. LC-MS (ES$^+$, m/z): 751.3.

Preparation of tert-butyl(3S,4R)-4-((2-(5-(aminomethyl)-1,3,4-thiadiazol-2-yl)-1-(2,2,2-trifluoroethyl)-1H-indol-4-yl)amino)-3-fluoropiperidine-1-carboxylate: To a solution of tert-butyl (3S,4R)-4-((2-(5-(((((9H-fluoren-9-yl)methoxy)carbonyl)amino)methyl)-1,3,4-thiadiazol-2-yl)-1-(2,2,2-trifluoroethyl)-1H-indol-4-yl)amino)-3-fluoropiperidine-1-carboxylate (800 mg, 1.07 mmol, 1 eq) in DMF (3 mL) was added piperidine (3623 mg, 4.26 mmol, 421 µL, 4 eq). The reaction was stirred at 25° C. for 4 hr, and completion of the reaction was confined using TLC analysis. The reaction mixture was poured into water (60 mL) and extracted with EA (40 mL×3). The combined organic phase was washed with brine (30 mL), dried with anhydrous sodium sulfate, filtered, and concentrated in vacuo. The crude residue was purified by column chromatography (SiO$_2$, PE:EA=3:1 to 0:1, R$_f$=0.17) to afford (+/−) tert-butyl (3S,4R)-4-((2-(5-(aminomethyl)-1,3,4-thiadiazol-2-yl)-1-(2,2,2-trifluoroethyl)-1H-indol-4-yl)amino)-3-fluoropiperidine-1-carboxylate (500 mg, 945.96 µmol, 88.78% yield) as a yellow oil. LC-MS (ES$^-$, m/z): 551.2.

Preparation of (+/−) tert-butyl (3S,4R)-4-((2-(5-(cyclopentanecarboxamidomethyl)-1,3,4-thiadiazol-2-yl)-1-(2,2,2-trifluoroethyl)-1H-indol-4-yl)amino)-3-fluoropiperidine-1-carboxylate: To a solution of cyclopentanecarboxylic acid (51.83 mg, 454.06 µmol, 49.4 µL, 1 eq) in DMF (10 mL) were added TEA (230 mg, 2.27 mmol, 316 µL, 5 eq) and HATU (345.3 mg. 908 µmol, 2 eq). Tert-butyl (3S,4R)-4-((2-(5-(aminomethyl)-1,3,4-thiadiazol-2-yl)-1-(2,2,2-trifluoroethyl)-1H-indol-4-yl)amino)-3-fluoropiperidine-1-carboxylate (240 mg, 454 µmol, 1 eq) was then added to the reaction, and the mixture was stirred at 25° C. for 1 hr. Completion of the reaction was monitored using LC-MS analysis. The reaction mixture was poured into water (50 mL) and extracted with EA (40 mL×3). The combined organic phase was washed with brine (30 mL), dried with anhydrous sodium sulfate, filtered, and concentrated in vacuo. The crude residue was purified by preparative-TLC (SiO$_2$, PE:EA=1:1, R$_f$=0.50) to afford (+/−) tert-butyl (3S, 4R)-4-((2-(5-(cyclopentanecarboxamidomethyl)-1,3,4-thiadiazol-2-yl)-1-(2,2,2-trifluoroethyl)-1H-indol-4-yl)amino)-3-fluoropiperidine-1-carboxylate (275 mg, 440.22 µmol, 96.95% yield) as a light yellow solid. LC-MS (ES$^-$, m/z): 625.3.

Preparation of (+/−)N-((5-(4-(((3S,4R)-3-fluoropiperidin-4-yl)amino)-1-(2,2,2-trifluoroethyl)-1H-indol-2-yl)-1,3,4-thiadiazol-2-yl)methyl)cyclopentanecarboxamide: A solution of tert-butyl (3S,4R)-4-((2-(5-(cyclopentanecarboxamidomethyl)-1,3,4-thiadiazol-2-yl)-1-(2,2,2-trifluoroethyl)-1H-indol-4-yl)amino)-3-fluoropiperidine-1-carboxylate (265 mg, 424 µmol, 1 eq) in TFA (2 mL) and DCM (20 mL) was stirred at 25° C. for 1 hr. Completion of the reaction was confirmed using TLC analysis. The reaction mixture was poured into a saturated aqueous sodium carbonate solution (30 mL) and was extracted with DCM (20 mL×3). The combined organic phase was washed with brine (10 mL), dried with anhydrous sodium sulfate, filtered, and concentrated in vacuo to afford (+/−)N-((5-(4-(((3S,4R)-3-fluoropiperidin-4-yl)amino)-1-(2,2,2-trifluoroethyl)-1H-indol-2-yl)-1,3,4-thiadiazol-2-yl)methyl)cyclopentanecarboxamide (260 mg, crude) as a light yellow oil. LC-MS (ES$^+$, m/z): 525.2.

Preparation of (+/−)N-((5-(4-(((3S,4R)-3-fluoro-1-methylpiperidin-4-yl)amino)-1-(2,2,2-trifluoroethyl)-1H-indol-2-yl)-1,3,4-thiadiazol-2-yl)methyl)cyclopentanecarboxamide (Compound 83C): To a mixture of N-((5-(4-(((3S,4R)-3-fluoropiperidin-4-yl)amino)-1-(2,2,2-trifluoroethyl)-1H-indol-2-yl)-1,3,4-thiadiazol-2-yl)methyl)cyclopentanecarboxamide (210 mg, 400 µmol, 1 eq) and paraformaldehyde (60.1 mg, 2 mmol, 5 eq) in MeOH (15 mL) were added acetic acid (1.05 g, 17.5 mmol, 1 mL, 43.7 eq) and sodium cyanoborohydride (125.8 mg, 2 mmol, 5 eq). The mixture was stirred at 50° C. for 1.5 h, and completion of the reaction was confirmed using TLC analysis. The reaction mixture was poured into water (50 mL) and extracted with EA (40 mL×3). The combined organic phase was washed with brine (30 mL), dried with anhydrous sodium sulfate, filtered, and concentrated in vacuo. The crude residue was purified by preparative-HPLC to afford (+/−)N-((5-(4-(((3S,4R)-3-fluoro-1-methylpiperidin-4-yl)amino)-1-(2,2,2-trifluoroethyl)-1H-indol-2-yl)-1,3,4-thiadiazol-2-yl)methyl)cyclopentanecarboxamide (Compound 83B) (20.2 mg, 37.2 µmol, 9.3% yield) as a yellow solid. LC-MS (ES$^+$, m/z): 539.2.

Example 31: Synthesis (+/−)-N-((3S,4R)-3-fluoro-1-methylpiperidin-4-yl)-2-(5-(((2-methoxy-4-(methylsulfonyl)phenyl)amino)methyl)-1,3,4-thiadiazol-2-yl)-1-(2,2,2-trifluoroethyl)-1H-indol-4-amine (Compound 84B)

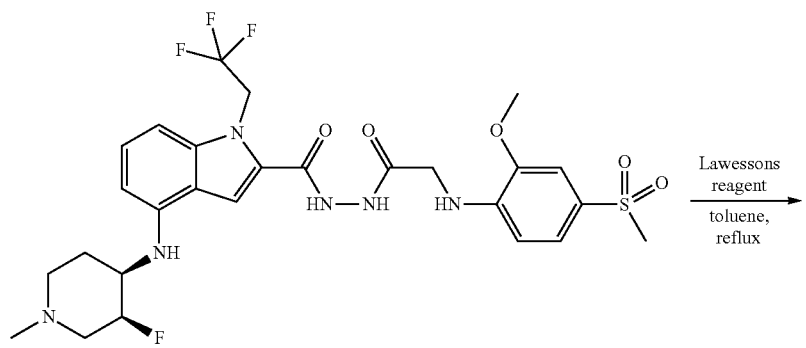

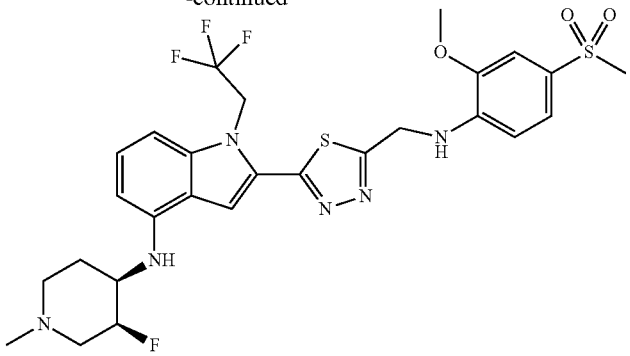

To a mixture of (+/−)-4-(((3S,4R)-3-fluoro-1-methylpiperidin-4-yl)amino)-N'-((2-methoxy-4-(methylsulfonyl)phenyl)glycyl)-1-(2,2,2-trifluoroethyl)-1H-indole-2-carbohydrazide (0.3 g, 477 μmol, 1 eq) in toluene (4 mL) was added Lawesson's Reagent (772 mg, 1.91 mmol, 4 eq) in one portion under a nitrogen atmosphere. The mixture was heated and stirred at 130° C. for 12 hr, and completion of the reaction was confirmed using LC-MS analysis. The residue was poured into ice water (w/w=1/1) (50 mL) and stirred for 20 min. The aqueous phase was extracted with EA (20 mL×3). The combined organic phase was washed with brine (20 mL×3), dried with anhydrous sodium sulfate, filtered, and concentrated in vacuo. The crude residue was purified by preparative-HPLC to afford N-((3S,4R)-3-fluoro-1-methylpiperidin-4-yl)-2-(5-(((2-methoxy-4-(methylsulfonyl)phenyl)amino)methyl)-1,3,4-thiadiazol-2-yl)-1-(2,2,2-trifluoroethyl)-1H-indol-4-amine (Compound 84B) (27 mg, 42.0 μmol, 8.8% yield) as a yellow solid. LC-MS (ES⁻, m/z): 627.1.

Example 32: Synthesis of N-((5-(4-(((3S,4R)-3-fluoro-1-methylpiperidin-4-yl)amino)-1-(2,2,2-trifluoroethyl)-1H-indol-2-yl)-1,3,4-thiadiazol-2-yl)methyl)benzamide (Compound 85B) and N-((5-(4-(((3S,4R)-3-fluoro-1-methylpiperidin-4-yl)amino)-1-(2,2,2-trifluoroethyl)-1H-indol-2-yl)-1,3,4-thiadiazol-2-yl)methyl)cyclopropanecarboxamide (Compound 86B)

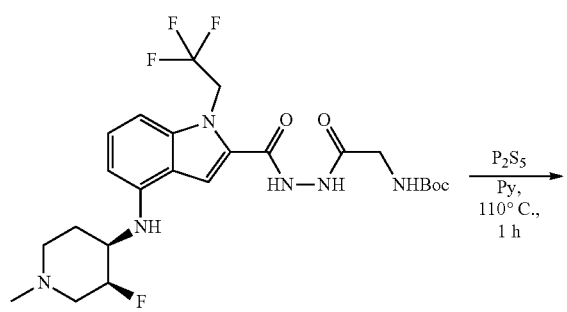

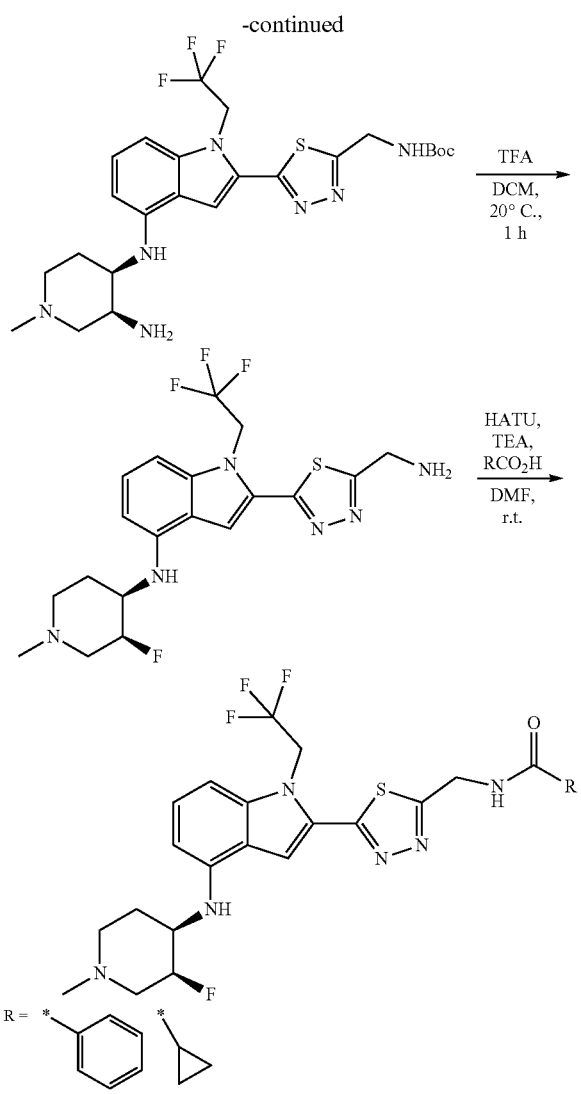

Preparation of tert-butyl ((5-(4-(((3S,4R)-3-amino-1-methylpiperidin-4-yl)amino)-1-(2,2,2-trifluoroethyl)-1H-indol-2-yl)-1,3,4-thiadiazol-2-yl)methyl)carbamate: To a mixture of tert-butyl (2-(2-(4-(((3S,4R)-3-fluoro-1-methylpiperidin-4-yl)amino)-1-(2,2,2-trifluoroethyl)-1H-indole-2-carbonyl)hydrazinyl)-2-oxoethyl)carbamate (1 g, 1.84 mmol, 1 eq) in pyridine (20 mL) was added P₂S₅ (816.4 mg, 3.67 mmol, 390.61 μL, 2 eq) in one portion at 110° C.

under a nitrogen atmosphere. The mixture was stirred at 110° C. for 60 min. The residue was poured into ice water (w/w=1/1) (50 mL), and the aqueous phase was extracted with EA (25 mL×3). The combined organic phase was washed with brine (25 mL×3), dried with anhydrous sodium sulfate, filtered, and concentrated in vacuo to afford tert-butyl ((5-(4-(((3S,4R)-3-amino-1-methylpiperidin-4-yl)amino)-1-(2,2,2-trifluoroethyl)-1H-indol-2-yl)-1,3,4-thiadiazol-2-yl)methyl)carbamate. LC-MS (ES+, m/z): 627.1.

Preparation of 2-(5-(aminomethyl)-1,3,4-thiadiazol-2-yl)-N-((3S,4R)-3-fluoro-1-methylpiperidin-4-yl)-1-(2,2,2-trifluoroethyl)-1H-indol-4-amine: To a mixture of tert-butyl ((5-(4-(((3S,4R)-3-amino-1-methylpiperidin-4-yl)amino)-1-(2,2,2-trifluoroethyl)-JH-indol-2-yl)-1,3,4-thiadiazol-2-yl)methyl)carbamate (300 mg, 552.90 μmol, 1 eq) in DCM (2 mL) was added TFA (3.08 g, 27.01 mmol, 2 mL, 48.86 eq) in one portion at 20° C. under a nitrogen atmosphere. The mixture was stirred at 20° C. for 1 hr., and completion of the reaction was confirmed using TLC analysis. The residue was poured into water (50 mL), and the aqueous phase was extracted with DCM (10 mL×3). The aqueous phase was poured into a saturated aqueous sodium bicarbonate solution to adjust the pH of the residue to 7-8. The aqueous phase was extracted with EA (25 mL×3). The combined organic phase was washed with brine (25 mL×3), dried with anhydrous sodium sulfate, filtered, and concentrated in vacuo to afford 2-(5-(aminomethyl)-1,3,4-thiadiazol-2-yl)-N-((3S,4R)-3-fluoro-1-methylpiperidin-4-yl)-1-(2,2,2-trifluoroethyl)-1H-indol-4-amine.

Synthesis of N-((5-(4-(((3S,4R)-3-fluoro-1-methylpiperidin-4-yl)amino)-1-(2,2,2-trifluoroethyl)-1H-indol-2-yl)-1,3,4-thiadiazol-2-yl)methyl)benzamide (Compound 85B) and N-((5-(4-(((3S,4R)-3-fluoro-1-methylpiperidin-4-yl)amino)-1-(2,2,2-trifluoroethyl)-1H-indol-2-yl)-1,3,4-thiadiazol-2-yl)methyl)cyclopropanecarboxamide (Compound 86B): To a solution of 2-(5-(aminomethyl)-1,3,4-thiadiazol-2-yl)-N-((3S,4R)-3-fluoro-1-methylpiperidin-4-yl)-1-(2,2,2-trifluoroethyl)-H-indol-4-amine (1 eq) in DMF were added HATU (2 eq) and TEA (114 mg, 1.13 mmol, 157 μL, 5 eq) in one portion at 20° C. under a nitrogen atmosphere. The mixture was stirred at 20° C. for 5 min, and RCO$_2$H (100 mg, 226 μmol, 1 eq) was added. The resulting mixture was stirred at 20° C. for 15 min, and completion of the reaction was confirmed using LC-MS analysis. The residue was poured into ice water (w/w=1/1) (40 mL). The aqueous phase was extracted with EA (20 mL×3), and the combined organic phase was washed with brine (20 mL×3), dried with anhydrous sodium sulfate, filtered, and concentrated in vacuo. The crude residue was purified by preparative-HPLC to afford N-((5-(4-(((3S,4R)-3-fluoro-1-methylpiperidin-4-yl)amino)-1-(2,2,2-trifluoroethyl)-1H-indol-2-yl)-1,3,4-thiadiazol-2-yl)methyl)benzamide (Compound 85B) and N-((5-(4-(((3S,4R)-3-fluoro-1-methylpiperidin-4-yl)amino)-1-(2,2,2-trifluoroethyl)-H-indol-2-yl)-1,3,4-thiadiazol-2-yl)methyl)cyclopropanecarboxamide (Compound 86B). Compound 85B, LC-MS (ES+, m/z): 547.1. Compound 86B, LC-MS (ES+, m/z): 511.2.

Example 33: Synthesis of (+/−)-N-{[5-(4-{[(3R,4S)-3-fluoro-1-methylpiperidin-4-yl]amino}-1-(2,2,2-trifluoroethyl)-1H-indol-2-yl)-1,3,4-thiadiazol-2-yl]methyl}oxetane-3-carboxamide (Compound 36B), (+/−)-N-{[5-(4-{[(3R,4S)-3-fluoro-1-methylpiperidin-4-yl]amino}-1-(2,2,2-trifluoroethyl)-1H-indol-2-yl)-1,3,4-thiadiazol-2-yl]methyl}cyclobutanecarboxamide (Compound 37B), and (+/−)-N-{[5-(4-{[(3R,4S)-3-fluoro-1-methylpiperidin-4-yl]amino}-1-(2,2,2-trifluoroethyl)-1H-indol-2-yl)-1,3,4-thiadiazol-2-yl]methyl}-1-methylpiperidine-4-carboxamide (Compound 40B)

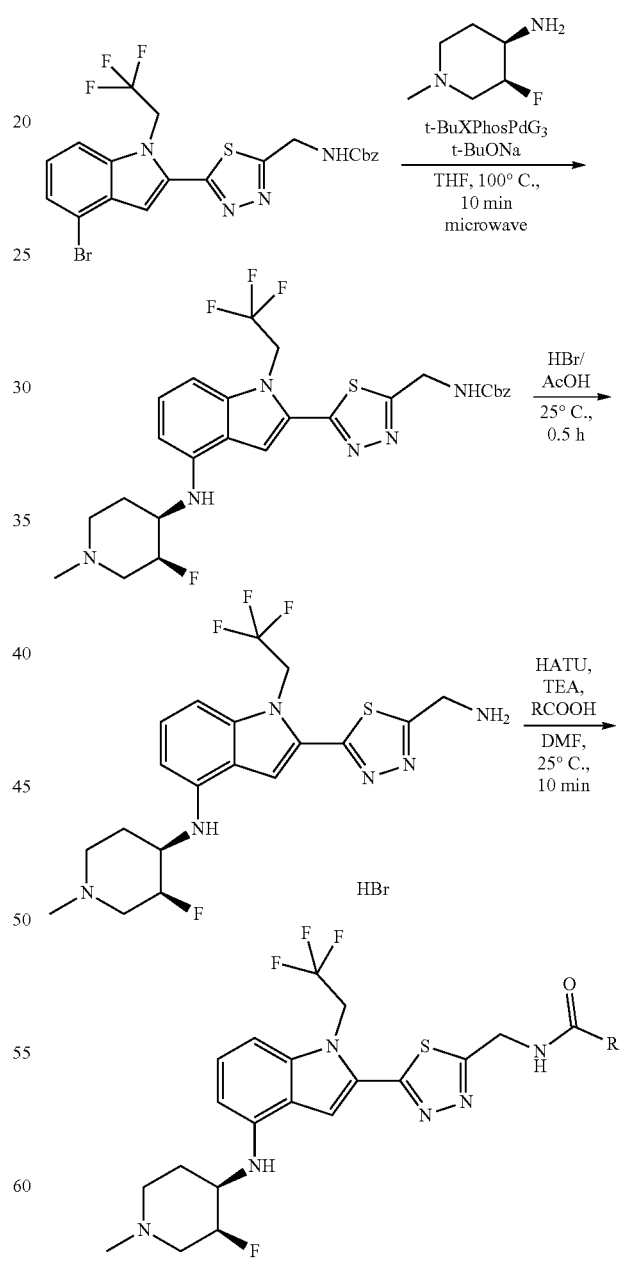

Preparation of (+/−)-benzyl ((5-(4-(((3S,4R)-3-fluoro-1-methylpiperidin-4-yl)amino)-1-(2,2,2-trifluoroethyl)-1H-indol-2-yl)-1,3,4-thiadiazol-2-yl)methyl)carbamate: To a solution of (+/−)-(3S,4R)-3-fluoro-1-methylpiperidin-4-amine (629 mg, 3.07 mmol, 3.2 eq, HCl) in THF (8 mL) were added t-BuONa (2 M (THF), 2.86 mL, 6 eq), benzyl ((5-(4-(((3S,4R)-3-fluoro-1-methylpiperidin-4-yl)amino)-1-(2,2,2-trifluoroethyl)-1H-indol-2-yl)-1,3,4-thiadiazol-2-yl)methyl)carbamate (500 mg, 952 μmol, 1 eq), and t-BuXPhos Palladium Generation 3 (75.6 mg, 95.2 μmol, 0.1 eq). The sealed vial was irradiated in the microwave at 100° C. for 10 mins. Completion of the reaction was confirmed using TLC analysis. The reaction mixture was poured into a 2M aqueous EDTA solution (100 mL) and stirred at 25° C. for 2 h, then extracted with EA (60 mL×3). The combined organic layers were washed with brine (50 mL), dried with sodium sulfate, filtered, and concentrated in vacuo. The crude residue was purified by column chromatography (SiO$_2$, PE:EA=1:1 to DCM:MeOH=10:1) to give benzyl (+/−)-((5-(4-(((3S,4R)-3-fluoro-1-methylpiperidin-4-yl)amino)-1-(2,2,2-trifluoroethyl)-1H-indol-2-yl)-1,3,4-thiadiazol-2-yl)methyl)carbamate (1.1 g, 1.91 mmol, 50.1% yield) as a brown solid.

Preparation of (+/−)-2-(5-(aminomethyl)-1,3,4-thiadiazol-2-yl)-N-((3S,4R)-3-fluoro-1-methylpiperidin-4-yl)-1-(2,2,2-trifluoroethyl)-1H-indol-4-amine hydrogen bromide: To a solution of (+/−)-benzyl ((5-(4-(((3S,4R)-3-fluoro-1-methylpiperidin-4-yl)amino)-1-(2,2,2-trifluoroethyl)-1H-indol-2-yl)-1,3,4-thiadiazol-2-yl)methyl)carbamate (1 g, 1.73 mmol, 1 eq) was added hydrogen bromide in acetic acid (37.25 g, 151.9 mmol, 25 mL, 33% wt, 87.60 eq). The mixture was stirred at 25° C. for 1 h, and completion of the reaction was confirmed using TLC analysis. The reaction mixture was poured into a saturated aqueous sodium carbonate solution (150 mL) to adjust the pH of the mixture to 9. The mixture was stirred for 15 mins and extracted with EA (50 mL×3). The combined organic layers were washed with brine (40 mL), dried with anhydrous sodium sulfate, and filtered. 4M HCl in EA (4 M, 15 mL) was added to the filtrate, and the filtrate solution was concentrated in vacuo. The crude product was triturated with methyl tert-butyl ether (MTBE) (40 mL) at 25° C. for 10 min and filtered to give (+/−)-2-(5-(aminomethyl)-1,3,4-thiadiazol-2-yl)-N-((3S,4R)-3-fluoro-1-methylpiperidin-4-yl)-1-(2,2,2-trifluoroethyl)-1H-indol-4-amine (650 mg, crude, HCl salt) in 78% yield as a yellow solid. LC-MS (ES$^+$, m/z): 443.0.

Preparation of (+/−)-N-{[5-(4-{[(3R,4S)-3-fluoro-1-methylpiperidin-4-yl]amino}-1-(2,2,2-trifluoroethyl)-1H-indol-2-yl]-1,3,4-thiadiazol-2-yl]methyl}oxetane-3-carboxamide (Compound 36B), (+/−)-N-{[5-(4-{[(3R,4S)-3-fluoro-1-methylpiperidin-4-yl]amino}-1-(2,2,2-trifluoroethyl)-1H-indol-2-yl]-1,3,4-thiadiazol-2-yl]methyl}cyclobutanecarboxamide (Compound 37B), and (+/−)-N-{[5-(4-{[(3R,4S)-3-fluoro-1-methylpiperidin-4-yl]amino}-1-(2,2,2-trifluoroethyl)-1H-indol-2-yl]-1,3,4-thiadiazol-2-yl]methyl}-1-methylpiperidine-4-carboxamide (Compound 40B): To a solution of RCOOH (1 eq) in DMF were added TEA (5 eq) and HATU (2 eq) in one portion at 25° C. under a nitrogen atmosphere. The mixture was stirred at 25° C. for 5 min, and (+/−)-2-(5-(aminomethyl)-1,3,4-thiadiazol-2-yl)-N-((3S,4R)-3-fluoro-1-methylpiperidin-4-yl)-1-(2,2,2-trifluoroethyl)-1H-indol-4-amine (1 eq, HCl) was added to the reaction at 25° C. The mixture was stirred for 5 min, and completion of the reaction was confirmed using LC-MS analysis. The residue was poured into ice water (w/w=1/1) (50 mL) and stirred for 5 min. The aqueous phase was extracted with EA (20 mL×3), and the combined organic phase was washed with brine (30 mL), dried with anhydrous sodium sulfate, filtered, and concentrated in vacuo. The crude residue was purified by preparative-TLC (DCM:MeOH=4:1) or preparative-HPLC to afford (+/−)-N-{[5-(4-{[(3R,4S)-3-fluoro-1-methylpiperidin-4-yl]amino}-1-(2,2,2-trifluoroethyl)-1H-indol-2-yl]-1,3,4-thiadiazol-2-yl]methyl}oxetane-3-carboxamide (Compound 36B) in 35% yield (LC-MS (ES$^+$, m/z): 568.3); (+/−)-N-{[5-(4-{[(3R,4S)-3-fluoro-1-methylpiperidin-4-yl]amino}-1-(2,2,2-trifluoroethyl)-1H-indol-2-yl]-1,3,4-thiadiazol-2-yl]methyl}cyclobutanecarboxamide (Compound 37B) in 38% yield (LC-MS (ES$^+$, m/z): 525.2); and (+/−)-N-{[5-(4-{[(3R,4S)-3-fluoro-1-methylpiperidin-4-yl]amino}-1-(2,2,2-trifluoroethyl)-1H-indol-2-yl]-1,3,4-thiadiazol-2-yl]methyl}-1-methylpiperidine-4-carboxamide (Compound 40B) in 32% yield (LC-MS (ES$^+$, m/z): 527.2).

Example 34: Synthesis of (+/−)-N-[(3R,4S)-3-fluoro-1-methylpiperidin-4-yl]-2-{5-[(methylamino)methyl]-1,3,4-thiadiazol-2-yl}-1-(2,2,2-trifluoroethyl)-1H-indol-4-amine (Compound 43B)

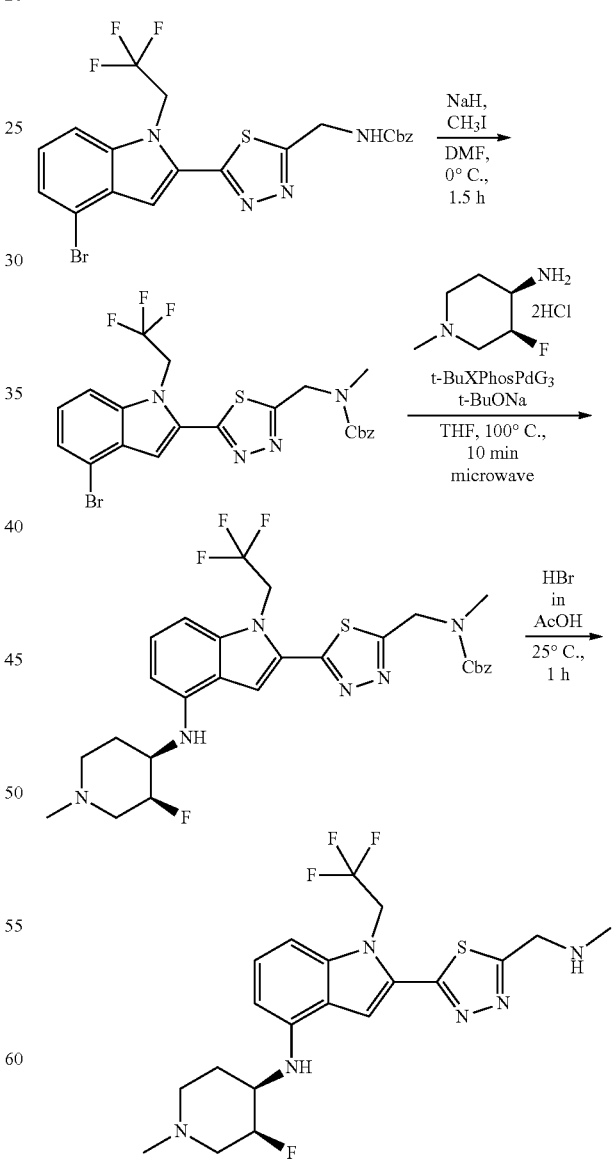

Preparation of benzyl ((5-(4-bromo-1-(2,2,2-trifluoroethyl)-1H-indol-2-yl)-1,3,4-thiadiazol-2-yl)methyl)(methyl)

carbamate: To a solution of benzyl ((5-(4-bromo-1-(2,2,2-trifluoroethyl)-1H-indol-2-yl)-1,3,4-thiadiazol-2-yl)methyl)carbamate (650 mg, 1.24 mmol, 1 eq) in DMF (10 mL) was added sodium hydride (99 mg, 2.47 mmol, 60% purity, 2 eq) at 0° C. The mixture was stirred at 0° C. for 0.5 h, and iodomethane (351.2 mg, 2.47 mmol, 2 eq) was added. The resulting mixture was stirred at 25° C. for 1 hr. The reaction mixture was poured into a saturated ammonium chloride solution (30 mL) and extracted with EA (20 mL×3). The combined organic phase was washed with brine (20 mL), dried with anhydrous sodium sulfate, filtered, and concentrated in vacuo. The crude residue was purified by column chromatography (SiO₂, PE:EA=10:1 to 2:1) to give benzyl ((5-(4-bromo-1H-(2,2,2-trifluoroethyl)-1H-indol-2-yl)-1,3,4-thiadiazol-2-yl)methyl)(methyl)carbamate (400 mg, 741.6 μmol, 60% yield) as a yellow solid. LC-MS (ES⁺, m/z): 539.1.

Preparation of (+/−)-benzyl ((5-(4-(((3S,4R)-3-fluoro-1-methylpiperidin-4-yl)amino)-1-(2,2,2-trifluoroethyl)-1H-indol-2-yl)-1,3,4-thiadiazol-2-yl)methyl)(methyl)carbamate: To a solution of (3S,4R)-3-fluoro-1-methylpiperidin-4-amine (428.55 mg, 2.09 mmol, 3.22 eq, 2HCl) in THF (5 mL) were added t-BuONa (2 M (TH-F), 1.95 mL, 6 eq), benzyl ((5-(4-bromo-1-(2,2,2-trifluoroethyl)-1H-indol-2-yl)-1,3,4-thiadiazol-2-yl)methyl)(methyl)carbamate (350 mg, 648.9 μmol, 1 eq), and t-BuXPhos Palladium Generation 3 (51.6 mg, 64.9 μmol, 0.1 eq). The resulting mixture was degassed and purged with nitrogen. The sealed vial was irradiated in the microwave at 100° C. for 10 min. The reaction mixture was poured into a 2M aqueous EDTA solution (50 mL) and stirred for 2 h, then extracted with EA (40 mL×3). The combined organic layers were washed with brine (40 mL), dried with anhydrous sodium sulfate, filtered, and concentrated in vacuo. The residue was purified by column chromatography (SiO₂, DCM:MeOH=40:1 to 10:1) to give (+/−)-benzyl ((5-(4-(((3S,4R)-3-fluoro-1-methylpiperidin-4-yl)amino)-1-(2,2,2-trifluoroethyl)-1H-indol-2-yl)-1,3,4-thiadiazol-2-yl)methyl)(methyl)carbamate (140 mg, 237 μmol, 36.5% yield) as a black-brown solid.

Preparation of (+/−)-N-[(3R,4S)-3-fluoro-1-methylpiperidin-4-yl]-2-{5-[(methylamino)methyl]-1,3,4-thiadiazol-2-yl}-1-(2,2,2-trifluoroethyl)-1H-indol-4-amine (Compound 43B): A solution of (+/−)-benzyl ((5-(4-(((3S,4R)-3-fluoro-1-methylpiperidin-4-yl)amino)-1-(2,2,2-trifluoroethyl)-1H-indol-2-yl)-1,3,4-thiadiazol-2-yl)methyl)(methyl)carbamate (120 mg, 203 μmol, 1 eq) in HBr (8.94 g, 36.5 mmol, 6 mL, 33% purity, 179.5 eq) was stirred at 25° C. for 1 hr under a nitrogen atmosphere. The reaction mixture was poured into a saturated aqueous sodium carbonate solution (50 mL) to adjust the pH of the mixture to 9. The mixture was extracted with EA (40 mL×3), washed with brine (20 mL), dried with anhydrous sodium sulfate, filtered, and concentrated in vacuo. The residue was purified by preparative-HPLC (basic condition) to afford (+/−)-N-[(3R,4S)-3-fluoro-1-methylpiperidin-4-yl]-2-{5-[(methylamino)methyl]-1,3,4-thiadiazol-2-yl}-1-(2,2,2-trifluoroethyl)-1H-indol-4-amine (Compound 43B) (23.2 mg, 50.8 μmol, 25.0% yield) as a yellow solid. LC-MS (ES⁺, m/z): 457.2.

Example 35: Synthesis of (+/−) 2-(5-((dimethylamino)methyl)-1,3,4-thiadiazol-2-yl)-N-((3S,4R)-3-fluoro-1-methylpiperidin-4-yl)-1-(2,2,2-trifluoroethyl)-1H-indol-4-amine (Compound 87B)

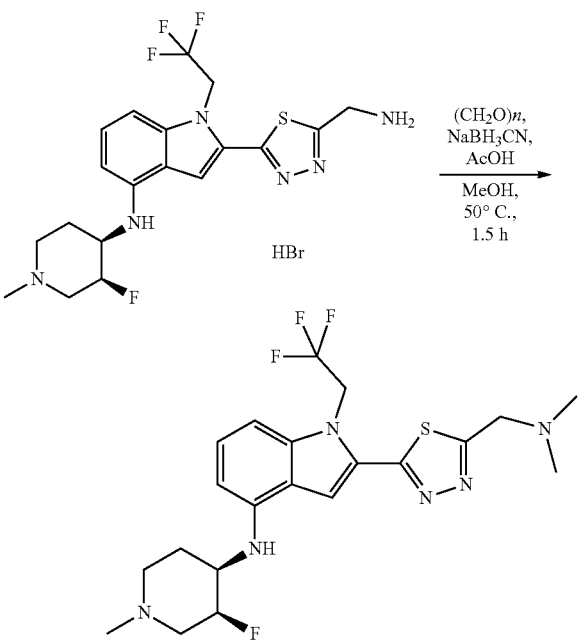

To a mixture of (+/−) 2-(5-(aminomethyl)-1,3,4-thiadiazol-2-yl)-N-((3S,4R)-3-fluoro-1-methylpiperidin-4-yl)-1-(2,2,2-trifluoroethyl)-1H-indol-4-amine (20 mg, 29.46 μmol, 1 eq, HBr) and paraformaldehyde (4.42 mg, 147 μmol, 4.06 μL, 5 eq) in MeOH (2 mL) were added acetic acid (77 mg, 1.29 mmol, 74 μL, 43.7 eq) and sodium cyanoborohydride (9.25 mg, 147.3 mol, 5 eq). The mixture was stirred at 50° C. for 1.5 hr. The reaction mixture was poured into water (30 mL) and then extracted with EA (15 mL×3). The combined organic phase was washed with brine (10 mL), dried with anhydrous sodium sulfate, filtered, and concentrated in vacuo. The crude residue was purified by preparative-HPLC (basic conditions) to give 2-(5-((dimethylamino)methyl)-1,3,4-thiadiazol-2-yl)-N-((3S,4R)-3-fluoro-1-methylpiperidin-4-yl)-1-(2,2,2-trifluoroethyl)-1H-indol-4-amine (Compound 87B) (1.9 mg, 4.0 μmol, 13.5% yield) as a yellow solid. LC-MS (ES⁺, m/z): 471.1.

Example 36: Synthesis of (+/−)-methyl N-{[5-(4-{[(3R,4S)-3-fluoro-1-methylpiperidin-4-yl]amino}-1-(2,2,2-trifluoroethyl)-1H-indol-2-yl)-1,3,4-thiadiazol-2-yl]methyl}carbamate (Compound 38B)

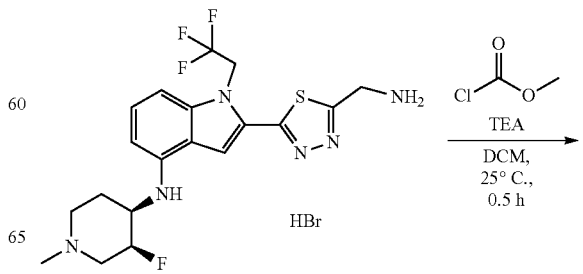

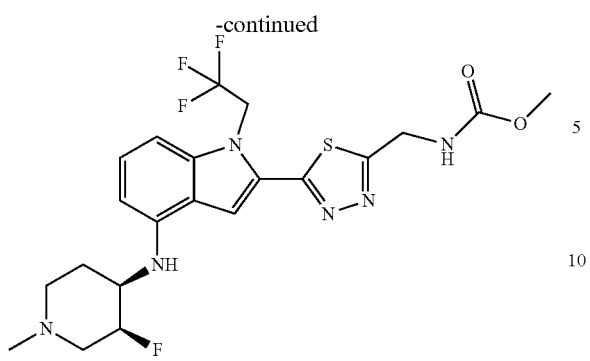

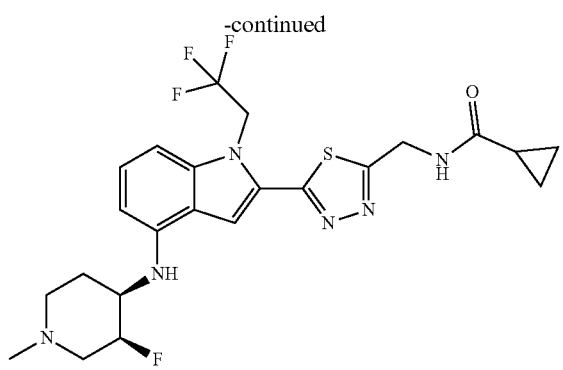

To a solution of (+/−)-2-(5-(aminomethyl)-1,3,4-thiadiazol-2-yl)-N-((3S,4R)-3-fluoro-1-methylpiperidin-4-yl)-1-(2,2,2-trifluoroethyl)-1H-indol-4-amine (100 mg, 147.28 µmol, 1 eq, 2HBr) in DCM (4 mL) was added TEA (59.61 mg, 589.11 µmol, 82 µL, 4 eq). Methyl carbonochloridate (13.92 mg, 147.28 µmol, 11.41 µL, 1 eq) was added to the mixture, and the combined mixture was stirred at 25° C. for 0.5 hr. The reaction mixture was poured into water (30 mL) and extracted with DCM (20 mL×3). The combined organic phase was washed with brine (20 mL), dried with anhydrous sodium sulfate, filtered, and concentrated in vacuo. The residue was purified by preparative-HPLC) to afford (+/−)-methyl N-{[5-(4-{[(3R,4S)-3-fluoro-1-methylpiperidin-4-yl]amino}-1-(2,2,2-trifluoroethyl)-1H-indol-2-yl)-1,3,4-thiadiazol-2-yl]methyl}carbamate (Compound 38B) (20.5 mg, 39.03 µmol, 26.50% yield) as a yellow solid. LC-MS (ES+, m/z): 501.1.

Example 37: Synthesis of N-{[5-(4-{[(3S,4R)-3-fluoro-1-methylpiperidin-4-yl]amino}-1-(2,2,2-trifluoroethyl)-1H-indol-2-yl)-1,3,4-thiadiazol-2-yl]methyl}cyclopropanecarboxamide (Compound 47B) and N-{[5-(4-{[(3R,4S)-3-fluoro-1-methylpiperidin-4-yl]amino}-1-(2,2,2-trifluoroethyl)-1H-indol-2-yl)-1,3,4-thiadiazol-2-yl]methyl}cyclopropanecarboxamide (Compound 48B)

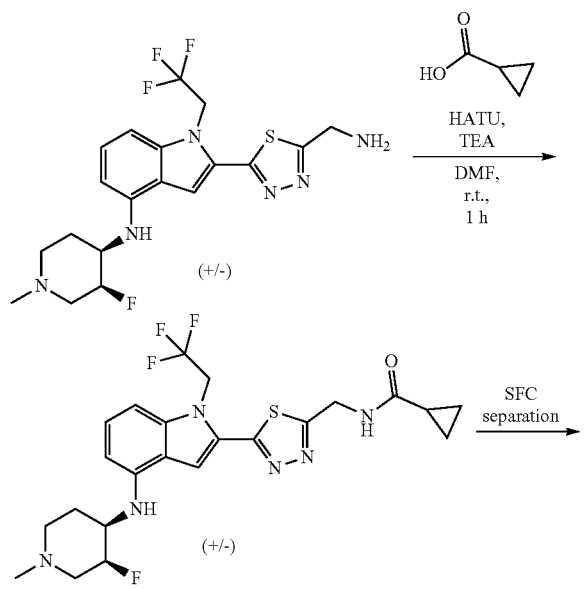

To a solution of cyclopropanecarboxylic acid (166.30 mg, 375.83 µmol, 1 eq, HCl) in DMF (2 mL) were added HATU (214.35 mg, 563.75 µmol, 1.5 eq), TEA (190.15 mg, 1.88 mmol, 261.56 µL, 5 eq), and (+/−)-2-(5-(aminomethyl)-1,3,4-thiadiazol-2-yl)-N-((3S,4R)-3-fluoro-1-methylpiperidin-4-yl)-1-(2,2,2-trifluoroethyl)-1H-indol-4-amine (32.36 mg, 375.83 µmol, 29.69 µL, 1 eq). The mixture was stirred at 20° C. for 1 hr. TLC analysis detected one major new spot with lower polarity than that of the starting material. The reaction mixture was diluted with H2O (50 mL) and was extracted with EA (20 mL×3). The combined organic layers were washed with brine (20 mL×3), dried over anhydrous sodium sulfate, filtered, and concentrated in vacuo. The crude residue was purified by preparative-TLC (SiO2, DCM: MeOH=4:1) to afford the desired compound as a yellow solid, which was further separated by chiral SFC to give N-{[5-(4-{[(3S,4R)-3-fluoro-1-methylpiperidin-4-yl]amino}-1-(2,2,2-trifluoroethyl)-1H-indol-2-yl)-1,3,4-thiadiazol-2-yl]methyl}cyclopropanecarboxamide (Compound 47B) (19 mg, 37.21 µmol, 9.90% yield; LC-MS (ES+, m/z): 511.1) and N-{[5-(4-{[(3R,4S)-3-fluoro-1-methylpiperidin-4-yl]amino}-1-(2,2,2-trifluoroethyl)-1H-indol-2-yl)-1,3,4-thiadiazol-2-yl]methyl}cyclopropanecarboxamide (Compound 48B) (26 mg, 50.93 µmol, 13.55% yield; LC-MS (ES+, m/z): 511.1) as yellow solids.

Example 38: Synthesis of N-[(3R,4S)-3-fluoro-1-methylpiperidin-4-yl]-2-(5-{[(4-methanesulfonyl-2-methoxyphenyl)amino]methyl}-1,3,4-thiadiazol-2-yl)-1-(2,2,2-trifluoroethyl)-1H-indol-4-amine (Compound 61B) and N-[(3S,4R)-3-fluoro-1-methylpiperidin-4-yl]-2-(5-{[(4-methanesulfonyl-2-methoxyphenyl)amino]methyl}-1,3,4-thiadiazol-2-yl)-1-(2,2,2-trifluoroethyl)-1H-indol-4-amine (Compound 62B)
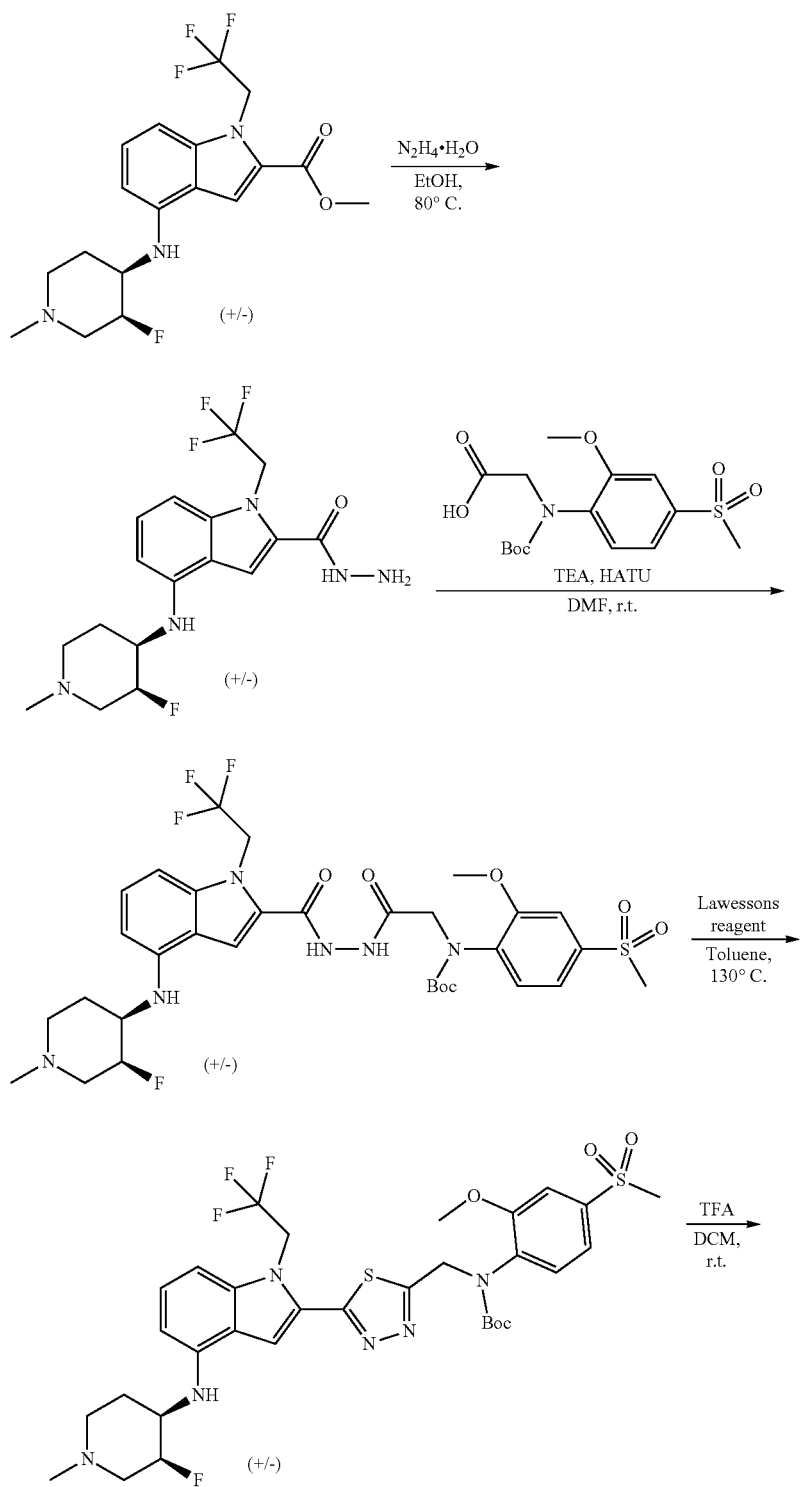

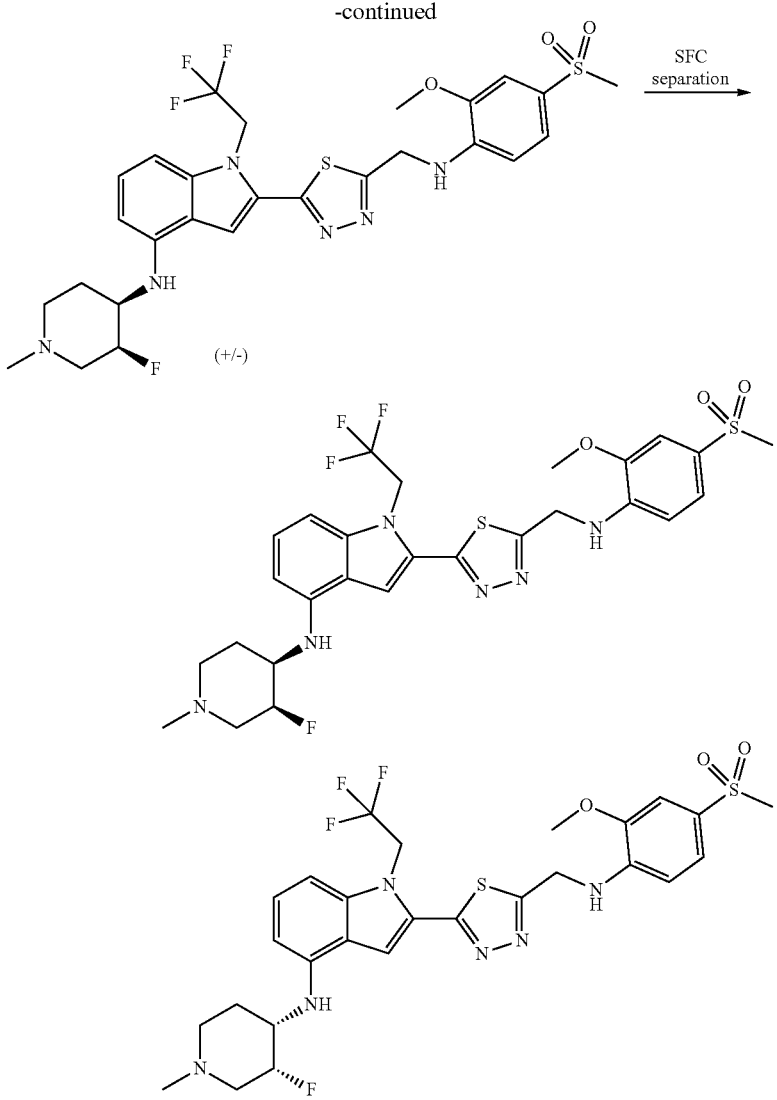

Preparation of (+/−)-4-(((3S,4R)-3-fluoro-1-methylpiperidin-4-yl)amino)-1-(2,2,2-trifluoroethyl)-1H-indole-2-carbohydrazide: To a solution of (+/−)-methyl 4-(((3S,4R)-3-fluoro-1-methylpiperidin-4-yl)amino)-1-(2,2,2-trifluoroethyl)-1H-indole-2-carboxylate (4 g, 10.33 mmol, 1 eq) in ethanol (20 mL) was added hydrazine hydrate (20 mL). The mixture was stirred at 80° C. for 1 hr, and completion of the reaction was confirmed using LC-MS analysis. The mixture was extracted with DCM (50 mL×2), and the organic phase was washed with water (50 mL) and brine (50 mL). The combined organic phase was dried with anhydrous sodium sulfate and concentrated in vacuo. The crude residue was purified using column chromatography (SiO₂, PE/EA=1:1) to afford (+/−)-4-(((3S,4R)-3-fluoro-1-methylpiperidin-4-yl)amino)-1-(2,2,2-trifluoroethyl)-1H-indole-2-carbohydrazide in 75% yield as a yellow solid. LC-MS (ES⁺, m/z): 388.2.

Preparation of (+/−)-tert-butyl (2-(2-(4-(((3S,4R)-3-fluoro-1-methylpiperidin-4-yl)amino)-1-(2,2,2-trifluoroethyl)-1H-indole-2-carbonyl)hydrazinyl)-2-oxoethyl)(2-methoxy-4-(methylsulfonyl)phenyl)carbamate: To a solution of (+/−)-4-(((3S,4R)-3-fluoro-1-methylpiperidin-4-yl)amino)-1-(2,2,2-trifluoroethyl)-1H-indole-2-carbohydrazide (1 g, 2.58 mmol, 1 eq) and N-(tert-butoxycarbonyl)-N-(2-methoxy-4-(methylsulfonyl)phenyl)glycine (1.39 g, 3.87 mmol, 1.5 eq) in DMF (20 mL) was added TEA (1.31 g, 12.9 mmol, 1.80 mL, 5 eq). HATU (1.47 g, 3.87 mmol, 1.5 eq) was added to the mixture, and the resulting reaction was stirred at 25° C. for 1 hr. The reaction was diluted with water, and the mixture was extracted with DCM (10 mL×2). The organic phase was washed with water (10 mL) and brine (10 mL), dried with anhydrous sodium sulfate, filtered, and concentrated in vacuo. The residue was purified using preparative-TLC (SiO₂, DCM:MeOH=10:1) to afford (+/−)-tert-butyl (2-(2-(4-(((3S,4R)-3-fluoro-1-methylpiperidin-4-yl)amino)-1-(2,2,2-trifluoroethyl)-1H-indole-2-carbonyl)hydrazinyl)-2-oxoethyl)(2-methoxy-4-(methylsulfonyl)phenyl)carbamate (600 mg) in 31.8% yield as a yellow solid.

Preparation of (+/−)-tert-butyl ((5-(4-(((3S,4R)-3-fluoro-1-methylpiperidin-4-yl)amino)-1-(2,2,2-trifluoroethyl)-1H-indol-2-yl)-1,3,4-thiadiazol-2-yl)methyl)(2-methoxy-4-(methylsulfonyl)phenyl)carbamate: To a solution of (+/−)-tert-butyl (2-(2-(4-(((3S,4R)-3-fluoro-1-methylpiperidin-4-yl)amino)-1-(2,2,2-trifluoroethyl)-1H-indole-2-carbonyl)

hydrazinyl)-2-oxoethyl)(2-methoxy-4-(methylsulfonyl) phenyl)carbamate (200 mg, 274.44 μmol, 1 eq) in toluene (3 mL) was added Lawesson's Reagent (222 mg, 549 μmol, 2 eq). The reaction mixture was heated and stirred at 130° C. for 1 hr. The mixture was extracted with DCM (10 mL×2), and the organic phase was washed with water (10 mL) and brine (10 mL), dried with anhydrous sodium sulfate, and concentrated in vacuo to afford (+/−)-tert-butyl ((5-(4-(((3S,4R)-3-fluoro-1-methylpiperidin-4-yl)amino)-1-(2,2,2-trifluoroethyl)-1H-indol-2-yl)-1,3,4-thiadiazol-2-yl)methyl)(2-methoxy-4-(methylsulfonyl)phenyl)carbamate (50 mg) as a yellow solid.

Preparation of N-[(3R,4S)-3-fluoro-1-methylpiperidin-4-yl]-2-(5-{[(4-methanesulfonyl-2-methoxyphenyl)amino]methyl}-1,3,4-thiadiazol-2-yl)-1-(2,2,2-trifluoroethyl)-1H-indol-4-amine and N-[(3S,4R)-3-fluoro-1-methylpiperidin-4-yl]-2-(5-[(4-methanesulfonyl-2-methoxyphenyl)amino]methyl}-1,3,4-thiadiazol-2-yl)-1-(2,2,2-trifluoroethyl)-1H-indol-4-amine: To a solution of (+/−)-tert-butyl ((5-(4-(((3S,4R)-3-fluoro-1-methylpiperidin-4-yl)amino)-1-(2,2,2-trifluoroethyl)-1H-indol-2-yl)-1,3,4-thiadiazol-2-yl)methyl)(2-methoxy-4-(methylsulfonyl)phenyl)carbamate (150 mg, 206.4 μmol, 1 eq) in DCM (5 mL) was added TFA (2.31 g, 20.26 mmol, 1.50 mL, 98.2 eq). The mixture was stirred at 25° C. for 1 hr. The mixture was poured into water and saturated sodium bicarbonate solution, then extracted with DCM (10 mL×2). The organic phase was washed with water (10 mL) and brine (10 mL), dried with anhydrous sodium sulfate, filtered, and concentrated in vacuo. The crude residue was purified by preparative-HPLC and then by SFC to afford the desired compounds. N-[(3R,4S)-3-fluoro-1-methylpiperidin-4-yl]-2-(5-{[(4-methanesulfonyl-2-methoxyphenyl)amino]methyl}-1,3,4-thiadiazol-2-yl)-1-(2,2,2-trifluoroethyl)-1H-indol-4-amine (Compound 61B), 29.5 mg; LC-MS (ES+, m/z): 627.1; N-[(3S,4R)-3-fluoro-1-methylpiperidin-4-yl]-2-(5-{[(4-methanesulfonyl-2-methoxyphenyl)amino]methyl}-1,3,4-thiadiazol-2-yl)-1-(2,2,2-trifluoroethyl)-1H-indol-4-amine (Compound 62B), 28.9 mg, 22.5% yield; LC-MS (ES+, m/z): 627.2.

Example 39: Synthesis of N-{[5-(4-{[(3R,4S)-3-fluoro-1-methylpiperidin-4-yl]amino}-1-(2,2,2-trifluoroethyl)-1H- indol-2-yl)-1,3,4- thiadiazol-2-yl]methyl}cyclopropanecarboxamide (Compound 25B) and N-{[5-(4-{[(3R,4S)-3-fluoro-1-methylpiperidin-4-yl]amino}-1-(2,2,2-trifluoroethyl)-1H-indol-2-yl)-1,3,4-thiadiazol-2-yl]methyl}benzamide (Compound 26B)

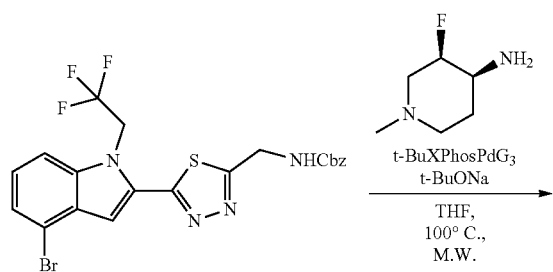

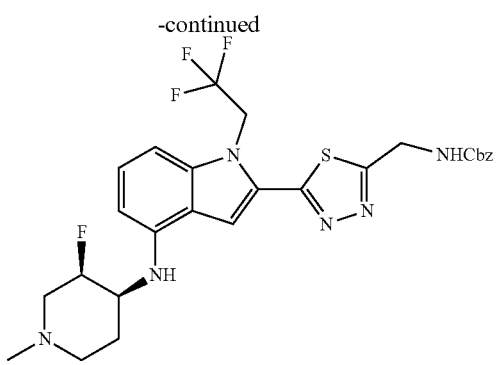

A mixture of benzyl ((5-(4-bromo-1-(2,2,2-trifluoroethyl)-1H-indol-2-yl)-1,3,4-thiadiazol-2-yl)methyl)carbamate (500 mg, 951.76 μmol, 1 eq), (3R,4S)-3-fluoro-1-methylpiperidin-4-amine dihydrochloride (629.01 mg, 3.07 mmol, 3.22 eq), t-BuXPhos Palladium Generation 2 (75.61 mg, 95.18 mol, 0.1 eq), and sodium tert-butoxide (1 M, 5.71 mL, 6 eq) in THF (2 mL) was degassed and purged with nitrogen. The sealed vial was irradiated by microwave at 100° C. for 10 min. The residue was poured into basic (pH=8) 2M aqueous EDTA solution (50 mL) and stirred for 60 min. The aqueous phase was extracted with EA (30 mL×2). The combined organic phase was washed with brine (20 mL×3), dried with anhydrous sodium sulfate, filtered, and concentrated in vacuo. The residue was purified by silica gel chromatography (DCM:MeOH=40:1 to 10:1) to afford benzyl ((5-(4-(((3R,4S)-3-fluoro-1-methylpiperidin-4-yl)amino)-1-(2,2,2-trifluoroethyl)-1H-indol-2-yl)-1,3,4-thiadiazol-2-yl)methyl)carbamate (1.1 g, 50% yield) as a yellow solid. LC-MS (M+H+)=577.2.

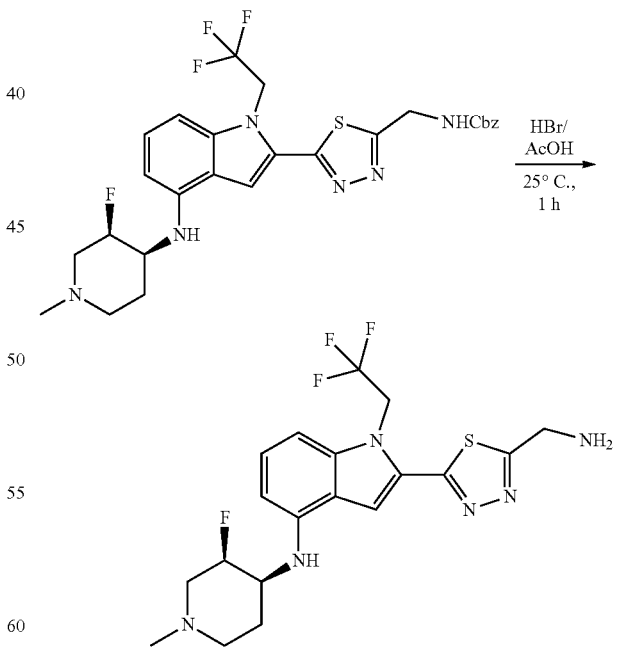

A solution of benzyl ((5-(4-(((3R,4S)-3-fluoro-1-methylpiperidin-4-yl)amino)-1-(2,2,2-trifluoroethyl)-1H-indol-2-yl)-1,3,4-thiadiazol-2-yl)methyl)carbamate (800 mg, 1.39 mmol, 1 eq) in HBr in acetic acid (30% wt) was prepared. The solution was stirred at 20° C. for 1 hr. The reaction solution was added dropwise into MTBE (100 mL), then filtered to give 2-(5-(aminomethyl)-1,3,4-thiadiazol-2-yl)-N-((3R,4S)-3-fluoro-1-methylpiperidin-4-yl)-1-(2,2,2-trifluoroethyl)-1H-indol-4-amine (680 mg, 1.20 mmol, 86.4% yield) as a yellow solid. LC-MS (M+H⁺)=443.0.

To a solution of RCOOH (1 eq) in DMF (1 mL) were added HATU (2 eq) and TEA (5 eq) in one portion at 20° C. under nitrogen. The mixture was stirred at 20° C. for 5 min, and then 2-(5-(aminomethyl)-1,3,4-thiadiazol-2-yl)-N-((3R,4S)-3-fluoro-1-methylpiperidin-4-yl)-1-(2,2,2-trifluoroethyl)-1H-indol-4-amine (1 eq) was added in one portion. The mixture was stirred at 20° C. for 15 min. The residue was poured into ice water (w/w=1/1) (40 mL). The aqueous phase was extracted with EA (20 mL×3). The combined organic phase was washed with brine (20 mL×3), dried with anhydrous sodium sulfate, filtered, and concentrated in vacuo. The crude product was purified by preparative-HPLC to afford the desired amide product. N-((5-(4-(((3R,4S)-3-fluoro-1-methylpiperidin-4-yl)amino)-1-(2,2,2-trifluoroethyl)-1H-indol-2-yl)-1,3,4-thiadiazol-2-yl)methyl)cyclopropanecarboxamide (Compound 25B), LC-MS (M+H⁺)=511.1; N-((5-(4-(((3R,4S)-3-fluoro-1-methylpiperidin-4-yl)amino)-1-(2,2,2-trifluoroethyl)-1H-indol-2-yl)-1,3,4-thiadiazol-2-yl)methyl)benzamide (Compound 26B), yield 9%, LC-MS (M+H⁻)=547.1.

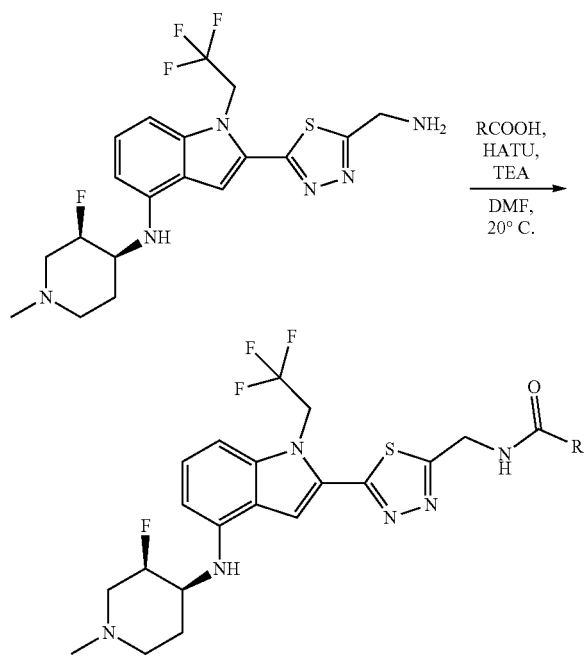

Example 40: N-{[5-(4-{[(3S,4R)-3-fluoro-1-methylpiperidin-4-yl]amino}-1-(2,2,2-trifluoroethyl)-1H-indol-2-yl)-1,3,4-thiadiazol-2-yl]methyl}-1-(4-methyloxan-4-yl)-1H-pyrrole-3-carboxamide (Compound 287B)

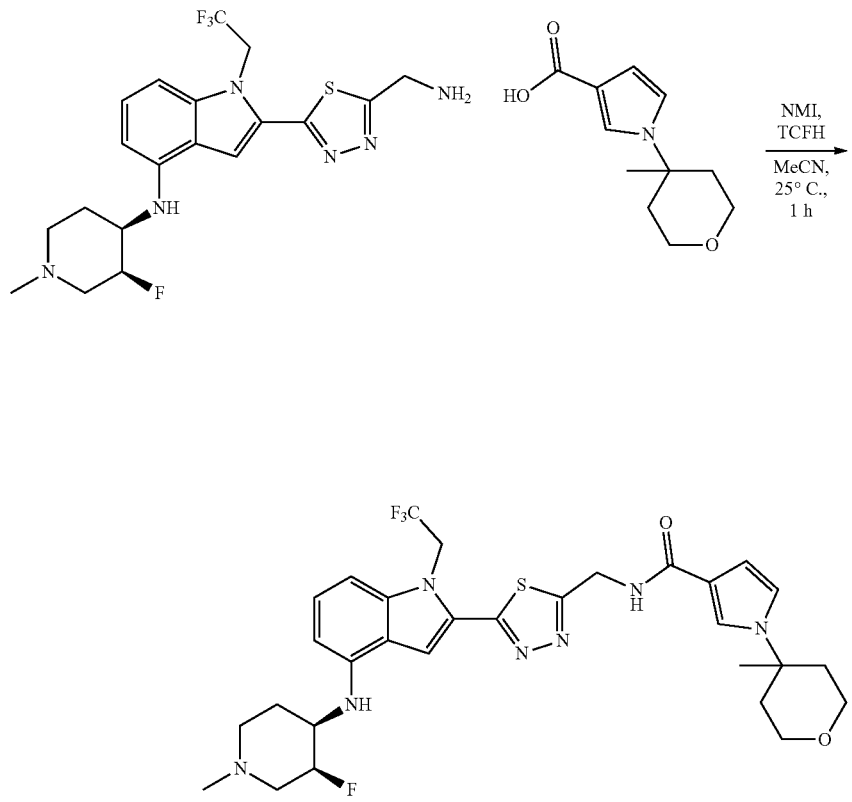

To a solution of 1-(4-methyltetrahydropyran-4-yl)pyrrole-3-carboxylic acid (24.9 mg, 119 μmol, 1 eq) in acetonitrile (2 mL) were added 2-[5-(aminomethyl)-1,3,4-thiadiazol-2-yl]-N-[(3S,4R)-3-fluoro-1-methyl-4-piperidyl]-1-(2,2,2-trifluoroethyl)indol-4-amine (90 mg, 119 μmol, 1 eq, 2HBr) and [chloro(dimethylamino)methylene]-dimethyl-ammonium hexafluorophosphate (50.1 mg, 179 μmol, 1.5 eq), 1-methylimidazole (357 μmol, 29 μL, 3 eq). The mixture was stirred at 25° C. for 0.5 h, then poured into water (50 mL) and extracted with EA (30 mL×3). The combined organic layers were washed with brine (30 mL×1), dried over anhydrous sodium sulfate, filtered, and concentrated in vacuo to give a residue. The residue was purified by prep-HPLC (column: Waters Xbridge Prep OBD C18 150×40 mm×10 um; mobile phase: [water (0.05% $NH_3H_2O$+10 mM $NH_4HCO_3$)-ACN]; B %: 30%-55%, 8 min) to give the desired product N-{{5-(4-{[(3S,4R)-3-fluoro-1-methylpiperidin-4-yl]amino}-1-(2,2,2-trifluoroethyl)-1H-indol-2-yl)-1,3,4-thiadiazol-2-yl]methyl}-1-(4-methyloxan-4-yl)-1H-pyrrole-3-carboxamide (21.7 mg, 33.6 μmol, 28.2% yield, 98% purity). LC-MS (ES+, m/z): 634.4 [(M+H)+]. $^1$H NMR (400 MHz, DMSO-$d_6$) δ=8.83 (t, J=6.0 Hz, 1H), 7.84 (s, 1H), 7.59 (s, 1H), 7.12 (t, J=8.0 Hz, 1H), 7.03 (t, J=2.6 Hz, 1H), 6.89 (d, J=8.2 Hz, 1H), 6.56 (d, J=1.9 Hz, 1H), 6.30 (d, J=7.8 Hz, 1H), 5.82-5.66 (m, 3H), 4.93-4.73 (m, 3H), 3.72-3.51 (m, 5H), 3.10-3.00 (m, 1H), 2.83 (br d, J=10.9 Hz, 1H), 2.36-2.28 (m, 1H), 2.20 (s, 3H), 2.18-2.10 (m, 3H), 1.97-1.87 (m, 3H), 1.78-1.68 (m, 1H), 1.44 (s, 3H).

Example 41: 1-tert-butyl-N-{[5-(4-{[(3S,4R)-3-fluoro-1-methylpiperidin-4-yl]amino}-1-(2,2,2-trifluoroethyl)-1H-indol-2-yl)-1,3,4-thiadiazol-2-yl]methyl}-1H-pyrrole-3-carboxamide (Compound 386B)

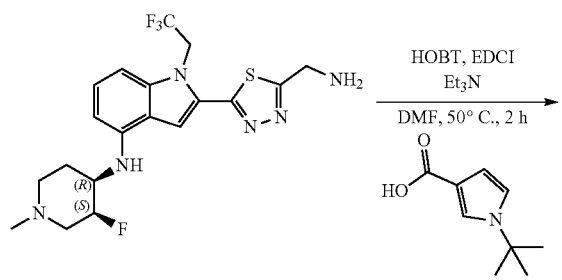

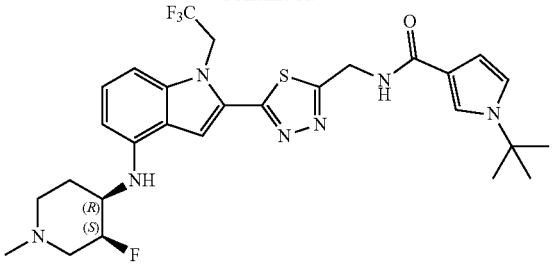

To a mixture of 2-[5-(aminomethyl)-1,3,4-thiadiazol-2-yl]-N-[(3S,4R)-3-fluoro-1-methyl-4-piperidyl]-1-(2,2,2-trifluoroethyl)indol-4-amine (60 mg, 91.7 μmol, 1 eq, HBr salt) and 1-tertbutylpyrrole-3-carboxylic acid (18.4 mg, 110 μmol, 1.2 eq) in DMF (2 mL) were added TEA (920 mmol, 130 μL 10 eq), HOBt (37.18 mg, 275.13 μmol, 3 eq) and EDCI (52.74 mg, 275.13 μmol, 3 eq), and the reaction was heated to 50° C. under nitrogen for 2 h. The residue was diluted with water (50 mL) and extracted with EA (2×50 mL). The combined organic layers were washed with brine (2×50 mL), dried over anhydrous $Na_2SO_4$, filtered, and concentrated in vacuo to give a residue. The residue was purified by prep-HPLC to give the product 1-tert-butyl-N-{[5-(4-{[(3S,4R)-3-fluoro-1-methylpiperidin-4-yl]amino}-1-(2,2,2-trifluoroethyl)-1H-indol-2-yl)-1,3,4-thiadiazol-2-yl]methyl}-1H-pyrrole-3-carboxamide (22.6 mg, 41.7% yield, 100% purity). LC-MS (ES+, m/z): 592.4 [(M+H)+]. $^1$H NMR (DMSO-d6, 400 MHz): δ (ppm) 8.78 (t, J=5.8 Hz, 1H), 8.19 (s, 1H), 7.80 (s, 1H), 7.52 (t, J=2.0 Hz, 1H), 7.09 (t, J=8.0 Hz, 1H), 6.95-6.97 (t, J=2.6 Hz, 1H), 6.86 (d, J=8.4 Hz, 1H), 6.48 (dd, J=2.8, 1.9 Hz, 1H), 6.27 (d, J=7.9 Hz, 1H), 5.66-5.75 (m, 3H), 4.73-4.81 (m, 2H), 3.55-3.62 (m, 1H), 3.02 (br t, J=10.5 Hz, 1H), 2.79 (br d, J=11.0 Hz, 1H), 2.25-2.30 (m, 1H), 2.17 (s, 3H), 2.05-2.13 (m, 1H), 1.90 (br dd, J=12.0, 3.4 Hz, 111), 1.69 (br d, J=9.9 Hz, 1H), 1.47 (s, 9H).

TABLE 5 shows compounds prepared with a 2-(1H-indol-2-yl)-1,3,4-thiadiazole core.

TABLE 5

| Compound No. | Structure | IUPAC | LC-MS (ES+, m/z) |
|---|---|---|---|
| 24B | (structure shown) | 2-(5-{[(4-methanesulfonyl-phenyl)amino]methyl}-1,3,4-thiadiazol-2-yl)-N-(1-methylpiperidin-4-yl)-1-(2,2,2-trifluoroethyl)-1H-indol-4-amine | 579.1 |

TABLE 5-continued

| Compound No. | Structure | IUPAC | LC-MS (ES+, m/z) |
|---|---|---|---|
| 25B | 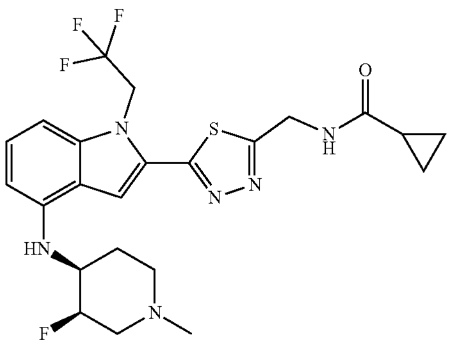 [SMILES: CN1CC[C@H](Nc2cccc3c2cc(-c2nnc(CNC(=O)C4CC4)s2)n3CC(F)(F)F)[C@H](F)C1] | N-{5-(4-{[(3R,4S)-3-fluoro-1-methylpiperidin-4-yl]amino}-1-(2,2,2-trifluoroethyl)-1H-indol-2-yl)-1,3,4-thiadiazol-2-yl]methyl}cyclopropanecarboxamide | 511.1 |
| 26B | 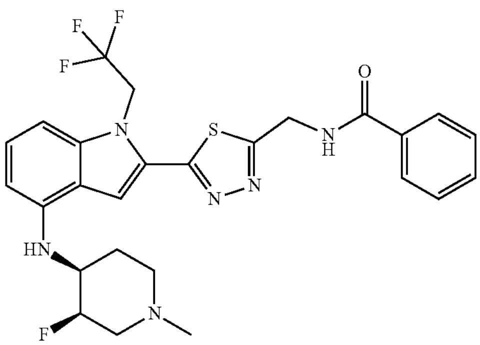 [SMILES: CN1CC[C@H](Nc2cccc3c2cc(-c2nnc(CNC(=O)c4ccccc4)s2)n3CC(F)(F)F)[C@H](F)C1] | N-{5-(4-{[(3R,4S)-3-fluoro-1-methylpiperidin-4-yl]amino}-1-(2,2,2-trifluoroethyl)-1H-indol-2-yl)-1,3,4-thiadiazol-2-yl]methyl}benzamide | 547.1 |
| 27B | 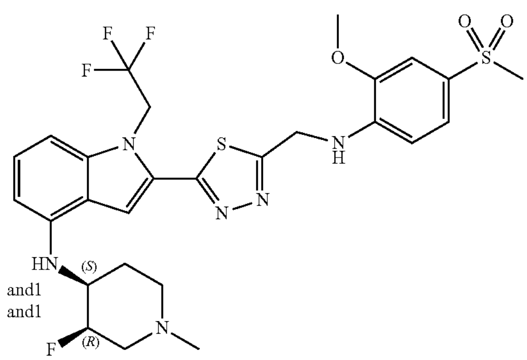 | (+/−)-N-[(3R,4S)-3-fluoro-1-methylpiperidin-4-yl]-2-(5-{[(4-methanesulfonyl-2-methoxyphenyl)amino]methyl}-1,3,4-thiadiazol-2-yl)-1-(2,2,2-trifluoroethyl)-1H-indol-4-amine | 627.1 |
| 28B | 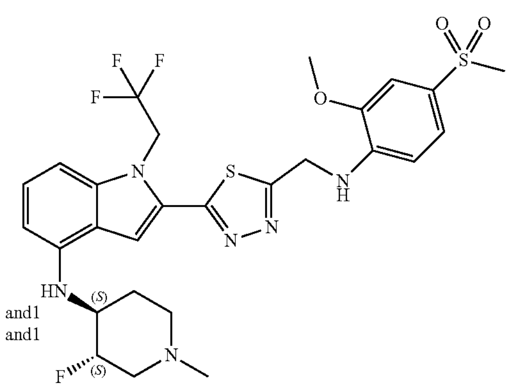 | (+/−)-N-[(3R,4R)-3-fluoro-1-methylpiperidin-4-yl]-2-(5-{[(4-methanesulfonyl-2-methoxyphenyl)amino]methyl}-1,3,4-thiadiazol-2-yl)-1-(2,2,2-trifluoroethyl)-1H-indol-4-amine | 627.2 |

TABLE 5-continued

| Compound No. | Structure | IUPAC | LC-MS (ES+, m/z) |
|---|---|---|---|
| 29B | 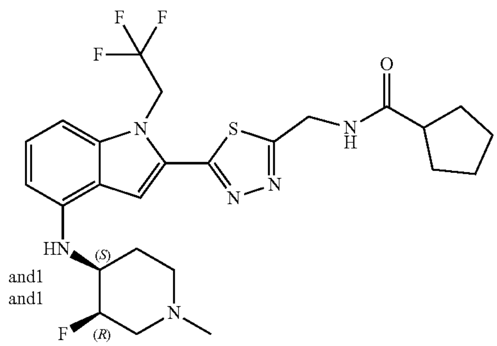 | (+/−)-N-{[5-(4-{[(3R,4S)-3-fluoro-1-methylpiperidin-4-yl]amino}-1-(2,2,2-trifluoroethyl)-1H-indol-2-yl)-1,3,4-thiadiazol-2-yl]methyl}cyclopentanecarboxamide | 539.2 |
| 30B | 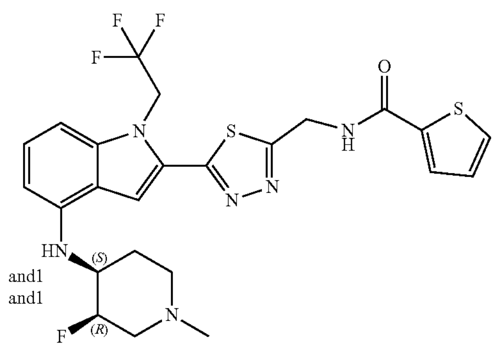 | (+/−)-N-{[5-(4-{[(3R,4S)-3-fluoro-1-methylpiperidin-4-yl]amino}-1-(2,2,2-trifluoroethyl)-1H-indol-2-yl)-1,3,4-thiadiazol-2-yl]methyl}thiophene-2-carboxamide | 553.1 |
| 31B | 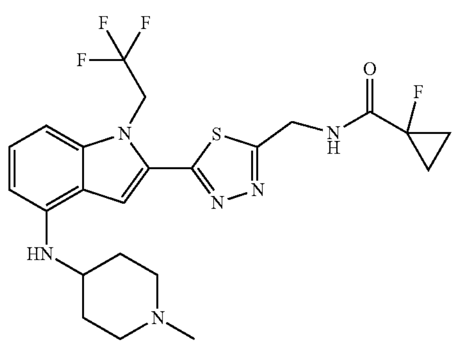 [SMILES: CN1CCC(Nc2cccc3c2cc(-c2nnc(CNC(=O)C4(F)CC4)s2)n3CC(F)(F)F)CC1] | 1-fluoro-N-[(5-{4-[(1-methylpiperidin-4-yl)amino]-1-(2,2,2-trifluoroethyl)-1H-indol-2-yl}-1,3,4-thiadiazol-2-yl)methyl]cyclopropane-1-carboxamide | 511.1 |
| 32B | 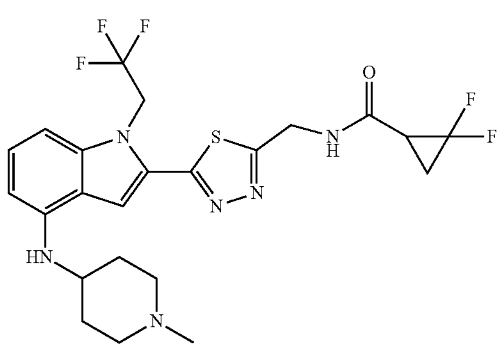 [SMILES: CN1CCC(Nc2cccc3c2cc(-c2nnc(CNC(=O)C4CC4(F)F)s2)n3CC(F)(F)F)CC1] | (+/−)-2,2-difluoro-N-[(5-{4-[(1-methylpiperidin-4-yl)amino]-1-(2,2,2-trifluoroethyl)-1H-indol-2-yl}-1,3,4-thiadiazol-2-yl)methyl]cyclopropane-1-carboxamide | 529.1 |

TABLE 5-continued

| Compound No. | Structure | IUPAC | LC-MS (ES+, m/z) |
|---|---|---|---|
| 33B | 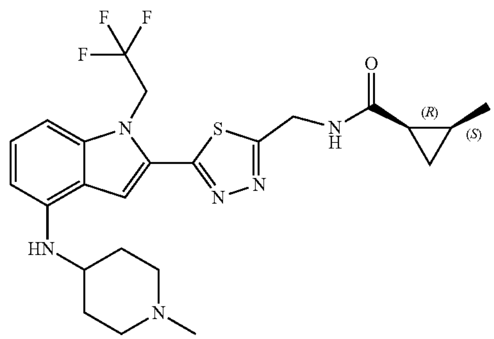 | (+/−)-(1R,2S)-2-methyl-N-[(5-{4-[(1-methylpiperidin-4-yl)amino]-1-(2,2,2-trifluoroethyl)-1H-indol-2-yl}-1,3,4-thiadiazol-2-yl)methyl]cyclopropane-1-carboxamide | 507.1 |
| 34B | 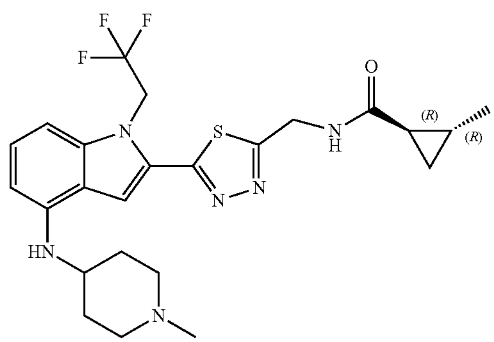 | (+/−)-(1R,2R)-2-methyl-N-[(5-{4-[(1-methylpiperidin-4-yl)amino]-1-(2,2,2-trifluoroethyl)-1H-indol-2-yl}-1,3,4-thiadiazol-2-yl)methyl]cyclopropane-1-carboxamide | 507.2 |
| 35B | 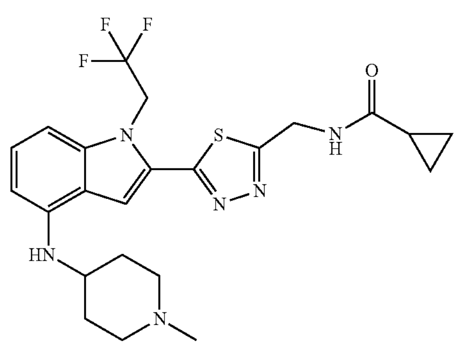 [SMILES: CN1CCC(Nc2cccc3c2cc(-c2nnc(CNC(=O)C4CC4)s2)n3CC(F)(F)F)CC1] | N-[(5-{4-[(1-methylpiperidin-4-yl)amino]-1-(2,2,2-trifluoroethyl)-1H-indol-2-yl}-1,3,4-thiadiazol-2-yl)methyl]cyclopropanecarboxamide | 493.2 |
| 36B | 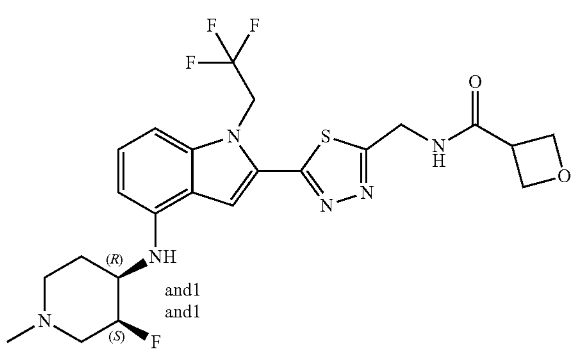 | (+/−)-N-{5-(4-{[(3R,4S)-3-fluoro-1-methylpiperidin-4-yl]amino}-1-(2,2,2-trifluoroethyl)-1H-indol-2-yl)-1,3,4-thiadiazol-2-yl]methyl}oxetane-3-carboxamide | 527.2 |

TABLE 5-continued

| Compound No. | Structure | IUPAC | LC-MS (ES+, m/z) |
|---|---|---|---|
| 37B | 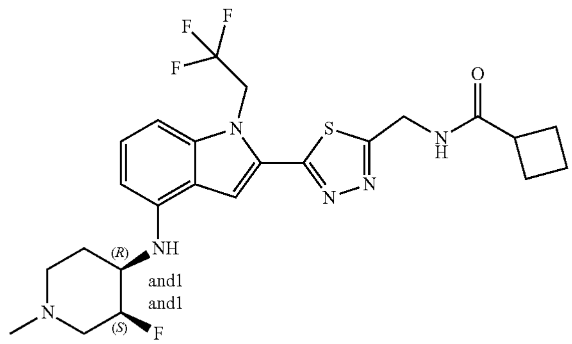 | (+/−)-N-{[5-(4-{[(3R,4S)-3-fluoro-1-methylpiperidin-4-yl]amino}-1-(2,2,2-trifluoroethyl)-1H-indol-2-yl)-1,3,4-thiadiazol-2-yl]methyl}cyclobutanecarboxamide | 525.2 |
| 38B | 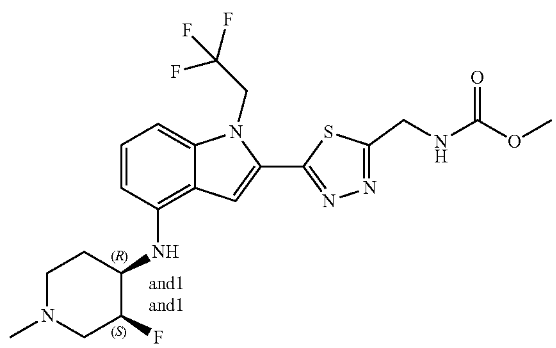 | (+/−)-methyl N-{[5-(4-{[(3R,4S)-3-fluoro-1-methylpiperidin-4-yl]amino}-1-(2,2,2-trifluoroethyl)-1H-indol-2-yl)-1,3,4-thiadiazol-2-yl]methyl}carbamate | 501.1 |
| 39B | 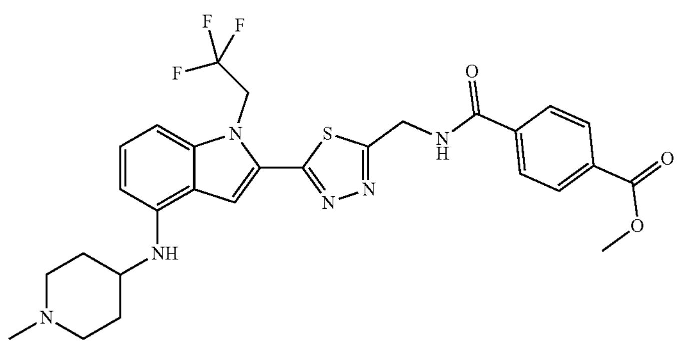 [SMILES: COC(=O)c1ccc(C(=O)NCc2nnc(-c3cc4c(NC5CCN(C)CC5)cccc4n3CC(F)(F)F)s2)cc1] | methyl 4-{[(5-{4-[(1-methylpiperidin-4-yl)amino]-1-(2,2,2-trifluoroethyl)-1H-indol-2-yl}-1,3,4-thiadiazol-2-yl)methyl]carbamoyl}benzoate | 587.3 |
| 40B | 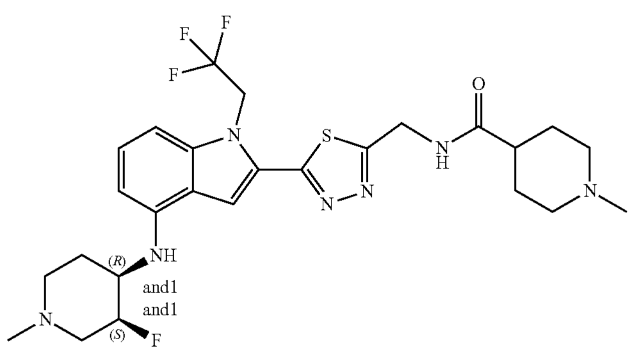 | (+/−)-N-{[5-(4-{[(3R,4S)-3-fluoro-1-methylpiperidin-4-yl]amino}-1-(2,2,2-trifluoroethyl)-1H-indol-2-yl)-1,3,4-thiadiazol-2-yl]methyl}-1-methylpiperidine-4-carboxamide | 568.3 |

TABLE 5-continued

| Compound No. | Structure | IUPAC | LC-MS (ES+, m/z) |
|---|---|---|---|
| 41B | 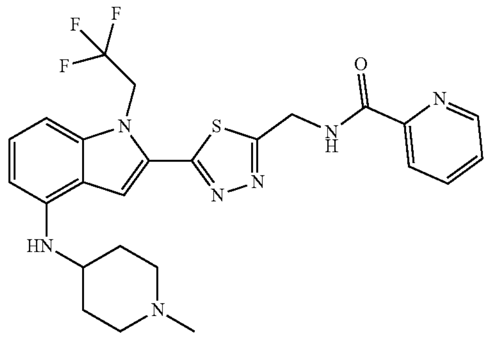 [SMILES: CN1CCC(Nc2cccc3c2cc(-c2nnc(CNC(=O)c4ccccn4)s2)n3CC(F)(F)F)CC1] | N-[(5-{4-[(1-methylpiperidin-4-yl)amino]-1-(2,2,2-trifluoroethyl)-1H-indol-2-yl}-1,3,4-thiadiazol-2-yl)methyl]pyridine-2-carboxamide | 530.3 |
| 42B | 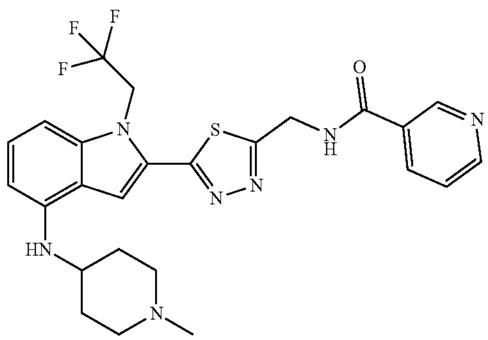 [SMILES: CN1CCC(Nc2cccc3c2cc(-c2nnc(CNC(=O)c4cccnc4)s2)n3CC(F)(F)F)CC1] | N-[(5-{4-[(1-methylpiperidin-4-yl)amino]-1-(2,2,2-trifluoroethyl)-1H-indol-2-yl}-1,3,4-thiadiazol-2-yl)methyl]pyridine-3-carboxamide | 530.3 |
| 43B | 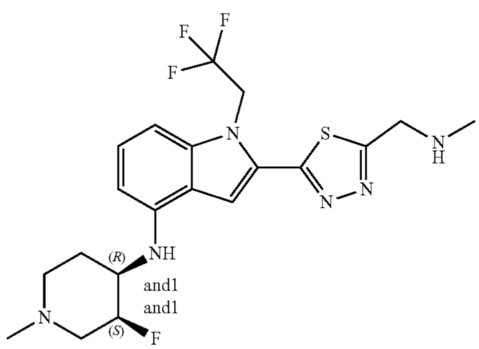 | (+/−)-N-[(3R,4S)-3-fluoro-1-methylpiperidin-4-yl]-2-{5-[(methylamino)methyl]-1,3,4-thiadiazol-2-yl}-1-(2,2,2-trifluoroethyl)-1H-indol-4-amine | 457.2 |
| 44B | 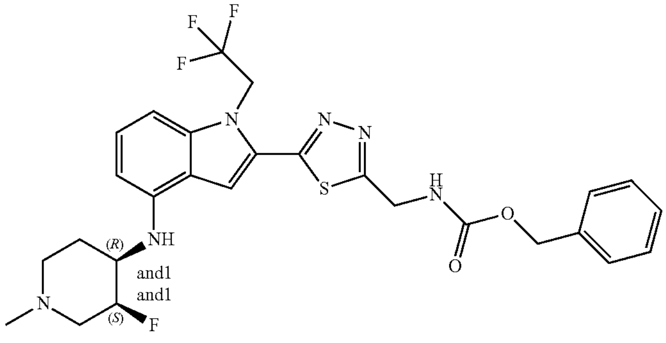 | (+/−)-benzyl N-{[5-(4-{[(3R,4S)-3-fluoro-1-methylpiperidin-4-yl]amino}-1-(2,2,2-trifluoroethyl)-1H-indol-2-yl)-1,3,4-thiadiazol-2-yl]methyl}carbamate | 576.9 |

TABLE 5-continued

| Compound No. | Structure | IUPAC | LC-MS (ES+, m/z) |
|---|---|---|---|
| 45B | 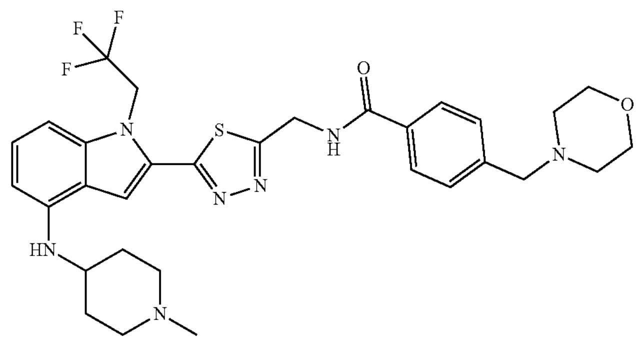 [SMILES: CN1CCC(Nc2cccc3c2cc(-c2nnc(CNC(=O)c4ccc(CN5CCOCC5)cc4)s2)n3CC(F)(F)F)CC1] | N-[(5-{4-[(1-methylpiperidin-4-yl)amino]-1-(2,2,2-trifluoroethyl)-1H-indol-2-yl}-1,3,4-thiadiazol-2-yl)methyl]-4-[(morpholin-4-yl)methyl]benzamide | 628.3 |
| 46B | 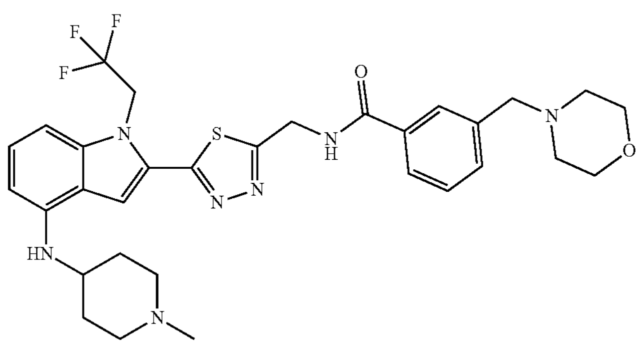 [SMILES: CN1CCC(Nc2cccc3c2cc(-c2nnc(CNC(=O)c4cccc(CN5CCOCC5)c4)s2)n3CC(F)(F)F)CC1] | N-[(5-{4-[(1-methylpiperidin-4-yl)amino]-1-(2,2,2-trifluoroethyl)-1H-indol-2-yl}-1,3,4-thiadiazol-2-yl)methyl]-3-[(morpholin-4-yl)methyl]benzamide | 628.3 |
| 47B | 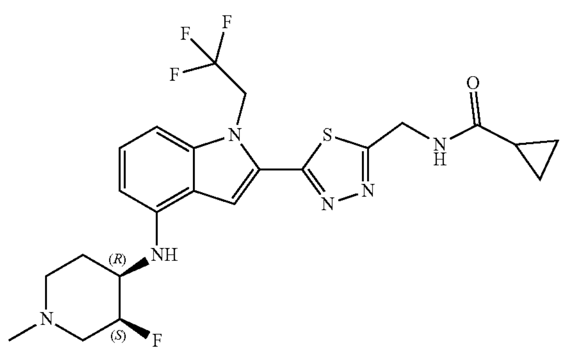 | N-{[5-(4-{[(3S,4R)-3-fluoro-1-methylpiperidin-4-yl]amino}-1-(2,2,2-trifluoroethyl)-1H-indol-2-yl)-1,3,4-thiadiazol-2-yl]methyl}cyclopropanecarboxamide | 511.1 |
| 48B | 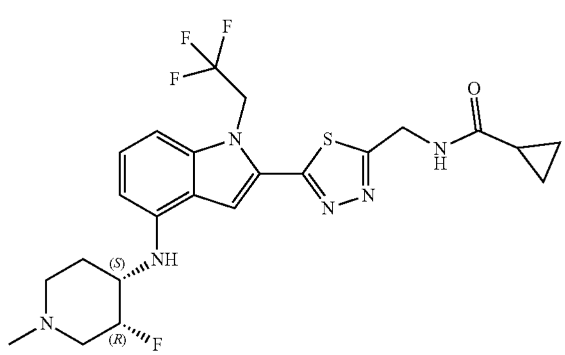 | N-{[5-(4-{[(3R,4S)-3-fluoro-1-methylpiperidin-4-yl]amino}-1-(2,2,2-trifluoroethyl)-1H-indol-2-yl)-1,3,4-thiadiazol-2-yl]methyl}cyclopropanecarboxamide | 511.1 |

TABLE 5-continued

| Compound No. | Structure | IUPAC | LC-MS (ES+, m/z) |
|---|---|---|---|
| 49B | 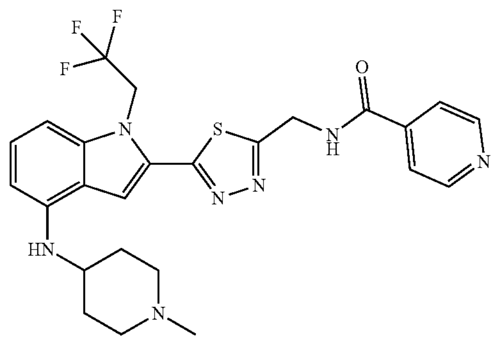 [SMILES: CN1CCC(Nc2cccc3c2cc(-c2nnc(CNC(=O)c4ccncc4)s2)n3CC(F)(F)F)CC1] | N-[(5-{4-[(1-methylpiperidin-4-yl)amino]-1-(2,2,2-trifluoroethyl)-1H-indol-2-yl}-1,3,4-thiadiazol-2-yl)methyl]pyridine-4-carboxamide | 530.2 |
| 50B | 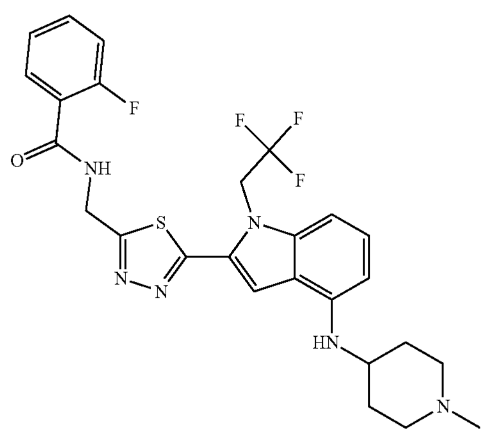 [SMILES: CN1CCC(Nc2cccc3c2cc(-c2nnc(CNC(=O)c4ccccc4F)s2)n3CC(F)(F)F)CC1] | 2-fluoro-N-[(5-{4-[(1-methylpiperidin-4-yl)amino]-1-(2,2,2-trifluoroethyl)-1H-indol-2-yl}-1,3,4-thiadiazol-2-yl)methyl]benzamide | 546.9 |
| 51B | 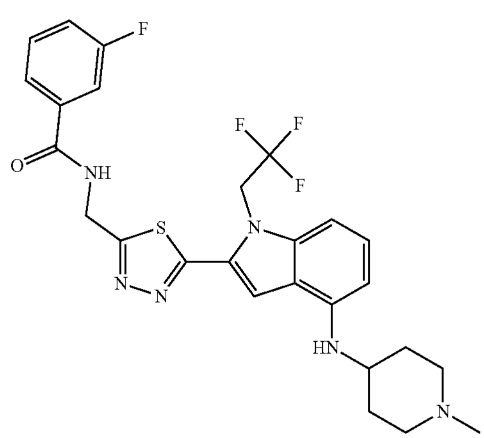 [SMILES: CN1CCC(Nc2cccc3c2cc(-c2nnc(CNC(=O)c4cccc(F)c4)s2)n3CC(F)(F)F)CC1] | 3-fluoro-N-[(5-{4-[(1-methylpiperidin-4-yl)amino]-1-(2,2,2-trifluoroethyl)-1H-indol-2-yl}-1,3,4-thiadiazol-2-yl)methyl]benzamide | 546.9 |

TABLE 5-continued

| Compound No. | Structure | IUPAC | LC-MS (ES+, m/z) |
|---|---|---|---|
| 52B | 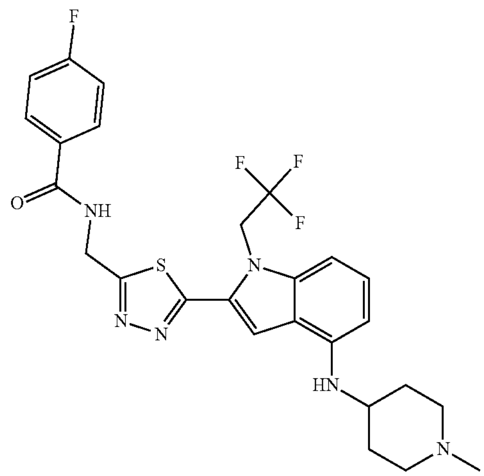 [SMILES: CN1CCC(Nc2cccc3c2cc(-c2nnc(CNC(=O)c4ccc(F)cc4)s2)n3CC(F)(F)F)CC1] | 4-fluoro-N-[(5-{4-[(1-methylpiperidin-4-yl)amino]-1-(2,2,2-trifluoroethyl)-1H-indol-2-yl}-1,3,4-thiadiazol-2-yl)methyl]benzamide | 546.9 |
| 53B | 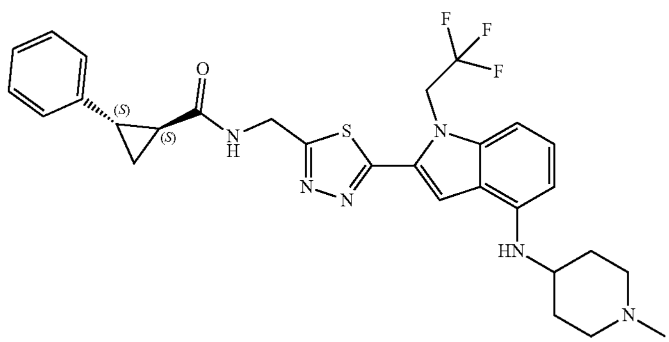 | (+/−)-(1S,2S)-N-[(5-{4-[(1-methylpiperidin-4-yl)amino]-1-(2,2,2-trifluoroethyl)-1H-indol-2-yl}-1,3,4-thiadiazol-2-yl)methyl]-2-phenylcyclopropane-1-carboxamide | 568.9 |
| 54B | 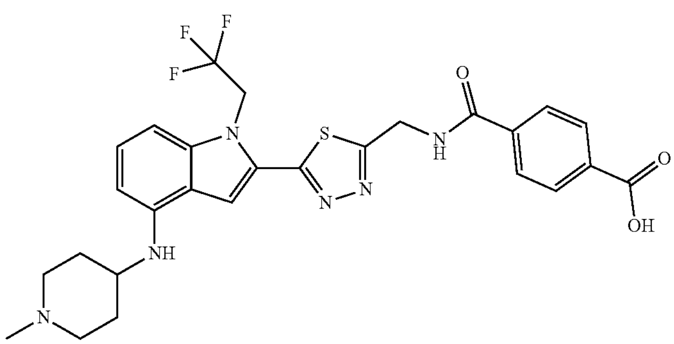 [SMILES: CN1CCC(Nc2cccc3c2cc(-c2nnc(CNC(=O)c4ccc(C(=O)O)cc4)s2)n3CC(F)(F)F)CC1] | 4-{[(5-{4-[(1-methylpiperidin-4-yl)amino]-1-(2,2,2-trifluoroethyl)-1H-indol-2-yl}-1,3,4-thiadiazol-2-yl)methyl]carbamoyl}benzoic acid | 573.1 |
| 55B | 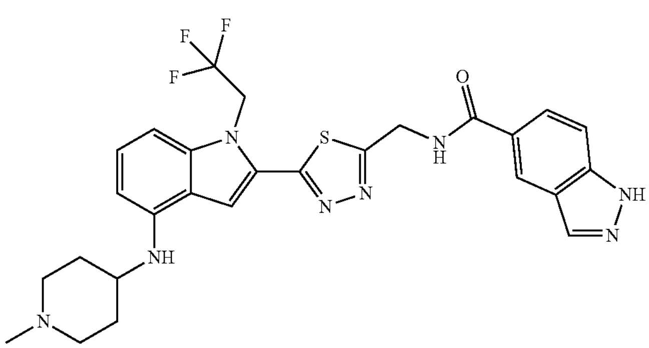 [SMILES: CN1CCC(Nc2cccc3c2cc(-c2nnc(CNC(=O)c4ccc5[nH]ncc5c4)s2)n3CC(F)(F)F)CC1] | N-[(5-{4-[(1-methylpiperidin-4-yl)amino]-1-(2,2,2-trifluoroethyl)-1H-indol-2-yl}-1,3,4-thiadiazol-2-yl)methyl]-1H-indazole-5-carboxamide | 569.2 |

TABLE 5-continued

| Compound No. | Structure | IUPAC | LC-MS (ES+, m/z) |
|---|---|---|---|
| 56B | 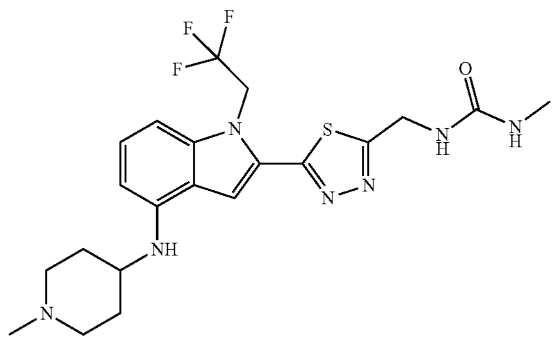 | 3-methyl-1-[(5-{4-[(1-methylpiperidin-4-yl)amino]-1-(2,2,2-trifluoroethyl)-1H-indol-2-yl}-1,3,4-thiadiazol-2-yl)methyl]urea | 482.2 |
| 57B | 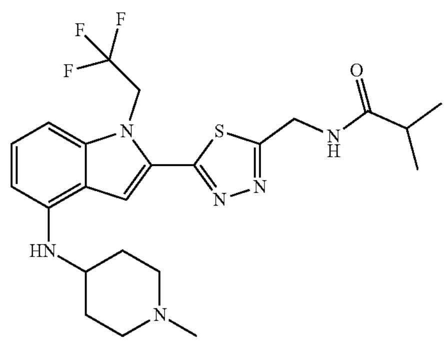 [SMILES: CC(C)C(=O)NCc1nnc(-c2cc3c(NC4CCN(C)CC4)cccc3n2CC(F)(F)F)s1] | 2-methyl-N-[(5-{4-[(1-methylpiperidin-4-yl)amino]-1-(2,2,2-trifluoroethyl)-1H-indol-2-yl}-1,3,4-thiadiazol-2-yl)methyl]propanamide | 495.2 |
| 58B | 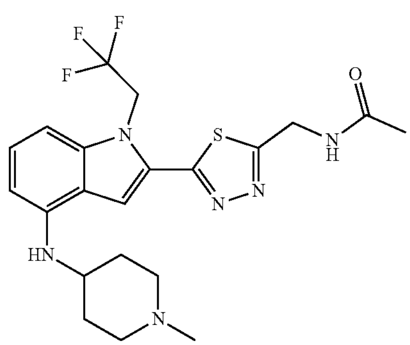 [SMILES: CC(=O)NCc1nnc(-c2cc3c(NC4CCN(C)CC4)cccc3n2CC(F)(F)F)s1] | N-[(5-{4-[(1-methylpiperidin-4-yl)amino]-1-(2,2,2-trifluoroethyl)-1H-indol-2-yl}-1,3,4-thiadiazol-2-yl)methyl]acetamide | 467.1 |
| 59B | 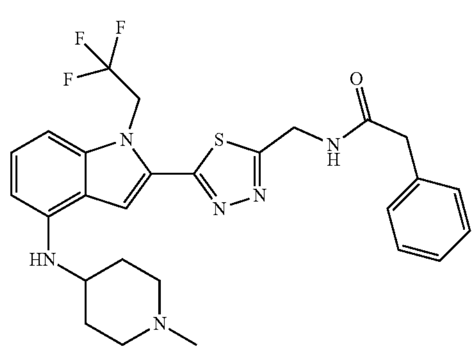 [SMILES: CN1CCC(Nc2cccc3c2cc(-c2nnc(CNC(=O)Cc4ccccc4)s2)n3CC(F)(F)F)CC1] | N-[(5-{4-[(1-methylpiperidin-4-yl)amino]-1-(2,2,2-trifluoroethyl)-1H-indol-2-yl}-1,3,4-thiadiazol-2-yl)methyl]-2-phenylacetamide | 543.3 |

TABLE 5-continued

| Compound No. | Structure | IUPAC | LC-MS (ES+, m/z) |
|---|---|---|---|
| 60B | 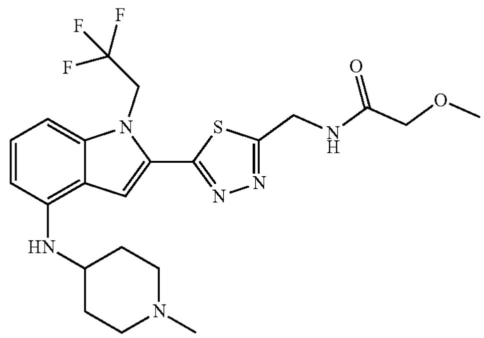 [SMILES: COCC(=O)NCc1nnc(-c2cc3c(NC4CCN(C)CC4)cccc3n2CC(F)(F)F)s1] | 2-methoxy-N-[(5-{4-[(1-methylpiperidin-4-yl)amino]-1-(2,2,2-trifluoroethyl)-1H-indol-2-yl}-1,3,4-thiadiazol-2-yl)methyl]acetamide | 497.1 |
| 61B | 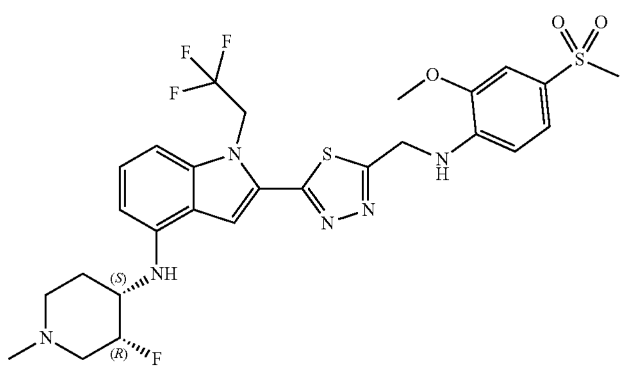 | N-[(3R,4S)-3-fluoro-1-methylpiperidin-4-yl]-2-(5-{[(4-methanesulfonyl-2-methoxyphenyl)amino]methyl}-1,3,4-thiadiazol-2-yl)-1-(2,2,2-trifluoroethyl)-1H-indol-4-amine | 627.2 |
| 62B | 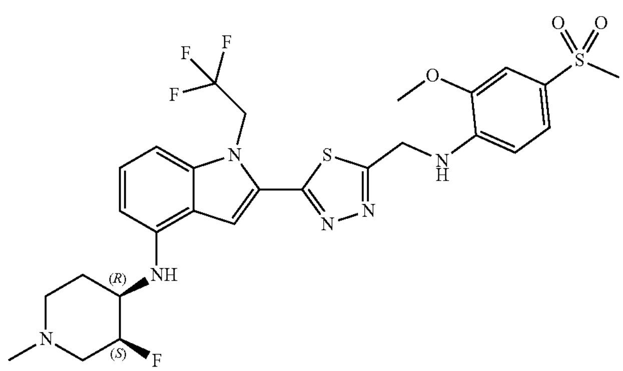 | N-[(3S,4R)-3-fluoro-1-methylpiperidin-4-yl]-2-(5-{[(4-methanesulfonyl-2-methoxyphenyl)amino]methyl}-1,3,4-thiadiazol-2-yl)-1-(2,2,2-trifluoroethyl)-1H-indol-4-amine | 627.2 |
| 63B | 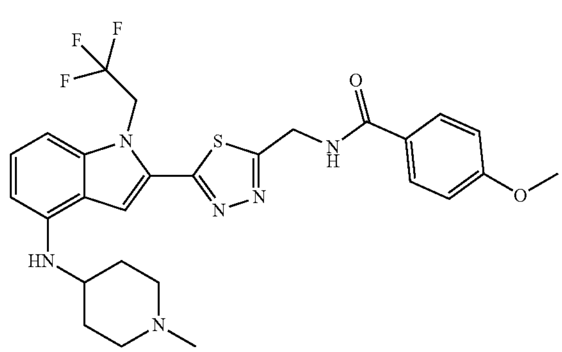 [SMILES: COc1ccc(C(=O)NCc2nnc(-c3cc4c(NC5CCN(C)CC5)cccc4n3CC(F)(F)F)s2)cc1] | 4-methoxy-N-[(5-{4-[(1-methylpiperidin-4-yl)amino]-1-(2,2,2-trifluoroethyl)-1H-indol-2-yl}-1,3,4-thiadiazol-2-yl)methyl]benzamide | 559.2 |

TABLE 5-continued

| Compound No. | Structure | IUPAC | LC-MS (ES+, m/z) |
|---|---|---|---|
| 64B | 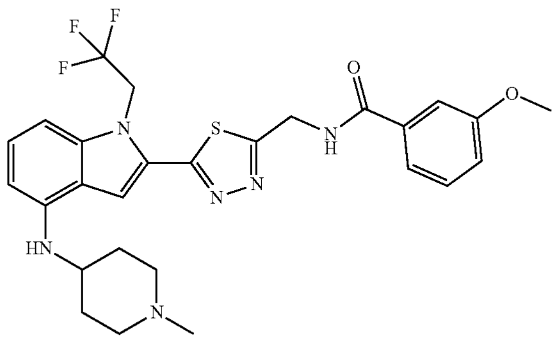 [SMILES: COc1cccc(C(=O)NCc2nnc(-c3cc4c(NC5CCN(C)CC5)cccc4n3CC(F)(F)F)s2)c1] | 3-methoxy-N-[(5-{4-[(1-methylpiperidin-4-yl)amino]-1-(2,2,2-trifluoroethyl)-1H-indol-2-yl}-1,3,4-thiadiazol-2-yl)methyl]benzamide | 559.2 |
| 65B | 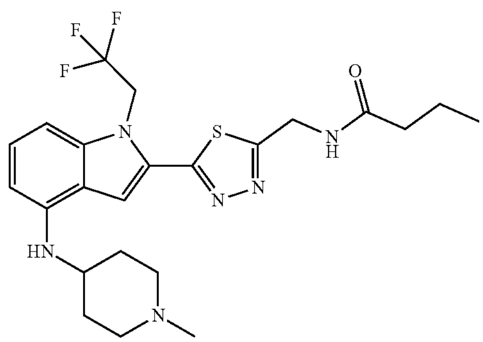 [SMILES: CCCC(=O)NCc1nnc(-c2cc3c(NC4CCN(C)CC4)cccc3n2CC(F)(F)F)s1] | N-[(5-{4-[(1-methylpiperidin-4-yl)amino]-1-(2,2,2-trifluoroethyl)-1H-indol-2-yl}-1,3,4-thiadiazol-2-yl)methyl]butanamide | 495.2 |
| 66B | 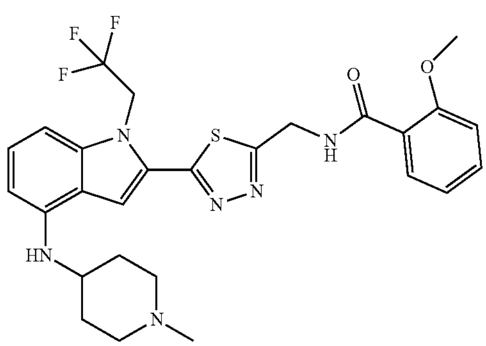 [SMILES: COc1ccccc1C(=O)NCc1nnc(-c2cc3c(NC4CCN(C)CC4)cccc3n2CC(F)(F)F)s1] | 2-methoxy-N-[(5-{4-[(1-methylpiperidin-4-yl)amino]-1-(2,2,2-trifluoroethyl)-1H-indol-2-yl}-1,3,4-thiadiazol-2-yl)methyl]benzamide | 559.2 |
| 67B | 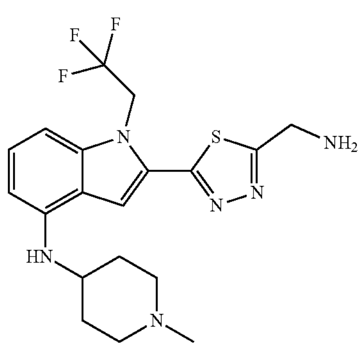 [SMILES: CN1CCC(Nc2cccc3c2cc(-c2nnc(CN)s2)n3CC(F)(F)F)CC1] | 2-[5-(aminomethyl)-1,3,4-thiadiazol-2-yl]-N-(1-methylpiperidin-4-yl)-1-(2,2,2-trifluoroethyl)-1H-indol-4-amine | 425.2 |

TABLE 5-continued

| Compound No. | Structure | IUPAC | LC-MS (ES+, m/z) |
|---|---|---|---|
| 68B | 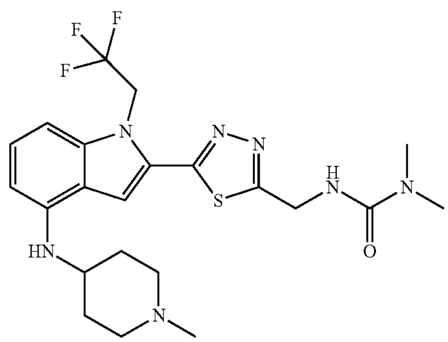 [SMILES: CN1CCC(Nc2cccc3c2cc(-c2nnc(CNC(=O)N(C)C)s2)n3CC(F)(F)F)CC1] | 3,3-dimethyl-1-[(5-{4-[(1-methylpiperidin-4-yl)amino]-1-(2,2,2-trifluoroethyl)-1H-indol-2-yl}-1,3,4-thiadiazol-2-yl)methyl]urea | 496.2 |
| 69B | 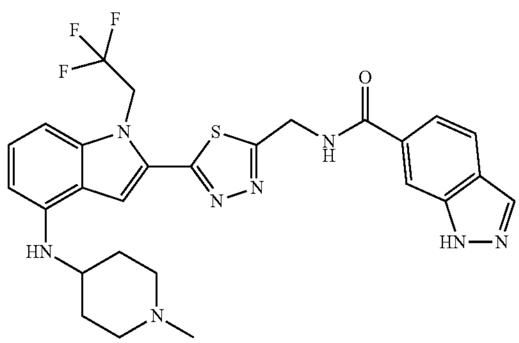 [SMILES: CN1CCC(Nc2cccc3c2cc(-c2nnc(CNC(=O)c4ccc5cn[nH]c5c4)s2)n3CC(F)(F)F)CC1] | N-[(5-{4-[(1-methylpiperidin-4-yl)amino]-1-(2,2,2-trifluoroethyl)-1H-indol-2-yl}-1,3,4-thiadiazol-2-yl)methyl]-1H-indazole-6-carboxamide | 569.3 |
| 70B | 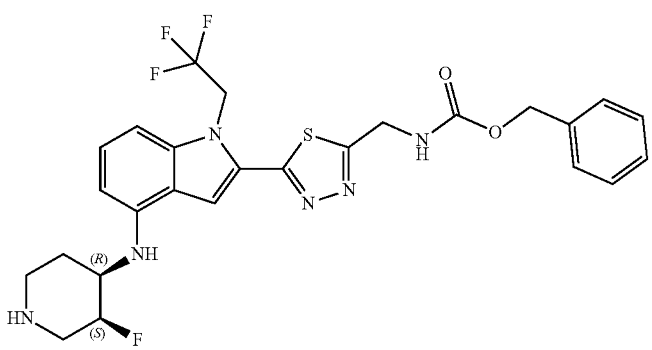 | benzyl N-{[5-(4-{[(3S,4R)-3-fluoropiperidin-4-yl]amino}-1-(2,2,2-trifluoroethyl)-1H-indol-2-yl)-1,3,4-thiadiazol-2-yl]methyl}carbamate | 563.2 |
| 71B | 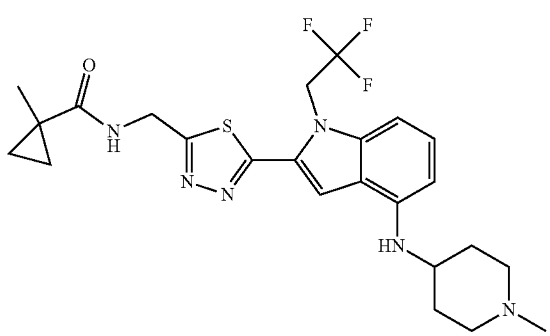 [SMILES: CN1CCC(Nc2cccc3c2cc(-c2nnc(CNC(=O)C4(C)CC4)s2)n3CC(F)(F)F)CC1] | 1-methyl-N-[(5-{4-[(1-methylpiperidin-4-yl)amino]-1-(2,2,2-trifluoroethyl)-1H-indol-2-yl}-1,3,4-thiadiazol-2-yl)methyl]cyclopropane-1-carboxamide | 507.2 |

TABLE 5-continued

| Compound No. | Structure | IUPAC | LC-MS (ES+, m/z) |
|---|---|---|---|
| 72B | 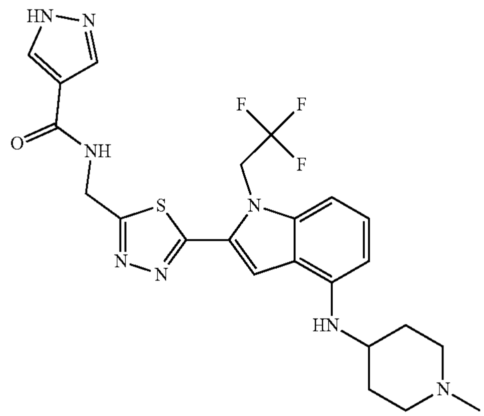 [SMILES: CN1CCC(Nc2cccc3c2cc(-c2nnc(CNC(=O)c4cn[nH]c4)s2)n3CC(F)(F)F)CC1] | N-[(5-{4-[(1-methylpiperidin-4-yl)amino]-1-(2,2,2-trifluoroethyl)-1H-indol-2-yl}-1,3,4-thiadiazol-2-yl)methyl]-1H-pyrazole-4-carboxamide | 518.9 |
| 73B | 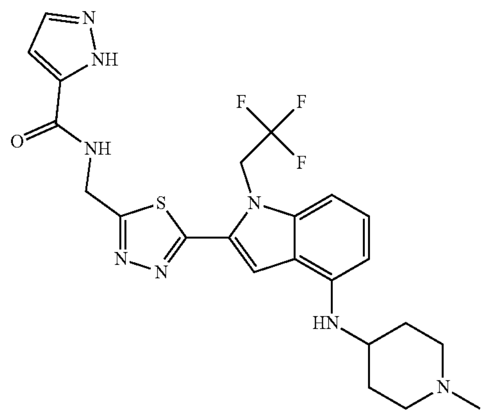 [SMILES: CN1CCC(Nc2cccc3c2cc(-c2nnc(CNC(=O)c4ccn[nH]4)s2)n3CC(F)(F)F)CC1] | N-[(5-{4-[(1-methylpiperidin-4-yl)amino]-1-(2,2,2-trifluoroethyl)-1H-indol-2-yl}-1,3,4-thiadiazol-2-yl)methyl]-1H-pyrazole-5-carboxamide | 218.9 |
| 74B | 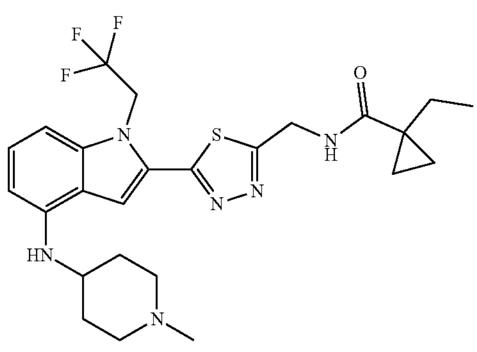 [SMILES: CCC1(C(=O)NCc2nnc(-c3cc4c(NC5CCN(C)CC5)cccc4n3CC(F)(F)F)s2)CC1] | 1-ethyl-N-[(5-{4-[(1-methylpiperidin-4-yl)amino]-1-(2,2,2-trifluoroethyl)-1H-indol-2-yl}-1,3,4-thiadiazol-2-yl)methyl]cyclopropane-1-carboxamide | 521.2 |
| 75B | 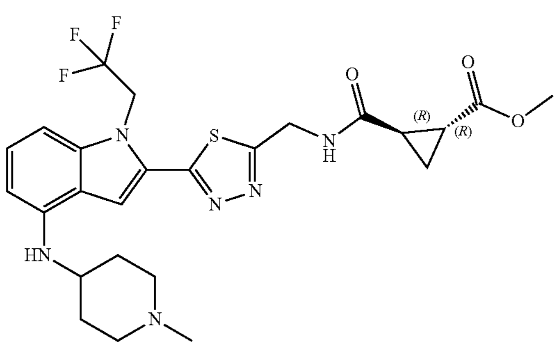 | (+/−)-methyl (1R,2R)-2-{[(5-{4-[(1-methylpiperidin-4-yl)amino]-1-(2,2,2-trifluoroethyl)-1H-indol-2-yl}-1,3,4-thiadiazol-2-yl)methyl]carbamoyl}cyclopropane-1-carboxylate | 551.2 |

TABLE 5-continued

| Compound No. | Structure | IUPAC | LC-MS (ES+, m/z) |
|---|---|---|---|
| 76B | 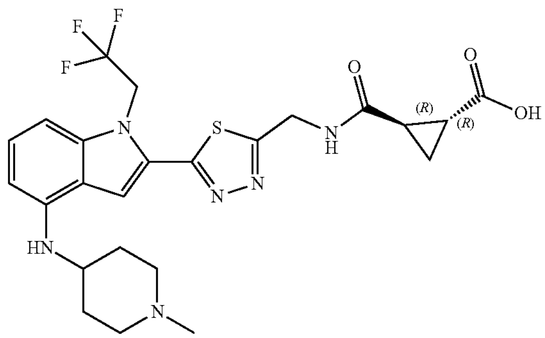 | (+/−)-(1R,2R)-2-{[(5-{4-[(1-methylpiperidin-4-yl)amino]-1-(2,2,2-trifluoroethyl)-1H-indol-2-yl}-1,3,4-thiadiazol-2-yl)methyl]carbamoyl}cyclopropane-1-carboxylic acid | 537.2 |
| 77B | 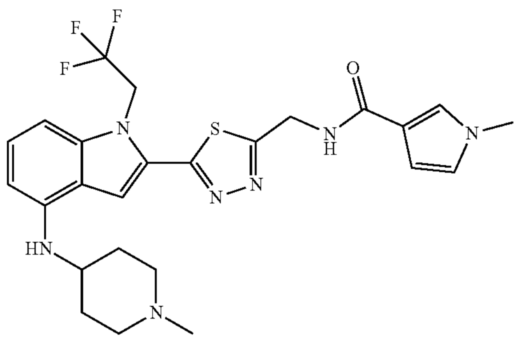 [SMILES: CN1CCC(Nc2cccc3c2cc(-c2nnc(CNC(=O)c4ccn(C)c4)s2)n3CC(F)(F)F)CC1] | 1-methyl-N-[(5-{4-[(1-methylpiperidin-4-yl)amino]-1-(2,2,2-trifluoroethyl)-1H-indol-2-yl}-1,3,4-thiadiazol-2-yl)methyl]-1H-pyrrole-3-carboxamide | 532.3 |
| 78B | 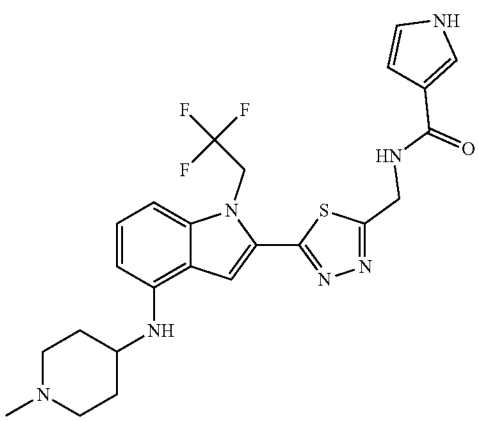 [SMILES: CN1CCC(Nc2cccc3c2cc(-c2nnc(CNC(=O)c4cc[nH]c4)s2)n3CC(F)(F)F)CC1] | N-[(5-{4-[(1-methylpiperidin-4-yl)amino]-1-(2,2,2-trifluoroethyl)-1H-indol-2-yl}-1,3,4-thiadiazol-2-yl)methyl]-1H-pyrrole-3-carboxamide | 518.1 |
| 79B | 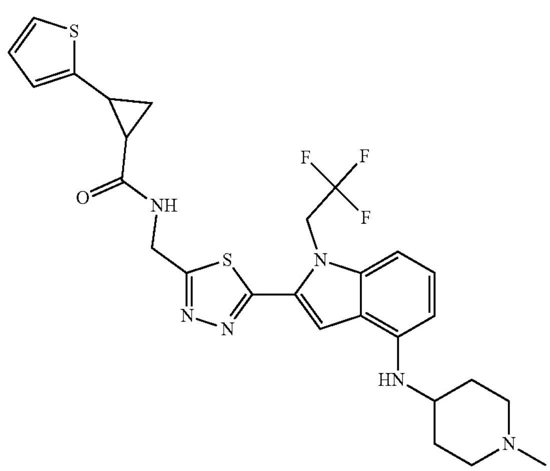 [SMILES: CN1CCC(Nc2cccc3c2cc(-c2nnc(CNC(=O)C4CC4c4cccs4)s2)n3CC(F)(F)F)CC1] | N-[(5-{4-[(1-methylpiperidin-4-yl)amino]-1-(2,2,2-trifluoroethyl)-1H-indol-2-yl}-1,3,4-thiadiazol-2-yl)methyl]-2-(thiophen-2-yl)cyclopropane-1-carboxamide | 574.9 |

TABLE 5-continued

| Compound No. | Structure | IUPAC | LC-MS (ES+, m/z) |
|---|---|---|---|
| 80B | 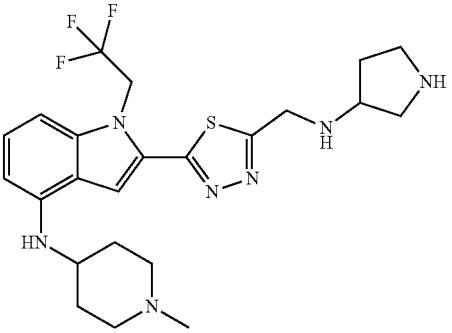 [SMILES: CN1CCC(Nc2cccc3c2cc(-c2nnc(CNC4CCNC4)s2)n3CC(F)(F)F)CC1] | N-(1-methylpiperidin-4-yl)-2-(5-{[(pyrrolidin-3-yl)amino]methyl}-1,3,4-thiadiazol-2-yl)-1-(2,2,2-trifluoroethyl)-1H-indol-4-amine | 494.2 |
| 81B | 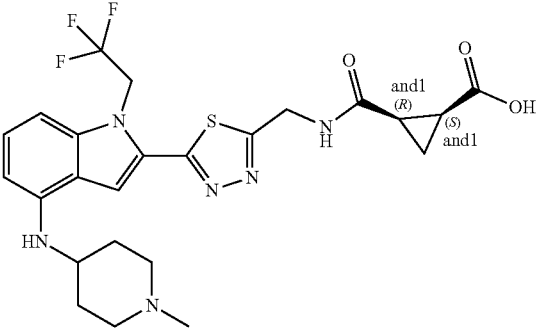 | (+/−)-(1R,2S)-2-{[(5-{4-[(1-methylpiperidin-4-yl)amino]-1-(2,2,2-trifluoroethyl)-1H-indol-2-yl}-1,3,4-thiadiazol-2-yl)methyl]carbamoyl}cyclopropane-1-carboxylic acid | 537.1 |
| 82B | 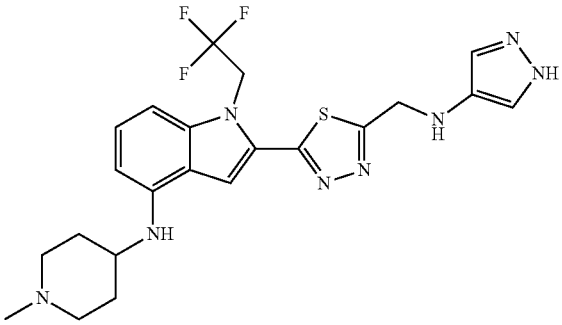 [SMILES: CN1CCC(Nc2cccc3c2cc(-c2nnc(CNc4cn[nH]c4)s2)n3CC(F)(F)F)CC1] | N-(1-methylpiperidin-4-yl)-2-(5-{[(1H-pyrazol-4-yl)amino]methyl}-1,3,4-thiadiazol-2-yl)-1-(2,2,2-trifluoroethyl)-1H-indol-4-amine | 491.1 |
| 83B | 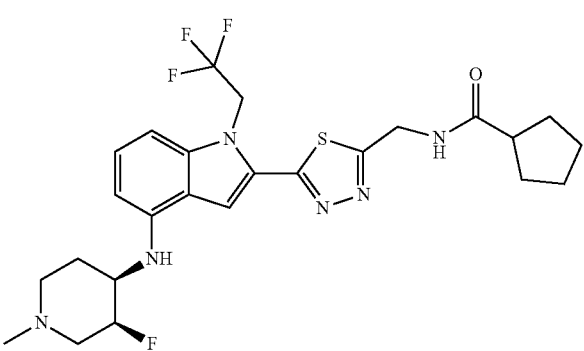 [SMILES: CN1CC[C@@H](Nc2cccc3c2cc(-c2nnc(CNC(=O)C4CCCC4)s2)n3CC(F)(F)F)[C@@H](F)C1] | N-((5-(4-(((3S,4R)-3-fluoro-1-methylpiperidin-4-yl)amino)-1-(2,2,2-trifluoroethyl)-1H-indol-2-yl)-1,3,4-thiadiazol-2-yl)methyl)cyclopentanecarboxamide | 539.2 |

TABLE 5-continued

| Compound No. | Structure | IUPAC | LC-MS (ES+, m/z) |
|---|---|---|---|
| 84B | 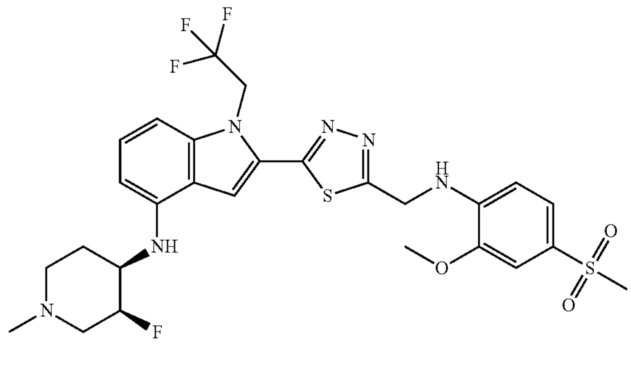 | N-((3S,4R)-3-fluoro-1-methylpiperidin-4-yl)-2-(5-(((2-methoxy-4-(methylsulfonyl)phenyl)amino)methyl)-1,3,4-thiadiazol-2-yl)-1-(2,2,2-trifluoroethyl)-1H-indol-4-amine | 627.1 |
| 85B | 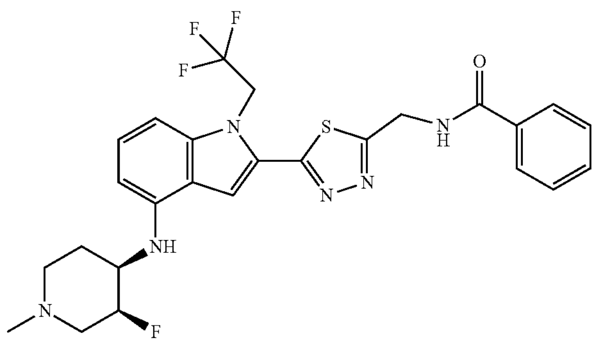 [SMILES: CN1CC[C@@H](Nc2cccc3c2cc(-c2nnc(CNC(=O)c4ccccc4)s2)n3CC(F)(F)F)[C@@H](F)C1] | N-((5-(4-(((3S,4R)-3-fluoro-1-methylpiperidin-4-yl)amino)-1-(2,2,2-trifluoroethyl)-1H-indol-2-yl)-1,3,4-thiadiazol-2-yl)methyl)benzamide | |
| 86B | 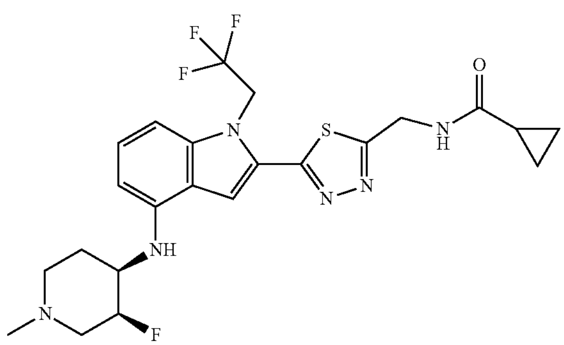 [SMILES: CN1CC[C@@H](Nc2cccc3c2cc(-c2nnc(CNC(=O)C4CC4)s2)n3CC(F)(F)F)[C@@H](F)C1] | N-((5-(4-(((3S,4R)-3-fluoro-1-methylpiperidin-4-yl)amino)-1-(2,2,2-trifluoroethyl)-1H-indol-2-yl)-1,3,4-thiadiazol-2-yl)methyl)cyclopropanecarboxamide | 511.2 |
| 87B | 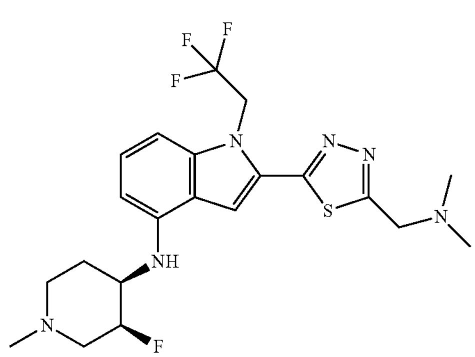 | 2-(5-((dimethylamino)methyl)-1,3,4-thiadiazol-2-yl)-N-((3S,4R)-3-fluoro-1-methylpiperidin-4-yl)-1-(2,2,2-trifluoroethyl)-1H-indol-4-amine | |

TABLE 5-continued

| Compound No. | Structure | IUPAC | LC-MS (ES+, m/z) |
|---|---|---|---|
| 88B | 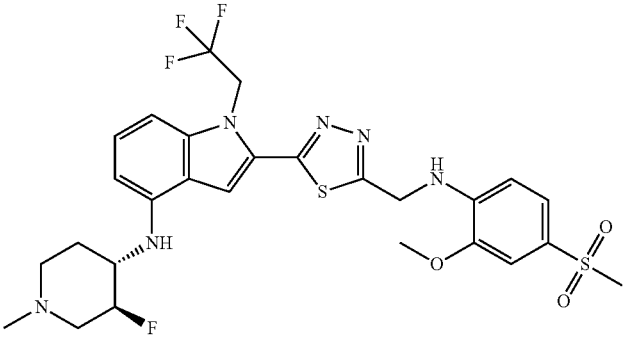 | N-((3S,4S)-3-fluoro-1-methylpiperidin-4-yl)-2-(5-(((2-methoxy-4-(methylsulfonyl)phenyl)amino)methyl)-1,3,4-thiadiazol-2-yl)-1-(2,2,2-trifluoroethyl)-1H-indol-4-amine | |
| 286B | 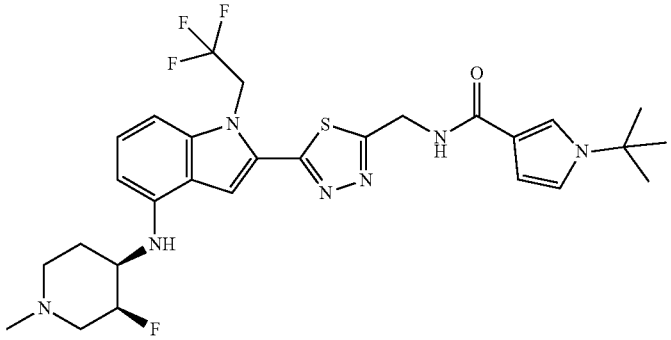 [SMILES: CN1CC[C@@H](Nc2cccc3c2cc(-c2nnc(CNC(=O)c4ccn(C(C)(C)C)c4)s2)n3CC(F)(F)F)[C@@H](F)C1] | 1-tert-butyl-N-{[5-(4-{[(3S,4R)-3-fluoro-1-methylpiperidin-4-yl]amino}-1-(2,2,2-trifluoroethyl)-1H-indol-2-yl)-1,3,4-thiadiazol-2-yl]methyl}-1H-pyrrole-3-carboxamide | 592.4 |
| 287B | 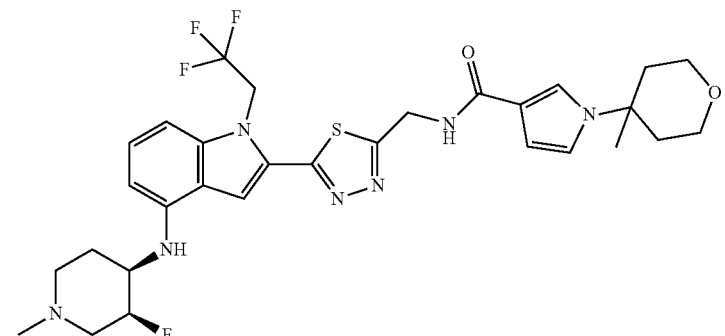 | N-{[5-(4-{[(3S,4R)-3-fluoro-1-methylpiperidin-4-yl]amino}-1-(2,2,2-trifluoroethyl)-1H-indol-2-yl)-1,3,4-thiadiazol-2-yl]methyl}-1-(4-methyloxan-4-yl)-1H-pyrrole-3-carboxamide | 634.4 |

Example 42: Synthesis of 2-(4-(aminomethyl)thiazol-2-yl)-N-((3S,4R)-3-fluoro-1-methylpiperidin-4-yl)-1-(2,2,2-trifluoroethyl)-1H-indol-4-amine (Compound 97B), N-{[2-(4-{[(3S,4R)-3-fluoro-1-methylpiperidin-4-yl]amino}-1-(2,2,2-trifluoroethyl)-1H-indol-2-yl)-1,3-thiazol-4-yl]methyl}cyclopropanecarboxamide (Compound 89B), and N-{[2-(4-{[(3S,4R)-3-fluoro-1-methylpiperidin-4-yl]amino}-1-(2,2,2-trifluoroethyl)-1H-indol-2-yl)-1,3-thiazol-4-yl]methyl}benzamide (Compound 90B)

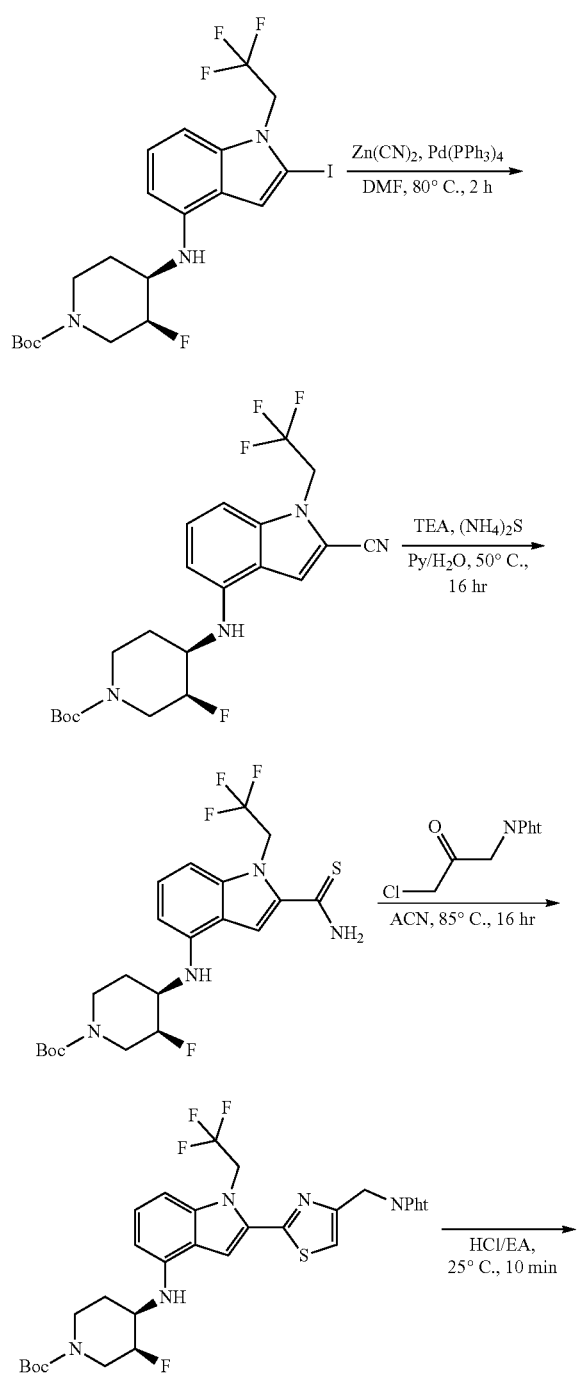

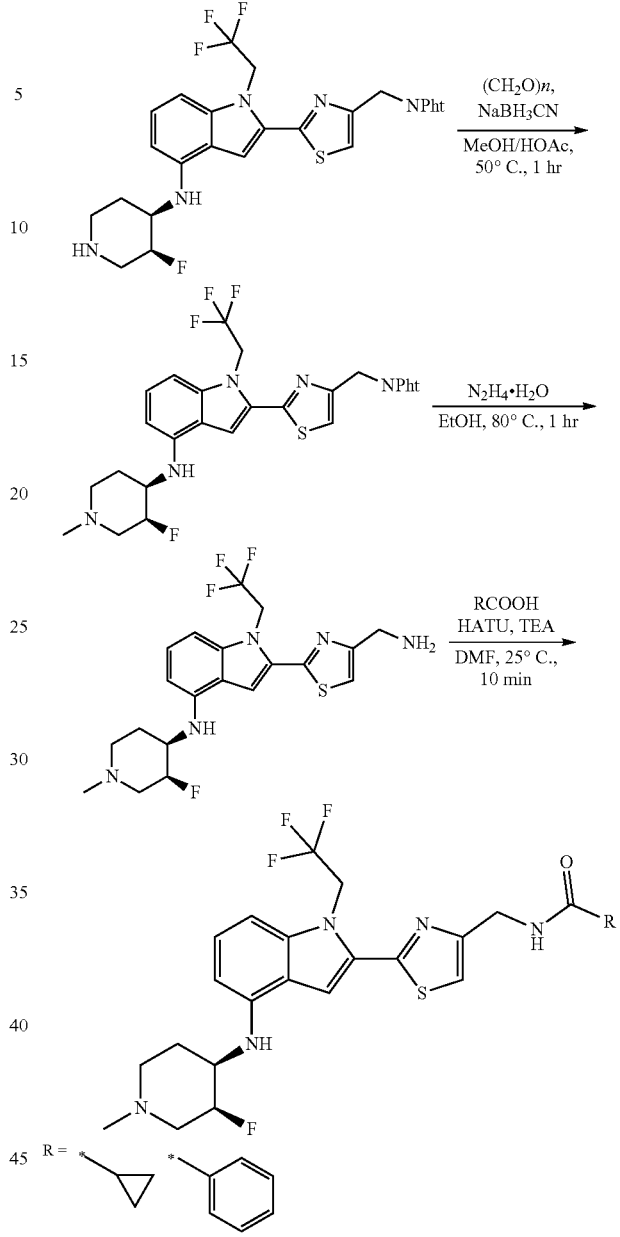

Preparation of (+/−) tert-butyl (3S,4R)-4-((2-cyano-1-(2,2,2-trifluoroethyl)-1H-indol-4-yl)amino)-3-fluoropiperidine-1-carboxylate: To a solution of (+/−) tert-butyl (3S,4R)-3-fluoro-4-((2-iodo-1-(2,2,2-trifluoroethyl)-1H-indol-4-yl)amino)piperidine-1-carboxylate (5 g, 9.24 mmol, 1 eq) in DMF (2 mL) were added zinc cyanide (3.25 g, 27.7 mmol, 3 eq) and tetrakis(triphenylphoshine)palladium(0) (3.20 g, 2.77 mmol, 0.3 eq). The mixture was stirred at 80° C. for 2 hr under nitrogen. TLC analysis indicated that the starting material was consumed and one new spot had formed. The reaction mixture was poured into an 2M aqueous EDTA solution (50 mL) and stirred for 1 hr. The reaction mixture was extracted with EA (50 mL×2). The combined organic layers were washed with brine (50 mL), dried over anhydrous sodium sulfate, filtered, and concentrated in vacuo. The crude residue was purified by column chromatography (SiO$_2$, PE/EA=5:1 to 3:1) to afford (+/−) tert-butyl (3S,4R)-4-((2-cyano-1-(2,2,2-trifluoroethyl)-1H-indol-4-yl)amino)-

3-fluoropiperidine-1-carboxylate (6 g, 13.62 mmol) as a brown solid. LC-MS (ES+, m/z): 441.3.

Preparation of (+/−) tert-butyl (3S,4R)-4-((2-carbonothioyl-1-(2,2,2-trifluoroethyl)-1H-indol-4-yl)amino)-3-fluoropiperidine-1-carboxylate: To a solution of tert-butyl (3S, 4R)-4-((2-cyano-1-(2,2,2-trifluoroethyl)-1H-indol-4-yl)amino)-3-fluoropiperidine-1-carboxylate (5 g, 11.4 mmol, 1 eq) in pyridine (50 mL) and water (2 mL) were added TEA (1.26 g, 12.5 mmol, 1.74 mL, 1.1 eq) and ammonium sulfide (10.64 g, 12.49 mmol, 1.1 eq). The mixture was stirred at 50° C. for 16 hr. TLC analysis indicated that the starting material was consumed and one new spot had formed. The reaction mixture was extracted with EA (50 mL×2). The combined organic layers were washed with brine (50 mL), dried over anhydrous sodium sulfate, filtered, and concentrated in vacuo. The residue was purified by column chromatography (SiO$_2$, PE/EA=5/1 to 3/1) to afford (+/−)-tert-butyl (3S,4R)-4-((2-carbonothioyl-1-(2,2,2-trifluoroethyl)-1H-indol-4-yl)amino)-3-fluoropiperidine-1-carboxylate (5 g, 10.54 mmol, 92.8% yield) as a yellow solid.

Preparation of (+/−)-2-((((2-(4-(((3S,4R)-1-(tert-butoxycarbonyl)-3-fluoropiperidin-4-yl)amino)-1-(2,2,2-trifluoroethyl)-1H-indol-2-yl)thiazol-4-yl)methyl)-12-azaneyl)carbonyl)benzoic acid: To a solution of 2-(3-chloro-2-oxopropyl)isoindoline-1,3-dione (325.5 mg, 1.37 mmol, 1.3 eq) in acetonitrile (15 mL) was added (+/−)-tert-butyl (3R,4S)-4-[[2-carbonothioyl-1-(2,2,2-trifluoroethyl)indol-4-yl]amino]-3-fluoro-piperidine-1-carboxylate (500 mg, 1.05 mmol, 1 eq). The mixture was stirred at 85° C. for 16 hr. The reaction mixture was extracted with EA (50 mL×2). The combined organic layers were washed with saturated brine (50 mL), dried over anhydrous sodium sulfate, filtered, and concentrated in vacuo to afford (+/−)-tert-butyl (3R,4S)-4-[[2-[4-[(1,3-dioxoisoindolin-2-yl)methyl]thiazol-2-yl]-1-(2,2,2-trifluoroethyl)indol-4-yl]amino]-3-fluoro-piperidine-1-carboxylate (600 mg, crude) as yellow solid.

Preparation of (+/−)-2-((((2-(4-(((3S,4R)-3-fluoropiperidin-4-yl)amino)-1-(2,2,2-trifluoroethyl)-1H-indol-2-yl)thiazol-4-yl)methyl)-12-azaneyl)carbonyl)benzoic acid; Route A: (+/−)-2-((((2-(4-(((3S,4R)-1-(tert-butoxycarbonyl)-3-fluoropiperidin-4-yl)amino)-1-(2,2,2-trifluoroethyl)-1H-indol-2-yl)thiazol-4-yl)methyl)-12-azaneyl)carbonyl)benzoic acid (800 mg, 1.22 mmol, 1 eq) was added to 4N hydrogen chloride in EA (5 mL). The mixture was stirred at 25° C. for 10 min. The reaction mixture was poured into saturated aqueous sodium carbonate (10 mL). The reaction mixture was diluted with water (10 mL) and extracted with EA (5 mL×2). The combined organic layers were washed with brine (10 mL), dried over anhydrous sodium sulfate, filtered, and concentrated in vacuo. The residue was purified by preparative-TLC (SiO$_2$, DCM:MeOH=10:1) to afford (+/−)-2-((((2-(4-(((3S,4R)-3-fluoropiperidin-4-yl)amino)-1-(2,2,2-trifluoroethyl)-1H-indol-2-yl)thiazol-4-yl)methyl)-12-azaneyl)carbonyl)benzoic acid (270 mg, 484 μmol, 39.8% yield) as a yellow solid. LC-MS (ES+, m/z): 542.1.

Preparation of (+/−)-2-((((2-(4-(((3S,4R)-3-fluoropiperidin-4-yl)amino)-1-(2,2,2-trifluoroethyl)-1H-indol-2-yl)thiazol-4-yl)methyl)-12-azaneyl)carbonyl)benzoic acid; Route B: To 2-(((3-chloro-2-oxopropyl)-12-azaneyl)carbonyl)benzoic acid (2.45 g, 10.33 mmol, 1.4 eq) in acetonitrile (105 mL) was added (+/−)-tert-butyl (3S,4R)-4-((2-carbamothioyl-1-(2,2,2-trifluoroethyl)-1H-indol-4-yl)amino)-3-fluoropiperidine-1-carboxylate (3.5 g, 7.38 mmol, 1 eq). The mixture was stirred at 85° C. for 16 hr. The reaction mixture was diluted with EA (50 mL), dried over anhydrous sodium sulfate, filtered, and concentrated in vacuo. The residue was purified by column chromatography (SiO$_2$, DCM:MeOH=100/1 to 10/1) to afford (+/−)-2-((((2-(4-(((3S,4R)-3-fluoropiperidin-4-yl)amino)-1-(2,2,2-trifluoroethyl)-1H-indol-2-yl)thiazol-4-yl)methyl)-12-azaneyl)carbonyl)benzoic acid (1.5 g, 2.28 mmol, 30.9% yield) as a yellow solid. LC-MS (ES+, m/z): 542.1.

Preparation of 2-((((2-(4-(((3S,4R)-3-fluoro-1-methylpiperidin-4-yl)amino)-1-(2,2,2-trifluoroethyl)-1H-indol-2-yl)thiazol-4-yl)methyl)-12-azaneyl)carbonyl)benzoic acid: To a solution of 2-((((2-(4-(((3S,4R)-3-fluoropiperidin-4-yl)amino)-1-(2,2,2-trifluoroethyl)-1H-indol-2-yl)thiazol-4-yl)methyl)-12-azaneyl)carbonyl)benzoic acid (1.60 g, 2.87 mmol, 1 eq) in MeOH (6 mL) were added paraformaldehyde (430.8 mg, 14.4 mmol, 5 eq), acetic acid (27.98 mmol, 1.60 mL, 9.75 eq), and sodium cyanoborohydride (901.7 mg, 14.4 mmol, 5 eq). The mixture was stirred at 50° C. for 1 hr. The reaction mixture was diluted with EA, washed with brine (20 mL), dried over anhydrous sodium sulfate, filtered, and concentrated in vacuo. The residue was purified by preparative-TLC (SiO$_2$, DCM:MeOH=10:1) to afford (+/−)-2-((((2-(4-(((3S,4R)-3-fluoro-1-methylpiperidin-4-yl)amino)-1-(2,2,2-trifluoroethyl)-1H-indol-2-yl)thiazol-4-yl)methyl)-12-azaneyl)carbonyl)benzoic acid (400 mg, 700 μmol, 24.4% yield) as a yellow solid. LC-MS (ES+, m/z): 572.2.

Preparation of (+/−)-2-(4-(aminomethyl)thiazol-2-yl)-N-((3S,4R)-3-fluoro-1-methylpiperidin-4-yl)-1-(2,2,2-trifluoroethyl)-1H-indol-4-amine (Compound 9713): To a solution of (+/−)-2-((((2-(4-(((3S,4R)-3-fluoro-1-methylpiperidin-4-yl)amino)-1-(2,2,2-trifluoroethyl)-1H-indol-2-yl)thiazol-4-yl)methyl)-12-azaneyl)carbonyl)benzoic acid (230 mg, 402 μmol, 1 eq) in ethanol (3 mL) was added hydrazine hydrate (3 mL). The mixture was stirred at 80° C. for 1 hr. The reaction mixture was extracted with EA (10 mL×2). The combined organic layers were washed with brine (20 mL), dried over anhydrous sodium sulfate, filtered, and concentrated in vacuo. The residue was purified by preparative-TLC (SiO$_2$, DCM:MeOH=10:1) or preparative-HPLC to afford (+/−)-2-(4-(aminomethyl)thiazol-2-yl)-N-((3S,4R)-3-fluoro-1-methylpiperidin-4-yl)-1-(2,2,2-trifluoroethyl)-1H-indol-4-amine (Compound 97B) (70 mg, 154.4 μmol, 38.4% yield) as a yellow solid. LC-MS (ES+, m/z): 442.1.

Preparation of (+/−)-N-{[2-(4-{1[(3S,4R)-3-fluoro-1-methylpiperidin-4-yl]amino}-1-(2,2,2-trifluoroethyl)-1H-indol-2-yl)-1,3-thiazol-4-yl]methyl}cyclopropanecarboxamide (Compound 89B) and N-{[2-(4-{1[(3S,4R)-3-fluoro-1-methylpiperidin-4-yl]amino}-1-(2,2,2-trifluoroethyl)-1H-indol-2-yl)-1,3-thiazol-4-yl]methyl}benzamide (Compound 90B): To a solution of RCOOH (1.5 eq) in DMF were added TEA (5 eq) and HATU (2 eq). Then (+/−)-2-(4-(aminomethyl)thiazol-2-yl)-N-((3S,4R)-3-fluoro-1-methylpiperidin-4-yl)-1-(2,2,2-trifluoroethyl)-1H-indol-4-amine (90 mg, 203.86 μmol, 1 eq) was added to the mixture. The mixture was stirred at 25° C. for 10 min. The reaction mixture was diluted with EA, washed with brine (20 mL), dried over anhydrous sodium sulfate, filtered, and concentrated in vacuo. The crude product was purified by preparative-HPLC to afford the desired product. (+/−)-N-{[2-(4-{[(3S,4R)-3-fluoro-1-methylpiperidin-4-yl]amino}-1-(2,2,2-trifluoroethyl)-1H-indol-2-yl)-1,3-thiazol-4-yl]methyl}cyclopropanecarboxamide (Compound 89B), 18.8% yield, LC-MS (ES−, m/z): 546.2; (+/−)-N-{[2-(4-{[(3S,4R)-3-fluoro-1-methylpiperidin-4-yl]amino}-1-(2,2,2-trifluoroethyl)-1H-indol-2-yl)-1,3-thiazol-4-yl]methyl}benzamide (Compound 90B), 19.3% yield, LC-MS (ES+, m/z): 510.1.

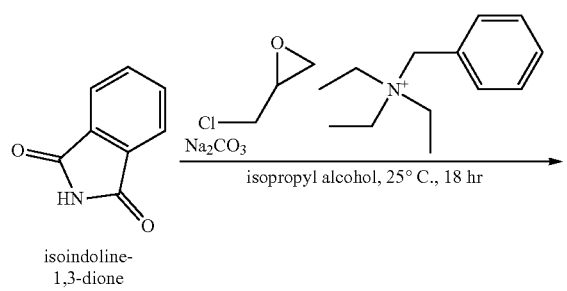

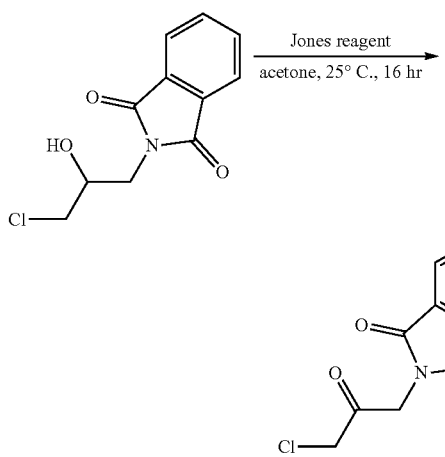

Preparation of 2-(3-chloro-2-hydroxypropyl)isoindoline-1,3-dione: A mixture of isoindoline-1,3-dione (15 g, 101.95 mmol, 1 eq), 2-(chloromethyl)oxirane (16.98 g, 183.51 mmol, 14.4 mL, 1.8 eq), N-benzyl-N,N-diethyl-ethanaminium (3.92 g, 20.4 mmol, 0.2 eq), and sodium carbonate (2.16 g, 20.4 mmol, 0.2 eq) in isopropyl alcohol (5 mL) was degassed and purged with nitrogen (×3), and the mixture was stirred at 25° C. for 18 hr under nitrogen. TLC analysis indicated that the starting material was consumed and one new spot had formed. The reaction mixture was diluted with EA, washed with brine (50 mL), dried over anhydrous sodium sulfate, filtered, and concentrated in vacuo. The crude residue was washed with PE (30 mL) to afford 2-(3-chloro-2-hydroxypropyl)isoindoline-1,3-dione (21 g, crude) as a white solid. LC-MS (ES⁺, m/z): 240.0.

Preparation of 2-(3-chloro-2-oxopropyl)isoindoline-1,3-dione: To a solution of 2-(3-chloro-2-hydroxypropyl)isoindoline-1,3-dione (6 g, 25 mmol, 1 eq) in acetone (50 mL) was added a solution of Jones reagent (2.68 M, 11.21 mL, 1.2 eq). The mixture was stirred at 25° C. for 16 hr. TLC analysis indicated that the starting material was consumed and one new spot had formed. The reaction mixture was diluted with EA, washed with brine (50 mL), dried over anhydrous sodium sulfate, filtered, and concentrated in vacuo. The crude residue was purified by column chromatography to afford 2-(3-chloro-2-oxopropyl)isoindoline-1,3-dione (5 g, 21 mmol, 84.0% yield) as a white solid. LC-MS (ES⁺, m/z): 256.0.

Example 43: Synthesis of (+/−)-N-{12-(4-{[(3R,4S)-3-fluoro-1-methylpiperidin-4-yl]amino}-1-(2,2,2-trifluoroethyl)-1H-indol-2-yl)-1,3-thiazol-5-yl]methyl}benzamide (Compound 91B) and N-[(2-{4-[(1-methylpiperidin-4-yl)amino]-1-(2,2,2-trifluoroethyl)-1H-indol-2-yl}-1,3-thiazol-5-yl)methyl]benzamide (Compound 92B)

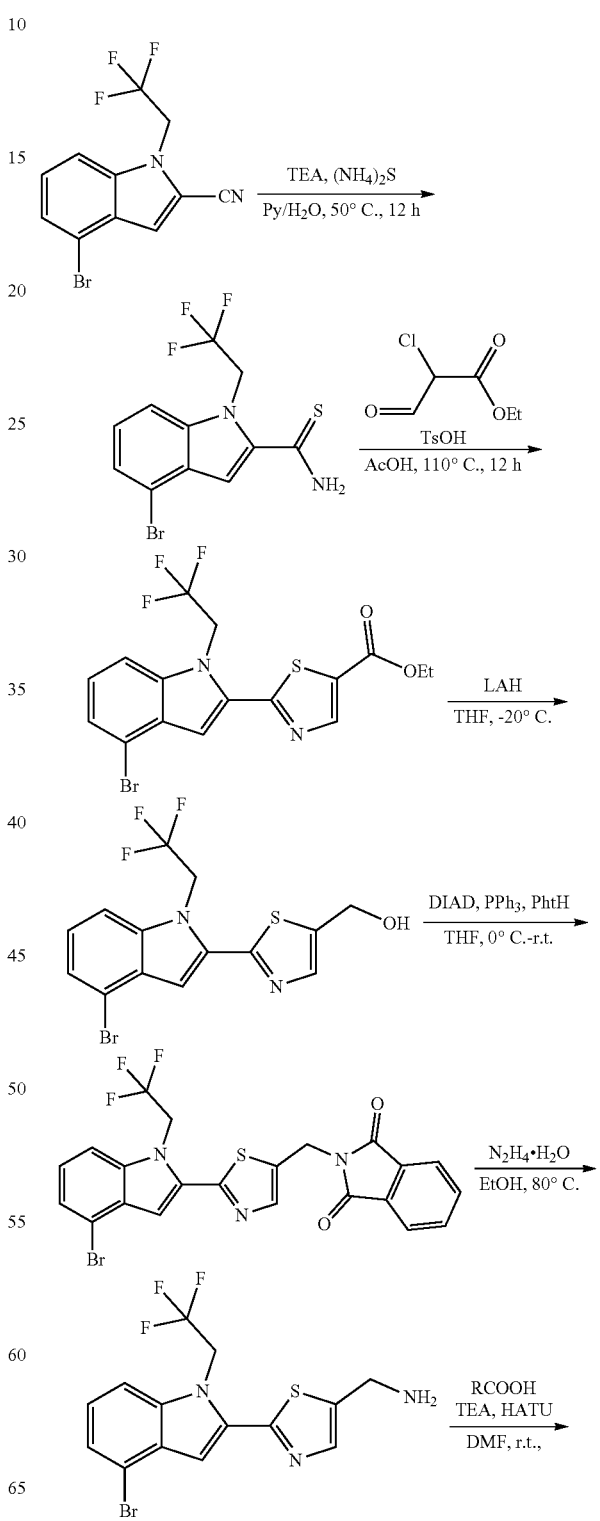

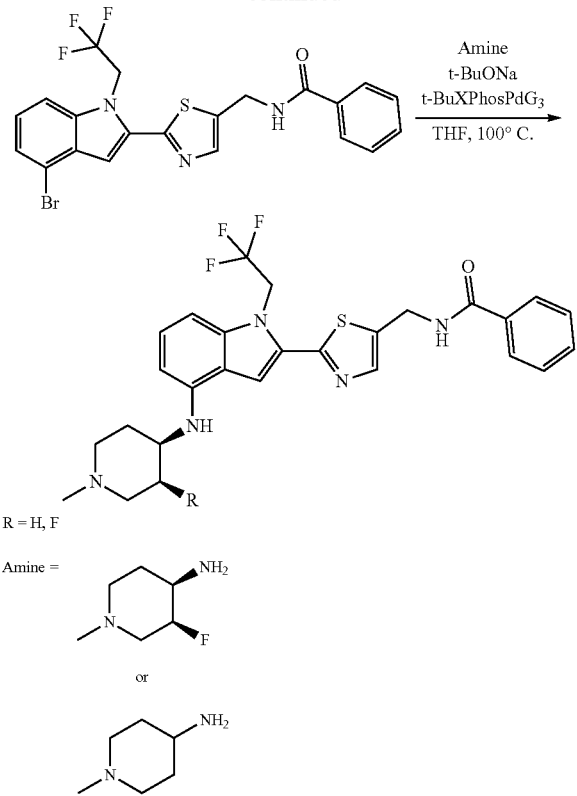

R = H, F

Preparation of 4-bromo-1-(2,2,2-trifluoroethyl)-1H-indole-2-carbothioamide: To a solution of 4-bromo-1-(2,2,2-trifluoroethyl)-1H-indole-2-carbonitrile (1 g, 3.30 mmol, 1 eq) in pyridine (10 mL) and water (5 mL) were added TEA (667.75 mg, 6.60 mmol, 918.50 µL, 2 eq) and ammonium sulfide (224.8 mg, 3.30 mmol, 225.5 µL, 1 eq). The mixture was heated and stirred at 50° C. for 12 hr. TLC analysis showed one major new spot with greater polarity than that of the starting material. The reaction mixture was diluted with water (200 mL) and extracted with EA (50 mL×3). The combined organic layers were washed with brine (100 mL), dried over anhydrous sodium sulfate, filtered, and concentrated in vacuo to afford 4-bromo-1-(2,2,2-trifluoroethyl)-1H-indole-2-carbothioamide (5.1 g, crude, 80% yield) as a white solid.

Preparation of ethyl 2-(4-bromo-1-(2,2,2-trifluoroethyl)-1H-indol-2-yl)thiazole-5-carboxylate: A mixture of 4-bromo-1-(2,2,2-trifluoroethyl)-1H-indole-2-carbothioamide (2 g, 5.93 mmol, 1 eq), ethyl 2-chloro-3-oxopropanoate (937.8 mg, 6.23 mmol, 1.05 eq), and TsOH (92.7 mg, 593 µmol, 0.1 eq) in acetic acid (20 mL) was degassed and purged with nitrogen (×3). The mixture was then stirred at 110° C. for 12 hr under nitrogen. TLC analysis indicated that the starting material was consumed and one new spot had formed. The mixture was added to water (50 mL), filtered, and concentrated in vacuo. The residue was washed with PE (10 mL) and concentrated to afford ethyl 2-(4-bromo-1-(2,2,2-trifluoroethyl)-1H-indol-2-yl)thiazole-5-carboxylate (1.9 g, crude, 80% yield) as a brown solid.

Preparation of (2-(4-bromo-1-(2,2,2-trifluoroethyl)-1H-indol-2-yl)thiazol-5-yl)methanol: To a solution of ethyl 2-(4-bromo-1-(2,2,2-trifluoroethyl)-1H-indol-2-yl)thiazole-5-carboxylate (1 g, 2.31 mmol, 1 eq) in THF (5 mL) was added a solution of lithium aluminum hydride (105.1 mg, 2.77 mmol, 1.2 eq) in THF (5 mL). The mixture was stirred at −20° C. for 30 min. The reaction mixture was quenched with water (0.1 mL) at −20° C., diluted with a 15% sodium hydroxide solution (0.1 mL), and extracted with EA (10 mL×2). The combined organic layers were washed with brine (10 mL×2), dried over anhydrous sodium sulfate, filtered, and concentrated in vacuo. The residue was washed with PE (5 mL), and concentrated in vacuo to afford (2-(4-bromo-1-(2,2,2-trifluoroethyl)-1H-indol-2-yl)thiazol-5-yl)methanol (740 mg, 1.89 mmol, 81.9% yield) as a yellow solid. LC-MS (ES$^+$, m/z): 390.9.

Preparation of 2-((2-(4-bromo-1-(2,2,2-trifluoroethyl)-1H-indol-2-yl)thiazol-5-yl)methyl)isoindoline-1,3-dione: DIAD (573.8 mg, 2.84 mmol, 552 µL, 1.5 eq) was added to a solution of phthalimide (417.5 mg, 2.84 mmol, 1.5 eq), (2-(4-bromo-1-(2,2,2-trifluoroethyl)-1H-indol-2-yl)thiazol-5-yl)methanol (740 mg, 1.89 mmol, 1 eq), and triphenylphosphine (744.22 mg, 2.84 mmol, 1.5 eq) in THF (10 mL) at 0° C. The mixture was stirred at 25° C. for 1 hr. The reaction mixture was extracted with EA (10 mL×2). The combined organic layers were washed with brine (20 mL), dried over anhydrous sodium sulfate, filtered, and concentrated in vacuo. The residue was purified by preparative-TLC to afford 2-((2-(4-bromo-1-(2,2,2-trifluoroethyl)-1H-indol-2-yl)thiazol-5-yl)methyl)isoindoline-1,3-dione (650 mg, 1.25 mmol, 66.0% yield) as a yellow solid.

Preparation of (2-(4-bromo-1-(((difluoro-13-methyl)-12-fluoranyl)methyl)-1H-indol-2-yl)thiazol-5-yl)methanamine: To a mixture of 2-((2-(4-bromo-1-(2,2,2-trifluoroethyl)-1H-indol-2-yl)thiazol-5-yl)methyl)isoindoline-1,3-dione (300 mg, 576.57 µmol, 1 eq) in hydrazine hydrate (5 mL) was added ethanol (5 mL). The mixture was heated and stirred at 80° C. for 1 hr. The reaction mixture was extracted with EA (10 mL×2). The combined organic layers were washed with brine (20 mL), dried over anhydrous sodium sulfate, filtered, and concentrated in vacuo. The residue was purified by preparative-TLC to afford (2-(4-bromo-1-(((difluoro-13-methyl)-12-fluoranyl)methyl)-1H-indol-2-yl)thiazol-5-yl)methanamine (200 mg, 513 µmol, 88.9% yield) as a white solid. LC-MS (ES$^+$, m/z): 389.9.

Preparation of R-substituted N-((2-(4-bromo-1-(2,2,2-trifluoroethyl)-1H-indol-2-yl)thiazol-5-yl)methyl)formamide: To a solution of benzoic acid (46.9 mg, 384.40 µmol, 1.5 eq) in DMF (2 mL) were added TEA (130 mg, 1.28 mmol, 178 µL, 5 eq) and HATU (194.9 mg, 512.5 µmol, 2 eq). Then, (2-(4-bromo-1-(((difluoro-13-methyl)-12-fluoranyl)methyl)-1H-indol-2-yl)thiazol-5-yl)methanamine (100 mg, 256 µmol, 1 eq) was added to the mixture. The mixture was stirred at 25° C. for 10 min. The reaction mixture was extracted with EA (10 mL×2). The combined organic layers were washed with brine (20 mL), dried over anhydrous sodium sulfate, filtered, and concentrated in vacuo. The product was washed with a solution of PE:EA=3:1 (3 mL) and concentrated to afford the desired product (110 mg, crude, 85% yield) as a yellow solid.

Preparation of (+/−)-N-{[2-(4-{[(3R,4S)-3-fluoro-1-methylpiperidin-4-yl]amino}-1-(2,2,2-trifluoroethyl)-1H-indol-2-yl)-1,3-thiazol-5-yl]methyl}benzamide (Compound 91B) and N-[(2-{4-[(1-methylpiperidin-4-yl)amino]-1-(2,2,2-trifluoroethyl)-1H-indol-2-yl}-1,3-thiazol-5-yl)methyl]benzamide (Compound 92B): To a mixture of R-substituted N-((2-(4-bromo-1-(2,2,2-trifluoroethyl)-1H-indol-2-yl)thiazol-5-yl)methyl)formamide (100 mg, 202.30 µmol, 1 eq) and (+/−)-(3S,4R)-3-fluoro-1-methylpiperidin-4-amine (~3 eq) in THF (3 mL) were added t-BuXPhos palladium Generation 3 (~0.1 eq) and t-BuONa (~5 eq) each in one portion under nitrogen. The mixture was stirred at 100° C.

for 30 min. A solution of 2M aqueous EDTA (30 mL) was added to the mixture, and the resulting mixture was stirred for 1 hr. The reaction mixture was extracted with EA (20 mL×2). The combined organic layers were washed with brine (20 mL), dried over anhydrous sodium sulfate, filtered, and concentrated in vacuo. The residue was purified by preparative-TLC to afford the desired compounds as brown solids. (+/−)-N-{[2-(4-{[(3R,4S)-3-fluoro-1-methylpiperidin-4-yl]amino}-1-(2,2,2-trifluoroethyl)-1H-indol-2-yl)-1,3-thiazol-5-yl]methyl}benzamide (Compound 91B), 10.3% yield, LC-MS (ES+, m/z): 546.2; Following the same procedure using 4-amino-1-methylpiperidine, was obtained N-[(2-{4-[(1-methylpiperidin-4-yl)amino]-1-(2,2,2-trifluoroethyl)-1H-indol-2-yl}-1,3-thiazol-5-yl)methyl]benzamide (Compound 92B), 40.6% yield, LC-MS (ES+, m/z): 528.2.

Example 44: Synthesis of (+/−)-N-[(3R,4S)-3-fluoro-1-methylpiperidin-4-yl]-2-(1,3-thiazol-2-yl)-1-(2,2,2-trifluoroethyl)-1H-indol-4-amine (Compound 93B)

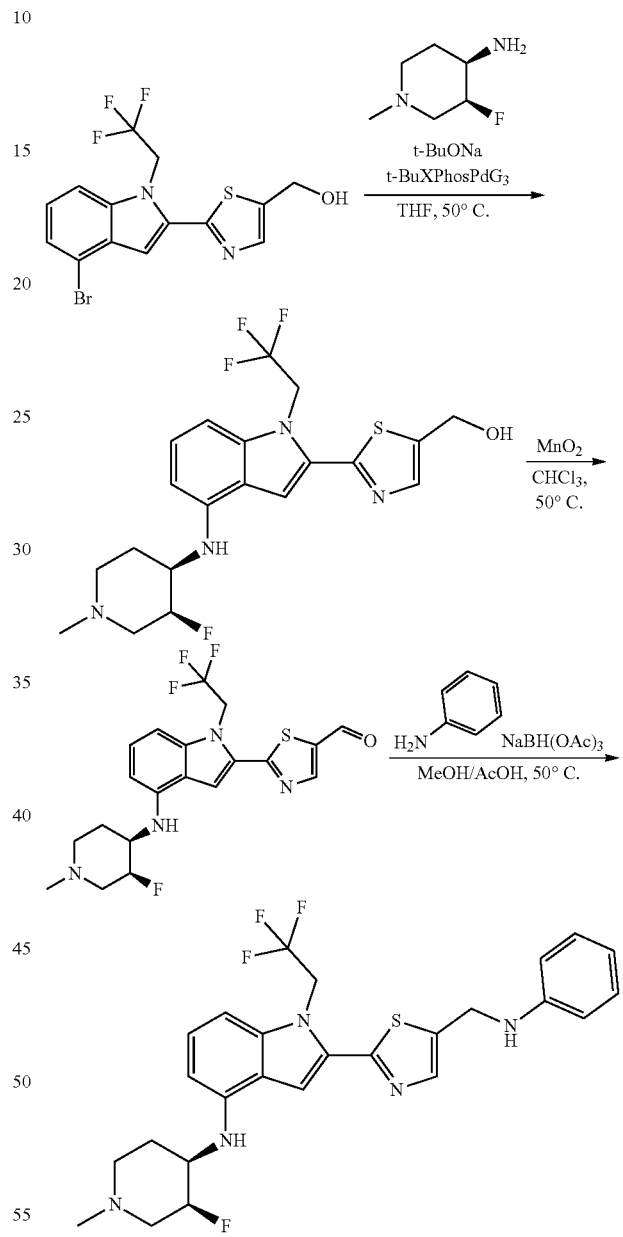

To a mixture of (2-(4-bromo-1-(2,2,2-trifluoroethyl)-1H-indol-2-yl)thiazol-5-yl)methanol (30 mg, 76.69 μmol, 1 eq) and (+/−)-(3S,4R)-3-fluoro-1-methylpiperidin-4-amine (23.83 mg, 180.32 μmol, 2.35 eq, HCl) in THF (2 mL) were added t-BuONa (22.11 mg, 230.06 μmol, 3 eq) and t-BuXPhos Palladium Generation 3 (6.09 mg, 7.67 μmol, 0.1 eq). The resulting reaction mixture was stirred at 100° C. for 1 hr. The mixture was poured into a solution of 2M aqueous EDTA (10 mL) and stirred for 2 hr. The mixture was extracted with DCM (10 mL×2). The organic phase was washed with water (10 mL) and brine (10 mL), dried with sodium sulfate, filtered, and concentrated in vacuo. The residue was purified by preparative-TLC (SiO₂, DCM: MeOH=10:1) to afford (2-(4-(((3S,4R)-3-fluoro-1-methylpiperidin-4-yl)amino)-1-(2,2,2-trifluoroethyl)-1H-indol-2-yl)thiazol-5-yl)methanol as a yellow solid. The byproduct, (+/−)-N-[(3R,4S)-3-fluoro-1-methylpiperidin-4-yl]-2-(1,3-thiazol-2-yl)-1-(2,2,2-trifluoroethyl)-1H-indol-4-amine (Compound 93B) (9.8 mg, 30.6% yield), was also obtained as a yellow solid. LC-MS (ES+, m/z): 413.2.

Example 45: Synthesis of (+/−)-N-[(3R,4S)-3-fluoro-1-methylpiperidin-4-yl]-2-{5-[(phenylamino)methyl]-1,3-thiazol-2-yl}-1-(2,2,2-trifluoroethyl)-1H-indol-4-amine (Compound 98B)

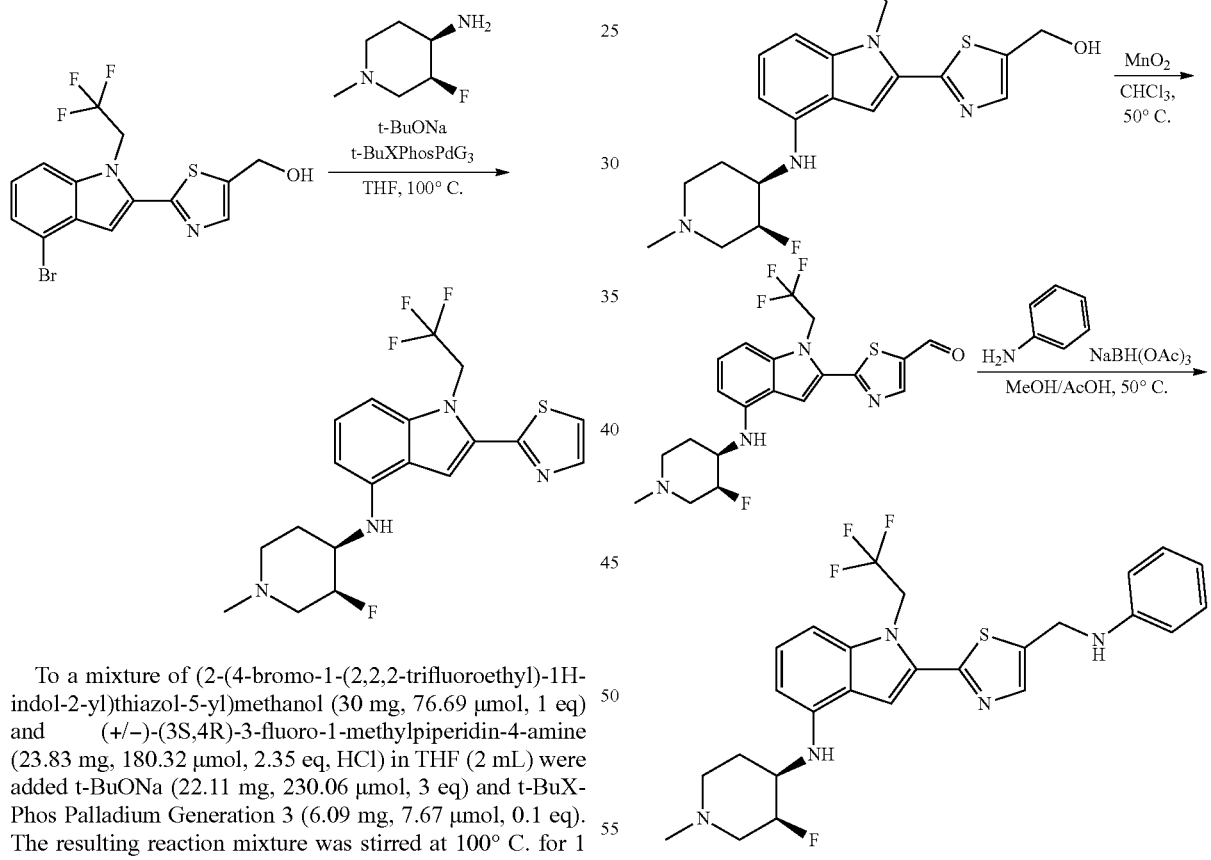

Preparation of (2-(4-(((3S,4R)-3-fluoro-1-methylpiperidin-4-yl)amino)-1-(2,2,2-trifluoroethyl)-1H-indol-2-yl)thiazol-5-yl)methanol: (2-(4-(((3S,4R)-3-fluoro-1-methylpiperidin-4-yl)amino)-1-(2,2,2-trifluoroethyl)-1H-indol-2-yl)thiazol-5-yl)methanol was prepared using the method described in EXAMPLE 44.

Preparation of 2-(4-(((3S,4R)-3-fluoro-1-methylpiperidin-4-yl)amino)-1-(2,2,2-trifluoroethyl)-1H-indol-2-yl)thiazole-5-carbaldehyde: To a solution of (2-(4-(((3S,4R)-3-fluoro-1-methylpiperidin-4-yl)amino)-1-(2,2,2- trifluoroethyl)-1H-indol-2-yl)thiazol-5-yl)methanol (200 mg, 452 µmol, 1 eq) in chloroform (5 mL) was added manganese dioxide (196.5 mg, 2.26 mmol, 5 eq). The reaction mixture was stirred at 50° C. for 1 hr. The mixture was diluted with DCM (10 mL×2), and the organic phase was washed with water (10 mL) and brine (10 mL), dried with sodium sulfate, filtered, and concentrated in vacuo. The residue was purified by preparative-TLC (SiO$_2$, DCM: MeOH=10:1) to afford 2-(4-(((3S,4R)-3-fluoro-1-methylpiperidin-4-yl)amino)-1-(2,2,2-trifluoroethyl)-1H-indol-2-yl) thiazole-5-carbaldehyde (130 mg) as a yellow solid.

Preparation of (+/−)-N-[(3R,4S)-3-fluoro-1-methylpiperidin-4-yl]-2-{5-[(phenylamino)methyl]-1,3-thiazol-2-yl}-1-(2,2,2-trifluoroethyl)-1H-indol-4-amine (Compound 98B): To a mixture of (+/−)-2-(4-(((3S,4R)-3-fluoro-1-methylpiperidin-4-yl)amino)-1-(2,2,2-trifluoroethyl)-1H-indol-2-yl) thiazole-5-carbaldehyde (80 mg, 182 µmol, 1 eq) and aniline (50.7 mg, 544.9 µmol, 49.8 µL, 3 eq) in MeOH (1 mL) acetic acid (3 mL) was added sodium triacetoxyborohydride (115.5 mg, 545 µmol, 3 eq). The reaction mixture was stirred at 50° C. for 1 hr. The mixture was diluted with DCM (10 mL×2), and the organic phase was washed with water (10 mL) and brine (10 mL), dried with sodium sulfate, filtered, and concentrated in vacuo. The residue was purified by preparative-HPLC to afford (+/−)-N-[(3R,4S)-3-fluoro-1-methylpiperidin-4-yl]-2-{5-[(phenylamino)methyl]-1,3-thiazol-2-yl}-1-(2,2,2-trifluoroethyl)-1H-indol-4-amine (Compound 9813) (16.5 mg, 16.9% yield) as a yellow solid. LC-MS (ES$^+$, m/z): 518.1.

Example 46: Synthesis of (+/−)-2-[5-(aminomethyl)-1,3-thiazol-2-yl]-N-[(3R,4S)-3-fluoro-1-methylpiperidin-4-yl]-1-(2,2,2-trifluoroethyl)-1H-indol-4-amine (Compound 96B)

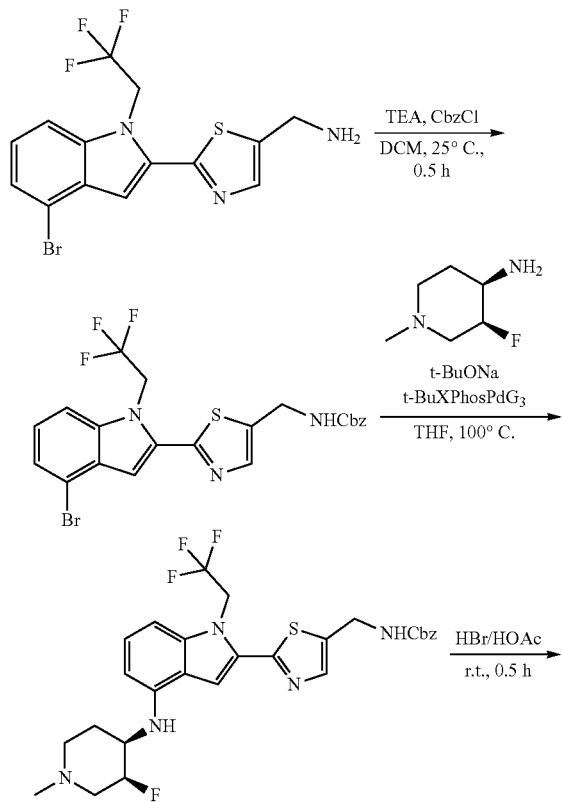

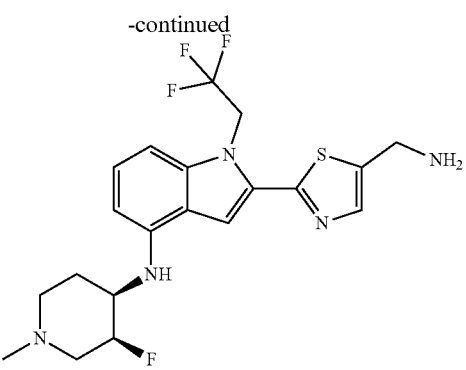

Preparation of benzyl ((2-(4-bromo-1-(2,2,2-trifluoroethyl)-1H-indol-2-yl)thiazol-5-yl)methyl)carbamate: To a solution of (2-(4-bromo-1-(2,2,2-trifluoroethyl)-1H-indol-2-yl)thiazol-5-yl)methanamine (160 mg, 410.02 µmol, 1 eq) in DCM (8 mL) was added TEA (83 mg, 820.05 µmol, 114 µL, 2 eq). Then, CbzCl (83.9 mg, 492 µmol, 70 µL, 1.2 eq) was added, and the resulting mixture was stirred at 25° C. for 0.5 hr. The reaction mixture was poured into water (50 mL), then extracted with DCM (30 mL×3). The combined organic phase was washed with brine (20 mL), dried with anhydrous sodium sulfate, filtered, and concentrated in vacuo. The residue was purified by preparative-TLC (SiO$_2$, PE:EA=2:1, R$_f$=0.65) to afford benzyl ((2-(4-bromo-1-(2,2,2-trifluoroethyl)-1H-indol-2-yl)thiazol-5-yl)methyl)carbamate as a white solid in 65.1% yield. LC-MS (ES$^+$, m/z): 524.1.

Preparation of (+/−)-benzyl ((2-(4-(((3S,4R)-3-fluoro-1-methylpiperidin-4-yl)amino)-1-(2,2,2-trifluoroethyl)-1H-indol-2-yl)thiazol-5-yl)methyl)carbamate: To a mixture of benzyl ((2-(4-bromo-1-(2,2,2-trifluoroethyl)-1H-indol-2-yl)thiazol-5-yl)methyl)carbamate (120 mg, 229 µmol, 1 eq) and (+/−)-(3S,4R)-3-fluoro-1-methylpiperidin-4-amine (150.2 mg, 732 µmol, 3.2 eq, HCl) in THF (4 mL) were added t-BuXPhos Palladium Generation 3 (18.2 mg, 22.9 µmol, 0.1 eq) and t-BuONa (2 M (THF), 572 µL, 5 eq). The reaction mixture was stirred at 100° C. for 1 hr. The reaction mixture was poured into a 2M aqueous EDTA solution (100 mL) and stirred for 2 hr. The reaction mixture was then extracted with EA (50 mL×3). The combined organic phase was washed with brine (30 mL), dried with anhydrous sodium sulfate, filtered, and concentrated in vacuo. The residue was purified by preparative-TLC to give benzyl (+/−)-((2-(4-(((3S,4R)-3-fluoro-1-methylpiperidin-4-yl)amino)-1-(2,2,2-trifluoroethyl)-1H-indol-2-yl)thiazol-5-yl)methyl)carbamate (60 mg, 104.2 µmol, 45.1% yield) as a light yellow oil. LC-MS (ES$^+$, m/z): 576.2.

Preparation of (+/−)-2-[5-(aminomethyl)-1,3-thiazol-2-yl]-N-[(3R,4S)-3-fluoro-1-methylpiperidin-4-yl]-1-(2,2,2-trifluoroethyl)-1H-indol-4-amine (Compound 96B): A solution of (+/−)-benzyl ((2-(4-(((3S,4R)-3-fluoro-1-methylpiperidin-4-yl)amino)-1-(2,2,2-trifluoroethyl)-1H-indol-2-yl)thiazol-5-yl)methyl)carbamate (50 mg, 86.86 µmol, 1 eq) in HBr (33% in acetic acid) (2 mL) was stirred at 25° C. for 1 hr. The mixture was poured into MTBE (10 mL) and filtered, and 2M aqueous sodium carbonate (10 mL) (pH-8) was added to the solid. The reaction mixture was extracted with DCM (10 mL×2), and the organic phase was washed with water (10 mL) and brine (10 mL), dried with sodium sulfate, filtered, and concentrated in vacuo. The residue was purified by preparative-HPLC to afford (+/−)-2-[5-(aminomethyl)-1,3-thiazol-2-yl]-N-[(3R,4S)-3-fluoro-1-methylpiperidin-4-yl]-1-(2,2,2-trifluoroethyl)-1H-indol-4-amine (Compound 96B) (21.5 mg, 53.2% yield) as a yellow solid. LC-MS (ES⁻, m/z): 442.1.

Example 47: Synthesis of N-[(2-{4-[(1-methylpiperidin-4-yl)amino]-1-(2,2,2-trifluoroethyl)-1H-indol-2-yl}-1,3-thiazol-5-yl)methyl]cyclopropanecarboxamide (Compound 94B) and (+/−)-N-{[2-(4-{[(3R,4S)-3-fluoro-1-methylpiperidin-4-yl]amino}-1-(2,2,2-trifluoroethyl)-1H-indol-2-yl)-1,3-thiazol-5-yl]methyl}cyclopropanecarboxamide (Compound 95B)

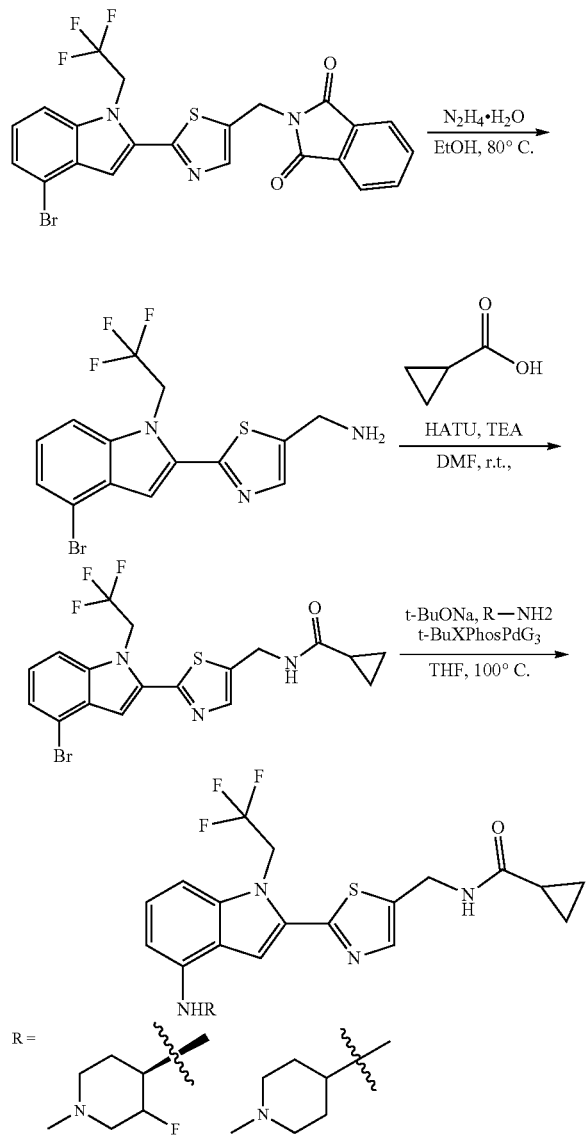

Preparation of (2-(4-bromo-1-(2,2,2-trifluoroethyl)-1H-indol-2-yl)thiazol-5-yl)methanamine: To a solution of 2-((2-(4-bromo-1-(2,2,2-trifluoroethyl)-1H-indol-2-yl)thiazol-5-yl)methyl)isoindoline-1,3-dione (1 g, 1.92 mmol, 1 eq) in ethanol (5 mL) was added hydrazine hydrate (97.7 mmol, 5 mL, 95% purity, 50.9 eq). The mixture was stirred at 80° C. for 1 hr. The mixture was diluted with water (10 mL), extracted with DCM (10 mL×2), and the organic phase was washed with brine (10 mL), dried with anhydrous sodium sulfate, filtered, and concentrated in vacuo to afford (2-(4-bromo-1-(2,2,2-trifluoroethyl)-1H-indol-2-yl)thiazol-5-yl)methanamine (600 mg).

Preparation of N-((2-(4-bromo-1-(2,2,2-trifluoroethyl)-1H-indol-2-yl)thiazol-5-yl)methyl)cyclopropanecarboxamide: To a solution of cyclopropanecarboxylic acid (132.4 mg, 1.54 mmol, 121 µL, 2 eq) in DMF (5 mL) were added HATU (438.48 mg, 1.15 mmol, 1.5 eq), TEA (3.84 mmol, 535 µL, 5 eq), and (2-(4-bromo-1-(2,2,2-trifluoroethyl)-1H-indol-2-yl)thiazol-5-yl)methanamine (300 mg, 769 µmol, 1 eq). The mixture was stirred at 25° C. for 1 hr. The reaction was diluted with water. The mixture was extracted with DCM (10 mL×2), and the organic phase was washed with water (10 mL) and brine (10 mL), dried with anhydrous sodium sulfate, filtered, and concentrated in vacuo to afford N-((2-(4-bromo-1-(2,2,2-trifluoroethyl)-1H-indol-2-yl)thiazol-5-yl)methyl)cyclopropanecarboxamide (300 mg) as a yellow solid.

Preparation of N-[(2-{4-[(1-methylpiperidin-4-yl)amino]-1-(2,2,2-trifluoroethyl)-1H-indol-2-yl}-1,3-thiazol-5-yl)methyl]cyclopropanecarboxamide (Compound 94B) and (+/−)-N-{[2-(4-{[(3R,4S)-3-fluoro-1-methylpiperidin-4-yl]amino}-1-(2,2,2-trifluoroethyl)-1H-indol-2-yl)-1,3-thiazol-5-yl]methyl}cyclopropanecarboxamide (Compound 95B): To a solution of N-((2-(4-bromo-1-(2,2,2-trifluoroethyl)-1H-indol-2-yl)thiazol-5-yl)methyl)cyclopropanecarboxamide (1 eq) and R—NH₂ (5 eq) in THF (2 mL) were added t-BuONa (2 M in THF, 87 µL, 1 eq) and t-BuXPhos Palladium Generation 3 (13.9 mg, 17.5 µmol, 0.1 eq). The mixture was stirred at 100° C. for 1 hr. The mixture was poured into a 2M aqueous EDTA solution (10 mL) and stirred. The mixture was extracted with DCM (10 mL×2), and the organic phase was washed with water (10 mL) and brine (10 mL), dried with anhydrous sodium sulfate, filtered, and concentrated in vacuo. The residue was purified by preparative-TLC (SiO₂, DCM:MeOH=10:1) to afford the desired product. (+/−)-N-{[2-(4-{[(3R,4S)-3-fluoro-1-methylpiperidin-4-yl]amino}-1-(2,2,2-trifluoroethyl)-1H-indol-2-yl)-1,3-thiazol-5-yl]methyl}cyclopropanecarboxamide (Compound 95B), 23.4% yield, LC-MS (ES⁺, m/z): 510.2; and N-[(2-{4-[(1-methylpiperidin-4-yl)amino]-]-(2,2,2-trifluoroethyl)-1H-indol-2-yl}-1,3-thiazol-5-yl)methyl]cyclopropanecarboxamide (Compound 94B), 28.7% yield, LC-MS (ES⁺, m/z): 492.2.

TABLE 6 shows compounds with a 2-(1H-indol-2-yl)thiazole core.

TABLE 6

| Compound No. | Structure | IUPAC | LC-MS (ES+, m/z) |
|---|---|---|---|
| 89B | 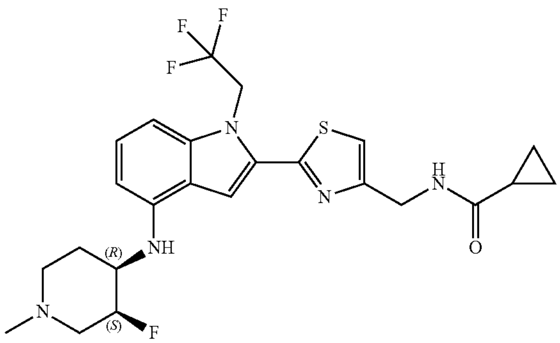 | N-{[2-(4-{[(3S,4R)-3-fluoro-1-methylpiperidin-4-yl]amino}-1-(2,2,2-trifluoroethyl)-1H-indol-2-yl)-1,3-thiazol-4-yl]methyl}cyclopropanecarboxamide | 510.1 |
| 90B | 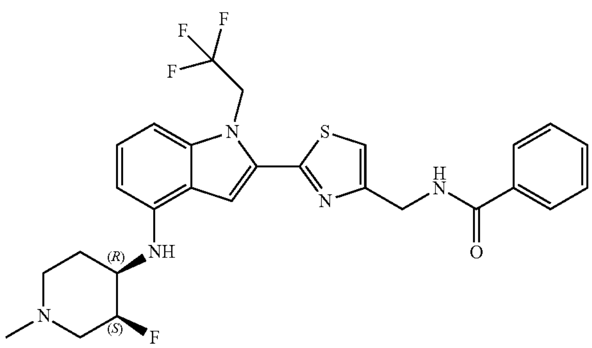 | N-{[2-(4-{[(3S,4R)-3-fluoro-1-methylpiperidin-4-yl]amino}-1-(2,2,2-trifluoroethyl)-1H-indol-2-yl)-1,3-thiazol-4-yl]methyl}benzamide | 546.2 |
| 91B | 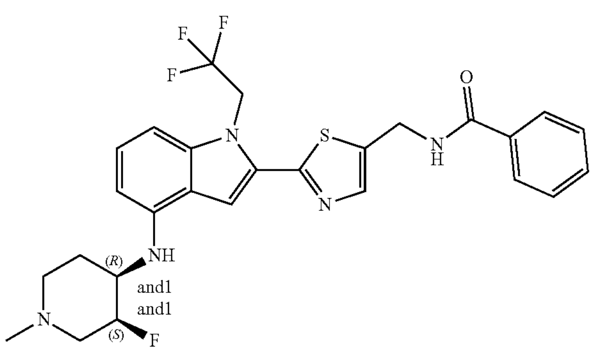 | (+/−)-N-{[2-(4-{[(3R,4S)-3-fluoro-1-methylpiperidin-4-yl]amino}-1-(2,2,2-trifluoroethyl)-1H-indol-2-yl)-1,3-thiazol-5-yl]methyl}benzamide | 546.2 |
| 92B | 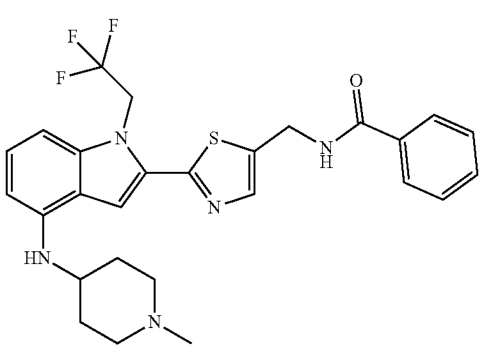 [SMILES: CN1CCC(Nc2cccc3c2cc(-c2ncc(CNC(=O)c4ccccc4)s2)n3CC(F)(F)F)CC1] | N-[(2-{4-[(1-methylpiperidin-4-yl)amino]-1-(2,2,2-trifluoroethyl)-1H-indol-2-yl}-1,3-thiazol-5-yl)methyl]benzamide | 528.2 |

TABLE 6-continued

| Compound No. | Structure | IUPAC | LC-MS (ES+, m/z) |
| --- | --- | --- | --- |
| 93B | 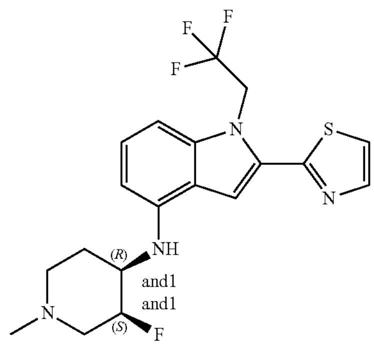 | (+/−)-N-[(3R,4S)-3-fluoro-1-methylpiperidin-4-yl]-2-(1,3-thiazol-2-yl)-1-(2,2,2-trifluoroethyl)-1H-indol-4-amine | 413.2 |
| 94B | 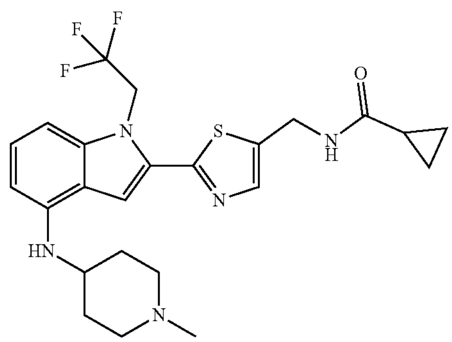 [SMILES: CN1CCC(Nc2cccc3c2cc(-c2ncc(CNC(=O)C4CC4)s2)n3CC(F)(F)F)CC1] | N-[(2-{4-[(1-methylpiperidin-4-yl)amino]-1-(2,2,2-trifluoroethyl)-1H-indol-2-yl}-1,3-thiazol-5-yl)methyl]cyclopropanecarboxamide | 492.2 |
| 95B | 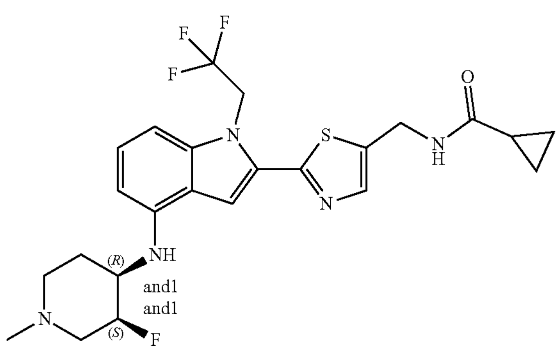 | (+/−)-N-{[2-(4-{[(3R,4S)-3-fluoro-1-methylpiperidin-4-yl]amino}-1-(2,2,2-trifluoroethyl)-1H-indol-2-yl)-1,3-thiazol-5-yl]methyl}cyclopropanecarboxamide | 510.2 |
| 96B | 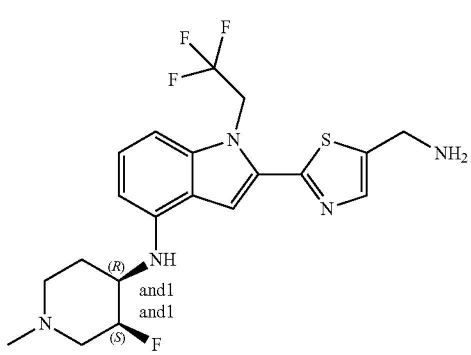 | (+/−)-2-[5-(aminomethyl)-1,3-thiazol-2-yl]-N-[(3R,4S)-3-fluoro-1-methylpiperidin-4-yl]-1-(2,2,2-trifluoroethyl)-1H-indol-4-amine | 442.1 |

TABLE 6-continued

| Compound No. | Structure | IUPAC | LC-MS (ES+, m/z) |
|---|---|---|---|
| 97B | 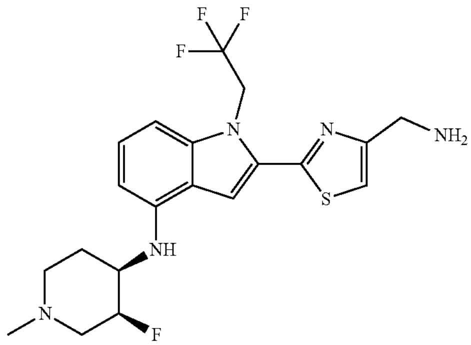 [SMILES: CN1CC[C@@H](Nc2cccc3c2cc(-c2nc(CN)cs2)n3CC(F)(F)F)[C@@H](F)C1] | 2-(4-(aminomethyl)thiazol-2-yl)-N-((3S,4R)-3-fluoro-1-methylpiperidin-4-yl)-1-(2,2,2-trifluoroethyl)-1H-indol-4-amine | 442.1 |
| 98B | 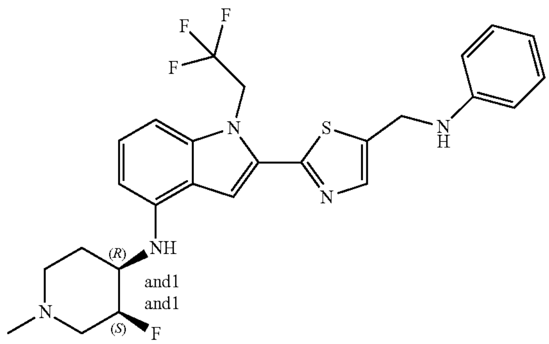 | (+/−)-N-[(3R,4S)-3-fluoro-1-methylpiperidin-4-yl]-2-{5-[(phenylamino)methyl]-1,3-thiazol-2-yl}-1-(2,2,2-trifluoroethyl)-1H-indol-4-amine | 518.1 |
| 99B | 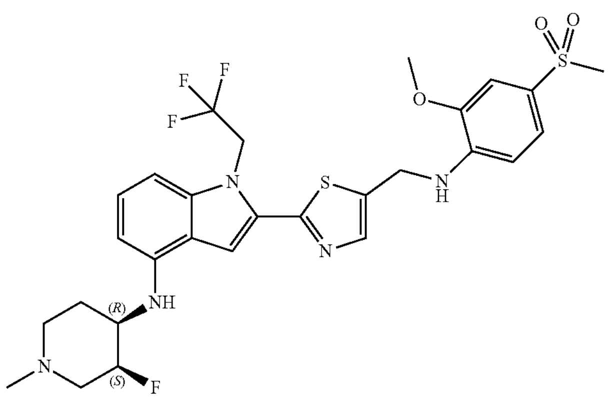 | N-[(3S,4R)-3-fluoro-1-methylpiperidin-4-yl]-2-(5-{[(4-methanesulfonyl-2-methoxyphenyl)amino]methyl}-1,3-thiazol-2-yl)-1-(2,2,2-trifluoroethyl)-1H-indol-4-amine | 626.2 |

Example 48: Synthesis of (+/−)-N-{[5-(4-{[(3R,4S)-3-fluoro-1-methylpiperidin-4-yl]amino}-1-(2,2,2-trifluoroethyl)-1H-indol-2-yl)thiophen-2-yl]methyl}cyclopropanecarboxamide (Compound 103B) and N-((5-(4-(((3S,4R)-3-fluoro-1-methylpiperidin-4-yl)amino)-1-(2,2,2-trifluoroethyl)-1H-indol-2-yl)thiophen-2-yl)methyl)benzamide (Compound 105B)

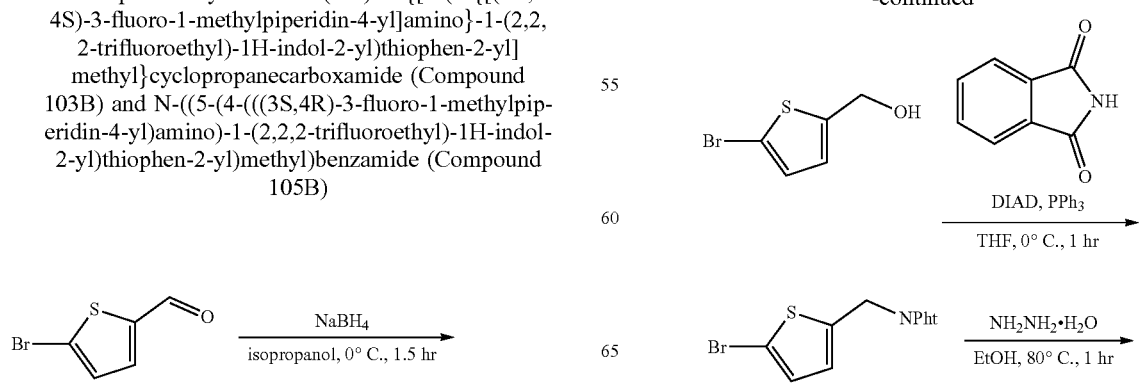

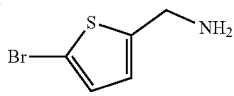

Preparation of (5-bromothiophen-2-yl)methanol: To a solution of 5-bromothiophene-2-carbaldehyde (3 g, 15.70 mmol, 1.86 mL, 1 eq) in isopropanol (30 mL) was added NaBH$_4$ (297.04 mg, 7.85 mmol, 0.5 eq). The mixture was stirred at 0° C. for 1.5 hr. The reaction mixture was quenched with water and extracted with EA (10 mL×2). The combined organic layers were washed with brine (10 mL), dried over anhydrous sodium sulfate, filtered, and concentrated in vacuo. The residue was purified by column chromatography (SiO$_2$, PE/EA=5/1 to 1:1) to afford (5-bromothiophen-2-yl)methanol (2.8 g, 14.5 mmol, 92.4% yield) as a colorless oil.

Preparation of 2-((((5-bromothiophen-2-yl)methyl)-12-azaneyl)carbonyl)benzoic acid: DIAD (4.24 g, 20.98 mmol, 4.08 mL, 1.5 eq) was added to a solution of isoindoline-1,3-dione (3.09 g, 20.98 mmol, 1.5 eq), (5-bromothiophen-2-yl)methanol (2.7 g, 13.99 mmol, 1 eq), and triphenylphosphine (5.50 g, 20.98 mmol, 1.5 eq) in THF (20 mL) at 0° C. The mixture was stirred at 0° C. for 1 hr. Water was added, and the reaction mixture was extracted with EA (10 mL×2). The combined organic layers were washed with brine (10 mL), dried over anhydrous sodium sulfate, filtered, and concentrated in vacuo. The crude residue was purified by column chromatography (SiO$_2$, PE/EA=0:1 to 3:1) to afford 2-((((5-bromothiophen-2-yl)methyl)-12-azaneyl)carbonyl) benzoic acid (3.1 g, 9.62 mmol, 68.8% yield) as a white solid.

Preparation of (5-bromothiophen-2-yl)methanamine: 2-((((5-Bromothiophen-2-yl)methyl)-12-azaneyl)carbonyl) benzoic acid (2.3 g, 7.14 mmol, 1 eq) was added to a mixture of hydrazine hydrate (10 mL) and ethanol (10 mL). The mixture was heated and stirred at 80° C. for 1 hr. The reaction mixture was extracted with EA (10 mL×2). The combined organic layers were washed with brine (10 mL), dried over anhydrous sodium sulfate, filtered, and concentrated in vacuo to afford (5-bromothiophen-2-yl)methanamine (1.3 g, crude) as a yellow oil.

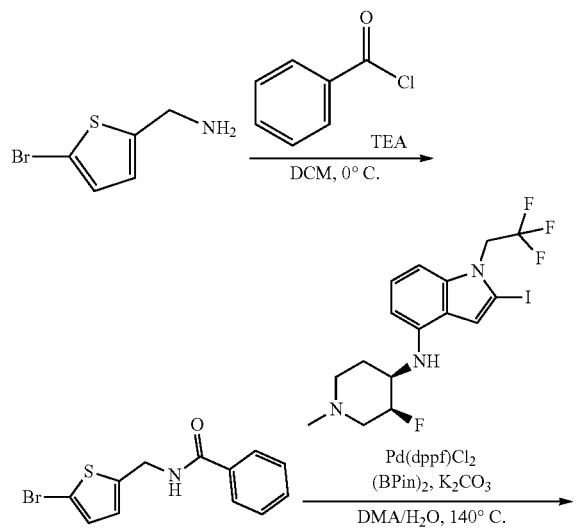

Preparation of N-[(5-bromothiophen-2-yl)methyl]benzamide: To a solution of (5-bromothiophen-2-yl)methanamine (600 mg, 3.12 mmol, 1 eq) in DCM (10 mL) was added TEA (6.25 mmol, 870 μL, 2 eq). Then, benzoyl chloride (6.25 mmol, 726 μL, 2 eq) was added to the mixture. The mixture was stirred at 0° C. for 5 min. Water was added, and the reaction mixture was extracted with EA (10 mL×2). The combined organic layers were washed with brine (10 mL), dried over anhydrous sodium sulfate, filtered, and concentrated in vacuo. The crude residue was purified by preparative-TLC to afford the desired product (550 mg, 1.86 mmol, 59.5% yield) as a white solid. LC-MS (ES$^+$, m/z): 297.9.

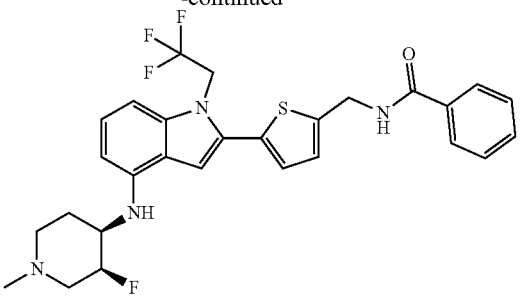

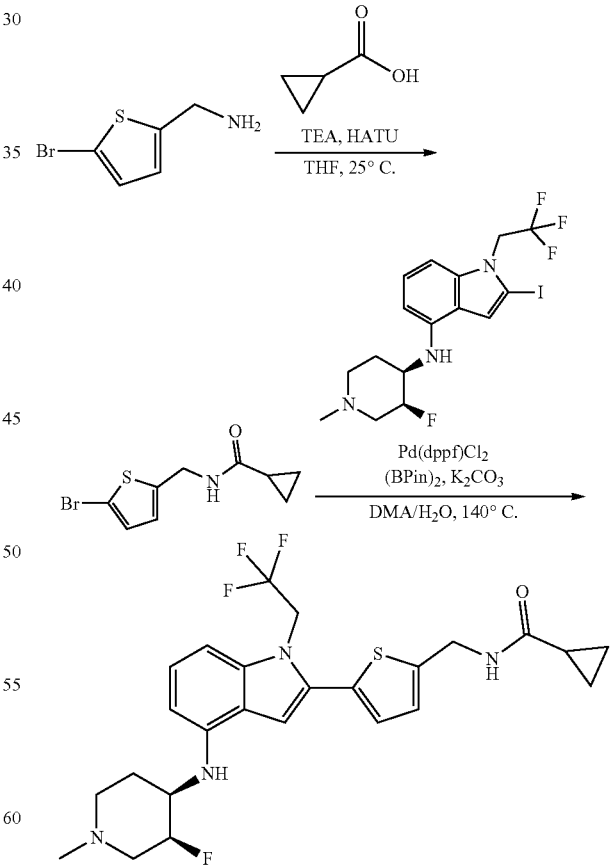

Preparation of N-[(5-bromothiophen-2-yl)methyl]cyclopropanecarboxamide: To a solution of (5-bromothiophen-2-yl)methanamine (500 mg, 2.60 mmol, 1 eq) in DMF (5 mL) were added TEA (5.21 mmol, 725 μL, 2 eq), cyclopropane carboxylic acid (336.2 mg, 3.90 mmol, 308.4 µL, 1.5 eq), and HATU (1.98 g, 5.21 mmol, 2 eq). The mixture was stirred at 25° C. for 1 hr. The residue was poured into water, and extracted with EA (10 mL×2). The combined organic layers were washed with brine (10 mL), dried over anhydrous sodium sulfate, filtered, and concentrated in vacuo. The crude residue was purified by preparative-TLC to afford N-[(5-bromothiophen-2-yl)methyl]cyclopropanecarboxamide (0.6 g, 2.31 mmol, 88.60% yield) as a white solid. LC-MS (ES$^+$, m/z): 259.9.

Preparation of (+/−)-N-{15-(4-{[(3R,4S)-3-fluoro-1-methylpiperidin-4-yl]amino}-1-(2,2,2-trifluoroethyl)-1H-indol-2-yl)thiophen-2-yl]methyl}cyclopropanecarboxamide (Compound 103B) and N-((5-(4-(((3S,4R)-3-fluoro-1-methylpiperidin-4-yl)amino)-1-(2,2,2-trifluoroethyl)-1H-indol-2-yl)thiophen-2-yl)methyl)benzamide (Compound 105B): To a solution of (+/−)-N-((3S,4R)-3-fluoro-1-methylpiperidin-4-yl)-2-iodo-1-(2,2,2-trifluoroethyl)-1H-indol-4-amine (1.1 eq), bis(pinacolato)diboron (1.5 eq), and N-((5-bromothiophen-2-yl)methyl)aniline or N-((5-bromothiophen-2-yl)methyl)cyclopropanamine (1 eq) in DMA (2 mL) and water (0.5 mL) were added potassium carbonate (187 mg, 1.35 mmol, 2 eq) and Pd(dppf)Cl$_2$ (1 eq). The mixture was heated and stirred at 140° C. for 5 min. The reaction was cooled and a 2M aqueous EDTA solution (30 mL) was added to the mixture, and the resulting reaction mixture was stirred for 1 hr. The reaction mixture was diluted with water and extracted with EA (40 mL). The combined organic layers were washed with brine (20 mL), dried over anhydrous sodium sulfate, filtered, and concentrated in vacuo. The crude residue was purified by preparative-TLC to afford the desired product. (+/−)-N-{[5-(4-{[(3R,4S)-3-fluoro-1-methylpiperidin-4-yl]amino}-1-(2,2,2-trifluoroethyl)-1H-indol-2-yl)thiophen-2-yl]methyl}cyclopropanecarboxamide (Compound 103B), LC-MS (ES$^+$, m/z): 509.2; Following the same procedure: N-((5-(4-(((3S,4R)-3-fluoro-1-methylpiperidin-4-yl)amino)-1-(2,2,2-trifluoroethyl)-1H-indol-2-yl)thiophen-2-yl)methyl)benzamide (Compound 105B), LC-MS (ES$^+$, m/z): 545.1.

Example 49: Synthesis of (+/−)-N-((3S,4R)-3-fluoro-1-methylpiperidin-4-yl)-2-(5-(((2-methoxy-4-(methylsulfonyl)phenyl)amino)methyl)thiophen-2-yl)-1-(2,2,2-trifluoroethyl)-1H-indol-4-amine (Compound 106B)

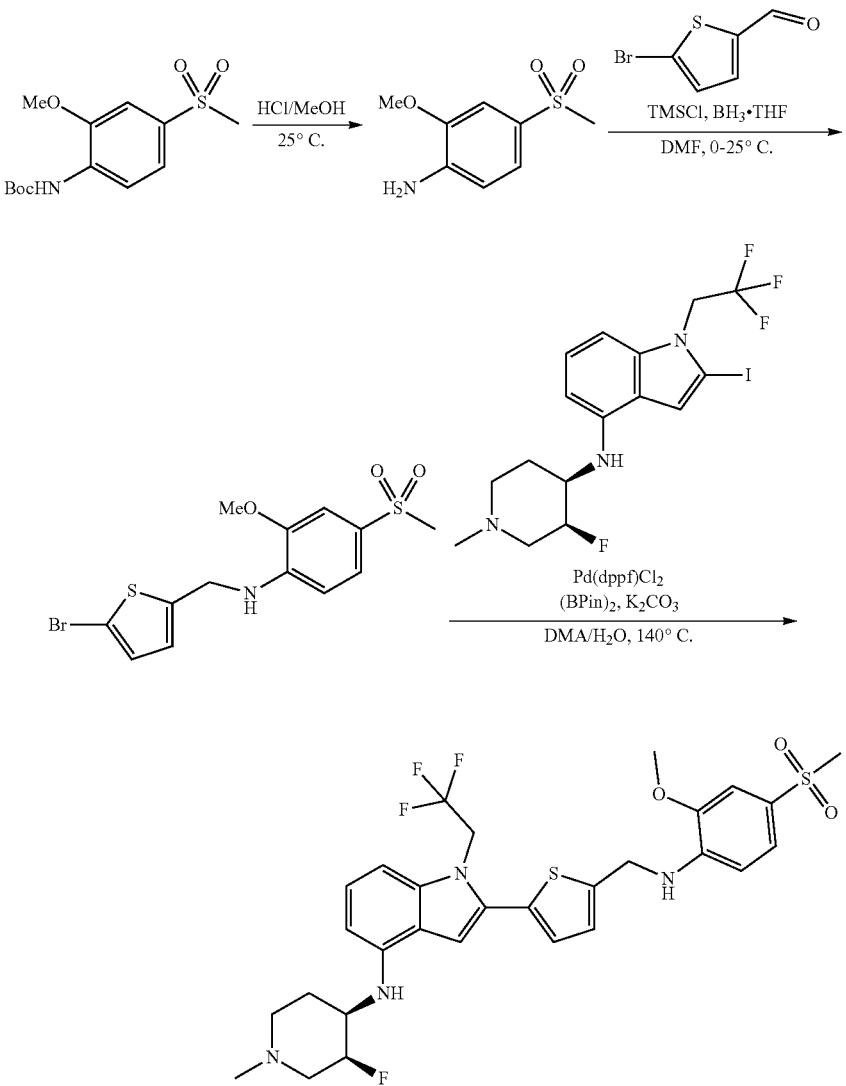

Preparation of 2-methoxy-4-(methylsulfonyl)aniline: Tert-butyl (2-methoxy-4-(methylsulfonyl)phenyl)carbamate (8 g, 26.55 mmol, 1 eq) was added to HCl/MeOH (80 mL; 4 M). The mixture was stirred at 25° C. for 1 hr. Saturated aqueous sodium bicarbonate was added to the mixture until the pH was adjusted to 8-9. The reaction mixture was extracted with EA (30 mL×2). The combined organic layers were washed with brine (10 mL), dried over anhydrous sodium sulfate, filtered, and concentrated in vacuo to afford 2-methoxy-4-(methylsulfonyl)aniline as a white solid. LC-MS (ES$^+$, m/z): 219.0.

Preparation of N-((5-bromothiophen-2-yl)methyl)-2-methoxy-4-(methylsulfonyl)aniline: To a solution of 5-bromothiophene-2-carbaldehyde (700.6 mg, 3.67 mmol, 1.2 eq) and 2-methoxy-4-(methylsulfonyl)aniline (615 mg, 3.06 mmol, 1 eq) in DMF (2 mL) was added chlorotrimethylsilane (7.64 mmol, 970 µL, 2.5 eq). The mixture was stirred at 0° C. for 2 hr. Then borane-THF complex (1 M, 15.3 mL, 5 eq) was added to the reaction mixture under nitrogen. The mixture was stirred at 25° C. for 1 hr. The reaction mixture was diluted with water (20 mL) and extracted with EA (20 mL). The combined organic layers were washed with brine (20 mL), dried over anhydrous sodium sulfate, filtered, and concentrated in vacuo. The crude residue was washed with PE and concentrated to afford N-((5-bromothiophen-2-yl)methyl)-2-methoxy-4-(methylsulfonyl)aniline as a brown solid in 87.0% yield.

Preparation of N-((3S,4R)-3-fluoro-1-methylpiperidin-4-yl)-2-(5-(((2-methoxy-4-(methylsulfonyl)phenyl)amino)methyl)thiophen-2-yl)-1-(2,2,2-trifluoroethyl)-1H-indol-4-amine (Compound 106B): To a solution of N-((3S,4R)-3-fluoro-1-methylpiperidin-4-yl)-2-iodo-1-(2,2,2-trifluoroethyl)-1H-indol-4-amine (266.2 mg, 585 µmol, 1.1 eq), (BPin)$_2$ (202.5 mg, 797 µmol, 1.5 eq), and N-((5-bromothiophen-2-yl)methyl)-2-methoxy-4-(methylsulfonyl)aniline (200 mg, 532 µmol, 1 eq) in DMA (8 mL) and water (2 mL) were added potassium carbonate (146.9 mg, 1.06 mmol, 2 eq) and Pd(dppf)Cl$_2$ (388.9 mg, 52 µmol, 1 eq). The mixture was heated and stirred at 140° C. for 5 min. A 2M aqueous EDTA solution (30 mL) was added, and the reaction mixture was stirred for 1 hr. The reaction mixture was extracted with EA (20 mL×2). The combined organic layers were washed with brine (20 mL), dried over anhydrous sodium sulfate, filtered, and concentrated in vacuo. The residue was purified by preparative-HPLC to obtain N-((3S,4R)-3-fluoro-1-methylpiperidin-4-yl)-2-(5-(((2-methoxy-4-(methylsulfonyl)phenyl)amino)methyl)thiophen-2-yl)-1-(2,2,2-trifluoroethyl)-1H-indol-4-amine (Compound 106B) as a white solid in 18% yield. LC-MS (ES$^+$, m/z): 625.2.

Example 50: Synthesis of N-(1-methylpiperidin-4-yl)-2-(5-(((4-(methylsulfonyl)phenyl)amino)methyl)thiophen-2-yl)-1-(2,2,2-trifluoroethyl)-1H-indol-4-amine (Compound 104B)

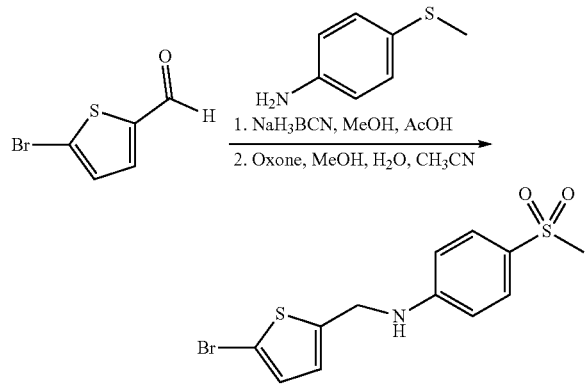

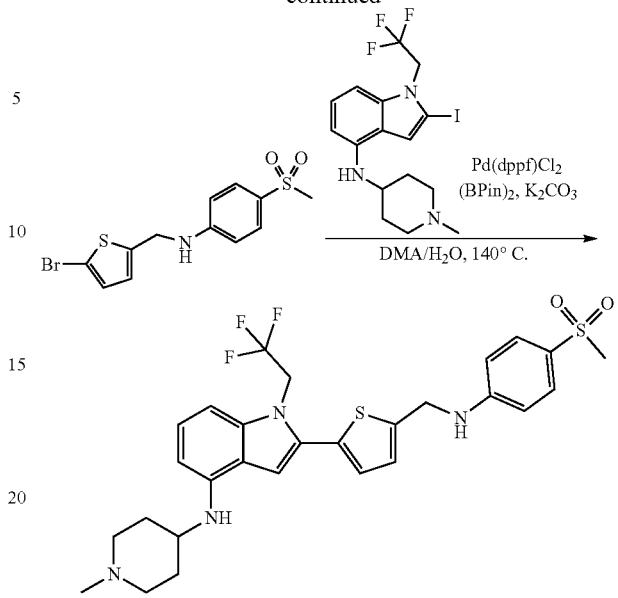

To a solution of 5-bromothiophene-2-carbaldehyde (5 g, 26.17 mmol, 3.11 mL, 1 eq) and 4-(methylthio)aniline (3.64 g, 26.2 mmol, 3.20 mL, 1 eq) in MeOH (50 mL) was added acetic acid (8.70 mmol, 497 µL, 1 eq). The mixture was stirred at 55° C. for 0.5 hr, and sodium cyanoborohydride (9.87 g, 157 mmol, 6 eq) was added. The mixture was stirred at 55° C. for 1.5 hr. The reaction mixture was poured into water (100 mL), and the aqueous phase was extracted with EA (100 mL×3). The combined organic layers were washed with brine (50 mL), dried over anhydrous sodium sulfate, filtered, and concentrated in vacuo. The crude residue was purified by column chromatography (SiO$_2$, PE/EA=0/1 to 20/1) to give the methylthio intermediate (5.3 g, 16.9 mmol, 64% yield) as a red oil. LC-MS (ES$^+$, m/z): 313.9.

To a solution of the methylthio intermediate compound (5.18 g, 13.7 mmol, 1 eq) in MeOH (20 mL), water (20 mL), and acetonitrile (20 mL) was added oxone (12.62 g, 20.5 mmol, 1.5 eq) at 0° C. The mixture was stirred at 0° C. for 1 hr. The reaction mixture was extracted with EA (100 mL×3). The combined organic layers were washed with brine (50 mL), dried over anhydrous sodium sulfate, filtered, and concentrated in vacuo to give N-((5-bromothiophen-2-yl)methyl)-4-(methylsulfonyl)aniline (1.6 g, 4.62 mmol, 33% yield) as a light yellow solid.

To a solution of N-((5-bromothiophen-2-yl)methyl)-4-(methylsulfonyl)aniline (250 mg, 722 µmol, 1 eq), bis(pinacolato)diboron (183.3 mg, 722 µmol, 1 eq), and 2-iodo-N-(1-methylpiperidin-4-yl)-1-(2,2,2-trifluoroethyl)-1H-indol-4-amine (315.7 mg, 722 µmol, 1 eq) in DMA (10 mL) and water (2.5 mL) were added potassium carbonate (200 mg, 1.44 mmol, 2 eq) and Pd(dppf)Cl$_2$ (52.8 mg, 72.2 µmol, 0.1 eq). The mixture was heated and stirred at 140° C. for 10 mins. The reaction mixture was poured into a 2M aqueous EDTA solution (50 mL), and then extracted with EA (20 mL×3). The combined organic layers were washed with brine (20 mL), dried over anhydrous sodium sulfate, filtered, and concentrated in vacuo to give a residue. The residue was purified by preparative-HPLC to afford N-(1-methylpiperidin-4-yl)-2-(5-(((4-(methylsulfonyl)phenyl)amino)methyl)thiophen-2-yl)-1-(2,2,2-trifluoroethyl)-1H-indol-4-amine (Compound 104B) (25.3 mg, 42.5 µmol, 5% yield) as a brown oil. LC-MS (ES$^+$, m/z): 577.1.

Example 51: 1-tert-butyl-N-{[5-(4-{[(3S,4R)-3-fluoro-1-methylpiperidin-4-yl]amino}-1-(2,2,2-trifluoroethyl)-1H-indol-2-yl)thiophen-3-yl]methyl}-1H-pyrrole-3-carboxamide (Compound 283B)

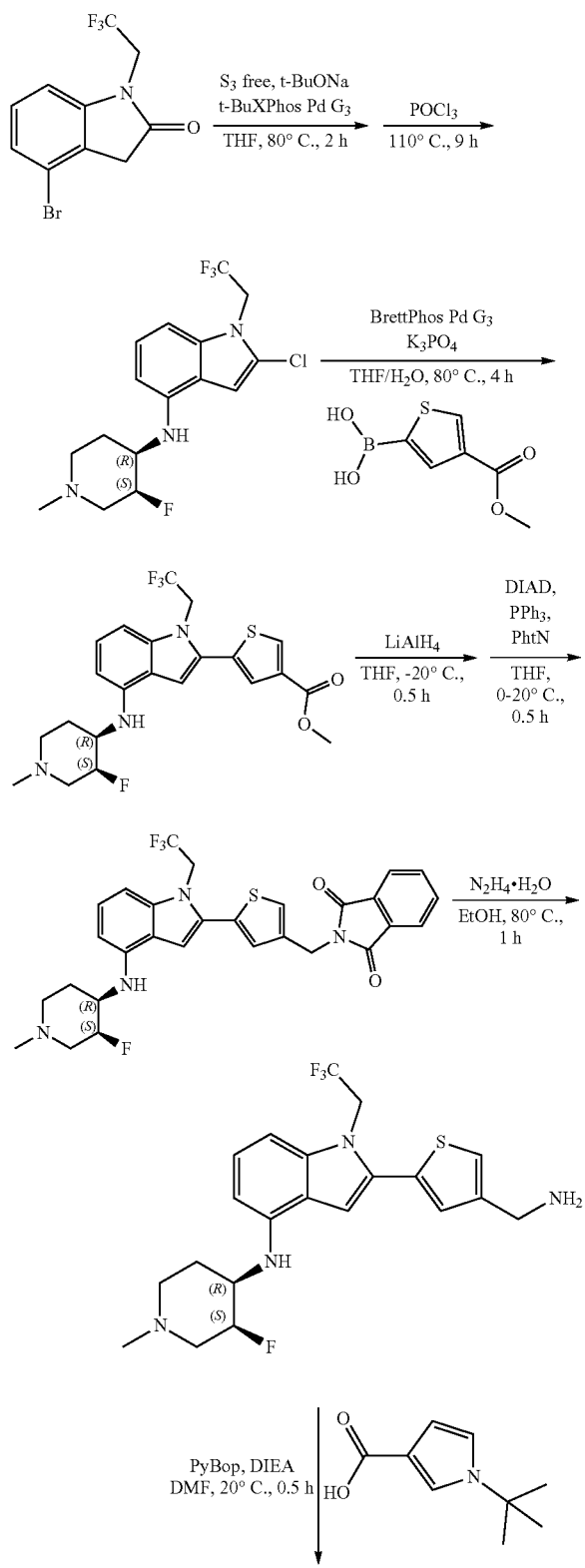

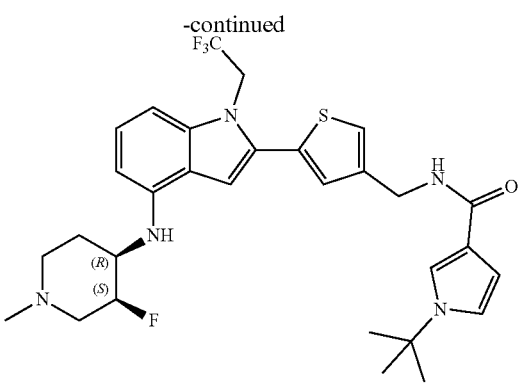

To a solution of 4-bromo-1-(2,2,2-trifluoroethyl)indolin-2-one (2.2 g, 7.48 mmol, 1 eq) and (3S,4R)-3-fluoro-1-methylpiperidin-4-amine (1.11 g, 8.23 mmol, 1.1 eq, free base) in THF (22 mL) were added t-Butyl-XPhos Palladium Generation 3 (1.19 g, 1.50 mmol, 0.2 eq) and sodium t-butoxide (2 M in THF, 7.5 mL, 2 eq). The mixture was stirred at 80° C. for 2 h. The reaction mixture was concentrated in vacuo, and the resulting residue was purified by column chromatography (SiO$_2$, DCM: MeOH=100/1 to 40/1) to provide 4-[[(3S,4R)-3-fluoro-1-methyl-4-piperidyl]amino]-1-(2,2,2-trifluoroethyl)indolin-2-one (1.0 g, 2.64 mmol, 35.2% yield, 91% purity) as a yellow solid. LC-MS (ES$^+$, m/z): 360.2 [(M+H)$^+$].

To a solution of 4-[[(3S,4R)-3-fluoro-1-methyl-4-piperidyl]amino]-1-(2,2,2-trifluoroethyl)indolin-2-one (1 g, 2.66 mmol, 1 eq) was added phosphorus oxychloride (215.2 mmol, 20 mL, 80.8 eq). The mixture was stirred at 110° C. for 9 h. The reaction mixture was concentrated in vacuo to give a residue the was used directly in the next reaction. 2-chloro-N-[(3S,4R)-3-fluoro-1-methyl-4-piperidyl]-1-(2,2,2-trifluoroethyl)indol-4-amine and (2-chloro-1-(2,2,2-trifluoroethyl)-1H-indol-4-yl)((3S,4R)-3-fluoro-1-methylpiperidin-4-yl)phosphoramidic dichloride (1.4 g, crude) was obtained as a yellow solid.

To a mixture of 2-chloro-N-[(3S,4R)-3-fluoro-1-methyl-4-piperidyl]-1-(2,2,2-trifluoroethyl)indol-4-amine and (2-chloro-1-(2,2,2-trifluoroethyl)-1H-indol-4-yl) ((3S,4R)-3-fluoro-1-methylpiperidin-4-yl)phosphoramidic dichloride (0.3 g, 1 eq) were added (4-methoxycarbonyl-2-thienyl) boronic acid (30 mg, 1.65 mmol, 2 eq), THF (15 mL) and water (3.75 mL), followed by BrettPhos Palladium Generation 3 (74.8 mg, 82.5 µmol, 0.1 eq) and potassium phosphate (2.45 g, 11.6 mmol, 14 eq). The mixture was stirred at 80° C. for 4 h. The reaction mixture was quenched by adding sat. EDTA (30 mL) and stirred at 20° C. for 1 h, diluted with water (30 mL), and extracted with eEA/THF (1/1) (5×40 mL). The combined organic layers were washed with brine (2×20 mL), dried over anhydrous Na$_2$SO$_4$, filtered, and concentrated in vacuo to give a residue. The residue was purified by prep-TLC (SiO$_2$, DCM: MeOH=10:1) to afford methyl 5-[4-[[(3S,4R)-3-fluoro-1-methyl-4-piperidyl]amino]-1-(2,2,2-trifluoroethyl)indol-2-yl]thiophene-3-carboxylate (140 mg, 36.2% yield) as a yellow solid. LC-MS (ES$^+$, m/z): 470.2 [(M+H)$^+$].

To a solution of methyl 5-[4-[[(3S,4R)-3-fluoro-1-methyl-4-piperidyl] amino]-1-(2,2,2-trifluoroethyl)indol-2-yl]thiophene-3-carboxylate (140 mg, 298 µmol, le eq) in THF (2 mL) was added lithium aluminum hydride (13.6 mg, 357 µmol, 1.2 eq) at −20° C. The mixture was stirred at −20° C. for 0.5 h. The reaction mixture was quenched by adding water (0.1 mL) at −20° C., then diluted with 15% sodium hydroxide solution (0.1 mL) and EA (20 mL), filtered with diatomite to give a mixture, then extracted with EA (3×30 mL). The combined organic layers were washed with brine (2×10 mL), dried over anhydrous sodium sulfate, filtered, and concentrated in vacuo to give a residue. The residue was purified by prep-TLC (SiO$_2$, DCM: MeOH=10:1) to provide [5-[4-[[(3S,4R)-3-fluoro-1-methyl-4-piperidyl]amino]-1-(2, 2,2-trifluoroethyl)indol-2-yl]-3-thienyl]methanol (110 mg, 83.6% yield) as a yellow solid.

DIAD (374 μmol, 73 μL 1.5 eq) was added to a solution of [5-[4-[[(3S,4R)-3-fluoro-1-methyl-4-piperidyl]amino]-1-(2,2,2-trifluoroethyl)indol-2-yl]-3-thienyl]methanol (110 mg, 249 μmol, 1 eq), isoindoline 1,3-dione (55 mg, 374 μmol, 1.5 eq) and triphenylphosphine (98 mg, 374 μmol, 1.5 eq) in THF (2 mL) at 0° C. The mixture was stirred at 20° C. for 0.5 h. TLC (DCM:MeOH=10:1, R$_f$=0.41) indicated one new spot had formed. The reaction mixture was concentrated in vacuo to give a residue. The residue was purified by prep-TLC (SiO$_2$, DCM: MeOH=10:1) to provide 2-[[5-[4-[[(3S,4R)-3-fluoro-1-methyl-4-piperidyl]amino]-1-(2,2, 2-trifluoroethyl)indol-2-yl]-3-thienyl]methyl]isoindoline-1, 3-dione (90 mg, 63.3% yield) as a yellow solid.

To a solution of 2-[[5-[4-[[(3S,4R)-3-fluoro-1-methyl-4-piperidyl]amino]-1-(2,2,2-trifluoroethyl)indol-2-yl]-3-thienyl]methyl]isoindoline-1,3-dione (90 mg, 158 mol, 1 eq) in ethanol (1 mL) was added hydrazine hydrate (2.2 g, 43.1 mmol, 2.14 mL, 98% purity, 273 eq). The mixture was stirred at 80° C. for 1 h. The reaction mixture was diluted by adding water (10 mL), and extracted with EA (2×10 mL). The combined organic layers were washed with brine (2×10 mL), dried over anhydrous Na$_2$SO$_4$, filtered, and concentrated in vacuo to give the crude product 2-[4-(aminomethyl)-2-thienyl]-N-[(3S,4R)-3-fluoro-1-methyl-4-piperidyl]-1-(2,2,2-trifluoroethyl)indol-4-amine (90 mg, crude) as a yellow solid.

To a solution of 2-[4-(aminomethyl)-2-thienyl]-N-[(3S, 4R)-3-fluoro-1-methyl-4-piperidyl]-1-(2,2,2-trifluoroethyl) indol-4-amine (40 mg, 90.8 μmol, 1 eq), 1-tert-butylpyrrole-3-carboxylic acid (18.2 mg, 109 μmol, 1.2 eq) in DMF (1 mL) were added PYBOP (94.5 mg, 181.6 μmol, 2 eq) and DIEA (908 μmol, 160 μL 10 eq). The mixture was stirred at 20° C. for 0.5 h. LCMS and TLC analysis (DCM: MeOH=10:1, R$_f$=0.48) indicated that one major new spot had formed. The reaction mixture was quenched by adding water (30 mL), and extracted with EA (3×20 mL). The combined organic layers were washed with brine (2×20 mL), dried over anhydrous Na$_2$SO$_4$, filtered, and concentrated in vacuo to give a residue. The residue was purified by prep-TLC (SiO$_2$, DCM: MeOH=10:1), then by prep-HPLC (FA condition: column: Phenomenex Luna C18 75×30 mm×3 um; mobile phase: [water (0.2% FA)-ACN]; B %: 1%-50%, 8 min) to provide the desired product 1-tert-butyl-N-{[5-(4-{[(3S,4R)-3-fluoro-1-methylpiperidin-4-yl] amino}-1-(2,2,2-trifluoroethyl)-1H-indol-2-yl)thiophen-3-yl]methyl}-1H-pyrrole-3-carboxamide (23.9 mg, 22.3% yield) as a yellow solid. LC-MS (ES$^+$, m/z): 590.2 [(M+H)$^+$]. $^1$H NMR (400 MHz, DMSO-d6) δ=8.32-8.20 (m, 1H), 7.54-7.44 (m, 1H), 7.37-7.30 (m, 1H), 7.25-7.17 (m, 1H), 7.13-7.07 (m, 1H), 7.01-6.95 (m, 1H), 6.94-6.90 (m, 1H), 6.85-6.79 (m, 1H), 6.51-6.41 (m, 1H), 6.30-6.18 (m, 1H), 5.60-5.46 (m, 1H), 5.21-5.02 (m, 2H), 4.92-4.72 (m, 1H), 4.51-4.30 (m, 2H), 3.67-3.46 (m, 1H), 3.10-2.96 (m, 1H), 2.84-2.76 (m, 1H), 2.29-2.14 (m, 4H), 2.13-2.03 (m, 1H), 2.00-1.84 (m, 1H), 1.76-1.63 (m, 1H), 1.48-1.43 (m, 9H).

Example 52: Compound 284B: N-[(3S,4R)-3-fluoro-1-methylpiperidin-4-yl]-2-(4-{[(4-methanesulfonylphenyl)amino]methyl}thiophen-2-yl)-1-(2,2, 2-trifluoroethyl)-1H-indol-4-amine To a solution of the previously prepared 2-[4-(aminomethyl)-2-thienyl]-N-[(3S,4R)-3-fluoro-1-methyl-4-piperidyl]-1-(2,2,2-trifluoroethyl)indol-4-amine (70 mg, 159 μmol, 1 eq) and 1-bromo-4-methylsulfonyl-benzene (35.1 mg, 149 μmol, 0.94 eq) in THF (7 mL) were added sodium t-butoxide (2 M in THF, 0.35 mL, 4.4 eq), t-Butyl Xphos (35 mg, 82 μmol, 5.19e-1 eq) and t-butyl-XPhos Palladium Generation 3 (35 mg, 44 μmol, 2.77e-1 eq). The mixture was stirred at 80° C. for 2 h. The reaction mixture was quenched by addition water (30 mL), and then extracted with EA (3×30 mL). The combined organic layers were washed with brine (2×30 mL), dried over anhydrous Na$_2$SO$_4$, filtered, and concentrated in vacuo to give a residue. The residue was purified by prep-TLC (SiO$_2$, DCM: MeOH=10:1), followed by further purification by prep-HPLC (FA condition:column: Phenomenex Luna C18 75×30 mm×3 um; mobile phase: [water (0.2% FA)-ACN]; B %: 1%-50%, 8 min) to provide the desired product N-[(3S,4R)-3-fluoro-1-methylpiperidin-4-yl]-2-(4-{[(4-methanesulfonylphenyl)amino] methyl}thiophen-2-yl)-1-(2,2,2-trifluoroethyl)-1H-indol-4-amine (20.9 mg, 22.1% yield) as a yellow solid. LC-MS (ES$^+$, m/z): 595.1 [(M+H)$^+$]. $^1$H NMR (400 MHz, DMSO-d6) S=7.64-7.52 (m, 2H), 7.49-7.42 (m, 1H), 7.28-7.24 (m, 1H), 7.23-7.18 (m, 1H), 7.17-7.10 (m, 1H), 7.04-6.96 (m, 1H), 6.88-6.82 (m, 1H), 6.80-6.70 (m, 2H), 6.31-6.24 (m, 1H), 5.58-5.48 (m, 1H), 5.18-5.01 (m, 2H), 4.93-4.69 (m, 1H), 4.41-4.33 (m, 2H), 3.63-3.57 (m, 1H), 3.03 (s, 4H), 2.82-2.80 (m, 1H), 2.19 (s, 4H), 2.10 (br s, 1H), 1.98-1.94 (m, 1H), 1.74-1.69 (m, 1H).

TABLE 7 shows compounds with a 2-(thiophen-2-yl)-1H-indole core.

TABLE 7

| Compound No. | Structure | IUPAC | LC-MS (ES$^+$, m/z) |
|---|---|---|---|
| 100B | 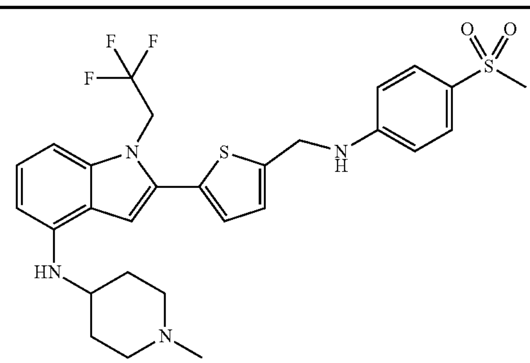 | 2-(5-{[(4-methanesulfonyl-phenyl)amino]methyl}thiophen-2-yl)-N-(1-methylpiperidin-4-yl)-1-(2,2,2-trifluoroethyl)-1H-indol-4-amine | 577.1 |

TABLE 7-continued

| Compound No. | Structure | IUPAC | LC-MS (ES+, m/z) |
|---|---|---|---|
| 101B | 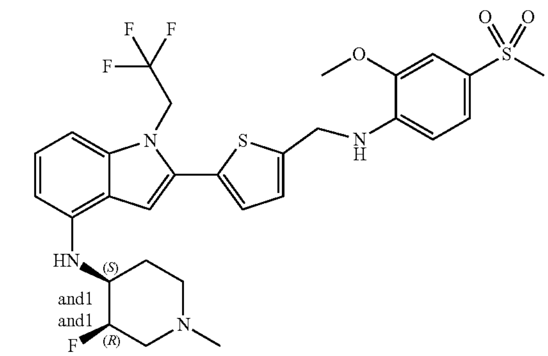 | (+/−)-N-[(3R,4S)-3-fluoro-1-methylpiperidin-4-yl]-2-(5-{[(4-methanesulfonyl-2-methoxyphenyl)amino]methyl}thiophen-2-yl)-1-(2,2,2-trifluoroethyl)-1H-indol-4-amine | 625.2 |
| 102B | 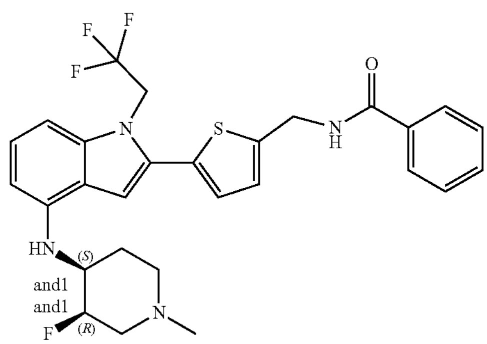 | (+/−)-N-{[5-(4-{[(3R,4S)-3-fluoro-1-methylpiperidin-4-yl]amino}-1-(2,2,2-trifluoroethyl)-1H-indol-2-yl)thiophen-2-yl]methyl}benzamide | 545.1 |
| 103B | 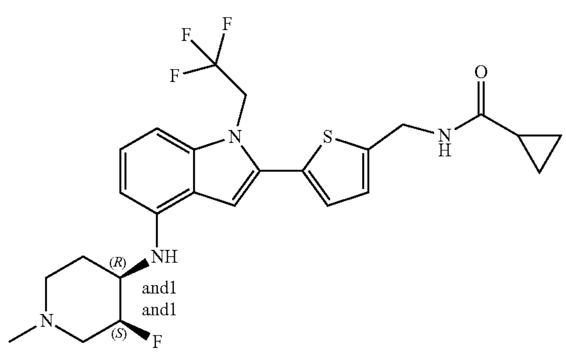 | (+/−)-N-{[5-(4-{[(3R,4S)-3-fluoro-1-methylpiperidin-4-yl]amino}-1-(2,2,2-trifluoroethyl)-1H-indol-2-yl)thiophen-2-yl]methyl}cyclopropanecarboxamide | 509.2 |
| 104B | 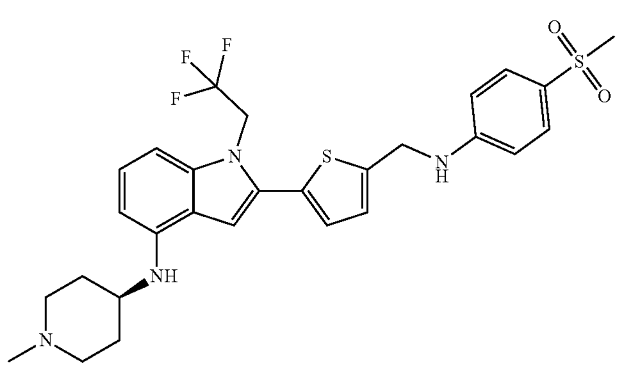 | N-(1-methylpiperidin-4-yl)-2-(5-(((4-(methylsulfonyl)phenyl)amino)methyl)thiophen-2-yl)-1-(2,2,2-trifluoroethyl)-1H-indol-4-amine | 577.1 |

TABLE 7-continued

| Compound No. | Structure | IUPAC | LC-MS (ES+, m/z) |
|---|---|---|---|
| 105B | 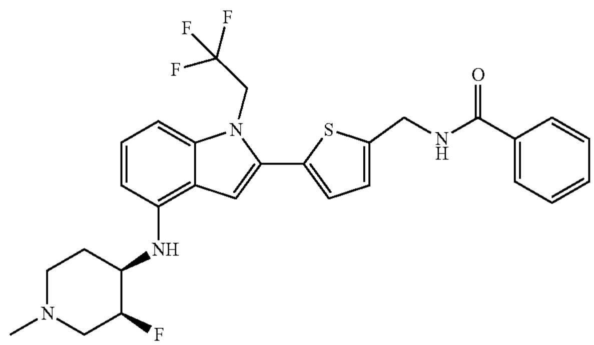 [SMILES: CN1CC[C@@H](Nc2cccc3c2cc(-c2ccc(CNC(=O)c4ccccc4)s2)n3CC(F)(F)F)[C@@H](F)C1] | N-((5-(4-(((3S,4R)-3-fluoro-1-methylpiperidin-4-yl)amino)-1-(2,2,2-trifluoroethyl)-1H-indol-2-yl)thiophen-2-yl)methyl)benzamide | 545.1 |
| 106B | 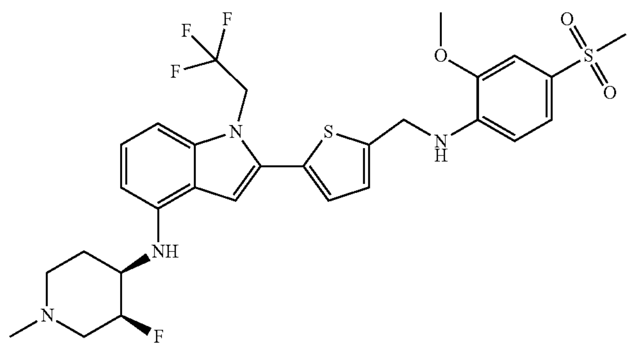 | N-((3S,4R)-3-fluoro-1-methylpiperidin-4-yl)-2-(5-(((2-methoxy-4-(methylsulfonyl)phenyl)amino)methyl)thiophen-2-yl)-1-(2,2,2-trifluoroethyl)-1H-indol-4-amine | 625.2 |
| 283B | 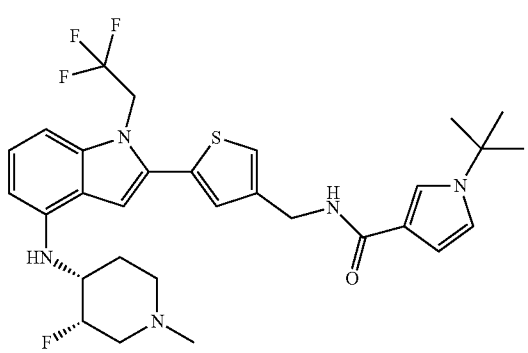 [SMILES: CN1CC[C@@H](Nc2cccc3c2cc(-c2cc(CNC(=O)c4ccn(C(C)(C)C)c4)cs2)n3CC(F)(F)F)[C@@H](F)C1] | 1-tert-butyl-N-{[5-(4-{[(3S,4R)-3-fluoro-1-methylpiperidin-4-yl]amino}-1-(2,2,2-trifluoroethyl)-1H-indol-2-yl}thiophen-3-yl]methyl}-1H-pyrrole-3-carboxamide | 590.2 |
| 284B | 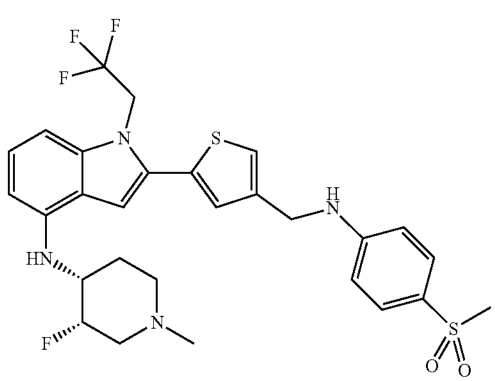 [SMILES: CN1CC[C@@H](Nc2cccc3c2cc(-c2cc(CNc4ccc(S(C)(=O)=O)cc4)cs2)n3CC(F)(F)F)[C@@H](F)C1] | N-[(3S,4R)-3-fluoro-1-methylpiperidin-4-yl]-2-(4-{[(4-methanesulfonylphenyl)amino]methyl}thiophen-2-yl)-1-(2,2,2-trifluoroethyl)-1H-indol-4-amine | 595.1 |

Example 53: General Procedure for Oxadiazole Benzylic Amides and Amines

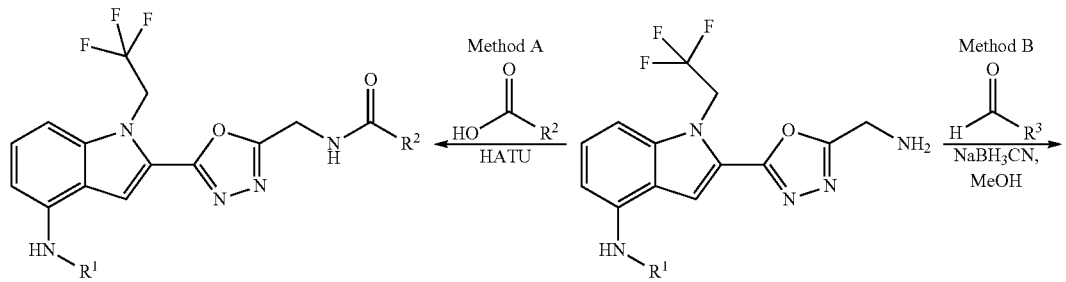

Method A: To a mixture of R¹-substituted 2-(5-(aminomethyl)-1,3,4-oxadiazol-2-yl)-1-(2,2,2-trifluoroethyl)-1H-indol-4-amine (1 eq) and a R²COOH (1 eq) in DMF (1 mL) were added HATU (1.5-2 eq) and TEA (3-5 eq) at 25° C. or 20° C. under nitrogen. The mixture was stirred at 20° C. or 25° C. until LC-MS analysis showed that the reaction was complete. The residue was poured into ice water (w/w=1/1) and stirred for 5 min. The aqueous phase was extracted with EA (×3). The combined organic phase was washed with brine, dried with anhydrous sodium sulfate, filtered, and concentrated in vacuo. The crude product was purified by preparative-HPLC to afford the desired amide product.

Method B: To a mixture of R¹-substituted 2-(5-(aminomethyl)-1,3,4-oxadiazol-2-yl)-1-(2,2,2-trifluoroethyl)-1H-indol-4-amine (1 eq) and R³-aldehyde (0.5 eq) in MeOH (2 mL) were added acetic acid (2 eq) and sodium cyanoborohydride (17.68 mg, 281.4 µmol, 3 eq) in one portion at 50° C. under nitrogen. The mixture was stirred at 50° C. for 1 h. The residue was poured into ice water (w/w=1/1) (50 mL) and stirred for 5 min. The aqueous phase was extracted with EA (20 mL×3). The combined organic phase was washed with brine (20 mL×3), dried with anhydrous sodium sulfate, filtered, and concentrated in vacuo. The crude product was purified by preparative-HPLC to afford the desired product.

(+/−)-N-{5-(4-{[(3R,4S)-3-fluoro-1-methylpiperidin-4-yl]amino}-1-(2,2,2-trifluoroethyl)-1H-indol-2-yl)-1,3,4-oxadiazol-2-yl]methyl}benzamide (Compound 118B) was synthesized using Method A as described above. Yield 25%. LC-MS (M+H⁺)=531.2.

(+/−)-N-{5-(4-{[(3R, 4S)-3-fluoro-1-methylpiperidin-4-yl]amino}-1-(2,2,2-trifluoroethyl)-1H-indol-2-yl)-1,3,4-oxadiazol-2-yl]methyl}thiophene-2-carboxamide (Compound 120B) was synthesized using Method A as described above. Yield 5%. LC-MS (M+H⁺)=537.1.

Example 54: Synthesis of 2-(5-(amino(cyclohexyl)methyl)-1,3,4-oxadiazol-2-yl)-N-(1-methylpiperidin-4-yl)-1-(2,2,2-trifluoroethyl)-1H-indol-4-amine (Compound 107B) and 2-(5-(amino(tetrahydro-2H-pyran-4-yl)methyl)-1,3,4-oxadiazol-2-yl)-N-(1-methylpiperidin-4-yl)-1-(2,2,2-trifluoroethyl)-1H-indol-4-amine (Compound 109B)

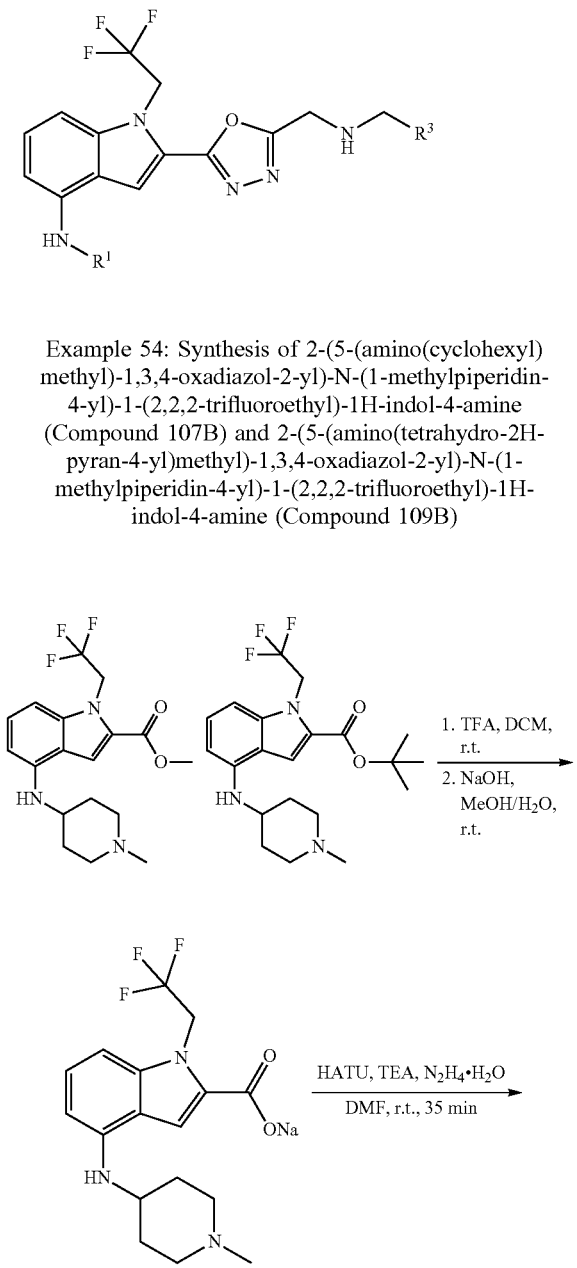

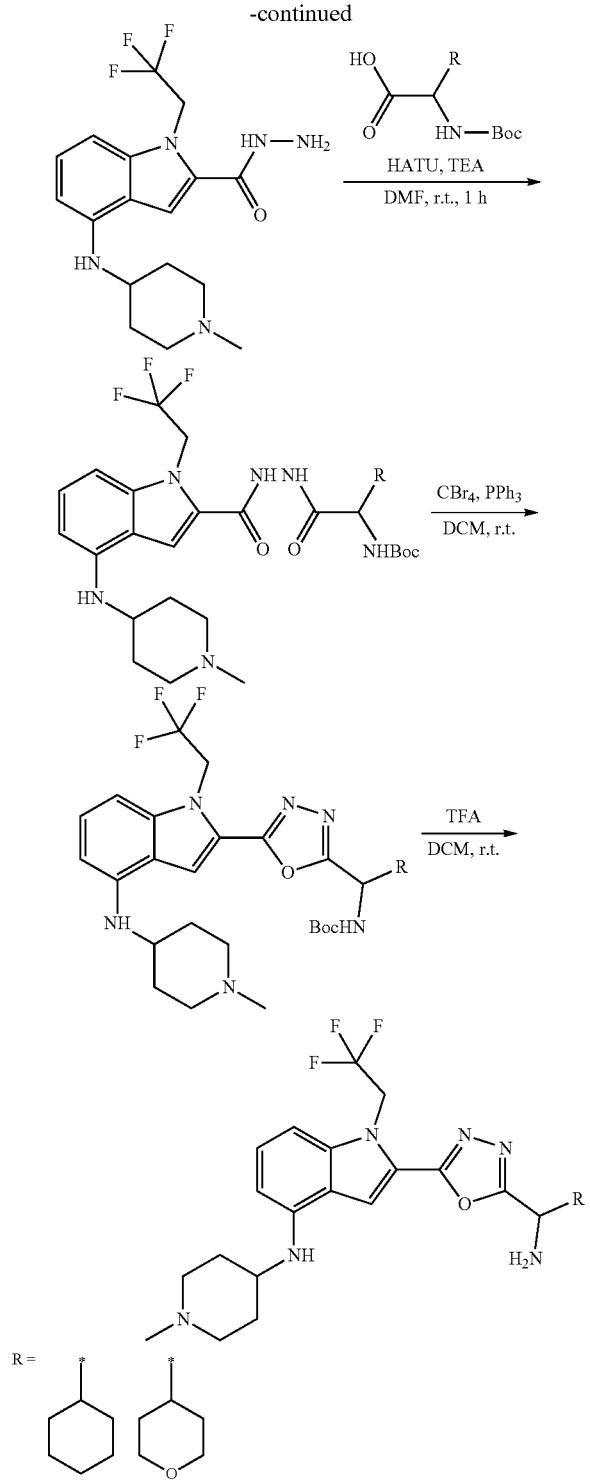

Preparation of sodium 4-((1-methylpiperidin-4-yl)amino)-1-(2,2,2-trifluoroethyl)-1H-indole-2-carboxylate: A solution of methyl 4-((1-methylpiperidin-4-yl)amino)-1-(2,2,2-trifluoroethyl)-1H-indole-2-carboxylate (1 g, 2.71 mmol, 1 eq) and tert-butyl 4-((1-methylpiperidin-4-yl)amino)-1-(2,2,2-trifluoroethyl)-1H-indole-2-carboxylate (1.11 g, 2.71 mmol, 1 eq) in DCM (10 mL) was prepared. To the solution, TFA (135.1 mmol, 10 mL, 49.9 eq) was added in one portion at 25° C. under a nitrogen atmosphere. The resulting mixture was stirred at 25° C. for 60 min, and MeOH (10 mL), water (2 mL), and sodium hydroxide (108.29 mg, 2.71 mmol, 1 eq) were added to the reaction mixture. The resulting mixture was stirred at 25° C. for 11 hours. Completion of the reaction was confirmed using TLC. The reaction mixture was filtered, and concentrated in vacuo to afford sodium 4-((1-methylpiperidin-4-yl)amino)-1-(2,2,2-trifluoroethyl)-1H-indole-2-carboxylate.

Preparation of 4-((1-methylpiperidin-4-yl)amino)-1-(2,2,2-trifluoroethyl)-1H-indole-2-carbohydrazide: To a solution of sodium 4-((1-methylpiperidin-4-yl)amino)-1-(2,2,2-trifluoroethyl)-1H-indole-2-carboxylate (2 g, 5.30 mmol, 1 eq) in DMF (20 mL) were added HATU (4.03 g, 10.60 mmol, 2 eq) and TEA (2.68 g, 26.50 mmol, 3.69 mL, 5 eq). The mixture was stirred at 25° C. for 5 min. hydrazine hydrate (10.60 mmol, 526 μL, 2 eq) was added to the mixture, and the resulting solution was stirred at 25° C. for 30 min. Completion of the reaction was confirmed using TLC analysis. The reaction mixture was poured into water (200 mL), and the aqueous phase was extracted with EA (100 mL×3). The combined organic phase was washed with brine (100 mL×3), dried with anhydrous sodium sulfate, filtered, and concentrated in vacuo. The residue was purified by column chromatography to afford 4-((1-methylpiperidin-4-yl)amino)-1-(2,2,2-trifluoroethyl)-1H-indole-2-carbohydrazide in 61.3% yield. LC-MS (ES$^+$, m/z): 370.2.

Preparation of R-substituted tert-butyl (2-(2-(4-((1-methylpiperidin-4-yl)amino)-1-(2,2,2-trifluoroethyl)-1H-indole-2-carbonyl)hydrazinyl)-2-oxoethyl)carbamate: To a solution of 4-((1-methylpiperidin-4-yl)amino)-1-(2,2,2-trifluoroethyl)-1H-indole-2-carbohydrazide (278.65 mg, 1.08 mmol, 2 eq) in DMF (3 mL) were added HATU (411.75 mg, 1.08 mmol, 2 eq) and TEA (2.71 mmol, 377 μL, 5 eq) in one portion at 20° C. under a nitrogen atmosphere. The reaction mixture was stirred at 20° C. for 10 min, and R-substituted (tert-butoxycarbonyl)glycine (200 mg, 541 μmol, 1 eq) was added to the mixture. The resulting mixture was stirred at 20° C. for 50 min. Completion of the reaction was confirmed using TLC analysis. The reaction mixture was poured into ice water (w/w=1/1) (30 mL), and the aqueous phase was extracted with EA (10 mL×3). The combined organic phase was washed with brine (10 mL×3), dried with anhydrous sodium sulfate, filtered, and concentrated in vacuo. The residue was purified using preparative-TLC to afford the desired R-substituted tert-butyl (2-(2-(4-((1-methylpiperidin-4-yl)amino)-1-(2,2,2-trifluoroethyl)-1H-indole-2-carbonyl)hydrazinyl)-2-oxoethyl)carbamate in 75.9% yield.

Preparation of R-substituted tert-butyl ((5-(4-((1-methylpiperidin-4-yl)amino)-1-(2,2,2-trifluoroethyl)-1H-indol-2-yl)-1,3,4-oxadiazol-2-yl)methyl)carbamate: To a solution of R-substituted tert-butyl (2-(2-(4-((1-methylpiperidin-4-yl)amino)-1-(2,2,2-trifluoroethyl)-1H-indole-2-carbonyl)hydrazinyl)-2-oxoethyl)carbamate (200 mg, 328.57 μmol, 1 eq) in DCM (1 mL) were added carbon tetrabromide (217.9 mg, 657.1 μmol, 2 eq) and triphenylphosphine (172.4 mg, 657.1 μmol, 2 eq) in one portion at 20° C. under a nitrogen atmosphere. The reaction mixture was stirred at 20° C. for 2 hr. Completion of the reaction was confirmed using TLC analysis. The reaction mixture was poured into ice water (w/w=1/1) (30 mL), and the aqueous phase was extracted with EA (10 mL×3). The combined organic phase was washed with brine, dried with anhydrous sodium sulfate, filtered, and concentrated in vacuo. The crude material was purified using preparative-TLC to afford the desired R-substituted tert-butyl ((5-(4-((1-methylpiperidin-4-yl)amino)-1-(2,2,2-trifluoroethyl)-1H-indol-2-yl)-1,3,4-oxadiazol-2-yl)methyl)carbamate product in 51.5% yield.

Preparation of 2-(5-(amino(cyclohexyl)methyl)-1,3,4-oxadiazol-2-yl)-N-(1-methylpiperidin-4-yl)-1-(2,2,2-trifluoroethyl)-1H-indol-4-amine (Compound 107B) and 2-(5-(amino(tetrahydro-2H-pyran-4-yl)methyl)-1,3,4-oxadiazol-2-yl)-N-(1-methylpiperidin-4-yl)-1-(2,2,2-trifluoroethyl)-1H-indol-4-amine (Compound 109B): To a mixture of R-substituted tert-butyl ((5-(4-((1-methylpiperidin-4-yl)amino)-1-(2,2,2-trifluoroethyl)-1H-indol-2-yl)-1,3,4-oxadiazol-2-yl)methyl)carbamate (100 mg, 169 μmol, 1 eq) in DCM (0.5 mL) was added TFA (6.75 mmol, 0.5 mL, 39.9 eq) in one portion at 20° C. under a nitrogen atmosphere. The mixture was stirred at 20° C. for 30 min, and completion of the reaction was confirmed using LC-MS analysis. The residue was poured into an aqueous solution of sodium bicarbonate to adjust the pH of the reaction to 7~8. The aqueous phase was extracted with DCM (20 mL×3). The combined organic phase was washed with brine (20 mL×3), dried with anhydrous sodium sulfate, filtered, and concentrated in vacuo. The crude residue was purified using preparative-HPLC to afford the desired product. 2-(5-(amino(cyclohexyl)methyl)-1,3,4-oxadiazol-2-yl)-N-(1-methylpiperidin-4-yl)-1-(2,2,2-trifluoroethyl)-1H-indol-4-amine (Compound 107B), LC-MS (ES+, m/z): 491.2; 2-(5-(amino(tetrahydro-2H-pyran-4-yl)methyl)-1,3,4-oxadiazol-2-yl)-N-(1-methylpiperidin-4-yl)-1-(2,2,2-trifluoroethyl)-1H-indol-4-amine (Compound 109B), LC-MS (ES+, m/z): 493.3.

Example 55: Synthesis of N-((5-(4-(((3S,4R)-3-fluoro-1-methylpiperidin-4-yl)amino)-1-(2,2,2-trifluoroethyl)-1H-indol-2-yl)-1,3,4-oxadiazol-2-yl)methyl)benzamide (Compound 129B), N-((5-(4-(((3S,4R)-3-fluoro-1-methylpiperidin-4-yl)amino)-1-(2,2,2-trifluoroethyl)-1H-indol-2-yl)-1,3,4-oxadiazol-2-yl)methyl)thiophene-2-carboxamide (Compound 130B), N-((5-(4-(((3S,4R)-3-fluoro-1-methylpiperidin-4-yl)amino)-1-(2,2,2-trifluoroethyl)-1H-indol-2-yl)-1,3,4-oxadiazol-2-yl)methyl)-2-methoxybenzamide (Compound 131B), N-((5-(4-(((3S,4R)-3-fluoro-1-methylpiperidin-4-yl)amino)-1-(2,2,2-trifluoroethyl)-1H-indol-2-yl)-1,3,4-oxadiazol-2-yl)methyl)-3-methoxybenzamide (Compound 132B), N-((5-(4-(((3S,4R)-3-fluoro-1-methylpiperidin-4-yl)amino)-1-(2,2,2-trifluoroethyl)-1H-indol-2-yl)-1,3,4-oxadiazol-2-yl)methyl)-4-methoxybenzamide (Compound 133B), and 2-(5-(((cyclopropylmethyl)amino)methyl)-1,3,4-oxadiazol-2-yl)-N-((3S,4R)-3-fluoro-1-methylpiperidin-4-yl)-1-(2,2,2-trifluoroethyl)-1H-indol-4-amine (Compound 134B)

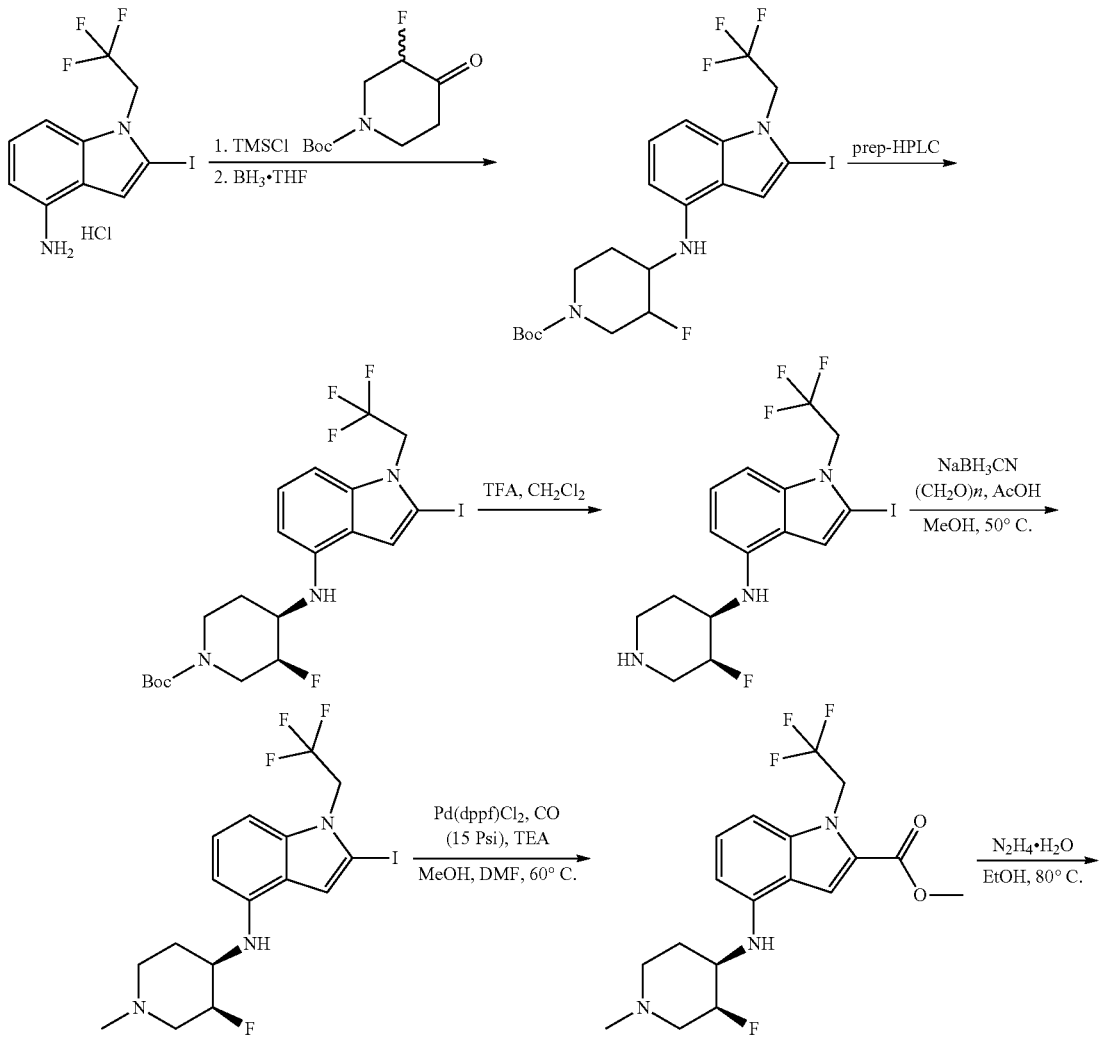

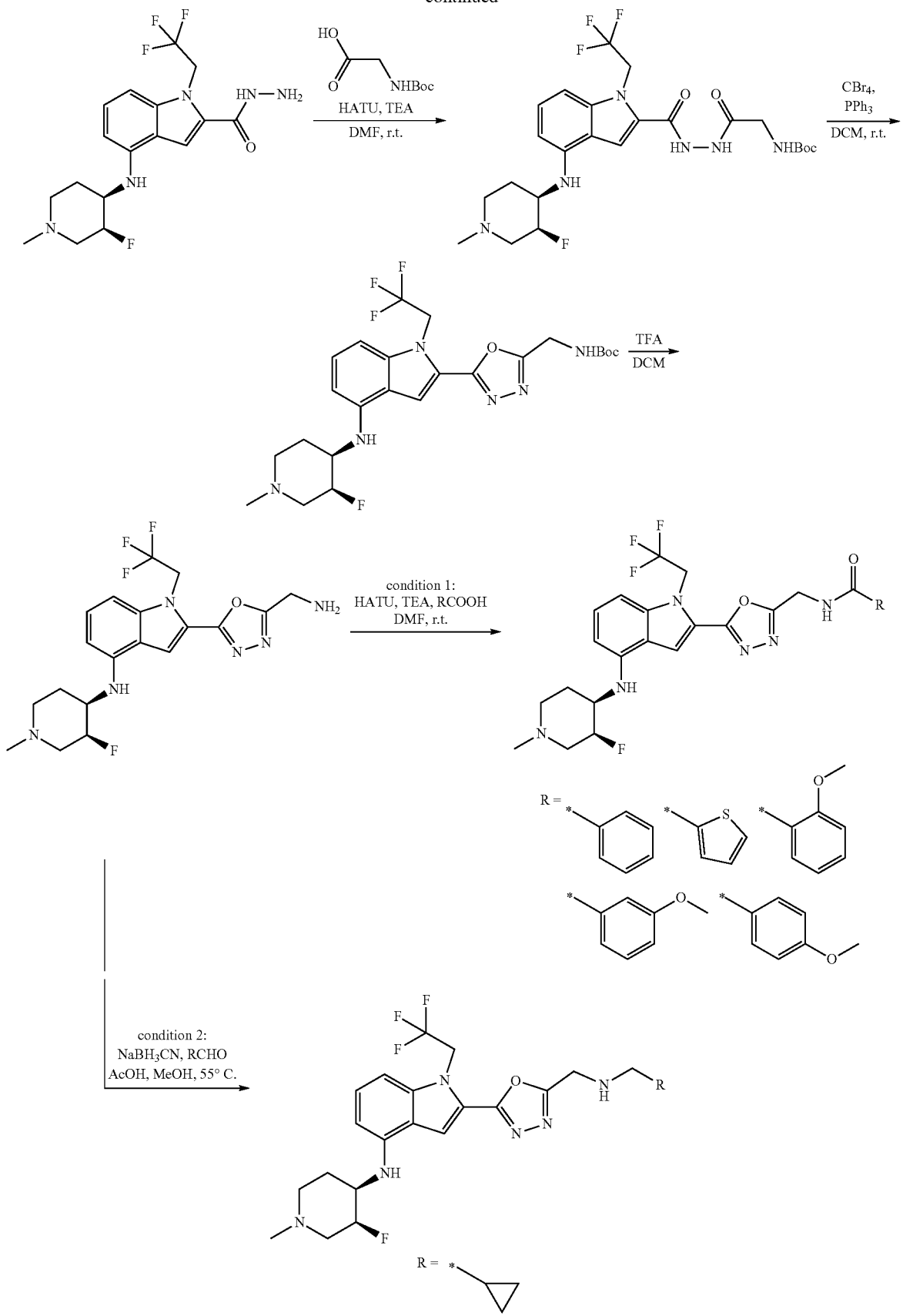

Preparation of (+/−)-tert-butyl (3S,4R)-3-fluoro-4-((2-iodo-1-(2,2,2-trifluoroethyl)-1H-indol-4-yl)amino)piperidine-1-carboxylate: To a solution of 2-iodo-1-(2,2,2-trifluoroethyl)-1H-indol-4-amine hydrogen chloride (10 g, 29.4 mmol, 1 eq) and tert-butyl 3-fluoro-4-oxopiperidine-1-carboxylate (31.9 g, 147 mmol, 5 eq) in DMF (100 mL) was added TMSCl (147 mmol, 18.7 mL, 5 eq) at 0° C. After 1 hr of stirring, $BH_3THF$ (1 M, 294 mL, 10 eq) was added, and the resulting reaction mixture was stirred at 0° C. for 2 hr. Completion of the reaction was confirmed using LC-MS analysis. The mixture was quenched with saturated aqueous sodium carbonate (500 mL).The reaction mixture was extracted with DCM (500 mL×2), the organic phase was washed with brine (500 mL), dried using anhydrous sodium sulfate, and concentrated in vacuo. The crude residue was purified using preparative-HPLC to afford (+/−)-tert-butyl (3S,4R)-3-fluoro-4-((2-iodo-1-(2,2,2-trifluoroethyl)-1H-indol-4-yl)amino)piperidine-1-carboxylate in 44.0% yield. LC-MS ($ES^+$, m/z): 542.0.

Alternative procedure for synthesizing (+/−)-tert-butyl (3S,4R)-3-fluoro-4-((2-iodo-1-(2,2,2-trifluoroethyl)-1H-indol-4-yl)amino)piperidine-1-carboxylate: To a solution of 2-iodo-1-(2,2,2-trifluoroethyl)-1H-indol-4-amine (2 g, 5.88 mmol, 1 eq, HCl) and tert-butyl 3-fluoro-4-oxopiperidine-1-carboxylate (6.39 g, 29.4 mmol, 5 eq) in DCE (20 mL) and acetic acid (60 mL) was added $NaBH(OAc)_3$ (6.23 g, 29.4 mmol, 5 eq) at 0° C. The reaction mixture was heated to 50° C. and stirred at 50° C. for 5 hr. Completion of the reaction was confirmed using LC-MS analysis. The residue was treated with saturated aqueous sodium carbonate to adjust the pH of the residue to 7-8, and the aqueous phase was extracted with EA (500 mL×3). The combined organic phase was washed with brine (500 mL×3), dried with anhydrous sodium sulfate, filtered, and concentrated in vacuo. The crude product was purified using preparative-HPLC to afford (+/−)-tert-butyl (3S,4R)-3-fluoro-4-((2-iodo-1-(2,2,2-trifluoroethyl)-1H-indol-4-yl)amino)piperidine-1-carboxylate in 59.7% yield as a light yellow solid. LC-MS ($ES^+$, m/z): 542.0.

Preparation of (+/−)-N-((3S,4R)-3-fluoropiperidin-4-yl)-2-iodo-1-(2,2,2-trifluoroethyl)-1H-indol-4-amine: To a solution of tert-butyl (3S,4R)-3-fluoro-4-((2-iodo-1-(2,2,2-trifluoroethyl)-1H-indol-4-yl)amino)piperidine-1-carboxylate (7 g, 12.93 mmol, 1 eq) in DCM (10 mL) was added TFA (157.6 mmol, 11.67 mL, 12.19 eq). The reaction mixture was stirred at 25° C. for 1 hr, and completion of the reaction was confirmed using LC-MS analysis. The mixture was quenched with saturated sodium carbonate (20 mL) and extracted with DCM (10 mL×2). The organic phase was washed with water (10 mL) and brine (10 mL), dried using anhydrous sodium sulfate, and concentrated in vacuo to afford (+/−)-N-((3S,4R)-3-fluoropiperidin-4-yl)-2-iodo-1-(2,2,2-trifluoroethyl)-1H-indol-4-amine. LC-MS ($ES^+$, m/z): 441.9.

Preparation of (+/−)-N-((3S,4R)-3-fluoro-1-methylpiperidin-4-yl)-2-iodo-1-(2,2,2-trifluoroethyl)-1H-indol-4-amine: To a solution of (+/−)-N-((3S,4R)-3-fluoropiperidin-4-yl)-2-iodo-1-(2,2,2-trifluoroethyl)-1H-indol-4-amine (1 g, 2.27 mmol, 1 eq) and paraformaldehyde (340.3 mg, 11.33 mmol, 5 eq) in MeOH (10 mL) were added sodium cyanoborohydride (712.1 mg, 11.33 mmol, 5 eq) and acetic acid (2 μmol, 0.1 μL, 0.001 eq). The reaction was stirred at 50° C. for 30 min, and completion of the reaction was confirmed using LC-MS analysis. The mixture was extracted with DCM (100 mL×2). The organic phase was washed with brine (100 mL), dried using anhydrous sodium sulfate, and concentrated in vacuo to afford (+/−)-N-((3S,4R)-3-fluoro-1-methylpiperidin-4-yl)-2-iodo-1-(2,2,2-trifluoroethyl)-1H-indol-4-amine. LC-MS ($ES^+$, m/z): 456.0.

Preparation of (+/−)-methyl 4-(((3S,4R)-3-fluoro-1-methylpiperidin-4-yl)amino)-1-(2,2,2-trifluoroethyl)-1H-indole-2-carboxylate: To a solution of (+/−)-N-((3S,4R)-3-fluoro-1-methylpiperidin-4-yl)-2-iodo-1-(2,2,2-trifluoroethyl)-1H-indol-4-amine (1 g, 10.98 mmol, 1 eq) in MeOH (5 mL) and DMF (5 mL) were added TEA (4.39 mmol, 612 μL, 2 eq) and $Pd(dppf)Cl_2$ (160.7 mg, 219.7 μmol, 0.1 eq). The mixture was stirred at 60° C. for 2 hr under 15 psi of carbon monoxide. Completion of the reaction was confirmed using HPLC analysis. The mixture was extracted with DCM (50 mL×2), and the organic phase was washed with brine (50 mL), dried with anhydrous sodium sulfate, and concentrated in vacuo to afford (+/−)-methyl 4-(((3S,4R)-3-fluoro-1-methylpiperidin-4-yl)amino)-1-(2,2,2-trifluoroethyl)-1H-indole-2-carboxylate (500 mg, crude). LC-MS ($ES^+$, m/z): 388.1.

Preparation of (+/−)-4-(((3S,4R)-3-fluoro-1-methylpiperidin-4-yl)amino)-1-(2,2,2-trifluoroethyl)-1H-indole-2-carbohydrazide: To a solution of methyl 4-(((3S,4R)-3-fluoro-1-methylpiperidin-4-yl)amino)-1-(2,2,2-trifluoroethyl)-1H-indole-2-carboxylate (4 g, 10.3 mmol, 1 eq) in EtOH (20 mL) was added $N_2H_4 \cdot H_2O$ (20 mL). The reaction mixture was stirred at 80° C. for 1 hr, and completion of the reaction was confirmed using LC-MS analysis. The mixture was extracted with DCM (50 mL×2). The organic phase was washed with brine (50 mL), dried with anhydrous sodium sulfate, and concentrated in vacuo. The crude residue was purified by column chromatography ($SiO_2$, PE/EA=1:1) to afford (+/−)-4-(((3S,4R)-3-fluoro-1-methylpiperidin-4-yl)amino)-1-(2,2,2-trifluoroethyl)-1H-indole-2-carbohydrazide in 75% yield (3 g, 7.74 mmol). LC-MS ($ES^+$, m/z): 388.2.

Preparation of (+/−)-tert-butyl (2-(2-(4-(((3S,4R)-3-fluoro-1-methylpiperidin-4-yl)amino)-1-(2,2,2-trifluoroethyl)-1H-indole-2-carbonyl)hydrazinyl)-2-oxoethyl)carbamate: To a mixture of 4-(((3S,4R)-3-fluoro-1-methylpiperidin-4-yl)amino)-1-(2,2,2-trifluoroethyl)-1H-indole-2-carbohydrazide (1 eq) and (N-tert-butoxycarbonyl)glycine (1~2.76 eq) in DMF (30 mL) were added HATU (2~3.5 eq) and TEA (5~6 eq) in one portion at 25° C. under a nitrogen atmosphere. The reaction mixture was stirred at 25° C. for 60 min, and completion of the reaction was confirmed using LC-MS analysis. The residue was poured into ice water (w/w=1/1) and stirred for 5 min. The aqueous phase was extracted three times with EA. The combined organic phase was washed with brine (×3), dried with anhydrous sodium sulfate, filtered, and concentrated in vacuo. The crude residue was purified by silica gel chromatography to afford (+/−)-tert-butyl (2-(2-(4-(((3S,4R)-3-fluoro-1-methylpiperidin-4-yl)amino)-1-(2,2,2-trifluoroethyl)-1H-indole-2-carbonyl)hydrazinyl)-2-oxoethyl)carbamate in 95% yield. LC-MS ($ES^+$, m/z): 545.3

Preparation of (+/−)-tert-butyl ((5-(4-(((3S,4R)-3-fluoro-1-methylpiperidin-4-yl)amino)-1-(2,2,2-trifluoroethyl)-1H-indol-2-yl)-1,3,4-oxadiazol-2-yl)methyl)carbamate: To a mixture of (+/−)-tert-butyl (2-(2-(4-(((3S,4R)-3-fluoro-1-methylpiperidin-4-yl)amino)-1-(2,2,2-trifluoroethyl)-1H-indole-2-carbonyl)hydrazinyl)-2-oxoethyl)carbamate (1 eq) in DCM were added $CBr_4$ (2 eq) and $PPh_3$ (2 eq) at 0° C. under a nitrogen atmosphere. The mixture was stirred at 0° C., and completion of the reaction was monitored using LC-MS analysis. The residue was poured into ice water (w/w=1/1) (100 mL) and stirred for 5 min. The aqueous phase was extracted with DCM (30 mL×3), and the combined organic phase was washed with brine (30 mL×3), dried with anhydrous sodium sulfate, filtered, and concentrated in vacuo. The residue was purified by silica gel chromatography (DCM:MeOH=40:1 to 10:1) or preparative-TLC to afford (+/−)-tert-butyl ((5-(4-(((3S,4R)-3-fluoro-1-methylpiperidin-4-yl)amino)-1-(2,2,2-trifluoroethyl)-1H-indol-2-yl)-1,3,4-oxadiazol-2-yl)methyl)carbamate in 62.1% yield. LC-MS (ES$^+$, m/z): 527.3.

Preparation of (+/−)-2-(5-(aminomethyl)-1,3,4-oxadiazol-2-yl)-N-((3S,4R)-3-fluoro-1-methylpiperidin-4-yl)-1-(2,2,2-trifluoroethyl)-1H-indol-4-amine: To a solution of (+/−)-tert-butyl ((5-(4-(((3S,4R)-3-fluoro-1-methylpiperidin-4-yl)amino)-1-(2,2,2-trifluoroethyl)-1H-indol-2-yl)-1,3,4-oxadiazol-2-yl)methyl)carbamate (30 mg, 57 μmol, 1 eq) in DCM (1 mL) was added TFA (13.5 mmol, 1 mL, 237 eq) at 20° C. under a nitrogen atmosphere. The mixture was stirred at 20° C. for 30 min, and completion of the reaction was confirmed using LC-MS analysis. The residue was poured into saturated sodium bicarbonate solution (aq) to adjust the pH of the residue to 7-8. The aqueous phase was extracted with DCM (10 mL×3), and the combined organic phase was washed with brine (10 mL×3), dried with anhydrous sodium sulfate, filtered, and concentrated in vacuo. The crude residue was purified by preparative-HPLC to afford (+/−)-2-(5-(aminomethyl)-1,3,4-oxadiazol-2-yl)-N-((3S,4R)-3-fluoro-1-methylpiperidin-4-yl)-1-(2,2,2-trifluoroethyl)-1H-indol-4-amine. LC-MS (ES$^+$, m/z): 427.1.

General procedure for R-substituted 2-(5-(aminomethyl)-1,3,4-oxadiazol-2-yl)-N-((3S,4R)-3-fluoro-1-methylpiperidin-4-yl)-1-(2,2,2-trifluoroethyl)-1H-indol-4-amine; condition 1: To a mixture of (+/−)-2-(5-(aminomethyl)-1,3,4-oxadiazol-2-yl)-N-((3S,4R)-3-fluoro-1-methylpiperidin-4-yl)-1-(2,2,2-trifluoroethyl)-1H-indol-4-amine (1 eq) and RCOOH (1 eq) in DMF (1 mL) were added HATU (1.5~2 eq) and TEA (3~5 eq) in one portion at 25° C. or 20° C. under a nitrogen atmosphere. The mixture was stirred at 20° C. or 25° C., and completion of the reaction was confirmed using LC-MS analysis. The residue was poured into ice water (w/w=1/1) and stirred for 5 min. The aqueous phase was extracted with EA (×3). The combined organic phase was washed with brine (×3), dried with anhydrous sodium sulfate, filtered, and concentrated in vacuo. The crude residue was purified by preparative-HPLC to afford the desired R-substituted (+/−)-2-(5-(aminomethyl)-1,3,4-oxadiazol-2-yl)-N-((3S,4R)-3-fluoro-1-methylpiperidin-4-yl)-1-(2,2,2-trifluoroethyl)-1H-indol-4-amine compound.

General procedure for R-substituted 2-(5-(aminomethyl)-1,3,4-oxadiazol-2-yl)-N-((3S,4R)-3-fluoro-1-methylpiperidin-4-yl)-1-(2,2,2-trifluoroethyl)-1H-indol-4-amine; condition 2: To a solution of 2-(5-(aminomethyl)-1,3,4-oxadiazol-2-yl)-N-((3S,4R)-3-fluoro-1-methylpiperidin-4-yl)-1-(2,2,2-trifluoroethyl)-1H-indol-4-amine (1 eq) and RCHO (0.5 eq) in MeOH (2 mL) were added acetic acid (2 eq) and sodium cyanoborohydride (17.68 mg, 281.42 μmol, 3 eq) in one portion at 50° C. under a nitrogen atmosphere. The mixture was stirred at 50° C. for 1 h, and completion of the reaction was confirmed using LC-MS analysis. The residue was poured into ice water (w/w=1/1) (50 mL) and stirred for 5 min. The aqueous phase was extracted with EA (20 mL×3). The combined organic phase was washed with brine (20 mL×3), dried with anhydrous sodium sulfate, filtered, and concentrated in vacuo. The crude product was purified by preparative-HPLC to afford desired R-substituted (+/−)-2-(5-(aminomethyl)-1,3,4-oxadiazol-2-yl)-N-((3S,4R)-3-fluoro-1-methylpiperidin-4-yl)-1-(2,2,2-trifluoroethyl)-1H-indol-4-amine compound.

(+/−)-N-((5-(4-(((3S,4R)-3-fluoro-1-methylpiperidin-4-yl)amino)-1-(2,2,2-trifluoroethyl)-1H-indol-2-yl)-1,3,4-oxadiazol-2-yl)methyl)benzamide (Compound 129B), LC-MS (ES$^+$, m/z): 531.2; (+/−)-N-((5-(4-(((3S,4R)-3-fluoro-1-methylpiperidin-4-yl)amino)-1-(2,2,2-trifluoroethyl)-1H-indol-2-yl)-1,3,4-oxadiazol-2-yl)methyl)thiophene-2-carboxamide (Compound 130B), LC-MS (ES$^+$, m/z): 537.1; (+/−)-N-((5-(4-(((3S,4R)-3-fluoro-1-methylpiperidin-4-yl)amino)-1-(2,2,2-trifluoroethyl)-1H-indol-2-yl)-1,3,4-oxadiazol-2-yl)methyl)-2-methoxybenzamide (Compound 131B), LC-MS (ES$^+$, m/z): 561.2; (+/−)-N-((5-(4-(((3S,4R)-3-fluoro-1-methylpiperidin-4-yl)amino)-1-(2,2,2-trifluoroethyl)-1H-indol-2-yl)-1,3,4-oxadiazol-2-yl)methyl)-3-methoxybenzamide (Compound 132B), LC-MS (ES$^+$, m/z): 561.2; (+/−)-N-((5-(4-(((3S,4R)-3-fluoro-1-methylpiperidin-4-yl)amino)-1-(2,2,2-trifluoroethyl)-1H-indol-2-yl)-1,3,4-oxadiazol-2-yl)methyl)-4-methoxybenzamide (Compound 133B), LC-MS (ES$^+$, m/z): 561.2; (+/−)-2-(5-(((cyclopropylmethyl)amino)methyl)-1,3,4-oxadiazol-2-yl)-N-((3S,4R)-3-fluoro-1-methylpiperidin-4-yl)-1-(2,2,2-trifluoroethyl)-1H-indol-4-anine (Compound 134B), LC-MS (ES$^+$, m/z): 481.1.

Example 56: Synthesis of (+/−)-N-[(3R,4R)-3-fluoro-1-methylpiperidin-4-yl]-2-(5-{1[(4-methanesulfonyl-2-methoxyphenyl)amino]methyl}-1,3,4-oxadiazol-2-yl)-1-(2,2,2-trifluoroethyl)-1H-indol-4-amine (Compound 123B)

To a solution of (9H-fluoren-9-yl)methyl (2-(2-(4-(((3S,4S)-3-fluoro-1-methylpiperidin-4-yl)amino)-1-(2,2,2-trifluoroethyl)-1H-indole-2-carbonyl)hydrazineyl)-2-oxoethyl)carbamate (300 mg, 477.22 μmol, 1 eq) in DCM (6 mL) were added triphenylphosphine (250.34 mg, 954.45 μmol, 2 eq) and carbon tetrabromide (316.52 mg, 954.45 μmol, 2 eq) at 0° C. The mixture was stirred at 0° C. for 0.5 hr. The reaction mixture was poured into water (60 mL) and extracted with DCM (30 mL×3). The combined organic phase was washed with brine (20 mL), dried with anhydrous sodium sulfate, filtered, and concentrated in vacuo to provide a residue. The residue was purified by prep-HPLC to give (+/−)-N-[(3R,4R)-3-fluoro-1-methylpiperidin-4-yl]-2-(5-{[(4-methanesulfonyl-2-methoxyphenyl)amino]methyl}-1,3,4-oxadiazol-2-yl)-1-(2,2,2-trifluoroethyl)-1H-indol-4-amine (Compound 123B) (25.8 mg, 42.25 μmol, 8.85% yield) as a white solid.

313

Example 57: Synthesis of (+/−)-N-((3S,4R)-3-fluoro-1-methylpiperidin-4-yl)-2-(5-(((2-methoxy-4-(methylsulfonyl)phenyl)amino)methyl)-1,3,4-oxadiazol-2-yl)-1-(2,2,2-trifluoroethyl)-1H-indol-4-amine (Compound 126B)

314

Preparation of (+/−)-methyl 4-(((3S,4R)-3-fluoro-1-methylpiperidin-4-yl)amino)-1-(2,2,2-trifluoroethyl)-1H-indole-2-carboxylate: To a solution of N-((3S,4R)-3-fluoro-1-methylpiperidin-4-yl)-2-iodo-1-(2,2,2-trifluoroethyl)-1H-indol-4-amine (500 mg, 1.10 mmol, 1 eq) in MeOH (5 mL) and

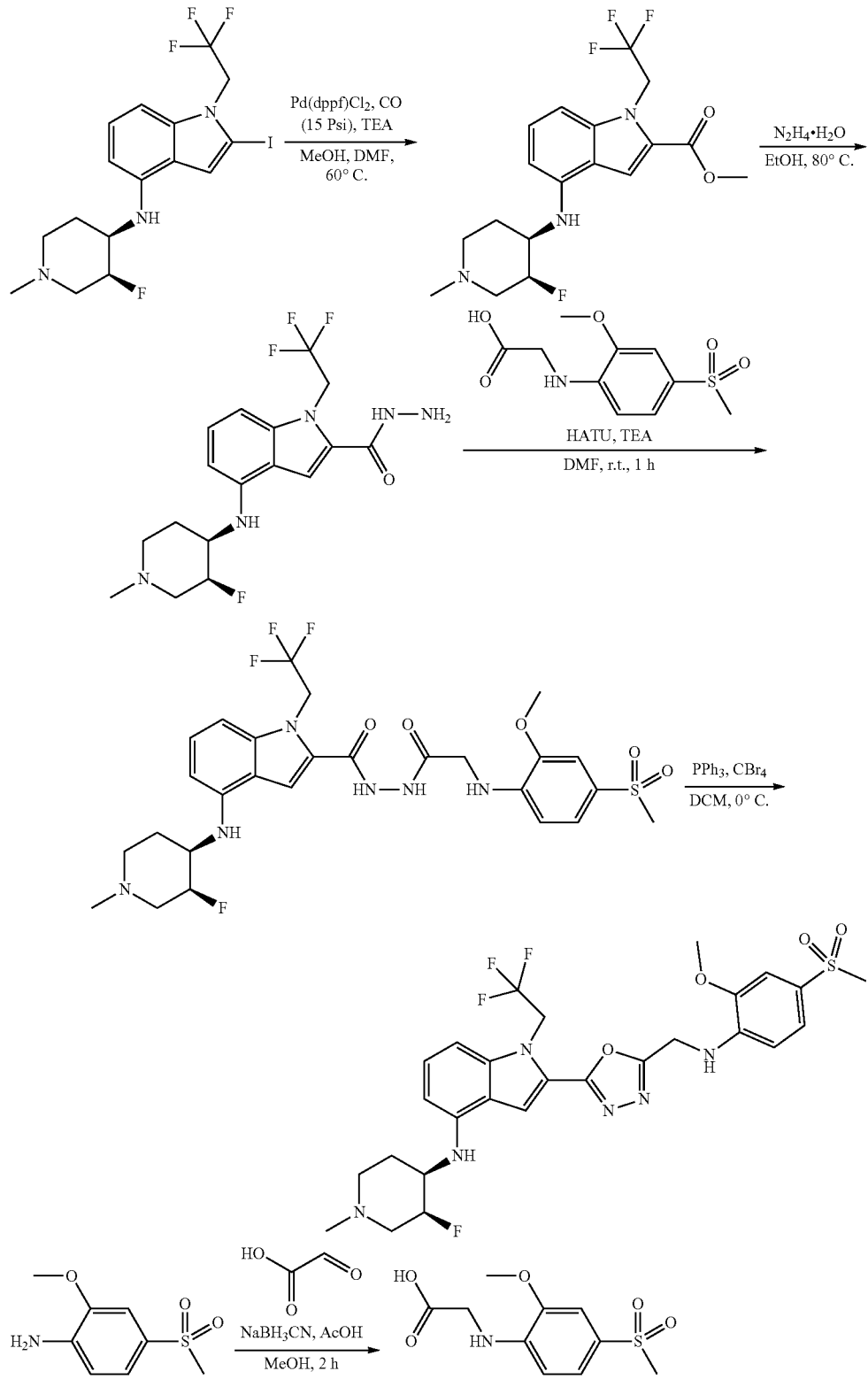

DMF (10 mL) were added TEA (2.20 mmol, 306 µL, 2 eq) and Pd(dppf)Cl₂ (89.7 mg, 110 µmol, 0.1 eq). The resulting mixture was flushed with CO (1.10 mmol, 1 eq) 3 times and stirred at 60° C. for 2 hr under a CO atmosphere. Completion of the reaction was confirmed using LC-MS analysis. The mixture was poured into a 2M aqueous EDTA solution (80 mL) and stirred for 2 h, then extracted with EA (50 mL×3). The combined organic phase was washed with brine (50 mL), dried with anhydrous sodium sulfate, filtered, and concentrated in vacuo to afford (+/−)-methyl 4-(((3S,4R)-3-fluoro-1-methylpiperidin-4-yl)amino)-1-(2,2,2-trifluoroethyl)-1H-indole-2-carboxylate (500 mg, crude) as a brown oil.

Preparation of (+/−)-4-(((3S,4R)-3-fluoro-1-methylpiperidin-4-yl)amino)-1-(2,2,2-trifluoroethyl)-1H-indole-2-carbohydrazide: To a solution of (+/−)-methyl 4-(((3S,4R)-3-fluoro-1-methylpiperidin-4-yl)amino)-1-(2,2,2-trifluoroethyl)-1H-indole-2-carboxylate (1.8 g, 2.79 mmol, 1 eq) in ethanol (10 mL) was added hydrazine hydrate (170.93 mmol, 8.31 mL, 61.3 eq). The resulting mixture was stirred at 80° C. for 1 h, and completion of the reaction was confirmed using TLC analysis. The reaction was poured into water (60 mL) and extracted with EA (30 mL×3), and the combined organic phase was washed with brine (20 mL), dried with anhydrous sodium sulfate, filtered, and concentrated in vacuo. The crude residue was purified by column chromatography (SiO₂, DCM:MeOH=1:0 to 10:1) to afford (+/−)-4-(((3S,4R)-3-fluoro-1-methylpiperidin-4-yl)amino)-1-(2,2,2-trifluoroethyl)-1H-indole-2-carbohydrazide (920 mg, 1.73 mmol, 62.2% yield) as a brown solid. LC-MS (ES⁺, m/z): 388.0

Preparation of N-(2-methoxy-4-(methylsulfonyl)phenyl)glycine: To a solution of 2-methoxy-4-(methylsulfonyl)aniline (1.4 g, 7 mmol, 1 eq) in MeOH (30 mL) were added 2-oxoacetic acid (566.5 mg, 7.65 mmol, 1.1 eq) and acetic acid (4.18 mg, 69.57 µmol, 3.98 µL, 0.01 eq). The reaction mixture was stirred at 25° C. for 2 h, then sodium cyanoborohydride (1.09 g, 17.4 mmol, 2.5 eq) was added, and the resulting mixture was stirred at 25° C. for 1 hr. Completion of the reaction was confirmed by TLC analysis. The reaction mixture was poured into a sodium hydroxide solution (6M, 60 mL), then extracted with EA (30 mL×3). The combined aqueous extracts were acidified at 0° C. to pH=2 with a 4M solution of HCl. The resulting precipitate was filtered and washed with water to afford N-(2-methoxy-4-(methylsulfonyl)phenyl)glycine (1 g, 3.47 mmol, 49.9% yield) as a white solid. LC-MS (ES⁺, m/z): 257.9.

Preparation of (+/−)-4-(((3S,4R)-3-fluoro-1-methylpiperidin-4-yl)amino)-N'-((2-methoxy-4-(methylsulfonyl)phenyl)glycyl)-1-(2,2,2-trifluoroethyl)-1H-indole-2-carbohydrazide: To a solution of N-(2-methoxy-4-(methylsulfonyl)phenyl)glycine (195.4 mg, 753.8 µmol, 1 eq) in DMF (10 mL) were added TEA (3.77 mmol, 524.6 µL, 5 eq) and HATU (573.2 mg, 1.51 mmol, 2 eq). 4-(((3S,4R)-3-Fluoro-1-methylpiperidin-4-yl)amino)-1-(2,2,2-trifluoroethyl)-1H-indole-2-carbohydrazide (400 mg, 754 µmol, 1 eq) was added to the mixture, and the resulting reaction mixture was stirred at 25° C. for 1 hr. Completion of the reaction was confirmed using TLC analysis. The reaction mixture was poured into water (50 mL) and extracted with EA (40 mL×3). The combined organic phase was washed with brine (30 mL), dried with anhydrous sodium sulfate, filtered, and concentrated in vacuo. The crude residue was purified by preparative-TLC (SiO₂, DCM:MeOH=10:1, R_f=0.41) to afford (+/−)-4-(((3S,4R)-3-fluoro-1-methylpiperidin-4-yl)amino)-N'-((2-methoxy-4-(methylsulfonyl)phenyl)glycyl)-1-(2,2,2-trifluoroethyl)-1H-indole-2-carbohydrazide (350 mg, 557 µmol, 73.9% yield) as a brown solid. LC-MS (ES⁺, m/z): 629.1.

Synthesis of (+/−)-N-((3S,4R)-3-fluoro-1-methylpiperidin-4-yl)-2-(5-(((2-methoxy-4-(methylsulfonyl)phenyl)amino)methyl)-1,3,4-oxadiazol-2-yl)-1-(2,2,2-trifluoroethyl)-1H-indol-4-amine (Compound 126B): To a solution of 4-(((3S,4R)-3-fluoro-1-methylpiperidin-4-yl)amino)-N'-((2-methoxy-4-(methylsulfonyl)phenyl)glycyl)-1-(2,2,2-trifluoroethyl)-1H-indole-2-carbohydrazide (300 mg, 477 µmol, 1 eq) in DCM (6 mL) were added triphenylphosphine (250.34 mg, 954.45 µmol, 2 eq) and carbon tetrabromide (316.52 mg, 954.45 µmol, 2 eq) at 0° C. The reaction mixture was stirred at 0° C. for 0.5 hr. Completion of the reaction was confirmed by TLC analysis. The reaction mixture was poured into water (60 mL) and extracted with DCM (30 mL×3). The combined organic phase was washed with brine (20 mL), dried with anhydrous sodium sulfate, filtered, and concentrated in vacuo. The crude residue was purified by preparative-HPLC to afford N-((3S,4R)-3-fluoro-1-methylpiperidin-4-yl)-2-(5-(((2-methoxy-4-(methylsulfonyl)phenyl)amino)methyl)-1,3,4-oxadiazol-2-yl)-1-(2,2,2-trifluoroethyl)-1H-indol-4-amine (Compound 126B) (25.8 mg, 42.3 µmol, 8.9% yield) as a white solid. LC-MS (ES⁺, m/z): 611.2.

Example 58: Synthesis of N-((3S,4R)-3-fluoro-1-methylpiperidin-4-yl)-2-(5-(((3-(methylsulfonyl)phenyl)amino)methyl)-1,3,4-oxadiazol-2-yl)-1-(2,2,2-trifluoroethyl)-1H-indol-4-amine (Compound 125B)

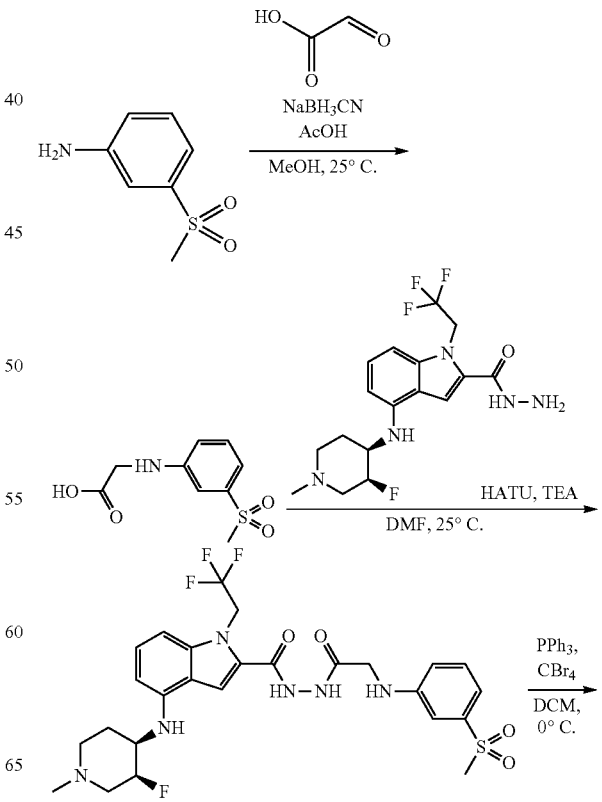

-continued

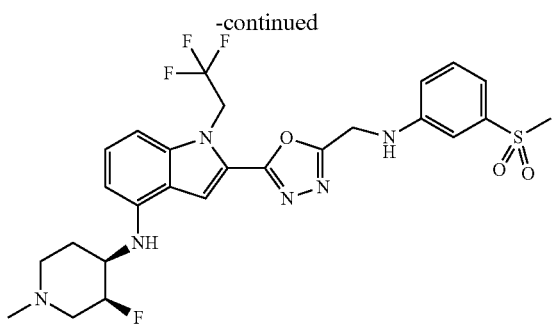

Preparation of (3-(methylsulfonyl)phenyl)glycine: To a solution of 2-oxoacetic acid (648.6 mg, 8.76 mmol, 1 eq) in MeOH (15 mL) were added sodium cyanoborohydride (3.30 g, 52.6 mmol, 6 eq) and acetic acid (8.76 mmol, 500 μL, 1 eq). 3-(Methylsulfonyl)aniline (1.5 g, 8.76 mmol, 1 eq) was added to the mixture. The resulting reaction mixture was stirred at 25° C. for 2 hr, and completion of the reaction was confirmed using LC-MS analysis. The reaction mixture was poured into a solution of sodium hydroxide (50 mL) and was extracted with EA 150 ml, (50 mL×3). The combined organic layers were washed with brine (50 mL), dried over anhydrous sodium sulfate, filtered, and concentrated in vacuo to afford (3-(methylsulfonyl)phenyl)glycine (1.5 g, 6.54 mmol, 74% yield) as a white solid.

Preparation of (+/−)-4-(((3S,4R)-3-fluoro-1-methylpiperidin-4-yl)amino)-N'-((3-(methylsulfonyl)phenyl)glycyl)-1-(2,2,2-trifluoroethyl)-1H-indole-2-carbohydrazide: To a solution of (+/−)-4-(((3S,4R)-3-fluoro-1-methylpiperidin-4-yl)amino)-1-(2,2,2-trifluoroethyl)-1H-indole-2-carbohydrazide (438.9 mg, 872.4 μmol, 1 eq) and (3-(methylsulfonyl)phenyl)glycine (200 mg, 872 μmol, 1 eq) in DMF (5 mL) were added TEA (4.36 mmol, 607.1 μL, 5 eq) and HATU (663 mg, 1.74 mmol, 2 eq). The mixture was stirred at 20° C. for 1 hr. Completion of the reaction was confirmed using LC-MS analysis. The reaction mixture was poured into water (60 mL) and extracted with EA (30 mL×3). The combined organic layers were washed with brine (20 mL), dried over anhydrous sodium sulfate, filtered, and concentrated in vacuo. The crude residue was purified by preparative-TLC (SiO₂, DCM:MeOH=5:1) to afford (+/−)-4-(((3S, 4R)-3-fluoro-1-methylpiperidin-4-yl)amino)-N'-((3-(methylsulfonyl)phenyl)glycyl)-1-(2,2,2-trifluoroethyl)-1H-indole-2-carbohydrazide (50 mg, 83.5 μmol, 27.8% yield) as a light yellow oil.

Synthesis of (+/−)-N-((3S,4R)-3-fluoro-1-methylpiperidin-4-yl)-2-(5-(((3-(methylsulfonyl)phenyl)amino)methyl)-1,3,4-oxadiazol-2-yl)-1-(2,2,2-trifluoroethyl)-1H-indol-4-amine (Compound 125B): To a solution of 4-(((3S,4R)-3-fluoro-1-methylpiperidin-4-yl)amino)-N'-((3-(methylsulfonyl)phenyl)glycyl)-1-(2,2,2-trifluoroethyl)-11H-indole-2-carbohydrazide (40 mg, 67 μmol, 1 eq) in DCM (8 mL) were added PPh₃ (35.1 mg, 134 μmol, 2 eq) and CBr₄ (44.3 mg, 134 μmol, 2 eq) at 0° C. The mixture was stirred at 0° C. for 0.5 h, and LC-MS analysis was used to confirm completion of the reaction. The reaction mixture was poured into water (60 mL) and extracted with DCM (30 mL×3). The combined organic phase was washed with brine (20 mL), dried with anhydrous sodium sulfate, filtered, and concentrated in vacuo. The residue was purified by preparative-HPLC to afford (+/−)-N-((3S,4R)-3-fluoro-1-methylpiperidin-4-yl)-2-(5-(((3-(methylsulfonyl)phenyl)amino)methyl)-1,3,4-oxadiazol-2-yl)-1-(2,2,2-trifluoroethyl)-1H-indol-4-amine (Compound 125B) (5.6 mg, 9.65 μmol, 14.4% yield) as a white solid. LC-MS (ES⁺, m/z): 581.2.

Example 59: Synthesis of N-(1-methylpiperidin-4-yl)-2-{5-[(phenylamino)methyl]-1,3,4-oxadiazol-2-yl}-1-(2,2,2-trifluoroethyl)-1H-indol-4-amine (Compound 108B)

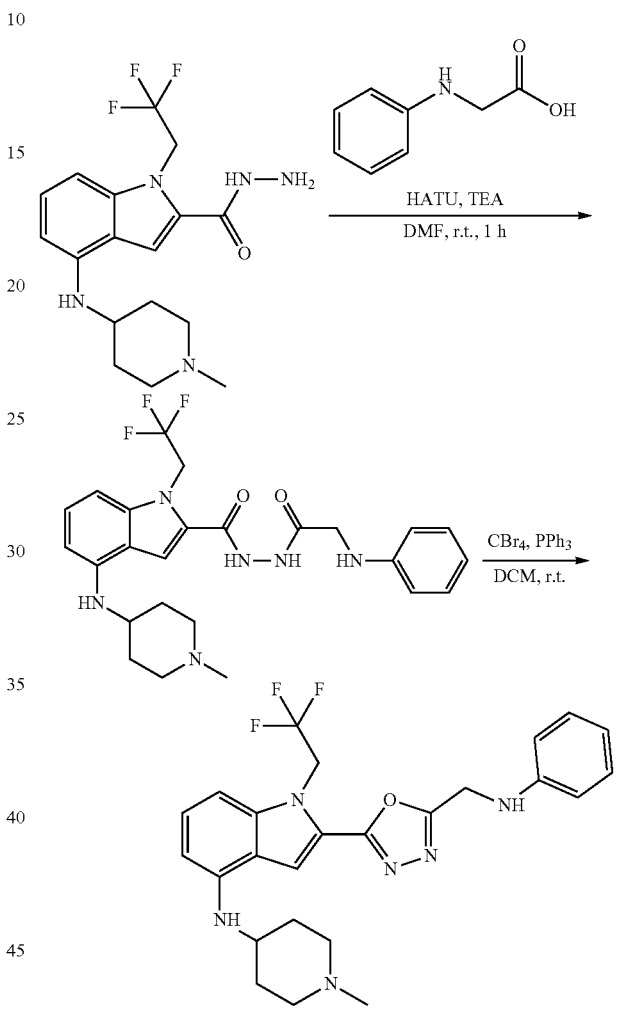

Preparation of 4-((1-methylpiperidin-4-yl)amino)-N'-(phenylglycyl)-1-(2,2,2-trifluoroethyl)-1H-indole-2-carbohydrazide: To a solution of phenylglycine (90 mg, 595.59 μmol, 2 eq) in DMF (3 mL) were added HATU (226.5 mg, 596 μmol, 2 eq) and TEA (1.49 mmol, 207.3 μL, 5 eq). The mixture was stirred at 20° C. for 5 min, and 4-((1-methylpiperidin-4-yl)amino)-1-(2,2,2-trifluoroethyl)-1H-indole-2-carbohydrazide (110 mg, 298 μmol, 1 eq) was added to the mixture. The resulting reaction mixture was stirred at 20° C. for 30 min. TLC analysis was used to confirm completion of the reaction. The residue was poured into water (50 mL), and the aqueous phase was extracted with EA (30 mL×3). The combined organic phase was washed with brine (30 mL×3), dried with anhydrous sodium sulfate, filtered, and concentrated in vacuo. The residue was purified by preparative-TLC to afford 4-((1-methylpiperidin-4-yl)amino)-N'-(phenylglycyl)-1-(2,2,2-trifluoroethyl)-1H-indole-2-carbohydrazide in 33.4% yield (50 mg, 99.5 μmol).

Preparation of N-(1-methylpiperidin-4-yl)-2-{5-[(phenylamino)methyl]-1,3,4-oxadiazol-2-yl}-1-(2,2,2-trifluoroethyl)-1H-indol-4-amine (Compound 108B): To a solution of 4-((1-methylpiperidin-4-yl)amino)-N'-(phenylglycyl)-1-(2,2,2-trifluoroethyl)-1H-indole-2-carbohydrazide (50 mg, 99.5 μmol, 1 eq) in DCM (3 mL) were added triphenylphosphine (52.2 mg, 199 μmol, 2 eq) and carbon tetrabromide (66 mg, 199 μmol, 2 eq). The mixture was stirred at 0° C. for 0.5 hr, and then stirred at 20° C. for 3 hr. TLC analysis was used to confirm completion of the reaction. The residue was poured into water (50 mL), and the aqueous phase was extracted with DCM (30 mL×3). The combined organic phase was washed with brine (30 mL×3), dried with anhydrous sodium sulfate, filtered, and concentrated in vacuo. The residue was purified by preparative-HPLC to afford N-(1-methylpiperidin-4-yl)-2-{5-[(phenylamino)methyl]-1,3,4-oxadiazol-2-yl}-1-(2,2,2-trifluoroethyl)-1H-indol-4-amine (Compound 108B) (5.4 mg, 11.0 μmol, 11.1% yield) as a light yellow solid. LC-MS (ES+, m/z): 485.3.

Example 60: Synthesis of N-[(5-{4-[(1-methylpiperidin-4-yl)amino]-1-(2,2,2-trifluoroethyl)-1H-indol-2-yl}-1,3,4-oxadiazol-2-yl)methyl]cyclopropanecarboxamide (Compound 110B)

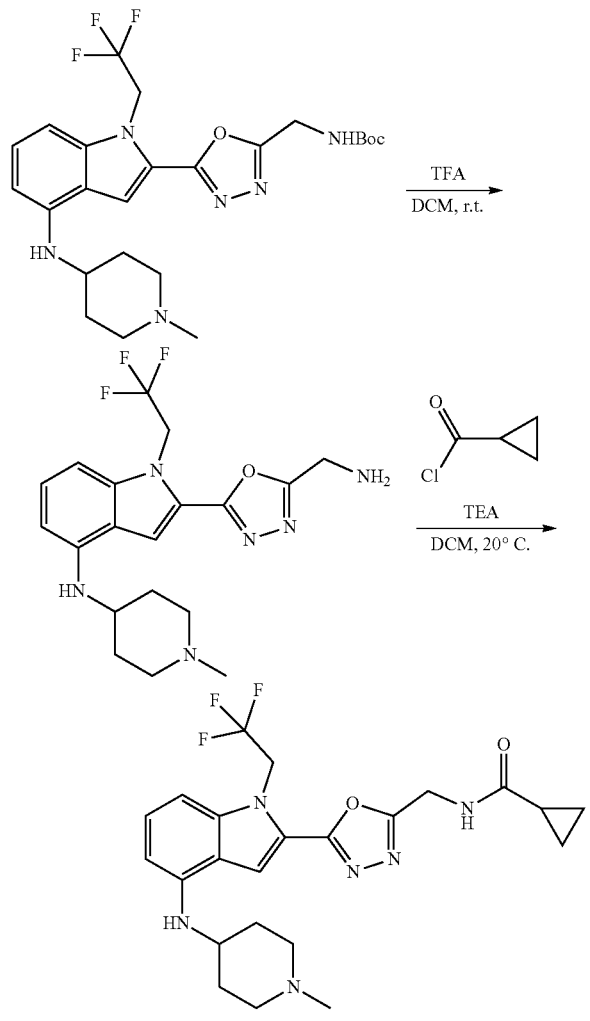

Preparation of 2-(5-(aminomethyl)-1,3,4-oxadiazol-2-yl)-N-(1-methylpiperidin-4-yl)-1-(2,2,2-trifluoroethyl)-1H-indol-4-amine: To a solution of tert-butyl ((5-(4-((1-methylpiperidin-4-yl)amino)-1-(2,2,2-trifluoroethyl)-1H-indol-2-yl)-1,3,4-oxadiazol-2-yl)methyl)carbamate (40 mg, 78.7 μmol 1 eq) in DCM (2 mL) was added TFA (27 mmol, 2 mL, 343 eq). The mixture was stirred at 20° C. for 15 min, and completion of the reaction was confirmed using TLC analysis. The reaction mixture was poured into saturated aqueous sodium bicarbonate (50 mL), and the aqueous phase was extracted with DCM (30 mL×3). The combined organic phase was washed with brine (30 mL×3), dried with anhydrous sodium sulfate, filtered, and concentrated in vacuo. The crude residue was purified by preparative-TLC to afford 2-(5-(aminomethyl)-1,3,4-oxadiazol-2-yl)-N-(1-methylpiperidin-4-yl)-1-(2,2,2-trifluoroethyl)-1H-indol-4-amine in 49.8% yield (16 mg, 39 μmol).

Preparation of N-[(5-{4-[(1-methylpiperidin-4-yl)amino]-1-(2,2,2-trifluoroethyl)-1H-indol-2-yl}-1,3,4-oxadiazol-2-yl)methyl]cyclopropanecarboxamide (Compound 110B): To a solution of 2-(5-(aminomethyl)-1,3,4-oxadiazol-2-yl)-N-(1-methylpiperidin-4-yl)-1-(2,2,2-trifluoroethyl)-1H-indol-4-amine (15 mg, 36.7 μmol, 1 eq) in DCM (1 mL) were added TEA (10.8 mmol, 1.50 mL, 293.4 eq) and cyclopropanecarbonyl chloride (36.73 μmol, 3.3 μL, 1 eq.). The mixture was stirred at 0° C. for 0.5 hr, and TLC analysis was used to confirm completion of the reaction. The residue was poured into water (50 mL), and the aqueous phase was extracted with DCM (30 mL×3). The combined organic phase was washed with brine (30 mL×3), dried with anhydrous sodium sulfate, filtered, and concentrated in vacuo, The crude residue was purified by preparative-HPLC to afford N-[(5-{4-[(1-methylpiperidin-4-yl)amino]-1-(2,2,2-trifluoroethyl)-1H-indol-2-yl}-1,3,4-oxadiazol-2-yl)methyl]cyclopropanecarboxamide (Compound 110B) (4.1 mg, 8.6 μmol, 23.4% yield) as a light yellow solid. LC-MS (ES+, m/z): 477.3.

Example 61: Synthesis of 2-(5-{[(4-methanesulfonylphenyl)amino]methyl}-1,3,4-oxadiazol-2-yl)-N-(1-methylpiperidin-4-yl)-1-(2,2,2-trifluoroethyl)-1H-indol-4-amine (Compound 111B)

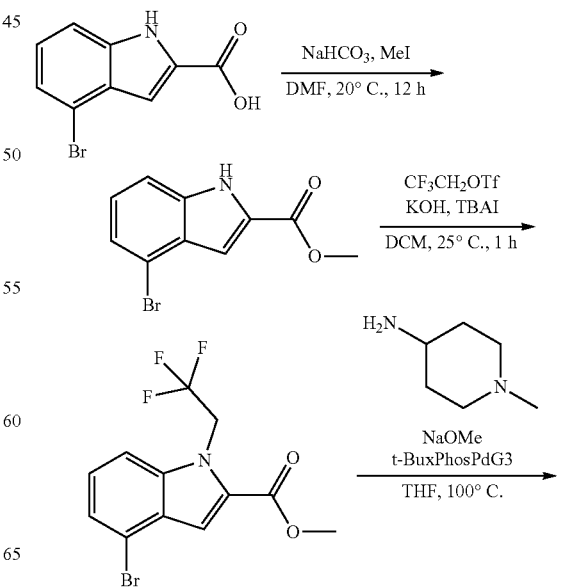

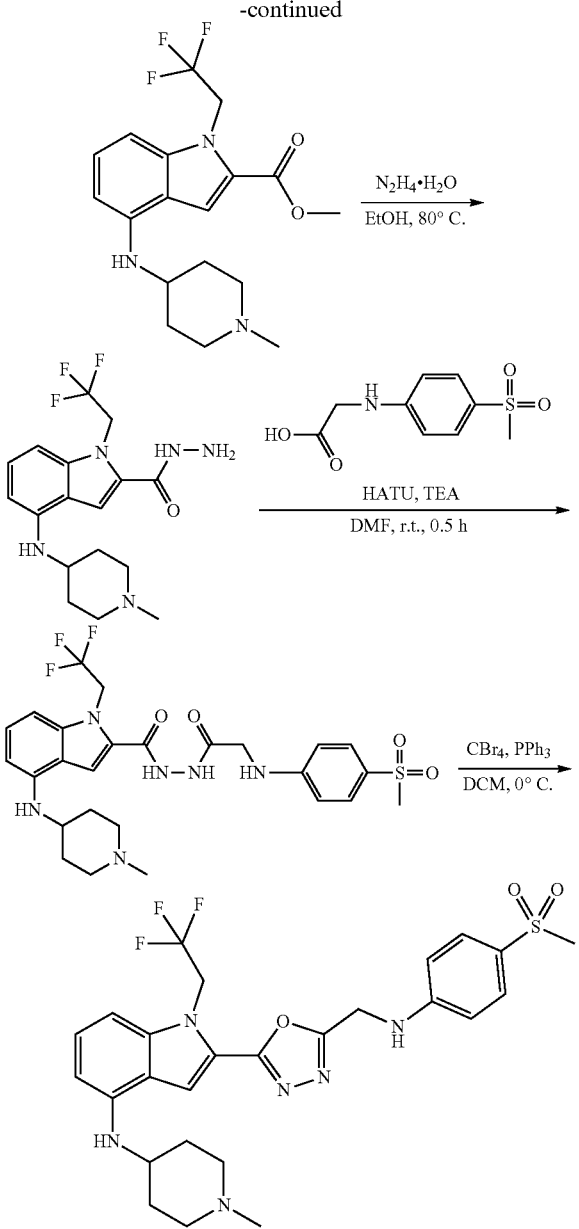

Preparation of methyl 4-bromo-1H-indole-2-carboxylate: To a mixture of 4-bromo-1H-indole-2-carboxylic acid (5 g, 20.8 mmol, 1 eq) in DMF (100 mL) were added sodium bicarbonate (3.50 g, 41.7 mmol, 2 eq) and iodomethane (80.32 mmol, 5 mL, 3.9 eq) in one portion at 20° C. under a nitrogen atmosphere. The mixture was stirred at 20° C. for 12 hours, and TLC analysis was used to confirm completion of the reaction. The residue was poured into ice water (w/w=1/1) (200 mL), and the aqueous phase was extracted with EA (50 mL×3). The combined organic phase was washed with brine (50 mL×3), dried with anhydrous sodium sulfate, filtered, and concentrated in vacuo. The residue was purified by silica gel chromatography to afford methyl 4-bromo-1H-indole-2-carboxylate in 66.1% yield.

Preparation of methyl 4-bromo-1-(2,2,2-trifluoroethyl)-1H-indole-2-carboxylate: To a mixture of methyl 4-bromo-1H-indole-2-carboxylate (7 g, 27.6 mmol, 1 eq) and 2,2,2-trifluoroethyl trifluoromethanesulfonate (12.8 g, 55.1 mmol, 2 eq) in DCM (20 mL) were added crushed potassium hydroxide (4.64 g, 82.7 mmol, 3 eq) and TBAI (2.04 g, 5.51 mmol, 0.2 eq) in one portion at 25° C. under a nitrogen atmosphere. The mixture was stirred at 25° C. for 60 min, and TLC analysis was used to confirm completion of the reaction. The residue was poured into ice water (w/w=1/1) (300 mL), and the aqueous phase was extracted with EA (100 mL×3). The combined organic phase was washed with brine, dried with anhydrous sodium sulfate, filtered, and concentrated in vacuo. The residue was purified by silica gel chromatography to provide methyl 4-bromo-1-(2,2,2-trifluoroethyl)-1H-indole-2-carboxylate in 66.8% yield.

Preparation of methyl 4-((1-methylpiperidin-4-yl)amino)-1-(2,2,2-trifluoroethyl)-1H-indole-2-carboxylate: To a mixture of methyl 4-bromo-1-(2,2,2-trifluoroethyl)-1H-indole-2-carboxylate (1 g, 3 mmol, 1 eq) and 1-methylpiperidin-4-amine (407.7 mg, 3.57 mmol, 1.2 eq) in THF (2 mL) were added t-BuXPhos Palladium Generation 3 (118.2 mg, 148.8 µmol, 0.05 eq) and sodium methoxide (321 mg, 5.95 mmol, 2 eq) under a nitrogen atmosphere. The mixture was heated and stirred at 100° C. for 15 min, and TLC analysis was used to confirm completion of the reaction. The residue was poured into a 2M aqueous EDTA (40 mL) and stirred for 60 min. The aqueous phase was extracted with EA (20 mL×3). The combined organic phase was washed with brine (20 mL×3), dried with anhydrous sodium sulfate, filtered, and concentrated in vacuo. The crude product was purified by silica gel chromatography to afford methyl 4-((1-methylpiperidin-4-yl)amino)-1-(2,2,2-trifluoroethyl)-1H-indole-2-carboxylate in 72.8% yield. LC-MS (ES+, m/z): 370.1.

Preparation of 4-((1-methylpiperidin-4-yl)amino)-1-(2,2,2-trifluoroethyl)-1H-indole-2-carbohydrazide: To a mixture of methyl 4-((1-methylpiperidin-4-yl)amino)-1-(2,2,2-trifluoroethyl)-1H-indole-2-carboxylate (1 eq) in ethanol (2~5 mL) was added hydrazine hydrate (2-5 mL, 98% purity) in one portion under a nitrogen atmosphere. The mixture was heated and stirred at 80° C. for 60 min, and TLC analysis was used to confirm completion of the reaction. The residue was poured into ice water (w/w=1/1) (30 mL), and the aqueous phase was extracted with EA (15 mL×3). The combined organic phase was washed with brine, dried with anhydrous sodium sulfate, filtered, and concentrated in vacuo. The residue was purified by silica gel chromatography to afford 4-((1-methylpiperidin-4-yl)amino)-1-(2,2,2-trifluoroethyl)-1H-indole-2-carbohydrazide in 87.5% yield.

Preparation of 4-((1-methylpiperidin-4-yl)amino)-N'-((4-(methylsulfonyl)phenyl)glycyl)-1-(2,2,2-trifluoroethyl)-1H-indole-2-carbohydrazide: To a mixture of 4-((1-methylpiperidin-4-yl)amino)-1-(2,2,2-trifluoroethyl)-1H-indole-2-carbohydrazide (100 mg. 271 µmol, 1 eq) and (4-(methylsulfonyl)phenyl)glycine (62.1 mg, 271 µmol mol, 1 eq) in DMF (1 mL) were added HATU (205.9 mg, 541.4 µmol, 2 eq) and TEA (1.35 mmol, 188 µL, 5 eq) in one portion at 20° C. under a nitrogen atmosphere. The mixture was stirred at 20° C. for 30 min, and LC-MS analysis was used to confirm completion of the reaction. The residue was poured into ice water (w/w=1/1) (30 mL), and the aqueous phase was extracted with EA (10 mL×3). The combined organic phase was washed with brine (10 mL×3), dried with anhydrous sodium sulfate, filtered, and concentrated in vacuo. The crude product was purified by preparative-TLC (SiO2, DCM:MeOH=8:1) to afford 4-((1-methylpiperidin-4-yl)amino)-N'-((4-(methylsulfonyl)phenyl)glycyl)-1-(2,2,2-trifluoroethyl)-1H-indole-2-carbohydrazide in 72.8% yield. LC-MS (ES+, m/z): 581.2.

Preparation of 2-(5-{[(4-methanesulfonylphenyl)amino]methyl}-1,3,4-oxadiazol-2-yl)-N-(1-methylpiperidin-4-yl)-

1-(2,2,2-trifluoroethyl)-1H-indol-4-amine (Compound 111B): To a mixture of 4-((1-methylpiperidin-4-yl)amino)-N'-((4-(methylsulfonyl)phenyl)glycyl)-1-(2,2,2-trifluoroethyl)-1H-indole-2-carbohydrazide (20 mg, 34 µmol, 1 eq) in DCM (1 mL) were added triphenylphosphine (18.1 mg, 68.9 µmol, 2 eq) and carbon tetrabromide (22.9 mg, 68.9 µmol, 2 eq) at 0° C. under a nitrogen atmosphere. The mixture was stirred at 0° C. for 15 min, and LC-MS analysis showed completion of the reaction. The residue was poured into ice water (w/w=1/1) (40 mL), and the aqueous phase was extracted with DCM (20 mL×3). The combined organic phase was washed with brine (20 mL×3), dried with anhydrous sodium sulfate, filtered, and concentrated in vacuo. The residue was purified by preparative-TLC and preparative-HPLC to afford 2-(5-{[(4-methanesulfonylphenyl)amino]methyl}-1,3,4-oxadiazol-2-yl)-N-(1-methylpiperidin-4-yl)-1-(2,2,2-trifluoroethyl)-1H-indol-4-amine (Compound 1111B). LC-MS (ES$^+$, m/z): 563.2.

Example 62: Synthesis of 2-(5-(aminomethyl)-1,3,4-oxadiazol-2-yl)-N-(1-methylpiperidin-4-yl)-1-(2,2,2-trifluoroethyl)-1H-indol-4-amine (Compound 113B)

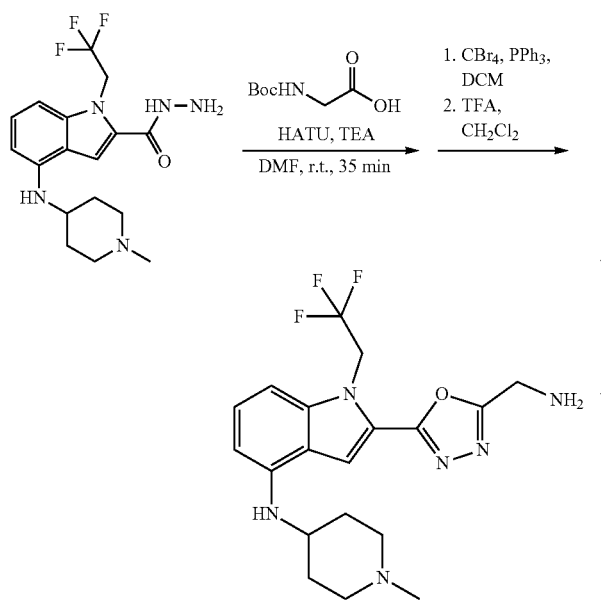

To a solution of N-Boc-glycine (94.9 mg, 541 µmol, 1 eq) in DMF (3 mL) were added HATU (411.7 mg, 1.08 mmol, 2 eq) and TEA (2.71 mmol, 377 µL, 5 eq). The mixture was stirred at 25° C. for 5 min, then 4-((1-methylpiperidin-4-yl)amino)-1-(2,2,2-trifluoroethyl)-1H-indole-2-carbohydrazide (200 mg, 541 µmol, 1 eq) was added. The mixture was stirred at 25° C. for 30 min. The residue was poured into water (50 mL). The aqueous phase was extracted with EA (30 mL×3). The combined organic phase was washed with brine (30 mL×3), dried with anhydrous sodium sulfate, filtered, and concentrated in vacuo. The residue was purified by preparative-TLC to afford the diacyl intermediate (90 mg, 171 µmol, 31.6% yield) as a yellow solid. LC-MS (M+H$^+$)= 527.3.

To a solution of the diacyl intermediate (90 mg, 170.9 µmol, 1 eq) in DCM (2 mL) were added triphenylphosphine (89.7 mg, 342 µmol, 2 eq) and carbon tetrabromide (113.4 mg, 341.8 µmol, 2 eq). The mixture was stirred at 0° C. for 0.5 hr, then at 25° C. for 0.5 hr. The residue was poured into water (50 mL). The aqueous phase was extracted with DCM (30 mL×3). The combined organic phase was washed with brine (30 mL×3), dried with anhydrous sodium sulfate, filtered, and concentrated in vacuo. The residue was purified by preparative-TLC to give the oxazole Boc intermediate (60 mg, 118 µmol, 69.0% yield) as a yellow solid.

To a solution of the oxazole Boc intermediate (40 mg, 78.66 µmol 1 eq) in DCM (2 mL) was added TFA (27 mmol, 2 mL, 343 eq). The mixture was stirred at 20° C. for 15 min. The residue was poured into saturated sodium bicarbonate solution (50 mL). The aqueous phase was extracted with DCM (30 mL×3). The combined organic phase was washed with brine (30 mL×3), dried with anhydrous sodium sulfate, filtered, and concentrated in vacuo. The residue was purified by preparative-TLC to provide the desired 2-(5-(aminomethyl)-1,3,4-oxadiazol-2-yl)-N-(1-methylpiperidin-4-yl)-1-(2,2,2-trifluoroethyl)-1H-indol-4-amine (Compound 11313) (16 mg, 39.2 µmol, 49.8% yield).

Example 63: Synthesis of (+/−)-2-(5-(aminomethyl)-1,3,4-oxadiazol-2-yl)-N-((3S,4R)-3-fluoro-1-methylpiperidin-4-yl)-1-(2,2,2-trifluoroethyl)-1H-indol-4-amine (Compound 127B)

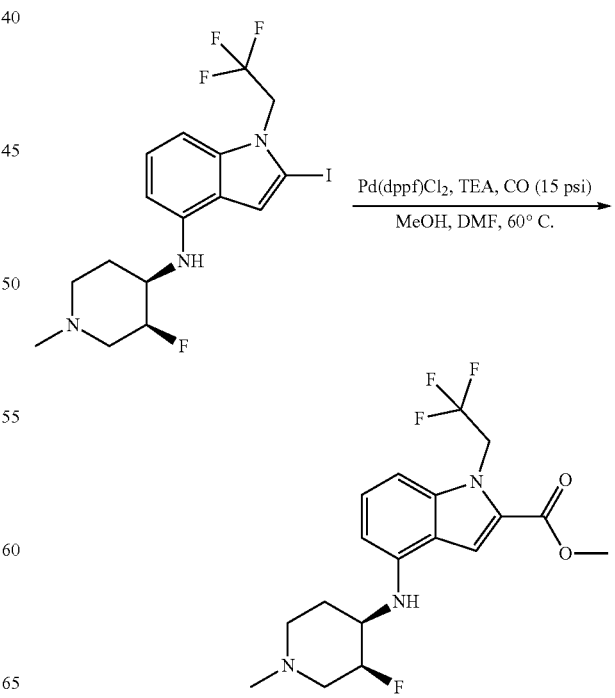

325

To a solution of (+/−)-N-((3S,4R)-3-fluoro-1-methylpiperidin-4-yl)-2-iodo-1-(2,2,2-trifluoroethyl)-1H-indol-4-amine (1 g, 11 mmol, 1 eq) in MeOH (5 mL) DMF (10 mL) were added TEA (4.39 mmol, 612 L, 2 eq) and Pd(dppf)Cl$_2$ (160.7 mg, 220 μmol, 0.1 eq). The mixture was stirred under a carbon monoxide atmosphere (15 psi) at 60° C. for 2 hr. The mixture was extracted with DCM (50 mL×2), and the organic phase was washed with brine (50 mL), dried over anhydrous sodium sulfate, filtered, and concentrated in vacuo to afford (+/−)-methyl 4-(((3S,4R)-3-fluoro-1-methylpiperidin-4-yl)amino)-1-(2,2,2-trifluoroethyl)-1H-indole-2-carboxylate (500 mg, crude).

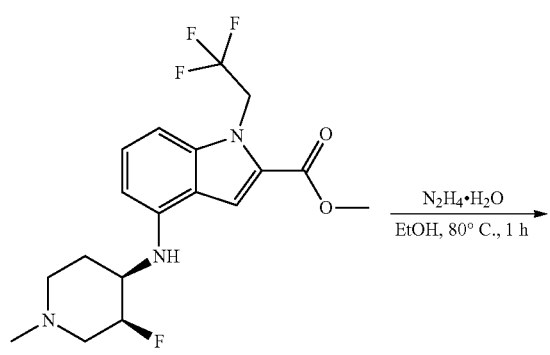

326

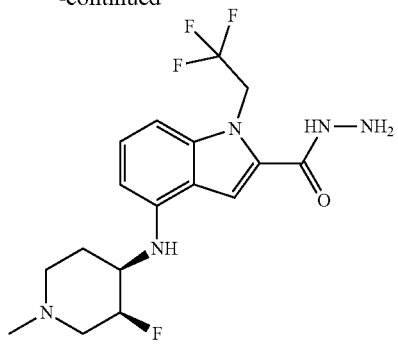

To a solution of the (+/−)-methyl 4-(((3S,4R)-3-fluoro-1-methylpiperidin-4-yl)amino)-1-(2,2,2-trifluoroethyl)-1H-indole-2-carboxylate (4 g, 10.3 mmol, 1 eq) in ethanol (20 mL) was added hydrazine hydrate (20 mL). The mixture was stirred at 80° C. for 1 hr. The mixture was extracted with DCM (50 mL×2), and the organic phase was washed with brine (50 mL), dried over anhydrous sodium sulfate, filtered, and concentrated in vacuo. The residue was purified by column chromatography (silica gel, PE/EA=1:1) to provide the desired (+/−)-4-(((3S,4R)-3-fluoro-1-methylpiperidin-4-yl)amino)-1-(2,2,2-trifluoroethyl)-1H-indole-2-carbohydrazide (3 g, 7.74 mmol, 75.0% yield). LC-MS (M+H$^+$)=388.2.

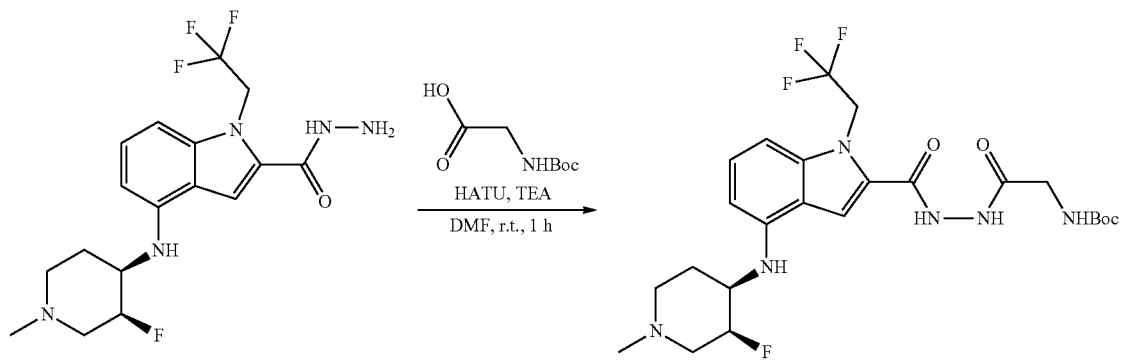

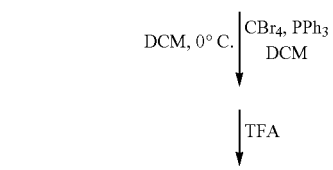

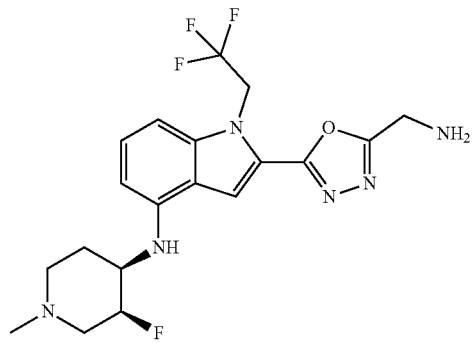

To a mixture of (+/−)-4-(((3S,4R)-3-fluoro-1-methylpiperidin-4-yl)amino)-1-(2,2,2-trifluoroethyl)-1H-indole-2-carbohydrazide (3 g, 6.20 mmol, 1 eq) and N-Boc glycine (3 g, 17 mmol, 2.8 eq) in DMF (30 mL) was added HATU (8.25 g, 21.7 mmol, 3.5 eq). Then, TEA (37.2 mmol, 5.17 mL, 6 eq) was added, and the reaction mixture was stirred at 25° C. under nitrogen. The mixture was stirred at 25° C. for 60 min, at which time LC-MS analysis showed completion of the reaction. The residue was poured into ice water (w/w=1/1) (50 mL) and stirred for 5 min. The aqueous phase was extracted with EA (20 mL×3). The combined organic phase was washed with brine (20 mL×3), dried over anhydrous sodium sulfate, filtered, and concentrated in vacuo. The residue was purified by silica gel chromatography to afford (+/−)-tert-butyl (2-(2-(4-(((3S,4R)-3-fluoro-1-methylpiperidin-4-yl)amino)-1-(2,2,2-trifluoroethyl)-1H-indole-2-carbonyl)hydrazineyl)-2-oxoethyl)carbamate (3.2 g, 5.88 mmol, 94.9% yield). LC-MS (M (−tBu)+H⁺)=486.3.

To a solution of (+/−)-tert-butyl (2-(2-(4-(((3S,4R)-3-fluoro-1-methylpiperidin-4-yl)amino)-1-(2,2,2-trifluoroethyl)-1H-indole-2-carbonyl)hydrazineyl)-2-oxoethyl)carbamate (4 g, 7.35 mmol, 1 eq) in DCM (30 mL) were added carbon tetrabromide (4.87 g, 14.7 mmol, 2 eq) and triphenylphosphine (3.85 g, 14.7 mmol, 2 eq) at 0° C. under nitrogen. The mixture was stirred at 0° C. for 1 h. The residue was poured into ice water (w/w=1/1) (100 mL) and stirred for 5 min. The aqueous phase was extracted with DCM (30 mL×3). The combined organic phase was washed with brine (30 mL×3), dried with anhydrous sodium sulfate, filtered, and concentrated in vacuo. The residue was purified by silica gel chromatography (DCM:MeOH=40:1 to 10:1) to afford the intermediate Boc oxadiazole (1.6 g, 3.04 mmol, 41.4% yield).

To a solution of the Boc oxadiazole intermediate (1.5 g, 2.85 mmol, 1 eq) in DCM (10 mL) was added TFA (127 mmol, 9.38 mL, 44.5 eq) in one portion at 20° C. under nitrogen. The mixture was stirred at 20° C. for 30 min. The residue was poured into water (50 mL). The aqueous phase was washed with DCM (10 mL×3), and the organic washings were discarded. The aqueous phase was poured into saturated sodium bicarbonate solution to adjust the pH to 7-8. The aqueous phase was extracted with EA (25 mL×3). The combined organic phase was washed with brine (25 mL×3), dried with anhydrous sodium sulfate, filtered, and concentrated in vacuo. The residue was purified by preparative-HPLC to provide the desired (+/−)-2-(5-(aminomethyl)-1,3,4-oxadiazol-2-yl)-N-((3S,4R)-3-fluoro-1-methylpiperidin-4-yl)-1-(2,2,2-trifluoroethyl)-1H-indol-4-amine (Compound 127B) (1 g, crude). LC-MS (M+H⁺)=427.1.

Example 64: Synthesis of (+/−)-N-((3R,4R)-3-fluoro-1-methylpiperidin-4-yl)-2-(5-(((2-methoxy-4-(methylsulfonyl)phenyl)amino)methyl)-1,3,4-oxadiazol-2-yl)-1-(2,2,2-trifluoroethyl)-1H-indol-4-amine (Compound 135B)

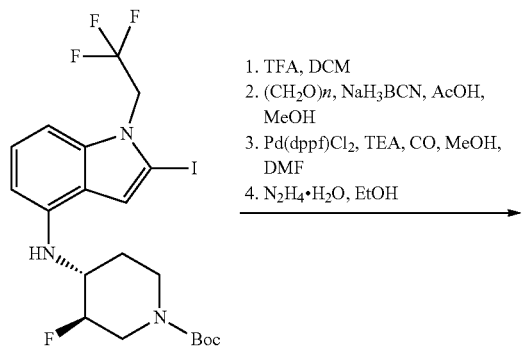

1. TFA, DCM
2. (CH₂O)n, NaH₃BCN, AcOH, MeOH
3. Pd(dppf)Cl₂, TEA, CO, MeOH, DMF
4. N₂H₄·H₂O, EtOH -continued

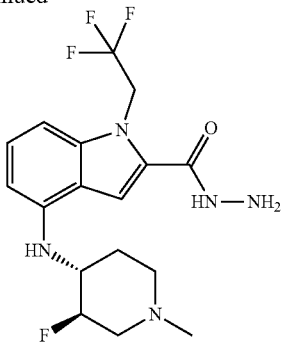

To a solution of tert-butyl (+/−)-(3R,4R)-3-fluoro-4-((2-iodo-1-(2,2,2-trifluoroethyl)-1H-indol-4-yl)amino)piperidine-1-carboxylate (10 g, 18.5 mmol, 1 eq) in DCM (30 mL) was added TFA (68 mmol, 5 mL, 3.7 eq) at 20° C. under nitrogen. The mixture was stirred at 20° C. for 30 min. The residue was poured into saturated sodium carbonate (aq) to adjust the pH to 7~8. The aqueous phase was extracted with DCM (200 mL×3). The combined organic phase was washed with brine (200 mL×3), dried with anhydrous sodium sulfate, filtered, and concentrated in vacuo. The residue was washed with DCM (30 mL), then with PE (60 mL) to provide the desired piperidine intermediate (6.5 g, 14.7 mmol, 79.8% yield).

To a mixture of (+/−)-N-[(3S)-3-fluoro-4-piperidyl]-2-iodo-1-(2,2,2-trifluoroethyl)indol-4-amine (5 g, 11.3 mmol, 1 eq) and paraformaldehyde (1.70 g, 56.7 mmol, 5 eq) in MeOH (80 mL) were added sodium cyanoborohydride (3.56 g, 56.7 mmol, 5 eq) and acetic acid (35 mmol, 2 mL, 3.09 eq) at 50° C. under a nitrogen atmosphere. The mixture was stirred at 50° C. for 2 hr. Completion of the reaction was confirmed using LC-MS analysis. The reaction residue was poured into ice water (w/w=1/1) (200 mL). The aqueous phase was extracted with EA (100 mL×3). The combined organic phase was washed with saturated brine (100 mL×3), dried with anhydrous sodium sulfate, filtered, and concentrated in vacuo. The residue was purified by silica gel chromatography to afford N-((3S,4S)-3-fluoro-1-methylpiperidin-4-yl)-2-iodo-1-(2,2,2-trifluoroethyl)-1H-indol-4-amine in 58.2% yield. LC-MS (ES⁺, m/z): 456.0.

To a mixture of the methyl piperidine iodide intermediate (3 g, 6.6 mmol, 1 eq) in DMF (20 mL) and MeOH (10 mL) were added Pd(dppf)Cl₂ (1.45 g, 1.98 mmol, 0.3 eq), TEA (32.95 mmol, 4.59 mL, 5 eq), and carbon monoxide (1 ATM) at 60° C. The mixture was stirred at 60° C. for 2 hours. The residue was poured into a 2M aqueous EDTA solution (100 mL) and stirred for 60 min. The aqueous phase was extracted with EA (50 mL×3). The combined organic phase was washed with brine (50 ml, ×3), dried with anhydrous sodium sulfate, filtered, and concentrated in vacuo. The residue was washed with EA (20 mL) and PE (60 mL) to provide the desired methyl ester intermediate (2 g, 5.16 mmol, 78.4% yield). LC-MS (M+H⁻)=388.1.

To a solution of the methyl ester intermediate (2 g, 5.16 mmol, 1 eq) in ethanol (15 mL) was added hydrazine hydrate (205.8 mmol, 10.20 mL, 39.9 eq) under nitrogen. The mixture was stirred at 80° C. for 3 hours. The residue was poured into ice water (w/w=1/1) (200 mL). The aqueous phase was extracted with EA (100 mL×3). The combined organic phase was washed with brine (100 mL×3), dried with anhydrous sodium sulfate, filtered, and concentrated in vacuo. The residue was purified by silica gel chromatography to provide (+/−)-4-(((3R,4R)-3-fluoro-1-methylpiperidin-4-yl)amino)-1-(2,2,2-trifluoroethyl)-1H-indole-2-carbohydrazide (1.2 g, 2.66 mmol, 510.6% yield). LC-MS (M+H⁺)=388.2.

Preparation of (+/−)-N-((3R,4R)-3-fluoro-1-methylpiperidin-4-yl)-2-(5-(((2-methoxy-4-(methylsulfonyl)phenyl)amino)methyl)-1,3,4-oxadiazol-2-yl)-1-(2,2,2-trifluoroethyl)-1H-indol-4-amine (Compound 135B): To a solution of 4-(((3R,4R)-3-fluoro-1-methylpiperidin-4-yl)amino)-1-(2,2,2-trifluoroethyl)-1H-indole-2-carbohydrazide (70 mg, 111 μmol, 1 eq) in DCM (1 mL) were added carbon tetrabromide (73.9 mg, 223 μmol, 2 eq) and triphenylphosphine (58.4 mg, 223 μmol, 2 eq) at 0° C. under nitrogen. The mixture was stirred at 0° C. for 15 min. The residue was poured into ice water (w/w=1/1) (40 mL). The aqueous phase was extracted with EA (20 mL×3). The combined organic phase was washed with brine (20 mL×3), dried with anhydrous sodium sulfate, filtered, and concentrated in vacuo. The residue was purified by preparative-HPLC to provide (+/−)-N-((3R,4R)-3-fluoro-1-methylpiperidin-4-yl)-2-(5-(((2-methoxy-4-(methylsulfonyl)phenyl)amino)methyl)-1,3,4-oxadiazol-2-yl)-1-(2,2,2-trifluoroethyl)-1H-indol-4-amine (6.1 mg, 10.0 μmol, 9.0% yield). LC-MS (M+H⁺)=611.3.

Example 65: Synthesis of (+/−)-4-(((3S,4S)-3-fluoro-1-methylpiperidin-4-yl)amino)-N'-((2-methoxy-4-(methylsulfonyl)phenyl)glycyl)-1-(2,2,2-trifluoroethyl)-1H-indole-2-carbohydrazide intermediate compound

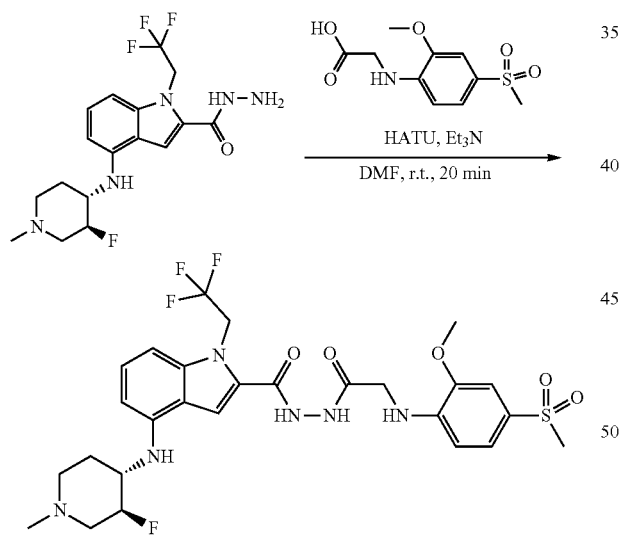

To a solution of (2-methoxy-4-(methylsulfonyl)phenyl) glycine (796.5 mg, 3.07 mmol, 2 eq) in DMF (10 mL) were added HATU (1.17 g, 3.07 mmol, 2 eq) and TEA (7.68 mmol, 1.07 mL, 5 eq) at 20° C. under nitrogen. The mixture was stirred at 20° C. for 5 min, and then 4-(((3S,4S)-3-fluoro-1-methylpiperidin-4-yl)amino)-1-(2,2,2-trifluoroethyl)-1H-indole-2-carbohydrazide (0.7 g, 1.5 mmol, 1 eq) was added. The mixture was stirred at 20° C. for 15 min. The residue was poured into ice water (w/w=1/1) (80 mL), and the aqueous phase was extracted with EA (30 mL×3). The combined organic phase was washed with brine (30 mL×3), dried with anhydrous sodium sulfate, filtered, and concentrated in vacuo. The residue was purified by silica gel chromatography to provide the diacyl intermediate 4-(((3S,4S)-3-fluoro-1-methylpiperidin-4-yl)amino)-N'-((2-methoxy-4-(methylsulfonyl)phenyl)glycyl)-1-(2,2,2-trifluoroethyl)-1H-indole-2-carbohydrazide (0.4 g, 636 μmol, 41.4% yield) as a yellow solid.

Example 66: Synthesis of (+/−)-2-(5-{[(cyclopropylmethyl)amino]methyl}-1,3,4-oxadiazol-2-yl)-N-[(3R,4S)-3-fluoro-1-methylpiperidin-4-yl]-1-(2,2,2-trifluoroethyl)-1H-indol-4-amine (Compound 121B)

(+/−)-4-(((3S,4S)-3-fluoro-1-methylpiperidin-4-yl) amino)-N'-((2-methoxy-4-(methylsulfonyl)phenyl)glycyl)-1-(2,2,2-trifluoroethyl)-1H-indole-2-carbohydrazide was prepared using the method described in EXAMPLE 65. (3-(Methylsulfonyl)phenyl)glycine (438.9 mg, 872.4 μmol, 1 eq), HATU (663.4 mg, 1.74 mmol, 2 eq), and TEA (4.36 mmol, 607 μL, 5 eq) provided the desired diacyl intermediate as a light yellow oil.

(+/−)-4-(((3S,4S)-3-fluoro-1-methylpiperidin-4-yl) amino)-N'-((2-methoxy-4-(methylsulfonyl)phenyl)glycyl)-1-(2,2,2-trifluoroethyl)-1H-indole-2-carbohydrazide (40 mg, 67 μmol, 1 eq) was reacted with triphenylphosphine (35.1 mg, 134 μmol, 2 eq) and carbon tetrabromide (44.3 mg, 134 μmol, 2 eq) following the method described in EXAMPLE 64 to provide (+/−)-(+/−)-2-(5-{[(cyclopropylmethyl)amino]methyl}-1,3,4-oxadiazol-2-yl)-N-[(3R,4S)-3-fluoro-1-methylpiperidin-4-yl]-1-(2,2,2-trifluoroethyl)-1H-indol-4-amine (Compound 121B) (5.6 mg, 9.7 μmol, 14.4% yield) as a white solid. LC-MS (M+H⁺)=581.2.

Example 67: 1-tert-butyl-N-{[5-(4-{[(3S,4R)-3-fluoro-1-methylpiperidin-4-yl]amino}-1-(2,2,2-trifluoroethyl)-1H-indol-2-yl)-1,2,4-oxadiazol-3-yl]methyl}-1H-pyrrole-3-carboxamide (Compound 552B)

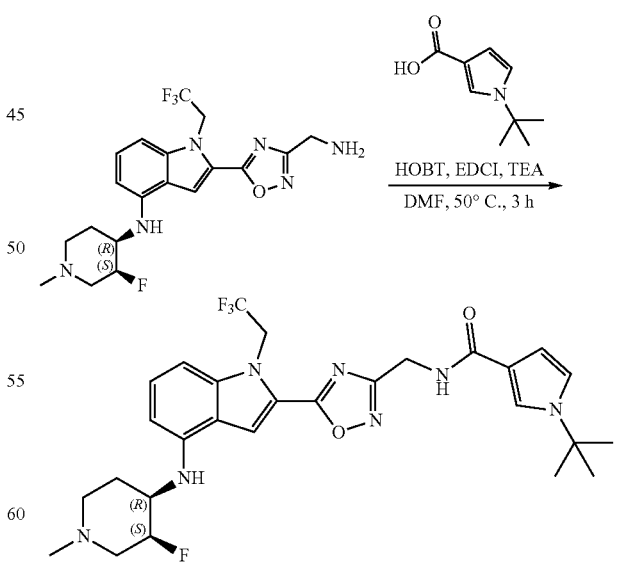

2-[3-(aminomethyl)-1,2,4-oxadiazol-5-yl]-N-[(3S,4R)-3-fluoro-1-methyl-4-piperidyl]-1-(2,2,2-trifluoroethyl)indol-4-amine (50 mg, 108 μmol, 1 eq, HCl) and 1-tert-butylpyrrole-3-carboxylic acid (19.9 mg, 118 μmol, 1.1 eq) were coupled under method A. The crude reaction was purified by prep-TLC (SiO$_2$, DCM:MeOH=10:1) to provide the desired product 1-tert-butyl-N-{[5-(4-{[(3S,4R)-3-fluoro-1-methylpiperidin-4-yl]amino}-1-(2,2,2-trifluoroethyl)-1H-indol-2-yl)-1,2,4-oxadiazol-3-yl]methyl}-1H-pyrrole-3-carboxamide (25.8 mg, 38.3% yield, 92.2% purity). LC-MS (ES$^+$, m/z): 576.4 [(M+H)$^+$]. $^1$H NMR (400 MHz, DMSO-d6) δ ppm 8.43 (t, J=5.73 Hz, 1H), 8.17 (s, 1H), 7.52 (t, J=1.87 Hz, 1H), 7.18 (t, J=8.05 Hz, 1H), 6.96 (t, J=2.65 Hz, 1H), 6.91 (d, J=8.38 Hz, 1H), 6.48 (dd, J=2.76, 1.87 Hz, 1H), 6.32 (d, J=7.94 Hz, 1H), 6.10 (br d, J=8.38 Hz, 1H), 5.61 (q, J=8.89 Hz, 2H), 4.94-4.77 (m, 1H), 4.58 (d, J=5.73 Hz, 2H), 3.70-3.54 (m, 1H), 3.10-3.00 (m, 1H), 2.83 (br d, J=9.70 Hz, 1H) 2.33-2.17 (m, 4H), 2.12 (br t, J=11.36 Hz, 1H), 2.06-1.93 (m, 1H), 1.72 (br d, J=11.03 Hz, 1H), 1.48 (s, 9H).

Example 68: 1-tert-butyl-N-{[5-(4-{[(3S,4R)-3-fluoro-1-methylpiperidin-4-yl]amino}-1-(2,2,2-trifluoroethyl)-1H-indol-2-yl)-1,3,4-oxadiazol-2-yl]methyl}-1H-pyrrole-3-carboxamide (Compound 288B)

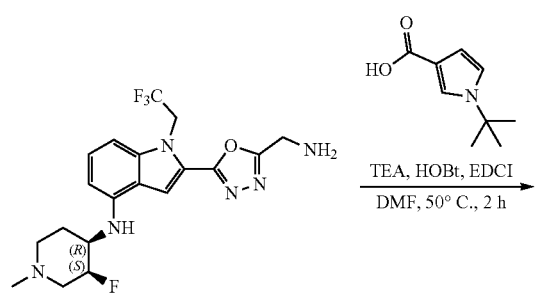

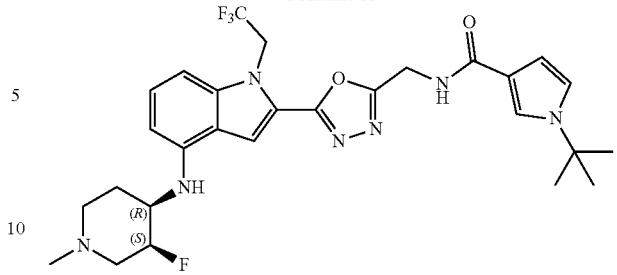

2-[5-(aminomethyl)-1,3,4-oxadiazol-2-yl]-N-[(3S,4R)-3-fluoro-1-methyl-4-piperidyl]-1-(2,2,2-trifluoroethyl) indol-4-amine (100 mg, 235 μmol, 1 eq) and 1-tert-butylpyrrole-3-carboxylic acid (78.4 mg, 469 μmol, 2 eq) were coupled under method A. The crude product was purified by prep-HPLC (neutral condition, column: Waters Xbridge Prep OBD C18 150×40 mm×10 um; mobile phase: [water (10 mM NH$_4$HCO$_3$)-ACN]; B %: 35%-60%, 8 min) to afford 1-tert-butyl-N-{[5-(4-{1[(3S,4R)-3-fluoro-1-methylpiperidin-4-yl]amino}-1-(2,2,2-trifluoroethyl)-1H-indol-2-yl)-1,3,4-oxadiazol-2-yl]methyl}-1H-pyrrole-3-carboxamide (18.7 mg, 13.9% yield, 100% purity) as a white solid. LC-MS (ES$^+$, m/z): 576.4 [(M+H)$^+$]. $^1$H NMR (400 MHz, DMSO-d$_6$) δ=8.52 (t, J=5.5 Hz, 1H), 7.86 (s, 1H), 7.53 (t, J=2.0 Hz, 1H), 7.14 (t, J=8.0 Hz, 1H), 6.97 (t, J=2.7 Hz, 1H), 6.89 (d, J=8.2 Hz, 1H), 6.49 (dd, J=1.8, 2.8 Hz, 1H), 6.29 (d, J=7.9 Hz, 1H), 6.07 (d, J=8.3 Hz, 1H), 5.62 (q, J=8.9 Hz, 2H), 4.94-4.75 (m, 1H), 4.71 (d, J=5.6 Hz, 2H), 3.69-3.49 (m, 1H), 3.11-2.97 (m, 1H), 2.81 (br d, J=10.5 Hz, 1H), 2.33-2.25 (m, 1H), 2.19 (s, 3H), 2.14-2.05 (m, 1H), 2.03-1.92 (m, 1H), 1.69 (br d, J=9.7 Hz, 1H), 1.48 (s, 9H).

TABLE 8 shows compounds with a 2-(1H-indol-2-yl)-1,3,4-oxadiazole core.

TABLE 8

| Compound No. | Structure | IUPAC | LC-MS (ES$^+$, m/z) |
|---|---|---|---|
| 107B | 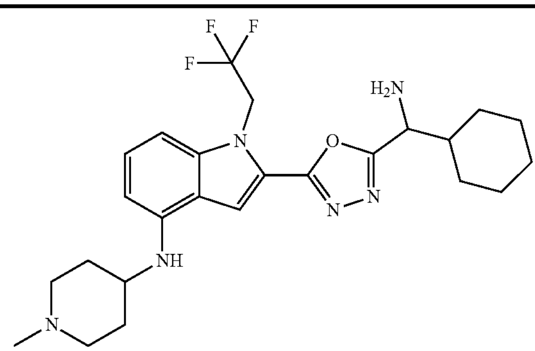 | 2-(5-(amino(cyclohexyl)methyl)-1,3,4-oxadiazol-2-yl)-N-(1-methylpiperidin-4-yl)-1-(2,2,2-trifluoroethyl)-1H-indol-4-amine | 491.2 |
| 108B | 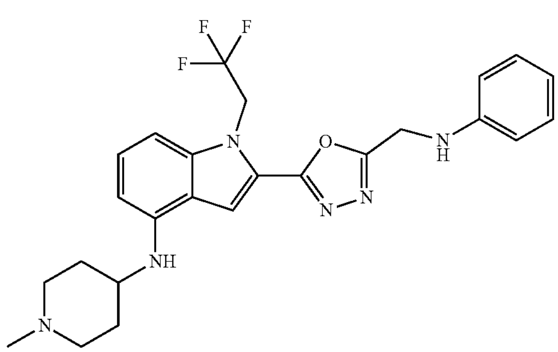 [SMILES: CN1CCC(Nc2cccc3c2cc(-c2nnc(CNc4ccccc4)o2)n3CC(F)(F)F)CC1] | N-(1-methylpiperidin-4-yl)-2-{5-[(phenylamino)methyl]-1,3,4-oxadiazol-2-yl}-1-(2,2,2-trifluoroethyl)-1H-indol-4-amine | 485.3 |

TABLE 8-continued

| Compound No. | Structure | IUPAC | LC-MS (ES+, m/z) |
|---|---|---|---|
| 109B | 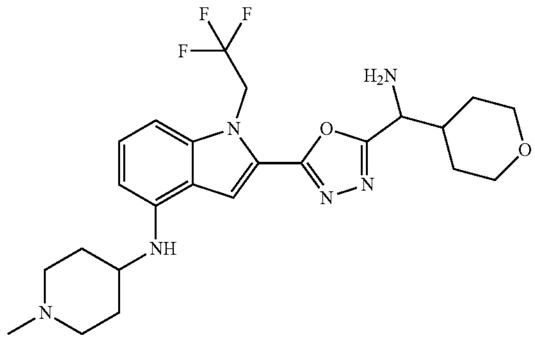 [SMILES: CN1CCC(Nc2cccc3c2cc(-c2nnc(C(N)C4CCOCC4)o2)n3CC(F)(F)F)CC1] | 2-(5-(amino(tetrahydro-2H-pyran-4-yl)methyl)-1,3,4-oxadiazol-2-yl)-N-(1-methylpiperidin-4-yl)-1-(2,2,2-trifluoroethyl)-1H-indol-4-amine | 493.3 |
| 110B | 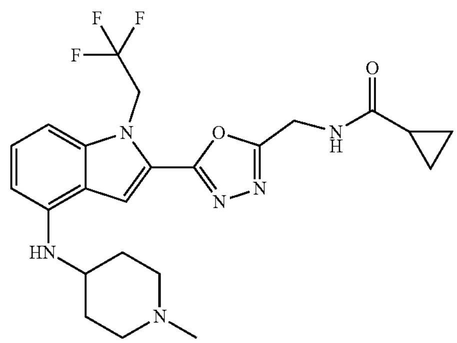 [SMILES: CN1CCC(Nc2cccc3c2cc(-c2nnc(CNC(=O)C4CC4)o2)n3CC(F)(F)F)CC1] | N-[(5-{4-[(1-methylpiperidin-4-yl)amino]-1-(2,2,2-trifluoroethyl)-1H-indol-2-yl}-1,3,4-oxadiazol-2-yl)methyl]cyclopropanecarbox-amide | 477.3 |
| 111B | 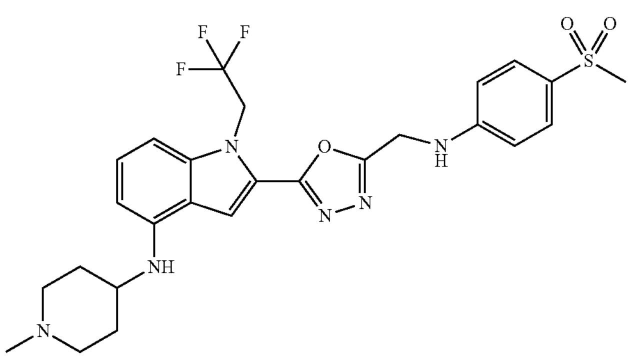 | 2-(5-{[(4-methanesulfonyl-phenyl)amino]methyl}-1,3,4-oxadiazol-2-yl)-N-(1-methylpiperidin-4-yl)-1-(2,2,2-trifluoroethyl)-1H-indol-4-amine | 563.2 |
| 112B | 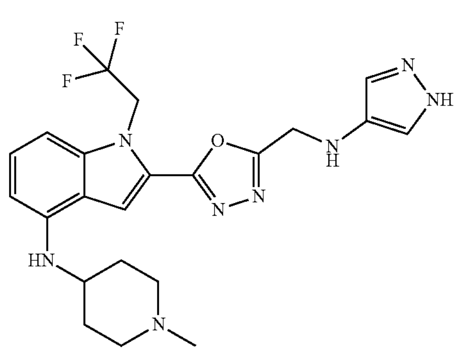 [SMILES: CN1CCC(Nc2cccc3c2cc(-c2nnc(CNc4cn[nH]c4)o2)n3CC(F)(F)F)CC1] | N-(1-methylpiperidin-4-yl)-2-(5-{[(1H-pyrazol-4-yl)amino]methyl}-1,3,4-oxadiazol-2-yl)-1-(2,2,2-trifluoroethyl)-1H-indol-4-amine | 475.2 |

TABLE 8-continued

| Compound No. | Structure | IUPAC | LC-MS (ES+, m/z) |
|---|---|---|---|
| 113B | 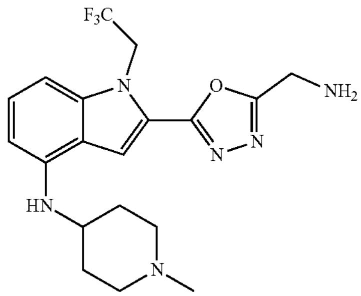 [SMILES: CN1CCC(Nc2cccc3c2cc(-c2nnc(CN)o2)n3CC(F)(F)F)CC1] | 2-(5-(aminomethyl)-1,3,4-oxadiazol-2-yl)-N-(1-methylpiperidin-4-yl)-1-(2,2,2-trifluoroethyl)-1H-indol-4-amine | |
| 114B | 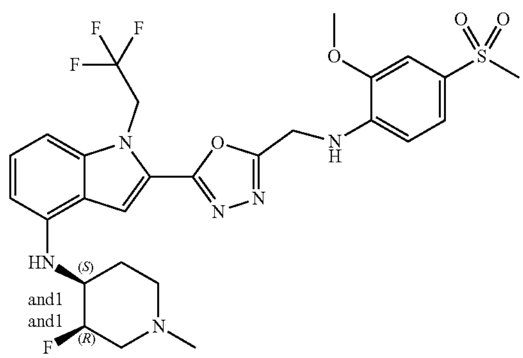 | (+/−)-N-[(3R,4S)-3-fluoro-1-methylpiperidin-4-yl]-2-(5-{[(4-methanesulfonyl-2-methoxyphenyl)amino]methyl}-1,3,4-oxadiazol-2-yl)-1-(2,2,2-trifluoroethyl)-1H-indol-4-amine | 611.2 |
| 115B | 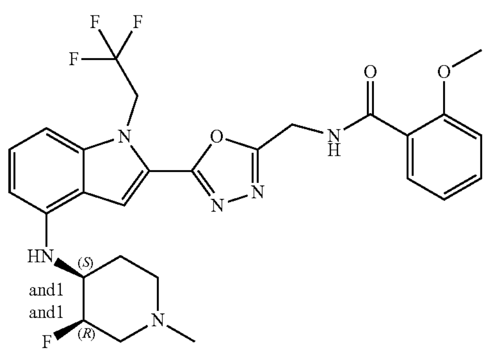 | (+/−)-N-{[5-(4-{[(3R,4S)-3-fluoro-1-methylpiperidin-4-yl]amino}-1-(2,2,2-trifluoroethyl)-1H-indol-2-yl)-1,3,4-oxadiazol-2-yl]methyl}-2-methoxybenzamide | 561.2 |
| 116B | 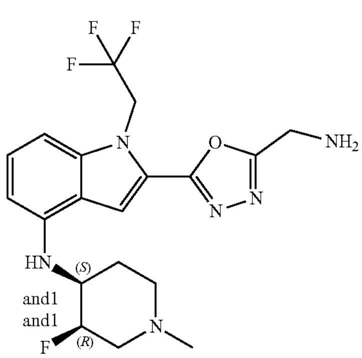 | (+/−)-2-[5-(aminomethyl)-1,3,4-oxadiazol-2-yl]-N-[(3R,4S)-3-fluoro-1-methylpiperidin-4-yl]-1-(2,2,2-trifluoroethyl)-1H-indol-4-amine | 427.1 |

TABLE 8-continued

| Compound No. | Structure | IUPAC | LC-MS (ES+, m/z) |
| --- | --- | --- | --- |
| 117B | 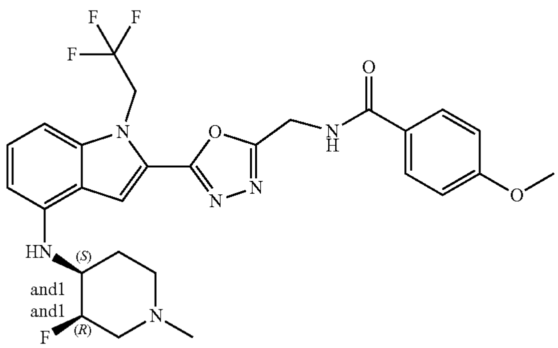 | (+/−)-N-{[5-(4-{[(3R,4S)-3-fluoro-1-methylpiperidin-4-yl]amino}-1-(2,2,2-trifluoroethyl)-1H-indol-2-yl)-1,3,4-oxadiazol-2-yl]methyl}-4-methoxybenzamide | 561.2 |
| 118B | 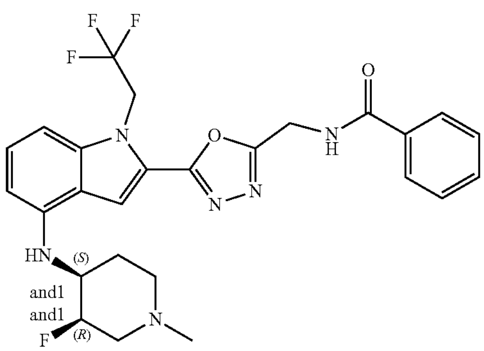 | (+/−)-N-{[5-(4-{[(3R,4S)-3-fluoro-1-methylpiperidin-4-yl]amino}-1-(2,2,2-trifluoroethyl)-1H-indol-2-yl)-1,3,4-oxadiazol-2-yl]methyl}benzamide | 531.2 |
| 119B | 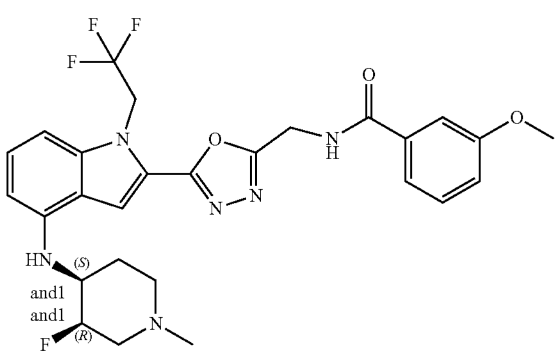 | (+/−)-N-{[5-(4-{[(3R,4S)-3-fluoro-1-methylpiperidin-4-yl]amino}-1-(2,2,2-trifluoroethyl)-1H-indol-2-yl)-1,3,4-oxadiazol-2-yl]methyl}-3-methoxybenzamide | 561.2 |
| 120B | 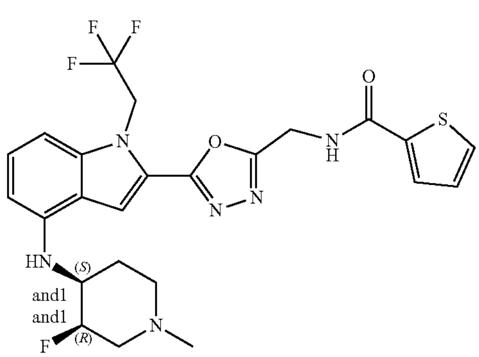 | (+/−)-N-{[5-(4-{[(3R,4S)-3-fluoro-1-methylpiperidin-4-yl]amino}-1-(2,2,2-trifluoroethyl)-1H-indol-2-yl)-1,3,4-oxadiazol-2-yl]methyl}thiophene-2-carboxamide | 537.1 |

TABLE 8-continued

| Compound No. | Structure | IUPAC | LC-MS (ES+, m/z) |
|---|---|---|---|
| 121B | 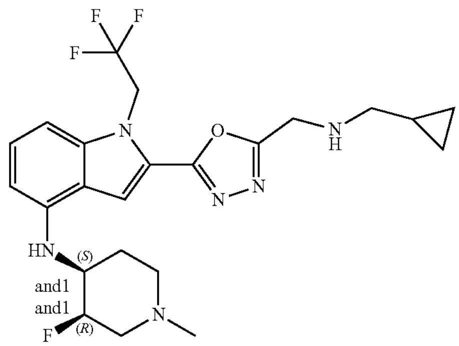 | (+/−)-2-(5-{[(cyclopropyl-methyl)amino]methyl}-1,3,4-oxadiazol-2-yl)-N-[(3R,4S)-3-fluoro-1-methylpiperidin-4-yl]-1-(2,2,2-trifluoroethyl)-1H-indol-4-amine | 481.1 |
| 122B | 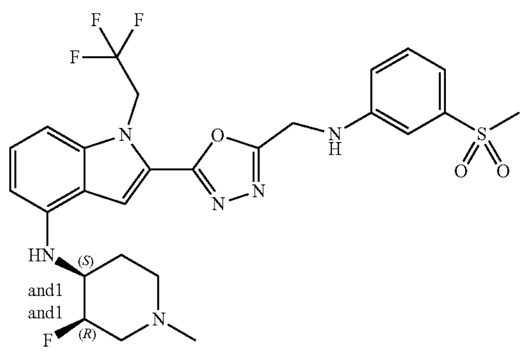 | (+/−)-N-[(3R,4S)-3-fluoro-1-methylpiperidin-4-yl]-2-(5-{[(3-methanesulfonyl-phenyl)amino]methyl}-1,3,4-oxadiazol-2-yl)-1-(2,2,2-trifluoroethyl)-1H-indol-4-amine | 581.2 |
| 123B | 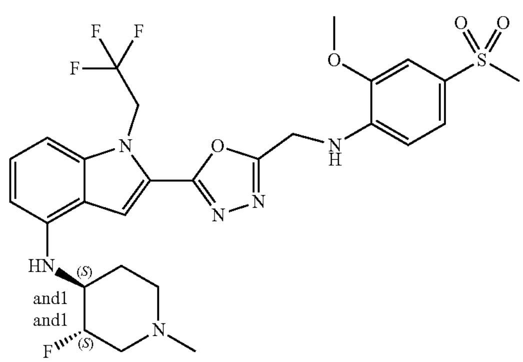 | (+/−)-N-[(3R,4R)-3-fluoro-1-methylpiperidin-4-yl]-2-(5-{[(4-methanesulfonyl-2-methoxyphenyl)amino]methyl}-1,3,4-oxadiazol-2-yl)-1-(2,2,2-trifluoroethyl)-1H-indol-4-amine | 611.3 |
| 124B | 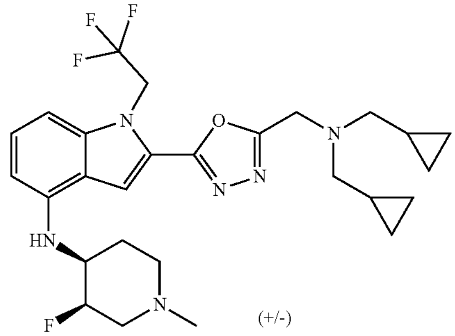 [SMILES: CN1CC[C@H](Nc2cccc3c2cc(-c2nnc(CN(CC4CC4)CC4CC4)o2)n3CC(F)(F)F)[C@H](F)C1] | (+/−)-2-(5-((bis(cyclopropyl-methyl)amino)methyl)-1,3,4-oxadiazol-2-yl)-N-((3R,4S)-3-fluoro-1-methylpiperidin-4-yl)-1-(2,2,2-trifluoroethyl)-1H-indol-4-amine | 481.1 |

TABLE 8-continued

| Compound No. | Structure | IUPAC | LC-MS (ES+, m/z) |
|---|---|---|---|
| 125B | 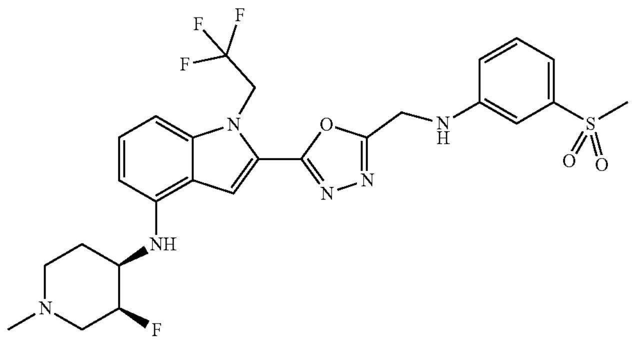 | (+/−)-N-((3S,4R)-3-fluoro-1-methylpiperidin-4-yl)-2-(5-(((3-(methylsulfonyl)phenyl)amino)methyl)-1,3,4-oxadiazol-2-yl)-1-(2,2,2-trifluoroethyl)-1H-indol-4-amine | 581.2 |
| 126B | 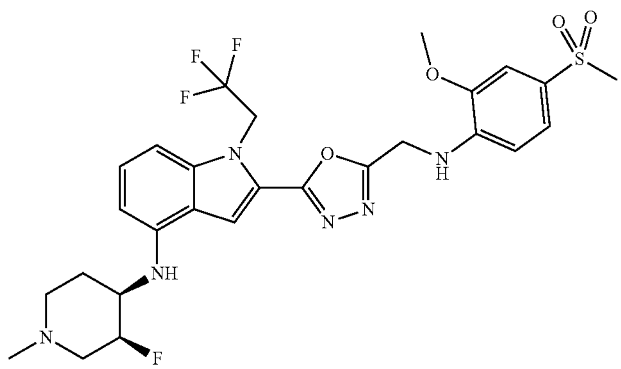 | (+/−)-N-((3S,4R)-3-fluoro-1-methylpiperidin-4-yl)-2-(5-(((2-methoxy-4-(methylsulfonyl)phenyl)amino)methyl)-1,3,4-oxadiazol-2-yl)-1-(2,2,2-trifluoroethyl)-1H-indol-4-amine | 611.2 |
| 127B | 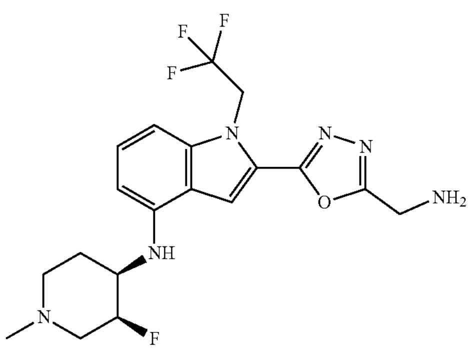 [SMILES: CN1CC[C@@H](Nc2cccc3c2cc(-c2nnc(CN)o2)n3CC(F)(F)F)[C@@H](F)C1] | (+/−)-2-(5-(aminomethyl)-1,3,4-oxadiazol-2-yl)-N-((3S,4R)-3-fluoro-1-methylpiperidin-4-yl)-1-(2,2,2-trifluoroethyl)-1H-indol-4-amine | 427.1 |
| 128B | 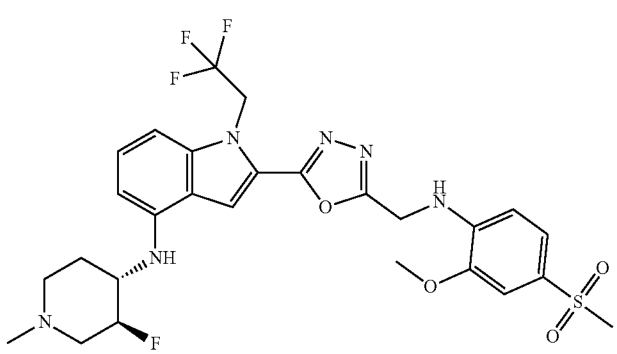 | (+/−)-N-((3S,4S)-3-fluoro-1-methylpiperidin-4-yl)-2-(5-(((2-methoxy-4-(methylsulfonyl)phenyl)amino)methyl)-1,3,4-oxadiazol-2-yl)-1-(2,2,2-trifluoroethyl)-1H-indol-4-amine | |

TABLE 8-continued

| Compound No. | Structure | IUPAC | LC-MS (ES+, m/z) |
|---|---|---|---|
| 129B | 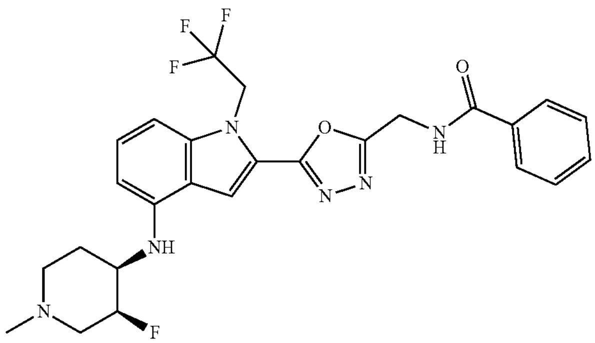 [SMILES: CN1CC[C@@H](Nc2cccc3c2cc(-c2nnc(CNC(=O)c4ccccc4)o2)n3CC(F)(F)F)[C@@H](F)C1] | N-((5-(4-(((3S,4R)-3-fluoro-1-methylpiperidin-4-yl)amino)-1-(2,2,2-trifluoroethyl)-1H-indol-2-yl)-1,3,4-oxadiazol-2-yl)methyl)benzamide | 531.2 |
| 130B | 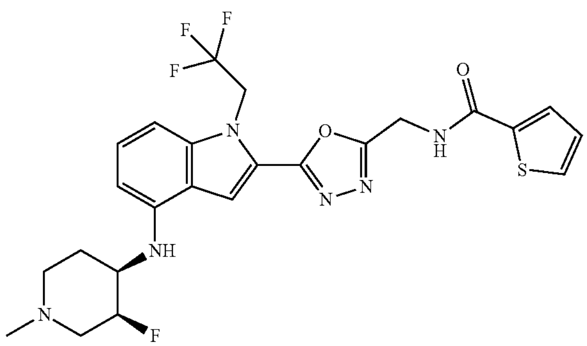 [SMILES: CN1CC[C@@H](Nc2cccc3c2cc(-c2nnc(CNC(=O)c4cccs4)o2)n3CC(F)(F)F)[C@@H](F)C1] | (+/−)-N-((5-(4-(((3S,4R)-3-fluoro-1-methylpiperidin-4-yl)amino)-1-(2,2,2-trifluoroethyl)-1H-indol-2-yl)-1,3,4-oxadiazol-2-yl)methyl)thiophene-2-carboxamide | 537.1 |
| 131B | 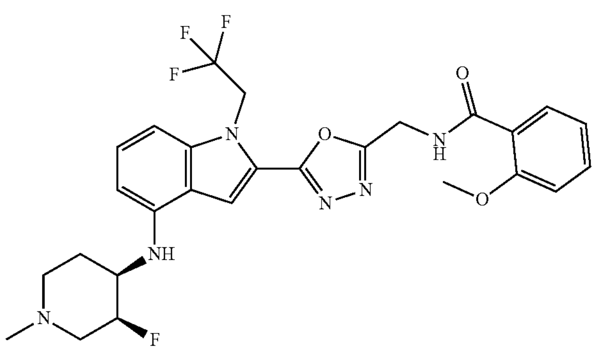 [SMILES: COc1ccccc1C(=O)NCc1nnc(-c2cc3c(N[C@@H]4CCN(C)C[C@@H]4F)cccc3n2CC(F)(F)F)o1] | (+/−)-N-((5-(4-(((3S,4R)-3-fluoro-1-methylpiperidin-4-yl)amino)-1-(2,2,2-trifluoroethyl)-1H-indol-2-yl)-1,3,4-oxadiazol-2-yl)methyl)-2-methoxybenzamide | 561.2 |
| 132B | 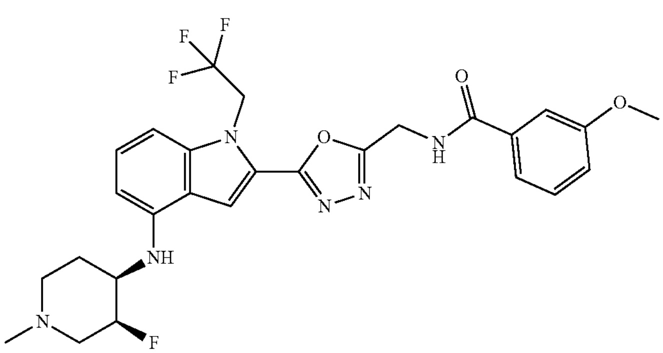 | (+/−)-N-((5-(4-(((3S,4R)-3-fluoro-1-methylpiperidin-4-yl)amino)-1-(2,2,2-trifluoroethyl)-1H-indol-2-yl)-1,3,4-oxadiazol-2-yl)methyl)-3-methoxybenzamide | 561.2 |

TABLE 8-continued

| Compound No. | Structure | IUPAC | LC-MS (ES+, m/z) |
|---|---|---|---|
| 133B | 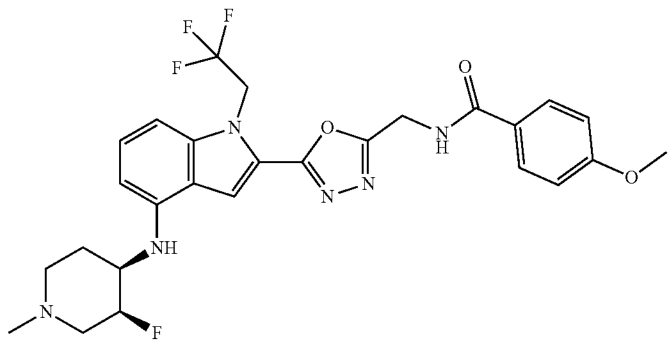 | (+/−)-N-((5-(4-(((3S,4R)-3-fluoro-1-methylpiperidin-4-yl)amino)-1-(2,2,2-trifluoroethyl)-1H-indol-2-yl)-1,3,4-oxadiazol-2-yl)methyl)-4-methoxybenzamide | 561.2 |
| 134B | 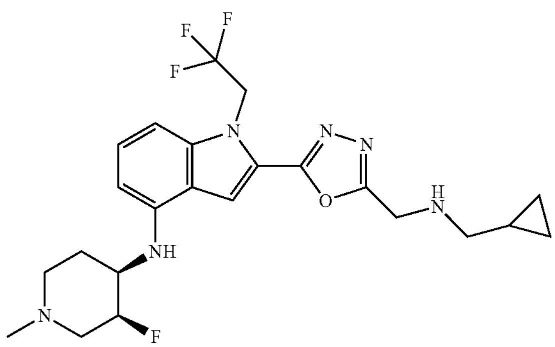 [SMILES: CN1CC[C@@H](Nc2cccc3c2cc(-c2nnc(CNCC4CC4)o2)n3CC(F)(F)F)[C@@H](F)C1] | (+/−)-2-(5-(((cyclopropylmethyl)amino)methyl)-1,3,4-oxadiazol-2-yl)-N-((3S,4R)-3-fluoro-1-methylpiperidin-4-yl)-1-(2,2,2-trifluoroethyl)-1H-indol-4-amine | 481.1 |
| 135B | 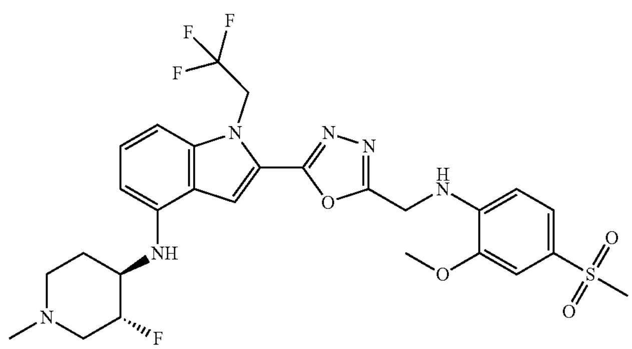 | (+/−)-N-((3R,4R)-3-fluoro-1-methylpiperidin-4-yl)-2-(5-(((2-methoxy-4-(methylsulfonyl)phenyl)amino)methyl)-1,3,4-oxadiazol-2-yl)-1-(2,2,2-trifluoroethyl)-1H-indol-4-amine | |
| 288B | 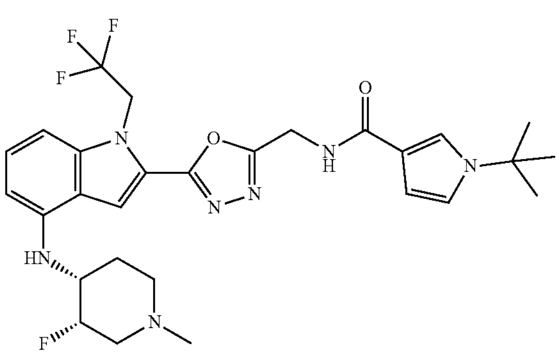 [SMILES: CN1CC[C@@H](Nc2cccc3c2cc(-c2nnc(CNC(=O)c4ccn(C(C)(C)C)c4)o2)n3CC(F)(F)F)[C@@H](F)C1] | 1-tert-butyl-N-{[5-(4-{[(3S,4R)-3-fluoro-1-methylpiperidin-4-yl]amino}-1-(2,2,2-trifluoroethyl)-1H-indol-2-yl)-1,3,4-oxadiazol-2-yl]methyl}-1H-pyrrole-3-carboxamide | 576.3 |

Example 69: Synthesis of Compounds 143B-152B and 154B-156B

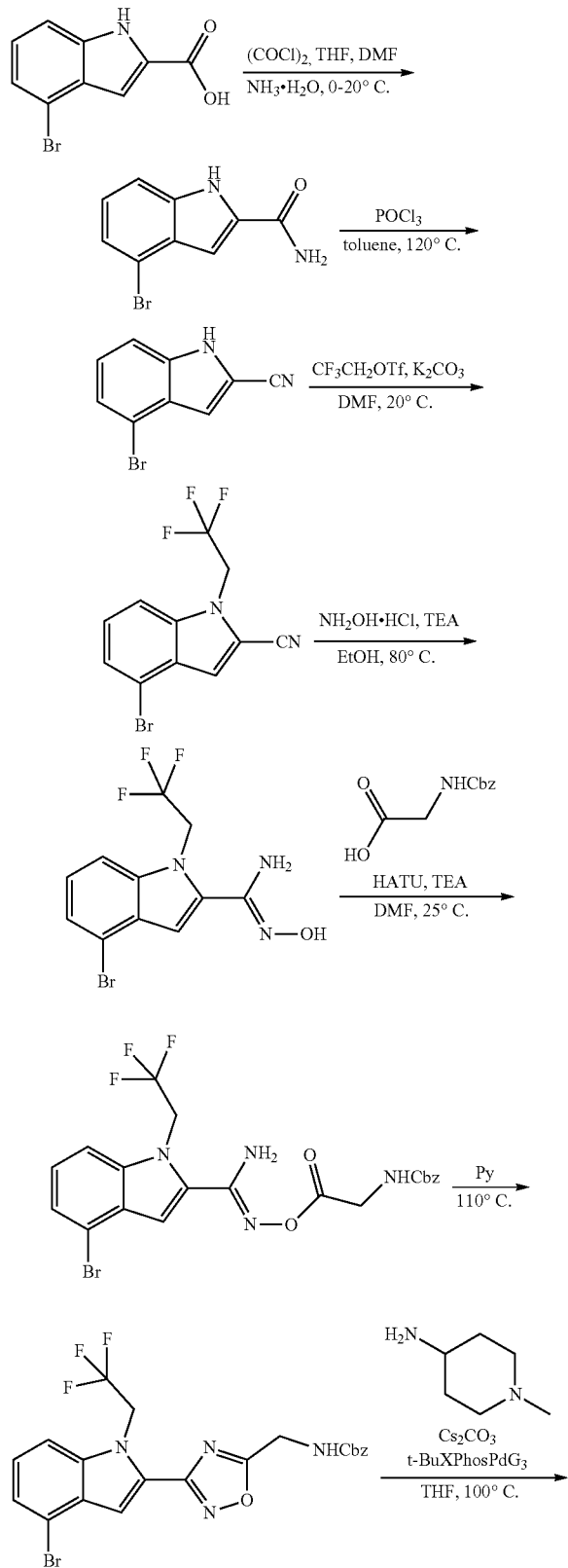

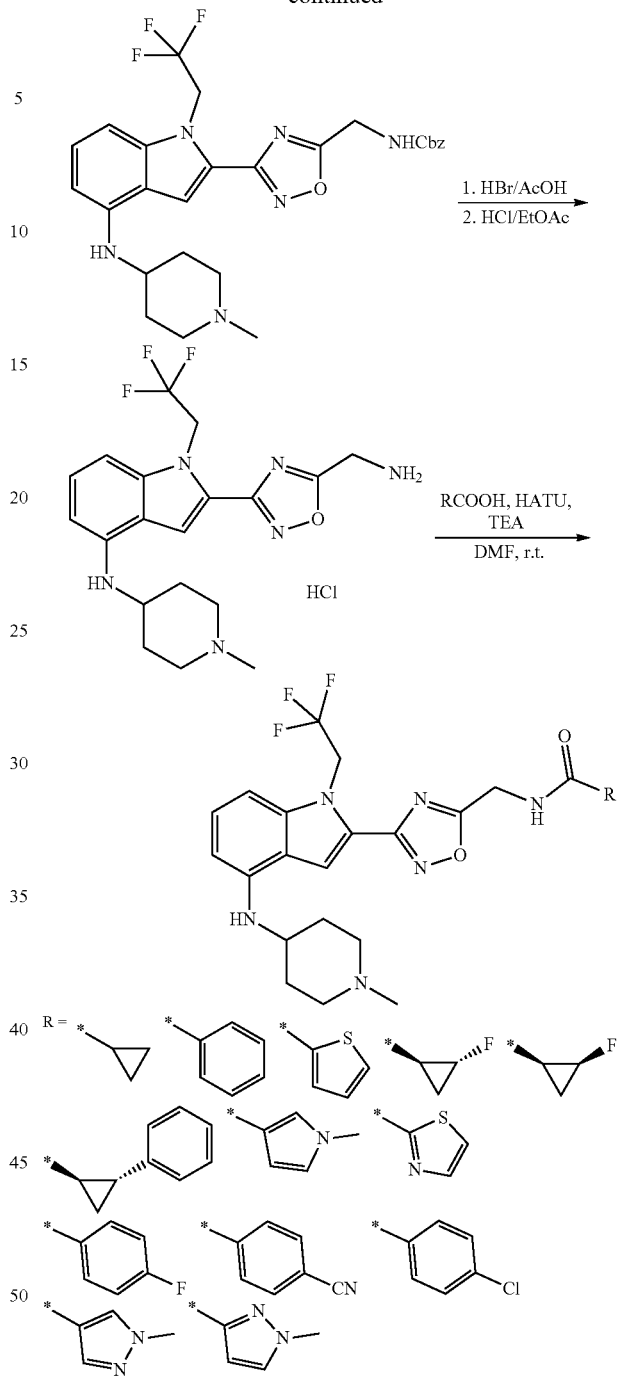

Preparation of 4-bromo-1H-indole-2-carboxamide: To a mixture of 4-bromo-1H-indole-2-carboxylic acid (15 g, 62.5 mmol, 1 eq) and oxalyl chloride (81.23 mmol, 7.11 mL, 1.3 eq) in THF (40 mL) was added DMF (6.25 mmol, 481 μL, 0.1 eq) in one portion at 0° C. under nitrogen. The mixture was stirred at 0° C. for 5 min. The reaction was further stirred at 20° C. for 115 min, and ammonium hydroxide (62.5 mmol, 8.59 mL, 28% purity, 1 eq) was added. The resulting mixture was stirred at 0° C. for 5 min, and at 20° C. for 10 min. The residue was poured into ice water (w/w=1/1) (200 mL). The aqueous phase was extracted with EA (100 mL×3). The combined organic phase was washed with brine (100 mL×3), dried with anhydrous sodium sulfate, filtered, and concentrated in vacuo. The residue was washed with PE (60 mL) and EA (20 mL) to afford 4-bromo-1H-indole-2-carboxamide (11 g, 46 mmol, 73.6% yield) as a light yellow solid. LC-MS (ES+, m/z): 239.0.

Preparation of 4-bromo-1H-indole-2-carbonitrile: To a mixture of 4-bromo-1H-indole-2-carboxamide (11 g, 46.01 mmol, 1 eq) in toluene (20 mL) was added phosphorus oxychloride (184.1 mmol, 17.10 mL, 4 eq) in one portion under nitrogen. The mixture was heated and stirred at 120° C. for 30 min. The residue was poured into ice water (w/w=1/1) (200 mL). The aqueous phase was extracted with EA (100 mL×3). The combined organic phase was washed with brine (100 mL×3), dried with anhydrous sodium sulfate, filtered, and concentrated in vacuo. The residue was purified by silica gel chromatography (PE/EA=1:0 to 2:1) to afford 4-bromo-1H-indole-2-carbonitrile as a light-yellow solid in 88.5% yield.

Preparation of 4-bromo-1-(2,2,2-trifluoroethyl)-1H-indole-2-carbonitrile: To a mixture of 4-bromo-1H-indole-2-carbonitrile (9 g, 40.7 mmol, 1 eq) and $CF_3CH_2OTf$ (18.9 g, 81.4 mmol, 2 eq) in DMF (90 mL) was added potassium carbonate (16.88 g, 122.1 mmol, 3 eq) at 20° C. under nitrogen. The mixture was stirred at 20° C. for 30 min. The residue was poured into ice water (w/w=1/1) (300 mL). The aqueous phase was extracted with EA (100 mL×3). The combined organic phase was washed with brine (100 mL×3), dried with anhydrous sodium sulfate, filtered, and concentrated in vacuo. The residue was purified by silica gel chromatography to afford 4-bromo-1-(2,2,2-trifluoroethyl)-1H-indole-2-carbonitrile (11 g, 36.3 mmol, 89.1% yield) as a white solid.

Preparation of 4-bromo-N'-hydroxy-1-(2,2,2-trifluoroethyl)-1H-indole-2-carboximidamide: To a mixture of 4-bromo-1-(2,2,2-trifluoroethyl)-1H-indole-2-carbonitrile (4 g, 13.20 mmol, 1 eq) in ethanol (40 mL) were added hydroxylamine hydrochloride (1.38 g, 19.80 mmol, 1.5 eq) and TEA (2.67 g, 26.40 mmol, 3.67 mL, 2 eq) in one portion under nitrogen. The mixture was heated and stirred at 80° C. for 30 min. The residue was poured into ice water (w/w=1/1) (300 mL). The aqueous phase was extracted with EA (100 mL×3). The combined organic phase was washed with brine (100 mL×3), dried with anhydrous sodium sulfate, filtered, and concentrated in vacuo to afford 4-bromo-N'-hydroxy-1-(2,2,2-trifluoroethyl)-1H-indole-2-carboximidamide (4 g, crude) as a light-yellow solid. LC-MS (ES+, m/z): 336.0.

Preparation of benzyl (2-(((amino(4-bromo-1-(2,2,2-trifluoroethyl)-1H-indol-2-yl)methylene)amino)oxy)-2-oxoethyl)carbamate: To a solution of ((benzyloxy)carbonyl)glycine (2.80 g, 13.4 mmol, 1.5 eq) in DMF (30 mL) were added HATU (4.07 g, 10.7 mmol, 1.2 eq) and TEA (44.6 mmol, 6.21 mL, 5 eq) in one portion at 20° C. under nitrogen. The mixture was stirred at 20° C. for 5 min, and then 4-bromo-N'-hydroxy-1-(2,2,2-trifluoroethyl)-1H-indole-2-carboximidamide (3 g, 8.9 mmol, 1 eq) was added. The mixture was stirred at 20° C. for 5 min. The residue was poured into ice water (w/w=1/1) (150 mL). The aqueous phase was extracted with EA (50 mL×3). The combined organic phase was washed with brine (50 mL×3), dried with anhydrous sodium sulfate, filtered, and concentrated in vacuo. The crude product was purified by silica gel chromatography to afford benzyl (2-(((amino(4-bromo-1-(2,2,2-trifluoroethyl)-1H-indol-2-yl)methylene)amino)oxy)-2-oxoethyl)carbamate (4 g, 7.59 mmol, 85.0% yield) as a white solid. LC-MS (ES+, m/z): 527.0.

Preparation of benzyl ((3-(4-bromo-1-(2,2,2-trifluoroethyl)-1H-indol-2-yl)-1,2,4-oxadiazol-5-yl)methyl)carbamate: Benzyl (2-(((amino(4-bromo-1-(2,2,2-trifluoroethyl)-1H-indol-2-yl)methylene)amino)oxy)-2-oxoethyl)carbamate (4 g, 7.6 mmol, 1 eq) was added to pyridine (10 mL) under nitrogen. The mixture was heated and stirred at 110° C. for 2 hrs. The residue was poured into ice water (w/w=1/1) (50 mL). The aqueous phase was extracted with EA (20 mL×3). The combined organic phase was washed with brine (20 mL×3), dried with anhydrous sodium sulfate, filtered, and concentrated in vacuo. The reaction was washed with DCM (30 mL) and PE (50 mL) to afford benzyl ((3-(4-bromo-1-(2,2,2-trifluoroethyl)-1H-indol-2-yl)-1,2,4-oxadiazol-5-yl)methyl)carbamate (3 g, 5.9 mmol, 77.7% yield) as a white solid. LC-MS (ES+, m/z): 509.1.

Preparation of benzyl ((3-(4-((1-methylpiperidin-4-yl)amino)-1-(2,2,2-trifluoroethyl)-1H-indol-2-yl)-1,2,4-oxadiazol-5-yl)methyl)carbamate: To a mixture of benzyl ((3-(4-bromo-1-(2,2,2-trifluoroethyl)-1H-indol-2-yl)-1,2,4-oxadiazol-5-yl)methyl)carbamate (2.3 g, 4.5 mmol, 1 eq) and 1-methylpiperidin-4-amine (5.16 g, 45.2 mmol, 10 eq) in THF (20 mL) were added t-BuXPhos Palladium Generation 3 (1.08 g, 1.35 mmol, 0.3 eq) and cesium carbonate (4.41 g, 13.55 mmol, 3 eq). The mixture was heated and stirred at 100° C. for 4 hours. TLC analysis showed~10% of the starting material remained. The residue was poured into a 2M aqueous EDTA solution (w/w=1/1) (100 mL) and stirred for 60 min. The aqueous phase was extracted with EA (50 mL×3). The combined organic phase was washed with brine (50 mL×3), dried with anhydrous sodium sulfate, filtered, and concentrated in vacuo. The residue was purified by silica gel chromatography to afford benzyl ((3-(4-((1-methylpiperidin-4-yl)amino)-1-(2,2,2-trifluoroethyl)-1H-indol-2-yl)-1,2,4-oxadiazol-5-yl)methyl)carbamate (1.4 g, 2.58 mmol, 57.1% yield) as a brown oil. LC-MS (ES+, m/z): 543.2.

Preparation of 2-(5-(aminomethyl)-1,2,4-oxadiazol-3-yl)-N-(1-methylpiperidin-4-yl)-1-(2,2,2-trifluoroethyl)-1H-indol-4-amine: Benzyl ((3-(4-((1-methylpiperidin-4-yl)amino)-1-(2,2,2-trifluoroethyl)-1H-indol-2-yl)-1,2,4-oxadiazol-5-yl)methyl)carbamate (1.4 g, 2.6 mmol, 1 eq) was added to hydrogen bromide/acetic acid (2.58 mmol, 5 mL, 1 eq) at 20° C. The mixture was stirred at 20° C. for 30 min. The residue was poured into 2 M aqueous sodium carbonate (50 mL) and stirred for 5 min. The aqueous phase was extracted with EA (20 mL×3). The combined organic phase was washed with brine (20 mL×3), dried with anhydrous sodium sulfate, and filtered. 4 M HCl/EA (10 mL) was added to the filtrate, and the filtrate was concentrated in vacuo to afford 2-(5-(aminomethyl)-1,2,4-oxadiazol-3-yl)-N-(1-methylpiperidin-4-yl)-1-(2,2,2-trifluoroethyl)-1H-indol-4-amine (1.1 g, crude, HCl) as a brown solid. LC-MS (ES+, m/z): 409.1.

Preparation of compounds 143B-152B and 154B-156B: To a solution of RCOOH (1 eq) in DMF (1~3 mL) were added HATU (2 eq) and TEA (5 eq) in one portion at 20° C. under nitrogen. The mixture was stirred at 20° C. for 5 min, and 2-(5-(aminomethyl)-1,2,4-oxadiazol-3-yl)-N-(1-methylpiperidin-4-yl)-1-(2,2,2-trifluoroethyl)-1H-indol-4-amine (100 mg, 195.3 μmol, 1 eq, 2HCl) was added. The mixture was stirred at 20° C. for 5 min. The residue was poured into ice water (w/w=1/1) (100 mL). The aqueous phase was extracted with EA (50 mL×3). The combined organic phase was washed with brine (50 mL×3), dried with anhydrous sodium sulfate, filtered, and concentrated in vacuo. The crude product was purified by preparative-TLC to afford the desired product as a light-yellow solid. N-[(3-{4-[(1-methylpiperidin-4-yl)amino]-1-(2,2,2-trifluoroethyl)-1H-indol-2-yl}-1,2,4-oxadiazol-5-yl)methyl]cyclopropanecarboxamide (Compound 146B), 20.4% yield, LC-MS (ES+, m/z):

577.1; N-[(3-{4-[(1-methylpiperidin-4-yl)amino]-1-(2,2,2-trifluoroethyl)-1H-indol-2-yl}-1,2,4-oxadiazol-5-yl)methyl]benzamide (Compound 144B), 19.8% yield, LC-MS (ES+, m/z): 513.2; N-[(3-{4-[(1-methylpiperidin-4-yl)amino]-1-(2,2,2-trifluoroethyl)-1H-indol-2-yl}-1,2,4-oxadiazol-5-yl)methyl]thiophene-2-carboxamide (Compound 143B), 19.4% yield, LC-MS (ES+, m/z): 519.2; (1S,2R)-2-fluoro-N-[(3-{4-[(1-methylpiperidin-4-yl)amino]-1-(2,2,2-trifluoroethyl)-1H-indol-2-yl}-1,2,4-oxadiazol-5-yl)methyl]cyclopropane-1-carboxamide (Compound 145B), 19.4% yield, LC-MS (ES+, m/z): 495.2; (1S,2S)-2-fluoro-N-[(3-{4-[(1-methylpiperidin-4-yl)amino]-1-(2,2,2-trifluoroethyl)-1H-indol-2-yl}-1,2,4-oxadiazol-5-yl)methyl]cyclopropane-1-carboxamide (Compound 147B), 16.7% yield, LC-MS (ES+, m/z): 495.2; (+/−)-(1R,2R)—N-[(3-{4-[(1-methylpiperidin-4-yl)amino]-1-(2,2,2-trifluoroethyl)-1H-indol-2-yl}-1,2,4-oxadiazol-5-yl)methyl]-2-phenylcyclopropane-1-carboxamide (Compound 156B), 17.1% yield, LC-MS (ES+, m/z): 553.3; 1-methyl-N-[(3-{4-[(1-methylpiperidin-4-yl)amino]-1-(2,2,2-trifluoroethyl)-1H-indol-2-yl}-1,2,4-oxadiazol-5-yl)methyl]-1H-pyrrole-3-carboxamide (Compound 152B), 19.55% yield, LC-MS (ES+, m/z): 516.2; N-[(3-{4-[(1-methylpiperidin-4-yl)amino]-1-(2,2,2-trifluoroethyl)-1H-indol-2-yl}-1,2,4-oxadiazol-5-yl)methyl]-1,3-thiazole-2-carboxamide (Compound 149B), 26.9% yield, LC-MS (ES+, m/z): 520; 4-fluoro-N-[(3-{4-[(1-methylpiperidin-4-yl)amino]-1-(2,2,2-trifluoroethyl)-1H-indol-2-yl}-1,2,4-oxadiazol-5-yl)methyl]benzamide (Compound 150B), 19.8% yield, LC-MS (ES+, m/z): 531.2; 4-cyano-N-[(3-{4-[(1-methylpiperidin-4-yl)amino]-1-(2,2,2-trifluoroethyl)-1H-indol-2-yl}-1,2,4-oxadiazol-5-yl)methyl]benzamide (Compound 151B), 18.9% yield, LC-MS (ES+, m/z): 538.1; 4-chloro-N-[(3-{4-[(1-methylpiperidin-4-yl)amino]-1-(2,2,2-trifluoroethyl)-1H-indol-2-yl}-1,2,4-oxadiazol-5-yl)methyl]benzamide (Compound 148B), 19.4% yield, LC-MS (ES+, m/z): 547; 1-methyl-N-[(3-{4-[(1-methylpiperidin-4-yl)amino]-1-(2,2,2-trifluoroethyl)-1H-indol-2-yl}-1,2,4-oxadiazol-5-yl)methyl]-1H-pyrazole-4-carboxamide (Compound 154B), 35.90% yield, LC-MS (ES+, m/z): 517.2; 1-methyl-N-[(3-{4-[(1-methylpiperidin-4-yl)amino]-1-(2,2,2-trifluoroethyl)-1H-indol-2-yl}-1,2,4-oxadiazol-5-yl)methyl]-1H-pyrazole-3-carboxamide (Compound 155B), 35.44% yield, LC-MS (ES+, m/z): 517.2.

Example 70: Synthesis of 3-1(3-{4-[(1-methylpiperidin-4-yl)amino]-1-(2,2,2-trifluoroethyl)-1H-indol-2-yl}-1,2,4-oxadiazol-5-yl)methyl]-1-phenylurea (Compound 153B)

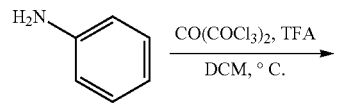

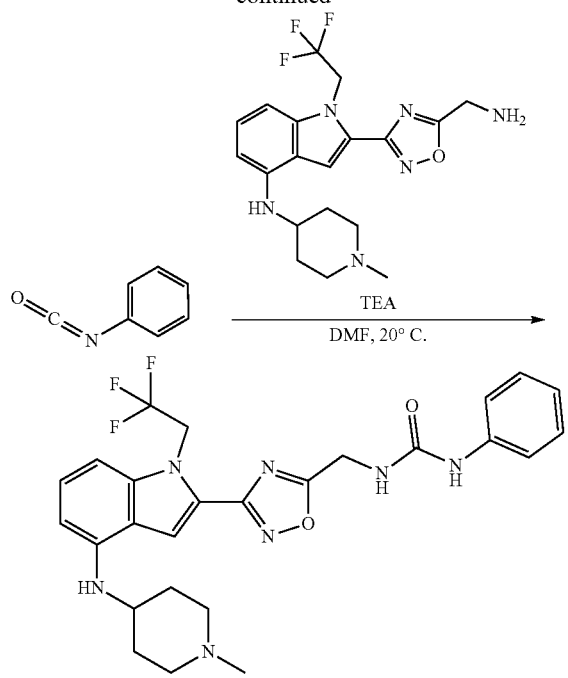

Preparation of isocyanatobenzene: To a mixture of aniline (500 mg, 5.37 mmol, 490.20 µL, 1 eq) and triphosgene (1.59 g, 5.37 mmol, 1 eq) in DCM (5 mL) was added TEA (4.67 mmol, 650 µL, 0.87 eq) at 0° C. under nitrogen. The mixture was stirred at 0° C. for 1 hour. The solution quenched with benzylamine. The reaction was concentrated in vacuo to afford isocyanatobenzene (0.3 g, crude) as a red solid.

Preparation of 3-[(3-{4-[(1-methylpiperidin-4-yl)amino]-1-(2,2,2-trifluoroethyl)-1H-indol-2-yl}-1,2,4-oxadiazol-5-yl)methyl]-1-phenylurea (Compound 153B): To a mixture of 2-(5-(aminomethyl)-1,2,4-oxadiazol-3-yl)-N-(1-methylpiperidin-4-yl)-1-(2,2,2-trifluoroethyl)-1H-indol-4-amine (100 mg, 245 µmol, 1 eq) and isocyanatobenzene (87.5 mg, 735 µmol, 79.5 µL, 3 eq) in DMF (1 mL) was added TEA (735 µmol, 102 µL, 3 eq) at 20° C. under nitrogen. The mixture was stirred at 20° C. for 10 min. The residue was poured into ice water (w/w=1/1) (100 mL). The aqueous phase was extracted with EA (30 mL×3). The combined organic phase was washed with brine (30 mL×3), dried with anhydrous sodium sulfate, filtered, and concentrated in vacuo. The crude product was purified by preparative-TLC to afford 3-[(3-{4-[(1-methylpiperidin-4-yl)amino]-1-(2,2,2-trifluoroethyl)-1H-indol-2-yl}-1,2,4-oxadiazol-5-yl)methyl]-1-phenylurea (Compound 153B) (19.5 mg, 36.3 µmol, 14.8% yield) as a light yellow solid. LC-MS (ES+, m/z): 528.3.

Example 71: Synthesis of compounds (+/−)-N-{[3-(4-{[(3R,4S)-3-fluoro-1-methylpiperidin-4-yl]amino}-1-(2,2,2-trifluoroethyl)-1H-indol-2-yl)-1,2,4-oxadiazol-5-yl]methyl}cyclopropanecarboxamide (Compound 171B), (+/−)-N-{[3-(4-{[(3R,4S)-3-fluoro-1-methylpiperidin-4-yl]amino)-1-(2,2,2-trifluoroethyl)-1H-indol-2-yl)-1,2,4-oxadiazol-5-yl]methyl}benzamide (Compound 172B), (+/−)-N-{[3-(4-{[(3R,4S)-3-fluoro-1-methylpiperidin-4-yl]amino}-1-(2,2,2-trifluoroethyl)-1H-indol-2-yl)-1,2,4-oxadiazol-5-yl]methyl}thiophene-2-carboxamide (Compound 175B), (+/−)-N-{[3-(4-{[(3R,4S)-3-fluoro-1-methylpiperidin-4-yl]amino}-1-(2,2,2-trifluoroethyl)-1H-indol-2-yl)-1,2,4-oxadiazol-5-yl]methyl}thiophene-3-carboxamide (Compound 176B), and (+/−)-N-{[3-(4-{[(3R,4S)-3-fluoro-1-methylpiperidin-4-yl]amino}-1-(2,2,2-trifluoroethyl)-1H-indol-2-yl)-1,2,4-oxadiazol-5-yl]methyl}-1,3-thiazole-5-carboxamide (Compound 178B)

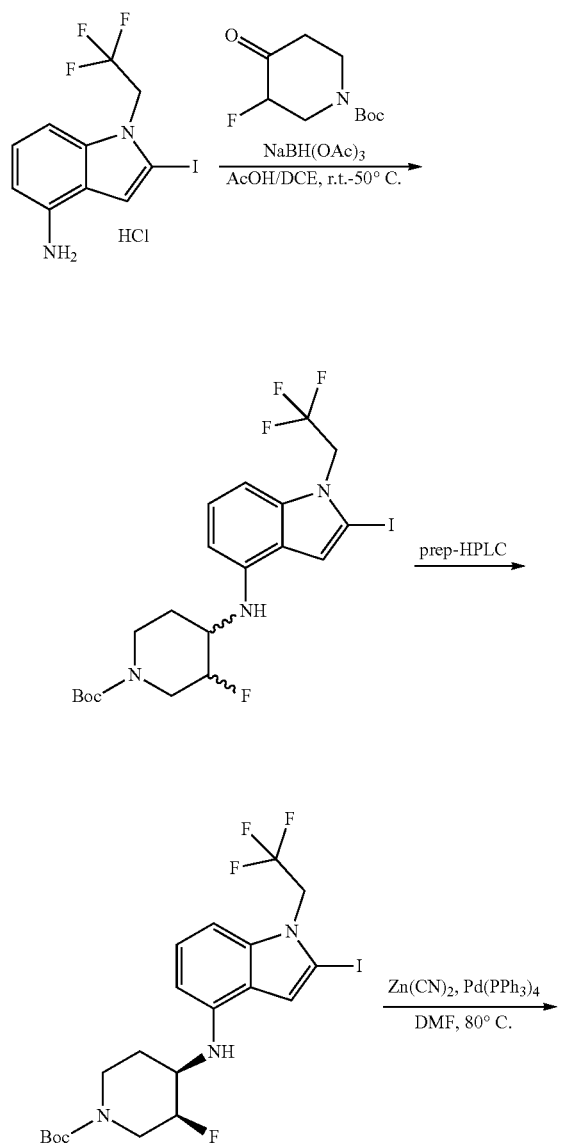

-continued

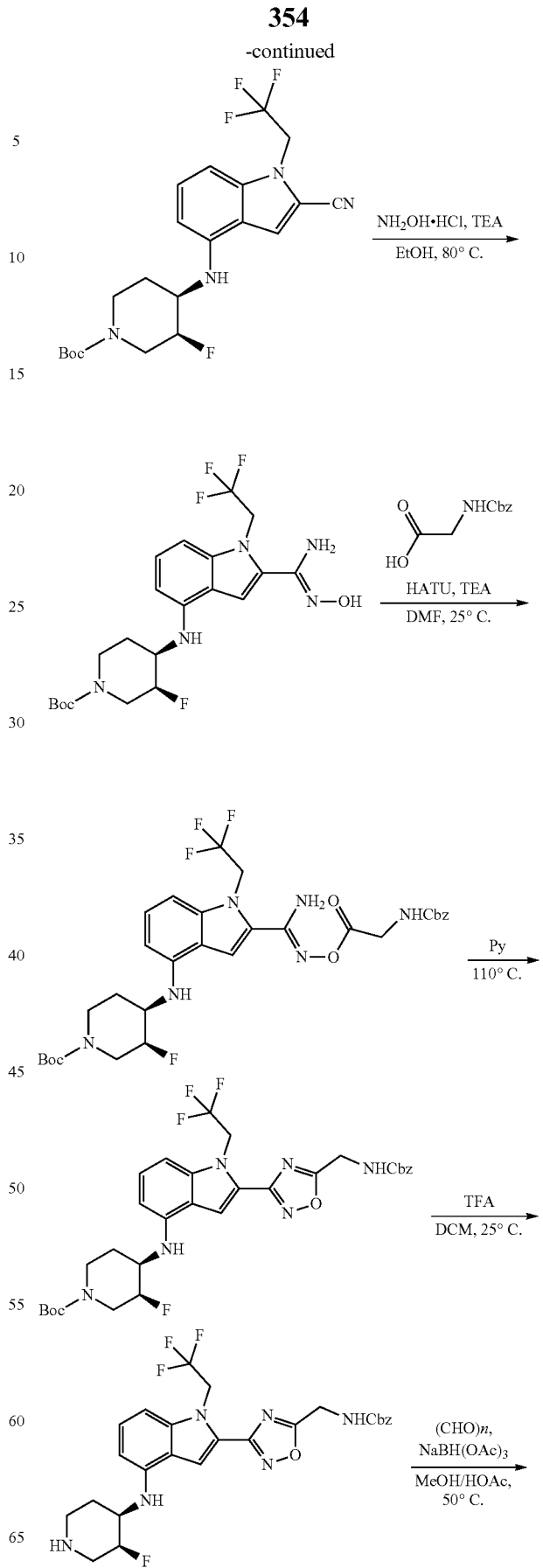

-continued

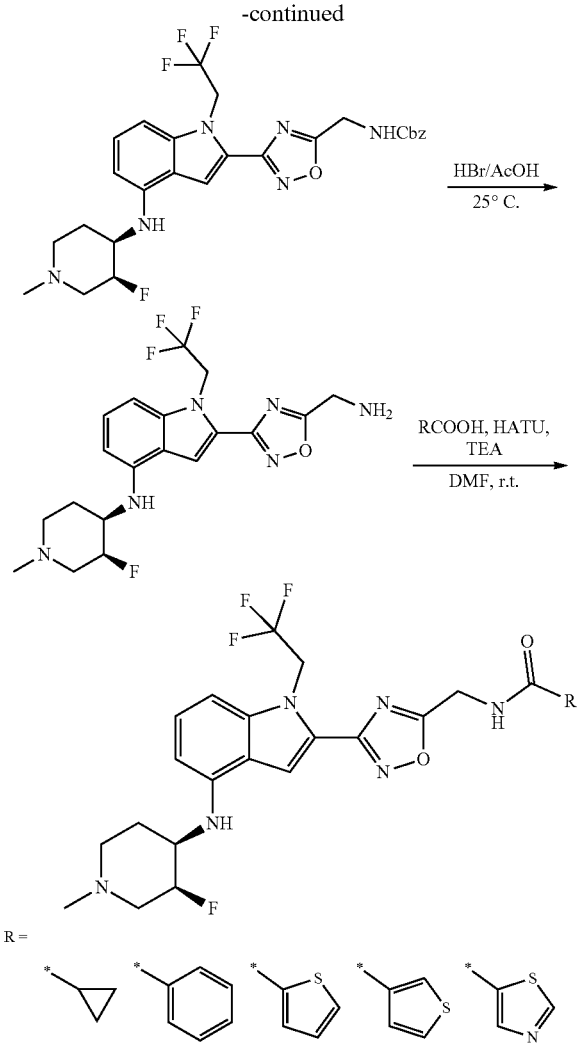

Preparation of (+/−)-tert-butyl (3S,4R)-3-fluoro-4-((2-iodo-1-(2,2,2-trifluoroethyl)-1H-indol-4-yl)amino)piperidine-1-carboxylate: To a solution of 2-iodo-1-(2,2,2-trifluoroethyl)-1H-indol-4-amine (30 g, 79.7 mmol, 1 eq, HCl) and tert-butyl 3-fluoro-4-oxopiperidine-1-carboxylate (86.54 g, 398.4 mmol, 5 eq) in acetic acid (900 mL) and 1,2-dichloroethane (300 mL) was added sodium triacetoxyborohydride (25.33 g, 119.5 mmol, 1.5 eq) at 25° C. After 30 min of stirring, sodium triacetoxyborohydride (25.33 g, 119.5 mmol, 1.5 eq) was added again in three equal portions (one portion every half hour). The resulting reaction mixture was stirred at 20-50° C. for 1.5 hr. The mixture was extracted with DCM (1000 mL×2). The organic phase was washed with water (1000 mL) and brine (1000 mL), dried with anhydrous sodium sulfate, filtered, and concentrated in vacuo. The residue was purified by preparative-HPLC to afford (+/−)-tert-butyl (3S,4R)-3-fluoro-4-((2-iodo-1-(2,2,2-trifluoroethyl)-1H-indol-4-yl)amino)piperidine-1-carboxylate (28 g, 64.9% yield) as a yellow solid. LC-MS (ES+, m/z): 542.1.

Preparation of (+/−)-tert-butyl (3S,4R)-4-((2-cyano-1-(2,2,2-trifluoroethyl)-11H-indol-4-yl)amino)-3-fluoropiperidine-1-carboxylate: To a solution of (+/−)-tert-butyl (3S,4R)-3-fluoro-4-((2-iodo-1-(2,2,2-trifluoroethyl)-1H-indol-4-yl)amino)piperidine-1-carboxylate (5.0 g, 9.24 mmol, 1 eq) in DMF (50 mL) were added zinc cyanide (3.25 g, 27.7 mmol, 3 eq) and tetrakis(triphenylphosphine)Palladium(0) (3.20 g, 2.77 mmol, 0.3 eq). The mixture was stirred at 80° C. for 2 hr. The mixture was poured into an 2M aqueous EDTA solution (10 mL) and stirred for 2 hr. The reaction was extracted with DCM (10 mL×2), and the organic phase was washed with water (10 mL) and brine (10 mL), dried with anhydrous sodium sulfate, filtered, and concentrated in vacuo. The residue was purified by column chromatography (SiO$_2$, PE:EA=1:1) to afford (+/−)-tert-butyl (3S,4R)-4-((2-cyano-1-(2,2,2-trifluoroethyl)-1H-indol-4-yl)amino)-3-fluoropiperidine-1-carboxylate (3.5 g, 86.0% yield) as a yellow solid. LC-MS (ES+, m/z): 441.2.

Preparation of (+/−)-tert-butyl (3S,4R)-3-fluoro-4-((2-(N'-hydroxycarbamimidoyl)-1-(2,2,2-trifluoroethyl)-1H-indol-4-yl)amino)piperidine-1-carboxylate: To a solution of (+/−)-tert-butyl (3S,4R)-4-((2-cyano-1-(2,2,2-trifluoroethyl)-1H-indol-4-yl)amino)-3-fluoropiperidine-1-carboxylate (5.0 g, 11.4 mmol, 1 eq) in ethanol (50 mL) were added hydroxylamine hydrochloride (1.18 g, 17.03 mmol, 1.5 eq) and TEA (22.70 mmol, 3.16 mL, 2 eq). The mixture was stirred at 80° C. for 2 hr. The residue was poured into ice water (w/w=1/1). The mixture was extracted with DCM (10 mL×2), and the organic phase was washed with water (10 mL) and brine (10 mL), dried with anhydrous sodium sulfate, filtered, and concentrated in vacuo to afforded (+/−)-tert-butyl (3S,4R)-3-fluoro-4-((2-(N'-hydroxycarbamimidoyl)-1-(2,2,2-trifluoroethyl)-1H-indol-4-yl)amino)piperidine-1-carboxylate (4 g) as a yellow solid.

Preparation of (+/−)-tert-butyl (3S,4R)-4-((2-(N'-((((benzyloxy)carbonyl)glycyl) oxy)carbamimidoyl)-1-(2,2,2-trifluoroethyl)-1H-indol-4-yl)amino)-3-fluoropiperidine-1-carboxylate: To a solution of (+/−)-((benzyloxy)carbonyl)glycine (2.98 g, 14.26 mmol, 1.5 eq) in DMF (50 mL) were added HATU (5.42 g, 14.3 mmol, 1.5 eq) and TEA (47.5 mmol, 6.61 mL, 5 eq). Tert-butyl (3S,4R)-3-fluoro-4-((2-(N'-hydroxycarbamimidoyl)-1-(2,2,2-trifluoroethyl)-1H-indol-4-yl)amino)piperidine-1-carboxylate (4.5 g, 9.50 mmol, 1 eq) was added to the reaction, and the resulting reaction mixture was stirred at 25° C. for 2 hr. The residue was poured into ice water (w/w=1/1). The mixture was extracted with DCM (10 mL×2), and the organic phase was washed with water (10 mL) and brine (10 mL), dried with anhydrous sodium sulfate, filtered, and concentrated in vacuo. The residue was purified by column chromatography (SiO$_2$, PE/EA=1:1) to afford (+/−)-tert-butyl (3S,4R)-4-((2-(N'-((((benzyloxy)carbonyl)glycyl)oxy)carbamimidoyl)-1-(2,2,2-trifluoroethyl)-1H-indol-4-yl)amino)-3-fluoropiperidine-1-carboxylate (5 g, 79.2% yield) as a yellow solid.

Preparation of (+/−)-tert-butyl (3S,4R)-4-((2-(5-((((benzyloxy)carbonyl)amino)methyl)-1,2,4-oxadiazol-3-yl)-1-(2,2,2-trifluoroethyl)-1H-indol-4-yl)amino)-3-fluoropiperidine-1-carboxylate: (+/−)-Tert-butyl (3S,4R)-4-((2-(N'-((((benzyloxy)carbonyl)glycyl)oxy) carbamimidoyl)-1-(2,2,2-trifluoroethyl)-1H-indol-4-yl)amino)-3-fluoropiperidine-1-carboxylate (3.5 g, 5.27 mmol, 1 eq) was dissolved in pyridine (20 mL) and stirred at 110° C. for 1 hr. The mixture was extracted with DCM (10 mL×2). The organic phase was washed with water (10 mL) and brine (10 mL), dried with anhydrous sodium sulfate, filtered, and concentrated in vacuo. The residue was purified by column chromatography (SiO$_2$, PE/EA=1:1) to afford (+/−)-tert-butyl (3S,4R)-4-((2-(5-((((benzyloxy)carbonyl)amino)methyl)-1,2,4-oxadiazol-3-yl)-1-(2,2,2-trifluoroethyl)-1H-indol-4-yl)amino)-3-fluoropiperidine-1-carboxylate (2 g, 58.7% yield) as a yellow solid.

Preparation of (+/−)-benzyl ((3-(4-(((3S,4R)-3-fluoropiperidin-4-yl)amino)-1-(2,2,2-trifluoroethyl)-1H-indol-2-yl)-

1,2,4-oxadiazol-5-yl)methyl)carbamate: To a solution of (+/−)-tert-butyl (3S,4R)-4-((2-(5-((((benzyloxy)carbonyl)amino)methyl)-1,2,4-oxadiazol-3-yl)-1-(2,2,2-trifluoroethyl)-1H-indol-4-yl)amino)-3-fluoropiperidine-1-carboxylate (1.8 g, 2.78 mmol, 1 eq) in DCM (18 mL) was added TFA (121.56 mmol, 9 mL, 43.7 eq). The mixture was stirred at 25° C. for 1 hr. The reaction mixture was poured into a saturated aqueous sodium carbonate solution. The mixture was extracted with DCM (10 mL×2), and the organic phase was washed with water (10 mL) and brine (10 mL), dried with anhydrous sodium sulfate, filtered, and concentrated in vacuo. The residue was purified by column chromatography (SiO$_2$, PE/EA=1:1) to afford (+/−)-benzyl ((3-(4-(((3S,4R)-3-fluoropiperidin-4-yl)amino)-1-(2,2,2-trifluoroethyl)-1H-indol-2-yl)-1,2,4-oxadiazol-5-yl)methyl)carbamate (1 g, 65.7% yield) as a yellow solid.

Preparation of (+/−)-benzyl ((3-(4-(((3S,4R)-3-fluoro-1-methylpiperidin-4-yl)amino)-1-(2,2,2-trifluoroethyl)-1H-indol-2-yl)-1,2,4-oxadiazol-5-yl)methyl)carbamate: To a solution of (+/−)-benzyl ((3-(4-(((3S,4R)-3-fluoropiperidin-4-yl)amino)-1-(2,2,2-trifluoroethyl)-1H-indol-2-yl)-1,2,4-oxadiazol-5-yl)methyl)carbamate (500 mg, 914.89 mol, 1 eq) and paraformaldehyde (137.35 mg, 4.57 mmol, 126.01 μL, 5 eq) in MeOH (2 mL) were added sodium cyanoborohydride (287.5 mg, 4.57 mmol, 5 eq) and acetic acid (8.74 mmol, 0.5 mL, 9.56 eq). The mixture was stirred at 50° C. for 1 hr. The mixture was extracted with DCM (10 mL×2), and the organic phase was washed with water (10 mL) and brine (10 mL), dried with anhydrous sodium sulfate, filtered, and concentrated in vacuo to afford benzyl (+/−)-((3-(4-(((3S,4R)-3-fluoro-1-methylpiperidin-4-yl)amino)-1-(2,2,2-trifluoroethyl)-1H-indol-2-yl)-1,2,4-oxadiazol-5-yl)methyl)carbamate (350 mg) as a yellow solid. LC-MS (ES$^-$, m/z): 561.3.

Preparation of (+/−)-2-(5-(aminomethyl)-1,2,4-oxadiazol-3-yl)-N-((3S,4R)-3-fluoro-1-methylpiperidin-4-yl)-1-(2,2,2-trifluoroethyl)-1H-indol-4-amine: (+/−)-Benzyl (3-(4-(((3S,4R)-3-fluoro-1-methylpiperidin-4-yl)amino)-1-(2,2,2-trifluoroethyl)-1H-indol-2-yl)-1,2,4-oxadiazol-5-yl)methyl)carbamate (100 mg, 178.4 μmol, 1 eq) was dissolved in a solution of hydrogen bromide (2 mL) and stirred at 25° C. for 1 hr. The mixture was poured into MTBE (10 mL) and stirred for 10 min, filtered, and concentrated to afford (+/−)-2-(5-(aminomethyl)-1,2,4-oxadiazol-3-yl)-N-((3S,4R)-3-fluoro-1-methylpiperidin-4-yl)-1-(2,2,2-trifluoroethyl)-1H-indol-4-amine (30 mg) as a yellow solid. LC-MS (ES$^+$, m/z): 427.1

General procedure for the preparation of compounds 171B, 172B, 175B, 176B, and 178B: To a solution of RCOOH (469 μmol, 2 eq) in DMF (2 mL) were added HATU (351.8 μmol, 1.5 eq), TEA (163 μL, 5 eq), and 2-(5-(aminomethyl)-1,2,4-oxadiazol-3-yl)-N-((3S,4R)-3-fluoro-1-methylpiperidin-4-yl)-1-(2,2,2-trifluoroethyl)-1H-indol-4-amine (235 μmol, 1 eq). The mixture was stirred at 25° C. for 1 hr. The mixture was extracted with DCM (10 mL×2), and the organic phase was washed with water (10 mL) and brine (10 mL), dried with anhydrous sodium sulfate, filtered, and concentrated in vacuo. The residue was purified by preparative-HPLC to afford the desired compounds. (+/−)-N-{[3-(4-{[(3R,4S)-3-fluoro-1-methylpiperidin-4-yl]amino}-1-(2,2,2-trifluoroethyl)-1H-indol-2-yl)-1,2,4-oxadiazol-5-yl]methyl}cyclopropanecarboxamide (Compound 171B), 12.1% yield, LC-MS (ES$^+$, m/z): 495.2; (+/−)-N-{[3-(4-{[(3R,4S)-3-fluoro-1-methylpiperidin-4-yl]amino}-1-(2,2,2-trifluoroethyl)-1H-indol-2-yl)-1,2,4-oxadiazol-5-yl]methyl}benzamide (Compound 172B), 15.3% yield, LC-MS (ES$^+$, m/z): 531.3; (+/−)-N-{[3-(4-{[(3R,4S)-3-fluoro-1-methylpiperidin-4-yl]amino}-1-(2,2,2-trifluoroethyl)-1H-indol-2-yl)-1,2,4-oxadiazol-5-yl]methyl}thiophene-2-carboxamide (Compound 175B), 16.6% yield, LC-MS (ES$^+$, m/z): 537.2; (+/−)-N-{[3-(4-{[(3R,4S)-3-fluoro-1-methylpiperidin-4-yl]amino}-1-(2,2,2-trifluoroethyl)-1H-indol-2-yl)-1,2,4-oxadiazol-5-yl]methyl}thiophene-3-carboxamide (Compound 176B), 21.1% yield, LC-MS (ES$^+$, m/z): 537.2; (+/−)-N-{[3-(4-{[(3R,4S)-3-fluoro-1-methylpiperidin-4-yl]amino}-1-(2,2,2-trifluoroethyl)-1H-indol-2-yl)-1,2,4-oxadiazol-5-yl]methyl}-1,3-thiazole-5-carboxamide (Compound 178B), 20.8% yield, LC-MS (ES$^+$, m/z): 538.2.

Example 72: Synthesis of N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}cyclopropanecarboxamide (Compound 173B) and N-{[3-(4-{[(3R,4S)-3-fluoro-1-methylpiperidin-4-yl]amino}-1-(2,2,2-trifluoroethyl)-1H-indol-2-yl)-1,2,4-oxadiazol-5-yl]methyl}cyclopropanecarboxamide (Compound 174B)

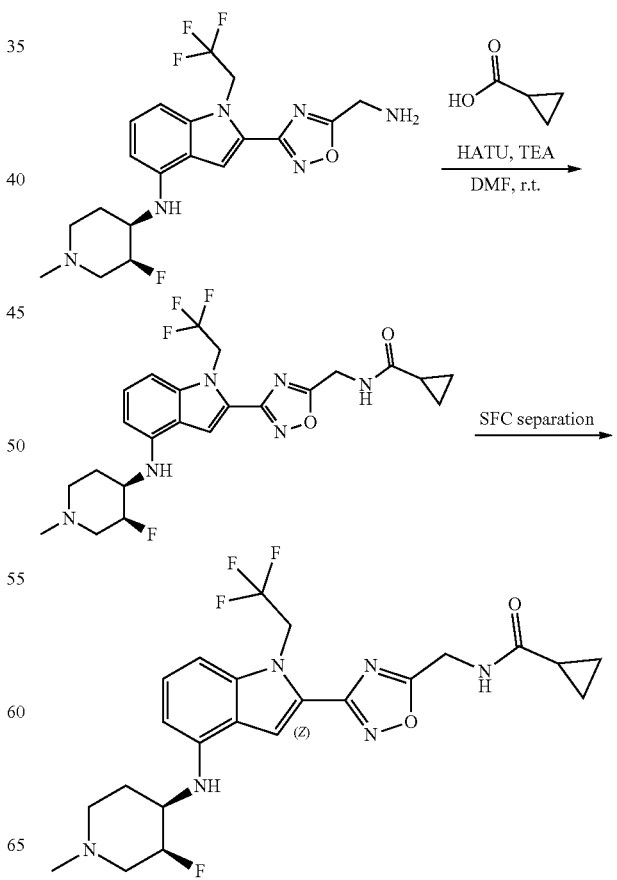

-continued

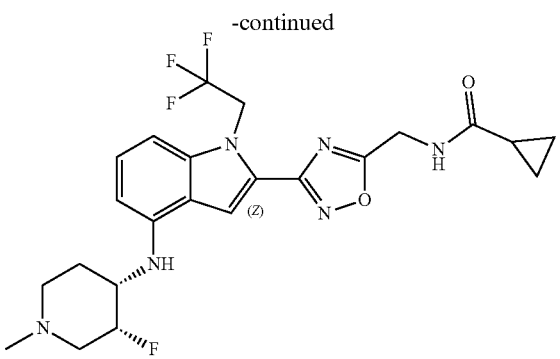

To a solution of cyclopropanecarboxylic acid (100.9 mg, 1.17 mmol, 92.6 μL, 2 eq) in DMF (3 mL) were added HATU (334 mg, 879 μmol, 1.5 eq), TEA (2.93 mmol, 408.02 μL, 5 eq), and (+/−)-2-(5-(aminomethyl)-1,2,4-oxadiazol-3-yl)-N-((3S,4R)-3-fluoro-1-methylpiperidin-4-yl)-1-(2,2,2-trifluoroethyl)-1H-indol-4-amine (250 mg, 586 μmol, 1 eq). The reaction mixture was stirred at 25° C. for 1 hr. The mixture was extracted with DCM (10 mL×2), and the organic phase was washed with water (10 mL) and brine (10 mL), dried with anhydrous sodium sulfate, filtered, and concentrated in vacuo. The crude residue was purified by preparative-HPLC to afford a mixture of compounds (50 mg, 16.4% yield) as a yellow solid. Chiral supercritical fluid chromatography was used to separate the mixture to afford N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}cyclopropanecarboxamide (Compound 173B) (16.5 mg) and N-{[3-(4-{[(3R,4S)-3-fluoro-1-methylpiperidin-4-yl]amino}-1-(2,2,2-trifluoroethyl)-1H-indol-2-yl)-1,2,4-oxadiazol-5-yl]methyl}cyclopropanecarboxamide (Compound 174B) (18.4 mg) as yellow solids. N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}cyclopropanecarboxamide (Compound 173B), 35.1% yield, LC-MS (ES+, m/z): 495.2; N-{[3-(4-{[(3R,4S)-3-fluoro-1-methylpiperidin-4-yl]amino}-1-(2,2,2-trifluoroethyl)-1H-indol-2-yl)-1,2,4-oxadiazol-5-yl]methyl}cyclopropanecarboxamide (Compound 174B), LC-MS (ES+, m/z): 495.2.

Example 73: Synthesis of (+/−)-N-[(3R,4S)-3-fluoro-1-methylpiperidin-4-yl]-2-(5-{[(4-methanesulfonylphenyl)amino]methyl}-1,2,4-oxadiazol-3-yl)-1-(2,2,2-trifluoroethyl)-1H-indol-4-amine (Compound 177B)

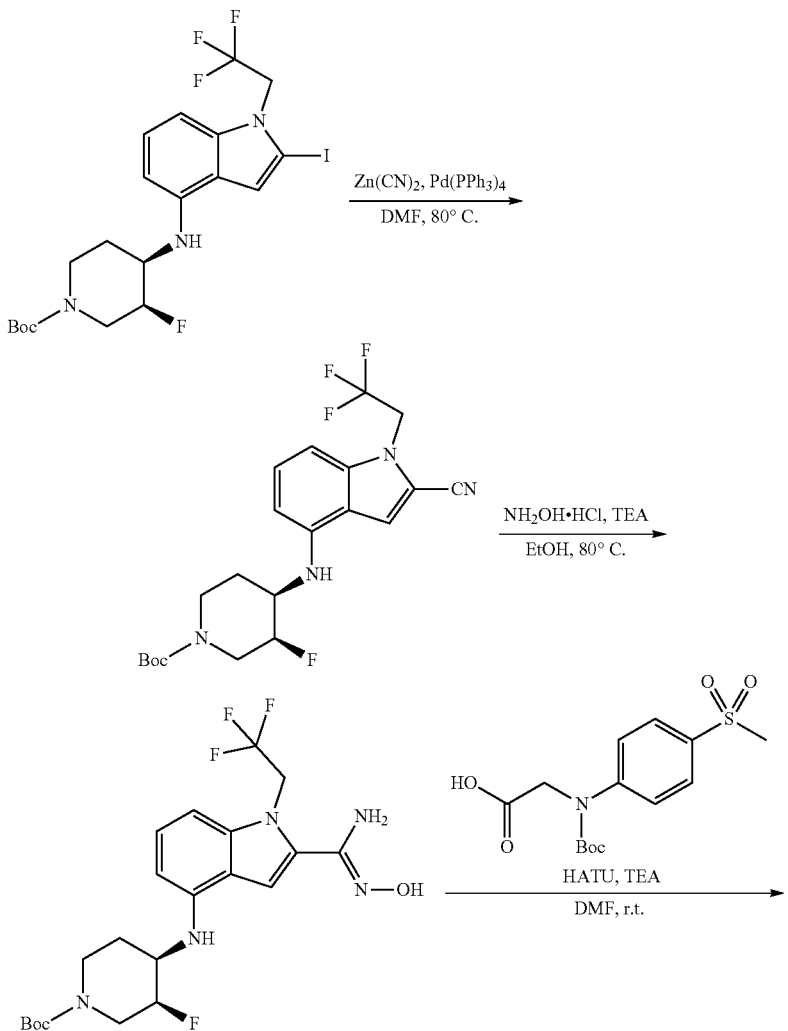

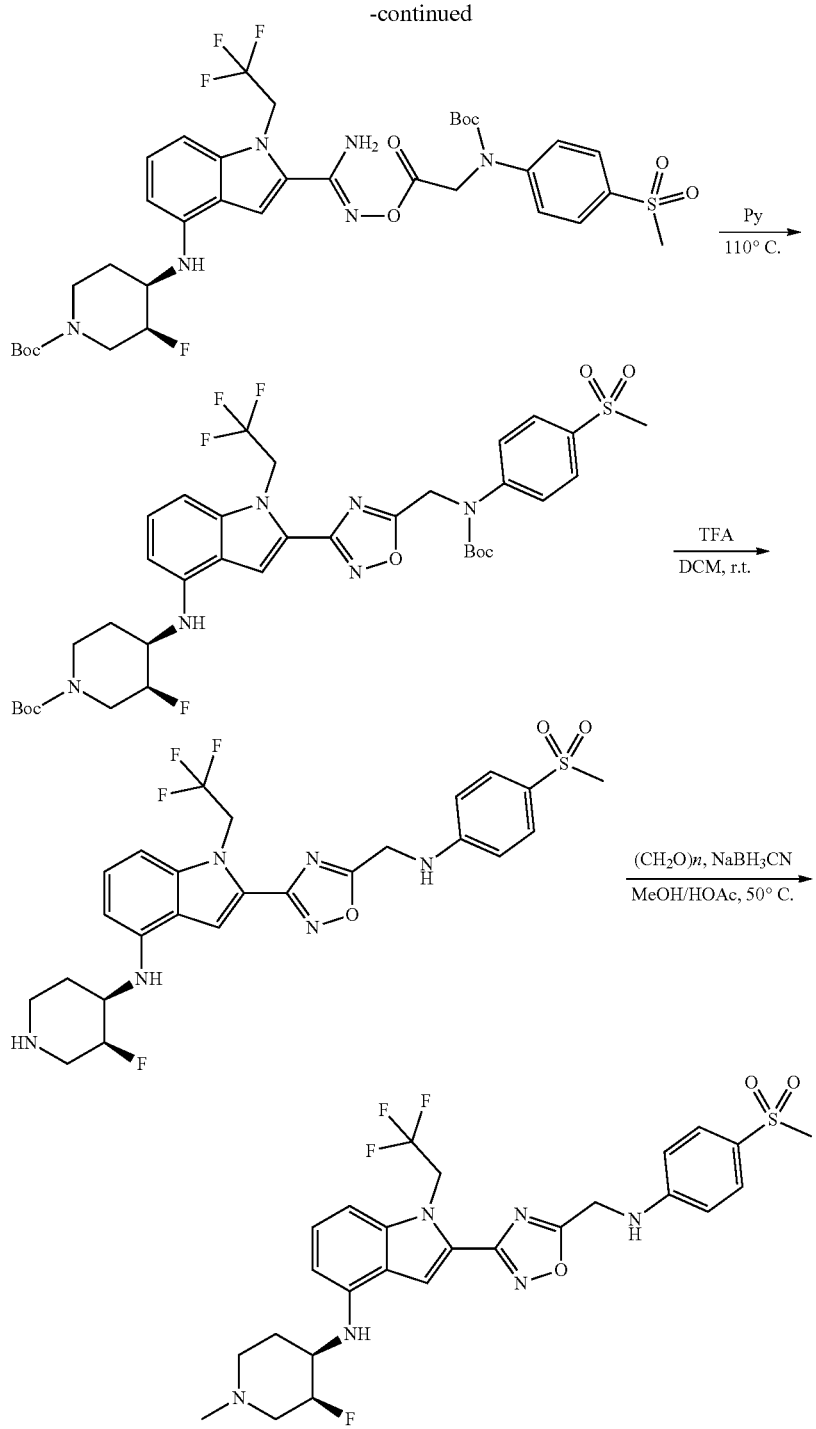

Preparation of (+/−)-tert-butyl (3S,4R)-4-((2-cyano-1-(2,2,2-trifluoroethyl)-1H-indol-4-yl)amino)-3-fluoropiperidine-1-carboxylate: To a solution of tert-butyl (3S,4R)-3-fluoro-4-((2-iodo-1-(2,2,2-trifluoroethyl)-1H-indol-4-yl)amino)piperidine-1-carboxylate (3 g, 5.54 mmol, 1 eq) in DMF (30 mL) were added zinc cyanide (1.95 g, 16.6 mmol, 3 eq) and tetrakis(triphenylphosphine)palladium(0) (640.4 mg, 554.2 μmol, 0.1 eq). The mixture was stirred at 80° C. for 2 hr. The residue was poured into a 2M aqueous EDTA solution (200 mL) and stirred for 1 hr. The aqueous phase was extracted with EA (100 mL×3). The combined organic phase was washed with brine (100 mL×3), dried with anhydrous sodium sulfate, filtered, and concentrated in vacuo. The residue was washed with EA and PE and concentrated to afford the crude product in 94.2% yield.

Preparation of (+/−)-tert-butyl (3S,4R)-3-fluoro-4-((2-(N'-hydroxycarbamimidoyl)-1-(2,2,2-trifluoroethyl)-1H-indol-4-yl)amino)piperidine-1-carboxylate: To a solution of tert-butyl (3S,4R)-4-((2-cyano-1-(2,2,2-trifluoroethyl)-1H-indol-4-yl)amino)-3-fluoropiperidine-1-carboxylate (2.3 g, 5.2 mmol, 1 eq) in ethanol (46 mL) were added hydroxylamine hydrochloride (544 mg, 7.83 mmol, 1.5 eq) and TEA (10.4 mmol, 1.45 mL, 2 eq). The mixture was stirred at 80° C. for 2 hr. The residue was poured into water (200 mL), and the aqueous phase was extracted with EA (100 mL×3). The combined organic phase was washed with brine (100 mL×3), dried with anhydrous sodium sulfate, filtered, and concentrated in vacuo. The residue was washed with EA and PE to afford (+/−)-tert-butyl (3S,4R)-3-fluoro-4-((2-(N'-hydroxycarbamimidoyl)-1-(2,2,2-trifluoroethyl)-1H-indol-4-yl)amino)piperidine-1-carboxylate in 89% yield. LC-MS (ES$^+$, m/z): 474.2.

Preparation of (+/−)-tert-butyl (3S,4R)-4-((2-(N'-((N-(tert-butoxycarbonyl)-N-(4-(methylsulfonyl)phenyl)glycyl)oxy)carbamimidoyl)-1-(2,2,2-trifluoroethyl)-1H-indol-4-yl)amino)-3-fluoropiperidine-1-carboxylate: To a solution of N-(tert-butoxycarbonyl)-N-(4-(methylsulfonyl)phenyl)glycine (1.25 g, 3.80 mmol, 1.5 eq) in DMF (24 mL) were added (+/−)-tert-butyl (3S,4R)-3-fluoro-4-((2-(N'-hydroxycarbamimidoyl)-1-(2,2,2-trifluoroethyl)-1H-indol-4-yl)amino)piperidine-1-carboxylate (1.2 g, 2.53 mmol, 1 eq) and TEA (12.67 mmol, 1.76 mL, 5 eq). HATU (1.93 g, 5.07 mmol, 2 eq) was then added, and the resulting reaction mixture was stirred at 20° C. for 0.5 hr. The residue was poured into water (100 mL), and the aqueous phase was extracted with EA (50 mL×3). The combined organic phase was washed with brine (50 mL×3), dried with anhydrous sodium sulfate, filtered, and concentrated in vacuo. The residue was purified by column chromatography to afford (+/−)-tert-butyl (3S,4R)-4-((2-(N'-((N-(tert-butoxycarbonyl)-N-(4-(methylsulfonyl)phenyl)glycyl)oxy)carbamimidoyl)-1-(2,2,2-trifluoroethyl)-1H-indol-4-yl)amino)-3-fluoropiperidine-1-carboxylate in 65.4% yield.

Preparation of (+/−)-tert-butyl (3S,4R)-4-((2-(5-(((tert-butoxycarbonyl)(4-(methylsulfonyl)phenyl)amino)methyl)-1,2,4-oxadiazol-3-yl)-1-(2,2,2-trifluoroethyl)-1H-indol-4-yl)amino)-3-fluoropiperidine-1-carboxylate: Compound (+/−)-tert-butyl (3S,4R)-4-((2-(N'-((N-(tert-butoxycarbonyl)-N-(4-(methylsulfonyl)phenyl)glycyl)oxy)carbamimidoyl)-1-(2,2,2-trifluoroethyl)-1H-indol-4-yl)amino)-3-fluoropiperidine-1-carboxylate (800 mg, 1.02 mmol, 1 eq) was dissolved in pyridine (8 mL), and the mixture was heated and stirred at 110° C. for 4 hr. The residue was poured into water (100 mL), and the aqueous phase was extracted with EA (50 mL×3). The combined organic phase was washed with brine (50 mL×3), dried with anhydrous sodium sulfate, filtered, and concentrated in vacuo. The crude residue was washed with PE and EA and concentrated to afford (+/−)-tert-butyl (3S,4R)-4-((2-(5-(((tert-butoxycarbonyl)(4-(methylsulfonyl)phenyl)amino)methyl)-1,2,4-oxadiazol-3-yl)-1-(2,2,2-trifluoroethyl)-1H-indol-4-yl)amino)-3-fluoropiperidine-1-carboxylate in 70.4% yield.

Preparation of (+/−)-N-((3S,4R)-3-fluoropiperidin-4-yl)-2-(5-(((4-(methylsulfonyl)phenyl)amino)methyl)-1,2,4-oxadiazol-3-yl)-1-(2,2,2-trifluoroethyl)-1H-indol-4-amine: To a solution of tert-butyl (3S,4R)-4-((2-(5-(((tert-butoxycarbonyl)(4-(methylsulfonyl)phenyl)amino)methyl)-1,2,4-oxadiazol-3-yl)-1-(2,2,2-trifluoroethyl)-1H-indol-4-yl)amino)-3-fluoropiperidine-1-carboxylate (550 mg, 717 μmol, 1 eq) in DCM (10 mL) was added TFA (67.53 mmol, 5 mL, 94 eq). The mixture was stirred at 20° C. for 0.5 hr. The residue was poured into saturated aqueous sodium carbonate (100 mL), and the aqueous phase was extracted with DCM (50 mL×3). The combined organic phase was washed with brine (50 mL×3), dried with anhydrous sodium sulfate, filtered, and concentrated in vacuo. The residue was washed with PE and EA and concentrated to afford (+/−)-N-((3S,4R)-3-fluoropiperidin-4-yl)-2-(5-(((4-(methylsulfonyl)phenyl)amino) methyl)-1,2,4-oxadiazol-3-yl)-1-(2,2,2-trifluoroethyl)-1H-indol-4-amine in 73.8% yield.

Preparation of N-[(3R,4S)-3-fluoro-1-methylpiperidin-4-yl]-2-(5-{1[(4-methanesulfonylphenyl)amino]methyl}-1,2,4-oxadiazol-3-yl)-1-(2,2,2-trifluoroethyl)-1H-indol-4-amine (Compound 177B): To a solution of N-((3S,4R)-3-fluoropiperidin-4-yl)-2-(5-(((4-(methylsulfonyl)phenyl)amino)methyl)-1,2,4-oxadiazol-3-yl)-1-(2,2,2-trifluoroethyl)-1H-indol-4-amine (150 mg, 265 μmol, 1 eq) in MeOH (3 mL) were added sodium cyanoborohydride (83.2 mg, 1.32 mmol, 5 eq), acetic acid (17.5 mmol, 1 mL, 66 eq), and paraformaldehyde (39.75 mg, 1.32 mmol, 5 eq). The mixture was stirred at 50° C. for 1 hr. The residue was poured into saturated aqueous sodium carbonate (aq) (50 mL), and the aqueous phase was extracted with EA (30 mL×3). The combined organic phase was washed with brine (30 mL×3), dried with anhydrous sodium sulfate, filtered, and concentrated in vacuo. The residue was purified by preparative-TLC to afford (+/−)-N-[(3R,4S)-3-fluoro-1-methylpiperidin-4-yl]-2-(5-{[(4-methanesulfonylphenyl)amino]methyl}-1,2,4-oxadiazol-3-yl)-1-(2,2,2-trifluoroethyl)-1H-indol-4-amine (Compound 177B) in 13.6% yield. LC-MS (ES$^+$, m/z): 581.2.

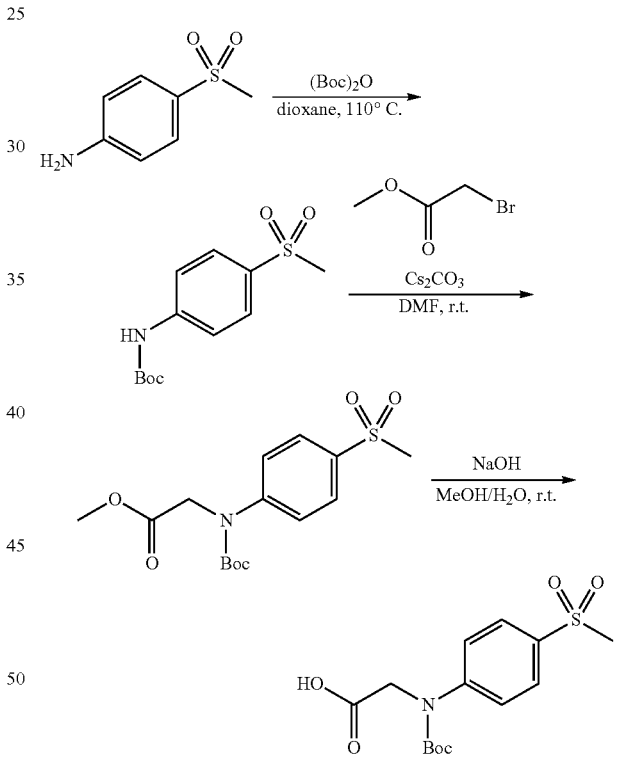

To a solution of 4-(methylsulfonyl)aniline (5.3 g, 31 mmol, 1 eq) in 1,4-dioxane (53 mL) was added (Boc)$_2$O (20.27 g, 92.9 mmol, 3 eq). The mixture was stirred at 110° C. for 18 hr. The residue was poured into water (200 mL). The aqueous phase was extracted with EA (100 mL×3). The combined organic phase was washed with brine (100 mL×3), dried with anhydrous sodium sulfate, filtered, and concentrated in vacuo. The residue was washed with PE and EA to afford tert-butyl (4-(methylsulfonyl)phenyl)carbamate in 85.7% yield.

Preparation of methyl N-(tert-butoxycarbonyl)-N-(4-(methylsulfonyl)phenyl)glycinate: To a solution of tert-butyl (4-(methylsulfonyl)phenyl)carbamate (3.5 g, 12.9 mmol, 1 eq) in DMF (70 mL) was added cesium carbonate (12.61 g, 38.70 mmol, 3 eq). The mixture was stirred at 20° C. for 10 min. Methyl 2-bromoacetate (23.22 mmol, 2.19 mL, 1.8 eq) was then added, and the resulting mixture was stirred at 20° C. for 1 hr. The residue was poured into water (200 mL). The aqueous phase was extracted with EA (100 mL×3). The combined organic phase was washed with brine (100 mL×3), dried with anhydrous sodium sulfate, filtered, and concentrated in vacuo. The residue was washed with PE and EA and concentrated to afford methyl N-(tert-butoxycarbonyl)-N-(4-(methylsulfonyl)phenyl)glycinate in 70.4% yield.

Preparation of N-(tert-butoxycarbonyl)-N-(4-(methylsulfonyl)phenyl)glycine: To a solution of methyl N-(tert-butoxycarbonyl)-N-(4-(methylsulfonyl)phenyl)glycinate (3 g, 8.74 mmol, 1 eq) in MeOH (48 mL) were added sodium hydroxide (1 g, 25 mmol, 2.86 eq) and water (12 mL). The mixture was stirred at 20° C. for 16 hr. The reaction mixture was concentrated in vacuo, and the crude residue was purified by preparative-HPLC to afford N-(tert-butoxycarbonyl)-N-(4-(methylsulfonyl)phenyl)glycine.

Example 74: Synthesis of N-[(3-{4-[(oxan-4-yl)amino]-1-(2,2,2-trifluoroethyl)-1H-indol-2-yl}-1,2,4-oxadiazol-5-yl)methyl]cyclopropanecarboxamide (Compound 159B)

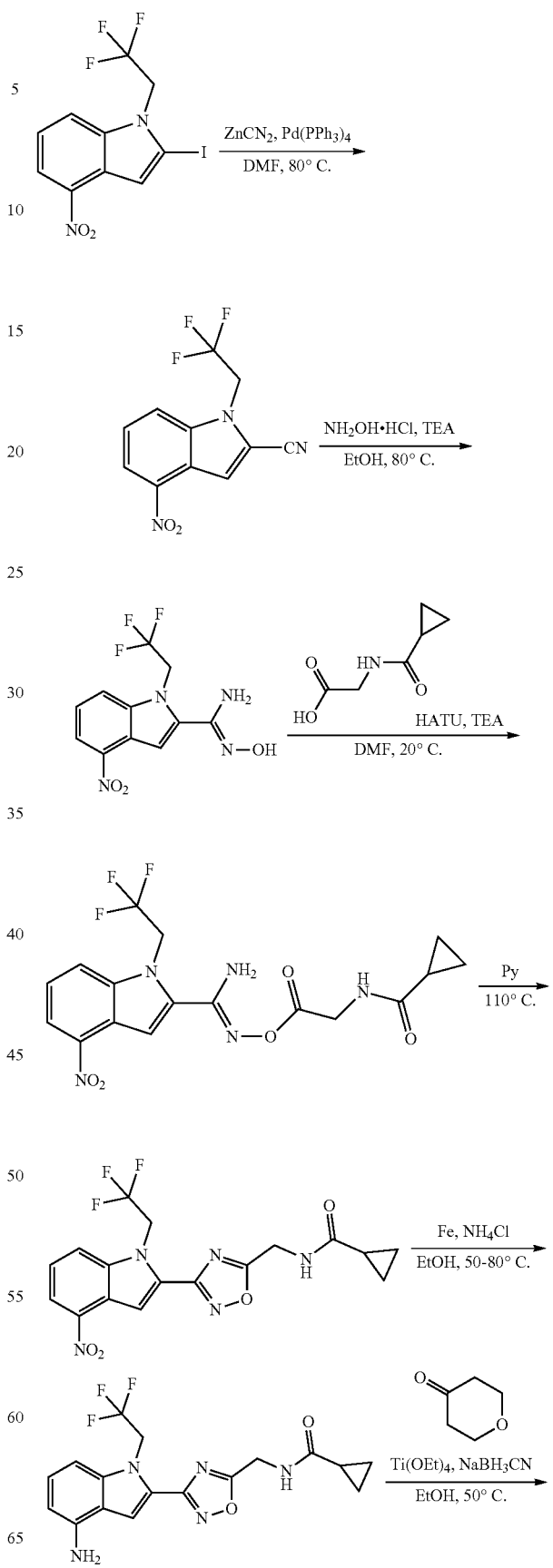

Preparation of (cyclopropanecarbonyl)glycine: To a solution of glycine (6 g, 79.9 mmol, 1 eq) in THF (100 mL) and water (100 mL) were added sodium hydroxide (3.84 g, 96 mmol, 1.20 eq) and sodium carbonate (10.20 g, 96.2 mmol, 1.20 eq) in one portion at 20° C. under a nitrogen atmosphere. Cyclopropanecarbonyl chloride (88.4 mmol, 8.03 mL, 1.11 eq) was added to the mixture at 0° C., and the resulting reaction mixture was stirred at 20° C. for 4 hours. Completion of the reaction was confirmed using TLC analysis. The residue was poured into 1N HCl to adjust the pH of the mixture to 2. The aqueous phase was extracted with EA (100 mL×3). The combined organic phase was washed with brine (100 mL×3), dried with anhydrous sodium sulfate, filtered, and concentrated in vacuo. The reaction was washed with EA (20 mL) and concentrated in vacuo to afford (cyclopropanecarbonyl)glycine (10 g, 69.9 mmol, 87.4% yield) as a white solid.

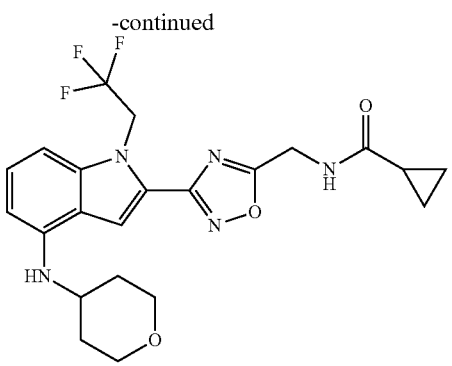

Preparation of 4-nitro-1-(2,2,2-trifluoroethyl)-1H-indole-2-carbonitrile: To a solution of 2-iodo-4-nitro-1-(2,2,2-trifluoroethyl)-1H-indole (20 g, 54 mmol, 1 eq) in DMF (200 mL) were added zinc cyanide (19.04 g, 162.1 mmol, 3 eq) and tetrakis(triphenylphosphine)palladium(0) (12.49 g, 10.81 mmol, 0.2 eq) in one portion under a nitrogen atmosphere. The mixture was heated and stirred at 80° C. for 2 hours, and TLC analysis was used to confirm completion of the reaction. The residue was poured into a 2M aqueous EDTA (300 mL) and stirred for 60 min. The aqueous phase was extracted with EA (200 mL×3). The combined organic phase was washed with brine (200 mL×3), dried with anhydrous sodium sulfate, filtered, and concentrated in vacuo. The crude product was purified using silica gel chromatography to afford 4-nitro-1-(2,2,2-trifluoroethyl)-1H-indole-2-carbonitrile (9 g, 33.4 mmol, 61.9% yield) as a yellow solid.

Preparation of N'-hydroxy-4-nitro-1-(2,2,2-trifluoroethyl)-1H-indole-2-carboximidamide: To a solution of 4-nitro-1-(2,2,2-trifluoroethyl)-1H-indole-2-carbonitrile (9 g, 33.4 mmol, 1 eq) in ethanol (70 mL) were added hydroxylamine hydrochloride (3.49 g, 50.15 mmol, 1.5 eq) and TEA (66.9 mmol, 9.31 mL, 2 eq) under a nitrogen atmosphere. The mixture was heated and stirred at 80° C. for 2 hours, and TLC analysis was used to confirm completion of the reaction. The residue was poured into ice water (w/w=1/1) (200 mL), and the aqueous phase was extracted with EA (100 mL×3). The combined organic phase was washed with brine (100 mL×3), dried with anhydrous sodium sulfate, filtered, and concentrated in vacuo. The residue was washed with PE (50 mL) and concentrated to afford N'-hydroxy-4-nitro-1-(2,2,2-trifluoroethyl)-1H-indole-2-carboximidamide (8 g, 26.5 mmol, 79.2% yield) as a yellow solid. LC-MS (ES+, m/z): 303.0.

Preparation of N-(2-(((amino(4-nitro-1-(2,2,2-trifluoroethyl)-1H-indol-2-yl)methylene)amino)oxy)-2-oxoethyl)cyclopropanecarboxamide: To a mixture of (cyclopropanecarbonyl)glycine (5.68 g, 39.7 mmol, 1.5 eq) in DMF (160 mL) were added HATU (15.10 g, 39.7 mmol, 1.5 eq) and TEA (132.4 mmol, 18.42 mL, 5 eq) in one portion at 20° C. under a nitrogen atmosphere. The mixture was stirred at 20° C. for 5 min, and N'-hydroxy-4-nitro-1-(2,2,2-trifluoroethyl)-1H-indole-2-carboximidamide (8 g, 26.5 mmol, 1 eq) was added. The resulting reaction mixture was stirred at 20° C. for 5 min, and TLC analysis was used to confirm completion of the reaction. The residue was poured into ice water (w/w=1/1) (500 mL), and the aqueous phase was extracted with EA (200 mL×3). The combined organic phase was washed with brine (200 mL×3), dried with anhydrous sodium sulfate, filtered, and concentrated in vacuo. The residue was washed with EA (100 mL) and concentrated to afford N-(2-(((amino(4-nitro-1-(2,2,2-trifluoroethyl)-1H-indol-2-yl)methylene)amino)oxy)-2-oxoethyl)cyclopropanecarboxamide (7.5 g, 17.6 mmol, 66.3% yield) as a yellow solid. LC-MS (ES, m/z): 428.1

Preparation of N-((3-(4-nitro-1-(2,2,2-trifluoroethyl)-1H-indol-2-yl)-1,2,4-oxadiazol-5-yl)methyl)cyclopropanecarboxamide: N-(2-(((amino(4-nitro-1-(2,2,2-trifluoroethyl)-1H-indol-2-yl)methylene)amino)oxy)-2-oxoethyl)cyclopropanecarboxamide (7.5 g, 17.6 mmol, 1 eq) was added to pyridine (100 mL) under a nitrogen atmosphere, then heated at 110° C. and stirred for 2 hrs. TLC analysis was used to confirm completion of the reaction. The residue was poured into 1N HCl to adjust the pH of the residue to 2~3. The aqueous phase was extracted with EA (50 mL×3). The combined organic phase was washed with brine (50 mL×3), dried with anhydrous sodium sulfate, filtered, and concentrated in vacuo. The reaction was washed with EA (20 mL) and concentrated to afford N-((3-(4-nitro-1-(2,2,2-trifluoroethyl)-1H-indol-2-yl)-1,2,4-oxadiazol-5-yl)methyl)cyclopropanecarboxamide (5.5 g, 13.4 mmol, 76.6% yield) as a yellow solid. LC-MS (ES+, m/z): 410.0.

Preparation of N-((3-(4-amino-1-(2,2,2-trifluoroethyl)-1H-indol-2-yl)-1,2,4-oxadiazol-5-yl)methyl)cyclopropanecarboxamide: To a mixture of N-((3-(4-nitro-1-(2,2,2-trifluoroethyl)-1H-indol-2-yl)-1,2,4-oxadiazol-5-yl)methyl)cyclopropanecarboxamide (0.5 g, 1.22 mmol, 1 eq) and ammonium chloride (326.7 mg, 6.11 mmol, 5 eq) in ethanol (4 mL) and water (1 mL) was added iron powder (341.1 mg, 6.11 mmol, 5 eq) in one portion at 50° C. under nitrogen. The mixture was stirred at 50° C. for 10 min, then heated to 80° C. and stirred for an additional 50 min. The residue was filtered by Celite® and poured into ice water (w/w=1/1) (100 mL), and the aqueous phase was extracted with EA (30 mL×3). The combined organic phase was washed with brine (30 mL×3), dried with anhydrous sodium sulfate, filtered, and concentrated in vacuo. The crude product was purified using silica gel chromatography to afford N-((3-(4-amino-1-(2,2,2-trifluoroethyl)-1H-indol-2-yl)-1,2,4-oxadiazol-5-yl)methyl)cyclopropanecarboxamide (100 mg. 263.6 μmol, 21.6% yield) as a light yellow solid. LC-MS (ES+, m/z): 380.0.

Preparation of N-[(3-{4-[(oxan-4-yl)amino]-1-(2,2,2-trifluoroethyl)-1H-indol-2-yl}-1,2,4-oxadiazol-5-yl)methyl]cyclopropanecarboxamide (Compound 159B): To a mixture of N-((3-(4-amino-1-(2,2,2-trifluoroethyl)-1H-indol-2-yl)-1,2,4-oxadiazol-5-yl)methyl)cyclopropanecarboxamide (100 mg, 263.6 μmol, 1 eq) and tetrahydro-4H-pyran-4-one (132 mg, 1.32 mmol, 5 eq) in ethanol (3 mL) was added titanium (IV) ethoxide (300.7 mg, 1.32 mmol, 5 eq) in one portion under a nitrogen atmosphere. The mixture was stirred at 50° C. for 2 hours, and sodium cyanoborohydride (82.8 mg, 1.32 mmol, 5 eq) was added. The mixture was stirred at 50° C. for 1 hour. The residue was poured into saturated aqueous sodium carbonate to adjust the pH of the residue to ~7. The aqueous phase was extracted with EA (20 mL×3). The combined organic phase was washed with brine (20 mL×3), dried with anhydrous sodium sulfate, filtered, and concentrated in vacuo. The residue was purified by preparative-HPLC to afford N-[(3-{4-[(oxan-4-yl)amino]-1-(2,2,2-trifluoroethyl)-1H-indol-2-yl}-1,2,4-oxadiazol-5-yl)methyl]cyclopropanecarboxamide (Compound 159B) (20.3 mg, 42.3 μmol, 16.05% yield) as a light yellow solid. LC-MS (ES+, m/z): 464.1.

Example 75: Synthesis of N-(1-methylpiperidin-4-yl)-2-{5-[(phenylamino)methyl]-1,2,4-oxadiazol-3-yl}-1-(2,2,2-trifluoroethyl)-1H-indol-4-amine (Compound 142B)

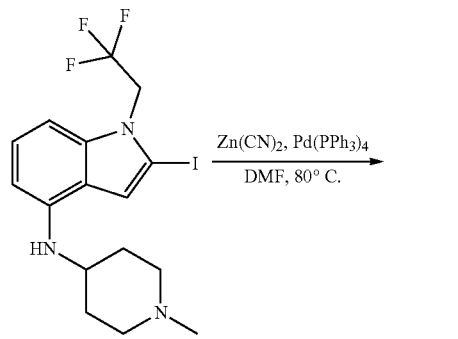

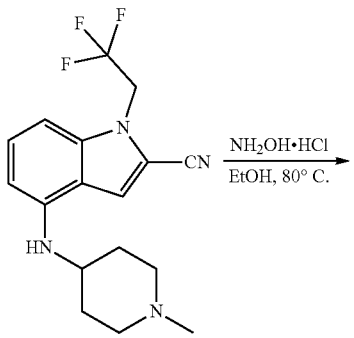

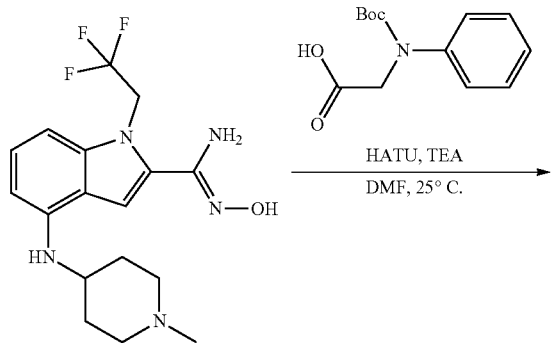

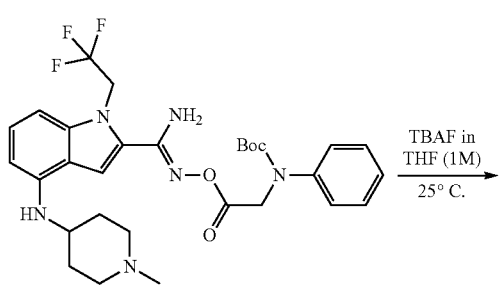

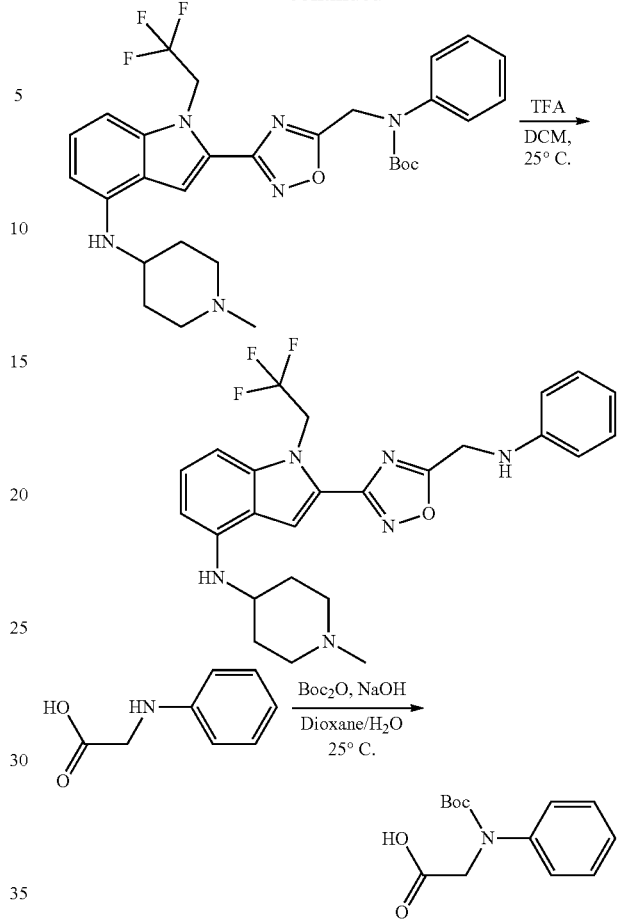

Preparation of 4-((1-methylpiperidin-4-yl)amino)-1-(2,2,2-trifluoroethyl)-1H-indole-2-carbonitrile: To a solution of 2-iodo-N-(1-methylpiperidin-4-yl)-1-(2,2,2-trifluoroethyl)-1H-indol-4-amine (1 g, 2.29 mmol, 1 eq) in DMF (10 mL) were added zinc cyanide (805.7 mg, 6.86 mmol, 3 eq) and tetrakis(triphenylphosphine)palladium(0) (264.3 mg, 229 μmol, 0.1 eq). The reaction mixture was stirred at 80° C. for 1 h, and TLC analysis was used to confirm completion of the reaction. The reaction mixture was poured into a 2M aqueous EDTA solution (50 mL) and stirred for 2 h, then extracted with EA (40 mL×3). The combined organic phase was washed with brine (30 mL), dried with anhydrous sodium sulfate, filtered, and concentrated in vacuo. The crude residue was purified by preparative-TLC (SiO$_2$, DCM:MeOH=10:1, Rr=0.34) to give 4-((1-methylpiperidin-4-yl)amino)-1-(2,2,2-trifluoroethyl)-1H-indole-2-carbonitrile (650 mg, 1.93 mmol, 84.5% yield) as a light yellow oil. LC-MS (ES$^+$, m/z): 337.2.

Preparation of N'-hydroxy-4-((1-methylpiperidin-4-yl)amino)-1-(2,2,2-trifluoroethyl)-1H-indole-2-carboximidamide: To a solution of 4-((1-methylpiperidin-4-yl)amino)-1-(2,2,2-trifluoroethyl)-1H-indole-2-carbonitrile (650 mg, 1.93 mmol, 1 eq) in ethanol (10 mL) were added TEA (3.86 mmol, 538 KL, 2 eq) and hydroxylamine hydrochloride (201.4 mg, 2.90 mmol, 1.5 eq). The mixture was stirred at 80° C. for 2 h, and LC-MS analysis was used to confirm completion of the reaction. The reaction mixture was poured into water (30 mL) and extracted with EA (20 mL×3). The combined organic phase was washed with brine (20 mL), dried with anhydrous sodium sulfate, filtered, and concentrated in vacuo. The crude residue was purified by preparative-TLC (SiO$_2$, DCM:MeOH=10:1, R$_f$=0.17) to give N'-hydroxy-4-((1-methylpiperidin-4-yl)amino)-1-(2,2,2-trifluoroethyl)-1H-indole-2-carboximidamide (420 mg, 1.14 mmol, 58.8% yield) as a brown solid. LC-MS (ES$^+$, m/z): 370.0.

Preparation of N-(tert-butoxycarbonyl)-N-phenylglycine: To a solution of N-phenylglycine (2 g, 13.2 mmol, 1 eq) in dioxane (24 mL) and water (12 mL) were added sodium hydroxide (1 M, 13.2 mL, 1 eq) and Boc$_2$O (3.18 g, 14.55 mmol, 1.1 eq). The mixture was stirred at 25° C. for 16 h, and LC-MS analysis was used to confirm completion of the reaction. The reaction mixture was poured into a citric acid solution (1M, 50 mL) and extracted with EA (40 mL×3). The combined organic phase was dried with anhydrous sodium sulfate, filtered, and concentrated in vacuo. The residue was purified by column chromatography (SiO$_2$, PE/EA=10/1 to 3:1, PE:EA=1:1, R$_f$=0.39) to give N-(tert-butoxycarbonyl)-N-phenylglycine (1.6 g, 6.37 mmol, 48.1% yield) as a light yellow oil. LC-MS (ES$^+$, m/z): 250.0 [M*].

Preparation of tert-butyl (2-(((amino(4-((1-methylpiperidin-4-yl)amino)-1-(2,2,2-trifluoroethyl)-1H-indol-2-yl)methylene)amino)oxy)-2-oxoethyl)(phenyl)carbamate: To a solution of N-(tert-butoxycarbonyl)-N-phenylglycine (251.7 mg, 1 mmol, 1 eq) in DMF (6 mL) were added TEA (5.01 mmol, 697.1 µL, 5 eq) and HATU (761.7 mg, 2 mmol, 2 eq). N'-hydroxy-4-((1-methylpiperidin-4-yl)amino)-1-(2,2,2-trifluoroethyl)-1H-indole-2-carboximidamide (370 mg, 1 mmol, 1 eq) was added to this mixture, and the reaction was stirred at 25° C. for 0.5 hr. TLC analysis was used to confirm completion of the reaction. The reaction mixture was poured into water (40 mL) and extracted with EA (30 mL×3). The combined organic phase was washed with brine (20 mL), dried with anhydrous sodium sulfate, filtered, and concentrated in vacuo. The crude residue was purified by preparative-TLC (SiO$_2$, DCM:MeOH=10:1, R$_f$=0.41) to give tert-butyl (2-(((amino(4-((1-methylpiperidin-4-yl)amino)-1-(2,2,2-trifluoroethyl)-1H-indol-2-yl)methylene)amino)oxy)-2-oxoethyl)(phenyl)carbamate (180 mg, 299 µmol, 29.8% yield) as a red oil. LC-MS (ES$^+$, m/z): 603.2.

Preparation of tert-butyl (3-(4-((1-methylpiperidin-4-yl)amino)-1-(2,2,2-trifluoroethyl)-1H-indol-2-yl)-1,2,4-oxadiazol-5-yl)methyl)(phenyl)carbamate: To a solution of tert-butyl (2-(((amino(4-((1-methylpiperidin-4-yl)amino)-1-(2,2,2-trifluoroethyl)-1H-indol-2-yl)methylene)amino)oxy)-2-oxoethyl)(phenyl)carbamate (180 mg, 299 µmol, 1 eq) in THF (4 mL) was added TBAF (1 M, 448 µL, 1.5 eq). The reaction mixture was stirred at 25° C. for 0.5 h, and TLC analysis was used to confirm completion of the reaction. The reaction mixture was poured into water (50 mL) and extracted with EA (20 mL×3). The combined organic phase was washed with brine (20 mL), dried with anhydrous sodium sulfate, filtered, and concentrated in vacuo. The crude product was purified using preparative-TLC (SiO$_2$, DCM:MeOH=10:1, R$_f$=0.46) to give tert-butyl ((3-(4-((1-methylpiperidin-4-yl)amino)-1-(2,2,2-trifluoroethyl)-1H-indol-2-yl)-1,2,4-oxadiazol-5-yl)methyl)(phenyl)carbamate (120 mg, 205 µmol, 68.7% yield) as a light yellow oil. LC-MS (ES$^+$, m/z): 585.1.

Preparation of N-(1-methylpiperidin-4-yl)-2-{5-[(phenylamino)methyl]-1,2,4-oxadiazol-3-yl}-1-(2,2,2-trifluoroethyl)-1H-indol-4-amine (Compound 142B): A solution of tert-butyl ((3-(4-((1-methylpiperidin-4-yl)amino)-1-(2,2,2-trifluoroethyl)-1H-indol-2-yl)-1,2,4-oxadiazol-5-yl)methyl)(phenyl)carbamate (110 mg, 188 µmol, 1 eq) in TFA (0.6 mL) and DCM (6 mL) was stirred at 25° C. until LC-MS analysis confirmed completion of the reaction. The reaction mixture was poured into a saturated aqueous sodium carbonate solution (30 mL) and extracted with DCM (20 mL×3). The combined organic phase was washed with brine (10 mL), dried with anhydrous sodium sulfate, filtered, and concentrated in vacuo to give a residue. The crude residue was purified by preparative-HPLC and preparative-TLC (SiO$_2$, DCM:MeOH=10:1, R$_f$=0.35) to afford N-(1-methylpiperidin-4-yl)-2-{5-[(phenylamino)methyl]-1,2,4-oxadiazol-3-yl}-1-(2,2,2-trifluoroethyl)-1H-indol-4-amine (Compound 142B) (5.8 mg, 11.5 µmol, 6.1% yield) as a red solid. LC-MS (ES$^-$, m/z): 485.1.

Example 76: Synthesis of N-(1-methylpiperidin-4-yl)-2-(3-(((4-(methylsulfonyl)phenyl)amino)methyl)-1,2,4-oxadiazol-5-yl)-1-(2,2,2-trifluoroethyl)-1H-indol-4-amine (Compound 136B)

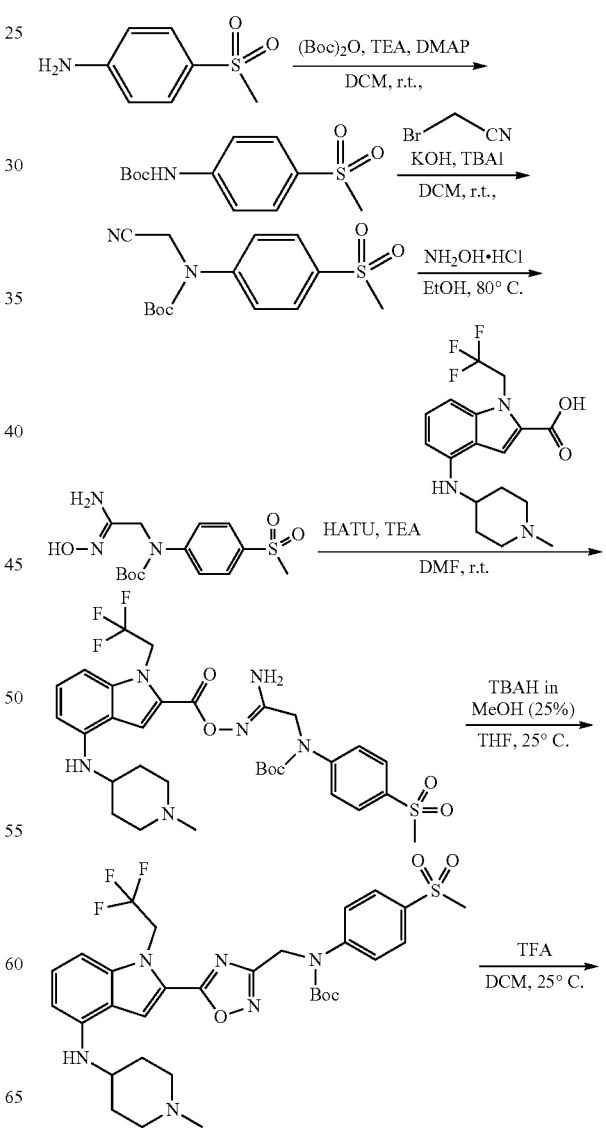

-continued

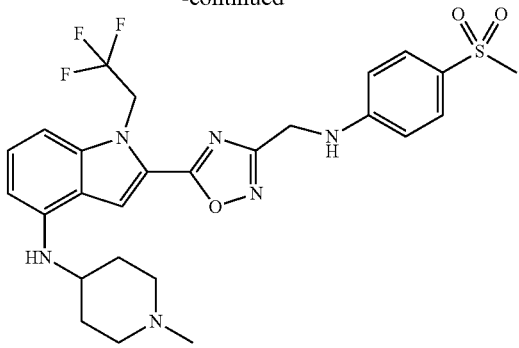

Preparation of tert-butyl (4-(methylsulfonyl)phenyl)carbamate: To a solution of 4-(methylsulfonyl)aniline (5 g, 29.2 mmol, 1 eq) in DCM (50 mL) were added (Boc)$_2$O (7.65 g, 35 mmol, 1.2 eq), DMAP (356.76 mg, 2.92 mmol, 0.1 eq) and TEA (58.4 mmol, 8.13 mL, 2 eq). The mixture was stirred at 20° C. for 2 hr. The reaction mixture was poured into water (100 mL), and then extracted with EA 300 mL (100 mL×3). The combined organic layers were washed with brine (100 mL), dried over anhydrous sodium sulfate, filtered, and concentrated in vacuo to give a residue. The residue was purified by column chromatography (SiO$_2$, PE/EA=5:1 to 3:1 to 1:1, R$_f$=0.6) to afford tert-butyl (4-(methylsulfonyl)phenyl)carbamate (2.6 g, 9.58 mmol, 32.8% yield) was obtained as a white solid.

Preparation of tert-butyl (cyanomethyl)(4-(methylsulfonyl)phenyl)carbamate: To a solution of tert-butyl (4-(methylsulfonyl)phenyl)carbamate (1 g, 3.69 mmol, 1 eq) in DCM (2 mL) were added potassium hydroxide (620 mg, 11.1 mmol, 3 eq), TBAI (2.04 g, 5.53 mmol, 1.5 eq), and 2-bromoacetonitrile (663.1 mg, 5.53 mmol, 1.5 eq). The mixture was stirred at 25° C. for 1 hr, and LC-MS analysis was used to confirm completion of the reaction. The mixture was extracted with DCM (10 mL×2), and the organic phase was washed with water (10 mL) and brine (10 mL), dried with anhydrous sodium sulfate, filtered, and concentrated in vacuo. The crude residue was purified by preparative-TLC (SiO$_2$, PE:EA=1:1) to afford tert-butyl (cyanomethyl)(4-(methylsulfonyl)phenyl)carbamate (500 mg, 1.61 mmol, 43.7% yield) as a white solid.

Preparation of tert-butyl (2-amino-2-(hydroxyimino) ethyl)(4-(methylsulfonyl)phenyl)carbamate: To a solution of tert-butyl (cyanomethyl)(4-(methylsulfonyl)phenyl)carbamate (450 mg, 1.45 mmol, 1 eq) in ethanol (5 mL) were added hydroxylamine hydrochloride (151.1 mg, 2.17 mmol, 1.5 eq) and TEA (2.90 mmol, 403.6 μL, 2 eq) at 25° C. The mixture was stirred at 80° C. for 1 hr. The reaction mixture was poured into water (20 mL) and extracted with EA (10 mL×3). The combined organic layers were washed with brine (10 mL), dried over anhydrous sodium sulfate, filtered, and concentrated in vacuo. The crude residue was purified by column chromatography (SiO$_2$, PE/EA=8:1 to 1:1, DCM: MeOH=30:1 to 20:1, EA=1, R$_f$=0.35) to afford tert-butyl (2-amino-2-(hydroxyimino)ethyl)(4-(methylsulfonyl)phenyl)carbamate (490 mg, 1.43 mmol, 98.4% yield) as a white solid.

Preparation of tert-butyl (2-amino-2-(((4-((1-methylpiperidin-4-yl)amino)-1-(2,2,2-trifluoroethyl)-1H-indole-2-carbonyl)oxy)imino)ethyl)(4-(methylsulfonyl)phenyl)carbamate: To a solution of 4-((1-methylpiperidin-4-yl)amino)-1-(2,2,2-trifluoroethyl)-1H-indole-2-carboxylic acid (248.4 mg, 699 μmol, 1 eq) in DMF (1 mL) were added HATU (398.61 mg, 1.05 mmol, 1.5 eq) and TEA (3.49 mmol, 486 μL, 5 eq). The mixture was stirred at 25° C. under a nitrogen atmosphere for 5 min. Tert-butyl (2-amino-2-(hydroxyimino)ethyl)(4-(methylsulfonyl)phenyl)carbamate (240 mg, 699 μmol, 1 eq) was added to the reaction, and the mixture was stirred at 25° C. under a nitrogen atmosphere until the reaction was 50% complete by LC-MS analysis. The reaction mixture was diluted with water (50 mL) and extracted with EA (20 mL×3). The combined organic layers were washed with brine (10 mL×3), dried over sodium sulfate, filtered, and concentrated in vacuo. The crude residue was purified by preparative-TLC (SiO$_2$, DCM:MeOH=10:1) to afford tert-butyl (2-amino-2-(((4-((1-methylpiperidin-4-yl) amino)-1-(2,2,2-trifluoroethyl)-1H-indole-2-carbonyl)oxy) imino)ethyl)(4-(methylsulfonyl)phenyl)carbamate (200 mg, 293.8 μmol, 42.0% yield) as a yellow solid.

Preparation of tert-butyl ((5-(4-((1-methylpiperidin-4-yl) amino)-1-(2,2,2-trifluoroethyl)-1H-indol-2-yl)-1,2,4-oxadiazol-3-yl)methyl)(4-(methylsulfonyl)phenyl)carbamate: To a solution of tert-butyl (2-amino-2-(((4-((1-methylpiperidin-4-yl)amino)-1-(2,2,2-trifluoroethyl)-1H-indole-2-carbonyl) oxy)imino)ethyl)(4-(methylsulfonyl)phenyl)carbamate (200 mg, 293.8 μmol, 1 eq) in THF (0.5 mL) was added tetrabutylammonium hydroxide (76.2 mg, 293.8 μmol, 1 eq). The mixture was stirred at 25° C. for 0.5 hr. LC-MS analysis showed several new peaks, and ~40% of desired compound was detected. The reaction mixture was diluted with water (50 mL) and extracted with EA (20 mL×3). The combined organic layers were washed with brine (20 mL×3), dried over sodium sulfate, filtered, and concentrated in vacuo. The crude residue was purified by preparative-TLC (SiO$_2$, DCM: MeOH=10:1) to afford tert-butyl ((5-(4-((1-methylpiperidin-4-yl)amino)-1-(2,2,2-trifluoroethyl)-1H-indol-2-yl)-1,2, 4-oxadiazol-3-yl)methyl)(4-(methylsulfonyl)phenyl) carbamate (60 mg, 90.5 μmol, 30.8% yield) as a yellow solid.

Preparation of 2-(3-{[(4-methanesulfonylphenyl)amino] methyl}-1,2,4-oxadiazol-5-yl)-N-(1-methylpiperidin-4-yl)-1-(2,2,2-trifluoroethyl)-1H-indol-4-amine (Compound 136B): To a solution of tert-butyl ((5-(4-((1-methylpiperidin-4-yl)amino)-1-(2,2,2-trifluoroethyl)-1H-indol-2-yl)-1,2, 4-oxadiazol-3-yl)methyl)(4-(methylsulfonyl)phenyl)carbamate (45 mg, 67.9 μmol, 1 eq) in DCM (1 mL) was added TFA (1 mL). The mixture was stirred at 25° C. until~70% of desired compound was detected by LC-MS analysis. The reaction mixture was diluted with water (20 mL) and extracted with EA (10 mL×3). The combined organic layers were washed with brine (10 mL×3), dried over sodium sulfate, filtered, and concentrated in vacuo. The crude residue was purified by preparative-TLC (SiO$_2$, DCM: MeOH=10:1) to afford N-(1-methylpiperidin-4-yl)-2-(3-(((4-(methylsulfonyl)phenyl)amino)methyl)-1,2,4-oxadiazol-5-yl)-1-(2,2,2-trifluoroethyl)-1H-indol-4-amine (5.2 mg, 8.50 μmol, 12.5% yield) as a yellow solid. LC-MS (ES$^+$, m/z): 563.2.

Example 77: Synthesis of (+/−)-N-{[5-(4-{[(3R,4S)-3-fluoro-1-methylpiperidin-4-yl]amino}-1-(2,2,2-trifluoroethyl)-1H-indol-2-yl)-1,2,4-oxadiazol-3-yl]methyl}cyclopropanecarboxamide (Compound 275B), (+/−)-N-{[5-(4-{[(3R,4S)-3-fluoro-1-methylpiperidin-4-yl]amino}-1-(2,2,2-trifluoroethyl)-1H-indol-2-yl)-1,2,4-oxadiazol-3-yl]methyl}benzamide (Compound 276B), (+/−)-N-{[5-(4-{1[(3R,4S)-3-fluoro-1-methylpiperidin-4-yl]amino}-1-(2,2,2-trifluoroethyl)-1H-indol-2-yl)-1,2,4-oxadiazol-3-yl]methyl}thiophene-2-carboxamide (Compound 277B), (+/−)-N-{[5-(4-{[(3R,4S)-3-fluoro-1-methylpiperidin-4-yl]amino}-1-(2,2,2-trifluoroethyl)-1H-indol-2-yl)-1,2,4-oxadiazol-3-yl]methyl}thiophene-3-carboxamide (Compound 278B), and (+/−)-N-{[5-(4-{[(3R,4S)-3-fluoro-1-methylpiperidin-4-yl]amino}-1-(2,2,2-trifluoroethyl)-1H-indol-2-yl)-1,2,4-oxadiazol-3-yl]methyl}-1,3-thiazole-5-carboxamide (Compound 279B)

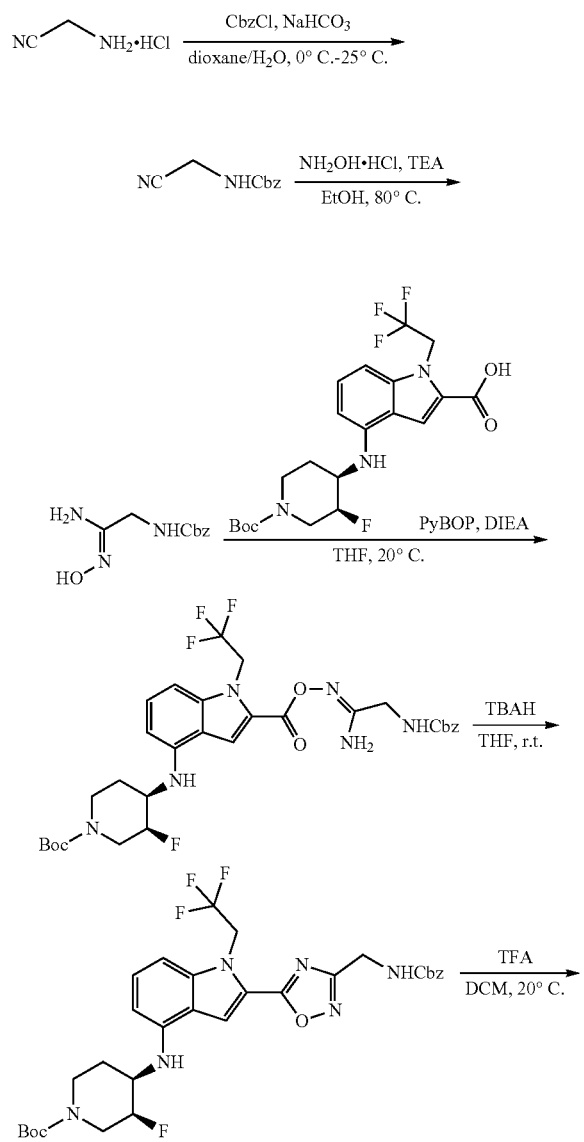

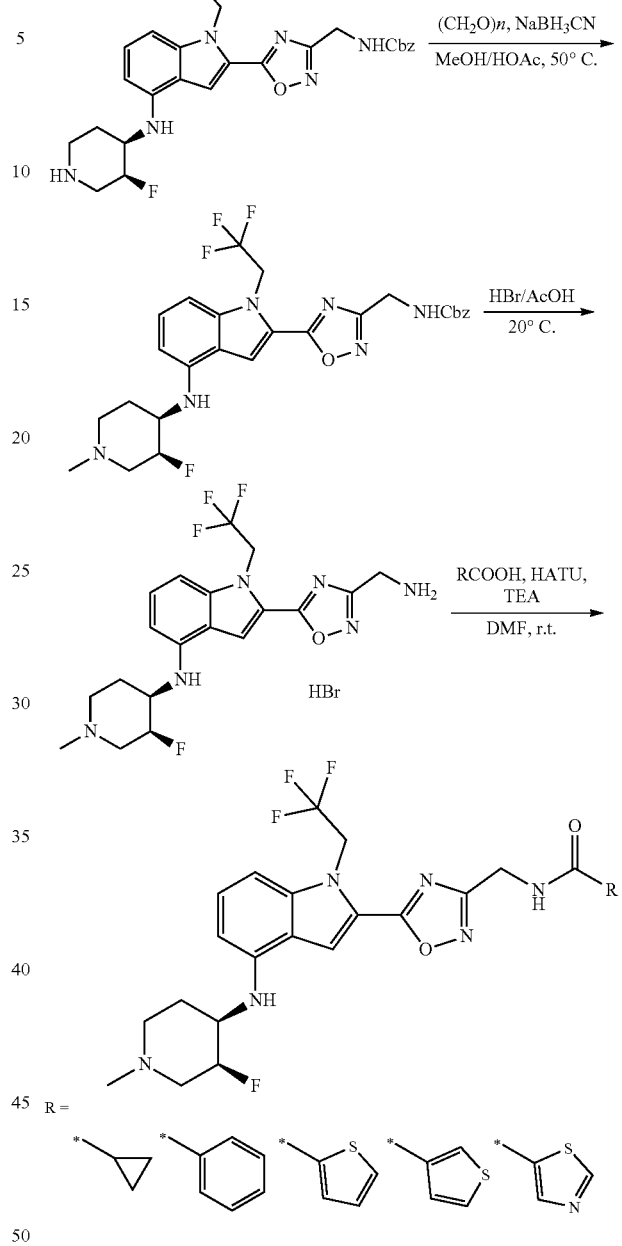

Preparation of benzyl (cyanomethyl)carbamate: To a solution of 2-aminoacetonitrile hydrochloride (20 g, 216 mmol, 1 eq, HCl) in dioxane (250 mL) and water (450 mL) were added sodium bicarbonate (54.48 g, 648.46 mmol, 25.22 mL, 3 eq) and benzyl chloroformate (432.3 mmol, 61.46 mL, 2 eq). The mixture was stirred at 0-25° C. for 2 hr. The mixture was extracted with DCM (1000 mL×2), and the organic phase was washed with water (1000 mL) and brine (1000 mL), dried with sodium sulfate, filtered, and concentrated in vacuo. The residue was purified by column chromatography (SiO$_2$, PE/EA=1:1) to afford benzyl (cyanomethyl)carbamate (35 g, 184 mmol, 85.1% yield) as a yellow solid. LC-MS (ES$^+$, m/z): 190.1.

Preparation of benzyl (2-amino-2-(hydroxyimino)ethyl)carbamate: To a solution of benzyl (cyanomethyl)carbamate (33 g, 173.5 mmol, 1 eq) in ethanol (250 mL) were added hydroxylamine hydrochloride (18.09 g, 260.3 mmol, 1.5 eq) and TEA (347 mmol, 48.3 mL, 2 eq). The mixture was stirred at 80° C. for 2 hr. The mixture was extracted with DCM (1000 mL×2), and the organic phase was washed with water (1000 mL) and brine (1000 mL), dried with anhydrous sodium sulfate, filtered, and concentrated in vacuo. The residue was purified by column chromatography to afford benzyl (2-amino-2-(hydroxyimino)ethyl)carbamate (35 g, 156.8 mmol, 90.4% yield) as a white solid.

Preparation of (+/−)-tert-butyl (3S,4R)-4-((2-(4-amino-7-oxo-9-phenyl-2,8-dioxa-3,6-diazanon-3-enoyl)-1-(2,2,2-trifluoroethyl)-1H-indol-4-yl)amino)-3-fluoropiperidine-1-carboxylate: To a mixture of (+/−)-4-(((3S,4R)-1-(tert-butoxycarbonyl)-3-fluoropiperidin-4-yl)amino)-1-(2,2,2-trifluoroethyl)-1H-indole-2-carboxylic acid (3 g, 6.53 mmol, 1 eq), benzyl (2-amino-2-(hydroxyimino)ethyl)carbamate (4.37 g, 19.6 mmol, 3 eq), and PyBOP (3.74 g, 7.18 mmol, 1.1 eq) in THF (20 mL) was added DIEA (16.3 mmol, 2.84 mL, 2.5 eq) at 20° C. under nitrogen. The mixture was stirred at 20° C. for 10 min. The residue was poured into ice water (w/w=1/1) (200 mL), and the aqueous phase was extracted with EA (100 mL×3). The combined organic phase was washed with brine (100 mL), dried with anhydrous sodium sulfate, filtered, and concentrated in vacuo to afford (+/−)-tert-butyl (3S,4R)-4-((2-(4-amino-7-oxo-9-phenyl-2,8-dioxa-3,6-diazanon-3-enoyl)-1-(2,2,2-trifluoroethyl)-1H-indol-4-yl)amino)-3-fluoropiperidine-1-carboxylate (3.5 g, crude) as a brown oil. LC-MS (ES+, m/z): 665.2.

Preparation of (+/−)-tert-butyl (3S,4R)-4-((2-(3-((((benzyloxy)carbonyl)amino)methyl)-1,2,4-oxadiazol-5-yl)-1-(2,2,2-trifluoroethyl)-1H-indol-4-yl)amino)-3-fluoropiperidine-1-carboxylate: To a mixture of (+/−)-tert-butyl (3S,4R)-4-((2-(4-amino-7-oxo-9-phenyl-2,8-dioxa-3,6-diazanon-3-enoyl)-1-(2,2,2-trifluoroethyl)-1H-indol-4-yl)amino)-3-fluoropiperidine-1-carboxylate (3.5 g, 5.27 mmol, 1 eq) in THF (40 mL) was added tetrabutylammonium hydroxide (2.73 g, 10.5 mmol, 2 eq) in one portion at 20° C. under nitrogen. The mixture was stirred at 20° C. for 3 hours. The residue was poured into ice water (w/w=1/1) (200 mL), and the aqueous phase was extracted with EA (100 mL×3). The combined organic phase was washed with brine (100 mL×3), dried with anhydrous sodium sulfate, filtered, and concentrated in vacuo. The residue was purified by silica gel chromatography to afford (+/−)-tert-butyl (3S,4R)-4-((2-(3-((((benzyloxy)carbonyl)amino)methyl)-1,2,4-oxadiazol-5-yl)-1-(2,2,2-trifluoroethyl)-1H-indol-4-yl)amino)-3-fluoropiperidine-1-carboxylate (1.6 g, 2.47 mmol, 47.0% yield) as a brown oil. LC-MS (ES+, m/z): 647.1

Preparation of (+/−)-benzyl ((5-(4-(((3S,4R)-3-fluoropiperidin-4-yl)amino)-1-(2,2,2-trifluoroethyl)-1H-indol-2-yl)-1,2,4-oxadiazol-3-yl)methyl)carbamate: To a mixture of (+/−)-tert-butyl (3S,4R)-4-((2-(3-((((benzyloxy)carbonyl)amino)methyl)-1,2,4-oxadiazol-5-yl)-1-(2,2,2-trifluoroethyl)-1H-indol-4-yl)amino)-3-fluoropiperidine-1-carboxylate (1.6 g, 2.47 mmol, 1 eq) in DCM (20 mL) was added TFA (15.40 g, 135.1 mmol, 10 mL, 54.6 eq) at 20° C. under nitrogen. The mixture was stirred at 20° C. for 30 min. The residue was poured into saturated aqueous sodium carbonate to adjust the pH of the residue to 7-8. The aqueous phase was extracted with DCM (50 mL×3). The combined organic phase was washed with brine (50 mL×3), dried with anhydrous sodium sulfate, filtered, and concentrated in vacuo to afford (+/−)-benzyl ((5-(4-(((3S,4R)-3-fluoropiperidin-4-yl)amino)-1-(2,2,2-trifluoroethyl)-1H-indol-2-yl)-1,2,4-oxadiazol-3-yl)methyl)carbamate (1.2 g, crude) as a yellow solid.

Preparation of (+/−)-benzyl ((5-(4-(((3S,4R)-3-fluoro-1-methylpiperidin-4-yl)amino)-1-(2,2,2-trifluoroethyl)-1H-indol-2-yl)-1,2,4-oxadiazol-3-yl)methyl)carbamate: To a mixture of benzyl ((5-(4-(((3S,4R)-3-fluoropiperidin-4-yl)amino)-1-(2,2,2-trifluoroethyl)-1H-indol-2-yl)-1,2,4-oxadiazol-3-yl)methyl)carbamate (1 g, 1.83 mmol, 1 eq) and paraformaldehyde (274.7 mg, 9.15 mmol, 5 eq) in MeOH (20 mL) were added sodium cyanoborohydride (574.9 mg, 9.15 mmol, 5 eq) and acetic acid (26.23 mmol, 1.5 mL, 14.3 eq) sequentially at 50° C. under nitrogen. The mixture was stirred at 50° C. for 5 hours. The residue was poured into saturated aqueous sodium carbonate to adjust the pH of the residue to 7~8. The aqueous phase was extracted with EA (30 mL×3). The combined organic phase was washed with brine (30 mL×3), dried with anhydrous sodium sulfate, filtered, and concentrated in vacuo. The reaction was washed with PE (20 mL) and EA (5 mL) to afford (+/−)-benzyl ((5-(4-(((3S,4R)-3-fluoro-1-methylpiperidin-4-yl)amino)-1-(2,2,2-trifluoroethyl)-1H-indol-2-yl)-1,2,4-oxadiazol-3-yl)methyl)carbamate (0.9 g, 1.61 mmol, 87.8% yield) as a yellow solid.

Preparation of (+/−)-2-(3-(aminomethyl)-1,2,4-oxadiazol-5-yl)-N-((3S,4R)-3-fluoro-1-methylpiperidin-4-yl)-1-(2,2,2-trifluoroethyl)-1H-indol-4-amine: (+/−)-Benzyl ((5-(4-(((3S,4R)-3-fluoro-1-methylpiperidin-4-yl)amino)-1-(2,2,2-trifluoroethyl)-1H-indol-2-yl)-1,2,4-oxadiazol-3-yl)methyl)carbamate (0.9 g, 1.61 mmol, 1 eq) was dissolved in HBr/acetic acid (2 mL) at 20° C. under nitrogen. The mixture was stirred at 20° C. for 30 min. The residue was poured into MTBE (200 mL) and stirred for 10 min. The mixture was filtered to afford (+/−)-2-(3-(aminomethyl)-1,2,4-oxadiazol-5-yl)-N-((3S,4R)-3-fluoro-1-methylpiperidin-4-yl)-1-(2,2,2-trifluoroethyl)-1H-indol-4-amine (0.7 g, crude, HBr) as a light green solid. LC-MS (ES+, m/z): 427.2.

General procedure for the preparation of Compounds 275B, 276B, 277B, 278B, and 279B: To a mixture of RCOOH (1 eq) in DMF (2 mL) was added HATU (2 eq) and TEA (5 eq) each in one portion at 20° C. under nitrogen. The mixture was stirred at 20° C. for 5 min, and (+/−)-2-(3-(aminomethyl)-1,2,4-oxadiazol-5-yl)-N-((3S,4R)-3-fluoro-1-methylpiperidin-4-yl)-1-(2,2,2-trifluoroethyl)-1H-indol-4-amine (1 eq) was added. The resulting reaction mixture was stirred at 20° C. for 5 min. The residue was poured into ice water (w/w=1/1) (100 mL), and the aqueous phase was extracted with EA (30 mL×3). The combined organic phase was washed with brine (30 mL×3), dried with anhydrous sodium sulfate, filtered, and concentrated in vacuo. The residue was purified by preparative-TLC (SiO₂, DCM: MeOH=10:1) to afford the desired compounds. (+/−)-N-{[5-(4-{[(3R,4S)-3-fluoro-1-methylpiperidin-4-yl]amino}-1-(2,2,2-trifluoroethyl)-1H-indol-2-yl)-1,2,4-oxadiazol-3-yl]methyl}cyclopropanecarboxamide (Compound 275B), 28.1% yield, LC-MS (ES+, m/z): 495.2; (+/−)-N-{[5-(4-{[(3R,4S)-3-fluoro-1-methylpiperidin-4-yl]amino}-1-(2,2,2-trifluoroethyl)-1H-indol-2-yl)-1,2,4-oxadiazol-3-yl]methyl}benzamide (Compound 276B), 26.1% yield, LC-MS (ES+, m/z): 531.2; (+/−)-N-{[5-(4-{[(3R,4S)-3-fluoro-1-methylpiperidin-4-yl]amino}-1-(2,2,2-trifluoroethyl)-1H-indol-2-yl)-1,2,4-oxadiazol-3-yl]methyl}thiophene-2-carboxamide (Compound 277B), 13.8% yield, LC-MS (ES+, m/z): 537.0; (+/−)-N-{[5-(4-{[(3R,4S)-3-fluoro-1-methylpiperidin-4-yl]amino}-1-(2,2,2-trifluoroethyl)-1H-indol-2-yl)-1,2,4-oxadiazol-3-yl]methyl}thiophene-3-carboxamide (Compound 278B), 20.2% yield, LC-MS (ES+, m/z): 537.2; (+/−)-N-{[5-(4-{[(3R,4S)-3-fluoro-1-methylpiperidin-4-yl]amino}-1-(2,2,2-trifluoroethyl)-1H-indol-2-yl)-1,2,4-oxadiazol-3-yl]methyl}-1,3-thiazole-5-carboxamide (Compound 279B), 18.2% yield, LC-MS (ES+, m/z): 538.2.

Example 78: Synthesis of N-[(5-{4-[(1-methylpiperidin-4-yl)amino]-1-(2,2,2-trifluoroethyl)-1H-indol-2-yl}-1,2,4-oxadiazol-3-yl)methyl]cyclopropanecarboxamide (Compound 137B), N-[(5-{4-[(1-methylpiperidin-4-yl)amino]-1-(2,2,2-trifluoroethyl)-1H-indol-2-yl}-1,2,4-oxadiazol-3-yl)methyl]benzamide (Compound 138B), N-[(5-{4-[(1-methylpiperidin-4-yl)amino]-1-(2,2,2-trifluoroethyl)-1H-indol-2-yl}-1,2,4-oxadiazol-3-yl)methyl]thiophene-2-carboxamide (Compound 139B), 1-methyl-N-[(5-{4-[(1-methylpiperidin-4-yl)amino]-1-(2,2,2-trifluoroethyl)-1H-indol-2-yl}-1,2,4-oxadiazol-3-yl)methyl]-1H-pyrazole-4-carboxamide (Compound 140B), and 1-methyl-N-[(5-{4-[(1-methylpiperidin-4-yl)amino]-1-(2,2,2-trifluoroethyl)-1H-indol-2-yl}-1,2,4-oxadiazol-3-yl)methyl]-1H-pyrazole-3-carboxamide (Compound 141B)

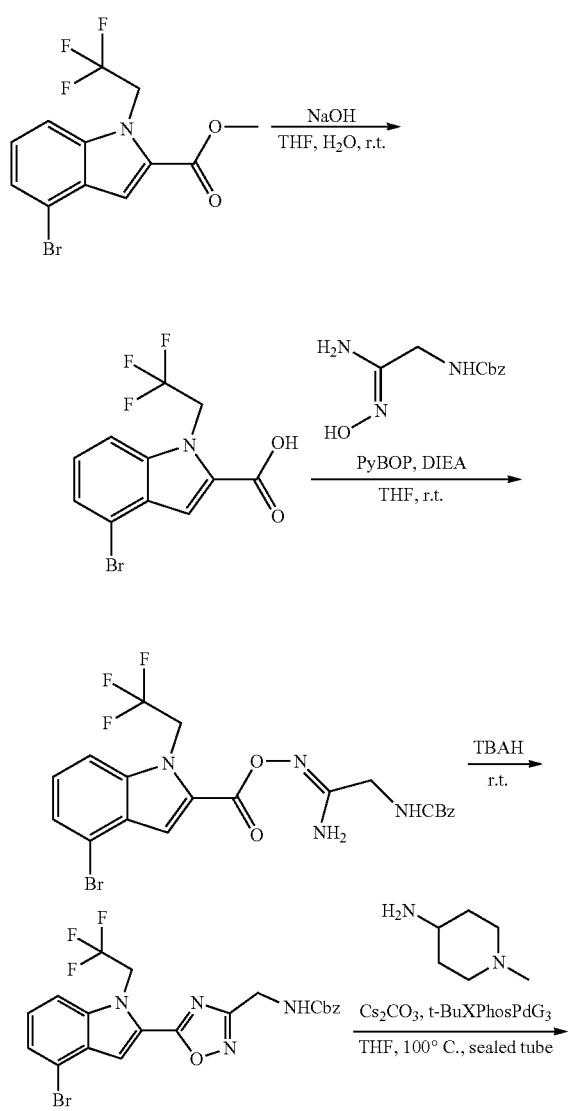

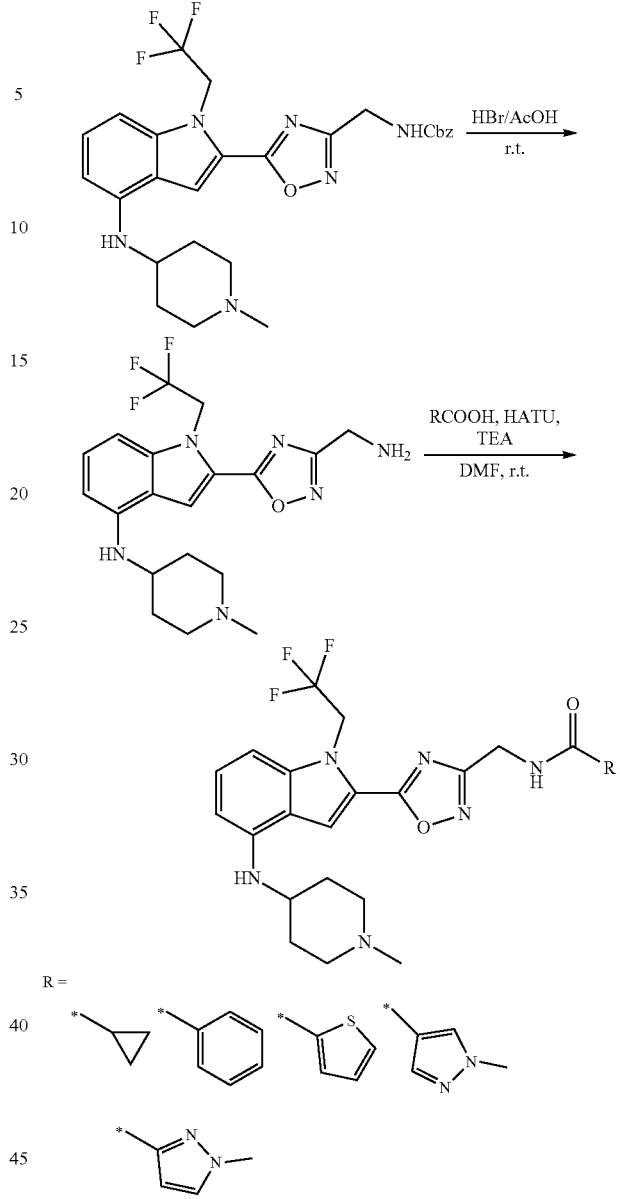

Preparation of 4-bromo-1-(2,2,2-trifluoroethyl)-1H-indole-2-carboxylic acid: To a solution of methyl 4-bromo-1-(2,2,2-trifluoroethyl)-1H-indole-2-carboxylate (5 g, 14.9 mmol, 1 eq) in THF (50 mL) was added 2M sodium hydroxide (46.1 mL, 6.2 eq). The mixture was stirred at 25° C. for 1 hr. 1M HCl (20 mL) was then added to the reaction. The reaction was extracted with DCM (50 mL×2), and the organic phase was washed with water (50 mL) and brine (50 mL), dried with sodium sulfate, filtered, and concentrated in vacuo to afford 4-bromo-1-(2,2,2-trifluoroethyl)-1H-indole-2-carboxylic acid (4.5 g) as a white solid. LC-MS (ES+, m/z): 322.0.

Preparation of benzyl (2-amino-2-(((4-bromo-1-(2,2,2-trifluoroethyl)-1H-indole-2-carbonyl)oxy)imino)ethyl)carbamate: To a solution of 4-bromo-1-(2,2,2-trifluoroethyl)-1H-indole-2-carboxylic acid (3 g, 9.31 mmol, 1 eq) in THF (10 mL) were added benzyl (2-amino-2-(hydroxyimino)ethyl)carbamate (6.24 g, 27.9 mmol, 3 eq), DIEA (23.3 mmol, 4.06 mL, 2.5 eq), and PyBOP (5.33 g, 10.25 mmol, 1.1 eq). The mixture was stirred at 25° C. for 1 hr. The mixture was extracted with DCM (10 mL×2). The organic phase was washed with water (10 mL) and brine (10 mL), dried with sodium sulfate, filtered, and concentrated in vacuo to afford benzyl (2-amino-2-(((4-bromo-1-(2,2,2-trifluoroethyl)-1H-indole-2-carbonyl)oxy)imino)ethyl)carbamate (4.5 g) as a white solid.

Preparation of benzyl ((5-(4-bromo-1-(2,2,2-trifluoroethyl)-1H-indol-2-yl)-1,2,4-oxadiazol-3-yl)methyl)carbamate: To a solution of benzyl (2-amino-2-(((4-bromo-1-(2,2, 2-trifluoroethyl)-1H-indole-2-carbonyl)oxy)imino)ethyl) carbamate (4 g, 7.59 mmol, 1 eq) in THF (10 mL) was added TBAH (3.94 g, 15.17 mmol, 2 eq). The mixture was stirred at 25° C. for 1 hr. The mixture was extracted with DCM (10 mL×2). The organic phase was washed with water (10 mL) and brine (10 mL), dried with sodium sulfate, filtered, and concentrated in vacuo to afford benzyl ((5-(4-bromo-1-(2,2, 2-trifluoroethyl)-1H-indol-2-yl)-1,2,4-oxadiazol-3-yl) methyl)carbamate (3.5 g) as a white solid.

Preparation of benzyl ((5-(4-((1-methylpiperidin-4-yl) amino)-1-(2,2,2-trifluoroethyl)-1H-indol-2-yl)-1,2,4-oxadiazol-3-yl)methyl)carbamate: To a solution of benzyl ((5-(4-bromo-1-(2,2,2-trifluoroethyl)-1H-indol-2-yl)-1,2,4-oxadiazol-3-yl)methyl)carbamate (200 mg, 393 µmol, 1 eq) and 1-methylpiperidin-4-amine (448.4 mg, 3.93 mmol, 10 eq) in THF (2 mL) were added t-BuXPhos Palladium Generation 3 (93.6 mg, 117.8 µmol, 0.3 eq) and cesium carbonate (383.9 mg, 1.18 mmol, 3 eq). The mixture was stirred at 100° C. for 12 hr. The mixture was poured into a 2M aqueous EDTA solution (10 mL) and stirred for 2 h, The mixture was extracted with DCM (10 mL×2). The organic phase was washed with water (10 mL) and brine (10 mL), dried with sodium sulfate, filtered, and concentrated in vacuo. The residue was purified using preparative-TLC (SiO$_2$, DCM:MeOH=10:1) to afford benzyl ((5-(4-((1-methylpiperidin-4-yl)amino)-1-(2,2,2-trifluoroethyl)-1H-indol-2-yl)-1,2,4-oxadiazol-3-yl)methyl)carbamate (500 mg) in 29.3% yield.

Preparation of 2-(3-(aminomethyl)-1,2,4-oxadiazol-5-yl)-N-(1-methylpiperidin-4-yl)-1-(2,2,2-trifluoroethyl)-1H-indol-4-amine: Benzyl ((5-(4-((1-methylpiperidin-4-yl) amino)-1-(2,2,2-trifluoroethyl)-1H-indol-2-yl)-1,2,4-oxadiazol-3-yl)methyl)carbamate (500 mg, 921.6 µmol, 1 eq) was dissolved in HBr/acetic acid (2 mL) and stirred at 25° C. for 1 hr. The mixture was poured into MTBE (10 mL) and stirred for 10 min, then filtered. The mixture was poured into water (10 mL), and a solution of EA and HCl was added dropwise to adjust the pH to 3. The solvent was removed in vacuo to afford 2-(3-(aminomethyl)-1,2,4-oxadiazol-5-yl)-N-(1-methylpiperidin-4-yl)-1-(2,2,2-trifluoroethyl)-1H-indol-4-amine (330 mg) hydrochloride as a yellow solid.

Preparation of Compounds 137B, 138B, 139B, 140B, and 141B: To a solution of RCOOH in DMF were added HATU (1.5 eq), TEA (5 eq), and 2-(3-(aminomethyl)-1,2,4-oxadiazol-5-yl)-N-(1-methylpiperidin-4-yl)-1-(2,2,2-trifluoroethyl)-1H-indol-4-amine (1 eq, HCl). The mixture was stirred at 25° C. for 1 hr. Then mixture was extracted with DCM (10 mL×2), and the organic phase was washed with water (10 mL) and brine (10 mL), dried with sodium sulfate, filtered, and concentrated in vacuo. The residue was purified using preparative-TLC (SiO$_2$, DCM:MeOH=5:1) to afford the desired compound. N-[(5-{4-[(1-methylpiperidin-4-yl) amino]-1-(2,2,2-trifluoroethyl)-1H-indol-2-yl}-1,2,4-oxadiazol-3-yl)methyl]cyclopropanecarboxamide (Compound 137B), 32.6% yield, LC-MS (ES$^+$, m/z): 477.2; N-[(5-{4-[(1-methylpiperidin-4-yl)amino]-1-(2,2,2-trifluoroethyl)-1H-indol-2-yl}-1,2,4-oxadiazol-3-yl)methyl]benzamide (Compound 138B), 22.2% yield, LC-MS (ES$^+$, m/z): 513.1; N-[(5-{4-[(1-methylpiperidin-4-yl)amino]-1-(2,2,2-trifluoroethyl)-1H-indol-2-yl}-1,2,4-oxadiazol-3-yl)methyl]thiophene-2-carboxamide (Compound 139B), 23.3% yield, LC-MS (ES$^+$, m/z): 519.0; 1-methyl-N-[(5-{4-[(1-methylpiperidin-4-yl)amino]-1-(2,2,2-trifluoroethyl)-1H-indol-2-yl}-1,2,4-oxadiazol-3-yl)methyl]-1H-pyrazole-4-carboxamide (Compound 140B), 23.7% yield, LC-MS (ES$^+$, m/z): 517.2; 1-methyl-N-[(5-{4-[(1-methylpiperidin-4-yl) amino]-1-(2,2,2-trifluoroethyl)-1H-indol-2-yl}-1,2,4-oxadiazol-3-yl)methyl]-1H-pyrazole-3-carboxamide (Compound 141B), 9.7% yield, LC-MS (ES$^-$, m/z): 517.3.

Example 79: Preparation of 2-[5-(aminomethyl)-1, 2,4-oxadiazol-3-yl]-N-[(3S,4R)-3-fluoro-1-methylpiperidin-4-yl]-1-(2,2,2-trifluoroethyl)-1H-indol-4-amine bis(hydrochloride), Amine 1

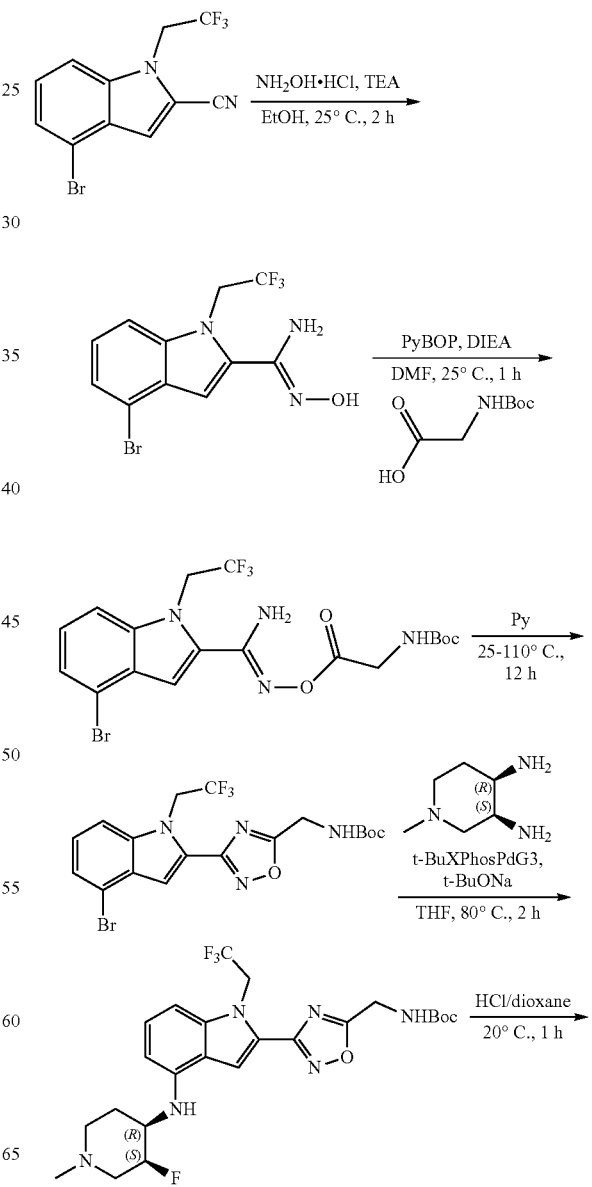

-continued

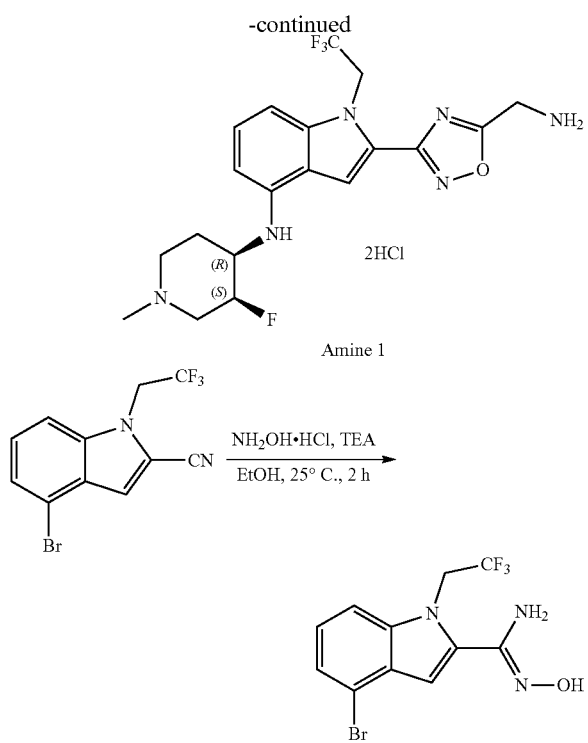

Amine 1

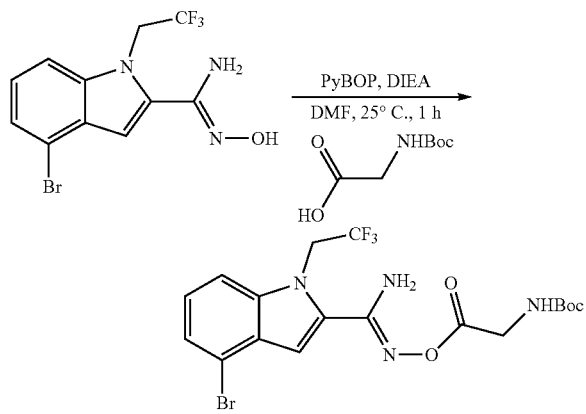

Step 1: 4-bromo-N'-hydroxy-1-(2,2,2-trifluoroethyl)indole-2-carboxamidine: To a mixture of 4-bromo-1-(2,2,2-trifluoroethyl)indole-2-carbonitrile (100 g, 330 mmol, 1 eq) and in ethanol (1 L) were added hydroxylamine hydrochloride (34.39 g, 494.9 mmol, 1.5 eq) and TEA (660 mmol, 91.9 mL, 2 eq) at 25° C. under nitrogen. The mixture was stirred at 25° C. for 2 h. The residue was poured into ice water (w/w=1/1) (1 L), and the aqueous phase was extracted with EA (3×300 mL). The combined organic phase was washed with brine (3×300 mL), dried over anhydrous sodium sulfate, filtered, and concentrated in vacuo. The crude product was triturated with PE:EA=20:1 at 25° C. for 12 h, then the product was collected by filtration and dried in vacuo to provide 4-bromo-N'-hydroxy-1-(2,2,2-trifluoroethyl)indole-2-carboxamidine (110 g, crude) as a white solid. LC-MS (ES+, m/z): 336.0/337.9 [(M+H)+]. $^1$H NMR (400 MHz, DMSO-d6) δ=9.97 (s, 1H), 7.67 (d, J=8.4 Hz, 1H), 7.35 (d, J=8 Hz, 1H), 7.20 (t, J=7.9 Hz, 1H), 7.01 (s, 1H), 6.06 (s, 2H), 5.70 (q, J=9.2 Hz, 2H).

Step 2: 2-1[amino-[4-bromo-1-(2,2,2-trifluoroethyl)indol-2-yl]methylene]amino]2-(tert-butoxycarbonylamino) acetate: To a mixture of 4-bromo-N'-hydroxy-1-(2,2,2-trifluoroethyl)indole-2-carboxamidine (92 g, 273 mmol, 1 eq) and 2-(tert-butoxycarbonylamino)acetic acid (71.93 g, 410.6 mmol, 1.5 eq) in DMF (2 L) were added PYBOP (170.93 g, 328.5 mmol, 1.2 eq) and DIEA (821.2 mmol, 143 mL, 3 eq) at 25° C. under nitrogen. The mixture was stirred at 25° C. for 60 min. The residue was poured into ice-water (w/w=1/1) (1 L). The aqueous phase was extracted with EA (3×300 mL). The combined organic phase was washed with brine (3×300 mL), dried over anhydrous sodium sulfate, filtered, and concentrated in vacuo. The crude product was triturated with PE:EA=10:1 at 25° C. for 2 h, then the solid was collected by filtration and dried in vacuo to provide the intermediate 2-[[amino-[4-bromo-1-(2,2,2-trifluoroethyl)indol-2-yl]methylene]amino]-2-(tert-butoxycarbonylamino) acetate (111 g, crude) as a white solid. $^1$H NMR (400 MHz, DMSO-d6) δ=7.76 (d, J=8.3 Hz, 1H), 7.42 (d, J=7.3 Hz, 1H), 7.32-7.25 (m, 2H), 7.18 (br s, 1H), 5.76 (q, J=9.0 Hz, 2H), 3.93 (d, J=6.1 Hz, 2H), 1.45-1.33 (m, 9H).

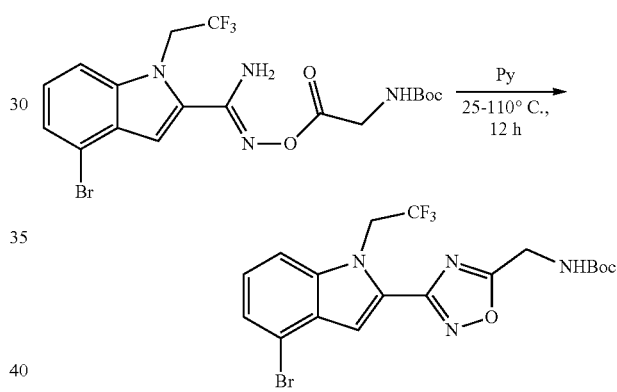

Step 3-tert-butyl N-[[3-[4-bromo-1-(2,2,2-trifluoroethyl)indol-2-yl]-1,2,4-oxadiazol-5-yl]methyl]carbamate: 2-[[amino-[4-bromo-1-(2,2,2-trifluoroethyl)indol-2-yl]methylene]amino]-2-(tert-butoxycarbonylamino)acetate (Ill g, 225.03 mmol, 1 eq) was treated with pyridine (8.25 mol, 666 mL, 36.7 eq) at 25° C. under nitrogen. The mixture was heated and stirred at 110° C. for 12 h. The residue was poured into citric acid (saturated, 1 L) and stirred for 30 min. The aqueous phase was extracted with EA (3×300 mL). The combined organic phase was washed with brine (3×300 mL), dried over anhydrous sodium sulfate, filtered, and concentrated in vacuo. The crude product was triturated with PE:EA=10:1 at 25° C. for 12 h. The product was collected by filtration and dried in vacuo to provide tert-butyl N-[[3-[4-bromo-1-(2,2,2-trifluoroethyl)indol-2-yl]-1,2,4-oxadiazol-5-yl]methyl]carbamate (100 g, crude) as a white solid. LC-MS (ES+, m/z): 375.0/377.0 [(M+H)+]. $^1$H NMR (400 MHz, DMSO-d6) δ=7.84 (d, J=8.3 Hz, 1H), 7.77 (br t, J=5.8 Hz, 1H), 7.48 (d, J=7.5 Hz, 1H), 7.39-7.32 (m, 1H), 7.27 (s, 1H), 5.68 (q, J=8.7 Hz, 2H), 4.63-4.46 (m, 2H), 3.02 (dt, J=3.9, 6.6 Hz, 1H), 1.42 (s, 9H).

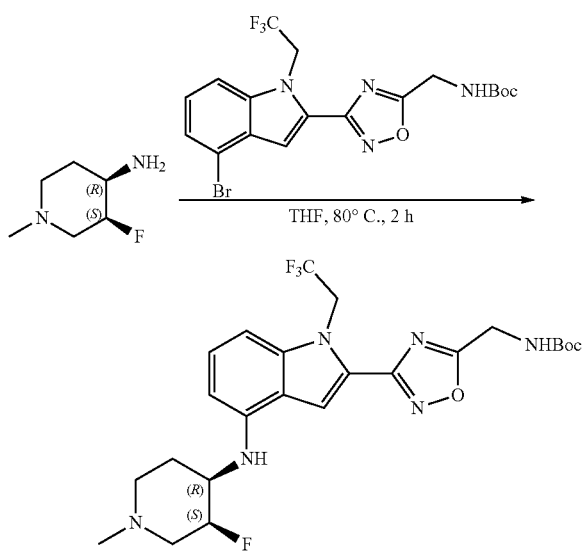

Step 4: N-[[3-[4-[[(3S,4R)-3-fluoro-1-methyl-4-piperidyl]amino]-1-(2,2,2-trifluoroethyl)indol-2-yl]-1,2,4-oxadiazol-5-yl]methyl]carbamate: To a solution of (3S,4R)-3-fluoro-1-methyl-piperidin-4-amine (11.43 g, 78.69 mmol, free base, 1.1 eq) and tert-butyl N-[[3-[4-bromo-1-(2,2,2-trifluoroethyl)indol-2-yl]-1,2,4-oxadiazol-5-yl]methyl]carbamate (34 g, 71.54 mmol, 1 eq) in THF (380 mL) were added t-Bu-XPhos Pd Generation 3 (11.37 g, 14.31 mmol, 0.2 eq) and sodium t-butoxide (2M in THF, 71.5 mL, 2 eq). The mixture was stirred at 80° C. for 2 h under nitrogen. The reaction mixture was quenched by adding saturated aqueous EDTA (400 mL) at 20° C. The mixture was stirred at 20° C. for 1 h, and then extracted with EA (3×250 mL). The combined organic layers were washed with brine (3×100 mL), dried over anhydrous sodium sulfate, filtered, and concentrated in vacuo to give a residue. This procedure was carried out twice on this scale, and the resulting crude products combined at this stage. The crude material was then purified by column chromatography (SiO$_2$, PE/EA=5/1 to 2/1 to DCM/methanol=100/1 to 60/1) to afford the title compound tert-butyl N-[[3-[4-[[(3S,4R)-3-fluoro-1-methyl-4-piperidyl]amino]-1-(2,2,2-trifluoroethyl)indol-2-yl]-1,2,4-oxadiazol-5-yl]methyl]carbamate (34 g, 64.57 mmol, 45.1% yield) as a yellow solid. $^1$H NMR (400 MHz, DMSO-d6) δ=7.99-7.87 (m, 1H), 7.78-7.62 (m, 1H), 7.17-7.04 (m, 1-1), 6.97-6.76 (m, 1H), 6.45-6.17 (m, 1H), 6.10-5.95 (m, 1H), 5.67-5.41 (m, 2H), 4.91 (br s, 1H), 4.58-4.37 (m, 2H), 3.71-3.46 (m, 1H), 3.12-2.96 (m, 1H), 2.90-2.72 (m, 1H), 2.14 (br d, J=4.1 Hz, 1H), 2.13-1.99 (m, 2H), 1.80-1.58 (m, 1H), 1.48-1.23 (m, 1H).

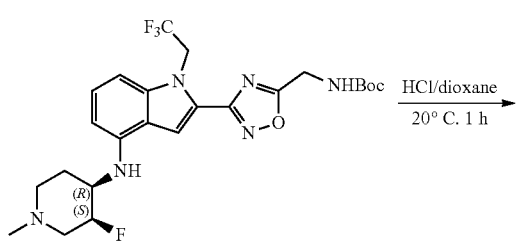

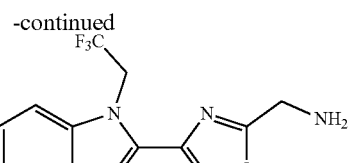

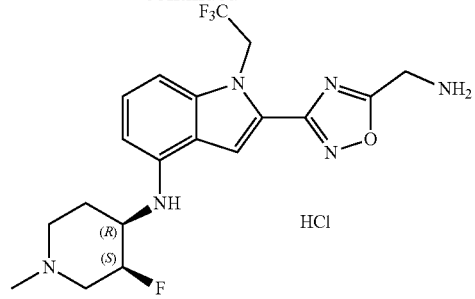

Amine 1

Step 5: 2-[5-(aminomethyl)-1,2,4-oxadiazol-3-yl]-N-[(3S,4R)-3-fluoro-1-methyl-4-piperidyl]-1-(2,2,2-trifluoroethyl)indol-4-amine hydrochloride, (Amine 1): A mixture of tert-butyl N-[[3-[4-[[(3S,4R)-3-fluoro-1-methyl-4-piperidyl]amino]-1-(2,2,2-trifluoroethyl)indol-2-yl]-1,2,4-oxadiazol-5-yl]methyl]carbamate (40 g, 68.4 mmol, 90% purity, 1 eq) in HCl/dioxane (4 M, 720 mL, 42 eq) was stirred at 20° C. for 1 h under nitrogen atmosphere. The reaction mixture was concentrated in vacuo to afford the title compound 2-[5-(aminomethyl)-1,2,4-oxadiazol-3-yl]-N-[(3S,4R)-3-fluoro-1-methyl-4-piperidyl]-1-(2,2,2-trifluoroethyl)indol-4-amine (Amine 1, HCl salt) (50 g, 96.6% yield, 90% purity, HCl) as a yellow solid. LC-MS (ES$^+$, m/z): 427.2 [(M+H)$^1$]. $^1$H NMR (400 MHz, DMSO-d6) δ=7.99-7.87 (m, 1H), 7.26-7.08 (m, 1H), 7.07-6.89 (m, 1H), 6.47-6.28 (m, 1H), 5.64-5.48 (m, 2H), 5.26-5.01 (m, 1H), 4.58 (br d, J=3.9 Hz, 2H), 4.50-4.04 (m, 14H), 4.00-3.91 (m, 1H), 3.83-3.74 (m, 1H), 3.69-3.59 (m, 1H), 3.51-3.44 (m, 1H), 3.28-3.17 (m, 1H), 2.88 (br d, J=4.4 Hz, 1H), 2.39-2.22 (m, 1H), 2.03-1.93 (m, 1H).

Example 80: 1-tert-butyl-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-pyrrole-3-carboxamide (Compound 194B)

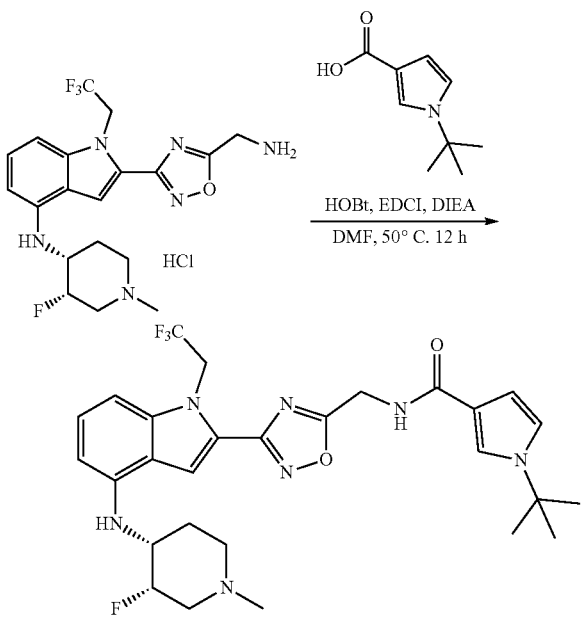

A mixture of 2-[5-(aminomethyl)-1,2,4-oxadiazol-3-yl]-N-[(3S,4R)-3-fluoro-1-methyl-4-piperidyl]-1-(2,2,2-trifluoroethyl)indol4-amine (Amine 1) (23.5 g, 30.7 mmol, 89% purity, 1 eq, HCl salt) and 1-tert-butylpyrrole-3-carboxylic acid (5.64 g, 33.8 mmol, 1.1 eq) was treated with HOBt (8.29 g, 61.37 mmol, 2 eq), EDCI (11.76 g, 61.37 mmol, 2 eq), and DIEA (307 mmol, 53.5 mL, 10 eq) in DMF (230 mL). The mixture was then degassed and purged with nitrogen 3 times, and the mixture was stirred at 50° C. for 12 h under nitrogen atmosphere. TLC (DCM:methanol=10:1, Rr-0.5) indicated one new spot had formed. The reaction mixture was quenched by adding water (800 mL) at 20° C., then extracted with EA (3××350 mL). The combined organic layers were washed with brine (3××200 mL), dried over anhydrous sodium sulfate, filtered, and concentrated in vacuo to give a residue. The residue was purified by column chromatography (SiO$_2$, PE/EA=5/1 to 2/1, then using DCM/methanol=100/1 to 60/1). The obtained product was further purified by prep-HPLC (basic condition: column: Agela DuraShell C18 250×80 mm×10 um; mobile phase: [water (10 mM NH$_4$HCO$_3$)-ACN]; B %: 55%-55%, 20 min) to afford Compound 194 1-tert-butyl-N-[[3-[4-[[(3S,4R)-3-fluoro-1-methyl-4-piperidyl]amino]-1-(2,2,2-trifluoroethyl)indol-2-yl]-1,2,4-oxadiazol-5-yl]methyl]pyrrole-3-carboxamide (20.32 g, 100.0% purity) as a yellow solid. LC-MS (ES$^+$, m/z): 576.4[(M+H)$^+$]. $^1$H NMR (400 MHz, DMSO-d6) δ=8.73-8.59 (m, 1H), 7.95-7.80 (m, 1H), 7.59-7.47 (m, 1H), 7.21-7.08 (m, 1H), 7.01-6.96 (m, 1H), 6.93-6.84 (m, 1H), 6.54-6.45 (m, 1H), 6.34-6.24 (m, 1H), 6.12-5.94 (m, 1H), 5.62-5.33 (m, 2H), 4.99-4.68 (m, 3H), 3.71-3.49 (m, 1H), 3.10-2.95 (m, 1H), 2.88- 2.75 (m, 1H), 2.31-2.15 (m, 4H), 2.13-2.05 (m, 1H), 2.05-1.92 (m, 1H), 1.73-1.62 (m, 1H), 1.54-1.45 (m, 9H).

Example 81: 1-tert-butyl-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-pyrrole-3-carboxamide (Compound 231B)

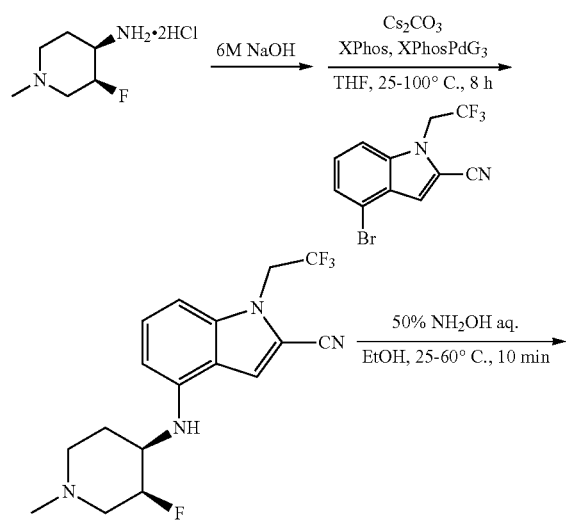

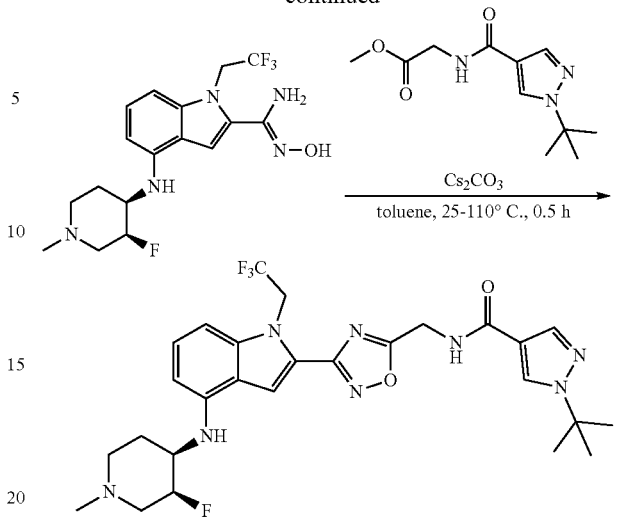

To a mixture of (3S,4R)-3-fluoro-1-methyl-piperidin-4-amine (18 g, 87.8 mmol, 1 eq, 2 HCl) in DCM (30 mL) was added sodium hydroxide (6 M, 56.3 mL, 3.85 eq) in one portion at 25° C. The mixture was stirred at 25° C. for 30 min. The reaction mixture was extracted with DCM (30 mL×8). The combined organic layers were dried over anhydrous sodium sulfate, filtered, and concentrated in vacuo with no heating to give a residue. (3S,4R)-3-fluoro-1-methyl-piperidin-4-amine (9.7 g, crude) was obtained as a yellow oil. $^1$H NMR (400 MHz, DMSO-d6) δ=5.76 (s, 1H), 4.57-4.40 (m, 1H), 2.96-2.76 (m, 1H), 2.74-2.54 (m, 2H), 2.17-2.03 (m, 4H), 2.00-1.91 (m, 1H), 1.58-1.31 (m, 4H).

To a mixture of (3S,4R)-3-fluoro-1-methyl-piperidin-4-amine (7.61 g, 56.9 mmol, 1.15 eq) and 4-bromo-1-(2,2,2-trifluoroethyl)indole-2-carbonitrile (15 g, 49.49 mmol, 1 eq) in THF (150 mL) was added XPhos (2.36 g, 4.95 mmol, 0.1 eq). The reaction was degassed by bubbling with nitrogen for 1 min, then XPhos-Pd Generation 3 was added in one portion (4.19 g, 4.95 mmol, 0.1 eq) and the reaction was degassed again by nitrogen bubbling for 1 min.

Cesium carbonate (32.25 g, 98.98 mmol, 2 eq) was then added to the reaction, and the reaction was degassed a final time by nitrogen bubbling for 1 min, then the sealed reaction was heated to 100° C. and stirred for 8 h. The residue was poured into saturated EDTA aqueous solution at 0° C. and stirred for 1 h (150 mL). The aqueous phase was extracted with EA (50 mL×4), then the organic phase was adjusted to pH=2 with 3M HCl, and the mixture was extracted with water 300 mL (50 mL×6). The aqueous phase (containing the product) was adjusted to pH=10 with 6M NaOH. The mixture was extracted with EA (80 mL×6). The combined organic phase was washed with brine (200 mL×1), dried over anhydrous sodium sulfate, filtered, and concentrated in vacuo. The product was triturated with PE:EA=20:1 (100 mL) at 25° C. for 30 mins, and the product collected by filtration. The filter cake was washed with PE:EA=20:1 (50 mL), and the solid dried in vacuo to provide the intermediate 4-[[(3S,4R)-3-fluoro-1-methyl-4-piperidyl]amino]-1-(2,2,2-trifluoroethyl)indole-2-carbonitrile (16 g, 88% yield, 96.4% purity) as a yellow solid. LC-MS (ES$^-$, m/z): 355.2 [(M+H)$^+$]. $^1$H NMR (400 MHz, DMSO-d6) δ=7.95 (s, 1H), 7.21 (t, J=8.0 Hz, 1H), 6.92 (d, J=8.3 Hz, 1H), 6.34 (d, J=7.7 Hz, 1H), 5.93 (d, J=8.5 Hz, 1H), 5.23 (q, J=9.2 Hz, 2H), 4.91-4.75 (m, 1H), 3.69-3.56 (m, 1H), 3.09-3.00 (m, 1H), 2.82 (br d, J=11.2 Hz, 1H), 2.33-2.19 (m, 4H), 2.14-2.07 (m, 1H), 2.01-1.90 (m, 1H), 1.72 (br dd, J=3.2, 12.9 Hz, 1H).

To a mixture of 4-[[(3S,4R)-3-fluoro-1-methyl-4-piperidyl]amino]-1-(2,2,2-trifluoroethyl)indole-2-carbonitrile (16 g, 43.5 mmol, 1 eq) in ethanol (80 mL) was added hydroxylamine (aq.) (43.5 mmol, 80 mL, 50% purity, 1 eq) at 25° C. under nitrogen, and the reaction was heated to 60° C. and stirred for 10 mins. The residue was poured into ice-water (w/w=1/1) (200 mL). The aqueous phase was extracted with EA (60 mL×6). The combined organic phase was washed with brine (200 mL×1), dried over anhydrous sodium sulfate, filtered, and concentrated in vacuo. The product was triturated with PE:EA=20:1 (120 mL) at 25° C. for 30 mins. The mixture was filtered and the filter cake was washed with PE (50 mL), then dried in vacuo to provide the intermediate hydroxamidine 4-[[(3S,4R)-3-fluoro-1-methyl-4-piperidyl]amino]-N'-hydroxy-1-(2,2,2-trifluoroethyl)indole-2-carboxamidine (15.8 g, 92.2% yield, 98.4% purity) as a yellow solid. LC-MS (ES+, m/z): 388.2 [(M+H)+]. 1H NMR (400 MHz, DMSO-d6) δ=9.75 (s, 1H), 7.23 (s, 1H), 7.05-6.97 (m, 1H), 6.82 (d, J=8.2 Hz, 1H), 6.28 (d, J=7.7 Hz, 1H), 5.78 (s, 2H), 5.51 (q, J=8.9 Hz, 2H), 5.23 (d, J=8.8 Hz, 1H), 4.94-4.71 (m, 1H), 4.03 (q, J=7.1 Hz, 1H), 3.71-3.51 (m, 1H), 3.10-2.97 (m, 1H), 2.81 (br d, J=11.0 Hz, 1H), 2.33-2.18 (m, 4H), 2.10 (brt, J=10.8 Hz, 1H), 1.99 (s, 1H), 1.96-1.83 (m, 1H), 1.80-1.70 (m, 1H), 1.17 (t, J=7.1 Hz, 1H).

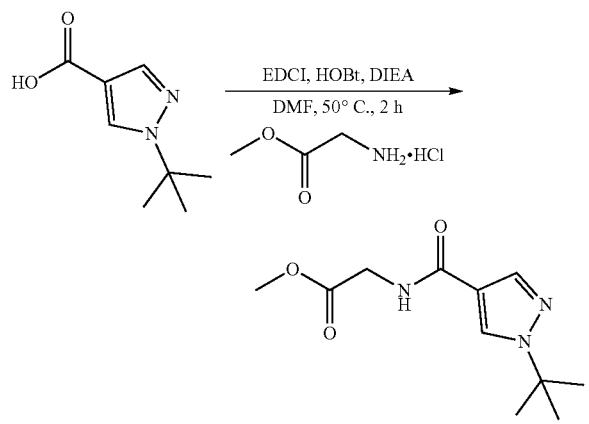

Representative Procedure: Method A. A mixture of methyl 2-aminoacetate hydrochloride (35.83 g, 285.4 mmol, 1.2 eq) and 1-tert-butylpyrazole-4-carboxylic acid (40 g, 237.82 mmol, 1 eq) were treated with HOBT (64.27 g, 475.7 mmol, 2 eq), EDCI (91.18 g, 475.7 mmol, 2 eq) and DIEA (2.38 mol, 414 mL, 10 eq) in DMF (400 mL), then stirred and heated at 50° C. for 2 h under nitrogen atmosphere. The mixture was cooled and quenched by adding brine (1000 mL) at 25° C., then extracted with EA (200 mL×5). The combined organic layers were washed with brine (500 mL×1), dried over anhydrous sodium sulfate, filtered, and concentrated in vacuo to give a residue. The residue was a colorless oil (53 g, crude product). The colorless oil (53 g, crude product) was triturated with hexane (200 mL) and stirred at 60° C. for 1 h, and then stirred and allowed to cool to 25° C. over 12 hrs. The reaction was then filtered to collect the solid, and the solid was dried in vacuo to provide the desired intermediate methyl 2-[(1-tert-butylpyrazole-4-carbonyl)amino]acetate (46 g, 81% yield, 98.5% purity) as a white solid. LC-MS (ES+, m/z): 240.1 [(M+H)+]. 1H NMR (400 MHz, DMSO-d6) δ ppm 8.49 (br t, J=5.81 Hz, 1H) 8.28 (s, 1H) 7.87 (s, 1H) 3.95 (d, J=5.99 Hz, 2H) 3.64 (s, 3H) 1.53 (s, 9H).

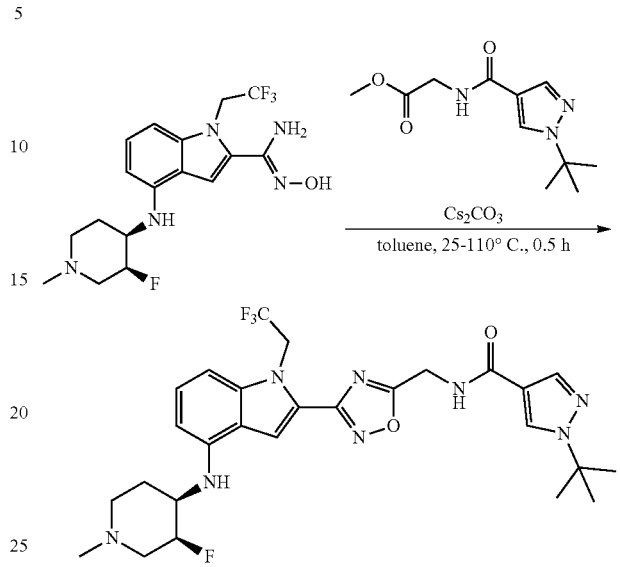

Representative Procedure: Method C. To a mixture of methyl 2-[(1-tert-butylpyrazole-4-carbonyl)amino]acetate (23.75 g, 97.76 mmol, 98.5% purity, 1.7 eq) and 4-[[(3S,4R)-3-fluoro-1-methyl-4-piperidyl]amino]-N'-hydroxy-1-(2,2,2-trifluoroethyl)indole-2-carboxamidine (23.8 g, 57.5 mmol, 1 eq) in toluene (240 mL) was added cesium carbonate (56.21 g, 172.5 mmol, 3 eq) at 25° C. under nitrogen, and the mixture was heated to 110° C. and stirred for 0.5 h. The reaction was cooled and poured into ice-water (w/w=1/1) (200 mL). The aqueous phase was extracted with EA (60 mL×4). The organic phase was adjusted to pH=2 with 3M HCl. The mixture was extracted with water (80 mL×6), and the aqueous phase (containing the product) was adjusted to pH=9 with 6M NaOH. The mixture was extracted with EA (100 mL×6). The combined organic phase was washed with brine (300 mL×1), dried over anhydrous sodium sulfate, filtered, and concentrated in vacuo. The residue was purified by prep-HPLC (column: Phenomenex Titank C18 Bulk 250×100 mm, 10 um; mobile phase: [water (10 mM NH4HCO3)-ACN]; B %: 40%-65%, 20 min.) to provide 1-tert-butyl-N-[[3-[4-[[(3S,4R)-3-fluoro-1-methyl-4-piperidyl]amino]-1-(2,2,2-trifluoroethyl)indol-2-yl]-1,2,4-oxadiazol-5-yl]methyl]pyrazole-4-carboxamide (20.79 g, 55.1% yield, 99.0% purity) was obtained as a green solid. LC-MS (ES+, m/z): 577.3 [(M+H)+]. 1H NMR (400 MHz, DMSO-d6) δ=8.97 (t, J=5.7 Hz, 1H), 8.34 (s, 1H), 7.93 (s, 1H), 7.89 (s, 1H), 7.15-7.08 (m, 1H), 6.88 (d, J=8.2 Hz, 1H), 6.28 (d, J=7.9 Hz, 1H), 6.01 (d, J=8.3 Hz, 1H), 5.50 (q, J=9.0 Hz, 2H), 4.93-4.74 (m, 3H), 3.69-3.50 (m, 1H), 3.08-2.98 (m, 1H), 2.81 (br d, J=9.9 Hz, 1H), 2.31-2.17 (m, 4H), 2.12-2.06 (m, 1H), 2.05-1.97 (m, 1H), 1.72-1.64 (m, 1H), 1.54 (s, 9H).

Example 82: N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(2-methoxyethyl)-1H-pyrazole-4-carboxamide (Compound 290B)

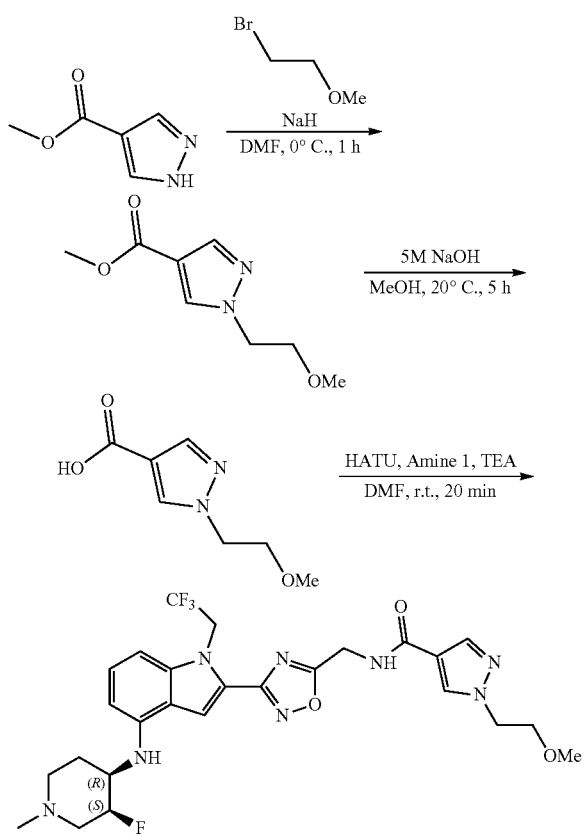

To a mixture of the pyrazole ester (1 g, 7.93 mmol, 1 eq) in DMF (10 mL) was added sodium hydride (634.3 mg, 15.9 mmol, 60% purity, 2 eq) at 0° C. under nitrogen. The mixture was stirred at 0° C. for 5 min, followed by the bromide (1.10 g, 7.93 mmol, 1 eq). The mixture was stirred at 0° C. for 55 h. The residue was poured into ammonium chloride (sat., 200 mL) and stirred for 5 min. The aqueous phase was extracted with EA (30 mL×3). The combined organic phase was washed with brine (30 mL×3), dried over anhydrous sodium sulfate, filtered, and concentrated in vacuo. The reaction was purification by silica gel chromatography to provide the product (1 g, 68.5% yield) as a yellow oil. LC-MS (ES+, m/z): 185.1 [(M+H)+].

To a mixture of the ester (1 g, 5.43 mmol, 1 eq) in methanol (5 mL) was added sodium hydroxide (5 M, 4.7 mL, 4.30 eq) in one portion at 20° C. under nitrogen. The mixture was stirred at 20° C. for 5 h. The residue was treated with 1N HCl to adjust pH=5~6. The aqueous phase was extracted with EA (30 mL×3). The combined organic phase was washed with brine (30 mL×3), dried over anhydrous sodium sulfate, filtered, and concentrated in vacuo to provide the intermediate (0.7 g, crude) as a white solid. LC-MS (ES·, m/z): 171.1 [(M+H)+].

Method B: To the carboxylic acid (30.7 mg, 180 μmol, 2 eq) in DMF (2 mL) were added HATU (68.5 mg, 180 μmol, 2 eq), TEA (900 μmol, 125 μL 10 eq) in one portion at 20° C. under nitrogen. The mixture was stirred at 20° C. for 10 min, followed by addition of Amine 1 (50 mg, 90.1 μmol, 1 eq, 2HCl). The mixture was stirred at 20° C. for 10 min. The residue was poured into ice-water (w/w=1/1) (100 mL). The aqueous phase was extracted with EA (30 mL×3). The combined organic phase was washed with brine (30 mL×3), dried over anhydrous sodium sulfate, filtered, and concentrated in vacuo. The residue was purified by prep-TLC to provide (20 mg, 36.8% yield, 95.9% purity) as a light yellow solid. $^1$H NMR (400 MHz, DMSO-d$_6$) δ ppm 1.68 (br d, J=9.78 Hz, 1H) 2.00 (br d, J=11.37 Hz, 1H) 2.06-2.13 (m, 1H) 2.20 (br s, 3H) 2.27 (br s, 1H) 2.82 (br d, J=9.05 Hz, 1H) 3.05 (br d, J=8.68 Hz, 1H) 3.24 (s, 3H) 3.50-3.63 (m, 1H) 3.69 (t, J=5.07 Hz, 2H) 4.30 (t, J=5.07 Hz, 2H) 4.74-4.93 (m, 3H) 5.50 (q, J=8.76 Hz, 2H) 6.03 (br d, J=8.19 Hz, 1H) 6.28 (d, J=7.95 Hz, 1H) 6.88 (br d, J=7.95 Hz, 1H) 7.11 (t, J=8.07 Hz, 1H) 7.91 (d, J=10.88 Hz, 2H) 8.22 (s, 1H) 9.01 (t, J=5.50 Hz, 1H).

Example 83: N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(1-methoxypropan-2-yl)-1H-pyrrole-3-carboxamide (Compound 289B)

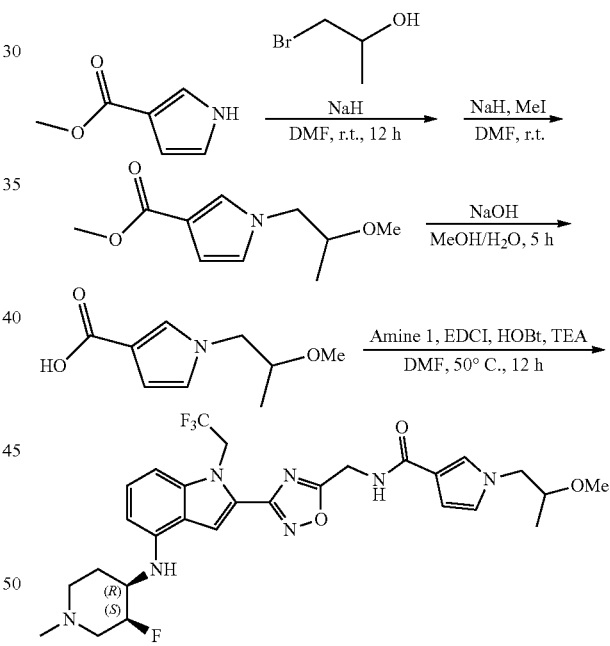

To a solution of the pyrrole (1 g, 7.99 mmol, 1 eq) in DMF (10 mL) was added sodium hydride (639 mg, 16 mmol, 60% purity, 2 eq) at 0° C., and the reaction was stirred at 0° C. for 0.5 h. The bromoalcohol (2.22 g, 16 mmol, 2 eq) was then added, and the mixture was stirred and warmed to 25° C. over 16 h. The reaction mixture was poured into sat. ammonium chloride (100 mL), then extracted with EA (50 mL×3). The combined organic phase was washed with brine (30 mL×1), dried over anhydrous sodium sulfate, filtered, and concentrated in vacuo to give a residue. The residue was purified by column chromatography to provide the intermediate ester (1 g, 68.3% yield) as a light yellow oil. $^1$H NMR (400 MHz, DMSO-d$_6$) δ=7.41 (t, J=1.90 Hz, 1H) 6.76-6.82

(m, 1H) 6.37 (dd, J=2.81, 1.71 Hz, 1H) 4.85-4.92 (m, 1H) 3.82-3.91 (m, 2H) 3.74-3.81 (m, 1H) 3.67 (s, 3H) 0.99 (d, J=5.99 Hz, 3H).

To a solution of the intermediate alcohol (300 mg, 1.64 mmol, 1 eq) in DMF (5 mL) was added sodium hydride (328 mg, 8.19 mmol, 60% purity, 5 eq) at 0° C., and the reaction was stirred at 0° C. for 0.5 h, followed by addition of iodomethane (3.28 mmol, 204 µL 2 eq). The mixture was stirred and warmed to 25° C. over 1.5 h. The reaction mixture was poured into sat. ammonium chloride (100 mL), then extracted with EA (50 mL×3). The combined organic phase was washed with brine (30 mL×1), dried over anhydrous sodium sulfate, filtered, and concentrated in vacuo to give a residue. The residue was purified by prep-TLC to give the intermediate methyl ether (200 mg. 61.9% yield) as a light yellow oil. LCMS (ES+, m/z): 198.1 [(M+H)+].

To a solution of the above intermediate (200 mg, 1.01 mmol, 1 eq) in methanol (3 mL) and water (3 mL) was added sodium hydroxide (81.1 mg, 2.03 mmol, 2 eq), then the mixture was stirred at 50° C. for 16 h.

The reaction mixture was poured into water (30 mL), and aq. HCl solution (1N) was added to pH=4, then the aqueous solution was extracted with EA (30 mL×3). The combined organic phase was dried over anhydrous sodium sulfate, filtered, and concentrated in vacuo to give the carboxylic acid (150 mg, crude) as a light yellow solid. LCMS (ES+, m/z): 184.1 [(M+H)+].

To a solution of the carboxylic acid (66 mg, 360 µmol, 2 eq) and Amine 1 (100 mg, 180.2 µmol, 1 eq, 2HCl) in DMF (5 mL) were added TEA (1.80 mmol, 251 µL 10 eq), EDCI (172.76 mg, 901.20 µmol, 5 eq) and HOBt (121.77 mg, 901.20 µmol, 5 eq), then the mixture was stirred at 50° C. for 16 h. The reaction mixture was poured into water (150 mL), then extracted with EA (60 mL×3). The combined organic phase was washed with brine (50 mL×1), dried over anhydrous sodium sulfate, filtered, and concentrated in vacuo to give a residue. The residue was purified by prep-TLC to give N-{[3-(4-{[(3S,4R)-3-fluoro-1-methylpiperidin-4-yl] amino}-1-(2,2,2-trifluoroethyl)-1H-indol-2-yl)-1,2,4-oxadiazol-5-yl]methyl}-1-(1-methoxypropan-2-yl)-1H-pyrrole-3-carboxamide (28.4 mg, 25.8% yield) as a white solid. LCMS (ES+, m/z): 592.2 [(M+H)+]. 1H NMR (400 MHz, DMSO-d6) δ=8.65 (t, J=5.69 Hz, 1H) 7.89 (s, 1H) 7.35 (t, J=1.83 Hz, 1H) 7.11 (t, J=8.01 Hz, 1H) 6.88 (d, 0.1=8.31 Hz, 1H) 6.77 (t, 0.1=2.45 Hz, 1H) 6.49 (dd, J=2.63, 1.90 Hz, 1H) 6.28 (d, 0.1=7.82 Hz, 1H) 6.01 (d, J=8.31 Hz, 1H) 5.50 (q, J=8.97 Hz, 2H) 4.76-4.91 (m, 1H) 4.72 (d, J=5.75 Hz, 2H) 3.96-4.03 (m, 1H) 3.83-3.91 (m, 1H) 3.51-3.67 (m, 2H) 3.21 (s, 3H) 2.99-3.08 (m, 1H) 2.82 (br d, J=11.00 Hz, 1H) 2.17-2.31 (m, 4H) 1.95-2.13 (m, 2H) 1.64-1.72 (m, 1H) 1.02 (d, J=6.24 Hz, 3H).

Example 84: N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(1-fluoropropan-2-yl)-1H-pyrrole-3-carboxamide (Compound 291B)

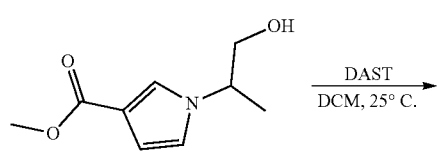

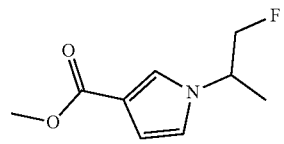

Step 1: To a solution of the intermediate alcohol obtained above (500 mg, 2.73 mmol, 1 eq) in DCM (10 mL) was added DAST (527.9 mg, 3.28 mmol, 432.71 µL 1.2 eq) at 0° C., and the reaction was then stirred at 25° C. for 1 h. The reaction mixture was poured into Sat. ammonium chloride (150 mL), then extracted with EA (60 mL×3). The combined organic phase was washed with brine (50 mL×1), dried over anhydrous sodium sulfate, filtered, and concentrated in vacuo to give a residue. The residue was purified by prep-TLC to give the desired fluoride ester (360 mg, 71.2% yield) as a light yellow oil. LCMS (ES+, m/z): 186.0 [(M+H)+].

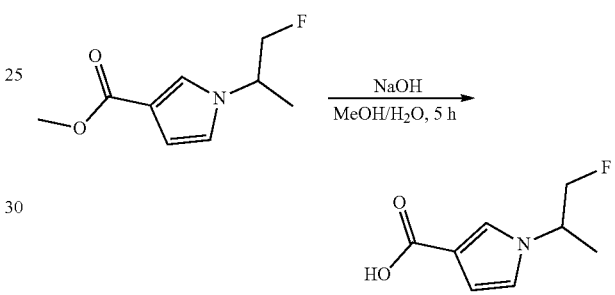

Step 2: To a solution of the difluoride ester intermediate (200 mg, 1.08 mmol, 1 eq) in methanol (3 mL) and water (3 mL) was added sodium hydroxide (172.8 mg, 4.32 mmol, 4 eq), then the mixture was stirred at 50° C. for 16 h. The reaction mixture was poured into water (80 mL), added aq. 1M HCl to pH=4, then extracted with EA (40 mL×3). The combined organic phase was dried over anhydrous sodium sulfate, filtered, and concentrated in vacuo to give the intermediate acid (150 mg, crude) as a light yellow solid. LCMS (ES+, m/z): 172.1 [(M+H)+].

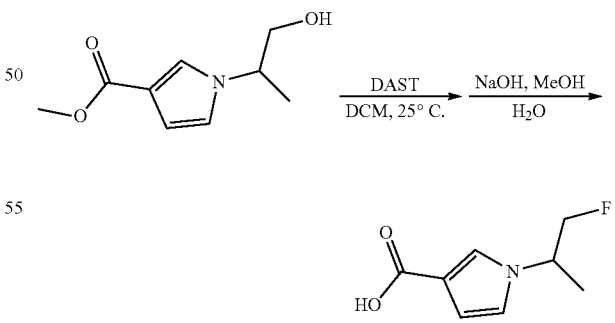

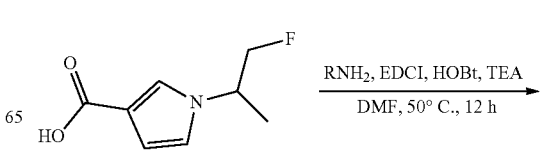

-continued

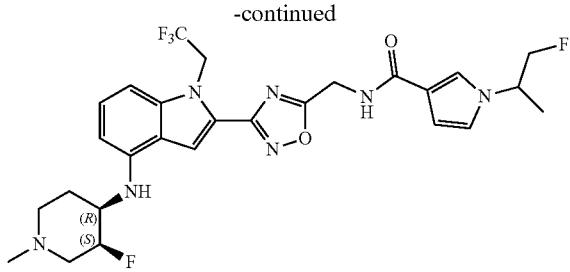

To a solution of the fluoro acid (37 mg, 216 μmol, 2 eq) and Amine 1 (60 mg, 108.1 μmol, 1 eq, 2HCl) in DMF (5 mL) were added TEA (1.08 mmol, 150 μL 10 eq), EDCI (103.7 mg, 541 μmol, 5 eq) and HOBt (73.1 mg, 541 μmol, 5 eq), then the mixture was heated and stirred at 50° C. for 16 h. The reaction mixture was poured into water (150 mL), then extracted with EA (60 mL×3). The combined organic phase was washed with brine (50 mL×1), dried over anhydrous sodium sulfate, filtered, and concentrated in vacuo to give a residue. The residue was purified by prep-TLC to give compound N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(1-fluoropropan-2-yl)-1H-pyrrole-3-carboxamide (21.3 mg, 32.7% yield) as a white solid. LCMS (ES$^+$, m/z): 580.1 [(M+H)$^+$]. $^1$H NMR (400 MHz, DMSO-d$_6$) δ=8.70 (t, J=5.75 Hz, 1H) 7.89 (s, 1H) 7.38 (s, 1H) 7.11 (t, J=8.01 Hz, 1H) 6.88 (d, J=8.19 Hz, 1H) 6.80 (t, J=2.32 Hz, 1H) 6.53 (dd, J=2.69, 1.83 Hz, 1H) 6.28 (d, J=7.82 Hz, 1H) 6.02 (br d, J=8.31 Hz, 1H) 5.50 (q, J=9.01 Hz, 2H) 4.78-4.99 (m, 2H) 4.73 (d, J=5.75 Hz, 2H) 4.15-4.27 (m, 1H) 4.02-4.13 (m, 1H) 3.51-3.68 (m, 1H) 3.00-3.10 (m, 1H) 2.83 (br d, J=9.29 Hz, 1H) 2.17-2.28 (m, 4H) 1.99-2.14 (m, 2H) 1.69 (br d, J=10.88 Hz, 1H) 1.21-1.29 (m, 3H).

Example 85: 1-tert-butyl-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-imidazole-4-carboxamide (Compound 292B)

To a mixture of the previously prepared ethyl (Z)-3-(dimethylamino)-2-isocyano-prop-2-enoate (1.18 g, 5.95 mmol, 1 eq) was added 2-methylpropan-2-amine (23.8 mmol, 2.50 mL, 4 eq), and the reaction was heated at 140° C. in a sealed tube for 10 h. The residue was poured into ice-water (200 mL). The aqueous phase was extracted with EA (3×50 mL). The combined organic phase was washed with brine (3×50 mL), dried over anhydrous sodium sulfate, filtered, and concentrated in vacuo. The residue was purified by silica gel chromatography (silica gel, PE/EA=1/0, 0/1) to provide ethyl 1-tert-butylimidazole-4-carboxylate (0.5 g, 2.55 mmol, 42.9% yield) as a brown solid.

Ethyl 1-tert-butylimidazole-4-carboxylate (500 mg, 2.55 mmol, 1 eq) was saponified in MeOH (2 mL) with aq. NaOH (5 M, 2 mL, 3.9 eq) under standard conditions. The reaction mixture was poured into 3N HCl to adjust pH=6-7, then concentrated in vacuo to provide 1-tert-butylimidazole-4-carboxylic acid (250 mg, crude) as a brown solid. LC-MS (ES$^+$, m/z): 169.1 [(M+H)$^+$]. 1-tert-butyl-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-imidazole-4-carboxamide was prepared from the above carboxylic acid to provide the product. LCMS (ES$^+$, m/z): 577.1 [(M+H)$^+$].

Example 86: N-{[3-(4-{[(3S,4R)-1-ethyl-3-fluoropiperidin-4-yl]amino}-1-(2,2,2-trifluoroethyl)-1H-indol-2-yl)-1,2,4-oxadiazol-5-yl]methyl}-1-(2-fluoroethyl)-1H-pyrrole-3-carboxamide (Compound 293B)

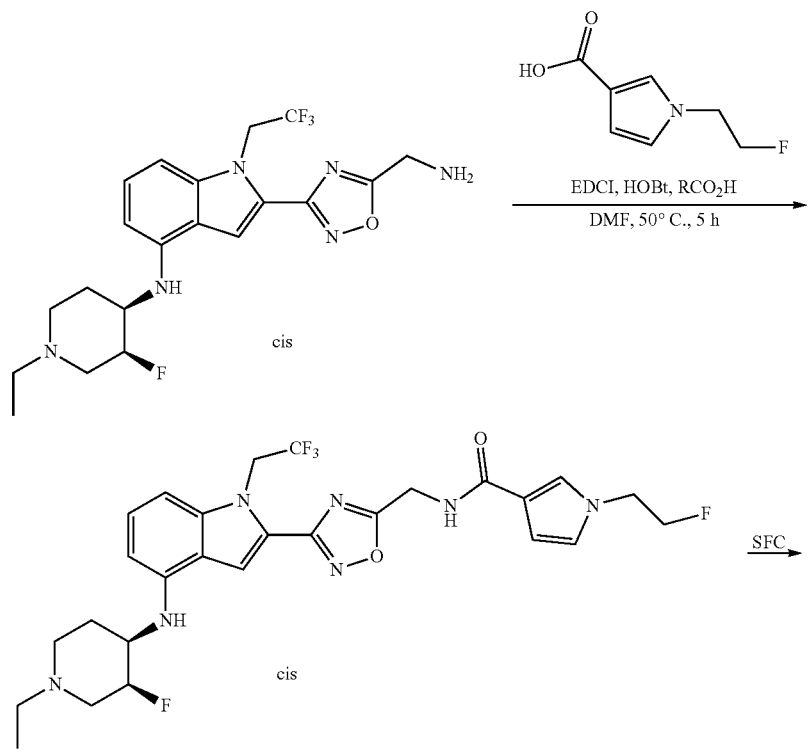

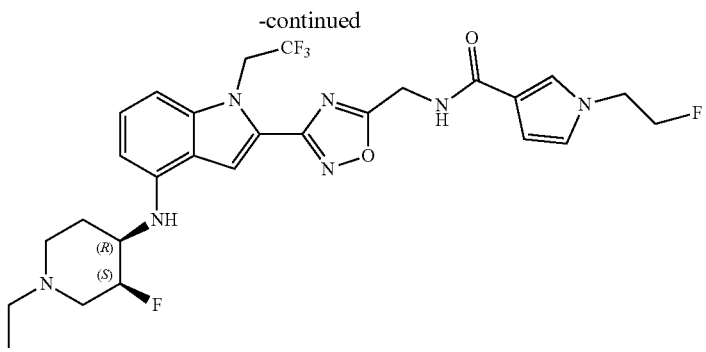

To a solution of the amine (300 mg, 0.44 mmol, 1 eq,), (74.3 mg, 0.44 mmol, 1 eq) in DMF (8 mL) were added TEA (4.39 mmol, 611 μL 10 eq), EDCI (252.5 mg, 1.32 mmol, 3 eq) and HOBt (178 mg, 1.32 mmol, 3 eq), and the mixture was stirred at 50° C. for 2 h. The reaction mixture was poured into water (20 mL), then extracted with EA (10 mL×3). The combined organic phase was washed with brine (20 mL×1), dried over anhydrous sodium sulfate, filtered, and concentrated in vacuo to give a residue. The residue was purified by prep-TLC to give N-{[3-(4-{[(3S,4R)-1-ethyl-3-fluoropiperidin-4-yl]amino}-1-(2,2,2-trifluoroethyl)-1H-indol-2-yl)-1,2,4-oxadiazol-5-yl]methyl}-(2-fluoroethyl)-1H-pyrrole-3-carboxamide (100 mg, 25.3% yield), a white solid, as a mixture of enantiomers. Resolution of the two enantiomers with chiral SFC provided the desired pure enantiomer N-{[3-(4-{[(3S,4R)-1-ethyl-3-fluoropiperidin-4-yl]amino}-1-(2,2,2-trifluoroethyl)-1H-indol-2-yl)-1,2,4-oxadiazol-5-yl]methyl}-1-(2-fluoroethyl)-1H-pyrrole-3-carboxamide. LCMS (ES+, m/z): 535.1 [(M+H)+]. $^1$H NMR (400 MHz, DMSO-d$_6$) δ=1.63-1.72 (m, 1H), 1.92-2.14 (m, 2H), 2.15-2.31 (m, 4H), 2.82 (br d, 1H), 2.96-3.10 (m, 1H), 3.50-3.70 (m, 1H), 3.87 (s, 3H), 4.69-4.96 (m, 3H), 5.50 (q, 2H), 6.02 (d, 1H), 6.28 (d, 1H), 6.88 (d, 1H), 7.11 (t, 1H), 7.89 (d, 2H), 8.19 (s, 1H), 9.00 (t, 1H).

Example 87: N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-methyl-1H-pyrazole-4-carboxamide (Compound 294B)

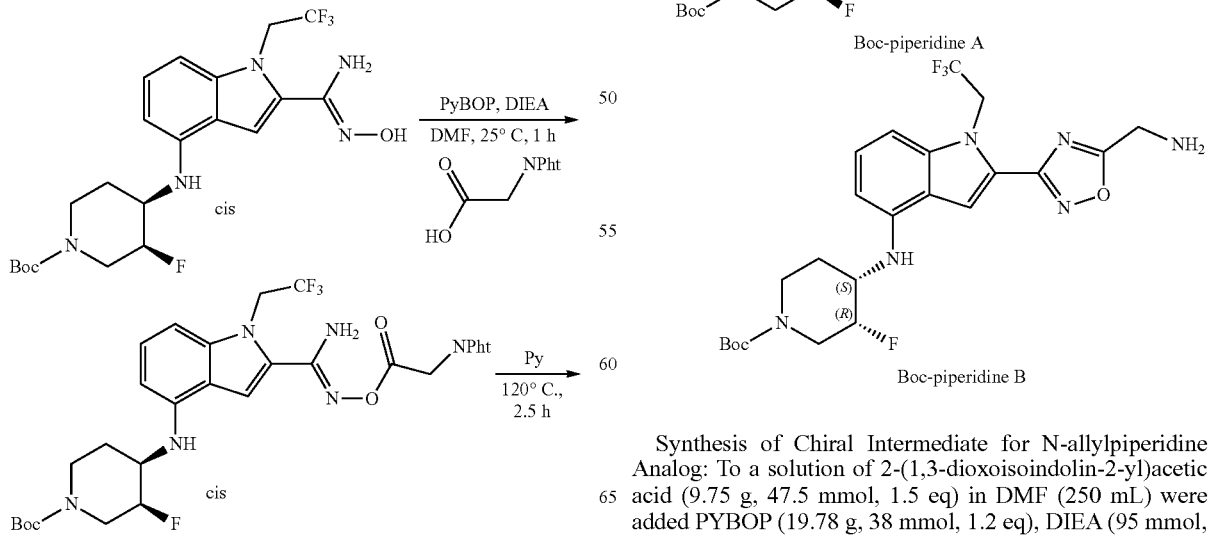

Synthesis of Chiral Intermediate for N-allylpiperidine Analog: To a solution of 2-(1,3-dioxoisoindolin-2-yl)acetic acid (9.75 g, 47.5 mmol, 1.5 eq) in DMF (250 mL) were added PYBOP (19.78 g, 38 mmol, 1.2 eq), DIEA (95 mmol, 16.6 mL, 3 eq) and racemic tert-butyl (3S,4R)-3-fluoro-4-

[[2-[(Z)—N'-hydroxycarbamimidoyl]-1-(2,2,2-trifluoroethyl)indol-4-yl]amino]piperidine-1-carboxylate (15 g, 31.7 mmol, 1 eq). The mixture was stirred at 25° C. for 1 h. The reaction mixture was poured into water (600 mL) then filtered, and the filter cake was dried in vacuo to give a residue. The residue was purified by column chromatography (SiO$_2$, PE:EA=10/1 to 1/1) to give the product (17 g, 81.2% yield). LC-MS (ES$^+$, m/z): 661.3 [(M+H)$^+$]. $^1$H NMR (400 MHz, DMSO-d6) δ=8.02-7.87 (m, 4H), 7.71-7.53 (m, 2H), 7.52-7.42 (m, 1H), 7.09 (t, J=8.0 Hz, 1H), 6.90 (d, J=8.4 Hz, 1H), 6.40-6.30 (m, 1H), 5.70 (d, J=8.8 Hz, 1H), 5.61-5.46 (m, 2H), 5.01-4.79 (m, 11H), 4.70 (s, 2H), 4.23 (br s, 1H), 4.16-4.03 (m, 1H), 3.95-3.78 (m, 1H), 3.19-2.90 (m, 2H), 1.91-1.68 (m, 2H), 1.42 (s, 9H).

Racemic tert-butyl (3S,4R)-4-[[2-[(Z)—N'-[2-(1,3-dioxoisoindolin-2-yl)acetyl]oxycarbamimidoyl]-1-(2,2,2-trifluoroethyl)indol-4-yl]amino]-3-fluoro-piperidine-1-carboxylate (17 g, 25.7 mmol, 1 eq) was dissolved in pyridine (170 mL), and the reaction was stirred at 120° C. for 2.5 hrs. The reaction was poured into water (300 mL), filtered, and the solid was concentrated in vacuo to give a residue. The residue was purified by trituration with 300 mL (PE:EA=5:1) to give the cyclized product (12 g, 72.6% yield) as brown solid. LC-MS (ES$^+$, m/z): 643.6 [(M+H)$^+$]. $^1$H NMR (400 MHz, DMSO-d6) δ=8.03-7.89 (m, 4H), 7.81 (s, 1H), 7.11 (t, J=8.0 Hz, 1H), 6.87 (d, J=8.2 Hz, 1H), 6.30 (d, J=7.9 Hz, 1H), 6.09 (br d, J=8.6 Hz, 1H), 5.46 (q, J=8.7 Hz, 2H), 5.25 (s, 2H), 4.93-4.74 (m, 1H), 4.32-4.13 (m, 1H), 4.10-4.00 (m, 1H), 3.91-3.71 (m, 1H), 2.88 (br s, 2H), 1.92-1.72 (m, 1H), 1.64 (br d, J=10.4 Hz, 1H), 1.39 (s, 11H).

Racemic tert-butyl (3S,4R)-4-[[2-[5-[(1,3-dioxoisoindolin-2-yl)methyl]-1,2,4-oxadiazol-3-yl]-1-(2,2,2-trifluoroethyl)indol-4-yl]amino]-3-fluoro-piperidine-1-carboxylate (9 g, 14 mmol, 1 eq) in ethanol (65 mL) was treated with hydrazine hydrate (65 mL, 98% purity), and the reaction was stirred at 80° C. for 1 h. The mixture was added to water (300 mL), filtered, and the solid was dried in vacuo to give a residue. The residue was purified by column chromatography (SiO$_2$, PE:EA=5/1 to 1/3).The racemic product was then further purified by SFC to resolve into separate enantiomers (column: DAICEL CHIRALPAK AD (250 mm×50 mm, 10 um); mobile phase: [0.1% NH3H$_2$O IPA]; B %: 50%-50%, 7 min) to give Boc-piperidine A (2.8 g, 39.0% yield) and Boc-piperidine B (2.9 g, 40.4% yield).

Example 88: 1-tert-butyl-N-{[3-(4-{[(3S,4R)-1-ethyl-3-fluoropiperidin-4-yl]amino}-1-(2,2,2-trifluoroethyl)-1H-indol-2-yl)-1,2,4-oxadiazol-5-yl]methyl}-1H-pyrrole-3-carboxamide (Compound 298B), and 1-tert-butyl-N-{[3-(4-{[(3R,4S)-1-ethyl-3-fluoropiperidin-4-yl]amino}-1-(2,2,2-trifluoroethyl)-1H-indol-2-yl)-1,2,4-oxadiazol-5-yl]methyl}-1H-pyrrole-3-carboxamide (Compound 299B)

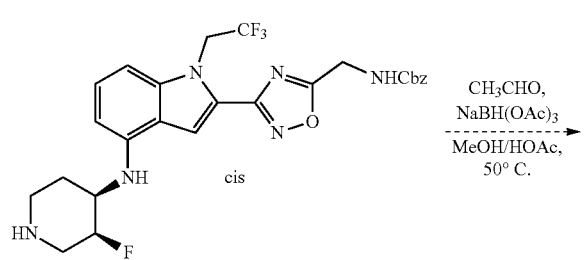

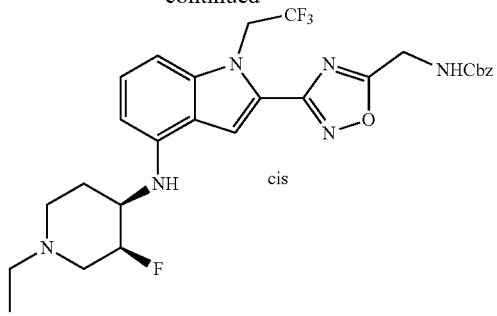

The piperidine starting material was prepared according to EXAMPLE 64. To a solution of the piperidine (1.2 g, 2.20 mmol, 1 eq) in DMF (20 mL) were added potassium carbonate (1.52 g, 11 mmol, 3 eq) and iodoethane (3.29 mmol, 263 μL 1.5 eq), then the reaction was stirred at r.t. for 2 h. The reaction mixture was poured into water (50 mL), then extracted with EA (30 mL×3). The combined organic phase was washed with brine (50 mL×1), dried over anhydrous sodium sulfate, filtered, and concentrated in vacuo to give a residue. The residue was purified by column chromatography to give the desired N-ethyl intermediate racemate (1.1 g, 87.1% yield) as a yellow solid. LC-MS (ES$^+$, m/z): 575.3 [(M+H)$^+$.

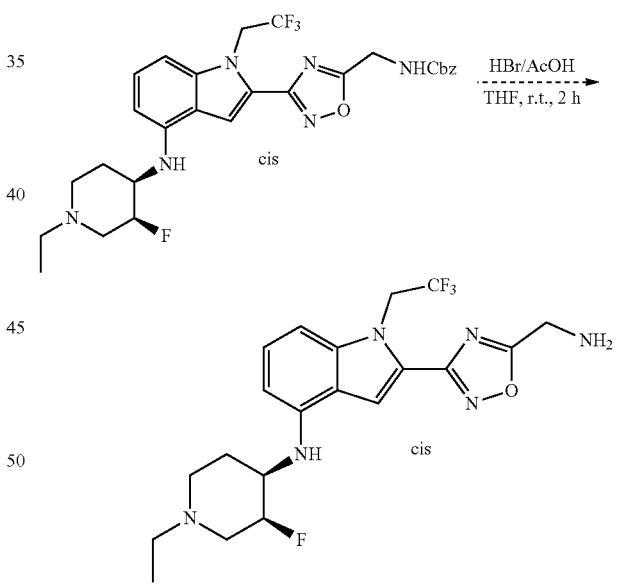

To a solution of the racemic N-ethyl piperidine (1 g, 1.74 mmol, 1 eq) in THF (0.3 mL) was added hydrogen bromide (29.80 g, 122 mmol, 69.8 eq, 33%), and the mixture was stirred at r.t. for 0.5 h. The reaction mixture was poured into MTBE (200 mL), and a yellow solid was collected by filtration, then washed with EA (30 mL×3). The solid was dried in vacuo to give the desired intermediate (1.6 g, 88.1% yield) as a yellow solid. LC-MS (ES$^+$, m/z): 441.1 [(M+H)$^+$].

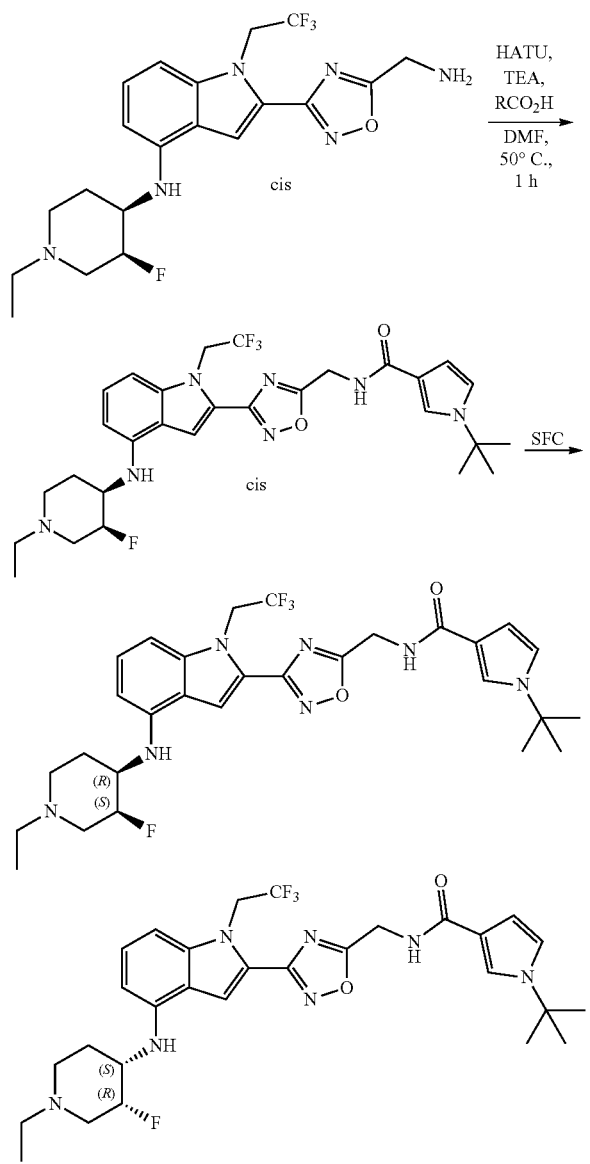

To a solution of the t-butylpyrrole acid (122.4 mg, 732 µmol, 1 eq) and the above intermediate (556 mg, 732 µmol, 1 eq, HBr) in DMF (15 mL) were added TEA (7.32 mmol, 1.02 mL, 10 eq), EDCI (701.5 mg, 3.66 mmol, 5 eq) and HOBT (494.5 mg, 3.66 mmol, 5 eq), and the mixture was stirred at 50° C. for 1 h. The reaction mixture was poured into water (150 mL), then extracted with EA (60 mL×3). The combined organic phase was washed with brine (50 mL), dried over anhydrous sodium sulfate, filtered, and concentrated in vacuo to give a residue. The residue was purified by prep-TLC (SiO$_2$, DCM: methanol=10:1) and washed by EA: PE=1: 2 to get a yellow solid as a racemate. The racemate was separated by SFC to give the desired enantiomers 1-tert-butyl-N-{[3-(4-{[(3S,4R)-1-ethyl-3-fluoropiperidin-4-yl]amino}-1-(2,2,2-trifluoroethyl)-1H-indol-2-yl)-1,2,4-oxadiazol-5-yl]methyl}-1H-pyrrole-3-carboxamide (Compound 298B) LC-MS (ES$^+$, m/z): 590.1 [(M+H)$^+$]. $^1$H NMR (400 MHz, DMSO-d$_6$) δ=0.83 (br s, 1H), 1.00 (br s, 3H), 1.49 (br s, 9H), 1.71 (br s, 1H), 1.98 (br s, 1H), 2.02-2.25 (m, 2H), 2.37 (br s, 2H), 2.89 (br s, 1H), 3.12 (br s, 1H), 3.52-3.62 (m, 1H), 4.59-5.09 (m, 3H), 5.50 (br d, 2H), 6.01 (br d, 1H), 6.29 (br s, 1H), 6.50 (br s, 1H), 6.77-7.26 (m, 3H), 7.55 (br s, 1H), 7.89 (br s, 1H), 8.66 (br s, 1H) (53 mg, 86.3 µmol, 26.8% yield, 96% purity); 1-tert-butyl-N-{[3-(4-{[(3R,4S)-1-ethyl-3-fluoropiperidin-4-yl]amino}-1-(2,2,2-trifluoroethyl)-1H-indol-2-yl)-1,2,4-oxadiazol-5-yl]methyl}-1H-pyrrole-3-carboxamide (Compound 299B) (53 mg, 26.2% yield, 94% purity). LC-MS (ES$^+$, m/z): 590.2 [(M+H)$^+$]. $^1$H NMR (400 MHz, DMSO-d$_6$) δ=1.00 (br t, 3H), 1.49 (s, 9H), 1.70 (br d, 1H), 1.90-2.00 (m, 1H), 2.00-2.11 (m, 1H), 2.11-2.34 (m, 2H), 2.37 (br d, 2H), 2.91 (br d, 1H), 3.12 (br t, 1H), 3.51-3.70 (m, 1H), 4.68-4.95 (m, 3H), 5.44-5.56 (m, 2H), 6.01 (br d, 1H), 6.28 (br d, 1H), 6.50 (br s, 1H), 6.88 (br d, 1H), 6.99 (br s, 1H), 7.11 (br t, 1H), 7.54 (br s, 1H), 7.89 (s, 1H), 8.66 (br t, 1H).

Example 89: 1-benzyl-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-pyrazole-4-carboxamide (Compound 300B)

The analog was prepared from the requisite N-benzyl pyrazolo carboxylic acid and Amine 1. LC-MS (ES$^+$, m/z): 610.9 [(M+H)$^+$]. $^1$H NMR (500 MHz, DMSO-d6) δ 9.09 (t, J=5.7 Hz, 1H), 8.38 (s, 1H), 8.00 (s, 1H), 7.93 (s, 1H), 7.47-7.30 (m, 5H), 7.16 (t, J=8.0 Hz, 1H), 6.93 (d, J=8.3 Hz, 1H), 6.33 (d, J=7.9 Hz, 1H), 6.08 (d, J=8.3 Hz, 1H), 5.55 (q, J=8.8 Hz, 2H), 5.43 (s, 2H), 4.97-4.76 (m, 3H), 3.73-3.56 (m, 2H), 3.09 (s, 1H), 2.87 (d, J=11.0 Hz, 1H), 2.32 (d, J=13.3 Hz, OH), 2.24 (s, 3H), 2.13 (d, J=10.1 Hz, 1H), 2.09-1.99 (m, 1H), 1.86-1.77 (m, 1H), 1.73 (d, J=12.3 Hz, 1H).

N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl[-1-(2-fluoroethyl)-1H-pyrazole-4-carboxamide (Compound 301B) was prepared from Amine 1 and the corresponding pyrazole acid. LCMS (ES$^+$, m/z): 567.1 [(M+H)]. $^1$H NMR (400 MHz, DMSO-d$_6$) δ ppm 1.65-1.76 (m, 1H), 1.89-2.07 (m, 1H), 2.08-2.31 (m, 1H), 2.09-2.29 (m, 3H), 2.33-2.48 (m, 1H), 2.34 (br s, 1H), 2.34-2.47 (m, 1H), 2.35-2.42 (m, 1H), 2.77-2.95 (m, 1H), 3.00-3.17 (m, 1H), 3.01-3.14 (m, 1H), 3.55-3.68 (m, 1H), 3.55-3.66 (m, 1H), 4.45 (t, J=4.74 Hz, 1H), 4.41-4.47 (m, 1H), 4.48-4.56 (m, 1H), 4.67-4.98 (m, 5H), 5.44-5.56 (m, 2H), 6.00-6.09 (m, 1H), 6.28 (d, J=7.72 Hz, 1H), 6.88 (d, J=7.94 Hz, 1H), 7.06-7.17 (m, 1H), 7.89 (s, 1H), 7.97 (s, 1H), 8.29 (s, 1H), 9.06 (t, J=5.62 Hz, 1H).

Example 90: N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl)-1-(1-methoxypropan-2-yl)-1H-pyrazole-4-carboxamide (Compound 302B)

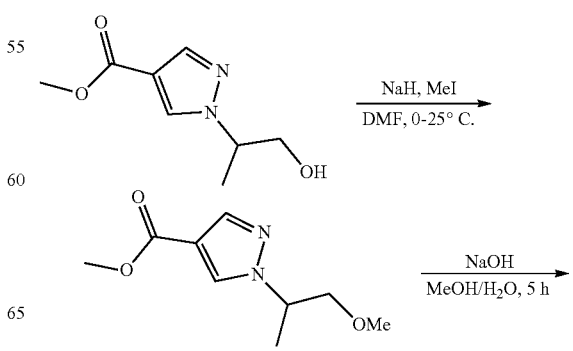

-continued

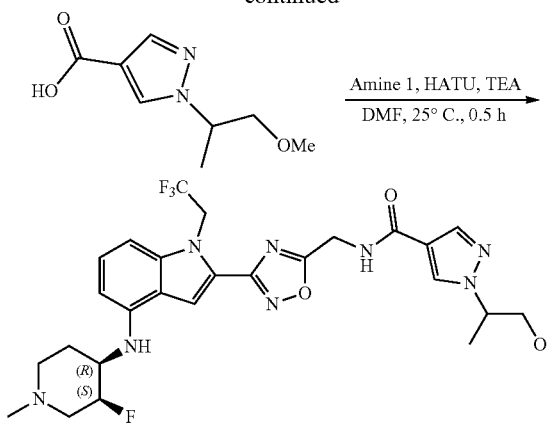

To a solution of the previously prepared methyl 1-(2-hydroxy-1-methyl-ethyl)pyrazole-4-carboxylate (500 mg, 2.71 mmol, 1 eq) in DMF (2 mL) was added sodium hydride (217.1 mg, 5.43 mmol, 60% purity, 2 eq) at 0° C. for 1 h, followed by iodomethane (5.43 mmol, 340 μL 2 eq). The mixture was stirred at 0-25° C. for 2 h under nitrogen atmosphere. The reaction mixture was quenched by adding ammonium chloride (10 mL) at 0° C., then was poured into water (50 mL) and extracted with EA (30 mL×3). The combined organic layers were washed with brine (30 mL×1), dried over anhydrous sodium sulfate, filtered, and concentrated in vacuo to give the desired product as a white oil that was used without further purification 1-(2-methoxy-1-methyl-ethyl)pyrazole-4-carboxylate (400 mg, crude). LC-MS (ES$^+$, m/z): 199.1 [(M+H)$^+$].

To a solution of methyl 1-(2-methoxy-1-methyl-ethyl)pyrrole-3-carboxylate (200 mg, 1.01 mmol, 1 eq) in methanol (2 mL) and water (0.5 mL) was added sodium hydroxide (81.1 mg, 2.03 mmol, 2 eq). The mixture was stirred at 25° C. for 2 h. The reaction mixture was poured into water (50 mL), and the mixture was adjusted to pH 2 with HCl (5M), then extracted with EA (30 mL×3). The combined organic layers were washed with brine (30 mL×1), dried over anhydrous sodium sulfate, filtered, and concentrated in vacuo to give a residue. The crude product was used without further purification. 1-(2-methoxy-1-methyl-ethyl)pyrrole-3-carboxylic acid (180 mg, crude) was obtained as a white solid. LC-MS (ES$^+$, m/z): 183.0 [(M+H)$^+$]. N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(1-methoxypropan-2-yl)-1H-pyrazole-4-carboxamide was obtained from the above acid using method B. LC-MS (ES$^+$, m/z): 593.1 [(M+H)$^+$]. $^1$H NMR (400 MHz, DMSO-d$_6$) δ ppm 9.03 (t, J=5.69 Hz, 1H), 8.19 (s, 1H), 7.91 (d, J=9.29 Hz, 2H), 7.12 (t, J=8.07 Hz, 1H), 6.88 (d, J=8.31 Hz, 1H), 6.28 (d, J=7.95 Hz, 1H), 6.02 (d, J=8.31 Hz, 1H), 5.50 (q, J=8.84 Hz, 2H), 4.73-4.93 (m, 3H), 4.09-4.26 (m, 2H), 3.70 (td, J=6.39, 4.34 Hz, 1H), 3.51-3.66 (m, 1H), 3.20 (s, 3H), 2.99-3.10 (m, 1H), 2.82 (br d, J=10.39 Hz, 1H), 2.17-2.34 (m, 4H), 2.06-2.16 (m, 1H), 2.00 (br dd, J=11.98, 3.18 Hz, 1H), 1.68 (br d, J=10.27 Hz, 1H), 1.06 (d, J=6.36 Hz, 3H).

Example 91: N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(1-fluoropropan-2-yl)-1H-pyrazole-4-carboxamide (Compound 303B)

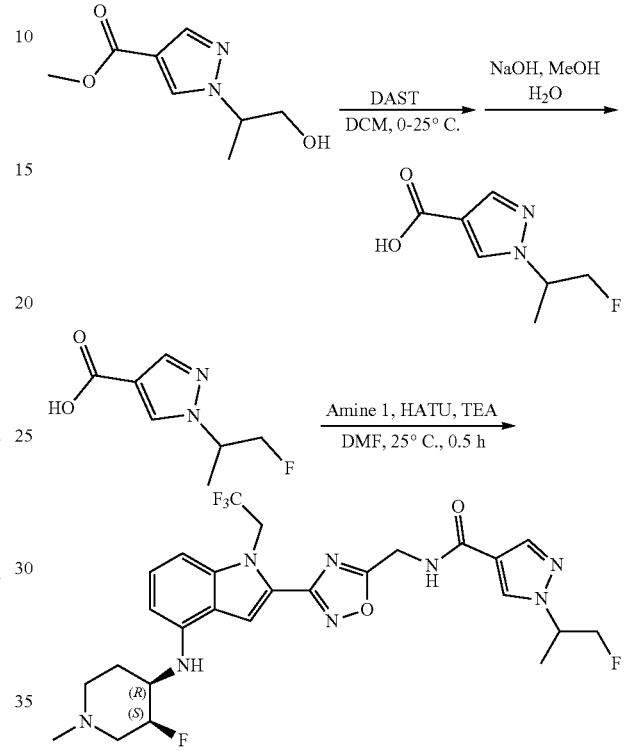

To a solution of the above alcohol in DCM (5 mL) was added DAST (9.77 mmol, 1.29 mL, 3 eq) at 0° C. The mixture was stirred at 25° C. for 2 h under nitrogen atmosphere. The reaction mixture was quenched by adding ammonium chloride (10 mL) at 0° C., then poured into water (50 mL) and extracted with EA (30 mL×3). The combined organic layers were washed with brine (30 mL×1), dried over anhydrous sodium sulfate, filtered, and concentrated in vacuo to give a residue to give the product (400 mg, crude). LC-MS (ES$^+$, m/z): 186.0 [(M+H)$^+$].

To a solution of the ester (200 mg, 1.07 mmol, 1 eq) in methanol (2 mL) and water (1 mL) was added sodium hydroxide (129 mg, 3.22 mmol, 3 eq). The mixture was stirred at 25° C. for 5 h. The reaction mixture was adjusted to pH 7 with HCl (2M), then filtered, and concentrated in vacuo to give the desired acid intermediate (180 mg, crude). LC-MS (ES$^+$, m/z): 172.0 [(M+H)$^+$].

N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(1-fluoropropan-2-yl)-1H-pyrazole-4-carboxamide was obtained from the above acid and Amine 1. LC-MS (ES$^+$, m/z): 581.1 [(M+H)$^+$]. $^1$H NMR (400 MHz, DMSO-d$_6$) δ ppm 9.03 (br t, J=5.62 Hz, 1H), 8.23 (s, 1H), 8.21-8.24 (m, 1H), 7.94 (s, 1H), 7.92-7.92 (m, 1H), 7.87 (s, 1H), 7.10 (t, J=7.94 Hz, 1H), 6.86 (d, J=8.16 Hz, 1H), 6.26 (d, J=7.94 Hz, 1H), 5.99 (br d, J=8.38 Hz, 1H), 5.48 (q, J=8.75 Hz, 2H), 5.07 (br d, J=2.65 Hz, 1H), 4.73-4.90 (m, 3H), 4.29-4.47 (m, 2H), 3.50-3.66 (m, 1 H), 3.02 (br t, J=10.36 Hz, 1H), 2.80 (br d, J=10.36 Hz, 1H), 2.16-2.30 (m, 1H), 2.15-2.32 (m, 4H), 2.04-2.12 (m, 1H), 1.98 (br dd, J=11.36, 2.98 Hz, 1H), 1.66 (br d, J=11.47 Hz, 1H), 1.24-1.34 (m, 3H).

1-tert-butyl-N-{[3-(4-{[(3S,4R)-1-ethyl-3-fluoropiperidin-4-yl]amino}-1-(2,2,2-trifluoroethyl)-1H-indol-2-yl)-1,2,4-oxadiazol-5-yl]methyl}-1H-pyrazole-4-carboxamide (Compound 304B) was obtained from the N-ethyl piperidine intermediate using method B. LC-MS (ES⁻, m/z): 591.1 [(M+H)⁺]. ¹H NMR (400 MHz, DMSO-d₆) δ ppm 8.95 (s, 1H), 8.32 (s, 1H), 7.91 (s, 1H), 7.87 (s, 1H), 7.00-7.16 (m, 1H), 6.86 (d, J=8.16 Hz, 1H), 6.27 (d, J=7.94 Hz, 1H), 5.99 (br d, J=8.38 Hz, 1H), 5.48 (br d, J=8.82 Hz, 2H), 4.76 (d, J=5.51 Hz, 3H), 3.49-3.71 (m, 1H), 3.12 (br d, J=9.70 Hz, 1H), 2.90 (br d, J=10.36 Hz, 1H), 2.36 (br d, J=6.17 Hz, 2H), 2.14-2.27 (m, 1H), 2.07 (br d, J=10.14 Hz, 1H), 1.91-2.01 (m, 1H), 1.69 (br d, J=9.26 Hz, 1H), 1.52 (s, 10H).

1-tert-butyl-N-{[3-(4-{[(3S,4R)-1-ethyl-3-fluoropiperidin-4-yl]amino}-1-(2,2,2-trifluoroethyl)-1H-indol-2-yl)-1,2,4-oxadiazol-5-yl]methyl}-1H-imidazole-4-carboxamide (Compound 305B) was obtained from the imidazole acid using method B. LC-MS (ES⁺, m/z): 591.1 [(M+H)⁺]. ¹H NMR (400 MHz, DMSO-d₆) δ ppm 8.79 (t, J=5.99 Hz, 1H), 7.92-7.94 (m, 2H), 7.89 (s, 1H), 7.05-7.18 (m, 1H), 6.88 (d, J=8.31 Hz, 1H), 6.29 (d, J=7.95 Hz, 1H), 6.03 (br d, J=8.31 Hz, 1H), 5.42-5.59 (m, 2H), 4.75-4.94 (m, 3H), 3.47-3.73 (m, 2H), 3.07-3.20 (m, 1H), 2.87-2.97 (m, 1H), 2.38 (br d, J=5.14 Hz, 1H), 2.17-2.31 (m, 1H), 2.05-2.16 (m, 1H), 1.93-2.04 (m, 1H), 1.65-1.76 (m, 1H).

Example 92: N-{[3-(4-{[(3S,4R)-3-fluoro-1-methylpiperidin-4-yl]amino[1-(2,2,2-trifluoroethyl)-1H-indol-2-yl)-1,2,4-oxadiazol-5-yl]methyl}-1-(2-fluoroethyl)-1H-imidazole-4-carboxamide (Compound 306B)

A mixture of ethyl (Z)-3-(dimethylamino)-2-isocyanoprop-2-enoate (10 g, 50.5 mmol, 1 eq) and 2-aminoethanol (101 mmol, 6.11 mL, 2 eq) was stirred at 70° C. for 5 h. The residue was purified directly by column chromatography (SiO₂, DCM/MeOH=25/1 to 15/1) to afford ethyl 1-(2-hydroxyethyl)-1H-imidazole-4-carboxylate (5.5 g, 54.4% yield, 92% purity) as a yellow oil. LC-MS (ES⁺, m/z): 185.1 [(M+H)⁺].

To a solution of ethyl 1-(2-hydroxyethyl)imidazole-4-carboxylate (2 g, 9.99 mmol, 1 eq) in DCM (10 mL) was added DAST (99.9 mmol, 13.2 mL, 10 eq) at 0° C. The mixture was stirred at 25° C. for 2 hrs. The mixture was added dropwise to aq. sodium bicarbonate (50 mL), then extracted with DCM (3×30 mL). The organic phase was washed with brine (1×20 mL), dried over sodium sulfate, and concentrated in vacuo. The residue was purified by prep-TLC (SiO₂, DCM: MeOH=8:1) to afford ethyl 1-(2-fluoroethyl)-1H-imidazole-4-carboxylate (120 mg, 4.8% yield, 90% purity) as a yellow oil. LC-MS (ES⁺, m/z): 187.0 [(M+H)⁺].

Ethyl 1-(2-fluoroethyl)-1H-imidazole-4-carboxylate (102.2 mg, 494 μmol, 1 eq) was saponified under standard conditions using aq. sodium hydroxide (1 M, 1.92 mL, 3.9 eq) and methanol (4 mL) to provide the desired carboxylic acid (250 mg, 64.0% yield) as white solid after lyophilization of the reaction, which was used directly in the next step. LC-MS (ES⁺, m/z): 159.0 [(M+H)⁺].

N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(2-fluoroethyl)-1H-imidazole-4-carboxamide was obtained from the fluoroethyl imidazole acid using method B. LC-MS (ES⁺, m/z): 567.1 [(M+H)⁺]. ¹H NMR (400 MHz, DMSO-d₆) δ=1.68 (br d, 1H), 1.92-2.14 (m, 2H), 2.19 (s, 3H), 2.25-2.36 (m, 1H), 2.82 (br d, 1H), 3.04 (br t, 1H), 3.48-3.72 (m, 1H), 4.30-4.45 (m, 2H), 4.63-4.94 (m, 5H), 5.50 (q, 2H), 6.04 (br d, 1H), 6.28 (br d, 1H), 6.88 (br d, 1H), 7.11 (br t, 1H), 7.81 (br d, 2H), 7.88 (s, 1H), 8.80 (br t, 1H).

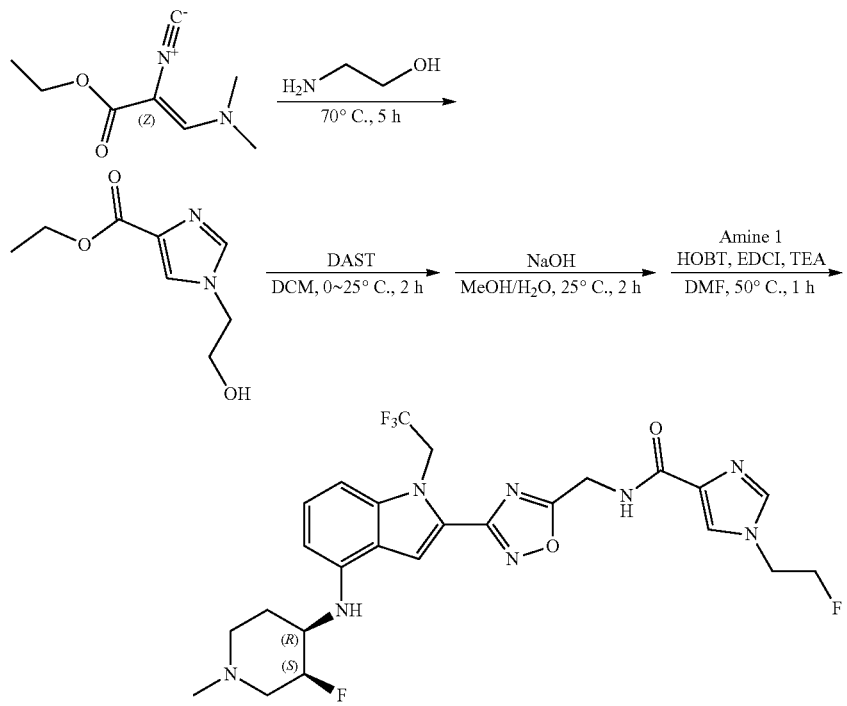

Example 93: N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(2-fluoroethyl)-1H-imidazole-4-carboxamide (Compound 307B)

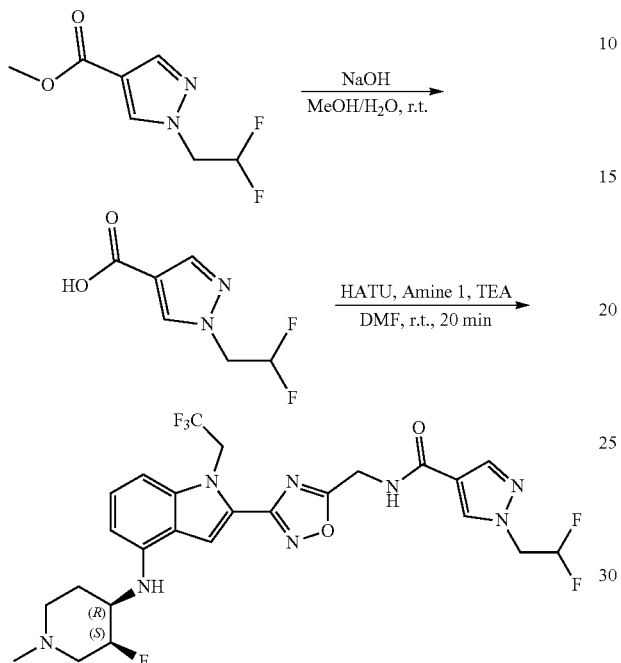

To a mixture of methyl 1-(2,2-difluoroethyl)pyrazole-4-carboxylate (300 mg, 1.58 mmol, 1 eq) in methanol (3 mL) sodium hydroxide (5 M, 3 mL, 9.51 eq) at 20° C. under nitrogen. The mixture was stirred at 20° C. for 30 min. 1N hydrochloric acid was added to adjust the pH to neutral, and the reaction was concentrated in vacuo to provide 1-(2,2-difluoroethyl)pyrazole-4-carboxylic acid as a white solid. LC-MS (ES+, m/z): 176.12 [(M+H)+]. H NMR (400 MHz, DMSO-d6) δ ppm 1.63-1.69 (m, 1H), 1.88-2.03 (m, 1H), 2.03-2.12 (m, 1H), 2.12-2.19 (m, 3H), 2.19-2.29 (m, 1H), 2.77-2.84 (m, 1H), 2.97-3.07 (m, 1H), 3.49-3.64 (m, 1H), 4.69 (td, 0.1=15.27, 3.42 Hz, 2H), 4.74-4.90 (m, 3H), 5.48 (q, 0.1=9.41 Hz, 2H), 6.01 (br d, J=8.16 Hz, 1H), 6.19-6.56 (m, 2H), 6.80-6.91 (m, 1H), 7.09 (t, J=8.05 Hz, 1H), 7.87 (s, 1H), 7.98 (s, 1H), 8.29 (s, 1H), 9.10 (t, J=5.62 Hz, 1H).

N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(2-fluoroethyl)-1H-imidazole-4-carboxamide was prepared using method B in 31% yield. LC-MS (ES+, m/z): 585.3 [(M+H)+]. 1H NMR (400 MHz, DMSO-d6) δ=1.68 (br d, 1H), 1.92-2.14 (m, 2H), 2.19 (s, 3H), 2.25-2.36 (m, 1H), 2.82 (br d, 1H), 3.04 (br t, 1H), 3.48-3.72 (m, 1H), 4.30-4.45 (m, 2H), 4.63-4.94 (m, 5H), 5.50 (q, 2H), 6.04 (br d, 1H), 6.28 (br d, 1H), 6.88 (br d, 1H), 7.11 (br t, 1H), 7.81 (br d, 2H), 7.88 (s, 1H), 8.80 (br t, 1H).

N-{[3-(4-{1[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-phenyl-1H-pyrazole-4-carboxamide (Compound 308B) was prepared using method B to provide the desired product in 40% yield. LC-MS (ES+, m/z): 597.1. 1H NMR (400 MHz, DMSO-d6) δ ppm 1.68 (br d, J=10.27 Hz, 1H) 1.99 (br d, J=11.86 Hz, 1H) 2.08 (br d, J=11.37 Hz, 1H) 2.19 (s, 3H) 2.28 (br d, J=13.69 Hz, 1H) 2.81 (br d, J=8.80 Hz, 1H) 3.03 (br s, 1H) 3.51-3.66 (m, 1H) 4.75-4.90 (m, 3H) 5.51 (br d, J=8.68 Hz, 2H) 6.01 (br d, J=7.70 Hz, 1H) 6.28 (br d, J=7.95 Hz, 1H) 6.88 (br d, J=8.56 Hz, 1H) 7.12 (br t, J=7.95 Hz, 1H) 7.36-7.41 (m, 1H) 7.54 (br t, J=7.58 Hz, 2H) 7.85-7.94 (m, 3H) 8.23 (s, 1H) 9.00 (s, 1H) 9.19 (br s, 1H).

N-{[3-(4-{[(3S,4R)-3-fluoro-1-methylpiperidin-4-yl]amino)-1-(2,2,2-trifluoroethyl)-1H-indol-2-yl)-1,2,4-oxadiazol-5-yl]methyl}-1-phenyl-1H-imidazole-5-carboxamide (Compound 309B) was prepared using method B. LC-MS (ES−, m/z): 597.1.

Example 94: 1-(2,2-difluoroethyl)-N-{[3-(4-{[(3S,4R)-3-fluoro-1-methylpiperidin-4-yl]amino)-1-(2,2,2-trifluoroethyl)-1H-indol-2-yl)-1,2,4-oxadiazol-5-yl]methyl}-1H-imidazole-4-carboxamide (Compound 310B)

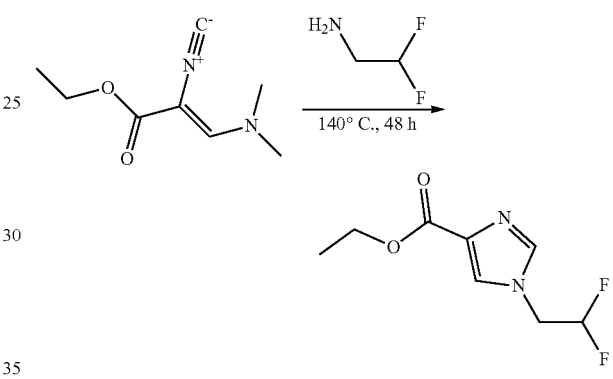

General Procedure for synthesis of 1-N-alkyl-4-carboxy-imidazoles: A mixture of 2,2-difluoroethylamine (965 mg, 11.9 mmol, 2 eq) and ethyl (Z)-3-(dimethylamino)-2-isocyano-prop-2-enoate (1 g, 5.95 mmol, 1 eq) was prepared, and the mixture was stirred at 70° C. for 2 h. The reaction mixture was poured into water (100 mL) and extracted with EA (100 mL×3). The combined organic phase was washed with brine (20 mL×3), dried over anhydrous sodium sulfate, filtered, and concentrated in vacuo to give a residue. The residue was purified by column chromatography (SiO2, PE/EA=1/0 to 1/1) to give the intermediate ester (1 g, 3.92 mmol, 65.9% yield, 80% purity). LC-MS (ES+, m/z): 152.0.

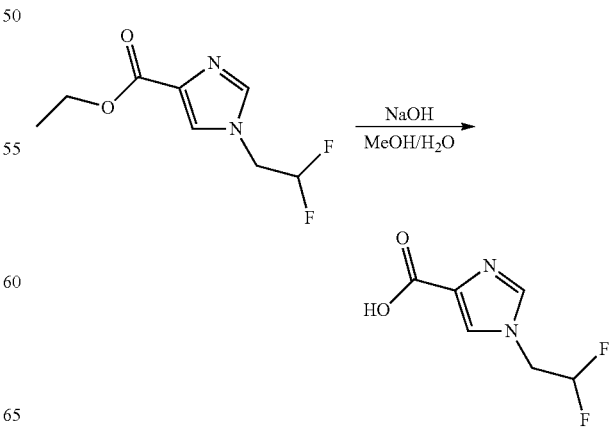

A solution of the ester (536.9 mg, 2.63 mmol, 1 eq) and sodium hydroxide (105 mg, 2.63 mmol, 1 eq) in water (3 mL) and methanol (3 mL) was stirred at 25° C. for 2 h. The reaction mixture was neutralized with HCl to pH 7. The reaction was filtered, and concentrated in vacuo to give a residue. The solid phase was extracted with DCM (60 mL×2). The reaction mixture was filtered and dried over anhydrous sodium sulfate, filtered, and concentrated in vacuo. The crude product was used without further purification (300 mg, crude). LC-MS (ES$^+$, m/z): 174.0.

1-(2,2-difluoroethyl)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-imidazole-4-carboxamide was prepared using method B to provide the desired product in 22% yield. LC-MS (ES$^+$, m/z): 585.1. $^1$H NMR (400 MHz, DMSO-d$_6$) δ ppm 8.83-8.87 (m, 1H), 8.85 (t, J=5.95 Hz, 1H), 8.82-8.87 (m, 1H), 7.88 (s, 1H), 7.80 (d, J=9.26 Hz, 2H), 7.11 (t, J=8.05 Hz, 1H), 6.88 (d, J=8.38 Hz, 1H), 6.33-6.67 (m, 1H), 6.28 (d, J=7.94 Hz, 1H), 6.04 (br d, J=8.16 Hz, 1H), 5.50 (q, J=8.97 Hz, 2H), 4.73-5.03 (m, 3H), 4.60 (td, J=15.93, 2.98 Hz, 2H), 3.46-3.77 (m, 1H), 3.07 (br s, 1H), 2.85 (br dd, J=8.49, 1.21 Hz, 1H), 2.08-2.32 (m, 5H), 1.88-2.05 (m, 1H), 1.69 (br d, J=11.69 Hz, 1H).

N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-3-methyl-1-(propan-2-yl)-1H-pyrazole-4-carboxamide (Compound 311B) was prepared using method B in 19% yield. LC-MS (ES$^+$, m/z): 577.1. $^1$H NMR (400 MHz, DMSO-d$_6$) δ ppm 8.66-8.73 (m, 1H), 8.25 (s, 1H), 7.88 (s, 1H), 7.04-7.14 (m, 1H), 6.86 (d, J=8.16 Hz, 1H), 6.27 (d, J=7.94 Hz, 1H), 5.99 (br d, 0.1=8.38 Hz, 1H), 5.48 (br d, J=8.82 Hz, 2H), 4.69-4.91 (m, 3H), 4.35-4.48 (m, 1H), 3.46-3.73 (m, 1H), 3.01 (br s, 1H), 2.78 (br s, 1H), 2.30 (s, 4H), 2.15-2.19 (m, 3H), 2.08 (br s, 1H), 2.03-2.12 (m, 1H), 1.94-2.03 (m, 1H), 1.66 (br d, J=10.36 Hz, 1H), 1.39 (d, J=6.62 Hz, 7H).

Example 95: 1-cyclopentyl-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-pyrazole-4-carboxamide (Compound 312B)

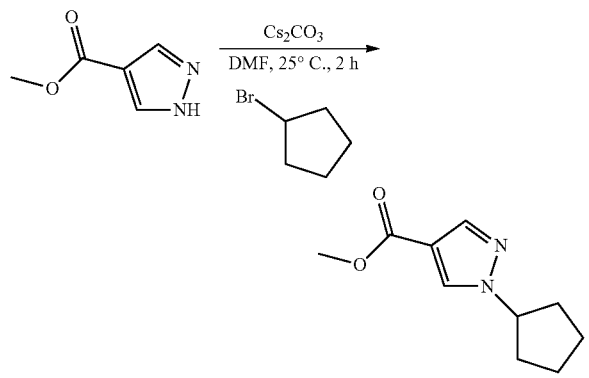

To a mixture of methyl 1H-pyrazole-4-carboxylate (1 g, 7.93 mmol, 1 eq) and bromocyclopentane (15.9 mmol, 1.70 mL, 2 eq) in DMF (8 mL) was added cesium carbonate (5.17 g, 15.9 mmol, 2 eq) at 20° C. under nitrogen. The mixture was stirred at 20° C. for 2 h. The residue was poured into ice-water (w/w=1/1) (100 mL). The aqueous phase was extracted with EA (30 mL×3). The combined organic phase was washed with brine (30 mL×3), dried over anhydrous sodium sulfate, filtered, and concentrated in vacuo. The residue was purified by silica gel chromatography to give methyl 1-cyclopentylpyrazole-4-carboxylate as a white solid in 88.8% yield. LC-MS (ES$^+$, m/z): 194.2 [(M+H)$^+$].

To methyl 1-cyclopentylpyrazole-4-carboxylate (500 mg, 2.57 mmol, 1 eq) were added sodium hydroxide solution (5 M, 3 mL, 5.83 eq) and methanol (5 mL) at 20° C. under nitrogen The mixture was stirred at 20° C. for 30 min. 1N hydrochloric acid was added to adjust the pH to neutral, and the reaction was then concentrated in vacuo. The residue was purified by silica gel chromatography to provide 1-cyclopentylpyrazole-4-carboxylic acid in 71% yield.

1-cyclopentyl-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-pyrazole-4-carboxamide was prepared using method B in 33% yield. LC-MS (ES$^+$, m/z): 589.3. $^1$H NMR (400 MHz, DMSO-dr$_6$) δ ppm 1.55-1.70 (m, 3H), 1.71-1.82 (m, 2H), 1.84-2.01 (m, 3H), 2.07 (td, J=12.84, 7.39 Hz, 3H), 2.19 (s, 3H), 2.21-2.29 (m, 1H), 2.82 (br d, J=10.36 Hz, 1H), 2.99-3.09 (m, 1H), 3.50-3.66 (m, 1H), 4.67-4.73 (m, 1H), 4.74-4.91 (m, 3H), 5.48 (q, J=8.97 Hz, 2H), 6.00 (br d, J=8.16 Hz, 1H), 6.26 (d, J=7.94 Hz, 1H), 6.86 (d, J=8.38 Hz, 1H), 7.09 (t, J=8.05 Hz, 1H), 7.87 (s, 1H), 7.89 (s, 1H), 8.26 (s, 1H), 8.96 (t, J=5.62 Hz, 1H).

Example 96: N-{[3-(4-{[(3S,4R)-1-ethyl-3-fluoropiperidin-4-yl]amino}-1-(2,2,2-trifluoroethyl)-1H-indol-2-yl)-1,2,4-oxadiazol-5-yl]methyl}-1-(oxolan-3-yl)-1H-pyrazole-4-carboxamide (Compound 314B)

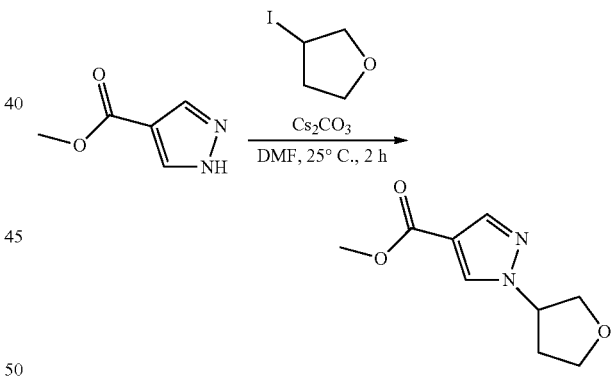

To a mixture of methyl 1H-pyrazole-4-carboxylate (800 mg, 6.34 mmol, 1 eq) and 3-iodotetrahydrofuran (1.51 g, 7.61 mmol, 1.2 eq) in DMF (8 mL) was added cesium carbonate (4.13 g, 12.7 mmol, 2 eq) at 20° C. under nitrogen. The mixture was stirred at 20° C. for 4 h. The residue was poured into ice-water (w/w=1/1) (100 mL). The aqueous phase was extracted with EA (30 mL×3). The combined organic phase was washed with brine (30 mL×3), dried over anhydrous sodium sulfate, filtered, and concentrated in vacuo. The residue was purified by silica gel chromatography to give methyl 1-cyclopentylpyrazole-4-carboxylate as a white solid in 71.1% yield. LC-MS (ES$^+$, m/z): 198.0 [(M+H)$^+$].

To a mixture of methyl 1-tetrahydrofuran-3-ylpyrazole-4-carboxylate (670 mg, 3.41 mmol, 1 eq) and sodium hydroxide (5 M, 3 mL, 4.39 eq) was added methanol (4 mL)

at 20° C. The mixture was stirred at 20° C. for 1 h. 1N hydrochloric acid was added to bring the pH to neutral, and the reaction was concentrated in vacuo. The residue was purified by silica gel chromatography to provide 1-tetrahydrofuran-3-ylpyrazole-4-carboxylic acid in 75.8% yield.

To a solution of the N-ethyl piperidine (1 g, 1.74 mmol, 1 eq) in THF (0.3 mL) was added hydrogen bromide (29.80 g, 121.5 mmol, 69.83 eq, 33%), and the mixture was stirred at rt for 0.5 h. The reaction mixture was poured into MTBE (200 mL), and a yellow solid was collected by filtration and washed with EA (30 mL×3), then concentrated in vacuo to give the intermediate amine hydrobromide salt (1.6 g, 88.1% yield) as a yellow solid. LC-MS (ES⁺, m/z): 441.1 [(M+H)].

N-{[3-(4-{[(3S,4R)-1-ethyl-3-fluoropiperidin-4-yl]amino}-1-(2,2,2-trifluoroethyl)-1H-indol-2-yl)-1,2,4-oxadiazol-5-yl]methyl}-1-(oxolan-3-yl)-1H-pyrazole-4-carboxamide was obtained from Amine 1 using method B in 35% yield. LC-MS (ES⁺, m/z): 605.1. ¹H NMR (400 MHz, DMSO-d₆) δ ppm 0.98 (t, J=7.17 Hz, 3H), 1.68 (br d, J=10.36 Hz, 1H), 1.87-2.01 (m, 1H), 2.07 (br t, J=10.91 Hz, 1H), 2.15-2.31 (m, 2H), 2.32-2.44 (m, 3H), 2.89 (br d, J=10.14 Hz, 1H), 3.10 (br t, J=10.03 Hz, 1H), 3.52-3.66 (m, 1H), 3.80 (td, J=8.38, 5.29 Hz, 1H), 3.85-3.90 (m, 1H), 3.91-3.99 (m, 2H), 4.67-4.93 (m, 3H), 5.00-5.09 (m, 1H), 5.48 (q, J=8.89 Hz, 2H), 6.00 (br d, J=8.38 Hz, 1H), 6.26 (d, J=7.94 Hz, 1H), 6.86 (d, J=8.16 Hz, 1H), 7.02-7.14 (m, 1H), 7.87 (s, 1H), 7.92 (s, 1H), 8.29 (s, 1H), 9.01 (t, J=5.62 Hz, 1H).

Example 97: 1-tert-butyl-N-{[3-(4-{[(3S,4R)-1-cyclopropyl-3-fluoropiperidin-4-yl]amino}-1-(2,2,2-trifluoroethyl)-1H-indol-2-yl)-1,2,4-oxadiazol-5-yl]methyl}-1H-pyrazole-4-carboxamide (Compound 315B)

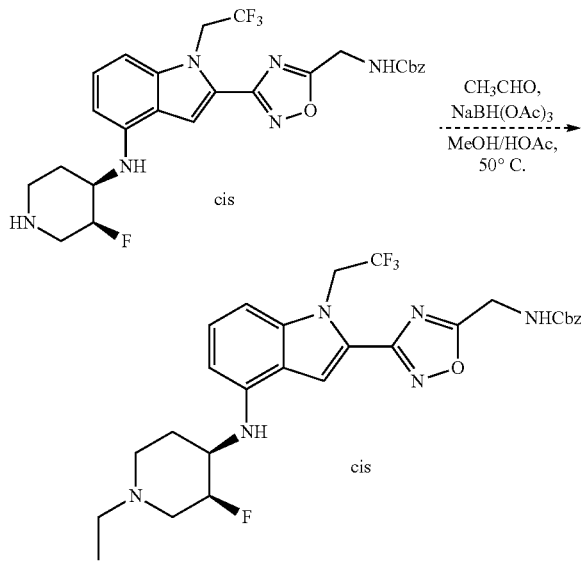

To a solution of the piperidine (1.2 g, 2.20 mmol, 1 eq) in DMF (20 mL) were added potassium carbonate (1.52 g, 11 mmol, 3 eq) and iodoethane (3.29 mmol, 263 μL 1.5 eq), then the reaction was stirred at rt for 2 h. The reaction mixture was poured into water (50 mL), then extracted with EA (30 mL×3). The combined organic phase was washed with brine (50 mL×1), dried over anhydrous sodium sulfate, filtered, and concentrated in vacuo to give a residue. The residue was purified by column chromatography to give the ethyl piperidine (1.1 g, 87.1% yield) as a yellow solid. LC-MS (ES⁺, m/z): 575.3 [(M+H)⁺]

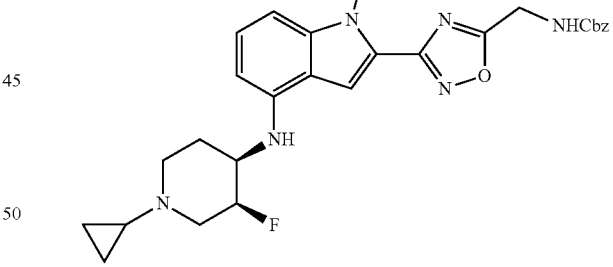

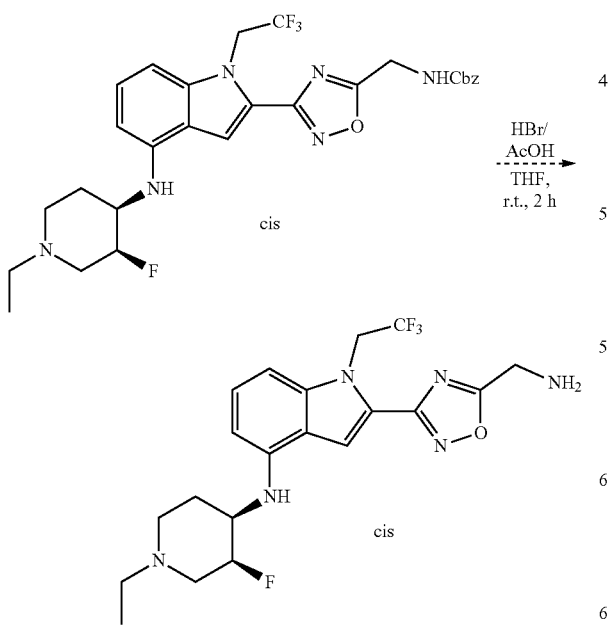

A mixture of the piperidine (0.4 g, 517 μmol, 1 eq), cyclopropylboronic acid (221.9 mg, 2.58 mmol, 5 eq), copper (II) acetate (187.7 mg, 1.03 mmol, 2 eq), 2,2'-bipyridine (161.4 mg, 1.03 mmol, 2 eq) and sodium carbonate (273.8 mg, 2.58 mmol, 5 eq) in DCE (50 mL) was heated and stirred at 70° C. for 3 h under air atmosphere. The reaction mixture was poured into water (20 mL). The mixture was extracted with EA (20 mL×3). The organic phase was washed with brine (20 mL), dried over anhydrous sodium sulfate, and concentrated in vacuo to give a residue. The residue was purified by prep-TLC (SiO₂, DCM: methanol=10:1) to provide the desired cyclopropyl piperidine (240 mg, 36.5% yield) as light yellow solid. LC-MS(ES⁺, m/z): 587.2 [(M+H)⁺].

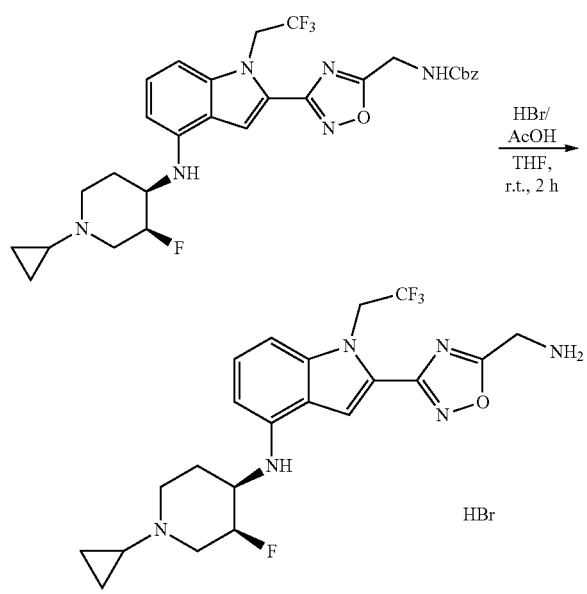

To a solution of the cyclopropyl piperidine (0.24 g, 409 μmol, 1 eq) in THF (3 mL) were added HBr (18.2 mmol, 3 mL, 33%, 44.6 eq) and acetic acid (157 mmol, 9 mL). The mixture was stirred at 20° C. for 1 h. The reaction mixture was added dropwise into ether (10 mL) to precipitate the product, which was collected by filtration and dried in vacuo to provide the primary amine (240 mg, crude, HBr salt) as a gray solid.

1-tert-butyl-N-{[3-(4-{[(3S,4R)-1-cyclopropyl-3-fluoropiperidin-4-yl]amino}-1-(2,2,2-trifluoroethyl)-1H-indol-2-yl)-1,2,4-oxadiazol-5-yl]methyl}-1H-pyrazole-4-carboxamide was prepared from the above amine by method B in 11% yield. LC-MS (ES+, m/z): 603.2 [(M+H)+]. $^1$H NMR (400 MHz, DMSO-d$_6$) δ=8.98-8.97 (d, J=2.4 Hz, 1H), 8.33 (s, 1H), 7.93 (s, 1H), 7.87 (s, 1H), 7.13-7.12 (m, 1H), 6.89-6.86 (m, 1H), 6.30-6.28 (m, 1H), 5.99-5.97 (d, J=8.0 Hz, 1H), 5.53-5.49 (m, 2H), 4.90-4.77 (m, 3H), 3.62-3.58 (m, 1H), 3.18-3.10 (m, 1H), 1.90-1.75 (m, 2H), 1.67-1.66 (m, 1H), 1.59 (s, 9H), 1.26-1.23 (m, 2H), 0.76-0.56 (m, 1H), 0.43-0.42 (m, 2H), 0.43-0.42 (m, 2H).

Example 98: 1-tert-butyl-N-{[3-(4-{[(3S,4R)-3-fluoro-1-(propan-2-yl)piperidin-4-yl]amino}-1-(2,2,2-trifluoroethyl)-1H-indol-2-yl)-1,2,4-oxadiazol-5-yl]methyl}-1H-pyrazole-4-carboxamide (Compound 316B)

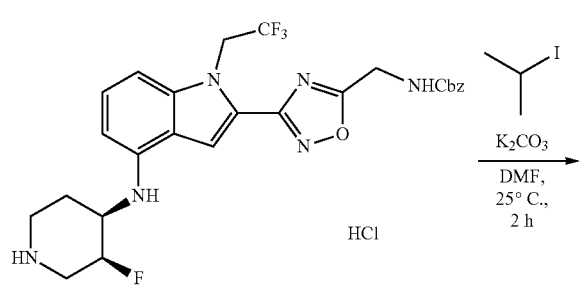

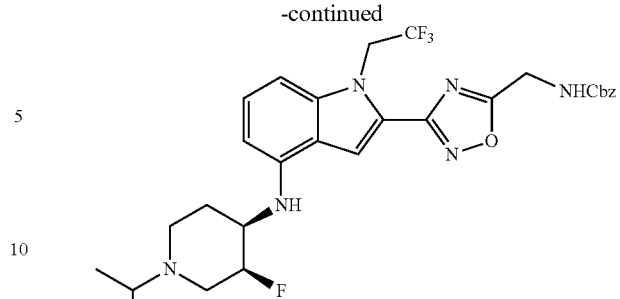

To a mixture of the piperidine (657.2 mg, 875 μmol, 1 eq, HCl) in DMF (9 mL) were added 2-iodopropane (1.75 mmol, 175 μL 2 eq) and potassium carbonate (604.5 mg, 4.37 mmol, 5 eq). The mixture was heated and stirred at 50° C. for 16 h. The mixture was quenched by adding water (20 mL), then was extracted with EA (30 mL×3). The organic phase was washed with brine (30 mL), dried over sodium sulfate, concentrated in vacuo. The residue was purified by column chromatography (SiO$_2$, DCM: methanol=30/1 to 10/1) to give the desired isopropylpiperidine (600 mg, 823.7 μmol, 94.2% yield, 80.8% purity) as a yellow oil. LC-MS (ES+, m/z): 589.2 [(M+H)+].

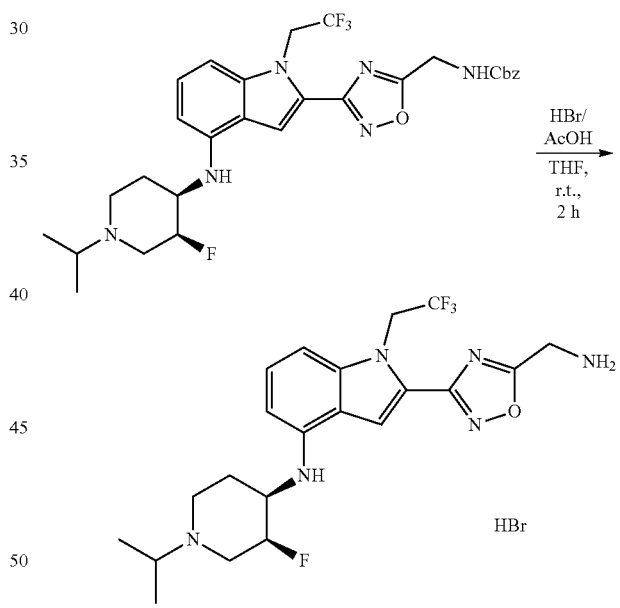

To a mixture of the isopropylpiperidine (743.5 mg, 1.19 mmol, 1 eq) in THF (10 mL) was added HBr/AcOH (10 mL, 33% purity). The mixture was stirred at 25° C. for 2 h. The mixture was added to MTBE (50 mL) and stirred for 10 min, then the product was collected by filtration and dried in vacuo to provide the primary amine (500 mg, 54.6% yield, 80% purity, 2HBr) as yellow solid. LC-MS (ES+, m/z): 455.3 [(M+H)+].

1-tert-butyl-N-{{3-(4-{[(3S,4R)-3-fluoro-1-(propan-2-yl)piperidin-4-yl]amino}-1-(2,2,2-trifluoroethyl)-1H-indol-2-yl)-1,2,4-oxadiazol-5-yl]methyl}-1H-pyrazole-4-carboxamide was prepared using method B to provide the desired product in 44% yield. LC-MS (ES+, m/z): 605.1 [(M+H)+]. $^1$H NMR (400 MHz, DMSO-d$_6$) δ=0.97 (dd, 6H), 1.54 (s, 9H), 1.71 (br d, 1H), 1.99 (s, 1H), 2.26-2.36 (m, 1H), 2.39-2.46 (m, 1H), 2.65-2.86 (m, 2H), 3.04 (br s, 1H), 3.49-3.70 (m, 1H), 4.71-4.97 (m, 3H), 5.50 (br d, 2H), 5.98 (br d, 1H), 6.28 (d, 1H), 6.88 (d, 1H), 7.11 (t, 1H), 7.91 (d, 2H), 8.34 (s, 1H), 8.97 (t, 1H).

1-tert-butyl-N-{[3-(4-{[(3S,4R)-3-fluoro-1-(propan-2-yl)piperidin-4-yl]amino}-1-(2,2,2-trifluoroethyl)-1H-indol-2-yl)-1,2,4-oxadiazol-5-yl]methyl}-1H-pyrrole-3-carboxamide (Compound 317B) was prepared from the isopropyl piperidine intermediate using method B in 46% yield. LC-MS (ES$^+$, m/z): 604.2 [(M+H)$^+$]. $^1$H NMR (400 MHz, DMSO-d$_6$) δ=0.98 (dd, 6H), 1.49 (s, 9H), 1.71 (br d, 1H), 1.93 (br dd, 1H), 2.26-2.37 (m, 2H), 2.64-2.87 (m, 2H), 2.99-3.10 (m, 1H), 3.49-3.67 (m, 1H), 4.69-4.94 (m, 3H), 5.50 (q, 2H), 5.97 (br d, 1H), 6.28 (d, 1H), 6.50 (dd, 1H), 6.87 (d, 1H), 6.99 (t, 1H), 7.11 (t, 1H), 7.54 (t, 1H), 7.88 (s, 1H), 8.63 (t, 1H).

1-tert-butyl-N-{[3-(4-{[(3S,4R)-3-fluoro-1-(propan-2-yl)piperidin-4-yl]amino}-1-(2,2,2-trifluoroethyl)-1H-indol-2-yl)-1,2,4-oxadiazol-5-yl]methyl}-1H-imidazole-4-carboxamide (Compound 318B) was prepared from the isopropylpiperidine intermediate using method B in 41% yield. LC-MS (ES$^+$, m/z): 605.2 [(M+H)$^+$]. $^1$H NMR (400 MHz, DMSO-d$_6$) δ=0.98 (br s, 6H), 1.54 (s, 9H), 1.71 (br d, 1H), 1.93 (br d, 1H), 2.24-2.37 (m, 2H), 2.63-2.89 (m, 2H), 3.04 (br s, 1H), 3.55 (br s, 1H), 4.70-4.96 (m, 3H), 5.50 (q, 2H), 5.99 (br d, 1H), 6.28 (br d, 1H), 6.88 (br d, 1H), 7.11 (br t, 1H), 7.88 (s, 1H), 7.92 (d, 2H), 8.77 (br t, 1H).

1-cyclopentyl-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-pyrrole-3-carboxamide (Compound 319B) was prepared using Amine 1 using method B to provide the desired product. LC-MS (ES$^+$, m/z): 588.2 [(M+H)$^+$].

1-cyclopentyl-N-{[3-(4-{[(3S,4R)-1-ethyl-3-fluoropiperidin-4-yl]amino}-1-(2,2,2-trifluoroethyl)-1H-indol-2-yl)-1,2,4-oxadiazol-5-yl]methyl}-1H-pyrrole-3-carboxamide (Compound 320B) was prepared from the N-ethyl piperidine intermediate using method A in 39% yield. LC-MS (ES$^+$, m/z): 602.2 [(M+H)-]. $^1$H NMR (400 MHz, DMSO-d6) δ=1.01 (t, 3H), 1.57-1.86 (m, 7H), 1.89-2.04 (m, 1H), 2.11 (br d, 2H), 2.26-2.43 (m, 4H), 2.91 (br d, 1H), 3.05-3.20 (m, 1H), 3.50-3.74 (m, 1H), 4.40-4.52 (m, 1H), 4.73 (d, 3H), 5.50 (br d, 2H), 5.99 (br d, 1H), 6.29 (d, 1H), 6.49 (dd, 1H), 6.82-6.93 (m, 2H), 7.12 (t, 1H), 7.45 (t, J=1.90 Hz, 1H), 7.88 (s, 1H), 8.63 (t, 1H).

N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(oxolan-3-yl)-1H-pyrazole-4-carboxamide (Compound 321B) was prepared from Amine 1 an the previously prepared THF-pyrazole acid in 24% yield using method B. LC-MS (ES$^-$, m/z): 591.1 [(M+H)$^+$]. $^1$H NMR (400 MHz, DMSO-d$_6$) δ ppm 1.71 (br d, J=10.80 Hz, 1H) 1.96-2.10 (m, 2H) 2.27 (br s, 4H) 2.37 (br s, 4H) 2.88 (br s, 5H) 3.06-3.21 (m, 2H) 3.52-3.70 (m, 1H) 4.74-4.94 (m, 3H) 4.97 (br s, 1H) 5.50 (q, J=9.19 Hz, 2H) 6.05 (br d, J=8.38 Hz, 1H) 6.29 (d, J=7.94 Hz, 1H) 6.89 (br d, J=8.16 Hz, 1H) 7.04-7.18 (m, 1H) 7.89 (s, 1H) 7.92 (s, 1H) 8.33 (s, 1H) 9.03 (t, J=5.51 Hz, 1H).

1-tert-butyl-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-5-methyl-1H-pyrazole-4-carboxamide (Compound 322B) was prepared from Amine 1 using method B in 32% yield. LC-MS (ES$^+$, m/z): 591.1 [(M+H)$^+$]. $^1$H NMR (400 MHz, DMSO-d$_6$) δ ppm 8.82 (t, J=5.73 Hz, 1H), 8.79-8.87 (m, 1H), 7.87 (s, 2H), 7.05-7.13 (m, 1H), 6.86 (d, J=8.38 Hz, 1H), 6.26 (d, J=7.72 Hz, 1H), 6.00 (br d, J=8.38 Hz, 1H), 5.48 (q, J=8.67 Hz, 2H), 4.73-4.75 (m, 1H), 4.58-4.97 (m, 3H), 3.48-3.66 (m, 1H), 2.95-3.11 (m, 1H), 2.76-2.86 (m, 1H), 2.65-2.69 (m, 3H), 2.14-2.30 (m, 4H), 2.04-2.13 (m, 1H), 1.91-2.02 (m, 1H), 1.67 (br d, J=9.04 Hz, 1H), 1.57 (s, 9H).

Example 99: N-{[3-(4-{1[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(oxolan-3-yl)-1H-pyrrole-3-carboxamide (Compound 323B)

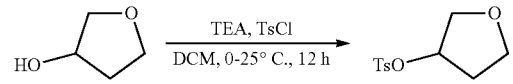 [SMILES: OC1CCOC1 ; "TEA, TsCl" ; Cc1ccc(S(=O)(=O)OC2CCOC2)cc1]

To a solution of 3-hydroxytetrahydrofuran (5 g, 4.6 mL, 1 eq) in DCM (50 mL) was added TEA (39.5 mL, 5 eq). The mixture was stirred at 0° C. for 0.5 h, then p-TsCl (5.41 g, 0.5 eq) was added to the mixture. The mixture was stirred at 0° C. for 0.5 h, at which time another portion of TsCl (5.41 g, 0.5 eq) was added. After a further 0.5 h of stirring at 0° C., a final portion of TsCl (5.41 g, 0.5 eq) was added. The mixture was warmed and stirred at 25° C. for 10.5 h. The reaction mixture was quenched by adding water (50 mL) and extracted with DCM (50 mL×2). The combined organic layers were washed with DCM (50 mL×3), dried over sodium sulfate, filtered, and concentrated in vacuo to give a residue. The residue was purified by column chromatography (SiO$_2$, PE/EA=100/1 to 10/1) to give a product as a yellow oil in 80% yield.

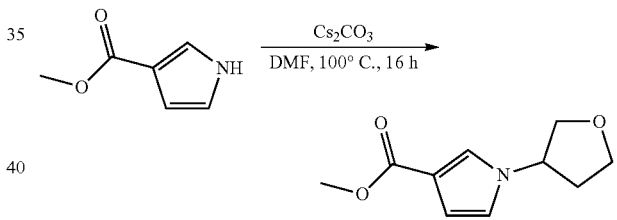

To a solution of methyl pyrrole-3-carboxylic acid (500 mg, 1 eq) and cesium carbonate (3.91 g, 3 eq) in DMF (10 mL) was added the intermediate tosylate (3.87 g, 4 eq). The reaction was stirred and heated at 100° C. for 16 h. The reaction mixture was diluted with water (100 mL) and extracted with EA (150 mL) (50 mL×3). The combined organic layers were washed with brine (50 mL×3), dried over sodium sulfate, filtered, and concentrated in vacuo to give a residue. The residue was purified by column chromatography (SiO$_2$, PE/EA=50/1 to 5/1) to give a product as a light yellow liquid in 83% yield. LCMS (ES$^+$, m/z): 196.1[(M+H)$^+$].

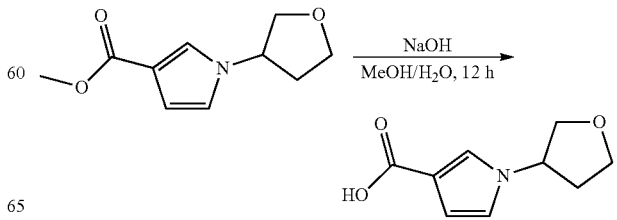

A mixture of the methyl ester (1.8 g, 1 eq) and sodium hydroxide (5 M, 8.30 mL, 5.42 eq) in methanol (10 mL) was stirred at 25° C. for 12 h. The reaction mixture was concentrated in vacuo to remove methanol. The mixture was adjusted to pH=2 with HCl (12 M) at 0° C. The mixture was extracted with EA (20 mL×3). The combined organic layers were washed with brine (20 mL×3), dried over sodium sulfate, filtered, and concentrated in vacuo to give the acid as a light yellow solid. LCMS (ES$^+$, m/z): 182.1[(M+H)$^+$].

N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(oxolan-3-yl)-1H-pyrrole-3-carboxamide was prepared from Amine 1 using method B in 30% yield. LCMS (ES$^+$, m/z): 196.1[(M+H)$^+$]. $^1$H NMR (400 MHz, DMSO-d$_6$) δ=8.77-8.63 (t, J=5.6 Hz, 1H), 7.89 (s, 1H), 7.51-7.44 (t, J=1.6 Hz, 1H), 7.15-7.06 (t, J=8.0 Hz, 1H), 6.93-6.81 (m, 2H), 6.53-6.49 (m, 1H), 6.34-6.23 (d, J=8.8 Hz, 1H), 6.11-5.97 (d, J=8.4 Hz, 1H), 5.56-5.40 (m, 2H), 4.90 (brs, 1H), 4.87-4.81 (m, 1H), 4.78 (brs, 1H), 4.75-4.69 (d, J=6.0 Hz, 2H), 4.06-3.97 (m, 1H), 3.91-3.83 (m, 1H), 3.82-3.74 (m, 2H), 3.68-3.51 (m, 1H), 3.09-2.99 (t, J=9.8 Hz, 1H), 2.87-2.78 (d, J=9.6 Hz, 1H), 2.46-2.38 (m, 1H), 2.31-2.29 (m, 4H), 2.13-1.96 (m, 3H), 1.73-1.64 (m, 1H).

N-{[3-(4-{[(3S,4R)-1-ethyl-3-fluoropiperidin-4-yl]amino}-1-(2,2,2-trifluoroethyl)-1H-indol-2-yl)-1,2,4-oxadiazol-5-yl]methyl}-1-(oxolan-3-yl)-1H-pyrrole-3-carboxamide (Compound 324B) was prepared from the N-ethyl piperidine intermediate using method B in 12% yield. LCMS (ES$^+$, m/z): 604.3 [(M+H)$^+$]. $^1$H NMR (400 MHz, DMSO-d$_6$) δ=8.75-8.66 (t, J=5.6 Hz, 1H), 7.92-7.84 (d, J=7.6 Hz, 1H), 7.50-7.41 (d, J=2.0 Hz, 1H), 7.15-7.05 (t, J=8.0 Hz, 1H), 6.92-6.80 (m, 2H), 6.56-6.46 (t, J=2.0 Hz, 1H), 6.34-6.23 (d, J=8.0 Hz, 1H), 6.06-5.97 (d, J=8.0 Hz, 1H), 5.64-5.39 (m, 2H), 4.90 (brs, 1H), 4.88-4.81 (m, 1H), 4.79 (brs, 1H), 4.75-4.68 (d, J=5.6 Hz, 2H), 4.06-3.96 (m, 1H), 3.92-3.84 (m, 1H), 3.83-3.73 (m, 2H), 3.68-3.53 (m, 1H), 3.18-3.07 (t, J=9.4 Hz, 1H), 2.96-2.85 (d, J=10.0 Hz, 1H), 2.46-2.21 (m, 4H), 2.14-1.91 (m, 3H), 1.76-1.65 (d, J=10.8 Hz, 1H), 1.00 (t, J=7.1 Hz, 3H).

Example 100: N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(oxan-4-yl)-1H-pyrazole-4-carboxamide (Compound 325B)

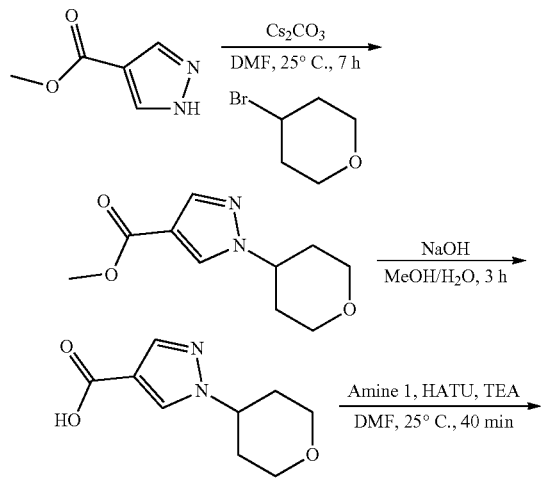

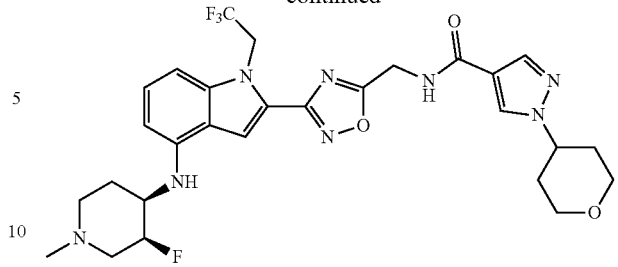

A mixture of methyl pyrazole-4-carboxylate (1 g, 7.93 mmol, 1 eq), cesium carbonate (7.75 g, 23.8 mmol, 3 eq), and 4-bromotetrahydropyran (2.62 g, 15.9 mmol, 2 eq) in DMF (10 mL) was degassed and purged with nitrogen 3 times, then the mixture was stirred at 25° C. for 7 h under nitrogen atmosphere. The reaction mixture was quenched by adding water (100 mL) and extracted with EA (50 mL×6). The combined organic layers were washed with brine (20 mL×3), dried over sodium sulfate, filtered, and concentrated in vacuo to give a residue. The residue was purified by column chromatography (SiO$_2$, PE/EA=10/1 to 3/1) to give a product as a white solid in 12% yield. LCMS (ES$^+$, m/z): 211.3[(M+H)$^+$].

A mixture of the THP ester (200 mg, 951 μmol, 1 eq), sodium hydroxide (114 mg, 2.85 mmol, 3 eq), methanol (2 mL), and water (2 mL) was degassed and purged with nitrogen 3 times, then the mixture was stirred at 25° C. for 3 h under nitrogen atmosphere. The reaction mixture was quenched by adding HCl to adjust pH=7, and the mixture was frozen and lyophilized to give the acid as a white solid. LCMS (ES$^-$, m/z): 197.0[(M+H)$^+$].

N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(oxan-4-yl)-1H-pyrazole-4-carboxamide was prepared from Amine 1 using method B in 34% yield. LCMS (ES$^+$, m/z): 605.1 [(M+H)$^+$]. $^1$H NMR (400 MHz, DMSO-d$_6$) δ=9.08-8.92 (t, J=5.2 Hz, 1H), 8.31 (s, 1H), 7.95 (s, 1H), 7.89 (s, 1H), 7.18-7.01 (t, J=8.0 Hz, 1H), 6.94-6.80 (d, J=8.4 Hz, 1H), 6.35-6.24 (d, J=8.0 Hz, 1H), 6.08-5.94 (d, J=11.6 Hz, 1H), 5.62-5.41 (m, 2H), 4.95-4.75 (m, 3H), 4.57-4.37 (m, 1H), 4.02-3.92 (d, J=10.0 Hz, 2H), 3.68-3.55 (m, 1H), 3.46 (br t, J=10.8 Hz, 2H), 3.10-3.02 (m, 1H), 2.88-2.80 (m, 1H), 2.29-2.18 (m, 4H), 2.16-2.09 (m, 1H), 2.05-1.97 (m, 3H), 1.96-1.87 (m, 2H), 1.73-1.64 (in, 1H).

Example 101: 1-cyclohexyl-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-pyrazole-4-carboxamide (Compound 326B)

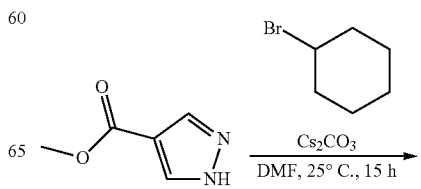

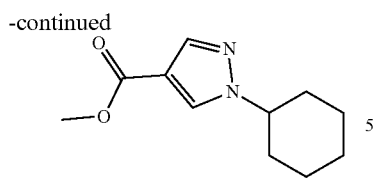

A mixture of the pyrazole ester (1 g, 7.93 mmol, 1 eq), cesium carbonate (7.75 g, 23.8 mmol, 3 eq) and bromocyclohexane (15.9 mmol, 1.96 mL, 2 eq) in DMF (10 mL) was degassed and purged with nitrogen 3 times, and the mixture was heated and stirred at 40° C. for 15 h under nitrogen atmosphere. The reaction mixture was quenched by adding water (100 mL), then extracted with EA (50 mL×6). The combined organic layers were washed with brine (20 mL×3), dried over sodium sulfate, filtered, and concentrated in vacuo to give a residue. The residue was purified by prep-TLC (SiO$_2$, PE:EA=3:1) to give the product as a white solid in 11% yield. LCMS (ES$^+$, m/z): 209.3[(M+H)].

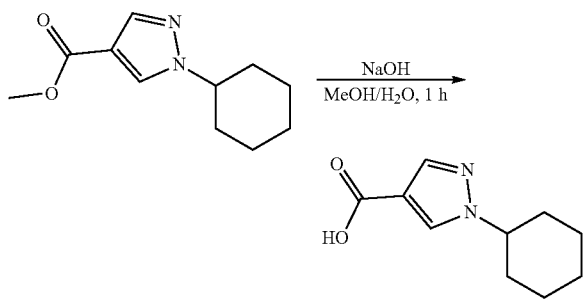

A mixture of the ester (0.15 g, 720 μmol, 1 eq) sodium hydroxide (144.04 mg, 3.60 mmol, 5 eq) in methanol (1 mL) and water (1 mL) was degassed and purged with nitrogen for 3 times, and then the mixture was stirred at 25° C. for 1 h under nitrogen atmosphere. The reaction mixture was quenched by adding 1N HCl aq to pH<7 at 0° C., then diluted with water (10 mL), and concentrated in vacuo to remove methanol. Freeze-drying gave the product as a white solid in 18% yield. LCMS (ES$^+$, m/z): 195.1[(M+H)].

1-cyclohexyl-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-pyrazole-4-carboxamide was prepared from Amine 1 using method B to provide the desired product in 29% yield. LCMS (ES$^+$, m/z): 603.1[(M+H)].

Example 102: General Procedure for Synthesis of Imidazoles Via Isocyanide: 1-cyclopropyl-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-imidazole-4-carboxamide (Compound 327B)

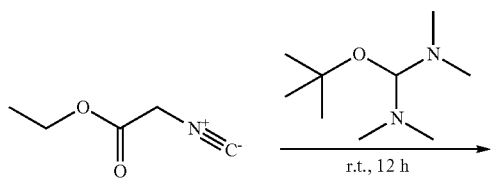

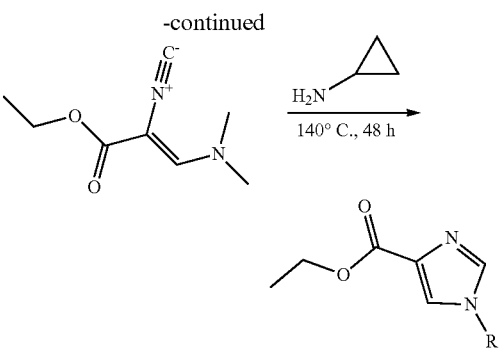

A mixture of the isocyanide (88.4 mmol, 9.71 mL, 1 eq) and 1-tert-butoxy-N,N,N',N'-tetramethyl-methanediamine (177 mmol, 36.5 mL, 2 eq) was stirred at 25° C. for 24 h. The reaction was used for next step directly without further purification.

A mixture of cyclopropylamine (965 mg, 11.9 mmol, 2 eq) and ethyl (Z)-3-(dimethylamino)-2-isocyano-prop-2-enoate (1 g, 5.95 mmol, 1 eq) was stirred at 70° C. for 2 h. The reaction mixture was poured into water (100 mL) and extracted with EA (100 mL×3). The combined organic phase was washed with brine (20 mL×3). dried over anhydrous sodium sulfate, filtered, and concentrated in vacuo to give a residue. The residue was purified by column chromatography (SiO$_2$, PE/EA=I/O to 1/1) to give the product (1 g, 3.92 mmol, 46.2% yield, 80% purity).

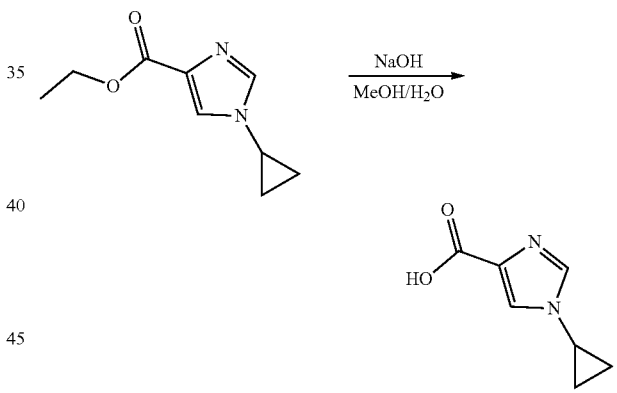

A solution of the ester (537 mg, 2.63 mmol, 1 eq), sodium hydroxide (105.2 mg, 2.63 mmol, 1 eq), water (3 mL), and methanol (3 mL) was stirred at 25° C. for 2 h. The reaction mixture was acidified with 1N HCl to pH 7. The reaction was filtered, and concentrated in vacuo to give a residue. The solid was extracted with DCM (60 mL×2). The organic solution was dried over anhydrous sodium sulfate, filtered, and concentrated in vacuo to give the desired product.

1-cyclopropyl-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-imidazole-4-carboxamide was prepared from Amine 1 using method B to provide the desired product in 33% yield. LCMS (ES$^+$, m/z): 603.1[(M+H)]. $^1$H NMR (400 MHz, DMSO-d$_6$) δ ppm 8.75 (t, J=6.06 Hz, 1H), 7.86 (s, 1H), 7.85-7.87 (m, 1H), 7.83 (d, J=1.10 Hz, 1H), 7.73 (d, J=1.10 Hz, 1H), 7.04-7.13 (m, 1H), 6.86 (d, J=8.38 Hz, 1H), 6.26 (d, J=7.72 Hz, 1H), 6.01 (d, J=8.38 Hz, 1H), 5.48 (q, J=8.97 Hz, 2H), 4.68-4.91 (m, 3H), 3.48-3.64 (m, 2H), 3.02 (br t, J=10.03 Hz, 1H), 2.80 (br d, J=10.36 Hz, 1H), 2.32-2.36 (m, 1H), 2.16-2.34 (m, 4H), 2.05-2.13 (m, 1H), 1.95-2.04 (m, 1H), 1.59-1.71 (m, 1H).

Example 103: 1-tert-butyl-N-[(3-{4-[(4,4-difluorocyclohexyl)amino]-1-(2,2,2-trifluoroethyl)-1H-indol-2-yl}-1,2,4-oxadiazol-5-yl)methyl]-1H-pyrrole-3-carboxamide (Compound 328B)

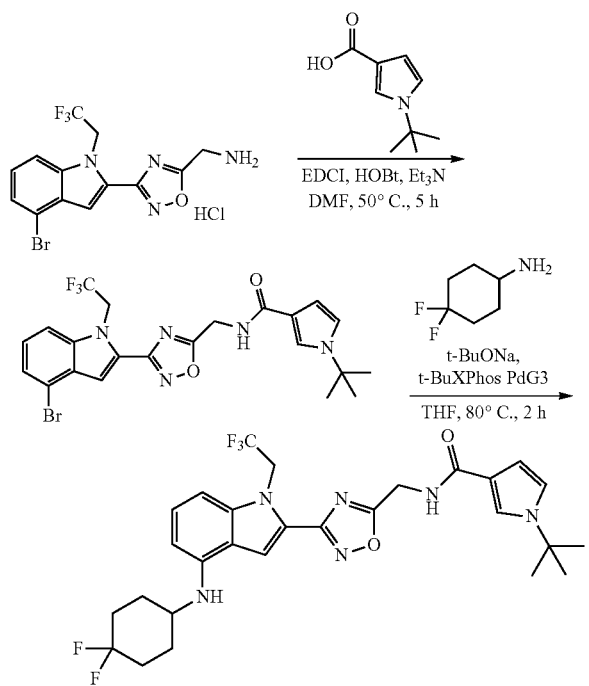

To a mixture of the primary amine (200 mg, 420 μmol, 1 eq, 2HCl) and the pyrrole acid (77.2 mg, 462 μmol, 1.1 eq) in DMF (4 mL) were added HOBt (170.1 mg, 1.26 mmol, 3 eq), EDCI (241.3 mg, 1.26 mmol, 3 eq), and TEA (4.2 mmol, 0.58 mL, 10 eq) at 50° C. under nitrogen. The mixture was stirred at 50° C. for 2 h. The reaction was poured into ice-water (w/w=1/1) (100 mL). The aqueous phase was extracted with EA (30 mL×3). The combined organic phase was washed with brine (30 mL×3), dried over anhydrous sodium sulfate, filtered, and concentrated in vacuo. The reaction was purified by prep-TLC to provide the desired bromoindole amide intermediate (80 mg, 152 μmol, 36.4% yield) as a light yellow solid. LC-MS (ES+, m/z): 524.0/526.0 [(M+H)+].

To a mixture of the above bromide intermediate (80 mg, 153 μmol, 1 eq) and 4,4-difluorocyclohexylamine (82.5 mg, 610 μmol, 4 eq) in THF (1 mL) were added t-BuXPhos generation 3 (48.5 mg, 61.0 μmol, 0.4 eq), sodium t-butoxide (2 M, 305 μL 4 eq), and the reaction was heated at 80° C. under nitrogen for 4 h. The residue was poured into ice-water (w/w=1/1) (100 mL). The aqueous phase was extracted with EA (30 mL×3). The combined organic phase was washed with brine (30 mL×3), dried over anhydrous sodium sulfate, filtered, and concentrated in vacuo. The residue was purified by prep-TLC to provide the product 1-tert-butyl-N-[(3-{4-[(4,4-difluorocyclohexyl)amino]-1-(2,2,2-trifluoroethyl)-1H-indol-2-yl}-1,2,4-oxadiazol-5-yl)methyl]-1H-pyrrole-3-carboxamide (19.6 mg, 20.8% yield, 93.8% purity) as a light yellow solid. LCMS (ES+, m/z): 603.1[(M+H)]. $^1$H NMR (400 MHz, DMSO-d$_6$) δ ppm 1.49 (s, 9H) 1.54-1.68 (m, 2H) 1.92-2.04 (m, 4H) 2.09 (br d, J=10.03 Hz, 2H) 3.62 (br d, J=5.75 Hz, 1H) 4.73 (d, J=5.75 Hz, 2H) 5.49 (q, J=9.05 Hz, 2H) 5.99 (d, J=7.95 Hz, 1H) 6.27 (d, J=7.95 Hz, 1H) 6.47-6.57 (m, 1H) 6.85 (d, J=8.07 Hz, 1H) 6.99 (t, J=2.63 Hz, 1H) 7.12 (t, J=8.07 Hz, 1H) 7.54 (t, J=2.02 Hz, 1H) 7.78 (s, 1H) 8.63 (t, J=5.75 Hz, 1H).

1-tert-butyl-N-{[3-(4-{(3S,4R)-1-cyclopropyl-3-fluoropiperidin-4-yl]amino}-1-(2,2,2-trifluoroethyl)-1H-indol-2-yl)-1,2,4-oxadiazol-5-yl]methyl}-1H-imidazole-4-carboxamide (Compound 329B) was prepared from the previously prepared N-cyclopropylpiperidine using method B in 28% yield. LCMS (ES+, m/z): 603.4 [(M+H)+]. $^1$H NMR (400 MHz, DMSO-d$_6$) δ=8.77 (s, 1H), 7.91-7.86 (m, 3H), 7.14-7.01 (m, 1H), 6.88-6.86 (m, 1H), 6.29-6.27 (m, 1H), 6.00-5.97 (m, 1H), 5.50-5.47 (m, 2H), 4.90-4.75 (m, 3H), 3.65-3.56 (m, 1H), 3.20-3.17 (m, 1H), 2.96-2.93 (m, 1H), 2.67-2.56 (m, 1H), 2.49-2.33 (m, 1H), 1.91-1.88 (m, 1H), 1.67-1.63 (m, 2H), 1.53 (s, 9H), 0.43-0.27 (m, 4H).

1-tert-butyl-N-{[3-(4-{[(3S,4R)-1-cyclopropyl-3-fluoropiperidin-4-yl]amino}-1-(2,2,2-trifluoroethyl)-1H-indol-2-yl)-1,2,4-oxadiazol-5-yl]methyl}-1H-pyrrole-3-carboxamide (Compound 330B) was prepared from the previously prepared N-cyclopropylpiperidine using method B in 20% yield. LCMS (ES+, m/z): 602.2 [(M+H)+]. $^1$H NMR (400 MHz, DMSO-d$_6$) δ=8.65-8.62 (m, 1H), 7.87 (s, 1H), 7.55 (s, 1H), 7.34-7.22 (m, 1H), 7.14-7.10 (m, 1H), 6.89-6.87 (m, 1H), 6.51-6.49 (m, 1H), 6.30-6.28 (m, 1H), 5.51-5.49 (m, 2H), 4.90-4.78 (d, J=8.0 Hz, 1H), 4.73-4.72 (m, 2H), 3.67-3.60 (m, 1H), 3.32 (t, 1H), 2.96-2.90 (m, 1H), 2.67-2.66 (m, 1H), 2.49-2.33 (m, 1H), 1.68-1.67 (m, 1H), 1.67-1.66 (m, 2H), 1.49 (s, 9H), 0.44-0.27 (m, 4H).

Example 104: 1-tert-butyl-N-({3-[4-({4H,5H,6H,7H-pyrazolo[1,5-a]pyridin-5-yl}amino)-1-(2,2,2-trifluoroethyl)-1H-indol-2-yl]-1,2,4-oxadiazol-5-yl}methyl)-1H-pyrrole-3-carboxamide (Compound 332B)

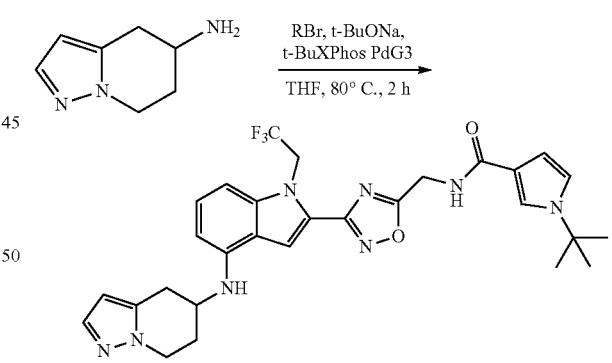

To a solution of N-[[3-[4-bromo-1-(2,2,2-trifluoroethyl)indol-2-yl]-1,2,4-oxadiazol-5-yl]methyl]-1-tert-butyl-pyrrole-3-carboxamide (RBr) (150 mg, 286 μmol, 1 eq) and the amine (117.7 mg, 858 μmol, 3 eq) in THF (3 mL) were added sodium t-butoxide (2 M, 570 μL 4 eq) and t-BuXPhos Pd Gen. 3 (113.6 mg, 143 μmol, 0.5 eq). The mixture was stirred at 80° C. for 2 h under nitrogen. The mixture was poured into EDTA (Sat. aq, 50 mL) and stirred at 25° C. for 1 h. The mixture was extracted with EA (50 mL×3). The combined organic layers were washed with brine 150 mL (50 mL×3), dried over sodium sulfate, filtered, and concentrated in vacuo to give a residue, which was purified by prep-TLC (PE:EA:TEA=50:100:3, R$_f$=0.3) to afford 1-tert-butyl-N-({3-[4-({4H,5H,6l1,7H-pyrazolo[1,5-a]pyridin-5-yl}amino)-1-(2,2,2-trifluoroethyl)-1H-indol-2-yl]-1,2,4-oxadiazol-5-yl}methyl)-1H-pyrrole-3-carboxamide (22.9 mg, 13.7% yield, 99.6% purity) as a light yellow solid. LC-MS (ES$^+$, m/z): 581.3 [(M+H)$^+$]. H NMR (400 MHz, DMSO-d$_6$)=8.64 (t, J=5.8 Hz, 1H), 7.78 (s, 1H), 7.54 (t, J=2.0 Hz, 1H), 7.36 (d, J=1.7 Hz, 1H), 7.15 (t, J=8.0 Hz, 1H), 6.99 (t, J=2.7 Hz, 1H), 6.90 (d, J=8.2 Hz, 1H), 6.50 (dd, J=1.8, 2.8 Hz, 1H), 6.37 (d, J=7.9 Hz, 1H), 6.18 (d, J=7.8 Hz, 1H), 6.02 (s, 1H), 5.51 (q, J=8.6 Hz, 2H), 4.73 (d, J=5.6 Hz, 2H), 4.36-4.24 (m, 1H), 4.22-4.11 (m, 1H), 4.00 (br s, 1H), 3.21 (br dd, J=4.9, 15.9 Hz, 1H), 2.79 (dd, J=9.4, 16.1 Hz, 1H), 2.36 (br s, 1H), 2.08-1.89 (m, 1H), 1.52-1.46 (m, 9H).

N-{[3-(4-{[(3S,4R)-1-ethyl-3-fluoropiperidin-4-yl]amino}-1-(2,2,2-trifluoroethyl)-1H-indol-2-yl)-1,2,4-oxadiazol-5-yl]methyl}-1-(oxan-4-yl)-1H-pyrrole-3-carboxamide (Compound 333B) was prepared from the previously prepared N-ethylpiperidine and 1-(oxan-4-yl)-1H-pyrrole-3-carboxylic acid using method B in 26% yield. LCMS (ES$^+$, m/z): 618.1 [(M+H)$^+$]. $^1$H NMR (400 MHz, DMSO-d$_6$) δ ppm 8.64 (t, J=5.73 Hz, 1H), 7.86 (s, 1H), 7.46 (t, J=1.87 Hz, 1H), 7.04-7.13 (m, 1H), 6.91 (t, J=2.54 Hz, 1H), 6.86 (d, J=8.38 Hz, 1H), 6.49 (dd, J=2.65, 1.76 Hz, 1H), 6.26 (d, J=7.72 Hz, 1H), 6.00 (br d, J=8.38 Hz, 1H), 5.48 (q, J=9.04 Hz, 2H), 4.75-4.91 (m, 1H), 4.74-4.92 (m, 1H), 4.71 (d, J=5.73 Hz, 1H), 4.66-4.74 (m, 1H), 4.09-4.24 (m, 1H), 3.94 (br dd, J=10.80, 3.97 Hz, 2H), 3.51-3.66 (m, 1H), 3.41 (td, J=11.63, 2.09 Hz, 1H), 3.36 (br s, 1H), 3.04-3.13 (m, 1H), 2.83-2.94 (m, 1H), 2.28-2.38 (m, 2H), 2.02-2.25 (m, 1H), 1.77-2.00 (m, 5H), 1.62-1.74 (m, 1H), 1.61-1.72 (m, 1H), 0.98 (br t, J=7.06 Hz, 2H), 0.92-1.04 (m, 1H).

N-{[3-(4-{[(3S,4R)-1-ethyl-3-fluoropiperidin-4-yl]amino)-1-(2,2,2-trifluoroethyl)-1H-indol-2-yl)-1,2,4-oxadiazol-5-yl]methyl}-1-(oxan-4-yl)-1H-pyrazole-4-carboxamide (Compound 334B) was prepared using the previously prepared N-ethylpiperidine and the previously prepared 1-(oxan-4-yl)-1H-pyrazole-4-carboxylic acid using method B in 33.9% yield. LC-MS (ES$^+$, m/z): 619.1 [(M+H)$^+$]. $^1$H NMR (400 MHz, DMSO-d$_6$) δ ppm 8.98 (t, J=5.73 Hz, 1H), 8.28 (s, 1H), 7.93 (s, 1H), 7.86-7.88 (m, 1H), 7.87 (s, 1H), 7.05-7.13 (m, 1H), 6.86 (d, J=8.16 Hz, 1H), 6.26 (d, J=7.72 Hz, 1H), 5.99 (br d, J=8.16 Hz, 1H), 5.48 (q, J=9.04 Hz, 2H), 4.73-4.91 (m, 3H), 4.38-4.48 (m, 1H), 3.94 (br dd, J=10.69, 2.98 Hz, 2H), 3.52-3.67 (m, 1H), 3.39-3.50 (m, 3H), 3.04-3.16 (m, 1H), 2.89 (br d, J=9.48 Hz, 1H), 2.31-2.39 (m, 2H), 2.04-2.22 (m, 1H), 1.85-2.02 (m, 6H), 1.68 (br d, J=10.14 Hz, 1H).

N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(oxan-4-yl)-1H-pyrrole-3-carboxamide (Compound 335B) was synthesized using the above prepared carboxylic acid and Amine 1 under method B to provide the desired product in 37% yield. LC-MS (ES$^+$, m/z): 604.1 [(M+H)$^+$]. $^1$H NMR (400 MHz, DMSO-d$_6$) δ ppm 8.63 (t, J=5.62 Hz, 1H), 7.86 (s, 1H), 7.46 (s, 1H), 7.09 (t, J=8.05 Hz, 1H), 6.91 (t, J=2.43 Hz, 1H), 6.86 (d, J=8.16 Hz, 11H), 6.50 (dd, J=2.65, 1.76 Hz, 1H), 6.26 (d, J=7.94 Hz, 1H), 5.99 (br d, J=8.16 Hz, 1H), 5.48 (q, J=8.89 Hz, 2H), 4.73-4.93 (m, 1H), 4.73-4.92 (m, 1H), 4.71 (d, J=5.73 Hz, 2H), 4.11-4.24 (m, 1H), 3.94 (br dd, J=11.25, 3.31 Hz, 2H), 3.49-3.65 (m, 1H), 3.36-3.46 (m, 2H), 3.02 (br t, J=10.36 Hz, 1H), 2.80 (br d, J=10.36 Hz, 1H), 2.16-2.33 (m, 1H), 2.04-2.13 (m, 1H), 1.94-2.03 (m, 1H), 1.78-1.91 (m, 4H), 1.66 (br d, J=10.80 Hz, 1H).

Example 105: N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(propan-2-yl)-1H-imidazole-2-carboxamide (Compound 336B)

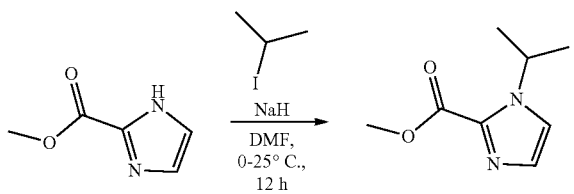

To a solution of methyl 2-imidazolecarboxylic acid (0.5 g, 3.96 mmol, 1 eq) in DMF (5 mL) was added sodium hydride (316.8 mg, 7.92 mmol, 60% purity, 2 eq) at 0° C., then 2-iodopropane (4.75 mmol, 475 μL 1.2 eq) was added. The mixture was stirred at 25° C. for 12 h. The reaction mixture was quenched by adding saturated ammonium chloride (40 mL) at 0° C., then diluted with water 10 mL and extracted with EA (50 mL×3). The combined organic layers were washed with brine (30 mL×3), dried over sodium sulfate, filtered, and concentrated in vacuo to give a residue. The residue was purified by prep-TLC (SiO$_2$, PE:EA=2:1) to give the intermediate as colorless oil in 15% yield.

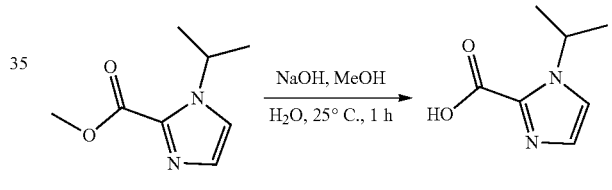

To a solution of the ester (0.1 g, 590 μmol, 1 eq) in methanol (3 mL) and water (3 mL) was added sodium hydroxide (119 mg, 2.97 mmol, 5 eq). The mixture was stirred at 25° C. for 1 h. The reaction mixture was quenched by adding 1N HCl to pH<7 at 0° C., then diluted with water (10 mL), and concentrated in vacuo to remove excess methanol. The solution was freeze-dried in vacuo to give a residue. The residue was purified by prep-HPLC (FA condition: column: Phenomenex Luna C18 200×40 mm×10 um; mobile phase: [water (0.2% FA)-ACN];B %: 1%-10%, 10 min) to give the product as a colorless oil in 51% yield. LCMS (ES$^+$, m/z): 155.1 [(M+H)$^+$.

N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(propan-2-yl)-1H-imidazole-2-carboxamide was prepared from the above carboxylic acid and Amine 1 using method B in 23% yield. LC-MS (ES$^+$, m/z): 563.1 [(M+H)$^+$]. $^1$H NMR (400 MHz, DMSO-d6) δ=9.31-9.15 (t, J=5.2 Hz, 1H), 7.89 (s, 1H), 7.64 (s, 1H), 7.18-7.07 (m, 2H), 6.93-6.83 (d, J=8.4 Hz, 1H), 6.31-6.22 (d, 1=8.0 Hz, 1H), 6.04-5.93 (d, J=8.0 Hz, 1H), 5.64-5.43 (m, 3H), 4.94-4.69 (m, 3H), 3.68-3.52 (m, 11H), 3.09-2.99 (m, 1H), 2.86-2.75 (m, 1H), 2.33-2.27 (m, 11H), 2.20-2.15 (m, 3H), 2.12-2.06 (m, 1H), 2.04-1.96 (m, 1H), 1.68 (br d, J=10.3 Hz, 1H), 1.43-1.36 (d, J=6.8 Hz, 6H).

Example 106: 1-tert-butyl-N-{[3-(4-{[(3S,4R)-3-fluoro-1-(2-methoxyethyl)piperidin-4-yl]amino}-1-(2,2,2-trifluoroethyl)-1H-indol-2-yl)-1,2,4-oxadiazol-5-yl]methyl}-1H-pyrrole-3-carboxamide (Compound 337B)

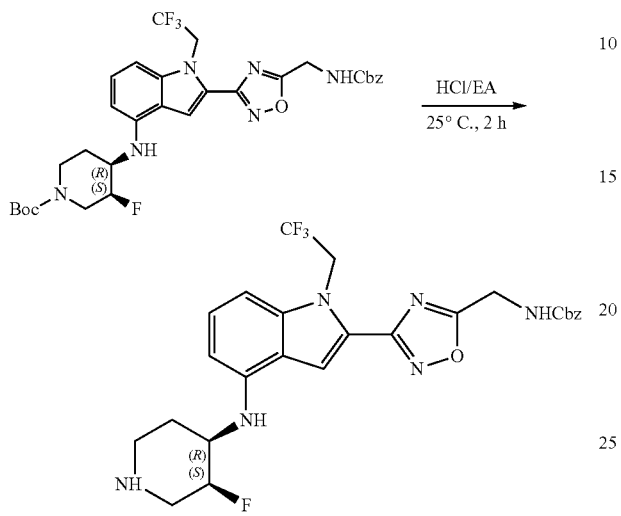

A mixture of the Boc-piperidine (1 g, 1.55 mmol, 1 eq) in HCl/EA (4 M, 10 mL, 25.9 eq) was stirred at 25° C. for 2 h. The reaction mixture was concentrated in vacuo to remove HCl/EA. The residue was diluted with sodium carbonate (Sat., 100 mL) and extracted with EA (90 mL×3). The combined organic layers were washed with brine (60 mL×3), dried over sodium sulfate, filtered, and concentrated in vacuo to give a residue. The residue was purified by column chromatography (SiO$_2$, PE/EA/TEA=2/1/0.001 to 1/2/0.01) to give the product as a yellow solid. LCMS (ES+, m/z): 605.3[(M+H)$^+$].

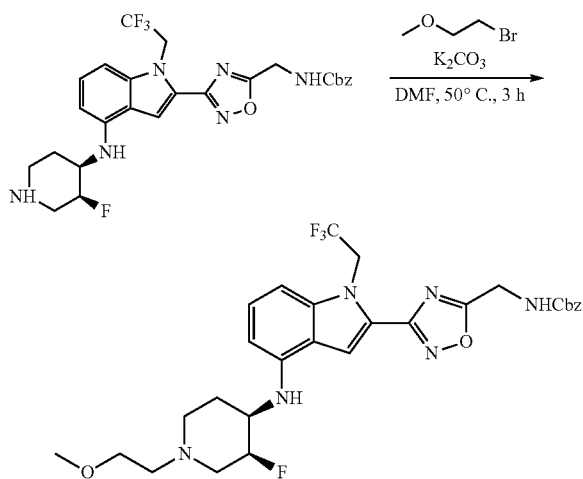

A mixture of the piperidine intermediate (0.3 g, 549 μmol, 1 eq), bromoethyl methyl ether (1.10 mmol, 103 μL 2 eq), potassium carbonate (379.3 mg, 2.74 mmol, 5 eq) in DMF (3 mL) was degassed and purged with nitrogen 3 times, then the mixture was heated and stirred at 50° C. for 3 h under nitrogen atmosphere. The reaction mixture was quenched by adding water (30 mL) and extracted with EA (30 mL×3). The combined organic layers were washed with brine (30 mL×3), dried over sodium sulfate, filtered, and concentrated in vacuo to give a residue. The residue was purified by prep-TLC (PE:EA:TEA=60:60:5) to give a product as a yellow oil in 45% yield.

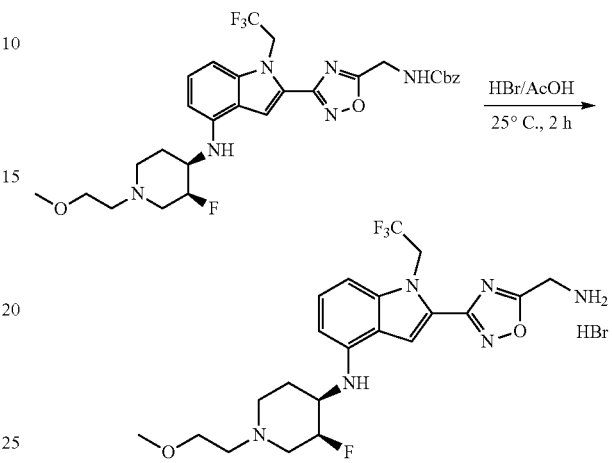

To the methoxyethyl piperidine intermediate (0.2 g, 331 μmol, 1 eq) was added HBr(AcOH) (330 μmol, 5 mL, 33% purity, 1 eq). The mixture was stirred at 25° C. for 2 h. The residue was triturated with TBME (10 mL), then filtered to collect the crude product. The crude product was triturated with PE:EA=20:1 at 25° C. for 12 h, then collected by filtration and dried in vacuo to give the product as a yellow solid. LCMS (ES+, m/z): 471.2[(M+H)$^+$] in 57% yield. 1-tert-butyl-N-{[3-(4-{[(3S,4R)-3-fluoro-1-(2-methoxyethyl)piperidin-4-yl]amino}-1-(2,2,2-trifluoroethyl)-1H-indol-2-yl)-1,2,4-oxadiazol-5-yl]methyl}-1H-pyrrole-3-carboxamide was prepared using method D using the pyrrole carboxylic acid in 28% yield. LCMS (ES+, m/z): 471.2[(M+H)$^+$]. $^1$H NMR (400 MHz, DMSO-d6) δ=8.70-8.57 (m, 1H), 7.88 (s, 1H), 7.55 (s, 1H), 7.19-7.08 (t, J=7.6 Hz, 1H), 6.99 (s, 1H), 6.94-6.80 (d, J=7.2 Hz, 1H), 6.57-6.39 (d, J=7.6 Hz, 1H), 6.34-6.20 (m, 1H), 6.08-5.94 (m, 1H), 5.67-5.45 (m, 2H), 4.94-4.69 (m, 3H), 3.64-3.53 (m, 1H), 3.46-3.41 (m, 2H), 3.24 (s, 3H), 3.15 (m, 1H), 2.92 (m, 1H), 2.44-2.31 (m, 3H), 2.28-2.12 (m, 1H), 2.02-1.91 (m, 1H), 1.71-1.63 (m, 1H), 1.49 (s, 9H).

Example 107: Method D-1-tert-butyl-N-{[3-(4-{[(3S,4R)-3-fluoro-1-(2-methoxyethyl)piperidin-4-yl]amino}-1-(2,2,2-trifluoroethyl)-1H-indol-2-yl)-1,2,4-oxadiazol-5-yl]methyl}-1H-pyrazole-4-carboxamide (Compound 338B)

To a solution of the pyrazole carboxylic acid in DMF (2 mL) were added TEA (522 μmol, 73 μL 5 eq) and PyBOP (81.6 mg, 157 μmol, 1.5 eq). The mixture was stirred at 50° C. for 15 min, and then the above amine (0.08 g, 104 μmol, 1 eq, HBr) was added into the mixture. The resulting mixture was stirred at 50° C. for 4.75 h. The reaction mixture was quenched by adding water (10 mL) and extracted with EA (10 mL×3). The combined organic layers were washed with brine (10 mL×3), dried over sodium sulfate, filtered, and concentrated in vacuo to give a residue. The residue was purified by prep-TLC (SiO$_2$, DCM: methanol=20:1) to give the product in 30% yield. LCMS (ES+, m/z): 621.3[(M+

H)+]. 1H NMR (400 MHz, DMSO-d6) δ=9.08-8.90 (m, LH), 8.35 (s, 1H), 8.06-7.80 (d, J=17.6 Hz, 2H), 7.20-7.01 (m, 1H), 6.96-6.78 (m, 1H), 6.36-6.22 (d, J=8.4 Hz, 1H), 6.09-5.92 (m, 1H), 5.60-5.43 (m, 2H), 4.97-4.70 (m, 3H), 3.68-3.54 (m, 1H), 3.46-3.41 (m, 2H), 3.26-3.20 (m, 3H), 3.18-3.10 (m, 1H), 2.97-2.87 (m, 1H), 2.48-2.31 (m, 3H), 2.25-2.16 (m, 1H), 2.03-1.91 (m, 1H), 1.74-1.63 (m, 1H), 1.58-1.47 (m, 9H).

Example 108: N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(3-fluorocyclopentyl)-1H-pyrazole-4-carboxamide (Compound 339B)

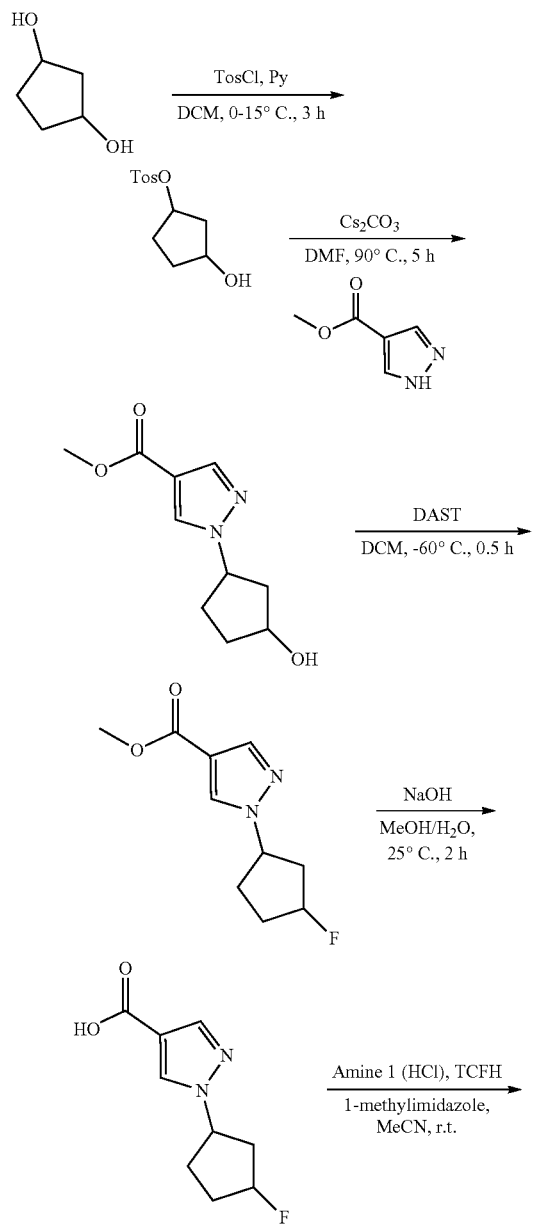

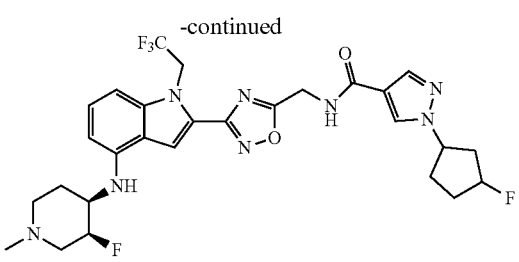

To a solution of cyclopentane-1,3-diol (0.5 g, 4.9 mmol, 1 eq) and pyridine (18.6 mmol, 1.5 mL, 3.8 eq) in DCM (3 mL) was added dropwise a solution of 4-methylbenzenesulfonyl chloride (886 mg, 4.7 mmol, 0.9 eq) in DCM (9 mL) at 0° C. over 5 min. The mixture was stirred at 15° C. for 3 hrs. The reaction mixture was diluted with DCM (50 mL) and washed with 1N HCl (5 mL×3). The organic layer was washed with brine, dried over sodium sulfate, filtered, and concentrated in vacuo to give a residue. The residue was purified by prep-TLC (SiO2, PE/EA=1:1) to give the monotosylate (0.5 g, 1.9 mmol, 39.8% yield) as a yellow oil. 1H NMR (400 MHz, CDCl3-d) δ=7.84-7.76 (m, 2H), 7.35 (d, J=8.0 Hz, 2H), 5.06 (tt, J=3.3, 6.3 Hz, 1H), 4.51-4.41 (m, 1H), 2.46 (s, 3H), 2.12-2.03 (m, 2H), 1.97-1.77 (m, 3H), 1.64-1.54 (m, 1H).

To a solution of the intermediate tosylate (250 mg, 975 μmol, 1 eq) and methyl 1H-pyrazole-4-carboxylate (184 mg, 1.5 mmol, 1.5 eq) in DMF (2 mL) was added cesium carbonate (635 mg, 1.9 mmol, 2 eq). The mixture was heated and stirred at 90° C. for 5 h. The reaction was quenched by addition water 10 mL at 20° C., then extracted with EA (10 mL×3). The combined organic layers were washed with brine (5 mL×2), dried over sodium sulfate, filtered, and concentrated in vacuo to give a residue. The residue was purified by prep-TLC (SiO2, PE/EA=1:1) to give the product (200 mg, 951 μmol, 97.5% yield) as a yellow oil. LC-MS: (ES+, m/z): 211.1 [(M+H)+].

To a solution of methyl 1-(3-hydroxycyclopentyl)pyrazole-4-carboxylate (200 mg, 951 μmol, 1 eq) in DCM (5 mL) was added DAST (951 μmol, 125 μL 1 eq) at −60° C. The mixture was stirred at −60° C. for 0.5 h. The reaction mixture was diluted with DCM (10 mL) and quenched with addition aqueous ammonium chloride (10 mL) at 0° C., then the mixture was extracted with DCM (10 mL×3). The combined organic layers were washed with brine (5 mL×2), dried over sodium sulfate, filtered, and concentrated in vacuo to give a residue. The residue was purified by prep-TLC (SiO2, PE/EA=3:1) to give the product (130 mg, 613 μmol, 64.3% yield) as a yellow solid. LC-MS: (ES+, m/z): 213.0 [(M+H)+].

To a solution of methyl 1-(3-fluorocyclopentyl)pyrazole-4-carboxylate (130 mg, 612 μmol, 1 eq) in methanol (0.2 mL) and water (0.1 mL) was added sodium hydroxide (49 mg, 1.2 mmol, 2 eq). The mixture was stirred at 25° C. for 2 h. The reaction mixture was acidified with 2 N HCl to pH=3 and extracted with EA (10 mL×3). The combined organic layers were washed with brine (5 mL), dried over sodium sulfate, filtered, and concentrated in vacuo to give the carboxylic acid (110 mg, 90.9% yield) as a yellow solid. LC-MS: (ES+, m/z): 197.1 [(M−H)+].

Example 109: Method E-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(3-fluorocyclopentyl)-1H-pyrazole-4-carboxamide A mixture of 1-(3-fluorocyclopentyl)pyrazole-4-carboxylic acid (36 mg, 182 μmol, 1.3 eq), Amine 1 (60 mg, 140

µmol, 1 eq), 1-methylimidazole (1.8 mmol, 145 µL 13 eq), [chloro(dimethylamino)methylene]dimethylammonium hexafluorophosphate (TFCH, 394 mg, 1.4 mmol, 10 eq) in acetonitrile (5 mL) was degassed and purged with nitrogen 3 times, then the mixture was stirred at 20° C. for 2 h under nitrogen atmosphere. The reaction mixture was diluted with water (10 mL), then extracted with EA (10 mL×3). The combined organic layers were washed with brine (5 mL×3), dried over sodium sulfate, filtered, and concentrated in vacuo to give a residue. The residue was purified by prep-HPLC to give the product N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(3-fluorocyclopentyl)-1H-pyrazole-4-carboxamide (23 mg, 35.8 µmol, 25.4% yield) as a light yellow solid. LC-MS: (ES+, m/z): 607.1 [(M+H)+].

Example 110: 1-tert-butyl-N-{[3-(4-{1(1S,2S)-2-fluorocyclohexyl]amino}-1-(2,2,2-trifluoroethyl)-1H-indol-2-yl)-1,2,4-oxadiazol-5-yl]methyl)-1H-pyrrole-3-carboxamide (Compound 340B)

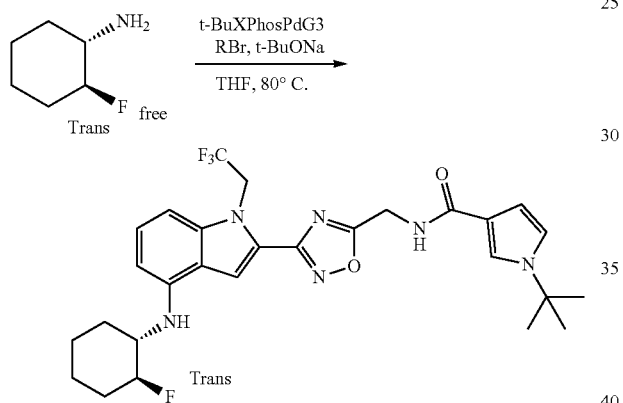

Method F: To a mixture of the bromide (100 mg, 0.191 mmol, 1 eq), (+/−)-trans-2-fluorocylohexylamine (62.3 mg, 531 µmol, 2.79 eq), t-BuXPhos Palladium Generation 3 (60.6 mg, 76. µmol, 0.4 eq) and sodium t-butoxide (2 M, 380 uL(THF), 4 eq) was added dioxane (2 mL) at 20° C. under nitrogen. The mixture was heated and stirred at 80° C. for 3 hrs, The mixture was cooled to 20° C. and concentrated in vacuo at 20° C. The residue was poured into EDTA (50 mL) and stirred for 1 h. The aqueous phase was extracted with EA (30 mL×3). The combined organic phase was washed with brine (30 mL×3), dried over anhydrous sodium sulfate, filtered, and concentrated in vacuo. The residue was purified by prep-HPLC (FA condition, column: Phenomenex Luna C18 200×40 mm×10 um; mobile phase: [water (0.2% FA)-ACN];B %: 60%-100%, 10 min) to afford the desired product (20.1 mg, 18.2% yield, 96.6% purity). LC-MS: (ES+, m/z): 561.1 [(M+H)+].

Compound 341B:N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(oxan-4-yl)-1H-imidazole-4-carboxamide. The imidazole acid was prepared using the General Procedure for synthesis of 1-N-alkyl-4-carboxyimidazoles. This acid was coupled with Amine 1 under method B to provide the desired product. LC-MS: (ES+, m/z): 605.1 [(M+H)+].

Example 111: N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(1-fluoro-2-methylpropan-2-yl)-1H-imidazole-4-carboxamide (Compound 342B)

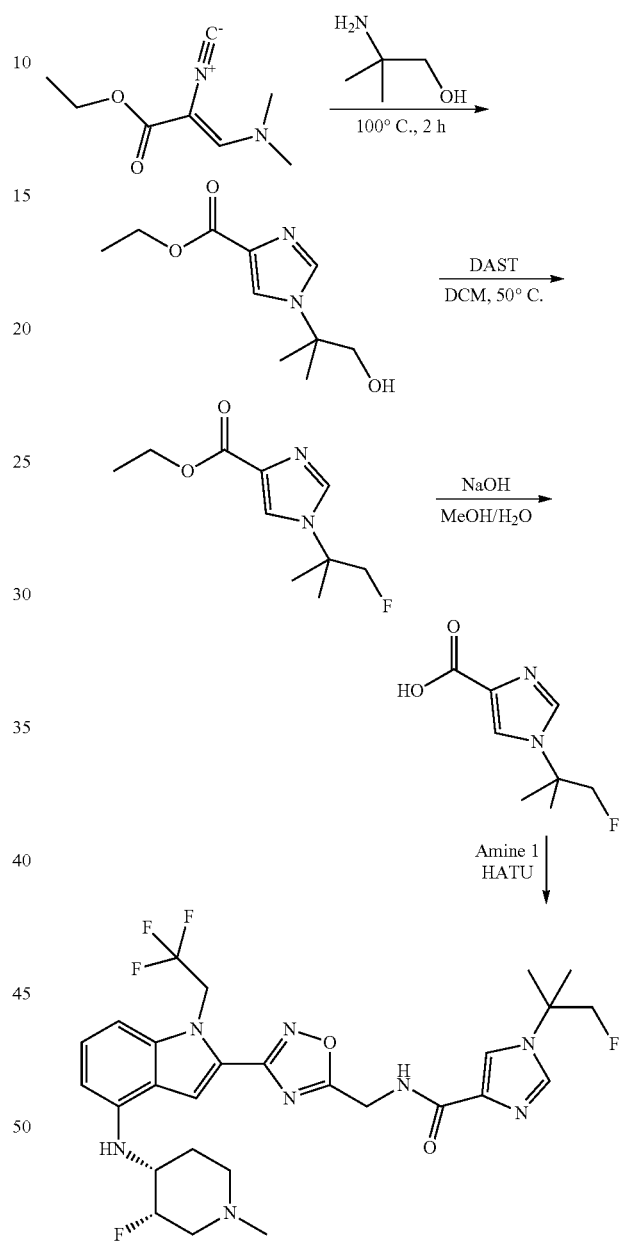

A mixture of the isocyanide (1 g, 5.95 mmol, 1 eq) in 2-amino-2-methyl-propan-1-ol (119 mmol, 11.4 mL, 20 eq) was heated and stirred at 100° C. for 2 h. The reaction mixture was poured into water (100 mL), then extracted with EA (50 mL×3). The combined organic layers were washed with brine (30 mL×1), dried over anhydrous sodium sulfate, filtered, and concentrated in vacuo to give a residue. The residue was purified by prep-HPLC to give product (440 mg, 1.66 mmol, 27.9% yield, 80% purity). LC-MS (ES+, m/z): 212.1[(M+H)+].

To a mixture of the above imidazole (300 mg, 1.41 mmol, 1 eq) in DCM (12 mL) was added DAST (31.8 mmol, 4.20 mL, 22 eq) at 0° C. under nitrogen. The mixture was stirred at 25° C. for 1 h, then stirred at 50° C. for 4 h. The reaction mixture was poured into water (100 mL), then extracted with EA (50 mL×3). The combined organic layers were washed with brine (50 mL×1), dried over anhydrous sodium sulfate, filtered, and concentrated in vacuo to give a residue. The residue was purified by prep-HPLC to give the fluoro intermediate ester (100 mg, 467 μmol, 33.0% yield). LC-MS (ES+, m/z): 214.1[(M+H)+].

To a solution of the ester intermediate (50 mg, 210 μmol, 1 eq) in methanol (2 mL) and water (1 mL) was added sodium hydroxide (25.2 mg, 630 μmol, 3 eq). The mixture was stirred at 25° C. for 2.5 h. The mixture was adjusted to pH 7 with HCl (2M). The reaction mixture was filtered, and concentrated in vacuo to give a residue (40 mg, crude). LC-MS (ES+, m/z): 186.0[(M+H)−]. The above carboxylic acid was coupled with Amine 1 using method B to provide the desired product. LC-MS (ES+, m/z): 595.2 [(M+H)+].

Example 112: 1-tert-butyl-N-{[3-(4-{[(1s,4s)-4-fluorocyclohexyl]amino}-1-(2,2,2-trifluoroethyl)-1H-indol-2-yl)-1,2,4-oxadiazol-5-yl]methyl}-1H-pyrrole-3-carboxamide (Compound 343B)

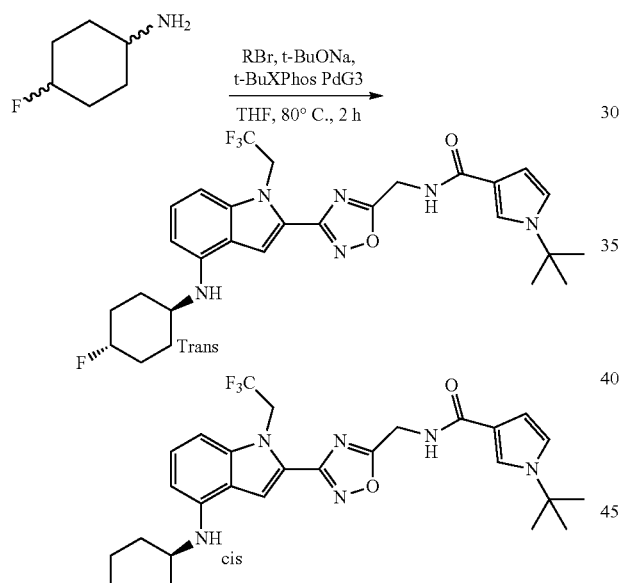

General Buchwald method F was used to provide the desired crude product as a mixture of cis and trans, which was then purified by prep-TLC and then purified by prep-HPLC (FA condition, column: Phenomenex Luna C18 200× 40 mm×10 um; mobilephase: [water (0.2% FA)-ACN];B %: 40%-80%, 10 min to provide the separated stereoisomers.

Cis-1-tert-butyl-N-{[3-(4-{[(1s,4s)-4-fluorocyclohexyl]amino}-1-(2,2,2-trifluoroethyl)-1H-indol-2-yl)-1,2,4-oxadiazol-5-yl]methyl}-1H-pyrrole-3-carboxamide. LC-MS (ES+, m/z): 561.3 [(M+H)+]. 1HNMR (400 MHz, DMSO-d6) δ ppm 1.33 (s, 9H), 1.38-1.46 (m, 2H), 1.47-1.62 (m, 2H), 1.63-1.73 (m, 2H), 1.75-1.86 (m, 2H), 3.25-3.33 (m, 1H), 4.56 (d, J=5.73 Hz, 2H), 4.59-4.75 (m, 1H), 5.32 (q, J=8.89 Hz, 2H), 5.83 (d, J=7.94 Hz, 1H), 6.07 (d, J=7.94 Hz, 1H), 6.30-6.37 (m, 1H), 6.65 (d, J=8.16 Hz, 1H), 6.83 (t, J=2.54 Hz, 1H), 6.94 (t, J=8.05 Hz, 1H), 7.38 (t, J=1.87 Hz, 1H), 7.64 (s, 1H), 8.48 (t, J=5.62 Hz, 1H).

Trans-1-tert-butyl-N-{[3-(4-{[(1s,4s)-4-fluorocyclohexyl]amino}-1-(2,2,2-trifluoroethyl)-1H-indol-2-yl)-1,2,4-oxadiazol-5-yl]methyl}-11H-pyrrole-3-carboxamide LC-MS (ES+, m/z): 561.3 [(M+H)+]. 1HNMR (400 MHz, DMSO-d6) δ ppm 1.33-1.42 (m, 2H), 1.49 (s, 9H), 1.56-1.66 (m, 2H), 2.00-2.10 (m, 4H), 3.41-3.47 (m, 1H), 4.51-4.69 (m, 1 11), 4.72 (d, J=5.75 Hz, 2H), 5.49 (q, J=9.05 Hz, 2H), 5.92 (d, J=7.70 Hz, 1H), 6.22 (d, J=7.82 Hz, 1H), 6.50 (dd, J=2.81, 1.83 Hz, 1H), 6.83 (d, J=8.07 Hz, 1H), 6.99 (t, J=2.63 Hz, 1H), 7.11 (t, J=8.07 Hz, 1H), 7.54 (t, J=2.02 Hz, 1H), 7.77 (s, 1H), 8.63 (t, J=5.69 Hz, 1H).

Example 113: 1-(3,3-difluorocyclopentyl)-N-{[3-(4-{1[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-pyrazole-4-carboxamide (Compound 344B)

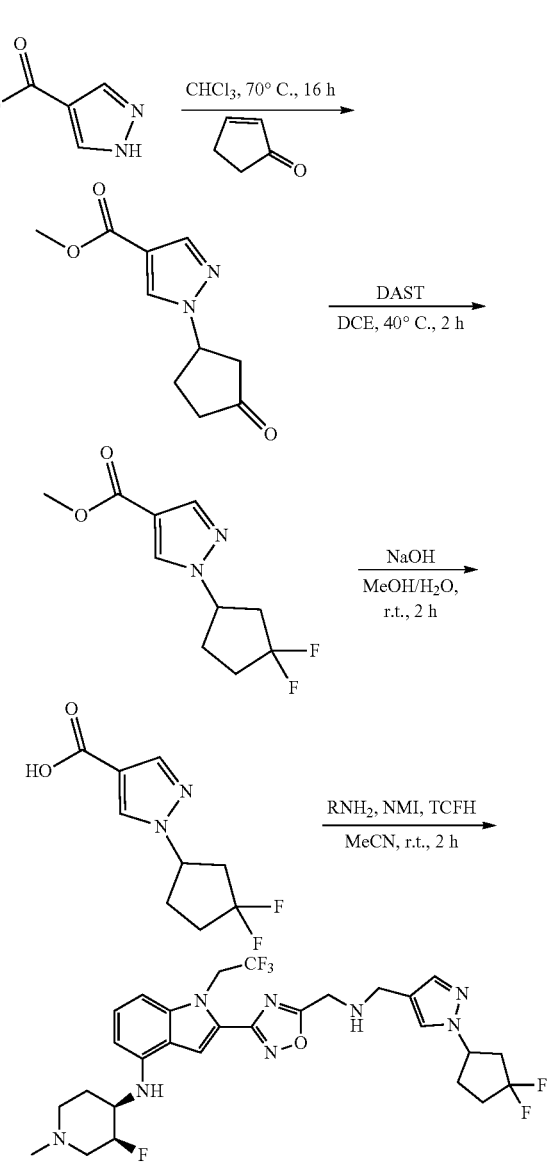

A mixture of methyl 1H-pyrazole-4-carboxylate (500 mg, 3.96 mmol, 1 eq) and cyclopent-2-en-1-one (7.93 mmol, 665 μL 2 eq) in chloroform (7 mL) was heated at 70° C. under nitrogen and stirred for 16 h. The aqueous phase was extracted with EA (30 mL×3). The combined organic phase was washed with brine (30 mL×3), dried over anhydrous sodium sulfate, filtered, and concentrated in vacuo. The crude was purified by prep-TLC (SiO$_2$, PE/EA=1/1) to afford methyl 1-(3-oxocyclopentyl) pyrazole-4-carboxylate (600 mg, 2.88 mmol, 72.7% yield) as a yellow oil. LC-MS (ES$^-$, m/z): 209.1[(M+H)$^+$].

To a mixture of methyl 1-(3-oxocyclopentyl)pyrazole-4-carboxylate (500 mg, 2.40 mmol, 1 eq) and DCE (2.5 mL) was added DAST (2 M, 2.50 mL, 2.08 eq) in one portion at 40° C. under nitrogen. The solution was stirred for 2 h in a sealed tube. The residue was poured into a mixture of ice-ammonium chloride (20 mL) and stirred for 10 min. The aqueous phase was extracted with EA (20 mL×3). The combined organic phase was washed with brine (20 mL×3), dried over anhydrous sodium sulfate, filtered, and concentrated in vacuo. The crude product was purified by pre-TLC (SiO$_2$, PE/EA=1/1) to afford methyl 1-(3,3-difluorocyclopentyl)pyrazole-4-carboxylate (300 mg, 1.30 mmol, 54.3% yield) as a yellow oil. LC-MS (ES$^+$, m/z): 231.1 [(M+H)$^+$].

Methyl 1-(3,3-difluorocyclopentyl)pyrazole-4-carboxylate (300 mg, 1.30 mmol, 1 eq) in methanol (2 mL) was treated with sodium hydroxide (104.24 mg, 2.61 mmol, 2 eq) and water (2 mL) at 20° C. under nitrogen and stirred for 2 h. The mixture was cooled to 0° C. The residue was poured into ammonium chloride (20 mL) and stirred for 10 min. The aqueous phase was extracted with EA (20 mL×3). The combined organic phase was washed with brine (20 mL×3), dried over anhydrous sodium sulfate, filtered, and concentrated in vacuo to provide the intermediate 1-(3,3-difluorocyclopentyl)pyrazole-4-carboxylic acid (250 mg, crude) as white oil. LC-MS (ES$^+$, m/z): 217.1[(M+H)$^+$].

The above acid was coupled with Amine 1 using method E to provide the desired product (22 mg, 0.35 mmol, 37.4% yield, 99.7% purity) as yellow solid. LC-MS (ES$^+$, m/z): 625.1 [(M+H)$^+$]. $^1$H NMR (400 MHz, DMSO-d$_6$) δ=9.03 (t, J=5.56 Hz, 1H), 8.33 (s, 1H), 7.99 (s, 1H), 7.89 (s, 1H), 7.12 (t, J=8.01 Hz, 1H), 6.88 (d, J=8.31 Hz, 1H), 6.29 (d, J=7.95 Hz, 1H), 6.01 (d, J=8.31 Hz, 1H), 5.50 (d, J=8.84 Hz, 2H), 5.01 (d, J=7.55 Hz, 1H), 4.72-4.93 (m, 3H), 3.64 (s, 1H), 3.05 (t, J=10.39 Hz, 1H), 2.54-2.89 (m, 4H), 2.23-2.46 (m, 4H), 2.20 (s, 4H), 2.09-2.18 (m, 2H), 1.95-2.07 (m, 1H), 1.95-2.07 (m, 1H).

Example 114: N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(3-fluorocyclopentyl)-1H-pyrrole-3-carboxamide (Compound 345B)

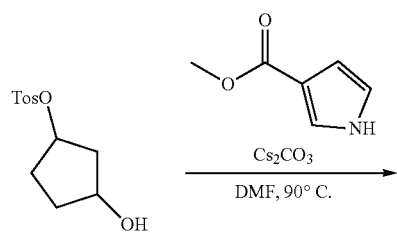

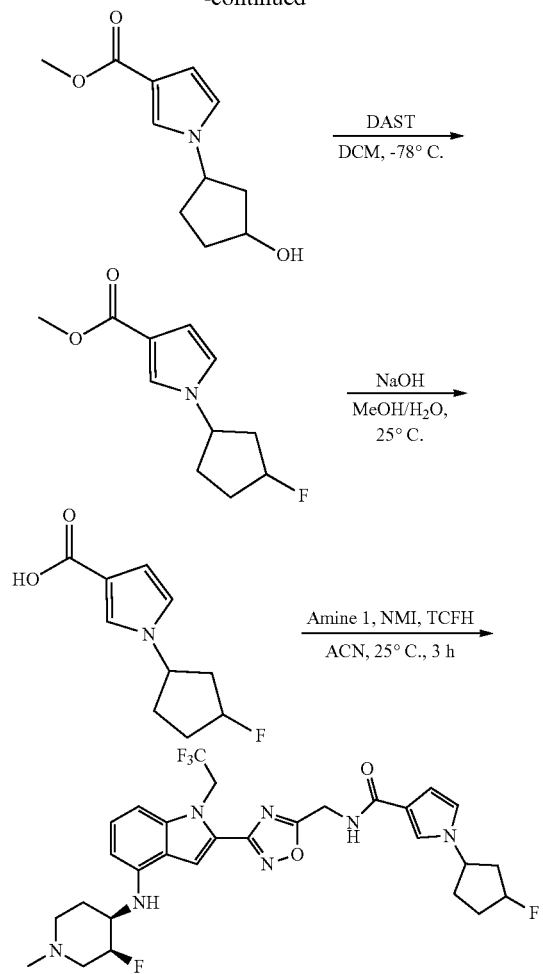

To a solution of the previously prepared mono-tosylate (900 mg, 3.51 mmol, 1 eq) and methyl 3-pyrrole carboxylate (439 mg, 3.51 mmol, 1 eq) in DMF (10 mL) was added cesium carbonate (2.29 g, 7.02 mmol, 2 eq), and the reaction was heated and stirred at 90° C. for 1 h. The mixture was extracted with DCM (10 mL×2), the organic phase was washed with water (10 mL) and brine (10 mL), then dried over sodium sulfate. The solvent was removed in vacuo to afford the intermediate (600 mg, crude) as a yellow solid. LC-MS (ES$^+$, m/z): 209.2 [(M+H)$^+$].

To a solution of the above intermediate (400 mg, 1.91 mmol, 1 eq) in DCM (15 mL) was added DAST (19.1 mmol, 2.53 mL, 10 eq) in DCM (5 mL), and the reaction was stirred at rt for 1 h. The reaction was quenched with ammonium chloride (10 mL), and the mixture was extracted with DCM (10 mL×2). The organic phase was washed by water (10 mL) and brine (10 mL), then dried over sodium sulfate, and the solvent was removed in vacuo. The residue was purified by column chromatography (SiO$_2$, PE/EA=1/1) to afford the fluorocyclopentyl ester (200 mg, 947 µmol, 49.5% yield) as a yellow solid. LC-MS (ES$^+$, m/z): 211.2 [(M+H)$^+$].

To a solution of the above ester (200 mg, 947 µmol, 1 eq) in methanol (4 mL) water (1 mL) was added sodium hydroxide (113.6 mg, 2.84 mmol, 3 eq), and the reaction was stirred at 60° C. for 3 h. The mixture was extracted with DCM (10 mL×2), and the organic phase was washed by water (10 mL) and brine (10 mL). The solution was dried over sodium sulfate, and the solvent was removed in vacuo to afford the carboxylic acid intermediate (100 mg, crude) as a yellow solid. LC-MS (ES⁺, m/z): 197.2 [(M+H)⁺].

The carboxylic acid was coupled with Amine 1 using method E to provide the desired product (23.6 mg, 26.6% yield, 96% purity) as a yellow solid. LC-MS (ES⁺, m/z): 605.6 [(M+H)⁺]. ¹H NMR (400 MHz, DMSO-d₆) δ ppm 8.65 (br t), 7.88 (s), 7.43-7.59 (m), 7.05-7.18 (m), 6.83-6.96 (m), 6.52 (br s), 6.28 (d), 6.01 (br d), 5.50 (q), 5.14-5.42 (m), 4.75-4.95 (m), 4.73 (br d), 3.64 (s), 3.57 (br s), 2.99-3.13 (m), 2.84 (br d), 2.28-2.34 (m), 2.25 (br s), 2.19 (br s), 2.09-2.18 (m), 1.97-2.09 (m), 1.78-1.96 (m), 1.63-1.77 (m).

Example 115: 1-(3,3-difluorocyclopentyl)-N-{[3-(4-{[(3S,4R)-1-ethyl-3-fluoropiperidin-4-yl]amino}-1-(2,2,2-trifluoroethyl)-1H-indol-2-yl)-1,2,4-oxadiazol-5-yl]methyl}-1H-pyrrole-3-carboxamide (Compound 346B)

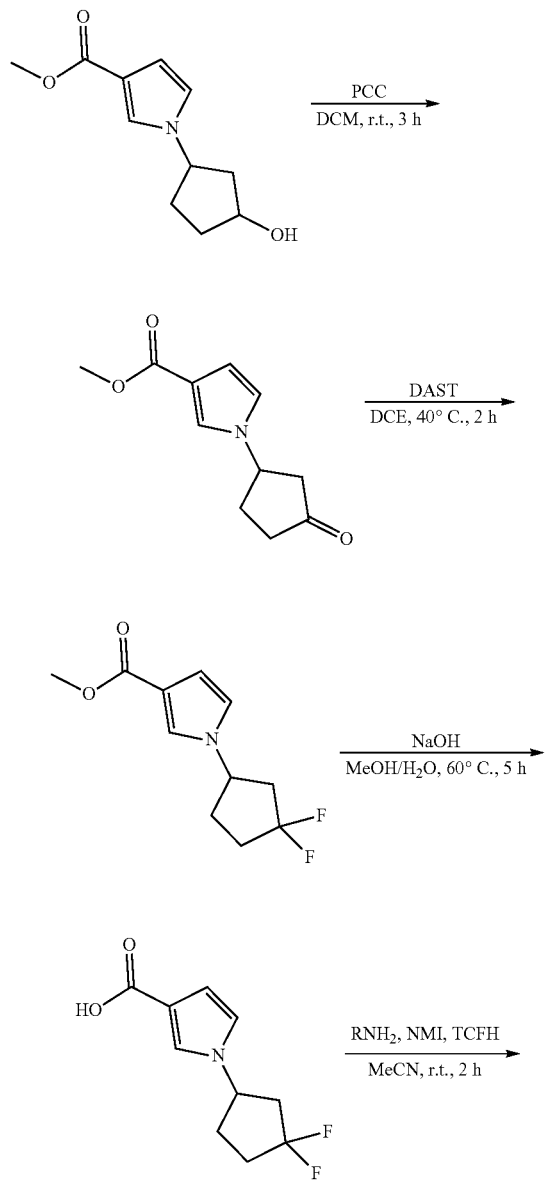

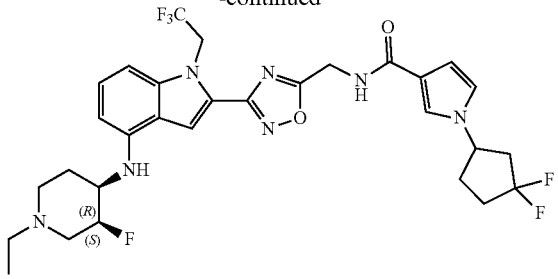

To a mixture of methyl 1-(3-hydroxycyclopentyl)pyrrole-3-carboxylate (600 mg, 2.87 mmol, 1 eq) in DCM (15 mL) was added PCC (1.24 g, 5.74 mmol, 2 eq) in one portion at 20° C. under nitrogen. The mixture was stirred at 20° C. for 3 h. The residue was poured into ice-water (30 mL) and stirred for 2 min. The aqueous phase was extracted with EA (30 mL×3). The combined organic phase was washed with brine (30 mL×3), dried over anhydrous sodium sulfate, filtered, and concentrated in vacuo. The residue was purified by prep-TLC to afford methyl 1-(3-oxocyclopentyl)pyrrole-3-carboxylate (200 mg, 965 μmol, 33.7% yield) as yellow solid. LC-MS (ES⁺, m/z): 208.1 [(M+H)⁺].

To a mixture of methyl 1-(3-oxocyclopentyl)pyrrole-3-carboxylate (200 mg, 965 μmol, 1 eq) in 1,2-dichloroethane (1 mL) was added DAST (18.9 mmol, 2.50 mL, 19.6 eq) in one portion at 20° C. under nitrogen. The mixture was heated and stirred at 40° C. for 12 h. The residue was poured into ice-water (30 mL) and stirred for 3 min. The aqueous phase was extracted with EA (30 mL×3). The combined organic phase was washed with brine (30 mL×3), dried over anhydrous sodium sulfate, filtered, and concentrated in vacuo. The residue was purified by prep-TLC to afford methyl 1-(3,3-difluorocyclopentyl)pyrrole-3-carboxylate (90 mg, 393 μmol, 40.7% yield) as a yellow oil.

To a mixture of methyl 1-(3,3-difluorocyclopentyl)pyrrole-3-carboxylate (150 mg, 654 μmol, 1 eq) in methanol (2 mL) and water (0.5 mL) was added sodium hydroxide (78.5 mg, 1.96 mmol, 3 eq) at 20° C. under nitrogen. The mixture was heated and stirred at 60° C. for 5 h. The residue was poured into ice-water (30 mL) and stirred for 3 min. The aqueous phase was extracted with EA (30 mL×3). The combined organic phase was washed with brine (30 mL×3), dried over anhydrous sodium sulfate, filtered, and concentrated in vacuo. The residue was purified by prep-TLC to provide 1-(3,3-difluorocyclopentyl)pyrrole-3-carboxylic acid (120 mg, 558 μmol, 85.2% yield) as a yellow oil. LC-MS (ES⁺, m/z): 216.1 [(M+H)⁺].

1-(3,3-difluorocyclopentyl)-N-[[3-[4-[[(3S,4R)-1-ethyl-3-fluoro-4-piperidyl]amino]-1-(2,2,2-trifluoroethyl)indol-2-yl]-1,2,4-oxadiazol-5-yl]methyl]pyrrole-3-carboxamide was synthesized from the previously prepared N-ethyl piperidine intermediate using method E to provide the product as a yellow solid in 22% yield. LC-MS (ES⁺, m/z): 638.3 [(M+H)⁺]. ¹H NMR (400 MHz, DMSO-d6) δ ppm 8.68 (t, J=5.81 Hz, 1H), 8.14 (s, 1H), 7.89 (s, 1H), 7.52 (s, 1H), 7.12 (t, J=8.01 Hz, 1H), 6.95 (d, J=2.45 Hz, 1H), 6.88 (d, J=8.44 Hz, 1H), 6.54 (br s, 1H), 6.29 (d, J=7.83 Hz, 1H), 6.01 (br d, J=7.95 Hz, 1H), 5.42-5.55 (m, 2H), 4.79-4.96 (m, 1H), 4.73 (br d, J=5.50 Hz, 2H), 3.48-3.74 (m, 1H), 3.14 (br s, 1H), 2.66-2.99 (m, 4H), 2.40 (br s, 4H), 1.94-2.26 (m, 5H), 1.73 (br s, 1H), 1.01 (t, J=7.03 Hz, 3H).

1-(3,3-difluorocyclopentyl)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl)-1H- pyrrole-3-carboxamide (Compound 347B) was prepared from the previously synthesized pyrrole carboxylic acid and Amine 1 using method E to provide the desired product (27.4 mg, 32.1 μmol, 13.8% yield) as white solid. LC-MS (ES+, m/z): 2.235 [(M+H)+]. $^1$H NMR (400 MHz, DMSO-$d_6$) δ ppm 8.70 (t, J=5.62 Hz, 1H), 8.14 (s, 1H), 7.89 (s, 1H), 7.52 (t, J=1.87 Hz, 1H), 7.11 (t, J=8.05 Hz, 1H), 6.95 (t, J=2.54 Hz, 1H), 6.88 (d, J=8.16 Hz, 1H), 6.54 (dd, J=2.87, 1.76 Hz, 1H), 6.28 (d, J=7.94 Hz, 1H), 6.03 (br d, J=8.38 Hz, 1H), 5.45-5.56 (m, 2H), 4.74-4.95 (m, 2H), 4.67-4.74 (m, 2H), 3.50-3.70 (m, 1H), 3.05 (br d, J=9.26 Hz, 1H), 2.57-2.90 (m, 4H), 2.24-2.47 (m, 4H), 2.19-2.24 (m, 3H), 1.93-2.17 (m, 3H), 1.69 (br d, J=10.36 Hz, 1H).

Example 116: N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-[(1R,2R)-2-methoxycyclopentyl]-1H-pyrazole-4-carboxamide (Compound 348B)

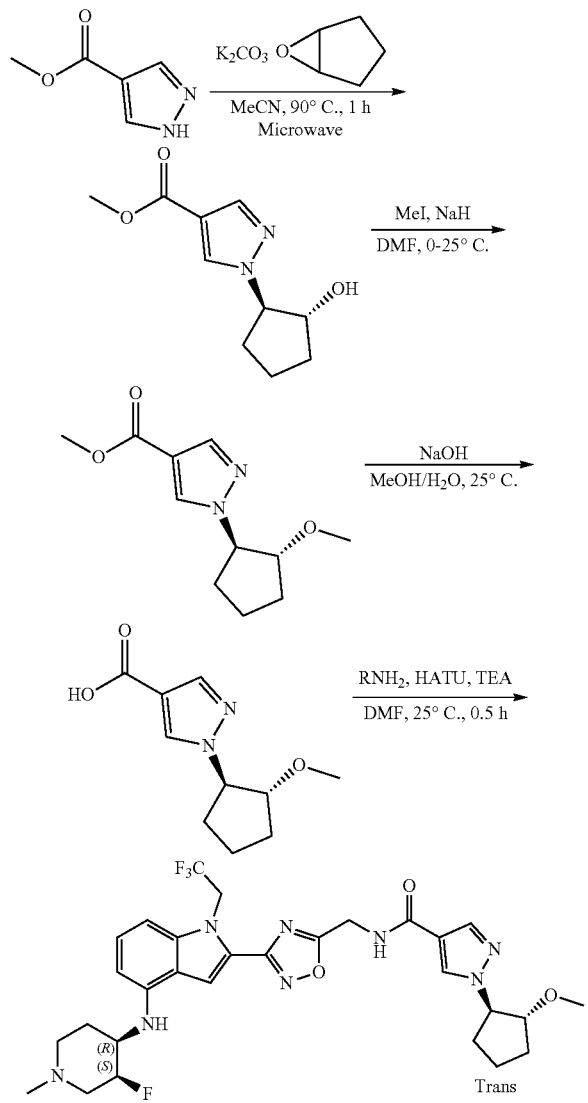

To a solution of cyclopentene oxide (5.94 mmol, 519 μL 2 eq) and methyl 1H-pyrazole-4-carboxylate (374.8 mg, 2.97 mmol, 1 eq) in acetonitrile (5 mL) was added cesium carbonate (2.42 g, 7.43 mmol, 2.5 eq). The mixture was heated by microwave and stirred at 90° C. for 1 h. The reaction mixture was poured into water (50 mL), then extracted with EA (30 mL×3). The combined organic layers were washed with brine (30 mL×1), dried over anhydrous sodium sulfate, filtered, and concentrated in vacuo to give a residue. The residue was purified by prep-TLC (SiO$_2$, PE:EA=1:1) to give the alcohol product (250 mg, 1.19 mmol, 40.0% yield). LC-MS (ES+, m/z): 210.1 [(M+H)−].

To a solution of the alcohol in DMF (4 mL) was added sodium hydride (76.1 mg, 1.90 mmol, 60% purity, 2 eq) at 0° C. for 0.5 h, followed by iodomethane (4.76 mmol, 296 μL 5 eq). The mixture was stirred and warmed to 25° C. over 2 h. The reaction mixture was quenched by ammonium chloride (50 mL), then extracted with EA (30 mL×3). The combined organic layers were washed with brine (30 mL×1), dried over anhydrous sodium sulfate, filtered, and concentrated in vacuo to give a residue. The residue was purified by prep-TLC (SiO$_2$, PE:EA=2:1) to give the methyl ether product (60 mg, 28.1% yield). LC-MS (ES+, m/z): 224.1 [(M+H)+].

To a solution of the above intermediate (60 mg, 268 μmol, 1 eq) in methanol (5 mL) and water (2 mL) was added sodium hydroxide (32.1 mg, 803 μmol, 3 eq). The mixture was stirred at 25° C. for 1 h. The reaction mixture was adjusted to pH 7 with HCl (2M), then filtered, and concentrated in vacuo to give the carboxylic acid (100 mg, crude). LC-MS (ES+, m/z): 210.1[(M+H)+]. N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-[(1R,2R)-2-methoxycyclopentyl]-1H-pyrazole-4-carboxamide was prepared from Amine 1 using method B to provide the desired product (18.6 mg, 23.4% yield, 98.0% purity). LC-MS (ES+, m/z): 618.2 [(M+H)+]. $^1$H NMR (400 MHz, DMSO-$d_6$) δ ppm 8.99 (t, J=5.62 Hz, 1H), 8.30 (s, 1H), 7.93 (s, 1H), 7.87 (s, 1H), 7.03-7.14 (m, 1H), 6.85 (d, J=8.38 Hz, 1H), 6.26 (d, J=7.72 Hz, 1H), 6.00 (br d, J=8.60 Hz, 1H), 5.32-5.64 (m, 2H), 4.70-4.99 (m, 3H), 4.42-4.66 (m, 1H), 3.84-4.01 (m, 1H), 3.84-4.01 (m, 1H), 3.67-4.04 (m, 1H), 3.48-3.66 (m, 1H), 3.48-3.66 (m, 1H), 3.46-3.67 (m, 1H), 3.46-3.67 (m, 1H), 3.20-3.26 (m, 1H), 3.16 (s, 3H), 2.95-3.07 (m, 1H), 2.76-2.83 (m, 1H), 2.16-2.18 (m, 1H), 2.15-2.28 (m, 2H), 2.15-2.21 (m, 1H), 2.04-2.13 (m, 1H), 1.92-2.02 (m, 3H), 1.86-2.12 (m, 1H), 1.86-2.12 (m, 1H), 1.55-1.82 (m, 4H).

Example 117: N-{[3-(4-{1[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(1-methylpiperidin-4-yl)-1H-pyrazole-4-carboxamide (Compound 350B)

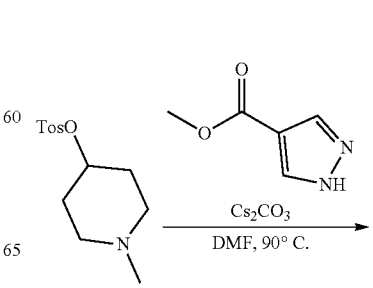

439

-continued

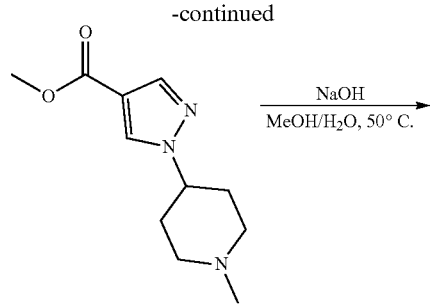

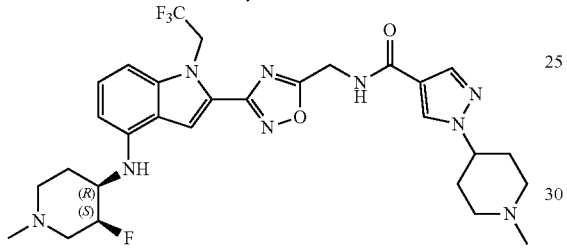

To a solution of methyl 1H-pyrazole-4-carboxylate (250 mg, 1.98 mmol, 1 eq) and (1-methyl-4-piperidyl) 4-methylbenzenesulfonate (640.8 mg, 2.38 mmol, 1.2 eq) in DMF (3 mL) was added cesium carbonate (1.94 g, 5.95 mmol, 3 eq), and the mixture was heated and stirred at 90° C. 3 h. The mixture was extracted with DCM (10 mL×2), and the organic phase was washed with water (10 mL) and brine (10 mL), then dried over sodium sulfate and the solvent removed in vacuo to provide methyl 1-(1-methyl-4-piperidyl)pyrazole-4-carboxylate (180 mg, crude) as a yellow solid. LC-MS (ES+, m/z): 223.2 [(M+H)+].

To a solution of methyl 1-(1-methyl-4-piperidyl)pyrazole-4-carboxylate (100 mg, 448 µmol, 1 eq) in methanol (4 mL) and water (1 mL) was added sodium hydroxide (53.75 mg, 1.34 mmol, 3 eq), and the reaction was stirred at 60° C. for 3 h. The mixture was extracted with DCM (10 mL×2), and the organic phase was washed with water (10 mL) and brine (10 mL), then dried over sodium sulfate and the solvent removed in vacuo. The residue was purified by prep-HPLC (FA condition) to provide 1-(1-methyl-4-piperidyl)pyrazole-4-carboxylic acid (30 mg, 143 µmol, 10.7% yield) as a yellow solid. LC-MS (ES+, m/z): 209.2 [(M+H)+].

N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(1-methylpiperidin-4-yl)-1H-pyrazole-4-carboxamide was prepared from the above carboxylic acid and Amine 1 using method E and purified by prep-HPLC (neutral condition) to provide the product (24.5 mg, 37.7 µmol, 26.8% yield, 95.1% purity) as a yellow solid. LC-MS (ES+, m/z): 617.6 [(M+H)+]. ¹H NMR (400 MHz, DMSO-d₆) δ ppm 8.97 (t), 8.27 (s), 7.92 (s), 7.88 (s), 7.10 (t), 6.87 (d), 6.27 (d), 6.00 (d), 5.49 (q), 4.89 (br s), 4.76 (br d), 4.06-4.23 (m), 3.49-3.69 (m), 3.02 (br t), 2.76-2.88 (m), 2.27 (br d), 2.18 (d), 1.88-2.10 (m), 1.67 (br d).

440

N-{[3-(4-{1[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(1-methylpyrrolidin-3-yl)-1H-pyrazole-4-carboxamide (Compound 349B): The required carboxylic acid was prepared using the same method used above to prepare 1-(1-methyl-4-piperidyl)pyrazole-4-carboxylic acid above. This acid was coupled with Amine 1 using method E to provide the desired product.

Example 118: N-{13-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(1-methylpyrrolidin-3-yl)-1H-pyrrole-3-carboxamide (Compound 351B)

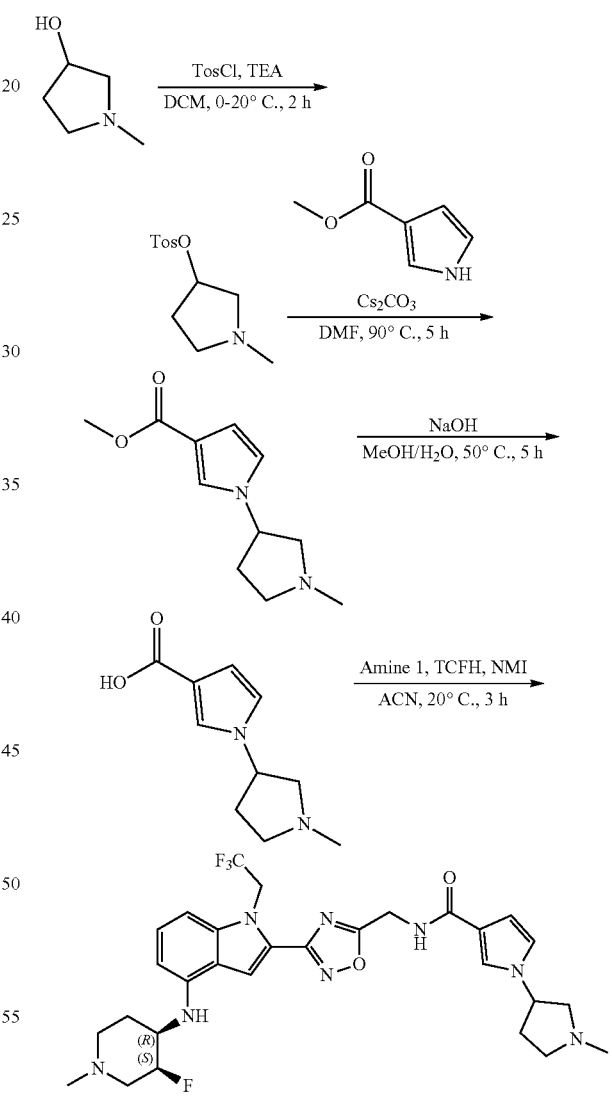

To a mixture of the alcohol (4 g, 39.6 mmol, 1 eq) in DCM (40 mL) were added TEA (39.6 mmol, 5.50 mL, 1 eq) followed by p-TosCl (7.58 g, 39.7 mmol, 1 eq) at 0° C. under nitrogen. The mixture was warmed and stirred at 20° C. for 2 h. The residue was poured into ice-water (w/w=1/1) (500 mL). The aqueous phase was extracted with EA (200 mL×3). The combined organic phase was washed with brine (200 mL×3), dried over anhydrous sodium sulfate, filtered, and concentrated in vacuo. The residue was purified by silica gel chromatography (column height: 250 mm, diameter: 100 mm, 100-200 mesh silica gel, PE/EA=1/0, 0/1) to afford (1-methylpyrrolidin-3-yl) 4-methylbenzenesulfonate (5 g, 19.6 mmol, 49.5% yield) as a yellow oil.

To a mixture of the methyl pyrrole-3-carboxylate (500 mg, 4 mmol, 1 eq) and the tosylate (1.53 g, 5.99 mmol, 1.5 eq) in DMF (5 mL) was added cesium carbonate (2.60 g, 7.99 mmol, 2 eq) under nitrogen. The mixture was heated and stirred at 90° C. for 5 h. The residue was poured into ice-water (w/w=1/1) (100 mL). The aqueous phase was extracted with EA (30 mL×3). The combined organic phase was washed with brine (30 mL×3), dried over anhydrous sodium sulfate, filtered, and concentrated in vacuo. The residue was purified by silica gel chromatography (column height: 250 mm, diameter: 100 mm, 100-200 mesh silica gel, PE/EA=1/0, 0/1) to afford the desired intermediate (0.6 g, 2.88 mmol, 72.1% yield) as a yellow oil. LC-MS (ES+, m/z): 209.1 [(M+H)+].

To a mixture of the ester intermediate (0.6 g, 2.88 mmol, 1 eq) in methanol (8 mL), water (2 mL) was added sodium hydroxide (230 mg, 5.76 mmol, 2 eq) at 50° C. The mixture was stirred at 50° C. for 10 h. The residue was poured into 1N HCl to adjust to pH=7, then concentrated in vacuo to afford the carboxylic acid (450 mg, crude) as a white solid. LC-MS (ES+, m/z): 195.2 [(M+H)+]

To a mixture of Amine 1 (70 mg, 126 μmol, 1 eq, 2HCl) and the above carboxylic acid (36.8 mg, 189 μmol, 1.5 eq) in ACN (2 mL) were added TCFH (42.5 mg, 151 μmol, 1.2 eq), NMI (442 μmol, 35 μL 3.5 eq) in one portion at 20° C. under nitrogen. The mixture was stirred at 20° C. for 3 h. The residue was poured into ice-water (w/w=1/1) (100 mL). The aqueous phase was extracted with EA (30 mL×3). The combined organic phase was washed with brine (30 mL×3), dried over anhydrous sodium sulfate, filtered, and concentrated in vacuo. The reaction was purified by prep-HPLC to afford N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(1-methylpyrrolidin-3-yl)-1H-pyrrole-3-carboxamide (6.5 mg, 10.5 μmol, 8.3% yield, 97.5% purity) as a light yellow solid. LC-MS (ES+, m/z): 603.4 [(M+H)+]. 1H NMR (400 MHz, DMSO-d6) δ ppm 1.67 (br d, J=12.13 Hz, 1H) 1.80-1.90 (m, 1H) 1.94-2.03 (m, 1H) 2.03-2.13 (m, 1H) 2.19 (s, 3H) 2.24-2.32 (m, 4H) 2.32-2.45 (m, 1H) 2.63-2.66 (m, 1H) 2.67 (s, 1H) 2.67-2.72 (m, 1H) 2.81 (br d, J=10.58 Hz, 1H) 2.84-2.91 (m, 1H) 3.03 (br t, J=9.92 Hz, 1H) 3.48-3.70 (m, 1H) 4.64-4.70 (m, 1H) 4.72 (d, J=5.73 Hz, 2H) 4.75-4.93 (m, 1H) 5.50 (q, J=8.89 Hz, 2H) 6.02 (d, J=8.38 Hz, 1H) 6.28 (d, J=7.94 Hz, 1H) 6.48 (dd, J=2.65, 1.76 Hz, 1H) 6.85-6.93 (m, 2H) 7.08-7.15 (m, 1H) 7.50 (t, J=1.87 Hz, 1H) 7.89 (s, 1H) 8.68 (t, J=5.73 Hz, 1H).

N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(1-methylpyrrolidin-3-yl)-1H-pyrrole-3-carboxamide (Compound 352B) was prepared from the N-ethylpiperidine intermediate (81.5 mg, 0.18 mmol, 1 eq) and 1-(3,3-difluorocyclopentyl)pyrazole-4-carboxylic acid (40 mg, 0.18 mmol, 1 eq) using method E to provide the desired product (10.5 mg, 0.02 mmol, 8.9% yield, 100% purity) as yellow solid. LC-MS (ES+, m/z): 639.1 [(M+H)+]. 1H NMR (400 MHz, DMSO-d6) δ=9.03 (t, J=5.62 Hz, 1H), 8.33 (s, 1H), 8.13 (s, 1H), 7.99 (s, 1H), 7.88 (s, 1H), 7.12 (t, J=8.01 Hz, 1H), 6.89 (d, J=8.44 Hz, 1H), 6.30 (d, J=7.82 Hz, 1H), 6.04 (d, J=6.85 Hz, 1H), 5.44-5.55 (m, 2H), 4.82-5.07 (m, 2H), 4.78 (d, J=5.62 Hz, 2H), 3.63-3.74 (m, 1H), 2.95-3.18 (m, 1H), 2.55-2.95 (m, 4H), 2.35-2.43 (m, 4H), 2.07-2.31 (m, 5H), 1.70-2.00 (m, 2H), 1.05 (s, 3H).

Example 119: 1-tert-butyl-N-{13-(4-{[(3S)-piperidin-3-yl]amino}-1-(2,2,2-trifluoroethyl)-1H-indol-2-yl)-1,2,4-oxadiazol-5-yl]methyl}-1H-pyrazole-4-carboxamide (Compound 353B)

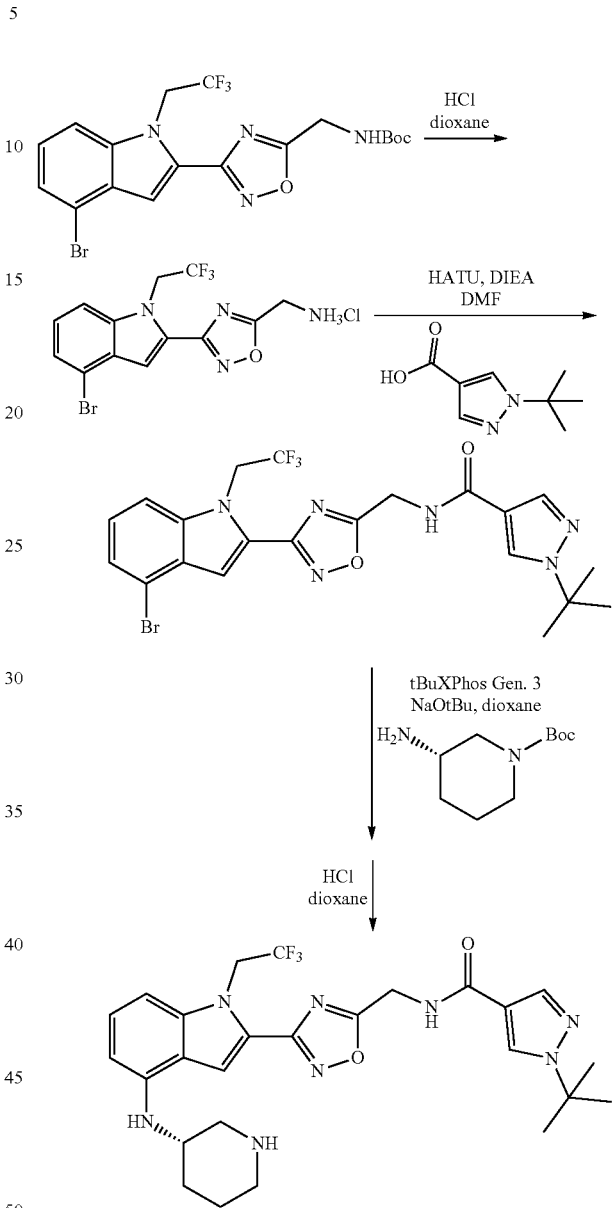

The bromide (207.1 mg, 0.436 mmol) was dissolved into dioxane (2 mL), and 4N HCl/dioxane (2 mL, 8 mmol) was added. After 1.5 h, the solid was collected by filtration and dried in vacuo to provide the desired intermediate as a white solid (136 mg, 76%).

To the amine salt (98 mg, 0.238 mmol, 1 eq) were added 1-tert-butyl-1H-pyrazole-4-carboxylic acid (51.8 mg, 0.308 mmol, 1.3 eq), HATU (144.7 mg, 0.381 mmol, 1.6 eq) and DMF (2 mL). DIEA (0.10 mL, 0.575 mmol, 2.4 eq) was added and the reaction was stirred for 15 min. The reaction was diluted with DCM and washed with 10% citric acid. The organic layer was removed, and the aqueous layer extracted with DCM. The organic solution was dried over magnesium sulfate, filtered, and concentrated. The crude product was purified by silica column (30-80% EA/hexanes) to provide the desired intermediate as a white solid (90.4 mg, 72%).

The above amide (45.7 mg, 0.087 mmol, 1 eq), (S)-1-Boc-3-aminopiperidine (35 mg, 0.174 mmol, 2 eq), tBuX-Phos Generation 3 (18.2 mg, 0.023 mmol, 0.26 eq), and sodium t-butoxide (16.6 mg, 0.173 mmol, 2 eq) were weighed into a vial with a septum cap. The vial was flushed with nitrogen through a needle, and degassed dioxane was added via syringe. The vial was placed to stir in a preheated block at 80° C. for 16 h. The reaction was then filtered, and the filtrate was purified by silica column (20-80% EA/hexanes) to provide the desired intermediate (25.7 mg, 46%).

The above intermediate (25.7 mg) was dissolved in dioxane (1 mL) and treated with 4N HCl/dioxane (1 mL) for 0.5 h, then concentrated to a solid. The crude solid was purified by reverse phase HPLC, and the resulting formic acid salt neutralized using a Strata X-C sulfonic acid column to provide the desired product as the free base (13.4 mg, 62% yield). LC-MS (ES−, m/z): 545.2 [(M+H)-]. ¹H NMR (500 MHz, DMSO-d6) δ 8.97 (t, J=5.8 Hz, 1H), 8.35 (s, 1H), 7.94 (s, 1H), 7.78 (s, 1H), 7.12 (t, J=8.0 Hz, 1H), 6.84 (d, J=8.4 Hz, 1H), 6.25 (dd, J=15.1, 7.7 Hz, 1H), 5.92 (d, J=8.2 Hz, 1H), 5.50 (q, J=8.8 Hz, 2H), 4.79 (d, J=5.6 Hz, 2H), 3.43 (s, 1H), 3.17 (d, J=12.3 Hz, 1H), 2.88 (d, J=12.1 Hz, 1H), 2.40 (dd, J=20.5, 9.5 Hz, 2H), 1.98 (d, J=12.2 Hz, 1H), 1.68 (d, J=6.5 Hz, 1H), 1.55 (s, 9H), 1.50-1.35 (m, 2H).

Example 120: N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-[(1R,2R)-2-methoxycyclopentyl]-1H-pyrrole-3-carboxamide (Compound 355B)

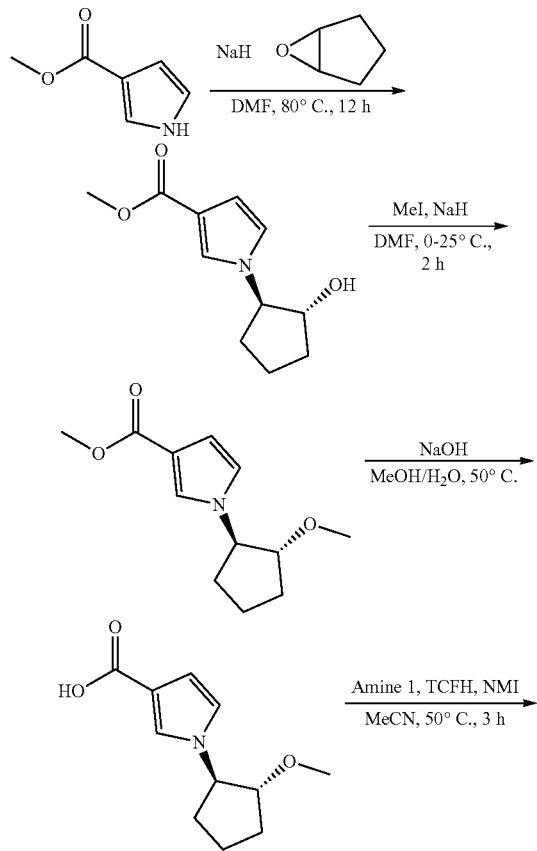

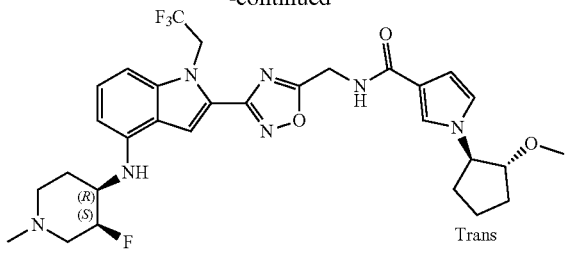

Trans

To a solution of methyl pyrrole-3-carboxylate (500 mg, 4 mmol, 1 eq) in DMF (7 mL) was added sodium hydride (320 mg, 7.99 mmol, 60% purity, 2 eq) at 0° C., and the reaction was stirred for 0.5 h, followed by addition of cyclopentene oxide (336 mg, 4 mmol, 1 eq). The mixture was then heated and stirred at 80° C. for 2 h. The reaction mixture was poured into water (50 mL), then extracted with EA (30 mL×3). The combined organic layers were washed with brine (30 mL×1), dried over anhydrous sodium sulfate, filtered, and concentrated in vacuo to give a residue. The residue was purified by prep-TLC (SiO₂, PE:EA=2: 1) to provide the desired product (170 mg, 812 µmol, 20.3% yield). LC-MS (ES+, m/z): 209.1[(M+H)+].

To a solution of the above alcohol (150 mg, 717 µmol, 1 eq) in DMF (2 mL) was added sodium hydride (57.4 mg, 1.43 mmol, 60% purity, 2 eq) at 0° C., and the reaction was stirred for 0.5 h, followed by addition of iodomethane (3.58 mmol, 223 µL 5 eq). The mixture was warmed to rt and stirred at 25° C. for 2 h. The reaction mixture was quenched with saturated ammonium chloride (50 mL), then extracted with EA (30 mL×3). The combined organic layers were washed with brine (30 mL×1), dried over anhydrous sodium sulfate, filtered, and concentrated in vacuo to give a residue. The residue was purified by prep-TLC (SiO₂, PE:EA=2:1) to provide the desired product (100 mg, 448 µmol, 62.5% yield). LC-MS (ES+, m/z): 223.1 [(M+H)+].

To a solution of the above intermediate (100 mg, 448 µmol, 1 eq) in methanol (5 mL) and water (2 mL) was added sodium hydroxide (53.7 mg, 1.34 mmol, 3 eq). The mixture was heated and stirred at 50° C. for 5 h. The reaction mixture was adjusted to pH=7 with HCl (2M), and was then filtered, and concentrated in vacuo to provide the crude product as a residue (130 mg, crude). LC-MS (ES+, m/z): 209.1[(M+H)+].

Amine 1 (60 mg, 108 µmol, 1 eq, 2HCl) and the above carboxylic acid (33.9 mg, 162 µmol, 1.5 eq) were treated under method E to provide the desired product N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-[(1R,2R)-2-methoxycyclopentyl]-1H-pyrrole-3-carboxamide after Prep-TLC purification. LC-MS (ES+, m/z): 618.3 [(M+H)+]. ¹H NMR (400 MHz, DMSO-d₆) δ ppm 8.67 (t, J=5.69 Hz, 1H), 7.90 (s, 1H), 7.48 (s, 1H), 7.12 (t, J=8.01 Hz, 1H), 6.85-6.93 (m, 2H), 6.52 (d, J=1.83 Hz, 1H), 6.29 (d, J=7.95 Hz, 1H), 6.02 (d, J=8.31 Hz, 1H), 5.51 (q, J=8.93 Hz, 2H), 4.65-4.95 (m, 3H), 4.26-4.35 (m, 1H), 3.83 (q, J=6.24 Hz, 1H), 3.51-3.68 (m, 1H), 3.19 (s, 3H), 3.04 (br t, J=10.88 Hz, 1H), 2.82 (br d, J=10.39 Hz, 1H), 2.19-2.35 (m, 4H), 1.97-2.14 (m, 3H), 1.66-1.89 (m, 4H), 1.55-1.65 (m, 1H).

Example 121: 1-tert-butyl-N-{[3-(4-{[(3S)-6-oxopi-peridin-3-yl]amino}-1-(2,2,2-trifluoroethyl)-1H-indol-2-yl)-1,2,4-oxadiazol-5-yl]methyl}-1H-pyrrole-3-carboxamide (Compound 356B)

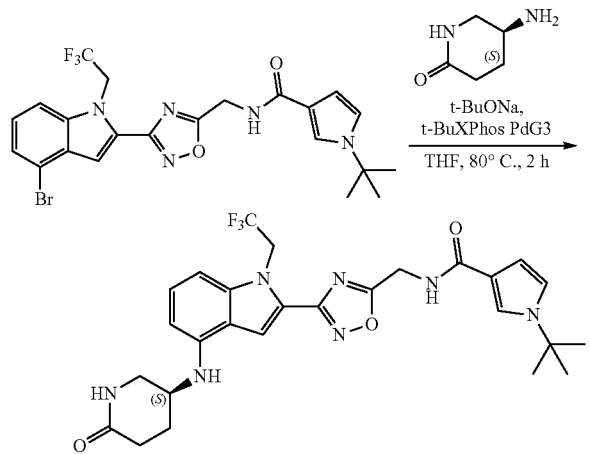

The intermediate bromide (20 mg, 0.038 mmol, 1 eq) was reacted with the amino piperidinone (87.1 mg, 0.76 mmol, 20 eq) under Buchwald conditions to provide the desired product (3.3 mg, 14.2% yield, 91.7% purity) as white solid. LC-MS (ES+, m/z): 558.2 [(M+H)+]. $^1$H NMR (400 MHz, DMSO-d6) δ=8.58-8.70 (m, 1H), 7.78 (s, 1H), 7.54 (s, 1H), 7.41 (s, 1H), 7.14 (t, J=8.07 Hz, 1H), 6.97-7.02 (m, 1H), 6.89 (d, J=8.44 Hz, 1H), 6.50 (s, 1H), 6.31 (d, J=7.95 Hz, 1H), 6.07 (d, J=7.70 Hz, 1H). 5.50 (d, J=9.09 Hz, 2H), 4.73 (d, J=5.62 Hz, 2H), 3.78-3.93 (m, 1H), 3.04-3.17 (m, 1H), 1.96-2.15 (m, 3H), 1.70-1.86 (m, 2H), 1.45-1.57 (m, 1H), 1.45-1.57 (m, 1H).

Example 122: rac-N-{[3-(4-{[(3R,4S)-1-tert-butyl-3-fluoropiperidin-4-yl]amino}-1-(2,2,2-trifluoro-ethyl)-1H-indol-2-yl)-1,2,4-oxadiazol-5-yl]methyl}-1-(1-methoxypropan-2-yl)-1H-pyrrole-3-carboxamide (Compound 357B), and rac-N-{[3-(4-{1[(3R,4R)-1-tert-butyl-3-fluoropiperidin-4-yl]amino}-1-(2,2,2-trifluoroethyl)-1H-indol-2-yl)-1,2,4-oxadiazol-5-yl]methyl}-1-(1-methoxypropan-2-yl)-1H-pyrrole-3-carboxamide (Compound 358B)

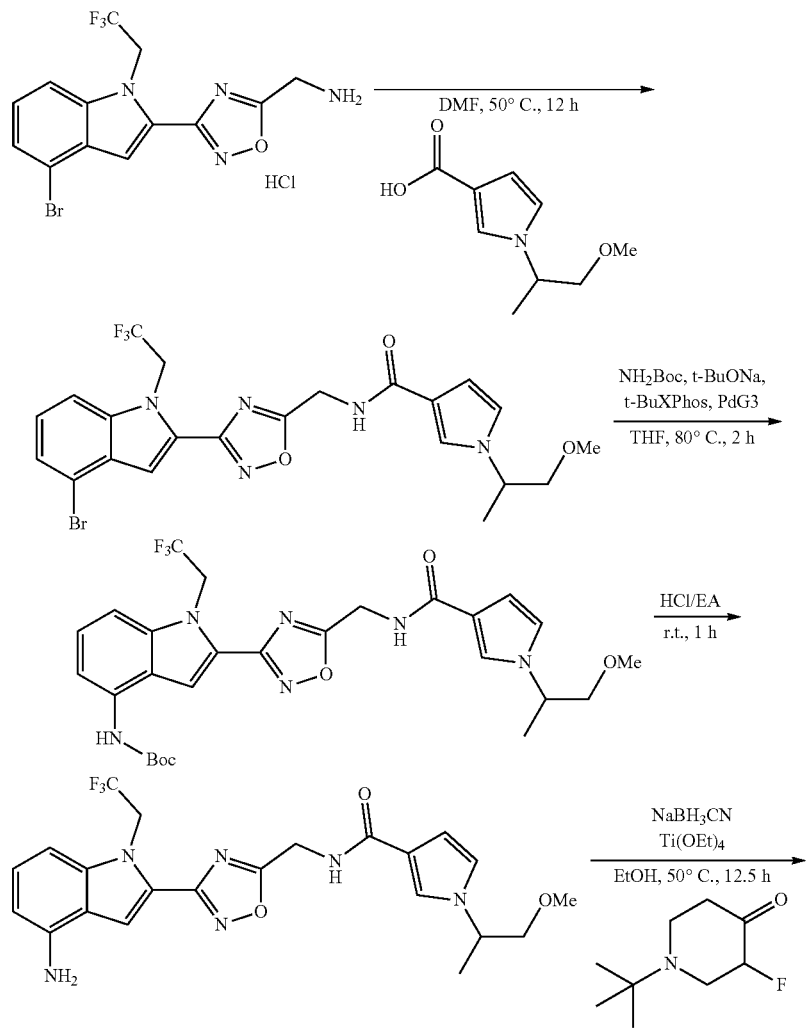

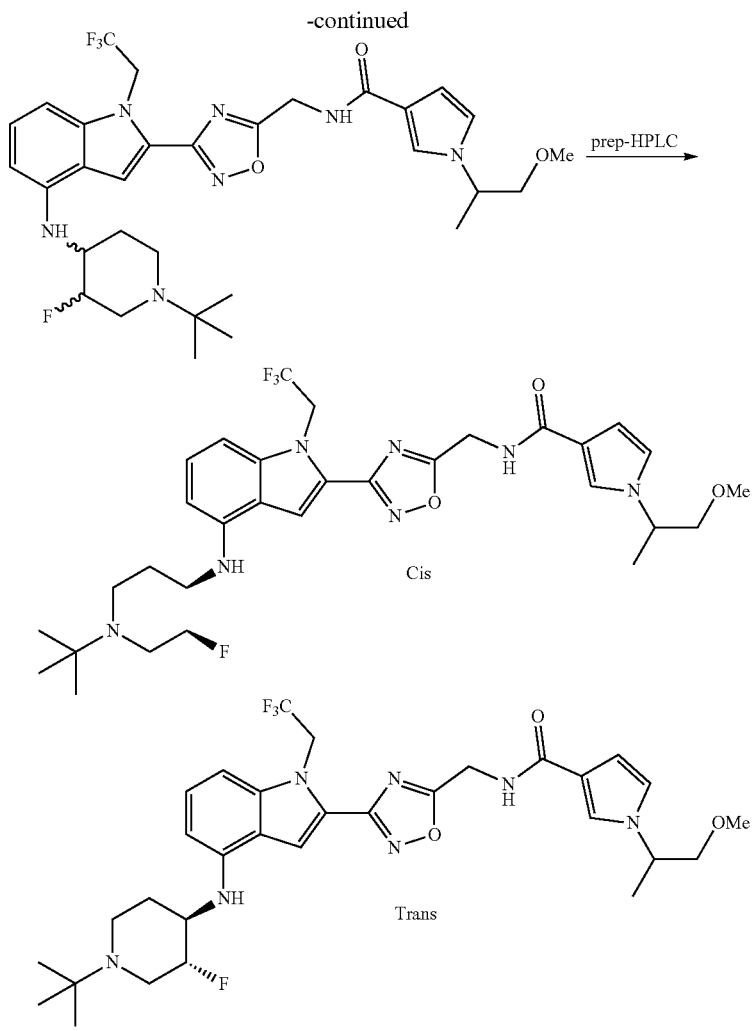

Cis

Trans

A mixture of [3-[4-bromo-1-(2,2,2-trifluoroethyl)indol-2-yl]-1,2,4-oxadiazol-5-yl]methanamine (2.5 g, 6.07 mmol, 1 eq, HCl) and 1-(2-methoxy-1-methyl-ethyl)pyrrole-3-carboxylic acid (1.33 g, 7.28 mmol, 1.20 eq) in DMF (30 mL) were treated with EDCI (3.49 g, 18.2 mmol, 3 eq), HOBt (2.46 g, 18.22 mmol, 3 eq), and TEA (60.7 mmol, 8.45 mL, 10 eq). The mixture was stirred at 50° C. for 12 h. The mixture was poured into water (300 mL) and extracted with EA (50 mL×3). The combined organic layers were washed with brine (100 mL×3), dried over sodium sulfate, filtered, and concentrated in vacuo to give a residue. The residue was purified by column chromatography (SiO$_2$, PE:EA=50:1 to 1:1) to afford N-[[3-[4-bromo-1-(2,2,2-trifluoroethyl)indol-2-yl]-1,2,4-oxadiazol-5-yl]methyl]-1-(2-methoxy-1-methyl-ethyl)pyrrole-3-carboxamide (2.3 g, 63.8% yield, 91% purity) as a yellow solid. LC-MS (ES$^+$, m/z): 540.1 [(M+H)$^+$].

To a solution of N-[[3-[4-bromo-1-(2,2,2-trifluoroethyl)indol-2-yl]-1,2,4-oxadiazol-5-yl]methyl]-1-(2-methoxy-1-methylethyl) pyrrole-3-carboxamide (1.3 g, 2.19 mmol, 1 eq) and tert-butyl carbamate (384.7 mg, 3.28 mmol, 1.5 eq) in THF (30 mL) were added sodium t-butoxide (2 M, 2.19 mL, 2 eq) and t-BuXphos (347.8 mg, 438 µmol, 0.2 eq) at 25° C. The mixture was stirred at 80° C. for 2 h under nitrogen. The reaction mixture was poured into EDTA (Sat. aq. 100 mL). The mixture was stirred at 25° C. for 1 h. The mixture was then extracted with EA (50 mL×3). The combined organic layers were washed with brine (50 mL×3), dried over sodium sulfate, filtered, and concentrated in vacuo to give a residue which was purified by column chromatography (SiO$_2$, PE/EA=10/1 to 1/2) to afford the desired compound tert-butyl N-[2-[5-[[[1-(2-methoxy-1-methyl-ethyl)pyrrole-3-carbonyl]amino]methyl]-1,2,4-oxadiazol-3-yl]-1-(2,2,2-trifluoroethyl)indol-4-yl]carbamate (0.6 g, 35.7% yield, 75% purity) as a yellow solid. LC-MS (ES$^+$, m/z): 521.1 [(M+H)$^+$].

A mixture of tert-butyl N-[2-[5-[[[1-(2-methoxy-1-methyl-ethyl)pyrrole-3-carbonyl]amino]methyl]-1,2,4-oxadiazol-3-yl]-1-(2,2,2-trifluoroethyl)indol-4-yl]carbamate (600 mg, 780.5 µmol, 1 eq) in HCl/EA (4 M, 1 eq) was stirred at 25° C. for 1 h. The reaction mixture was concentrated in vacuo to afford N-[[3-[4-amino-1-(2,2,2-trifluoroethyl)indol-2-yl]-1,2,4-oxadiazol-5-yl]methyl]-1-(2-methoxy-1-methyl-ethyl)pyrrole-3-carboxamide (0.5 g, crude, HCl) as a yellow solid.

To a solution of N-[[3-[4-amino-1-(2,2,2-trifluoroethyl)indol-2-yl]-1,2,4-oxadiazol-5-yl]methyl]-1-(2-methoxy-1-methylethyl)pyrrole-3-carboxamide (500 mg, 975 µmol, 1 eq, HCl) and 1-tert-butyl-3-fluoro-piperidin-4-one (613.2 mg, 2.92 mmol, 3 eq, HCl) in ethanol (10 mL) was added titanium ethoxide (9.75 mmol, 2.02 mL, 10 eq) at 50° C. The mixture was stirred at 50° C. for 12 h, then sodium cyanoborohydride (306.3 mg, 4.87 mmol, 5 eq) was added into the mixture. The mixture was stirred at 50° C. for 30 min. The reaction mixture was diluted with EA (200 mL) and poured into sodium bicarbonate (Sat., 50 mL). The mixture was stirred at 25° C. for 1 h. The mixture was then extracted with EA (200 mL×3). The combined organic layers were washed with brine (300 mL×2), dried over sodium sulfate, filtered, and concentrated in vacuo to give a residue which was purified by prep-TLC (DCM:methanol=20:1, $R_f$=0.3) to afford N-[[3-[4-[(1-tert-butyl-3-fluoro-4-piperidyl)amino]-1-(2,2,2-trifluoroethyl) indol-2-yl]-1,2,4-oxadiazol-5-yl]methyl]-1-(2-methoxy-1-methyl-ethyl)pyrrole-3-carboxamide (0.3 g, 48.6% yield) as a yellow solid.

The mixture of isomers was separated by prep-HPLC (column: Phenomenex luna C18 250×50 mm×10 um; mobile phase: [water (0.225% FA)-ACN];B %: 20%-40%, 10 min) to provide the separated cis and trans isomers: Cis-N-[[3-[4-[[(3S,4R)-1-tert-butyl-3-fluoro-4-piperidyl]amino]-1-(2,2,2-trifluoroethyl) indol-2-yl]-1,2,4-oxadiazol-5-yl]methyl]-1-(2-methoxy-1-methyl-ethyl)pyrrole-3-carboxamide (21.9 mg, 97.3% purity, FA salt) as a yellow solid. LC-MS (ES+, m/z): 634.4 [(M+H)+]. $^1$H NMR (400 MHz, DMSO-$d_6$) δ=8.68 (t, J=5.6 Hz, 1H), 8.22 (s, 1H), 7.89 (s, 11H), 7.35 (s, 1H), 7.17-7.07 (m, 1H), 6.87 (d, J=8.4 Hz, 1H), 6.77 (t, J=2.3 Hz, 1H), 6.49 (d, J=1.8 Hz, 1H), 6.28 (d, J=7.9 Hz, 1H), 5.97 (br d, J=8.2 Hz, 1H), 5.50 (q, J=9.0 Hz, 2H), 4.96-4.76 (m, 1H), 4.72 (d, J=5.5 Hz, 2H), 4.00 (br dd, J=4.0, 13.9 Hz, 1H), 3.87 (br dd, J=6.5, 14.0 Hz, 1H), 3.67-3.51 (m, 2H), 3.30-3.20 (m, 4H), 3.03 (br d, J=8.8 Hz, 1H), 2.47-2.35 (m, 1H), 2.24 (br t, J=11.0 Hz, 1H), 1.99-1.86 (m, 1H), 1.73 (br d, J=10.4 Hz, 1H), 1.07-0.98 (m, 12H); Trans-N-[[3-[4-[[(3R,4R)-1-tert-butyl-3-fluoro-4-piperidyl]amino]-1-(2,2,2-trifluoroethyl)indol-2-yl]-1,2,4-oxadiazol-5-yl]methyl]-1-(2-methoxy-1-methyl-ethyl)pyrrole-3-carboxamide (22.4 mg, 98.6% purity, FA salt) as a yellow solid. LC-MS (ES+, m/z): 634.4 [(M+H)+]. $^1$H NMR (400 MHz, DMSO-$d_6$) δ=8.66 (t, J=5.7 Hz, 1H), 8.22 (s, 1H), 7.78 (s, 1H), 7.35 (t, J=1.8 Hz, 1H), 7.10 (t, J=8.1 Hz, 1H), 6.84 (d, J=8.2 Hz, 1H), 6.77 (t, J=2.4 Hz, 1H), 6.49 (dd, J=1.8, 2.7 Hz, 1H), 6.28 (d, J=7.9 Hz, 1H), 6.11 (d, J=8.2 Hz, 1H), 5.50 (q, J=8.8 Hz, 2H), 4.73 (d, J=5.6 Hz, 2H), 4.62-4.34 (m, 1H), 4.06-3.96 (m, 1H), 3.93-3.83 (m, 1H), 3.63-3.51 (m, 2H), 3.21 (s, 4H), 2.93 (br d, J=10.8 Hz, 1H), 2.25-2.11 (m, 2H), 2.03 (br s, 1H), 1.46-1.30 (m, 1H), 1.12-0.95 (m, 12H).

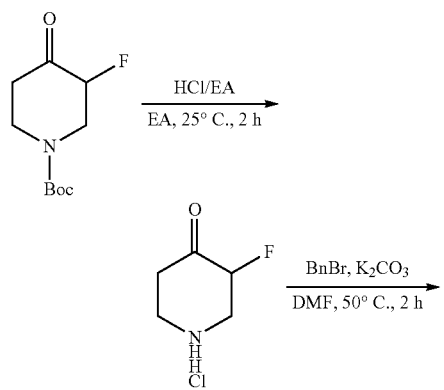

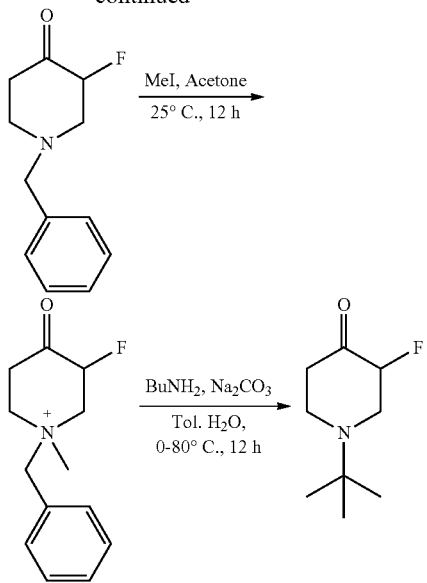

Preparation of N-t-butyl piperidinone: To a solution of tert-butyl 3-fluoro-4-oxo-piperidine-1-carboxylate (20 g, 92.1 mmol, 1 eq) in EA (30 mL) was added HCl/EA (4 M, 200 mL, 8.69 eq). The mixture was stirred at 25° C. for 1 h. The reaction mixture was concentrated in vacuo to afford 3-fluoropiperidin-4-one (14 g, 80.0% yield, 2HCl) as a white solid. $^1$H NMR (400 MHz, DMSO-$d_6$) δ=5.56-5.26 (m, 1H), 3.85-3.75 (m, 1H), 3.06 (br d, J=11.9 Hz, 1H), 2.92-2.85 (m, 1H), 2.60-2.51 (m, 1H), 1.97-1.84 (m, 1H), 1.77-1.64 (m, 1H).

To a solution of 3-fluoropiperidin-4-one (10 g, 85.4 mmol, 1 eq, HCl) in DMF (50 mL) was added in portions potassium carbonate (59.0 g, 427 mmol, 5 eq) at 25° C. Then, benzyl bromide (170.8 mmol, 20.3 mL, 2 eq) was added dropwise into the mixture at 0° C. The resulting mixture was heated and stirred at 50° C. for 2 h. The reaction mixture was quenched by adding water (400 mL) and extracted with EA (400 mL×3). The combined organic layers were washed with brine (400 mL×3), dried over sodium sulfate, filtered, and concentrated in vacuo to give a residue which was purified by column chromatography (SiO$_2$, PE/EA=10/1 to 4/1) to provide 1-benzyl-3-fluoro-piperidin-4-one (9 g, 50.9% yield) as a yellow oil. $^1$H NMR (400 MHz, DMSO-$d_6$) d=7.40-7.31 (m, 4H), 7.31-7.26 (m, 1H), 5.37-5.08 (m, 1H), 3.71-3.66 (m, 2H), 3.37 (br s, 1H), 3.06-2.96 (m, 1H), 2.66 (td, 1=6.5, 13.2 Hz, 1H), 2.42-2.32 (m, 2H), 2.31-2.23 (m, 1H).

A mixture of 1-benzyl-3-fluoro-piperidin-4-one (9 g, 43.4 mmol, 1 eq) and iodomethane (651 mmol, 40.6 mL, 15 eq) in acetone (20 mL) was stirred at 25° C. for 16 h. The reaction mixture was filtered, and the filter cake washed with PE (20 mL). The filter cake was dried in vacuo to provide 1-benzyl-3-fluoro-1-methyl-piperidin-1-ium-4-one hydrochloride(7 g, crude) as a white solid.

To a solution of 1-benzyl-3-fluoro-1-methyl-piperidin-1-ium-4-one hydrochloride (5 g, 22.5 mmol, 1 eq) in toluene (20 mL) and water (2 mL) were added sodium carbonate (2.38 g, 22.5 mmol, 1 eq) and 2-methylpropan-2-amine (45 mmol, 4.73 mL, 2 eq) at 0° C. The mixture was stirred at 80° C. for 12 h. The reaction mixture was concentrated in vacuo to remove solvent, giving a residue which was purified by prep-HPLC (column: Phenomenex Luna C18 100×30 mm×5 um; mobile phase: [water (0.1% TFA)-ACN]; B %: 1%-18%, 12 min) to afford 1-tert-butyl-3-fluoro-piperidin-4-one (500 mg, 2.89 mmol, 12.8% yield), a mixture of stereoisomers, as a yellow solid. LC-MS (ES+, m/z): 206.2 [(M+MeOH)+].

Example 123: N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl)-1-[(1R,3S)-3-methoxycyclopentyl]-1H-pyrrole-3-carboxamide (Compound 359B), and N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl)-1-[(1R,3R)-3-methoxycyclopentyl]-1H-pyrrole-3-carboxamide (Compound 360B)

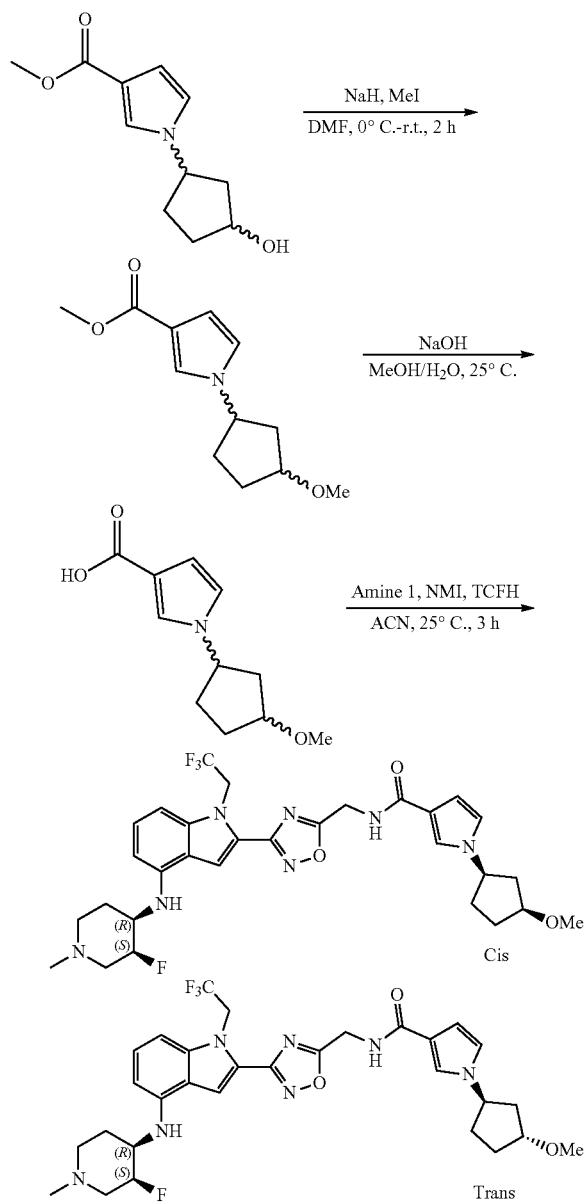

To a mixture of methyl 1-(3-hydroxycyclopentyl)pyrrole-3-carboxylate (1.5 g, 7.2 mmol, 1 eq) in DMF (20 mL) were added sodium hydride (573 mg, 14.3 mmol, 60% purity, 2 eq) and iodomethane (35.8 mmol, 2.23 mL, 5 eq) at 0° C. under nitrogen. The mixture was stirred at 0° C. for 30 min, then heated to 25° C. and stirred for 1.5 h. The residue was poured into saturated ammonium chloride (30 mL) and stirred for 5 min. The aqueous phase was extracted with EA (30 mL×3). The combined organic phase was washed with brine (30 mL×3), dried over anhydrous sodium sulfate, then filtered, and concentrated in vacuo. The residue was purified by column chromatography to afford methyl 1-(3-methoxycyclopentyl)pyrrole-3-carboxylate (900 mg, 4.03 mmol, 56.2% yield) as a yellow oil. LC-MS (ES+, m/z): 1.054 [(M+H)+].

To a mixture of methyl 1-(3-methoxycyclopentyl)pyrrole-3-carboxylate (500 mg, 2.24 mmol, 1 eq) in methanol (6 mL) and water (1.5 mL) was added sodium hydroxide (269 mg, 6.72 mmol, 3 eq) at 20° C. under nitrogen. The mixture was then heated and stirred at 60° C. for 5 h. The residue was poured into HCl (2M, 20 mL) and stirred for 3 min. The aqueous phase was extracted with EA (20 mL×3). The combined organic phase was washed with brine (20 mL×3), dried over anhydrous sodium sulfate, then filtered and concentrated in vacuo without further purification to afford 1-(3-methoxycyclopentyl)pyrrole-3-carboxylic acid (200 mg, 956 µmol, 42.7% yield) as a yellow oil. LC-MS (ES+, m/z): 0.927 [(M+H)~].

1-(3-methoxycyclopentyl)pyrrole-3-carboxylic acid (100 mg, 477.92 µmol, 1 eq) and Amine 1 (203.8 mg, 478 µmol, 1 eq) were reacted under method E, followed by separation of the cis and trans stereoisomers by SFC, to provide the desired products. Cis-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-[(1R,3S)-3-methoxycyclopentyl]-1H-pyrrole-3-carboxamide (30 mg, 48.6 µmol, 10.2% yield), a white solid. LC-MS (ES+, m/z): 618.3 [(M+H)+]. 1H NMR (400 MHz, DMSO-d6) δ ppm 8.67 (t, J=5.62 Hz, 1H), 7.89 (s, 1H), 7.46 (s, 1H), 7.11 (t, J=8.16 Hz, 1H), 6.83-6.93 (m, 2H), 6.49 (br s, 1H), 6.28 (d, J=8.16 Hz, 1H), 6.03 (br d, J=8.60 Hz, 1H), 5.50 (q, J=8.75 Hz, 2H), 4.75-4.93 (m, 1H), 4.72 (d, J=5.95 Hz, 2H), 4.45-4.54 (m, 1H), 3.84 (br s, 1H), 3.50-3.67 (m, 1H), 3.05 (br s, 1H), 2.83 (br s, 1H), 2.40-2.46 (m, 1H), 2.20 (br s, 3H), 2.02-2.19 (m, 3H), 1.88-2.02 (m, 1H), 1.60-1.88 (m, 5H); Trans-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-[(1 R,3S)-3-methoxycyclopentyl]-1H-pyrrole-3-carboxamide (30 mg, 48.6 µmol, 10.2% yield), a white solid. LC-MS (ES+, m/z): 618.3 [(M+H)+]. 1H NMR (400 MHz, DMSO-d6) δ ppm 8.64 (t, J=5.62 Hz, 1H), 7.89 (s, 1H), 7.43-7.48 (m, 1H), 7.11 (t, J=8.05 Hz, 1H), 6.85-6.93 (m, 2H), 6.48-6.52 (m, 1H), 6.48-6.52 (m, 1H), 6.28 (d, J=7.72 Hz, 1H), 6.01 (d, J=8.16 Hz, 1H), 5.50 (q, J=9.04 Hz, 2H), 4.75-4.92 (m, 1H), 4.72 (d, J=5.73 Hz, 2H), 4.52-4.61 (m, 1H), 3.95 (dt, J=5.73, 2.87 Hz, 1H), 3.50-3.67 (m, 1H), 2.98-3.09 (m, 1H), 2.76-2.85 (m, 1H), 2.16-2.31 (m, 6H), 1.89-2.15 (m, 4H), 1.61-1.78 (m, 3H).

Example 124: 1-[(1R,3R)-3-(dimethylamino)cyclopentyl]-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-pyrrole-3-carboxamide (Compound 361B)

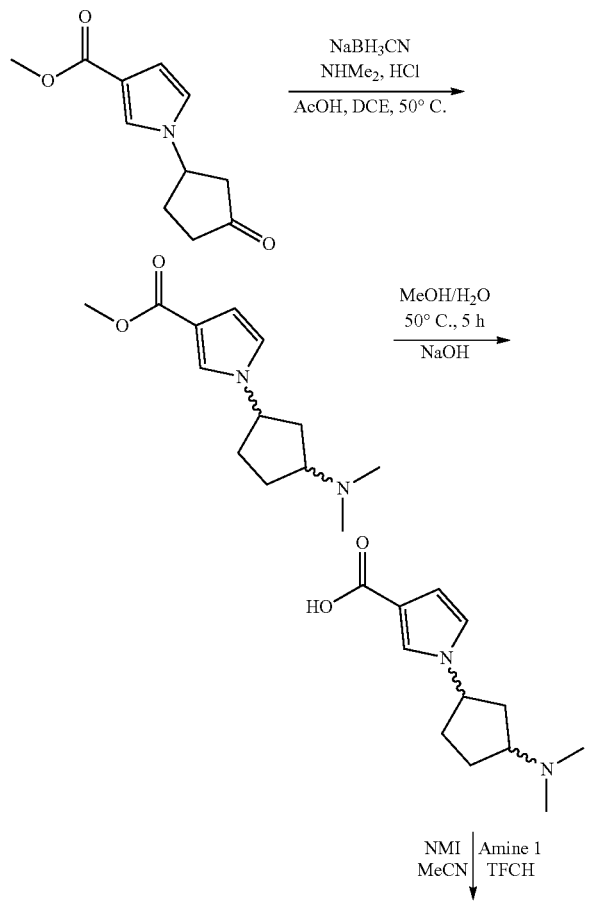

To a mixture of the previously prepared ketone (300 mg, 1.45 mmol, 1 eq) and dimethylamine hydrochloride (472.2 mg, 5.79 mmol, 4 eq) in DCE (4 mL) were added acetic acid (6.51 mmol, 373 μL 4.5 eq) and sodium triacetoxyborohydride (614 mg, 2.90 mmol, 2 eq) at 50° C. under nitrogen. The mixture was stirred at 50° C. for 5 h. The residue was diluted with saturated sodium carbonate to a final pH=7-8. The aqueous phase was extracted with EA (30 mL×3). The combined organic phase was washed with brine (30 mL×3), dried over anhydrous sodium sulfate, filtered, and concentrated in vacuo. The reaction was purified by prep-TLC to afford the tertiary amine product (150 mg, 635 μmol, 43.9% yield) as a colorless oil. LC-MS (ES+, m/z): 237.1 [(M+H)+].

The intermediate ester (150 mg, 635 μmol, 1 eq) was treated with methanol (2 mL) and water (0.5 mL) to form a mixture to which was added sodium hydroxide (101.6 mg, 2.54 mmol, 4 eq) in one portion at 50° C. under nitrogen. The mixture was stirred at 50° C. for 5 h. 1N HCl was added to adjust pH=7, and the reaction concentrated in vacuo to afford the carboxylic acid (120 mg, crude) as a white solid. LC-MS (ES+, m/z): 223.1 [(M+H)+].

To a mixture of Amine 1 (200 mg, 360 μmol, 1 eq, 2HCl) and the above carboxylic acid (96.2 mg, 433 μmol, 1.2 eq) in DMF (2 mL) were added HOBt (146.1 mg, 1.08 mmol, 3 eq), EDCI (207.3 mg, 1.08 mmol, 3 eq), TEA (3.60 mmol, 0.50 L, 10 eq). The mixture was heated and stirred at 50° C. for 5 h. The residue was poured into ice-water (w/w=1/1) (100 mL), and the aqueous phase was extracted with EA (30 mL×3). The combined organic phase was washed with brine (30 mL×3), dried over anhydrous sodium sulfate, filtered, and concentrated in vacuo. The reaction was purified by prep-TLC to afford the separated cis and trans stereoisomers.

Trans-1-[(1R,3R)-3-(dimethylamino)cyclopentyl]-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-pyrrole-3-carboxamide (Compound 361B) (22.2 mg, 9.3% yield, 95.6% purity), a white solid. LC-MS (ES+, m/z): 631.4 [(M+H)+]. $^1$H NMR (400 MHz, DMSO-$d_6$) δ ppm 1.52-1.62 (m, 1H) 1.69 (br d, J=12.96 Hz, 1H) 1.77-1.86 (m, 1H) 1.89-2.06 (m, 3H) 2.10 (br d, J=12.47 Hz, 2H) 2.20 (s, 3H) 2.23-2.33 (m, 6H) 2.41 (br s, 1H) 2.83 (br d, J=10.51 Hz, 1H) 2.92-3.14 (m, 3H) 3.63 (br s, 1H) 4.50-4.66 (m, 1H) 4.70-4.95 (m, 2H) 5.38-5.77 (m, 2H) 6.02 (br d, J=8.44 Hz, 1H) 6.28 (d, J=7.95 Hz, 1H) 6.50 (br s, 1H) 6.84-6.93 (m, 2H) 7.11 (t, J=8.01 Hz, 1H) 7.46 (s, 1H) 7.88 (s, 1H) 8.67 (br t, J=5.50 Hz, 1H); Cis-1-[(1R,3R)-3-(dimethylamino)cyclopentyl]-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-pyrrole-3-carboxamide (Compound 362B) (27 mg, 11.8% yield, 98.9% purity), a white solid. LC-MS (ES+, m/z): 631.3 [(M+H)+]. $^1$H NMR (400 MHz, DMSO-$d_6$) δ ppm 1.64-1.79 (m, 3H) 1.80-1.91 (m, 2H) 1.95-2.05 (m, 1H) 2.07-2.15 (m, 2H) 2.20 (br d, J=6.62 Hz, 9H) 2.28-2.41 (m, 2H) 2.61 (br s, 1H) 2.82 (br d, J=10.36 Hz, 1H) 2.98-3.10 (m, 1H) 3.51-3.66 (m, 1H) 4.41-4.55 (m, 1H) 4.68-4.96 (m, 3H) 5.50 (q, J=8.82 Hz, 2H) 6.01 (d, J=8.38 Hz, 1H) 6.28 (d, J=7.72 Hz, 1H) 6.50 (dd, J=2.87, 1.76 Hz, 1H) 6.85-6.95 (m, 2H) 7.11 (t, J=8.05 Hz, 1H) 7.49 (t, J=1.76 Hz, 1H) 7.89 (s, 1H) 8.66 (t, J=5.73 Hz, 1H).

Example 125: N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl)-1-(1-methylpiperidin-4-yl)-1H-pyrrole-3-carboxamide (Compound 363B)

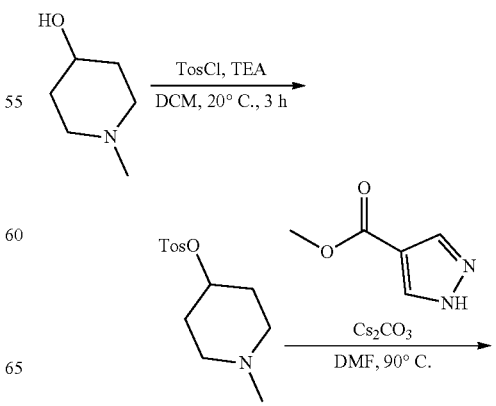

-continued

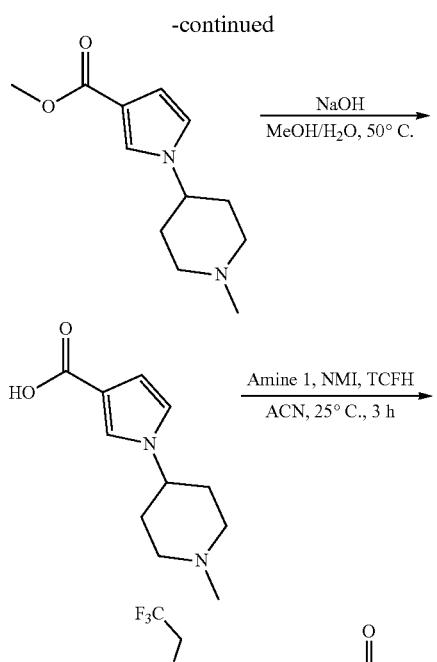

To a solution of 1-methylpiperidin-4-ol (86.8 mmol, 10.2 mL, 1 eq) in DCM (200 mL) were added 4-methylbenzenesulfonyl chloride (33.1 g, 174 mmol, 2 eq) and TEA (86.8 mmol, 12.1 mL, 1 eq), and the reaction was stirred at 25° C. for 1 h. The mixture was extracted with DCM (10 mL×2), and the organic phase was washed with water (10 mL) and brine (10 mL), then dried over anhydrous sodium sulfate. The solvent was removed in vacuo to afford (1-methyl-4-piperidyl) 4-methylbenzenesulfonate (10 g, crude) as a yellow solid. LC-MS (ES+, m/z): 269.3 [(M+H)+].

To a solution of methyl 1H-pyrrole-3-carboxylate (100 mg, 800 µmol, 1 eq) (1-methyl-4-piperidyl) 4-methylbenzenesulfonate (258.3 mg, 959 µmol, 1.2 eq) in DMF (15 mL) was added cesium carbonate (781 mg, 2.40 mmol, 3 eq), and the reaction was heated and stirred at 90° C. for 3 h. The mixture was extracted with DCM (10 mL×2), the organic phase was washed with water (10 mL) and brine (10 mL), then dried over anhydrous sodium sulfate. The solvent was removed in vacuo to afford methyl 1-(1-methyl-4-piperidyl) pyrrole-3-carboxylate (50 mg, crude) as a yellow solid. LC-MS (ES+, m/z): 222.2 [(M+H)+].

To a solution of methyl 1-(1-methyl-4-piperidyl) pyrrole-3-carboxylate (30 mg, 135 µmol, 1 eq) in methanol (4 mL) water (1 mL) was added sodium hydroxide (16.2 mg, 405 µmol, 3 eq), and the reaction was heated and stirred at 60° C. for 3 h. The mixture was extracted with DCM (10 mL×2), and the organic phase was washed with water (10 mL), brine (10 mL), and was then dried by sodium sulfate. The solvent was removed in vacuo and the residue was purified by prep-HPLC (formic acid conditions) to afford 1-(1-methyl-4-piperidyl) pyrrole-3-carboxylic acid (28 mg, 134 µmol, 99.6% yield) as a yellow solid. LC-MS (ES+, m/z): 208.2 [(M+H)+].

To a solution of Amine 1 (50 mg, 100 µmol, 1 eq. 2HCl) and 1-(1-methyl-4-piperidyl) pyrrole-3-carboxylic acid (20.9 mg, 100 µmol, 1 eq) were reacted under method E, followed by purification by prep-HPLC (neutral condition) to afford N-[[3-[4-[[(3S,4R)-3-fluoro-1-methyl-4-piperidyl]amino]1-(2,2,2-trifluoroethyl)indol-2-yl]-1,2,4-oxadiazol-5-yl]methyl]-1-(1-methyl-4-piperidyl) pyrrole-3-carboxamide (6.2 mg, 9.79 µmol, 9.8% yield, 97.4% purity) as a yellow solid. LC-MS (ES+, m/z): 617.3 [(M+H)+]. 1H NMR (400 MHz, DMSO-d6) δ ppm 8.63 (t), 7.88 (s), 7.46 (s), 7.11 (t), 6.81-6.95 (m), 6.50 (br s), 6.28 (d), 6.00 (br d), 5.50 (q), 4.76-4.94 (m), 4.72 (d), 3.83-3.99 (m), 3.46-3.65 (m), 3.03 (br t), 2.79-2.89 (m), 2.52-2.54 (m), 2.28 (br d), 2.19 (s), 2.06-2.14 (m), 1.96-2.05 (m), 1.89-1.95 (m), 1.86 (br d), 1.83 (br d), 1.68 (br d).

Example 126: N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-[(1R,2S)-2-methoxycyclopentyl]-1H-pyrrole-3-carboxamide (Compound 364B)

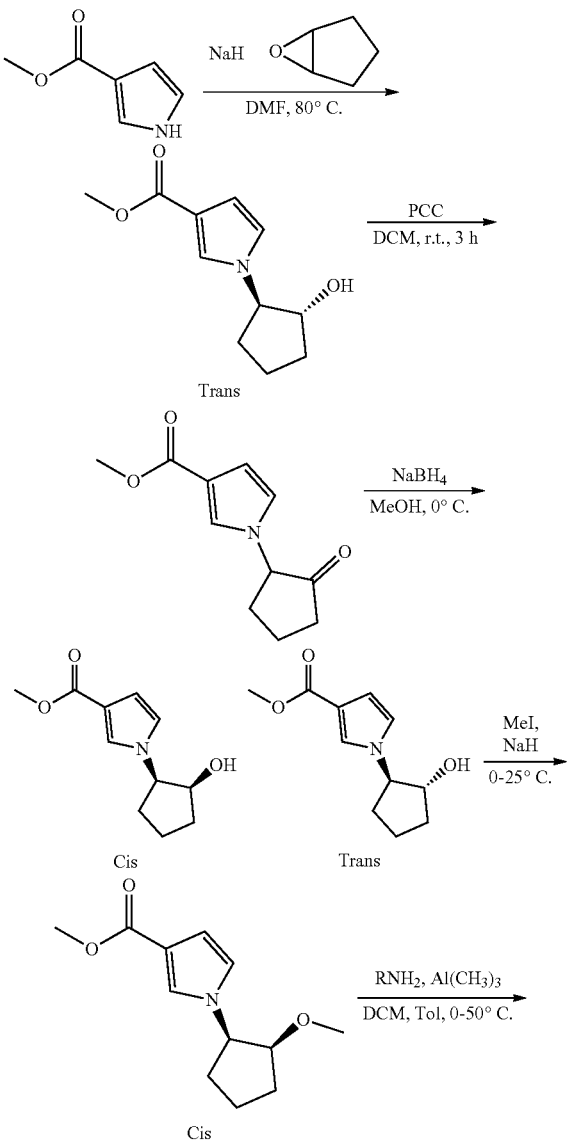

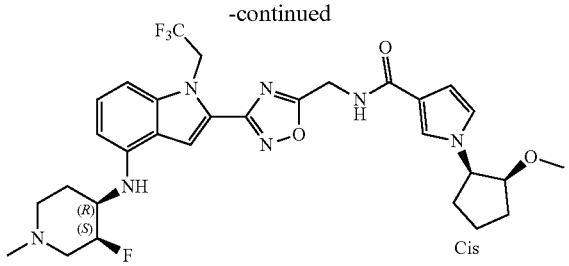

To a mixture of cyclopentene oxide (40 mmol, 3.49 mL, 1 eq) and methyl pyrrole-3-carboxylate (5 g, 40 mmol, 1 eq) in DMF (50 mL) was added sodium hydride (3.20 g, 79.9 mmol, 60% purity, 2 eq) in one portion at 0° C. under nitrogen. The mixture was stirred at 0° C. for 1 h, then heated to 80° C. and stirred for 4 h. The residue was poured into ammonium chloride solution (100 mL). The aqueous phase was extracted with EA (3×30 mL). The combined organic phase was washed with brine (3×50 mL), dried over anhydrous sodium sulfate, filtered, and concentrated in vacuo, then purified by silica gel chromatography to give the trans alcohol (68.0% yield, 97.5% purity). LC-MS(ES+, m/z): 210.1 [(M+H)+].

To a mixture of methyl 1-[(1R,2R)-2-hydroxycyclopentyl]pyrrole-3-carboxylate (1.3 g, 6.21 mmol, 1 eq) in DCM (2 mL) was added PCC (2.68 g, 12.4 mmol, 2 eq) in one portion at 20° C. under nitrogen. The mixture was stirred at 20° C. for 3 h. The reaction mixture was poured into water (50 mL), then extracted with DCM (3×30 mL). The combined organic layers were washed with brine (3×50 mL), dried over anhydrous sodium sulfate, filtered, and concentrated in vacuo to give a residue. The residue was purified by prep-TLC, to give product LC-MS (ES+, m/z): 208.0[(M+H)+].

To a mixture of methyl 1-[(1R)-2-oxocyclopentyl]pyrrole-3-carboxylate (400 mg, 1.93 mmol, 1 eq) in methanol (3 mL) and added sodium borohydride (73 mg, 1.93 mmol, 1 eq) in one portion at 0° C. The mixture was stirred at 0° C. for 15 min, then heated to 25° C. and stirred for 30 min. The residue was poured into sodium carbonate (aq.) to adjust pH=9~1. The aqueous phase was extracted with EA (3×80 mL). The combined organic phase was washed with brine (3×50 mL), dried over anhydrous sodium sulfate, filtered, and concentrated in vacuo. The residue was purified by prep-TLC. LC-MS (ES+, m/z): 210.0 [(M+H)+].

To a mixture of methyl 1-1(1R, 2S)-2-hydroxycyclopentyl]pyrrole-3-carboxylate (185 mg, 884.15 μmol, 1 eq) in DMF (2 mL) was added sodium hydride (106.1 mg, 2.65 mmol, 60% purity, 3 eq) at 0° C. under nitrogen. The mixture was stirred at 0° C. for 30 min, then iodomethane (1.77 mmol, 110 μL 2 eq) was added, and the mixture was stirred at 20° C. for 30 min. The residue was poured into ammonium chloride (50 mL). The aqueous phase was extracted with EA (3×50 mL). The combined organic phase was washed with brine (3×30 mL), dried over anhydrous sodium sulfate, filtered, and concentrated in vacuo. The reaction was purified by prep-TLC to provide the product LC-MS (ES+, m/z): 224.2[(M+H)+].

Method H: To a mixture of Amine 1 (84 mg, 197 μmol, 1.1 eq) in DCM (1 mL) and toluene (1 mL) was added trimethylaluminum (2 M, 450 μL 5 eq) in one portion at 0° C. under nitrogen. The mixture was stirred at 0° C. for 30 min, followed by addition of methyl 1-[(1R,2S)-2-methoxycyclopentyl]pyrrole-3-carboxylate (40 mg, 179.16 μmol, 1 eq), and the reaction was heated to 50° C. and stirred for 10 h. The residue was poured into sat. ammonium chloride (100 mL). The aqueous phase was extracted with EA (3×30 mL). The combined organic phase was washed with brine (3×30 mL), dried over anhydrous sodium sulfate, filtered, and concentrated in vacuo. The reaction was purified by prep-TLC to provide the desired product N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-[(1R,2S)-2-methoxycyclopentyl]-1H-pyrrole-3-carboxamide (20.2 mg, 17.8% yield, 97.5% purity) LC-MS (ES+, m/z): 618.4 [(M+H)+]. 1H NMR (400 MHz, DMSO-d6) δ=8.65 (t, J=5.62 Hz, 1H), 7.89 (s, 1H), 7.43 (s, 1H), 7.15-7.07 (m, 1H), 6.92-6.81 (m, 2H), 6.48 (dd, J=2.65, 1.76 Hz, 1H), 6.28 (d, J=7.72 Hz, 1H), 6.01 (br d, J=8.38 Hz, 1H), 5.54-5.45 (m, 2H), 4.41 (td, J=8.71, 4.63 Hz, 1H), 4.92-4.76 (m, 1H), 4.72 (d, J=5.73 Hz, 2H), 3.78-3.71 (m, 1H), 3.64-3.54 (m, 1H), 3.02 (s, 3H), 2.86-2.80 (m, 1H), 2.20 (br s, 3H), 2.08-1.94 (m, 3H), 1.86-1.74 (m, 3H), 1.72-1.55 (m, 2H).

Example 127: 1-[(dimethylcarbamoyl)methyl]-N-{[3-(4-{[(3S,4R)-1-ethyl-3-fluoropiperidin-4-yl]amino}-1-(2,2,2-trifluoroethyl)-1H-indol-2-yl)-1,2,4-oxadiazol-5-yl]methyl}-1H-pyrrole-3-carboxamide (Compound 365B)

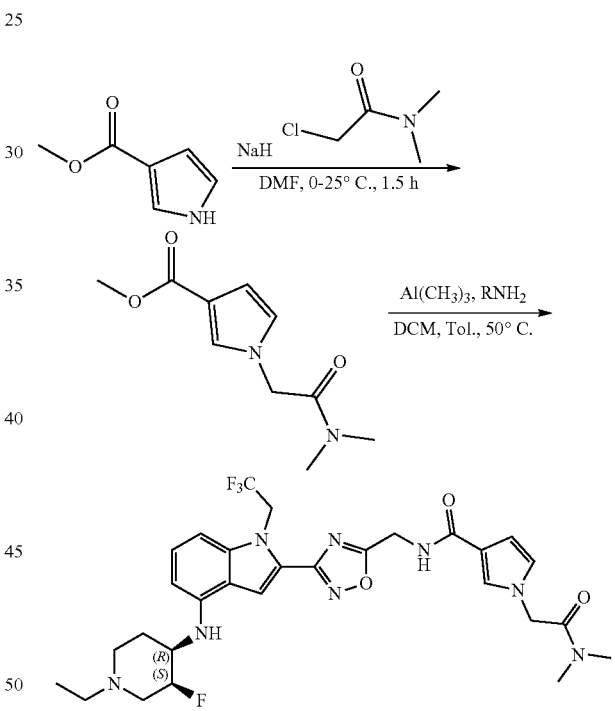

To a mixture of methyl 1H-pyrrole-3-carboxylate (1 g, 8 mmol, 1 eq) in DMF (10 mL) was added sodium hydride (352 mg, 8.79 mmol, 60% purity, 1.1 eq) in one portion at 0° C. under nitrogen. The mixture was stirred at 0° C. for 30 min, followed by addition of 2-chloro-N, N-dimethyl-acetamide (7.95 mmol, 820 μL 1 eq), and the reaction was heated to 25° C. and stirred for 1 h. The residue was poured into sat. ammonium chloride (50 mL) and stirred for 3 min. The aqueous phase was extracted with EA (3×30 mL). The combined organic phase was washed with brine (3×30 mL), dried over anhydrous sodium sulfate, filtered, and concentrated in vacuo. The residue was purified by column chromatography (SiO2, PE/EA=10:1 to 0:1) to give the product (1 g, 4.76 mmol, 59.5% yield) as a white solid. LC-MS (ES+, m/z): 211.2 I(M+H)+].

To a mixture of the N-ethylpiperidine amine previously prepared (83.8 mg, 190 μmol, 1 eq, free base) in DCM (5 mL) and toluene (5 mL) was added trimethylaluminum (2 M, 0.48 mL, 5 eq) in one portion at 0° C. under nitrogen. The mixture was stirred at 0° C. for 30 min, followed by addition of methyl 1-[2-(dimethylamino)-2-oxo-ethyl]pyrrole-3-carboxylate (40 mg, 190 μmol, 1 eq), and the reaction was heated to 50° C. and stirred for 2 h. The mixture was cooled to 0° C. The residue was poured into sodium hydroxide (4M, 5 mL) and stirred for 3 min. The aqueous phase was extracted with DCM (3×20 mL). The combined organic phase was washed with brine (3×20 mL), dried over anhydrous sodium sulfate, filtered, and concentrated in vacuo. The residue was purified by prep-HPLC (FA condition) to give product (30 mg, 48.5 μmol, 25.5% yield) LC-MS (ES+, m/z): 619.3 [(M+H)+]. ¹H NMR (400 MHz, DMSO-d₆) δ=8.66 (t, J=5.84 Hz, 1H), 8.14 (s, 1H), 7.90 (s, 1H), 7.30-7.25 (m, 1H), 7.11 (t, J=8.05 Hz, 1H), 6.87 (d, J=8.38 Hz, 1H), 6.69 (t, J=2.43 Hz, 1H), 6.48 (dd, J=2.65, 1.76 Hz, 1H), 6.28 (d, J=7.94 Hz, 1H), 6.07 (br d, J=8.38 Hz, 1H), 5.50 (q, J=9.11 Hz, 2H), 4.92 (s, 3H), 4.72 (d, J=5.73 Hz, 2H), 3.67-3.55 (m, 1H), 3.21-3.11 (m, 1H), 3.01 (s, 3H), 2.94 (br d, J=10.80 Hz, 1H), 2.85 (s, 3H), 2.40 (br d, J=7.06 Hz, 2H), 2.32-1.91 (m, 3H), 1.71 (br d, J=11.25 Hz, 1H), 1.01 (t, J=7.06 Hz, 3H).

Example 128: 1-tert-butyl-N-({3-[4-({5H,6H,7H,8H-imidazo[1,2-a]pyridin-7-yl}amino)-1-(2,2,2-trifluoroethyl)-1H-indol-2-yl]-1,2,4-oxadiazol-5-yl}methyl)-1H-pyrrole-3-carboxamide (Compound 366B)

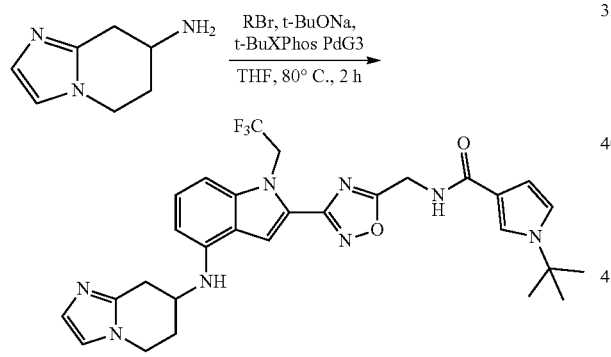

To a solution of N-[[3-[4-bromo-1-(2,2,2-trifluoroethyl)indol-2-yl]-1,2,4-oxadiazol-5-yl]methyl]-1-tert-butyl-pyrrole-3-carboxamide (10 mg, 19.1 μmol, 1 eq) and 5,6,7,8-tetrahydroimidazo[1,2-a]pyridin-7-amine (7.9 mg, 57 μmol, 3 eq) in THF (3 mL) were added sodium t-butoxide (2 M, 40 μL 4 eq) and [2-(2-aminophenyl)phenyl]-methylsulfonyloxy-palladium di-tert-butyl-[2-(2,4,6-triisopropylphenyl)phenyl]phosphane (t-Butyl-XPhos Gen.3) (7.6 mg, 9.54 μmol, 0.5 eq). The mixture was stirred at 80° C. for 2 h under nitrogen. The residue was purified by prep-TLC (SiO₂, DCM: methanol=10:1). This process was repeated eight times, and the resulting material combined. This material was further purified by prep-HPLC (FA condition:column: Phenomenex Luna C18 200×40 mm×10 um; mobile phase: [water (0.2% FA)-ACN]; B %: 30%-70%, 8 min) to give the desired product 1-tert-butyl-N-({3-[4-({5H,6H, 7H,8H-imidazo[1,2-a]pyridin-7-yl}amino)-1-(2,2,2-trifluoroethyl)-1H-indol-2-yl]-1,2,4-oxadiazol-5-yl}methyl)-1H-pyrrole-3-carboxamide (12 mg, 20.7 μmol, 13.6% yield). LC-MS (ES+, m/z): 581.3 [(M+H)+]. ¹H NMR (400 MHz, DMSO-d₆) δ=8.65-8.62 (t, J=5.6 Hz, 1H), 8.14 (s, 1H), 7.78 (s, 1H), 7.55-7.54 (t, J=2.2 Hz, 1H), 7.17-7.13 (t, J=8.0 Hz, 1H), 7.034-7.032 (d, J=0.8 Hz, 1H), 7.00-6.98 (t, J=2.8 Hz, 1H), 6.91-6.89 (d, J=8.0 Hz, 1H), 6.843-6.840 (d, J=1.2 Hz, 1H), 6.51-6.50 (m, 1H), 6.37-6.35 (d, J=7.6 Hz, 1H), 6.21-6.19 (d, J=8.0 Hz, 1H), 5.55-5.48 (m, 2H), 4.74-4.72 (d, J=5.6 Hz, 2H), 4.15-4.11 (m, 1H), 4.06-3.99 (m, 2H), 3.20-3.14 (m, 1H), 2.82-2.76 (m, 1H), 2.32-2.25 (m, 1H), 1.92-1.87 (m, 1H), 1.49 (s, 9H).

1-tert-butyl-N-{[3-(4-{[(3R)-6-oxopiperidin-3-yl]amino}-1-(2,2,2-trifluoroethyl)-1H-indol-2-yl)-1,2,4-oxadiazol-5-yl]methyl}-1H-pyrrole-3-carboxamide (Compound 367B) was prepared using the same method F as for the opposite enantiomer above using N-[[3-[4-bromo-1-(2,2,2-trifluoroethyl)indol-2-yl]-1,2,4-oxadiazol-5-yl]methyl]-1-tert-butyl-pyrrole-3-carboxamide (20 mg, 38.1 μmol, 1 eq) and (5S)-5-aminopiperidin-2-one hydrochloride (23 mg, 152 μmol, 4 eq) to afford the product (9.1 mg, 15.7.mol, 8.2% yield, 96% purity) as white solid. LC-MS (ES+, m/z): 558.3 [(M+H)+]. ¹H NMR (400 MHz, DMSO-d6) δ=8.64 (t, J=5.7 Hz, 1H), 7.78 (s, 1H), 7.54 (t, J=2.08 Hz, 1H), 7.40 (s, 1H), 7.14 (t, J=8.08 Hz, 1H), 6.99 (t, J=2.68 Hz, 1H), 6.89 (d, J=8.32 Hz, 1H), 6.50 (dd, J=2.94, 1.83 Hz, 1H), 6.31 (d, J=7.82 Hz, 1H), 6.07 (d, J=7.70 Hz, 1H), 5.50 (d, J=8.84 Hz, 2H), 4.73 (d, J=5.74 Hz, 2H), 3.77-3.88 (m, 1H), 3.33-3.49 (m, 1H), 3.11 (dd, J=10.94, 8.50 Hz, 1H), 2.31-2.36 (m, 2H), 2.05 (dd, J=12.90, 5.20 Hz, 1H), 1.72-1.85 (m, 1H), 1.49 (s, 9H).

Example 129: 1-tert-butyl-N-[(3-{4-[(2-methyl-4,5,6,7-tetrahydro-1,3-benzothiazol-6-yl)amino]-1-(2,2,2-trifluoroethyl)-1H-indol-2-yl}-1,2,4-oxadiazol-5-yl)methyl]-1H-pyrrole-3-carboxamide (Compound 368B)

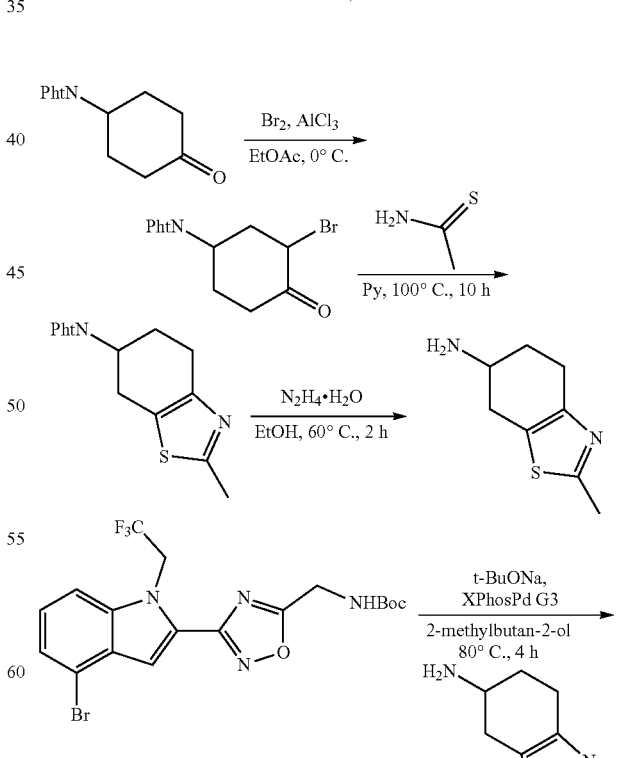

-continued

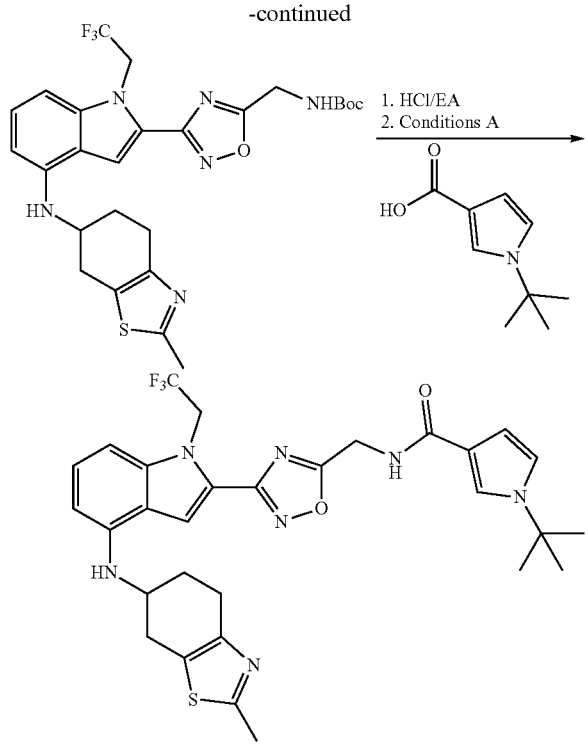

To a solution of 2-(4-oxocyclohexyl)isoindoline-1,3-dione (5 g, 20.6 mmol, 1 eq) in EA (50 mL) was added aluminum chloride (150 mg, 1.1 mmol). A solution of bromine (985.4 mg, 6.2 mmol, 1 eq) in EA (8 mL) was then added as dropwise at 0° C. over 5 min. The mixture was stirred at this temperature for 0.5 h. The reaction mixture was quenched by adding saturated sodium thiosulfate (50 mL), then extracted with EA (3×50 mL). The combined organic layers were washed with brine (2×15 mL), dried over sodium sulfate, filtered, and concentrated in vacuo to give the product (6 g, crude) as a light yellow solid. LC-MS (ES+, m/z): 321.9, 323.9 [(M+H)+].

To a solution of thioacetamide (1.2 g, 16.1 mmol, 1.3 eq) in DMF (40 mL) was added 2-(3-bromo-4-oxocyclohexyl)isoindoline-1,3-dione (4.0 g, 12.4 mmol, 1 eq). The reaction mixture was stirred at 100° C. for 10 hrs. The reaction mixture was quenched by adding water (100 mL), and then extracted with EA (3×80 mL). The combined organic layers were washed with brine (2×50 mL), dried over sodium sulfate, filtered, and concentrated in vacuo to give a residue. The residue was purified by column chromatography (SiO2, PE/EA=1:0 to 10:1) to give the product (3 g, 10.1 mmol, 81.0% yield) as a light yellow solid. LC-MS (ES+, m/z): 299.0 [(M+H)+].

To a solution of 2-(2-methyl-4,5,6,7-tetrahydro-1,3-benzothiazol-6-yl)isoindoline-1,3-dione (3 g, 10.1 mmol, 1 eq) in ethanol (50 mL) was added hydrazine hydrate (3.4 g, 20.1 mmol, 3.3 mL, 30% purity, 2 eq).

The reaction mixture was stirred at 60° C. for 2 hrs. The reaction mixture was filtered to remove the solid. The filtration was concentrated in vacuo to remove solvent and give a residue. The residue was purified by prep-HPLC (column: Welch Xtimate C18 250×50 mm×10 um; mobile phase: [water (10 mM NH4HCO3)-ACN]; B %: 5%-30%, 20 min). The product (0.3 g, 1.8 mmol, 17.7% yield) was obtained as a dark brown solid. LC-MS (ES+, m/z): 169.1 [(M+H)+]. 1H NMR (400 MHz, CDCl3) δ=3.27 (br s, 1H), 2.97 (br dd, J=4.3, 15.8 Hz, 1H), 2.92-2.82 (m, 1H), 2.81-2.71 (m, 1H), 2.61 (s, 3H), 2.48 (br dd, J=8.1, 15.8 Hz, 1H), 2.06-1.94 (m, 1H), 1.77-1.66 (m, 1H).

A mixture of tert-butyl N-[[3-[4-bromo-1-(2,2,2-trifluoroethyl)indol-2-yl]-1,2,4-oxadiazol-5-yl]methyl]carbamate (51 mg, 107 μmol, 1 eq), 2-methyl-4,5,6,7-tetrahydro-1,3-benzothiazol-6-amine (27.1 mg, 161 μmol, 1.5 eq), XPhos Pd G3 (13.6 mg, 16.1 μmol, 0.2 eq), sodium t-butoxide (2 M, 270 μL 5 eq) in 2-methylbutan-2-ol (2 mL) was degassed and purged with nitrogen 3 times, then the mixture was stirred at 80° C. for 4 h under nitrogen atmosphere. This process was repeated 7 times, and the mixtures were combined and quenched by adding water 50 mL, then extracted with EA (3×30 mL). The combined organic layers were washed with brine (3×20 mL), dried over sodium sulfate, filtered, and concentrated in vacuo to give a residue. The residue was purified by prep-TLC (SiO2, PE/EA=1:2) to give compound product (50 mg, 88.9 μmol, 82.8% yield) as a yellow solid. LC-MS (ES+, m/z): 563.2 [(M+H)+].

Treatment of the intermediate under standard conditions to remove Boc (HCl/EA) gave the desired primary amine (40 mg). LC-MS (ES+, m/z): 463.0 [(M+H)+]. N-[2-[5-(aminomethyl)-1,2,4-oxadiazol-3-yl]-1-(2,2,2-trifluoroethyl)indol-4-yl]-2-methyl-4,5,6,7-tetrahydro-1,3-benzothiazol-6-amine (40 mg, 86.5 μmol, 1 eq) and 1-tert-butylpyrrole-3-carboxylic acid (21.7 mg, 129.7 μmol, 1.5 eq) were reacted under method A to provide the desired product 1-tert-butyl-N-[(3-{4-[(2-methyl-4,5,6,7-tetrahydro-1,3-benzothiazol-6-yl)amino]-1-(2,2,2-trifluoroethyl)-1H-indol-2-yl}-1,2,4-oxadiazol-5-yl)methyl]-1H-pyrrole-3-carboxamide (5.2 mg, 7.9 μmol, 9.1% yield, 92.4% purity) as a light yellow solid. LC-MS (ES+, m/z): 612.3 [(M+H)+]. 1H NMR (400 MHz, DMSO-d6) δ=8.71-8.58 (m, 1H), 7.78 (s, 1H), 7.55 (s, 1H), 7.13 (t, J=7.9 Hz, 1H), 6.99 (s, 1H), 6.87 (d, J=8.8 Hz, 1H), 6.50 (br s, 111), 6.32 (d, J=8.2 Hz, 1H), 6.14 (d, J=8.2 Hz, 1H), 5.56-5.45 (m, 2H), 4.72 (d, J=5.7 Hz, 2H), 3.90 (br s, 1H), 3.18-3.11 (m, 1H), 2.83-2.71 (m, 3H), 2.57 (s, 3H), 2.16 (br s, 1H), 1.77 (br s, 1H), 1.49 (s, 9H).

1-cyclobutyl-N-{[3-(4-{1[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-pyrazole-4-carboxamide (Compound 369B): Amine 1 (47 mg, 0.099 mmol, 1 eq, HCl) was coupled with 1-cyclobutyl-4-pyrazole carboxylic acid (22.3 mg, 0.134 mmol. 1.43 eq) under method B to provide the desired amide product (10.3 mg, 18%) after reverse-phase HPLC purification. LC-MS (ES+, m/z): 575.3 [(M+H)+]. 1H NMR (500 MHz, DMSO-d6) δ 9.05 (t, J=5.7 Hz, 1H), 8.37 (s, 1H), 8.00 (s, 1H), 7.94 (s, 1H), 7.17 (t, J=8.0 Hz, 1H), 6.93 (d, J=8.3 Hz, 1H), 6.33 (d, J=7.8 Hz, 1H), 6.09 (d, J=8.2 Hz, 1H), 5.81 (s, OH), 5.55 (d, J=8.9 Hz, 2H), 5.01-4.86 (m, 1H), 4.82 (d, J=5.7 Hz, 2H), 3.65 (d, J=28.9 Hz, 1H), 3.10 (s, 1H), 2.88 (s, 1H), 2.51-2.39 (m, 4H), 2.33-1.95 (m, 4H), 1.85 (ddt, J=14.0, 10.3, 5.4 Hz, 2H), 1.74 (d, J=11.9 Hz, 1H).

Example 130: N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-[(1R,2S)-2-methoxycyclopentyl]-1H-pyrazole-4-carboxamide (Compound 370B)

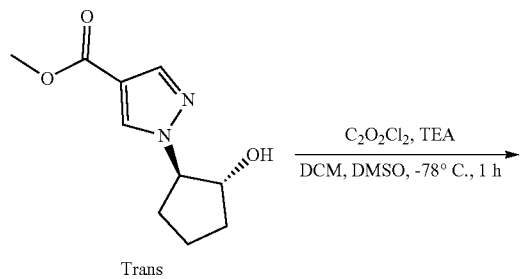
Trans

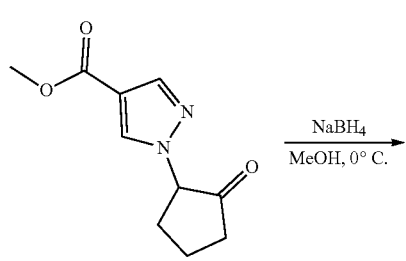

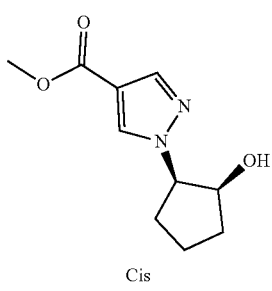
Cis

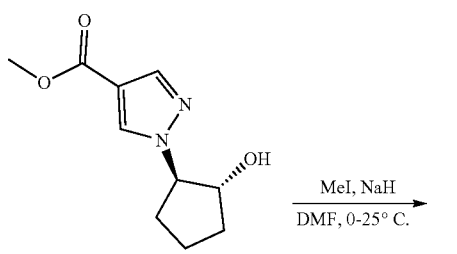
Trans

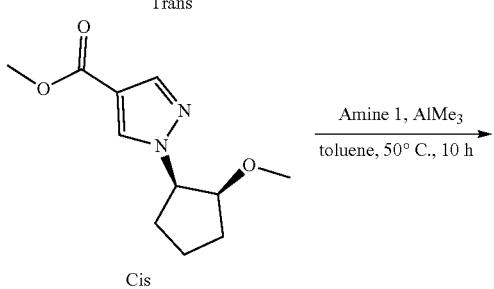
Cis

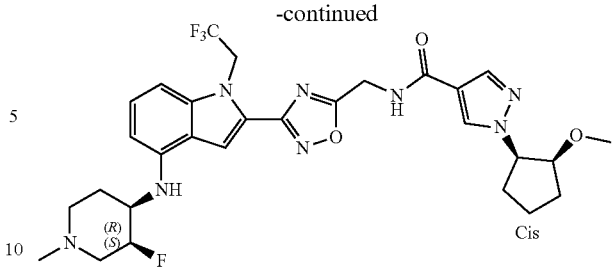
Cis

To a mixture of DMSO (9.51 mmol, 740 μL 2 eq) in DCM (5 mL) was added oxalyl chloride (9.51 mmol, 833 μL 2 eq) at −78° C. under nitrogen. The mixture was stirred at −78° C. for 15 min, followed by addition of the previously prepared racemic methyl 1-[(1R,2R)-2-hydroxycyclopentyl]pyrazole-4-carboxylate (1 g, 4.76 mmol, 1 eq) in DCM (2 mL) at −78° C. under nitrogen. The mixture was stirred at −78° C. for 35 min, followed by addition of TEA (23.8 mmol, 3.3 mL, 5 eq) at −78° C. The mixture was stirred and warmed to 0° C. over 10 min. The residue was poured into sat. ammonium chloride (100 mL). The aqueous phase was extracted with EA (3×30 mL). The combined organic phase was washed with brine (3×30 mL), dried over anhydrous sodium sulfate, filtered, and concentrated in vacuo. The reaction was purified by prep-TLC to give the product (633 mg, 3.04 mmol, 63.9% yield).

To a mixture of methyl 1-[(1R)-2-oxocyclopentyl]pyrazole-4-carboxylate (630 mg, 3.03 mmol, 1 eq) in methanol (10 mL) was added sodium borohydride (57.2 mg, 1.51 mmol, 0.5 eq) in one portion at 0° C. under nitrogen. The mixture was stirred at 0° C. for 30 min. The residue was poured into sodium carbonate to adjust pH=7-8. The aqueous phase was extracted with EA (100 mL×3). The combined organic phase was washed with brine (3×100 mL), dried over anhydrous sodium sulfate, filtered, and concentrated in vacuo. The residue was purified by prep-TLC to give the alcohol product (200 mg, 951 μmol, 31.4% yield).

To a mixture of racemic methyl 1-[(1R,2S)-2-hydroxycyclopentyl]pyrazole-4-carboxylate (100 mg, 476 μmol, 1 eq) in DMF (2 mL) was added sodium hydride (57.1 mg, 1.43 mmol, 60% purity, 3 eq) in one portion at 0° C. under nitrogen. The mixture was stirred at 0° C. for 30 min, followed by addition of iodomethane (950 μmol, 60 μL 2 eq). The mixture was stirred at 25° C. for 30 min. The residue was poured into ammonium chloride (100 mL). The aqueous phase was extracted with EA (3×30 mL). The combined organic phase was washed with brine (3×30 mL), dried over anhydrous sodium sulfate, filtered, and concentrated in vacuo. The reaction was purified by prep-TLC. To give product (63 mg, 281 μmol, 59.1% yield).

To a mixture of the previously prepared Amine 1 (99 mg, 178 μmol, 1 eq, 2 HCl) in DCM (1 mL) and toluene (1 mL) was added trimethylaluminum (2 M, 890 μL 10 eq) in one portion at 0° C. under nitrogen. The mixture was stirred at 0° C. for 30 min, followed by addition of methyl 1-[(1R,2S)-2-methoxycyclopentyl]pyrazole-4-carboxylate (40 mg, 179 μmol, 1 eq) and was then heated to 50° C. and stirred for 10 hrs. The residue was poured into ammonium chloride (100 mL). The aqueous phase was extracted with EA (3×30 mL). The combined organic phase was washed with brine (3×30 mL), dried over anhydrous sodium sulfate, filtered, and concentrated in vacuo. The reaction was purified by prep-TLC to give the product N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-[(1R,2S)-2- methoxycyclopentyl]-1H-pyrazole-4-carboxamide (20.2 mg, 17% yield, 92.8% purity) as a yellow solid. LC-MS (ES+, m/z) 619.3 [(M+H)+]. 1H NMR (400 MHz, DMSO-d6) δ ppm 9.00 (t, J=5.62 Hz, 1H), 8.25 (s, 1H), 7.89 (d, J=2.20 Hz, 2H), 7.14-7.07 (m, 1H), 6.88 (d, J=8.38 Hz, 1H), 6.28 (d, J=7.72 Hz, 1H), 6.04 (br d, J=8.16 Hz, 1H), 5.50 (q, J=8.82 Hz, 2H), 4.92-4.74 (m, 3H), 4.70 (td, J=7.99, 4.96 Hz, 1H), 3.83 (q, J=4.781-Hz, 1H), 3.65-3.51 (m, 1H), 3.30 (s, 7H), 3.05 (s, 3H), 2.85-2.78 (m, 1H), 2.19 (br s, 3H), 2.15-2.06 (m, 3H), 2.05-1.94 (m, 1H), 1.91-1.76 (m, 3H), 1.70-1.59 (m, 2H).

Example 131: N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(4-methyloxan-4-yl)-1H-pyrrole-3-carboxamide (Compound 371B)

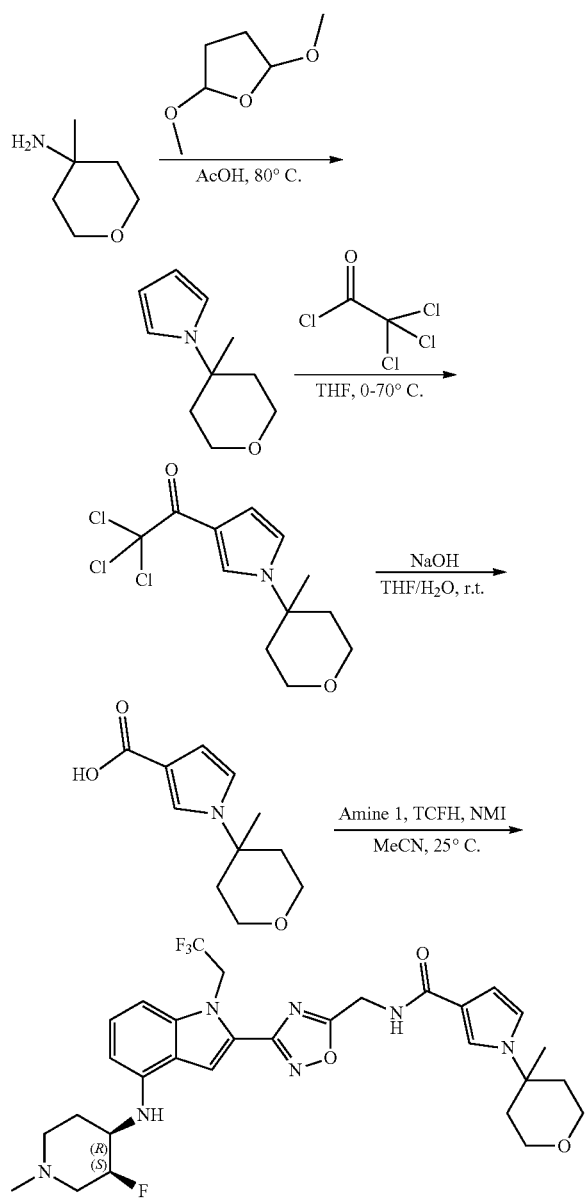

A mixture of 2,5-dimethoxytetrahydrofuran (434 mmol, 56.2 mL, 5 eq) and 4-methyltetrahydropyran-4-amine (10 g, 86.8 mmol, 1 eq) was treated in portions with acetic acid (60 mL), and was then stirred at 80° C. for 24 h. The reaction mixture was concentrated in vacuo to remove solvent. The residue was diluted with EA (300 mL), washed with sodium hydroxide (3 M, 2×200 mL), dried over sodium sulfate, filtered, and concentrated in vacuo to give a residue. The residue was purified by prep-HPLC (column: Phenomenex luna c18 250 mm×100 mm×10 um; mobile phase:[water (0.1% TFA)-ACN]; B %: 20%-50%, 40 min). The mixture was concentrated in vacuo to remove acetonitrile, followed by addition of sodium carbonate (Sat. aq) to pH>9. The mixture was extracted with EA (3×300 mL). The combined organic layers were washed with brine (3×300 mL), dried over sodium sulfate, filtered, and concentrated in vacuo to give the product (5 g, 27.2 mmol, 31.4% yield) LC-MS (ES+, m/z): 166.2 [(M+H)+]. 1H NMR (400 MHz, CHLOROFORM-d) δ=6.84 (t, J=2.2 Hz, 2H), 6.22 (t, J=2.2 Hz, 2H), 3.80-3.71 (m, 4H), 2.26 (td, J=5.6, 13.4 Hz, 2H), 1.95 (td, J=5.3, 13.5 Hz, 2H), 1.50 (s, 3H).

To a solution of 2,2,2-trichloroacetyl chloride (16.3 mmol, 1.8 mL, 3 eq) in THF (10 mL) was added 1-(4-methyltetrahydropyran-4-yl)pyrrole (1 g, 5.5 mmol, 1 eq) at 0° C. The mixture was stirred at 0° C. for 1 h, then stirred at 70° C. for 3 h. The mixture was poured into sodium carbonate (Sat., 20 mL). The mixture was extracted with EA (60 mL). The combined organic layers were washed with brine (60 mL), dried over sodium sulfate, filtered, and concentrated in vacuo to give a residue. The residue was purified by prep-TLC (PE:EA=10:1, Rf=0.4) to give the product (1.5 g, 4.4 mmol, 79.8% yield) as a light yellow solid. 1H NMR (399 MHz, DMSO-d6) δ=7.95 (t, J=2.0 Hz, 1H), 7.26-7.18 (m, 1H), 6.76 (dd, J=1.8, 3.1 Hz, 1H), 3.71-3.61 (m, 2H), 3.61-3.54 (m, 2H), 2.20-2.11 (m, 2H), 2.02-1.92 (m, 2H), 1.49 (s, 3H).

To a solution of 2,2,2-trichloro-1-[1-(4-methyltetrahydropyran-4-yl)pyrrol-3-yl]ethanone (1 g, 3.22 mmol, 1 eq) in THF (5 mL) and water (5 mL) was added sodium hydroxide (3 M, 5 mL, 4.7 eq) and. The mixture was stirred at 25° C. for 1 h. The reaction mixture was quenched by adding 1N HCl to pH<5 at 0° C., then extracted with EA (3×30 mL). The combined organic layers were washed with brine (3×30 mL), dried over sodium sulfate, filtered, and concentrated in vacuo to give the product (0.5 g, 2.39 mmol, 74.2% yield).

1-(4-methyltetrahydropyran-4-yl)pyrrole-3-carboxylic acid (68.7 mg, 328 μmol, 2 eq) was coupled with Amine 1 (0.07 g, 164 μmol, 1 eq) under method E, then purified by prep-TLC (SiO2, DCM: methanol=10:1). The residue was further purified by prep-HPLC (FA condition: column: Phenomenex Luna C18 200×40 mm×10 um; mobile phase: [water (0.2% FA)-ACN];B %: 30%-70%, 8 min) to give the desired product N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(4-methyloxan-4-yl)-1H-pyrrole-3-carboxamide (23 mg, 36.4 μmol, 22.1% yield). LC-MS (ES+, m/z): 138.1 [(M+H)+]. 1H NMR (400 MHz, chloroform-d) δ=8.71-8.60 (t, J=5.6 Hz, 1H), 7.92-7.84 (s, 1H), 7.61-7.53 (t, J=2.0 Hz, 1H), 7.16-7.07 (t, J=8.0 Hz, 1H), 7.04-7.00 (t, J=2.4 Hz, 1H), 6.93-6.83 (d, J=8.0 Hz, 1H), 6.58-6.48 (dt, J=2.0 Hz, 1H), 6.35-6.24 (d, J=6.0 Hz, 1H), 6.04-5.94 (d, J=8.4 Hz, 1H), 5.60-5.38 (dt, J=8.8 Hz, 2H), 4.96-4.67 (m, 3H), 3.69-3.52 (m, 5H), 3.07-2.99 (m, 1H), 2.85-2.77 (m, 1H), 2.31-2.26 (m, 1H), 2.23-2.17 (m, 3H), 2.17-2.06 (m, 3H), 2.05-1.97 (m, 1H), 1.95-1.88 (m, 2H), 1.72-1.64 (m, 1H), 1.47-1.37 (s, 3H).

Example 132: N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(oxetan-3-yl)-1H-pyrazole-4-carboxamide (Compound 372B)

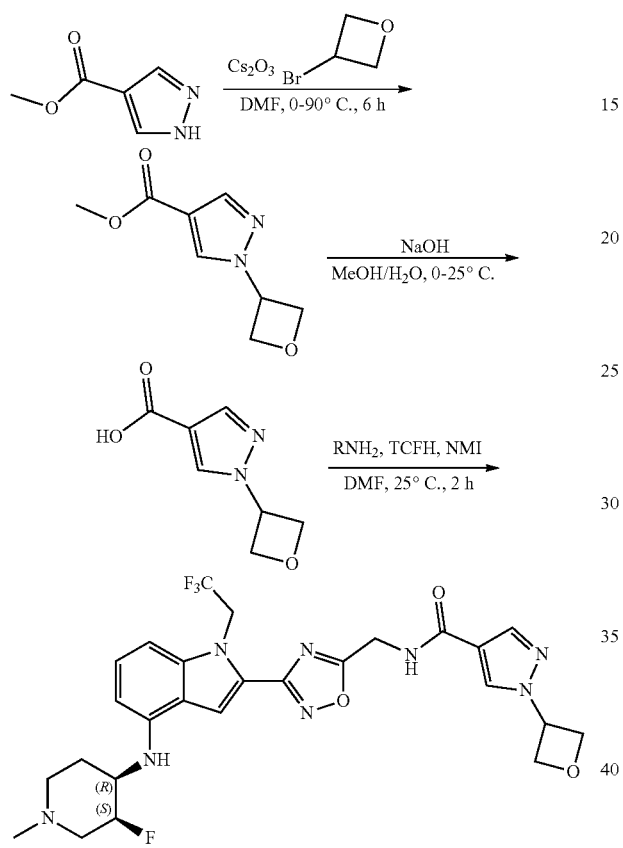

To a solution of methyl 1H-pyrazole-4-carboxylate (500 mg, 3.96 mmol, 1 eq) in DMF (5 mL) was added cesium carbonate (1.29 g, 3.96 mmol, 1 eq) at 0° C. The mixture was stirred at 90° C. for 1 h, followed by addition of 3-bromooxetane (652 mg, 4.76 mmol, 1.2 eq), the mixture was stirred at 90° C. for 5 h. The reaction mixture was poured into water (50 mL), then extracted with EA (30 mL×3). The combined organic layers were washed with brine (30 mL×1), dried over anhydrous sodium sulfate, filtered, and concentrated in vacuo to give a residue. The residue was purified by prep-TLC (SiO$_2$, PE:EA=2:1) to give the expected product (400 mg, 2.20 mmol, 55.4% yield). LC-MS (ES$^+$, m/z): 182.1 [(M+H)$^+$].

To a solution of methyl 1-(oxetan-3-yl)pyrazole-4-carboxylate (200 mg, 1.10 mmol, 1 eq) in water (3 mL) and methanol (6 mL) was added sodium hydroxide (87.8 mg, 2.20 mmol, 2 eq) at 0° C. The mixture was warmed and stirred at 25° C. for 1 h. The combined organic layers were acidified with 1N HCl, filtered, and concentrated in vacuo to give a residue (140 mg, crude). LC-MS (ES$^+$, m/z): 168.0 [(M+H)$^+$].

Amine 1 (80 mg, 144 µmol, 1 eq, 2HCl) and 1-(oxetan-3-yl)pyrazole-4-carboxylic acid (36.37 mg, 216.29 µmol, 1.5 eq) were reacted under method E. The residue was purified by prep-TLC (SiO$_2$, DCM:methanol=10:1) to give the desired product N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(oxetan-3-yl)-1H-pyrazole-4-carboxamide (12 mg, 20 µmol, 13.8% yield, 95.9% purity). LC-MS (ES$^+$, m/z): 576.2 [(M+H)$^+$]. $^1$H NMR (400 MHz, DMSO-d$_6$) δ=9.08 (t, J=5.69 Hz, 1H), 8.40 (s, 1H), 8.08 (s, 1H), 7.89 (s, 1H), 7.12 (t, J=8.01 Hz, 1H), 6.89 (d, J=8.31 Hz, 1H), 6.29 (d, J=7.83 Hz, 1H), 6.02 (br d, J=8.19 Hz, 1H), 5.64 (quin, J=6.88 Hz, 1H), 5.51 (q, J=8.80 Hz, 2H), 4.98-4.85 (m, 5H), 4.79 (d, J=5.62 Hz, 2H), 3.71-3.50 (m, 1H), 3.70-3.49 (m, 1H), 3.13-2.99 (m, 1H), 3.19-2.98 (m, 1H), 2.89-2.79 (m, 1H), 2.89-2.79 (m, 1H), 2.30-2.26 (m, 1H), 2.21 (s, 4H), 2.13 (br d, J=11.98 Hz, 1H), 2.06-1.98 (m, 1H), 1.96 (br s, 1H), 2.06-1.96 (m, 1H), 1.69 (br d, J=10.76 Hz, 1H), 1.74-1.64 (m, 1H).

Example 133: Trans-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-[(1R,3R)-3-hydroxy-3-methylcyclopentyl]-1H-pyrrole-3-carboxamide (Compound 373B), and Cis-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-[(1R,3S)-3-hydroxy-3-methylcyclopentyl]-1H-pyrrole-3-carboxamide (Compound 374B)

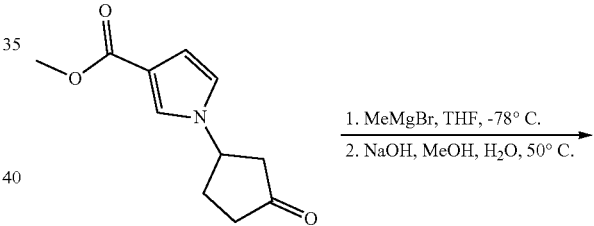

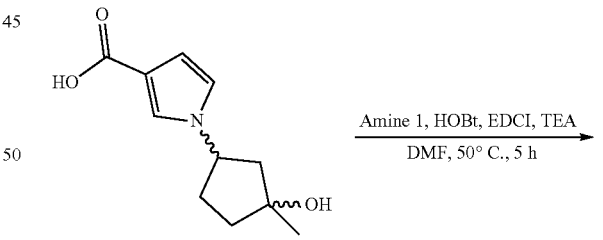

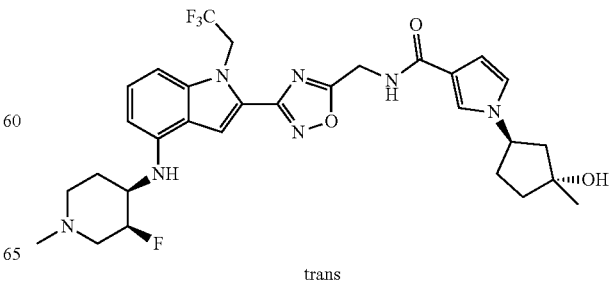

trans

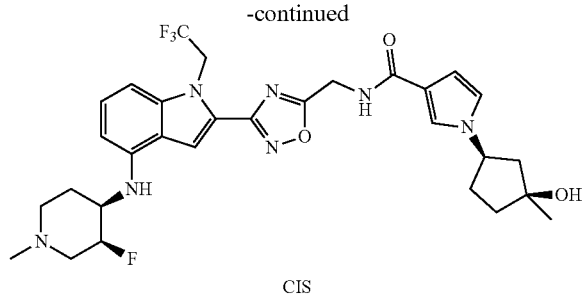

CIS

To a mixture of the previously prepared methyl 1-(3-oxocyclopentyl) pyrrole-3-carboxylate (0.4 g, 1.93 mmol, 1 eq) in THF (5 mL) was added bromo(methyl)magnesium (3 M, 3.22 mL, 5 eq) at −78° C. under nitrogen. The mixture was stirred at −78° C. for 2 h. The residue was poured into sat. ammonium chloride (100 mL). The aqueous phase was extracted with EA (3×30 mL). The combined organic phase was washed with brine (3×30 mL), dried over anhydrous sodium sulfate, filtered, and concentrated in vacuo. The residue was purified by prep-TLC (SiO$_2$, DCM: methanol=20: 1) to give the product (90 mg, 403 μmol, 20.9% yield). LC-MS (ES$^+$, m/z): 224.1 [(M+H)$^+$].

To a mixture of methyl 1-(3-hydroxy-3-methyl-cyclopentyl)pyrrole-3-carboxylate (60 mg, 269 μmol, 1 eq) in methanol (2 mL) and water (0.5 mL) was added sodium hydroxide (43 mg, 1.07 mmol, 4 eq) in one portion at 50° C. under nitrogen. The mixture was stirred at 50° C. for 12 h. The residue was poured into 2M HCl to adjust pH=7~8, then concentrated in vacuo to give the desired product (250 mg, crude) as a mixture of cis and trans LC-MS (ES$^-$, m/z): 210.0 [(M+H)~].

Amine 1 (100 mg, 180.24 μmol, 1 eq, 2HCl) and the above carboxylic acid (226.3 mg, 216 μmol, 1.2 eq) were reacted under method A. The reaction was purified by prep-TLC (SiO$_2$, DCM: methanol=10:1), to give the products as separated cis and trans isomers. Trans (8.2 mg, 12.6 μmol, 7.0% yield, 95.1% purity). LC-MS: ES$^+$, m/z: 618.3 [(M+H)$^+$]. $^1$H NMR (400 MHz, DMSO-d6) δ ppm 8.64 (t, J=5.60 Hz, 1H), 7.89 (s, 1H), 7.48 (s, 1H), 7.06-7.21 (m, 1H), 6.92-6.88 (m, 2H), 6.59-6.44 (m, 1H), 6.30 (d, J=7.80 Hz, 1H), 6.06 (br s, 1H), 5.58-5.45 (m, 2H), 5.04-4.49 (m, 1H), 4.76-4.66 (m, 3H), 4.51 (s, 1H), 3.68 (br s, 1H), 3.12 (br s, 1H), 2.90 (br s, 1H), 2.30 (br d, J=6.24 Hz, 3H), 2.15 (br s, 2H), 2.13-2.03 (m, 2H), 1.92-1.82 (m, 2H), 1.81-1.76 (m, 2H), 1.65-1.75 (m, 2H), 1.32 (s, 3H); Cis (17.5% yield). LC-MS: ES$^+$, m/z: 618.4 [(M+H)$^+$]. $^1$H NMR (400 MHz, DMSO-d6) δ ppm 8.64 (t, J=5.60 Hz, 1H), 7.89 (s, 1H), 7.47-7.58 (m, 1H), 7.11 (t, J=8.00 Hz, 1H), 6.95-6.85 (m, 2H), 6.53-6.44 (m, 1H), 6.28 (d, J=7.80 Hz, 1H), 6.02 (br d, J=8.30 Hz, 1H), 5.50 (q, J=8.40 Hz, 2H), 4.94-4.77 (m, 1H), 4.72 (d, J=5.60 Hz, 2H), 4.64 (s, 1H), 4.6-4.50 (m, 1H), 3.75-3.49 (m, 1H), 3.06 (br s, 11H), 2.83 (br s, 1H), 2.25-2.20 (m, 3H), 2.19-2.12 (m, 3H), 2.10-1.91 (m, 3H), 1.85-1.76 (m, 2H), 1.69 (br d, J=10.40 Hz, 1H), 1.54 (td, J=12.00, 7.27 Hz, 1H), 1.27 (s, 3H).

Example 134: Compound 375B: 1-[(1R,2R)-2-ethoxycyclopentyl]-N-{[3-(4-{[(3S,4R)-3-fluoro-1-methylpiperidin-4-yl]amino}-1-(2,2,2-trifluoro-ethyl)-1H-indol-2-yl)-1,2,4-oxadiazol-5-yl]methyl}-1H-pyrazole-4-carboxamide (Compound 375B)

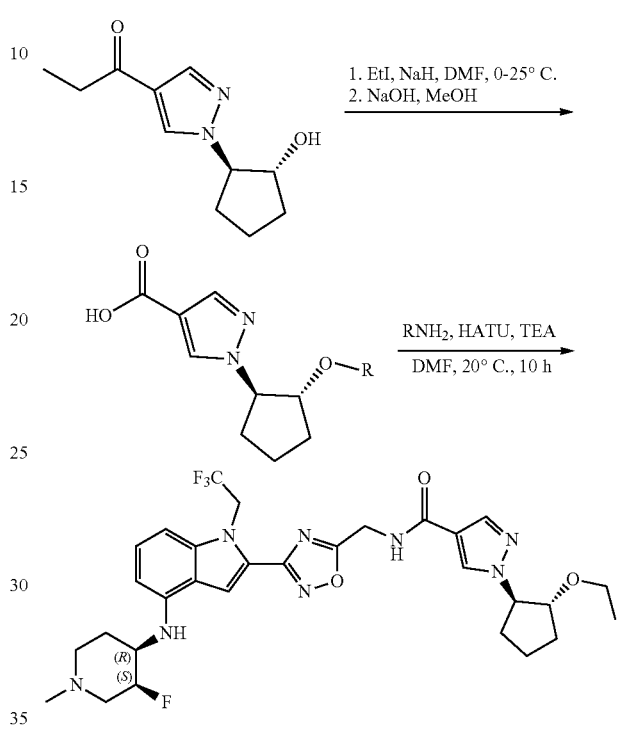

To a mixture of the previously prepared methyl 1-[(1R, 2R)-2-hydroxycyclopentyl]pyrazole-4-carboxylate (150 mg, 714 μmol, 1 eq) in DMF (2 mL) was added sodium hydride (85.6 mg, 2.14 mmol, 60% purity, 3 eq) at 0° C. under nitrogen. The mixture was stirred at 0° C. for 30 min, followed by addition of ethyl iodide (1.43 mmol, 114 μL 2 eq). The mixture was stirred at 20° C. for 30 min. The residue was poured into sat. ammonium chloride (100 mL). The aqueous phase was extracted with EA (3×30 mL). The combined organic phase was washed with brine (3×30 mL), dried over anhydrous sodium sulfate, filtered, and concentrated in vacuo. The residue was purified by prep-TLC to give the desired product (130 mg, 57.4% yield).

To a mixture of methyl 1-[(1R,2R)-2-ethoxycyclopentyl] pyrazole-4-carboxylate (100 mg, 420 μmol, 1 eq) in methanol (5 mL) was added sodium hydroxide (5 M, 170 μL 2 eq) in one portion at 20° C. The mixture was stirred at 20° C. for 4 hrs. The residue was poured into 1N HCl (aq) to adjust pH=7, then concentrated in vacuo to provide the carboxylic acid (760 mg, crude). LC-MS (ES$^+$,m/z): 225.0[(M+H)$^+$].

The 1-[(1R,2R)-2-ethoxycyclopentyl]pyrazole-4-carboxylic acid (323 mg, 216 μmol, 2 eq) in DMF (1 mL) was reacted with Amine 1 (60 mg, 108.1 μmol, 1 eq, 2HCl) under method B, then purified by prep-TLC to give the desired product (20.5 mg, 28.6% yield, 95.3% purity). LC-MS (ES$^+$,m/z): 633.3 [(M+H)$^+$]. $^1$H NMR (400 MHz, DMSO-d$_6$) δ ppm 1.04 (t, J=6.95 Hz, 1H), 9.00 (t, J=5.73 Hz, 1H)8.32 (s, 1H), 7.94-7.92(m, 1H), 7.89 (s, 1H), 7.17-7.05 (m, 1H), 6.88 (d, J=8.16 Hz, 1H), 6.28 (d, J=7.72 Hz, 1H), 6.02 (br d, J=8.16 Hz, 1H), 5.50-5.41 (m, 1H), 4.92-4.74 (m, 1H), 4.63-4.52 (m, 1H), 4.06 (q, J=5.95 Hz, 1H), 3.66-3.52

(m, 1H), 3.36 (q, J=7.20 Hz, 1H), 3.09-2.96 (m, 1H), 2.89-2.79 (m, 1H), 2.27-2.18 (m, 1H), 2.18-2.10 (m, 1H), 2.10-2.00 (m, 1H), 2.00-1.82 (m, 1H), 1.77 (dt, J=17.92, 7.14 Hz, 1H), 1.72-1.56 (m, 1H).

Example 135: 1-[(1R,2R)-2-ethoxycyclopentyl]-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-pyrrole-3-carboxamide (Compound 376B)

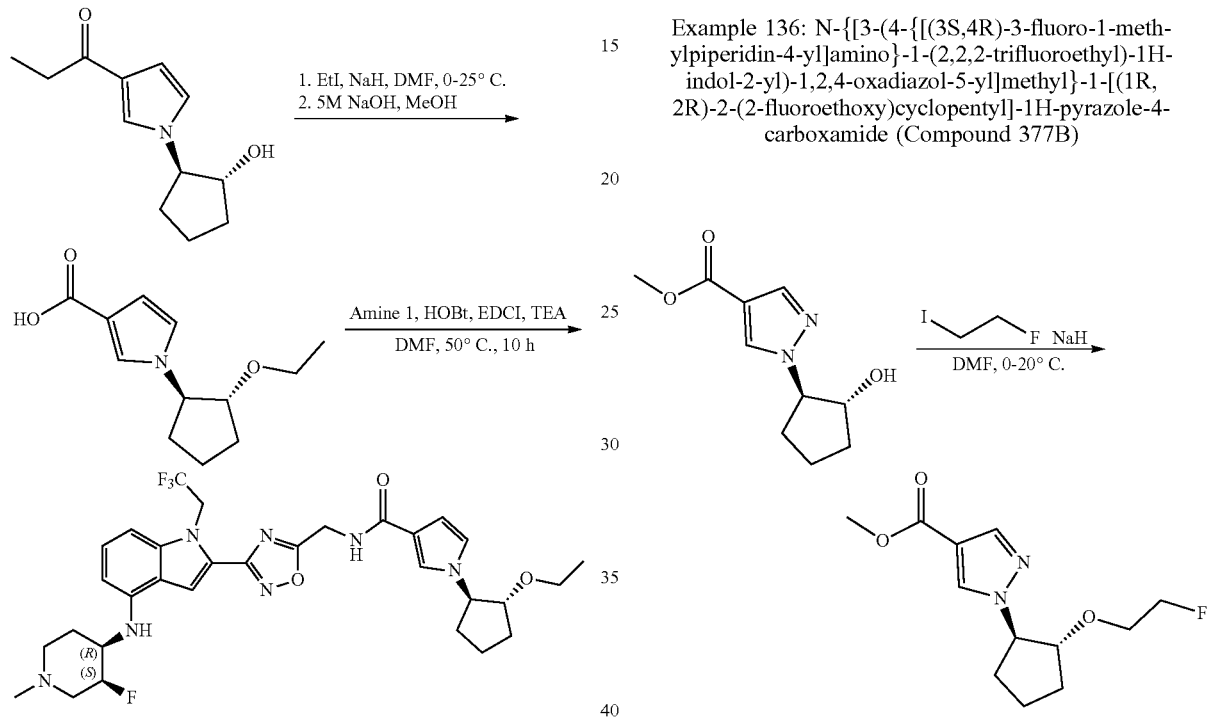

To a solution of methyl 1-[(1R,2R)-2-hydroxycyclopentyl]pyrrole-3-carboxylate (200 mg, 956 μmol, 1 eq) in DMF (2 mL) was added sodium hydride (114.7 mg, 2.87 mmol, 60% purity, 3 eq) in one portion at 0° C. under nitrogen. The mixture was stirred at 0° C. for 30 min, followed by addition of ethyl iodide (1.91 mmol, 153 μL 2.0 eq), and the mixture was warmed and stirred at 20° C. for 30 min. The residue was poured into ammonium chloride (100 mL). The aqueous phase was extracted with EA (3×30 mL). The combined organic phase was washed with brine (3×30 mL), dried over anhydrous sodium sulfate, filtered, and concentrated in vacuo. The residue was purified by prep-TLC to give the product (140 mg, 61.7% yield).

To a mixture of methyl 1-[(1R,2R)-2-ethoxycyclopentyl]pyrrole-3-carboxylate (130 mg, 548 μmol, 1 eq) in methanol (5 mL) was added sodium hydroxide (5 M, 1 mL, 9.1 eq) at 50° C. under nitrogen. The mixture was stirred at 50° C. for 10 h. The residue was poured into 1N HCl (aq) to adjust pH=7, then concentrated in vacuo to give the desired carboxylic acid product (823 mg, crude) LC-MS (ES+, m/z): 238.0 [(M+H)+].

Amine 1 (60 mg, 108 μmol, 1 eq, 2HCl) and 1-[(1R,2R)-2-ethoxycyclopentyl]pyrrole-3-carboxylic acid (644 mg, 433 μmol, 4 eq) were coupled under method A. The reaction was purified by prep-TLC to provide the desired product 1-[(1R,2R)-2-ethoxycyclopentyl]-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-pyrrole-3-carboxamide (23.2 mg, 33.2% yield, 97.6% purity). LC-MS (ES+, m/z): 632.3 [(M+H)~]. $^1$H NMR (400 MHz, DMSO-d6) δ=7.47 (s, 1H), 7.15-7.06 (m, 1H), 6.94-6.84 (m, 2H), 6.53-6.48 (m, 1H), 6.28 (d, J=7.94 Hz, 1H), 6.03 (br d, J=8.16 Hz, 1H), 5.50 (q, J=9.04 Hz, 1H), 4.93-4.75 (m, 1H), 4.72 (d, J=5.73 Hz, 1H), 4.33-4.20 (m, 1H), 3.91 (q, J=6.39 Hz, 1H), 3.70-3.51 (m, 1H), 3.42-3.32 (m, 1H), 3.11-2.97 (m, 1H), 2.87-2.77 (m, 1H), 2.19 (br s, 1H), 2.17-2.08 (m, 1H), 2.08-2.00 (m, 1H), 2.00-1.85 (m, 1H), 1.62-1.51 (m, 1H), 1.04 (t, J=6.95 Hz, 1H).

Example 136: N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-[(1R,2R)-2-(2-fluoroethoxy)cyclopentyl]-1H-pyrazole-4-carboxamide (Compound 377B)

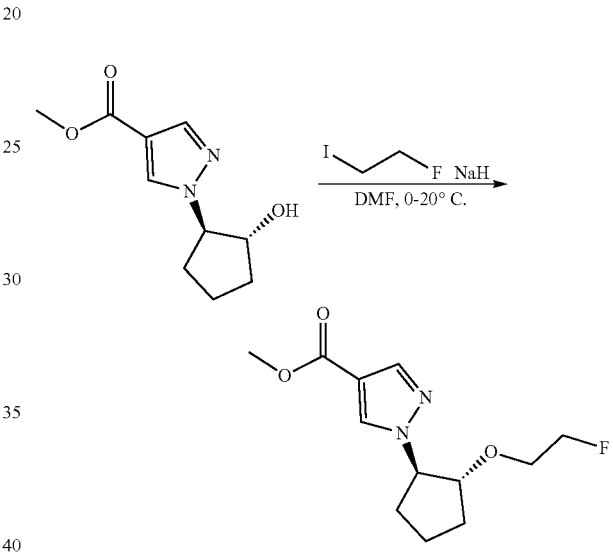

To a mixture of methyl 1-[(1R,2R)-2-hydroxycyclopentyl]pyrazole-4-carboxylate (150 mg, 714 mol, 1 eq) in DMF (2 mL) was added sodium hydride (85.6 mg, 2.14 mmol, 60% purity, 3 eq) in one portion at 0° C. under nitrogen. The mixture was stirred at 0° C. for 30 min, followed by addition of 1-fluoro-2-iodoethane (1.43 mmol, 114 μL 2 eq). The mixture was stirred at 20° C. for 30 min, then the residue was poured into ammonium chloride (100 mL). The aqueous phase was extracted with EA (3×30 mL). The combined organic phase was washed with brine (3×30 mL), dried over anhydrous sodium sulfate, filtered, and concentrated in vacuo. The residue was purified by prep-TLC, to give the product (48 mg, 13.6% yield). LC-MS (ES+,m/z): 257.1 [(M+H)+].

To a mixture of methyl 1-[(1R,2R)-2-ethoxycyclopentyl]pyrazole-4-carboxylate (100 mg, 420 μmol, 1 eq) in methanol (5 mL) was added sodium hydroxide (5 M, 170 μL2 eq) at 20° C. under nitrogen. The mixture was stirred at 20° C. for 4 hrs. To the reaction was added 1N HCl to adjust pH=7, then the reaction was concentrated in vacuo. The above acid was coupled with Amine 1 under method B to provide the crude product. The reaction was purified by prep-TLC to provide the desired product (23.7 mg, 32.5% yield, 96.2% purity). LC-MS (ES+,m/z): 651.3 [(M+H)+]. $^1$H NMR (400 MHz, CHLOROFORM-d) δ ppm 8.02 (s, 1H)7.90 (s, 1H), 7.41 (s, 1H), 7.22-7.21 (m, 1H), 6.81 (br d, J=8.16 Hz, 1H), 6.53 (br s, 1H), 6.32 (br d, J=7.50 Hz, 1H), 5.27 (br d, J=7.50 Hz, 1H), 4.95-4.80 (m, 1H), 4.55 (br s, 1H), 4.43 (br s, 1H), 4.19 (br d, J=5.73 Hz, 1H), 3.26 (br t, J=9.70 Hz, 1H), 2.97 (br d, J=10.14 Hz, 1H), 2.37 (br s, 1H), 1.79 (dt, J=12.84, 6.48 Hz, 1H), 2.32-2.21 (m, 1H), 2.19-2.11 (m, 1H), 2.11-2.00 (m, 1H), 1.96-1.88 (m, 1H), 1.79 (dt, J=12.84, 6.48 Hz, 1H).

Example 137: N-[(3S,4R)-3-fluoro-1-methylpiperidin-4-yl]-2-(5-{[(5-methoxypyridin-2-yl)amino]methyl}-1,2,4-oxadiazol-3-yl)-1-(2,2,2-trifluoroethyl)-1H-indol-4-amine (Compound 378B)

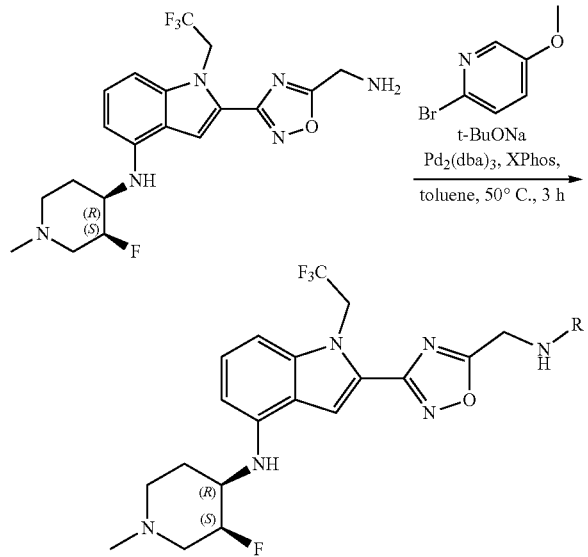

Amine 1 and 2-bromo-5-methoxypyridine were coupled under Buchwald conditions to provide the desired product in 5.0% yield, LC-MS (ES⁺, m/z): 534.2 [(M+H)-]. $^1$H NMR (400 MHz, DMSO-d$_6$) δ ppm 7.86 (s, 1H), 7.68 (d, J=2.87 Hz, 1H), 7.21 (dd, J=8.93, 2.98 Hz, 1H), 7.14-7.09 (m, 1H), 7.06 (t, J=6.06 Hz, 1H), 6.87 (d, J=8.16 Hz, 1H), 6.64 (d, J=9.04 Hz, 1H), 6.28 (d, J=7.50 Hz, 1H), 5.97 (br d, J=8.82 Hz, 1H), 5.48 (q, J=9.04 Hz, 2H), 4.92-4.77 (m, 3H), 3.67 (s, 3H), 3.57 (br s, 1H), 3.05 (br s, 1H), 2.83 (br s, 1H), 2.30-2.23 (m, 1H), 2.21 (br s, 3H), 2.12 (br s, 1H), 2.00 (br d, J=10.58 Hz, 1H), 1.71 (br s, LH).

Example 138: N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(oxetan-3-yl)-1H-pyrrole-3-carboxamide (Compound 379B)

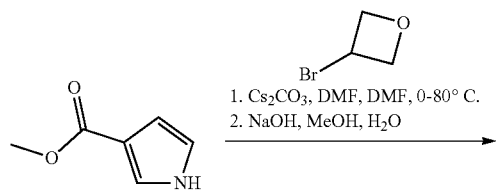

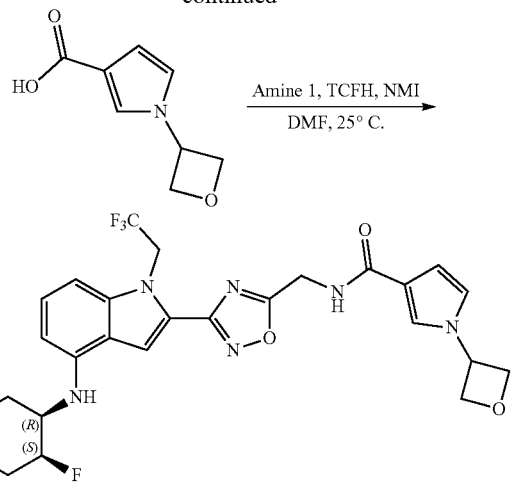

To a solution of methyl 1H-pyrrole-3-carboxylate (300 mg, 2.40 mmol, 1 eq) in DMF (5 mL) was added cesium carbonate (1.56 g, 4.80 mmol, 2 eq) at 0° C., followed by addition of 3-bromooxetane (394 mg, 2.88 mmol, 1.2 eq), and the mixture was heated and stirred at 80° C. for 4 h. The reaction mixture was poured into water (50 mL), then extracted with EA (3×30 mL). The combined organic layers were washed with brine (30 mL), dried over anhydrous sodium sulfate, filtered, and concentrated in vacuo to give a residue. The residue was purified by prep-TLC (SiO$_2$, DCM:methanol=2:1) to give the product (200 mg, 1.10 mmol, 46% yield). LC-MS (ES⁺, m/z): 182.1[(M+H)].

To a solution of methyl 1-(oxetan-3-yl)pyrrole-3-carboxylate (90 mg, 497 μmol, 1 eq) in water (2 mL) and methanol (4 mL) was added sodium hydroxide (39.7 mg, 993 μmol, 2 eq). The mixture was stirred at 50° C. for 1 h. The reaction was filtered, and concentrated in vacuo to give a residue. The reaction was without further worked-up as for previous to give the product (100 mg, crude). LC-MS (ES⁺, m/z): 166.0[(M+H)⁺].

Amine 1 (50 mg, 90.12 μmol, 1 eq, 2HCl) was coupled with the above 1-(oxetan-3-yl)pyrrole-3-carboxylic acid (22.60 mg, 135.18 μmol, 1.5 eq) using method E. The reaction was purified by prep-TLC (SiO$_2$, DCM:methanol=10:1) to give the desired product N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(oxetan-3-yl)-1H-pyrrole-3-carboxamide (20.4 mg 36.8% yield, 93.6% purity). LC-MS (ES⁺, m/z): 576.3[(M+H)⁺].

$^1$H NMR (400 MHz, DMSO-d6) δ=8.75 (t, J=5.62 Hz, 1H), 7.90 (s, 1H), 7.68 (t, J=1.77 Hz, 1H), 7.16-7.08 (m, 2H), 6.89 (d, J=8.44 Hz, 1H), 6.60 (dd, J=2.69, 1.83 Hz, 1H), 6.29 (d, J=7.82 Hz, 1H), 6.18-6.07 (m, 1H), 6.01 (br d, J=8.31 Hz, 1H), 5.51 (q, J=8.72 Hz, 2H), 5.39 (quin, J=6.85 Hz, 1H), 5.43-5.35 (m, 1H), 4.95 (t, J=7.27 Hz, 1H), 4.98-4.93 (m, 1H), 4.92-4.78 (m, 1H), 4.91-4.77 (m, 1H), 4.77-4.72 (m, 4H), 3.67-3.53 (m, 1H), 3.04 (br t, J=10.21 Hz, 1H), 2.82 (br d, J=10.39 Hz, 1H), 2.35-2.27 (m, 1H), 2.20 (s, 4H), 2.15-2.07 (m, 1H), 2.06-1.97 (m, 1H), 1.73-1.62 (m, 1H).

Example 139: N-[(3S,4R)-3-fluoro-1-methylpiperidin-4-yl]-2-(5-{[(4-methoxyphenyl)amino]methyl}-1,2,4-oxadiazol-3-yl)-1-(2,2,2-trifluoroethyl)-1H-indol-4-amine (Compound 380B)

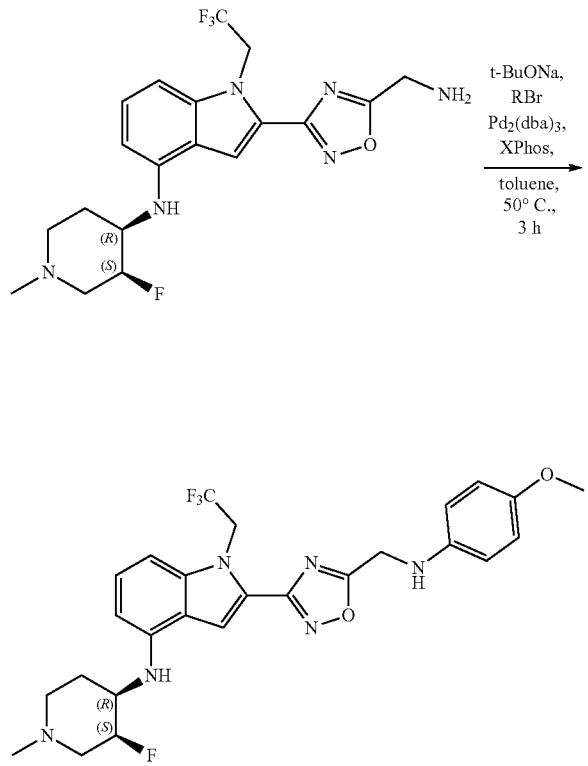

Example 140: N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-[(1R,2R)-2-(2-fluoroethoxy)cyclopentyl]-1H-pyrrole-3-carboxamide (Compound 381B)

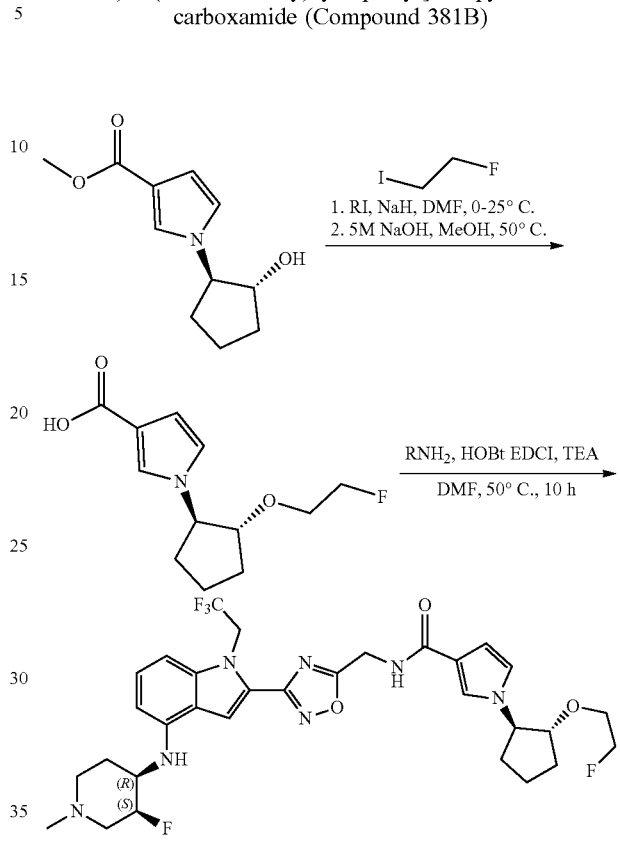

To a mixture of Amine 1 (100 mg, 235 μmol, 1 eq) and 1-bromo-4-methoxy-benzene (280 μmol, 35 μL 1.2 eq) in toluene (2 mL) were added sodium t-butoxide (31.6 mg, 328.mol, 1.4 eq), XPhos (13.4 mg, 28.1 μmol, 0.1 eq), and $Pd_2(dba)_3$ (12.9 mg, 14.1 μmol, 0.1 eq) at 50° C. under nitrogen. The mixture was stirred at 50° C. for 3 h. The residue was poured into EDTA (sat., 100 mL), and stirred for 60 min. The aqueous phase was extracted with EA (3×30 mL). The combined organic phase was washed with brine (3×30 mL), dried over anhydrous sodium sulfate, filtered, and concentrated in vacuo. The reaction was purified by prep-TLC ($SiO_2$, DCM/methanol=20:1) to provide the product (10.3 mg, 18.41 μmol, 7.9% yield, 95.2% purity) as a white solid. LC-MS (ES$^+$, m/z):533.2 [(M+H)$^+$]. $^1$H NMR (400 MHz, DMSO-$d_6$) δ ppm 7.91 (s, 1H), 7.13 (t, J=8.00 Hz, 1H), 6.90 (br d, J=7.88 Hz, 1H), 6.76 (br d, J=8.88 Hz, 2H), 6.65 (br d, J=8.50 Hz, 2H), 6.12 (br t, J=6.32 Hz, 1H), 6.02 (br d, J=8.00 Hz, 1H), 5.57-5.42 (m, 2H), 4.96-4.78 (m, 1H), 4.74-4.65 (m, 2H), 3.65 (s, 3H), 3.58 (br s, 1H), 3.06 (br t, J=11.26 Hz, 1H), 2.84 (br d, J=9.76 Hz, 1H), 2.32 (br s, 1H), 2.21 (s, 3H), 2.10 (br d, J=11.76 Hz, 1H), 2.02 (br d, J=9.63 Hz, 1H), 1.71 (br d, J=10.76 Hz, 1H).

To a mixture of methyl 1-[(1R,2R)-2-hydroxycyclopentyl]pyrrole-3-carboxylate (200 mg, 956 μmol, 1 eq) in DMF (2 mL) was added sodium hydride (114.7 mg, 2.87 mmol, 60% purity, 3 eq) at 0° C. under nitrogen. The mixture was stirred at 0° C. for 30 min, and then 1-fluoro-2-iodoethane was added (1.91 mmol, 153 μL 2 eq). The mixture was stirred at 20° C. for 30 min. The residue was poured into ammonium chloride (100 mL). The aqueous phase was extracted with EA (3×30 mL). The combined organic phase was washed with brine (3×30 mL), dried over anhydrous sodium sulfate, filtered, and concentrated in vacuo. The residue was purified by prep-TLC to give the product (42 mg, 164.5 μmol, 13.2% yield).

To a mixture of methyl 1-[(1R,2R)-2-ethoxycyclopentyl]pyrrole-3-carboxylate (130 mg, 548 mol, 1 eq) in methanol (5 mL) was added sodium hydroxide (5 M, 1 mL, 9.1 eq) at 50° C. under nitrogen. The mixture was stirred at 50° C. for 10 h. The residue was poured into HCl (aq) to adjust pH=7, then concentrated in vacuo to give the acid product (400 mg, crude).

Amine 1 and the above acid were coupled under method A to provide the desired product N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-[(1R,2R)-2-(2-fluoroethoxy)cyclopentyl]-1H-pyrrole-3-carboxamide. LC-MS (ES$^+$, m/z): 650.3 [(M+H)$^+$]. $^1$H NMR (400 MHz, DMSO-d6) δ=8.66 (t, J=5.62 Hz, 1H), 7.89 (s, 1H), 7.48 (t, J=1.76 Hz, 1H), 7.16-7.06 (m, 1H), 6.92 (t, J=2.54 Hz, 1H), 6.87 (d, J=8.16 Hz, 1H), 6.52 (dd, J=2.65, 1.76 Hz, 1H), 6.28 (d, J=7.72 Hz, 11H), 6.00 (br d, J=8.38

Hz, 1H), 5.50 (q, J=8.75 Hz, 1H), 4.92-4.75 (m, 1H), 4.73 (d, J=5.73 Hz, 1H), 4.51 (t, J=4.08 Hz, 1H), 4.39 (t, J=3.97 Hz, 1H), 4.37-4.29 (m, 1H), 4.00 (q, J=6.17 Hz, 1H), 3.65-3.55 (m, 1H), 3.54-3.49 (m, 1-1), 3.09-2.96 (m, 1H), 2.86-2.76 (m, 1H), 2.26 (br d, J=11.25 Hz, 1H), 2.21-2.13 (m, 1H), 2.12-1.93 (m, 1H), 1.89-1.72 (m, 1H), 1.71-1.58 (m, 1H).

Example 141: rac-1-tert-butyl-N-{[3-(4-{[(3R,4S)-4-fluoropiperidin-3-yl]amino}-1-(2,2,2-trifluoro-ethyl)-1H-indol-2-yl)-1,2,4-oxadiazol-5-yl]methyl}-1H-pyrrole-3-carboxamide (Compound 382B)

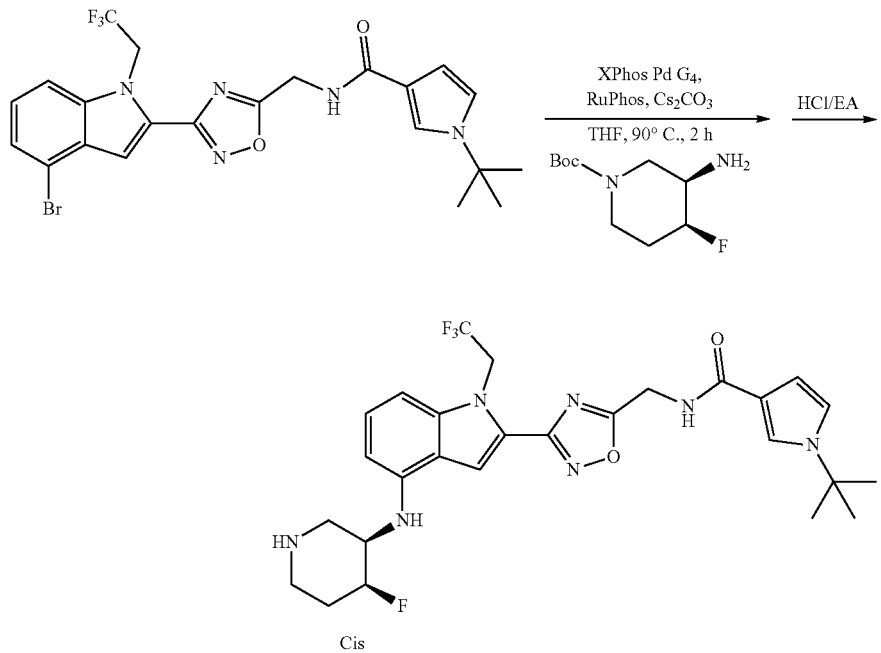

To a solution of N-[[3-[4-bromo-1-(2,2,2-trifluoroethyl)indol-2-yl]-1,2,4-oxadiazol-5-yl]methyl]-1-tert-butyl-pyrrole-3-carboxamide (120 mg, 229 µmol, 1 eq) and tert-butyl (3R,4S-3-amino-4-fluoro-piperidine-1-carboxylate (59.9 mg, 275 µmol, 1.2 eq) in THF (5 mL) were added cesium carbonate (223.7 mg, 687 µmol, 3 eq), XPhos Generation 4 (21.1 mg, 22.9 µmol, 0.1 eq), and dicyclohexyl-[2-(2,6-diisopropoxyphenyl) phenyl]phosphane (21.4 mg, 45.8 µmol, 0.2 eq), and the reaction was stirred at 90° C. for 2 h. The mixture was poured into EDTA (sat., 10 mL) and stirred for 2 h. Then mixture was extracted with DCM (2×10 mL), and the organic phase was washed with water (10 mL) and brine (10 mL), dried over sodium sulfate, and concentrated. The residue was purified by prep-TLC (SiO$_2$, DCM: methanol=20:1) to afford tert-butyl (3R,4S)-3-[[2-[5-[[(1-tert-butylpyrrole-3-carbonyl)amino]methyl]-1,2,4-oxadiazol-3-yl]-1-(2,2,2-trifluoroethyl) indol-4-yl]amino]-4-fluoro-piperidine-1-carboxylate (10.4 mg, 15.26 µmol, 6.7% yield, 97.1% purity) as a yellow solid. LC-MS (ES$^+$, m/z): 662.7 [(M+H)$^+$]. $^1$H NMR (400 MHz, DMSO-d$_6$) δ=8.64 (t, J=5.7 Hz, 1H), 7.88 (s, 1H), 7.54 (t, J=2.0 Hz, 1H), 7.13 (t, J=8.1 Hz, 1H), 6.99 (t, J=2.6 Hz, 1H), 6.93 (d, J=8.3 Hz, 1H), 6.50 (dd, J=1.8, 2.8 Hz, 1H), 6.36 (d, J=7.9 Hz, 1H), 6.04 (br d, J=7.2 Hz, 1H), 5.52 (q, J=8.8 Hz, 2H), 5.12-4.91 (m, 1H), 4.73 (d, J=5.7 Hz, 2H), 3.74 (br s, 2H), 3.31 (s, 2H), 3.06 (br t, J=11.4 Hz, 1H), 2.12-1.74 (m, 2H), 1.49 (s, 9H), 1.33 (br s, 9H).

tert-butyl (3R,4S)-3-[[2-[5-[[(1-tert-butylpyrrole-3-carbonyl) amino]methyl]-1,2,4-oxadiazol-3-yl]-1-(2,2,2-trifluoroethyl)indol-4-yl]amino]-4-fluoro-piperidine-1-carboxylate (35 mg, 52.9 µmol, 1 eq) was treated with HCl/EA (4 M, 5 mL) and stirred at 25° C. 2 h. The solvent was removed in vacuo. The residue was purified by prep-HPLC (FA condition) to afford 1-tert-butyl-N-[[3-[4-[[(3R,4S)-4-fluoro-3-piperidyl]amino]-1-(2,2,2-trifluoroethyl)indol-2-yl]-1,2,4-oxadiazol-5-yl]methyl]pyrrole-3-carboxamide (21.6 mg, 72.7% yield, 100% purity) LC-MS (ES$^+$, m/z): 562.5 [(M+H)$^+$]. $^1$H NMR (400 MHz, DMSO-d$_6$) δ=8.65 (t, J=5.6 Hz, 1H), 8.18 (s, 1H), 7.86 (s. 1H), 7.55 (t, J=2.1 Hz, 1H), 7.17-7.09 (m, 1H), 6.99 (t, J=2.6 Hz, 1H), 6.91 (d, J=8.2 Hz, 1H), 6.51 (dd, J=2.0, 2.9 Hz, 1H), 6.31 (d, J=7.9 Hz, 1H), 5.98 (d, J=8.4 Hz, 1H), 5.51 (q, J=8.9 Hz, 2H), 5.15-4.88 (m, 1H), 4.74 (d, J=5.7 Hz, 2H), 3.89-3.60 (m, 1H), 2.98-2.87 (m, 2H), 2.81 (br d, J=6.0 Hz, 2H), 2.04-1.73 (m, 2H), 1.50 (s, 9H).

Example 142: N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(1-methoxy-2-methylpropan-2-yl)-1H-pyrrole-3-carboxamide (Compound 383B)

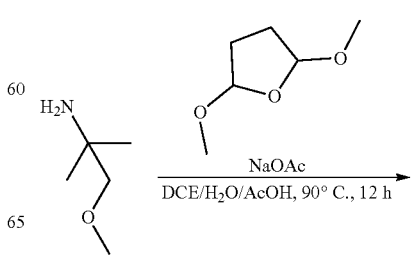

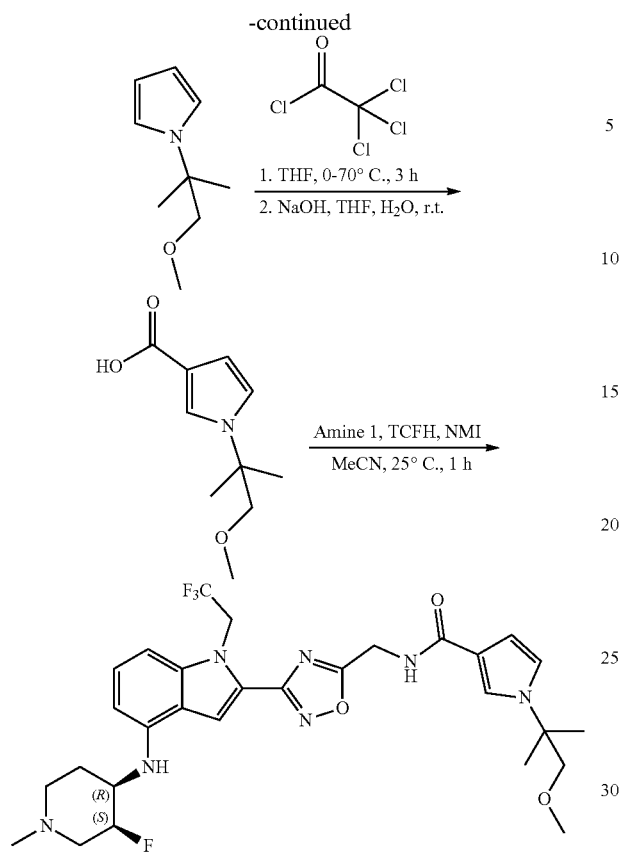

To a solution of 1-methoxy-2-methyl-propan-2-amine (3 g, 29.1 mmol, 1 eq) in DCE (20 mL), water (12 mL), and acetic acid (4 mL) was added sodium acetate (3.58 g, 43.6 mmol, 1.5 eq). After 30 minutes, 2,5-dimethoxytetrahydrofuran (29.1 mmol, 3.77 mL, 1 eq) was added, and the reaction was stirred 11.5 h at 90° C. The residue was poured into ice-water (w:w=1:1) (10 mL) and stirred for 10 min. The aqueous phase was extracted with EA (3×10 mL). The combined organic phase was washed with brine (3×10 mL), dried over anhydrous sodium sulfate, filtered, and concentrated in vacuo to afford the pyrrole product (3 g, crude) LC-MS (ES$^+$, m/z): 154.2 [(M+H)$^+$]. $^1$H NMR (400 MHz, DMSO-d$_6$) δ=6.86 (t, J=2.1 Hz, 2H), 5.96 (t, J=2.2 Hz, 2H), 3.41 (s, 2H), 3.17 (s, 3H), 1.43 (s, 6H).

To a solution of 1-(2-methoxy-1,1-dimethyl-ethyl)pyrrole (300 mg, 1.96 mmol, 1 eq) in THF (5 mL) was added 2,2,2-trichloroacetyl chloride (5.87 mmol, 655 μL 3 eq) at 0° C. After 30, the reaction was heated to 70° C. for 2.5 h. The residue was poured into ice/water (w:w=1:1) (10 mL) and stirred for 10 min. The aqueous phase was extracted with EA (3×10 mL). The combined organic phase was washed with brine (3×10 mL), dried over anhydrous sodium sulfate, filtered, and concentrated in vacuo to afford the ketone product (200 mg, crude) LC-MS (ES$^+$, m/z): 298.0 [(M+H)$^+$].

To a solution of 2,2,2-trichloro-11-[-(2-methoxy-1,1-dimethyl-ethyl)pyrrol-3-yl]ethanone (200 mg, 670 μmol, 1 eq) in THF (2 mL) was added sodium hydroxide (3 M, 13.3 mL, 60 eq) and the reaction stirred at 25° C. for 2 h. The residue was poured into HCl (4 M) (10 mL) and stirred for 10 min. The aqueous phase was extracted with EA (3×10 mL). The combined organic phase was washed with brine (3×10 mL), dried over anhydrous sodium sulfate, filtered, and concentrated in vacuo to provide the acid (90 mg, crude). LC-MS (ES$^+$, m/z): 198.2[(M+H)$^+$]. $^1$H NMR (400 MHz, DMSO-d6) δ=7.42 (s, 1H), 6.94 (t, J=2.5 Hz, 1H), 6.35 (dd, J=1.8, 2.6 Hz, 1H), 3.45 (s, 2H), 3.19 (s, 4H), 1.45 (s, 6H).

Amine 1 (200 mg, 401 μmol, 1 eq, 2HCl) was coupled with 1-(2-methoxy-1,1-dimethyl-ethyl)pyrrole-3-carboxylic acid (79 mg, 401 μmol, 1 eq) using method E. The residue was purified by prep-HPLC (FA condition) to provide the desired product N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(1-methoxy-2-methylpropan-2-yl)-1H-pyrrole-3-carboxamide (87.5 mg, 36.0% yield, 99.7% purity). LC-MS (ES$^+$, m/z): 606.3[(M+H)$^+$]. $^1$H NMR (400 MHz, DMSO-d6) δ=8.66 (t, J=5.6 Hz, 1H), 7.89 (s, 1H), 7.52 (s, 1H), 7.17-7.06 (m, 1H), 6.96 (t, J=2.5 Hz, 1H), 6.88 (d, J=8.4 Hz, 1H), 6.49 (br s, 1H), 6.28 (d, J=7.7 Hz, 1H), 6.02 (br d, J=8.4 Hz, 1H), 5.55-5.45 (m, 2H), 4.94-4.77 (m, 1H), 4.73 (d, J=5.5 Hz, 2H), 3.69-3.52 (m, 1H), 3.46 (s, 2H), 3.21 (s, 3H), 3.11-2.98 (m, 1H), 2.83 (br d, J=9.3 Hz, 1H), 2.35-2.24 (m, 1H), 2.20 (s, 3H), 2.17-1.94 (m, 2H), 1.68 (br d, J=11.0 Hz, 1H), 1.47 (s, 6H).

Example 143: N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-[(1R,2R)-2-methoxycyclohexyl]-1H-pyrrole-3-carboxamide (Compound 384B)

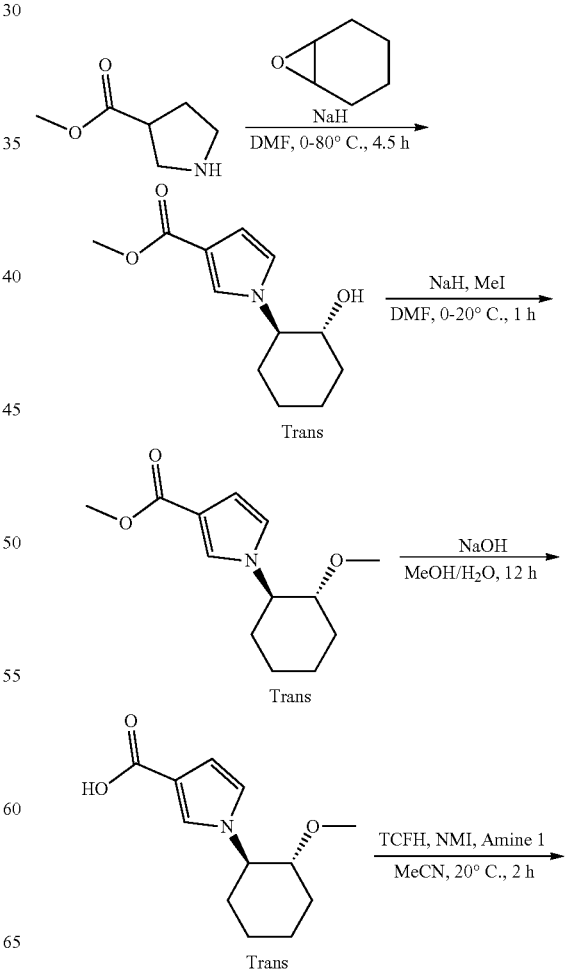

-continued

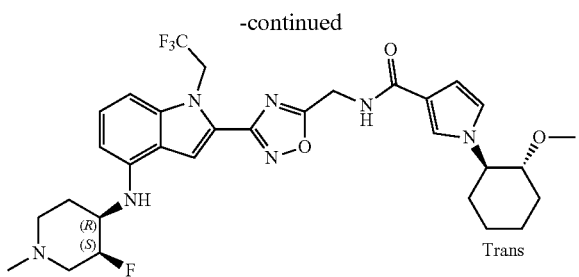

Trans

To a mixture of methyl 1H-pyrrole-3-carboxylate (2 g, 16 mmol, 1 eq) and cyclohexene oxide (16 mmol, 1.62 mL, 1 eq) in DMF (25 mL) was added sodium hydride (1.28 g, 32 mmol, 60% purity, 2 eq) in one portion at 0° C. under nitrogen. The mixture was stirred at 0° C. for 30 min, then heated to 80° C. and stirred for 4 h. The residue was poured into sat. ammonium chloride (20 mL) and stirred for 3 min. The aqueous phase was extracted with EA (3×20 mL). The combined organic phase was washed with brine (3×20 mL), dried over anhydrous sodium sulfate, filtered, and concentrated in vacuo. The residue was purified by column chromatography (SiO$_2$, PE/EA=1:0 to 0:1) to afford the alcohol product (800 mg, 3.58 mmol, 22.4% yield). LC-MS (ES$^+$, m/z): 224.2 [(M+H)$^-$].

To a mixture of methyl 1-[(1R,2R)-2-hydroxycyclohexyl]pyrrole-3-carboxylate (500 mg, 2.24 mmol, 1 eq) in DMF (5 mL) was added sodium hydride (268.7 mg, 6.72 mmol, 60% purity, 3 eq) in one portion at 0° C. The mixture was stirred at 0° C. for 30 min, followed by addition of iodomethane (4.48 mmol, 280 µL 2 eq), and the reaction was warmed to rt and stirred for 30 min. The residue was poured into ammonium chloride (30 mL) and stirred for 3 min. The aqueous phase was extracted with EA (3×30 mL). The combined organic phase was washed with brine (3×30 mL), dried over anhydrous sodium sulfate, filtered, and concentrated in vacuo. The residue was purified by prep-TLC (SiO$_2$, PE:EA=1:1) to provide the methyl ether product (420 mg, 1.77 mmol, 79.0% yield). LC-MS (ES$^+$, m/z): 238.2 [(M+H)].

To a mixture of methyl 1-[(1R, $^2$R)-2-methoxycyclohexyl]pyrrole-3-carboxylate (420 mg, 1.77 mmol, 1 eq) in methanol (6 mL) and water (1.5 mL) was added sodium hydroxide (212.4 mg, 5.31 mmol, 3 eq) at 20° C. The mixture was stirred at 50° C. for 12 h. The residue was poured into HCl (2 M, 5 mL) and stirred for 3 min. The aqueous phase was extracted with EA (3×20 mL). The combined organic phase was washed with brine (3×20 mL), dried over anhydrous sodium sulfate, filtered, and concentrated in vacuo. The reaction was without further purification (390 mg, 1.75 mmol, 98.7% yield). LC-MS (ES$^+$, m/z): 224.1 [(M+H)$^+$].

Amine 1 (40 mg, 80.11 µmol, 1 eq, 2HCl) was coupled with 1-[(1 R,2R)-2-methoxycyclohexyl]pyrrole-3-carboxylic acid (21.5 mg, 96.1 µmol, 1.2 eq) under method E. The crude product was purified by prep-TLC (SiO$_2$, DCM:methanol=10:1) to provide the desired product N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-[(1R,2R)-2-methoxycyclohexyl]-1H-pyrrole-3-carboxamide (29 mg, 45.9 µmol, 57.3% yield). LC-MS (ES$^+$, m/z): 632.3 [(M+H)-]. $^1$H NMR (400 MHz, DMSO-d$_6$) δ=8.63 (t, J=5.62 Hz, 1H), 8.14 (s, 1H), 7.90 (s, 1H), 7.44 (s, 1H), 7.11 (t, J=7.95 Hz, 1H), 6.91-6.84 (m, 2H), 6.49 (br s, 1H), 6.28 (d, J=7.83 Hz, 1H), 6.01 (br d, J=8.19 Hz, 1H), 5.57-5.43 (m, 2H), 4.94-4.68 (m, 3H), 3.82-3.70 (m, 1H), 3.65-3.54 (m, 1H), 3.08-3.01 (m, 1H), 2.98 (s, 3H), 2.83 (br d, J=10.27 Hz, 1H), 2.32-2.22 (m, 1H), 2.21 (s, 3H), 2.19-2.15 (m, 1H), 2.15-1.90 (m, 1H), 1.88 (br s, 1H), 1.72 (br d, 0.1=6.85 Hz, 4H), 1.31 (br t, 0.1=9.78 Hz, 2H), 1.16 (br d, J=9.90 Hz, 1H).

Example 144: N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-[(1R,2R)-2-methoxycyclohexyl]-1H-pyrazole-4-carboxamide (Compound 385B)

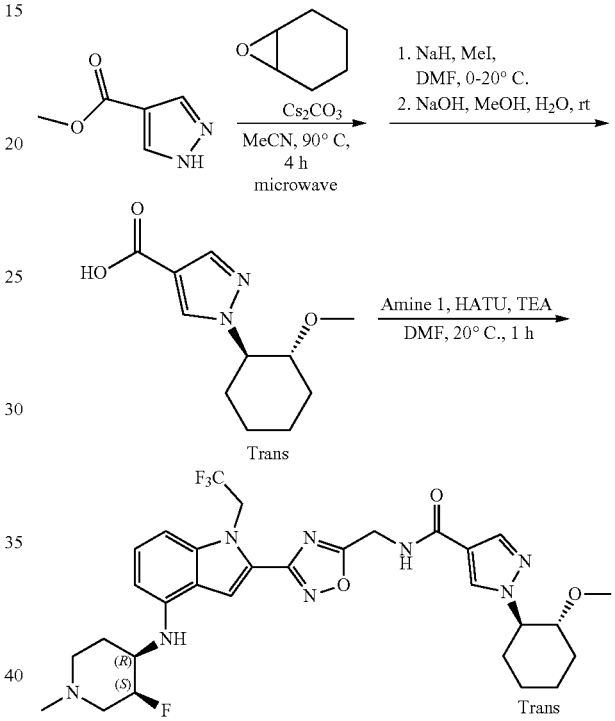

Trans

To a mixture of methyl 1H-pyrazole-4-carboxylate (3 g, 23.8 mmol, 1 eq) and cyclohexene oxide (47.6 mmol, 4.81 mL, 2 eq) in acetonitrile (25 mL) was added cesium carbonate (19.38 g, 59.5 mmol, 2.5 eq) in acetonitrile (10 mL). The sealed tube was heated at 90° C. for 4 h under microwave. The residue was poured into ice-water (30 mL) and stirred for 3 min. The aqueous phase was extracted with EA (3×30 mL). The combined organic phase was washed with brine (3×30 mL), dried over anhydrous sodium sulfate, filtered, and concentrated in vacuo. The residue was purified by column chromatography (SiO$_2$, PE/EA=1:0 to 0:1) to afford the alcohol product (2 g, 8.92 mmol, 37.5% yield) as white solid. LC-MS (ES$^+$, m/z): 225.2 [(M+H)$^+$].

To a mixture of methyl 1-[(1R,2R)-2-hydroxycyclohexyl]pyrazole-4-carboxylate (500 mg, 2.23 mmol, 1 eq) in DMF (5 mL) was added sodium hydride (267.6 mg, 6.69 mmol, 60% purity, 3 eq) in portions at 0° C. under nitrogen. The mixture was stirred at 0° C. for 30 min, followed by addition of iodomethane (4.46 mmol, 280 µL 2 eq) and heating to 20° C. The residue was poured into ammonium chloride (30 mL) and stirred for 3 min. The aqueous phase was extracted with EA (3×30 mL). The combined organic phase was washed with brine (3×30 mL), dried over anhydrous sodium sulfate, filtered, and concentrated in vacuo. The residue was purified by prep-TLC (SiO$_2$, PE/EA=1:1) to provide the product (500 mg, 2.10 mmol, 94.1% yield) as a yellow oil.

To a mixture of methyl 1-[(1R,2R)-2-methoxycyclohexyl]pyrazole-4-carboxylate (200 mg, 839 μmol, 1 eq) in methanol (2 mL) and water (0.5 mL) was added sodium hydroxide (100.7 mg, 2.52 mmol, 3 eq) at 20° C. The mixture was stirred at 20° C. for 5 h. The reaction was poured into HCl (2 M, 5 mL) and stirred for 3 min. The aqueous phase was extracted with EA (3×20 mL). The combined organic phase was washed with brine (3×20 mL), dried over anhydrous sodium sulfate, filtered, and concentrated in vacuo. The product was without further purification as a yellow oil (170 mg, 90.3% yield). LC-MS (ES$^+$, m/z): 225.1 [(M+H)$^+$].

1-[(1R,2R)-2-methoxycyclohexyl]pyrazole-4-carboxylic acid (53.9 mg, 240.3 μmol, 1.2 eq) was coupled with Amine 1 (100 mg, 200.27 μmol, 1 eq, 2HCl) using method B to provide the product. The crude was purified by prep-TLC (SiO$_2$, DCM/methanol=10:1) to provide the desired product N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-[(1R,2R)-2-methoxycyclohexyl]-1H-pyrazole-4-carboxamide (24 mg, 18.9% yield) as yellow solid. LC-MS (ES$^+$, m/z): 633.3 [(M+H)$^+$]. $^1$H NMR (400 MHz, DMSO-d$_6$) δ ppm 8.99 (t, 0.1=5.73 Hz, 1H), 8.22 (s, 1H), 7.94 (s, 1H), 7.90 (s, 1H), 7.15-7.07 (m, 1H), 6.88 (d, J=8.38 Hz, 1H), 6.28 (d, J=7.94 Hz, 1H), 6.02 (d, J=8.16 Hz, 1H), 5.50 (q, J=9.04 Hz, 2H), 4.92-4.75 (m, 3H), 4.11-4.01 (m, 1H), 3.67-3.52 (m, 1H), 3.48 (td, J=10.31, 4.30 Hz, 1H), 3.09-3.01 (m, 1H), 2.99 (s, 3H), 2.82 (br d, J=10.36 Hz, 11H), 2.29 (br d, J=13.01 Hz, 1H), 2.19 (s, 3H), 2.18-2.04 (m, 2H), 2.04-1.89 (m, 2H), 1.86-1.65 (m, 4H), 1.37-1.28 (m, 2H), 1.23-1.13 (m, 1H).

Example 145: N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(3-methyloxetan-3-yl)-1H-pyrrole-3-carboxamide (Compound 386B)

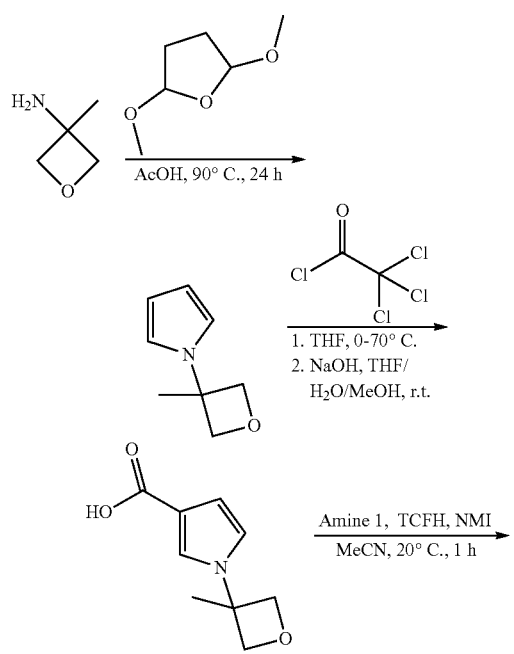

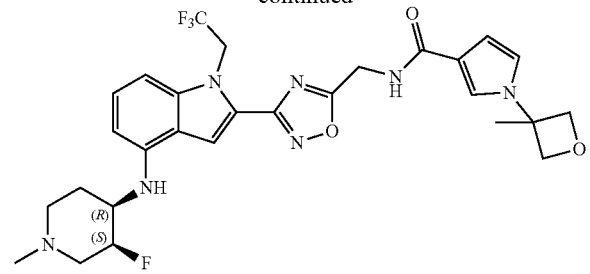

A mixture of 2,5-dimethoxytetrahydrofuran (230 mmol, 29.7 mL, 5 eq) and 3-methyloxetan-3-amine (4 g, 45.9 mmol, 1 eq) in acetic acid (18 mL) was stirred at 90° C. for 24 h. The reaction mixture was diluted with EA (100 mL) and washed with sodium hydroxide (3 M, 2×200 mL), dried over anhydrous sodium sulfate, filtered, and concentrated in vacuo to give a residue. The crude product was distilled under vacuum (120° C., pressure). The residue was further purified by prep-HPLC (TFA condition: column: Phenomenex luna C18 250 mm×100 mm×10 um; mobile phase: [water (0.1% TFA)-ACN]; B %: 10%-40%, 30 min) to give the product (49 g, 17.9 mmol, 24.5% yield). Due to volatility of the product, the product was maintained as an acetonitrile solution, and the amount estimated from $^1$H NMR purity of the solution. LC-MS (ES$^+$, m/z): 138.1 [(M+H)$^+$]. $^1$H NMR (400 MHz, CHCl$_3$-d) δ=6.77-6.70 (t, J=2.0 Hz, 2H), 6.14-6.06 (t, J=2.0 Hz, 2H), 4.88-4.82 (d, J=6.0 Hz, 2H), 4.59-4.49 (d, J=6.4 Hz, 2H), 1.78 (s, 3H).

To a solution of 1-(3-methyloxetan-3-yl)pyrrole (2 g, 14.6 mmol, 1 eq) in THF (20 mL) was added 2,2,2-trichloroacetyl chloride (8.0 g, 43.7 mmol, 4.9 mL, 3 eq) at 0° C. The mixture was stirred at 70° C. for 3 h. The reaction mixture was poured into water (50 mL) at 0° C., then extracted with EA (3×50 mL). The combined organic phase was washed with brine (50 mL), dried over anhydrous sodium sulfate, filtered, and concentrated in vacuo to give a residue. The residue was purified by prep-HPLC (FA condition:column: Phenomenex luna C18 250×80 mm×10 um; mobile phase: [water (0.225% FA)-ACN]; B %: 20%-50%, 20 min) to give the ketone product (0.1 g, 320 μmol, 2.2% yield). LC-MS (ES$^+$, m/z): 284.0 [(M+H)$^+$] $^1$H NMR (400 MHz, Chloroform-d) δ=7.80-7.69 (t, J=2.0 Hz, 1H), 6.99-6.87 (m, 2H), 5.08-4.91 (d, J=6.4 Hz, 2H), 4.80-4.62 (d, J=6.8 Hz, 2H), 1.95 (s, 3H).

To a solution of 2,2,2-trichloro-1-[1-(3-methyloxetan-3-yl)pyrrol-3-yl]ethanone (0.1 g, 354 μmol, 1 eq) in THF (1 mL), water (1 mL), methanol (1 mL) was added sodium hydroxide (3 M, 120 μL 1 eq). The mixture was stirred at 25° C. for 1 h. The reaction mixture concentrated in vacuo to remove methanol, acidified with HCl, then diluted with water (5 mL) and extracted with EA (3×10 mL). The combined organic layers were washed with brine (3×10 mL), dried over sodium sulfate, filtered, and concentrated in vacuo to give a residue. The combined water layers were washed with brine (3×10 mL), dried over sodium sulfate, filtered, and concentrated in vacuo to give the carboxylic acid (50 mg, 276 μmol, 78.0% yield) as a yellow solid LC-MS (ES$^-$, m/z): 180.0 [(M+H)$^+$].

1-(3-methyloxetan-3-yl)pyrrole-3-carboxylic acid (41.1 mg, 227 μmol, 1.5 eq) was coupled with Amine 1 (70 mg, 151 μmol, 1 eq, HCl), using method E. The crude was purified by prep-TLC (SiO2, DCM: methanol=14:1) to give the desired product N-{[3-(4-{[(3S,4R)-3-fluoro-1-methylpiperidin-4-yl]amino}-1-(2,2,2-trifluoroethyl)-1H-indol- 2-yl)-1,2,4-oxadiazol-5-yl]methyl}-1-(3-methyloxetan-3-yl)-1H-pyrrole-3-carboxamide (23 mg, 23.7% yield). LC-MS (ES+, m/z): 590.2 [(M+H)+]. ¹H NMR (400 MHz, CHLOROFORM-d) δ=8.84-8.65 (t, J=5.6 Hz, 1H), 7.95-7.84 (s, 1H), 7.65-7.56 (s, 1H), 7.18-7.01 (m, 2H), 6.93-6.84 (d, J=8.4 Hz, 1H), 6.66-6.53 (s, 1H), 6.33-6.19 (d, J=7.6 Hz, 1H), 6.08-5.94 (d, J=8.4 Hz, 1H), 5.62-5.41 (dt, J=8.8 Hz, 2H), 4.96-4.71 (m, 5H), 4.66-4.57 (d, J=6.8 Hz, 2H), 3.64-3.53 (m, 1H), 3.12-3.00 (m, 1H), 2.87-2.76 (m 1H), 2.32-2.16 (m, 4H), 2.16-2.07 (m, 1H), 2.06-1.94 (m, 1H), 1.77 (s, 3H), 1.72-1.65 (m, 1H).

Example 146: cis-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-[(1R,3S)-3-methoxy-3-methylcyclopentyl]-1H-pyrrole-3-carboxamide (Compound 387B), and trans-N-{[3-(4-{[(3S,4R)-3-fluoro-1-methylpiperidin-4-yl]aminol-1-(2,2,2-trifluoroethyl)-1H-indol-2-yl)-1,2,4-oxadiazol-5-yl]methyl}-1-[(1R,3R)-3-methoxy-3-methylcyclopentyl]-1H-pyrrole-3-carboxamide (Compound 388B)

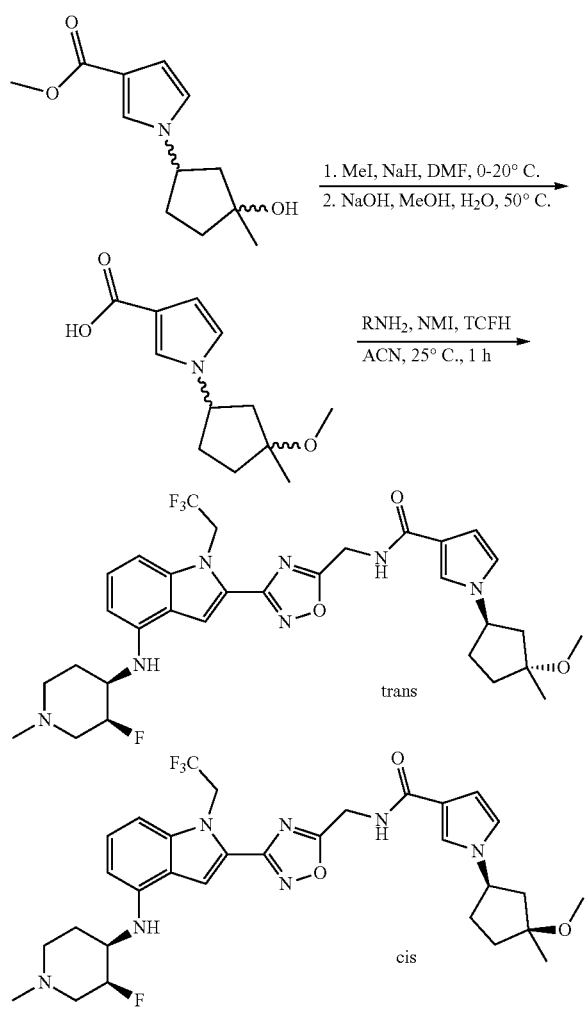

To a cis/trans mixture of methyl 1-(3-hydroxy-3-methyl-cyclopentyl)pyrrole-3-carboxylate (160 mg, 717 μmol, 1 eq) in DMF (3 mL) was added sodium hydride (86 mg, 2.15 mmol, 60% purity, 3 eq) in one portion at 0° C. under nitrogen. The mixture was stirred at 0° C. for 30 min, followed by addition of iodomethane (3.58 mmol, 220 μL 5 eq). The mixture was stirred at 20° C. for 30 min. The residue was poured into ammonium chloride (aq. 100 mL). The aqueous phase was extracted with EA (3×30 mL). The combined organic phase was washed with brine (3×30 mL), dried over anhydrous sodium sulfate, filtered, and concentrated in vacuo. The residue was purified by prep-TLC to give the ether products as a cis/trans mixture (130 mg, 76.5% yield) LC-MS (ES+, m/z): 238.2 [(M+H)+].

To a mixture of methyl 1-(3-methoxy-3-methyl-cyclopentyl)pyrrole-3-carboxylate (130 mg, 548 mol, 1 eq) in methanol (2 mL) and water (1 mL) was added sodium hydroxide (131.5 mg, 3.29 mmol, 6 eq) at 50° C. under nitrogen. The mixture was stirred at 50° C. for 10 h. The residue was poured into HCl to pH=7-8, filtered, and concentrated in vacuo to give the product (0.7 g, crude).

1-(3-methoxy-3-methyl-cyclopentyl) pyrrole-3-carboxylic acid (79.7 mg, 357 μmol, 1.1 eq) was coupled with Amine 1 (180 mg, 324 μmol, 1 eq, 2HCl) under method E. The residue was purified by prep-TLC (SiO₂, DCM: methanol=20:1), then purified again by SFC (column: DAICEL CHIRALPAK AD (250 mm×30 mm, 10 um); mobile phase: [0.1% NH₃H₂O ETOH]; B %: 60%-60%, 15 min) to obtain the racemic, separated cis and trans isomers. Cis:(20.7 mg, 32.8 mol, 10.1% yield, 100% purity). LC-MS (ES+, m/z): 632.3 [(M+H)+] ¹H NMR (DMSO-d₆, 400 MHz): δ=,8.69 (t, J=5.9 Hz, 1H), 7.91 (s, 1H), 7.48 (s, 1H), 7.16-7.10 (m, 1H), 6.93-6.86 (m, 2H), 6.52-6.47 (m, 1H), 6.30 (d, J=7.9 Hz, 1H), 6.06 (br d, J=7.9 Hz, 1H), 5.52 (q, J=8.9 Hz, 2H), 4.93 (m, 1H), 4.74 (d, J=5.6 Hz, 2H), 4.66-4.52 (m, 1H), 3.65-3.58 (M, 1H), 3.16 (s, 3H), 3.08 (br s, 1H), 2.84 (br s, 1H), 2.22-2.19 (m, 7H), 2.19-2.16 (m, 4H), 1.72 (br s, 1H), 1.63-1.38 (m, 1H), 1.28 (s, 3H). Trans: (11.5 mg, 18.21 μmol, 5.61% yield, 97.7% purity). LC-MS (ES+, m/z): 632.3 [(M+H)+]. ¹H NMR (DMSO-d₆, 400 MHz): δ=8.61 (br t, 1H), 7.85 (s, 1H), 7.46 (s, 1H), 7.08 (t, 1H), 6.95-6.78 (m, 2H), 6.46 (br s, 1H), 6.25 (br d, 1H), 6.01 (br d, 1H), 5.52-5.35 (m, 2H), 4.88 (br dd, 1H), 4.80-4.64 (m, 2H), 4.59-4.52 (m, JH), 3.59-3.51 (m, 1H), 3.12-3.03 (m, 4H), 2.60-2.59 (m, 1H), 2.35-2.29 (m, 7H), 1.99-1.83 (m, 1H), 1.82-1.65 (m, 4H), 1.26 (s, 3H).

Example 147: rac-1-tert-butyl-N-{[3-(4-{[(3R,4S)-4-fluoro-1-methylpiperidin-3-yl]amino}-1-(2,2,2-trifluoroethyl)-1H-indol-2-yl)-1,2,4-oxadiazol-5-yl]methyl}-1H-pyrrole-3-carboxamide (Compound 389B)

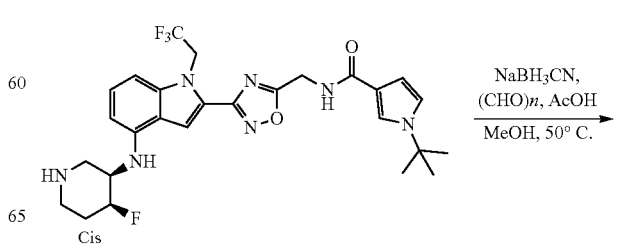

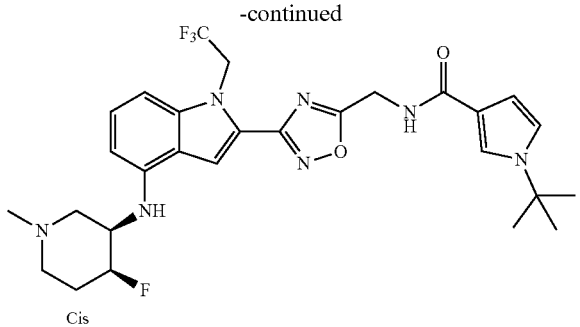

Cis

To a solution of the previously prepared piperidine (40 mg, 71.2 µmol, 1 eq) and paraformaldehyde (21.4 mg, 712 µmol, 10 eq) in methanol (2 mL) was added sodium cyanoborohydride (13.4 mg, 214 µmol, 3 eq), then acetic acid (710 µmol, 41 mL, 10 eq), and the reaction was stirred at 50° C. for 1 h. The residue was poured into ice-water (w/w=1/1) (10 mL) and stirred for 10 min. The aqueous phase was extracted with EA (3×10 mL). The combined organic phase was washed with brine (3×10 mL), dried over anhydrous sodium sulfate, filtered, and concentrated in vacuo. The residue was purified by prep-TLC (SiO$_2$, DCM: methanol=20:1) to provide 1-tert-butyl-N-[[3-[4-[[(3R,4S)-4-fluoro-1-methyl-3-piperidyl]amino]-1-(2,2,2-trifluoroethyl)indol-2-yl]-1,2,4-oxadiazol-5-yl] methyl]pyrrole-3-carboxamide (15.8 mg, 38.5% yield, 99.8% purity) as a white solid. LC-MS (ES$^+$, m/z): 576.6 [(M+H)$^+$]. 1H NMR (400 MHz, DMSO-d$_6$) δ=8.65 (t, J=5.7 Hz, 1H), 7.87 (s, 1H), 7.54 (s, 1H), 7.15-7.09 (m, 1H), 6.99 (t, J=2.6 Hz, 1H), 6.89 (d, J=8.4 Hz, 1H), 6.50 (br s, 1H), 6.31 (d, J=7.9 Hz, 1H), 5.97 (br d, J=8.6 Hz, 1H), 5.51 (q, J=8.8 Hz, 2H), 4.98 (br s, 1H), 4.73 (d, J=5.5 Hz, 2H), 3.91-3.63 (m, 1H), 2.69 (br s, 1H), 2.60-2.55 (m, 1H), 2.32-2.27 (m, 1H), 2.22 (s, 3H), 2.15 (br s, 1H), 2.02-1.85 (m, 2H), 1.49 (s, 9H).

Example 148: 2-(5-{[(1-tert-butyl-LH-pyrazol-3-yl)amino]methyl}-1,2,4-oxadiazol-3-yl)-N-[(3S,4R)-3-fluoro-1-methylpiperidin-4-yl]-1-(2,2,2-trifluoroethyl)-1H-indol-4-amine (Compound 390B)

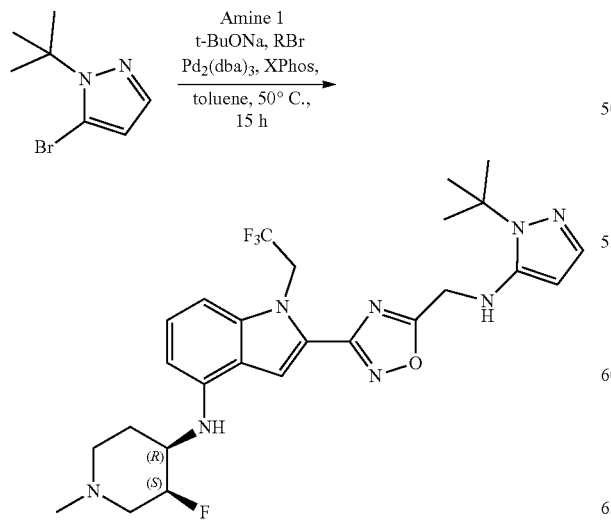

Amine 1 (30 mg, 70.4 µmol, 1 eq) and 5-bromo-1-tert-butyl-pyrazole (28.6 mg, 141 µmol, 2 eq) were added to toluene (1 mL), to which were added sodium t-butoxide (9.5 mg, 98.5 µmol, 1.4 eq), Pd$_2$(dba)$_3$ (6.4 mg, 7.04 µmol, 0.1 eq), and XPhos (4 mg, 8.4 µmol, 0.1 eq) at 20° C. under nitrogen. The mixture was stirred at 50° C. for 15 h. The residue was poured into (1 M) EDTA (10 mL) and stirred for 2 h. The aqueous phase was extracted with EA (3×10 mL). The combined organic phase was washed with brine (3×10 mL), dried over anhydrous sodium sulfate, filtered, and concentrated in vacuo. The residue was purified by prep-TLC (SiO$_2$, DCM/methanol=10:1) to afford the desired product 2-(5-{[(1-tert-butyl-1H-pyrazol-3-yl)amino]methyl}-1,2,4-oxadiazol-3-yl)-N-[(3S,4R)-3-fluoro-1-methylpiperidin-4-yl]-1-(2,2,2-trifluoroethyl)-1H-indol-4-amine (1.8 mg, 4.7% yield) as yellow solid. LC-MS (ES$^+$, m/z): 549.3 [(M+H)$^+$]. 1H NMR (400 MHz, DMSO-d$_6$) δ ppm 7.87 (s, 1H), 7.12 (t, J=8.01 Hz, 1H), 7.04 (d, J=1.71 Hz, 1H), 6.88 (d, J=8.44 Hz, 1H), 6.30 (d, J=7.82 Hz, 1H), 5.97 (br d, J=8.19 Hz, 1H), 5.86 (t, J=5.99 Hz, 1H), 5.56-5.44 (m, 3H), 4.95-4.75 (m, 1H), 4.62 (d, J=5.99 Hz, 2H), 3.70-3.50 (m, 1H), 3.05 (br s, 1H), 2.83 (br d, J=9.41 Hz, 1H), 2.28 (br s, 1H), 2.20 (s, 3H), 2.10 (br d, J=11.25 Hz, 1H), 2.06-1.99 (m, 1H), 1.71 (br d, J=13.94 Hz, 1H), 1.57 (s, 9H), 1.31-1.19 (m, 4H), 0.91-0.84 (m, 1H).

Example 149: N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(1-methoxy-2-methylpropan-2-yl)-1H-pyrazole-4-carboxamide (Compound 391B)

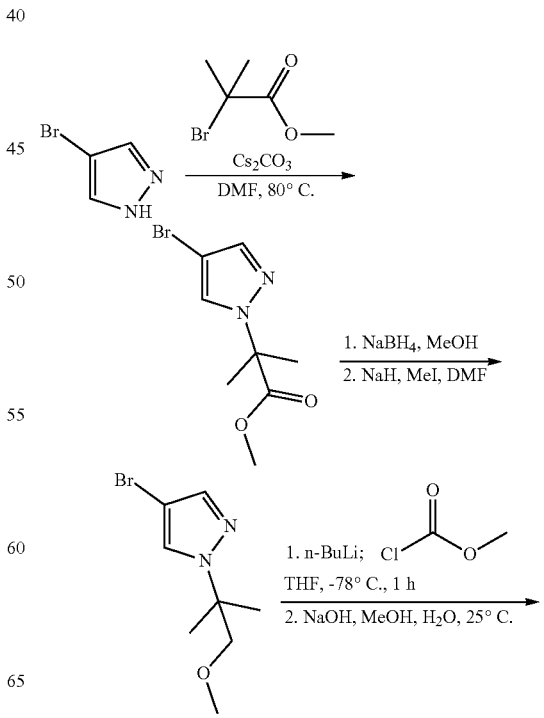

-continued

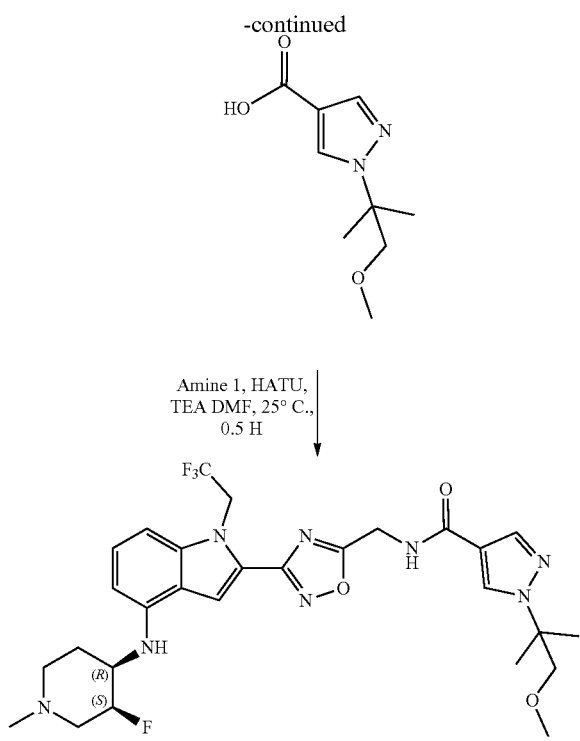

Amine 1, HATU, TEA DMF, 25° C., 0.5 H

To a solution of 4-bromo-1H-pyrazole (5.0 g, 34 mmol, 1 eq) and methyl 2-bromo-2-methyl-propanoate (12.3 g, 68 mmol, 8.8 mL, 2 eq) in DMF (50 mL) was added cesium carbonate (33.3 g, 102.1 mmol, 3 eq), and the mixture was stirred at 80° C. for 2 h. The reaction mixture was poured into water (300 mL), then extracted with EA (150 mL×3). The combined organic phase was washed with brine (100 mL×1), dried over anhydrous sodium sulfate, filtered, and concentrated in vacuo to give a residue. The residue was purified by column chromatography (SiO$_2$, PE/EA=20/1 to 5/1) to give the ester product (6.0 g, 24.3 mmol, 71.4% yield) as a colorless oil. LCMS (ES$^+$, m/z): 246.9 [(M+H)$^+$].

To a solution of methyl 2-(4-bromo-1H-pyrazol-1-yl)-2-methylpropanoate (3.0 g, 12.1 mmol, 1 eq) in methanol (50 mL) was added sodium borohydride (918.6 mg, 24.3 mmol, 2 eq) at 0° C., then the mixture was stirred at 50° C. for 4 h. The reaction mixture was poured into sat. sodium carbonate (200 mL), then extracted with EA (80 mL×3). The combined organic phase was washed with brine (80 mL×1), dried over anhydrous sodium sulfate, filtered, and concentrated in vacuo to give a residue. The residue was purified by column chromatography (SiO$_2$, PE/EA=20/1 to 5/1) to give the product (1.8 g, 8.2 mmol, 67.7% yield) as a colorless oil. LCMS (ES$^+$, m/z): 218.9 [(M+H)$^+$].

To a solution of 2-(4-bromo-1H-pyrazol-1-yl)-2-methyl-propan-1-ol (1.8 g, 8.2 mmol, 1 eq) in DMF (30 mL) was added sodium hydride (1.64 g, 41.1 mmol, 60% purity, 5 eq) at 0° C., and the reaction was stirred at 0° C. for 0.5 h, then iodomethane (16.4 mmol, 1.02 mL, 2 eq) was added, and the mixture was stirred at 25° C. for 1.5 h. The reaction mixture was poured into sat. ammonium chloride (100 mL), then extracted with EA (50 mL×3). The combined organic phase was washed with brine (30 mL×1), dried over anhydrous sodium sulfate, filtered, and concentrated in vacuo to give a residue. The residue was purified by column chromatography (SiO$_2$, PE/EA=40/1 to 8/1) to give the methyl ether product (900 mg, 3.86 mmol, 47.0% yield) as a colorless oil. LCMS (ES$^-$, m/z): 232.9 [(M+H)$^+$].

To a solution of 4-bromo-1-(l-methoxy-2-methylpropan-2-yl)-1H-pyrazole (300 mg, 1.29 mmol, 1 eq) in THF (12 mL) was added n-butyllithium (2.5 M, 1.03 mL, 2 eq) at −78° C., and the reaction was stirred at −78° C. for 0.5 h, followed by addition of methyl chloroformate (1.16 mmol, 90 μL 0.9 eq), and the mixture was stirred at −78° C. for 0.5 h under nitrogen atmosphere. The reaction mixture was poured into sat. ammonium chloride (150 mL), and was then extracted with EA (80 mL×3). The combined organic phase was washed with brine (80 mL×1), dried over anhydrous sodium sulfate, filtered, and concentrated in vacuo to give a residue. The residue was purified by column chromatography (SiO$_2$, PE/EA=20/1 to 8/1) to give the methyl ester product (280 mg, 1.32 mmol, 51.3% yield) as a colorless oil. LCMS (ES$^+$, m/z): 213.1 [(M+H)$^+$].

To a solution of methyl 1-(1-methoxy-2-methylpropan-2-yl)-1H-pyrazole-4-carboxylate (280 mg, 1.32 mmol, 1 eq) in methanol (4 mL) and water (2 mL) was added sodium hydroxide (158.3 mg, 3.96 mmol, 3 eq), and the mixture was stirred at 25° C. for 3 h. The reaction mixture was poured into water (150 mL), then 1N HCl solution was added to pH=4, and the mixture extracted with EA (80 mL×3). The combined organic phase was washed with brine (80 mL×1), dried over anhydrous sodium sulfate, filtered, and concentrated n vacuo to give the product (200 mg, crude) as a light yellow solid.

The 1-(1-methoxy-2-methylpropan-2-yl)-1H-pyrazole-4-carboxylic acid (142.9 mg, 721 μmol, 2 eq) was coupled with Amine 1 (200 mg, 360.5 μmol, 1 eq, 2HCl) under method B. The crude product was purified by prep-TLC (SiO$_2$, DCM: methanol=10:1, R$_f$=0.53) to give the desired product N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(1-methoxy-2-methylpropan-2-yl)-1H-pyrazole-4-carboxamide (74.5 mg, 33.6% yield) as a white solid. LCMS (ES$^+$, m/z): 607.3 [(M+H)$^+$]. $^1$H NMR (400 MHz, DMSO-d$_6$) δ=9.00 (br t, J=5.62 Hz, 1H) 8.30 (s, 1H), 7.91 (d, J=12.13 Hz, 2H), 7.12 (t, J=8.05 Hz, 1H), 6.88 (br d, J=8.16 Hz, 1H), 6.28 (d, J=7.94 Hz, 1H), 6.04 (br d, J=8.16 Hz, 1H), 5.46-5.55 (m, 2H), 4.77-4.91 (m, 3H), 3.53-3.65 (m, 3H), 3.15-3.23 (m, 3H), 3.01-3.08 (m, 1H), 2.80-2.86 (m, 1H), 2.18-2.32 (m, 4H), 2.08-2.15 (m, 1H), 1.95- 2.04 (m, 1H), 1.68 (br d, J=10.36 Hz, 1H), 1.51 (s, 6H).

Example 150: N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-[(1R,2R)-2-fluorocyclopentyl]-1H-pyrrole-3-carboxamide (Compound 392B)

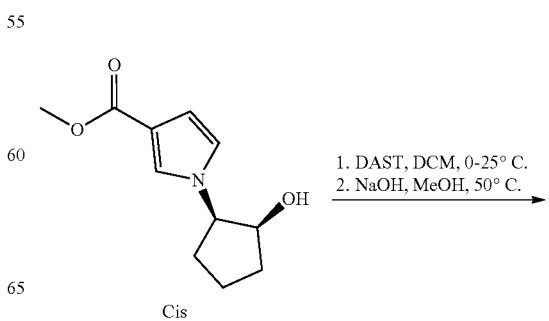

1. DAST, DCM, 0-25° C.
2. NaOH, MeOH, 50° C.

Cis

-continued

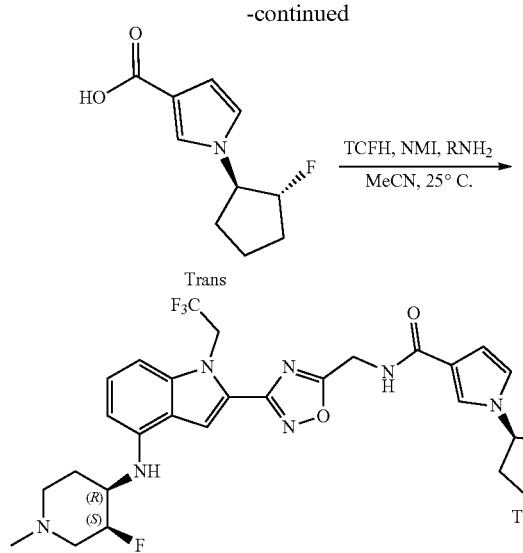

Trans cis-Methyl 1-[(1R,2S)-2-hydroxycyclopentyl]pyrrole-3-carboxylate (150 mg, 717 µmol, 1 eq), previously prepared by reduction of the ketone previously described, was treated with DCM (2 mL) and DAST (231.11 mg, 1.43 mmol, 189.43 µL 2 eq) at 0° C. The mixture was stirred at 25° C. for 2 h. The reaction mixture was poured into sodium carbonate (50 mL), then extracted with EA (3×30 mL). The combined organic layers were washed with brine (30 mL), dried over anhydrous sodium sulfate, filtered, and concentrated in vacuo to give a residue. The residue was purified by prep-TLC (SiO$_2$, PE:EA=2:1) to give the trans-fluoro product (80 mg, 52.8% yield). LC-MS (ES$^+$, m/z): 212.2[(M+H)$^+$].

To a mixture of methyl 1-[(1R,2R)-2-fluorocyclopentyl]pyrrole-3-carboxylate (80 mg, 379 µmol, 1 eq) in methanol (2 mL) was added sodium hydroxide (75.8 mg, 1.89 mmol, 5 eq). The mixture was stirred at 50° C. for 3 h. The reaction mixture was filtered and concentrated in vacuo to give a residue. The reaction was without further purification and give a product (80 mg, crude). LC-MS (ES$^+$, m/z): 198.2 [(M+H)$^+$].

Amine 1 (70 mg, 126 µmol, 1 eq, 2HCl) was coupled with trans-1-[(1R)-2-fluorocyclopentyl]pyrrole-3-carboxylic acid (37.3 mg, 189 µmol, 1.5 eq) under method E. The crude product was purified by prep-TLC (SiO$_2$, DCM:methanol=10:1) to give the desired product N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-[(1R,2R)-2-fluorocyclopentyl]-1H-pyrrole-3-carboxamide (21.4 mg, 27.5% yield, 98.3% purity). LC-MS (ES$^+$, m/z): 606.3 [(M+H)$^+$]. $^1$H NMR (400 MHz, DMSO-d6) δ=8.70 (t, J=5.69 Hz, 1H), 7.89 (s, 1H), 7.50 (t, J=1.77 Hz, 1H), 7.16-7.09 (m, 1H), 6.94 (t, J=2.51 Hz, 1H), 6.89 (d, J=8.44 Hz, 1H), 6.56 (dd, J=2.63, 1.77 Hz, 1H), 6.29 (d, J=7.95 Hz, 1H), 6.01 (br d, J=8.31 Hz, 1H), 5.51 (q, J=8.93 Hz, 2H), 5.23-5.03 (m, 1H), 4.91-4.77 (m, 1H), 4.74 (d, J=5.62 Hz, 2H), 4.68-4.54 (m, 1H), 3.56 (br s, 1H), 3.67-3.50 (m, 1H), 3.09-3.00 (m, 1H), 3.04 (br t, J=10.45 Hz, 1H), 2.82 (br d, J=10.03 Hz, 1H), 2.33 (br d, J=1.71 Hz, 1H), 2.29 (br d, J=12.47 Hz, 1H), 2.25 (br s, 1H), 2.20 (s, 3H), 2.16-2.06 (m, 2H), 2.00 (br dd, J=11.80, 3.24 Hz, 1H), 2.04-1.97 (m, 1H), 1.94-1.89 (m, 1H), 1.86-1.82 (m, 2H), 1.73-1.65 (m, 1H), 1.73-1.63 (m, 1H).

Example 151: 1-tert-butyl-N-{[3-(4-{[(3S,4R)-1-tert-butyl-3-fluoropiperidin-4-yl]amino}-1-(2,2,2-trifluoroethyl)-1H-indol-2-yl)-1,2,4-oxadiazol-5-yl]methyl}-1H-pyrrole-3-carboxamide (Compound 393B)

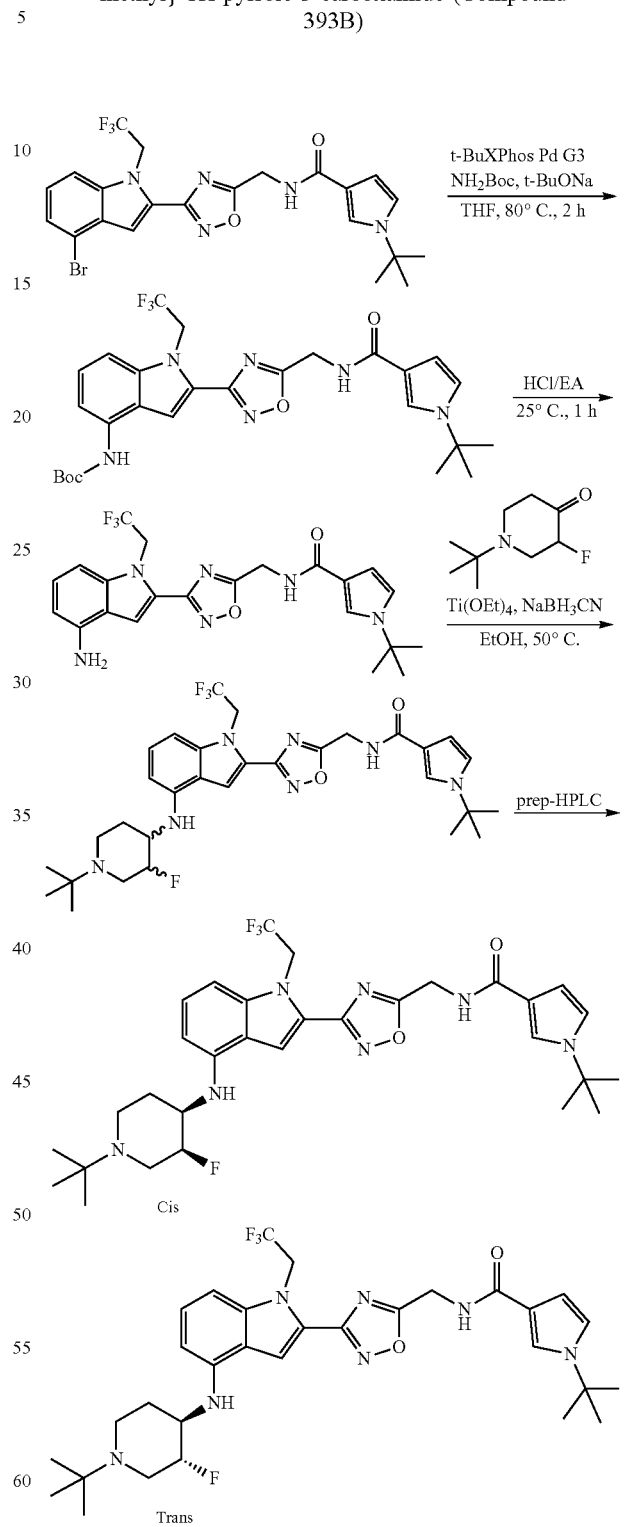

To a solution of N-[[3-[4-bromo-1-(2,2,2-trifluoroethyl)indol-2-yl]-1,2,4-oxadiazol-5-yl]methyl]-1-tert-butyl-pyrrole-3-carboxamide (910 mg, 1.74 mmol, 1 eq) and tert-butyl carbamate (305 mg, 2.60 mmol, 1.5 eq) in THF (23 mL) were added sodium t-butoxide (2 M, 1.74 mL, 2 eq) and [2-(2-aminophenyl)phenyl]-methylsulfonyloxy-palladium di-tert-butyl-[2-(2,4,6-triisopropylphenyl)phenyl]phosphane (t-butyl-XPhos Generation 3) (276 mg, 347 μmol, 0.2 eq) at 25° C. The mixture was stirred at 80° C. for 2 h under nitrogen. The reaction mixture was diluted with EDTA (sat., 100 mL) and extracted with EA (3×50 mL). The combined organic layers were washed with brine (100 mL), dried over sodium sulfate, filtered, and concentrated in vacuo to give a residue. The residue was purified by column chromatography (SiO$_2$, PE:EA=20:1 to 1:2), to give the carbamate product (0.45 g, 803 μmol, 46.2% yield) LC-MS (ES$^+$, m/z): 561.2 [(M+H)$^+$]. $^1$H NMR (400 MHz, DMSO-d6) δ=9.41 (s, 1H), 8.65 (br t, J=5.6 Hz, 1H), 7.86 (s, 1H), 7.65-7.47 (m, 2H), 7.38 (br d, J=8.3 Hz, 1H), 7.34-7.24 (m, 1H), 6.99 (t, J=2.5 Hz, 1H), 6.51 (br s, 1H), 5.59 (q, J=8.8 Hz, 2H), 4.74 (br d, J=5.5 Hz, 2H), 1.49 (s, 18H).

A solution of tert-butyl N-[2-[5-[[(1-tert-butylpyrrole-3-carbonyl)amino]methyl]-1,2,4-oxadiazol-3-yl]-1-(2, 2, $^2$-trifluoroethyl)indol-4-yl]carbamate (0.45 g, 803 μmol, 1 eq) in HCl/EA (4 M, 20 mL) was stirred at 25° C. for 1 h. The reaction mixture was concentrated in vacuo to give the product (0.35 g, crude, HCl) LC-MS (ES$^+$, m/z): 461.3 [(M+H)$^+$].

To a solution of N-[[3-[4-amino-1-(2,2,2-trifluoroethyl) indol-2-yl]-1,2,4-oxadiazol-5-yl]methyl]-1-tert-butyl-pyrrole-3-carboxamide (0.1 g, 201 μmol, 1 eq, HCl) and 1-tert-butyl-3-fluoro-piperidin-4-one (127 mg, 604 μmol, 3 eq, HCl) in ethanol (4 mL) was added titanium ethoxide (2.01 mmol, 417 μL 10 eq) at 50° C.

The mixture was stirred at 50° C. for 12 h, then sodium cyanoborohydride (63 mg, 1.01 mmol, 5 eq) was added to the mixture. The mixture was stirred at 50° C. for 30 min. The reaction mixture was diluted with sodium bicarbonate (Sat., 150 mL) and extracted with EA (3×50 mL). The combined organic layers were washed with brine (100 mL), dried over sodium sulfate, filtered, and concentrated in vacuo to give a residue. The residue was purified by prep-TLC (PE:EA=2:1 and then DCM:methanol=10:1), and was then further purified by prep-HPLC to separate the cis and trans diastereomers (column: Phenomenex Luna C18 200×40 mm×10 um; mobile phase:[water (0.2% FA)-ACN];B %: 30%-70%, 8mi).

Cis (Compound 393B) (0.03 g, 45.2 μmol, 22.5% yield, FA salt). LC-MS (ES$^+$, m/z): 618.3 [(M+H)$^+$]. $^1$H NMR (400 MHz, DMSO-d6) δ=8.74-8.55 (t, J=5.6 Hz, 1H), 7.88 (s, 1H), 7.65-7.49 (m, 1H), 7.18-7.07 (t, J=8.0 Hz, 1H), 7.01-6.95 (t, J=2.4 Hz, 1H), 6.93-6.82 (d, J=8.4 Hz, 1H), 6.57-6.46 (m, 1H), 6.37-6.21 (d, J=8.0 Hz, 1H), 6.06-5.85 (d, J=8.0 Hz, 1H), 5.63-5.42 (dt, J=8.8 Hz, 2H), 4.95- 4.68 (m, 3H), 3.68-3.53 (m, 1H), 3.24-3.15 (m, 1H), 3.08-2.97 (m, 1H), 2.41-2.16 (m, 2H), 1.98-1.84 (m, 1H), 1.78-1.66 (m, 1H), 1.49 (s, 9H), 1.04 (s, 9H). Trans (Compound 394B) (15 mg, 22.6 μmol, 11.2% yield, FA). LC-MS (ES$^+$, m/z): 618.3 [(M+H)$^+$]. $^1$H NMR (400 MHz, DMSO-d6) δ=8.72-8.56 (t, J=5.6 Hz, 1H), 8.17 (s, 1H), 7.77 (s, 1H), 7.55 (s, 1H), 7.15-7.06 (t, J=8.0 Hz, 1H), 7.02-6.94 (t, J=2.4 Hz, 1H), 6.92-6.76 (d, J=8.4 Hz, 1H), 6.52-6.45 (d, J=2.0 Hz, 1H), 6.34-6.25 (d, J=8.0 Hz, 1H), 6.16-6.04 (d, J=8.4 Hz, 1H), 5.59-5.36 (dt, J=8.4 Hz, 2H), 4.82-4.67 (d, J=5.6 Hz, 2H), 4.62-4.37 (m, 1H), 3.59-3.48 (m, 1H), 3.26-3.20 (m, 1H), 3.00-2.87 (m, 1H), 2.23-2.11 (m, 2H), 2.08-2.00 (m, 1H), 1.49 (s, 9H), 1.43-1.33 (m, 1H), 1.05 (s, 9H).

Example 152: N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-[(1R,2R)-2-fluorocyclopentyl]-1H-pyrazole-4-carboxamide (Compound 395B)

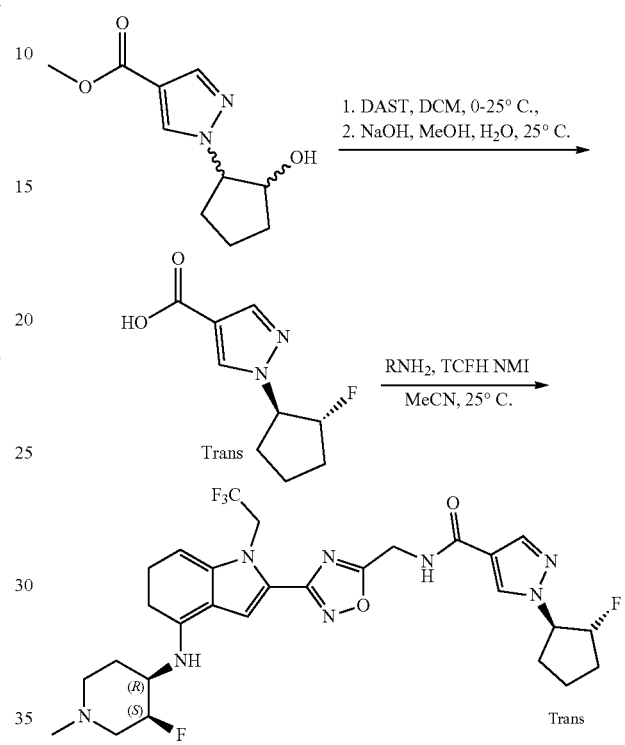

To a mixture of cis/trans methyl 1-[(1R,2S)-2-hydroxycyclopentyl]pyrazole-4-carboxylate (300 mg, 1.43 mmol, 1 eq), were added DCM (1 mL), then DAST (2.85 mmol, 377 μL 2 eq) at 0° C. under nitrogen. The mixture was stirred at 0° C. for 2.5 h. The reaction mixture was poured into sat. ammonium chloride (50 mL), then extracted with EA (3×30 mL). The combined organic layers were washed with brine (1×30 mL), dried over anhydrous sodium sulfate, filtered, and concentrated in vacuo to give a residue. The residue was purified by prep-TLC (SiO$_2$, PE/EA=5:1) to give the products. The trans isomer was isolated as the desired product (160 mg, 754 μmol, 52.8% yield). LC-MS (ES$^+$, m/z): 212.1 [(M+H)$^+$].

To a mixture of methyl 1-[(1R,2R)-2-fluorocyclopentyl] pyrrole-3-carboxylate (80 mg, 379 μmol, 1 eq) in water (1 mL) and methanol (2 mL) was added sodium hydroxide (75.8 mg, 1.89 mmol, 5 eq). The mixture was stirred at 25° C. for 2 h. The reaction mixture was adjusted to pH 7 with 1-Cl (2M), then was filtered, and concentrated in vacuo to give a residue to give a product (80 mg, crude).

1-[(1R,2R)-2-fluorocyclopentyl]pyrazole-4-carboxylic acid (25.7 mg, 130 μmol, 1.2 eq) was coupled with Amine 1 (60 mg, 108.14 μmol, 1 eq, 2 HCl) under method B. The crude product was purified by prep-TLC (SiO$_2$,DCM/methanol=10:1) to give the desired product N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-[(1R,2R)-2-fluorocyclopentyl]-1H-pyrazole-4-carboxamide (25.7 mg, 37.1% yield, 94.8% purity). LC-MS (ES$^+$, m/z): 606.2 [(M+H)$^+$]. $^1$H NMR (400 MHz, DMSO-d$_6$) δ=9.02 (t, J=5.73 Hz, 1H), 9.07-8.95 (m, 1H), 8.35 (s, 1H), 7.97 (s, 1H), 7.87 (s, 1H), 7.13-7.07 (m, 1H), 6.86 (d, J=8.38 Hz, 1H), 6.26 (d, J=7.94 Hz, 1H), 6.00 (d, J=8.38 Hz, 1H), 5.53-5.43 (m, 2H), 5.32-5.12 (m, 1H), 4.94-4.72 (m, 4H), 3.66-3.49 (m, 1H), 3.02 (br t, J=10.36 Hz, 1H), 2.80 (br d, J=10.58 Hz, 1H), 2.31-2.21 (m, 2H), 2.17 (s, 3H), 2.13-2.04 (m, 2H), 2.03-1.95 (m, 2H), 1.94-1.79 (m, 3H), 1.70-1.62 (m, 1H).

Example 153: 2-(5-{[(1-tert-butyl-1H-pyrazol-5-yl)amino]methyl}-1,2,4-oxadiazol-3-yl)-N-[(3S,4R)-3-fluoro-1-methylpiperidin-4-yl]-1-(2,2,2-trifluoroethyl)-1H-indol-4-amine (Compound 396B)

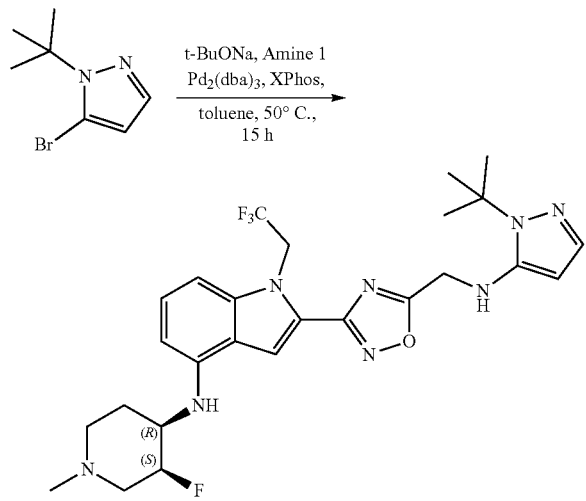

To a mixture of Amine 1 (30 mg, 70 μmol, 1 eq, free base) and 5-bromo-1-tert-butyl-pyrazole (28.6 mg, 141 μmol, 2 eq) in toluene (1 mL) were added sodium t-butoxide (9.5 mg, 99 μmol, 1.4 eq), $Pd_2(dba)_3$ (6.4 mg, 7.0 μmol, 0.1 eq) and XPhos (4 mg, 8.4 mol, 0.1 eq) at 20° C. under nitrogen. The mixture was stirred at 50° C. for 15 h. The residue was poured into (1 M) EDTA (10 mL) and stirred for 2 h. The aqueous phase was extracted with EA (3×10 mL). The combined organic phase was washed with brine (3×10 mL), dried over anhydrous sodium sulfate, filtered, and concentrated in vacuo. The residue was purified by prep-TLC ($SiO_2$, DCM/methanol=10:1) to afford the product (1.8 mg, 3.28 μmol, 4.7% yield) as yellow solid. LC-MS ($ES^+$, m/z): 549.3 [$(M+H)^+$]. $^1H$ NMR (400 MHz, DMSO-$d_6$) δ ppm 7.87 (s, 1H), 7.12 (t, J=8.01 Hz, 1H), 7.04 (d, J=1.71 Hz, 1H), 6.88 (d, J=8.44 Hz, 1H), 6.30 (d, J=7.82 Hz, 1H), 5.97 (br d, J=8.19 Hz, 1H), 5.86 (t, J=5.99 Hz, 1H), 5.56-5.44 (m, 3H), 4.95-4.75 (m, 1H), 4.62 (d, J=5.99 Hz, 2H), 3.70-3.50 (m, 1H), 3.05 (br s, 1H), 2.83 (br d, J=9.41 Hz, 1H), 2.28 (br s, 1H), 2.20 (s, 3H), 2.10 (br d, J=11.25 Hz, 1H), 2.06-1.99 (m, 1H), 1.71 (br d, J=13.94 Hz, 1H), 1.57 (s, 9H), 1.31-1.19 (m, 4H), 0.91-0.84 (m, 1H).

Example 154: N-{[3-(4-{[(3S,4R)-1-tert-butyl-3-fluoropiperidin-4-yl]amino}-1-(2,2,2-trifluoroethyl)-1H-indol-2-yl)-1,2,4-oxadiazol-5-yl]methyl}-1-methyl-1H-pyrrole-3-carboxamide (Compound 397B)

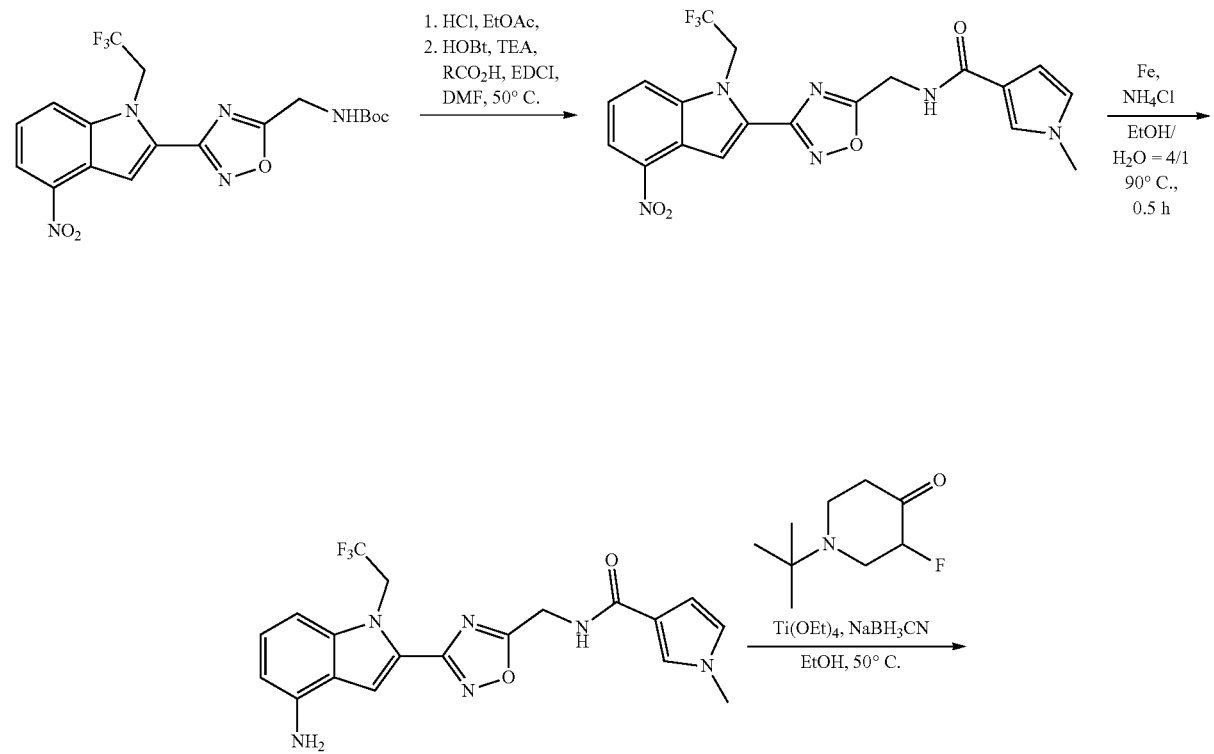

-continued

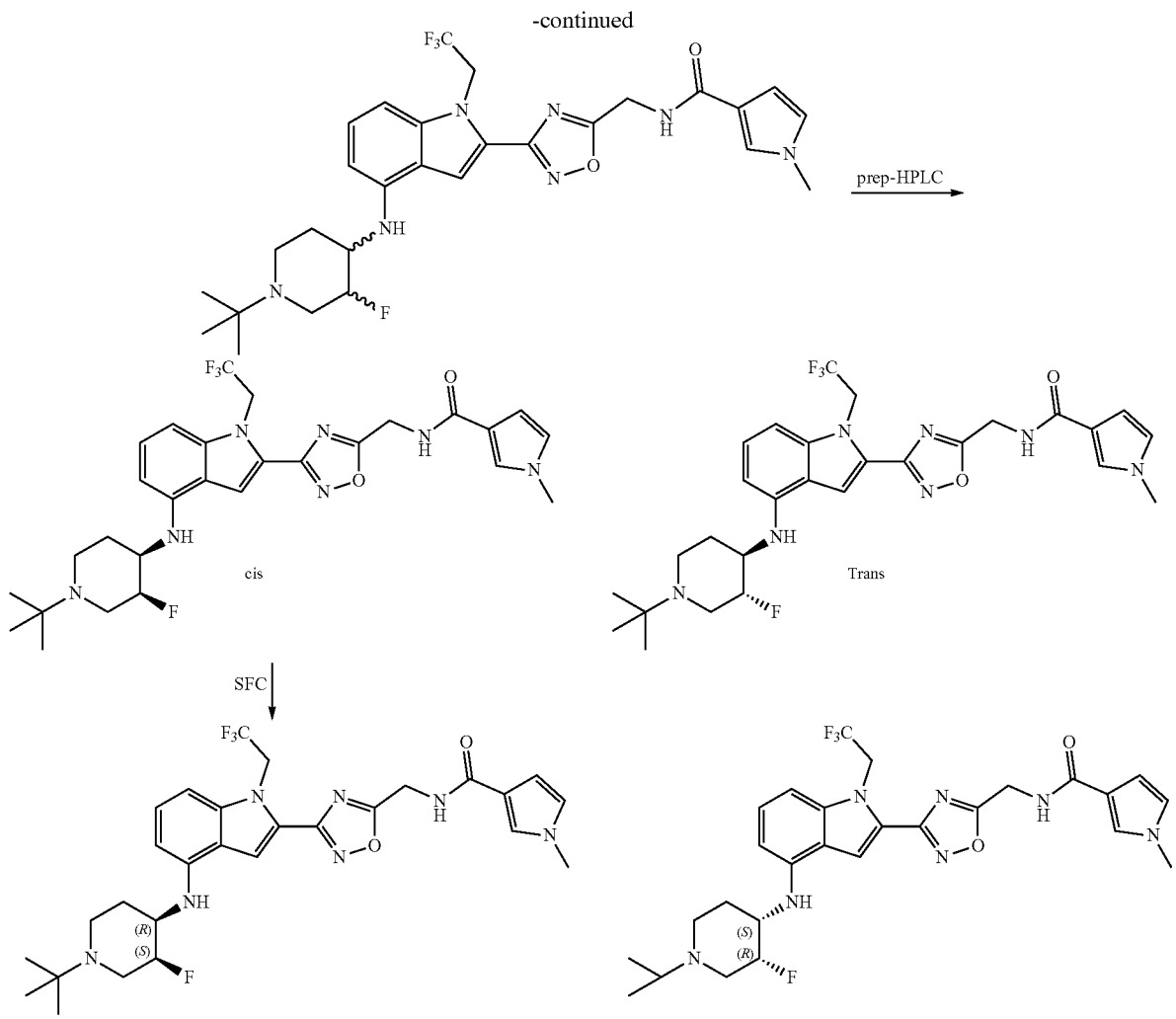

To a solution of tert-butyl N-[[3-[4-nitro-1-(2,2,2-trifluoroethyl)indol-2-yl]-1,2,4-oxadiazol-5-yl]methyl]carbamate (5.0 g, 11.3 mmol, 1 eq) in EA (10 mL) was added HCl/EA (4 M, 40 mL, 14.1 eq). The mixture was stirred at 25° C. for 1 h. The reaction mixture was concentrated in vacuo to give a product (3.9 g, 9.4 mmol, 83.1% yield, 2 HCl) LC-MS (ES+, m/z): 342.0 [(M+H)+].

A mixture of [3-[4-nitro-1-(2,2,2-trifluoroethyl)indol-2-yl]-1,2,4-oxadiazol-5-yl] methanamine (906 mg, 2.4 mmol, 1 eq, HCl), 1-methylpyrrole-3-carboxylic acid (0.3 g, 2.4 mmol, 1 eq), HOBt (648 mg, 4.8 mmol, 2 eq), EDCI (919 mg, 4.8 mmol, 2 eq), TEA (12 mmol, 1.7 mL, 5 eq) in DMF (9 mL) was degassed and purged with nitrogen 3 times, then the mixture was stirred at 50° C. for 4 h under nitrogen atmosphere. The reaction mixture was quenched by adding water (90 mL), filtered under reduced pressure to give a residue. The crude product was triturated with EA (20 mL) for 12 h to give the product (0.73 g, 1.6 mmol, 67.9% yield) LC-MS (ES+, m/z): 449.1 [(M+H)+]. $^1$H NMR (400 MHz, DMSO-d6) δ=8.81-8.59 (t, J=6.0 Hz, 1H), 8.43-8.29 (d, J=8.0 Hz, 1H), 8.27-8.21 (d, J=8.0 Hz, 1H), 7.88 (s, 1H), 7.73-7.57 (t, J=8.0 Hz, 1H), 7.38-7.23 (t, J=1.6 Hz, 1H). 6.82-6.70 (t, J=2.4 Hz, 1H), 6.56-6.42 (t, J=2.2 Hz, 1H), 5.87-5.75 (dt, J=8.0 Hz, 2H), 4.84-4.68 (d, J=5.6 Hz, 2H), 3.65 (s, 3H).

To a solution of 1-methyl-N-[[3-[4-nitro-1-(2,2,2-trifluoroethyl)indol-2-yl]-1,2,4-oxadiazol-5-yl]methyl]pyrrole-3-carboxamide(0.7 g, 1.4 mmol, 1 eq) and ammonium chloride (451 mg, 8.4 mmol, 6 eq) in ethanol (60 mL) and water (6 mL) was added iron powder (235 mg, 4.2 mmol, 3 eq). The mixture was stirred at 90° C. for 1 h. The reaction mixture was concentrated in vacuo to remove ethanol. The residue was diluted with water (50 mL) and extracted with EA (3×50 mL). The combined organic layers were washed with brine (3×50 mL), dried over sodium sulfate, filtered, and concentrated in vacuo to give a residue. The residue was purified by prep-TLC (SiO$_2$, EA=1) to give the product (0.4 g, 60.7% yield). LC-MS (ES+, m/z): 419.3 [(M+H)+].

To a solution of 1-tert-butyl-3-fluoro-piperidin-4-one (484.4 mg, 2.8 mmol, 6 eq) in ethanol (60 mL) were added N-[[3-[4-amino-1-(2,2,2-trifluoroethyl)indol-2-yl]-1,2,4-oxadiazol-5-yl]methyl]-1-methyl-pyrrole-3-carboxamide (195 mg, 466 µmol, 1 eq) and titanium ethoxide (9.3 mmol, 1.9 mL, 20 eq). The mixture was stirred at 50° C. for 10 h. Sodium cyanoborohydride (87.9 mg, 1.40 mmol, 3 eq) was then added. The mixture was stirred at 50° C. for 1 h. The reaction mixture was quenched by addition aqueous sodium carbonate (50 mL), then the solid was filtered off, and the filtrate was extracted with EA (4×20 mL). The combined organic layers were washed with brine (2×20 mL), dried over sodium sulfate, filtered, and concentrated in vacuo to product LC-MS (ES+, m/z): 576.4 [(M+H)+].

The crude products were purified by prep-TLC (SiO2, PE:EA=1:5) to give 300 mg. The mixture was then further purified by prep-HPLC (column: Phenomenex luna C18 250×80 mm×10 um; mobile phase: [water (0.225% FA)-ACN]; B %: 15%-45%, 20 min). The enantiomers of the cis isomers were resolved by SFC (column: DAICEL CHIRAL-PAK AD(250 mm×30 mm, 10 um); mobile phase: [0.1% NH3H20 methanol]; B %: 60%) to give the resolved cis enantiomers.

Cis-(Compound 397B): (71 mg, 5.9% yield). LC-MS (ES+, m/z): 576.3 [(M+H)+]. 1H NMR (400 MHz, DMSO-d6) δ=8.65 (t, J=5.6 Hz, 1H), 7.88 (s, 1H), 7.32 (s, 1H), 7.11 (t, J=8.0 Hz, 1H), 6.87 (br d, J=8.3 Hz, 1H), 6.74 (d, J=2.0 Hz, 1H), 6.49 (s, 1H), 6.28 (br d, J=7.6 Hz, 1H), 5.96 (br d, J=8.1 Hz, 1H), 5.50 (q, J=8.9 Hz, 2H), 4.93-4.76 (m, 1H), 4.72 (d, J=5.6 Hz, 2H), 3.65 (s, 3H), 3.54 (br s, 1H), 3.24 (br d, J=11.8 Hz, 1H), 3.02 (br d, J=10.4 Hz, 1H), 2.38-2.31 (m, 1H), 2.22 (br t, J=11.0 Hz, 1H), 1.97-1.84 (m, 1H), 1.72 (br d, J=11.6 Hz, 1H), 1.03 (s, 9H). Cis-(Compound 398B): (83 mg, 6.7% yield). LC-MS (ES+, m/z): 576.3 [(M+H)+] 1H NMR (400 MHz, DMSO-d6) δ=8.64 (br t, J=5.6 Hz, 1H), 7.88 (s, 1H), 7.32 (s, 1H), 7.11 (t, J=8.0 Hz, 1H), 6.87 (br d, J=8.1 Hz, 1H), 6.74 (br s, 1H), 6.49 (br s, 1H), 6.28 (br d, J=7.8 Hz, 1H), 5.94 (br d, J=7.8 Hz, 1H), 5.50 (q, J=8.7 Hz, 2H), 4.94-4.76 (m, 1H), 4.72 (br d, J=5.6 Hz, 2H), 3.65 (s, 3H), 3.55 (br s, 1H), 3.27-3.16 (m, 1H), 3.02 (br d, J=8.1 Hz, 1H), 2.45-2.35 (m, 1H), 2.22 (br t, J=9.9 Hz, 1H), 1.91 (br d, J=9.8 Hz, 1H), 1.74 (br s, 1H), 1.04 (br s, 9H).

N-{[3-(4-{[(3R,4R)-1-tert-butyl-3-fluoropiperidin-4-yl]amino}-1-(2,2,2-trifluoroethyl)-1H-indol-2-yl)-1,2,4-oxadiazol-5-yl]methyl}-1-methyl-1H-pyrrole-3-carboxamide (Compound 399B): The trans isomers from the above reaction were further purified to obtain the pure, trans racemate (20 mg, 24.1% yield). Prep-TLC (SiO2, DCM: methanol=10:1). LC-MS (ES+, m/z): 576.3 [(M+H)]. 1H NMR (400 MHz, DMSO-d6) δ=8.65 (brt, J=5.6 Hz, 1H), 7.77 (s, 1H), 7.32 (s, 1H), 7.10 (t, J=8.0 Hz, 1H), 6.84 (br d, J=8.2 Hz, 1H), 6.75 (t, J=2.2 Hz, 1H), 6.49 (br s, 1H), 6.28 (br d, J=7.7 Hz, 1H), 6.12 (br d, J=6.4 Hz, 1H), 5.50 (q, J=8.7 Hz, 2H), 4.72 (d, J=5.5 Hz, 2H), 4.63-4.39 (m, 1H), 3.65 (s, 3H), 3.49 (br d, J=17.0 Hz, 1H), 3.41-3.36 (m, 1H), 2.99-2.87 (m, 1H), 2.17 (br d, J=7.3 Hz, 2H), 2.05 (br s, 1H), 1.46-1.31 (m, 1H), 1.13-0.96 (m, 9H).

Example 155: 1-tert-butyl-N-{[3-(4-{[(3S,4R)-1-tert-butyl-3-fluoropiperidin-4-yl]amino}-1-(2,2,2-trifluoroethyl)-1H-indol-2-yl)-1,2,4-oxadiazol-5-yl]methyl}-1H-pyrazole-4-carboxamide. (Compound 400B)

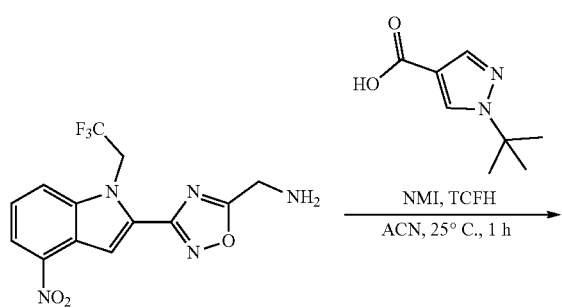

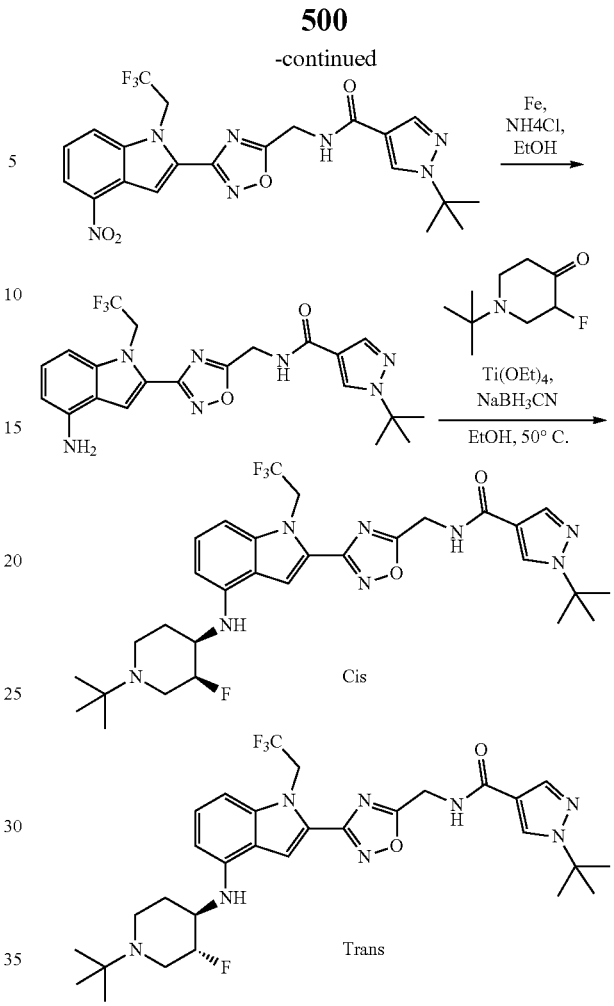

To a solution of [3-[4-nitro-1-(2,2,2-trifluoroethyl)indol-2-yl]-1,2,4-oxadiazol-5-yl] methanamine (0.3 g, 88 μmol, 1 eq) and 1-tert-butylpyrazole-4-carboxylic acid (148 mg, 879 μmol, 1 eq) in acetonitrile (3 mL) were added 1-methylimidazole (2.6 mmol, 210 μL 3 eq), then [chloro(dimethylamino)methylene]-dimethyl-ammonium hexafluorophosphate (370 mg, 1.3 mmol, 1.5 eq). The mixture was stirred at 25° C. for 1 h. The mixture was diluted with water (50 mL) and extracted with EA (3×50 mL). The combined organic layers were washed with brine (3×50 mL), dried over sodium sulfate, filtered, and concentrated in vacuo to give a residue. The crude product was triturated with PE/EA=1:1(20 mL) at 25° C. for 30 min to give the product (0.3 g, 610 μmol, 69.4% yield). LC-MS (ES+, m/z): 492.2 [(M+H)+].

To a solution of 1-tert-butyl-N-[[3-[4-nitro-1-(2,2,2-trifluoroethyl)indol-2-yl]-1,2,4-oxadiazol-5-yl]methyl]pyrazole-4-carboxamide (0.3 g, 48 μmol, 1 eq, 2HCl) and ammonium chloride (154 mg, 2.9 mmol, 6 eq) in water (4 mL) and ethanol (40 mL) was added iron powder (80.2 mg, 1.4 mmol, 3 eq). The mixture was stirred at 90° C. for 1 h. The reaction mixture was filtered under reduced pressure to remove ethanol. The residue was diluted with water (50 mL) and extracted with EA (3×50 mL). The combined organic layers were washed with brine (3×50 mL), dried over sodium sulfate, filtered, and concentrated in vacuo to give a residue. The residue was purified by prep-TLC (SiO2, PE/EA=1:1) to give product (0.15 g, 315 μmol, 65.9% yield). LC-MS (ES+, m/z): 462.3 [(M+H)+].

To a solution of N-[[3-[4-amino-1-(2,2,2-trifluoroethyl)
indol-2-yl]-1,2,4-oxadiazol-5-yl]methyl]-1-tert-butyl-pyrazole-4-carboxamide (50 mg, 108 μmol, 1 eq) and 1-tert-butyl-3-fluoro-piperidin-4-one (68.2 mg, 325 μmol, 3 eq, HCl) in ethanol (6 mL) was added titanium ethoxide (1.1 mmol, 225 μL 10 eq). The mixture was stirred at 50° C. for 12 h, then sodium cyanoborohydride (34.1 mg. 542 μmol, 5 eq) was added to the mixture. The resulting mixture was stirred at 50° C. for 0.5 h. The reaction mixture was quenched by adding sodium carbonate (aq.) to pH>7 and filtered under reduced pressure to give a residue, then extracted with EA (3×50 mL). The combined organic layers were washed with brine (3×50 mL), dried over sodium sulfate, filtered, and concentrated in vacuo. This residue was purified by prep-TLC (SiO$_2$, DCM/methanol=10:1). The crude product was then further purified by prep-HPLC (FA condition: column: Phenomenex Luna C18 100×30 mm×5 um; mobile phase: [water (0.2% FA)-ACN]; B %: 25%-55%, 9 min) to give the products.

Cis (Compound 400B) (31 mg, 49.9 μmol, 23.0% yield). LC-MS (ES$^+$, m/z): 619.4 [(M+H)$^+$] $^1$H NMR (400 MHz, DMSO-d6) δ=9.04-8.88 (t, J=5.6 Hz, 1H), 8.34 (s, 11H), 7.93 (s, 1H), 7.88 (s, 2H), 7.20-7.02 (t, J=8.0 Hz, 1H), 6.97-6.81 (d, J=8.4 Hz, 1H), 6.31-6.20 (d, J=8.0 Hz, 1H), 6.03-5.88 (d, J=8.4 Hz, 1H), 5.62-5.39 (dt, J=8.8 Hz, 211), 4.98-4.67 (m, 3H), 3.67-3.52 (m, 1H), 3.24-3.19 (m, 1H), 3.07- 2.97 (m, 1H), 2.40-2.33 (m, 1H), 2.26-2.19 (m, 1H), 1.96-1.85 (m, 1H), 1.77-1.69 (m, 1H), 1.54 (s, 9H), 1.04 (s, 9H). Trans (Compound 40213) (12 mg, 19.3 μmol, 8.9% yield). LC-MS (ES$^+$, m/z): 619.4 [(M+H)$^+$]$^1$H NMR (400 MHz, DMSO-d6) δ=9.05-8.89 (t, J=5.6 Hz, 1H), 8.34 (s, 1H), 7.93 (s, 1H), 7.77 (s, 1H), 7.15-7.04 (t, J=8.0 Hz, 1H), 6.90-6.76 (d, J=8.4 Hz, 1H), 6.34-6.22 (d, J=8.0 Hz, 1H), 6.16-6.03 (d, J=8.4 Hz, 1H), 5.58-5.40 (dt, J=8.4 Hz, 2H), 4.86-4.72 (d, J=5.6 Hz, 2H), 4.63-4.35 (m, 1H), 3.57-3.49 (m, 1H), 3.25-3.20 (m, 1H), 2.97-2.90 (m, 1H), 2.22-2.13 (m, 2H), 2.09-2.01 (m, 1H), 1.54 (s, 9H), 1.43-1.33 (m, 1H), 1.05 (s, 9H).

Example 156: N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(3-methyloxolan-3-yl)-1H-pyrrole-3-carboxamide.
(Compound 401B)

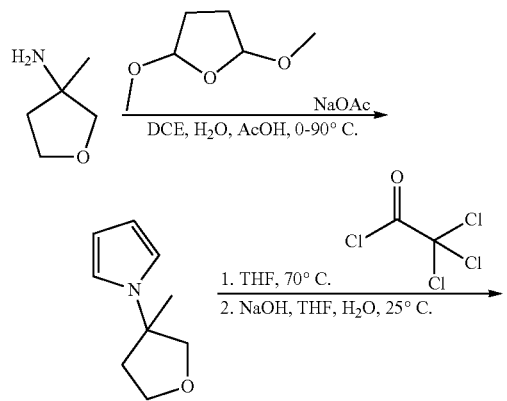

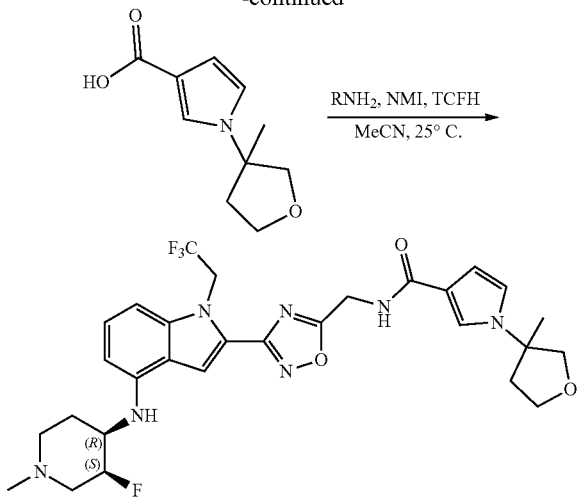

To a solution of 3-methyltetrahydrofuran-3-amine (1 g, 9.89 mmol, 1 eq) in DCE (5 mL) and water (3 mL), were added sodium acetate (1.22 g, 14.8 mmol, 1.5 eq) and acetic acid (1 mL), and the mixture was stirred at 0° C. for 0.5 h, then 2,5-dimethoxytetrahydrofuran (9.89 mmol, 1.28 mL, 1 eq) was added. The mixture was stirred at 90° C. for 12 h. The reaction mixture was poured into ammonium chloride (sat., 50 mL), then extracted with DCM (3×30 mL). The combined organic layers were washed with brine (30 mL), dried over anhydrous sodium sulfate, filtered, and concentrated in vacuo to give a residue (700 mg, crude). LC-MS (ES$^+$, m/z): 152.3[(M+H)$^+$]. $^1$H NMR (400 MHz, CHLOROFORM-d) δ=6.81 (t, J=2.20 Hz, 1H), 6.82-6.80 (m, 1H), 6.81 (br d, J=11.91 Hz, 1H), 6.18 (t, J=2.20 Hz, 1H), 6.23-6.10 (m, 1H), 4.11 (br s, 1H), 4.12 (d, J=8.82 Hz, 1H), 4.07-3.99 (m, 1H), 3.84 (d, J=8.82 Hz, 1H), 3.86-3.81 (m, 1H), 2.47-2.38 (m, 1H), 2.24-2.15 (m, 1H), 2.20 (ddd, J=12.68, 7.72, 6.73 Hz, 1H), 2.01 (s, 1H), 2.05 (s, 1H), 1.67 (s, 3H), 1.68 (br s, 1H), 1.26 (t, J=7.06 Hz, 1H).

To a solution of 1-(3-methyltetrahydrofuran-3-yl)pyrrole (200 mg, 1.32 mmol, 1 eq) in THE (1 mL) was added 2,2,2-trichloroacetyl chloride (3.97 mmol, 440 μL 3 eq). The mixture was stirred at 70° C. for 8 h. The reaction mixture was poured into sodium carbonate (50 mL), then extracted with EA (3×30 mL). The combined organic layers were washed with brine (30 mL), dried over anhydrous sodium sulfate, filtered, and concentrated in vacuo to give a residue. The residue was purified by prep-TLC (SiO$_2$, PE:EA=2:1) to give the ketone product (150 mg, 38.2% yield). LC-MS (ES$^+$, m/z): 295.9[(M+H)$^+$].

To a solution of 2,2,2-trichloro-1-[1-(3-methyltetrahydrofuran-3-yl)pyrrol-3-yl] ethanone (150 mg, 506 μmol, 1 eq) in THF (1 mL) was added sodium hydroxide (3 M, 2.50 mL, 14.8 eq). The mixture was stirred at 25° C. for 2 h. The reaction mixture was adjusted to pH<7 with 2M HCl, then was poured into water (50 mL) and extracted with EA (3×30 mL). The combined organic layers were washed with brine (30 mL), dried over anhydrous sodium sulfate, filtered, and concentrated in vacuo to give a residue to give the carboxylic acid product (85 mg, crude). LC-MS (ES$^+$, m/z): 194.0 [(M+H)$^+$].

Amine 1 (100 mg, 160 μmol, 1 eq, 2HCl) and 1-(3-methyltetrahydrofuran-3-yl)pyrrole-3-carboxylic acid (37.5 mg, 192 μmol, 1.2 eq) were coupled under method E. The crude was purified by prep-TLC (SiO$_2$, DCM:methanol=10:

1) to give the desired product N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(3-methyloxolan-3-yl)-1H-pyrrole-3-carboxamide (58.5 mg, 59.5% yield, 98.4% purity). LC-MS (ES+, m/z): 604.3[(M+H)+]. 1H NMR (400 MHz, DMSO-d6) δ=8.70 (t, J=5.62 Hz, 1H), 8.72-8.67 (m, 1H), 7.90 (s, 1H), 7.92-7.86 (m, 1H), 7.59-7.53 (m, 1H), 7.56 (d, J=1.71 Hz, 1H), 7.15-7.09 (m, 1H), 7.15-7.09 (m, 1H), 6.99 (t, J=2.57 Hz, 1H), 7.01-6.97 (m, 1H), 6.89 (d, J=8.31 Hz, 1H), 6.91-6.86 (m, 1H), 6.55-6.52 (m, 1H), 6.56-6.52 (m, 1H), 6.31-6.27 (m, 1H), 6.29 (d, J=7.82 Hz, 1H), 6.08-6.00 (m, 1H), 6.03 (br d, J=8.31 Hz, 1H), 5.58-5.42 (m, 1H), 5.51 (q, J=8.72 Hz, 1H), 4.92-4.77 (m, 1H), 4.94-4.77 (m, 1H), 4.74 (d, J=5.62 Hz, 1H), 4.76-4.72 (m, 1H), 4.00 (d, J=9.17 Hz, 1H), 4.02-3.98 (m, 1H), 3.93-3.87 (m, 1H), 3.93-3.87 (m, 1H), 3.77-3.73 (m, 1H), 3.75 (d, J=9.05 Hz, 1H), 3.67-3.52 (m, 1H), 3.68-3.51 (m, 1H), 3.09-2.99 (m, 1H), 3.04 (br t, J=10.82 Hz, 1H), 2.82 (br d, J=9.90 Hz, 1H), 2.82-2.79 (m, 1H), 2.85-2.79 (m, 1H), 2.86-2.78 (m, 1H), 2.41 (dt, J=13.14, 6.76 Hz, 1H), 2.45-2.37 (m, 1H), 2.26 (br d, J=7.70 Hz, 1H), 2.27-2.22 (m, 1H), 2.23 (br d, J=2.08 Hz, 1H), 2.21-2.19 (m, 1H), 2.20 (s, 2H), 2.15-2.07 (m, 1H), 2.04-1.97 (m, 1H), 1.96 (br d, J=2.93 Hz, 1H), 1.91 (s, 1H), 1.72-1.65 (m, 1H), 1.68 (br d, J=10.27 Hz, 1H), 1.59 (s, 3H).

Example 157: Compound 403B: N-{[3-(4-{[(3R,4S)-4-fluoro-1-methylpiperidin-3-yl]amino}-1-(2,2,2-trifluoroethyl)-1H-indol-2-yl)-1,2,4-oxadiazol-5-yl]methyl}-1-(4-methyloxan-4-yl)-1H-pyrrole-3-carboxamide; Compound 420B: N-{[3-(4-{[(3R,4S)-4-fluoropiperidin-3-yl]amino}-1-(2,2,2-trifluoroethyl)-1H-indol-2-yl)-1,2,4-oxadiazol-5-yl]methyl}-1-(4-methyloxan-4-yl)-1H-pyrrole-3-carboxamide; Compound 421B: N-{[3-(4-{[(3S,4R)-4-fluoropiperidin-3-yl]amino}-1-(2,2,2-trifluoroethyl)-1H-indol-2-yl)-1,2,4-oxadiazol-5-yl]methyl}-1-(4-methyloxan-4-yl)-1H-pyrrole-3-carboxamide; and Compound 416B: N-{[3-(4-{1[(3S,4R)-4-fluoro-1-methylpiperidin-3-yl]amino}-1-(2,2,2-trifluoroethyl)-1H-indol-2-yl)-1,2,4-oxadiazol-5-yl]methyl}-1-(4-methyloxan-4-yl)-1H-pyrrole-3-carboxamide

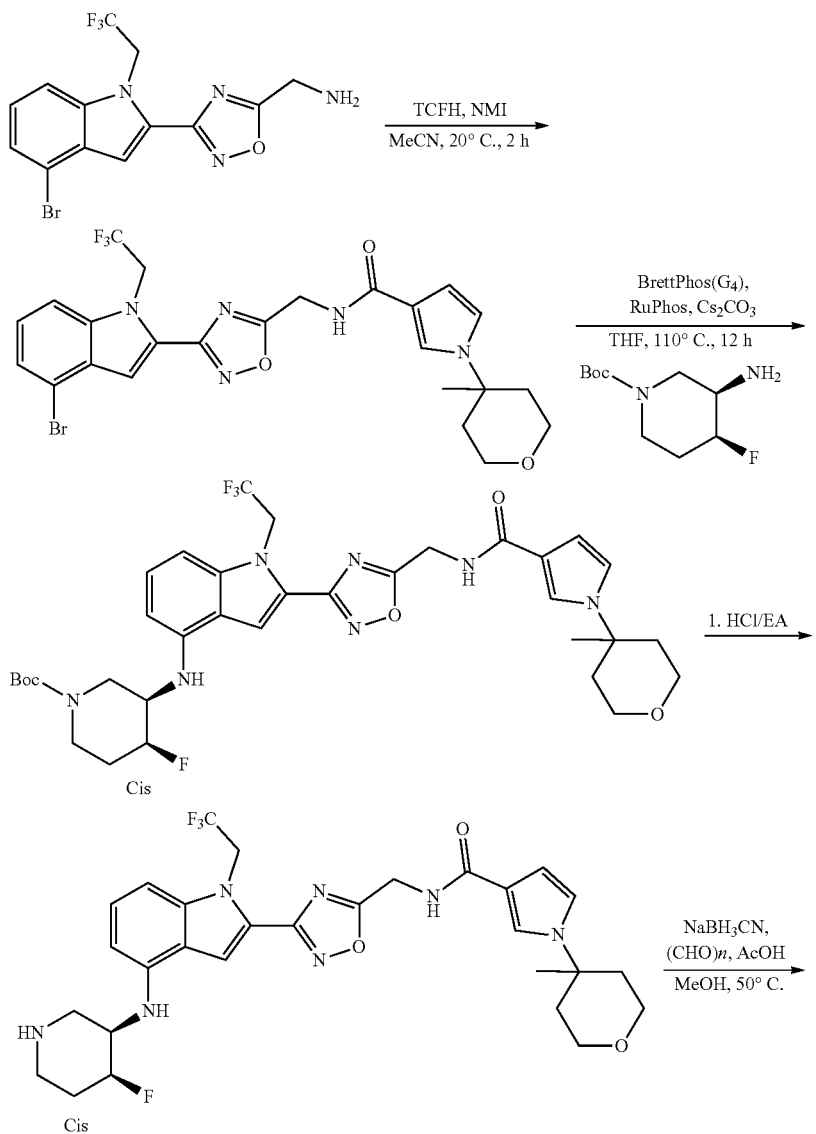

-continued

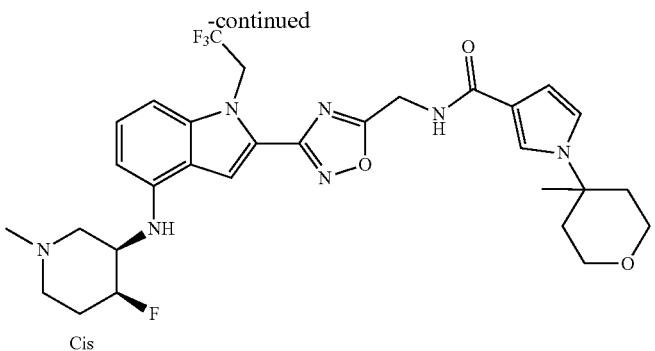
Cis

To a mixture of the previously prepared 1-(4-methyltetrahydropyran-4-yl)pyrrole-3-carboxylic acid (934 mg, 4.46 mmol, 2 eq) and [3-[4-bromo-1-(2,2,2-trifluoroethyl)indol-2-yl]-1,2,4-oxadiazol-5-yl]methanamine (1 g, 2.23 mmol, 1 eq, 2HCl) in acetonitrile (30 mL) were added 1-methylimidazole (6.70 mmol, 530 µL 3 eq) and [chloro(dimethylamino)methylene]-dimethyl-ammonium hexafluorophosphate (940 mg, 3.35 mmol, 1.5 eq) in one portion at 20° C. under nitrogen. The mixture was stirred at 20° C. for 2 h. The residue was poured into ice-water (30 mL) and stirred for 3 min. The aqueous phase was extracted with EA (3×30 mL). The combined organic phase was washed with brine (3×30 mL), dried over anhydrous sodium sulfate, filtered, and concentrated in vacuo. The residue was purified by prep-HPLC (FA condition) to afford the product (900 mg, 1.59 mmol, 71.2% yield) as yellow solid. LC-MS (ES$^+$, m/z): 566.2 [(M+H)$^+$].

To a mixture of N-[[3-[4-bromo-1-(2,2,2-trifluoroethyl)indol-2-yl]-1,2,4-oxadiazol-5-yl]methyl]-1-(4-methyltetrahydropyran-4-yl)pyrrole-3-carboxamide (200 mg, 353 µmol, 1 eq) and cis-tert-butyl-3-amino-4-fluoro-piperidine-1-carboxylate (231.2 mg, 1.06 mmol, 3 eq) in THF (4 mL) were added cesium carbonate (345 mg, 1.06 mmol, 3 eq) and [2-(2-aminophenyl)phenyl]palladium(1+); dicyclohexyl-[2-(2,4,6-triisopropylphenyl)phenyl]phosphane methanesulfonate (89.7 mg, 106 µmol, 0.3 eq) at 20° C. under nitrogen. The reaction was heated to 110° C. and stirred for 12 h. The residue was poured into EDTA (1M, 50 mL) and stirred for 2 h. The aqueous phase was extracted with EA (3×20 mL). The combined organic phase was washed with brine (3×20 mL), dried over anhydrous sodium sulfate, filtered, and concentrated in vacuo. The residue was purified by prep-TLC (SiO$_2$, DCM/methanol=20:1) to provide the product (190 mg, 25.5% yield) as yellow solid. LC-MS (ES$^+$, m/z): 604.4 [(M+H)$^+$].

To a mixture of tert-butyl (3R,4S)-4-fluoro-3-[[2-[5-[[[1-(4-methyltetrahydropyran-4-yl)pyrrole-3-carbonyl]amino]methyl]-1,2,4-oxadiazol-3-yl]-1-(2,2,2-trifluoroethyl)indol-4-yl]amino]piperidine-1-carboxylate (190 mg, 270 µmol, 1 eq) was added 4N HCl/EA (10 mL) at 20° C., and the reaction was heated to 20° C. and stirred for 4 h. The reaction was concentrated to afford the product (160 mg, 265 µmol, 98% yield) as yellow solid. A portion of this racemic material prepared by the above method was further separated by SFC (column: DAICEL CHIRALPAK AD (250 mm×30 mm, 10 um); mobile phase: [0.1% NH$_3$H$_2$O IPA]; B %: 60%, 40 min) to provide the resolved enantiomers.

Compound 420B: N-{[3-(4-{[(3R,4S)-4-fluoropiperidin-3-yl]amino}-1-(2,2,2-trifluoroethyl)-1H-indol-2-yl)-1,2,4-oxadiazol-5-yl]methyl}-1-(4-methyloxan-4-yl)-1H-pyrrole-3-carboxamide $^1$H NMR (400 MHz, DMSO-d6) δ ppm 8.67 (br t, J=5.69 Hz, 1H), 8.21 (br s, 1H), 7.87 (s, 1H), 7.59 (s, 1H), 7.12 (t, J=8.07 Hz, 1H), 7.02 (t, J=2.51 Hz, 1H), 6.89 (br d, J=8.07 Hz, 1H), 6.55 (br s, 1H), 6.30 (d, J=7.82 Hz, 1H), 5.93 (br d, J=8.44 Hz, 1H), 5.58-5.44 (m, 2H), 5.08-4.48 (m, 1H), 4.74 (br d, J=5.62 Hz, 2H), 3.75 (br s, 1H), 3.69-3.63 (m, 2H), 3.59-3.52 (m, 2H), 2.88 (br s, 2H), 2.73 (br s, 2H), 2.16-2.09 (m, 2H), 2.02-1.85 (m, 4H), 1.75 (br s, 1H), 1.43 (s, 3H).

Compound 421B: N-{[3-(4-{[(3S,4R)-4-fluoropiperidin-3-yl]amino}-1-(2,2,2-trifluoroethyl)-1H-indol-2-yl)-1,2,4-oxadiazol-5-yl]methyl}-1-(4-methyloxan-4-yl)-1H-pyrrole-3-carboxamide $^1$H NMR (400 MHz, DMSO-d6) δ ppm 8.66 (br t, J=5.56 Hz, 1H), 8.20 (br s, 1H), 7.86 (s, 1H), 7.59 (s, 1H), 7.12 (t, J=8.07 Hz, 1H), 7.02 (t, J=2.57 Hz, 1H), 6.89 (br d, J=8.07 Hz, 1H), 6.55 (br s, 1H), 6.31 (d, J=7.95 Hz, 1H), 5.94 (br d, J=7.70 Hz, 1H), 5.51 (q, J=8.48 Hz, 2H), 5.11-4.88 (m, 1H), 4.74 (d, J=5.62 Hz, 2H), 3.77 (br s, 1H), 3.68-3.62 (m, 2H), 3.60-3.52 (m, 2H), 2.89 (br s, 2H), 2.75 (br s, 2H), 2.19-2.08 (m, 2H), 1.98-1.87 (m, 4H), 1.75 (br s, 1H), 1.43 (s, 3H).

Compound 403B: N-{[3-(4-{[(3R,4S)-4-fluoro-1-methylpiperidin-3-yl]amino}-1-(2,2,2-trifluoroethyl)-1H-indol-2-yl)-1,2,4-oxadiazol-5-yl]methyl}-1-(4-methyloxan-4-yl)-1H-pyrrole-3-carboxamide and Compound 416B: N-{[3-(4-{1(3S,4R)-4-fluoro-1-methylpiperidin-3-yl]amino}-1-(2,2,2-trifluoroethyl)-1H-indol-2-yl)-1,2,4-oxadiazol-5-yl]methyl}-1-(4-methyloxan-4-yl)-1H-pyrrole-3-carboxamide: To a mixture of racemic N-[[$^3$-[4-[[(3R,4S)-4-fluoro-3-piperidyl]amino]-1-(2,2,2-trifluoroethyl)indol-2-yl]-1,2,4-oxadiazol-5-yl]methyl]-1-(4-methyltetrahydropyran-4-yl)pyrrole-3-carboxamide (160 mg, 265 µmol, 1 eq) and paraformaldehyde (79.6 mg, 2.65 mmol, 10 eq) in methanol (4 mL) were added sodium cyanoborohydride (50 mg, 795 µmol, 3 eq) and acetic acid (2.65 mmol, 150 µL 10 eq) at 25° C. under nitrogen. The mixture was stirred at 50° C. for 2 h. The residue was poured into sodium bicarbonate (10 mL) and stirred for 10 min. The aqueous phase was extracted with EA (3×20 mL). The combined organic phase was washed with brine (3×20 mL), dried over anhydrous sodium sulfate, filtered, and concentrated in vacuo. The residue was purified by prep-TLC (SiO$_2$, DCM/methanol=20:1) to afford the racemic product (120 mg, 69.1 µmol, 52.2% yield) as yellow solid. LC-MS (ES$^+$, m/z): 618.3 [(M+H)$^+$]. The residue was further separated by SFC (column: DAICEL CHIRALPAK AD (250 mm×30 mm, 10 um); mobile phase: [0.1% NH$_3$H$_2$O IPA] to afford the resolved enantiomers.

Compound 403B: N-{[3-(4-{1[(3R,4S)-4-fluoro-1-methylpiperidin-3-yl]amino}-1-(2,2,2-trifluoroethyl)-1H-indol-2-yl)-1,2,4-oxadiazol-5-yl]methyl}-1-(4-methyloxan-4-yl)-1H-pyrrole-3-carboxamide (42.8 mg, 26.1% yield, 99.8% purity). LC-MS (ES$^+$, m/z): 618.3 [(M+H)$^+$]. $^1$H NMR (400

MHz, DMSO-d( ) δ ppm 8.68 (t, J=5.62 Hz, 1H), 7.87 (s, 1H), 7.58 (s, 1H), 7.12 (t, J=7.94 Hz, 1H), 7.02 (t, J=2.54 Hz, 1H), 6.90 (d, J=8.16 Hz, 1H), 6.55 (br s, 1H), 6.31 (d, J=7.72 Hz, 1H), 5.98 (br d, J=8.82 Hz, 1H), 5.51 (q, J=8.75 Hz, 2H), 5.01-4.82 (m, 1H), 4.74 (d, J=5.51 Hz, 2H), 3.87-3.75 (m, 1H), 3.69-3.62 (m, 2H), 3.59-3.53 (m, 2H), 2.69 (br d, J=15.66 Hz, 2H), 2.57 (br s, 2H), 2.25 (br s, 3H), 2.14 (dt, J=13.40, 3.67 Hz, 2H), 2.01-1.79 (m, 4H), 1.43 (s, 3H).

Compound 419B: N-{[3-(4-{[(3S,4R)-4-fluoro-1-methylpiperidin-3-yl]amino}-1-(2,2,2-trifluoroethyl)-1H-indol-2-yl)-1,2,4-oxadiazol-5-yl]methyl}-1-(4-methyloxan-4-yl)-1H-pyrrole-3-carboxamide (33.4 mg, 20.0% yield, 97.93% purity), a yellow solid. LC-MS (ES+, m/z): 618.3 [(M+H)+]. 1H NMR (400 MHz, DMSO-d6) δ ppm 8.68 (t, J=5.29 Hz, 1H), 7.87 (s, 1H), 7.58 (s, 1H), 7.16-7.07 (m, 1H), 7.02 (br s, 1H), 6.90 (br d, J=8.16 Hz, 1H), 6.55 (br s, 1H), 6.32 (d, J=7.94 Hz, 1H), 6.00 (br d, J=7.28 Hz, 1H), 5.51 (q, J=8.82 Hz, 2H), 5.03-4.83 (m, 1H), 4.74 (d, J=5.73 Hz, 2H), 3.87-3.74 (m, 1H), 3.68-3.62 (m, 2H), 3.60-3.53 (m, 2H), 2.83-2.53 (m, 4H), 2.28 (br s, 3H), 2.17-2.10 (m, 2H), 2.03-1.82 (m, 4H), 1.43 (s, 3H).

Example 158: Compound 404B: N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(4-methyloxan-4-yl)-1H-pyrazole-4-carboxamide

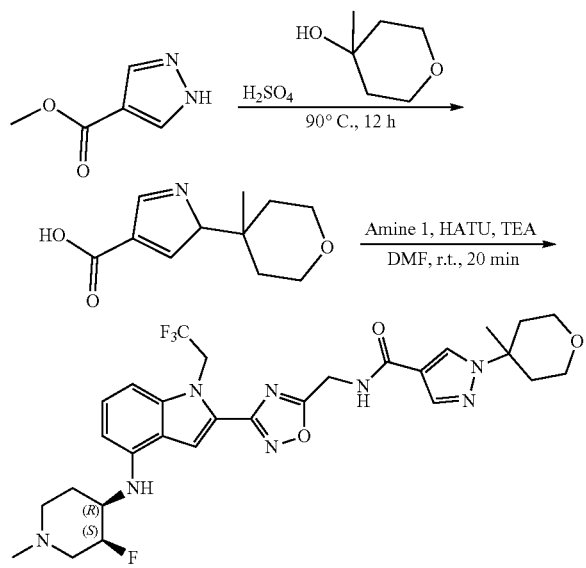

To a mixture of methyl 1H-pyrazole-4-carboxylate (0.6 g, 4.8 mmol, 1 eq) and 4-methyltetrahydropyran-4-ol (3.81 g, 32.8 mmol, 6.9 eq), sulfuric acid (4.85 mmol, 260 μL 1.02 eq) in one portion at 90° C. under nitrogen. The mixture was stirred at 90° C. for 12 h. The reaction was concentrated in vacuo, and the residue was purified by prep-HPLC (TFA conditions, column: Nano-micro Kromasil C18 100×40 mm 10 um; mobile phase: [water (0.1 % TFA)-ACN]; B %: 1%-28%, 8 min) to provide the desired product (160 mg, 16.0% yield) as a white solid. LC-MS (ES+, m/z):211.1 [(M+H)+].

To a mixture of 1-(4-methyltetrahydropyran-4-yl)pyrazole-4-carboxylic acid (80.8 mg, 385 μmol, 1.2 eq) in DMF (3 mL) were added HATU (243.7 mg, 640.9 μmol, 2 eq) and TEA (3.20 mmol, 445 μL 10 eq) at 20° C. under nitrogen. The mixture was stirred at 20° C. for 10 min, followed by addition of Amine 1 (200 mg, 320.4 μmol, 1 eq, 2HCl). The mixture was stirred at 20° C. for 10 min. The residue was poured into ice-water (w/w=1/1) (100 mL). The aqueous phase was extracted with EA (30 mL×3). The combined organic phase was washed with brine (30 mL×3), dried over anhydrous sodium sulfate, filtered, and concentrated in vacuo. The reaction was purified by prep-TLC (SiO2 DCM: methanol=10:1) to afford the product N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(4-methyloxan-4-yl)-1H-pyrazole-4-carboxamide (58.8 mg, 29.3% yield, 98.6% purity). LC-MS (ES+, m/z): 619.3 [(M+H)+]. 1H NMR (400 MHz, DMSO-d6) δ ppm 9.00 (t, J=5.60 Hz, 1H), 8.43 (s, 1H), 7.98 (s, 1H), 7.90 (s, 1H), 7.12 (t, J=8.00 Hz, 1H), 6.88 (d, J=8.40 Hz, 1H), 6.28 (d, J=8.00 Hz, 1H), 6.03 (br d, J=8.00 Hz, 1H), 5.50 (q, J=9.00 Hz, 2H), 4.94-4.75 (m, 3H), 3.75-3.64 (m, 2H), 3.56 (br s, 1H), 3.49-3.42 (m, 2H), 3.04 (br s, 1H), 2.82 (br d, J=9.20 Hz, 1H), 2.39-2.32 (m, 2H), 2.20 (br s, 4H), 2.09 (br d, J=10.40 Hz, 1H), 2.05-1.96 (m, 1H), 1.96-1.87 (m, 2H), 1.68 (br d, J=10.00 Hz, 1H), 1.45 (s, 3H).

Example 159: Compound 40513: N-{[3-(4-{[(3S,4R)-1-tert-butyl-3-fluoropiperidin-4-yl]amino}-1-(2,2,2-trifluoroethyl)-1H-indol-2-yl)-1,2,4-oxadiazol-5-yl]methyl}-1-methyl-1H-pyrazole-4-carboxamide; Compound 40613: N-{[3-(4-{[(3R,4S)-1-tert-butyl-3-fluoropiperidin-4-yl]amino}-1-(2,2,2-trifluoroethyl)-1H-indol-2-yl)-1,2,4-oxadiazol-5-yl]methyl}-1-methyl-1H-pyrazole-4-carboxamide; and Compound 407B: N-{[3-(4-{[(3R,4R)-1-tert-butyl-3-fluoropiperidin-4-yl]amino}-1-(2,2,2-trifluoroethyl)-1H-indol-2-yl)-1,2,4-oxadiazol-5-yl]methyl}-1-methyl-1H-pyrazole-4-carboxamide

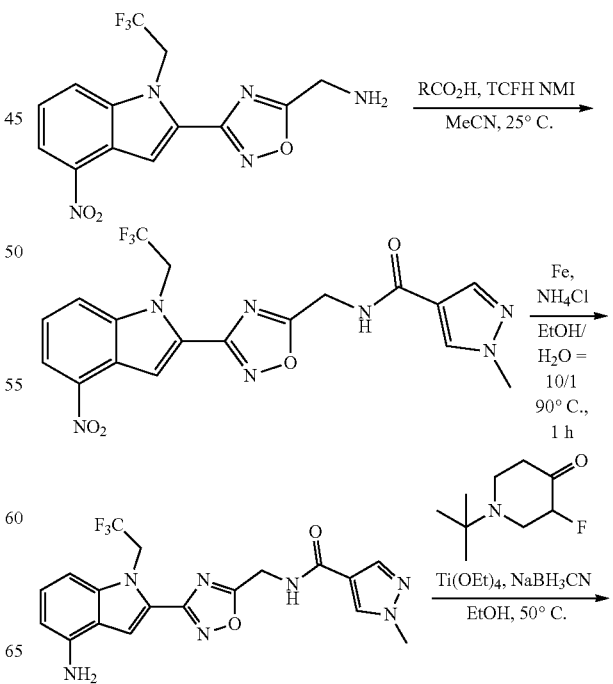

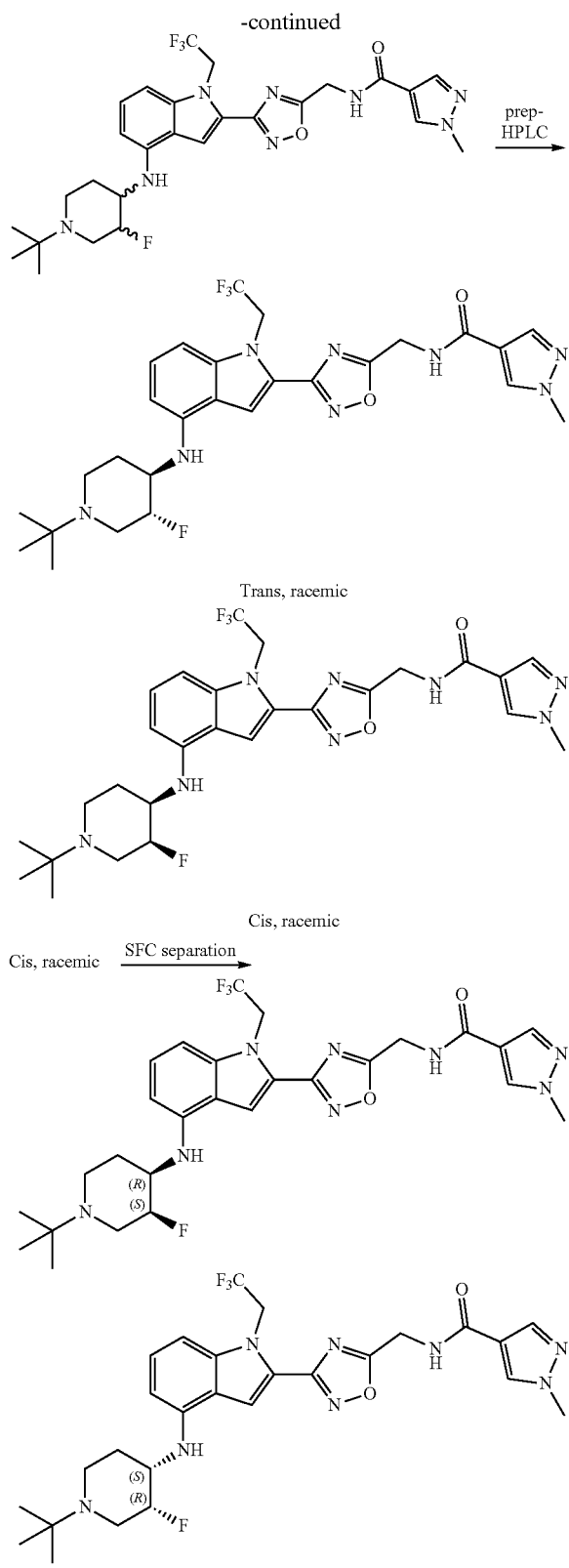

A mixture of [3-[4-nitro-1-(2,2,2-trifluoroethyl)indol-2-yl]-1,2,4-oxadiazol-5-yl] methanamine (1.5 g, 3.97 mmol, 1 eq, HCl), 1-methylpyrazole-4-carboxylic acid (601 mg, 4.77 mmol, 1.2 eq), [chloro(dimethylamino)methylene]-dimethylammonium; hexafluorophosphate (1.67 g, 5.96 mmol, 1.5 eq), and 1-methylimidazole (11.9 mmol, 950 μL 3 eq) in acetonitrile (15 mL) was stirred at 25° C. for 1 h under nitrogen atmosphere. The reaction mixture was quenched by adding water (50 mL), then filtered in vacuo to give a residue. The crude product was triturated with EA (20 mL) for 12 h, then filtered and dried to give the product (1.1 g, 2.45 mmol, 61.6% yield). LC-MS (ES+, m/z): 450.1 [(M+H)+]. $^1$H NMR (400 MHz, DMSO-d6) 5=9.14-9.00 (t, J=5.6 Hz, 1H), 8.40-8.30 (d, J=8.4 Hz, 1H), 8.27-8.23 (d, J=8.0 Hz, 1H), 8.20 (s, 1H), 7.90 (s, 1H), 7.88 (s, 1H), 7.69-7.61 (t, J=8.4 Hz, 1H), 5.88-5.71 (dt, J=8.4 Hz, 2H), 4.95-4.76 (d, J=5.6 Hz, 2H), 3.88 (s, 3H).

To a mixture of 1-methyl-N-[[3-[4-nitro-1-(2,2,2-trifluoroethyl)indol-2-yl]-1,2,4-oxadiazol-5-yl]methyl]pyrazole-4-carboxamide (1 g, 2 mmol, 1 eq) and ammonium chloride (642.8 mg, 12 mmol, 6 eq) in ethanol (100 mL) and water (10 mL) was added iron powder (335.6 mg, 6.01 mmol, 3 eq). The mixture was stirred at 90° C. for 1 h. The reaction mixture was concentrated in vacuo to remove ethanol. The residue was diluted with water (50 mL) and extracted with EA (3×50 mL). The combined organic layers were washed with brine (3×50 mL), dried over sodium sulfate, filtered, and concentrated in vacuo to give a residue. The residue was purified by column chromatography (SiO$_2$, PE:EA=10:1 to 0:1) to give the product (0.55 g, 1.27 mmol, 63.5% yield, 97% purity) LC-MS (ES+, m/z): 420.1 [(M+H)+]$^1$H NMR (400 MHz, DMSO-d6) δ=9.06-8.90 (t, J=5.6 Hz, 1H), 8.19 (s, 1H), 7.90 (s, 1H), 7.61 (s, 1H), 7.11-6.93 (t, J=8.0 Hz, 1H), 6.87-6.66 (d, J=8.0 Hz, 1H), 6.42-6.14 (d, J=7.6 Hz, 1H), 5.70 (s, 2H), 5.55-5.34 (dt, J=8.4 Hz, 2H), 4.83-4.68 (d, J=5.6 Hz, 2H), 3.87 (s, 3H).

To a solution of N-[[3-[4-amino-1-(2,2,2-trifluoroethyl)indol-2-yl]-1,2,4-oxadiazol-5-yl]methyl]-1-methyl-pyrazole-4-carboxamide (250 mg, 596 μmol, 1 eq) and 1-tert-butyl-3-fluoro-piperidin-4-one (620 mg, 3.6 mmol, 6.0 eq) in ethanol (15 mL) was added titanium ethoxide (1.7 g, 6 mmol, 1.2 mL, 10 eq) at 50° C. The mixture was stirred at 50° C. for 12 h, then sodium cyanoborohydride (187 mg, 3.0 mmol, 5.0 eq) was added to the mixture. The mixture was stirred at 50° C. for 30 min. The mixture was diluted with sodium carbonate (100 mL) and stirred at 25° C. for 1 h. The mixture was filtered, and the filter cake was washed with EA (3×100 mL). The filtrate was concentrated in vacuo to give a residue. The residue was purified by prep-TLC (DCM: methanol=10:1), then purified by prep-HPLC (column: Phenomenex Luna C18 200×40 mm×10 um; mobile phase: [water (0.2% FA)-ACN]; B %: 20%-50%, 8 min to provide pure, racemic Compound 407B: trans-N-{[3-(4-{[(3R,4R)-1-tert-butyl-3-fluoropiperidin-4-yl]amino}-1-(2,2,2-trifluoroethyl)-1H-indol-2-yl)-1,2,4-oxadiazol-5-yl]methyl}-1-methyl-1H-pyrazole-4-carboxamide (30 mg, 8.7% yield). LC-MS (ES+, m/z): 577.3 [(M+H)+]. $^1$H NMR (400 MHz, DMSO-d6) δ=9.10-8.82 (t, J=5.6 Hz, 1H), 8.19 (s, 1H), 7.90 (s, 1H), 7.77 (s, 1H), 7.18-7.01 (t, J=8.0 Hz, 1H), 6.90-6.71 (d, J=8.0 Hz, 1H), 6.35-6.21 (d, J=7.6 Hz, 1H), 6.19-6.02 (d, J=8.4 Hz, 1H), 5.60-5.37 (dt, J=8.4 Hz, 2H), 4.84-4.73 (d, J=5.6 Hz, 2H), 4.61-4.33 (m, 1H), 3.88 (s, 3H), 3.58-3.47 (m, 1H), 3.31-3.26 (m, 1H), 2.99-2.89 (m, 1H), 2.24-2.02 (m, 3H), 1.42-1.33 (m, 1H), 1.05 (s, 9H).

The racemic mixture of cis diasteromers was further purified by SFC (column: DAICEL CHIRALCELOD(250 mm×50 mm, 10 um); mobile phase: [0.1% NH$_3$H$_2$O ETOH];B %: 38%-38%,min) to resolve the enantiomers.

Compound 405B: N-{[3-(4-{[(3S,4R)-1-tert-butyl-3-fluoropiperidin-4-yl]amino}-1-(2,2,2-trifluoroethyl)-1H-indol-2-yl)-1,2,4-oxadiazol-5-yl]methyl}-1-methyl-1H-pyrazole-4-carboxamide (110 mg, 190.78 μmol, 16.0% yield).

LC-MS (ES+, m/z): 577.3 [(M+H)+]. 1H NMR (400 MHz, DMSO-d6) δ=9.09-8.95 (t, J=6.0 Hz, 1H), 8.20 (s, 1H), 7.94-7.79 (d, J=7.2 Hz, 2H), 7.17-7.02 (t, J=8.0 Hz, 1H), 6.93-6.81 (d, J=8.0 Hz, 1H), 6.34-6.23 (d, J=8.0 Hz, 1H), 6.09-5.91 (d, J=8.4 Hz, 1H), 5.62-5.44 (dt, J=8.8 Hz, 2H), 4.96-4.74 (m, 3H), 3.87 (s, 3H), 3.65-3.53 (m, 1H), 3.25-3.20 (m, 1H), 3.06-2.98 (m, 1H), 2.43-2.35 (m, 1H), 2.26-2.18 (t, J=11.2 Hz, 1H), 1.97-1.86 (m, 1H), 1.77-1.67 (m, 1H), 1.03 (s, 9H).

Compound 406B: N-{[3-(4-{[(3R,4S)-1-tert-butyl-3-fluoropiperidin-4-yl]amino}-1-(2,2,2-trifluoroethyl)-1H-indol-2-yl)-1,2,4-oxadiazol-5-yl]methyl}-1-methyl-1H-pyrazole-4-carboxamide (30 mg, 52.0 µmol, 8.7% yield). LC-MS (ES+, m/z): 577.3 [(M+H)+]. 1H NMR (400 MHz, DMSO-d6) δ=9.10-8.82 (t, J=5.6 Hz, 1H), 8.19 (s, 1H), 7.90 (s, 1H), 7.77 (s, 1H), 7.18-7.01 (t, J=8.0 Hz, 1H), 6.90-6.71 (d, J=8.0 Hz, 1H), 6.35-6.21 (d, J=7.6 Hz, 1H), 6.19-6.02 (d, J=8.4 Hz, 1H), 5.60-5.37 (dt, J=8.4 Hz, 2H), 4.84-4.73 (d, J=5.6 Hz, 2H), 4.61-4.33 (m, 1H), 3.88 (s, 3H), 3.58-3.47 (m, 1H), 3.31-3.26 (m, 1H), 2.99-2.89 (m, 1H), 2.24-2.02 (m, 3H), 1.42-1.33 (m, 1H), 1.05 (s, 9H).

Example 160: Compound 408B: 1-tert-butyl-N-{[3-(4-{[(3R,4S)-4-fluoro-1-methylpiperidin-3-yl]amino}-1-(2,2,2-trifluoroethyl)-1H-indol-2-yl)-1,2,4-oxadiazol-5-yl]methyl}-1H-pyrazole-4-carboxamide

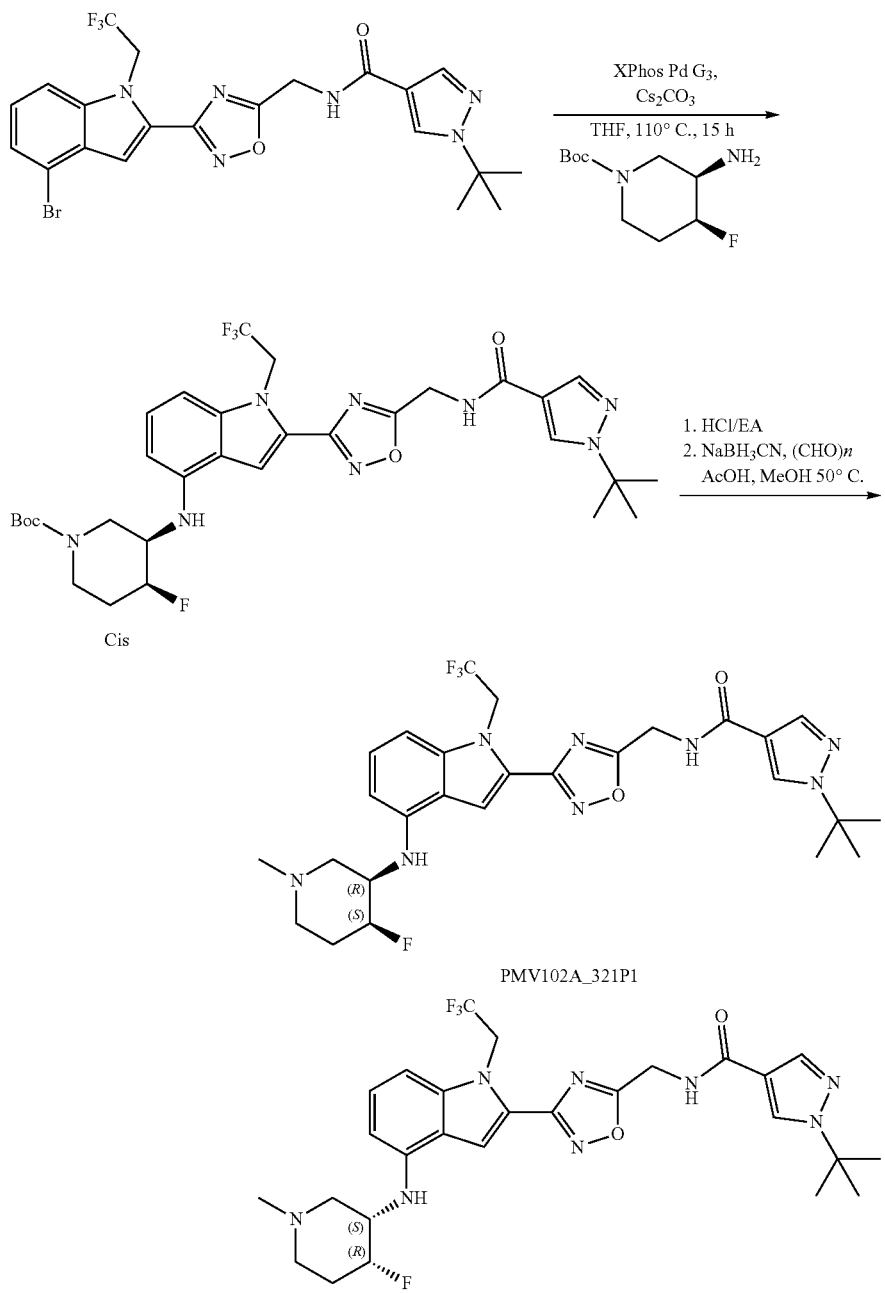

A mixture of the previously prepared N-[[3-[4-bromo-1-(2,2,2-trifluoroethyl)indol-2-yl]-1,2,4-oxadiazol-5-yl]methyl]-1-tert-butyl-pyrazole-4-carboxamide (200 mg, 381 µmol, 1 eq), racemic tert-butyl (3R,4S)-3-amino-4-fluoro-piperidine-1-carboxylate (249.3 mg, 1.14 mmol, 3 eq), cesium carbonate (372.1 mg, 1.14 mmol, 3 eq), and XPhos Palladium Generation 3 (96.7 mg, 114 µmol, 0.3 eq) in THF (4 mL) was degassed and purged with nitrogen 3 times, then the mixture was heated and stirred at 110° C. for 15 hrs in a sealed tube. Sat. EDTA (20 mL) was added to the mixture, which was stirred for 1 h. The reaction mixture was diluted with water (50 mL) and extracted with EA (2×20 mL). The combined organic layers were washed with brine (50 mL), dried over sodium sulfate, filtered, and concentrated in vacuo to give a residue. The residue was purified by prep-TLC (SiO$_2$, PE:EA=1:2) to give the product (280 mg, 22.2% yield). LC-MS (ES$^+$, m/z): 663.3 [(M+H)$^+$].

tert-Butyl (3R,4S)-3-[[2-[5-[[(1-tert-butylpyrazole-4-carbonyl)amino]methyl]-1,2,4-oxadiazol-3-yl]-1-(2,2,2-trifluoroethyl)indol-4-yl]amino]-4-fluoro-piperidine-1-carboxylate (320 mg, 483 µmol, 1 eq) was added to 4N HCl/EA (6 mL) and the mixture was stirred at 25° C. for 10 min under nitrogen atmosphere. The reaction mixture was concentrated in vacuo to give the product (310 mg, crude). LC-MS (ES$^−$, m/z): 563.2 [(M+H)$^+$].

A mixture of 1-tert-butyl-N-[[3-[4-[[(3R,4S)-4-fluoro-3-piperidyl]amino]-1-(2,2,2-trifluoroethyl) indol-2-yl]-1,2,4-oxadiazol-5-yl]methyl]pyrazole-4-carboxamide (310 mg, 551 µmol, 1 eq), paraformaldehyde (165.5 mg, 5.51 mmol, 10 eq), sodium cyanoborohydride (103.9 mg, 1.65 mmol, 3 eq), acetic acid (5.51 mmol, 315 µL 10 eq) in methanol (10 mL) was degassed and purged with nitrogen 3 times, then the mixture was stirred at 50° C. for 1 h under nitrogen atmosphere. The reaction mixture was poured into sodium bicarbonate (sat., aq., 20 mL). The reaction mixture was diluted with water (50 mL) and extracted with EA (2×25 mL). The combined organic layers were washed with brine (50 mL), dried over sodium sulfate, filtered, and concentrated in vacuo to give a residue. The residue was purified by prep-TLC (SiO$_2$, DCM: methanol=10:1), and the enantiomers resolved by SFC (column: DAICEL CHIRALPAK AD(250 mm×50 mm, 10 um); mobile phase: [0.1% NH$_3$H$_2$O ETOH]; B %: 50%) to provide the products.

Compound 408B: Tert-butyl-N-[[3-[4-[[(3R,4S)-4-fluoro-1-methyl-3-piperidyl]amino]-1-(2,2,2-trifluoroethyl)indol-2-yl]-1,2,4-oxadiazol-5-yl]methyl]pyrazole-4-carboxamide (69.1 mg, 32.6% yield, 99.1% purity) was obtained as white solid. LC-MS (ES$^+$, m/z): 577.3 [(M+H)$^+$]. $^1$H NMR (DMSO-d$_6$, 400 MHz): δ (ppm) 8.98 (t, J=5.6 Hz, 1H), 8.35 (s, 1H), 7.99-7.84 (m, 2H), 7.13 (t, J=8.1 Hz, 1H), 6.90 (d, J=8.3 Hz, 1H), 6.32 (d, J=7.9 Hz, 1H), 5.97 (br d, J=8.8 Hz, 1H), 5.51 (q, J=8.8 Hz, 2H), 5.05-4.73 (m, 3H), 3.91-3.69 (m, 1H), 2.74-2.68 (m, 1H), 2.36-2.27 (m, 2H), 2.23 (s, 3H), 2.17 (br d, J=9.6 Hz, 1H), 2.00-1.95 (m, 1H), 1.83 (br s, 1H), 1.55 (s, 9H).

Compound 409B: Tert-butyl-N-[[3-[4-[[(3S,4R)-4-fluoro-1-methyl-3-piperidyl]amino]-1-(2,2,2-trifluoroethyl)indol-2-yl]-1,2,4-oxadiazol-5-yl]methyl]pyrazole-4-carboxamide (56.6 mg, 26.8% yield, 99.3% purity) was obtained as white solid. LC-MS (ES$^+$, m/z): 577.3 [(M+H)$^+$]. $^1$H NMR (DMSO-d$_6$, 400 MHz): S=9.00 (t, J=5.6 Hz, 1H), 8.36 (s, 1H), 7.98-7.86 (m, 2H), 7.21-7.08 (m, 1H), 6.91 (d, J=8.4 Hz, 1H), 6.33 (d, J=7.9 Hz, 1H), 6.00 (br d, J=8.8 Hz, 1H), 5.52 (q, J=8.8 Hz, 2H), 5.05-4.73 (m, 3H), 3.93-3.68 (m, 1H), 2.69 (br s, 1H), 2.35 (br s, 2H), 2.25 (br s, 3H), 2.19 (br d, J=8.3 Hz, 1H), 2.02-1.82 (m, 2H), 1.56 (s, 9H).

Example 161: Compound 410B: N-{[3-(4-{[(3R,4S)-4-fluoro-1-methylpiperidin-3-yl]amino}-1-(2,2,2-trifluoroethyl)-1H-indol-2-yl)-1,2,4-oxadiazol-5-yl]methyl}-1-[(1R,2R)-2-methoxycyclopentyl]-1H-pyrrole-3-carboxamide

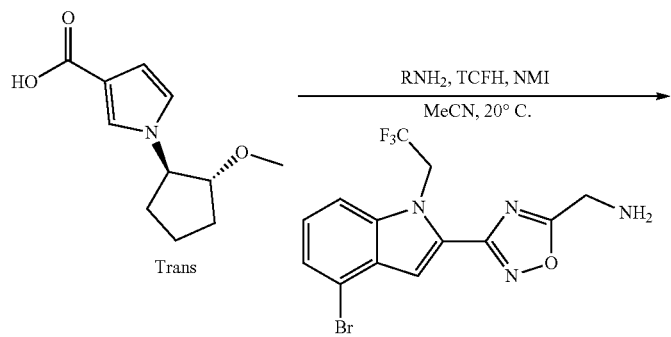

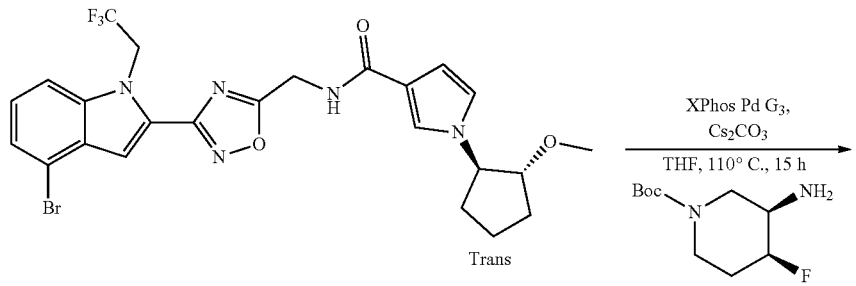

-continued

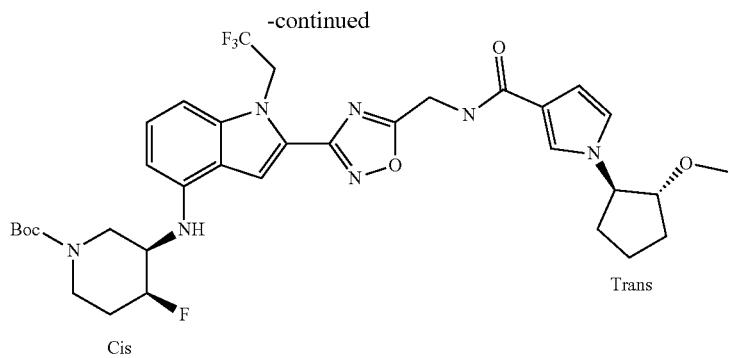

1. HCl, EtOAc
2. NaBH₃CN, (CHO)n, AcOH

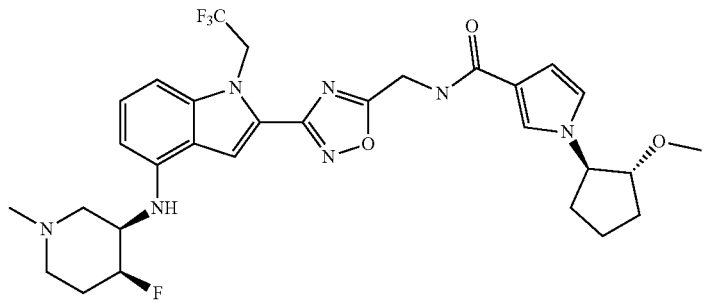

A mixture of the previously prepared [3-[4-bromo-1-(2,2,2-trifluoroethyl)indol-2-yl]-1,2,4-oxadiazol-5-yl] methanamine (0.5 g, 1.1 mmol, 1 eq, 2HCl) and the previously prepared 1-[(1R,2R)-2-methoxycyclopentyl] pyrrole-3-carboxylic acid (280 mg, 1.34 mmol, 1.2 eq), [chloro(dimethylamino) methylene]-dimethyl-ammonium; hexafluorophosphate (470 mg, 1.67 mmol, 1.5 eq), and 1-methylimidazole (3.35 mmol, 270 μL 3 eq) in acetonitrile (6 mL) was degassed and purged with nitrogen 3 times, and then the mixture was stirred at 20° C. for 1 h under nitrogen atmosphere. The mixture was filtered, and concentrated in vacuo to give a residue. This residue was diluted with water (50 mL) and extracted with EA (3×50 mL). The combined organic layers were washed with brine (3×50 mL), dried over sodium sulfate, filtered, and concentrated in vacuo to give a residue. The residue was purified by column chromatography (SiO₂, PE:EA=10:1 to 1:1, DCM:methanol=20:1, Rt=0.5) to give the product (0.5 g, 70.4% yield).

A mixture of N-[[3-[4-bromo-1-(2,2,2-trifluoroethyl)indol-2-yl]-1,2,4-oxadiazol-5-yl] methyl]-1-[(1R,2R)-2-methoxycyclopentyl]pyrrole-3-carboxamide (0.2 g, 35 μmol, 1 eq), cis-tert-butyl (3R,4S)-3-amino-4-fluoro-piperidine-1-carboxylate (231 mg, 1.06 mmol, 3 eq), cesium carbonate (345 mg, 1.06 mmol, 3 eq), and XPhos Palladium Generation 3 (89.7 mg, 106 μmol, 0.3 eq) in THF (2 mL) was degassed and purged with nitrogen 3 times, then the mixture was stirred at 110° C. for 15 h under nitrogen atmosphere. The reaction mixture was quenched by adding water (20 mL) and extracted with EA (3×20 mL). The combined organic layers were washed with brine (3×20 mL), dried over sodium sulfate, filtered, and concentrated in vacuo to give a residue. The residue was purified by prep-TLC (SiO₂, PE:EA=10:1, R$_f$=0.1) to give the product (0.06 g, 24.1% yield).

To a solution of tert-butyl (3R,4S)-4-fluoro-3-[[2-[5-[[[1-[(1R,2R)-2-methoxycyclopentyl]pyrrole-3-carbonyl]amino]methyl]-1,2,4-oxadiazol-3-yl]-1-(2,2,2-trifluoroethyl)indol-4-yl]amino]piperidine-1-carboxylate (80 mg, 114 μmol, 1 eq) in EA (2 mL) was added HCl/EA (4 M, 6 mL, 210 eq). The mixture was stirred at 20° C. for 0.5 h. The reaction mixture was concentrated in vacuo to give the product (50 mg, 68.7% yield, HCl).

To a solution of N-[[3-[4-[[(3R,4S)-4-fluoro-3-piperidyl]amino]-1-(2,2,2-trifluoroethyl)indol-2-yl]-1,2,4-oxadiazol-5-yl]methyl]-1-[(1R,2R)-2-methoxycyclopentyl]pyrrole-3-carboxamide (50 mg, 78.1 μmol, 1 eq, HCl), paraformaldehyde (23.5 mg, 781 μmol, 10 eq) in methanol (2 mL) were added sodium cyanoborohydride (14.7 mg, 234 μmol, 3 eq) and acetic acid (781 μmol, 45 μL 10 eq). The mixture was stirred at 50° C. for 1 h. The reaction mixture was quenched by adding water (10 mL) and extracted with EA (3×10 mL). The combined organic layers were washed with brine (3×10 mL), dried over sodium sulfate, filtered, and concentrated in vacuo to give a residue. The residue was purified by prep-TLC (SiO₂, DCM: methanol=20:1, R$_f$=0.3) to give the desired product N-{[3-(4-{[(3R,4S)-4-fluoro-1-methylpiperidin-3-yl]amino}-1-(2,2,2-trifluoroethyl)-1H-indol-2-yl)-1,2,4-oxadiazol-5-yl]methyl}-1-[(1R,2R)-2-methoxycyclopentyl]-1H-pyrrole-3-carboxamide (21 mg, 40.9% yield). LC-MS (ES⁺, m/z): 618.3 [(M+H)]. ¹H NMR (400 MHz, DMSO-d6) δ=8.73-8.62 (t, J=5.6 Hz, 1H), 7.87 (s, 1H), 7.53-7.43 (m, 1H), 7.18-7.08 (t, J=8.0 Hz, 1H), 6.95-6.83 (m, 2H), 6.57-6.45 (m, 1H), 6.37-6.26 (d, J=7.6 Hz, 1H), 6.05-5.93 (d, J=8.8 Hz, 1H), 5.58-5.42 (dt, J=8.8 Hz, 2H), 5.03-4.81 (m, 1H), 4.77-4.70 (d, J=5.6 Hz, 2H), 4.37-4.25 (dt, J=8.0 Hz, 1H), 3.90-3.71 (m, 2H), 3.19 (s, 3H), 2.79-2.68 (m, 1H), 2.59-2.53 (m, 1H), 2.35- 2.22 (br s, 4H), 2.22-2.10 (m, 2H), 2.09-1.92 (m, 2H), 1.90-1.66 (m, 4H), 1.64-1.54 (m, 1H) $^1$H NMR (400 MHz, DMSO-d6) δ=8.87-8.69 (t, J=5.6 Hz, 1H), 7.81 (s, 1H), 7.53-7.39 (m, 11H), 7.20-7.04 (t, J=8.0 Hz, 1H), 6.96-6.76 (m, 2H), 6.55-6.42 (m, 1H), 6.37-6.20 (d, J=8.0 Hz, 1H), 5.58-5.36 (dt, J=8.8 Hz, 2H), 5.01-4.78 (m, 1H), 4.74-4.66 (m, 2H), 4.38-4.17 (dt, J=8.0 Hz, 1H), 3.89-3.72 (m, 2H), 3.16 (s, 3H), 2.72-2.62 (m, 1H), 2.31-2.23 (m, 1H), 2.22-2.09 (m, 5H), 2.07-1.90 (m, 3H), 1.87-1.64 (m, 4H), 1.62-1.52 (m, 1H).

Example 162: Compound 411B: N-{[3-(4-{1[(3R,4R)-1-tert-butyl-3-fluoropiperidin-4-yl]amino}-1-(2,2,2-trifluoroethyl)-1H-indol-2-yl)-1,2,4-oxadiazol-5-yl]methyl}-1-(1-methoxy-2-methylpropan-2-yl)-1H-pyrazole-4-carboxamide; Compound 412B: N-{[3-(4-{[(3S,4R)-1-tert-butyl-3-fluoropiperidin-4-yl]amino}-1-(2,2,2-trifluoroethyl)-1H-indol-2-yl)-1,2,4-oxadiazol-5-yl]methyl}-1-(1-methoxy-2-methylpropan-2-yl)-1H-pyrazole-4-carboxamide; and Compound 413B: N-{13-(4-{1[(3R,4S)-1-tert-butyl-3-fluoropiperidin-4-yl]amino}-1-(2,2,2-trifluoroethyl)-1H-indol-2-yl)-1,2,4-oxadiazol-5-yl]methyl}-1-(1-methoxy-2-methylpropan-2-yl)-1H-pyrazole-4-carboxamide

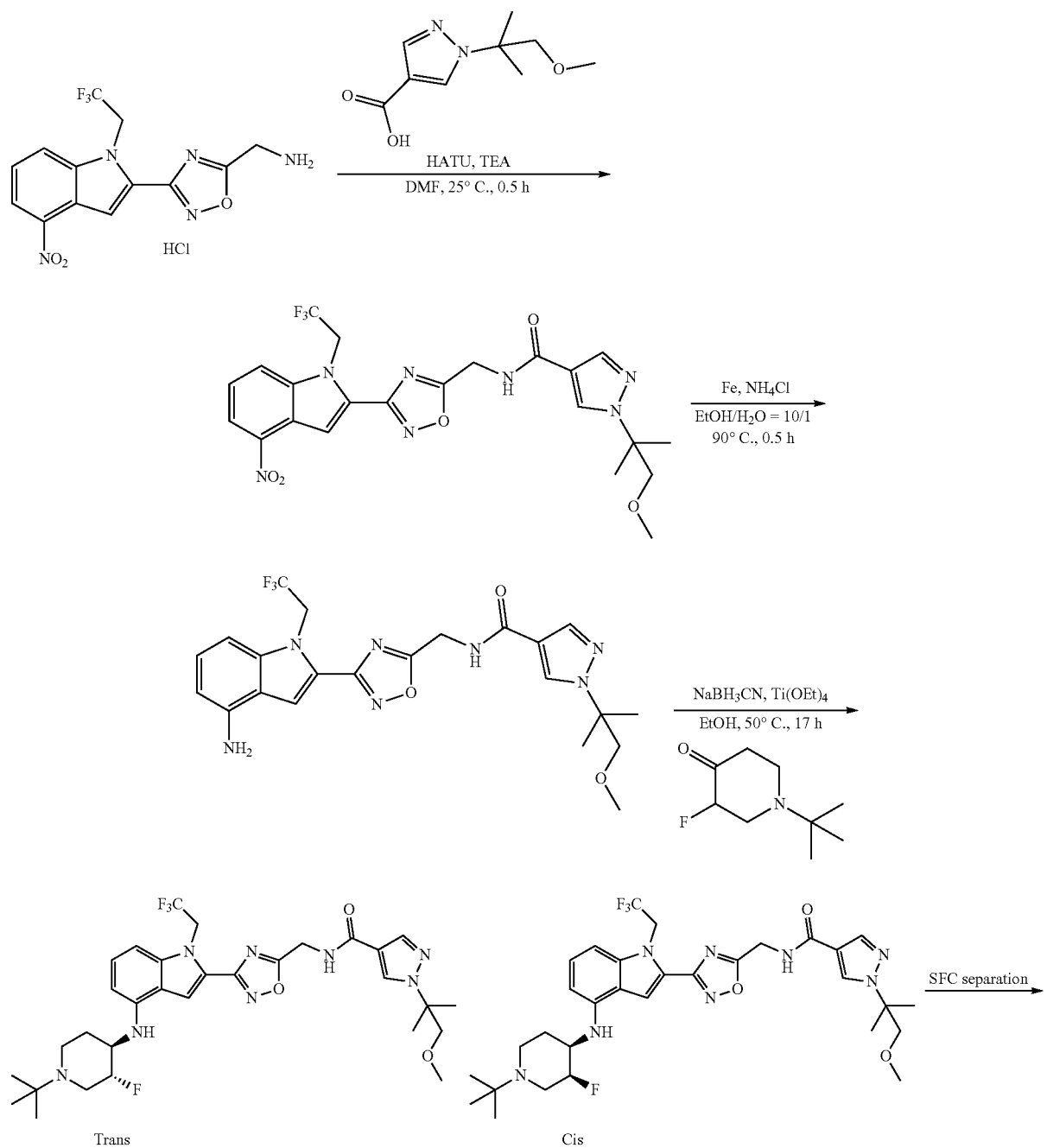

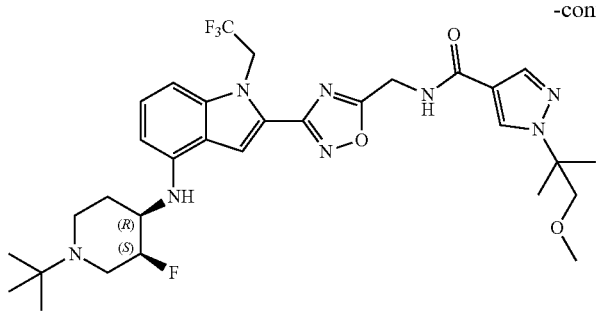
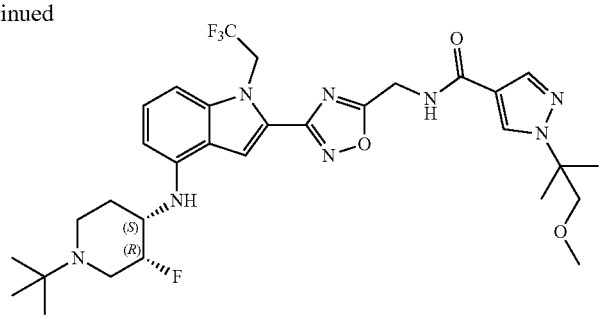

To a solution of the previously prepared 1-(1-methoxy-2-methylpropan-2-yl)-1H-pyrazole-4-carboxylic acid (387.7 mg, 1.96 mmol, 2 eq) in DMF (4 mL) were added TEA (9.78 mmol, 1.36 mL, 10 eq) and HATU (743.6 mg, 1.96 mmol, 2 eq), followed by (3-(4-nitro-1-(2,2,2-trifluoroethyl)-1H-indol-2-yl)-1,2,4-oxadiazol-5-yl)methanamine hydrochloride (450 mg, 978 μmol, 1 eq, 2HCl). The mixture was stirred at 25° C. for 0.5 h. The reaction mixture was poured into water (200 mL), then extracted with EA (80 mL×3). The combined organic phase was washed with brine (60 mL×1), dried over anhydrous sodium sulfate, filtered, and concentrated in vacuo to give a residue. The residue was purified by column chromatography ($SiO_2$, PE/EA=20/1 to 2/1) to give the product (450 mg, 88.3% yield) as a yellow solid. LCMS ($ES^+$, m/z): 522.2 $[(M+H)^+]$.

To a solution of 1-(1-methoxy-2-methylpropan-2-yl)-N-((3-(4-nitro-1-(2,2,2-trifluoroethyl)-1H-indol-2-yl)-1,2,4-oxadiazol-5-yl)methyl)-]H-pyrazole-4-carboxamide (350 mg, 671 μmol, 1 eq) in ethanol (15 mL) and water (1.5 mL) were added iron powder (112.5 mg, 2.01 mmol, 3 eq) and ammonium chloride (215.4 mg, 4.03 mmol, 6 eq), and the mixture was stirred at 90° C. for 0.5 h. The reaction mixture was filtered and poured into water (100 mL), then extracted with EA (80 mL×3). The combined organic phase was washed with brine (100 mL×1), dried over anhydrous sodium sulfate, filtered, and concentrated in vacuo to give a residue. The residue was purified by column chromatography ($SiO_2$, PE:EA=10:1 to 1:2) to give product (200 mg, 60.6% yield) as a yellow solid. LCMS ($ES^+$, m/z): 492.2 $[(M+H)^+]$.

To a solution of N-((3-(4-amino-1-(2,2,2-trifluoroethyl)-1H-indol-2-yl)-1,2,4-oxadiazol-5-yl)methyl)-1-(1-methoxy-2-methylpropan-2-yl)-1H-pyrazole-4-carboxamide (150 mg, 305 μmol, 1 eq) and 1-tert-butyl-3-fluoro-piperidin-4-one (192 mg, 916 μmol, 3 eq, HCl) in ethanol (12 mL) was added titanium ethoxide (3.05 mmol, 630 μL 10 eq). The reaction was heated to 50° C. and stirred for 16 h, then sodium cyanoborohydride (95.9 mg, 1.53 mmol, 5 eq) was added, and the reaction was stirred at 50° C. for 1 h. The reaction mixture was poured into sat. sodium carbonate solution (250 mL), then extracted with EA (100 mL×3). The combined organic phase was washed with brine (100 mL), dried over anhydrous sodium sulfate, filtered, and concentrated in vacuo to give a residue. The residue was purified by prep-HPLC (FA condition: column: Phenomenex Luna C18 200×40 mm×10 um; mobile phase: [water (0.2% FA)-ACN]; B %: 30%-56%, 8 mm) to give the cis products as the racemate (70 mg, 35.4% yield), a white solid, as well as the racemic trans isomer (14.6 mg, 22.51 μmol, 7.4% yield) as a white solid. LCMS ($ES^+$, m/z): 649.3 $[(M+H)^+]$.

Compound 411B: Trans-N-{[3-(4-{[(3R,4R)-1-tert-butyl-3-fluoropiperidin-4-yl]amino}-1-(2,2,2-trifluoroethyl)-1H-indol-2-yl)-1,2,4-oxadiazol-5-yl]methyl}-1-(1-methoxy-2-methylpropan-2-yl)-1H-pyrazole-4-carboxamide (14.6 mg, 22.51 μmol, 7.4% yield), a white solid. LCMS ($ES^+$, m/z): 649.3 $[(M+H)^+]$. $^1$H NMR (400 MHz, DMSO-$d_6$) δ=8.98 (t, J=5.62 Hz, 1H), 8.29 (s, 1H), 7.93 (s, 1H), 7.77 (s, 1H), 7.10 (t, J=8.07 Hz, 1H), 6.84 (br d, J=8.44 Hz, 1H), 6.28 (d, J=7.70 Hz, 1H), 6.11 (br d, J=8.19 Hz, 1H), 5.50 (q, J=8.76 Hz, 2H), 4.78 (d, J=5.62 Hz, 2H), 4.39-4.62 (m, 1H), 3.41-3.60 (m, 3H), 3.28-3.30 (m, 1H), 3.19 (s, 3H), 2.93 (br d, J=9.78 Hz, 1H), 2.11-2.23 (m, 2H), 1.98-2.09 (m, 1H), 1.51 (s, 6H), 1.32-1.43 (m, 1H), 1.05 (s, 9H).

The racemic cis isomers were resolved by SFC (column: REGIS (s,s) WHELK-O1 (250 mm×50 mm, 10 um); mobile phase: [0.1% $NH_3H_2O$ EtOH]; B %: 39%).

Compound 412B: cis-N-{[3-(4-{[(3S,4R)-1-tert-butyl-3-fluoropiperidin-4-yl]amino}-1-(2,2,2-trifluoroethyl)-1H-indol-2-yl)-1,2,4-oxadiazol-5-yl]methyl}-1-(1-methoxy-2-methylpropan-2-yl)-1H-pyrazole-4-carboxamide (24 mg, 33.9% yield). LCMS ($ES^+$, m/z): 592.4 $[(M+H)^+]$. $^1$H NMR (400 MHz, DMSO-$d_6$) δ=8.98 (t, J=5.62 Hz, 1H), 8.29 (s, 1H), 7.91 (d, J=15.89 Hz, 2H), 7.11 (t, J=8.01 Hz, 1H), 6.88 (br d, J=8.31 Hz, 1H), 6.28 (d, J=7.82 Hz, 1H), 5.95 (br d, J=7.82 Hz, 1H), 5.50 (q, J=8.76 Hz, 2H), 4.73-4.94 (m, 3H), 3.47-3.69 (m, 3H), 3.19 (s, 4H), 3.02 (br d, J=8.56 Hz, 1H), 2.36-2.44 (m, 1H), 2.22 (br t, J=10.09 Hz, 1H), 1.83-1.97 (m, 1H), 1.65-1.78 (m, 1H), 1.51 (s, 6H), 1.04 (br s, 9H).

Compound 413B: cis-N-{[3-(4-{[(3R,4S)-1-tert-butyl-3-fluoropiperidin-4-yl]amino}-1-(2,2,2-trifluoroethyl)-1H-indol-2-yl)-1,2,4-oxadiazol-5-yl]methyl}-1-(1-methoxy-2-methylpropan-2-yl)-1H-pyrazole-4-carboxamide (21.2 mg, 29.9% yield) as a white solid. LCMS ($ES^+$, m/z): 592.4 $[(M+H)^+]$. $^1$H NMR (400 MHz, DMSO-$d_6$) 5=8.98 (t, J=5.62 Hz, 1H), 8.29 (s, 1H), 7.91 (d, J=15.89 Hz, 2H), 7.11 (t, J=8.01 Hz, 1H), 6.88 (br d, J=8.31 Hz, 1H), 6.28 (d, J=7.82 Hz, 1H), 5.95 (br d, J=7.82 Hz, 1H), 5.50 (q, J=8.76 Hz, 2H), 4.73-4.94 (m, 3H), 3.47-3.69 (m, 3H), 3.19 (s, 4H), 3.02 (br d, J=8.56 Hz, 1H), 2.36-2.44 (m, 1H), 2.22 (br t, J=10.09 Hz, 1H), 1.83-1.97 (m, 1H), 1.65-1.78 (m, 1H), 1.51 (s, 6H), 1.04 (br s, 9H).

Compound 414B: 1-tert-butyl-N-{[3-(4-{[(3R,4S)-4-fluoro-1-methylpiperidin-3-yl]amino}-1-(2,2,2-trifluoroethyl)-1H-indol-2-yl)-1,2,4-oxadiazol-5-yl]methyl}-1H-pyrrole-3-carboxamide and Compound 415B: 1-tert-butyl-N-{[3-(4-{[(3S,4R)-4-fluoro-1-methylpiperidin-3-yl]amino}-1-(2,2,2-trifluoroethyl)-1H-indol-2-yl)-1,2,4-oxadiazol-5-yl]methyl}-1H-pyrazole-4-carboxamide: The analogues were prepared using the same procedure used to prepare the similar analogs previously described.

Compound 414B: 1-tert-butyl-N-{[3-(4-{[(3R,4S)-4-fluoro-1-methylpiperidin-3-yl]amino}-1-(2,2,2-trifluoroethyl)-1H-indol-2-yl)-1,2,4-oxadiazol-5-yl]methyl}-1H-pyrrole-3-carboxamide (32.2 mg, 20.0% yield, 99.3% purity). LC-MS (ES+, m/z): 575.6 [(M+H)+]. $^1$H NMR (400 MHz, DMSO-$d_6$) δ=8.64 (br t, J=5.7 Hz, 1H), 7.86 (s, 1H), 7.54 (s, 1H), 7.12 (t, J=8.1 Hz, 1H), 6.99 (t, J=2.6 Hz, 1H), 6.89 (d, J=8.4 Hz, 1H), 6.50 (br s, 1H), 6.31 (d, J=7.9 Hz, 1H), 5.96 (br d, J=8.8 Hz, 1H), 5.50 (q, J=8.8 Hz, 2H), 5.00-4.83 (m, 1H), 4.73 (d, J=5.6 Hz, 2H), 3.88-3.68 (m, 1H), 2.75-2.66 (m, 1H), 2.33-2.30 (m, 1H), 2.22 (s, 3H), 2.16 (br d, J=10.3 Hz, 1H), 1.96 (br d, J=10.9 Hz, 2H), 1.86 (br d, J=17.9 Hz, 1H), 1.49 (s, 9H).

Compound 415B: 1-tert-butyl-N-{[3-(4-{[(3S,4R)-4-fluoro-1-methylpiperidin-3-yl]amino}-1-(2,2,2-trifluoroethyl)-1H-indol-2-yl)-1,2,4-oxadiazol-5-yl]methyl}-1H-pyrrole-3-carboxamide (55.8 mg, 34.9% yield, 100% purity) as a yellow solid. $^1$H NMR (400 MHz, DMSO-$d_6$) δ=8.64 (t, J=5.6 Hz, 1H), 7.86 (s, 1H), 7.54 (s, 1H), 7.12 (t, J=8.1 Hz, 1H), 6.99 (t, J=2.5 Hz, 1H), 6.89 (d, J=8.3 Hz, 1H), 6.50 (d, J=2.2 Hz, 1H), 6.31 (d, J=7.9 Hz, 1H), 5.96 (br d, J=8.6 Hz, 1H), 5.51 (q, J=9.0 Hz, 2H), 5.00-4.83 (m, 1H), 4.73 (d, J=5.6 Hz, 2H), 3.94-3.68 (m, 1H), 2.72-2.66 (m, 1H), 2.47-2.44 (m, 1H), 2.32 (br d, J=7.6 Hz, 1H), 2.22 (s, 3H), 2.16 (br d, J=10.9 Hz, 1H), 2.01-1.83 (m, 2H), 1.49 (s, 9H).

Example 163: Compound 416B: N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(2-methylbutan-2-yl)-1H-pyrazole-4-carboxamide

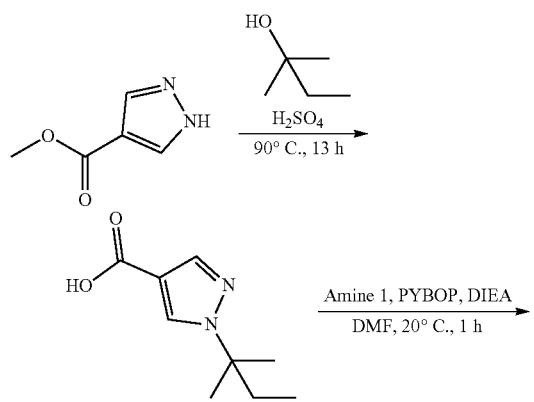

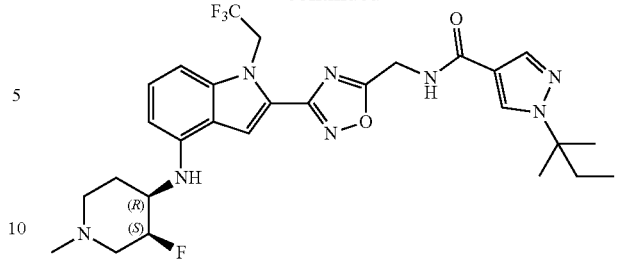

To a mixture of methyl 1H-pyrazole-4-carboxylate (0.5 g, 3.96 mmol, 1 eq) and 2-methylbutan-2-ol (27.4 mmol, 3 mL, 6.92 eq) was added sulfuric acid (4.04 mmol, 220 µL 1.02 eq), and the reaction heated at 90° C. under nitrogen for 12 h. The residue was concentrated in vacuo. The residue was purified by prep-HPLC (TFA condition, column: Nanomicro Kromasil C18 100×40 mm 10 um; mobile phase: [water (0.1% TFA)-ACN]; B %: 1%-44%, 8 min) to afford the product (110 mg, 604 µmol, 15.2% yield). LC-MS (ES+, m/z): 183.1 [(M+H)+]. The above ester was saponified using standard conditions for similar esters (sodium hydroxide, methanol, water).

Amine 1 (100 mg, 160 µmol, 1 eq, 2HCl) was coupled with 1-(1,1-dimethylpropyl)pyrazole-4-carboxylic acid (58.4 mg, 320 µmol, 2 eq) under method D. The crude product was purified by prep-TLC (SiO$_2$, DCM:methanol=10:1) to afford the desired product N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(2-methylbutan-2-yl)-1H-pyrazole-4-carboxamide (25 mg, 26.1% yield, 98.6% purity). LC-MS (ES+, m/z): 591.3. [(M+H)+]. $^1$H NMR (400 MHz, DMSO-d6) δ ppm 8.97 (br t, J=5.62 Hz, 1H), 8.31 (s, 1H), 7.94 (s, 1H), 7.89 (s, 1H), 7.15-7.08 (m, 1H), 6.88 (d, J=8.38 Hz, 1H, 6.28 (d, J=7.94 Hz, 1H), 6.03 (br d, J=8.60 Hz, 1H), 5.60-5.93 (m, 2H), 4.95-4.71 (m, 3H), 3.67-3.51 (m, 1H), 3.05 (br s, 1H), 2.81 (br s, 1H), 2.20 (br s, 4H), 2.13-1.93 (m, 2H), 1.84 (q, J=7.28 Hz, 2H), 1.68 (br d, J=10.14 Hz, 1H), 1.51 (s, 6H), 0.61 (t, J=7.39 Hz, 3H).

Example 164: Compound 417B: N-{[3-(4-{[(3R,4S)-4-fluoro-1-methylpiperidin-3-yl]amino}-1-(2,2,2-trifluoroethyl)-1H-indol-2-yl)-1,2,4-oxadiazol-5-yl]methyl}-1-(1-methoxy-2-methylpropan-2-yl)-1H-pyrrole-3-carboxamide, and Compound 418B: N-{[3-(4-{1[(3S,4R)-4-fluoro-1-methylpiperidin-3-yl]amino}-1-(2,2,2-trifluoroethyl)-1H-indol-2-yl)-1,2,4-oxadiazol-5-yl]methyl}-1-(1-methoxy-2-methylpropan-2-yl)-1H-pyrrole-3-carboxamide

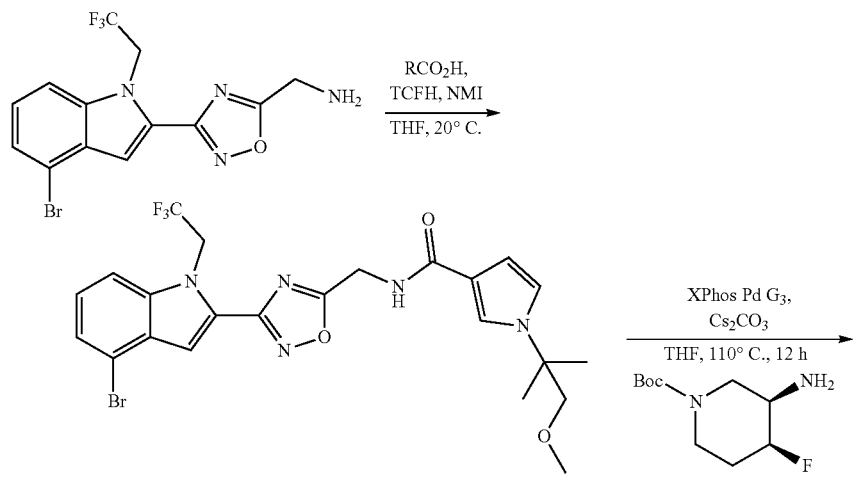

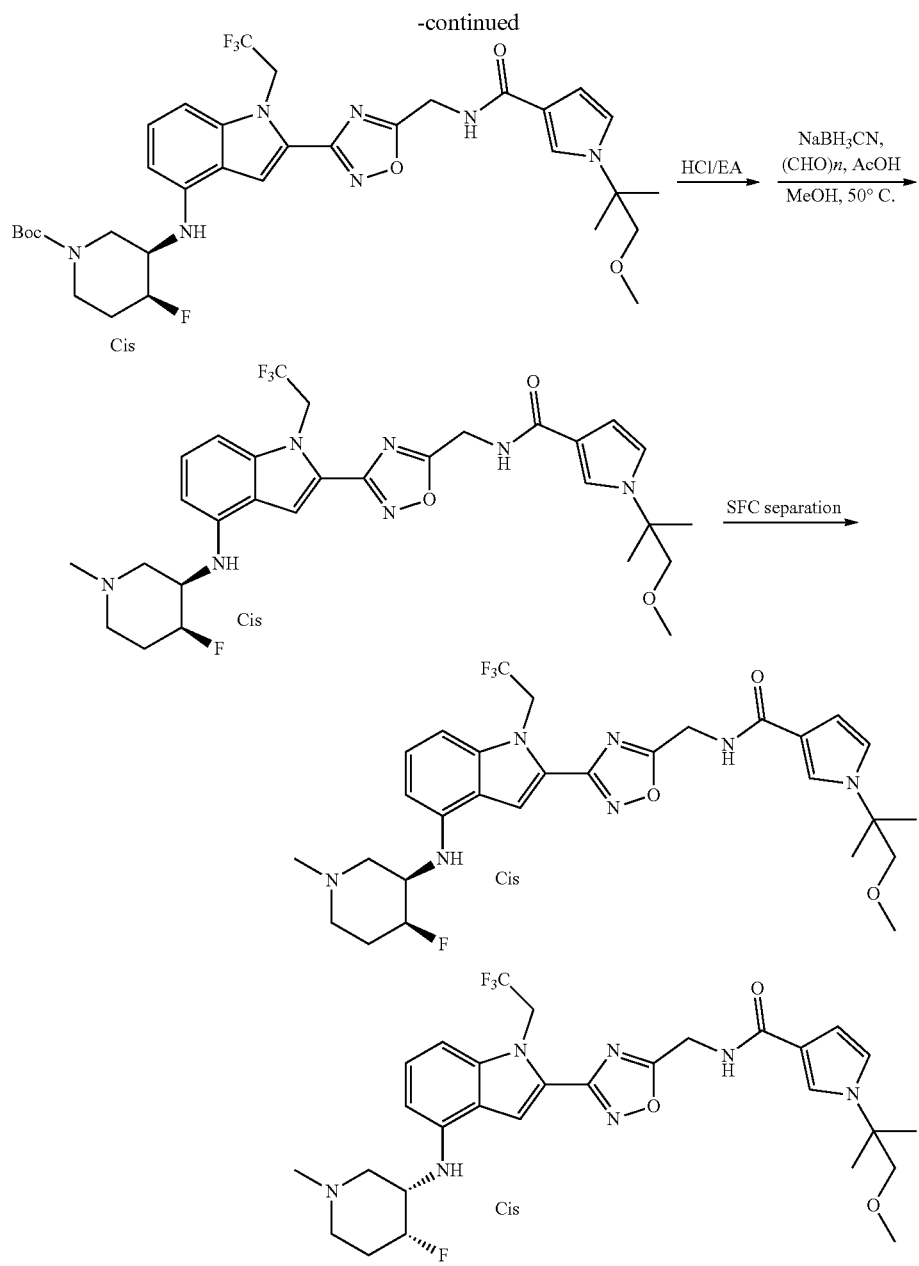

To a mixture of the previously prepared 1-(2-methoxy-1,1-dimethyl-ethyl)pyrrole-3-carboxylic acid (704.3 mg, 3.57 mmol, 2 eq) and [3-[4-bromo-1-(2,2,2-trifluoroethyl)indol-2-yl]-1,2,4-oxadiazol-5-yl]methanamine (800 mg, 1.79 mmol, 1 eq, 2HCl) in acetonitrile (1 mL) were added 1-methylimidazole (5.36 mmol, 430 μL 3 eq), then [chloro(dimethylamino)methylene]-dimethylammonium hexafluorophosphate (751.4 mg, 2.68 mmol, 1.5 eq) at 20° C. under nitrogen. The mixture was stirred at 20° C. for 2 h. The residue was poured into ice-water (30 mL) and stirred for 3 min. The aqueous phase was extracted with EA (3×30 mL). The combined organic phase was washed with brine (3×30 mL), dried over anhydrous sodium sulfate, filtered, and concentrated in vacuo. The residue was purified by column chromatography (SiO₂, PE/EA=1:0 to 0:1) to provide the amide product (860 mg, 1.55 mmol, 86.9% yield). LC-MS (ES⁺,m/z): 554.2 [(M+H)⁺].

A mixture of N-[[3-[4-bromo-1-(2,2,2-trifluoroethyl)indol-2-yl]-1,2,4-oxadiazol-5-yl]methyl]-1-(2-methoxy-1,1-dimethyl-ethyl)pyrrole-3-carboxamide (200 mg, 361 μmol, 1 eq) and tert-butyl (3R,4S)-3-amino-4-fluoro-piperidine-1-carboxylate (236.2 mg, 1.08 mmol, 3 eq), cesium carbonate (352.6 mg, 1.08 mmol, 3 eq), and XPhos Pd Gen. 3 (91.6 mg, 108.2 μmol, 0.3 eq) in THF (4 mL) was degassed and purged with nitrogen 3 times, then the mixture was stirred at 110° C. for 12 h in a sealed tube. The mixture was cooled to 20° C. and concentrated in vacuo at 20° C. The residue was poured into EDTA (20 mL, sat. aq.) and stirred for 1 h. The aqueous phase was extracted with EA (3×30 mL). The combined organic phase was washed with brine (3×30 mL), dried over anhydrous sodium sulfate, filtered, and concentrated in vacuo. The reaction was purified by prep-TLC (SiO₂, PE/EA=1:2) to give the product (10 mg). LC-MS (ES⁺,m/z): 592.4 [(M+H)⁺].

525

To a mixture of t-butyl(3R,4S)-4-fluoro-3-[[2-[5-[[[1-(2-methoxy-1,1-dimethyl-ethyl)pyrrole-3-carbonyl]amino]methyl]-1,2,4-oxadiazol-3-yl]-1-(2,2,2-trifluoroethyl)indol-4-yl]amino]piperidine-1-carboxylate (10 mg, 13.7 μmol, 1 eq, HCl) in HCl/EA (4 M, 1 mL, 1 eq). The mixture was stirred at 20° C. for 30 min. The reaction was concentrated to give the crude product (7 mg).

To a solution of N-[[3-[4-[[(3R,4S)-4-fluoro-3-piperidyl]amino]-1-(2,2,2-trifluoroethyl)indol-2-yl]-1,2,4-oxadiazol-5-yl]methyl]-1-(2-methoxy-1,1-dimethyl-ethyl)pyrrole-3-carboxamide (7 mg, 12 μmol, 1 eq) and paraformaldehyde (3.6 mg, 118 μmol, 10 eq) in methanol (1 mL) were added sodium cyanoborohydride (2.2 mg, 36 μmol, 3 eq) and acetic acid (118 μmol, 7 μL 10 eq) and the reaction was stirred at 50° C. for 1 h. The residue was poured into sodium bicarbonate (30 mL). The aqueous phase was extracted with EA (3×30 mL). The combined organic phase was washed with brine (3×30 mL), dried over anhydrous sodium sulfate, filtered, and concentrated in vacuo. The reaction was purified by prep-TLC (SiO$_2$, DCM/methanol=10:1). A larger batch of racemic material prepared as above was then purified by SFC to resolve the enantiomers.

Compound 417B: N-{[3-(4-{[(3R,4S)-4-fluoro-1-methylpiperidin-3-yl]amino}-1-(2,2,2-trifluoroethyl)-1H-indol-2-yl)-1,2,4-oxadiazol-5-yl]methyl}-1-(1-methoxy-2-methylpropan-2-yl)-1H-pyrrole-3-carboxamide LC-MS (ES$^+$,m/z): 606.3 [(M+H)$^+$]. $^1$H NMR (400 MHz, DMSO-d6) δ ppm 8.66 (t, J=5.73 Hz, 1H), 7.87 (s, 1H), 7.51 (t, J=1.87 Hz, 1H), 7.17-7.07 (m, 1H), 6.96 (t, J=2.65 Hz, 1H), 6.89 (d, J=8.16 Hz, 1H), 6.58-6.42 (m, 1H), 6.31 (d, J=7.94 Hz, 1H), 5.98 (br d, J=8.60 Hz, 1H), 5.51 (q, J=8.97 Hz, 2H), 5.03-4.80 (m, 1H), 4.73 (d, J=5.73 Hz, 2H), 3.88-3.70 (m, 1H), 3.46 (s, 2H), 3.21 (s, 3H), 2.76-2.67 (m, 1H), 2.61-2.55 (m, 1H), 2.34-2.20 (m, 4H), 2.15 (br s, 1H), 2.02-1.79 (m, 2H), 1.47 (s, 6H).

Compound 418B: N-{[3-(4-{[(3S,4R)-4-fluoro-1-methylpiperidin-3-yl]amino}-1-(2,2,2-trifluoroethyl)-1H-indol-2-yl)-1,2,4-oxadiazol-5-yl]methyl}-1-(1-methoxy-2-methylpropan-2-yl)-1H-pyrrole-3-carboxamide LC-MS (ES$^+$,m/z): 606.3 [(M+H)$^+$]. $^1$H NMR (400 MHz, DMSO-d6) δ ppm 8.66 (t, J=5.73 Hz, 1H), 7.87 (s, 1H), 7.56-7.45 (m, 1H), 7.18-7.08 (m, 1H), 6.96 (t, J=2.54 Hz, 1H), 6.89 (d, J=8.38 Hz, 1H), 6.23-6.46 (m, 1H), 6.31 (d, J=7.94 Hz, 1H), 5.98 (br d, J=8.82 Hz, 1H), 5.51 (q, J=8.82 Hz, 2H), 4.99-4.82 (m, 1H), 4.73 (d, J=5.51 Hz, 2H), 3.86-3.71 (m, 1H), 3.46 (s, 2H), 3.21 (s, 3H), 2.72-2.66 (m, 1H), 2.62-2.54 (m, 1H), 2.34-2.20 (m, 4H), 2.15 (br s, 1H), 2.01-1.79 (m, 2H), 1.47 (s, 6H).

Example 165: Compound 422B: 5-tert-butyl-N-{[3-(4-{1[(3S,4R)-3-fluoro-1-methylpiperidin-4-yl]amino}-1-(2,2,2-trifluoroethyl)-1H-indol-2-yl)-1,2,4-oxadiazol-5-yl]methyl}thiophene-2-carboxamide

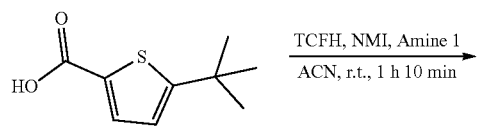

TCFH, NMI, Amine 1
ACN, r.t., 1 h 10 min

526

-continued

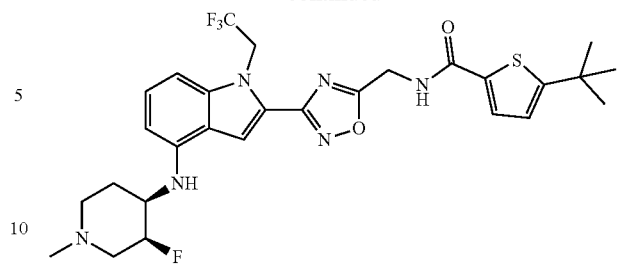

Amine 1 (70 mg, 121 μmol, 1 eq, HCl) and 5-tert-butylthiophene-2-carboxylic acid (33.4 mg, 181 μmol, 1.5 eq) were coupled under method E. The crude was purified by pre-TLC (SiO$_2$,DCM/methanol=10/1) to afford 5-tert-butyl-N-[[3-[4-[[(3S,4R)-3-fluoro-1-methyl-4-piperidyl]amino]-1-(2,2,2-trifluoroethyl)indol-2-yl]-1,2,4-oxadiazol-5-yl]methyl]thiophene-2-carboxamide (30.6 mg, 41.1% yield, 96.2% purity) as white solid. LC-MS (ES$^+$, m/z): 593.3 [(M+H)$^+$]. $^1$H NMR (400 MHz, DMSO-d$_6$) δ=9.31 (t, J=5.56 Hz, 1H), 7.89 (s, 1H), 7.68 (d, J=3.80 Hz, 1H), 7.12 (t, J=8.00 Hz, 1H), 6.99 (d, J=3.80 Hz, 1H), 6.88 (d, J=8.30 Hz, 1H), 6.28 (d, J=7.96 Hz, 1H), 6.03 (d, J=8.20 Hz, 1H), 5.50 (q, J=8.76 Hz, 2H), 4.75-4.93 (m, 3H), 3.50-3.69 (m, 1H), 3.03 (t, J=10.40 Hz, 1H), 2.81 (d, J=10.14 Hz, 1H), 2.15-2.35 (m, 4H), 1.93-2.15 (m, 2H), 1.68 (d, J=10.64 Hz, 1H), 1.35 (s, 9H).

Example 166: Compound 423B: 1-(2-cyclopropylpropan-2-yl)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-pyrrole-3-carboxamide

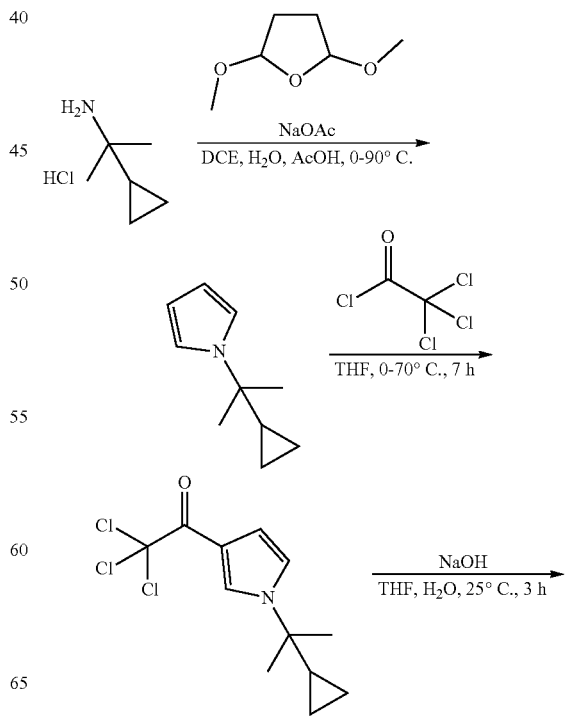

-continued

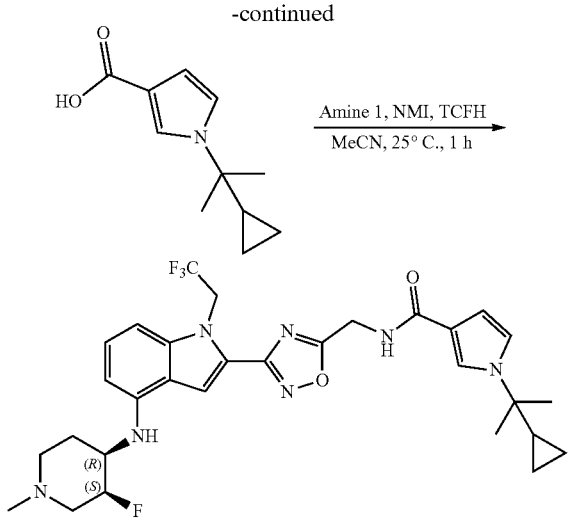

To a solution of 2-cyclopropylpropan-2-amine (150 mg, 1.11 mmol, 1 eq, HCl) in DCE (4.5 mL), acetic acid (0.9 mL) and water (2.7 mL) was added sodium acetate (136 mg, 1.66 mmol, 1.5 eq) at 0° C., then the mixture was stirred at 0° C. for 0.5 h, followed by addition of 2,5-dimethoxytetrahydrofuran (1.11 mmol, 143 μL 1 eq), and the mixture was then heated and stirred at 90° C. for 12 h. The reaction mixture was poured into water (100 mL), then extracted with EA (3×50 mL). The combined organic phase was washed with brine (80 mL), dried over anhydrous sodium sulfate, filtered, and concentrated in vacuo to give a residue. The residue was purified by prep-HPLC (column: Welch Xtimate C18 150×25 mm×5 um; mobile phase: [water (0.04% HCl)-ACN];B %: 40%-70%, 8 min) to give the desired pyrrole product (100 mg, 60.6% yield). LC-MS (ES+, m/z): 150.1 [(M+H)+].

To a solution of 1-(1-cyclopropyl-1-methyl-ethyl)pyrrole (100 mg, 670.10 μmol, 1 eq) in THF (3 mL) was added 2,2,2-trichloroacetyl chloride (2 mmol, 220 μL 3 eq) at 0° C., then the mixture was stirred at 70° C. for 7 h. The reaction mixture was poured into sat. sodium carbonate solution (150 mL), then extracted with DCM (3×80 mL). The combined organic phase was washed with brine (80 mL), dried over anhydrous sodium sulfate, filtered, and concentrated in vacuo to give a residue. The residue was purified by prep-TLC (SiO$_2$, PE:EA=5:1, R$_f$=0.62) to give the ketone product (100 mg, 50.7% yield). LC-MS (ES+, m/z): 295.9 [(M+H)+].

To a solution of 2,2,2-trichloro-1-[1-(1-cyclopropyl-1-methyl-ethyl)pyrrol-3-yl]ethanone (150 mg, 509 μmol, 1 eq) in THF (3 mL) was added sodium hydroxide (6 M, 250 μL 3 eq), then the mixture was stirred at 25° C. for 3 h. The reaction mixture was acidified with HCl solution (1.0 M) to pH=5, then extracted with DCM (3×50 mL). The combined organic phase was washed with brine (30 mL), dried over anhydrous sodium sulfate, then filtered, and concentrated in vacuo to give the product (80 mg, crude) LC-MS (ES+, m/z): 194.0 [(M+H)+].

Amine 1 (90 mg, 180 μmol, 1 eq, 2HCl) and 1-(1-cyclopropyl-1-methyl-ethyl)pyrrole-3-carboxylic acid (87.1 mg, 451 μmol, 2.5 eq) were coupled under method E. The crude product was purified by prep-TLC (DCM:methanol=10:1, R$_f$=0.3) and further purified by prep-HPLC (column: Phenomenex Luna C18 200×40 mm×10 um; mobile phase: [water (0.2% FA)-ACN]; B %: 20%-50%, 8 min) to give the desired product 1-(2-cyclopropylpropan-2-yl)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-pyrrole-3-carboxamide (30 mg, 27.7% yield). LC-MS (ES+, m/z): 620.3 [(M+H)+]. $^1$H NMR (400 MHz, DMSO-d6) δ=8.76-8.58 (t, J=5.6 Hz, 1H), 7.90 (s, 1H), 7.68-7.52 (m, 1H), 7.18-7.06 (t, J=8.0 Hz, 1H), 7.05-7.02 (t, J=2.4 Hz, 1H), 6.91-6.84 (d, J=7.6 Hz, 1H), 6.56-6.46 (m, 1H), 6.31-6.25 (d, J=8.0 Hz, 1H), 6.12-5.97 (d, J=8.4 Hz, 1H), 5.57-5.37 (dt, J=8.4 Hz, 2H), 4.93-4.67 (m, 3H), 3.64-3.56 (m, 1H), 3.09-3.01 (m, 1H), 2.86-2.78 (m, 1H), 2.33-2.16 (m, 4H), 2.13-1.93 (m, 2H), 1.73-1.64 (m, 1H), 1.37 (S, 6H), 1.26-1.16 (m, 1H), 0.54-0.34 (m, 4H).

Example 167: Compound 424B: N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl)-5-(2-hydroxypropan-2-yl)thiophene-2-carboxamide

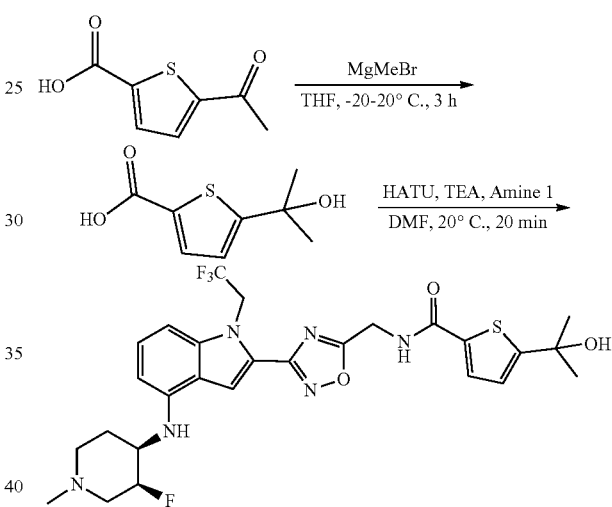

To a mixture of 5-acetylthiophene-2-carboxylic acid (2 g, 11.8 mmol, 1 eq) in THF (10 mL) was added bromo(methyl)magnesium (3 M, 9.8 mL, 2.5 eq) at −20° C. under nitrogen. The mixture was stirred at-20° C. for 3 h. The reaction mixture was quenched by slow addition of ammonium chloride (saturated solution, 10 mL), then diluted with HCl (12 M) to pH<5 and extracted with DCM (3×30 mL). The combined organic layers were washed with brine (3×20 mL), dried over sodium sulfate, filtered, and concentrated in vacuo to give 5-(1-hydroxy-1-methyl-ethyl)thiophene-2-carboxylic acid (1.9 g, crude) as a white solid.

5-(1-hydroxy-1-methyl-ethyl)thiophene-2-carboxylic acid (96.6 mg, 519 μmol, 1.2 eq) was coupled with Amine 1 (200 mg, 432 μmol, HCl) under method B. The reaction was purified by prep-TLC (SiO$_2$, DCM:methanol=1:1) to provide the desired product N-[[3-[4-[[(3S,4R)-3-fluoro-1-methyl-4-piperidyl]amino]-1-(2,2,2-trifluoroethyl)indol-2-yl]-1,2,4-oxadiazol-5-yl]methyl]-5-(1-hydroxy-1-methyl-ethyl)thiophene-2-carboxamide (55 mg, 20.2% yield, 94.5% purity) as a light yellow solid. LC-MS (ES+, m/z): 595.2 [(M+H)+]. $^1$H NMR (400 MHz, DMSO-d6) δ=9.27 (t, J=5.6 Hz, 1H), 7.89 (s, 1H), 7.66 (d, J=3.9 Hz, 1H), 7.12 (t, J=8.0 Hz, 1H), 6.97 (d, J=3.8 Hz, 1H), 6.88 (d, J=8.3 Hz, 1H), 6.29 (d, J=7.9 Hz, 1H), 6.04 (br d, J=8.3 Hz, 1H), 5.62 (s, 1H), 5.50 (q, J=9.0 Hz, 2H), 4.94-4.76 (m, 311), 3.68-3.52 (m, 1H), 3.07 (br s, 1H), 2.84 (br s, 1H), 2.22 (br s, 4H), 2.12-1.90 (m, 2H), 1.69 (br d, J=10.1 Hz, 1H), 1.50 (s, 6H).

Example 168: Compound 425B: N-{[3-(4-{[(3S, 4R)-3-fluoro-1-methylpiperidin-4-yl]amino}-1-(2,2, 2-trifluoroethyl)-1H-indol-2-yl)-1,2,4-oxadiazol-5-yl]methyl}-5-(2-hydroxypropan-2-yl)thiophene-3-carboxamide

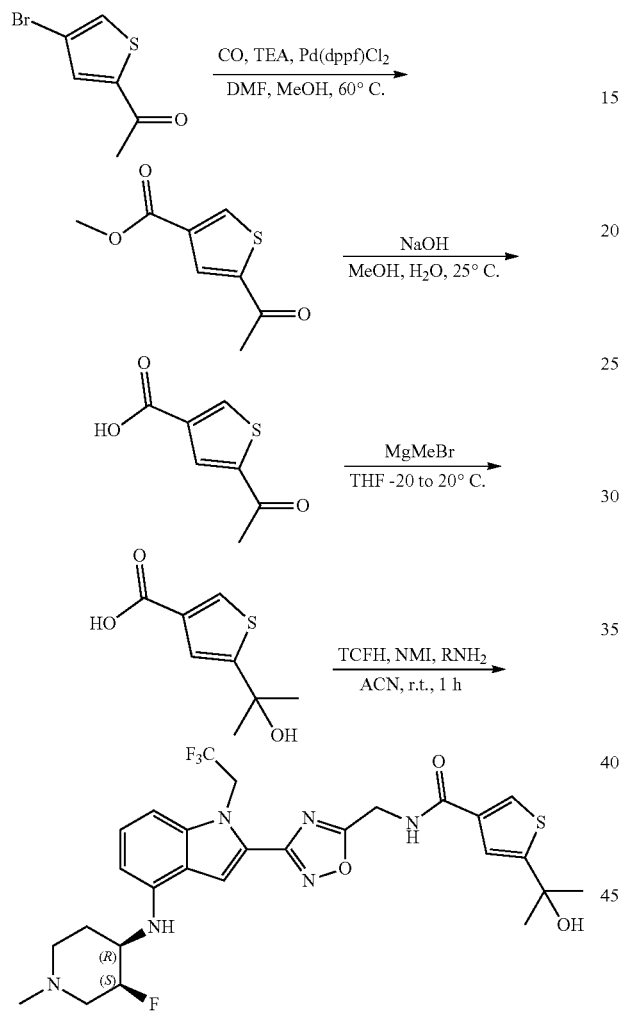

A solution of 1-(4-bromo-2-thienyl)ethanone (2.5 g, 12.2 mmol, 1 eq), methanol (5 mL), DMF (1 mL), Pd(dppf)Cl₂ (2.68 g, 3.66 mmol, 0.3 eq), and TEA (61 mmol, 85 mL, 5 eq) were stirred at 60° C. 1 h under a carbon monoxide atmosphere. The residue was poured into ice-water (w/w=1/1) (10 mL) and stirred for 10 min. The aqueous phase was extracted with EA (3×10 mL). The combined organic phase was washed with brine (3×10 mL), dried over anhydrous sodium sulfate, filtered, and concentrated in vacuo to provide methyl 5-acetylthiophene-3-carboxylate (1.5 g, crude) as a yellow solid. LC-MS (ES⁺, m/z): 185.2 [(M+H)⁺].

To a solution of methyl 5-acetylthiophene-3-carboxylate (1.5 g, 8.14 mmol, 1 eq) in methanol (20 mL) was added sodium hydroxide (3 M, 60 mL, 22 eq), and the reaction was stirred at 25° C. for 2 h. The mixture was acidified with HCl (3M, 10 mL) to pH-3, and was then extracted with DCM (2×10 mL). The organic phase was washed with water (10 mL) and brine (10 mL), then dried over sodium sulfate, and the solvent was removed in vacuo to give 5-acetylthiophene-3-carboxylic acid (900 mg, crude) as a yellow solid. LC-MS (ES⁺, m/z): 171.1.

To a solution of 5-acetylthiophene-3-carboxylic acid (600 mg, 3.53 mmol, 1 eq) in THF (5 mL) was added bromo(methyl)magnesium (3 M, 2.94 mL, 2.5 eq) at −20° C. for 0.5 h. The reaction was then warmed and stirred at 20° C. for 2.5 h. The mixture was quenched with ammonium chloride (10 mL) and HCl (3M, 5 mL) was added until pH-3. The mixture was extracted with DCM (2×10 mL), and the organic phase was washed with water (10 mL), brine (10 mL), then dried by sodium sulfate. The solvent was removed in vacuo to afford 5-(1-hydroxy-1-methyl-ethyl) thiophene-3-carboxylic acid (300 mg, crude) as a yellow solid.

Amine 1 (80 mg, 160 μmol, 1 eq, 2HCl) and 5-(1-hydroxy-1-methyl-ethyl) thiophene-3-carboxylic acid (59.7 mg, 320 μmol, 2 eq) were coupled under method E. The crude reaction was purified by prep-HPLC (FA condition) to afford the desired product N-[[3-[4-[[(3S,4R)-3-fluoro-1-methyl-4-piperidyl]amino]-1-(2,2,2-trifluoroethyl)indol-2-yl]-1,2,4-oxadiazol-5-yl]methyl]-5-(1-hydroxy-1-methyl-ethyl) thiophene-3-carboxamide (20 mg, 19.7% yield, 94% purity) as a white solid. LC-MS (ES⁺, m/z): 595.6 [(M+H)⁺]. ¹H NMR (400 MHz, DMSO-d₆) δ=9.16 (t, J=5.5 Hz, 1H), 8.15 (s, 1H), 8.01 (d, J=1.1 Hz, 1H), 7.90 (s, 1H), 7.35 (d, J=1.1 Hz, 1H), 7.12 (t, J=8.0 Hz, 1H1), 6.88 (d, J=8.2 Hz, 1H), 6.29 (d, J=7.9 Hz, 1H), 6.04 (d, J=8.4 Hz, 1H), 5.58 (s, 1H), 5.51 (q, J=8.8 Hz, 2H), 4.90 (br s, 1H), 4.79 (d, J=5.7 Hz, 2H), 3.71-3.48 (m, 1H), 3.05 (br t, J=10.3 Hz, 1H), 2.82 (br d, J=10.1 Hz, 1H), 2.35-2.27 (m, 1H), 2.20 (s, 311), 2.14-1.95 (m, 2H), 1.68 (br d, J=10.6 Hz, 1H), 1.52 (s, 611).

Example 169: Compound 426B: N-{[3-(4-{[(3S, 4R)-3-fluoro-1-methylpiperidin-4-yl]amino}-1-(2,2, 2-trifluoroethyl)-1H-indol-2-yl)-1,2,4-oxadiazol-5-yl]methyl}-1-[1-(methoxymethyl)cyclopropyl]-1H-pyrrole-3-carboxamide

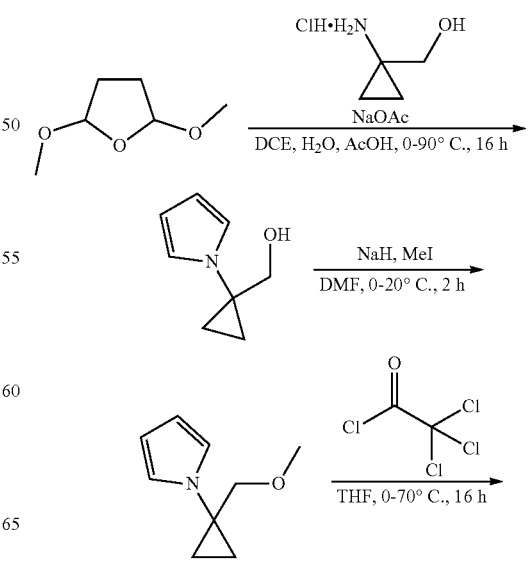

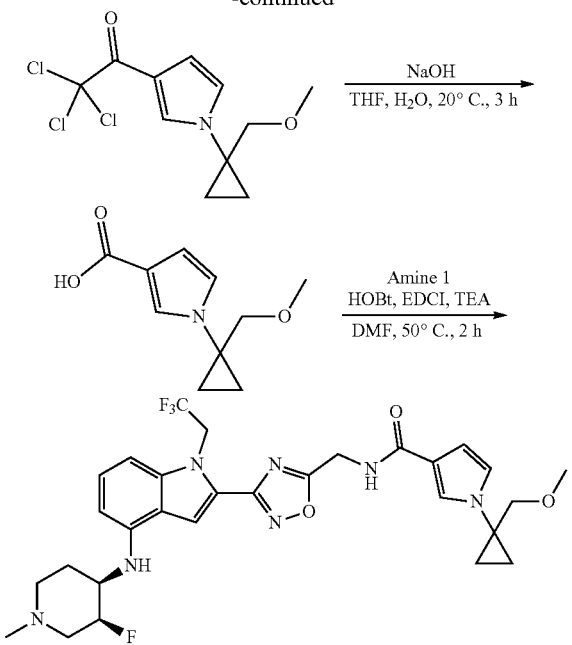

To a mixture of (I-aminocyclopropyl)methanol (3 g, 24.3 mmol, 1 eq, HCl) in DCE (20 mL), acetic acid (4 mL). and water (12 mL) was added sodium acetate (2.99 g, 36.4 mmol, 1.5 eq) at 0° C. under nitrogen. 2,5-dimethoxytetrahydrofuran (3.21 g, 24.28 mmol, 3.15 mL, 1 eq) was then added and the reaction heated to 90° C. and stirred for 16 h. The residue was poured into sodium bicarbonate (sat., 100 mL). The aqueous phase was extracted with DCM (30 mL×3). The combined organic phase was washed with brine (30 mL×3), dried over anhydrous sodium sulfate, filtered, and concentrated in vacuo. The residue was purified by prep-HPLC (FA condition, column: Phenomenex Luna C18 200×40 mm×10 um; mobile phase: [water (0.2% FA)-ACN]; B %: 1%-30%, 8 min) to provide (1-pyrrol-1-ylcyclopropyl)methanol (2.2 g, 16 mmol, 66.1% yield) as a yellow oil. LC-MS (ES$^+$, m/z): 138.2 [(M+H)$^+$].

To a mixture of (1-pyrrol-1-ylcyclopropyl)methanol (2.2 g, 16 mmol, 1 eq) in DMF (20 mL) was added sodium hydride (1.92 g, 48.1 mmol, 60% purity, 3 eq) at 0° C. under nitrogen. The mixture was stirred at 0° C. for 30 min, followed by addition of iodomethane (32.1 mmol, 2 mL, 2 eq). The mixture was stirred at 20° C. for 1 h 30 min. The residue was poured into ammonium chloride (saturated solution, 100 mL) and stirred for 5 min. The aqueous phase was extracted with EA (30 mL×3). The combined organic phase was washed with brine (saturated solution, 30 mL×3), dried over anhydrous sodium sulfate, filtered, and concentrated in vacuo to provide the methyl ether 1-[1-(methoxymethyl)cyclopropyl]pyrrole (2.9, crude) as a yellow oil. LC-MS (ES$^+$, m/z): 152.2 [(M+H)$^+$].

To a mixture of 1-[1-(methoxymethyl)cyclopropyl]pyrrole (2 g, 13.2 mmol, 1 eq) in THF (30 mL) was added 2,2,2-trichloroacetyl chloride (39.7 mmol, 4.43 mL, 3 eq) in one portion at 0° C. under nitrogen. The mixture was stirred at 70° C. for 16 h. The residue was poured into sodium bicarbonate (sat., 100 mL). The aqueous phase was extracted with EA (3×30 mL). The combined organic phase was washed with brine (3×30 mL), dried over anhydrous sodium sulfate, filtered, and concentrated in vacuo. The residue was purified by silica gel chromatography (column height: 250 mm, diameter: 100 mm, 100-200 mesh silica gel, PE/EA=100/, 95/5) to provide the ketone 2,2,2-trichloro-1-[1-[1-(methoxymethyl)cyclopropyl]pyrrol-3-yl]ethanone (580 mg, 14.8% yield) as a red-brown oil. LC-MS (ES$^+$, m/z): 296.0 [(M+H)$^+$]. $^1$H NMR (400 MHz, DMSO-d6) δ=7.86 (t, J=1.9 Hz, 1H), 7.03 (dd, J=2.1, 3.1 Hz, 1H), 6.65 (dd, J=1.8, 3.1 Hz, 1H), 3.50 (s, 2H), 3.22 (s, 3H), 1.22-1.14 (m, 2H), 1.07-0.99 (m, 2H).

To a mixture of 2,2,2-trichloro-1-[1-[1-(methoxymethyl)cyclopropyl]pyrrol-3-yl]ethanone (580 mg, 1.96 mmol, 1 eq) in THF (3 mL) was added sodium hydroxide (3 M, 2.10 mL, 3.25 eq) in one portion at 20° C. under nitrogen. The mixture was stirred at 20° C. for 3 h. The residue was poured into ice-water (w/w=1/1, 30 mL). The aqueous phase was extracted with DCM (3×10 mL). The aqueous phase was adjusted to pH=5-6 by adding 1 M HCl, then extracted with DCM (3×10 mL). The combined organic phase was washed with brine (10 mL×3), dried over anhydrous sodium sulfate, filtered, and concentrated in vacuo to provide 1-[1-(methoxymethyl)cyclopropyl]pyrrole-3-carboxylic acid (300 mg, crude) as a brown solid.

Amine 1 (200 mg, 432 μmol, 1 eq, HCl) was coupled with 1-[1-(methoxymethyl)cyclopropyl]pyrrole-3-carboxylic acid (101.2 mg, 519 μmol, 1.2 eq) under method A. The crude reaction was purified by prep-TLC (SiO$_2$, DCM:methanol=8:1) to provide the desired product N-[[3-[4-[[(3S,4R)-3-fluoro-1-methyl-4-piperidyl]amino]-1-(2,2,2-trifluoroethyl)indol-2-yl]-1,2,4-oxadiazol-5-yl]methyl]-1-[1-(methoxymethyl)cyclopropyl]pyrrole-3-carboxamide (77.2 mg, 29.6% yield, 100.0% purity) as a light yellow solid. LC-MS (ES$^+$, m/z): 604.4 [(M+H)$^+$]. $^1$H NMR (400 MHz, DMSO-d6) δ=8.71 (t, J=5.7 Hz, 1H), 7.90 (s, 1H), 7.45 (s, 1H), 7.11 (t, J=8.0 Hz, 1H), 6.92-6.85 (m, 2H), 6.46 (br s, 1H), 6.28 (d, J=7.9 Hz, 1H), 6.06 (br d, J=8.5 Hz, 1H), 5.51 (q, J=8.7 Hz, 2H), 4.92-4.78 (m, 1H), 4.72 (br d, J=5.6 Hz, 2H), 3.72-3.52 (m, 1H), 3.46 (s, 2H), 3.21 (s, 3H), 3.05 (br s, 1H), 2.83 (br d, J=9.4 Hz, 1H), 2.20 (br s, 4H), 2.11 (br s, 1H), 2.05-1.96 (m, 1H), 1.68 (br d, J=10.1 Hz, 1H), 1.12-1.07 (m, 2H), 1.03-0.97 (m, 2H).

Example 170: Compound 427B: N-{[3-(4-{(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(2-methylbutan-2-yl)-1H-pyrrole-3-carboxamide

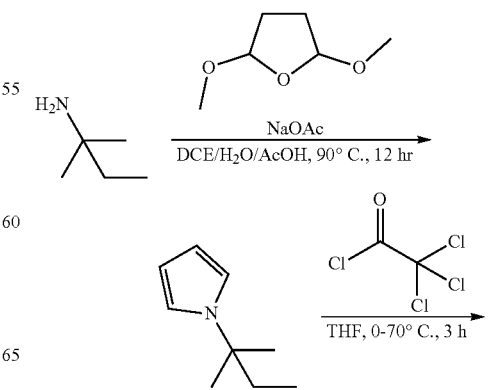

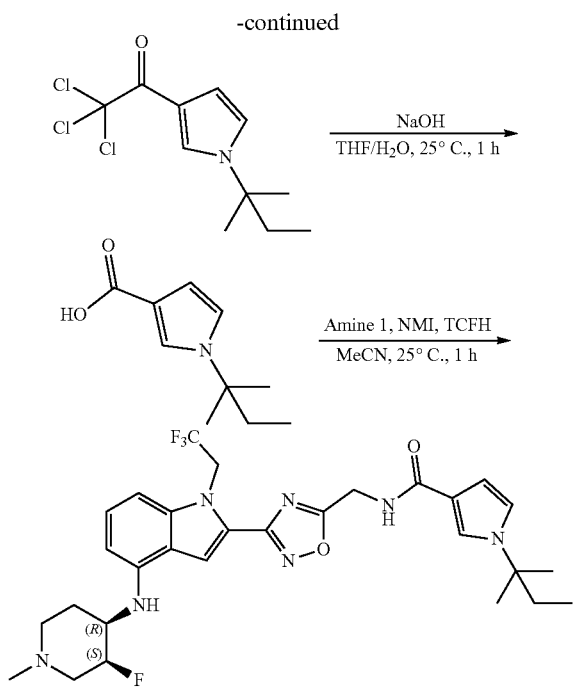

To a solution of 2-methylbutan-2-amine (57.4 mmol, 6.70 mL, 1 eq) in DCE (20 mL), water (12 mL), and acetic acid (4 mL) was added sodium acetate (7.06 g, 86 mmol, 1.5 eq). The mixture was stirred for 30 min, then 2,5-dimethoxytetrahydrofuran (57.3 mmol, 7.4 mL, 1 eq) was added to the mixture. The mixture was stirred at 90° C. for 11.5 h. The reaction mixture was poured into sodium carbonate (Sat., aq., 10 mL). The reaction mixture was diluted with water (100 mL) and extracted with EA 100 mL (2×50 mL). The combined organic layers were washed with brine (100 mL), dried over sodium sulfate, filtered, and concentrated in vacuo to give a residue. The residue was purified by prep-HPLC to give product (200 mg, 1.46 mmol, 2.5% yield). LC-MS (ES$^+$, m/z): 138.1 [(M+H)$^+$].

To a solution of 1-(1,1-dimethylpropyl)pyrrole (200 mg, 1.46 mmol, 1 eq) in THF (3 mL) was added 2,2,2-trichloroacetyl chloride (4.37 mmol, 490 μL 3 eq) at 0° C., then the reaction was stirred at 70° C. for 3 h. The reaction mixture was poured into sodium carbonate (sat., 10 mL). The reaction mixture was diluted with water (10 mL) and extracted with EA (2×5 mL). The combined organic layers were washed with brine (10 mL), dried over sodium sulfate, filtered, and concentrated in vacuo to give a residue. The residue was purified by prep-HPLC to give the product (80 mg, 19.4% yield). LC-MS (ES$^+$, m/z): 281.9 [(M+H)$^+$]. $^1$H NMR (400 MHz, DMSO-d$_6$) δ=7.86 (t, J=1.9 Hz, 1H), 7.16 (dd, J=2.4, 3.1 Hz, 1H), 6.75 (dd, J=1.8, 3.1 Hz, 1H), 1.81 (q, J=7.4 Hz, 2H), 1.52 (s, 6H), 0.64 (t, J=7.4 Hz, 3H).

To a solution of 2,2,2-trichloro-1-[1-(1,1-dimethylpropyl)pyrrol-3-yl]ethanone (80 mg, 283 μmol, 1 eq) in THF (2 mL) was added sodium hydroxide (3 M, 2 mL, 21 eq). The mixture was stirred at 25° C. for 2 h. 2M HCl was added to the mixture until pH 6-7. The reaction mixture was extracted with EA 60 mL (2×30 mL). The combined organic layers were washed with brine (10 mL), dried over sodium sulfate, filtered, and concentrated in vacuo to give the product (50 mg, crude). LC-MS (ES$^+$, m/z): 182.1 [(M+H)$^+$].

1-(1,1-dimethylpropyl)pyrrole-3-carboxylic acid (40 mg, 221 μmol, 1 eq) was coupled with Amine 1 (144.7 mg, 231.8 μmol, 1.1 eq, 2HCl) under method E. The residue was purified by prep-TLC (SiO$_2$, PE:EA=L:1) to give the desired product N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(2-methylbutan-2-yl)-1H-pyrrole-3-carboxamide (28.6 mg, 21.1% yield, 94.6% purity). LC-MS (ES$^+$, m/z): 590.3 [(M+H)$^+$]. $^1$H NMR (DMSO-d6, 400 MHz): δ=8.66 (br t, J=5.6 Hz, 1H), 7.90 (s, 1H), 7.51 (s, 1H), 7.12 (t, J=8.1 Hz, 1H), 6.98-6.83 (m, 2H), 6.52 (br d, J=1.6 Hz, 1H), 6.29 (d, J=7.8 Hz, 1H), 6.02 (br d, J=8.3 Hz, 1H), 5.51 (q, J=8.8 Hz, 2H), 4.93-4.72 (m, 3H), 3.71-3.46 (m, 1H), 3.04 (br t, J=10.6 Hz, 1H), 2.82 (br d, J=9.9 Hz, 1H), 2.29 (br d, J=13.0 Hz, 1H), 2.20 (s, 3H), 1.92-2.12 (m, 2H), 1.81-1.67 (m, 3H), 1.47 (s, 6H), 0.62 (m, 3H).

Example 171: Compound 428B: N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(1-methylcyclopropyl)-1H-pyrrole-3-carboxamide

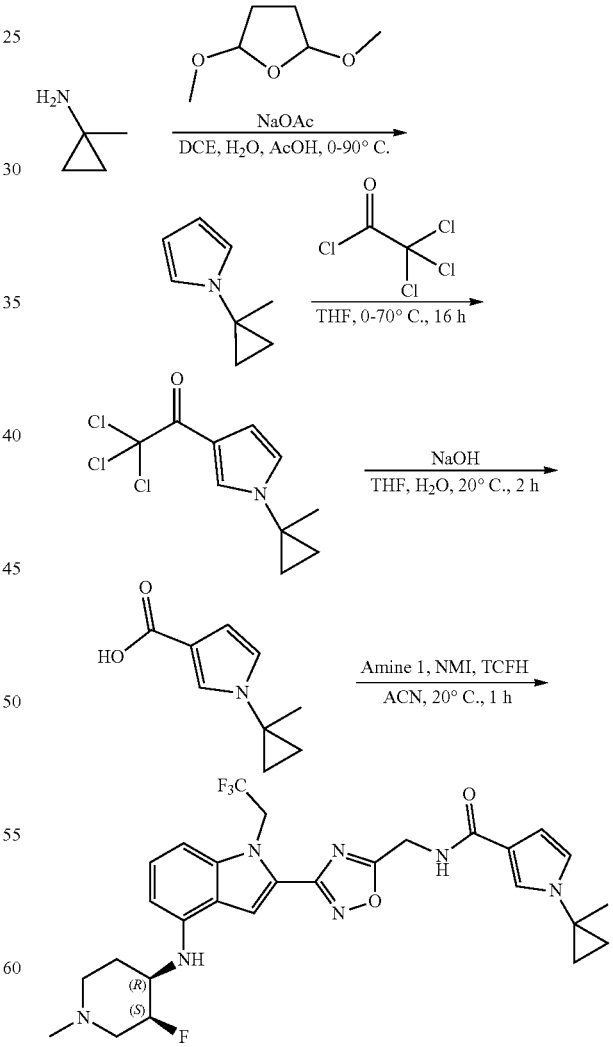

To a mixture of 1-methylcyclopropanamine (2 g, 18.6 mmol, 1 eq, HCl) in DCE (20 mL), acetic acid (4 mL), and water (12 mL) was added sodium acetate (2.29 g, 27.9 mmol, 1.5 eq) at 0° C. under nitrogen. The mixture was stirred at 0° C. for 30 min, followed by addition of 2,5-dimethoxytetrahydrofuran (18.6 mmol, 2.4 mL, 1 eq), and was then heated to 90° C. and stirred for 16 h. The residue was poured into sodium hydroxide (2 M, 20 mL). The aqueous phase was extracted with DCM (3×50 mL). The combined organic phase was washed with brine (3×30 mL), dried over anhydrous sodium sulfate, then filtered, and concentrated under weak vacuum with no heating to provide the product (2 g, crude) as yellow liquid, which was used for the next step. LC-MS (ES$^+$, m/z): 122.1[(M+H)$^+$].

1-(1-methylcyclopropyl)pyrrole (2 g, 16.5 mmol, 1 eq) was dissolved in THF (10 mL) and treated with 2,2,2-trichloroacetyl chloride (99 mmol, 11.1 mL, 6 eq) at 0° C., then heated to 70° C. and stirred for 16 h.

The residue was poured into sodium bicarbonate (30 mL). The aqueous phase was extracted with EA (3×30 mL). The combined organic phase was washed with brine (3×30 mL), dried over anhydrous sodium sulfate, filtered, and concentrated in vacuo. The crude product was purified by pre-HPLC, (column: Phenomenex Luna C18 200×40 mm×10 um; mobile phase: [water (0.2% FA)-ACN]; B %: 50%-80%, 8 min) to provide the ketone product (1.5 g, 34.1% yield) as a yellow oil. LC-MS (ES$^+$, m/z): 265.9/267.9 [(M+H)$^+$].

To a mixture of 2,2,2-trichloro-1-[1-(1-methylcyclopropyl)pyrrol-3-yl]ethanone (500 mg, 1.88 mmol, 1 eq) in THF (3 mL) was added sodium hydroxide (3 M, 3 mL, 4.8 eq) at 20° C., and the reaction was stirred for 2 h. The reaction was adjusted to pH=5 using HCl (2 M). The aqueous phase was extracted with EA (3×20 mL). The combined organic phase was washed with brine (3×20 mL), dried over anhydrous sodium sulfate, filtered, and concentrated in vacuo. The crude was purified by pre-TLC (SiO$_2$, PE/EA=1:1) to afford the product (280 mg, 90.4% yield) as a yellow oil. LC-MS (ES$^+$, m/z): 166.0 [(M+H)$^+$].

Amine 1 (80 mg, 172.83 μmol, 1 eq, HCl) was coupled with 1-(1-methylcyclopropyl)pyrrole-3-carboxylic acid (42.83 mg, 259.25 μmol, 1.5 eq) under method E. The crude reaction was purified by pre-TLC (SiO$_2$, DCM/methanol=10:1) to provide the desired product N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(1-methylcyclopropyl)-1H-pyrrole-3-carboxamide (41.8 mg, 41.3% yield, 98% purity) as white solid. LC-MS (ES$^+$, m/z): 574.3 [(M+H)$^+$]. $^1$H NMR (400 MHz, DMSO-d6) δ=8.67 (t, J=5.69 Hz, 1H), 7.88 (s, 1H), 7.46 (t, J=1.96 Hz, 1H), 7.11 (t, J=8.00 Hz, 1H), 6.91-6.82 (m, 2H), 6.46 (dd, J=2.81, 1.83 Hz, 1H), 6.28 (d, J=7.82 Hz, 1H), 6.01 (d, J=8.32 Hz, 1H), 5.50 (q, J=8.84 Hz, 2H), 4.93-4.76 (m, 1H), 4.72 (d, J=5.76 Hz, 2H), 3.68-3.50 (m, 1H), 3.10-2.97 (m, 1H), 2.81 (d, J=10.28 Hz, 1H), 2.30-2.17 (m, 4H), 2.13-1.93 (m, 2H), 1.68 (d, J=12.96 Hz, 1H), 1.53-1.45 (m, 3H), 1.08-1.02 (m, 2H), 0.90-0.81 (m, 2H).

Example 172: Compound 429B: 5-amino-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}thiophene-3-carboxamide

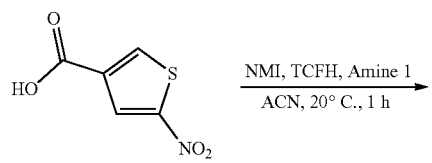

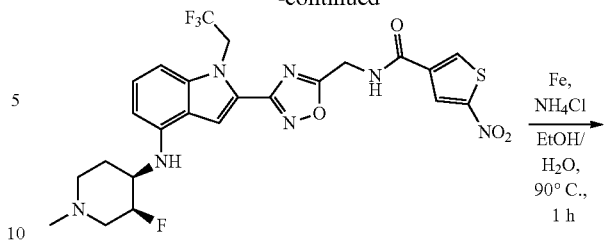

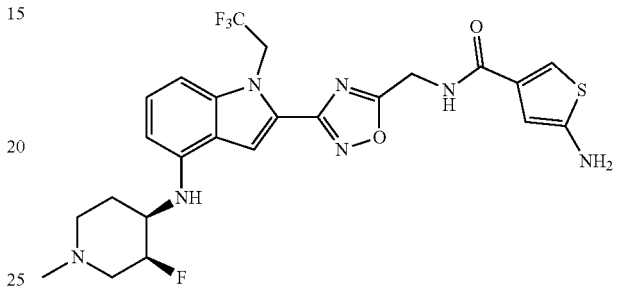

5-nitrothiophene-3-carboxylic acid (99.9 mg, 577 μmol, 2 eq) and Amine 12-[5-(aminomethyl)-1,2,4-oxadiazol-3-yl]-N-[(3S,4R)-3-fluoro-1-methyl-4-piperidyl]-1-(2,2,2-trifluoroethyl)indol-4-amine (0.2 g, 288 μmol, 1 eq, 2HCl), were coupled under method E. The crude product was purified by prep-TLC (SiO$_2$, DCM: methanol=10:1) to give the product (0.1 g, 59.6% yield). LC-MS (ES$^+$, m/z): 582.1 [(M+H)$^+$].

To a solution of N-[[3-[4-[[(3S,4R)-3-fluoro-1-methyl-4-piperidyl]amino]-1-(2,2,2-trifluoroethyl)indol-2-yl]-1,2,4-oxadiazol-5-yl]methyl]-5-nitro-thiophene-3-carboxamide (90 mg, 155 μmol, 1 eq) and ammonium chloride (49.7 mg, 929 μmol, 6 eq) in ethanol (2 mL) and water (0.2 mL) was added iron powder (25.9 mg, 464 μmol, 3 eq). The mixture was stirred at 90° C. for 1 h. The reaction mixture was quenched by adding water (30 mL), then extracted with EA (3×30 mL). The combined organic layers were washed with brine (3×30 mL), dried over sodium sulfate, filtered, and concentrated in vacuo to give a residue. The residue was purified by prep-HPLC (basic condition:column: Waters Xbridge Prep OBD C18 150×40 mm×10 um; mobile phase: [water (0.05% NH$_3$H$_2$O+10 mM NH$_4$HCO$_3$)-ACN]; B %: 25%-55%, 8 min) to give the desired product 5-amino-N-{13-(4-{1(3S,4R)-3-fluoro-1-methylpiperidin-4-yl]amino}-1-(2,2,2-trifluoroethyl)-1H-indol-2-yl)-1,2,4-oxadiazol-5-yl]methyl}thiophene-3-carboxamide (26 mg, 46.0 μmol, 29.7% yield, 97.6% purity). LC-MS (ES$^+$, m/z): 552.2 [(M+H)$^+$]. $^1$H NMR (400 MHz, DMSO-d6) δ=8.96-8.80 (t, J=5.6 Hz, 1H), 7.89 (s, 1H), 7.21-7.02 (m, 2H), 6.98-6.80 (d, J=8.0 Hz, 1H), 6.37-6.20 (m, 2H), 6.05-5.93 (m, 1H), 5.66 (s, 2H), 5.55-5.46 (dt, J=8.8 Hz, 2H), 4.95-4.64 (m, 3H), 3.68-3.51 (m, 2H), 3.10-3.01 (m, 2H), 2.89-2.78 (m, 11H), 2.30-2.22 (m, 1H), 2.20 (s, 3H), 2.15-1.97 (m, 3H), 1.74-1.61 (m, 1H).

Example 173: Compound 430B: N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-(propan-2-yl)-1,3-oxazole-4-carboxamide

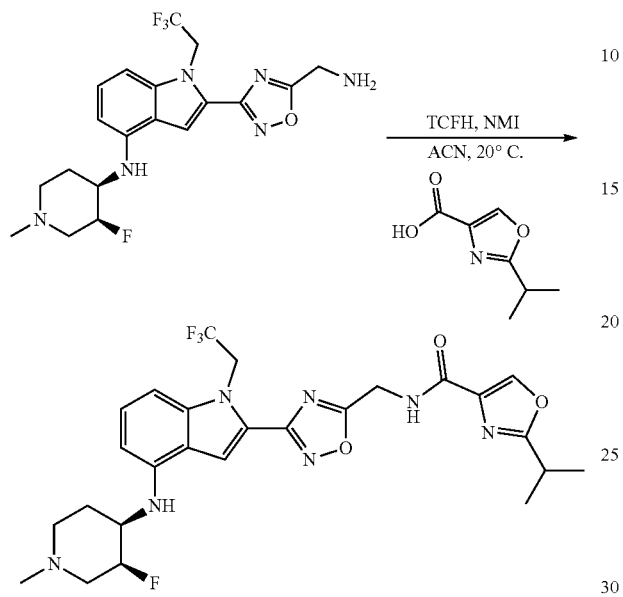

Amine 1 (2-[5-(aminomethyl)-1,2,4-oxadiazol-3-yl]-N-[(3S,4R)-3-fluoro-1-methyl-4-piperidyl]-1-(2,2,2-trifluoroethyl)indol-4-amine) (70 mg, 126 μmol, 1 eq, 2HCl) and 2-isopropyloxazole-4-carboxylic acid (23.5 mg, 151 μmol, 1.2 eq) were placed in acetonitrile (2 mL), to which were added [chloro(dimethylamino)methylene]-dimethyl-ammonium hexafluorophosphate (53.1 mg, 189 μmol, 1.5 eq) and 1-methylimidazole (31.1 mg, 379 μmol, 30.2 μL 3 eq). The mixture was stirred at 20° C. for 1 h. The reaction mixture was quenched by adding water (30 mL), and extracted with EA (3×30 mL). The combined organic layers were washed with brine (3×30 mL), dried over anhydrous sodium sulfate, filtered, and concentrated in vacuo to give a residue. The residue was purified by prep-TLC (SiO$_2$, DCM: methanol=10:1). The residue was further purified by prep-HPLC (FA condition: column: Phenomenex Luna C18 200×40 mm×10 um; mobile phase:[water (0.2% FA)-ACN];B %: 10%-50%, 8 min) to give the desired product N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-(propan-2-yl)-1,3-oxazole-4-carboxamide (0.03 g, 41.8% yield, 99.0% purity). LC-MS (ES$^+$, m/z): 564.3 [(M+H)$^+$]. $^1$H NMR (400 MHz, DMSO-d6) δ=9.03-8.93 (t, J=5.6 Hz, 1H), 8.59 (s, 1H), 7.89 (s, 1H), 7.19-7.02 (t, J=8.0 Hz, 1H), 6.92-6.82 (d, J=8.4 Hz, 1H), 6.39-6.20 (d, J=8.0 Hz, 1H), 6.07-5.92 (d, J=8.4 Hz, 1H), 5.57-5.43 (dt, J=8.4 Hz, 2H), 4.92-4.74 (m, 3H), 3.65-3.57 (m, 1H), 3.21-3.12 (m, 1H), 3.07-3.02 (m, 1H), 2.86-2.79 (m, 1H), 2.30-2.18 (m, 4H), 2.17-2.07 (m, 1H), 2.05-1.91 (m, 1H), 1.74-1.66 (m, 1H), 1.37-1.27 (d, J=6.8 Hz, 6H).

Example 174: Compound 431B: N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-(propan-2-yl)-1,3-thiazole-5-carboxamide

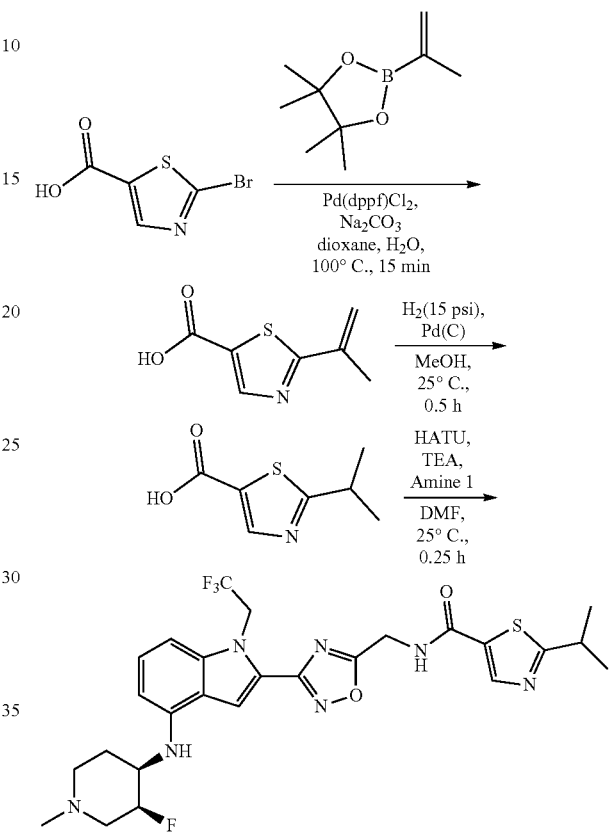

To a solution of 2-bromothiazole-5-carboxylic acid (1 g, 4.81 mmol, 1 eq) and 2-isopropenyl-4,4,5,5-tetramethyl-1,3,2-dioxaborolane (807.8 mg, 4.81 mmol, 1 eq) in dioxane (10 mL) and water (2.5 mL) were added Pd(dppf)Cl$_2$ (392.5 mg, 481 μmol, 0.1 eq) and sodium carbonate (1.53 g, 14.4 mmol, 3 eq), then the mixture was stirred at 100° C. for 15 mins. The reaction mixture was poured into saturated EDTA solution (200 mL) and stirred for 2 h, then extracted with EA (100 mL×3). The combined organic phase was washed with saturated brine (100 mL×1), dried over anhydrous sodium sulfate, filtered, and concentrated in vacuo to give 2-(prop-1-en-2-yl)thiazole-5-carboxylic acid (600 mg, crude) as a brown solid. LCMS (ES$^+$, m/z): 170.0 [(M+H)$^+$].

To a solution of 2-(prop-1-en-2-yl)thiazole-5-carboxylic acid (600 mg, 3.55 mmol, 1 eq) in methanol (30 mL) was added 10% Pd(C) (100 mg), then the mixture was degassed with hydrogen and stirred at 25° C. for 0.5 h under hydrogen atmosphere. The reaction mixture was filtered, then poured into saturated EDTA solution (100 mL) and stirred for 2 h, then the aqueous phase was acidified with HCl (1.0 M) to pH=4. The mixture was extracted with EA (60 mL×3), and the combined organic phase was washed with brine (60 mL×1), dried over anhydrous sodium sulfate, filtered, and concentrated in vacuo to give 2-isopropylthiazole-5-carboxylic acid (300 mg, crude) as a white solid. LCMS (ES$^+$, m/z): 172.0 [(M+H)$^+$].

2-isopropylthiazole-5-carboxylic acid (44.6 mg, 261 µmol, 2 eq) was coupled with Amine 1 (70 mg, 130.37 µmol, 1 eq, 2HCl) under method B. The crude reaction was purified by prep-TLC (SiO$_2$, DCM:methanol=10:1, R$_f$=0.5) to give the desired product N-((3-(4-(((3S,4R)-3-fluoro-1-methylpiperidin-4-yl)amino)-1-(2,2,2-trifluoroethyl)-1H-indol-2-yl)-1,2,4-oxadiazol-5-yl)methyl)-2-isopropylthiazole-5-carboxamide (20 mg, 26.5% yield, 100% purity) as a white solid. LCMS (ES$^+$, m/z): 580.3 [(M+H)$^+$]. $^1$H NMR (400 MHz, DMSO-d$_6$) δ=9.54 (t, J=5.56 Hz, 1H) 8.35 (s, 1H) 7.89 (s, 1H) 7.12 (t, J=8.07 Hz, 1H) 6.88 (d, J=8.31 Hz, 1H) 6.29 (d, J=7.95 Hz, 1H) 6.01 (br d, J=8.31 Hz, 1H) 5.50 (q, J=8.97 Hz, 2H) 4.77-4.92 (m, 3H) 3.52-3.67 (m, 1H) 2.99-3.11 (m, 1H) 2.83 (br d, J=10.27 Hz, 1H) 2.20 (s, 4H) 2.07-2.16 (m, 1H) 1.94-2.05 (m, 1H) 1.69 (br d, J=10.39 Hz, 1H) 1.34 (d, J=6.85 Hz, 6H). $^1$H NMR (400 MHz, DMSO-d$_6$+D$_2$O) δ=8.30 (s, 1H) 7.82 (s, 1H) 7.12 (t, J=8.01 Hz, 1H) 6.85 (d, J=8.44 Hz, 1H) 6.28 (d, J=7.82 Hz, 1H) 5.45 (q, J=8.80 Hz, 2H) 4.75-4.89 (m, 3H) 3.51-3.64 (m, 1H) 3.29 (dt, J=13.69, 6.85 Hz, 1H) 3.01 (br t, J=10.09 Hz, 1H) 2.79 (br d, J=10.64 Hz, 1H) 2.19-2.31 (m, 1H) 2.16 (s, 3H) 2.09 (br t, J=11.31 Hz, 1H) 1.91-2.01 (m, 1H) 1.63-1.71 (m, 1H) 1.32 (d, J=6.85 Hz, 6H).

Example 175: Compound 432B 2-(dimethylamino)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1,3-thiazole-5-carboxamide

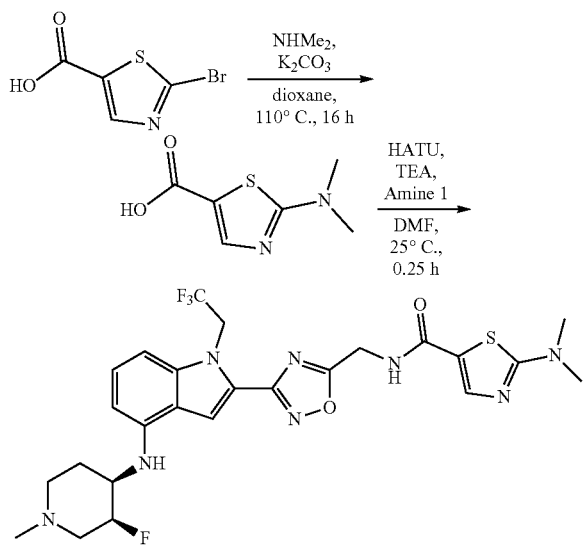

To a solution of 2-bromothiazole-5-carboxylic acid (1 g, 4.81 mmol, 1 eq) and dimethylamine hydrochloride (1.96 g, 24 mmol) in dioxane (10 mL) was added potassium carbonate (6.64 g, 48.1 mmol, 10 eq), then the mixture was stirred at 110° C. for 16 h in a sealed tube. The reaction mixture was concentrated in vacuo to give a residue. The residue was purified by prep-HPLC (column: Phenomenex luna C18 250×50 mm×10 um; mobile phase: [water (0.05% HCl)-ACN]; B %: 1%-30%, 10 min) to give compound 2-(dimethylamino)thiazole-5-carboxylic acid (200 mg, 1.16 mmol, 24.2% yield) as a white solid. LCMS (ES$^+$, m/z): 173.0 [(M+H)$^+$].

2-(dimethylamino)thiazole-5-carboxylic acid (44.9 mg, 261 µmol, 2 eq) was coupled with Amine 1 (70 mg, 130 µmol, 1 eq, 2HCl) under method B. The crude reaction was purified by prep-TLC (SiO$_2$, DCM:methanol=10:1, R$_1$=0.46) to give the desired product 2-(dimethylamino)-N-((3-(4-(((3S,4R)-3-fluoro-1-methylpiperidin-4-yl)amino)-1-(2,2,2-trifluoroethyl)-1H-indol-2-yl)-1,2,4-oxadiazol-5-yl)methyl)thiazole-5-carboxamide (37.1 mg, 48.2% yield, 98.4% purity) as a white solid. LCMS (ES$^+$, m/z): 581.3 [(M+H)$^+$]. $^1$H NMR (400 MHz, DMSO-d4) δ=9.08 (t, J=5.62 Hz, 1H) 7.91 (s, 2H) 7.12 (t, J=8.01 Hz, 1H) 6.88 (d, J=8.31 Hz, 1H) 6.29 (d, J=7.95 Hz, 1H) 6.02 (br d, J=8.31 Hz, 1H) 5.50 (q, J=8.76 Hz, 2H) 4.73-4.94 (m, 3H) 3.50-3.68 (m, 1H) 3.01-3.13 (m, 7H) 2.83 (br d, J=10.27 Hz, 1H) 2.20 (s, 4H) 2.07-2.15 (m, 1H) 1.95-2.06 (m, 1H) 1.69 (br d, J=11.001 Hz, 1H).

Example 176: Compound 433B N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(4-methyloxan-4-yl)-1H-imidazole-4-carboxamide

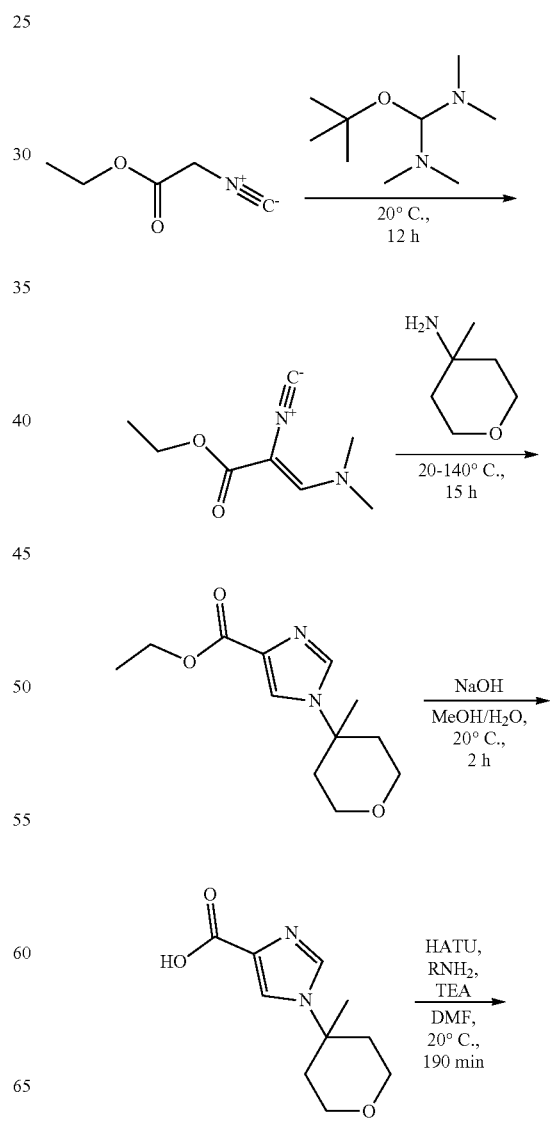

-continued

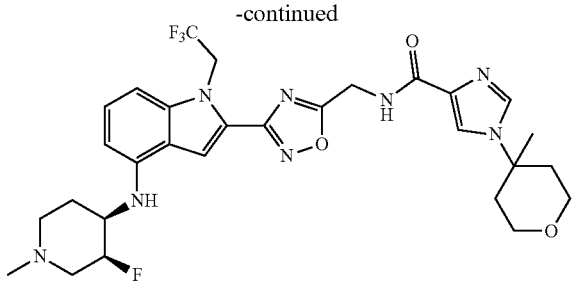

The required carboxylic acid was prepared using the General Synthesis of Imidazoles from the Isocyanide, followed by ester hydrolysis. 1-(4-methyltetrahydropyran-4-yl) imidazole-4-carboxylic acid (530.5 mg, 252 μmol, 2 eq) was coupled with Amine 1 (70 mg, 126 μmol, 1 eq, 2HCl) using method B. The crude product was purified by prep-TLC (SiO$_2$, DCM/methanol=10:1) to afford the desired product N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(4-methyloxan-4-yl)-1H-imidazole-4-carboxamide (32.2 mg, 39.2% yield, 95% purity) as yellow solid. LC-MS (ES$^+$, m/z): 619.3 [(M+H)$^+$]. $^1$H NMR (400 MHz, DMSO-d$_6$) δ=8.81 (t, J=5.95 Hz, 1H), 8.00 (d, J=1.32 Hz, 1H), 7.95 (d, J=1.10 Hz, 1H), 7.89 (s, 1H), 7.14-7.07 (m, 1H), 6.88 (d, J=8.38 Hz, 1H), 6.28 (d, J=7.72 Hz, 1H), 6.02 (br d, J=8.16 Hz, 1H), 5.50 (q, J=8.89 Hz, 2H), 4.92-4.72 (m, 3H), 3.72-3.63 (m, 2H), 3.56-3.49 (m, 2H), 3.08-2.98 (m, 1H), 2.81 (br d, 0.1=10.36 Hz, 1H), 2.30-2.21 (m, 2H), 2.19 (s, 3H), 2.08-2.18 (m, 2H), 2.08-1.99 (m, 2H), 1.99-1.92 (m, 2H), 1.67 (br d, J=10.36 Hz, 1H), 1.49 (s, 3H).

Example 177: Compound 434B:N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-(propan-2-yl)-1,3-thiazole-4-carboxamide

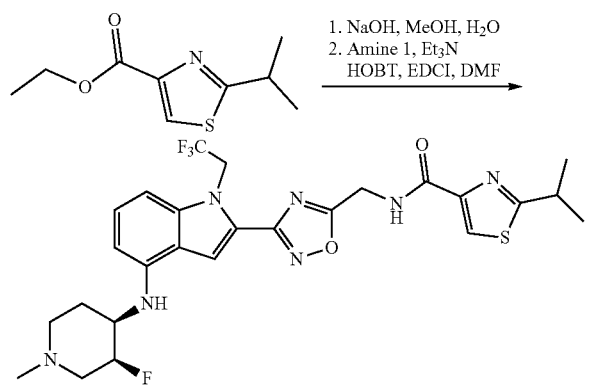

2-isopropylthiazole-4-carboxylic acid was prepared from the ethyl ester by sodium hydroxide saponification. 2-isopropylthiazole-4-carboxylic acid (30.2 mg, 176 μmol, 1.1 eq) was then coupled with Amine 1 (88.9 mg, 160 μmol, 1 eq, 2HCl) under method A. The residue was purified by prep-TLC (SiO$_2$, DCM: methanol=10:1) to give the desired product N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-(propan-2-yl)-1,3-thiazole-4-carboxamide (20.9 mg, 22.0% yield, 97.9% purity). LC-MS (ES$^+$, m/z): 580.3 [(M+H)$^-$]. $^1$H NMR (DMSO-d6, 400 MHz): δ=9.10 (t, J=6.0 Hz, 1H), 8.22 (s, 1H), 7.87 (s, 1H), 7.10 (t, J=8.0 Hz, 1H), 6.86 (d, J=8.2 Hz, 1H), 6.26 (d, J=7.9 Hz, 1H), 5.99 (d, J=8.4 Hz, 1H), 5.48 (br d, J=9.0 Hz, 2H), 4.72-4.90 (m, 3H), 3.48-3.67 (m, 1H), 3.48-3.67 (m, 1H), 3.02 (br t, J=10.1 Hz, 1H), 2.79 (br s, 1H), 2.24-2.34 (m, 1H), 2.18 (s, 3H), 2.07 (br d, J=12.6 Hz, 1H), 1.91-2.03 (m, 1H), 1.66 (br d, J=10.1 Hz, 1H), 1.38 (d, J=6.8 Hz, 6H).

Example 178: Compound 435B: 2-(dimethylamino)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1,3-thiazole-4-carboxamide

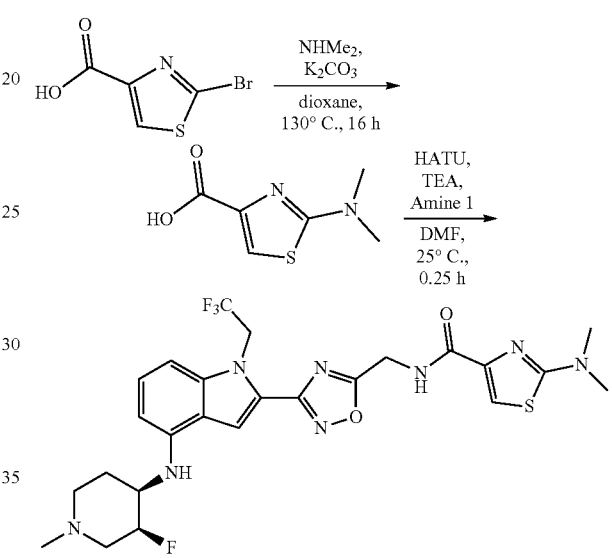

To a solution of 2-bromothiazole-4-carboxylic acid (500 mg. 2.40 mmol, 1 eq) and dimethylamine hydrochloride (980 mg, 12 mmol, 5 eq) in dioxane (20 mL) was added potassium carbonate (3.32 g, 24 mmol, 10 eq), and the mixture was stirred at 130° C. for 16 h in a sealed tube. The reaction mixture was concentrated in vacuo to give a residue. The residue was purified by prep-HPLC (column: Phenomenex luna C18 250×50 mm×10 um; mobile phase: [water (0.05% HCl)-ACN]; B %: 1%-30%. 10 min) to give 2-(dimethylamino)thiazole-4-carboxylic acid (120 mg, 40.0% yield) as a light yellow solid. LCMS (ES$^+$, m/z): 173.0 [(M+H)$^+$].

2-(dimethylamino)thiazole-4-carboxylic acid (44.9 mg, 261 μmol, 2 eq) was coupled with Amine 1 (70 mg, 130.37 μmol, 1 eq, 2HCl) under method B. The crude reaction was purified by prep-TLC (SiO$_2$, DCM: methanol=10:1, R$_f$=0.45) to provide the desired product 2-(dimethylamino)-N-((3-(4-(((3S,4R)-3-fluoro-1-methylpiperidin-4-yl)amino)-1-(2,2,2-trifluoroethyl)-1H-indol-2-yl)-1,2,4-oxadiazol-5-yl)methyl)thiazole-4-carboxamide (33.2 mg, 43.3% yield, 98.8% purity) as a white solid. LCMS (ES$^+$, m/z): 581.3 [(M+H)$^+$]. $^1$H NMR (400 MHz, DMSO-d( ) 6=8.86 (t, J=6.05 Hz, 1H) 7.89 (s, 1H) 7.43 (s, 1H) 7.12 (t, J=8.01 Hz, 1H) 6.88 (d, J=8.31 Hz, 1H) 6.28 (d, J=7.95 Hz, 1H) 6.02 (d, J=8.31 Hz, 1H) 5.50 (q, J=8.97 Hz, 2H) 4.77-4.92 (m, 3H) 3.52-3.67 (m, 1H) 3.02-3.11 (m, 7H) 2.83 (br d, J=10.03 Hz, 1H) 2.20 (s, 4H) 2.12 (br t, J=11.13 Hz, 1H) 1.95-2.06 (m, 1H) 1.69 (br d, J=10.64 Hz, 1H).

Example 179: Compound 436B: N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-5-(morpholin-4-yl)thiophene-3-carboxamide

Example 180: Compound 437B: 2-tert-butyl-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1,3-thiazole-5-carboxamide

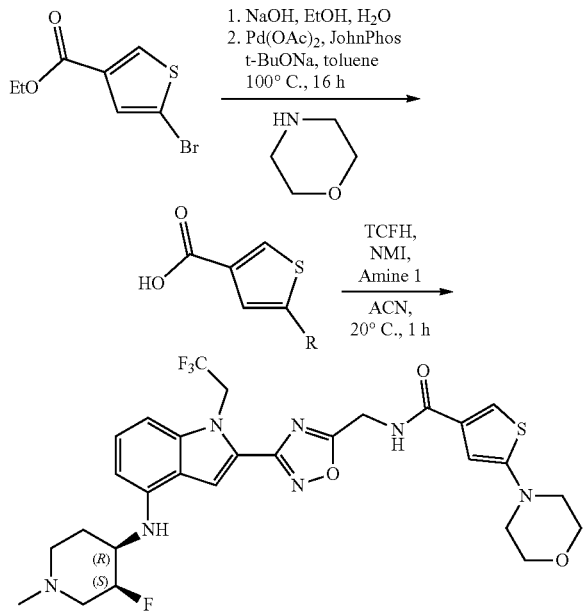

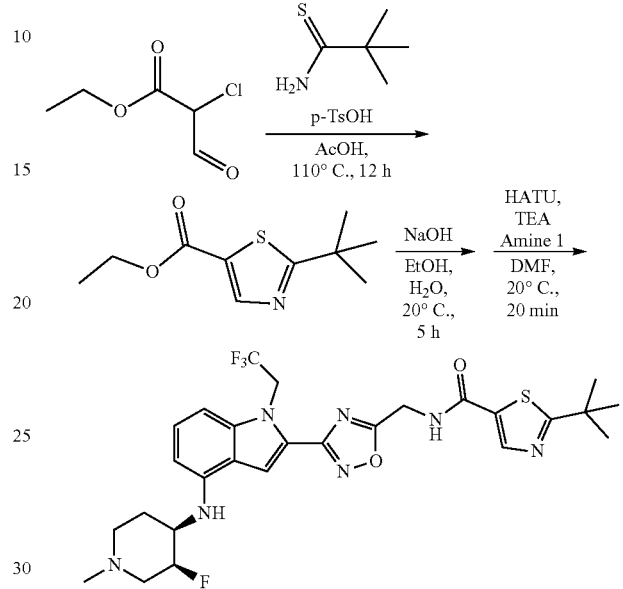

The ethyl ester was saponified under standard conditions to provide the carboxylic acid. To a mixture of morpholine (12.1 mmol, 1.06 mL, 5 eq) and 5-bromothiophene-3-carboxylic acid (500 mg, 2.41 mmol, 1 eq) in toluene (6 mL) were added di-tert-butyl-(2-phenylphenyl)phosphane (John-Phos) (144.1 mg, 483 μmol, 0.2 eq), diacetoxypalladium (54.2 mg, 241.49 μmol, 0.1 eq), sodium t-butoxide (2 M, 3.6 mL, 3 eq) at 20° C. under nitrogen. The reaction was then heated to 100° C. and stirred for 16 h. The reaction was poured into EDTA (sat., 30 mL) and stirred for 2 h. The aqueous phase was extracted with EA (3×20 mL). The combined organic phase was washed with brine (3×20 mL), dried over anhydrous sodium sulfate, filtered, and concentrated in vacuo. The crude product was purified by pre-HPLC, column: Phenomenex Luna C18 200×40 mm×10 um; mobile phase: [water (0.2% FA)-ACN];B %: 10%-50%, 8 min to give the desired intermediate (100 mg, 19.4% yield) as yellow solid. LC-MS (ES$^+$, m/z): 214.1 [(M+H)$^+$].

Amine 1 (80 mg, 173 μmol, 1 eq., HCl) and 5-morpholinothiophene-3-carboxylic acid (47.9 mg, 225 μmol, 1.3 eq) were coupled under method E. The crude product was purified by prep-HPLC, column: Phenomenex Luna C18 200×40 mm×10 um; mobile phase: [water (0.2% FA)-ACN]; B %: 10%-60%, 8 min to give the desired product (27 mg, 24.6% yield, 98% purity) as white solid. LC-MS (ES$^+$, m/z): 622.2 [(M+H)$^+$]. $^1$H NMR (400 MHz, DMSO-d6) δ=9.05 (t, J=5.62 Hz, 1H), 8.14 (s, 1H), 7.89 (s, 1H), 7.48 (d, J=1.59 Hz, 1H), 7.12 (t, J=8.01 Hz, 1H), 6.88 (d, J=8.31 Hz, 1H), 6.60 (d, J=1.59 Hz, 1H), 6.29 (d, J=7.95 Hz, 1H), 6.01 (d, J=8.19 Hz, 1H), 5.45-5.56 (m, 2H), 4.71-4.93 (m, 3H), 3.69-3.78 (m, 4H), 3.51-3.68 (m, 1H), 2.98-3.12 (m, 5H), 2.83 (d, J=10.64 Hz, 1H), 2.17-2.30 (m, 4H), 2.07-2.16 (m, 1H), 1.94-2.05 (m, 1H), 1.69 (d, J=9.90 Hz, 1H).

To a mixture of 2,2-dimethylpropanethioamide (300 mg, 2.56 mmol, 1 eq) and ethyl 2-chloro-3-oxo-propanoate (404.6 mg, 2.69 mmol, 1.05 eq) in acetic acid (3 mL) was added 4-methylbenzenesulfonic acid hydrate (97.4 mg, 512 μmol, 0.2 eq). The mixture was stirred at 110° C. for 12 h. The residue was poured into ice-water (w/w=1/1) (100 mL). The aqueous phase was extracted with EA (20 mL×3). The combined organic phase was washed with brine (20 mL×3), dried over anhydrous sodium sulfate, filtered, and concentrated in vacuo. The residue was purified by prep-TLC (SiO$_2$, PE:EA=5:1) to afford the thaizole product (350 mg, 64.1% yield) as a light yellow oil. LC-MS (ES$^+$, m/z):214.0 [(M+H)$^+$]. $^1$H NMR (400 MHz, CHLOROFORM-d) δ=8.27 (s, 1H), 4.35 (q, J=7.15 Hz, 2H), 1.46 (s, 9H), 1.37 (t, J=7.15 Hz, 3H). Ethyl 2-tert-butylthiazole-5-carboxylate (350 mg, 1.64 mmol, 1 eq) in methanol (1 mL) was saponified under standard conditions using added sodium hydroxide (6 M, 1 mL, 3.66 eq) to provide the carboxylic acid intermediate (150 mg, crude) as a white solid.

2-tert-butylthiazole-5-carboxylic acid (29 mg, 156 μmol, 1.2 eq) was coupled with Amine 1 (70 mg, 130.37 μmol, 1 eq, 2HCl) under method B. The crude product was purified by prep-HPLC (FA, column: Phenomenex Luna C18 200× 40 mm×10 um; mobile phase: [water (0.2% FA)-ACN];B %: 10%-60%,8 min) to provide the desired product 2-tert-butyl-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1,3-thiazole-5-carboxamide (23.4 mg, 30.2% yield) as a light yellow solid. LC-MS (ES$^+$, m/z): 594.3 [(M+H)$^+$]. $^1$H NMR (400 MHz, DMSO-d6) δ ppm 9.55 (t, J=5.62 Hz, 1H), 8.35 (s, 1H), 7.89 (s, 1H), 7.12 (t, J=8.16 Hz, 1H), 6.88 (d, J=8.16 Hz, 1H), 6.29 (d, J=7.94 Hz, 1H), 6.01 (d, J=8.38 Hz, 1H), 5.50 (q, J=9.04 Hz, 2H), 4.75-4.92 (m, 3H), 3.67-3.51 (m, 1H), 3.09-2.99

(m, 1H), 2.81 (br d, J=10.58 Hz, 1H), 2.31-2.16 (m, 4H), 2.14-2.05 (m, 1H), 2.05-1.93 (m, 1H), 1.68 (br d, J=10.58 Hz, 1H), 1.40 (s, 9H).

Example 181: Compound 438B: 2-tert-butyl-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1,3-thiazole-4-carboxamide

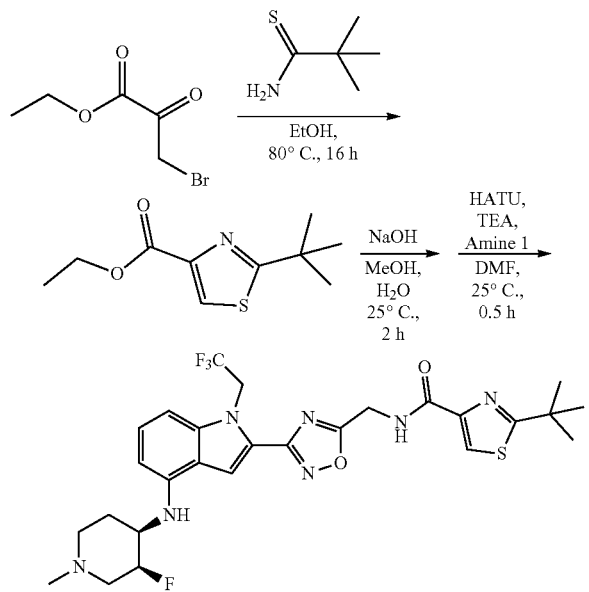

To a solution of ethyl 3-bromo-2-oxo-propanoate (1 g, 5.13 mmol, 1 eq) in ethanol (10 mL) was added 2,2-dimethylpropanethioamide (601 mg, 5.13 mmol, 1 eq). The mixture was stirred at 80° C. at reflux for 16 h. The reaction mixture was poured into water (200 mL), then extracted with EA (300 mL×3). The combined organic layers were washed with brine (100 mL×1), dried over anhydrous sodium sulfate, filtered, and concentrated in vacuo to give a residue. The crude product was purified by re-crystallization from EA (10 mL×3) at 25° C. to give the thiazole ester product (800 mg, 73.1% yield). LC-MS (ES$^+$, m/z): 214.2 [(M+H)$^+$].

Ethyl 2-tert-butylthiazole-4-carboxylate (400 mg, 1.88 mmol, 1 eq) in methanol (2 mL) and water (1 mL) was saponified using sodium hydroxide (75 mg, 1.88 mmol, 1 eq) under standard conditions. The crude product thus obtained was used directly without purification. LC-MS (ES$^+$, m/z): 186.2 [(M+H)$^+$]. 2-tert-butylthiazole-4-carboxylic acid (27.3 mg, 134 µmol, 1.2 eq) was coupled with Amine 1 (60 mg, 112 µmol, 1 eq, 2HCl) using method B. The crude reaction was purified by prep-TLC (SiO$_2$, DCM:methanol=10:1) to give the desired product 2-tert-butyl-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1,3-thiazole-4-carboxamide (30 mg, 43.9% yield, 97% purity). LC-MS (ES$^+$, m/z): 594.2 [(M+H)$^+$]. $^1$H NMR (400 MHz, DMSO-d6) δ=9.08 (t, J=6.0 Hz, 1H), 8.24 (s, 1H), 7.90 (s, 1H), 7.12 (t, J=8.1 Hz, 1H), 6.89 (d, J=8.3 Hz, 1H), 6.29 (d, J=7.9 Hz, 1H), 6.01 (d, J=8.3 Hz, 1H), 5.51 (q, J=9.0 Hz, 2H), 4.91-4.77 (m, 3H), 3.68-3.52 (m, 1H), 3.10-2.99 (m, 1H), 2.83 (br d, J=10.5 Hz, 1H), 2.29-2.16 (m, 4H), 2.15-2.07 (m, 1H), 2.05-1.97 (m, 1H), 1.69 (br d, J=10.3 Hz, 1H), 1.46 (s, 9H).

Example 182: Compound 439B: N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-5-(2-methoxypropan-2-yl)thiophene-2-carboxamide

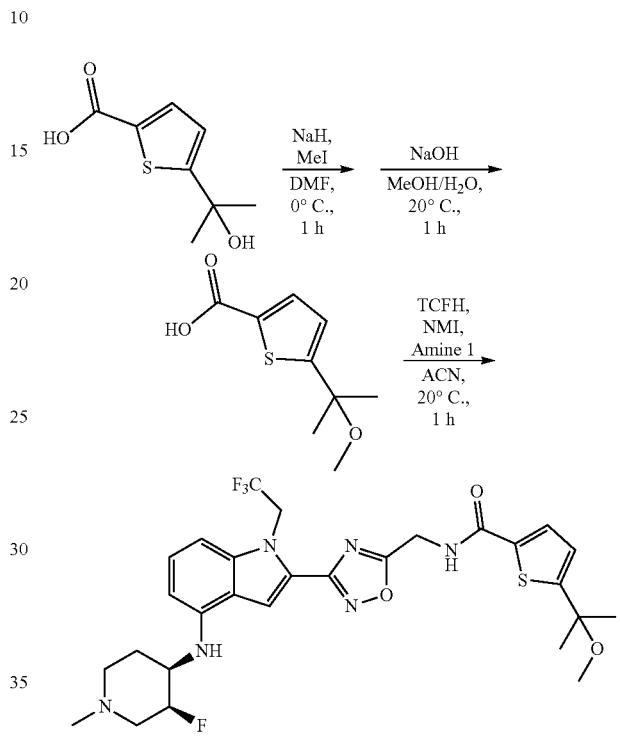

To a solution of the previously prepared 5-(1-hydroxy-1-methyl-ethyl)thiophene-2-carboxylic acid (0.1 g, 540 µmol, 1 eq) in DMF (10 mL) were added sodium hydride (258 mg, 6.44 mmol, 60% purity, 12 eq) and iodomethane (5.37 mmol, 330 µL 10 eq) at 0° C. The mixture was stirred and warmed to 20° C. over 1 h. The reaction mixture was quenched by adding saturated ammonium chloride (10 mL), then diluted with 1N HCl to pH<5 and extracted with DCM (3×30 mL). The combined organic layers were washed with brine (3×20 mL), dried over sodium sulfate, filtered, and concentrated in vacuo to give a residue. The residue was purified by prep-TLC (SiO$_2$, PE:EA=5:1) to give the product (60 mg, 52.1% yield). $^1$H NMR (400 MHz, CDCl$_3$) δ=7.68-7.64 (d, J=4.0 Hz, 1H), 6.95-6.91 (d, J=4.0 Hz, 1H), 3.88 (s, 3H), 3.16 (s, 3H), 1.61 (s, 6H).

To a solution of methyl 5-(1-methoxy-1-methyl-ethyl)thiophene-2-carboxylate (80 mg, 373 µmol, 1 eq) in methanol (5 mL) was added sodium hydroxide (5 M, 4 mL, 54 eq). The mixture was stirred at 20° C. for 1 h. The reaction mixture was quenched by adding water (10 mL), then diluted with HCl (1 N) to pH<5 and extracted with EA (3×30 mL). The combined organic layers were washed with brine (3×20 mL), dried over sodium sulfate, filtered, and concentrated in vacuo to give the product (60 mg, 80.3% yield).

Amine 1 (70 mg, 126 µmol, 1.0 eq., 2HCl) was coupled with 5-(1-methoxy-1-methyl-ethyl)thiophene-2-carboxylic acid (50.5 mg, 252 µmol, 2 eq) under method E. The crude product was purified by prep-TLC (SiO$_2$, DCM: methanol=10:1). The residue was further purified by prep-HPLC (FA condition: column: Phenomenex Luna C18 200×40 mm×10 um; mobile phase:[water (0.2% FA)-ACN];B %: 20%-60%, 8 min) to give the desired product N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-5-(2-methoxypropan-2-yl)thiophene-2-carboxamide (25 mg, 32.2% yield, 99% purity). LC-MS (ES+, m/z): 609.3 [(M+H)+]. $^{1}$H NMR (400 MHz, DMSO-d6) δ=9.45-9.32 (t, J=5.6 Hz, 1H), 7.90 (s, 1H), 7.76-7.63 (d, J=3.6 Hz, 1H), 7.16-7.03 (m, 2H), 6.95-6.81 (d, J=8.4 Hz, 1H), 6.46-6.21 (d, J=8.0 Hz, 1H), 6.12-5.95 (d, J=8.4 Hz, 1H), 5.58-5.39 (dt, J=8.8 Hz, 2H), 4.93-4.73 (m, 3H), 3.64-3.57 (m, 1H), 3.07-2.99 (m, 4H), 2.87-2.78 (m, 1H), 2.30-2.16 (m, 4H), 2.12- 2.04 (m, 1H), 2.04-1.94 (m, 1H), 1.74-1.62 (m, 1H), 1.53 (s, 6H).

Example 183: Compound 440B: 2-tert-butyl-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1,3-oxazole-4-carboxamide

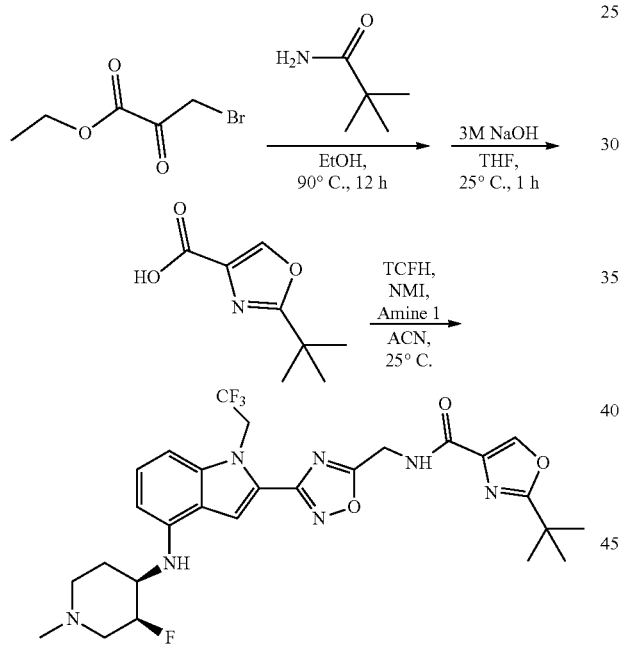

A mixture of 2,2-dimethylpropanamide (3.6 g, 35.6 mmol, 1 eq) and ethyl 3-bromo-2-oxo-propanoate (35.6 mmol, 4.45 mL, 1 eq) in ethanol (50 mL) was stirred at 90° C. for 12 h. The reaction mixture was concentrated in vacuo to give the product (8 g, crude) as a yellow solid. LC-MS (ES+, m:z): 198.5 [(M+H)+]. A mixture of ethyl 2-tert-butyloxazole-4-carboxylate (6.0 g, 30.4 mmol, 1 eq) and sodium hydroxide (3M, 30 mL) in THF (30 mL) was stirred at 25° C. for 1 h. The reaction mixture was diluted with water (30 mL) and HCl (12 M, 10 mL), and was then extracted with MTBE (3×50 mL). The combined organic layers were washed with brine (3×50 mL), dried over sodium sulfate, filtered, and concentrated in vacuo to give a residue, which was purified by prep-HLC (column: Phenomenex luna c18 250 mm×100 mm×10 um; mobile phase: [water (0.05% HCl)-ACN]; B %: 5%-35%, 30 min). The HPLC fractions were adjusted with sodium carbonate (sat., aq.) to pH=7~8, and the mixture was concentrated in vacuo to remove ACN. The mixture was then adjusted with HCl (3 M) to pH=3~4, and extracted with EA (3×50 mL). The combined organic layers were washed with brine (3×50 mL), dried over anhydrous sodium sulfate, filtered, and concentrated in vacuo to give the desired product. (0.4 g, 7.8% yield) as a yellow oil. LC-MS (ES+, m/z): 170.5 [(M+H)+].

Amine 1 (0.1 g, 200 μmol, 1 eq, 2HCl) was coupled with 2-tert-butyloxazole-4-carboxylic acid (40.7 mg, 240 μmol, 1.2 eq) under method E. The crude product was purified by prep-TLC (EA:TEA=10:1, R$_f$=0.3) and further purified by prep-HPLC (column: Phenomenex Luna C18 200×40 mm×10 um; mobile phase: [water (0.2% FA)-ACN];B %: 20%-60%, 8 min) to give the desired product 2-tert-butyl-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1,3-oxazole-4-carboxamide (0.035 g, 30.3% yield). LC-MS (ES+, m/z): 578.3 [(M+H)+]. $^{1}$H NMR (400 MHz, DMSO-d6) δ=9.00-8.90 (t, J=6.0 Hz, 1H), 8.61 (s, 1H), 7.90 (s, 1H), 7.19-7.06 (t, J=8.0 Hz, 1H), 6.95-6.84 (d, J=8.4 Hz, 1H), 6.36-6.15 (d, J=8.0 Hz, 1H), 6.10-5.96 (d, J=8.4 Hz, 1H), 5.62-5.39 (dt, J=8.8 Hz, 2H), 4.93-4.75 (m, 3H), 3.63-3.58 (m, 1H), 3.08-3.01 (m, 1H), 2.87-2.78 (m, 1H), 2.31-2.17 (m, 4H), 2.15-2.06 (m, 1H), 2.04-1.94 (m, 1H), 1.72-1.57 (m, 1H), 1.38 (s, 9H).

Example 184: Compound 441B: 5-(1-cyano-1-methylethyl)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}thiophene-2-carboxamide

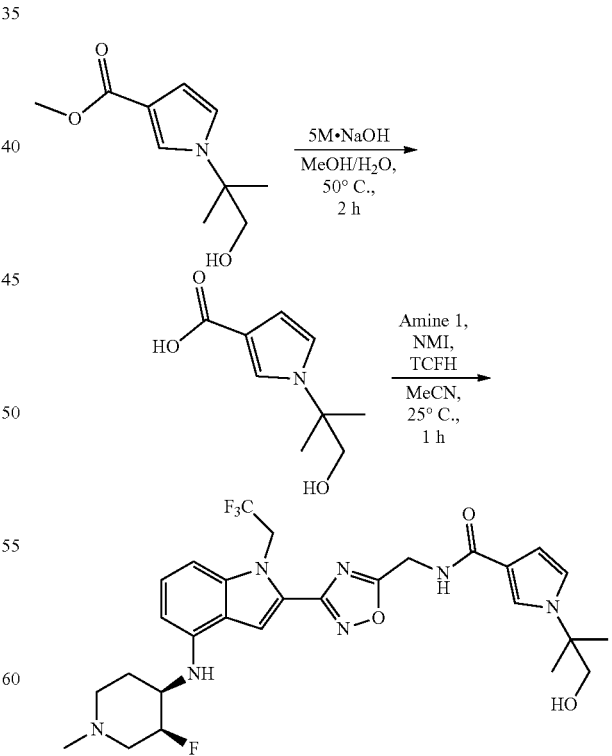

The hydroxy ester was prepared using the same procedure used to prepare the analogous methyl ether. A mixture of methyl 1-(2-hydroxy-1,1-dimethyl-ethyl)pyrrole-3-carboxylate (0.1 g, 507 µmol, 1 eq) and sodium hydroxide (5 M, 1 mL, 9.86 eq) in methanol (1 mL) was stirred at 50° C. for 2 h. The reaction mixture was adjusted with HCl (3M) to pH=3-4. The mixture was extracted with EA (3×30 mL). The combined organic layers were washed brine (3×30 mL), dried over anhydrous sodium sulfate, filtered, and concentrated in vacuo to give the carboxylic acid product (0.09 g, crude) as a yellow solid. LC-MS (ES+, m/z): 184.5 [(M+H)+].

Amine 1 (0.1 g, 200 µmol, 1 eq, 2HCl) was coupled with 1-(2-hydroxy-1,1-dimethyl-ethyl)pyrrole-3-carboxylic acid (44 mg, 240 µmol, 1.2 eq) under method E. The crude reaction was purified by prep-TLC (EA:TEA=10:1, $R_f$=0.1, then further purified by prep-HPLC (column: Phenomenex Luna C18 200×40 mm×10 um; (s, 1H), 7.52 (s, 1H), 7.15-7.06 (t, J=8.0 Hz, 1H), 6.98-6.91 (t, J=2.4 Hz, 1H), 6.90- 6.85 (d, J=8.0 Hz, 1H), 6.52-6.45 (m, 1H), 7.33-6.25 (d, J=7.6 Hz, 1H), 6.10-6.00 (d, J=8.0 Hz, 1H), 5.61-5.41 (dt, J=8.4 Hz, 2H), 5.08 (br s, 1H), 4.92-4.68 (m, 3H), 3.65-3.54 (m, 1H), 3.48 (s, 2H), 3.03 (br t, J=10.0 Hz, 1H), 2.86-2.77 (d, J=10.8 Hz, 1H), 2.31-2.26 (m, 1H), 2.19 (s, 3H), 2.13-2.06 (m, 1H), 2.04-1.95 (m, 1H), 1.71-1.62 (m, 1H), 1.43 (s, 6H).

Example 185: Compound 442B: 5-(1-cyano-1-methylethyl)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}thiophene-2-carboxamide

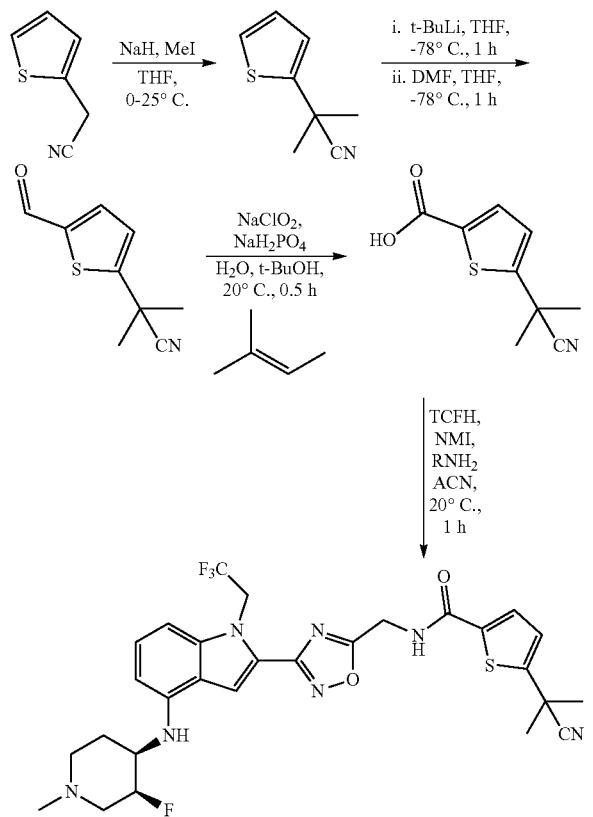

To a mixture of 2-(2-thienyl)acetonitrile (5 g, 40.6 mmol, 4.31 mL, 1 eq) in THF (7 mL) was added sodium hydride (4.87 g, 121.8 mmol, 60% purity, 3 eq) in one portion 0° C. under nitrogen. The mixture was stirred at 0° C. for 30 min, followed by addition of iodomethane (122 mmol, 7.6 mL, 3 eq), then the reaction was heated to 20° C. and stirred for 1.5 h. The residue was poured into ammonium chloride (saturated, 30 mL). The aqueous phase was extracted with EA (3×20 mL). The combined organic phase was washed with brine (3×20 mL), dried over anhydrous sodium sulfate, filtered, and concentrated in vacuo. The residue was purified by silica gel chromatography (column height: 250 mm, diameter: 100 mm, 100-200 mesh silica gel, PE/EA=99/1, 91/19) to afford the product (3.6 g, 58.6% yield) as white oil. 1H NMR (400 MHz, CHCl3-d) δ=7.28 (d, J=0.86 Hz, 1H), 7.27 (d, J=1.10 Hz, 1H), 7.12 (dd, J=3.55, 0.98 Hz, 1H), 6.99 (dd, J=5.01, 3.67 Hz, 1H), 1.82 (s, 6H).

To a mixture of 2-methyl-2-(2-thienyl)propanenitrile (600 mg, 3.97 mmol, 1 eq) in THF (6 mL) at-78° C. under nitrogen was added dropwise t-butyllithium (1.3 M, 3.80 mL, 1.2 eq). The mixture was stirred at −78° C. for 1 h, followed by addition of DMF (9.92 mmol, 760 µL 2.5 eq) in THF (6 mL) dropwise. The mixture was stirred at −78° C. for 1 h. The residue was then poured into ammonium chloride (20 mL, sat.). The aqueous phase was extracted with EA (3×20 mL). The combined organic phase was washed with brine (3×20 mL), dried over anhydrous sodium sulfate, filtered, and concentrated in vacuo to afford the product (600 mg, crude) as a yellow oil. LC-MS (ES+, m/z): 180.1 [(M+H)]. 1H NMR (400 MHz, DMSO-d6) δ=9.91 (s, 1H), 7.97 (d, J=3.97 Hz, 1H), 7.43 (d, J=3.97 Hz, 1H), 1.80 (s, 6H).

To a mixture of 2-methylbut-2-ene (42.5 mmol, 4.5 mL, 25.4 eq) and 2-(5-formyl-2-thienyl)-2-methyl-propanenitrile (300 mg, 1.67 mmol, 1 eq) in t-BuOH (7.5 mL) was added dropwise a solution of sodium phosphate (diacidic) (1.41 g, 11.7 mmol, 7 eq) and sodium chlorite (1.37 g, 18.4 mmol, 1.13 mL, 11 eq) in water (7 mL) at 20°. The mixture was stirred at 20° C. for 1 h. The residue was poured into sodium bicarbonate (sat., 20 mL) and 2N HCl was added to adjust pH=5. The aqueous phase was extracted with EA (3×30 mL). The combined organic phase was washed with brine (3×30 mL), dried over anhydrous sodium sulfate, filtered, and concentrated in vacuo. The crude product was triturated with PE/EA=5/1 at 20° C. for 30 min to afford the product (270 mg, 82.6% yield) as white solid. LC-MS (ES+, m/z): 196.1 [(M+H)+].

Amine 1 (80 mg, 173 µmol, 1 eq, HCl) was coupled with 5-(1-cyano-1-methyl-ethyl)thiophene-2-carboxylic acid (37.1 mg, 190 µmol, 1.1 eq) under method E. The crude product was purified by pre-TLC (SiO2, DCM/methanol=10/1) to afford the desired product 5-(1-cyano-1-methylethyl)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}thiophene-2-carboxamide (39.9 mg, 37.9% yield, 99% purity) as yellow solid. LC-MS (ES+, m/z): 604.3 [(M+H)]. 1H NMR (400 MHz, DMSO-d6) δ=9.49 (t, J=5.62 Hz, 1H), 7.89 (s, 1H), 7.78 (d, J=3.91 Hz, 1H), 7.29 (d, J=3.91 Hz, 1H), 7.10 (s, 1H), 6.88 (d, J=8.31 Hz, 1H), 6.28 (d, J=7.82 Hz, 1H), 6.02 (d, J=8.31 Hz, 1H), 5.50 (q, J=8.84 Hz, 2H), 4.72-4.95 (m, 3H), 3.51-3.69 (m, 1H), 3.04 (t, J=9.96 Hz, 1H), 2.82 (d, J=9.90 Hz, 1H), 2.17-2.32 (m, 4H), 2.05-2.15 (m, 1H), 1.93-2.04 (m, 1H), 1.78 (s, 6H), 1.68 (d, J=11.00 Hz, 1H), 1.63-1.73 (m, 1H).

Example 186: Compound 443B: 2-tert-butyl-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1,3-oxazole-5-carboxamide

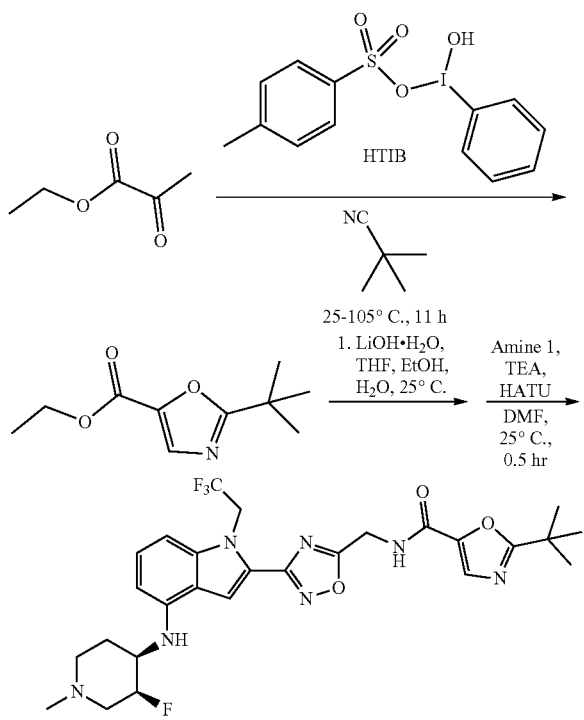

A solution of ethyl 2-oxopropanoate (1 g, 8.61 mmol, 1 eq) and [hydroxy(phenyl)-iodanyl] 4-methylbenzenesulfonate (HTIB, 4.05 g, 10.3 mmol, 1.2 eq) in trimethylacetonitrile (7 mL) was stirred at 105° C. for 3 h under nitrogen atmosphere, then the reaction was cooled to 25° C. 2,6-lutidine (861 μmol, 100 μL 0.1 eq) was added, the reaction was heated again and stirred for another 8 h at 105° C. The residue was diluted with water (50 mL) and extracted with EA (2×50 mL). The combined organic layers were washed with brine (2×50 mL), dried over anhydrous sodium sulfate, filtered, and concentrated in vacuo to give a residue. The residue was purified by prep-HPLC (column: Phenomenex Luna C18 200×40 mm×10 um; mobile phase: [water (0.2% FA)-ACN]; B %: 40%-80%, 8 min) and further purified by HPLC (column: Phenomenex luna C18 (250×70 mm×10 um); mobile phase: [water (0.05% HCl)-ACN]; B %: 25%-55%, 20 min) to give the product (0.2 g, 11.8% yield). LC-MS (ES+, m/z): 198.5 [(M+H)+]. 1H NMR (400 MHz, DMSO-d6) δ=8.72 (s, 1H), 4.33-4.23 (m, 2H), 1.33-1.15 (m, 12H).

A mixture of ethyl 2-tert-butyloxazole-5-carboxylate (200 mg, 1.01 mmol, 1 eq), lithium hydroxide hydrate (97.9 mg, 2.33 mmol, 2.3 eq) in THF (1 mL), water (1 mL), and ethanol (1 mL) was stirred at 25° C. for 2 h under nitrogen atmosphere. 3M HCl was added to the mixture until the pH was adjusted to 3-4. The reaction mixture was extracted with EA (2×30 mL). Since the desired product remained in the water phase, the water phase was lyophilized to obtain the crude product. The residue was triturated in DCM (5 mL) and stirred at 25° C. for 30 min, filtered, and concentrated in vacuo to give the product (50 mg, crude). LC-MS (ES+, m/z): 170.5 [(M+H)+]0.2-(tert-butyl)oxazole-5-carboxylic acid (22.7 mg, 130 μmol, 1.2 eq) was coupled with Amine 1 (60 mg, 108 μmol, 1 eq, 2HCl) under method B. The crude product was purified by prep-TLC (SiO2, DCM: methanol=10:1) to give the desired product 2-tert-butyl-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1,3-oxazole-5-carboxamide (26.8 mg, 42.9% yield, 100% purity). LC-MS (ES+, m/z): 578.3 [(M+H)+]. 1H NMR (400 MHz, DMSO-d6) δ=8.95 (t, J=5.9 Hz, 1H), 8.61 (s, 1H), 7.90 (s, 1H), 7.12 (t, J=8.0 Hz, 1H), 6.88 (d, J=8.3 Hz, 1H), 6.28 (d, J=7.9 Hz, 1H), 6.03 (d, J=8.3 Hz, 1H), 5.50 (br d, J=8.9 Hz, 2H), 4.93-4.74 (m, 3H), 3.71-3.51 (m, 1H), 3.04 (brt, J=10.4 Hz, 1H), 2.82 (br d, J=10.8 Hz, 1H), 2.32-2.13 (m, 4H), 2.13-1.95 (m, 2H), 1.69 (br s, 1H), 1.38 (s, 9H)

Example 187: Compound 444B: N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-5-(propan-2-yl)thiophene-2-carboxamide-isopropylthiophene-2-carboxylic acid was coupled with Amine 1 under method B. The crude product was purified by reverse-phase HPLC to provide the desired product N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-5-(propan-2-yl)thiophene-2-carboxamide. LC-MS (ES+, m/z): 579.2 [(M+H)+]. 1H NMR (300 MHz, DMSO-d6) δ 9.77 (s, 1H), 9.30-9.12 (m, 1H), 8.07 (d, J=1.4 Hz, 1H), 7.93 (s, 1H), 7.36 (s, 1H), 7.21 (t, J=8.0 Hz, 1H), 7.00 (d, J=8.2 Hz, 1H), 6.38 (d, J=7.9 Hz, 1H), 5.57 (d, J=8.8 Hz, 1H), 5.21 (d, J=47.7 Hz, 1H), 4.84 (d, J=5.6 Hz, 2H), 3.89 (s, 2H), 2.87 (d, J=4.4 Hz, 3H), 2.18 (dd, J=57.3, 22.7 Hz, 2H), 1.34 (d, J=6.8 Hz, 7H)

Example 188: Compound 445B: N-[(3S,4R)-3-fluoro-1-methylpiperidin-4-yl]-2-{5-[({thieno[2,3-c]pyridin-7-yl}amino)methyl]-1,2,4-oxadiazol-3-yl}-1-(2,2,2-trifluoroethyl)-1H-indol-4-amine Amine 1 (101.1 mg, 0.202 mmol, 1 eq.), 7-chlorothieno[2,3-C]pyridine (45.4 mg, 0.268 mmol, 1.3 eq.), potassium t-butoxide (60.5 mg, 0.539 mmol, 2.7 eq.), BrettPhos-Pd Generation 4 (13.9 mg, 0.0151 mmol, 0.075 eq.), and t-Butyl-XPhos Generation 3 (19.4 mg, 0.0244 mmol, 0.12 eq.) were placed in a vial and the vial flushed with nitrogen. Toluene (1.2 mL) was added, and the reaction was stirred and heated to 80° C. for 1.5 h. The reaction was then filtered, and concentrated. The crude product was purified by reverse-phase HPLC to provide the desired product N-[(3S,4R)-3-fluoro-1-methylpiperidin-4-yl]-2-{5-[({thieno[2,3-c]pyridin-7-yl}amino)methyl]-1,2,4-oxadiazol-3-yl}-1-(2,2,2-trifluoroethyl)-1H-indol-4-amine (15.4 mg, 13.6%). LC-MS (ES+, m/z): 560.2 [(M+H)]. 1H NMR (400 MHz, DMSO-d6) δ 8.02 (d, J=5.3 Hz, 1H), 7.90 (d, J=5.6 Hz, 2H), 7.85 (t, J=5.7 Hz, 1H), 7.49 (d, J=5.3 Hz, 1H), 7.24-7.11 (m, 2H), 6.92 (d, J=8.3 Hz, 1H), 6.32 (d, J=7.8 Hz, 1H), 6.02 (d, J=8.3 Hz, 1H), 5.53 (q, J=8.9 Hz, 2H), 5.04 (d, J=5.6 Hz, 2H), 3.64 (d, J=28.2 Hz, 1H), 3.34 (s, 1H), 3.09 (s, 1H), 2.88 (s, 1H), 2.43-1.90 (m, 5H), 1.74 (s, 1H), 1.29 (s, 2H).

Example 189: Compound 446B: N-{13-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-5-(1-methylcyclopropyl)thiophene-2-carboxamide

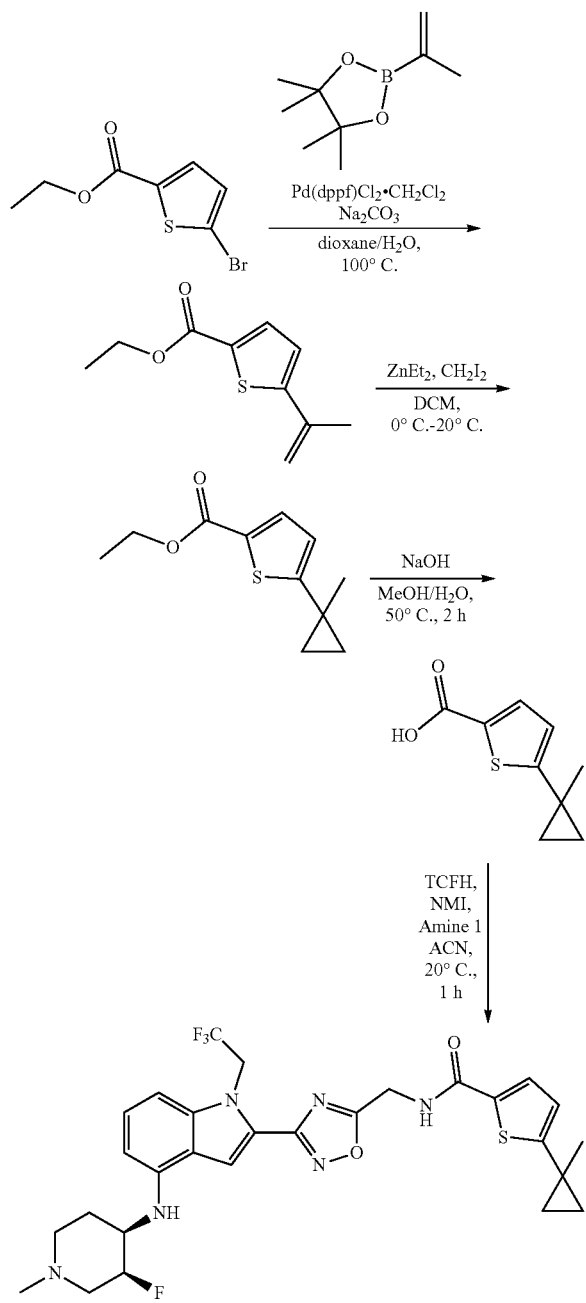

To a solution of ethyl 5-bromothiophene-2-carboxylate (3 g, 12.8 mmol, 1 eq) and 2-isopropenyl-4,4,5,5-tetramethyl-1,3,2-dioxaborolane (2.14 g, 12.8 mmol, 1 eq) in dioxane (30 mL) and water (7.5 mL) were added Pd(dppf)Cl$_2$·CH$_2$Cl$_2$ (1.04 g, 1.28 mmol, 0.1 eq) and sodium carbonate (4.06 g, 38.28 mmol, 3 eq), then the mixture was stirred at 100° C. for 15 min. The reaction mixture was poured into sat. EDTA solution (200 mL) and stirred at 25° C. for 2 h, then extracted with EA (3×100 mL). The combined organic phase was washed with brine (100 mL), dried over anhydrous sodium sulfate, filtered, and concentrated in vacuo to give a residue. The residue was purified by column chromatography (SiO$_2$, PE/EA=50:1 to 10:1, PE:EA=8:1, R$_f$=0.47) to give the product (1.7 g, 67.9% yield). LC-MS (ES$^+$, m/z): 197.0 [(M+H)$^+$].

To a solution of diethylzinc (1 M, 5.10 mL, 10 eq) at 0° C. in DCM (4 mL) was added a solution of TFA (5.10 mmol, 380 μL 10 eq) in DCM (2 mL) drop-wise over a period of 20 min under nitrogen, during which time the temperature was maintained below 0° C. A solution of diiodomethane (2.05 g, 7.64 mmol, 15 eq) in DCM (2 mL) was added dropwise and the reaction stirred for another 20 min. A solution of ethyl 5-isopropenylthiophene-2-carboxylate (0.1 g, 510 μmol, 1 eq) in DCM (2 mL) was added to the mixture at 0° C. The reaction mixture was stirred at 20° C. for another 3 h. The reaction mixture was quenched by adding saturated ammonium chloride (50 mL), then extracted with DCM (3×30 mL). The combined organic layers were washed with brine (3×20 mL), dried over sodium sulfate, filtered, and concentrated in vacuo to give a residue. The residue was purified by prep-TLC (SiO$_2$, PE:EA=10:1, R$_f$=0.3) to give the product (0.06 g, 53.2% yield, 95% purity) LC-MS (ES$^+$, m/z): 242.3 [(M+H)$^+$]. The ester (60 mg, 285.32 μmol, 1 eq) was saponified under standard conditions using sodium hydroxide (aq.) and methanol to provide the carboxylic acid product (0.03 g, 57.7% yield). LC-MS (ES$^+$, m/z): 183.4 [(M+H)$^+$].

Amine 1 (70 mg, 126 μmol, 1 eq, 2HCl) was coupled with 5-(1-methylcyclopropyl)thiophene-2-carboxylic acid (46 mg, 252 μmol, 2 eq) under method E. The crude product was purified by prep-TLC (SiO$_2$, DCM: methanol=10:1). The residue was further purified by prep-HPLC (FA condition: column: Phenomenex Luna C18 200×40 mm×10 um; mobile phase:[water (0.2% FA)-ACN]; B %: 20%-60%, 8 min) to give the desired product (0.037 g, 48.7% yield, 98% purity). LC-MS (ES$^+$, m/z): 591.3 [(M+H)]. $^1$H NMR (400 MHz, DMSO-d6) δ=9.36-9.23 (t, J=5.6 Hz, 1H), 7.96-7.84 (s, 1H), 7.72-7.63 (d, J=3.6 Hz, 1H), 7.19-7.03 (t, J=8.0 Hz, 1H), 6.99-6.84 (m, 2H), 6.39-6.18 (d, J=7.6 Hz, 1H), 6.09-5.93 (d, J=8.4 Hz, 1H), 5.59-5.38 (dt, J=8.8 Hz, 2H), 4.94-4.75 (m, 3H), 3.62-3.55 (m, 1H), 3.07-3.00 (m, 1H), 2.82 (br d, J=10.5 Hz, 1H), 2.32-2.15 (m, 4H), 2.14-1.94 (m, 2H), 1.72-1.63 (m, 1H), 1.45 (s, 3H), 0.94 (s, 4H).

Example 190: Compound 447B: N-{[3-(4-{1[(3S,4R)-3-fluoro-1-methylpiperidin-4-yl]amino}-1-(2,2,2-trifluoroethyl)-1H-indol-2-yl)-1,2,4-oxadiazol-5-yl]methyl)-5-(2-methoxypropan-2-yl)thiophene-3-carboxamide

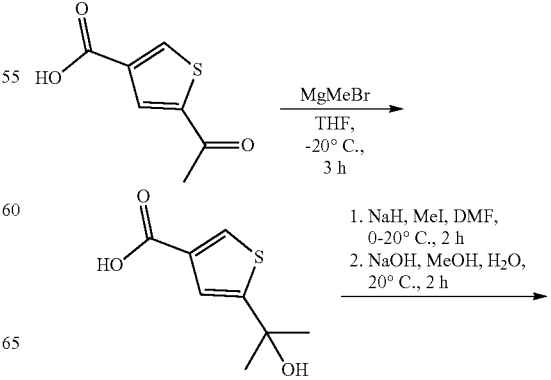

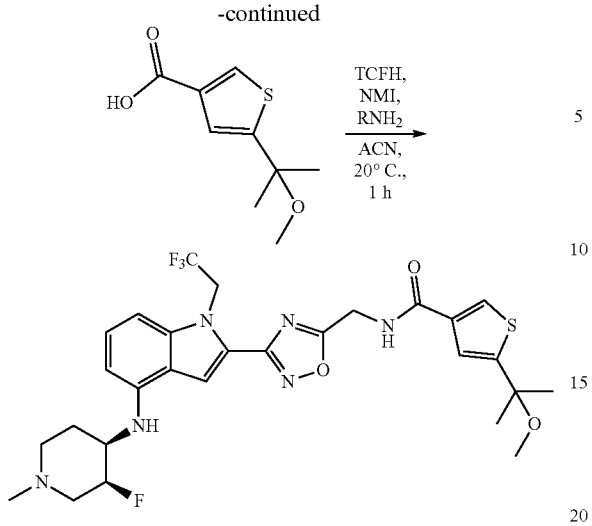

To a mixture of 5-acetylthiophene-3-carboxylic acid (600 mg, 3.53 mmol, 1 eq) in THF (10 mL) was added bromo(methyl)magnesium (3 M, 2.9 mL, 2.5 eq) at −20° C. under nitrogen. The mixture was stirred at −20° C. for 30 min, then heated to 20° C. and stirred for 2.5 h. The residue was poured into sat. ammonium chloride (20 mL), then added to HCl (3N) and stirred for 3 min. The aqueous phase was extracted with DCM (3×20 mL). The combined organic phase was washed with brine (3×20 mL), dried over anhydrous sodium sulfate, filtered, and concentrated in vacuo to give the product (600 mg, 91.4% yield) as a yellow solid. LC-MS (ES+, m/z): 185.0 [(M+H)+]. $^1$H NMR (400 MHz, DMSO-d$_6$) δ=12.55 (s, 1H), 8.02 (d, J=1.32 Hz, 1H), 7.18 (d, J=1.32 Hz, 1H), 5.55 (s, 1H), 3.31 (s, 2H), 1.49 (s, 6H).

To a mixture of 5-(1-hydroxy-1-methyl-ethyl)thiophene-3-carboxylic acid (800 mg, 4.30 mmol, 1 eq) in DMF (10 mL) was added sodium hydride (343.7 mg, 8.59 mmol, 60% purity, 2 eq) at 0° C. under nitrogen. The mixture was stirred at 0° C. for 30 min, then iodomethane (21.5 mmol, 1.34 mL, 5 eq) was added, and the reaction was warmed to 20° C. and stirred for 1.5 h. The residue was poured into sat. ammonium chloride (50 mL) and stirred for 3 min. The aqueous phase was extracted with EA (3×30 mL). The combined organic phase was washed with brine (3×30 mL) (saturated), dried over anhydrous sodium sulfate, filtered, and concentrated in vacuo. The residue was purified by column chromatography (SiO$_2$, PE/EA=1:0 to 0:1) to give the product (400 mg, 43.5% yield) as colourless oil. LC-MS (ES+, m/z): 183.1 [(M+H)+].

To a mixture of methyl 5-(1-methoxy-1-methyl-ethyl)thiophene-3-carboxylate (400 mg, 1.87 mmol, 1 eq) in methanol (4 mL) and water (1 mL) was added sodium hydroxide (224 mg, 5.60 mmol, 3 eq) in one portion at 20° C. under nitrogen. The mixture was stirred at 20° C. for 2 h. The reaction was poured into 2N HCl (10 mL) and stirred for 2 min. The aqueous phase was extracted with EA (3×30 mL). The combined organic phase was washed with brine (3×30 mL), dried over anhydrous sodium sulfate, filtered, and concentrated in vacuo. The residue was purified by prep-TLC (SiO$_2$, DCM:methanol=10:1) to afford the product (200 mg, 53.5% yield) as a yellow solid. LC-MS (ES+, m/z): 199.0 [(M+H)+].

Amine 1 (80 mg, 173 µmol, 1 eq, HCl) was coupled with 5-(1-methoxy-1-methyl-ethyl)thiophene-3-carboxylic acid (41.5 mg, 207 µmol, 1.2 eq) under method E. The crude reaction was purified by prep-TLC (SiO2, DCM:methanol=10/1) to afford the desired product N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-5-(2-methoxypropan-2-yl)thiophene-3-carboxamide (22.4 mg, 20.7% yield, 97.2% purity) as a yellow solid. LC-MS (ES+, m/z): 609.3 [(M+H)+]. $^1$H NMR (400 MHz, DMSO-d6) δ=9.21 (t, J=5.29 Hz, 1H), 8.15 (d, J=1.32 Hz, 1H), 7.89 (s, 1H), 7.43 (d, J=1.32 Hz, 1H), 7.17-7.06 (m, 1H), 6.88 (d, J=8.16 Hz, 1H), 6.28 (d, J=7.72 Hz, 1H), 6.01 (d, J=7.94 Hz, 1H), 5.50 (q, J=8.97 Hz, 2H), 4.92-4.75 (m, 3H), 3.68-3.53 (m, 1H), 3.04 (s, 3H), 3.01 (s, 1H), 2.81 (d, J=10.58 Hz, 1H), 2.28 (d, J=13.67 Hz, 1H), 2.19 (s, 3H), 2.11-2.03 (m, 1H), 2.02-1.92 (m, 1H), 1.68 (d. J=13.23 Hz, 1H), 1.54 (s, 6H).

Example 191: Compound 448B: N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(1-methylcyclopropyl)-1H-pyrazole-4-carboxamide

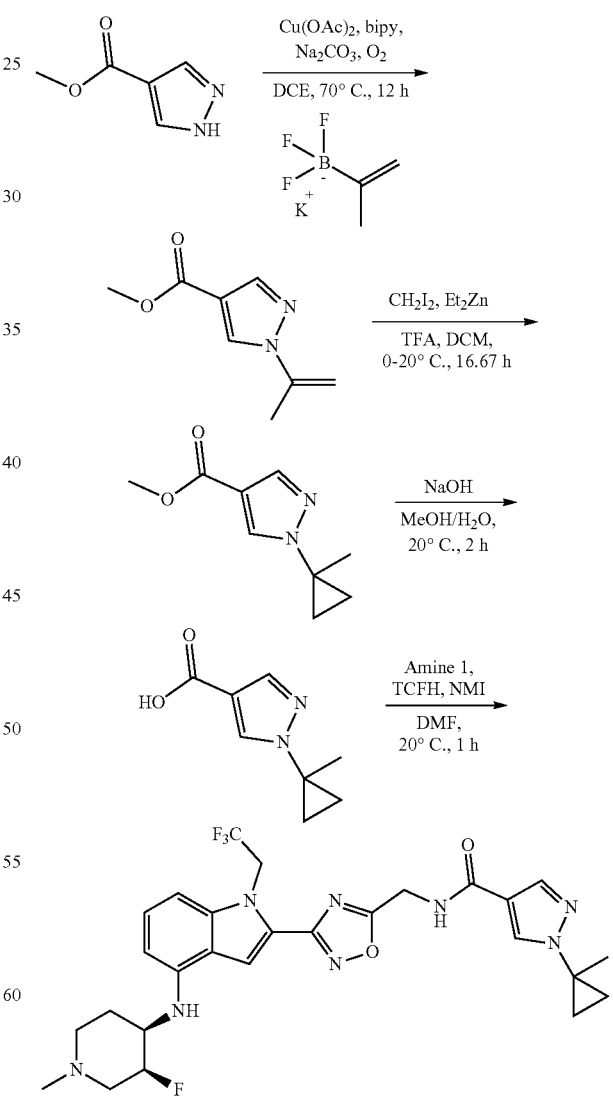

To a mixture of methyl 1H-pyrazole-4-carboxylate (1 g, 7.93 mmol, 1 eq) in DCE (20 mL) were added 2-(2-pyridyl)

pyridine (2.48 g, 15.9 mmol, 2 eq), copper acetate, sodium carbonate (1.68 g, 15.9 mmol, 2 eq), potassium trifluoro (isopropenyl)boronate (2.35 g, 15.7 mmol, 2 eq) at 20° C. and 15 psi oxygen, then the reaction was heated to 70° C. and stirred for 12 h. The residue was poured into EDTA (sat., 20 mL) and stirred for 120 min. The aqueous phase was extracted with EA (3×30 mL). The combined organic phase was washed with brine (3×30 mL), dried over anhydrous sodium sulfate, filtered, and concentrated in vacuo. The residue was purified by silica gel chromatography (column height: 250 mm, diameter: 100 mm, 100-200 mesh silica gel, PE/EA=99/1, 75/25) to give the product (1 g, 6.02 mmol, 75.9% yield) as white solid. LC-MS (ES+, m/z): 167.1 [(M+H)+].

A mixture of TFA (9.03 mmol, 670 μL 5 eq) in DCM (2 mL) was added dropwise to diethylzinc (1 M, 9 mL mL, 5 eq) in DCM (4 mL) under nitrogen at 0° C. and stirred for 20 min, then a solution of diiodomethane (4.84 g, 18.1 mmol, 10 eq) in DCM (2 mL) was added dropwise and stirred for another 20 min. A solution of methyl 1-isopropenylpyrazole-4-carboxylate (300 mg, 1.81 mmol, 1 eq) in DCM (1 mL) was added and heated 20° C. for 16 h. The reaction was quenched with water (20 mL), then extracted with EA (3×20 mL). The combined organic phase was washed with brine (3×20 mL), dried over anhydrous sodium sulfate, filtered, and concentrated in vacuo. The crude was purified by prep-HPLC (column: Phenomenex Luna 80×30 mm×3 um; mobile phase: [water (0.2% FA)-ACN]; B %: 14%-44%, 7 min) to give the cyclopropyl product (50 mg, 15.4% yield) as white oil.

To a mixture of methyl 1-(1-methylcyclopropyl)pyrazole-4-carboxylate (50 mg, 277 μmol, 1 eq) in methanol (2 mL) was added sodium hydroxide (3M, 2 mL, 21.6 eq) at 20° C. under nitrogen, and the reaction was stirred for 2 h. To the solution was added HCl (2 N) to pH=5. The reaction was added to water (20 mL), then extracted with EA (3×20 mL). The combined organic phase was washed with brine (3×10 mL), dried over anhydrous sodium sulfate, filtered, and concentrated in vacuo to give the product (30 mg, crude) as white solid. LC-MS (ES+, m/z): 167.1 [(M+H)+].

Amine 1 (60 mg, 120 μmol, 1 eq, 2HCl) was coupled with 1-(1-methylcyclopropyl)pyrazole-4-carboxylic acid (24 mg, 144 μmol, 1.2 eq) under method E. The crude was purified by prep-TLC (DCM:methanol=10:1; R$_f$=0.43) to give the desired product N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(1-methylcyclopropyl)-1H-pyrazole-4-carboxamide (23.9 mg, 32.2% yield, 93.1% purity) as white solid. LC-MS (ES+, m/z): 575.3 [(M+H)+]. $^1$H NMR (400 MHz, DMSO-d6) δ=8.99 (t, J=5.7 Hz, 1H), 8.32 (s, 1H), 7.89 (d, J=4.2 Hz, 2H), 7.16-7.05 (m, 1H), 6.88 (d, J=8.3 Hz, 1H), 6.28 (d, J=7.9 Hz, 1H), 6.03 (d, J=8.3 Hz, 1H), 5.50 (q, J=8.9 Hz, 2H), 4.95-4.73 (m, 3H), 3.71-3.51 (m, 1H), 3.09-2.99 (m, 1H), 2.81 (d, J=10.3 Hz, 1H), 2.32-2.16 (m, 4H), 2.13-1.93 (m, 2H), 1.68 (d, J=10.7 Hz, 1H), 1.58 (s, 3H), 1.25-1.17 (m, 3H), 0.99-0.88 (m, 2H).

Example 192: Compound 449B: N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-[(1r,3r)-3-methoxycyclobutyl]-1H-pyrrole-3-carboxamide

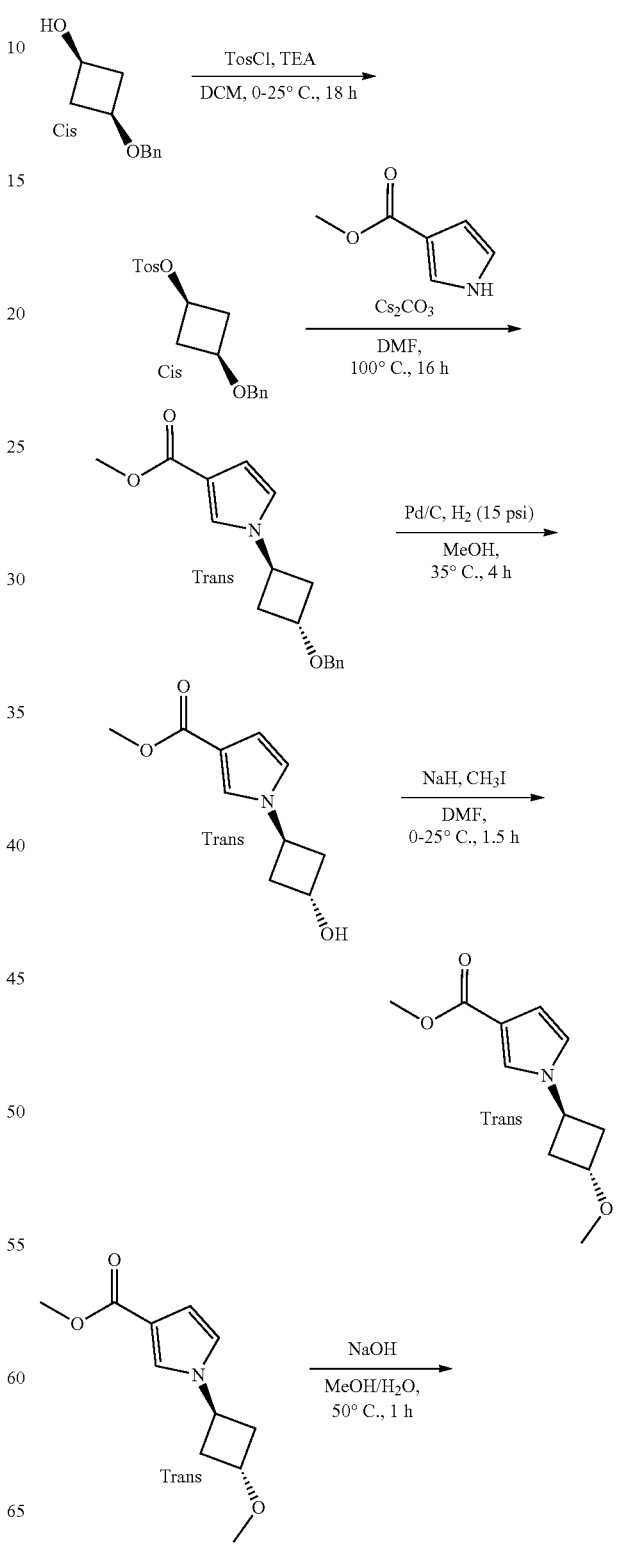

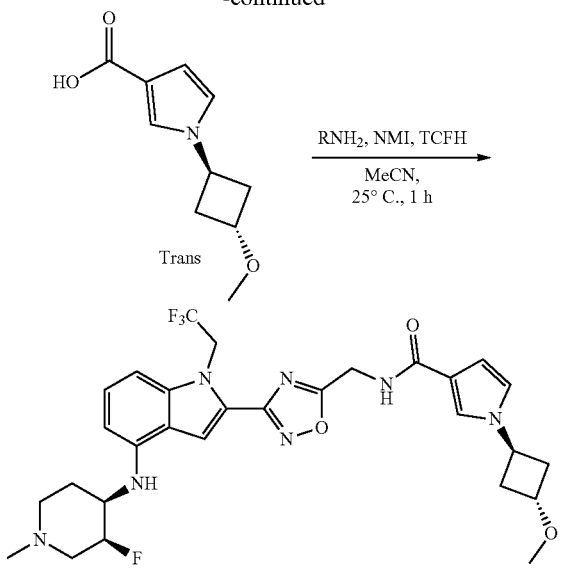

To solution of 3-benzyloxycyclobutanol (1.0 g, 5.6 mmol, 1 eq) and TEA (28.1 mmol, 3.90 mL, 5 eq) in DCM (10 mL) was added 4-methylbenzenesulfonyl chloride (1.60 g, 8.42 mmol, 1.5 eq) at 0° C. The mixture was stirred at 25° C. for 18 h under nitrogen. The mixture was diluted with water (60 mL) and extracted with DCM 60 mL (3×20 mL). The combined organic layers were washed with brine (3×20 mL), dried over anhydrous sodium sulfate, filtered, and concentrated in vacuo to give a residue, which was purified by column chromatography (SiO$_2$, PE/EA=20:1 to 10:1) to afford the product (1.7 g, 87.8% yield, 96.3% purity) as a yellow oil. LC-MS (ES$^+$, m/z): 333.2 [(M+H)$^+$].

To a solution of methyl 1H-pyrrole-3-carboxylate (600 mg, 4.80 mmol, 1 eq) and cesium carbonate (4.69 g, 14.4 mmol, 3 eq) in DMF (10 mL) was added (3-benzyloxycyclobutyl) 4-methylbenzenesulfonate (1.76 g, 5.28 mmol, 1.1 eq), and the reaction was heated at 100° C. for 16 h under nitrogen. The mixture was diluted with water (100 mL) and extracted with (3×50 mL). The combined organic layers were washed with brine (3×50 mL), dried over anhydrous sodium sulfate, filtered, and concentrated in vacuo to give the product (1.4 g, crude) as a yellow oil.

A mixture of methyl 1-(3-benzyloxycyclobutyl)pyrrole-3-carboxylate (1.40 g, 4.91 mmol, 1 eq) and 5% Pd(C) (200 mg, 94.0 μmol, 1.92e-2 eq) in methanol (10 mL) was stirred at 35° C. for 4 h under hydrogen (15 Psi). The reaction mixture was filtered, and concentrated in vacuo to give a residue, which was purified by column chromatography (SiO$_2$, PE/EA=20:1 to 1:1) to give the product (0.6 g, 57.1% yield, 91.2% purity) as a colorless oil. LC-MS (ES$^+$, m/z): 196.1 [(M+H)$^+$].

To a solution of methyl 1-(3-hydroxycyclobutyl)pyrrole-3-carboxylate (400 mg, 2.05 mmol, 1 eq) in DMF (4 mL) was added sodium hydride (122.9 mg, 3.07 mmol, 60% purity, 1.5 eq) at 0° C. The mixture was stirred at 0° C. for 30 min. Iodomethane (2.66 mmol, 165 μL 1.3 eq) was added to the mixture, and the reaction was stirred at 25° C. for 1 h under nitrogen. The mixture was diluted with saturated ammonium chloride (50 mL) and EDTA (sat., 50 mL) at 0° C. The mixture was stirred at 25° C. for 1 h and extracted with EA (3×50 mL). The combined organic layers were washed with brine (3×50 mL). dried over anhydrous sodium sulfate, filtered, and concentrated in vacuo to give the product (0.45 g, crude) as a yellow oil. LC-MS (ES$^+$, m/z): 210.1 [(M+H)$^+$].

A mixture of methyl 1-(3-methoxycyclobutyl)pyrrole-3-carboxylate (450 mg, 2.15 mmol, 1 eq) and sodium hydroxide (5 M, 5 mL, 11.6 eq) in methanol (5 mL) was stirred at 50° C. for 1 h. HCl (2 M) was added into the mixture to adjust pH=5-6 at 0° C. The mixture was extracted with EA (3×50 mL). The combined organic layers were washed with brine (3×50 mL), dried over anhydrous sodium sulfate, filtered, and concentrated in vacuo to give the product (0.3 g, crude) as a light yellow solid. LC-MS (ES$^+$, m/z): 196.0 [(M+H)$^+$]. $^1$H NMR (400 MHz, CDCl$_3$) δ=12.69-9.88 (m, 1H), 7.47 (t, J=1.9 Hz, 1H), 6.71-6.68 (m, 1H), 6.66 (dd, J=1.7, 2.9 Hz, 1H), 4.81-4.69 (m, 1H), 4.22-4.08 (m, 1H), 3.31 (s, 3H), 2.67-2.50 (m, 4H).

Amine 1 (0.12 g, 240 μmol, 1 eq, 2 HCl) was coupled with 1-(3-methoxycyclobutyl)pyrrole-3-carboxylic acid (56.3 mg, 288 μmol, 1.2 eq) under method E. The crude product was purified by prep-TLC (EA:TEA=10: 1, R$_f$=0.2), and further purified by prep-HPLC (column: Phenomenex Luna 80×30 mm×3 um; mobile phase: [water (0.2% FA)-ACN]; B %: 24%-54%, 7 min) to give the desired product N-{3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-1(1r,3r)-3-methoxycyclobutyl]-1H-pyrrole-3-carboxamide (35 mg, 24.1% yield, 100% purity). LC-MS (ES$^+$, m/z): 604.3 [(M+H)$^+$]. $^1$H NMR (400 MHz, DMSO-d$_6$) δ=8.78-8.55 (t, J=5.6 Hz, 1H), 7.89 (s, 1H), 7.53 (s, 1H), 7.23-7.06 (t, J=8.0 Hz, 1H), 6.98-6.91 (t, J=1.6 Hz, 1H), 6.90-6.84 (d, J=8.4 Hz, 1H), 6.63-6.40 (t, J=2.2 Hz, 1H), 6.36-6.23 (d, J=8.0 Hz, 1H), 6.11-5.93 (d, J=8.4 Hz, 1H), 5.61-5.39 (dt, J=8.8 Hz, 2H), 5.00-4.66 (m, 4H), 4.14-3.99 (m, 1H), 3.64-3.54 (m, 1H), 3.19 (s, 3H), 3.04 (br t, J=9.7 Hz, 1H), 2.82 (br d, J=10.0 Hz, 1H), 2.48-2.44 (m, 4H), 2.32-2.17 (m, 4H), 2.14-2.06 (m, 1H), 2.05-1.94 (m, 1H), 1.74-1.59 (m, 1H).

Example 193: Compound 450B: N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-[(1s,3s)-3-methoxycyclobutyl]-1H-pyrrole-3-carboxamide

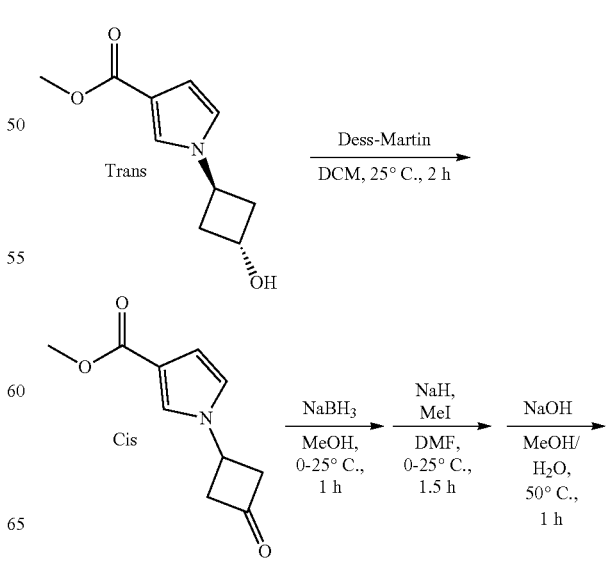

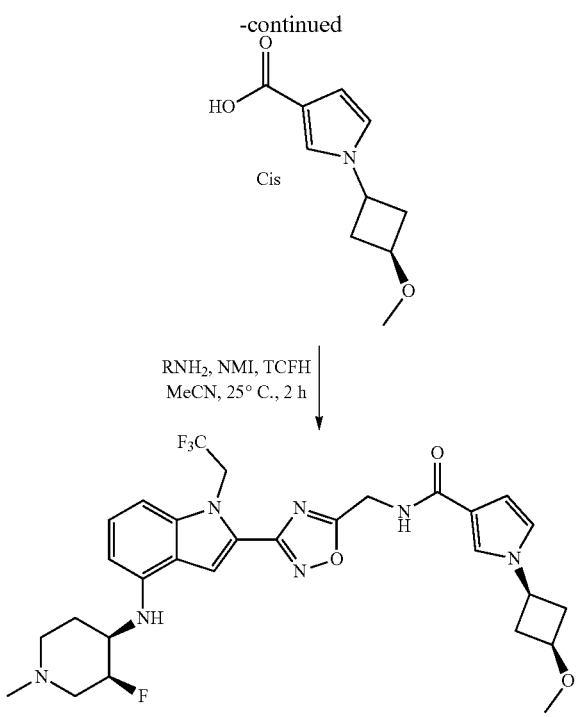

To a solution of the previously prepared trans methyl 1-(3-hydroxycyclobutyl)pyrrole-3-carboxylate (300 mg, 1.54 mmol, 1 eq) in DCM (3 mL) was added Dess-Martin Periodinane (977.7 mg, 2.31 mmol, 1.5 eq) at 25° C., and the reaction stirred for 2 h. TLC (PE:EA=1:1, R$_f$=0.3) indicated formation of product. The reaction mixture was diluted with sodium carbonate (sat., 20 mL) and extracted with DCM (3×20 mL). The combined organic layers were washed with brine (3×20 mL), dried over anhydrous sodium sulfate, filtered, and concentrated in vacuo to give a residue, which was purified by prep-TLC (PE:EA=1:1) to give the ketone product (0.2 g, 67.4% yield) as a light yellow oil.

To a solution of methyl 1-(3-oxocyclobutyl)pyrrole-3-carboxylate (0.2 g, 1.04 mmol, 1 eq) in methanol (2 mL) was added sodium borohydride (195.8 mg, 5.18 mmol, 5 eq) at 0° C.. The mixture was stirred at 25° C. for 1 h under nitrogen. The reaction was diluted with water (30 mL) and extracted with EA (3×30 mL). The combined organic layers were washed with brine (50 mL×3), dried over anhydrous sodium sulfate, filtered, and concentrated in vacuo to give the cis product (0.18 g, crude) as a light yellow oil.

To a solution of cis methyl 1-(3-hydroxycyclobutyl)pyrrole-3-carboxylate (0.18 g, 922 μmol, 1 eq) in DMF (4 mL) was added sodium hydride (55.3 mg, 1.38 mmol, 60% purity, 1.5 eq) at 0° C. The mixture was stirred at 0° C. for 30 min. Iodomethane (1.20 mmol, 75 μL 1.3 eq) was added into the reaction, and the mixture was stirred at 25° C. for 1 h under nitrogen. The mixture was diluted with saturated ammonium chloride (50 mL) and EDTA (Sat. aq., 50 mL) at 0° C. The mixture was stirred at 25° C. for 1 h and extracted with EA (3×50 mL). The combined organic layers were washed with brine (3×50 mL). dried over anhydrous sodium sulfate, filtered, and concentrated in vacuo to give the ether product (0.15 g, crude) as a yellow oil.

Cis methyl 1-(3-methoxycyclobutyl)pyrrole-3-carboxylate (150 mg, 717 μmol, 1 eq) was saponified under standard conditions as for the trans isomer to provide the product carboxylic acid (0.1 g, crude) as a light yellow solid. $^1$H NMR (400 MHz, CDCl3) δ=12.63-9.71 (m, 1H), 7.47 (s, 1H), 6.73 (t, J=2.5 Hz, 1H), 6.66-6.62 (m, 1H), 4.27-4.05 (m, 1H), 3.85-3.68 (m, 1H), 3.35-3.22 (m, 3H), 2.91 (dtd, J=3.1, 6.8, 9.6 Hz, 2H), 2.65-2.50 (m, 1H), 2.38-2.21 (m, 2H).

Amine 1 (0.08 g, 160 μmol, 1 eq, 2HCl) was coupled with 1-(3-methoxycyclobutyl)pyrrole-3-carboxylic acid (46.9 mg, 240 μmol, 1.5 eq) under method E. The crude product was purified by prep-HPLC (column: Phenomenex Luna 80×30 mm×3 um: mobile phase: [water (0.2% FA)-ACN];B %: 30%-60%, 7 min) to give the desired product N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-[(1s,3s)-3-methoxycyclobutyl]-1H-pyrrole-3-carboxamide (7.3 mg, 36.2% yield, 96.9% purity). LC-MS (ES$^+$, m/z): 604.3 [(M+H)$^+$]. $^1$H NMR (400 MHz, DMSO-d6) δ=8.77-8.62 (t, J=5.6 Hz, 1H), 7.89 (s, 1H), 7.62-7.47 (t, J=2.0 Hz, 1H), 7.17-7.07 (t, J=8.0 Hz, 1H), 6.95-6.84 (m, 2H), 6.52-6.45 (dt, J=1.6 Hz, 1H), 6.34-6.24 (d, J=7.6 Hz, 1H), 6.11-5.96 (d, J=8.0 Hz, 1H), 5.57-5.38 (dt, J=8.8 Hz, 2H), 4.92-4.71 (m, 3H), 4.40-4.19 (m, 1H), 3.73-3.67 (m, 1H), 3.64-3.55 (m, 1H), 3.21-3.17 (t, J=2.8 Hz, 3H), 3.08-3.00 (m, 1H), 2.86-2.75 (m, 3H), 2.32-2.17 (m, 4H), 2.16-2.06 (m, 3H), 2.05-1.93 (m, 1H), 1.76-1.60 (m, 1H).

Example 194: Compound 451B: 1-(3,3-difluorocyclobutyl)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-pyrrole-3-carboxamide

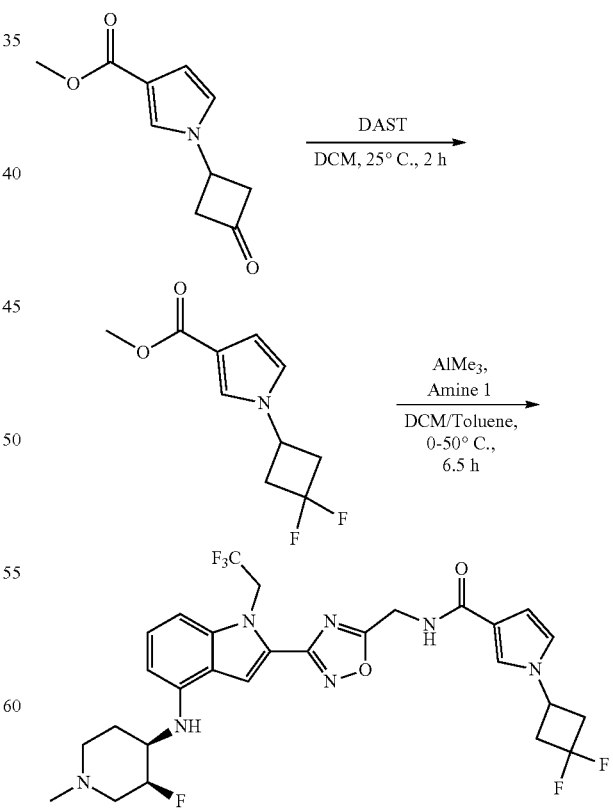

To a solution of the previously prepared methyl 1-(3-oxocyclobutyl)pyrrole-3-carboxylate (120 mg, 621 μmol, 1 eq) in DCM (2 mL) was added DAST (1.86 mmol, 245 μL 3 eq). The mixture was stirred at 25° C. for 2 h. The reaction mixture was poured into water (50 mL), then extracted with EA (30 mL×3). The combined organic layers were washed with brine (30 mL×1), dried over anhydrous sodium sulfate, filtered, and concentrated in vacuo to give a residue. The residue was purified by prep-TLC (SiO$_2$, PE:EA=3:1) to give the difluoro product (80 mg, 59% yield). LC-MS (ES$^+$, m/z): 216.0 [(M+H)$^+$].

Method H: To a solution of Amine 1 (70 mg, 153 μmol, 1 eq) in toluene (2 mL) and DCM (2 mL) was added trimethylaluminum (2 M, 380 μL 5 eq) at 0° C., and the solution was stirred for 30 min, followed by addition of methyl 1-(3,3-difluorocyclobutyl)pyrrole-3-carboxylate (34.6 mg, 153 μmol, 1 eq). The mixture was stirred at 50° C. for 6 h. The reaction mixture was poured into water (50 mL), then extracted with EA (30 mL×3). The combined organic layers were washed with brine (30 mL×1), dried over anhydrous sodium sulfate, filtered, and concentrated in vacuo to give a residue. The residue was purified by prep-TLC (SiO$_2$, DCM: methanol=10:1) to give the desired product 1-(3,3-difluorocyclobutyl)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-pyrrole-3-carboxamide (15.2 mg, 15.1% yield, 92.7% purity). LC-MS (ES$^+$, m/z): 610.3 [(M+H)$^+$]. $^1$H NMR (400 MHz, DMSO-d) δ=8.73 (t, J=5.6 Hz, 1H), 7.89 (s, 1H), 7.58 (d, J=1.7 Hz, 1H), 7.12 (t, J=8.0 Hz, 1H), 7.01 (t, J=2.5 Hz, 1H), 6.89 (d, J=8.2 Hz, 1H), 6.57 (dd, J=1.7, 2.7 Hz, 1H), 6.29 (d, J=7.8 Hz, 1H), 6.04 (br d, J=8.4 Hz, 1H), 5.51 (q, J=8.6 Hz, 2H), 4.96-4.68 (m, 4H), 3.70-3.53 (m, 1H), 3.24-3.13 (m, 2H), 3.11-2.94 (m, 3H), 2.91-2.80 (m, 1H), 2.36-2.08 (m, 5H), 2.07-1.95 (m, 1H), 1.75-1.65 (m, 1H).

Example 195: Compound 4521B: N-[(3S,4R)-3-fluoro-1-methylpiperidin-4-yl]-2-{5-[({1-methyl-1H-pyrazolo[4,3-c]pyridin-4-yl}amino)methyl]-1,2,4-oxadiazol-3-yl}-1-(2,2,2-trifluoroethyl)-1H-indol-4-amine To a solution of 4-chloro-1H-pyrazolo[4,3-c]pyridine (500 mg, 3.26 mmol, 1 eq) in DMF (10 mL) were added sodium hydride (195.4 mg, 4.88 mmol, 60% purity, 1.5 eq) and iodomethane (3.91 mmol, 240 μL 1.2 eq), and the reaction was stirred at 0° C. for 2 h. The residue was poured into saturated ammonium chloride (10 mL) and stirred for 10 min at 0° C. The aqueous phase was extracted with EA (3×10 mL). The combined organic phase was washed with brine (3×10 mL), dried over anhydrous sodium sulfate, filtered, and concentrated in vacuo. The residue was purified by prep-TLC (SiO$_2$, DCM: methanol=20: 1) to provide the product 4-chloro-1-methyl-pyrazolo[4,3-c]pyridine (250 mg, 45.8% yield) as a yellow solid. LC-MS (ES$^+$, m/z): 168.1 [(M+H)$^+$]. $^1$H NMR (400 MHz, CHLOROFORM-d) δ=8.22 (d, J=6.0 Hz, 1H), 8.17 (s, 1H), 7.29 (dd, J=5.6, 6.3 Hz, 1H), 4.13 (s, 3H).

To a mixture of Amine 1 (60 mg, 141 μmol, 1 eq) and 4-chloro-1-methyl-pyrazolo[4,3-c]pyridine (28.3 mg, 169 μmol, 1.2 eq) in toluene (2 mL) were added sodium t-butoxide (27 mg, 281 μmol, 2 eq) and t-Bu-XPhos Generation 3 (11.2 mg, 14.1 μmol, 0.1 eq), and the reaction was stirred at 80° C. for 2 h. The reaction was poured into EDTA (10 mL, sat.) and stirred for 2 h. The aqueous phase was extracted with EA (3×10 mL). The combined organic phase was washed with brine (3×10 mL), dried over anhydrous sodium sulfate, filtered, and concentrated in vacuo. The residue was purified by prep-HPLC (FA condition) to provide the desired product (0.022 g, 24.0% yield, 99.4% purity). LC-MS (ES$^+$, m/z): 558.3 [(M+H)$^+$]. $^1$H NMR (400 MHz, DMSO-d$_6$) δ=8.31-8.25 (t, J=5.6 Hz, 1H), 8.22 (s, 1H), 7.85 (s, 1H), 7.77-7.62 (d, J=6.0 Hz, 1H), 7.17-7.03 (t, J=8.2 Hz, 1H), 6.92-6.68 (t, J=6.4 Hz, 2H), 6.33-6.22 (d, J=8.0 Hz, 1H), 6.05-5.93 (d, J=8.0 Hz, 1H), 5.58-5.36 (dt, J=8.6 Hz, 2H), 5.10-4.96 (d, J=5.6 Hz, 2H), 4.93-4.69 (d, J=49.2 Hz, 1H), 3.95 (s, 3H), 3.65-3.54 (m, 1H), 3.05 (br t, J=10.5 Hz, 1H), 2.86-2.78 (m, 1H), 2.32-2.16 (m, 4H), 2.15-2.07 (m, 1H), 2.04-1.91 (m, 1H), 1.75-1.60 (m, 1H).

Example 196: Compound 45311: N-{[3-(4-{1[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-(morpholin-4-yl)-1,3-thiazole-5-carboxamide

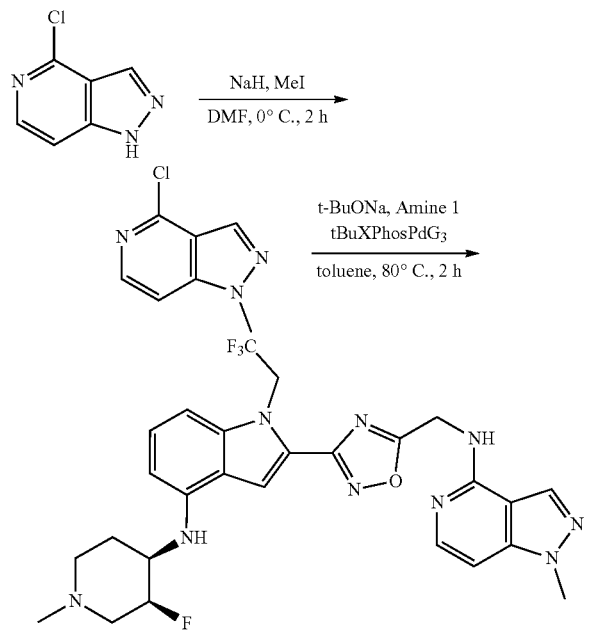

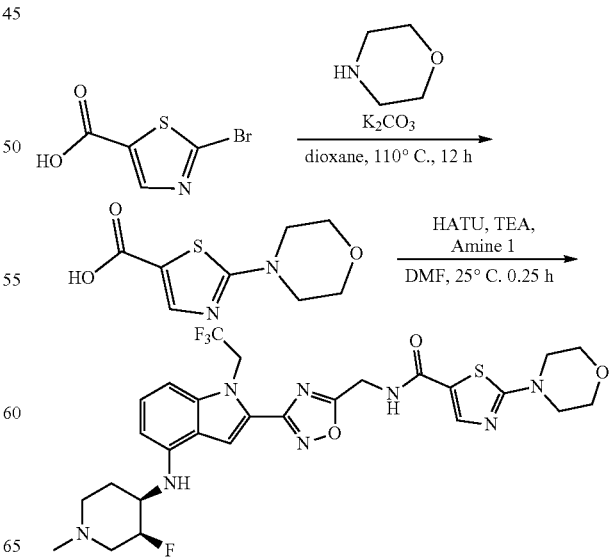

To a mixture of 2-bromothiazole-5-carboxylic acid (500 mg, 2.40 mmol, 1 eq) and morpholine (12 mmol, 1.06 mL, 5 eq) in dioxane (5 mL) was added potassium carbonate (3.32 g, 24 mmol, 10 eq), and the reaction was heated at 110° C. under nitrogen for 12 h. The residue was poured into water (30 mL) and extracted with EA (30 mL×3). The combined aqueous phase was concentrated in vacuo. The mixture was purified by pre-HPLC (column: Phenomenex luna C18 250×50 mm×10 um; mobile phase: [water (0.05% HCl)-ACN]; B %: 1%-30%, 10 min) to give the product (260 mg, 50.5% yield).

Amine 1 (70 mg, 126 μmol, 1 eq, 2HCl) and 2-morpholinothiazole-5-carboxylic acid (54.1 mg, 252 μmol, 2 eq) were coupled under method B. The crude reaction was purified by prep-TLC (SiO2, DCM: methanol=10:1) to give the desired product N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-(morpholin-4-yl)-1,3-thiazole-5-carboxamide (37.3 mg, 45.0% yield, 94.8% purity). LC-MS (ES$^+$, m/z): 623.3 [(M+H)$^+$]. $^1$H NMR (400 MHz, DMSO-d6) δ=9.16 (t, J=5.6 Hz, 1H), 7.94 (s, 1H), 7.90 (s, 1H), 7.12 (t, J=8.0 Hz, 1H), 6.88 (d, J=8.2 Hz, 1H), 6.29 (d, J=7.8 Hz, 1H), 6.00 (d, J=8.3 Hz, 1H), 5.50 (q, J=8.7 Hz, 2H), 4.95-4.73 (m, 3H), 3.76-3.68 (m, 4H), 3.65-3.52 (m, 1H), 3.50-3.43 (m, 4H), 3.06 (br t, J=10.6 Hz, 1H), 2.83 (br d, J=10.1 Hz, 1H), 2.21 (s, 4H), 2.18-2.07 (m, 1H), 2.06-1.94 (m, 1H), 1.70 (br d, J=9.5 Hz, 1H).

Example 197: Compound 454B: N-[(3S,4R)-3-fluoro-1-methylpiperidin-4-yl]-2-{5-[({1-methyl-1H-pyrrolo[3,2-c]pyridin-4-yl}amino)methyl]-1,2,4-oxadiazol-3-yl}-1-(2,2,2-trifluoroethyl)-1H-indol-4-amine

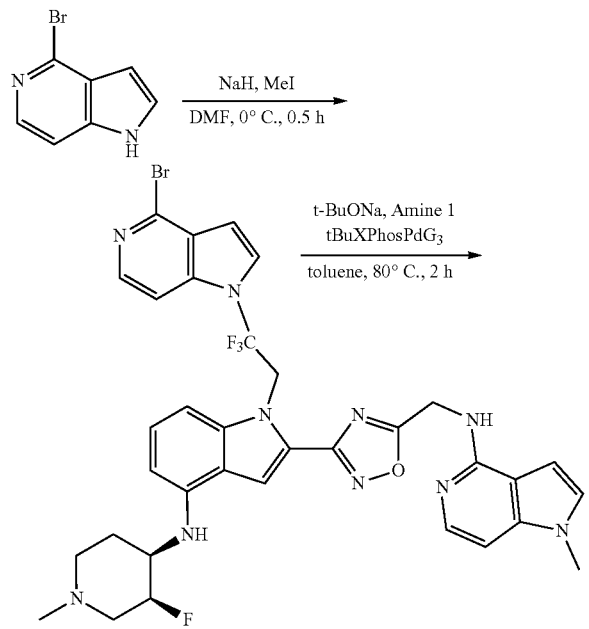

To 4-bromo-1H-pyrrolo[3,2-c]pyridine (220 mg, 1.12 mmol, 1 eq) in DMF (4 mL) was added sodium hydride (89.3 mg, 2.23 mmol, 60% purity, 2 eq) at 0° C., followed by iodomethane (1.67 mmol, 105 μL 1.5 eq) was added to the mixture and stirred for 0.5 h at 0° C. The reaction mixture was quenched by adding sat. ammonium chloride (10 mL) at 0° C., then diluted with water (100 mL) and extracted with EA (2×50 mL). The combined organic layers were washed with brine (50 mL) dried over anhydrous sodium sulfate, filtered, and concentrated in vacuo to give a residue. The residue was purified by prep-TLC (PE:EA=2:1) to give the product (200 mg, 84.9% yield). LC-MS (ES$^-$, m/z): 211.1 [(M+H)$^+$].

A mixture of 4-bromo-1-methyl-pyrrolo[3,2-c]pyridine (35.6 mg, 169 μmol, 1.2 eq), Amine 1 (60 mg, 141 μmol, 1 eq), sodium t-butoxide (27 mg, 280 μmol, 2 eq), t-BuXPhos Pd Generation 3 (11.2 mg, 14.1 μmol, 0.1 eq) in toluene (2.5 mL) was degassed and purged with nitrogen 3 times, then the mixture was stirred at 80° C. for 2 h under nitrogen atmosphere, then cooled to rt. EDTA solution (sat., 100 mL) was added to the mixture, and the mixture was stirred for 1 hr. The reaction mixture was diluted with water (100 mL) and extracted with EA (2×100 mL). The combined organic layers were washed with brine (100 mL), dried over anhydrous sodium sulfate, filtered, and concentrated in vacuo to give a residue. The residue was purified by prep-TLC (SiO$_2$, DCM: methanol=10:1). The residue was further purified by prep-HPLC to give the desired product N-[(3S,4R)-3-fluoro-1-methylpiperidin-4-yl]-2-{5-[({1-methyl-1H-pyrrolo[3,2-c]pyridin-4-yl}amino)methyl]-1,2,4-oxadiazol-3-yl}-1-(2,2,2-trifluoroethyl)-1H-indol-4-amine (20 mg, 24.6% yield, 96.3% purity). LC-MS (ES$^+$, m/z): 557.3 [(M+H)$^+$]. $^1$H NMR (400 MHz, DMSO-d6) δ=8.13 (s, 1H), 7.83 (s, 1H), 7.61-7.48 (m, 2H), 7.15 (d, J=3.1 Hz, 1H), 7.11-7.05 (m, 1H), 6.85 (d, J=8.2 Hz, 1H), 6.73 (d, J=6.0 Hz, 1H), 6.65 (d, J=3.1 Hz, 1H), 6.25 (d, J=7.9 Hz, 1H), 5.96 (d, J=8.4 Hz, 1H), 5.46 (br d, J=9.0 Hz, 2H), 4.95 (d, J=5.7 Hz, 2H), 4.90-4.72 (m, 1H), 3.70 (s, 3H), 3.64-3.49 (m, 1H), 3.02 (br t, J=10.0 Hz, 1H), 2.80 (brd, J=10.6 Hz, 1H), 2.32-2.24 (m, 1H), 2.18 (s, 3H), 2.14-2.03 (m, 1H), 2.03-1.89 (m, 1H), 1.65 (br d, J=10.1 Hz, 1H).

Example 198: Compound 455B: 2-{5-[({1-tert-butyl-1H-pyrazolo[4,3-c]pyridin-4-yl}amino)methyl]-1,2,4-oxadiazol-3-yl}-N-[(3S,4R)-3-fluoro-1-methylpiperidin-4-yl]-1-(2,2,2-trifluoroethyl)-1H-indol-4-amine, and Compound 456B: 2-{5-[({2-tert-butyl-2H-pyrazolo[4,3-c]pyridin-4-yl}amino)methyl]-1,2,4-oxadiazol-3-yl}-N-[(3S,4R)-3-fluoro-1-methylpiperidin-4-yl]-1-(2,2,2-trifluoroethyl)-1H-indol-4-amine

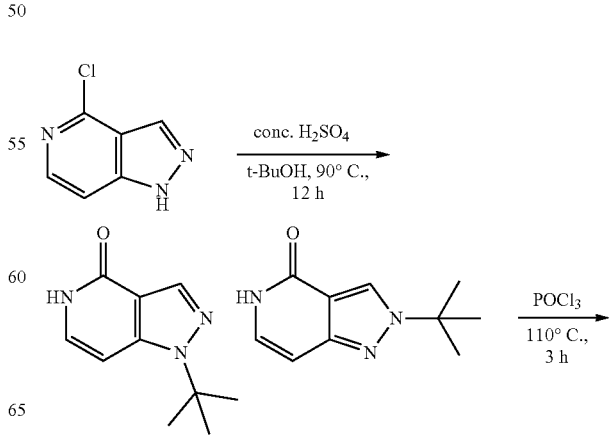

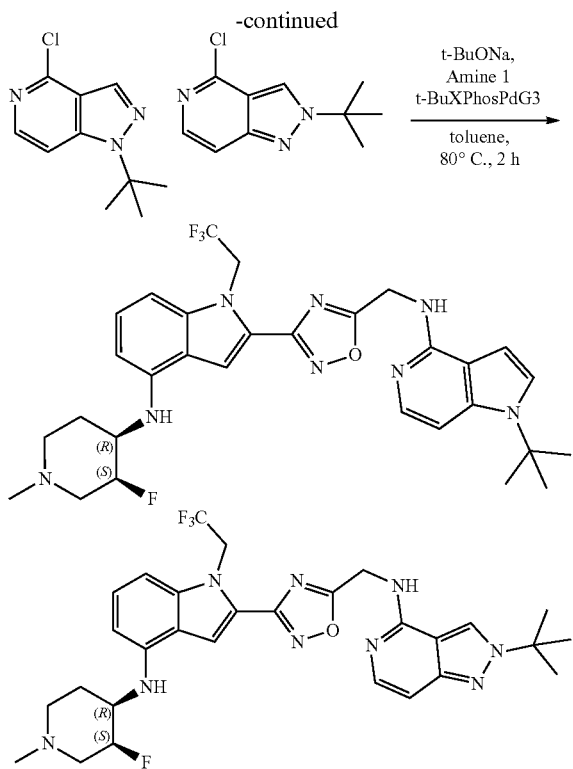

A mixture of 4-chloro-1H-pyrazolo[4,3-c]pyridine (5 g, 32.6 mmol, 1 eq) and sulfuric acid (33 mmol, 1.80 mL, 1.02 eq) were heated in t-butanol (100 mL) at 90° C. under nitrogen for 12 h. The residue was poured into sodium carbonate (sat.) to adjust pH=7-8. The aqueous phase was extracted with EA (3×50 mL). The combined organic phase was washed with brine (3×50 mL), dried over anhydrous sodium sulfate, filtered, and concentrated in vacuo to afford the products as a mixture of regioisomers (3 g, crude) as yellow solids.

To a mixture of 1-tert-butyl-5H-pyrazolo[4,3-c]pyrdin-4-one and 2-tert-butyl-5H-pyrazolo[4,3-c]pyridin-4-one (3 g, 15.7 mmol, 1 eq; mixture) was added phosphorus oxychloride (323 mmol, 30 mL, 20.6 eq) in one portion at 110° C. under nitrogen. The mixture was stirred at 110° C. for 3 h. The residue was poured into ice-water (w/w=1/1, 100 mL) followed by sodium carbonate (sat.) to adjust pH=7-8. The aqueous phase was extracted with EA (3×30 mL). The combined organic phase was washed with brine (3×30 mL), dried over anhydrous sodium sulfate, filtered, and concentrated in vacuo. The residue was purified by prep-HPLC (TFA condition, column: Phenomenex luna C18 (250×70 mm, 15 um); mobile phase: [water (0.1% TFA)-ACN]; B %: 25%-55%, 20 min) to provide the 1-N-t-butyl isomer (0.5 g, 15.2% yield) as a light yellow solid, as well as the 2-N-t-butyl isomer (100 mg, 3.04% yield) as a brown oil.

To a mixture of Amine 1 (100 mg, 235 μmol, 1 eq) and 1-tert-butyl-4-chloro-pyrazolo[4,3-c]pyridine (59 mg, 281 μmol, 1.2 eq) in toluene (2 mL) were added sodium t-butoxide (45 mg, 469 μmol, 2 eq), t-butylXPhos Generation 3 (18.6 mg, 23.5 μmol, 0.1 eq), and the reaction was heated at 80° C. under nitrogen for 2 h. The residue was poured into EDTA (sat., 60 mL) and stirred for 60 min. The aqueous phase was extracted with EA (3×20 mL). The combined organic phase was washed with brine (saturated solution) (3×20 mL), dried over anhydrous sodium sulfate, filtered, and concentrated in vacuo. The residue was purified by prep-TLC (SiO$_2$, DCM:methanol=10: 1) to provide the desired product 1-tert-butyl-N-[[3-[4-[[(3S,4R)-3-fluoro-1-methyl-4-piperidyl]amino]-1-(2,2,2-trifluoroethyl)indol-2-yl]-1,2,4-oxadiazol-5-yl]methyl]pyrazolo[4,3-c]pyridin-4-amine (22.3 mg, 15.5% yield, 97.6% purity) as a light yellow solid. LC-MS (ES$^+$, m/z): 600.3 [(M+H)$^+$]. $^1$H NMR (400 MHz, DMSO-d6) δ=8.30-8.19 (m, 2H), 7.85 (s, 1H), 7.64 (d, J=6.4 Hz, 1H), 7.15-7.07 (m, 1H), 7.01 (d, J=6.2 Hz, 1H), 6.87 (d, J=8.4 Hz, 1H), 6.27 (d, J=7.9 Hz, 1H), 5.99 (br d, J=8.4 Hz, 1H), 5.54-5.41 (m, 211), 5.00 (d, J=5.7 Hz, 2H), 4.93-4.76 (m, 1H), 3.67-3.52 (m, 1H), 3.05 (br s, 1H), 2.92-2.78 (m, 1H), 2.33-2.14 (m, 4H), 2.03 (br s, 1H), 1.99 (br d, J=9.3 Hz, 1H), 1.71 (br d, J=7.7 Hz, 1H), 1.66 (s, 9H).

The 2-t-butyl isomer was prepared using the same conditions using Amine 1 (100 mg, 235 μmol, 1 eq) and 2-tert-butyl-4-chloro-pyrazolo[4,3-c]pyridine (59 mg, 281 μmol, 1.2 eq). The crude reaction was purified by prep-HPLC (FA condition, column: Phenomenex Luna C18 200× 40 mm×10 um; mobile phase: [water (0.2% FA)-ACN] B %: 1%-50%, 8 min) to provide the desired product Compound 456B: 2-{5-[({2-tert-butyl-2H-pyrazolo[4,3-c]pyridin-4-yl}amino)methyl]-1,2,4-oxadiazol-3-yl}-N-[(3S,4R)-3-fluoro-1-methylpiperidin-4-yl]-1-(2,2,2-trifluoroethyl)-1H-indol-4-amine (20.5 mg, 14.5% yield, 99.4% purity) as a light yellow solid. LC-MS (ES$^+$, m/z): 600.3 [(M+H)$^+$]. $^1$H NMR (400 MHz, DMSO-d6) δ=8.63 (s, 1H), 8.28 (s, 1H), 8.12 (br s, 1H), 7.85 (s, 1H), 7.52 (d, J=6.2 Hz, 1H), 7.20-7.04 (m, 1H), 6.87 (d, J=8.4 Hz, 1H), 6.73 (d, J=6.4 Hz, 1-1), 6.27 (d, J=7.7 Hz, 1H), 5.97 (br d, J=7.1 Hz, 1H), 5.48 (q, J=8.7 Hz, 2H), 5.02 (d, J=5.7 Hz, 2H), 4.93-4.75 (m, 1H), 3.67-3.50 (m, 1H), 3.07-2.98 (m, 1H), 2.80 (br d, J=10.6 Hz, 1H), 2.31-2.16 (m, 4H), 2.13-2.04 (m, 1H), 2.03-1.93 (m, 1H), 1.68 (br d, J=3.5 Hz, 1H), 1.66 (s, 9H).

Example 199: Compound 457B: N-[(3S,4R)-3-fluoro-1-methylpiperidin-4-yl]-2-{5-[({thieno[3,2-c]pyridin-4-yl}amino)methyl]-1,2,4-oxadiazol-3-yl}-1-(2,2,2-trifluoroethyl)-1H-indol-4-amine The analogue was prepared using the same conditions as used for the other thienopyrimidine regioisomer previously described. Amine 1 (105 mg, 0.21 mmol, 1 eq, HCl salt) and 4-Chlorothieno[3,2-c]pyridine (51.8 mg, 0.305 mmol, 1.45 eq) provided after reverse-phase HPLC the desired product N-[(3S,4R)-3-fluoro-1-methylpiperidin-4-yl]-2-{5-[({thieno[3,2-c]pyridin-4-yl}amino)methyl]-1,2,4-oxadiazol-3-yl}-1-(2,2,2-trifluoroethyl)-1H-indol-4-amine as a formic acid salt (33.2 mg, 26.1% yield). LC-MS (ES$^+$, m/z): 600.3 [(M+H)$^+$]. $^1$H NMR (500 MHz, DMSO-d6) δ 8.15 (s, 1H), 8.09 (t, J=5.8 Hz, 1H), 7.85 (s, 1H), 7.79 (dd, J=9.0, 5.6 Hz, 2H), 7.71 (d, J=5.5 Hz, 1H), 7.25 (d, J=5.7 Hz, 1H), 7.11 (t, J=8.0 Hz, 1H), 6.87 (d, J=8.3 Hz, 1H), 6.28 (d, J=7.8 Hz, 1H), 5.97 (d, J=8.3 Hz, 1H), 5.48 (q, J=8.9 Hz, 2H), 5.01 (d, J=5.6 Hz, 2H), 4.84 (d, J=49.4 Hz, 1H), 3.60 (d, J=29.7 Hz, 1H), 3.06 (t, J=10.9 Hz, 1H), 2.83 (d, J=11.0 Hz, 1H), 2.41-2.25 (m, 1H), 2.21 (d, J=2.8 Hz, 3H), 2.13 (t, J=11.5 Hz, 1H), 1.99 (dd, J=12.3, 3.7 Hz, 1H), 1.68 (d, J=12.9 Hz, 1H).

Example 200: Compound 458B: N-{[3-(4-{[(3S, 4R)-3-fluoro-1-methylpiperidin-4-yl]amino}-1-(2,2, 2-trifluoroethyl)-1H-indol-2-yl)-1,2,4-oxadiazol-5-yl]methyl}-5-(methoxymethyl)thiophene-2-carboxamide Amine 1 (49 mg, 0.098 mmol, 1.00 eq.) and 5-(methoxymethyl)thiophene-2-carboxylic acid (22.4 mg, 0.13 mmol, 1.3 eq.) under method B to provide after reverse-phase HPLC the desired product N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-5-(methoxymethyl)thiophene-2-carboxamide as the formate salt (19.1 mg, 31%). LC-MS (ES+, m/z): 607.3 [(M+H)+].

Example 201: Compound 459B: N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-(pyrrolidin-1-yl)-1,3-thiazole-5-carboxamide

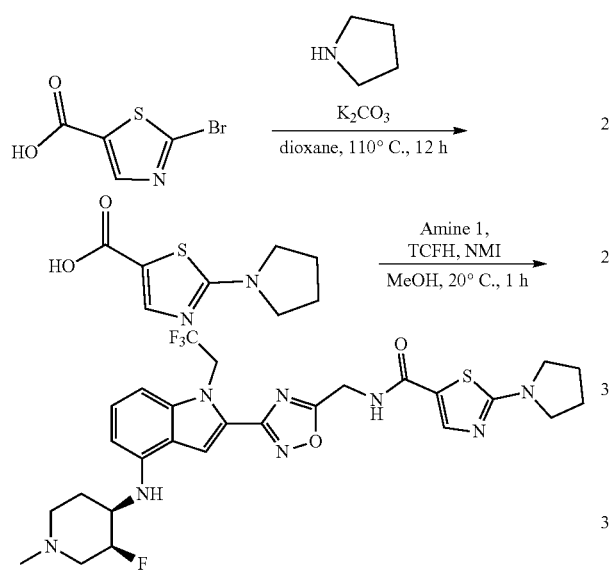

A mixture of 2-bromothiazole-5-carboxylic acid (0.5 g, 2.40 mmol, 1 eq), pyrrolidine (12 mmol, 1 mL, 5 eq) and potassium carbonate (3.32 g, 24 mmol, 10 eq) in dioxane (10 mL) was stirred at 110° C. for 12 h in a sealed tube. The reaction mixture was diluted with water (10 mL) and adjusted to pH to 7 using HCl (6 M). The mixture was concentrated in vacuo to give a residue. The residue was purified by prep-HPLC (column: Phenomenex luna C18 80×40 mm×3 um; mobile phase: [water (0.04% HCl)-ACN]; B %: 1%-25%, 7 min) to give the product (0.12 g, 25.2% yield). LC-MS (ES+, m/z): 199.1 [(M+H)+].

Amine 1 (80 mg, 144 μmol, 1 eq, 2HCl) was coupled with 2-pyrrolidin-1-ylthiazole-5-carboxylic acid (28.6 mg, 144 μmol, 1 eq) under method E. The crude reaction was purified by prep-TLC (SiO2, DCM: methanol=10:1). The residue was further purified by prep-HPLC (FA condition:column: Phenomenex Luna C18 200×40 mm×10 um; mobile phase: [water (0.2% FA)-ACN];B %: 20%-50%, 8 min) to give the desired product N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-(pyrrolidin-1-yl)-1,3-thiazole-5-carboxamide (31 mg, 34.7% yield, 98% purity) LC-MS (ES+, m/z): 607.3 [(M+H)+]. 1H NMR (400 MHz, DMSO-d6) δ=9.17-8.99 (t, J=5.6 Hz, 1H), 7.99-7.80 (d, J=5.2 Hz, 2H), 7.17-7.07 (t, J=8.0 Hz, 1H), 6.97-6.77 (d, J=8.4 Hz, 1H), 6.38-6.22 (d, J=8.0 Hz, 1H), 6.10-5.97 (d, J=8.0 Hz, 1H), 5.61-5.34 (dt, J=8.2 Hz, 2H), 4.96-4.73 (m, 3H), 3.64- 3.55 (m, 1H), 3.40 (br s, 4H), 3.04 (br t, J=10.5 Hz, 1H), 2.82 (br d, J=10.4 Hz, 1H), 2.32-2.17 (m, 4H), 2.16-1.93 (m, 6H), 1.74-1.63 (m, 1H).

Example 202: Compound 460B: N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-(pyrrolidin-1-yl)-1,3-thiazole-4-carboxamide

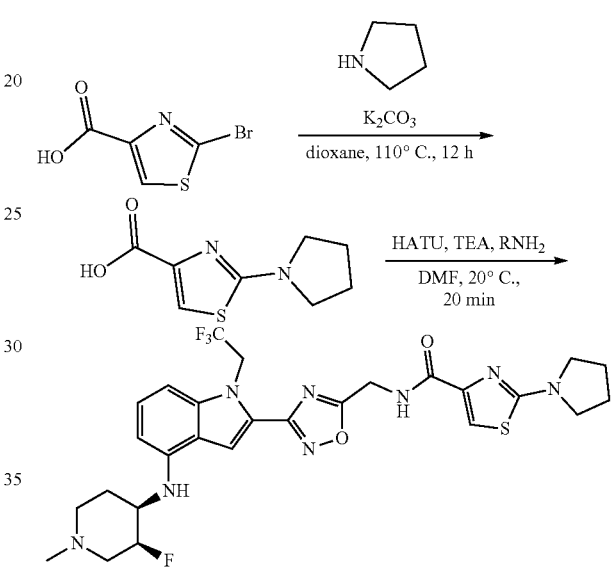

To a mixture of 2-bromothiazole-4-carboxylic acid (500 mg, 2.40 mmol, 1 eq) and pyrrolidine (7.21 mmol, 600 μL 3 eq) in dioxane (5 mL) was added potassium carbonate (3.32 g, 24 mmol, 10 eq), and the reaction was heated at 110° C. under nitrogen for 12 h in a sealed tube. The reaction was concentrated, and the residue was purified by prep-HPLC (HCl condition, column: Phenomenex luna C18 250×50 mm×10 um; mobile phase: [water (0.05% HCl)-ACN] B %: 1%-30%, 10 min) to provide the product 2-pyrrolidin-1-ylthiazole-4-carboxylic acid (30 mg, 6.30% yield) as a light yellow solid. LC-MS (ES+, m/z): 199.0 [(M+H)+].

2-pyrrolidin-1-ylthiazole-4-carboxylic acid (22.2 mg, 112 μmol, 1 eq) was coupled with Amine 1 (60 mg, 112 μmol, 1 eq, 2HCl) under method B. The crude product was purified by prep-TLC (SiO2, DCM:methanol=10:1) to afford the (21.1 mg, 30.6% yield, 98.4% purity) as a light yellow solid. LC-MS (ES+, m/z): 607.3 [(M+H)+]. 1 NMR (400 MHz, DMSO-d6) δ=8.79 (t, J=6.1 Hz, 1H), 7.89 (s, 1H), 7.40 (s, 1H), 7.15-7.08 (m, 1H), 6.88 (d, J=8.4 Hz, 1H), 6.28 (d, J=7.9 Hz, 1H), 6.04 (br d, J=8.4 Hz, 1H), 5.50 (q, J=8.8 Hz, 2H), 4.92-4.77 (m, 3H), 3.68-3.52 (m, 1H), 3.44 (br t, J=6.6 Hz, 4H), 3.05 (br s, 11H), 2.82 (br s, 1H), 2.20 (br s, 4H), 2.12 (br s, 1H), 2.00 (td, J=3.4, 6.5 Hz, 5H), 1.68 (br d, J=9.9 Hz, 1H).

Example 203: Compound 461B: N-[(3S,4R)-3-fluoro-1-methylpiperidin-4-yl]-2-{5-[({thieno[2,3-d]pyrimidin-4-yl}amino)methyl]-1,2,4-oxadiazol-3-yl}-1-(2,2,2-trifluoroethyl)-1H-indol-4-amine Amine 1 (19 mg, 44.7 μmol), 4-chlorothieno[2,3-d]pyrimidine (15.4 mg, 90.3 μmol), were weighed into a 20 mL EPA vial with a septum cap. DMSO (0.6 mL) was added, and the reaction was stirred and heated to 80° C. for 2 h, at which time LCMS showed complete reaction. The reaction was purified by reverse-phase HPLC, and the product was isolated as the free base by diluting the HPLC fractions with DCM, washing with water made basic with sodium bicarbonate solution. The organic layer was removed, dried over magnesium sulfate, filtered, and concentrated in a vacuum oven to provide the desired N-[[3-[4-[[(3S,4R)-3-fluoro-1-methyl-4-piperidyl]amino]-1-(2,2,2-trifluoroethyl)indol-2-yl]-1,2,4-oxadiazol-5-yl]methyl]thieno[2,3-d]pyrimidin-4-amine (14.8 mg, 59.1% yield) as the free base. LC-MS (ES$^+$, m/z): 561.2 [(M+H)$^+$]. $^1$H NMR (500 MHz, DMSO-d6) δ 9.00 (t, J=5.8 Hz, 1H), 8.41 (s, 1H), 7.90 (s, 1H), 7.74 (s, 2H), 7.15 (t, J=8.0 Hz, 1H), 6.92 (d, J=8.4 Hz, 1H), 6.32 (d, J=7.8 Hz, 1H), 6.06 (d, J=8.3 Hz, 1H), 5.53 (q, J=8.9 Hz, 2H), 5.14 (d, J=5.7 Hz, 2H), 4.87 (d, J 48.7 Hz, 1H), 3.74-3.52 (m, 1H), 3.08 (s, 1H), 2.86 (d, J=10.8 Hz, 1H), 2.14 (d, 0.1=99.3 Hz, 614), 1.71 (d, 0.1=12.5 Hz, 1H).

Example 204: Compound 462B: N-[(3S,4R)-3-fluoro-1-methylpiperidin-4-yl]-2-(5-{[(1-methyl-1H-indol-4-yl)amino]methyl}-1,2,4-oxadiazol-3-yl)-1-(2,2,2-trifluoroethyl)-1H-indol-4-amine Amine 1 (59.8 mg, 120 μmol, 2HCl), potassium t-butoxide (54 mg, 481 μmol), BrettPhos Pd Generation 4 (14.5 mg, 16.1 μmol) and t-Butyl-XPhos Generation 3 (16.4 mg, 20.7 μmol) were weighed into a 20 mL EPA vial with a septum cap. The vial was flushed with nitrogen through a needle. In a separate vial, toluene was degassed by 2 min nitrogen bubbling, then transferred to the reaction under nitrogen via syringe. The vial was placed to stir in an aluminum block at 80° C. for 1 h. The reaction was cooled, diluted with DCM, filtered through an Acrodisc, then concentrated and redissolved in DMSO. The crude solution was then purified by reverse-phase HPLC in acetonitrile:water 10-50% over 8 min 0.1% formic acid). The resulting fractions were diluted with DCM, washed with water made basic with saturated sodium bicarbonate. The organic layer was removed and the aqueous layer extracted with DCM. The organic solution was dried (magnesium sulfate), filtered, and concentrated. The brown oil was redissolved in acetonitrile. The product was dissolved in acetonitrile and 1N hydrochloric acid, then isolated as the hydrochloride salt by lyophilization to provide N-[(3S,4R)-3-fluoro-1-methyl-4-piperidyl]-2-[5-[[(1-methylindol-4-yl)amino]methyl]-1,2,4-oxadiazol-3-yl]-1-(2,2,2-trifluoroethyl)indol-4-amine (29.1 mg, 43.8% yield). LC-MS (ES$^+$, m/z): 556.2 [(M+H)$^+$]. $^1$H NMR (300 MHz, DMSO-d6) δ 9.79 (s, 2H), 7.89 (s, 1H1), 7.24-7.09 (m, 2H), 6.93 (dd, J=15.8, 8.0 Hz, 2H), 6.74 (d, J=8.2 Hz, 1H), 6.62 (d, J=3.2 Hz, 1H), 6.34 (d, J=7.8 Hz, 1H), 6.15 (d, J=7.6 Hz, 1H). 5.50 (t, J=9.0 Hz, 2H), 5.16 (d, J=47.4 Hz, 1H), 4.84 (s, 2H), 3.84 (s, 1H), 3.72 (s, 3H), 3.20 (d, J=12.0 Hz, 1H), 2.82 (d, J=4.4 Hz, 4H), 2.33-1.88 (m, 3H).

Example 205: Compound 463B: N-{13-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-methyl-1H-indazol-4-amine

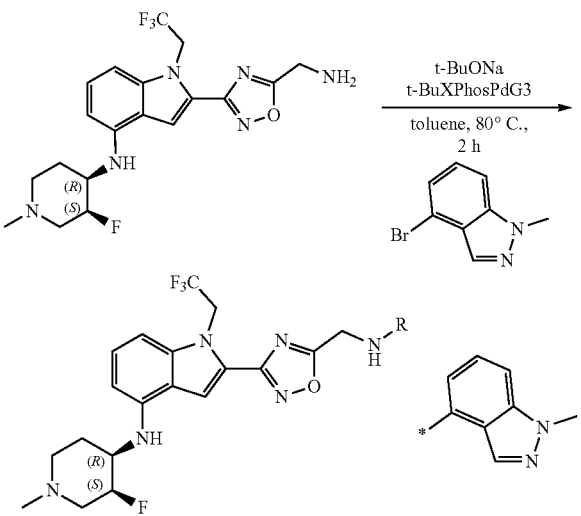

To a mixture of Amine 1 (100 mg, 235 μmol, 1 eq) and 4-bromo-1-methyl-indazole (59.4 mg, 281 μmol, 1.2 eq) in toluene (3 mL) were added sodium t-butoxide (45.1 mg, 469 μmol, 2 eq), t-butyl-XPhos Generation 3 (18.6 mg, 23.5 μmol, 0.1 eq), and the reaction heated to 80° C. under nitrogen for 2 h. The residue was poured into EDTA (saturated, 50 mL) and stirred for 60 min. The aqueous phase was extracted with EA (20 mL×3). The combined organic phase was washed with brine (20 mL×3), dried over anhydrous sodium sulfate, filtered, and concentrated in vacuo. The residue was purified by prep-TLC (SiO$_2$, DCM:methanol=10:1) to provide the desired product N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-methyl-1H-indazol-4-amine (17.8 mg, 13.6% yield, 100.0% purity) as a light yellow solid. LC-MS (ES$^+$, m/z): 557.3 [(M+H)$^+$]. $^1$H NMR (400 MHz, DMSO-d6) δ=8.16 (d, J=0.6 Hz, 1H), 7.89 (s, 1H), 7.24 (t, J=6.3 Hz, 1H), 7.12 (dt, J=3.9, 8.0 Hz, 2H), 6.88 (d, J=8.3 Hz, 1H), 6.82 (d, J=8.3 Hz, 1H), 6.28 (d, J=7.8 Hz, 1H), 6.15 (d, J=7.6 Hz, 1H), 6.02 (d, J=8.3 Hz, 1H), 5.49 (q, J=9.0 Hz, 2H), 4.96-4.75 (m, 3H), 3.95 (s, 3H), 3.70-3.51 (m, 1H), 3.04 (br t, J=10.0 Hz, 1H), 2.82 (br d, J=11.0 Hz, 1H), 2.28 (br d, J=12.7 Hz, 1H), 2.19 (s, 3H), 2.14-2.06 (m, 1H), 2.06-1.96 (m, 1H), 1.68 (br d, J=11.7 Hz, 1H).

Example 206: Compound 464B: N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-5-(methoxymethyl)thiophene-3-carboxamide

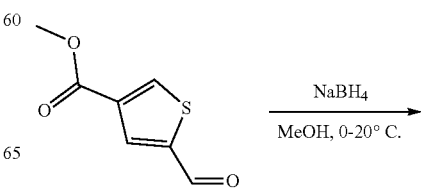

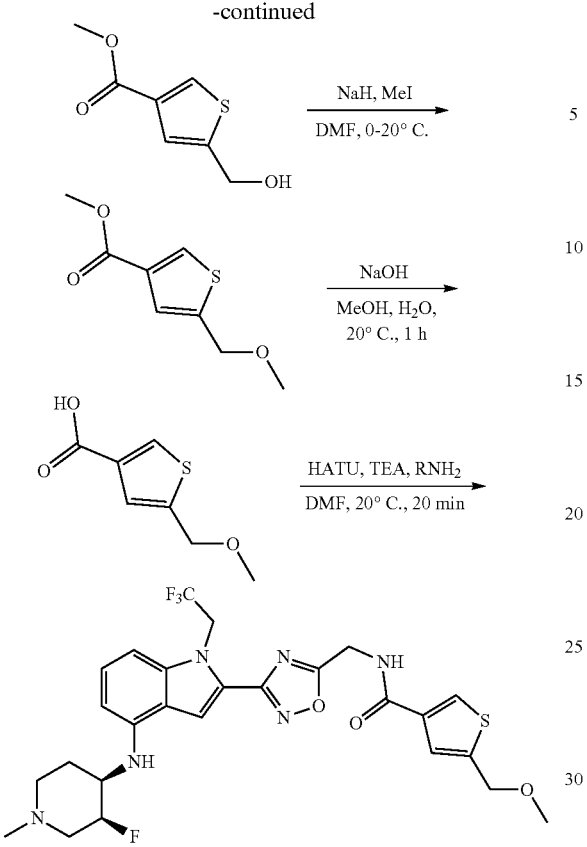

To a solution of methyl 5-formylthiophene-3-carboxylate (0.1 g, 588 µmol, 1 eq) in methanol (6 mL) was added sodium borohydride (44.5 mg, 1.18 mmol, 2 eq) at 0° C. The mixture was stirred at 20° C. for 30 min. The reaction mixture was quenched by addition sat. ammonium chloride (50 mL), then extracted with DCM (3×30 mL). The combined organic layers were washed with saturated brine (3×20 mL), dried over sodium sulfate, filtered, and concentrated in vacuo to give the crude product (0.06 g, 34 µmol, 59.3% yield) as a yellow oil. LC-MS (ES$^+$, m/z): 173.1[(M+H)$^+$]. $^1$H NMR (400 MHz, DMSO-d6) δ=8.24-8.20 (d, J=1.6 Hz, 1H), 7.31-7.25 (d, J=1.2 Hz, 1H), 5.64-5.55 (t, J=5.6 Hz, 1H), 4.65-4.62 (dt, J=5.6 Hz, 2H), 3.78 (s, 3H).

To a solution of methyl 5-(hydroxymethyl)thiophene-3-carboxylate (0.2 g, 1.16 mmol, 1 eq) in DMF (2 mL) was added sodium hydride (139 mg, 3.48 mmol, 60% purity, 3 eq) at 0° C. The mixture was stirred at 0° C. for 30 min. iodomethane (2.32 mmol, 145 µL 2 eq) was added at 0° C. The resulting mixture was stirred at 20° C. for 30 min. The reaction mixture was quenched by adding sat. ammonium chloride (50 mL) and extracted with DCM (3×30 mL). The combined organic layers were washed with saturated brine (3×20 mL), dried over sodium sulfate, filtered, and concentrated in vacuo to give a residue. The residue was purified by prep-TLC (SiO$_2$, PE:EA=5:1) to afford the product (0.1 g, 31.0% yield, 67% purity) as a colorless oil. LC-MS (ES$^+$, m/z): 187.1[(M+H)$^+$]

To a solution of methyl 5-(methoxymethyl)thiophene-3-carboxylate (0.1 g, 537 µmol, 1 eq) in methanol (2 mL) was added sodium hydroxide (4 M, 2 mL, 14.9 eq). The mixture was stirred at 20° C. for 1 h. The reaction mixture was quenched by adding water (10 mL), then diluted with HCl (1 N) to pH<5 and extracted with EA (3×30 mL). The combined organic layers were washed with brine (3×20 mL), dried over sodium sulfate, filtered, and concentrated in vacuo to give the product (0.07 g, 75.7% yield) as a yellow solid. LC-MS (ES$^+$, m/z): 170.8 [(M+H)$^+$].

5-(methoxymethyl)thiophene-3-carboxylic acid (43.5 mg, 252 µmol, 2 eq) and Amine 1 (70 mg, 126 mol, 90% purity, 1 eq, 2HCl) were coupled under method B. The crude reaction was purified by prep-TLC (SiO$_2$, DCM: methanol=10:1) to afford the desired N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-5-(methoxymethyl)thiophene-3-carboxamide product (0.02 g, 25.7% yield, 94% purity) as a yellow solid. LC-MS (ES$^+$, m/z): 581.2 [(M+H)$^+$]. $^1$H NMR (400 MHz, DMSO-d6) δ=9.32-9.22 (t, J=5.2 Hz, 1H), 8.26-8.18 (d, J=1.2 Hz, 1H), 7.90 (s, 1H), 7.61-7.45 (d, J=0.8 Hz, 1H), 7.20-7.08 (d, J=8.0 Hz, 1H), 6.93-6.83 (d, J=8.4 Hz, 1H), 6.40-6.24 (d, J=8.0 Hz, 1H), 6.12-6.00 (d, J=8.4 Hz, 1H), 5.67-5.42 (dt, J=17.6 Hz, 2H), 4.94-4.78 (m, 3H), 4.59 (s, 2H), 3.68-3.54 (m, 1H), 3.29 (s, 3H), 3.17-3.05 (m, 1H), 2.96-2.80 (m, 1H), 2.47-2.07 (m, 5H), 2.07-1.94 (m, 1H). 1.78-1.65 (m, 1H).

Example 207: Compound 465B: N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-(morpholin-4-yl)-1,3-thiazole-4-carboxamide

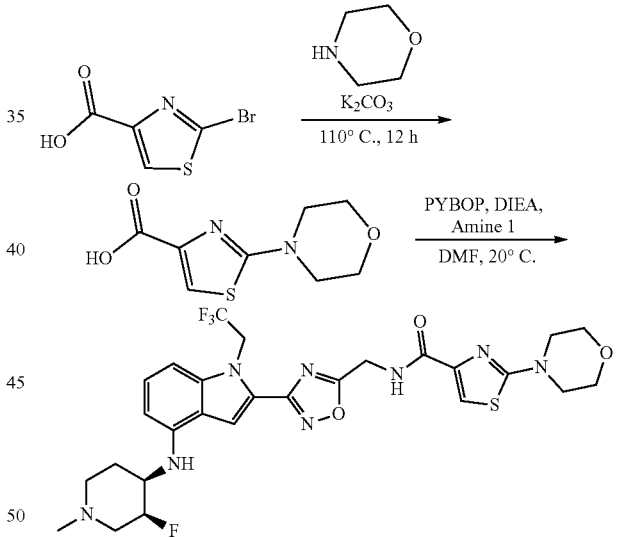

A mixture of 2-bromothiazole-4-carboxylic acid (2 g, 9.61 mmol, 1 eq) and morpholine (227 mmol, 20 mL, 23.6 eq) was heated and stirred at 110° C. for 12 h. The reaction was concentrated in vacuo, then purified by prep-HPLC (neutral condition, column: Xtimate C18 10 u 250 mm×80 mm; mobile phase: [water (10 mM NH$_4$HCO$_3$)-ACN]; B %: 0%-35%, 25 min) to provide the desired product 2-morpholinothiazole-4-carboxylic acid (68.0% yield) as a white solid. LC-MS (ES$^+$, m:z): 214.9 [(M+H)$^+$]. $^1$H NMR (400 MHz, DMSO-d6) δ=7.39 (s, 1H), 3.72-3.67 (m, 4D), 3.38-3.33 (m, 4H).

To a mixture of Amine 1 (6 g, 10.6 mmol, 1 eq, 2HCl) and 2-morpholinothiazole-4-carboxylic acid (4.25 g, 15.9 mmol, 1.5 eq) in DMF (60 mL) were added HOBt (2.86 g, 21.2 mmol, 2 eq), EDCI (4.05 g, 21.2 mmol, 2 eq), and DIEA (105.7 mmol, 18.4 mL, 10 eq), and the reaction was heated to 50° C. under nitrogen and stirred for 3 h. The residue was poured into ice-water (w/w=1/1) (50 mL). The aqueous phase was extracted with EA (20 mL×3). The combined organic phase was washed with brine (20 mL×3), dried over anhydrous sodium sulfate, filtered, and concentrated in vacuo. The residue was purified by silica gel chromatography (column height: 250 mm, diameter: 100 mm, 100-200 mesh silica gel, PE/EA=1/01, 23/77, DCM:methanol=1/0, 95/5). The resulting product was triturated with EA (10 mL)/MTBE(30 mL), then dried in vacuo to afford the desired product N-[[3-[4-[[(3S,4R)-3-fluoro-1-methyl-4-piperidyl]amino]-1-(2,2,2-trifluoroethyl)indol-2-yl]-1,2,4-oxadiazol-5-yl]methyl]-2-morpholino-thiazole-4-carboxamide (3 g, 45.6% yield, 100.0% purity) as a light yellow solid. LC-MS (ES+, m:z): 623.1 [(M+H)+]. $^1$H NMR (400 MHz, DMSO-d6) δ=8.94 (t, J=6.1 Hz, 1H), 7.89 (s, 1H), 7.55 (s, 1H), 7.12 (t, J=8.0 Hz, 1H), 6.88 (d, J=8.2 Hz, 1H), 6.28 (d, J=7.8 Hz, 1H), 6.03 (d, J=8.3 Hz, 1H), 5.50 (q, J=8.8 Hz, 2H), 4.93-4.75 (m, 3H), 3.78-3.70 (m, 4H), 3.66-3.53 (m, 1H), 3.51-3.44 (m, 4H), 3.04 (br t, J=10.1 Hz, 1H), 2.82 (br d, J=10.6 Hz, 1H), 2.31-2.16 (m, 4H), 2.13-2.05 (m, 1H), 2.04-1.94 (m, 1H), 1.68 (br d, J=10.1 Hz, 1H).

Example 208: Compound 466B: N-{[3-(4-{f(3S,4R)-3-fluoro-1-methylpiperidin-4-yl]amino}-1-(2,2,2-trifluoroethyl)-1H-indol-2-yl)-1,2,4-oxadiazol-5-yl]methyl}-5-[(pyrrolidin-1-yl)methyl]thiophene-3-carboxamide

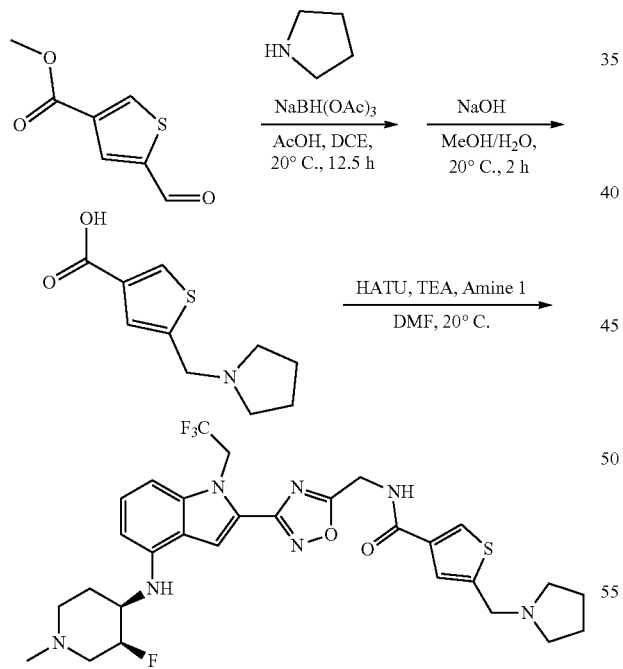

To a solution of methyl 5-formylthiophene-3-carboxylate (500 mg, 2.94 mmol, 1 eq) and pyrrolidine (2.94 mmol, 245 μL 1 eq) in DCE (10 mL) was added acetic acid (1.25 mL) at 25° C. The mixture was stirred at 50° C. for 30 min, then sodium triacetoxyborohydride (3.11 g, 14.7 mmol, 5 eq) was added and the resulting mixture was stirred at 50° C. for 12 h. The residue was poured into saturated sodium carbonate (30 mL) and stirred for 10 min. The aqueous phase was extracted with DCM (3×30 mL). The combined organic phase was washed with brine (3×30 mL), dried over anhydrous sodium sulfate, filtered, and concentrated in vacuo. The residue was purified by column chromatography to give the product (0.36 g, 52.2% yield, 96% purity). LC-MS (ES+, m/z): 226.1 [(M+H)+].

To a solution of methyl 5-(pyrrolidin-1-ylmethyl)thiophene-3-carboxylate (360 mg, 1.53 mmol, 96% purity, 1 eq) in methanol (2 mL) was added sodium hydroxide (4 M, 1.90 mL, 5 eq). The mixture was stirred at 20° C. for 2 h. The reaction mixture was quenched by adding HCl (3 M) aq to pH=7, then concentrated in vacuo to give the crude product (0.9 g, 1 mmol, 65.3% yield) as a yellow solid containing some sodium chloride as well.

5-(pyrrolidin-1-ylmethyl)thiophene-3-carboxylic acid (45.7 mg, 216 μmol, 2 eq) was coupled with Amine 1 (60 mg, 108.14 μmol, 90% purity, 1 eq, 2HCl) under method B. The crude product was purified by prep-TLC (SiO₂, DCM:methanol=7:1) to give the desired product N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-5-[(pyrrolidin-1-yl)methyl]thiophene-3-carboxamide (18 mg, 25.8% yield, 96% purity) as a yellow solid. LC-MS (ES+, m/z): 620.3 [(M+H)+]. 1H NMR (400 MHz, DMSO-d6) δ=9.30-9.04 (t, J=5.6 Hz, 1H), 8.12 (s, 1H), 7.89 (s, 1H), 7.40 (s, 1H), 7.18-7.03 (t, J=8.0 Hz, 1H), 6.94-6.75 (d, J=8.0 Hz, 1H), 6.35-6.22 (d, J=8.0 Hz, 1H), 6.14-5.96 (d, J=7.6 Hz, 1H), 5.59-5.39 (dt, J=18.0 Hz, 2H), 4.97-4.68 (m, 3H), 3.89-3.73 (m, 2H), 3.67-3.57 (m, 1H), 3.15-3.04 (m, 1H), 2.92-2.82 (m, 1H), 2.67-2.52 (m, 5H), 2.33-2.11 (m, 4H), 2.08-1.93 (m, 1H), 1.83-1.64 (m, 5H).

Example 209: Compound 467B: 5-[(dimethylamino)methyl]-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}thiophene-2-carboxamide

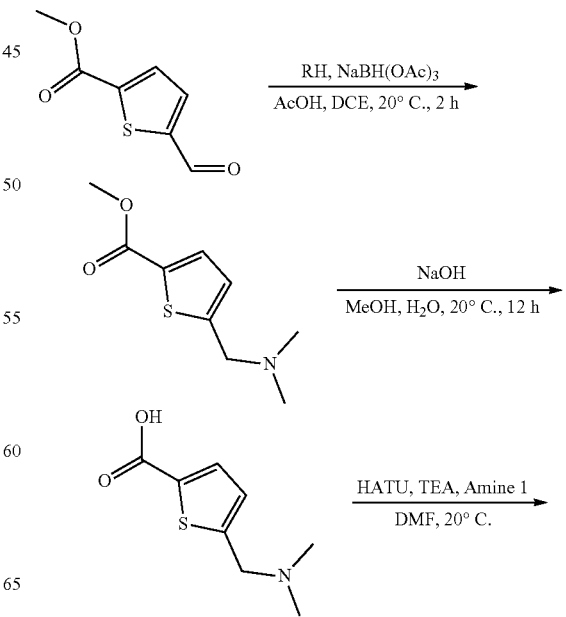

-continued

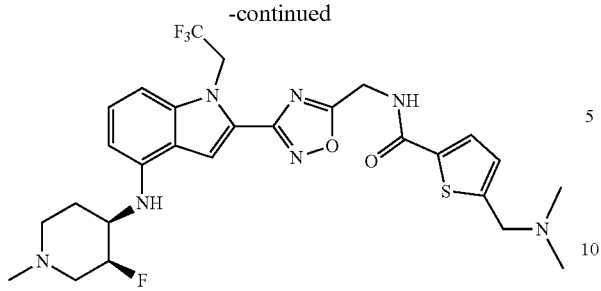

To a mixture of methyl 5-formylthiophene-2-carboxylate (300 mg, 1.76 mmol, 1 eq) in ethanol (5 mL) were added dimethylamine hydrochloride (718.7 mg, 8.81 mmol, 5 eq) and THF (1 mL), followed by acetic acid (1.76 mmol, 100 µL 1 eq), then sodium cyanoborohydride (553.9 mg, 8.81 mmol, 5 eq) at 20° C. under nitrogen. The mixture was stirred at 20° C. for 2 h. The reaction was poured into sodium bicarbonate (sat., 15 mL). The aqueous phase was extracted with EA (3×20 mL). The combined organic phase was washed with brine (3×20 mL), dried over anhydrous sodium sulfate, filtered, and concentrated in vacuo. The crude was purified by prep-TLC (SiO$_2$, PE/EA=2/1) to afford the product (80 mg, 22.8% yield) as a yellow oil. LC-MS (ES$^+$, m/z): 200.1 [(M+H)$^+$].

Methyl 5-[(dimethylamino)methyl]thiophene-2-carboxylate (80 mg, 401 µmol, 1 eq) was treated with methanol (2 mL), followed by sodium hydroxide (5 M, 0.5 mL, 6.2 eq) at 20° C., and stirred for 12 h. The solution was purified directly by prep-HPLC: column: Welch Xtimate C18 150× 25 mm×5 um; mobile phase: [water (0.04% HCl)-ACN] B %: 1%-5%, 8 min) to afford the acid product (60 mg, 80.7% yield) as white solid. LC-MS (ES$^+$, m/z): 186.1 [(M+H)-].

5-|(dimethylamino)methyl|thiophene-2-carboxylic acid (20 mg, 108 µmol, 1 eq) was coupled with Amine 1 (60 mg, 108 µmol, 90% purity, 1 eq, 2HCl) under method B. The crude product was purified by prep-TLC (SiO$_2$. DCM: methanol=7:1) to give the desired product 5-[(dimethylamino)methyl]-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}thiophene-2-carboxamide (15 mg, 22.2% yield, 95% purity) as a yellow solid. LC-MS (ES$^+$, m/z): 594.3 [(M+H)$^+$]. $^1$H NMR (400 MHz, DMSO-d6) δ=9.45-9.25 (t, J=5.6 Hz, 1H), 7.90 (s, 1H), 7.79-7.63 (d, J=3.6 Hz, 1H), 7.15-7.09 (t, J=8.0 Hz, 1H), 7.05-7.00 (d, J=3.6 Hz, 1H), 6.92-6.86 (d, J=8.4 Hz, 1H), 6.31-6.26 (d, J=7.6 Hz, 1H), 6.09-6.03 (d, J=8.0 Hz, 1H), 5.54-5.47 (dt, J=9.2 Hz, 2H), 4.94-4.80 (m, 3H), 3.66-3.57 (m, 3H), 3.17-3.06 (m, 1H), 2.92-2.84 (m, 1H), 2.33-2.10 (m, 11H), 2.09-1.95 (m, 1H), 1.78-1.65 (m, 1H).

Example 210: Compound 468B: N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-5-[(morpholin-4-yl)methyl]thiophene-3-carboxamide

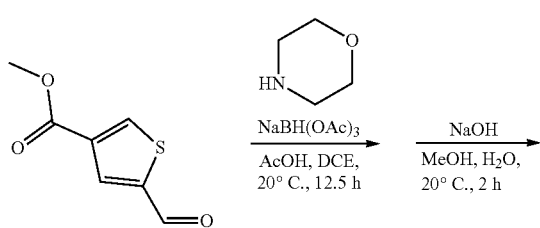

-continued

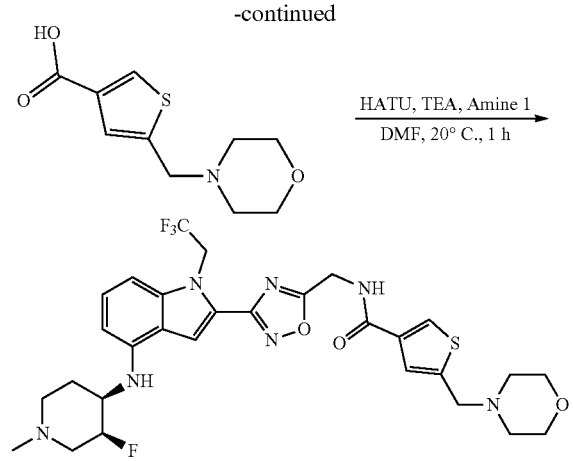

To a mixture of methyl 5-formylthiophene-3-carboxylate (200.8 mg, 1.18 mmol, 1 eq) and morpholine (1.14 mmol, 100 µL 1 eq) in DCE (4 mL) was added acetic acid (0.5 mL) at 25° C. under nitrogen. The mixture was heated and stirred at 50° C. for 30 min, followed by addition of sodium triacetoxyborohydride (1.25 g, 5.90 mmol, 5 eq) and stirring for 12 h at 50° C. The residue was poured into sat. sodium carbonate (30 mL) and stirred for 10 mins. The aqueous phase was extracted with EA (3×30 mL). The combined organic phase was washed with brine (3×30 mL), dried over anhydrous sodium sulfate, filtered, and concentrated in vacuo. The residue was purified by prep-TLC (SiO$_2$, PE/EA=4/1) to provide the tertiary amine product.

To a mixture of methyl 5-(morpholinomethyl)thiophene-3-carboxylate (200 mg, 829 µmol, 1 eq) in methanol (2 mL) was added sodium hydroxide (4 M, 2 mL, 9.6 eq) at 25° C. under nitrogen. The mixture was stirred at 25° C. for 2 h. The residue was poured into HCl (4M, 2 mL). The mixture was concentrated in vacuo. The residue was purified by prep-HPLC to afford 5-(morpholinomethyl)thiophene-3-carboxylic acid (210 mg, 89.2% yield, 80% purity).

Amine 1 (53.3 mg, 98.1 µmol, 92% purity, 1 eq, 2HCl) and 5-[(dimethylamino)methyl]thiophene-3-carboxylic acid (36.4 mg, 196.3 µmol, 2 eq) were coupled under method B. The crude product was purified by prep-TLC to provide the desired product 5-[(dimethylamino)methyl]-N-[[3-[4-[[(3S,4R)-3-fluoro-1-methyl-4-piperidyl]amino]-1-(2,2,2-trifluoroethyl)indol-2-yl]-1,2,4-oxadiazol-5-yl]methyl]thiophene-3-carboxamide (28.6 mg, 45.5% yield, 92.6% purity). LC-MS (ES$^+$, m/z): 636.3 [(M+H$^+$)]. $^1$H NMR (400 MHz, DMSO-d6) δ=9.22 (t, J=5.7 Hz, 1H), 8.14 (d, J=1.5 Hz, 1H), 7.89 (s, 1H), 7.39 (s, 1H), 7.16-7.07 (m, 1H), 6.89 (d, J=8.2 Hz, 1H), 6.29 (d, J=7.9 Hz, 1H), 6.08 (br d, J=8.8 Hz, 1H), 5.58-5.43 (m, 2H), 5.01-4.72 (m, 3H), 3.68 (s, 3H), 3.58 (br t, J=4.4 Hz, 4H), 3.21-2.84 (m, 2H), 2.41 (br s, 4H), 2.30 (br d, J=17.6 Hz, 2H), 2.04 (br s, 1H), 1.73 (br s, 1H).

Example 211: Compound 469B: N-[[3-[4-[[(3S,4R)-3-fluoro-1-methyl-4-piperidyl]amino]-1-(2,2,2-trifluoroethyl)indol-2-yl]-1,2,4-oxadiazol-5-yl]methyl]-5-(morpholinomethyl)thiophene-2-carboxamide Amine 1 (70 mg, 1 eq, 2HCl) and 5-(morpholinomethyl)thiophene-2-carboxylic acid (58.6 mg, 258 µmol, 2 eq) were coupled using method B. The residue was purified by prep-TLC (DCM:methanol=10: 1) to provide the desired product N-[[3-[4-[[(3S,4R)-3-fluoro-1-methyl-4-piperidyl]

amino]-1-(2,2,2-trifluoroethyl)indol-2-yl]-1,2,4-oxadiazol-5-yl]methyl]-5-(morpholinomethyl)thiophene-2-carboxamide (61 mg, 71.1% yield, 95.6% purity). LC-MS (ES+, m/z): 636.3 [(M+H)+]. ¹H NMR (400 MHz, DMSO-d6) δ=9.37 (t, J=5.7 Hz, 1H), 7.90 (s, 1H), 7.71 (d, J=3.7 Hz, 1H), 7.12 (t, J=8.0 Hz, 1H), 7.04 (d, J=3.7 Hz, 1H), 6.88 (d, J=8.6 Hz, 1H), 6.28 (d, J=7.9 Hz, 1H), 6.05 (d, J=8.4 Hz, 1H), 5.50 (q, J=8.8 Hz, 2H), 4.95-4.74 (m, 3H), 3.69 (s, 2H), 3.58 (br t, J=4.5 Hz, 5H), 3.05 (br t, J=10.7 Hz, 1H), 2.83 (br d, J=10.8 Hz, 1H), 2.46-2.32 (m, 4H), 2.29-2.14 (m, 4H), 2.10 (br d, J=10.6 Hz, 1H), 2.03-1.94 (m, 1H), 1.68 (br d, J=9.7 Hz, 1H).

Example 212: Compound 470B: N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-5-[(pyrrolidin-1-yl)methyl]thiophene-2-carboxamide 5-(dimethylaminomethyl)thiophene-2-carboxylic acid was coupled with Amine 1 under similar conditions as for the morpholinomethyl analog above, providing the desired product in 40.9% yield. LC-MS (ES+, m/z): 620.3 [(M+H)+]. ¹H NMR (400 MHz, DMSO-d6) δ=9.44-9.30 (m, 1H), 7.90 (s, 1H), 7.70 (d, J=3.7 Hz, 1H), 7.18-7.09 (m, 1H), 7.06 (br s, 1H), 6.90 (d, J=8.2 Hz, 1H), 6.29 (d, J=7.9 Hz, 1H), 6.08 (br d, J=8.2 Hz, 1H), 5.51 (q, J=8.9 Hz, 2H), 5.01-4.74 (m, 3H), 3.86 (br s, 2H), 3.63 (br d, J=7.7 Hz, 1H), 3.25-3.08 (m, 1H), 3.03-2.81 (m, 1H), 2.56 (br s, 4H), 2.32 (br d, J=8.2 Hz, 4H), 2.13-1.97 (m, 1H), 1.73 (br s, 5H).

Example 213: Compound 471B: N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl-1-[1-(methoxymethyl)cyclobutyl]-1H-pyrrole-3-carboxamide

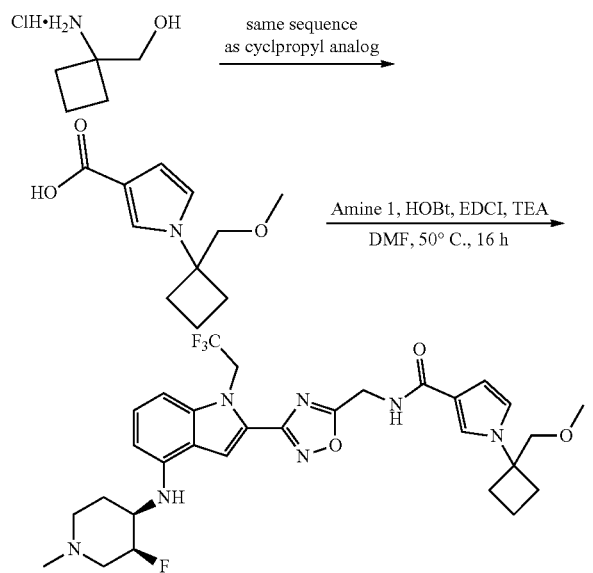

The required pyrrole carboxylic acid was prepared from (1-aminocyclobutyl)methanol using the same sequence as was used to prepare the analogous cyclopropyl analog previously.

Amine 1 (180 mg, 288 μmol, 1 eq, 2HCl) was coupled with 1-[1-(methoxymethyl)cyclobutyl]pyrrole-3-carboxylic acid (72.4 mg, 346 μmol, 1.2 eq) under method A. The residue was purified by prep-TLC (SiO₂, DCM: methanol=10:1) to give the desired product N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-[1-(methoxymethyl)cyclobutyl]-1H-pyrrole-3-carboxamide (75 mg, 41.7% yield, 99% purity) as a yellow solid. LC-MS (ES+, m/z): 618.3 [(M+H)+]. ¹H NMR (400 MHz, DMSO-d6) δ=8.77-8.59 (t, J=5.6 Hz, 1H), 7.90 (s, 1H), 7.41-7.31 (t, J=1.6 Hz, 1H), 7.20-7.05 (t, J=8.0 Hz, 1H), 6.96-6.83 (t, J=8.0 Hz, 1H), 6.80-6.71 (t, J=2.0 Hz, 1H), 6.54-6.43 (dt, J=2.8 Hz, 1H), 6.38-6.21 (d, J=8.0 Hz, 1H), 6.06-5.91 (d, J=8.4 Hz, 1H), 5.61-5.37 (dt, J=17.6 Hz, 2H), 4.96-4.69 (m, 3H), 3.66-3.54 (m, 3H), 3.20 (s, 3H), 3.08-2.99 (m, 1H), 2.89-2.76 (m, 1H), 2.39-2.30 (m, 4H), 2.27-2.17 (m, 4H), 2.14-2.07 (m, 1H), 2.05-1.97 (m, 1H), 1.96-1.84 (m, 2H), 1.75-1.62 (m, 1H)

Example 214: Compound 4721B: N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-[1-(hydroxymethyl)cyclopropyl]-1H-pyrrole-3-carboxamide

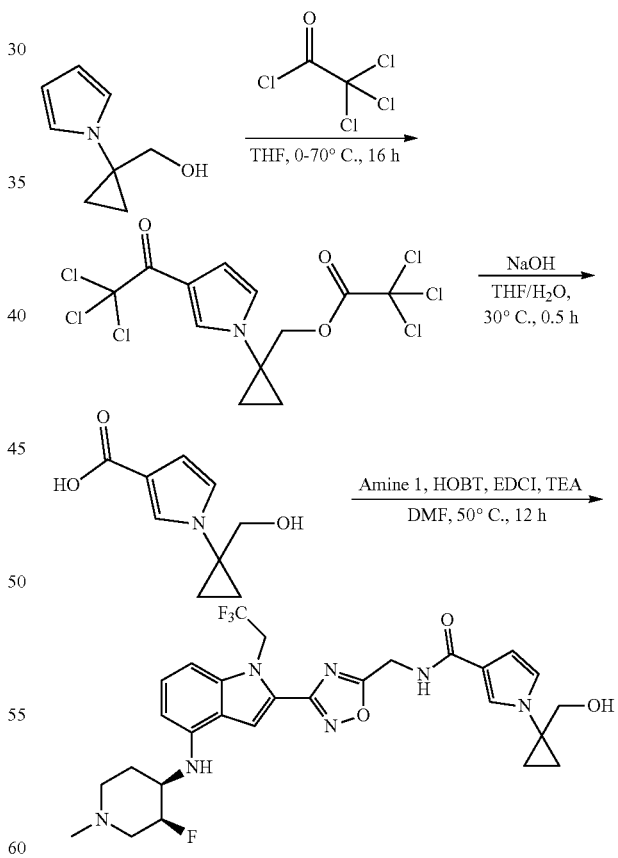

To a mixture of(I-pyrrol-1-ylcyclopropyl)methanol (2.5 g, 18.2 mmol, 1 eq) in THF (30 mL) was added 2,2,2-trichloroacetyl chloride (72.9 mmol, 8.13 mL, 4 eq) in one portion at 0° C. under nitrogen. The mixture was heated and stirred at 70° C. for 16 h. The residue was treated with sodium carbonate (saturated) to adjust pH=7-8. The aqueous phase was extracted with EA (40 mL×3). The combined organic phase was washed with brine (40 mL×3), dried over anhydrous sodium sulfate, filtered, and concentrated in vacuo. The residue was purified by silica gel chromatography (column height: 250 mm, diameter: 100 mm, 100-200 mesh silica gel, PE/EA=100/1, 97/3) to afford [1-[3-(2,2,2-trichloroacetyl)pyrrol-1-yl]cyclopropyl]methyl 2,2,2-trichloroacetate (900 mg, 2.10 mmol, 11.5% yield) as a yellow solid. LC-MS (ES+, m/z): 427.8[(M+H)+]. $^1$H NMR (400 MHz, DMSO-d6) δ=7.91 (t, J=1.7 Hz, 1H), 7.14-7.03 (m, 1H), 6.68 (dd, J=1.9, 2.8 Hz, 1H), 4.65 (s, 2H), 1.39-1.34 (m, 2H), 1.32-1.27 (m, 2H), as well as the other ketone regioisomer [1-[2-(2,2,2-trichloroacetyl)pyrrol-1-yl]cyclopropyl]methyl 2,2,2-trichloroacetate (3.6 g, 46.2% yield) as a light yellow solid.

To a solution of [1-[3-(2,2,2-trichloroacetyl)pyrrol-1-yl]cyclopropyl]methyl 2,2,2-trichloroacetate (200 mg, 467 μmol, 1 eq) in THF (1 mL) was added sodium hydroxide (3 M, 1 mL, 6.42 eq) at 30° C. under nitrogen, and the mixture was stirred for 30 min. The residue was treated with HCl (12 M) to adjust pH=5-6. The residue was concentrated in vacuo. The residue was washed with DCM:methanol=10:1 (10×3), then concentrated in vacuo to afford 1-[1-(hydroxymethyl)cyclopropyl]pyrrole-3-carboxylic acid (70 mg, crude) as a yellow oil. LC-MS (ES+, m/z): 182.1[(M+H)+].

Amine 1 (55 mg, 110 μmol, 1 eq, 2HCl) was coupled with 1-[1-(hydroxymethyl)cyclopropyl]pyrrole-3-carboxylic acid (20 mg, 110 μmol, 1 eq) were coupled under method A. The crude product was purified by prep-TLC (SiO$_2$. DCM: methanol=8:1) to provide N-[[3-[4-[[(3S,4R)-3-fluoro-1-methyl-4-piperidyl]amino]-1-(2,2,2-trifluoroethyl)indol-2-yl]-1,2,4-oxadiazol-5-yl]methyl]-1-[1-(hydroxymethyl)cyclopropyl]pyrrole-3-carboxamide (20.8 mg. 32.0% yield, 100.0% purity) as a light yellow solid. LC-MS (ES+, m/z): 590.3 [(M+H)+]. $^1$H NMR (400 MHz, DMSO-d6) δ=8.69 (t, J=5.4 Hz, 1H), 7.89 (s, 1H)7.45 (t, J=2.0 Hz, 1H), 7.15-7.07 (m, 1H), 6.88 (d, J=7.9 Hz, 1H), 6.86-6.84 (m, 1H), 6.45 (dd, J=1.8, 2.9 Hz, 1H), 6.28 (d, J=7.9 Hz, 1H), 6.06 (br d, J=8.8 Hz, 1H), 5.50 (q, J=8.7 Hz, 2H), 5.01 (t, J=5.7 Hz, 1H), 4.94-4.77 (m, 1H), 4.71 (d, J=5.7 Hz, 2H), 3.69-3.55 (m, 1H), 3.50 (d, J=5.7 Hz, 2H), 3.06 (br s, 1H), 2.84 (br s, 1H), 2.40-2.18 (m, 4H), 2.16-1.94 (m, 2H), 1.70 (br s, 1H), 1.03-0.99 (m, 2H), 0.98-0.94 (m, 2H).

Example 215: Compound 473B: N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-(4-methyloxan-4-yl)-1,3-thiazole-5-carboxamide

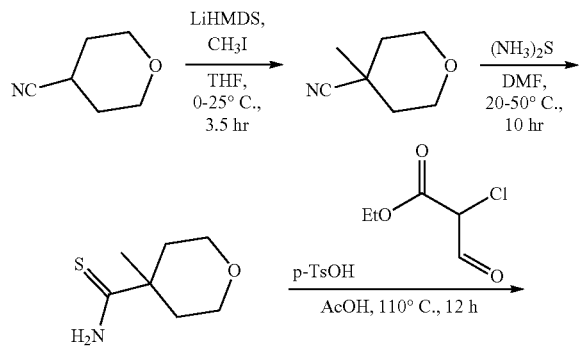

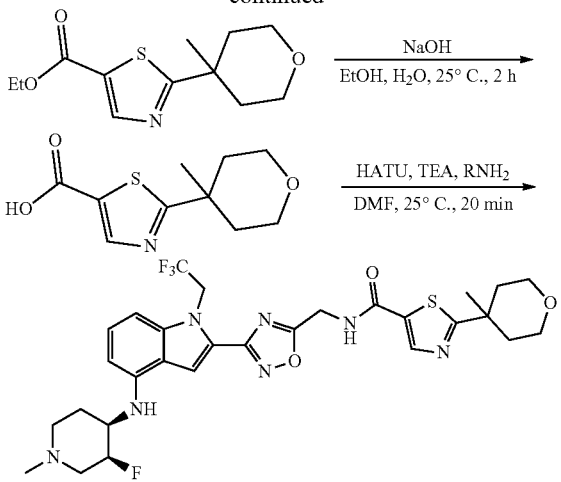

To a solution of tetrahydropyran-4-carbonitrile (5 g, 45 mmol, 1 eq) in THF (50 mL) was added LiHMDS (1 M, 54 mL, 1.2 eq) at 0° C. The reaction was stirred at 0° C. for 1.5 h, then iodomethane (135 mmol, 8.40 mL, 30 eq) was added to the mixture. The mixture was stirred at 25° C. for 2 hrs. The reaction mixture was quenched by adding sat. ammonium chloride (200 mL) at 0° C., then extracted with water (100 mL) and EA (100 mL×2). The combined organic layers were washed with brine (100 mL×2), dried over sodium sulfate, filtered, and concentrated in vacuo to give the product (4.8 g, crude). 1H NMR (DMSO-d6, 400 MHz): δ=3.91-3.79 (m, 2H), 3.44 (dt, J=2.1, 12.0 Hz, 2H), 1.86-1.72 (m, 2H), 1.54 (ddd, J=4.4, 11.9, 13.9 Hz, 2H), 1.34 (s, 31H).

To a mixture of 4-methyltetrahydropyran-4-carbonitrile (0.7 g, 5.59 mmol, 1 eq) in DMF (10 mL) was added ammonium sulfide (3.81 g, 11.2 mmol, 3.82 mL, 20% purity, 2 eq) at 20° C. The mixture was stirred at 50° C. for 10 hrs in a sealed tube. The reaction mixture was extracted with EA 60 mL (30 mL×2). The combined organic layers were washed with brine (100 mL), dried over sodium sulfate, filtered, and concentrated in vacuo to give the crude product. This process was repeated three times and the crude products combined. These were further purified by prep-TLC (SiO$_2$, PE:EA=1:1) to give the product (1.6 g, 59.9% yield). LC-MS (ES+, m/z): 160.1 [(M+H)+].

To a mixture of 4-methyltetrahydropyran-4-carbothioamide (400 mg, 2.51 mmol, 1 eq) and ethyl 2-chloro-3-oxopropanoate (397 mg, 2.64 mmol, 1.05 eq) in acetic acid (13 mL) was added 4-methylbenzenesulfonic acid hydrate (95.6 mg, 502 μmol, 0.2 eq), and the reaction was heated at 110° C. under nitrogen for 12 h. The reaction was poured into 50 mL sat. sodium carbonate, and extracted with EA (100 mL×2). The combined organic layers were washed with brine (100 mL), dried over sodium sulfate, filtered, and concentrated in vacuo to give a residue. The residue was purified by prep-TLC (SiO2, PE:EA=1:1) to give the thiazole product (600 mg, 2.35 mmol, 93.6% yield). LC-MS (ES+, m/z): 256.0 [(M+H)+].

Ethyl 2-(4-methyltetrahydropyran-4-yl)thiazole-5-carboxylate (600 mg, 2.35 mmol, 1 eq) was saponified under standard conditions to provide the carboxylic acid product. (450 mg, crude). LC-MS (ES+, m/z): 228.1 [(M+H)+].

2-(4-methyltetrahydropyran-4-yl)thiazole-5-carboxylic acid (38.23 mg, 168.22 μmol, 1.2 eq) and Amine 1 (70 mg, 140 μmol, 1 eq, 2HCl) were coupled under method B. The crude product was purified by prep-TLC (SiO₂, DCM: methanol=10:1) to give the desired product N-{[3-(4-{[(3S, 4R)-3-fluoro-1-methylpiperidin-4-yl]amino}-1-(2,2,2-trifluoroethyl)-1H-indol-2-yl)-1,2,4-oxadiazol-5-yl]methyl}-2-(4-methyloxan-4-yl)-1,3-thiazole-5-carboxamide (26.5 mg, 29.7% yield, 100% purity). LC-MS (ES⁺, m/z): 636.3 [(M+H)⁺]. ¹H NMR (400 MHz, DMSO-d₆) δ=9.55 (t, J=5.7 Hz, 1H), 8.36 (s, 1H), 7.86 (s, 1H), 7.08 (t, J=7.9 Hz, 1H), 6.85 (d, J=8.3 Hz, 1H), 6.25 (d, J=7.9 Hz, 1H), 5.99 (d, J=8.3 Hz, 1H), 5.47 (q, J=9.1 Hz, 2H), 4.92-4.73 (m, 3H), 3.74-3.64 (m, 2H), 3.63-3.52 (m, 1H), 3.47 (ddd, J=3.1, 8.2, 11.5 Hz, 2H), 3.02 (br s, 1H), 2.80 (br d, J=8.8 Hz, 1H), 2.17 (br s, 4H), 2.09 (ddd, J=3.1, 6.0, 13.3 Hz, 3H), 1.97 (br dd, J=3.1, 12.3 Hz, 1H), 1.77-1.63 (m, 3H), 1.34 (s, 3H).

Example 216: Compound 474B: N-{[3-(4-{[(3S, 4R)-3-fluoro-1-methylpiperidin-4-yl]amino}-1-(2,2, 2-trifluoroethyl)-1H-indol-2-yl)-1,2,4-oxadiazol-5-yl]methyl}-2-(4-methyloxan-4-yl)-1,3-thiazole-4-carboxamide

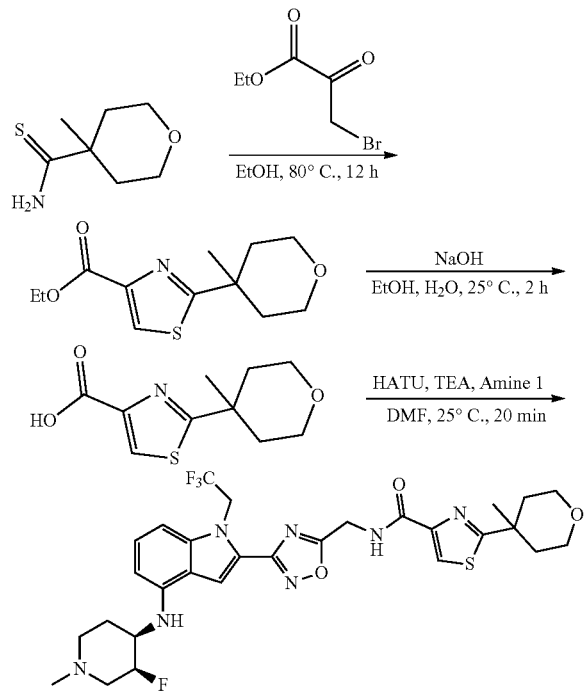

To a mixture of the previously prepared 4-methyltetrahydropyran-4-carbothioamide (400 mg, 2.51 mmol, 1 eq) in ethanol (13 mL) was added ethyl 3-bromo-2-oxo-propanoate (2.64 mmol, 330 μL 1.05 eq) under nitrogen. The mixture was stirred at 80° C. for 12 h. The reaction was extracted with water (100 mL) and (100 mL×2). The combined organic layers were washed with brine (100 mL) dried over sodium sulfate, filtered, and concentrated in vacuo to give a residue. The residue was by prep-TLC (SiO₂, PE:EA=1:1) to give the thiazole product (600 mg, 2.35 mmol, 93.6% yield). LC-MS (ES⁺, m/z): 256.0 [(M+H)⁺].

Ethyl 2-(4-methyltetrahydropyran-4-yl)thiazole-4-carboxylate (600 mg, 2.35 mmol, 1 eq) was saponified under the standard conditions to provide the carboxylic acid product (450 mg, crude). LC-MS (ES⁺, m/z): 228.1 [(M+H)⁺].

2-(4-methyltetrahydropyran-4-yl)thiazole-4-carboxylic acid (38.2 mg, 168 μmol, 1.2 eq) was coupled with Amine 1 (70 mg, 140 μmol, 1 eq, 2HCl) under method B. The crude product was purified by prep-TLC (SiO2, DCM: methanol=10:1) to give the desired product N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-(4-methyloxan-4-yl)-1,3-thiazole-4-carboxamide (20.8 mg, 23.3% yield, 100% purity). LC-MS (ES⁺, m/z): 636.3 [(M+H)⁺]. ¹H NMR (400 MHz, DMSO-d₆) δ=9.10 (t, J=6.1 Hz, 1H), 8.27 (s, 1H), 7.86 (s, 1H), 7.08 (t, J=7.9 Hz, 1H), 6.84 (d, J=8.3 Hz, 1H), 6.25 (d, J=7.9 Hz, 1H), 5.98 (br d, J=8.3 Hz, 1H), 5.47 (q, J=8.9 Hz, 2H), 4.91-4.65 (m, 3H), 3.74-3.66 (m, 2H), 3.53 (ddd, J=3.1, 8.0, 11.3 Hz, 2H), 3.59 (br d, J=3.1 Hz, 1H), 3.06-2.94 (m, 1H), 2.84-2.72 (m, LH), 2.32-2.22 (m, 1H), 2.19-2.14 (m, 5H), 2.11-2.01 (m, 1H), 1.96-1.76 (m, 1H), 1.79-1.69 (m, 2H), 1.68-1.60 (m, 1H), 1.40 (s, 3H).

Example 217: Compound 475B: N-{[3-(4-{[(3S, 4R)-3-fluoropiperidin-4-yl]amino}-1-(2,2,2-trifluoroethyl)-1H-indol-2-yl)-1,2,4-oxadiazol-5-yl] methyl}-1-[1-(methoxymethyl)cyclopropyl]-1H-pyrrole-3-carboxamide

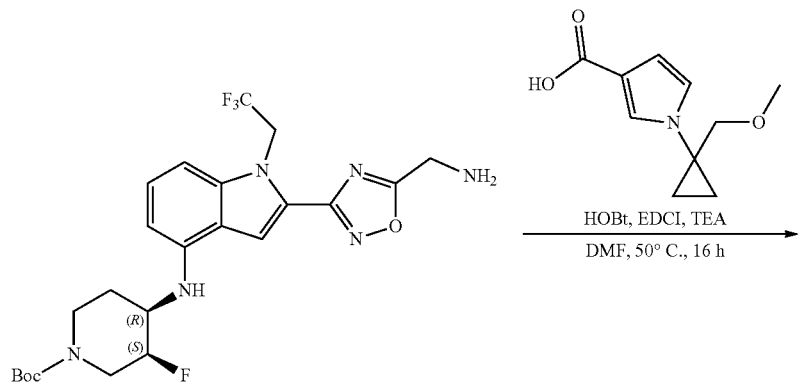

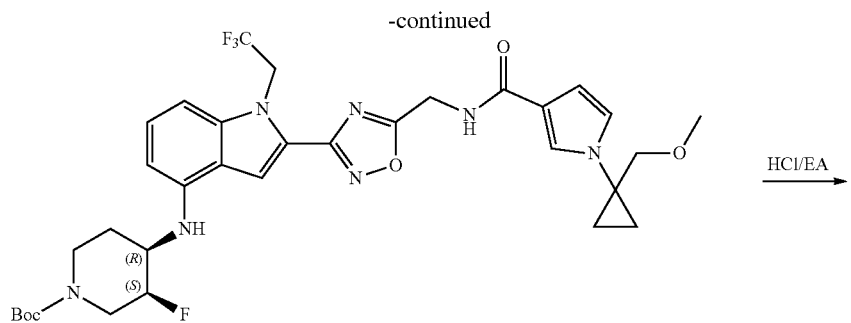

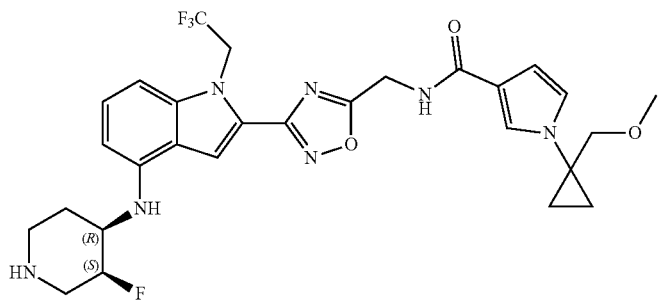

To a solution of 1-[1-(methoxymethyl)cyclopropyl]pyrrole-3-carboxylic acid (41.1 mg, 211 μmol, 1.2 eq) and the previously prepared tert-butyl (3S,4R)-4-[[2-[5-(aminomethyl)-1,2,4-oxadiazol-3-yl]-1-(2,2,2-trifluoroethyl)indol-4-yl]amino]-3-fluoro-piperidine-1-carboxylate (Boc-piperidine A) (90 mg, 176 μmol, 1 eq) in DMF (2 mL) were added HOBt (47.5 mg, 351 μmol, 2 eq) and EDCI (67.3 mg, 351 μmol, 2 eq), and TEA (874 μmol, 120 μL 5 eq). The mixture was stirred at 50° C. for 16 h. The reaction mixture was quenched by adding water (10 mL), then extracted with EA (3×30 mL). The combined organic layers were washed with brine (3×20 mL), dried over sodium sulfate, filtered, and concentrated in vacuo to give a residue. The residue was purified by prep-TLC (SiO$_2$, PE:EA=1:2) to give the product (80 mg, 62.8% yield, 95% purity) as a yellow solid LC-MS (ES$^+$, m:z): 690.2 [(M+H)~].

To a solution of the above intermediate (80 mg, 116 μmol, 1 eq) in EA (1 mL) was added HCl/EA (4 M, 2 mL, 68 eq). The mixture was stirred at 20° C. for 0.5 h. The reaction mixture was concentrated in vacuo to give a residue. The residue was triturated with EA 3 mL at 20° C. for 5 min, followed by filtering and drying, to give the desired product N-{[3-(4-{[(3S,4R)-3-fluoropiperidin-4-yl]amino}-1-(2,2,2-trifluoroethyl)-1H-indol-2-yl)-1,2,4-oxadiazol-5-yl]methyl}-1-[1-(methoxymethyl)cyclopropyl]-1H-pyrrole-3-carboxamide (30 mg, 43.9% yield) as a yellow solid. LC-MS (ES$^+$, m:/z): 590.2 [(M+H)$^+$]. $^1$H NMR (400 MHz, DMSO-d6) δ=9.36-9.12 (m, 1H), 8.74-8.69 (t, J=5.6 Hz, 1H), 7.79 (s, 1H), 7.62-7.32 (t, J=1.6 Hz, 1H), 7.24-7.06 (t, J=8.0 Hz, 1H), 6.98-6.91 (d, J=8.4 Hz, 1H), 6.89-6.83 (t, J=2.4 Hz, 1H), 6.51-6.42 (t, J=2.0 Hz, 1H), 6.38-6.32 (d, J=8.0 Hz, 1H), 6.25 (br s, 1H), 5.65-5.39 (dt, J=17.6 Hz, 2H), 5.18-5.00 (d, J=47.6 Hz, 1H), 4.81-4.63 (d, J=5.2 Hz, 2H), 4.03-3.90 (m, 1H), 3.70-3.65 (m, 1H), 3.47 (s, 2H), 3.44-3.30 (m, 2H), 3.22 (s, 3H), 3.13-3.01 (m, 1H), 2.22-2.04 (m, 1H), 1.97-1.85 (m, 1H), 1.17-0.92 (m, 4H).

Example 218: Compound 476B: N-{[3-(4-{[(3R,4S)-3-fluoropiperidin-4-yl]amino}-1-(2,2,2-trifluoroethyl)-1H-indol-2-yl)-1,2,4-oxadiazol-5-yl]methyl}-1-[1-(methoxymethyl)cyclopropyl]-1H-pyrrole-3-carboxamide

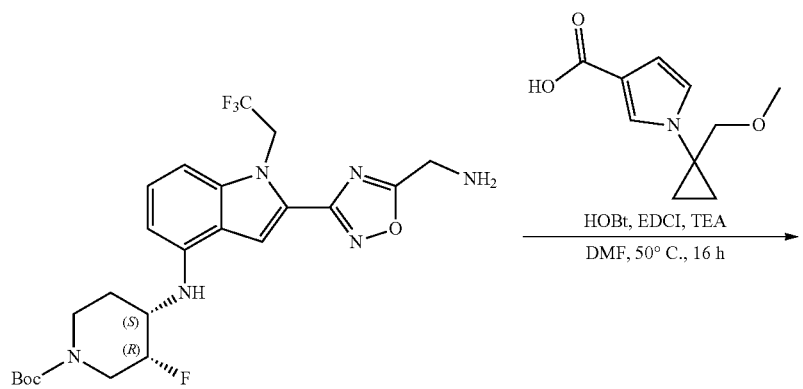

-continued

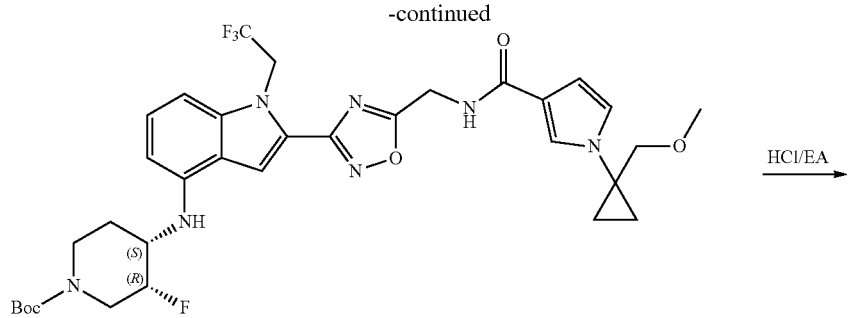

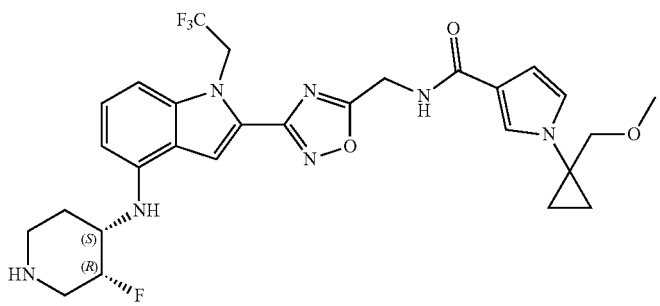

The 3R, 4S enantiomer was prepared using the identical procedure as was used for the opposite enantiomer of starting material previously described, to provide N-{[3-(4-{[(3R, 4S)-3-fluoropiperidin-4-yl]amino}-1-(2,2,2-trifluoroethyl)-1H-indol-2-yl)-1,2,4-oxadiazol-5-yl]methyl}-1-[1-(methoxymethyl)cyclopropyl]-1H-pyrrole-3-carboxamide. LC-MS (ES+, m/z): 590.2 [(M+H)+]. $^1$HNMR (400 MHz, DMSO-d6) δ=9.36-9.12 (m, 1H), 8.74-8.69 (t, J=5.6 Hz, 1H), 7.79 (s, 1H), 7.62-7.32 (t, J=1.6 Hz, 1H), 7.24-7.06 (t, J=8.0 Hz, 1H), 6.98-6.91 (d, J=8.4 Hz, 1H), 6.89-6.83 (t, J=2.4 Hz, 1H), 6.51-6.42 (t, J=2.0 Hz, 1H), 6.38-6.32 (d, J=8.0 Hz, 1H), 6.25 (br s, 1H), 5.65-5.39 (dt, J=17.6 Hz, 2H), 5.18-5.00 (d, J=47.6 Hz, 1H), 4.81-4.63 (d, J=5.2 Hz, 2H), 4.03-3.90 (m, 1H), 3.70-3.65 (m, 1H), 3.47 (s, 2H), 3.44-3.30 (m, 2H), 3.22 (s, 3H), 3.13-3.01 (m, 1H), 2.22-2.04 (m, 1H), 1.97-1.85 (m, 1H), 1.17-0.92 (m, 4H).

Example 219: Compound 477B: N-{[3-(4-{[(3S, 4R)-3-fluoropiperidin-4-yl]amino}-1-(2,2,2-trifluoroethyl)-1H-indol-2-yl)-1,2,4-oxadiazol-5-yl]methyl}-1-(4-methyloxan-4-yl)-1H-pyrrole-3-carboxamide

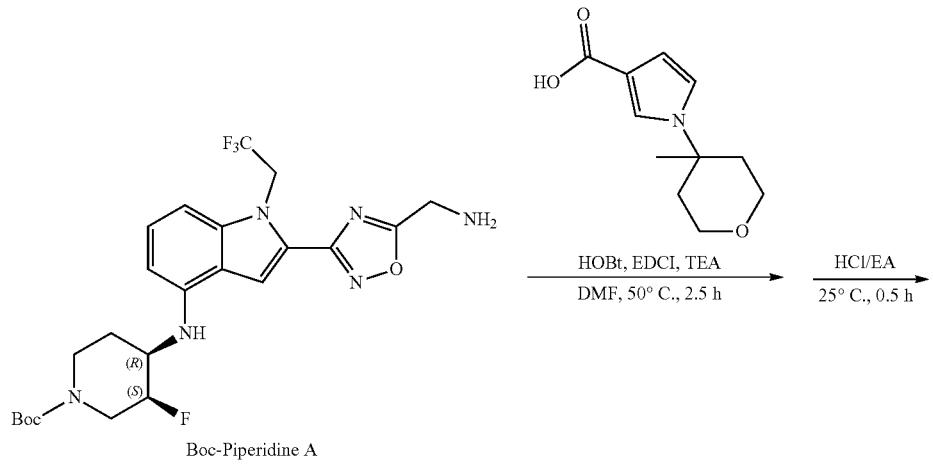

Boc-Piperidine A

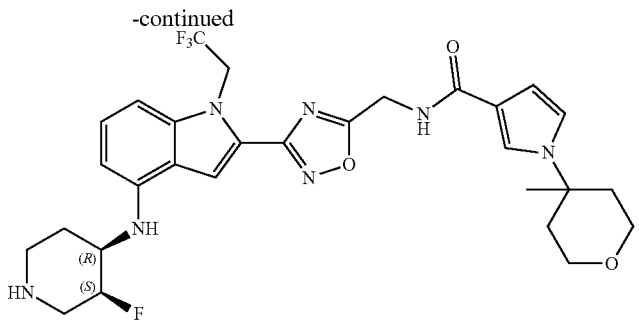

A mixture of tert-butyl (3S,4R)-4-[[2-[5-(aminomethyl)-1,2,4-oxadiazol-3-yl]-1-(2,2,2-trifluoroethyl)indol-4-yl]amino]-3-fluoropiperidine-1-carboxylate (Boc-piperidine A) (80 mg, 156.1 µmol, 1 eq), 1-(4-methyltetrahydropyran-4-yl)pyrrole-3-carboxylic acid (39.6 mg, 187 µmol, 99% purity, 1.2 eq), HOBt (42.2 mg, 312 µmol, 2 eq), EDCI (59.9 mg, 312 µmol, 2 eq) and TEA (780 µmol, 110 µL 5 eq) in DMF (3 mL) was degassed and purged with nitrogen 3 times, then the mixture was stirred at 50° C. for 2.5 hrs. The reaction mixture was diluted with water (50 mL) and extracted with EA 50 mL (2×25 mL). The combined organic layers were washed with brine (50 mL), dried over sodium sulfate, filtered, and concentrated in vacuo to give a residue. The residue was purified by prep-TLC (SiO$_2$, PE:EA=1:2) to give the product (90 mg, 81.9% yield). LC-MS (ES$^+$, m/z): 704.4 [(M+H)~].

Tert-butyl (3S,4R)-3-fluoro-4-[[2-[5-[[[1-(4-methyltetrahydropyran-4-yl)pyrrole-3-carbonyl]amino]methyl]-1,2,4-oxadiazol-3-yl]-1-(2,2,2-trifluoroethyl)indol-4-yl]amino]piperidine-1-carboxylate (90 mg, 128 µmol, 1 eq) was added to 4N HCl/EA (3 mL). The mixture was stirred at 25° C. for 0.5 h. The reaction mixture was concentrated in vacuo to give a residue. The residue was purified by trituration with EA (5 mL) to give the desired product N-{[3-(4-{[(3S,4R)-3-fluoropiperidin-4-yl]amino}-1-(2,2,2-trifluoroethyl)-1H-indol-2-yl)-1,2,4-oxadiazol-5-yl]methyl}-1-(4-methyloxan-4-yl)-1H-pyrrole-3-carboxamide (23.3 mg, 27.8% yield, 97.7% purity, HCl salt). LC-MS (ES$^+$, m/z): 604.4 [(M+H)$^+$]. $^1$H NMR (400 MHz, DMSO-d6) δ=9.35-9.21 (m, 1H), 8.77-8.57 (m, 2H), 7.90 (s, 1H), 7.60 (s, 1H), 7.16 (t, J=8.0 Hz, 1H), 7.03 (t, J=2.6 Hz, 1H), 6.95 (d, J=8.4 Hz, 1H), 6.60-6.52 (m, 1H), 6.35 (d, J=8.0 Hz, 1H), 6.26 (br s, 1H), 5.58-5.48 (m, 2H), 5.04-5.16 (m, 1H), 4.75 (br d, J=5.5 Hz, 2H), 4.06-3.90 (m, 1H), 3.53 (br s, 4H), 3.46 (br d, J=11.3 Hz, 1H), 3.33 (br d, J=11.0 Hz, 2H), 3.17-3.03 (m, 1H), 2.22-2.06 (m, 3H), 1.98-1.86 (m, 3H), 1.44 (s, 3H).

Example 220: Compound 478B: N-{[3-(4-{[(3R,4S)-3-fluoropiperidin-4-yl]amino}-1-(2,2,2-trifluoroethyl)-1H-indol-2-yl)-1,2,4-oxadiazol-5-yl]methyl}-1-(4-methyloxan-4-yl)-1H-pyrrole-3-carboxamide

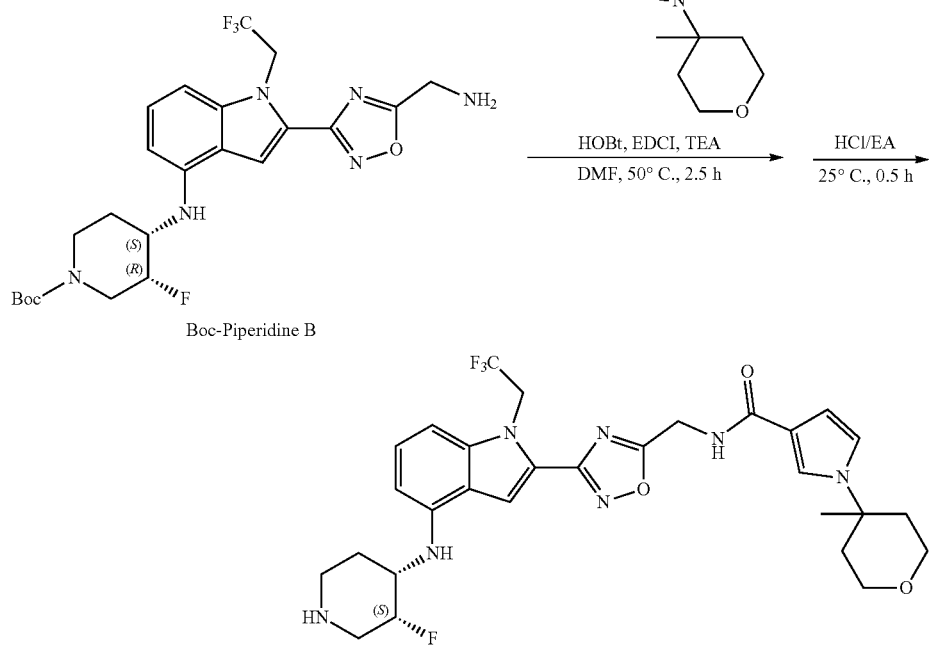

The 3R, 4S enantiomer was prepared from Boc-Piperidine B using the identical procedure as for the previously described enantiomer, to provide N-{[3-(4-{[(3R,4S)-3-fluoropiperidin-4-yl]amino}-1-(2,2,2-trifluoroethyl)-1H-indol-2-yl)-1,2,4-oxadiazol-5-yl]methyl}-1-(4-methyloxan-4-yl)-1H-pyrrole-3-carboxamide. LC-MS (ES+, m/z): 604.4 [(M+H)-]. ¹H NMR (400 MHz, DMSO-d6) δ=9.58 (br s, 1H), 8.73 (br s, 2H), 7.90 (s, 1H), 7.61 (s, 1H), 7.15 (t, J=8.1 Hz, 1H), 7.03 (t, J=2.5 Hz, 1H), 6.95 (br d, J=8.3 Hz, 1H), 6.56 (br s, 1H), 6.36 (br d, J=7.9 Hz, 1H), 5.53 (br d, J=9.0 Hz, 2H), 5.19-5.01 (m, 1H), 4.74 (br d, J=5.5 Hz, 2H), 4.06-3.90 (m, 1H), 3.66 (dt, J=3.5, 7.6 Hz, 2H), 3.61-3.51 (m, 3H), 3.32 (br d, J=11.8 Hz, 2H), 3.08 (br d, J=11.4 Hz, 1H), 2.22-2.08 (m, 3H), 1.98-1.86 (m, 3H), 1.44 (s, 3H).

Example 221: Compound 479B: N-{[3-(4-{[(3R,4S)-3-fluoropiperidin-4-yl]amino}-1-(2,2,2-trifluoroethyl)-1H-indol-2-yl)-1,2,4-oxadiazol-5-yl]methyl}-5-(2-methoxypropan-2-yl)thiophene-2-carboxamide A mixture of Boc-piperidine B (80 mg, 156 μmol, 1 eq), 5-(1-methoxy-1-methyl-ethyl)thiophene-2-carboxylic acid (41.7 mg, 187 μmol, 1.2 eq), HOBt (42.2 mg, 312 μmol, 2 eq), EDCI (59.9 mg, 312 μmol, 2 eq) and TEA (780 μmol, 110 μL 5 eq) in DMF (3 mL) was stirred at 50° C. for 2.5 hrs under nitrogen atmosphere. The reaction mixture was diluted with water (50 mL) and extracted with EA (2×25 mL). The combined organic layers were washed with brine (50) mL, dried over anhydrous sodium sulfate, filtered, and concentrated in vacuo to give a residue. The residue was purified by prep-TLC (SiO₂, PE:EA=1:1) to give the product (80 mg, 73.8% yield). LC-MS (ES+, m/z): 695.3 [(M+H)+].

To a solution of tert-butyl (3R,4S)-3-fluoro-4-[[2-[5-[[[5-(1-methoxy-1-methyl-ethyl) thiophene-2-carbonyl]amino]methyl]-1,2,4-oxadiazol-3-yl]-1-(2,2,2-trifluoroethyl)indol-4-yl]amino]piperidine-1-carboxylate (80 mg, 115 μmol, 1 eq) in DCM (1 mL) was added 2,6-dimethylpyridine (345 μmol, 40 μL 3 eq). then TMSI (345 μmol, 47 μL 3 eq) was added to the mixture. The mixture was stirred at 25° C. for 10 min. The reaction mixture was quenched by adding sat. sodium carbonate (10 mL), then diluted with water (100 mL) and extracted with EA (2×25 mL). The combined organic layers were washed with brine (50 mL), dried over anhydrous sodium sulfate, filtered, and concentrated in vacuo to give a residue. The residue was purified by prep-TLC (SiO₂, PE:EA=1:2) to give the desired product N-{[3-(4-{[(3R,4S)-3-fluoropiperidin-4-yl]amino}-1-(2,2,2-trifluoroethyl)-1H-indol-2-yl)-1,2,4-oxadiazol-5-yl]methyl}-5-(2-methoxypropan-2-yl)thiophene-2-carboxamide (21.8 mg, 31.8% yield, 100% purity). LC-MS (ES-, m/z): 595.2 [(M+H)~]. ¹H NMR (400 MHz, DMSO-d6) δ=9.38 (br t, J=5.6 Hz, 1H), 7.92 (s, 1H), 7.72 (d, J=3.8 Hz, 1H), 7.18-7.03 (m, 2H), 6.89 (d, J=8.2 Hz, 1H), 6.31 (d, J=7.8 Hz, 1H), 6.08 (br d, J=8.0 Hz, 1H), 5.52 (q, J=9.1 Hz, 2H), 4.89-4.65 (m, 3H), 3.83-

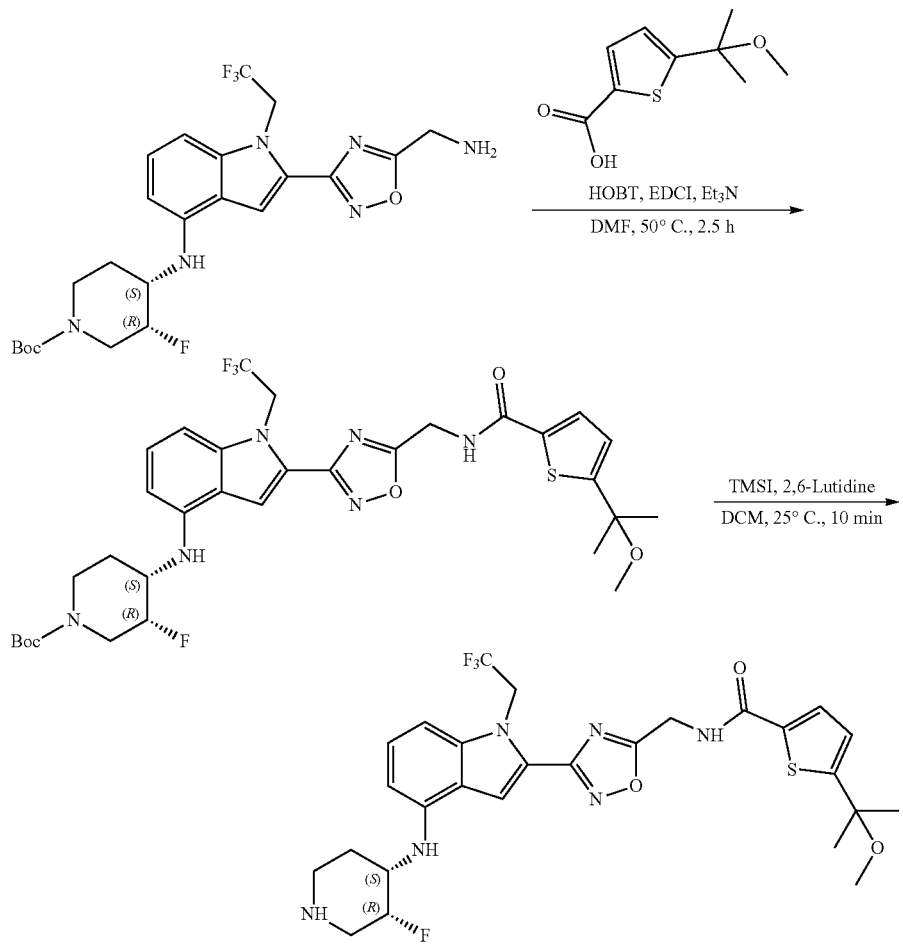

3.61 (m, 1H), 3.23-3.14 (m, 1H), 3.10-3.01 (m, 4H), 2.94-2.76 (m, 1H), 2.73- 2.65 (m, 1H), 1.94-1.74 (m, 2H), 1.83-1.64 (m, 8H).

Example 222: Compound 480B: N-{[3-(4-{1(3S, 4R)-3-fluoropiperidin-4-yl]amino}-1-(2,2,2-trifluoroethyl)-1H-indol-2-yl)-1,2,4-oxadiazol-5-yl] methyl}-5-(2-methoxypropan-2-yl)thiophene-2-carboxamide The analogue was prepared using the exact same conditions as for the opposite enantiomer, using Boc-piperidine A to provide the desired compound N-{[3-(4-{[(3S,4R)-3-fluoropiperidin-4-yl]amino}-1-(2,2,2-trifluoroethyl)-1H-indol-2-yl)-1,2,4-oxadiazol-5-yl]methyl}-5-(2-methoxypropan-2-yl)thiophene-2-carboxamide LC-MS (ES$^+$, m/z): 595.2 [(M+H)$^+$]. $^1$H NMR (400 MHz, DMSO-d6) δ=9.40 (br t, J=5.5 Hz, 1H), 7.92 (s, 1H), 7.72 (d, J=3.6 Hz, 1H), 7.21-7.04 (m, 2H), 6.90 (br d, J=8.3 Hz, 1H), 6.32 (d, J=7.9 Hz, 1H), 6.11 (br d, J=8.3 Hz, 1H), 5.53 (q, J=8.6 Hz, 2H), 4.93-4.67 (m, 3H), 3.88-3.67 (m, 1H), 3.22 (br t, J=11.4 Hz, 1H), 3.07 (s, 4H), 2.98-2.81 (m, 1H), 2.75-2.66 (m, 1H), 1.94-1.80 (m, 1H), 1.69 (br d, J=12.6 Hz, 1H), 1.55 (s, 6H).

Example 223: Compound 481B: 1-[1-(ethoxymethyl)cyclopropyl]-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-pyrrole-3-carboxamide

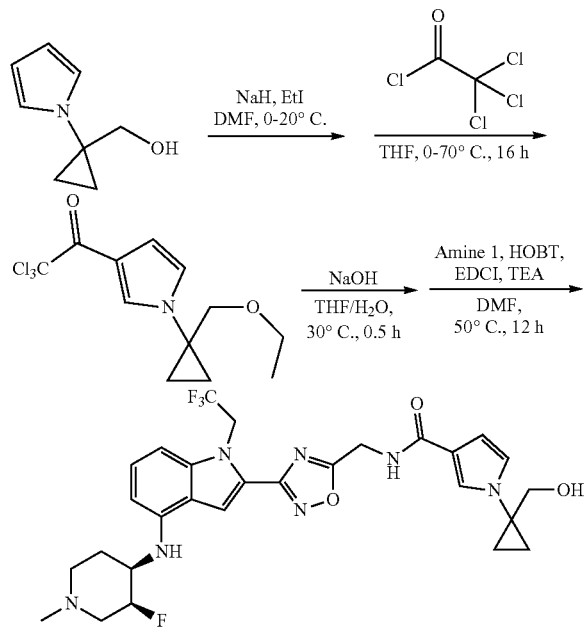

To a mixture of the previously prepared (1-pyrrol-1-ylcyclopropyl)methanol (1 g, 7.3 mmol, 1 eq) in DMF (10 mL) was added iodoethane (14.6 mmol, 1.17 mL, 2 eq) in one portion at 0° C. under nitrogen. The mixture was stirred at 0° C. for 30 min, followed by addition of sodium hydride (875 mg, 21.9 mmol, 60% purity, 3 eq). The mixture was stirred at 20° C. for 1 h 30 min. The residue was poured into ammonium chloride (sat., 100 mL) and stirred for 5 min. The aqueous phase was extracted with EA (30 mL×3). The combined organic phase was washed with brine (30 mL×3), dried over anhydrous sodium sulfate, filtered, and concentrated in vacuo to provide 1-[1-(ethoxymethyl)cyclopropyl] pyrrole (1.3 g, crude) as a yellow oil. LC-MS (ES$^+$, m:z): 166.2 [(M+H)$^+$].

To a solution of 1-[1-(ethoxymethyl)cyclopropyl]pyrrole (1.3 g, 7.87 mmol, 1 eq) in THF (20 mL) was added 2,2,2-trichloroacetyl chloride (23.6 mmol, 2.63 mL, 3 eq) at 0° C. The mixture was heated and stirred at 70° C. for 12 h. The residue was poured into sodium carbonate (sat.) to adjust pH>7. The aqueous phase was extracted with EA (20 mL×3). The combined organic phase was washed with brine (20 mL×3), dried over anhydrous sodium sulfate, filtered, and concentrated in vacuo. The residue was purified by silica gel chromatography (column height: 250 mm, diameter: 100 mm, 100-200 mesh silica gel, PE/EA=100/0, 98/2) to provide 2,2,2-trichloro-1-[1-[1-(ethoxymethyl)cyclopropyl] pyrrol-3-yl]ethanone (400 mg, 1.29 mmol, 16.4% yield) as a yellow oil. LC-MS (ES$^+$, m:z): 310.0 [(M+H)$^+$]. $^1$H NMR (400 MHz, DMSO-d6) δ=7.86 (t, J=1.9 Hz, 1H), 7.03 (dd, J=2.0, 3.1 Hz, 1H), 6.65 (dd, J=1.8, 3.1 Hz, 1H), 3.53 (s, 2H), 3.39 (q, J=7.1 Hz, 2H), 1.20-1.14 (m, 2H), 1.07-1.00 (m, 5H).

To a mixture of 2,2,2-trichloro-1-[1-[1-(ethoxymethyl) cyclopropyl]pyrrol-3-yl]ethanone (420 mg, 1.35 mmol, 1 eq) in THF (2 mL) was added sodium hydroxide (2 M, 2 mL, 3 eq) at 30° C. under nitrogen. The mixture was stirred at 30° C. for 0.5 h. The residue was poured into water (w/w=1/1) (30 mL). The aqueous phase was extracted with DCM (10 mL×3). The aqueous phase was treated with HCl (12 M) to adjust to pH=5~$^6$, then extracted with DCM (10 mL×3). The combined organic phase was washed with brine (10 mL×3), dried over anhydrous sodium sulfate, filtered, and concentrated in vacuo to provide 1-[1-(ethoxymethyl)cyclopropyl] pyrrole-3-carboxylic acid (0.2 g, crude) as a light yellow oil.

Amine 1 (70 mg, 140 μmol, 1 eq, 2HCl) was coupled with 1-[1-(ethoxymethyl)cyclopropyl]pyrrole-3-carboxylic acid (35.2 mg, 168 μmol, 1.2 eq) under method A. The crude product was purified by prep-TLC (SiO$_2$, DCM:methanol=8:1) to afford 1-[1-(ethoxymethyl)cyclopropyl]-N-[[3-[4-[[(3S,4R)-3-fluoro-1-methyl-4-piperidyl]amino]-1-(2,2,2-trifluoroethyl)indol-2-yl]-1,2,4-oxadiazol-5-yl]methyl] pyrrole-3-carboxamide (21.7 mg, 25.1% yield, 100% purity) as a light yellow solid. LC-MS (ES$^+$, m/z): 618.3 [(M+H)$^+$]. $^1$H NMR (400 MHz, DMSO-d6) δ=8.68 (br t, J=5.4 Hz, 1H), 7.89 (s, 1H), 7.45 (s, 1H), 7.11 (t, J=8.1 Hz, 1H), 6.95-6.81 (m, 2H), 6.46 (br s, 1H), 6.28 (d, J=7.8 Hz, 1H), 6.02 (br d, J=8.4 Hz, 1H), 5.57-5.44 (m, 2H), 4.93-4.70 (m, 3H), 3.64 (br s, 1H), 3.50 (s, 2H), 3.41-3.36 (m, 2H), 3.09-2.98 (m, 1H), 2.82 (br d, J=7.4 Hz, 1H), 2.32-2.14 (m, 4H), 2.13-2.04 (m, 1H), 2.05-1.83 (m, 1H), 1.74-1.63 (m, 1H), 1.13- 1.03 (m, 5H), 1.02-0.90 (m, 2H).

Example 224: Compound 482B: 1-{1-[(dimethylamino)methyl]cyclopropyl}-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl] methyl}-1H-pyrrole-3-carboxamide

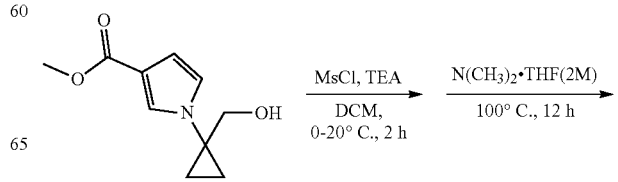

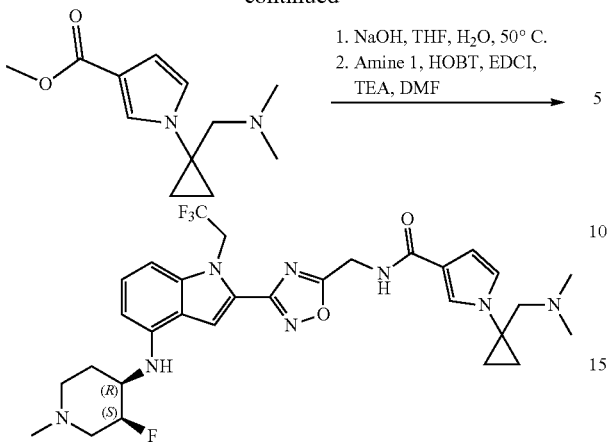

To a mixture of the previously prepared methyl 1-[1-(hydroxymethyl)cyclopropyl]pyrrole-3-carboxylate (110 mg, 563 μmol, 1 eq) and methanesulfonyl chloride (676 μmol, 52 μL 1.2 eq) in DCM (1 mL) was added TEA (676 μmol, 94 L 1.2 eq) at 0° C. under nitrogen. The mixture was stirred at 20° C. for 2 h. The residue was poured into ice-water (w/w=1/1) (40 mL). The aqueous phase was extracted with DCM (10 mL×3). The combined organic phase was washed with brine (10 mL×3), dried over anhydrous sodium sulfate, filtered, and concentrated in vacuo to provide methyl 1-[1-(methylsulfonyloxyethyl)cyclopropyl] pyrrole-3-carboxylate (140 mg, crude) as a yellow oil. LC-MS (ES$^+$, m/z): 274.1[(M+H)$^+$].

To methyl 1-[1-(methylsulfonyloxyethyl)cyclopropyl] pyrrole-3-carboxylate (140 mg, 512 μmol, 1 eq) was added dimethylamine (2 M (THF), 770 μL 3 eq) in a sealed tube. The mixture was stirred at 100° C. for 12 h. The residue was poured into ice-water (w/w=1/1) (40 mL). The aqueous phase was extracted with EA (10 mL×3). The combined organic phase was washed with brine (10 mL×3), dried over anhydrous sodium sulfate, filtered, and concentrated in vacuo. The residue was purified by prep-TLC (SiO$_2$, PE:EA=1:1) to provide methyl 1-[1-[(dimethylamino) methyl]cyclopropyl]pyrrole-3-carboxylate (70 mg, 314.9 μmol, 61.5% yield) as a yellow oil. LC-MS (ES$^+$, m/z): 223.1[(M+H)$^+$].

To a mixture of methyl 1-[1-[(dimethylamino)methyl] cyclopropyl]pyrrole-3-carboxylate (70 mg, 315 μmol, 1 eq) in methanol (1 mL) was added sodium hydroxide (3 M, 1 mL, 9.53 eq), and the reaction was heated at 50° C. under nitrogen for 12 h. HCl (12 M) was added dropwise into the reaction to adjust pH=7-8, then the reaction was concentrated in vacuo to afford 1-[1-[(dimethylamino)methyl]cyclopropyl]pyrrole-3-carboxylic acid (360 mg, crude) as a light yellow solid.

Amine 1 (70 mg, 140.2 μmol, 1 eq, 2HCl) and 1-[1-[(dimethylamino)methyl]cyclopropyl]pyrrole-3-carboxylic acid (233.6 mg, 168.2 μmol, 1.2 eq) were coupled under method A. The crude reaction was purified by prep-TLC (SiO$_2$, DCM:methanol=7:1) to provide 1-[1-[(dimethylamino)methyl]cyclopropyl]-N-[[3-[4-[[(3S,4R)-3-fluoro-1-methyl-4-piperidyl]amino]-1-(2,2,2-trifluoroethyl)indol-2-yl]-1,2,4-oxadiazol-5-yl]methyl]pyrrole-3-carboxamide (21.4 mg, 24.0% yield, 96.9% purity) as a light yellow solid. LC-MS (ES$^+$, m/z): [(M+H)$^+$]. $^1$H NMR (400 MHz, DMSO-d6) δ=8.68 (t, J=5.5 Hz, 1H), 7.91 (s, 1H), 7.43 (s, 1H), 7.11 (t, J=8.0 Hz, 1H), 6.93-6.79 (m, 2H), 6.44 (br s, 1H), 6.28 (d, J=7.8 Hz, 1H), 6.05 (br d, J=8.4 Hz, 1H), 5.59-5.43 (m, 2H), 4.96-4.76 (m, 1H), 4.72 (d, J=5.5 Hz, 2H), 3.69-3.48 (m, 1H), 3.31 (s, 2H), 2.28-2.18 (m, 4H), 2.14 (s, 6H), 2.10-1.97 (m, 1H), 2.09-1.95 (m, 1H), 1.72-1.63 (m, 1H), 1.12-1.03 (m, 2H), 0.91- 0.85 (m, 2H).

Example 225: Compound 483B: N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-5-[1-(methoxymethyl)cyclopropyl] thiophene-2-carboxamide

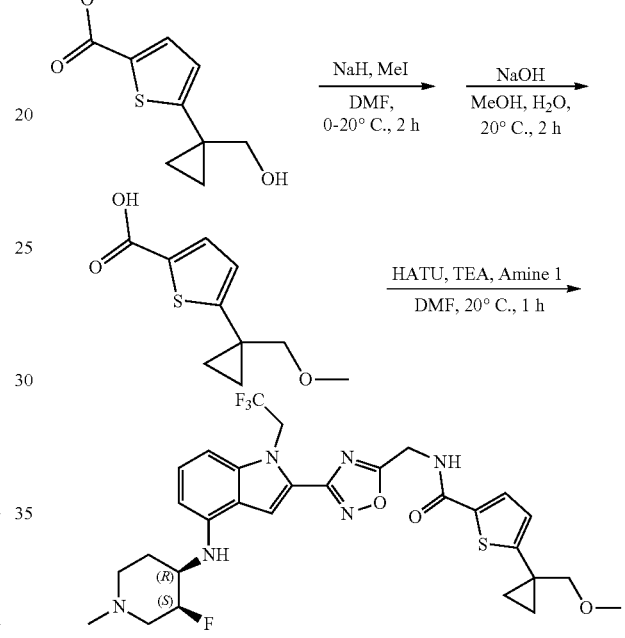

To a mixture of the previously prepared methyl 5-[1-(hydroxymethyl)cyclopropyl]thiophene-2-carboxylate (300 mg, 1.41 mmol, 1 eq) in DMF (4 mL) was added sodium hydride (282.6 mg, 7.07 mmol, 60% purity, 5 eq) at 0° C. under nitrogen. The mixture was stirred at 0° C. for 30 min, then heated to 20° C., followed by addition of iodomethane (4.24 mmol, 265 μL 3 eq) and stirring for 1.5 h. The residue was poured into ice-water (10 mL) and ammonium chloride (sat., 10 mL). The aqueous phase was extracted with EA (3×15 mL). The combined organic phase was washed with brine (3×15 mL), dried over anhydrous sodium sulfate, filtered, and concentrated in vacuo to provide methyl 5-[1-(methoxymethyl)cyclopropyl]thiophene-2-carboxylate (300 mg, crude) as a yellow oil, which without purification used next step. LC-MS (ES$^+$, m/z): 227.1 [(M+H)$^+$]

Methyl 5-[1-(methoxymethyl)cyclopropyl]thiophene-2-carboxylate (300 mg, 1.33 mmol, 1 eq), was saponified under standard conditions to provide the carboxylic acid product (150 mg, 53.3% yield) as white solid.

Amine 1 (80 mg, 160 μmol, 1 eq, 21HCl) was coupled with 5-[1-(methoxymethyl)cyclopropyl]thiophene-2-carboxylic acid (40.8 mg, 192 μmol, 1.2 eq) under method B. The crude product was purified by prep-TLC (SiO$_2$, DCM/MEOH=10/1) to give the desired product N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-5-

[1-(methoxymethyl)cyclopropyl]thiophene-2-carboxamide (44.7 mg, 45.0% yield) as white solid. LC-MS (ES+, m/z): 621.2 [(M+H)+]. $^1$H NMR (400 MHz, DMSO-d6) δ-7.89 (s, 1H), 7.65 (d, J=4.0 Hz, 1H), 7.12 (t, J=8.0 Hz, 1H), 6.93 (d, J=3.7 Hz, 1H), 6.88 (d, J=8.4 Hz, 1H), 6.28 (d, J=7.9 Hz, 1H), 6.03 (d, J=7.5 Hz, 1H), 5.50 (q, J=8.7 Hz, 2H), 4.94-4.75 (m, 3H), 3.69-3.52 (m, 1H), 3.47 (s, 2H), 3.30-3.26 (m, 3H), 3.12-3.00 (m, 1H), 2.90-2.77 (m, 1H), 2.21 (s, 4H), 2.12 (s, 1H), 2.06-1.93 (m, 1H), 1.69 (d, J=10.6 Hz, 1H), 1.08-0.92 (m, 4H).

Example 226: Compound 484B: 5-tert-butyl-N-{[3-(4-{1[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-pyrrole-3-carboxamide Amine 1 (42.7 mg, 85.9 μmol, 2Cl) was coupled with 5-tert-butyl-1H-pyrrole-3-carboxylic acid (18.4 mg, 110 μmol) under method B. The reaction was filtered through an Acrodisc using an additional 2 mL of DMF, then purified by reverse-phase HPLC in acetonitrile:water 10-60% over 9 min (0.1% formic acid). The fractions were combined, diluted with DCM, and sat. sodium bicarbonate solution. The organic layer was removed, and the aqueous layer extracted with DCM. The organic solution was dried over magnesium sulfate, filtered, and concentrated to provide the desired product 5-tert-butyl-N-[[3-[4-[[(3S,4R)-3-fluoro-1-methyl-4-piperidyl]amino]-1-(2,2,2-trifluoroethyl)indol-2-yl]-1,2,4-oxadiazol-5-yl]methyl]-1H-pyrrole-3-carboxamide (12.3 mg, 24.8% yield). LC-MS (ES+, m/z): 576.3 [(M+H)+]. $^1$H NMR (500 MHz, DMSO-d6) δ 11.08 (s, 1H), 8.62 (t, J=5.7 Hz, 1H), 7.93 (s, 1H), 7.31 (t, J=2.2 Hz, 1H), 7.16 (t, J=8.0 Hz, 1H), 6.93 (d, J=8.3 Hz, 1H), 6.33 (d, J=7.9 Hz, 111), 6.26 (t, J=2.2 Hz, 1H), 6.07 (d, J=8.3 Hz, 1H), 5.81 (s, OH), 5.55 (d, J=9.0 Hz, 1H), 4.89 (d, J=49.2 Hz, 1H), 4.76 (d, J=5.7 Hz, 2H), 3.65 (d, J=29.2 Hz, 1H), 3.10 (s, 1H), 2.97-2.77 (m, 1H), 2.39-1.97 (m, 4H), 1.74 (d, J=12.8 Hz, 1H), 1.29 (s, 9H).

Example 227: Compound 485B: N-{[3-(4-{1[(3S,4R)-3-fluoro-1-methylpiperidin-4-yl]amino}-1-(2,2,2-trifluoroethyl)-1H-indol-2-yl)-1,2,4-oxadiazol-5-yl]methyl}-5-(1-methoxy-2-methylpropan-2-yl)thiophene-3-carboxamide

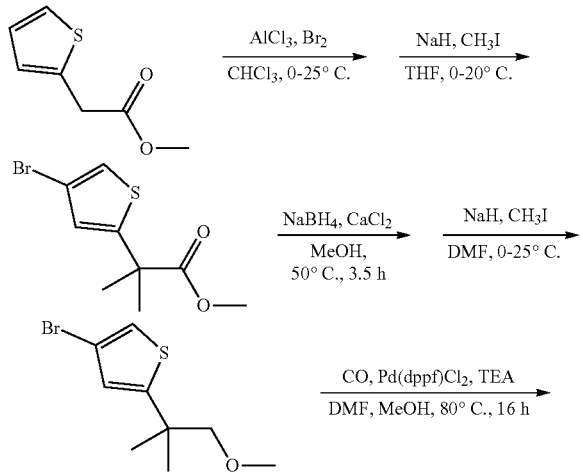

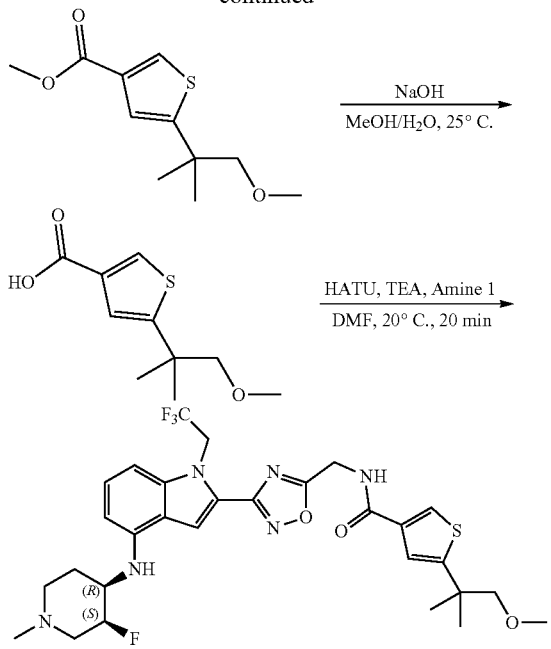

To a mixture of methyl 2-(2-thienyl)acetate (15 g, 96 mmol, 1 eq) in chloroform (100 mL) was added aluminum chloride (32.0 g, 240 mmol, 2.5 eq) at 0-5° C. under nitrogen, and dropwise bromine (96 mmol, 4.95 mL, 1 eq) in the solution. The mixture was stirred for 30 min, then heated to 20° C. and stirred for 2 h. The solution was added in ice water extracted with EA (3×50 mL). The combined organic phase was washed with brine (3×30 mL), dried over anhydrous sodium sulfate, filtered, and concentrated in vacuo. The crude product was purified by prep-HPLC (column: Phenomenex luna C18 250 mm×100 mm×15 um; mobile phase: [water (0.225% FA)-ACN] B %: 40%-75%, 30 min) to afford methyl 2-(4-bromo-2-thienyl)acetate (2.4 g, 9.19 mmol, 9.6% yield, 90% purity) as a yellow oil. $^1$H NMR (400 MHz, CHLOROFORM-d)=7.13 (d, J=1.5 Hz, 1H), 6.89 (d, J=1.2 Hz, 1H), 3.81 (d, J=0.7 Hz, 2H), 3.78-3.72 (m, 3H).

To a mixture of methyl 2-(4-bromo-2-thienyl)acetate (1.5 g, 6.38 mmol, 1 eq) in DMF (10 mL) was added sodium hydride (510.4 mg, 12.8 mmol, 60% purity, 2 eq) in one portion at 0° C. under nitrogen. The mixture was stirred at 0° C. for 30 min, followed by addition of iodomethane (19.1 mmol, 1.19 mL, 3 eq). The mixture was stirred at 20° C. for 30 min. The reaction mixture was quenched by adding ammonium chloride saturated solution (30 mL) at 0° C., and extracted with EA (3×30 mL). The combined organic layers were washed with saturated brine (3×20 mL), dried over anhydrous sodium sulfate, filtered, and concentrated in vacuo to give a residue. The residue was purified by column chromatography (SiO$_2$, PE/EA=1/0 to 50/1) to afford the product (1.4 g, 83.4% yield) as a yellow oil. LC-MS (ES+, m/z): 263.0 [(M+H)+].

A mixture of methyl 2-(4-bromo-2-thienyl)-2-methylpropanoate (1.4 g, 5.32 mmol, 1 eq) calcium chloride (590 mg, 5.32 mmol, 1 eq), sodium borohydride (1.01 g, 26.6 mmol, 5 eq) in methanol (14 mL) at 0° C. was stirred for 0.25 h, then heated to 50° C. and stirred for 3.5 h. The residue was poured into ice-water (10 mL) and HCl (1 N) stirred for 10 min. The aqueous phase was extracted with EA (3×40 mL). The combined organic phase was washed with brine (3×15 mL), dried over anhydrous sodium sulfate, filtered, and concentrated in vacuo to afford the product (1.1 g, 87.9% yield) as a yellow oil. LC-MS (ES$^+$, m/z): 236.9 [(M+H)$^+$].

To a solution of 2-(4-bromo-2-thienyl)-2-methyl-propan-1-ol (1.1 g, 4.68 mmol, 1 eq) in DMF (11 mL) was added sodium hydride (374.2 mg, 9.36 mmol, 60% purity, 2 eq) at 0° C. The mixture was stirred at 0° C. for 30 min, followed by addition of iodomethane (14 mmol, 875 μL 3 eq) at 0° C. The resulting mixture was warmed and stirred at 20° C. for 30 min. The reaction mixture was quenched by adding sat. ammonium chloride (30 mL), then extracted with EA (3×30 mL). The combined organic layers were washed with brine (3×20 mL), dried over anhydrous sodium sulfate, filtered, and concentrated in vacuo to give a residue. The residue was purified by column chromatography (silica gel, PE/EA=1/0 to 19/1) to afford the product (0.9 g, 77.2% yield) as a yellow oil. $^1$H NMR (400 MHz, DMSO-d6) δ=7.53-7.41 (d, J=1.2 Hz, 1H), 7.01-6.85 (d, J=1.6 Hz, 1H), 3.30 (s, 2H), 3.24 (s, 3H), 1.28 (s, 6H).

To a solution of 4-bromo-2-(2-methoxy-1,1-dimethyl-ethyl)thiophene (0.7 g, 2.81 mmol, 1 eq) in DMF (2 mL), methanol (0.4 mL) were added Pd(dppf)Cl$_2$ (1.03 g, 1.40 mmol, 0.5 eq) and TEA (14.1 mmol, 1.96 mL, 5 eq) under CO (15 psi) atmosphere. The mixture was stirred at 80° C. for 16 h. The reaction mixture was quenched by adding EDTA sat. (10 mL), and the mixture was stirred at 20° C. for 1 h, then diluted with water (10 mL) and extracted with EA (3×10 mL). The combined organic layers were washed with brine (3×10 mL), dried over anhydrous sodium sulfate, filtered, and concentrated in vacuo to give a residue. The residue was purified by column chromatography (SiO$_2$, PE/EA=1/0 to 17/1) to afford the ester product (0.6 g, 93.6% yield) as a yellow oil. $^1$H NMR (400 MHz, DMSO-d6) δ=8.22-8.05 (d, J=1.2 Hz, 1H), 7.35-7.06 (d, J=1.2 Hz, 1H), 3.77 (S, 3H), 3.32 (s, 2H), 3.25 (S, 3H), 1.31 (s, 6H).

Methyl 5-(2-methoxy-1,1-dimethyl-ethyl)thiophene-3-carboxylate (0.6 g, 2.63 mmol, 1 eq) was saponified under standard conditions to provide the product carboxylic acid (0.5 g, 88.8% yield) as a yellow solid.

Amine 1 (70 mg, 121 μmol, 1 eq, HCl) was coupled with 5-(2-methoxy-1,1-dimethyl-ethyl)thiophene-3-carboxylic acid (51.9 mg, 242 μmol, 2 eq) under method B. The crude reaction was purified by prep-TLC (DCM: methanol=10:1) to afford the desired product N-{{3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-5-(1-methoxy-2-methylpropan-2-yl)thiophene-3-carboxamide (21 mg, 27.9% yield) as a yellow solid. LC-MS (ES$^+$, m/z): 623.2 [(M+H)$^+$]. H NMR (400 MHz, DMSO-d6) 5=9.28-9.05 (t, J=5.6 Hz, 1H), 8.03 (s, 1H), 7.89 (s, 1H), 7.35 (s, 1H), 7.19-7.08 (t, J=8.0 Hz, 1H), 6.97-6.81 (d, J=8.0 Hz 1H), 6.40-6.24 (d, J=7.6 Hz 1H), 6.09-5.96 (t, J=8.0 Hz 1H), 5.60-5.39 (dt, J=17.6 Hz 2H), 4.93-4.73 (m, 3H), 3.65-3.53 (m, 1H), 3.32-3.31 (m, 2H), 3.26 (s, 3H), 3.10-3.01 (m, 1H), 2.88-2.77 (m, 1H), 2.26-2.12 (m, 5H), 2.02- 1.97 (m, 1H), 1.72-1.64 (m, 1H), 1.32 (s, 6H); $^1$H NMR (400 MHz, CDCl3) δ=7.81-7.79 (d, J=1.2 Hz, 1H), 7.44-7.39 (d, J=0.4 Hz, 1H), 7.26-7.20 (m, 2H), 6.88-6.77 (d, J=8.4 Hz, 1H), 6.65-6.50 (t, J=5.6 Hz, 1H), 6.40-6.27 (d, J=8.0 Hz, 1H), 5.35-5.23 (m, 2H), 4.96-4.81 (m, 3H), 4.47-4.30 (d, J=9.6 Hz, 1H), 3.66-3.52 (m, 1H), 3.38 (s, 2H), 3.36 (s, 3H), 3.31-3.22 (m, 1H), 3.03-2.88 (m, 1H), 2.25 (br d, J=12.8 Hz, 4H), 2.18 (br t, J=11.4 Hz, 1H), 2.11-2.03 (m, 1H), 2.00-1.90 (m, 1H), 1.40 (s, 6H).

Example 228: Compound 486B: N-{[3-(4-{[(3S, 4R)-3-fluoro-1-methylpiperidin-4-yl]amino}-1-(2,2,2-trifluoroethyl)-1H-indol-2-yl)-1,2,4-oxadiazol-5-yl]methyl}-5-[1-(hydroxymethyl)cyclopropyl] thiophene-2-carboxamide

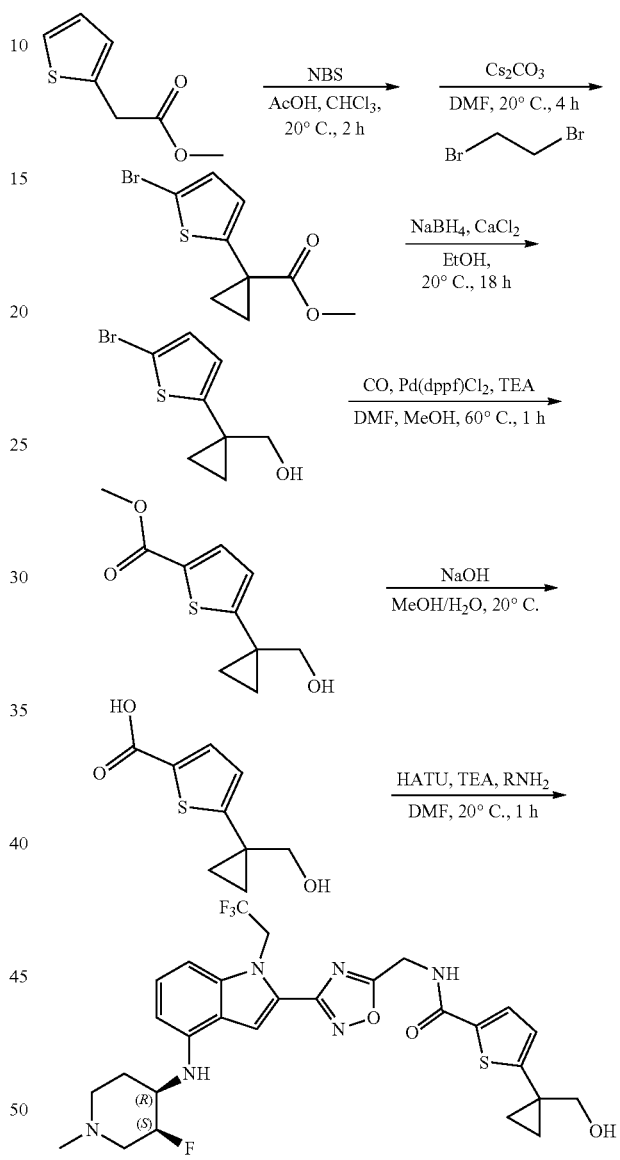

To a mixture of methyl 2-(2-thienyl)acetate (4 g, 25.6 mmol, 1 eq) in chloroform (20 mL) and acetic acid (20 mL) was added NBS (5.47 g, 30.7 mmol, 1.2 eq) at 20° C. under nitrogen. The reaction was stirred for 2 h. The reaction was adjusted to pH to 7 using sat. sodium carbonate (20 mL). The aqueous phase was extracted with EA (3×20 mL). The combined organic phase was washed with brine (3×20 mL), dried over anhydrous sodium sulfate, filtered, and concentrated in vacuo. The residue was purified by silica gel chromatography (column height: 250 mm, diameter: 100 mm, 100-200 mesh silica gel, PE/EA=99/1, 97/3) to give the product (5 g, 66.4% yield, 80% purity) as a yellow oil. $^1$H NMR (400 MHz, CHCl$_3$d) δ=6.91 (d, J=3.7 Hz, 1H), 6.70 (td, J=0.9, 3.7 Hz, 1H), 3.78 (d, J=0.7 Hz, 2H), 3.74 (s, 3H).

A mixture of methyl 2-(5-bromo-2-thienyl)acetate (2.5 g, 10.6 mmol, 1 eq) and 1,2-dibromoethane (26.6 mmol, 2 mL, 2.5 eq), cesium carbonate (13.86 g, 42.5 mmol, 4 eq) was stirred in DMF (20 mL) at 20° C. for 4 h. The aqueous phase was extracted with EA (3×30 mL). The combined organic phase was washed with brine (3×30 mL), dried over anhydrous sodium sulfate, filtered, and concentrated in vacuo. The residue was purified by silica gel chromatography (column height: 250 mm, diameter: 100 mm, 100-200 mesh silica gel, PE/EA=99/1, 97/3) to give the cyclopropyl product (2.4 g, 9.19 mmol, 43.2% yield) as a yellow oil. LC-MS (ES$^+$, m/z): 261.0/263.0 [(M+H)$^+$]. $^1$H NMR (400 MHz, CHCl$_3$-d) δ=6.87 (d, J=3.8 Hz, 1H), 6.67 (d, J=3.8 Hz, 1H), 3.70 (s, 3H), 1.72-1.67 (m, 2H), 1.33-1.29 (m, 2H).

A mixture of methyl 1-(5-bromo-2-thienyl)cyclopropanecarboxylate (2.4 g, 9.19 mmol, 1 eq), sodium borohydride (1.74 g, 45.95 mmol, 5 eq) and calcium chloride (510 mg, 4.60 mmol, 0.5 eq) in ethanol (25 mL) at 0° C. was stirred for 10 min, then heated to 20° C. and stirred for 18 h. The residue was poured into ice-water (30 mL) and 1N HCl (30 mL) and stirred for 10 min. The aqueous phase was extracted with EA (3×20 mL). The combined organic phase was washed with brine (3×20 mL), dried over anhydrous sodium sulfate, filtered, and concentrated in vacuo. The residue was purified by silica gel chromatography (column height: 250 mm, diameter: 100 mm, 100-200 mesh silica gel, PE/EA=99/1, 74/26) to give the product (2.1 g, 98.0% yield) as a yellow oil. $^1$H NMR (400 MHz, CHCl$_3$-d) δ=6.87 (d, J=3.8 Hz, 1H), 6.69 (d, J=3.8 Hz, 1H), 3.66 (s, 2H), 1.03-0.89 (m, 4H). A mixture of [1-(5-bromo-2-thienyl)cyclopropyl]methanol (2.1 g, 9.01 mmol, 1 eq), TEA (45.04 mmol, 6.27 mL, 5 eq) in DMF (20 mL) and methanol (4 mL) at 20° C. were stirred under carbon monoxide at 15 psi. Pd(dppf)Cl$_2$ (3.30 g, 4.50 mmol, 0.5 eq) was added and the reaction was then heated to 60° C. and stirred for 18 h under carbon monoxide. The residue was poured into EA (20 mL) and EDTA (30 mL) (saturated) and stirred for 2 h. The aqueous phase was extracted with EA (3×20 mL). The combined organic phase was washed with brine (3×20 mL), dried over anhydrous sodium sulfate, filtered, and concentrated in vacuo. The residue was purified by silica gel chromatography (column height: 250 mm, diameter: 100 mm, 100-200 mesh silica gel, PE/EA=99/1, 70/30) to give the product (1.7 g, 71.1% yield, 80% purity) as a yellow oil. $^1$H NMR (400 MHz, DMSO-d6) δ=7.61 (d, J=3.8 Hz, 1H), 6.96 (d, J=3.8 Hz, 1H), 4.98 (t, J=5.6 Hz, 1H), 3.78 (s, 3H), 3.56 (d, J=5.6 Hz, 2H), 1.05-0.99 (m, 2H), 0.94-0.88 (m, 2H).

Methyl 5-[1-(hydroxymethyl)cyclopropyl]thiophene-2-carboxylate (300 mg, 1.41 mmol, 1 eq) was saponified under standard conditions to provide the crude product, which was purified by prep-TLC to give the carboxylic acid product (230 mg, 82.1% yield) as white oil.

5-[1-(hydroxymethyl)cyclopropyl]thiophene-2-carboxylic acid (38.1 mg, 192 μmol, 1.2 eq) and Amine 1 (80 mg, 160 μmol, 1 eq, 2HCl) were coupled under method B. The crude product was purified by prep-TLC (SiO$_2$, DCM/methanol=10/1) to give the desired product N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-5-[-(hydroxymethyl)cyclopropyl]thiophene-2-carboxamide (35.7 mg, 36.1% yield, 98.4% purity) as a white solid. LC-MS (ES$^+$, m/z): 607.1 [(M+H)~]. $^1$H NMR (400 MHz, DMSO-d6) δ=9.26 (t, J=5.6 Hz, 1H), 7.89 (s, 1H), 7.65 (d, J=3.8 Hz, 1H), 7.12 (t, J=8.1 Hz, 1H), 6.94 (d, J=3.8 Hz, 1H), 6.88 (d, J=8.3 Hz, 1H), 6.28 (d, J=7.8 Hz, 1H), 6.03 (d, J=8.3 Hz, 1H), 5.50 (q, J=8.8 Hz, 2H), 4.99-4.72 (m, 4H), 3.71-3.49 (m, 3H), 3.06 (s, 1H), 2.84 (d, J=8.2 Hz, 1H), 2.26-2.07 (m, 6H), 2.06-1.89 (m, 1H), 1.69 (d, J=9.7 Hz, 1H), 1.04-0.96 (m, 2H), 0.92-0.84 (m, 2H).

Example 229: Compound 487B: N-{[3-(4-{[(3S, 4R)-3-fluoro-1-methylpiperidin-4-yl]amino}-1-(2,2,2-trifluoroethyl)-1H-indol-2-yl)-1,2,4-oxadiazol-5-yl]methyl}-5-[1-(hydroxymethyl)cyclopropyl]thiophene-3-carboxamide

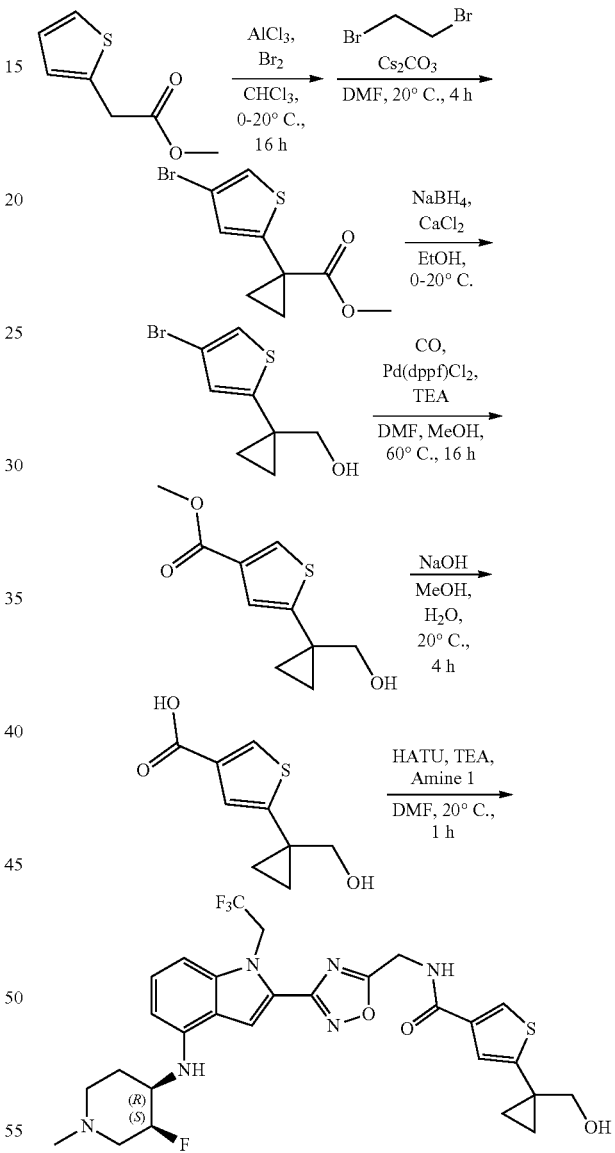

To a mixture of methyl 2-(2-thienyl)acetate (10 g, 64 mmol, 1 eq) in chloroform (100 mL) was added aluminum chloride (21.34 g, 160.1 mmol, 2.5 eq) at 0° C. under nitrogen. Bromine (64.02 mmol, 3.30 mL, 1 eq) was then added was dropwise. The mixture was stirred for 30 min at 0° C., then heated to 20° C. and stirred for 15.5 h. The solution was added to ice water (50 mL) extracted with EA (3×30 mL). The combined organic phase was washed with brine (3×20 mL), dried over anhydrous sodium sulfate, filtered, and concentrated in vacuo. The residue was purified by silica gel chromatography (column height: 250 mm, diameter: 100 mm, 100-200 mesh silica gel, PE/EA=99/1 to 97/3) to give the bromo product (6 g, 28% yield) as a yellow oil. $^1$H NMR (400 MHz, CHCl$_3$-d) δ=7.13 (d, J=1.5 Hz, 1H), 6.89 (d, J=1.2 Hz, 1H), 3.81 (d, J=0.6 Hz, 2H), 3.75 (s, 3H).

To a mixture of methyl 2-(4-bromo-2-thienyl)acetate (5 g, 21.27 mmol, 1 eq) and 1,2-dibromoethane (53.2 mmol, 4.01 mL, 2.5 eq) in DMF (70 mL) was added cesium carbonate (27.72 g, 85.07 mmol, 4 eq) at 20° C., and the reaction was stirred for 4 h. The aqueous phase was extracted with EA (3×30 mL). The combined organic phase was washed with brine (3×30 mL), dried over anhydrous sodium sulfate, filtered, and concentrated in vacuo. The residue was purified by silica gel chromatography (column height: 250 mm, diameter: 100 mm, 100-200 mesh silica gel, PE/EA=99/1 to 97/3) to give the cyclopropyl product (3 g, 54.0% yield) as a white oil. $^1$H NMR (400 MHz, CHC$_3$-d) δ=7.11 (d, J=1.5 Hz, 1H), 6.86 (d, J=1.5 Hz, 1H), 3.70 (s, 3H), 1.75-1.69 (m, 2H), 1.35-1.30 (m, 2H).

To a mixture of methyl 1-(4-bromo-2-thienyl)cyclopropanecarboxylate (3 g, 11.5 mmol, 1 eq) in ethanol (30 mL) were added sodium borohydride (2.17 g, 57.4 mmol, 5 eq) and calcium chloride (637.5 mg, 5.74 mmol, 0.5 eq) at 0° C., then the reaction was warmed to 20° C. and stirred for 18 h. TLC (PE:EA=3: 1, R$_f$=0.16) showed the desired product. The solution was adjusted to pH=7 using HCl (2 N), then extracted with EA (3×30 mL). The combined organic phase was washed with brine (3×30 mL), dried over anhydrous sodium sulfate, filtered, and concentrated in vacuo. The residue was purified by silica gel chromatography (column height: 250 mm, diameter: 100 mm, 100-200 mesh silica gel, PE/EA=99/1, 70/30) to give alcohol product (2.4 g, 89.6% yield) as white oil. $^1$H NMR (400 MHz, CHC$_3$-d) δ=7.05 (s, 1H), 6.87 (s, 1H), 3.69 (s, 2H), 1.06-0.91 (m, 4H).

To a mixture of [1-(4-bromo-2-thienyl)cyclopropyl] methanol (2.4 g, 10.29 mmol, 1 eq), TEA (51.5 mmol, 7.16 mL, 5 eq) in DMF (30 mL) and methanol (6 mL) was added Pd(dppf)Cl$_2$ (3.77 g, 5.15 mmol, 0.5 eq) at 20° C. under carbon monoxide at 15 psi. The mixture was heated to 60° C. and stirred for 16 h. The solution was added to EDTA (30 mL, saturated) and stirred for 2 h, then added extracted with EA (3×30 mL). The combined organic phase was washed with brine (3×30 mL), dried over anhydrous sodium sulfate, filtered, and concentrated in vacuo. The residue was purified by silica gel chromatography (column height: 250 mm, diameter: 100 mm, 100-200 mesh silica gel, PE/EA=99/1 to 65/35) to give the product (2 g, 91.5% yield) as gray oil. $^1$H NMR (400 MHz, DMSO-d6) δ=9.26 (t, J=5.6 Hz, 1H), 7.89 (s, 1H), 7.65 (d, J=3.8 Hz, 1H), 7.12 (t, J=8.1 Hz, 1H), 6.94 (d, J=3.8 Hz, 1H), 6.88 (d, J=8.3 Hz, 1H), 6.28 (d, J=7.8 Hz, 1H), 6.03 (d, J=8.3 Hz, 1H), 5.50 (q, J=8.8 Hz, 2H), 4.99-4.72 (m, 4H), 3.71-3.49 (m, 3H), 3.06 (s, 1H), 2.84 (d, J=8.2 Hz, 1H), 2.26-2.07 (m, 6H), 2.06-1.89 (m, 1H), 1.69 (d, J=9.7 Hz, 1H), 1.04-0.96 (m, 2H), 0.92-0.84 (m, 2H).

Methyl 5-[1-(hydroxymethyl)cyclopropyl]thiophene-3-carboxylate (300 mg, 1.41 mmol, 1 eq) was saponified under standard conditions. The crude was purified by prep-TLC to provide the carboxylic acid (150 mg, 53.5% yield) as white solid.

5-[1-(hydroxymethyl)cyclopropyl]thiophene-3-carboxylic acid (38.1 mg, 192 µmol, 1.2 eq) was coupled with Amine 1 (80 mg, 160.2 µmol, 1 eq, 2HCl) under method B. The crude was purified by prep-TLC to give the desired product N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-5-[1-(hydroxymethyl)cyclopropyl] thiophene-3-carboxamide (32.5 mg, 33.4% yield, 100% purity) as white solid. LC-MS (ES$^+$, m/z): 607.1 [(M+H)$^{+1.}$ $^1$H NMR (400 MHz, DMSO-d6) δ-9.14 (t, J=5.7 Hz, 1H), 7.97 (d, J=1.5 Hz, 1H), 7.89 (s, 1H), 7.32 (d, J=1.5 Hz, 1H), 7.12 (t, J=8.1 Hz, 1H), 6.88 (d, J=8.3 Hz, 1H), 6.28 (d, J=7.9 Hz, 1H), 6.04 (d, J=8.6 Hz, 1H), 5.50 (q, J=9.2 Hz, 2H), 4.99-4.73 (m, 4H), 3.70-3.50 (m, 3H), 3.05 (s, LH), 2.83 (d, J=10.1 Hz, 1H), 2.21 (s, 4H), 2.17-2.07 (m, 1H), 2.17-2.07 (m, 1H), 2.05-1.93 (m, 1H), 1.69 (d, J=11.0 Hz, 1H), 1.00-0.91 (m, 2H), 0.88-0.78 (m, 2H).

Example 230: Compound 488: N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl] methyl}-5-[1-(methoxymethyl)cyclopropyl] thiophene-3-carboxamide

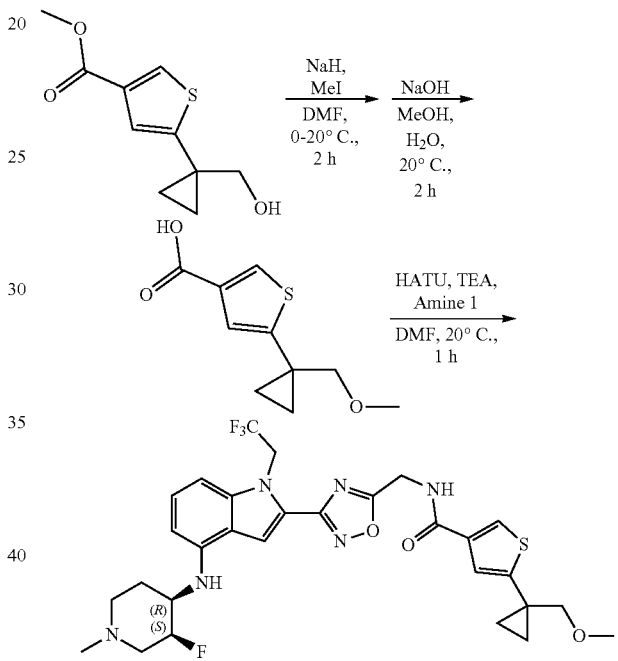

To a mixture of the previously prepared methyl 5-[1-(hydroxymethyl)cyclopropyl]thiophene-3-carboxylate (400 mg, 1.88 mmol, 1 eq) in DMF (4 mL) was added sodium hydride (376.9 mg, 9.42 mmL, 60% purity, 5 eq) at 0° C. The reaction was stirred for 30 min, followed by addition of iodomethane (5.65 mmol, 350 µL 3 eq), and the reaction was heated to 20° C. and stirred for 1.5 h. To the solution was added sat. ammonium chloride (20 mL), followed by extraction with EA (3×10 mL). The combined organic phase was washed with brine (3×10 mL), dried over anhydrous sodium sulfate, filtered, and concentrated in vacuo to give the methyl ether product (300 mg, crude) as a yellow oil, which was carried without purification to the next step.

Methyl 5-[1-(methoxymethyl)cyclopropyl]thiophene-3-carboxylate (300 mg, 1.33 mmol, 1 eq) was saponified under standard conditions. The crude was purified by prep-TLC to give product (150 mg, 53.3% yield) as white solid.

5-[1-(methoxymethyl)cyclopropyl]thiophene-3-carboxylic acid (40.8 mg, 192 µmol, 1.2 eq) was coupled with Amine 1 (80 mg, 160 µmol, 1 eq, 2HCl) under method B. The crude product was purified by prep-TLC to give the desired product N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-5-[1-(methoxymethyl)cyclopropyl] thiophene-3-carboxamide (35.6 mg, 35.5% yield, 99.1% purity) as a white solid. LC-MS (ES+, m/z): 621.1 [(M+H)+]. ¹H NMR (400 MHz, DMSO-d6) δ=9.15 (t, J=5.7 Hz, 1H), 7.98 (d, J=1.3 Hz, 1H), 7.89 (s, 1H), 7.30 (d, J=1.5 Hz, 1H), 7.12 (t, J=8.0 Hz, 1H), 6.88 (d, J=8.3 Hz, 1H), 6.28 (d, J=7.8 Hz, 1H), 6.04 (d, J=8.3 Hz, 1H), 5.50 (q, J=8.8 Hz, 2H), 4.96-4.73 (m, 3H), 3.71-3.53 (m, 1H), 3.45 (s, 2H), 3.28 (s, 3H), 3.09 (d, J=10.6 Hz, 1H), 2.85 (d, J=7.3 Hz, 1H), 2.22 (s, 5H), 2.08-1.93 (m, 1H), 1.69 (d, J=11.4 Hz, 1H), 1.01-0.96 (m, 2H), 0.96-0.91 (m, 2H).

Example 231: Compound 489B: N-{[3-(4-{[(3S,4R)-3-fluoropiperidin-4-yl]amino}-1-(2,2,2-trifluoroethyl)-1H-indol-2-yl)-1,2,4-oxadiazol-5-yl]methyl}-5-(2-methoxypropan-2-yl)thiophene-3-carboxamide eq) in DCM (1 mL) was added, 2,6-dimethylpyridine (300 µmol, 35 mL, 3 eq). TMSI (30 µmol, 41 mL, 3 eq) was added at 20° C. under nitrogen, and the mixture was stirred for 20 min. The reaction was adjusted pH to 7-8 using sodium bicarbonate (sat.). The aqueous phase was extracted with DCM (10 mL×3). The combined organic phase was washed with brine (10 mL×3), dried over anhydrous sodium sulfate, filtered, and concentrated in vacuo. The residue was purified by prep-TLC (SiO₂, DCM:methanol=10:1) to provide the desired product N-[[3-4-[[(3S,4R)-3-fluoro-4-piperidyl]amino]-1-(2,2,2-trifluoroethyl)indol-2-yl]-1,2,4-oxadiazol-5-yl]methyl]-5-(1-methoxy-1-methyl-ethyl)thiophene-3-carboxamide (22 mg, 36.7% yield, 100.0% purity) as a light yellow solid. LC-MS (ES+, m/z): 595.3 [(M+H)+]. ¹H NMR (400 MHz, DMSO-d6) δ=9.21 (t, J=5.6 Hz, 1H), 8.15 (d, J=1.3 Hz, 1H), 7.90 (s, 1H), 7.43 (d, J=1.5 Hz, 1H), 7.11 (t, J=8.0 Hz, 1H), 6.88 (d, J=8.2 Hz, 1H), 6.30 (d, J=7.9 Hz, 1H), 6.05 (d, J=8.2 Hz, 1H), 5.50 (q, J=8.8 Hz, 2H),

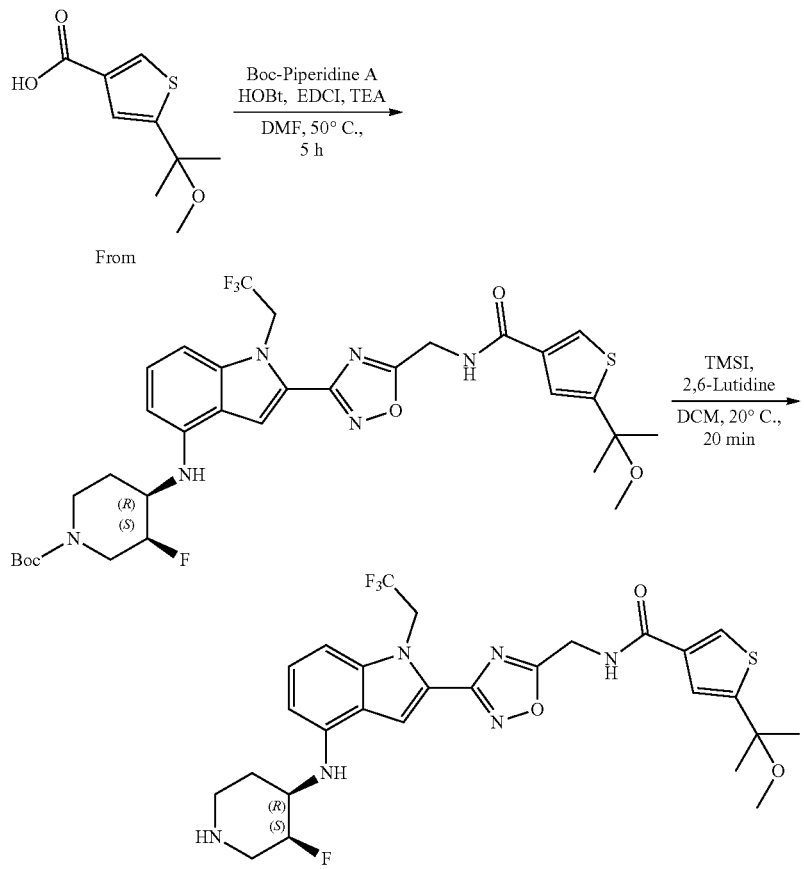

Boc-Piperidine A (100 mg, 195 µmol, 1 eq) was coupled with 5-(1-methoxy-1-methyl-ethyl)thiophene-3-carboxylic acid (46.9 mg, 234 µmol, 1.2 eq) under conditions. The crude reaction was purified by prep-TLC (SiO₂, PE:EA=1:1) to afford tert-butyl(3S,4R)-3-fluoro-4-[[2-[5-[[[5-(1-methoxy-1-methyl-ethyl)thiophene-3-carbonyl]amino]methyl]-1,2,4-oxadiazol-3-yl]-1-(2,2,2-trifluoroethyl)indol-4-yl]amino]piperidine-1-carboxylate (90 mg, 66.4% yield) as a yellow solid.

To a mixture of tert-butyl (3S,4R)-3-fluoro-4-[[2-[5-[[[5-(1-methoxy-1-methyl-ethyl)thiophene-3-carbonyl]amino]methyl]-1,2,4-oxadiazol-3-yl]-1-(2,2,2-trifluoroethyl)indol-4-yl]amino]piperidine-1-carboxylate (70 mg, 101 µmol, 1

4.87-4.68 (m, 3H), 3.20-3.12 (m, 1H), 3.04 (s, 4H), 2.88 (br d, J=14.3 Hz, 1H), 2.78 (br d, J=14.1 Hz, 1H), 2.65-2.59 (m, 1H), 1.89-1.76 (m, 1H), 1.71-1.60 (m, 1H), 1.54 (s, 6H).

Example 232: Compound 490B: N-{[3-(4-{[(3R,4S)-3-fluoropiperidin-4-yl]amino}-1-(2,2,2-trifluoroethyl)-1H-indol-2-yl)-1,2,4-oxadiazol-5-yl]methyl}-5-(2-methoxypropan-2-yl)thiophene-3-carboxamide The analogue was prepared from Boc-piperidine B using the identical procedure as for the other enantiomer above. N-{[3-(4-{[(3R,4S)-3-fluoropiperidin-4-yl]amino}-1-(2,2, 2-trifluoroethyl)-1H-indol-2-yl)-1,2,4-oxadiazol-5-yl]methyl}-5-(2-methoxypropan-2-yl)thiophene-3-carboxamide LC-MS (ES+, m/z): 595.2 [(M+H)+]. ¹H NMR (400 MHz, DMSO-d6) δ=9.21 (t, J=5.6 Hz, 1H), 8.15 (d, J=1.3 Hz, 1H), 7.90 (s, 1H), 7.43 (d, J=1.5 Hz, 1H), 7.11 (t, J=8.0 Hz, 1H), 6.88 (d, J=8.3 Hz, 1H), 6.30 (d, J=7.9 Hz, 1H), 6.05 (d, J=8.3 Hz, 1H), 5.50 (q, J=8.9 Hz, 2H), 4.87-4.68 (m, 3H), 3.78-3.64 (m, 1H), 3.19-3.12 (m, 1H), 3.06-2.97 (m, 4H), 2.90-2.74 (m, 1H), 2.07 (s, 1H), 1.91 (s, 1H), 1.89-1.76 (m, 1H), 1.69-1.61 (m, 1H), 1.54 (s, 6H).

Example 233: Preparation of THP-Amine A and THP-Amine B

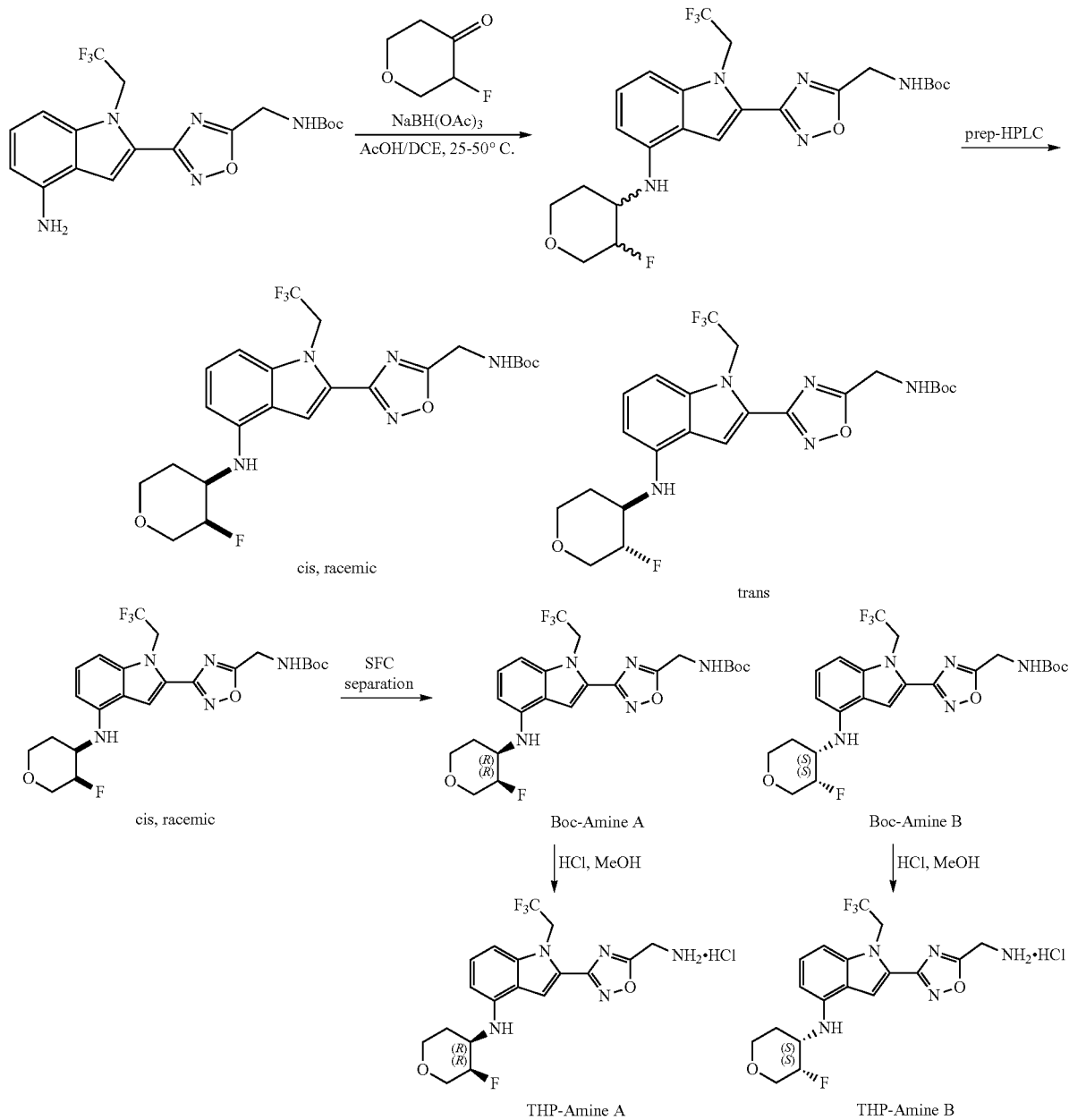

To a mixture of tert-butyl N-[[3-[4-bromo-1-(2,2,2-trifluoroethyl)indol-2-yl]-1,2,4-oxadiazol-5-yl]methyl]carbamate (3 g, 6.31 mmol, 1 eq) and 3-fluorotetrahydropyran-4-one (1.49 g, 12.6 mmol, 2 eq) in acetic acid (45 mL) and DCE (15 mL) was added sodium triacetoxyborohydride (4.01 g, 18.9 mmol, 3 eq) in one portion at 25° C. under nitrogen. The mixture was heated and stirred at 50° C. for 2 h. The reaction mixture was adjusted to pH 9 using saturated sodium carbonate, then extracted with DCM (3×300 mL). The combined organic layers were washed with brine (3×300 mL), dried over sodium sulfate, filtered, and concentrated in vacuo to give a residue. The residue was purified by prep-HPLC (neutral condition: column: Welch Xtimate C18 250×70 mm #10 um; mobile phase:[water (10 mM NH4HCO3)-ACN] B %: 42%-62%, 28 min) to provide the separated cis and trans products.

Cis product (6.1 g, 62.7% yield), a yellow solid. ¹H NMR (400 MHz, DMSO-d6) δ=7.92 (s, 1H), 7.83-7.64 (t, J=5.6 Hz, 1H), 7.17-7.08 (t, J=8.0 Hz, 1H), 6.96-6.87 (d, J=8.0 Hz, 1H), 6.49-6.32 (d, J=7.6 Hz, 1H), 6.17-6.02 (d, J=8.4 Hz, 1H), 5.60-5.40 (dt, J=17.6 Hz, 2H), 4.92-4.65 (d, J=48.8 Hz, 1H), 4.60-4.39 (d, J=5.6 Hz, 2H), 4.02-3.79 (m, 3H), 3.73-3.44 (m, 2H), 2.16-2.00 (m, 1H), 1.77-1.62 (m, 1H), 1.41 (s, 9H).

Trans product (1.4 g, 14.4% yield), a yellow solid. $^1$H NMR (400 MHz, DMSO-d6) δ=7.82 (s, 1H), 7.77-7.71 (t, J=5.6 Hz, 1H), 7.21-7.08 (t, J=8.0 Hz, 1H), 6.96-6.82 (d, J=8.4 Hz, 1H), 6.38-6.30 (d, J=7.6 H, 1H), 6.25-6.11 (d, J=8.0 Hz, 1H), 5.59-5.36 (dt, J=17.6 Hz, 2H), 4.67-4.41 (m, 3H), 4.12-4.00 (m, 1H), 3.94-3.78 (m, 2H), 3.59-3.39 (m, 2H), 2.17-2.04 (m, 1H), 1.63-1.52 (m, 1H), 1.43-1.18 (m, 9H).

The cis-tert-butyl ((3-(4-(((3R,4R)-3-fluorotetrahydro-2H-pyran-4-yl)amino)-1-(2,2,2-trifluoroethyl)-1H-indol-2-yl)-1,2,4-oxadiazol-5-yl)methyl)carbamate was separated by SFC (condition: column: DAICEL CHIRALPAK AD(250 mm×30 mm, 10 um); mobile phase: [0.1% NH3H20 IPA] B %: 56%-56%) to provide the separate enantiomers.

Boc-Amine A: cis-tert-butyl ((3-(4-(((3R,4R)-3-fluorotetrahydro-2H-pyran-4-yl)amino)-1-(2,2,2-trifluoroethyl)-1H-indol-2-yl)-1,2,4-oxadiazol-5-yl)methyl)carbamate (3.1 g, 43.7% yield) as a yellow solid.

Boc-Amine B: cis-tert-butyl ((3-(4-(((3S,4S)-3-fluorotetrahydro-2H-pyran-4-yl)amino)-1-(2,2,2-trifluoroethyl)-1H-indol-2-yl)-1,2,4-oxadiazol-5-yl)methyl)carbamate (3.2 g, 45.1% yield) as a yellow solid.

Each of the resolved cis enantiomers were deprotected separately under the same conditions. To a solution of (Boc-Amine A) tert-butyl N-[[3-[4-[[(3R,4R)-3-fluorotetrahydropyran-4-yl]amino]-1-(2,2,2-trifluoroethyl)indol-2-yl]-1,2,4-oxadiazol-5-yl]methyl]carbamate (2.0 g, 3.9 mmol, 1 eq) in methanol (20 mL) was added HCl (methanol) (4 M, 120 mL, 123.2 eq). The mixture was stirred at 20° C. for 3 h. The reaction mixture was concentrated in vacuo to afford the desired amine hydrochloride salt.

THP-Amine A 2-[5-(aminomethyl)-1,2,4-oxadiazol-3-yl]-N-[(3R,4R)-3-fluorotetrahydropyran-4-yl]-1-(2,2,2-trifluoroethyl)indol-4-amine (2.0 g, 98.2% yield, 3HCl) as a yellow solid. THP-Amine B 2-[5-(aminomethyl)-1,2,4-oxadiazol-3-yl]-N-[(3S,4S)-3-fluorotetrahydropyran-4-yl]-1-(2,2,2-trifluoroethyl)indol-4-amine (2.0 g, 93.6% yield, 3HCl).

Example 234: Compound 491B: N-{[3-(4-1[(3S, 4S)-3-fluorooxan-4-yl]amino}-1-(2,2,2-trifluoroethyl)-1H-indol-2-yl)-1,2,4-oxadiazol-5-yl]methyl}-1-(4-methyloxan-4-yl)-1H-pyrrole-3-carboxamide To a mixture of THP-Amine A (100 mg, 222 μmol, 1 eq, HCl) and the previously prepared 1-(4-methyltetrahydropyran-4-yl)pyrrole-3-carboxylic acid (56.4 mg, 267 μmol, 1.2 eq) in DMF (5 mL) were added HOBt (60.1 mg, 445 μmol, 2 eq), EDCI (85.2 mg, 445 μmol, 2 eq) and DIPEA (2.23 mmol, 390 μL 10 eq) in one portion at 25° C. under nitrogen. The mixture was stirred at 50° C. for 12 h. Water (50 mL) was poured into the mixture, and the aqueous phase was extracted with EA (30 mL×3). The combined organic phase was washed with brine (30 mL×3), dried over anhydrous sodium sulfate, filtered, and concentrated in vacuo. The residue was purified by prep-TLC (DCM:methanol=40:1) to afford the desired product N-{[3-(4-{[(3S,4S)-3-fluorooxan-4-yl]amino}-1-(2,2,2-trifluoroethyl)-1H-indol-2-yl)-1,2,4-oxadiazol-5-yl]methyl}-1-(4-methyloxan-4-yl)-1H-pyrrole-3-carboxamide in 48.4% yield. LC-MS (ES+, m/z): 605.3 [(M+H)+]. $^1$H NMR (400 MHz, DMSO-d6) δ=8.68 (t, J=5.6 Hz, 1H), 7.89 (s, 1H), 7.58 (t, J=2.0 Hz, 1H), 7.12 (t, J=8.1 Hz, 1H), 7.02 (t, J=2.7 Hz, 1H), 6.90 (d, J=8.4 Hz, 1H), 6.55 (dd, J=1.7, 2.9 Hz, 1H), 6.35 (d, J=7.8 Hz, 1H), 6.10 (d, J=8.3 Hz, 1H), 5.58-5.43 (m, 2H), 4.87-4.68 (m, 3H), 4.05-3.83 (m, 3H), 3.72-3.61 (m, 3H), 3.60-3.52 (m, 3H), 2.20-2.08 (m, 3H), 1.91 (br dd, J=3.2, 9.7 Hz, 2H), 1.67 (br d, J=9.9 Hz, 1H), 1.43 (s, 3H).

Example 235: Compound 492B: 1-tert-butyl-N-{[3-(4-{[(3S,4S)-3-fluorooxan-4-yl]amino}-1-(2,2,2-trifluoroethyl)-1H-indol-2-yl)-1,2,4-oxadiazol-5-yl]methyl}-1H-pyrrole-3-carboxamide To a solution of 1-tert-butylpyrrole-3-carboxylic acid (65.7 mg, 373 μmol, 1.2 eq) in DMF (4 mL) were added PYBOP (242.9 mg, 467 μmol, 1.5 eq) and DIEA (3.11 mmol, 540 μL 10 eq). THP-Amine B (140 mg, 311 μmol, 1 eq, HCl) was then added to the mixture, which was stirred at 25° C. for 1h. The reaction mixture was diluted with water (50 mL) and extracted with EA (2×25 mL). The combined organic layers were washed with brine (50 mL), dried over sodium sulfate, filtered, and concentrated to give a residue. The residue was purified by prep-TLC (SiO$_2$, PE:EA=1:2) to give the desired product 1-tert-butyl-N-{[3-(4-{[(3S,4S)-3-fluorooxan-4-yl]amino}-1-(2,2,2-trifluoroethyl)-1H-indol-2-yl)-1,2,4-oxadiazol-5-yl]methyl}-1H-pyrrole-3-carboxamide (52.7 mg, 29.9% yield, 99.2% purity). LC-MS (ES+, m/z): 563.2 [(M+H)+]. $^1$H NMR (400 MHz, DMSO-d6) δ=8.63 (t, J=5.6 Hz, 1H), 7.86 (s, 1H), 7.52 (t, J=2.0 Hz, 1H), 7.17-7.06 (m, 1H), 6.97 (t, J=2.6 Hz, 1H), 6.87 (d, J=8.4 Hz, 1H), 6.48 (dd, J=1.8, 2.9 Hz, 1H), 6.32 (d, J=7.9 Hz, 1H), 6.07 (d, J=8.4 Hz, 1H), 5.48 (q, J=8.9 Hz, 2H), 4.85-4.66 (m, 3H), 4.04-3.76 (m, 3H), 3.68-3.43 (m, 2H), 2.01 (br dd, J=4.3, 12.5 Hz, 1H), 1.65 (br dd, J=4.1, 13.6 Hz, 1H), 1.47 (s, 9H).

Example 236: Compound 493B: 1-tert-butyl-N-{[3-(4-{[(3R,4R)-3-fluorooxan-4-yl]amino}-1-(2,2,2-trifluoroethyl)-1H-indol-2-yl)-1,2,4-oxadiazol-5-yl]methyl}-1H-pyrrole-3-carboxamide The 3R, 4R enantiomer was prepared under identical conditions to the other enantiomer using THP-Amine A (150 mg, 1 eq, HCl) to provide the desired product 1-tert-butyl-N-{[3-(4-{[(3R,4R)-3-fluorooxan-4-yl]amino}-1-(2,2,2-trifluoroethyl)-1H-indol-2-yl)-1,2,4-oxadiazol-5-yl]methyl}-1H-pyrrole-3-carboxamide in 29.2% yield. LC-MS (ES+, m/z): 563.3 [(M+H)+]. $^1$H NMR (400 MHz, DMSO-d6) δ=8.65 (t, J=5.7 Hz, 1H), 7.89 (s, 1H), 7.55 (t, J=2.1 Hz, 1H), 7.18-7.06 (m, 1H), 6.99 (t, J=2.6 Hz, 1H), 6.89 (d, J=8.4 Hz, 1H), 6.50 (dd, J=1.8, 2.9 Hz, 1H), 6.35 (d, J=7.7 Hz, 1H), 6.09 (d, J=8.4 Hz, 1H), 5.51 (q, J=9.0 Hz, 2H), 4.89-4.68 (m, 3H), 4.05-3.90 (m, 2H), 3.83 (br s, 1H), 3.70-3.55 (m, 1H), 3.51 (brt, J=11.4 Hz, 1H), 2.10-1.96 (m, 1H), 1.74-1.63 (m, 1H), 1.49 (s, 9H).

Example 237: Compound 494B: N-((3-(4-(((3R,4R)-3-fluorotetrahydro-2H-pyran-4-yl)amino)-1-(2,2,2-trifluoroethyl)-1H-indol-2-yl)-1,2,4-oxadiazol-5-yl)methyl)-1-(4-methyltetrahydro-2H-pyran-4-yl)-1H-pyrrole-3-carboxamide THP-Amine B (150 mg, 333 μmol, 1 eq, HCl) and 1-(4-methyltetrahydropyran-4-yl)pyrrole-3-carboxylic acid (84.6 mg, 400 μmol, 1.2 eq) were coupled under the identical conditions as for the enantiomer to provide the desired product N-((3-(4-(((3R,4R)-3-fluorotetrahydro-2H-pyran-4- yl)amino)-1-(2,2,2-trifluoroethyl)-1H-indol-2-yl)-1,2,4-oxadiazol-5-yl)methyl)-1-(4-methyltetrahydro-2H-pyran-4-yl)-1H-pyrrole-3-carboxamide (51.2 mg, 24.2% yield, 95.1% purity). LC-MS (ES+, m/z): 605.2 [(M+H)+]. $^1$H NMR (400 MHz, DMSO-d6) δ=8.67 (t, J=5.6 Hz, 1H), 7.89 (s, 1H), 7.59 (t, J=2.0 Hz, 1H), 7.17-7.09 (m, 1H), 7.02 (t, J=2.6 Hz, 1H), 6.90 (d, J=8.4 Hz, 1H), 6.55 (dd, J=1.8, 2.9 Hz, 1H), 6.35 (d, J=7.7 Hz, 1H), 6.09 (d, J=8.4 Hz, 1H), 5.51 (q, J=8.9 Hz, 2H), 4.93-4.69 (m, 3H), 4.03-3.79 (m, 3H), 3.71-3.62 (m, 1H), 3.71-3.46 (m, 5H), 2.18-2.09 (m, 2H), 2.06-1.98 (m, 1H), 1.92 (ddd, J=3.3, 6.7, 13.4 Hz, 2H), 1.67 (br dd, J=3.5, 12.8 Hz, 1H), 1.46-1.40 (m, 3H).

Example 238: Compound 495B: N-{[3-(4-{[(3R,4R)-3-fluorooxan-4-yl]amino}-1-(2,2,2-trifluoroethyl)-1H-indol-2-yl)-1,2,4-oxadiazol-5-yl]methyl}-1-[1-(methoxymethyl)cyclopropyl]-1H-pyrrole-3-carboxamide

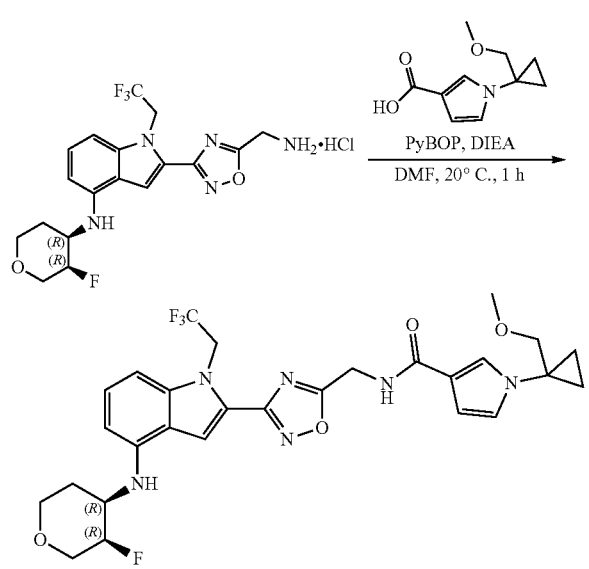

To a solution THP-Amine A (0.14 g, 311 μmol, 1 eq, HCl) and the previously prepared 1-[1-(methoxymethyl)cyclopropyl]pyrrole-3-carboxylic acid (72.9 mg, 373 μmol, 1.2 eq) in DMF (1 mL) were added PYBOP (323.9 mg, 622.5 μmol, 2 eq) and DIPEA (3.10 mmol, 540 μL 10 eq). The mixture was stirred at 20° C. for 20 min. The reaction mixture was quenched with water (10 mL) and extracted with EA (10 mL×3). The combined organic layers were washed with brine (10 mL×3), dried over sodium sulfate, filtered, and concentrated in vacuo to give a residue. The residue was purified by prep-TLC (SiO$_2$, PE:EA=1:2) to afford the desired product N-{[3-(4-{[(3R,4R)-3-fluorooxan-4-yl]amino}-1-(2,2,2-trifluoroethyl)-1H-indol-2-yl)-1,2,4-oxadiazol-5-yl]methyl}-1-[1-(methoxymethyl)cyclopropyl]-1H-pyrrole-3-carboxamide in 32.6% yield. LC-MS (ES+, m/z): 591.2 [(M+H)-]. $^1$H NMR (400 MHz, DMSO-d6) δ=8.79-8.48 (t, J=5.6 Hz, 1H), 7.89 (s, 1H), 7.45 (s, 1H), 7.27-7.07 (t, J=8.0 Hz, 1H), 6.96-6.75 (m, 2H), 6.60-6.41 (t, J=2.0 Hz, 1H), 6.39-6.26 (d, J=8.0 Hz, 1H), 6.15-5.99 (d, J=8.4 Hz, 1H), 5.60-5.39 (dt, J=17.6 Hz, 2H), 4.88-4.59 (m, 3H), 4.04-3.77 (m, 3H), 3.71-3.44 (m, 4H), 3.32 (s, 3H), 2.11-1.96 (m, 1H), 1.73-1.61 (m, 1H), 1.14-0.92 (m, 4H).

Example 239: Compound 496B: N-{[3-(4-{[(3S,4S)-3-fluorooxan-4-yl]amino}-1-(2,2,2-trifluoroethyl)-1H-indol-2-yl)-1,2,4-oxadiazol-5-yl]methyl}-1-[1-(methoxymethyl)cyclopropyl]-1H-pyrrole-3-carboxamide Using an identical procedure as for the other enantiomer, the desired product was obtained from THP-Amine B and 1-[1-(methoxymethyl)cyclopropyl]pyrrole-3-carboxylic acid to provide N-{[3-(4-{[(3S,4S)-3-fluorooxan-4-yl]amino}-1-(2,2,2-trifluoroethyl)-1H-indol-2-yl)-1,2,4-oxadiazol-5-yl]methyl}-1-[1-(methoxymethyl)cyclopropyl]-1H-pyrrole-3-carboxamide in 29.9% yield. LC-MS (ES+, m/z): 591.3 [(M+H)+]. $^1$H NMR (400 MHz, DMSO-d6) δ=8.70 (t, J=5.7 Hz, 1H), 7.89 (s, 1H), 7.45 (t, J=1.9 Hz, 1H), 7.12 (t, J=8.1 Hz, 1H), 6.94-6.85 (m, 2H), 6.46 (dd, J=1.8, 2.8 Hz, 1H), 6.35 (d, J=7.9 Hz, 1H), 6.11 (br d, J=8.4 Hz, 1H), 5.51 (q, J=8.8 Hz, 2H), 4.89-4.70 (m, 3H), 3.99 (br t, J=12.2 Hz, 1H), 3.94-3.79 (m, 2H), 3.70-3.55 (m, 11H), 3.54-3.48 (m, 1H), 3.46 (s, 2H), 3.21 (s, 3H), 2.03 (br dd, J=4.5, 12.3 Hz, 1H), 1.73-1.61 (m, 1H), 1.13-1.07 (m, 2H), 1.04-0.96 (m, 2H).

Example 240: Compound 497B: 1-tert-butyl-N-{[3-(4-{[(3R,4R)-3-fluorooxan-4-yl]amino}-1-(2,2,2-trifluoroethyl)-1H-indol-2-yl)-1,2,4-oxadiazol-5-yl]methyl}-1H-pyrazole-4-carboxamide The analogue was prepared using THP-Amine A and 1-t-butylpyrazole-4-carboxylic acid, following the identical procedure as for the above analog to give the desired product 1-tert-butyl-N-{[3-(4-{[(3R,4R)-3-fluorooxan-4-yl]amino}-1-(2,2,2-trifluoroethyl)-1H-indol-2-yl)-1,2,4-oxadiazol-5-yl]methyl}-1H-pyrazole-4-carboxamide in 39.9% yield. LC-MS (ES+, m/z): 564.1 [(M+H)+]. $^1$H NMR (400 MHz, DMSO-d6) δ=9.11-8.72 (t, J=5.6 Hz, 1H), 8.34 (s, 1H), 7.93 (s, 1H), 7.89 (s, 1H), 7.18-7.08 (t, J=8.0 Hz, 1H), 6.94-6.82 (d, J=8.0 Hz, 1H), 6.41-6.30 (d, J=8.0 Hz, 1H), 6.14-6.03 (d, J=8.0 Hz, 11H), 5.58-5.42 (dt, J=17.6 Hz, 2H), 4.88-4.71 (m, 3H), 4.05-3.78 (m, 3H), 3.71-3.45 (m, 2H), 2.08-1.97 (m, 1H), 1.72-1.60 (m, 1H), 1.54 (s, 9H).

Example 241: Compound 498B: 1-tert-butyl-N-{[3-(4-{[(3S,4S)-3-fluorooxan-4-yl]amino}-1-(2,2,2-trifluoroethyl)-1H-indol-2-yl)-1,2,4-oxadiazol-5-yl]methyl}-1H-pyrazole-4-carboxamide The analogue was prepared using THP-Amine B and 1-t-butylpyrazole-4-carboxylic acid, following the identical procedure as for the enantiomer to give the desired product 1-tert-butyl-N-{[3-(4-{[(3S,4S)-3-fluorooxan-4-yl]amino}-1-(2,2,2-trifluoroethyl)-1H-indol-2-yl)-1,2,4-oxadiazol-5-yl]methyl}-1H-pyrazole-4-carboxamide in 29.0% yield. LC-MS (ES+, m/z): 564.3 [(M+H)+]. $^1$H NMR (400 MHz, DMSO-d6) δ=8.98 (t, J=5.6 Hz, 1H), 8.34 (s, 1H), 7.93 (s, 1H), 7.89 (s, 1H), 7.12 (t, J=8.0 Hz, 1H), 6.90 (d, J=8.2 Hz, 1H), 6.35 (d, J=7.8 Hz, 1H), 6.11 (d, J=8.3 Hz, 1H), 5.51 (q, J=8.8 Hz, 2H), 4.90-4.70 (m, 3H), 3.99 (br t, J=12.2 Hz, 1H), 3.94-3.77 (m, 1H), 3.70-3.55 (m, 1H), 3.51 (br t, J=11.6 Hz, 1H), 2.03 (br dd, J=4.4, 12.5 Hz, 1H), 1.73-1.62 (m, 1H), 1.54 (s, 9H).

Example 242: Compound 557B: 6-(dimethylamino)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}pyridine-3-carboxamide

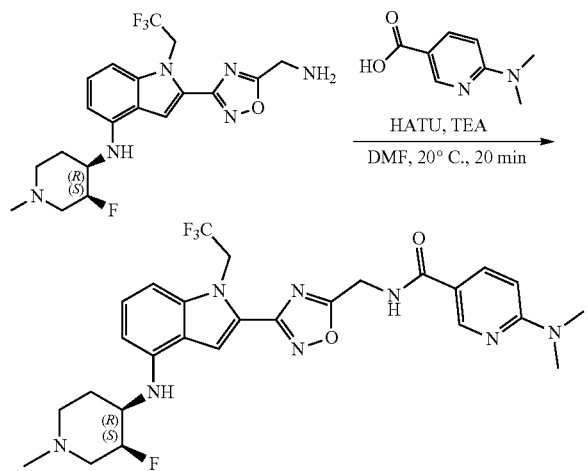

To a solution of 6-(dimethylamino)pyridine-3-carboxylic acid (30.2 mg, 181.5 μmol, 1.2 eq) in DMF (1 mL) were added HATU (115 mg, 302.4 μmol, 2 eq) and TEA (1.51 mmol, 210 mL, 10 eq) at 20° C. The mixture was stirred at this temperature for 10 min, then Amine 1 (70 mg, 151 μmol, 1 eq, HCl) was added at 20° C. The resulting mixture was stirred at 20° C. for 10 min, then quenched by adding water (100 mL) and extracted with EA (3×30 mL). The combined organic layers were washed with brine (3×20 mL), dried over anhydrous sodium sulfate, filtered, and concentrated in vacuo to give a residue. The residue was purified by prep-TLC (SiO$_2$, DCM: methanol=10:1) to afford the desired product 6-(dimethylamino)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}pyridine-3-carboxamide (30 mg, 33.8% yield, 98% purity) as a yellow solid. LC-MS (ES$^+$, m/z): 575.2 [(M+H)$^+$]. $^1$H NMR (400 MHz, DMSO-d6) δ=9.13 (t, J=5.6 Hz, 1H), 8.74-8.59 (d, J=2.0 Hz, 1H), 8.06-7.95 (dt, J=8.8 Hz, 1H), 7.90 (s, 1H), 7.24-7.08 (t, J=8.0 Hz, 1H), 7.00-6.81 (d, J=8.8 Hz, 1H), 6.75-6.65 (d, J=8.4 Hz, 1H), 6.39-6.22 (d, J=8.0 Hz, 1H), 6.10-5.93 (d, J=8.4 Hz, 1H), 5.62-5.38 (dt, J=17.6 Hz, 2H), 4.96-4.70 (m, 3H), 3.66-3.52 (m, 1H), 3.14 (br s, 6H), 3.07-3.00 (m, 1H), 2.87-2.78 (m, 1H), 2.32-2.15 (m, 4H), 2.12-2.06 (m, 1H), 2.04-1.94 (m, 1H), 1.73-1.62 (m, 1H).

Example 243: Compound 499B: N-{[3-(4-{[(3S,4S)-3-fluorooxan-4-yl]amino}-1-(2,2,2-trifluoroethyl)-1H-indol-2-yl)-1,2,4-oxadiazol-5-yl]methyl}-5-(2-methoxypropan-2-yl)thiophene-3-carboxamide The analogue was prepared under method D using THP-Amine B and the previously prepared 5-(]-methoxy-1-methyl-ethyl)thiophene-3-carboxylic acid, following the identical procedure as for the above analogues to give the desired product N-{[3-(4-{[(3S,4S)-3-fluorooxan-4-yl]amino}-(2,2,2-trifluoroethyl)-1H-indol-2-yl)-1,2,4-oxadiazol-5-yl]methyl}-5-(2-methoxypropan-2-yl)thiophene-3-carboxamide in 28.6% yield. LC-MS (ES$^+$, m/z): 564.2 [(M-OMe)$^+$]. $^1$H NMR (400 MHz, DMSO-d6) δ=9.24 (t, J=5.4 Hz, 1H), 8.16 (d, J=1.2 Hz, 1H), 7.90 (s, 1H), 7.44 (d, J=1.2 Hz, 1H), 7.16-7.09 (m, 1H), 6.90 (d, J=8.3 Hz, 1H), 6.35 (d, J=7.9 Hz, 1H), 6.12 (d, J=8.2 Hz, 1H), 5.51 (q, J=8.8 Hz, 2H), 4.88-4.72 (m, 3H), 4.04-3.95 (m, 1H), 3.94-3.79 (m, 2H), 3.70-3.55 (m, 1H), 3.51 (br t, J=11.4 Hz, 1H), 3.04 (s, 3H), 2.02 (br dd, J=4.4, 12.5 Hz, 1H), 1.67 (br dd, J=3.0, 12.8 Hz, 1H), 1.54 (s, 6H).

Example 244: Compound 500B:N-{[3-(4-{[(3R,4R)-3-fluorooxan-4-yl]amino}-1-(2,2,2-trifluoroethyl)-1H-indol-2-yl)-1,2,4-oxadiazol-5-yl]methyl}-5-(2-methoxypropan-2-yl)thiophene-3-carboxamide The analogue was prepared under method D using THP-Amine B and the previously prepared 5-(1-methoxy-1-methyl-ethyl)thiophene-3-carboxylic acid, following the identical procedure as for the enantiomer to give the desired product N-{[3-(4-{[(3R,4R)-3-fluorooxan-4-yl]amino}-1-(2,2,2-trifluoroethyl)-1H-indol-2-yl)-1,2,4-oxadiazol-5-yl]methyl}-5-(2-methoxypropan-2-yl)thiophene-3-carboxamide in 28.6% yield. LC-MS (ES$^+$, m/z): 596.2 [(M-OMe)]. $^1$H NMR (400 MHz, DMSO-d6) δ=9.24 (t, J=5.4 Hz, 1H), 8.16 (d, J=1.2 Hz, 1H), 7.90 (s, 1H), 7.44 (d, J=1.2 Hz, 1H), 7.16-7.09 (m, 1H), 6.90 (d, J=8.3 Hz, 1H), 6.35 (d, J=7.9 Hz, 1H), 6.12 (d, J=8.2 Hz, 1H), 5.51 (q, J=8.8 Hz, 2H), 4.88-4.72 (m, 3H), 4.04-3.95 (m, 1H), 3.94-3.79 (m, 2H), 3.70-3.55 (m, 1H), 3.51 (br t, J=11.4 Hz, 1H), 3.04 (s, 3H), 2.02 (br dd, J=4.4, 12.5 Hz, 1H1), 1.67 (br dd, J=3.0, 12.8 Hz, 1H), 1.54 (s, 6H).

Example 245: Compound 501B: 6-tert-butyl-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}pyridine-3-carboxamide 6-tert-butylpyridine-3-carboxylic acid (32.5 mg, 181 μmol, 1.2 eq) was coupled with Amine 1 (70 mg, 151 μmol, 1 eq, HCl) under method B. The crude product was purified by prep-TLC (SiO$_2$, DCM:methanol=10:1) to afford the desired product 6-tert-butyl-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}pyridine-3-carboxamide (30 mg, 32.8% yield, 97% purity) as a yellow solid. LC-MS (ES$^+$, m/z): 588.1 [(M+H)$^+$]. $^1$H NMR (400 MHz, DMSO-d6) δ=9.69-9.39 (t, J=5.6 Hz, 1H), 9.12-8.97 (d, J=2.4 Hz, 1H), 8.33-8.14 (dt, J=8.4 Hz, 11H), 7.89 (s, 1H), 7.72-7.54 (d, J=8.41z, 1H), 7.27-7.03 (t, J=8.0 Hz, 1H), 6.97-6.82 (d, J=8.4 Hz, 1H), 6.35-6.22 (d, J=8.0 Hz, 1H), 6.08-5.95 (d, J=8.4 Hz, 1H), 5.68-5.39 (dt, J=17.6 Hz, 2H), 5.00-4.69 (m, 3H), 3.67-3.51 (m, 1H), 3.12-2.99 (m, 1H), 2.88-2.76 (m, 1H), 2.29-2.15 (m, 4H), 2.12-1.94 (m, 2H), 1.72-1.62 (m, 1H), 1.34 (s, 9H).

Example 246: Compound 502B: 1-tert-butyl-N-{[3-(4-{[(3S,4R)-3-fluoropiperidin-4-yl]amino}-1-(2,2,2-trifluoroethyl)-1H-indol-2-yl)-1,2,4-oxadiazol-5-yl]methyl}-1H-pyrrole-3-carboxamide

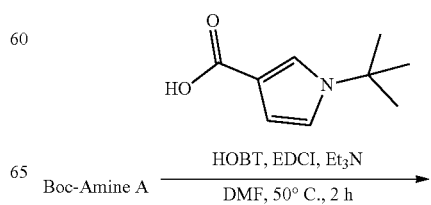

-continued

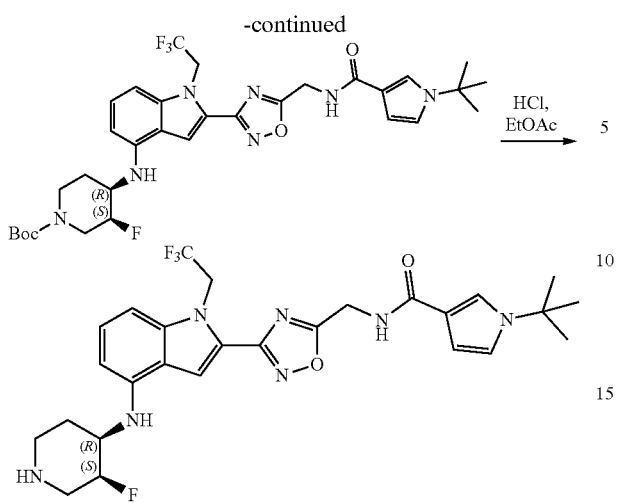

A mixture of Boc-Amine A (60 mg, 117 μmol, 1 eq) and 1-tert-butylpyrrole-3-carboxylic acid (23.5 mg, 140.5 μmol, 1.2 eq) were coupled under method A. The crude reaction was purified by prep-TLC (SiO$_2$, PE:EA=1:1) to provide the intermediate tert-butyl (3S,4R)-4-[[2-[5-[[(1-tert-butylpyrrole-3-carbonyl)amino]methyl]-1,2,4-oxadiazol-3-yl]-1-(2,2,2-trifluoroethyl)indol-4-yl]amino]-3-fluoro-piperidine-1-carboxylate (50 mg, 75.6 μmol, 64.5% yield) as white solid. LC-MS (ES$^+$, m/z): 661.3 [(M+H)$^+$].

Tert-butyl (3S,4R)-4-[[2-[5-[1(1-tert-butylpyrrole-3-carbonyl)amino]methyl]-1,2,4-oxadiazol-3-yl]-1-(2,2,2-trifluoroethyl)indol-4-yl]amino]-3-fluoro-piperidine-1-carboxylate (40 mg, 60.5 μmol, 1 eq) was added to HCl/EA (4 M, 1 mL, 66 eq), and the mixture was stirred at 25° C. for 0.5 h under nitrogen atmosphere. The reaction mixture was concentrated in vacuo to give a residue. The residue was washed with 5 mL EA to provide 1-tert-butyl-N-{[3-(4-{[(3S,4R)-3-fluoropiperidin-4-yl]amino}-1-(2,2,2-trifluoroethyl)-1H-indol-2-yl)-1,2,4-oxadiazol-5-yl]methyl}-1H-pyrrole-3-carboxamide (23.3 mg, 64.5% yield, 100% purity, HCl) as a white solid. LC-MS (ES$^+$, m/z): 561.3 [(M+H)$^+$]. $^1$H NMR (400 MHz, DMSO-d6) δ=9.24-9.09 (m, 1H), 8.73-8.56 (m, 2H), 7.88 (s, 1H), 7.59-7.53 (m, 1H), 7.15 (t, J=8.0 Hz, 1H), 7.03-6.90 (m, 2H), 6.54-6.47 (m, 1H), 6.35 (d, J=8.1 Hz, 1H), 6.30-6.15 (m, 1H), 6.31-6.12 (m, 1H), 5.60-5.45 (m, 2H), 5.24-4.98 (m, 1H), 4.73 (d, J=5.5 Hz, 2H), 4.07-3.86 (m, 1H), 3.68-3.52 (m, 1H), 3.50-3.36 (m, 2H), 3.19-3.01 (m, 1H), 2.23-2.04 (m, 1H), 1.98-1.84 (m, 1H), 1.50-1.40 (m, 9H). $^1$H NMR (400 MHz, DMSO-d6) δ=7.83 (s, 1H), 7.52 (t, J=2.1 Hz, 1H), 7.18-7.11 (m, 1H), 6.98 (t, J=2.6 Hz, 1H), 6.91 (d, J=8.4 Hz, 1H), 6.49 (dd, J=1.8, 2.9 Hz, 1H), 6.35 (d, J=8.2 Hz, 1H), 5.48 (q, J=8.5 Hz, 2H), 5.03 (br s, 1H), 4.70 (s, 2H), 4.03-3.88 (m, 1H), 3.62-3.58 (m, 1H), 3.43-3.30 (m, 2H), 3.13-3.06 (m, 1H), 3.11-3.03 (m, 1H), 2.20-2.02 (m, 1H), 1.93 (br d, J=11.5 Hz, 1H), 1.45 (br s, 9H).

Example 247: Compound 503B: N-{[3-(4-{[(3S,4R)-3-fluoropiperidin-4-yl]amino}-1-(2,2,2-trifluoroethyl)-1H-indol-2-yl)-1,2,4-oxadiazol-5-yl]methyl)-5-[1-(methoxymethyl)cyclopropyl]thiophene-2-carboxamide

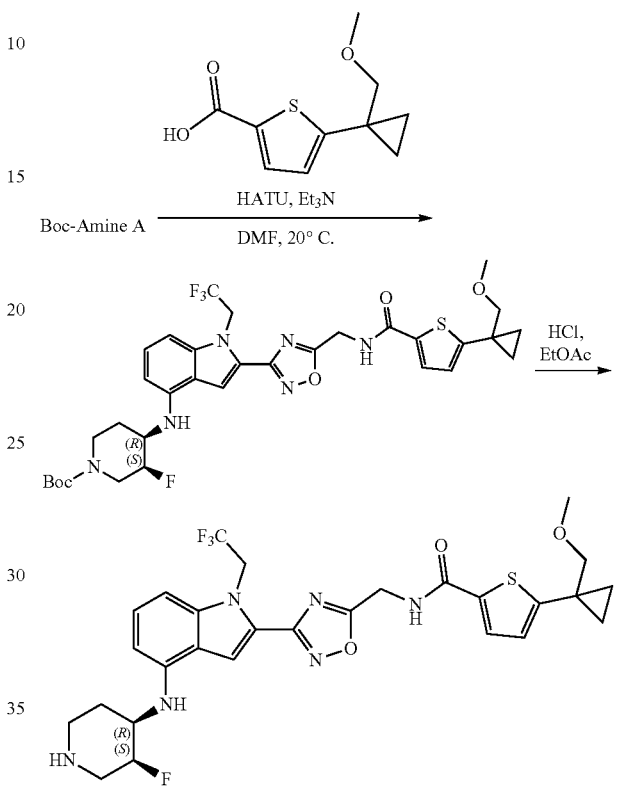

5-[1-(methoxymethyl)cyclopropyl]thiophene-2-carboxylic acid (29 mg, 137 μmol, 1 eq) was coupled with Boc-Amine A (70 mg, 137 μmol, 1 eq) under method B. The crude reaction was purified by prep-TLC (PE/EA=1:2) to afford the intermediate (60 mg, 62.2% yield) as a yellow solid.

To a solution of tert-butyl (3S,4R)-3-fluoro-4-[[2-[5-[[[5-[1-(methoxymethyl) cyclopropyl]thiophene-2-carbonyl]amino]methyl]-1,2,4-oxadiazol-3-yl]-1-(2,2,2-trifluoroethyl)indol-4-yl]amino]piperidine-1-carboxylate (60 mg, 84.9 μmol, 1 eq) in EA (2 mL) was added HCl(EA) (4 M, 6 mL).The mixture was stirred at 20° C. for 0.5 h. The reaction mixture was concentrated in vacuo to give a residue. The crude product was triturated with EA (10 mL) for 10 min, and the solid filtered and dried to afford the desired product N-{[3-(4-{[(3S,4R)-3-fluoropiperidin-4-yl]amino}-1-(2,2,2-trifluoroethyl)-1H-indol-2-yl)-1,2,4-oxadiazol-5-yl]methyl}-5-[1-(methoxymethyl)cyclopropyl]thiophene-2-carboxamide (30 mg, 55.3% yield, 95% purity) as a yellow solid. LC-MS (ES$^+$, m/z): 607.0 [(M+H)$^+$]. $^1$H NMR (400 MHz, DMSO-d6) δ=9.37-9.25 (t, J=5.6 Hz, 1H), 9.17-9.03 (m, 1H), 8.83-8.51 (m, 1H), 7.89 (s, 1H), 7.74-7.60 (d, J=4.0 Hz, 1H), 7.23-7.08 (d, J=8.0 Hz, 1H). 6.99-6.88 (m, 2H), 6.45-6.31 (d, J=7.6 Hz, 111), 6.29-6.19 (d, J=8.0 Hz, 1H), 5.67-5.40 (dt, J=17.6 Hz, 2H), 5.24-4.95 (d, J=46.8 Hz, 11), 4.85-4.70 (d, J=6.0 Hz, 2H), 4.06-3.86 (m, 1H), 3.64-3.54

(m, 1H), 3.47 (s, 2H), 3.45 (br s, 1H1), 3.27 (s, 3H), 3.15-3.03 (m, 1H), 2.20-2.06 (m, 1H), 1.97-1.84 (m, 1H), 1.06-0.94 (m, 4H).

Example 248: Synthesis of 3-Methyl-Amine A and 3-Methyl-Amine B

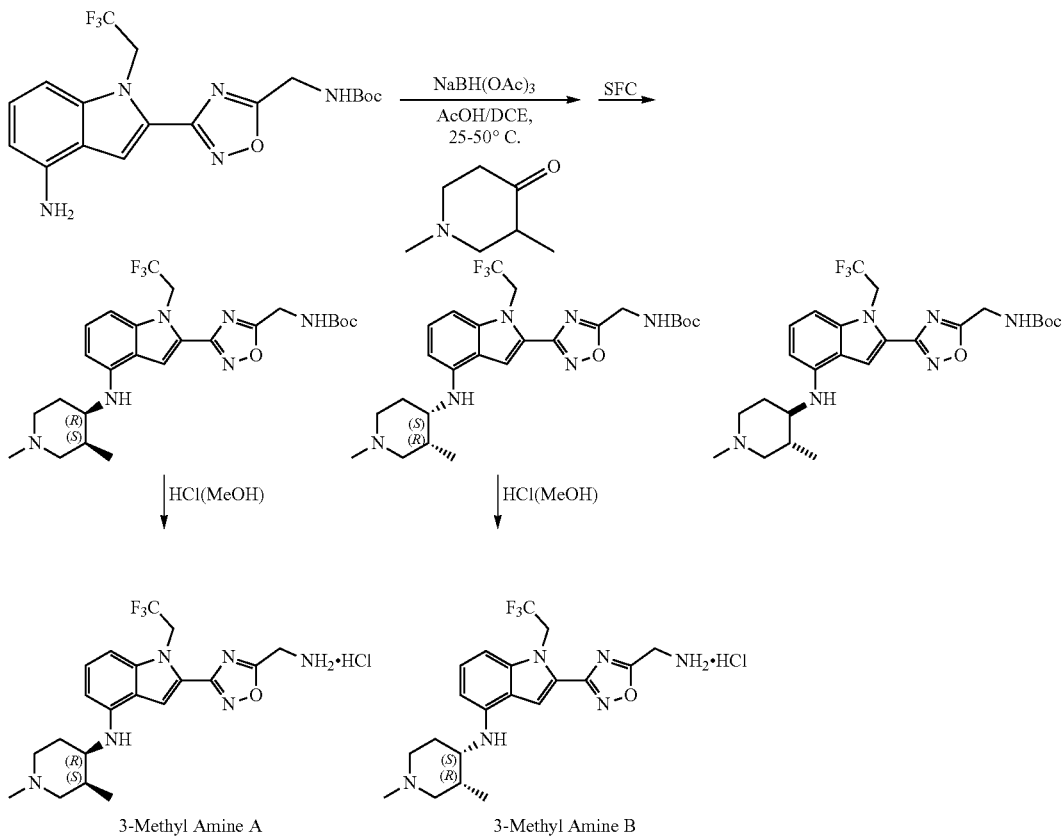

To a mixture of the previously prepared tert-butyl N-[[3-[4-amino-1-(2,2,2-trifluoroethyl)indol-2-yl]-1,2,4-oxadiazol-5-yl]methyl]carbamate (3 g, 7.29 mmol, 1 eq) and 1,3-dimethylpiperidin-4-one (2.78 g, 21.9 mmol, 3 eq) in acetic acid (45 mL) and DCE (15 mL) was added sodium triacetoxyborohydride (4.64 g, 21.9 mmol, 3 eq) at 25° C. under nitrogen. The mixture was stirred at 50° C. for 2 h. Sodium carbonate (sat.) was added to the mixture, and the pH was adjusted to 8-10, and then diluted with water (500 mL) and extracted with (250 mL×2). The combined organic layers were washed with brine (200 mL), dried over sodium sulfate, filtered, and concentrated in vacuo to give a residue. The residue was purified by column chromatography (SiO₂, DCM: methanol=50/1 to 10/1) to afford tert-butyl N-[[3-[4-[(1,3-dimethyl-4-piperidyl)amino]-1-(2,2,2-trifluoroethyl) indol-2-yl]-1,2,4-oxadiazol-5-yl]methyl]carbamate (3.2 g, 84.0% yield), a white solid, as a mixture of stereoisomers.

Tert-butyl N-[[3-[4-[(1,3-dimethyl-4-piperidyl)amino]-1-(2,2,2-trifluoroethyl)indol-2-yl]-1,2,4-oxadiazol-5-yl]methyl]carbamate (3.8 g) was purified by SFC: (column: REGIS (s,s) WHELK-01 (250 mm×50 mm, 10 um); mobile phase: [0.1% NH3H₂O ETOH]; B %: 42%). The residue was further purified by SFC (column: DAICEL CHIRALPAK AD(250 mm×30 mm, 10 um); mobile phase: [0.1% NH3H₂O IPA]; B %: 55%) to afford the separated cis isomers. tert-butyl N-[[3-[4-[[(3S,4R)-1,3-dimethyl-4-piperidyl]amino]-1-(2,2,2-trifluoroethyl)indol-2-yl]-1,2,4-oxadiazol-5-yl]methyl]carbamate (1.3, 34.2% yield) was obtained as white solid.

Trans (racemic): Tert-butyl N-[[3-[4-[[(3R,4R)-1,3-dimethyl-4-piperidyl]amino]-1-(2,2,2-trifluoroethyl)indol-2-yl]-1,2,4-oxadiazol-5-yl]methyl]carbamate (0.85 g, 22.4% yield) was obtained as white solid. Tert-butyl N-[[3-[4-[[(3R,4S)-1,3-dimethyl-4-piperidyl]amino]-1-(2,2,2-trifluoroethyl)indol-2-yl]-1,2,4-oxadiazol-5-yl]methyl]carbamate (1.3 g, 34.2% yield) was obtained as white solid. $^1$H NMR (400 MHz, DMSO-d6) δ=8.00 (s, 1H), 7.82-7.90 (m, 1H), 7.19-7.15 (m, 1H), 6.91-6.89 (d, J=8.0 Hz, 1H), 6.30-6.26 (m, 1H), 5.86 (s, 1H), 5.59-5.53 (m, 1H), 4.59-4.58 (d, J=8.0 Hz, 2H), 3.64 (s, 1H), 2.79-2.73 (m, 2H), 2.29 (s, 4H), 2.01-1.94 (m, 1H), 1.69-1.63 (m, 1H), 1.35 (s, 2H), 1.00-0.99 (d, J=4 Hz, 3H). Tert-butyl N-[[3-[4-[[(3S,4R)-1,3-dimethyl-4-piperidyl]amino]-1-(2,2,2-trifluoroethyl)indol-2-yl]-1,2,4-oxadiazol-5-yl]methyl]carbamate (1.3 g, 2.49 mmol, 1 eq) was added to HCl(methanol) (4 M, 50.00 mL, 80.4 eq) and the reaction was stirred at 25° C. for 0.5 h. The reaction mixture was concentrated in vacuo to give the desired enantiomerically pure Cis product 3-Methyl Amine A: 2-[5-(aminomethyl)-1,2,4-oxadiazol-3-yl]-N-[(3S,4R)-1,3-dimethyl-4-piperidyl]-1-(2,2,2-trifluoroethyl)indol-4-amine (1.3 g, crude, HCl) was obtained as white solid. LC-MS (ES⁻, m/z): 423.2 [(M+H)⁺]. 3-Methyl Amine B: The synthesis followed the identical procedure as for the enantiomer to provide 2-[5-(aminomethyl)-1,2,4-oxadiazol-3-yl]-N-[(3R,4S)-1,3-dimethyl-4-piperidyl]-1-(2,2,2-trifluoroethyl)indol-4-amine (1.3 g, crude, HCl) was obtained as white solid. LC-MS (ES⁺, m/z): 423.2 [(M+H)⁺].

Example 249: Compound 5041B: N-{[3-(4-{[(3S,4R)-1,3-dimethylpiperidin-4-yl]amino}-1-(2,2,2-trifluoroethyl)-1H-indol-2-yl)-1,2,4-oxadiazol-5-yl]methyl}-1-[1-(methoxymethyl)cyclopropyl]-1H-pyrrole-3-carboxamide

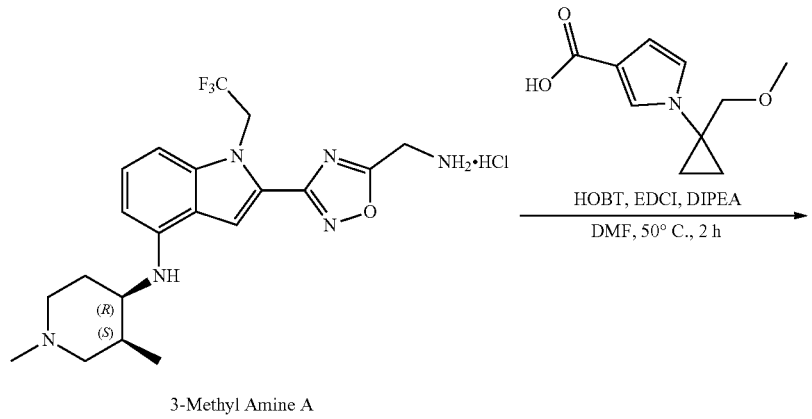

3-Methyl Amine A

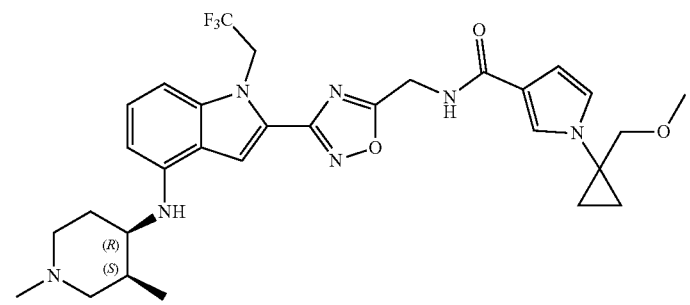

3-Methyl-Amine A (140 mg, 275 µmol, 1 eq, HCl) was coupled with 1-[1-(methoxymethyl)cyclopropyl]pyrrole-3-carboxylic acid (64.3 mg, 329 µmol, 1.2 eq) under method A. The crude product was purified by prep-TLC (SiO$_2$, DCM: methanol=10:1) to afford the desired product N-{[3-(4-{[(3S,4R)-1,3-dimethylpiperidin-4-yl]amino}-1-(2,2,2-trifluoroethyl)-1H-indol-2-yl)-1,2,4-oxadiazol-5-yl]methyl}-1-[1-(methoxymethyl)cyclopropyl]-1H-pyrrole-3-carboxamide (70 mg, 42.5% yield) as a yellow solid. LC-MS (ES$^+$, m:z): 600.2 [(M+H)$^+$]. $^1$H NMR (400 MHz, DMSO-d6) δ=8.77-8.61 (m, 1H), 7.96-7.87 (m, 1H), 7.52-7.43 (m, 1H), 7.17-7.07 (m, 1H), 6.89-6.85 (m, 1H), 6.85-6.80 (m, 1H), 6.50-6.44 (m, 1H), 6.27-6.17 (m, 1H), 5.84-5.75 (m, 1H), 5.55-5.42 (m, 2H), 4.76-4.68 (m, 2H), 3.60-3.51 (m, 1H), 3.49-3.45 (m, 2H), 3.41-3.36 (m, 1H), 3.25-3.19 (m, 3H), 2.67 (br s, 1H), 2.61-2.56 (m, 1H), 2.25-2.06 (m, 5H), 1.96-1.82 (m, 1H), 1.66-1.50 (m, 1H), 1.11-0.98 (m, 4H), 0.92 (d, J=6.8 Hz, 3H).

Example 250: Compound 506B: N-{[3-(4-{[(3R,4R)-3-fluorooxan-4-yl]amino}-1-(2,2,2-trifluoroethyl)-1H-indol-2-yl)-1,2,4-oxadiazol-5-yl]methyl}-5-(2-methoxypropan-2-yl)thiophene-2-carboxamide THP-Amine A (140 mg, 339 µmol, 1 eq) was coupled with 5-(1-methoxy-1-methyl-ethyl)thiophene-2-carboxylic acid (81.4 mg, 406.42 µmol, 1.2 eq) in DMF (5 mL) under method A. The crude product was purified by prep-TLC (PE:EA=1:1; R$_f$=0.3) to afford the desired product N-{[3-(4-{[(3R,4R)-3-fluorooxan-4-yl]amino}-1-(2,2,2-trifluoroethyl)-1H-indol-2-yl)-1,2,4-oxadiazol-5-yl]methyl}-5-(2-methoxypropan-2-yl)thiophene-2-carboxamide (54.9 mg, 95.8% purity, 26% yield). LC-MS (ES$^+$, m/z): 596.2 [(M+H)$^+$]. $^1$H NMR (400 MHz, DMSO-d6) δ=9.38 (t, J=5.7 Hz, 1H), 7.90 (s, 1H), 7.71 (d, J=3.8 Hz, 1H), 7.13 (t, J=8.0 Hz, 1H), 7.07 (d, J=3.9 Hz, 1H), 6.90 (d, J=8.3 Hz, 1H), 6.35 (d, J=7.9 Hz, 1H), 6.11 (br d, J=8.4 Hz, 1H), 5.51 (q, J=8.8 Hz, 2H), 4.90-4.71 (m, 3H), 3.99 (br t, J=12.0 Hz, 1H), 3.94-3.78 (m, 2H), 3.71-3.55 (m, 1H), 3.54-3.46 (m, 1H), 3.06 (s, 3H), 2.02 (br dd, J=4.2, 12.7 Hz, 11H), 1.71-1.64 (m, 1H), 1.53 (s, 6H).

Example 251: Compound 507B: N-{[3-(4-{[(3R,4R)-3-fluorooxan-4-yl]amino}-1-(2,2,2-trifluoroethyl)-1H-indol-2-yl)-1,2,4-oxadiazol-5-yl]methyl)-5-[1-(methoxymethyl)cyclopropyl]thiophene-3-carboxamide 5-[1-(methoxymethyl)cyclopropyl]thiophene-3-carboxylic acid (36.3 mg, 171 µmol, 1.1 eq) was coupled with THP-Amine A (70 mg, 156 µmol, 1 eq, HCl) under method D. The crude product was purified by prep-TLC (SiO$_2$, PE:EA=1:2) to give the desired product N-{[3-(4-{[(3R,4R)-3-fluorooxan-4-yl]amino}-1-(2,2,2-trifluoroethyl)-1H-indol-2-yl)-1,2,4-oxadiazol-5-yl]methyl}-5-[1-(methoxymethyl)cyclopropyl]thiophene-3-carboxamide (24.3 mg, 25.7% yield, 100% purity) as a white solid. LC-MS (ES$^+$, m/z): 608.3 [(M+H)$^+$]. $^1$H NMR (400 MHz, DMSO-d6) δ=9.16 (t, J=5.6 Hz, 1H), 7.99 (d, J=1.2 Hz, 1H), 7.93-7.85 (m, 1H), 7.31 (d, J=1.3 Hz, 1H), 7.13 (t, J=8.0 Hz, 1H), 6.90 (d, J=8.3 Hz, 1H), 6.35 (d, J=7.8 Hz, 1H), 6.12 (d, J=8.3 Hz, 1H), 5.61-5.45 (m, 2H), 4.88-4.69 (m, 3H), 4.05-3.77 (m, 3H), 3.67 (br d, J=13.1 Hz, 2H), 3.46 (s, 2H), 3.28 (s, 3H), 2.02 (br s, 1H), 1.69 (br d, J=2.9 Hz, 1H), 1.06-0.90 (m, 4H).

Example 252: Compound 508B: N-{[3-(4-{1[(3R,4R)-3-fluorooxan-4-yl]amino}-1-(2,2,2-trifluoroethyl)-1H-indol-2-yl)-1,2,4-oxadiazol-5-yl]methyl}-5-(1-methoxy-2-methylpropan-2-yl)thiophene-3-carboxamide THP-Amine A (70 mg, 153 μmol, 1 eq, HCl) was coupled with 5-(2-methoxy-1,1-dimethyl-ethyl)thiophene-3-carboxylic acid (65.4 mg, 305 μmol, 2 eq) under method A. The crude product was purified by prep-TLC (SiO₂, PE:EA=1:1) to afford the desired product N-{[3-(4-{[(3R,4R)-3-fluorooxan-4-yl]amino}-1-(2,2,2-trifluoroethyl)-1H-indol-2-yl)-1,2,4-oxadiazol-5-yl]methyl}-5-(1-methoxy-2-methylpropan-2-yl)thiophene-3-carboxamide (30 mg, 32.0% yield, 99% purity) as a yellow solid. LC-MS (ES⁺, m/z): 610.1 [(M+H)⁺]. ¹H NMR (400 MHz, DMSO-d6) δ=9.31-9.07 (t, J=5.6 Hz, 1H), 8.17-7.96 (d, J=0.8 Hz, 1H), 7.89 (s, 1H), 7.45-7.25 (d, J=1.2 Hz, 1H), 7.19-7.04 (t, J=8.0 Hz, 1H), 6.95-6.77 (t, J=8.4 Hz, 1H), 6.40-6.27 (t, J=7.6 Hz, 1H), 6.17-5.91 (t, J=7.6 Hz, 1H), 5.74-5.27 (dt, J=17.6 Hz, 2H), 4.95-4.63 (m, 3H), 4.06-3.78 (m, 3H), 3.68-3.46 (m, 2H), 3.33-3.31 (m, 2H), 3.26 (s, 3H), 2.07- 1.97 (m, 1H), 1.71-1.62 (m, 1H), 1.32 (s, 6H).

Example 253: Compound 509B: N-{[3-(4-{1[(3S,4R)-1,3-dimethylpiperidin-4-yl]amino}-1-(2,2,2-trifluoroethyl)-1H-indol-2-yl)-1,2,4-oxadiazol-5-yl]methyl}-5-(2-hydroxypropan-2-yl)thiophene-2-carboxamide 3-Methyl Amine A (150 mg, 327 μmol, 1 eq, HCl) was coupled with 5-(1-hydroxy-1-methyl-ethyl)thiophene-2-carboxylic acid (73.1 mg, 392 μmol, 1.2 eq) under method A. The crude reaction was purified by prep-TLC (SiO₂, DCM:methanol=10:1) to afford the desired product N-{[3-(4-{[(3S,4R)-1,3-dimethylpiperidin-4-yl]amino}-1-(2,2,2-trifluoroethyl)-1H-indol-2-yl)-1,2,4-oxadiazol-5-yl]methyl}-5-(2-hydroxypropan-2-yl)thiophene-2-carboxamide (62 mg, 30.8% yield, 96% purity) was obtained as a yellow solid. LC-MS (ES⁺, m:z): 591.1 [(M+H)⁺]. ¹H NMR (400 MHz, DMSO-d6) δ=9.36-9.13 (t, J=4.8 Hz, 1H), 7.91 (s, 1H), 7.71-7.55 (d, J=4.0 Hz, 1H), 7.25-7.04 (t, J=4.0 Hz, 1H), 7.03-6.92 (d, J=4.0 Hz, 1H), 6.89-6.75(d, J=8.4 Hz, 1H), 6.30-6.14 (d, J=8.4 Hz, 1H), 5.85-5.71 (m, 1H), 5.62 (s, 1H), 5.55-5.40 (dt, J=17.6 Hz, 2H), 4.85-4.72 (d, J=9.6 Hz, 2H), 3.67-3.49 (m, 1H), 2.76-2.66 (m, 2H), 2.29-2.05 (m, 6H), 1.94-1.86 (m, 1H), 1.66-1.56 (m, 1H), 1.50 (s, 6H), 0.95-0.87 (d, J=6.8 Hz, 3H).

Example 254: Compound 510B: 1-tert-butyl-N-{[3-(4-{[(3S,4R)-1,3-dimethylpiperidin-4-yl]amino}-1-(2,2,2-trifluoroethyl)-1H-indol-2-yl)-1,2,4-oxadiazol-5-yl]methyl}-1H-pyrazole-4-carboxamide 3-Methyl Amine A (140 mg, 305 μmol, 1 eq, HCl) was coupled with 1-tert-butylpyrazole-4-carboxylic acid (61.6 mg, 366 μmol, 1.2 eq) under method D. The crude product was purified by prep-TLC (SiO₂,DCM/methanol=10/1) to afford the desired product 1-tert-butyl-N-{[3-(4-{[(3S,4R)-1,3-dimethylpiperidin-4-yl]amino}-1-(2,2,2-trifluoroethyl)-1H-indol-2-yl)-1,2,4-oxadiazol-5-yl]methyl}-1H-pyrazole-4-carboxamide (70.1 mg, 39.7% yield, 99.1% purity) as a yellow solid. LC-MS (ES⁺, m/z): 573.2 [(M+H)⁺]. ¹H NMR (400 MHz, DMSO-d6) δ=8.98 (t, J=5.7 Hz, 1H), 8.34 (s, 1H), 7.98-7.86 (m, 214), 7.19-7.03 (m, 1H), 6.84 (d, J=8.1 Hz, 1H), 6.22 (d, J=7.8 Hz, 1H), 5.79 (s, 1H), 5.50 (q, J=8.9 Hz, 2H), 4.78 (d, J=5.6 Hz, 2H), 3.67-3.50 (m, 1H), 2.89- 2.67 (m, 1H), 2.30-2.07 (m, 4H), 2.01-1.82 (m, 1H), 1.74-1.59 (m, 1H), 1.54 (s, 10H), 1.58-1.46 (m, 1H), 0.92 (d, J=7.0 Hz, 31H).

Example 255: Compound 511B: 1-tert-butyl-N-{[3-(4-{[(3R,4S)-1,3-dimethylpiperidin-4-yl]amino}-1-(2,2,2-trifluoroethyl)-1H-indol-2-yl)-1,2,4-oxadiazol-5-yl]methyl}-1H-pyrazole-4-carboxamide The analogue was prepared using the same procedure as for the enantiomer. 3-Methyl Amine B (150 mg, 355 μmol, 1 eq, HCl) and 1-tert-butylpyrazole-4-carboxylic acid (65.7 mg, 391 μmol, 1.1 eq) provided the desired product (69.2 mg, 33.5% yield, 98.6% purity) as yellow solid. LC-MS (ES⁺, m/z): 573.2 [(M+H)⁺]. ¹H NMR (400 MHz, DMSO-d6) δ=8.98 (t, J=5.6 Hz, 1H), 8.34 (s, 1H), 7.98-7.84 (m, 21H), 7.11 (t, J=8.1 Hz, 1H), 6.85 (d, J=8.1 Hz, 1H), 6.23 (d, J=7.8 Hz, 1H), 5.78 (s, 1H), 5.50 (q, J=8.7 Hz, 2H), 4.78 (d, J=5.6 Hz, 2H), 3.64 (s, 1H), 2.88-2.71 (m, 1H), 2.33 (s, 2H), 2.23 (s, 2H), 1.99-1.87 (m, 114), 1.68 (d, J=13.6 Hz, 1H), 1.54 (s, 9H), 0.92 (d, J=7.0 Hz, 3H).

Example 256: Compound 512B: 1-tert-butyl-N-{[3-(4-{[(3S,4R)-3-fluorooxan-4-yl]amino}-1-(2,2,2-trifluoroethyl)-1H-indol-2-yl)-1,2,4-oxadiazol-5-yl]methyl}-1H-pyrrole-3-carboxamide

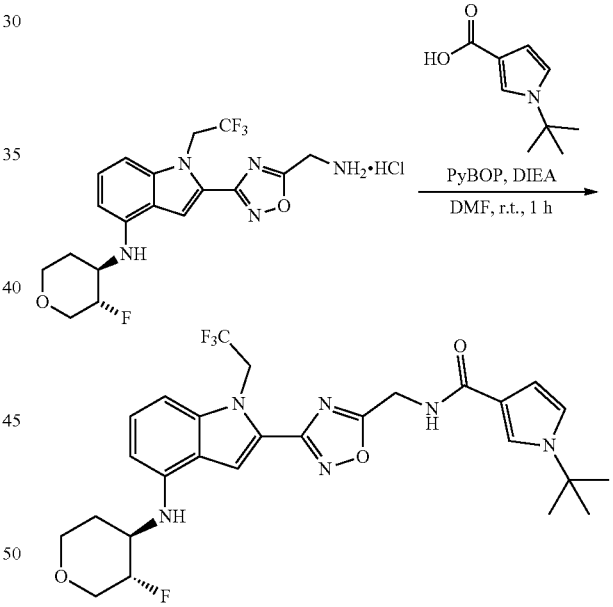

1-tert-butylpyrrole-3-carboxylic acid (32.7 mg, 186 μmol, 1.1 eq) was coupled with the previously prepared trans 3-fluoro-THP intermediate (76 mg, 169 μmol, 1 eq, HCl) using method D. The crude product was purified by prep-TLC (SiO₂, PE:EA=1:1) to provide the desired product 1-tert-butyl-N-{[3-(4-{[(3S,4R)-3-fluorooxan-4-yl]amino}-1-(2,2,2-trifluoroethyl)-1H-indol-2-yl)-1,2,4-oxadiazol-5-yl]methyl}-1H-pyrrole-3-carboxamide (20 mg, 20.2% yield, 95.8% purity) as a white solid. LC-MS (ES⁺, m/z): 563.3 [(M+H)⁺]. ¹H NMR (400 MHz, DMSO-d6) δ=8.64 (t, J=5.6 Hz, 1H), 7.79 (s, 1H), 7.55 (t, J=2.0 Hz, 1H), 7.21-7.05 (m, 1H), 6.99 (t, J=2.7 Hz, 1H), 6.88 (d, J=8.3 Hz, 1H), 6.51 (dd, J=1.8, 2.9 Hz, 1H), 6.33 (d, J=7.8 Hz, 1H), 6.17 (d, J=7.9 Hz, 1H), 5.51 (q, J=8.8 Hz, 2H), 4.74 (d, J=5.6 Hz, 2H), 4.60 (dt, J=4.5, 8.0 Hz, 1H), 4.03 (dt, J=4.3, 10.8 Hz, 1H), 3.94-3.73 (m, 2H), 3.58-3.34 (m, 2H), 2.32-2.04 (m, 1H), 1.65-1.42 (m, 9H).

Example 257: Compound 513B: 1-tert-butyl-N-{[3-(4-{[(3R,4S)-1,3-dimethylpiperidin-4-yl]amino}-1-(2,2,2-trifluoroethyl)-1H-indol-2-yl)-1,2,4-oxadiazol-5-yl]methyl}-1H-pyrrole-3-carboxamide 3-Methyl Amine B (150 mg, 355 µmol, 1 eq) was coupled with 1-tert-butylpyrrole-3-carboxylic acid (71.2 mg, 426 µmol, 1.2 eq) under method A. The crude product was purified by prep-TLC (SiO$_2$, DCM:methanol=10:1) to provide the desired product 1-tert-butyl-N-{[3-(4-{[(3R,4S)-1,3-dimethylpiperidin-4-yl]amino}-1-(2,2,2-trifluoroethyl)-1H-indol-2-yl)-1,2,4-oxadiazol-5-yl]methyl}-1H-pyrrole-3-carboxamide (60 mg, 28.8% yield, 97.4% purity). LC-MS (ES$^+$, m/z): 572.3 [(M+H)$^+$]. $^1$H NMR (400 MHz, DMSO-d6) δ=8.72-8.59 (m, 1H), 8.69-8.53 (m, 1H), 7.91 (s, 1H), 7.55 (s, 1H), 7.19-7.05 (m, 1H), 6.99 (t, J=2.6 Hz, 1H), 6.83 (br d, J=8.2 Hz, 11H), 6.57-6.44 (m, 1H), 6.22 (br d, J=7.5 Hz, 1H), 5.88-5.70 (m, 1H), 5.59-5.39 (m, 2H), 4.73 (d, J=5.7 Hz, 2H), 3.69-3.45 (m, 1H), 3.29 (s, 1H), 2.85-2.71 (m, 1H), 2.63-2.57 (m, 1H), 2.33-2.06 (m, 5H), 1.98-1.85 (m, 1H), 1.67-1.55 (m, 1H), 1.49 (s, 9H), 0.92 (d, J=6.8 Hz, 3H).

Example 258: Compound 514B: 1-tert-butyl-N-{[3-(4-{[(3S,4R)-1,3-dimethylpiperidin-4-yl]amino}-1-(2,2,2-trifluoroethyl)-1H-indol-2-yl)-1,2,4-oxadiazol-5-yl]methyl}-1H-pyrrole-3-carboxamide The analogue was prepared using the same procedure as for the enantiomer. 3-Methyl Amine A (140 mg, 305 µmol, 1 eq, HCl) and 1-tert-butylpyrrole-3-carboxylic acid (61.2 mg, 366 µmol, 1.2 eq) provided the desired product 1-tert-butyl-N-{[3-(4-{[(3S,4R)-1,3-dimethylpiperidin-4-yl]amino}-1-(2,2,2-trifluoroethyl)-1H-indol-2-yl)-1,2,4-oxadiazol-5-yl]methyl}-1H-pyrrole-3-carboxamide (63.9 mg, 36.6% yield, 100% purity). LC-MS (ES$^+$, m/z): 572.4 [(M+H)$^+$]. $^1$H NMR (400 MHz, DMSO-d6) δ=8.64 (t, J=5.6 Hz, 1H), 7.91 (s, 1H), 7.55 (t, J=1.9 Hz, 1H), 7.10 (t, J=8.0 Hz, 1H), 6.99 (t, J=2.5 Hz, 1H), 6.83 (br d, J=8.8 Hz, 1H), 6.50 (dd, J=1.8, 2.9 Hz, 1H), 6.27-6.18 (m, 1H), 5.84-5.73 (m, 1H), 5.49 (q, J=9.0 Hz, 2H), 4.73 (d, J=5.5 Hz, 2H), 3.66-3.52 (m, 1H), 3.29 (br s, 1H), 2.79-2.69 (m, 1H), 2.57 (br d, J=1.3 Hz, 1H), 2.36-2.09 (m, 4H), 1.99-1.83 (m, 1H), 1.67-1.56 (m, 1H), 1.49 (s, 9H), 0.92 (d, J=6.8 Hz, 3H).

Example 259: Compound 515B: N-{[3-(4-{[(3R,4S)-1,3-dimethylpiperidin-4-yl]amino}-1-(2,2,2-trifluoroethyl)-1H-indol-2-yl)-1,2,4-oxadiazol-5-yl]methyl)-5-(2-hydroxypropan-2-yl)thiophene-2-carboxamide The analogue was prepared using the same procedure as was used for the enantiomer. 3-Methyl Amine A provided the desired product in 32.3% yield. LC-MS (ES$^+$, m/z): 591.3 [(M+H)$^+$]. $^1$H NMR (400 MHz, DMSO-d6) δ=9.27 (br t, J=5.4 Hz, 1H), 7.91 (s, 1H), 7.66 (d, J=3.7 Hz, 1H), 7.10 (t, J=7.9 Hz, 1H), 6.98 (d, J=3.7 Hz, 1H), 6.83 (br d, J=8.4 Hz, 1H), 6.21 (br d, J=7.7 Hz, 1H), 5.85-5.74 (m, 1H), 5.62 (s, 1H), 5.49 (q, J=8.5 Hz, 2H), 4.80 (br d, J=5.5 Hz, 2H), 3.56 (br s, 11H), 3.31-3.28 (m, 1H), 2.79-2.64 (m, 2H), 2.21 (br s, 5H), 1.90 (br d, J=9.7 Hz, 1H), 1.61 (br s, 1H), 1.50 (s, 6H), 0.92 (br d, J=6.8 Hz, 3H).

Example 260: Compound 516B: N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-{8-oxa-3-azabicyclo[3.2.1]octan-3-yl}-1,3-thiazole-4-carboxamide

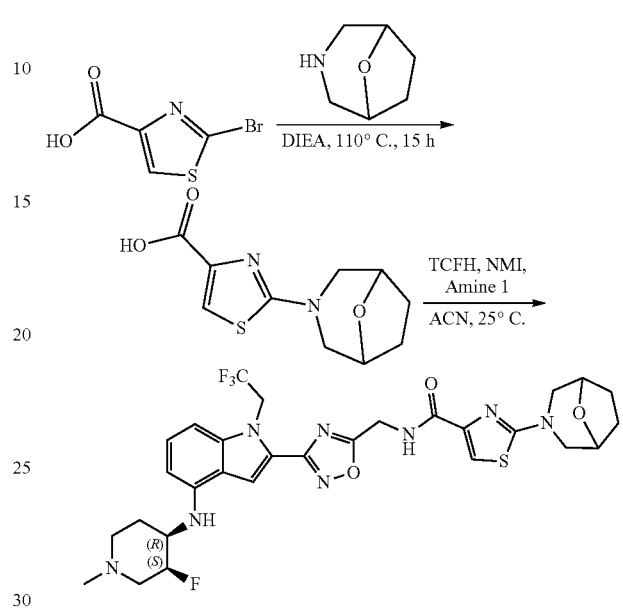

A mixture of 2-bromothiazole-4-carboxylic acid (0.5 g, 2.40 mmol, 1 eq), (1R,5S)-8-oxa-3-azabicyclo[3.2.1]octane (251.7 mg, 1.68 mmol, 0.7 eq, HCl) and DIEA (57.4 mmol, 10 mL, 23.9 eq) was stirred at 110° C. for 15 h in a sealed tube. The reaction mixture was concentrated in vacuo to give a residue, which was purified by prep-HPLC (column: Phenomenex luna C18 80×40 mm×3 um; mobile phase: [water (0.04% HCl)-ACN] B %: 4%-24%, 7 min) to afford the product (0.2 g, 41.2% yield, 96% purity, HCl) as a yellow solid. LC-MS (ES$^+$, m:z): 241.0 [(M+H)$^+$].

Amine 1 (0.13 g, 260 µmol, 1 eq, 2 HCl) was coupled with 2-(8-oxa-3-azabicyclo[3.2.1]octan-3-yl)thiazole-4-carboxylic acid (86.5 mg, 312 µmol, 1.2 eq, HCl) under method E. The crude product was purified by prep-TLC (PE:EA=5:1) to afford the desired product N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-{8-oxa-3-azabicyclo[3.2.1]octan-3-yl}-1,3-thiazole-4-carboxamide (55.2 mg, 32.7% yield, 98.5% purity) as a yellow solid. LC-MS (ES$^+$, m/z): 640.1 [(M+H)$^+$]. $^1$H NMR (400 MHz, DMSO-d6) δ=8.98-8.83 (t, J=2.0 Hz, 1H), 7.89 (s, 1H), 7.50 (s, 1H), 7.17-7.03 (t, J=8.0 Hz, 1H), 6.95-6.81 (d, J=8.0 Hz, 1H), 6.40-6.22 (d, J=7.6 Hz, 1H), 6.14-5.94 (d, J=8.0 Hz, 1H), 5.66-5.38 (dt, J=17.6 Hz, 2H), 4.94-4.73 (m, 3H), 4.54-4.39 (m, 2H), 3.67-3.51 (m, 3H), 3.26-3.20 (m, 2H), 3.08-2.99 (m, 1H), 2.88-2.76 (m, 1H), 2.31-2.17 (m, 4H), 2.14-2.06 (m, 1H), 2.05-1.96 (m, 1H), 1.93-1.84 (m, 2H), 1.83-1.73 (m, 2H), 1.72-1.63 (m, 1H).

Example 261: Compound 517B: 2-[(2S,6S)-2,6-dimethylmorpholin-4-yl]-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1,3-thiazole-4-carboxamide The analogue was prepared using the same process as for the 8-oxa-3-azabicyclo[3.2.1]octane analog previously described. 2-bromothiazole-4-carboxylic acid (500 mg, 2.40 mmol, 1 eq) and racemic, trans-(2S,6S)-2,6-dimethylmorpholine (1 g, 8.68 mmol, 1 mL, 3.6 eq) after HPLC purification provided the product 2-[(2S,6S)-2,6-dimethylmorpholin-4-yl]thiazole-4-carboxylic acid (300 mg, 51.5% yield) as yellow solid. LC-MS (ES$^+$, m/z): 243.1 [(M+H)$^-$].

Amine 1 (140 mg, 280 μmol, 1 eq, 2HCl) was coupled with 2-[(2S,6S)-2,6-dimethylmorpholin-4-yl]thiazole-4-carboxylic acid (101.9 mg, 421 μmol, 1.5 eq) under method A. The crude product was purified by prep-TLC (SiO$_2$, DCM/MEOH=10/1) to afford 2-[(2S,6S)-2,6-dimethylmorpholin-4-yl]-N-[[3-[4-[[(3S,4R)-3-fluoro-1-methyl-4-piperidyl]amino]-1-(2,2,2-trifluoroethyl)indol-2-yl]-1,2,4-oxadiazol-5-yl]methyl]thiazole-4-carboxamide (59.4 mg, 30.9% yield, 95% purity) as a white solid. LC-MS (ES$^+$, m/z): 651.0 [(M+H)$^+$]. $^1$H NMR (400 MHz, DMSO-d6) δ=8.93 (t, J=6.0 Hz, 1H), 7.89 (s, 1H), 7.51 (s, 1H), 7.12 (t, J=8.1 Hz, 1H), 6.88 (d, J=8.4 Hz, 1H), 6.28 (d, J=7.9 Hz, 1H), 6.04 (d, J=8.3 Hz, 1H), 5.50 (q, J=9.0 Hz, 2H), 4.96-4.72 (m, 3H), 4.15-4.01 (m, 2H), 3.60 (dd, J=3.3, 12.5 Hz, 3H), 3.18 (dd, J=6.1, 12.5 Hz, 2H), 3.06 (s, 1H), 2.83 (d, J=9.7 Hz, 1H), 2.29-2.08 (m, 5H), 2.06-1.94 (m, 1H), 2.06-1.94 (m, 1H), 1.69 (d, J=10.9 Hz, 1H), 1.19 (d, J=6.4 Hz, 6H).

Example 262: Compound 518B: N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-(4-methoxypiperidin-1-yl)-1,3-thiazole-4-carboxamide

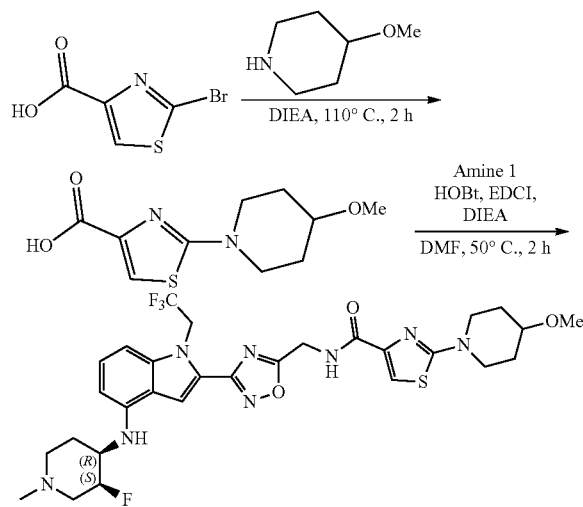

2-bromothiazole-4-carboxylic acid (500 mg, 2.40 mmol, 1 eq) and 4-methoxypiperidine (276.8 mg, 2.40 mmol, 1 eq) were added to DIEA (17.2 mmol, 3 mL, 7.2 eq) in a sealed tube, and the mixture was stirred at 110° C. for 2 h. The reaction mixture was dried by nitrogen flow to give a residue. The residue was purified by prep-HPLC (TFA condition: column: Phenomenex luna C18 250×50 mm×10 um; mobile phase: [water (0.04% HCl)-ACN]; B %: 5%-35%, 10 min) to provide 2-(4-methoxy-1-piperidyl)thiazole-4-carboxylic acid (500 mg, 85.9% yield) as a white solid. LC-MS (ES$^+$, m/z): 242.1 [(M+H)$^+$]. $^1$H NMR (400 MHz, DMSO-d6) δ=8.98-8.52 (m, 1H), 7.61 (s, 1H), 3.70-3.61 (m, 2H), 3.71-3.60 (m, 1H), 3.10 (br d, J=7.1 Hz, 3H), 2.98-2.88 (m, 1H), 2.00-1.85 (m, 2H), 1.71-1.61 (m, 1H), 1.52 (dtd, J=4.1, 8.6, 12.8 Hz, 2H).

2-(4-methoxy-1-piperidyl)thiazole-4-carboxylic acid (109.93 mg, 454 μmol, 1.5 eq) was coupled with Amine 1 (140 mg, 302 μmol, 1 eq, HCl) under method A.

The crude reaction was purified by prep-TLC (SiO$_2$, DCM: methanol=20:1) to provide the desired product N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-(4-methoxypiperidin-1-yl)-1,3-thiazole-4-carboxamide (55 mg, 27.8% yield, 99.3% purity) as a light yellow solid. LC-MS (ES$^+$, m/z): 650.3 [(M+H)$^+$]. $^1$H NMR (400 MHz, DMSO-d6) δ=8.94 (t, J=6.0 Hz, 1H), 7.90 (s, 1H), 7.48 (s, 1H), 7.11 (t, J=8.1 Hz, 1H), 6.88 (d, J=8.3 Hz, 1H), 6.28 (d, J=7.8 Hz, 1H), 6.04 (d, J=8.4 Hz, 1H), 5.50 (q, J=8.9 Hz, 2H), 4.92-4.72 (m, 3H), 3.79-3.69 (m, 2H), 3.49-3.40 (m, 1H), 3.29 (s, 3H), 3.11-2.98 (m, 1H), 2.82 (br d, J=10.1 Hz, 1H), 1.72-1.63 (m, 1H), 1.59-1.48 (m, 2H).

Example 263: Compound 519B: N-{[3-(4-{1[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-[(2S)-2-(methoxymethyl)pyrrolidin-1-yl]-1,3-thiazole-4-carboxamide The aminothiazole carboxylic acid was prepared using the same procedure as was used for the-methoxypiperidine analogue. 2-bromothiazole-4-carboxylic acid (0.5 g, 2.40 mmol, 1 eq) and (2S)-2-(methoxymethyl)pyrrolidine (8.09 mmol, 1 mL, 3.4 eq) provided the crude product, which was purified by prep-HPLC (column: Welch Xtimate C18 150× 25 mm×5 um; mobile phase: [water (0.04% HCl)-ACN]; B %: 1%-15%, 8 min) to afford the product (0.14 g, 19.9% yield, 95.3% purity, HCl) as a yellow solid. LC-MS (ES$^+$, m:z): 243.0 [(M+H)$^+$].

Amine 1 (0.05 g, 100 μmol, 1 eq, 2HCl) was coupled with 2-[(2S)-2-(methoxymethyl)pyrrolidin-1-yl]thiazole-4-carboxylic acid (35.2 mg, 120 μmol, 1.2 eq, HCl) under method E. The crude product was purified by prep-TLC (DCM: methanol=5:1) to afford the desired product N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-[(2S)-2-(methoxymethyl)pyrrolidin-1-yl]-1,3-thiazole-4-carboxamide (20.7 mg, 31.8% yield, 98.5% purity) as a yellow solid. LC-MS (ES$^+$, m/z): 65 1.1 [(M+H)$^+$]. $^1$H NMR (400 MHz, DMSO-d6) δ=8.90-8.60 (t, J=6.0 Hz, 1H), 7.89(s, 1H), 7.42 (s, 1H), 7.19-7.03 (t, J=8.0 Hz, 1H), 6.92-6.73 (d, J=8.0 Hz, 1H), 6.35-6.23 (d, J=8.0 Hz, 1H), 6.12-5.97 (d, J=8.0 Hz, 1H), 5.59-5.42 (dt, J=17.6 Hz, 2H), 4.94-4.71 (m, 3H), 4.09- 3.94 (m, 1H), 3.65-3.44 (m, 4H), 3.39-3.34 (m, 1H), 3.29 (s, 311), 3.10-2.99 (m, 1H), 2.90-2.76 (m, 1H), 2.32-2.15 (m, 4H), 2.14-1.91 (m, 6H), 1.75-1.62 (m, 1H).

Example 264: Compound 520B: N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-[(2R)-2-(methoxymethyl)pyrrolidin-1-yl]-1,3-thiazole-4-carboxamide The analoge was prepared using the same procedure as was used for the enantiomer. 2-bromothiazole-4-carboxylic acid (0.5 g, 2.40 mmol, 1 eq) and (2R)-2-(methoxymethyl) pyrrolidine (829 mg, 7.20 mmol, 3 eq) provided the product (0.5 g, 74.7% yield, HCl) after HPLC purification. as a yellow solid.

Amine 1 (0.05 g, 100 μmol, 1 eq, 2HCl) and 2-[(2R)-2-(methoxymethyl)pyrrolidin-1-yl]thiazole-4-carboxylic acid (33.5 mg, 120.2 μmol, 1.2 eq, HCl) were coupled under method E. TLC (DCM:methanol=5:1, R$_f$=0.6) indicated that one new spot formed. The reaction was worked up and purified as for the enantiomer to provide the desired product N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-[(2R)-2-(methoxymethyl)pyrrolidin-1-yl]-1,3-thiazole-4-carboxamide (25.6 mg, 39.3% yield, 99.7% purity) as a light yellow solid. LC-MS (ES$^+$, m:z): 651.1 [(M+H)$^+$]. $^1$H NMR (400 MHz, DMSO-d6) δ=8.85-8.67 (t, J=6.0 Hz, 1H), 7.89 (s, 1H), 7.42 (s, 1H), 7.18-7.04 (t, J=8.0 Hz, 1H), 6.93-6.75 (d, J=8.4 Hz, 1H), 6.35-6.21 (d, J=8.0 Hz, 1H), 6.11-5.94 (d, J=8.0 Hz, 1H), 5.65-5.37 (dt, J=17.6 Hz, 2H), 4.97-4.70 (m, 3H), 4.12-3.97 (m, 1H), 3.66-3.43 (m, 4H), 3.40-3.33 (m, 1H), 3.29 (s, 3H), 3.11-3.00 (m, 1H), 2.88-2.76 (m, 1H), 2.33-2.16 (m, 4H), 2.13-1.88 (m, 6H), 1.78-1.62 (m, 1H).

Example 265: Compound 521B: 3-ethyl-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1,2-oxazole-5-carboxamide To ethyl 3-ethylisoxazole-5-carboxylate (80 mg, 473 μmol, 1 eq) in ethanol (1 mL) was added sodium hydroxide (3 M, 1 mL, 1 eq). The mixture was stirred at 30° C. for 1 h. The reaction mixture was quenched by adding 1N HCl to pH=7 at 0° C., then concentrated in vacuo to give the carboxylic acid product (200 mg, 59.9% yield) as a yellow solid. LC-MS (ES$^+$, m:z): 139.9 [(M+H)$^+$].
Amine 1 (70 mg, 121 μmol, 1 eq, HCl) was coupled with 3-ethylisoxazole-5-carboxylic acid (85.4 mg, 120 μmol, 1 eq) under method E. The crude product was purified by prep-TLC (SiO$_2$, DCM:methanol=10:1) to afford the product (22.6 mg, 34% yield) as a yellow solid. LC-MS (ES$^+$, m/z): 550.1 [(M+H)$^+$]. $^1$H NMR (400 MHz, DMSO-d6) δ=9.62-9.49 (t, J=5.6 Hz, 1H), 7.90 (s, 1H), 7.23-7.03 (t, J=8.0 Hz, 1H), 6.98-6.82 (d, J=8.4 Hz, 1H), 6.65 (s, 1H), 6.36-6.23 (d, J=8.0 Hz, 1H), 6.07-5.93 (d, J=8.0 Hz, 1H), 5.62-5.36 (dt, J=17.6 Hz, 2H), 4.93-4.75 (m, 3H), 3.70-3.50 (m, 1H), 3.12-2.99 (m, 1H), 2.89-2.78 (m, 3H), 2.32-1.94 (m, 6H), 1.75-1.63 (m, 1H), 1.29-1.21 (t, J=7.2 Hz, 3H).

Example 266: Compound 552B: N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-[(3R)-3-methoxypyrrolidin-1-yl]-1,3-thiazole-4-carboxamide The aminothiazole was prepared as for similar analogues such as the 4-methoxypiperidine. Reaction of 2-bromothiazole-4-carboxylic acid (500 mg, 2.40 mmol, 1 eq) and (3R)-3-methoxypyrrolidine hydrochloride (500 mg, 3.63 mmol, 1.5 eq) provided, after prep-HPLC (column: Phenomenex Luna C18 100×30 mm×5 um; mobile phase: [water (0.04% HCl)-ACN];B %: 1%-18%, 10 min), the desired carboxylic acid product (250 mg, 45.6% yield) as a white solid. LC-MS (ES$^+$, m/z): 229.0 [(M+H)$^+$]. $^1$H NMR (400 MHz, DMSO-d6) δ=7.58 (d, J=0.7 Hz, 1H), 4.11 (br d, J=2.9 Hz, 1H). 3.61-3.36 (m, 4H), 3.31-3.23 (m, 3H), 2.16-2.05 (m, 2H).
2-[(3R)-3-methoxypyrrolidin-1-yl]thiazole-4-carboxylic acid (44.4 mg, 194 μmol, 1.5 eq) and Amine 1 (60 mg, 130 μmol, 1 eq, HCl) were coupled under method A. The crude reaction was purified by prep-TLC (SiO$_2$, DCM: metha-nol=15:1) to provide the desired product N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-[(3R)-3-methoxypyrrolidin-1-yl]-1,3-thiazole-4-carboxamide (25.8 mg, 30.6% yield, 98.0% purity) as a white solid. LC-MS (ES$^+$, m/z): 637.2 [(M+H)$^+$]. $^1$H NMR (400 MHz, DMSO-d6) δ=8.81 (br t, J=5.8 Hz, 1H), 7.89 (s, 1H), 7.42 (d, J=1.3 Hz, 1H), 7.16-7.09 (m, 1H), 6.88 (br d, J=8.6 Hz, 1H), 6.28 (d, J=8.2 Hz, 1H), 6.03 (br d, J=8.4 Hz, 1H), 5.50 (q, J=8.5 Hz, 2H), 4.93-4.77 (m, 3H), 4.16-4.08 (m, 1H), 3.65-3.49 (m, 6H), 3.28 (d, J=1.3 Hz, 3H), 3.11-2.99 (m, 1H), 2.86-2.78 (m, 1H), 2.20 (s, 3H), 2.13 (br s, 3H), 2.05-1.95 (m, 1H), 1.68 (br d, J=11.7 Hz, 1H).

Example 267: Compound 523B: N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-[(3S)-3-methoxypyrrolidin-1-yl]-1,3-thiazole-4-carboxamide The analogue was prepared using the same procedure used to prepare the enantiomer. 2-bromothiazole-4-carboxylic acid (500 mg, 2.40 mmol, 1 eq) and (3S)-3-methoxypyrrolidine (367 mg, 3.63 mmol, 1.5 eq, HCl) provided after purification the product (370 mg, 67.5% yield) as a white solid. LC-MS (ES$^+$, m/z): 229.0 [(M+H)$^+$].H NMR (400 MHz, DMSO-d6) δ=7.58 (s, 1H), 4.11 (br d, J=2.4 Hz, 1H), 3.60-3.39 (m, 4H), 3.29-3.22 (m, 3H), 2.17-2.04 (m, 2H).
2-[(3S)-3-methoxypyrrolidin-1-yl]thiazole-4-carboxylic acid (44.4 mg, 194 μmol, 1.5 eq) and Amine 1 (60 mg, 129.63 μmol, n/a purity, 1 eq, HCl) were coupled as for the enantiomer and purified to provide the desired product N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-[(3S)-3-methoxypyrrolidin-1-yl]-1,3-thiazole-4-carboxamide (4 mg, 4.7% yield, 96.4% purity) as a white solid. LC-MS (ES$^+$, m/z): 637.2 [(M+H)$^+$]. $^1$H NMR (400 MHz, DMSO-d6) Shift=8.81 (t, J=6.1 Hz, 1H), 7.89 (s, 1H), 7.42 (s, 1H), 7.15-7.05 (m, 1H), 6.88 (d, J=8.4 Hz, 1H), 6.28 (d, J=7.7 Hz, 1H), 6.03 (br d, J=8.6 Hz, 1H), 5.50 (q, J=8.8 Hz, 2H), 4.93-4.71 (m, 3H), 4.12 (br s, 1H), 3.67-3.50 (m, 4H), 3.47-3.37 (m, 2H), 3.27 (s, 3H), 3.04 (br s, 1H), 2.82 (br d, J=9.5 Hz, 1H), 2.19 (s, 3H), 2.13 (br t, J=9.0 Hz, 3H), 2.04-1.94 (m, 1H), 1.68 (br d, J=11.2 Hz, 1H).

Example 268: Compound 524B: 5-tert-butyl-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-pyrrole-2-carboxamide Amine 1 (50 mg, 100 μmol, 1 eq, 211C1) was coupled with 5-tert-butyl-1H-pyrrole-2-carboxylic acid (20.1 mg. 120 μmol, 1.2 eq) under method E. The crude product was purified by prep-TLC (DCM:methanol=8:1). The crude product was further purified by prep-HPLC (FA condition: column: Phenomenex Luna C18 200×40 mm×10 um; mobile phase: [water (0.2% FA)-ACN];B %: 10%-60%, 8 min) to provide the desired product 5-tert-butyl-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-pyrrole-2-carboxamide (22.6 mg, 75.3% yield) as a yellow solid. LC-MS (ES$^+$, m/z): 576.1 [(M+H)]. $^1$H NMR (400 MHz, DMSO-d$_6$) δ=11.13 (s, 1H), 8.85-8.69 (t, J=5.6 Hz, 1H), 7.89 (s, 1H), 7.22-7.03 (t, J=8.0 Hz, 1H), 6.96-6.79 (d, J=8.4 Hz, 1H), 6.77-6.67 (dt, J=3.6 Hz, 1H), 6.30-6.21 (d, J=8.0 Hz, 1H), 6.10-5.96 (d, J=8.4 Hz, 1H), 5.92-5.79 (dt, J=3.4 Hz, 1H), 5.64-5.34 (dt, J=18.0 Hz, 2H), 4.94-4.64 (m, 3H), 3.69-3.52 (m, 1H), 3.03 (brt, J=10.5 Hz, 1H), 2.88-2.74 (m, 1H), 2.32-2.14 (m, 4H), 2.14-2.06 (m, 1H), 2.05-1.92 (m, 1H), 1.72-1.59 (m, 1H), 1.26 (s, 9H).

Example 269: Compound 52513: N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-{6-oxa-3-azabicyclo[3.1.1]heptan-3-yl}-1,3-thiazole-4-carboxamide The required carboxylic acid was prepared using the same conditions used to prepare the 4-methoxypiperidine analogue. 2-bromothiazole-4-carboxylic acid (0.5 g, 2.40 mmol, 1 eq) and 6-oxa-3-azabicyclo[3.1.1.]heptane (0.25 g, 1.84 mmol, 7.67e-1 eq, HCl) provided 2-(6-oxa-3-azabicyclo[3.1.1]heptan-3-yl)thiazole-4-carboxylic acid (0.1 g, 18.4% yield) as a yellow oil. LC-MS (ES$^+$, m/z): 227.1[(M+H)$^+$].

Amine 1 (150 mg, 324 µmol, 1 eq, HCl) and 2-(6-oxa-3-azabicyclo[3.1.1]heptan-3-yl)thiazole-4-carboxylic acid (80.7 mg, 356 µmol, 1.1 eq) were coupled under method A. The reaction was purified by prep-TLC (SiO$_2$, DCM:methanol=10: 1) to provide the desired N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-5-(propan-2-yl)furan-3-carboxamide (59.1 mg, 27.6% yield, 96.2% purity) as a light yellow solid. LC-MS (ES$^+$, m/z): 651.1 [(M+H)$^+$]. $^1$H NMR (400 MHz, DMSO-d6) δ=8.86 (t, J=5.8 Hz, 1H), 7.88 (s, 1H), 7.48 (s, 1H), 7.10 (t, J=8.2 Hz, 1H), 6.87 (d, J=8.2 Hz, 1H), 6.27 (d, J=7.9 Hz, 1H), 6.01 (br d, J=8.6 Hz, 1H), 5.54-5.41 (m, 2H), 4.94-4.74 (m, 3H), 4.71 (d, J=6.6 Hz, 2H), 3.73-3.63 (m, 4H), 3.63-3.49 (m, 1H), 3.22-3.12 (m, 1H), 3.09-2.97 (m, 1H), 2.90-2.76 (m, 1H), 2.38-2.17 (m, 4H), 2.16-2.05 (m, 1H), 2.02-1.91 (m, 2H), 1.79- 1.52 (m, 1H).

Example 270: Compound 526B: N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-5-(propan-2-yl)furan-3-carboxamide To a mixture of 5-bromofuran-3-carboxylic acid (500 mg, 2.62 mmol, 1 eq) and 2-isopropenyl-4,4,5,5-tetramethyl-1,3,2-dioxaborolane (440 mg, 2.62 mmol, 1 eq) in dioxane (4 mL) and water (1 mL) were added Pd(dppf)Cl$_2$ (191.6 mg, 262 µmol, 0.1 eq) and sodium carbonate (832.5 mg, 7.85 mmol, 3 eq), and the reaction was heated at 100° C. under nitrogen for 1 h. The residue was poured into ice-water (w/w=1/1) (100 mL). The aqueous phase was extracted with EA (30 mL×3). To the aqueous phase was added HCl (3 M) to adjust pH=4-5. The aqueous phase was extracted with EA (30 mL×3). The combined organic phase washed with brine (30 mL×3), dried over anhydrous sodium sulfate, filtered, and concentrated in vacuo to provide the olefin product (350 mg, crude) as a light yellow solid. LC-MS (ES$^+$, m/z): 151.1[(M+H)$^+$].

To a mixture of 5-isopropenylfuran-3-carboxylic acid (350 mg, 2.30 mmol, 1 eq) in methanol (4 mL) was added 5% Pd(C) (2.30 mmol, 1 eq) at 20° C., and the reaction was stirred under H$_2$(15 psi) at 20° C. for 12 h. The residue was filtered through Celite and concentrated in vacuo. The residue was purified by prep-HPLC (HCl condition, column: Phenomenex luna C18 80×40 mm×3 um; mobile phase: [water (0.04% HCl)-ACN]; B %: 22%-42%, 7 min) to afford 5-isopropylfuran-3-carboxylic acid (60 mg, 389 µmol, 16.9% yield) as a white solid. LC-MS (ES$^+$, m/z): 153.1 [(M+H)$^+$].

Amine 1 (70 mg, 151 µmol, 1 eq, HC) and 5-isopropylfuran-3-carboxylic acid (28 mg, 181 µmol, 1.2 eq) were coupled under method A. The crude product was purified by prep-TLC (SiO$_2$, DCM:methanol=10:1) to afford the desired N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-5-(propan-2-yl)furan-3-carboxamide (23.2 mg, 27.3% yield, 100.0% purity) as a light yellow solid. LC-MS (ES$^+$, m/z): 563.2 [(M+H)$^+$]. $^1$H NMR (400 MHz, DMSO-d6) δ=9.04 (t, J=5.7 Hz, 1H), 8.13 (s, 1H), 7.89 (s, 1H), 7.12 (t, J=8.1 Hz, 1H), 6.88 (d, J=8.4 Hz, 1H), 6.51 (s, 1H), 6.29 (d, J=7.8 Hz, 1H), 6.03 (d, J=8.0 Hz, 1H), 5.50 (q, J=9.1 Hz, 2H), 4.93-4.75 (m, 3H), 3.68-3.52 (m, 1H), 3.11-3.02 (m, 1H), 2.94 (td, J=6.6, 13.7 Hz, 1H), 2.88-2.79 (m, 1H), 2.32-2.17 (m, 4H), 2.16-2.07 (m, 1H), 2.05-1.95 (m, 1H), 1.69 (br d, J=11.9 Hz, 1H), 1.21 (d, J=6.8 Hz, 6H).

Example 271: Compound 527B: N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-{2-oxa-6-azaspiro[3.3]heptan-6-yl}-1,3-thiazole-4-carboxamide

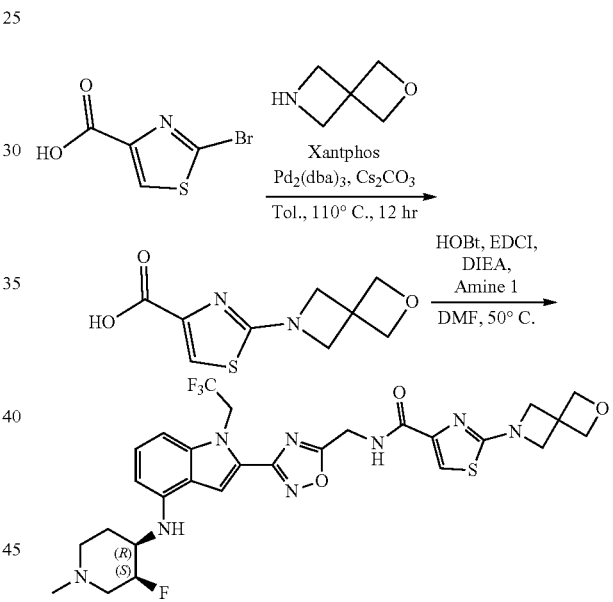

A mixture of 2-bromothiazole-4-carboxylic acid (500 mg, 2.40 mmol, 1 eq), 2-oxa-6-azaspiro[3.3]heptane (682 mg, 3.61 mmol, 1.5 eq, oxalate salt), Xantphos (139.1 mg, 240.3 µmol, 0.1 eq), Pd$_2$(dba)$_3$ (440.2 mg, 0.2 eq) and cesium carbonate (2.35 g, 7.21 mmol, 3 eq) in toluene (0.5 mL) was degassed and purged with nitrogen 3 times, then the mixture was stirred at 110° C. for 12 h under nitrogen atmosphere. The reaction mixture was concentrated in vacuo to remove toluene, then diluted with methanol (3 mL). The residue was purified by prep-HPLC (column: Phenomenex Gemini-NX C18 75×30 mm×3 um; mobile phase: [water (10 mM NH$_4$HCO$_3$)-ACN];B %: 1%-20%, 12 min).HPLC: ET34794-39-P1B1. The product was then further purified by column chromatography (SiO$_2$, PE/EA=1/1), and then further purified by column chromatography (SiO$_2$, methanol). The residue was purified by prep-HPLC (column: Phenomenex Gemini-NX C18 75×30 mm×3 um; mobile phase: [water (10 mM NH$_4$HCO$_3$)-ACN];B %: 5%-5%, 8 min). The 2-(2-oxa-6-azaspiro[3.3]heptan-6-yl)thiazole-4-carboxylic acid (13 mg, 2.4% yield) was obtained as a white solid LC-MS (ES+, m/z): 225.02 [(M+H)+].

2-(2-oxa-6-azaspiro[3.3]heptan-6-yl)thiazole-4-carboxylic acid (9.8 mg, 43 µmol, 1 eq) and Amine 1 (20 mg, 43.21 µmol, 1 eq, HCl) were coupled under method A. The crude reaction was purified by prep-TLC (SiO$_2$, DCM: methanol=15:1) to provide the desired product N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-{2-oxa-6-azaspiro[3.3]heptan-6-yl}-1,3-thiazole-4-carboxamide (12.7 mg, 23.2% yield, 100.0% purity) was obtained as a white solid. LC-MS (ES+, m/z): 635.2 [(M+H)+]. $^1$H NMR (400 MHz, DMSO-d6) 5=8.86-8.79 (m, 1H), 7.90-7.84 (m, 1H), 7.59-7.50 (m, 1H), 7.18-7.04 (m, 1H), 6.92-6.83 (m, 1H), 6.34-6.21 (m, 1H), 6.08-5.99 (m, 1H), 5.58-5.41 (m, 2H), 4.93-4.86 (m, 7H), 4.34-4.20 (m, 4H), 3.78-3.50 (m, 1H), 3.08- 2.97 (m, 1H), 2.83-2.77 (m, 1H), 2.52-2.32 (m, 4H), 2.21-2.09 (m, 1H), 1.93-1.85 (m, 1H), 1.73-1.62 (m, 1H). $^1$H NMR (400 MHz, DMSO-d6) δ=8.82 (t, J=6.1 Hz, 1H), 7.89 (s, 1H), 7.54 (s, 1H), 7.17-7.07 (m, 1H), 6.88 (d, J=8.2 Hz, 1H), 6.28 (d, J=7.7 Hz, 1H), 6.03 (d, J=8.6 Hz, 1H), 5.62-5.41 (m, 2H), 4.93-4.72 (m, 7H), 4.26 (s, 4H), 3.70-3.47 (m, 1H), 3.10-2.98 (m, 1H), 2.84-2.78 (m, 1H), 2.24-2.14 (m, 4H), 2.07-2.04 (m, 1H), 2.03-1.93 (m, 1H), 1.67 (br d, J=12.6 Hz, 1H).

Example 272: Compound 528B: 2-[tert-butyl (methyl)amino]-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1,3-thiazole-4-carboxamide

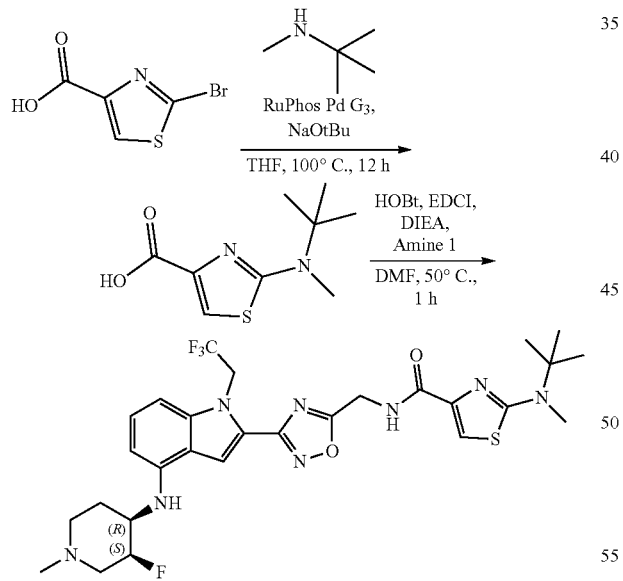

A mixture of 2-bromothiazole-4-carboxylic acid (500 mg, 3.06 mmol, 1 eq), t-butyl methylamine (346 mg, 3.97 mmol, 1.3 eq), sodium t-butoxide (587.5 mg, 6.11 mmol, 2 eq) and RuPhos Pd G$_3$ (255.6 mg, 306 µmol, 0.1 eq) were treated with THF (10 mL) in glovebox. The mixture was then stirred at 100° C. for 12 h under nitrogen. The reaction mixture was concentrated using nitrogen to give a residue. The residue was purified by prep-HPLC (HCl condition:column: Phenomenex luna C18 250×50 mm×10 um; mobile phase: [water (0.04% HCl)-ACN];B %: 20%-50%, 10 min) to provide the product (100 mg, 7.6% yield) as a yellow solid. LC-MS (ES+, m:z): 215.1 [(M+H)+]. $^1$H NMR (400 MHz, DMSO-d6) δ=7.59 (s, 1H), 2.97 (s, 3H), 1.46 (s, 9H).

Amine 1 (56 mg, 121 µmol, 1 eq, HCl) and 2-[tert-butyl (methyl)amino]thiazole-4-carboxylic acid (38.3 mg, 145 µmol, 1.2 eq, HCl) were coupled under method A. TLC (DCM:methanol=10:1, R$_f$=0.7) indicated formation of product. The reaction was worked up as for previous reactions, then purified by prep-TLC (SiO$_2$, DCM: methanol=10:1) to provide the desired product 2-[tert-butyl(methyl)amino]-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1,3-thiazole-4-carboxamide (28 mg, 37.2% yield) as a yellow solid. LC-MS (ES+, m/z): 623.2 [(M+H)+]. $^1$H NMR (400 MHz, DMSO-d6) δ=8.79-8.59 (t, J=6.0 Hz, 1H), 7.89 (s, 1H), 7.48 (s, 1H), 7.22-7.02 (t, J=8.0 Hz, 1H), 6.96-6.78 (d, J 8.4 Hz, 1H), 6.41-6.17 (d, J=8.0 Hz, 1H), 6.11-5.94 (d, J=8.4 Hz, 1H), 5.66-5.37 (d, J=17.6 Hz, 2H), 5.09-4.65 (m, 3H), 3.75-3.50 (m, 1H), 3.13-2.97 (m, 4H), 2.91-2.77 (m, 1H), 2.30-1.96 (m, 6H), 1.76-1.62 (m, 1H), 1.52 (s, 9H).

Example 273: Compound 529B: 1-tert-butyl-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-pyrazole-3-carboxamide 1-tert-butylpyrazole-3-carboxylic acid (28 mg, 166 µmol, 1.1 eq) was coupled with Amine 1 (70 mg, 151.23 µmol, N/A purity, 1 eq, HCl) under method B. The crude product was purified by prep-TLC (SiO$_2$, DCM:methanol=10:1) to afford the desired product 1-tert-butyl-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-pyrazole-3-carboxamide (22.8 mg, 39.5 µmol, 26.2% yield) as a light yellow solid LC-MS (ES+, m/z): 577.2 [(M+H)+].

Example 274: Compound 530B: N-{[3-(4-{1[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-(2-methoxypropan-2-yl)-1,3-thiazole-4-carboxamide

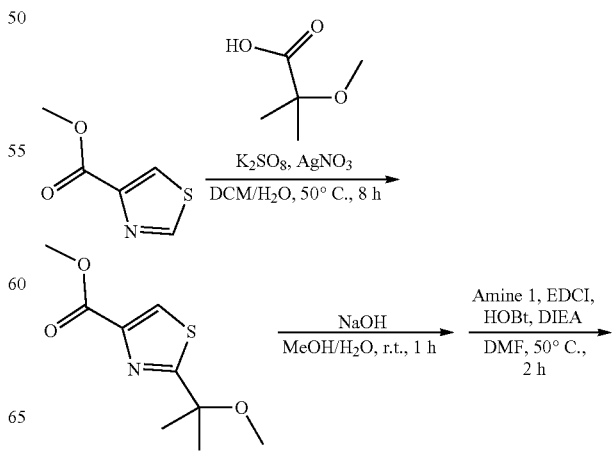

-continued

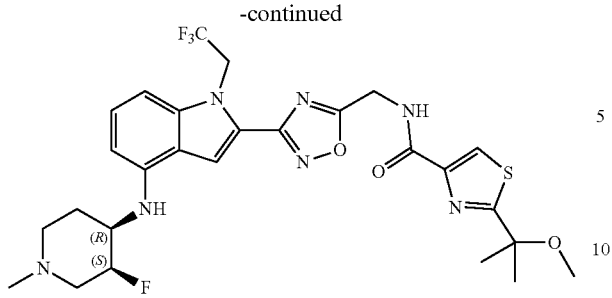

A mixture of methyl thiazole-4-carboxylate (700 mg, 4.89 mmol, 1 eq), 2-methoxy-2-methyl-propanoic acid (866 mg, 7.33 mmol, 1.5 eq), silver nitrate (830.6 mg, 4.89 mmol, 1 eq) and potassium persulfate (5.29 g, 19.56 mmol 4 eq) in DCM (4 mL) and water (4 mL) was degassed and purged with nitrogen 3 times, then the mixture was stirred at 50° C. for 8 h under nitrogen atmosphere. The reaction mixture was filtered and diluted with water (100 mL) and extracted with DCM (30 mL×2). The combined organic layers were washed with brine (100 mL), dried over anhydrous sodium sulfate, filtered, and concentrated in vacuo to give a residue. The residue was purified by prep-TLC (SiO$_2$, PE:EA=1:1) to give the product (220 mg, 1.02 mmol, 20.9% yield) as light yellow oil. LC-MS (ES$^+$, m/z): 216.1 [(M+H)-]. $^1$H NMR (400 MHz, CHLOROFORM-d) δ=8.16 (s, 1H), 3.94 (s, 3H), 3.28 (s, 3H), 1.66 (s, 6H). Methyl 2-(1-methoxy-1-methyl-ethyl)thiazole-4-carboxylate (200 mg, 929 μmol, 1 eq) in methanol (2 mL) was added sodium hydroxide (4 M, 2 mL, 8.6 eq), and the reaction was stirred at 25° C. for 1 h. 4M HCl was added to the mixture to adjust the pH to 7. The mixture was concentrated in vacuo to give the crude product as white solid. LC-MS (ES$^+$, m/z): 201.9 [(M+H)$^+$].

2-(1-methoxy-1-methyl-ethyl)thiazole-4-carboxylic acid (258.6 mg, 321 μmol, 1.3 eq) was coupled with Amine 1 (130 mg, 247 μmol, 1 eq, HCl) under method A. The crude reaction was purified by prep-TLC (SiO$_2$, DCM: methanol=10:1) to give the desired product N-{[3-(4-{[(3S,4R)-3-fluoro-1-methylpiperidin-4-yl]amino}-1-(2,2,2-trifluoro-ethyl)-1H-indol-2-yl)-1,2,4-oxadiazol-5-yl]methyl}-2-(2-methoxypropan-2-yl)-1,3-thiazole-4-carboxamide (51.9 mg, 33.8% yield, 98.2% purity) as a light yellow solid. LC-MS (ES$^+$, m/z): 610.3 [(M+H)$^+$]. $^1$H NMR (400 MHz, DMSO-d6) δ=9.15 (t, J=6.0 Hz, 1H), 8.34 (s, 1H), 7.90 (s, 1H), 7.19-7.04 (m, 1H), 6.88 (d, J=8.3 Hz, 1H), 6.28 (d, J=7.9 Hz, 1H), 6.06-5.97 (m, 1H), 5.57-5.46 (m, 2H), 4.94-4.72 (m, 3H), 3.69-3.51 (m, 1H), 3.23 (s, 3H), 3.08-2.99 (m, 1H), 2.85-2.77 (m, 1H), 2.28-2.15 (m, 4H), 2.14-2.05 (m, 1H), 2.04-1.94 (m, 1H), 1.61 (s, 7H).

Example 275: Compound 531B: N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-(1-hydroxy-2-methylpropan-2-yl)-1,3-thiazole-4-carboxamide

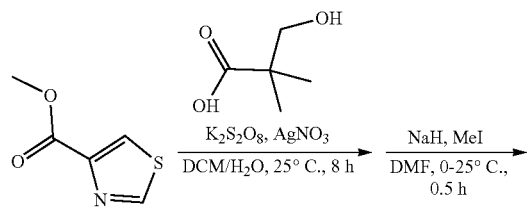

-continued

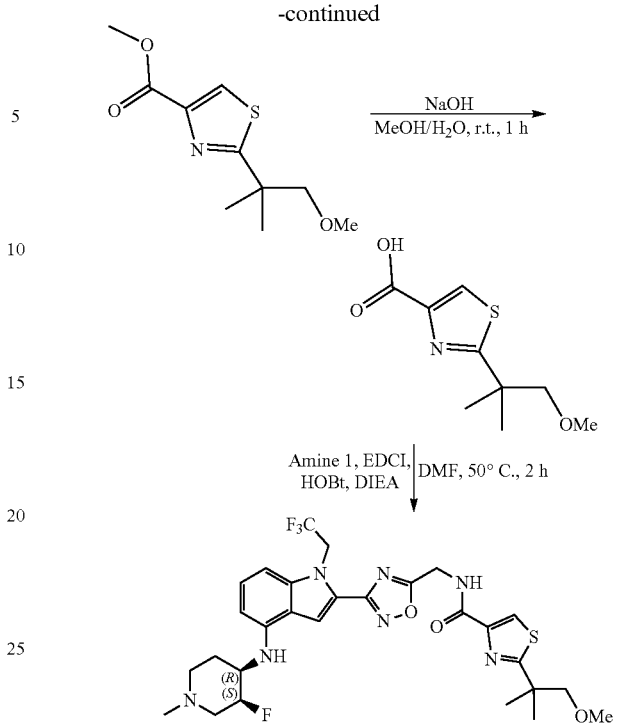

A mixture of methyl thiazole-4-carboxylate (3.0 g, 21 mmol, 1 eq), 3-hydroxy-2,2-dimethyl-propanoic acid (4.95 g, 41.9 mmol, 2 eq), potassium persulfate (22.66 g, 83.8 mmol, 4 eq), silver nitrate (3.56 g, 21 mmol, 1 eq) in DCM (20 mL) and water (20 mL) was degassed and purged with nitrogen for 3 times, and then the mixture was stirred at 25° C. for 8 h under nitrogen atmosphere. The reaction mixture was diluted with water (50 mL) and extracted with DCM (25 mL×2). The combined organic layers were washed with brine (50 mL), dried over sodium sulfate, filtered, and concentrated in vacuo to give a residue. The residue was purified by prep-HPLC (column: Agela DuraShell C18 250×80 mm×10 um; mobile phase: [water (10 mM NH4HCO3)-ACN]; B %: 5%-35%, 20 min) to give the product (260 mg, 5.8% yield) as brown oil. LC-MS (ES$^+$, m/z): 215.9 [(M+H)$^+$]. $^1$H NMR (400 MHz, CHLOROFORM-d) δ=8.08 (s, 1H), 3.92 (s, 3H), 3.77 (s, 2H), 3.48 (s, 1H), 1.44 (s, 6H).

To methyl 2-(2-hydroxy-1,1-dimethyl-ethyl)thiazole-4-carboxylate (0.2 g, 929 μmol, 1 eq) in DMF (5 mL) was added sodium hydride (74.3 mg, 1.86 mmol, 60% purity, 2 eq) at 0° C., and the reaction was stirred at 0° C. for 10 min. Iodomethane (1.86 mmol, 115 μL 2 eq) was added to the mixture, and the reaction stirred at 25° C. for 20 min. The reaction mixture was quenched by adding sat. ammonium chloride (20 mL), and then diluted with water (20 mL) and extracted with DCM (25 mL×2). The combined organic layers were washed with brine (100 mL), dried over sodium sulfate, filtered, and concentrated in vacuo to give a residue. The residue was purified by prep-TLC (SiO$_2$, PE:EA=1:1) to give the ether product (70 mg, 32.9% yield) as a light yellow oil. LC-MS (ES$^+$, m/z): 230.1 [(M+H)$^+$].

To methyl 2-(2-methoxy-1,1-dimethyl-ethyl)thiazole-4-carboxylate (70 mg, 305 μmol, 1 eq) in methanol (1 mL) was added sodium hydroxide (4 M, 1 mL, 13 eq), and the reaction was stirred at 25° C. for 1 h. 4M HCl was added to the mixture and adjusted to pH=7. The residue was freeze-dried to give the product (610 mg, crude) as a white solid. LC-MS (ES+, m/z): 216.0 [(M+H)+].

2-(2-methoxy-1,1-dimethyl-ethyl)thiazole-4-carboxylic acid (418.6 mg, 194.4 μmol, 1.5 eq) and Amine 1 (60 mg, 129.6 μmol, 1 eq, HCl) were coupled under method A. The crude product was purified by prep-TLC (SiO₂, DCM: methanol=10:1) to give the desired product (21.4 mg, 26.5% yield, 100% purity) as a light yellow solid. LC-MS (ES+, m/z): 624.2 [(M+H)+]. ¹H NMR (400 MHz, DMSO-d6) δ=9.10 (t, J=5.9 Hz, 1H), 8.25 (s, 1H), 7.90 (s, 1H), 7.11 (t, J=8.0 Hz, 1H), 6.88 (d, J=8.3 Hz, 1H), 6.28 (d, J=7.9 Hz, 1H), 6.04 (d, J=8.1 Hz, 1H), 5.51 (q, J=8.8 Hz, 2H), 4.92-4.75 (m, 3H), 3.51 (s, 4H), 3.28 (s, 3H), 3.04 (br s, 1H), 2.87-2.78 (m, 1H), 2.19 (s, 4H), 2.14-1.92 (m, 2H), 1.67 (br dd, J=1.9, 12.2 Hz, 1H), 1.41 (s, 6H).

Example 276: Compound 53213: N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-(1-hydroxy-2-methylpropan-2-yl)-1,3-thiazole-4-carboxamide The analogue was synthesized using the previously prepared methyl 2-(2-hydroxy-1,1-dimethyl-ethyl)thiazole-4-carboxylate, which was saponified under standard conditions. 2-(2-hydroxy-1,1-dimethyl-ethyl)thiazole-4-carboxylic acid (21.7 mg, 518.5 μmol, 4 eq) and Amine 1 (60 mg, 130 μmol, 1 eq, HCl) were coupled under method A.

The crude product was purified by prep-TLC (SiO₂, DCM: methanol=10:1) to give the desired product N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-(1-hydroxy-2-methylpropan-2-yl)-1,3-thiazole-4-carboxamide (22.8 mg, 28.6% yield, 99.1% purity) as light yellow solid. LC-MS (ES-, m/z): 610.1 [(M+H)-]. ¹H NMR (400 MHz, DMSO-d6) δ=9.12 (t, J=6.0 Hz, 1H), 8.24 (s, 1H), 7.91 (s, 1H), 7.12 (t, J=8.0 Hz, 1H), 6.89 (d, J=8.3 Hz, 1H), 6.29 (d, J=7.9 Hz, 1H), 6.05 (d, J=8.3 Hz, 1H), 5.51 (q, J=8.8 Hz, 2H), 5.07 (t, J=5.6 Hz, 1H), 4.93-4.75 (m, 3H), 3.57 (d, J=5.6 Hz, 3H), 3.04 (br t, J=10.9 Hz, 1H), 2.82 (br d, J=10.3 Hz, 1H), 2.31-2.18 (m, 4H), 2.13-2.08 (m, 1H), 2.03-1.95 (m, 1H), 1.68 (br d, J=11.8 Hz, 1H), 1.39 (s, 6H).

Example 277: Compound 533B: N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-5-[(propan-2-yloxy)methyl]thiophene-2-carboxamide Amine 1 (46.1 mg, 92.7 μmol, 2HCl) and 5-(isopropoxymethyl)thiophene-2-carboxylic acid (10.6 mg, 52.9 μmol) were coupled under method B. After 30 min, the reaction was filtered through an Acrodisk using additional DMF, then purified by reverse-phase HPLC in 10-70% acetonitrile/water (0.1% formic acid). The product was isolated as the formate salt by lyophilization to provide N-[[3-[4-[[(3S,4R)-3-fluoro-1-methyl-4-piperidyl]amino]-1-(2,2,2-trifluoroethyl)indol-2-yl]-1,2,4-oxadiazol-5-yl]methyl]-5-(isopropoxymethyl)thiophene-2-carboxamide (6 mg, 10.6% yield).

Example 278: Compound 534B: 1-ethyl-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-pyrrole-2-carboxamide

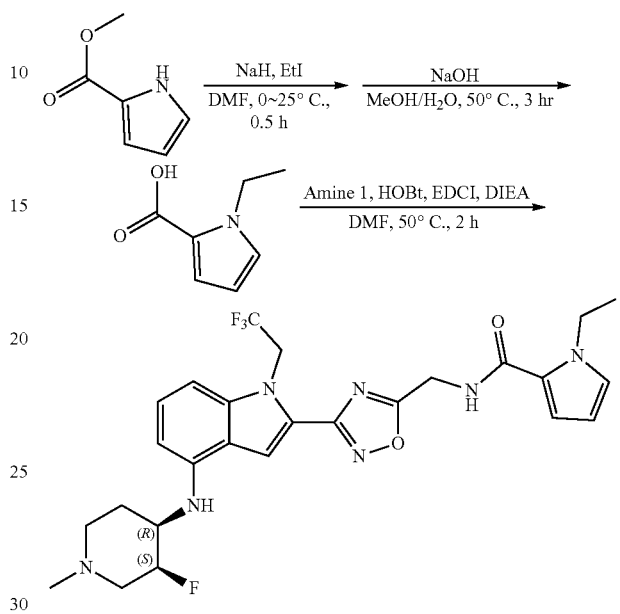

To methyl 1H-pyrrole-2-carboxylate (1 g, 8 mmol, 1 eq) in DMF (10 mL) was added sodium hydride (639.3 mg, 16 mmol, 60% purity, 2 eq) at 0° C., the reaction was stirred at 0° C. for 10 min, then iodoethane (24 mmol, 1.92 mL, 3 eq) was added to the mixture, and the reaction was stirred at 25° C. for 20 min. The reaction was poured into ammonium chloride (sat., 100 mL), and extracted with DCM (25 mL×2). The combined organic layers were washed with brine (100 mL), dried over sodium sulfate, filtered, and concentrated in vacuo to give a residue. The residue was purified by column chromatography (SiO₂, PE/EA=20/1 to 10/1). Methyl 1-ethylpyrrole-2-carboxylate (0.9 g, 5.88 mmol, 73.5% yield) was obtained as colorless oil. LC-MS (ES-, m/z): 154.0 [(M+H)-]. ¹H NMR (400 MHz, DMSO-d6) δ=7.15 (d, J=1.5 Hz, 1H), 6.93-6.68 (m, 1H), 6.09 (dd, J=2.6, 3.8 Hz, 1H), 4.29 (q, J=7.1 Hz, 2H), 3.80-3.64 (m, 3H), 1.27 (t, J=7.1 Hz, 3H).

A mixture of methyl 1-ethylpyrrole-2-carboxylate (950 mg, 6.20 mmol, n/a purity, 1 eq) and sodium hydroxide (3 M, 10 mL, 4.9 eq) in methanol (5 mL) was stirred at 50° C. for 3 h. 3M HCl (10 mL) was added to the mixture until the pH was adjusted to 4-5. The reaction mixture was extracted with DCM (30 mL×2). The combined organic layers were washed with brine (30 mL), dried over anhydrous sodium sulfate, filtered, and concentrated in vacuo to give the product. The crude product 1-ethylpyrrole-2-carboxylic acid (550 mg, crude) was obtained as a white solid, which was used into the next step without further purification. LC-MS (ES+, m/z): 140.0 [(M+H)+].

1-ethylpyrrole-2-carboxylic acid (27.1 mg, 194 μmol, 1.5 eq) was coupled with Amine 1 (60 mg, 129.6 μmol, 1 eq, HCl) under method A. The crude reaction was purified by prep-TLC (SiO₂, DCM: methanol=10:1) to provide the desired product 1-ethyl-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-pyrrole-2-carboxamide (25.5 mg, 34.9% yield, 97.1% purity) as a white solid. LC-MS (ES$^+$, m/z): 548.2 [(M+H)$^+$]. $^1$H NMR (400 MHz, DMSO-d6) δ=8.84 (t, J=5.7 Hz, 1H), 7.89 (s, 1H), 7.16-7.06 (m, 1H), 7.03 (t, J=2.1 Hz, 1H), 6.92-6.85 (m, 2H), 6.29 (d, J=7.9 Hz, 1H), 6.08-5.90 (dd, J=2.6, 4.0 Hz, 2H), 5.54-5.50 (q, J=8.9 Hz, 2H), 4.95-4.67 (m, 3H), 4.30 (q, J=7.1 Hz, 2H), 3.65-3.51 (m, 1H), 3.04 (br s, 1H), 2.82 (br d, J=11.0 Hz, 1H), 2.32-2.15 (m, 4H), 2.14-1.93 (m, 2H), 1.73-1.64 (m, 1H), 1.24 (t, J=7.1 Hz, 3H).

Example 279: Compound 535B:N-{[3-(4-{1[(3S, 4R)-3-fluoro-1-methylpiperidin-4-yl]amino}-1-(2,2, 2-trifluoroethyl)-1H-indol-2-yl)-1,2,4-oxadiazol-5-yl]methyl}-1-(2-methylpropyl)-1H-pyrrole-2-carboxamide 1-isobutylpyrrole-2-carboxylic acid as prepared using the same process used to prepare the N-ethyl pyrrole analogue, with 1-iodo-2-methyl-propane, to provide the desired carboxylic acid. LC-MS (ES$^+$, m/z): 168.1 [(M+H)$^+$].

1-isobutylpyrrole-2-carboxylic acid (37.9 mg, 227 µmol, 1.5 eq) and Amine 1 (70 mg, 151 µmol, 1 eq, HCl) were coupled under method A. The crude product was purified by prep-TLC (SiO2, DCM: methanol=10:1) to provide the desired product N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(2-methylpropyl)-1H-pyrrole-2-carboxamide (22.7 mg, 26.1% yield, 100% purity) was obtained as a white solid. LC-MS (ES$^+$, m/z): 576.2 [(M+H)$^+$]. $^1$H NMR (400 MHz, DMSO-d6) δ=8.80 (t, J=5.6 Hz, 1H), 7.86 (s, 1H), 7.10 (t, J=8.0 Hz, 1H), 6.96 (t, J=2.0 Hz, 1H), 6.91-6.84 (m, 2H), 6.27 (d, J=7.7 Hz, 1H), 6.05 (dd, J=2.8, 3.6 Hz, 1H), 5.95 (d, J=8.4 Hz, 1H), 5.49 (q, J=8.9 Hz, 2H), 4.93-4.67 (m, 3H), 4.08 (d, J=7.3 Hz, 2H), 3.66-3.50 (m, 1H), 3.02 (br s, 1H), 2.80 (br d, J=10.6 Hz, 1H), 2.18 (s, 4H), 2.07 (br d, J=11.2 Hz, 1H), 2.02-1.88 (m, 2H), 1.67 (br d, J=10.8 Hz, 1H), 0.73 (d, J=6.6 Hz, 6H).

Example 280: Compound 536B: N-{[3-(4-{1[(3S, 4R)-3-fluoro-1-methylpiperidin-4-yl]amino}-1-(2,2, 2-trifluoroethyl)-1H-indol-2-yl)-1,2,4-oxadiazol-5-yl]methyl}-2-[(2-methoxyethyl)(methyl)amino]-1,3-thiazole-4-carboxamide

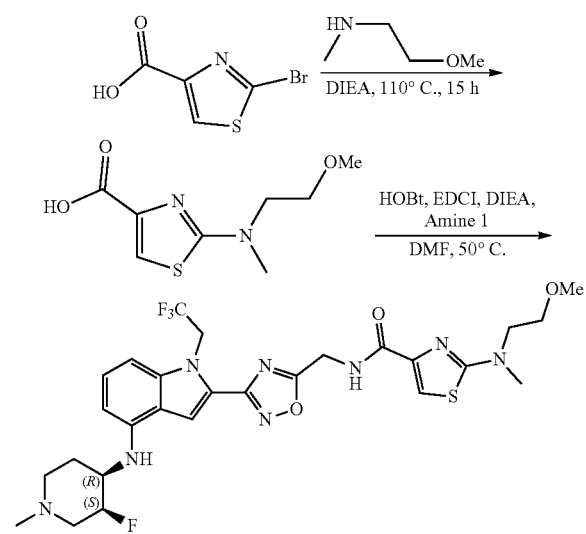

2-[2-methoxyethyl(methyl)amino]thiazole-4-carboxylic acid was prepared using the same conditions used to prepare the 4-methoxypiperidine thiazole analogue, to provide the intermediate carboxylic acid in 22% yield. LC-MS (ES$^+$, m/z): 216.9 [(M+H)$^+$]. $^1$H NMR (400 MHz, DMSO-d6) δ=7.09 (s, 1H), 3.61-3.50 (m, 4H), 3.26 (s, 3H), 3.01 (s, 3H).

2-[2-methoxyethyl(methyl)amino]thiazole-4-carboxylic acid (39.3 mg, 181 µmol, 1.2 eq) and Amine 1 (70 mg, 151 µmol, 1 eq, HCl) were coupled under method A. The crude product was purified by prep-TLC (SiO$_2$, DCM: methanol=10:1) to provide the desired product (20.2 mg, 21.4% yield) as a yellow solid. LC-MS (ES$^+$, m/z): 625.1 [(M+H)$^+$]. $^1$H NMR (400 MHz, DMSO-d6) δ=8.91-8.77 (t, J=7.0 Hz, 1H), 7.90 (s, 1H), 7.41 (s, 1H), 7.22-7.07 (t, J=8.0 Hz, 1H), 7.00-6.84 (d, J=8.4 Hz, 1H), 6.39-6.24 (d, J=7.6 Hz, 1H), 6.08-5.91 (d, J=7.6 Hz, 1H), 5.37 (br dd, J=6.1, 15.3 Hz, 2H), 4.94-4.75 (m, 3H), 3.72-3.67 (m, 2H), 3.65-3.54 (m, 3H), 3.28 (s, 3H), 3.12-3.00 (m, 4H), 2.89-2.78 (m, 1H), 2.30-2.18 (m, 4H), 2.14-2.07 (m, 1H), 2.04-1.97 (m, 1H), 1.74-1.63 (m, 1H).

Example 281: Compound 537B:N-{[3-(4-{[(3S, 4R)-3-fluoro-1-methylpiperidin-4-yl]amino}-1-(2,2, 2-trifluoroethyl)-1H-indol-2-yl)-1,2,4-oxadiazol-5-yl]methyl}-5-[(2S)-2-(methoxymethyl) pyrrolidine-1-yl]thiophene-3-carboxamide IDC 9,C3

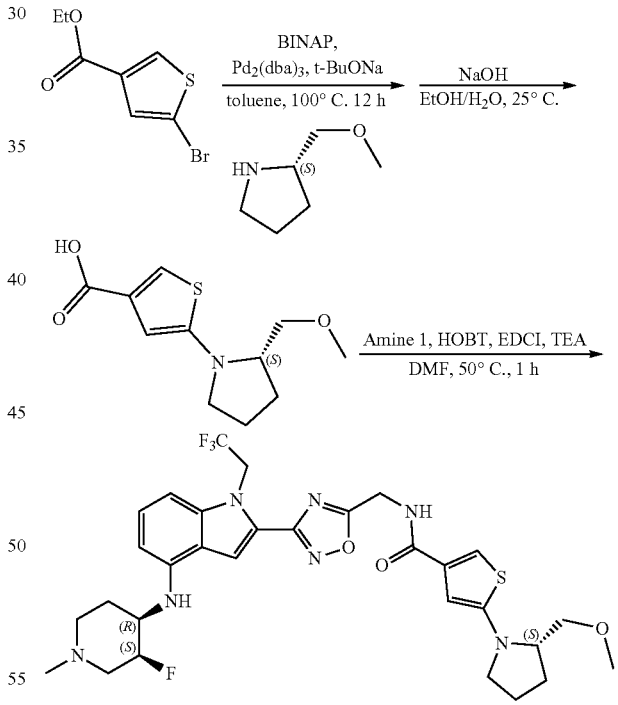

A mixture of ethyl 5-bromothiophene-3-carboxylate (500 mg, 2.13 mmol, 1 eq), (2S)-2-(methoxymethyl)pyrrolidine (270 mg, 2.34 mmol, 1.1 eq), BINAP (50.8 mg, 63.9 µmol, 0.03 eq), sodium t-butoxide (2 M, 2.13 mL, 2 eq) and Pd$_2$(dba)$_3$ (58.5 mg, 63.9 µmol, 0.03 eq) in toluene (15 mL) was degassed and purged with nitrogen 3 times, then the mixture was stirred at 100° C. for 12 h under nitrogen atmosphere. The reaction mixture was quenched by adding saturated EDTA solution (30 mL) and the mixture was stirred at 20° C. for 1 h under nitrogen atmosphere, then diluted with water (10 mL) and extracted with EA (30 mL×3). The combined organic layers were washed with brine (20 mL×3), dried over anhydrous sodium sulfate, filtered, and concentrated in vacuo to give a residue. The residue was purified by column chromatography (SiO$_2$, PE/EA=1/0 to 93/7) to afford the product (0.13 g, 22.7% yield) as a yellow oil. LC-MS (ES$^+$, m/z): 269.9 [(M+H)$^+$].

The ester was saponified under standard conditions to provide the desired carboxylic acid intermediate (0.4 g, 68.7% yield) as a yellow solid. LC-MS (ES$^+$, m/z): 240.0 [(M+H)$^+$]. $^1$H NMR (400 MHz, DMSO-d6) δ=6.81-6.63 (d, J=1.2 Hz, 1H), 6.19-5.97 (d, J=1.2 Hz, 1H), 3.59-3.46 (m, 1H), 3.41 (dd, J=3.7, 9.4 Hz, 1H), 3.31-3.21 (m, 5H), 3.03-2.92 (m, 1H), 2.03-1.82 (m, 4H).

Amine 1 (60 mg, 130 μmol, 1 eq, HCl) and 5-[(2S)-2-(methoxymethyl)pyrrolidin-1-yl]thiophene-3-carboxylic acid (187.7 mg, 155.6 μmol, 1.2 eq) were coupled under method A. The crude product was purified by prep-TLC (SiO$_2$, DCM: methanol=10:1) to provide the desired product N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-5-[(2S)-2-(methoxymethyl)pyrrolidin-1-yl]thiophene-3-carboxamide (25.4 mg, 30.2% yield) as a yellow solid. LC-MS (ES$^+$, m/z): 650.1 i(M+H)$^+$1. $^1$H NMR (400 MHz, DMSO-d6) δ=9.07-8.81 (t, J=5.6 Hz, 1H), 7.90 (s, 1H), 7.28-7.20 (d, J=1.6 Hz, 1H), 7.16-7.03 (t, J=8.0 Hz, 1H), 6.94-6.77 (d, J=8.4 Hz, 1H), 6.34-6.21 (m, 2H), 6.09-5.96 (d, J=8.0 Hz, 1H), 5.58-5.35 (dt, J=17.6 Hz, 2H), 4.92-4.71 (m, 3H), 3.64-3.51 (m, 2H), 3.43 (dd, J=3.9, 9.5 Hz, 1H), 3.38-3.34 (m, 1H), 3.30 (s, 1H), 3.29-3.27 (m, 3H), 3.09-3.00 (m, 2H), 2.85-2.78 (m, 1H), 2.30-2.17 (m, 4H), 2.12-2.06 (m, 1H), 2.04-1.87 (m, 5H), 1.72- 1.64 (m, 1H) $^1$H NMR (400 MHz, CDCl3, 298 K) δ (ppm)=7.42 (s, 1H), 7.24 (t, J=8.0 Hz, 1H), 7.07-6.98 (d, J=2.0 Hz, 1H), 6.88-6.78 (d, J=8.4 Hz, 1H), 6.59-6.49 (t J=5.6 Hz, 1H), 6.33 (d, J=7.7 Hz, 1H), 6.22-6.09 (d, J=2.0 Hz, 1H), 5.36-5.16 (m, 2H), 5.01-4.76 (m, 3H), 4.44-4.34 (d, J=9.6 Hz, 1H), 3.75-3.56 (m, 2H), 3.53 (dd, J=4.2, 9.5 Hz, 1H), 3.49-3.43 (m, 1H), 3.39 (s, 3H), 3.37-3.32 (m, 1H), 3.22-3.12 (m, 1H), 3.20-3.12 (m, 1H), 3.03-2.88 (m, 1H), 2.42-2.15 (m, 5H), 2.12-1.95 (m, 6H).

Example 282: Compound 538B: N-{[3-(4-{1[(3S, 4R)-3-fluoro-1-methylpiperidin-4-yl]amino}-1-(2,2,2-trifluoroethyl)-1H-indol-2-yl)-1,2,4-oxadiazol-5-yl]methyl}-1-(2-methoxyethyl)-1H-pyrrole-2-carboxamide 1-(2-methoxyethyl)-1H-pyrrole-2-carboxylic acid was prepared using the same process used to prepare the N-ethyl pyrrole carboxylic acid.

Amine 1 (60 mg, 130 μmol, 1 eq, HCl) and 1-(2-methoxyethyl)pyrrole-2-carboxylic acid (43.9 mg, 259 μmol, 2 eq) were coupled under method A. The crude reaction was purified by prep-TLC (SiO$_2$, DCM:methanol=1: 1) to provide the desire product N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(2-methoxyethyl)-1H-pyrrole-2-carboxamide (24.6 mg, 31.5% yield, 95.9% purity) as a light yellow solid. LC-MS (ES$^+$, m/z): 578.2 [(M+H)$^+$]. $^1$H NMR (400 MHz, DMSO-d6) δ=8.87 (t, J=5.7 Hz, 1H), 7.89 (s, 1H), 7.15-7.08 (m, 1H), 7.00 (t, J=2.1 Hz, 1H), 6.92 (dd, J=1.5, 4.0 Hz, 1H), 6.88 (d, J=8.4 Hz, 1H), 6.28 (d, J=7.9 Hz, 1H), 6.07 (dd, J=2.6, 3.7 Hz, 1H), 6.00 (d, J=8.4 Hz, 1H), 5.50 (q, J=8.7 Hz, 2H), 4.92-4.72 (m, 3H), 4.44 (t, J=5.5 Hz, 2H), 3.63 (br s, 1H), 3.17 (s, 3H), 3.04 (br t, J=10.4 Hz, 1H), 2.82 (br d, J=10.4 Hz, 1H), 2.31-2.16 (m, 4H), 2.14-2.06 (m, 1H), 2.05-1.94 (m, 1H), 1.68 (br d, J=10.6 Hz, 1H).

Example 283: Compound 539B: N-{[3-(4-{[(3S, 4R)-3-fluoro-1-methylpiperidin-4-yl]amino}-1-(2,2,2-trifluoroethyl)-1H-indol-2-yl)-1,2,4-oxadiazol-5-yl]methyl}-1-methyl-2-(propan-2-yl)-1H-imidazole-4-carboxamide

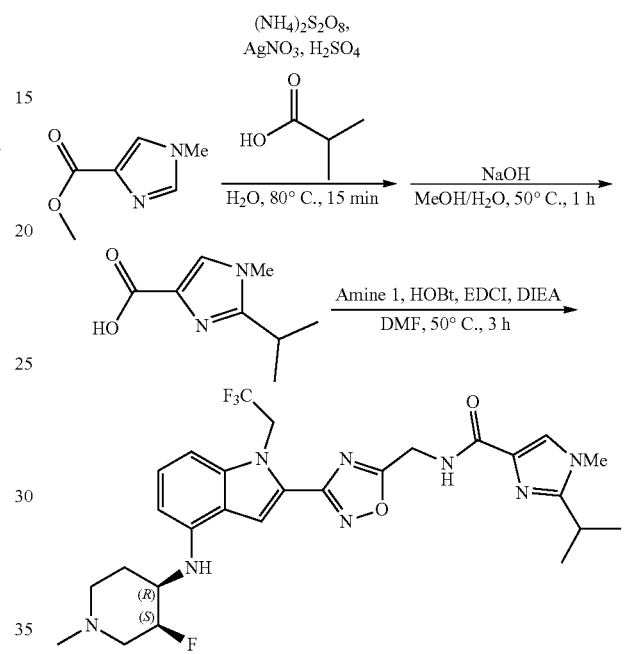

To a mixture of methyl 1-methylimidazole-4-carboxylate (200 mg, 1.43 mmol, 1 eq), 2-methylpropanoic acid (4.29 mmol, 400 μL 3 eq) in 10% sulfuric acid (26.8 mmol, 14.3 mL, 18.7 eq) was added silver nitrate (145 mg, 856 μmol, 0.6 eq) at 80° C. under nitrogen. Ammonium persulfate (977 mg, 4.28 mmol, 3 eq) in water (14 mL) was then added dropwise over 15 min. The reaction mixture was quenched with sodium carbonate (saturated) to adjust pH=7-8, then extracted with EA (10 mL×3). The combined organic layers were washed with brine (30 mL), dried over sodium sulfate, filtered, and concentrated in vacuo to give a residue. The residue was purified by prep-TLC (SiO$_2$, PE:EA=1:2) to afford the intermediate methyl 2-isopropyl-1-methyl-imidazole-4-carboxylate (40 mg, 15.4% yield) as a colorless oil. LC-MS (ES$^+$, m/z): 183.1 [(M+H)$^+$]. $^1$H NMR (400 MHz, DMSO-d6) δ=7.77 (s, 1H), 3.70 (s, 3H), 3.63 (s, 3H), 3.06 (td, J=6.8, 13.6 Hz, 1H), 1.20 (d, J=6.7 Hz, 6H).

To a mixture of methyl 2-isopropyl-1-methyl-imidazole-4-carboxylate (40 mg, 220 μmol, 1 eq) in methanol (1 mL) was added sodium hydroxide (3 M, 0.5 mL, 6.8 eq) at 50° C. The mixture was stirred at 50° C. for 1 h. The reaction mixture was quenched by adding 1N HCl to pH=5-6 at 0° C., then concentrated in vacuo to give a residue (160 mg) as a light yellow solid. LC-MS (ES$^+$, m/z): 169.1 [(M+H)$^+$].

Amine 1 (15 mg, 32.4 μmol, 1 eq, HCl) was coupled with 2-tert-butyl-1-methyl-imidazole-4-carboxylic acid (22.1 mg, 48.6 μmol, 1.5 eq) under method A. The reaction was purified by prep-TLC (SiO$_2$, DCM:methanol=10:1) to afford the desired product N-{[3-(4-{[(3S,4R)-3-fluoro-1-methylpiperidin-4-yl]amino}-1-(2,2,2-trifluoroethyl)-11H-indol- 2-yl)-1,2,4-oxadiazol-5-yl]methyl}-1-methyl-2-(propan-2-yl)-1H-imidazole-4-carboxamide (4.9 mg, 25.4% yield, 99.0% purity) as a light yellow solid. LC-MS (ES+, m/z): 577.2 [(M+H)+]. ¹H NMR (400 MHz, DMSO-d6) δ=8.46 (t, J=6.1 Hz, 1H), 7.89 (s, 1H), 7.63 (s, 1H), 7.16-7.08 (m, 1H), 6.88 (d, J=8.2 Hz, 1H), 6.28 (d, J=7.9 Hz, 1H), 6.02 (d, J=8.4 Hz, 1H), 5.50 (q, J=9.0 Hz, 2H), 4.93-4.75 (m, 3H), 3.79 (s, 3H), 3.66-3.51 (m, 1H), 3.04 (br t, J=10.4 Hz, 1H), 2.82 (br d, J=10.4 Hz, 1H), 2.29-2.15 (m, 4H), 2.14-1.95 (m, 2H), 1.68 (br d, J=10.4 Hz, 1H), 1.40 (s, 9H).

Example 284: Compound 540B: N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(2-fluoroethyl)-1H-pyrrole-2-carboxamide The required carboxylic acid was prepared using the same procedure as used to prepare the N-ethyl pyrrole carboxylic acid. Methyl 1H-pyrrole-2-carboxylate (1 g, 7.99 mmol 1 eq) and 1-fluoro-2-iodo-ethane (2.78 g, 16 mmol, 2 eq) provided the ester methyl 1-(2-fluoroethyl)pyrrole-2-carboxylate (1 g, 73.1% yield) as a colorless liquid. LC-MS (ES+, m/z): 172.0 [(M+H)+]. Saponification under standard conditions provided, after HPLC purification, the carboxylic acid 1-(2-fluoroethyl)pyrrole-2-carboxylic acid (35 mg, 19.1% yield) as a light yellow solid. LC-MS (ES+, m/z): 158.0 [(M+H)+].

Amine 1 (70 mg, 151 μmol, 1 eq, HCl) and 1-(2-fluoroethyl)pyrrole-2-carboxylic acid (28.5 mg, 181 μmol, 1.2 eq) were coupled under method A. The crude product was purified by prep-TLC (SiO₂, DCM:methanol=10:1) to provide the desired product N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(2-fluoroethyl)-1H-pyrrole-2-carboxamide (23 mg, 27% yield) as a light yellow solid. LC-MS (ES+, m/z):566.1 [(M+H)+]. ¹H NMR (400 MHz, DMSO-d6) δ=8.93 (t, J=5.7 Hz, 1H), 7.89 (s, 1H), 7.14-7.08 (m, 1H), 7.04 (t, J=1.9 Hz, 1H), 6.98 (dd, J=1.7, 3.9 Hz, 1H), 6.88 (d, J=8.4 Hz, 1H), 6.28 (d, J=7.7 Hz, 1H), 6.11 (dd, J=2.6, 4.0 Hz, 1H), 6.00 (d, J=8.4 Hz, 1H), 5.50 (q, J=8.9 Hz, 2H), 4.92-4.72 (m, 3H), 4.70-4.61 (m, 2H), 4.56 (s, 2H), 3.68-3.52 (m, 1H), 3.09-2.97 (m, 1H), 2.82 (br d, J=9.9 Hz, 1H), 2.19 (s, 4H), 2.14-1.91 (m, 2H), 1.68 (br d, J=10.4 Hz, 1H).

Example 285: Compound 541B: N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-5H,6H,7H,8H-imidazo[1,2-a]pyridine-2-carboxamide 5,6,7,8-tetrahydroimidazo[1,2-a]pyridine-2-carboxylic acid (23.2 mg, 115 μmol, HCl) and Amine 1 (49.3 mg, 99.1 μmol, 2HCl) were coupled under method B. The reaction was filtered through an Acrodisk using additional DMF, then purified by reverse-phase HPLC. The fractions were dried by lyophilization to provide the product as the formate salt N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-5H,6H, 7H,8H-imidazo[1,2-a]pyridine-2-carboxamide (16.8 mg. 27.3% yield, formate salt). LC-MS (ES+, m/z):556.8 [(M+H)+].

Example 286: Compound 542B:5-tert-butyl-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-methyl-1H-pyrrole-2-carboxamide

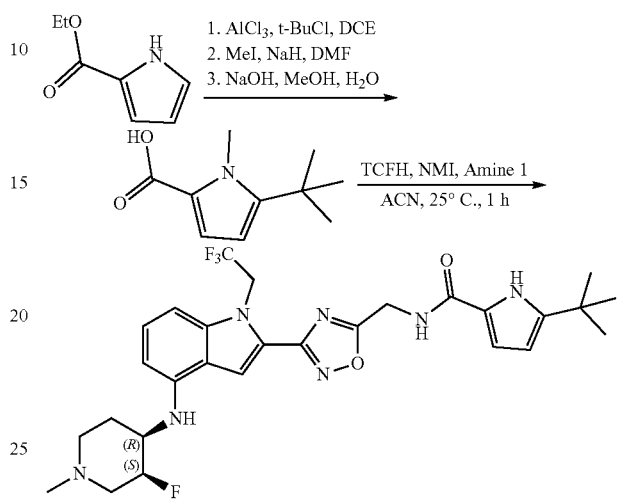

To a mixture of ethyl 1H-pyrrole-2-carboxylate (2 g, 14 mmol, 1 eq) and aluminum chloride (4.02 g, 30 mmol, 2.1 eq) in DCE (133 mL) was added 2-chloro-2-methyl-propane (14.4 mmol, 1.58 mL, 1 eq) at 25° C., and the reaction was stirred for 1 h under nitrogen. The reaction mixture was slowly poured into sodium bicarbonate (sat., 150 mL) at 0° C. The mixture was stirred 0.5 h and filtered. The filtrate was extracted with DCM (3×50 mL). The combined organic layers were washed with brine (3×100 mL), dried over anhydrous sodium sulfate, filtered, and concentrated in vacuo to give a residue, which was purified by column chromatography (SiO₂, PE/EA=50/1 to 20/1, TLC (SiO2, PE:EA=5:1, Rf=0.6)) to afford the product (2.5 g, 88.7% yield) as a white solid. LC-MS (ES+, m/z): 196.2 [(M+H)+]. ¹H NMR (400 MHz, CDCl₃) δ=8.84 (br s, 1H), 6.82 (dd, J=2.6, 3.7 Hz, 1H), 6.07-5.95 (m, 1H), 4.31 (q, J=7.1 Hz, 2H), 1.36 (t, J=7.1 Hz, 3H), 1.33 (s. 9H).

The pyrrole thus obtained was alkylated with iodomethane under the same conditions used for similar analogues, thus providing the desired N-methyl ester. The ester thus obtained was saponified under standard conditions to provide the desired carboxylic acid intermediate.

Amine 1 (50 mg, 100 μmol, 1 eq, 2HCl) and 5-tert-butyl-1H-pyrrole-2-carboxylic acid (20.1 mg, 120 μmol, 1.2 eq) were coupled under method E. TLC (DCM:methanol=5:1, Rf-0.6) indicated formation of product. The crude product after workup was purified by prep-HPLC (FA condition: column: Phenomenex Luna C18 200×40 mm×10 um; mobile phase:[water (0.2% FA)-ACN]; B %: 10%-60%, 8 min) to provide the desired product 5-tert-butyl-N-{[3-(4-{1(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-methyl-1H-pyrrole-2-carboxamide (22.6 mg, 75.3% yield) as a yellow solid. LC-MS (ES+, m/z): 576.1 [(M+H)]. ¹H NMR (400 MHz, DMSO-d₆) δ=11.13 (s, 1H), 8.85-8.69 (t, J=5.6 Hz, 1H), 7.89 (s, 1H), 7.22-7.03 (t, J=8.0 Hz, 1H), 6.96-6.79 (d, J=8.4 Hz, 1H), 6.77-6.67 (dt, J=3.6 Hz, 1H), 6.30-6.21 (d, J=8.0 Hz, 1H), 6.10-5.96 (d, J=8.4 Hz, 1H), 5.92- 5.79 (dt, J=3.4 Hz, 1H), 5.64-5.34 (dt, J=18.0

Hz, 2H), 4.94-4.64 (m, 3H), 3.69-3.52 (m, 1H), 3.03 (br t, J=10.5 Hz, 1H), 2.88-2.74 (m, 1H), 2.32-2.14 (m, 4H), 2.14-2.06 (m, 1H), 2.05-1.92 (m, 1H), 1.72-1.59 (m, 1H), 1.26 (s, 9H).

Example 287: Compound 543B: 5-tert-butyl-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1,2-oxazole-3-carboxamide

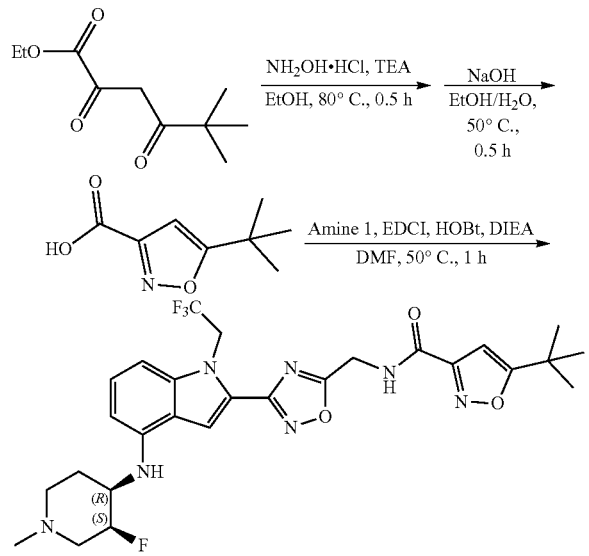

A mixture of ethyl 5,5-dimethyl-2,4-dioxo-hexanoate (1 g, 4.99 mmol, 1 eq), hydroxylamine hydrochloride (347 mg, 4.99 mmol, 1 eq), TEA (10 mmol, 1.40 mL, 2 eq) in ethanol (10 mL) was degassed and purged with nitrogen 3 times, then the mixture was stirred at 80° C. for 0.5 h under nitrogen atmosphere. The reaction mixture was quenched by adding water (30 mL), then extracted with EA (10 mL×3). The combined organic layers were washed with brine (10 mL×2), dried over anhydrous sodium sulfate, filtered, and concentrated in vacuo to give the crude isoxazole ester (0.2 g, 20.3% yield) as a yellow oil. LC-MS (ES$^+$, m:z): 198.1 [(M+H)$^+$].

To the ethyl 5-tert-butylisoxazole-3-carboxylate (400 mg, 2.03 mmol, 1 eq) in ethanol (2 mL) was added sodium hydroxide (2 mmol, 1 M, 2 mL, 1 eq). The mixture was stirred at 50° C. for 2 h. The reaction mixture was quenched by adding 3N HCl to pH<7, then diluted with water (20 mL) and extracted with EA (10 mL×3). The combined organic layers were washed with brine (10 mL×1), dried over anhydrous sodium sulfate, filtered, and concentrated in vacuo to give a residue. The residue was purified by prep-HPLC (FA condition:column: Phenomenex Luna C18 200× 40 mm×10 um; mobile phase: [water (0.2% FA)-ACN]; B %: 1%-50%, 8 min) to provide the carboxylic acid (0.1 g, 29.1% yield) as a yellow oil. LC-MS (ES$^+$, m/z): 169.9 [(M+H)$^+$]. $^1$H NMR (400 MHz, DMSO-d$_6$) δ=6.43 (s, 1H), 1.39 (s, 9H).

Amine 1 (70 mg, 123 μmol, 1 eq, 2HCl) and 5-tert-butylisoxazole-3-carboxylic acid (41.7 mg, 247 μmol, 2 eq) were coupled under method A. The crude product was purified by prep-TLC (SiO$_2$, DCM: methanol=10:1) to afford the desired product 5-tert-butyl-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1,2-oxazole-3-carboxamide (24.7 mg, 32.9% yield, 95% purity) as a yellow solid. LC-MS (ES$^+$, m/z): 578.1 [(M+H)$^+$]. $^1$H NMR (400 MHz, DMSO-d$_6$) δ=9.70-9.41 (t, J=5.6 Hz, 1H), 7.89 (s, 1H), 7.30-7.04 (t, J=8.0 Hz, 1H), 6.97-6.82 (d, J=8.4 Hz, 1H), 6.64 (s, 1H), 6.36-6.20 (d, J=8.0 Hz, 1H), 6.09-5.97 (d, J=8.4 Hz, 1H), 5.63-5.24 (dt, J=17.6 Hz, 2H), 5.09-4.65 (m, 3H), 3.75-3.44 (m, 1H), 3.08-2.99 (m, 1H), 2.81 (m, 1H), 2.31-2.17 (m, 4H), 2.14-2.06 (m, 1H), 2.05-1.94 (m, 1H), 1.73-1.64 (m, 1H), 1.34 (s, 9H).

Example 288: Compound 558B: 3-(4-{[(3S,4R)-3-fluoro-1-methylpiperidin-4-yl]amino}-1-(2,2,2-trifluoroethyl)-1H-indol-2-yl)-N-[(oxan-4-yl)methyl]-1,2,4-oxadiazole-5-carboxamide

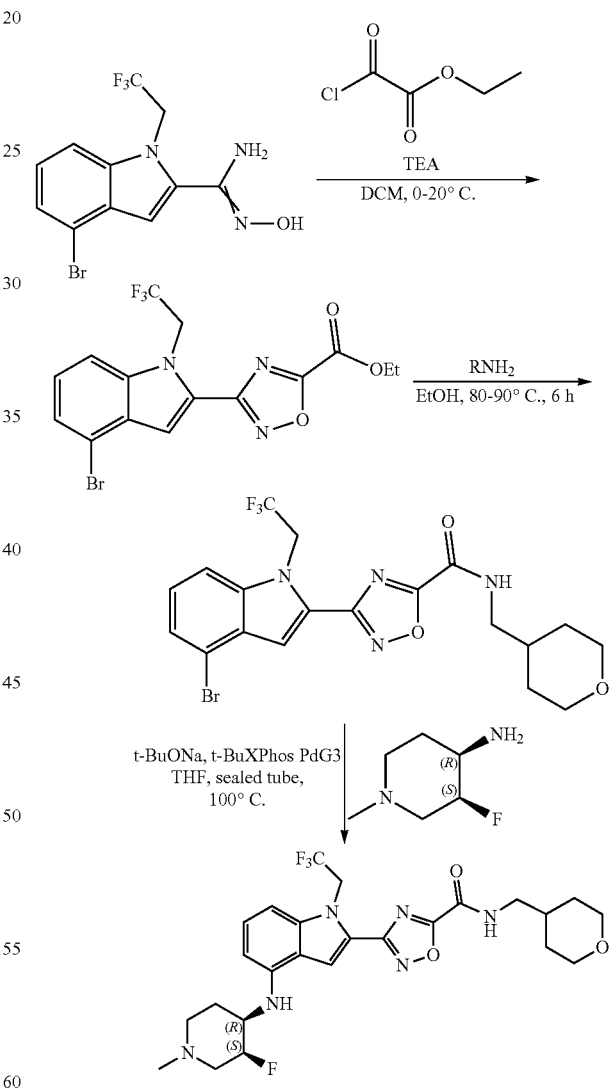

To a mixture of the previously prepared 4-bromo-N'-hydroxy-1-(2,2,2-trifluoroethyl)indole-2-carboxamidine (4 g, 11.9 mmol, 1 eq) in DCM (50 mL) was added TEA (23.7 mmol, 3.3 mL, 2 eq) in one portion at 0° C. Ethyl 2-chloro-2-oxo-acetate (13.09 mmol, 1.47 mL, 1.1 eq) was added, and the mixture was stirred at 20° C. for 5 h. The residue was poured into ice-water (w/w=1/1) (200 mL). The aqueous phase was extracted with EA (50 mL×3). The combined organic phase was washed with brine (50 mL×3), dried over anhydrous sodium sulfate, filtered, and concentrated in vacuo. The residue was purified by silica gel chromatography (column height: 250 mm, diameter: 100 mm, 100-200 mesh silica gel, PE/EA=1/0, 96/4) to provide ethyl 3-[4-bromo-1-(2,2,2-trifluoroethyl)indol-2-yl]-1,2,4-oxadiazole-5-carboxylate (2 g, 40.2% yield) as a light yellow solid. LC-MS (ES$^+$, m/z): 418.0/420.0 [(M+H)$^+$].

General Procedure for Acyl Oxadiazole Synthesis: Ethyl 3-[4-bromo-1-(2,2,2-trifluoroethyl)indol-2-yl]-1,2,4-oxadiazole-5-carboxylate (200 mg, 478 µmol, 1 eq) and tetrahydropyran-4-ylmethanamine (110 mg, 957 µmol, 2 eq) were combined in ethanol (2 mL). The mixture was stirred at 80° C. for 6 h. The reaction was adjusted to pH 4-5 with HCl (1 M), then extracted with EA (30 mL×3). The combined organic layers were washed with brine (30 mL), dried over anhydrous sodium sulfate, filtered, and concentrated in vacuo to give the amide as a residue N-benzyl-3-[4-bromo-1-(2,2,2-trifluoroethyl)indol-2-yl]-1,2,4-oxadiazole-5-carboxamide (150 mg, crude) as a white solid. LC-MS (ES$^+$, m/z): 487.0/489.0.

To a mixture of (3S,4R)-3-fluoro-1-methyl-piperidin-4-amine (167.9 mg, 1.27 mmol, 3 eq) and 1-[3-[4-bromo-1-(2,2,2-trifluoroethyl)indol-2-yl]-1,2,4-oxadiazol-5-yl]-2-tetrahydropyran-4-yl-ethanone (200 mg, 424 µmol, 1 eq) in THF (2 mL) were added sodium t-butoxide (1 M, 850 mL, 2 eq), t-Butyl-XPhos Generation 3 (134.6 mg, 169 µmol, 0.4 eq), and the reaction was heated at 100° C. in a sealed tube for 2 h. The residue was poured into EDTA (saturated solution) (40 mL) and stirred for 60 min. The aqueous phase was extracted with EA (20 mL×3). The combined organic phase was washed with brine (20 mL×3), dried over anhydrous sodium sulfate, filtered, and concentrated in vacuo. The residue was purified by prep-TLC (SiO$_2$, DCM:methanol=10:1) to provide the desired product 3-(4-{[(3S,4R)-3-fluoro-1-methylpiperidin-4-yl]amino}-1-(2,2,2-trifluoroethyl)-1H-indol-2-yl)-N-[(oxan-4-yl)methyl]-1,2,4-oxadiazole-5-carboxamide (21 mg, 8.7% yield, 94.0% purity) as a yellow solid. LC-MS (ES$^+$, m/z): 539.1 [(M+H)$^+$]. $^1$H NMR (400 MHz, DMSO-d6) S=9.50 (t, J=5.9 Hz, 1H), 7.99 (s, 1H), 7.19-7.10 (m, 1H), 6.93 (d, J=8.3 Hz, 1H), 6.31 (d, J=7.9 Hz, 1H), 6.01 (d, J=8.4 Hz, 1H), 5.55 (q, J=9.0 Hz, 2H), 4.98-4.71 (m, 1H), 3.85 (br dd, J=2.4, 11.3 Hz, 2H), 3.70-3.53 (m, 1H), 3.30-3.19 (m, 3H), 3.10-3.00 (m, 1H), 2.82 (br d, J=11.5 Hz, 1H), 2.31-2.18 (m, 4H), 2.15-2.07 (m, 1H), 2.05-1.96 (m, 1H), 1.91-1.80 (m, 1H), 1.76-1.67 (m, 1H), 1.61 (br d, J=11.5 Hz, 2H), 1.25-1.19 (m, 2H).

Example 289: Compound 544B: N-benzyl-3-(4-{[(3S,4R)-3-fluoro-1-methylpiperidin-4-yl]amino}-1-(2,2,2-trifluoroethyl)-1H-indol-2-yl)-1,2,4-oxadiazole-5-carboxamide The analogue was prepared using the general procedure above. 3-[4-bromo-1-(2,2,2-trifluoroethyl)indol-2-yl]-1,2,4-oxadiazole-5-carboxylate (200 mg, 478 µmol, 1 eq) and benzylamine (958 µmol, 105 µL 2 eq) provided the intermediate N-benzyl-3-[4-bromo-1-(2,2,2-trifluoroethyl)indol-2-yl]-1,2,4-oxadiazole-5-carboxamide (150 mg, crude) as a white solid. LC-MS (ES$^+$, m/z): 479.1/481.1 [(M+H)$^+$]. $^1$H NMR (400 MHz, DMSO-d6) δ=10.08 (br t, J=6.1 Hz, 1H), 7.87 (d, J=8.3 Hz, 1H), 7.49 (d, J=7.6 Hz, 1H), 7.42-7.33 (m, 6H), 7.32-7.25 (m, 1H), 5.72 (q, J=8.9 Hz, 2H), 4.53 (d, J=6.0 Hz, 2H).

Buchwald coupling of this intermediate (190 mg, 396 µmol, 1 eq) provided the desired product N-benzyl-3-(4-{[(3S,4R)-3-fluoro-1-methylpiperidin-4-yl]amino}-1-(2,2,2-trifluoroethyl)-1H-indol-2-yl)-1,2,4-oxadiazole-5-carboxamide (21.1 mg, 10.0% yield, 100.0% purity) as a yellow solid. LC-MS (ES$^+$, m/z): 531.1 [(M+H)$^+$]. $^1$H NMR (400 MHz, DMSO-d6) δ=10.02 (br t, J=6.0 Hz, 1H), 7.99 (s, 1H), 7.46-7.25 (m, 5H), 7.15 (t, J=8.0 Hz, 1H), 6.94 (d, J=8.2 Hz, 1H), 6.32 (d, J=7.8 Hz, 1H), 5.99 (br d, J=8.3 Hz, 1H), 5.68-5.47 (m, 2H), 4.98-4.74 (m, 1H), 4.54 (br d, J=5.9 Hz, 2H), 3.74-3.52 (m, 1H), 3.74-3.52 (m, 1H), 3.11-2.99 (m, 1H), 2.83 (br d, J=11.7 Hz, 1H), 2.32-2.17 (m, 4H), 2.15-2.07 (m, 1H), 2.07-1.95 (m, 1H), 1.72 (br d, J=10.0 Hz, 1H).

Example 290: Compound 545B: N-(cyclopropylmethyl)-3-(4-{[(3S,4R)-3-fluoro-1-methylpiperidin-4-yl]amino}-1-(2,2,2-trifluoroethyl)-1H-indol-2-yl)-1,2,4-oxadiazole-5-carboxamide The analogue was prepared using the general procedure above. Ethyl 3-[4-bromo-1-(2,2,2-trifluoroethyl)indol-2-yl]-1,2,4-oxadiazole-5-carboxylate (200 mg, 478 µmol, 1 eq) and cyclopropylmethanamine (68 mg, 956 µmol, 2 eq) provided the desired intermediate N-(cyclopropylmethyl)-3-[4-[[(3S,4R)-3-fluoro-1-methyl-4-piperidyl]amino]-1-(2,2,2-trifluoroethyl)indol-2-yl]-1,2,4-oxadiazole-5-carboxamide (190 mg, crude) as a white solid. LC-MS (ES$^+$, m/z): 443.1/445.1. Buchwald coupling of the intermediate (190 mg, 429 µmol, 1 eq) provided, after HPLC purification (FA condition, column: 3_Phenomenex Luna C18 75×30 mm×3 um; mobile phase: [water (0.2% FA)-ACN]; B %: 25%-60%, 8 min), the desired product N-(cyclopropylmethyl)-3-(4-{[(3S,4R)-3-fluoro-1-methylpiperidin-4-yl]amino}-1-(2,2,2-trifluoroethyl)-1H-indol-2-yl)-1,2,4-oxadiazole-5-carboxamide (24.3 mg, 11.5% yield, 100.0% purity) as a yellow solid. LC-MS (ES$^+$, m/z): 495.1 [(M+H)$^+$]. $^1$H NMR (400 MHz, DMSO-d6) δ=9.54 (br t, J=5.4 Hz, 1H), 8.18 (s, 1H), 8.22-8.15 (m, 1H), 8.00 (s, 1H), 7.27-7.06 (m, 1H), 6.93 (br d, J=8.3 Hz, 1H), 6.32 (br d, J=7.8 Hz, 1H), 5.98 (br d, J=8.3 Hz, 1H), 5.55 (q, J=9.1 Hz, 2H), 4.97-4.72 (m, 1H), 3.76-3.50 (m, 1H), 3.20 (br t, J=6.4 Hz, 2H), 3.10-3.00 (m, 1H), 2.87-2.78 (m, 1H), 2.28-2.16 (m, 4H), 2.15-2.07 (m, 1H), 2.06-1.96 (m, 1H), 1.78-1.67 (m, 1H), 1.15-0.99 (m, 1H), 0.58-0.38 (m, 2H), 0.33-0.20 (m, 2H).

Example 291: Compound 546I1: 3-(4-{[(3S,4R)-3-fluoro-1-methylpiperidin-4-yl]amino}-1-(2,2,2-trifluoroethyl)-1H-indol-2-yl)-N-1(1-methyl-1H-pyrazol-4-yl)methyl]-1,2,4-oxadiazole-5-carboxamide The analogue was prepared using the general procedure above. Ethyl 3-[4-bromo-1-(2,2,2-trifluoroethyl)indol-2-yl]-1,2,4-oxadiazole-5-carboxylate (200 mg, 478 µmol, 1 eq) and (1-methylpyrazol-4-yl)methanamine (106.3 mg, 957 µmol, 2 eq) provided the intermediate 3-[4-bromo-1-(2,2,2-trifluoroethyl)indol-2-yl]-N-[(1-methylpyrazol-4-yl)methyl]-1,2,4-oxadiazole-5-carboxamide (190 mg, crude) as a white solid. LC-MS (ES$^+$, m/z): 483.0/485.0. Buchwald coupling of the intermediate (190 mg, 393 µmol, 1 eq) provided the desired product 3-(4-{[(3S,4R)-3-fluoro-1-methylpiperidin-4-yl]amino}-1-(2,2,2-trifluoroethyl)-1H-indol-2-yl)-N-[(1-methyl-1H-pyrazol-4-yl)methyl]-1,2,4-oxadiazole-5-carboxamide (22.4 mg, 10.7% yield, 100.0% purity), after prep-TLC (SiO$_2$, DCM:methanol=10: 1) purification, as a yellow solid. LC-MS (ES$^+$, m/z): 535.1 [(M+H)$^+$]. $^1$H NMR (400 MHz, DMSO-d6) δ=9.81 (t, J=5.9 Hz, 1H), 7.97 (s, 1H), 7.66 (s, 1H), 7.39 (s, 1H), 7.14 (t, J=8.0

Hz, 1H), 6.92 (d, J=8.4 Hz, 1H), 6.31 (d, J=7.9 Hz, 1H), 5.97 (d, J=8.3 Hz, 1H), 5.54 (q, J=9.0 Hz, 2H), 4.94-4.75 (m, 1H), 4.34 (d, J=5.9 Hz, 2H), 3.79 (s, 3H), 3.69-3.54 (m, 1H), 3.11-2.98 (m, 1H), 2.82 (br d, J=11.0 Hz, 1H), 2.31-2.17 (m, 4H), 2.15-2.06 (m, 1H), 2.04-1.92 (m, 1H), 1.75-1.67 (m, 1H).

Example 292: Compound 54711: N-{[3-(4-{[(3S, 4R)-3-fluoro-1-methylpiperidin-4-yl]amino}-1-(2,2,2-trifluoroethyl)-1H-indol-2-yl)-1,2,4-oxadiazol-5-yl]methyl}-1-(1-methoxy-2-methylpropan-2-yl)-1H-pyrazole-3-carboxamide

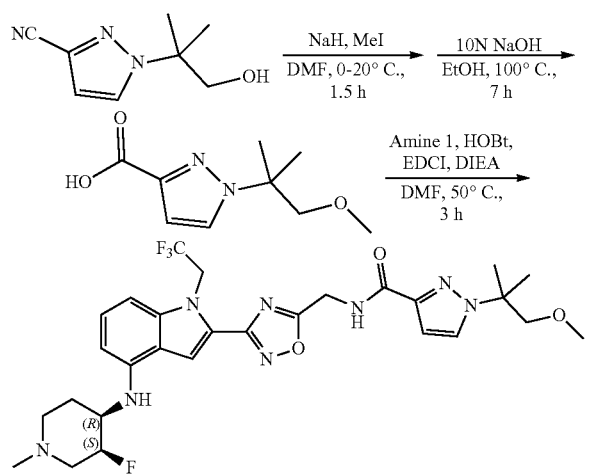

To a mixture of 1-(2-hydroxy-1,1-dimethyl-ethyl)pyrazole-3-carbonitrile (100 mg, 605 μmol, 1 eq) in DMF (3 mL) was added sodium hydride (72.6 mg, 1.82 mmol, 60% purity, 3 eq) at 0° C. under nitrogen. The mixture was stirred at 0° C. for 30 min, followed by addition of iodomethane (3.02 mmol, 190 μL 5 eq). The mixture was stirred at 20° C. for 60 min. The reaction was poured into sat. ammonium chloride (40 mL). The aqueous phase was extracted with EA (10 mL×3). The combined organic phase was washed with brine (10 mL×3), dried over anhydrous sodium sulfate, filtered, and concentrated in vacuo to provide 1-(2-methoxy-1,1-dimethyl-ethyl)pyrazole-3-carbonitrile (100 mg, crude) as a colorless oil. LC-MS (ES+, m/z): 180.0 [(M+H)+].

To a mixture of 1-(2-methoxy-1,l-dimethyl-ethyl)pyrazole-3-carbonitrile (100 mg, 558 μmol, 1 eq) in ethanol (1 mL) was added sodium hydroxide (10 M, 1 mL, 17.92 eq), and the reaction was heated at 100° C. for 7 h. The residue was treated with HCl (12 M) to adjust pH=3-4. The aqueous phase was extracted with DCM (10 mL×3). The combined organic phase was washed with brine (10 mL×3), dried over anhydrous sodium sulfate, filtered, and concentrated in vacuo to provide 1-(2-methoxy-1,1-dimethyl-ethyl)pyrazole-3-carboxylic acid (100 mg, crude) as a colorless oil. LC-MS (ES+, m:z): 199.0 [(M+H)+].

Amine 1 (90 mg, 159 μmol, 1 eq, 2HCl) was coupled with 1-(2-methoxy-1,1-dimethyl-ethyl)pyrazole-3-carboxylic acid (37.7 mg, 190 μmol, 1.2 eq) under method A. The crude product was purified by prep-TLC (SiO₂, DCM:methanol=10:1) to provide the desired product N-{[3-(4-{[(3S, 4R)-3-fluoro-1-methylpiperidin-4-yl]amino}-1-(2,2,2-trifluoroethyl)-1H-indol-2-yl)-1,2,4-oxadiazol-5-yl]methyl}-1-(I-methoxy-2-methylpropan-2-yl)-1H-pyrazole-3-carboxamide (24.6 mg, 25.6% yield, 100.0% purity) as a white solid. LC-MS (ES+, m/z):607.2 [(M+H)+]. ¹H NMR (400 MHz, DMSO-d6) δ=8.85 (t, J=5.9 Hz, 1H), 7.90 (d, J=2.0 Hz, 2H), 7.11 (t, J=8.1 Hz, 1H), 6.87 (d, J=8.4 Hz, 1H), 6.67 (d, J=2.5 Hz, 11H), 6.28 (d, J=8.0 Hz, 1H), 6.00 (d, J=8.4 Hz, 1H), 5.50 (q, J=8.7 Hz, 2H), 4.92-4.74 (m, 3H), 3.66-3.51 (m, 3H), 3.21 (s, 3H), 3.07-2.98 (m, 1H), 2.86-2.77 (m, 1H), 2.29-2.16 (m, 4H), 2.13-2.04 (m, 1H), 2.04-1.93 (m, 1H), 1.71- 1.63 (m, 1H), 1.55 (s, 61H).

Example 293: Compound 548B: N-{[3-(4-{[(3S, 4R)-3-fluoro-1-methylpiperidin-4-yl]amino}-1-(2,2,2-trifluoroethyl)-1H-indol-2-yl)-1,2,4-oxadiazol-5-yl]methyl}-1-(1-fluoro-2-methylpropan-2-yl)-1H-pyrazole-3-carboxamide

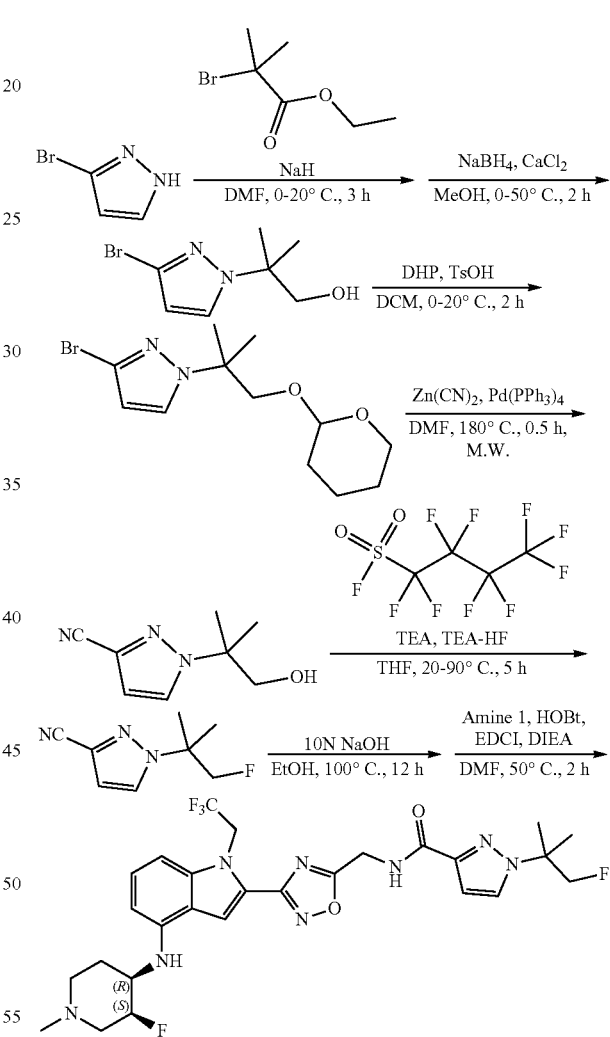

To a mixture of 3-bromo-1H-pyrazole (4 g, 27 mmol, 1 eq) in DMF (40 mL) was added sodium hydride (2.18 g, 54.4 mmol, 60% purity, 2 eq) at 0° C. under nitrogen. The mixture was stirred at 0° C. for 30 min, followed by addition of ethyl 2-bromo-2-methyl-propanoate (40.8 mmol, 6 mL, 1.5 eq). The mixture was stirred at 20° C. for 2 h 30 min. The residue was poured into sat. ammonium chloride (200 mL) and stirred for 5 min. The aqueous phase was extracted with EA (50 mL×2). The combined organic phase was washed with brine (50 mL×2), dried over anhydrous sodium sulfate, filtered, and concentrated in vacuo. The reaction was purified by prep-HPLC (TFA condition, column: Phenomenex luna c18 250 mm×100 mm×10 um; mobile phase: [water (0.1% TFA)-ACN]; B %: 35%-65%, 25 min) to provide ethyl 2-(3-bromopyrazol-1-yl)-2-methyl-propanoate (5.5 g, 77.4% yield) as a brown oil. LC-MS (ES$^+$, m/z): 261.2/263.2[(M+H)$^+$]. $^1$H NMR (400 MHz, DMSO-d6) δ=7.95 (d, J=2.5 Hz, 1H), 6.43 (d, J=2.5 Hz, 1H), 4.09 (q, J=7.2 Hz, 2H), 1.74 (s, 6H), 1.12 (t, J=7.1 Hz, 3H).

To a mixture of ethyl 2-(3-bromopyrazol-1-yl)-2-methyl-propanoate (5.5 g, 21 mmol, 1 eq), CaCl$_2$ (1.17 g, 10.5 mmol, 0.5 eq) in methanol (55 mL) was added sodium borohydride (2.47 g, 65.3 mmol, 3.1 eq) at 0° C. under nitrogen, then the reaction was heated to 50° C. and stirred for 2 h. The residue was poured into HCl (2N) to adjust the pH=7. The aqueous phase was extracted with EA (50 mL×3). The combined organic phase was washed with brine (50 mL×3), dried over anhydrous sodium sulfate, filtered, and concentrated in vacuo. The reaction was purified by prep-HPLC (TFA, column: Phenomenex luna C18 (250×70 mm, 15 um); mobile phase: [water (0.1% TFA)-ACN]; B %: 5%-45%, 20 min) to provide 2-(3-bromopyrazol-1-yl)-2-methyl-propan-1-ol (1.9 g, 41.2% yield) as brown oil. LC-MS (ES$^+$, m/z): 219.0/221.0[(M+H)$^-$].

To a mixture of 2-(3-bromopyrazol-1-yl)-2-methyl-propan-1-ol (1.9 g, 8.67 mmol, 1 eq) in DCM (20 mL) was added p-TsOH (149.3 mg, 867 μmol, 0.1 eq) at 0° C. under nitrogen, followed by 3,4-dihydro-2H-pyran (13.9 mmol, 1.27 mL, 1.6 eq). The mixture was stirred at 20° C. for 2 h. The residue was poured into sodium bicarbonate (sat., 80 mL). The aqueous phase was extracted with EA (20 mL×3). The combined organic phase was washed with brine (20 mL×3), dried over anhydrous sodium sulfate, filtered, and concentrated in vacuo. The residue was purified by prep-HPLC (TFA condition, column: Agela DuraShell C18 250× 70 mm×10 um; mobile phase: [water (10 mM NH4HCO3)-ACN]; B %: 40%) to provide 3-bromo-1-(1,1-dimethyl-2-tetrahydropyran-2-yloxy-ethyl)pyrazole (1.2 g, 45.6% yield) as a white solid. LC-MS (ES$^+$, m/z): 303.0/3.5.0[(M+H)$^+$]. $^1$H NMR (400 MHz, DMSO-d6) δ=7.81 (d, J=2.4 Hz, 1H), 6.35 (d, J=2.4 Hz, 1H), 4.40 (t, J=3.0 Hz, 1H), 3.75 (d, J=10.0 Hz, 1H), 3.49 (br d, J=9.9 Hz, 2H), 3.39-3.35 (m, 1H), 1.63-1.37 (m, 10H).

To a mixture of 3-bromo-1-(1,1-dimethyl-2-tetrahydropyran-2-yloxy-ethyl)pyrazole (500 mg, 1.65 mmol, 1 eq) in DMF (5 mL) were added Pd(PPh$_3$)$_4$(381.1 mg, 330 μmol, 0.2 eq), zinc cyanide (581 mg, 4.95 mmol, 3 eq), and the reaction was heated at 180° C. under microwave for 0.5 h. The residue was poured into EDTA (saturated solution, 50 mL) and stirred for 60 min. The aqueous phase was extracted with EA (30 mL×3). The combined organic phase was washed with brine (30 mL×3), dried over anhydrous sodium sulfate, filtered, and concentrated in vacuo. The reaction was purified by prep-HPLC (basic condition, column: Welch Xtimate C18 250×70 mm #10 um; mobile phase: [water (0.04% NH$_3$H$_2$O+10 mM NH4HCO3)-ACN]; B %: 10%-28%, 25 min) to provide 1-(2-hydroxy-1,1-dimethyl-ethyl)pyrazole-3-carbonitrile (0.3 g, 55.1% yield) as a light yellow oil. LC-MS (ES$^+$, m/z): 166.0 [(M+H)$^+$]. $^1$H NMR (400 MHz, DMSO-d6) δ=8.06 (d, J=2.6 Hz, 1H), 6.93 (d, J=2.6 Hz, 1H), 5.06 (t, J=5.5 Hz, 1H), 3.58 (d, J=5.7 Hz, 2H), 1.48 (s, 6H).

To a mixture of 1-(2-hydroxy-1,1-dimethyl-ethyl)pyrazole-3-carbonitrile (180 mg, 1.09 mmol, 1 eq) in THF (3 mL) were added TEA (13.1 mmol, 1.82 mL, 12 eq), N,N-diethylethanamine; trihydrofluoride (1.41 g, 8.72 mmol, 8 eq), and 1,1,2,2,3,3,4,4-nonafluorobutane-1-sulfonyl fluoride (8.72 mmol, 1.53 mL, 8 eq) at 20° C. in a sealed tube, and then heated to 90° C. for 5 h. The residue was poured into ice-water (w/w=1/1, 50 mL). The aqueous phase was extracted with EA (20 mL×3). The combined organic phase was washed with brine (20 mL×3), dried over anhydrous sodium sulfate, filtered, and concentrated in vacuo to provide 1-(2-fluoro-1,1-dimethyl-ethyl)pyrazole-3-carbonitrile (140 mg, crude) as a light yellow oil. LC-MS (ES$^+$, m/z): 168.0 [(M+H)$^+$].

To a mixture of 1-(2-fluoro-1,1-dimethyl-ethyl)pyrazole-3-carbonitrile (200 mg, 1.20 mmol, 1 eq) in ethanol (2 mL) was added sodium hydroxide (10 M, 940 μL 7.87 eq) at 20° C., and the reaction was heated to 100° C. for 12 h. The residue was poured into HCl (12 N) to adjust pH=3-4. The aqueous phase was extracted with DCM (10 mL×3). The combined organic phase was washed with brine (20 mL×3), dried over anhydrous sodium sulfate, filtered, and concentrated in vacuo to give 1-(2-fluoro-1,1-dimethyl-ethyl)pyrazole-3-carboxylic acid (210 mg, crude) as a yellow solid. LC-MS (ES$^+$, m/z): 168.0 [(M+H)$^+$].

Amine 1 (90 mg, 159 μmol, 1 eq, 2HCl) and 1-(2-fluoro-1,1-dimethyl-ethyl)pyrazole-3-carboxylic acid (35.4 mg, 190.3 μmol, 1.2 eq) were coupled under method A. The crude product was purified by prep-TLC (SiO$_2$, DCM: methanol=10:1) to provide the desired product N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(1-fluoro-2-methylpropan-2-yl)-1H-pyrazole-3-carboxamide (22.3 mg, 23.7% yield, 100% purity) as a white solid. LC-MS (ES$^+$, m/z): 595.2 [(M+H)$^+$]. $^1$H NMR (400 MHz, DMSO-d6) δ=8.91 (t, J=5.9 Hz, 1H), 7.99 (d, J=2.5 Hz, 1H). 7.90 (s, 1H), 7.15-7.08 (m, 1H), 6.88 (d, J=8.1 Hz, 1H), 6.72 (d, J=2.5 Hz, 1H), 6.28 (d, J=7.9 Hz, 1H), 6.01 (d, J=8.4 Hz, 1H), 5.50 (q, J=8.8 Hz, 2H), 4.92-4.75 (m, 3H), 4.75-4.60 (m, 2H), 3.67-3.51 (m, 1H), 3.10-2.98 (m, 1H), 2.81 (br d, J=10.6 Hz, 1H). 2.28 (br d, J=12.9 Hz, 1H), 2.14-2.05 (m, 1H), 2.05-1.93 (m, 1H), 1.72-1.65 (m, 1H), 1.60 (d, J=1.9 Hz, 6H).

Example 294: Compound 549B: N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-3-(2-hydroxypropan-2-yl)benzamide

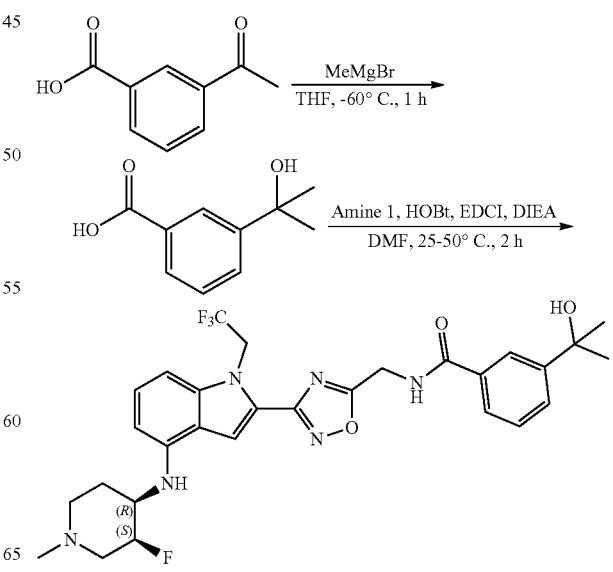

To a mixture of 3-acetylbenzoic acid (5 g, 30.46 mmol, 1 eq) in THF (50 mL) at −60° C. under $N_2$ was added methylmagnesium bromide (2.5 M, 30.5 mL, 2.5 eq) over 10 min, and the reaction was then stirred for 50 min. The reaction mixture was poured into saturated ammonium chloride (100 mL) and stirred for 5 min. The pH was adjusted to 3 using 1 M HCl(aq). The aqueous phase was extracted with EA (3×50 mL). The combined organic phase was washed with saturated brine (2×80 mL), dried over anhydrous sodium sulfate, filtered, and concentrated in vacuo to afford the tertiary alcohol 3-(1-hydroxy-1-methyl-ethyl)benzoic acid (5.8 g, crude) as a yellow oil. LC-MS ($ES^+$, m/z): 179.0 $[(M+H)^+]$.

A mixture of Amine 1 (70 mg, 140 μmol, 1 eq, 2HCl) and 3-(1-hydroxy-1-methyl-ethyl)benzoic acid (27.8 mg, 154.2 μmol, 1.1 eq) in DMF (3 mL) were coupled under conditions A. The crude product was purified by prep-TLC ($SiO_2$, DCM: MeOH=15:1) to afford the desired product N-[[3-[4-[[(3S,4R)-3-fluoro-1-methyl-4-piperidyl]amino]-1-(2,2,2-trifluoroethyl)indol-2-yl]-1,2,4-oxadiazol-5-yl]methyl]-3-(I-hydroxy-1-methyl-ethyl)benzamide (19.7 mg, 23.9% yield, 100% purity) as a light yellow powder. LC-MS ($ES^+$, m/z): 589.1 $[(M+H)^+]$. $^1H$ NMR (400 MHz, DMSO-d6) δ=9.40 (s, 1H), 8.04 (s, 1H), 7.89 (s, 1H), 7.75 (s, 1H), 7.67 (s, 1H), 7.47-7.39 (m, 1H), 7.10 (d, J=8.0 Hz, 1H), 6.89 (s, 1H), 6.28 (d, J=7.9 Hz, 1H), 6.02 (d, J=7.9 Hz, 1H), 5.51 (s, 2H), 5.17 (s, 1H), 4.84 (d, J=5.4 Hz, 3H), 2.69-2.65 (m, 2H), 2.35-2.30 (m, 2H), 2.18 (s, 4H), 2.08 (s, 1H), 1.46 (s, 6H).

Example 295: Compound 550B: N-{[3-(4-{[(3S, 4R)-3-fluoro-1-methylpiperidin-4-yl]amino}-1-(2,2,2-trifluoroethyl)-1H-indol-2-yl)-1,2,4-oxadiazol-5-yl]methyl}-2-(2-hydroxypropan-2-yl)pyridine-4-carboxamide

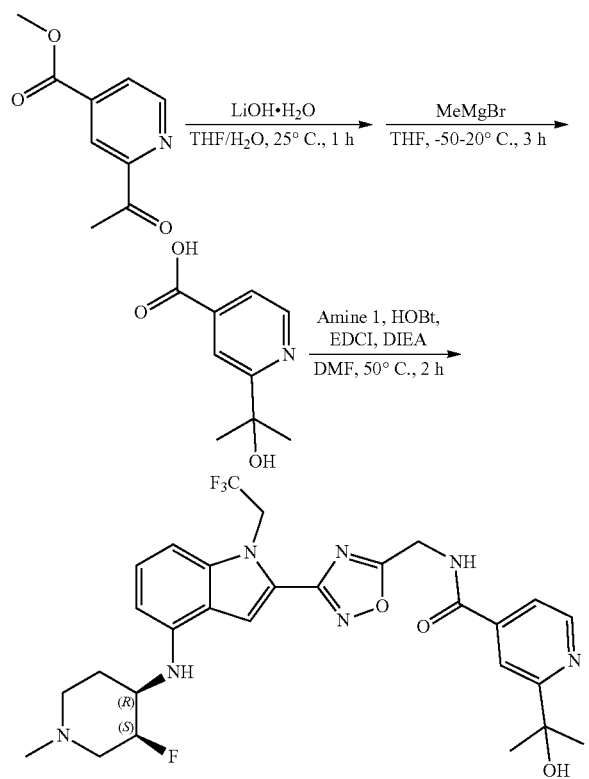

To a solution of methyl 2-acetylpyridine-4-carboxylate (2 g, 11.2 mmol, 1 eq) in THF (20 mL) and water (5 mL) was added lithium hydroxide hydrate (1.41 g, 33.5 mmol, 3 eq). The mixture was stirred at 25° C. for 1 h. The reaction mixture was quenched by adding 3N HCl to adjust pH<7 at 0° C., followed by extraction with EA (3×80 mL). The combined organic layers were dried over anhydrous sodium sulfate, filtered, and concentrated in vacuo to afford 2-acetylisonicotinic acid as a yellow solid (1.5 g, 9.08 mmol, 81.4% yield).

To a solution of 2-acetylpyridine-4-carboxylic acid (1 g, 6.06 mmol, 1 eq) in THF (40 mL) was added methylmagnesium bromide (3 M, 10.1 mL, 5 eq) at −50 L. The mixture was stirred at 20° C. for 3 h. The reaction mixture was quenched by adding sat. ammoniumn chloride (10 mL), and diluted with 1N HCl 1 to adjust pH<5, then extracted with DCM (3×30 mL). The combined organic layers were washed with brine (3×20 mL), dried over anhydrous sodium sulfate, filtered, and concentrated in vacuo to give a residue. The residue was purified by prep-HPLC (FA condition: column: Phenomenex luna C 18 (250×70 mm, 15 um); mobile phase: [water (0.225% FA)-ACN];B %: 0%-10%, 20 min) to afford 2-(2-hydroxypropan-2-yl)isonicotinic acid as a white solid. (0.4 g, 2.21 mmol, 36.5% yield). LC-MS ($ES^+$, mn/z): 181.9 $[(M+H)^+]$.

A solution of 5-(1-hydroxy-1-methyl-ethyl)pyridine-3-carboxylic acid (22.9 mg, 126 μmol, 1 eq), Amine 1 (70 mg, 126 μmol, 1 eq, 2H—C1) in DMF (3 mL) was coupled under conditions A. The residue was purified by prep-TLC ($SiO_2$, DCM: MeOH=10:1 $R_f$=0.45) to afford the desired compound N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-(2-hydroxypropan-2-yl)pyridine-4-carboxamide as a yellow solid (26.4 mg, 35.5% yield, 100% purity) LC-MS ($ES^+$, m/z): 590.2 $[(M+H)^+]$. $^1H$ NMR (400 MHz, DMSO-d6) δ=9.73 (t, J=5.6 Hz, 1H), 8.68 (d, J=5.0 Hz, 1H), 8.15 (d, J=0.7 Hz, 1H), 7.89 (s, 1H), 7.67 (dd, J=1.7, 5.1 Hz, 1H), 7.17-7.04 (m, 1H), 6.88 (d, J=8.3 Hz, 1H), 6.29 (d, J=7.8 Hz, 1H), 6.02 (br d, J=8.2 Hz, 1H), 5.50 (q, J=8.9 Hz, 2H), 5.38 (s, 1H), 4.96-4.73 (m, 3H), 3.70-3.53 (m, 1H), 3.08 (br s, 1H), 2.84 (br s, 1H), 2.30-1.91 (m, 6H), 1.70 (br d, J=10.6 Hz, 1H), 1.47 (s, 6H).

Example 296: Compound 551B: N-{[3-(4-{[(3S, 4R)-3-fluoro-1-methylpiperidin-4-yl]amino}-1-(2,2,2-trifluoroethyl)-1H-indol-2-yl)-1,2,4-oxadiazol-5-yl]methyl}-2-(methoxymethyl)-6-methylpyridine-4-carboxamide

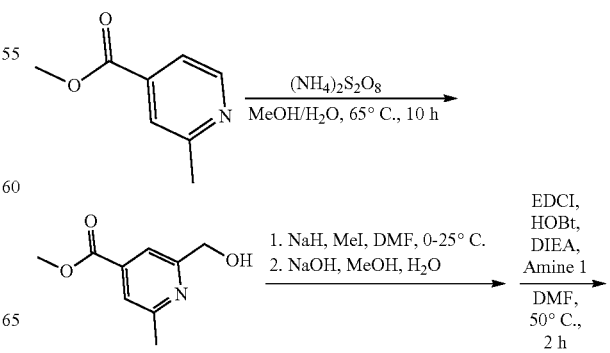

-continued

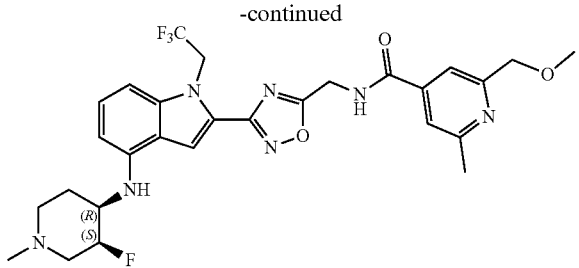

A solution of methyl 2-methylpyridine-4-carboxylate (1 g, 6.62 mmol, 1 eq), ammonium persulfate (4.98 g, 21.8 mmol, 3.3 eq) in water (12 mL) and methanol (100 mL) was degassed and purged with nitrogen 3 times, then the mixture was stirred at 60° C. for 1 h under nitrogen atmosphere. The reaction mixture was filtered, and concentrated in vacuo to give a residue. The residue was purified by prep-TLC (SiO$_2$, DCM:methanol=10:1) to provide the alcohol methyl 2-(hydroxymethyl)-6-methyl-pyridine-4-carboxylate (450 mg, 37.5% yield) as a red solid. LC-MS (ES$^+$, m/z):198.1 [(M+H)$^+$]. $^1$H NMR (400 MHz, DMSO-d6) δ=7.64 (d, J=6.2 Hz, 2H), 4.80 (s, 2H), 3.95 (s, 3H), 3.89-3.67 (m, 1H), 3.87-3.47 (m, 1H), 2.65 (s, 3H).

To a solution of methyl 2-(hydroxymethyl)-6-methyl-pyridine-4-carboxylate (400 mg, 1.77 mmol, 1 eq) in DMF (10 mL) was added sodium hydride (211.9 mg, 5.30 mmol, 60% purity, 3 eq) at 0° C., then the mixture was stirred at 0° C. for 0.5 h under N$_2$ atmosphere. Iodomethane (7.06 mmol, 0.44 mL, 4 eq) was added at 0° C., and then the mixture was stirred at 25° C. for 0.5 h under N$_2$ atmosphere. The reaction mixture was quenched by adding sat. ammonium chloride (200 mL) at 0° C., and extracted with EA (3×40 mL). The combined organic layers were washed with brine (2×40 mL), dried over anhydrous sodium sulfate, filtered, and concentrated in vacuo to give a residue. The residue was purified by prep-TLC (SiO$_2$, PE:EA=4:1) to afford methyl 2-(methoxymethyl)-6-methyl-pyridine-4-carboxylate (220 mg, 56.8% yield, 89% purity) as a colorless oil. LC-MS (ES$^+$, m/z):196.1 [(M+H)$^+$].

Methyl 2-(methoxymethyl)-6-methyl-pyridine-4-carboxylate (120 mg, 547 μmol, 1 eq) was saponified in methanol (2 mL) using sodium hydroxide (6 M, 91 μL 1 eq). The mixture was stirred at 25° C. for 1 h under N$_2$ atmosphere. The reaction mixture was adjusted to pH=7 with 3 M HCl, then filtered, and concentrated in vacuo to give a residue. The residue, which contained the desired product as well as residual reagent, was used directly for the next reaction. LC-MS (ES$^+$, m/z):182.0 [(M+H)$^+$].

2-(methoxymethyl)-6-methyl-pyridine-4-carboxylic acid (259.1 mg, crude) and Amine 1 (70 mg, 119 μmol, 1 eq, 2HCl) were coupled under conditions A. The residue was purified by prep-TLC (SiO$_2$, DCM: methanol=10:1 R$_f$=0.35) followed by prep-HPLC (FA condition) column: Phenomenex Luna C18 200×40 mm×10 um; mobile phase: [water (0.2% FA)-ACN]; B %: 20%-50%, 8 min) to provide the desired compound N-[[3-4-[[(3S,4R)-3-fluoro-1-methyl-4-piperidyl]amino]-1-(2,2,2-trifluoroethyl)indol-2-yl]-1,2,4-oxadiazol-5-yl]methyl]-2-(methoxymethyl)-6-methyl-pyridine-4-carboxamide (22.5 mg, 32.0% yield, 100% purity) as a yellow solid. LC-MS (ES$^+$, m/z):590.4 [(M+H)$^+$]. $^1$H NMR (400 MHz, DMSO-d6) δ=1.60-1.74 (m, 1H) 1.95-2.04 (m, 1H) 2.06-2.13 (m, 1H) 2.17-2.30 (m, 4H) 2.53-2.55 (m, 3H) 2.74-2.87 (m, 1H) 2.99-3.07 (m, 1H) 3.39-3.41 (m, 3H) 3.52-3.66 (m, 1H) 4.49-4.59 (m, 2H) 4.70-4.96 (m, 3H) 5.39-5.62 (m, 2H) 5.87-6.07 (m, 1H) 6.20-6.37 (m, 1H) 6.69-6.93 (m, 1H) 7.07-7.20 (m, 1H) 7.57-7.63 (m, 1H) 7.64-7.70 (m, 1H) 7.80-7.96 (m, 1H) 9.63-9.75 (m, 1H).

Example 297: Compound 553B: 1-tert-butyl-N-{[3-(4-{[(3S,4R)-3-fluoro-1-methylpiperidin-4-yl]amino}-1-(2,2,2-trifluoroethyl)-1H-indol-2-yl)-1,2-oxazol-5-yl]methyl}-1H-pyrrole-3-carboxamide

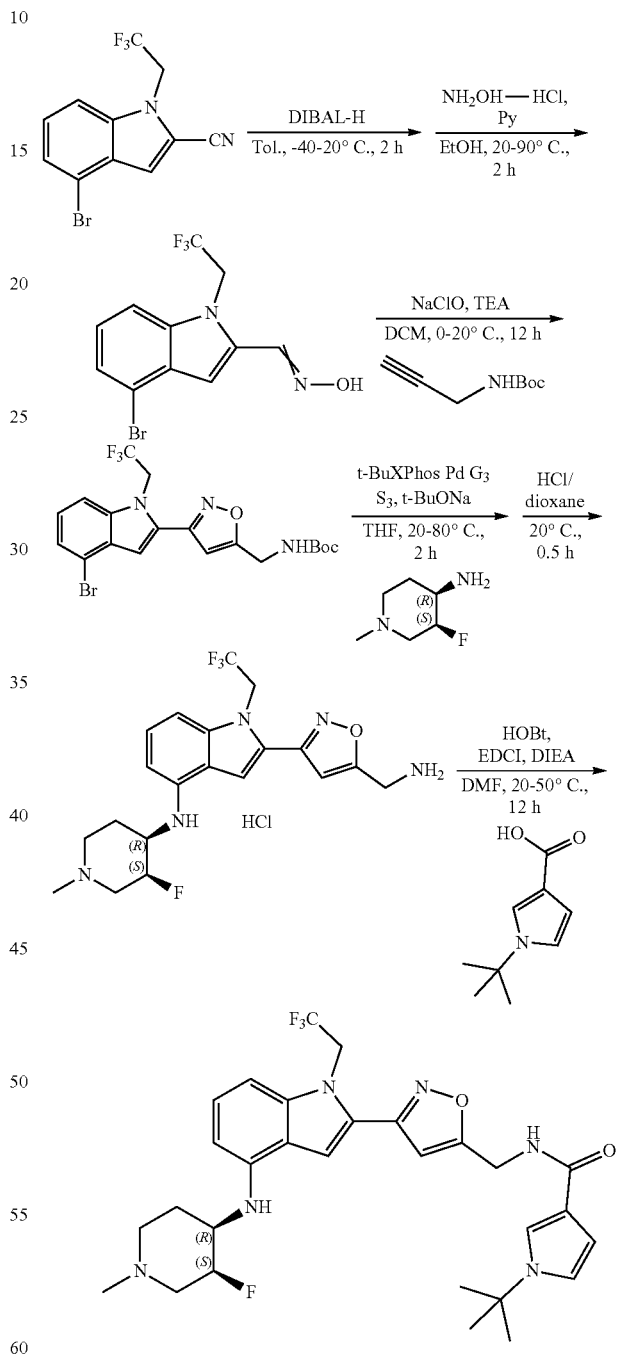

To a mixture of 4-bromo-1-(2,2,2-trifluoroethyl)indole-2-carbonitrile (5 g, 16.5 mmol, 1 eq) in toluene (50 mL) was added dropwise DIBAL (1 M, 33 mL, 2 eq) at −40° C. under nitrogen. The mixture was stirred at 20° C. for 2 h. The reaction was poured into ice-water (40 mL) and 15% sodium hydroxide (40 mL), and stirred 10 min. The mixture was filtered through Celite, and the aqueous phase was extracted with EA (2×30 mL). The combined organic phase was washed with brine (1×60 mL), dried over anhydrous sodium sulfate, filtered, and concentrated in vacuo. The residue was purified by silica gel chromatography (PE/EA=1/0 to 80/1) to provide the product 4-bromo-1-(2,2,2-trifluoroethyl)indole-2-carbaldehyde (2 g, 6.53 mmol, 39.6% yield) as a light yellow solid. $^1$H NMR (400 MHz, DMSO-d6) δ=9.98 (s, 1H), 7.83 (d, J=8.3 Hz, 1H), 7.60 (s, 1H), 7.52-7.47 (m, 1H), 7.45-7.39 (m, 1H), 5.58 (q, J=9.0 Hz, 2H).

To a mixture of 4-bromo-1-(2,2,2-trifluoroethyl)indole-2-carbaldehyde (2 g, 6.53 mmol, 1 eq) in ethanol (25 mL) was added pyridine (13.1 mmol, 1.05 mL, 2 eq) and hydroxylamine hydrochloride (545 mg, 7.84 mmol, 1.2 eq) at 20° C. under nitrogen. The mixture was stirred at 90° C. for 2 h. The residue was poured into citric acid (saturated, 30 mL). The aqueous phase was extracted with EA (3×10 mL). The combined organic phase was washed with brine (1×30 mL), dried over anhydrous sodium sulfate, filtered, and concentrated in vacuo. The residue was purified by silica gel chromatography (PE/EA=1/0, 20/1) to provide the oxime 4-bromo-1-(2,2,2-trifluoroethyl)indole-2-carbaldehyde oxime (1.8 g, 85.8% yield) as a white solid.

To a mixture of tert-butyl N-prop-2-yl]carbamate (483.3 mg, 3.11 mmol, 1 eq) in DCM (10 mL) were added sodium hypochlorite (3.21 g, 5.61 mmol, 2.65 mL, 13% purity, 1.8 eq), TEA (320 μmol, 45 μL 0.1 eq) in one portion at 0° C. 4-bromo-1-(2,2,2-trifluoroethyl)indole-2-carbaldehyde oxime (1 g, 3.1 mmol, 1 eq) in DCM (10 mL) was then added. The mixture was stirred at 20° C. for 12 h. The residue was poured into ice-water (30 mL). The aqueous phase was extracted with EA (3×10 mL). The combined organic phase was washed with brine (1×30 mL), dried over anhydrous sodium sulfate, filtered, and concentrated in vacuo. The residue was purified by silica gel chromatography (PE/EA=100/0, 97/3) to provide tert-butyl N-[[3-[4-bromo-1-(2,2,2-trifluoroethyl)indol-2-yl]isoxazol-5-yl]methyl]carbamate (0.5 g, 27.1% yield, 80% purity) as a light yellow solid. LC-MS (ES$^+$, m/z): 417.9/149.9 [(M+H)$^+$]. $^1$H NMR (400 MHz, DMSO-d6) δ=7.77 (d, J=8.3 Hz, 1H), 7.61 (br t, J=5.9 Hz, 1H), 7.42 (d, J=7.7 Hz, 1H), 7.34 (s, 1H), 7.27 (t, J=8.0 Hz, 1H), 7.11 (s, 1H), 5.69 (q, J=8.8 Hz, 2H), 4.35 (br d, J=5.9 Hz, 2H), 1.48-1.35 (m, 9H).

To a mixture of tert-butyl N-[[3-[4-bromo-1-(2,2,2-trifluoroethyl)indol-2-yl] isoxazol-5-yl]methyl]carbamate (400 mg, 675 μmol, 1 eq) and (3S,4R)-3-fluoro-1-methyl-piperidin-4-amine (111 mg, 810 μmol, 96% purity, 1.2 eq, free base) in THF (4 mL) were added sodium t-butoxide (2 M, 670 μL 2 eq), t-butyl-XPhos Palladium Generation 3 (107.2 mg, 135 μmol, 0.2 eq) at 20° C. under nitrogen. The mixture was stirred at 80° C. for 2 h. The residue was poured into EDTA (saturated, 50 mL) and stirred for 60 min. The aqueous phase was extracted with EA (3×20 mL). The combined organic phase was washed with brine (1×50 mL), dried over anhydrous sodium sulfate, filtered, and concentrated in vacuo. The residue was purified by prep-TLC (SiO$_2$, DCM:MeOH=10:1) to provide tert-butyl N-[[3-[4-[[(3S,4R)-3-fluoro-1-methyl-4-piperidyl]amino]-1-(2,2,2-trifluoroethyl)indol-2-yl]isoxazol-5-yl]methyl]carbamate (200 mg, crude) as a light yellow solid. LC-MS (ES$^+$, m/z): 526.2 [(M+H)].

To a mixture of tert-butyl N-[[3-[4-[[(3S,4R)-3-fluoro-1-methyl-4-piperidyl] amino]-1-(2,2,2-trifluoroethyl)indol-2-yl]isoxazol-5-yl]methyl]carbamate (200 mg, 381 μmol, 1 eq) in HCl/dioxane (4 M) at 20° C.. The mixture was stirred at 20° C. for 30 min. The residue was concentrated in vacuo to provide 2-[5-(aminomethyl)isoxazol-3-yl]-N-[(3S,4R)-3-fluoro-1-methyl-4-piperidyl]-1-(2,2,2-trifluoroethyl)indol-4-amine (200 mg, crude, 2HCl) as a brown solid.

To a mixture of 2-[5-(aminomethyl)isoxazol-3-yl]-N-[(3S,4R)-3-fluoro-1-methyl-4-piperidyl]-1-(2,2,2-trifluoroethyl)indol-4-amine (80 mg, 150 mol, 1 eq, 3HCL) and 1-tert-butylpyrrole-3-carboxylic acid (30 mg, 179.5 μmol, 1.2 eq) in DMF (2 mL) were added HOBt (40.4 mg, 300 μmol, 2 eq), EDCI (57.4 mg, 300 μmol, 2 eq), DIEA (1.50 mmol, 260 μL, 10 eq) in one portion at 20° C. under nitrogen. The mixture was stirred at 50° C. for 12 h. The residue was poured into ice-water (40 mL). The aqueous phase was extracted with EA (3×10 mL). The combined organic phase was washed with brine (1×30 mL), dried over anhydrous sodium sulfate, filtered, and concentrated in vacuo. The residue was purified by prep-TLC (SiO$_2$, DCM:MeOH=10:1) to provide the desired product 1-tert-butyl-N-{[3-(4-{[(3S,4R)-3-fluoro-1-methylpiperidin-4-yl]amino}-1-(2,2,2-trifluoroethyl)-1H-indol-2-yl)-1,2-oxazol-5-yl]methyl}-1H-pyrrole-3-carboxamide (23.5 mg, 27.3% yield, 100.0% purity) as a white solid. LC-MS (ES$^+$, m/z): 575.2 [(M+H)$^+$]. $^1$H NMR (400 MHz, DMSO-d6) δ=8.51 (t, J=6.0 Hz, 1H), 7.65 (s, 1H), 7.54 (t, J=2.0 Hz, 1H), 7.08 (t, J=8.0 Hz, 1H), 6.98 (t, J=2.6 Hz, 1H), 6.87 (d, J=8.3 Hz, 1H), 6.62 (s, 1H), 6.51 (dd, J=1.8, 2.8 Hz, 1H), 6.30 (d, J=7.8 Hz, 1H), 5.59-5.44 (m, 3H), 4.93-4.74 (m, 1H), 4.57 (d, J=5.7 Hz, 2H), 3.70-3.50 (m, 1H), 3.11-2.97 (m, 1H), 2.81 (br d, J=11.5 Hz, 1H), 2.31-2.17 (m, 4H), 2.15-2.06 (m, 1H), 1.97-1.82 (m, 1H), 1.79-1.68 (m, 1H), 1.49 (s, 9H).

Example 298: Compound 554B: 1-tert-butyl-N-{13-(4-{[(3S,4R)-3-fluoro-1-methylpiperidin-4-yl]amino}-1-(2,2,2-trifluoroethyl)-1H-indol-2-yl)-1,2-oxazol-5-yl]methyl}-1H-pyrazole-4-carboxamide The previously prepared 2-[5-(aminomethyl)isoxazol-3-yl]-N-[(3S,4R)-3-fluoro-1-methyl-4-piperidyl]-1-(2,2,2-trifluoroethyl)indol-4-amine (50 mg, 100 μmol, 1 eq, 2HCl) and 1-tert-butylpyrazole-4-carboxylic acid (20.3 mg, 120 μmol, 1.2 eq) in DMF (1 mL) were coupled under conditions A. The crude product was purified by prep-TLC (SiO$_2$, DCM: MeOH=10:1) to provide the desired product 1-tert-butyl-N-{[3-(4-{[(3S,4R)-3-fluoro-1-methylpiperidin-4-yl]amino}-1-(2,2,2-trifluoroethyl)-1H-indol-2-yl)-1,2-oxazol-5-yl]methyl}-1H-pyrazole-4-carboxamide (18.8 mg, 31.8% yield, 97.8% purity) as a white solid. LC-MS (ES$^+$, m/z): 270.9 [(M+H)$^+$]. $^1$H NMR (400 MHz, DMSO-d6) δ ppm 8.82 (br t, J=5.81 Hz, 1H) 8.34 (s, 1H) 7.93 (s, 1H) 7.64 (s, 1H) 7.08 (t, J=7.89 Hz, 1H) 6.88 (br d, J=8.55 Hz, 1H) 6.66 (s, 1H) 6.30 (d, J=7.89 Hz, 1H) 5.43-5.58 (m, 3H) 4.75-4.92 (m, 1H) 4.61 (br d, J=5.70 Hz, 2H) 3.52-3.72 (m, 1H) 3.05 (br d, J=1.32 Hz, 1H) 2.81 (br dd, J=11.62, 1.10 Hz, 1H) 2.20 (s, 4H) 1.87-1.87 (m, 1H)1.69-1.79 (m, 1H) 1.76 (br d, J=1.32 Hz, 1H) 1.54 (s, 911).

Example 299: Compound 555B: N-{[3-(4-{[(3S, 4R)-3-fluoro-1-methylpiperidin-4-yl]amino}-1-(2,2, 2-trifluoroethyl)-1H-indol-2-yl)-1,2-oxazol-5-yl] methyl}-5-(2-hydroxypropan-2-yl)thiophene-3-carboxamide The previously prepared 2-[5-(aminomethyl)isoxazol-3-yl]-N-[(3S,4R)-3-fluoro-1-methyl-4-piperidyl]-1-(2,2,2-trifluoroethyl)indol-4-amine (40 mg, 94 μmol, 1 eq) and the previously prepared 5-(1-hydroxy-1-methyl-ethyl)thiophene-3-carboxylic acid (21 mg, 113 μmol, 1.2 eq) were coupled under conditions A. The crude product was purified by prep-TLC (SiO$_2$, DCM: methanol=10:1) to provide the desired product N-[[3-[4-[[(3S,4R)-3-fluoro-1-methyl-4-piperidyl]amino]-1-(2,2,2-trifluoroethyl)indol-2-yl]isoxazol-5-yl]methyl]-5-(1-hydroxy-1-methyl-ethyl)thiophene-3-carboxamide (14 mg, 25.1% yield) as a yellow solid. LC-MS (ES+, m/z): 594.1 [(M+H)+]. $^1$H NMR (400 MHz, DMSO-d6) δ=9.08-8.93 (m, 1H), 8.05-7.95 (m, 1H), 7.64 (s, 1H), 7.35 (d, J=1.1 Hz, 1H), 7.06 (s, 1H), 6.92-6.85 (m, 1H), 6.72-6.61 (m, 1H), 6.35-6.28 (m, 1H), 5.65-5.39 (m, 4H), 4.95-4.74 (m, 1H), 4.72-4.55 (m, 2H), 3.67-3.58 (m, 1H), 3.12-3.03 (m, 1H), 2.82 (br dd, J=3.5, 6.4 Hz, 1H), 2.30-2.09 (m, 5H), 1.95-1.86 (m, 1H), 1.80-1.71 (m, 1H), 1.51 (s, 6H).

TABLE 9 shows compounds with a 5-(1H-indol-2-yl)-1,2,4-oxadiazole, 3-(1H-indol-2-yl)-1,2,4-oxadiazole, or 3-(1H-indol-2-yl)isoxazole core.

TABLE 9

| Compound No. | Structure | IUPAC | LC-MS (ES+, m/z) |
|---|---|---|---|
| 136B | 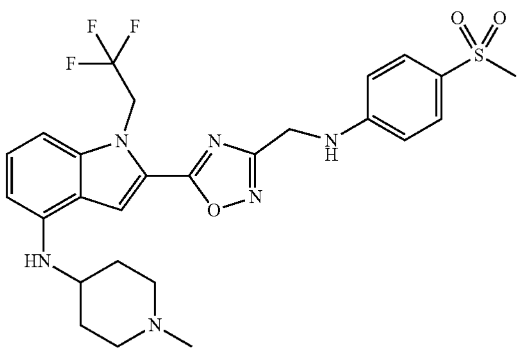 [SMILES: CN1CCC(Nc2cccc3c2cc(-c2nc(CNc4ccc(S(C)(=O)=O)cc4)no2)n3CC(F)(F)F)CC1] | 2-(3-{[(4-methanesulfonylphenyl)amino]methyl}-1,2,4-oxadiazol-5-yl)-N-(1-methylpiperidin-4-yl)-1-(2,2,2-trifluoroethyl)-1H-indol-4-amine | 563.2 |
| 137B | 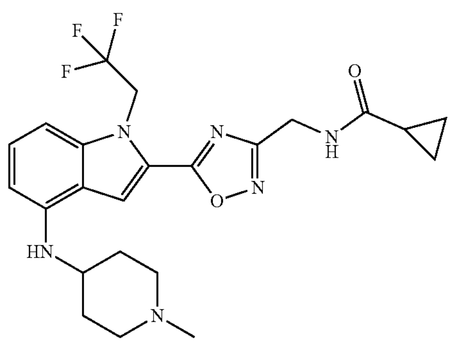 [SMILES: CN1CCC(Nc2cccc3c2cc(-c2nc(CNC(=O)C4CC4)no2)n3CC(F)(F)F)CC1] | N-[(5-{4-[(1-methylpiperidin-4-yl)amino]-1-(2,2,2-trifluoroethyl)-1H-indol-2-yl}-1,2,4-oxadiazol-3-yl)methyl]cyclopropanecarboxamide | 477.2 |
| 138B | 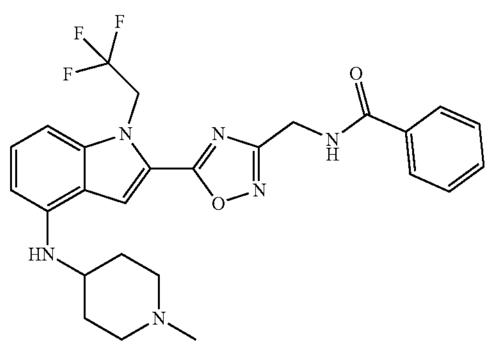 [SMILES: CN1CCC(Nc2cccc3c2cc(-c2nc(CNC(=O)c4ccccc4)no2)n3CC(F)(F)F)CC1] | N-[(5-{4-[(1-methylpiperidin-4-yl)amino]-1-(2,2,2-trifluoroethyl)-1H-indol-2-yl}-1,2,4-oxadiazol-3-yl)methyl]benzamide | 513.1 |
| 139B | 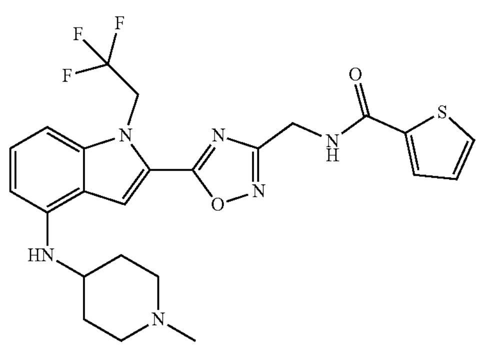 [SMILES: CN1CCC(Nc2cccc3c2cc(-c2nc(CNC(=O)c4cccs4)no2)n3CC(F)(F)F)CC1] | N-[(5-{4-[(1-methylpiperidin-4-yl)amino]-1-(2,2,2-trifluoroethyl)-1H-indol-2-yl}-1,2,4-oxadiazol-3-yl)methyl]thiophene-2-carboxamide | 519 |

TABLE 9-continued

| Compound No. | Structure | IUPAC | LC-MS (ES+, m/z) |
|---|---|---|---|
| 140B | 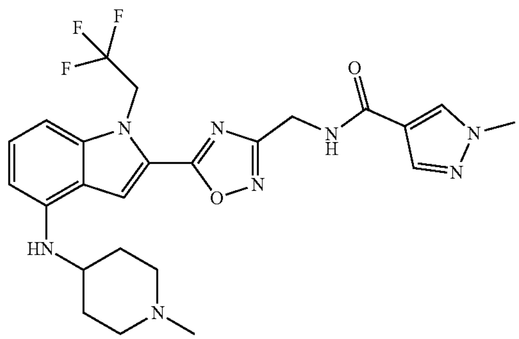 [SMILES: CN1CCC(Nc2cccc3c2cc(-c2nc(CNC(=O)c4cnn(C)c4)no2)n3CC(F)(F)F)CC1] | 1-methyl-N-[(5-{4-[(1-methylpiperidin-4-yl)amino]-1-(2,2,2-trifluoroethyl)-1H-indol-2-yl}-1,2,4-oxadiazol-3-yl)methyl]-1H-pyrazole-4-carboxamide | 517.2 |
| 141B | 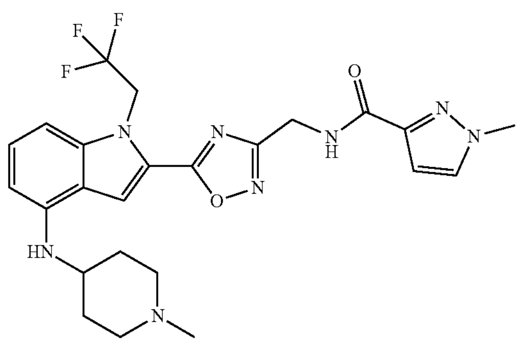 [SMILES: CN1CCC(Nc2cccc3c2cc(-c2nc(CNC(=O)c4ccn(C)n4)no2)n3CC(F)(F)F)CC1] | 1-methyl-N-[(5-{4-[(1-methylpiperidin-4-yl)amino]-1-(2,2,2-trifluoroethyl)-1H-indol-2-yl}-1,2,4-oxadiazol-3-yl)methyl]-1H-pyrazole-3-carboxamide | 517.3 |
| 142B | 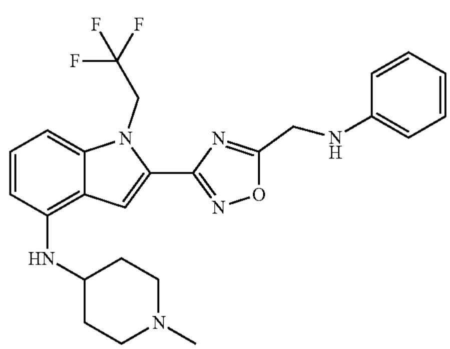 [SMILES: CN1CCC(Nc2cccc3c2cc(-c2noc(CNc4ccccc4)n2)n3CC(F)(F)F)CC1] | N-(1-methylpiperidin-4-yl)-2-{5-[(phenylamino)methyl]-1,2,4-oxadiazol-3-yl}-1-(2,2,2-trifluoroethyl)-1H-indol-4-amine | 485.1 |
| 143B | 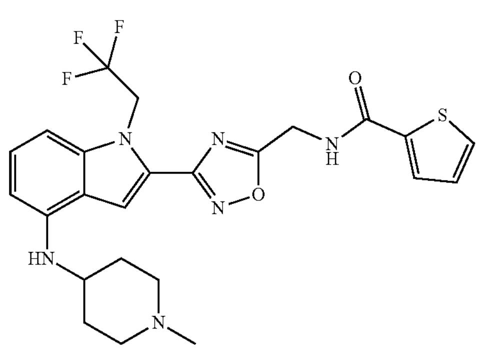 [SMILES: CN1CCC(Nc2cccc3c2cc(-c2noc(CNC(=O)c4cccs4)n2)n3CC(F)(F)F)CC1] | N-[(3-{4-[(1-methylpiperidin-4-yl)amino]-1-(2,2,2-trifluoroethyl)-1H-indol-2-yl}-1,2,4-oxadiazol-5-yl)methyl]thiophene-2-carboxamide | 519.2 |

TABLE 9-continued

| Compound No. | Structure | IUPAC | LC-MS (ES+, m/z) |
|---|---|---|---|
| 144B | 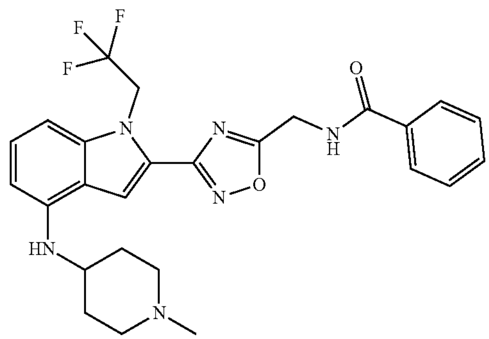 [SMILES: CN1CCC(Nc2cccc3c2cc(-c2noc(CNC(=O)c4ccccc4)n2)n3CC(F)(F)F)CC1] | N-[(3-{4-[(1-methylpiperidin-4-yl)amino]-1-(2,2,2-trifluoroethyl)-1H-indol-2-yl}-1,2,4-oxadiazol-5-yl)methyl]benzamide | 513.2 |
| 145B | 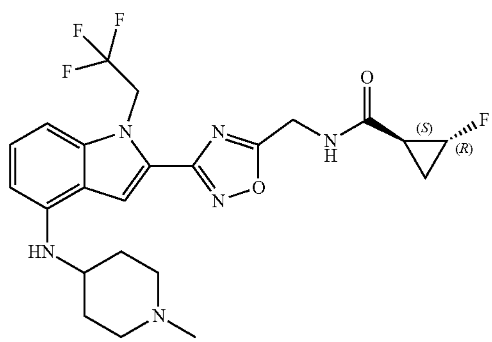 | (+/−)-(1S,2R)-2-fluoro-N-[(3-{4-[(1-methylpiperidin-4-yl)amino]-1-(2,2,2-trifluoroethyl)-1H-indol-2-yl}-1,2,4-oxadiazol-5-yl)methyl]cyclopropane-1-carboxamide | 495.2 |
| 146B | 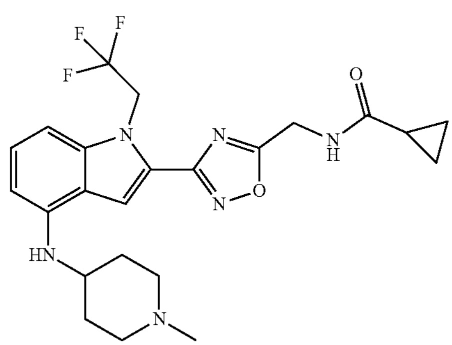 [SMILES: CN1CCC(Nc2cccc3c2cc(-c2noc(CNC(=O)C4CC4)n2)n3CC(F)(F)F)CC1] | N-[(3-{4-[(1-methylpiperidin-4-yl)amino]-1-(2,2,2-trifluoroethyl)-1H-indol-2-yl}-1,2,4-oxadiazol-5-yl)methyl]cyclopropanecarboxamide | 577.1 |
| 147B | 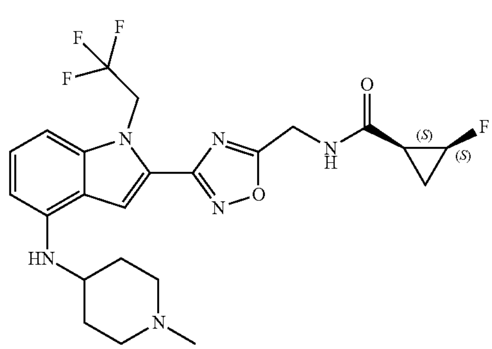 | (+/−)-(1S,2S)-2-fluoro-N-[(3-{4-[(1-methylpiperidin-4-yl)amino]-1-(2,2,2-trifluoroethyl)-1H-indol-2-yl}-1,2,4-oxadiazol-5-yl)methyl]cyclopropane-1-carboxamide | 495.1 |

TABLE 9-continued

| Compound No. | Structure | IUPAC | LC-MS (ES+, m/z) |
|---|---|---|---|
| 148B | 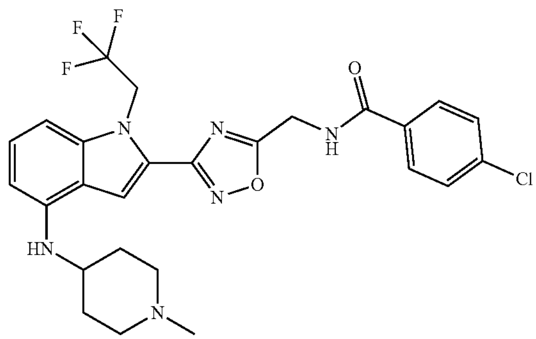 [SMILES: CN1CCC(Nc2cccc3c2cc(-c2noc(CNC(=O)c4ccc(Cl)cc4)n2)n3CC(F)(F)F)CC1] | 4-chloro-N-[(3-{4-[(1-methylpiperidin-4-yl)amino]-1-(2,2,2-trifluoroethyl)-1H-indol-2-yl}-1,2,4-oxadiazol-5-yl)methyl]benzamide | 547 |
| 149B | 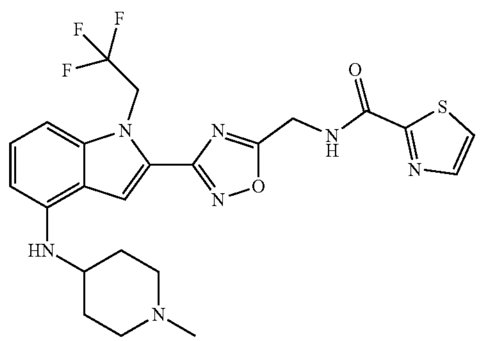 [SMILES: CN1CCC(Nc2cccc3c2cc(-c2noc(CNC(=O)c4nccs4)n2)n3CC(F)(F)F)CC1] | N-[(3-{4-[(1-methylpiperidin-4-yl)amino]-1-(2,2,2-trifluoroethyl)-1H-indol-2-yl}-1,2,4-oxadiazol-5-yl)methyl]-1,3-thiazole-2-carboxamide | 520 |
| 150B | 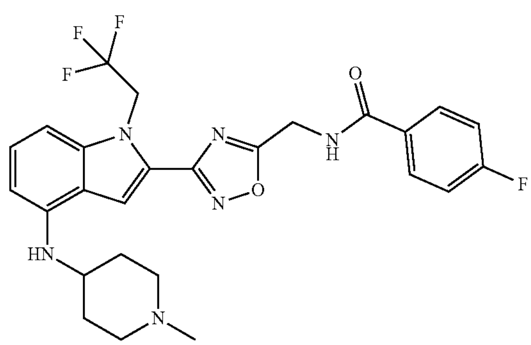 [SMILES: CN1CCC(Nc2cccc3c2cc(-c2noc(CNC(=O)c4ccc(F)cc4)n2)n3CC(F)(F)F)CC1] | 4-fluoro-N-[(3-{4-[(1-methylpiperidin-4-yl)amino]-1-(2,2,2-trifluoroethyl)-1H-indol-2-yl}-1,2,4-oxadiazol-5-yl)methyl]benzamide | 531.2 |
| 151B | 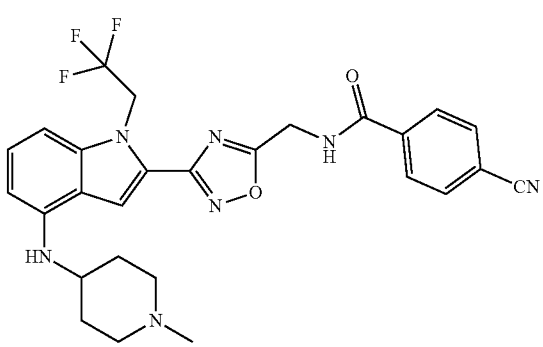 [SMILES: CN1CCC(Nc2cccc3c2cc(-c2noc(CNC(=O)c4ccc(C#N)cc4)n2)n3CC(F)(F)F)CC1] | 4-cyano-N-[(3-{4-[(1-methylpiperidin-4-yl)amino]-1-(2,2,2-trifluoroethyl)-1H-indol-2-yl}-1,2,4-oxadiazol-5-yl)methyl]benzamide | 538.1 |

TABLE 9-continued

| Compound No. | Structure | IUPAC | LC-MS (ES+, m/z) |
|---|---|---|---|
| 152B | 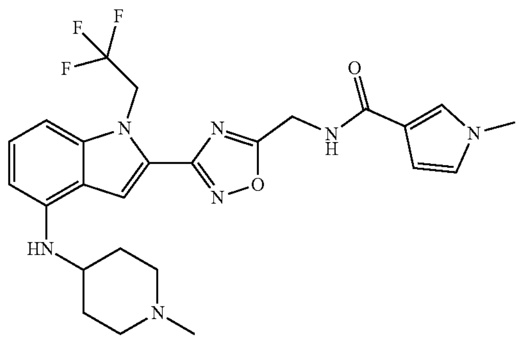 [SMILES: CN1CCC(Nc2cccc3c2cc(-c2noc(CNC(=O)c4ccn(C)c4)n2)n3CC(F)(F)F)CC1] | 1-methyl-N-[(3-{4-[(1-methylpiperidin-4-yl)amino]-1-(2,2,2-trifluoroethyl)-1H-indol-2-yl}-1,2,4-oxadiazol-5-yl)methyl]-1H-pyrrole-3-carboxamide | 516.2 |
| 153B | 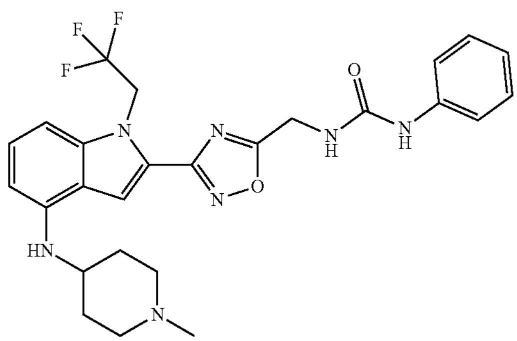 [SMILES: CN1CCC(Nc2cccc3c2cc(-c2noc(CNC(=O)Nc4ccccc4)n2)n3CC(F)(F)F)CC1] | 3-[(3-{4-[(1-methylpiperidin-4-yl)amino]-1-(2,2,2-trifluoroethyl)-1H-indol-2-yl}-1,2,4-oxadiazol-5-yl)methyl]-1-phenylurea | 528.3 |
| 154B | 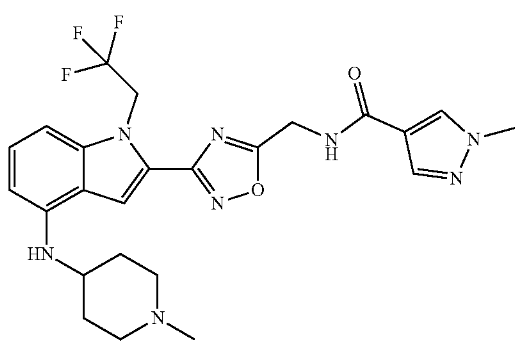 [SMILES: CN1CCC(Nc2cccc3c2cc(-c2noc(CNC(=O)c4cnn(C)c4)n2)n3CC(F)(F)F)CC1] | 1-methyl-N-[(3-{4-[(1-methylpiperidin-4-yl)amino]-1-(2,2,2-trifluoroethyl)-1H-indol-2-yl}-1,2,4-oxadiazol-5-yl)methyl]-1H-pyrazole-4-carboxamide | 517.2 |
| 155B | 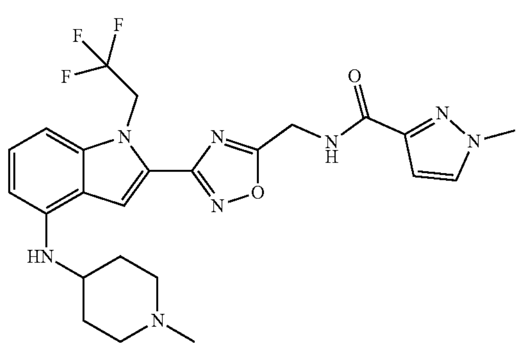 [SMILES: CN1CCC(Nc2cccc3c2cc(-c2noc(CNC(=O)c4ccn(C)n4)n2)n3CC(F)(F)F)CC1] | 1-methyl-N-[(3-{4-[(1-methylpiperidin-4-yl)amino]-1-(2,2,2-trifluoroethyl)-1H-indol-2-yl}-1,2,4-oxadiazol-5-yl)methyl]-1H-pyrazole-3-carboxamide | 517.2 |

TABLE 9-continued

| Compound No. | Structure | IUPAC | LC-MS (ES+, m/z) |
|---|---|---|---|
| 156B | 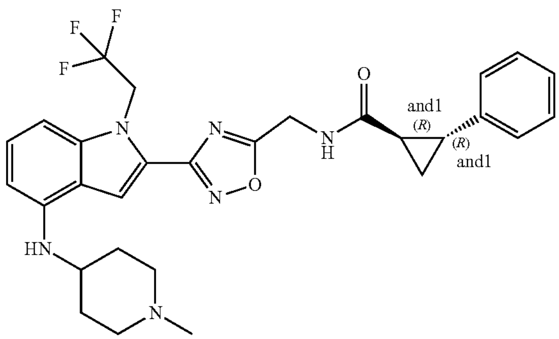 | (+/−)-(1R,2R)-N-[(3-{4-[(1-methylpiperidin-4-yl)amino]-1-(2,2,2-trifluoroethyl)-1H-indol-2-yl}-1,2,4-oxadiazol-5-yl)methyl]-2-phenylcyclopropane-1-carboxamide | 553.3 |
| 157B | 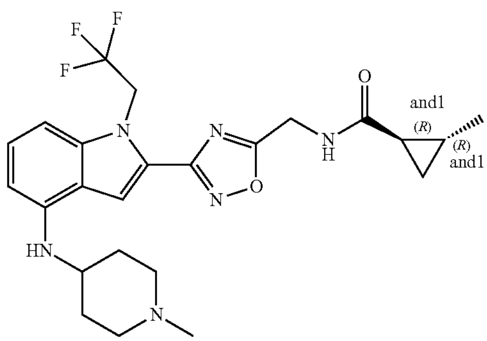 | (+/−)-(1R,2R)-2-methyl-N-[(3-{4-[(1-methylpiperidin-4-yl)amino]-1-(2,2,2-trifluoroethyl)-1H-indol-2-yl}-1,2,4-oxadiazol-5-yl)methyl]cyclopropane-1-carboxamide | 491.3 |
| 158B | 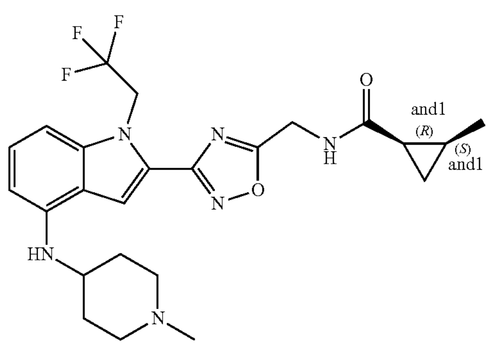 | (+/−)-(1R,2S)-2-methyl-N-[(3-{4-[(1-methylpiperidin-4-yl)amino]-1-(2,2,2-trifluoroethyl)-1H-indol-2-yl}-1,2,4-oxadiazol-5-yl)methyl]cyclopropane-1-carboxamide | 491.2 |
| 159B | 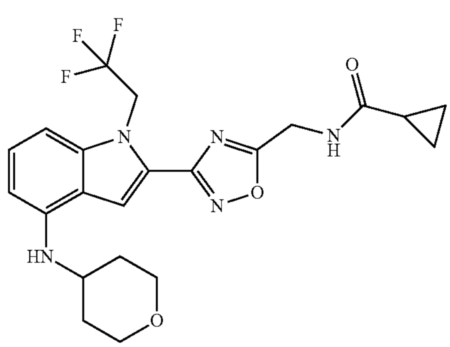 [SMILES: O=C(NCc1nc(-c2cc3c(NC4CCOCC4)cccc3n2CC(F)(F)F)no1)C1CC1] | N-[(3-{4-[(oxan-4-yl)amino]-1-(2,2,2-trifluoroethyl)-1H-indol-2-yl}-1,2,4-oxadiazol-5-yl)methyl]cyclopropanecarboxamide | 464.1 |

TABLE 9-continued

| Compound No. | Structure | IUPAC | LC-MS (ES+, m/z) |
| --- | --- | --- | --- |
| 160B | 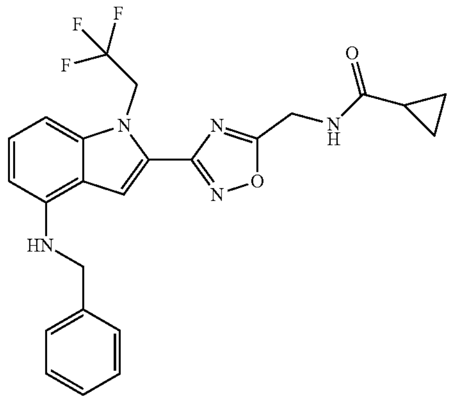 [SMILES: O=C(NCc1nc(-c2cc3c(NCc4ccccc4)cccc3n2CC(F)(F)F)no1)C1CC1] | N-({3-[4-(benzylamino)-1-(2,2,2-trifluoroethyl)-1H-indol-2-yl]-1,2,4-oxadiazol-5-yl}methyl)cyclopropanecarboxamide | 470.2 |
| 161B | 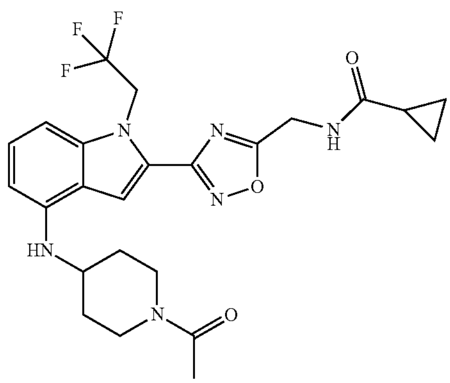 [SMILES: CC(=O)N1CCC(Nc2cccc3c2cc(-c2noc(CNC(=O)C4CC4)n2)n3CC(F)(F)F)CC1] | N-[(3-{4-[(1-acetylpiperidin-4-yl)amino]-1-(2,2,2-trifluoroethyl)-1H-indol-2-yl}-1,2,4-oxadiazol-5-yl)methyl]cyclopropanecarboxamide | 505.2 |
| 162B | 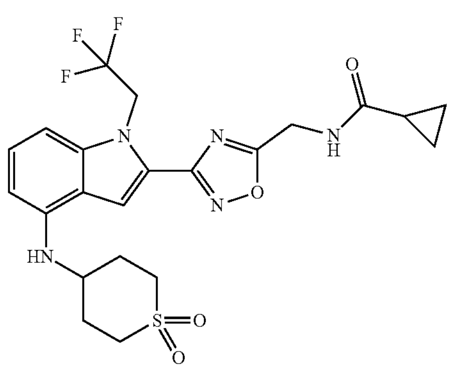 [SMILES: O=C(NCc1nc(-c2cc3c(NC4CCS(=O)(=O)CC4)cccc3n2CC(F)(F)F)no1)C1CC1] | N-[(3-{4-[(1,1-dioxo-1$\lambda^6$-thian-4-yl)amino]-1-(2,2,2-trifluoroethyl)-1H-indol-2-yl}-1,2,4-oxadiazol-5-yl)methyl]cyclopropanecarboxamide | 512.2 |

TABLE 9-continued

| Compound No. | Structure | IUPAC | LC-MS (ES+, m/z) |
|---|---|---|---|
| 163B | 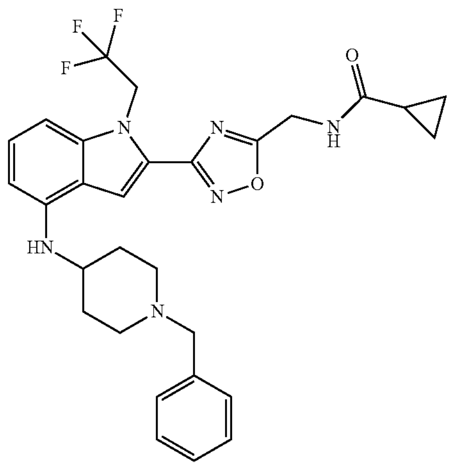 [SMILES: O=C(NCc1nc(-c2cc3c(NC4CCN(Cc5ccccc5)CC4)cccc3n2CC(F)(F)F)no1)C1CC1] | N-[(3-{4-[(1-benzylpiperidin-4-yl)amino]-1-(2,2,2-trifluoroethyl)-1H-indol-2-yl}-1,2,4-oxadiazol-5-yl)methyl]cyclopropanecarboxamide | 553.3 |
| 164B | 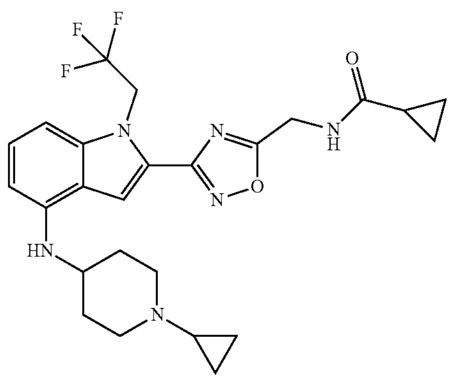 [SMILES: O=C(NCc1nc(-c2cc3c(NC4CCN(C5CC5)CC4)cccc3n2CC(F)(F)F)no1)C1CC1] | N-[(3-{4-[(1-cyclopropylpiperidin-4-yl)amino]-1-(2,2,2-trifluoroethyl)-1H-indol-2-yl}-1,2,4-oxadiazol-5-yl)methyl]cyclopropanecarboxamide | 503.2 |
| 165B | 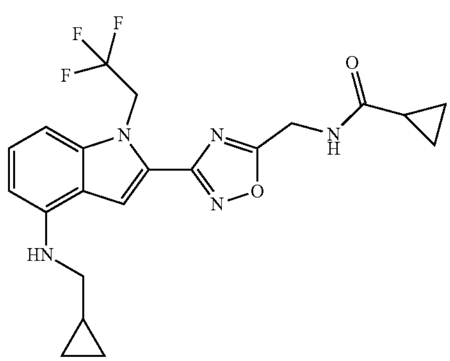 [SMILES: O=C(NCc1nc(-c2cc3c(NCC4CC4)cccc3n2CC(F)(F)F)no1)C1CC1] | N-[(3-{4-[(cyclopropylmethyl)amino]-1-(2,2,2-trifluoroethyl)-1H-indol-2-yl}-1,2,4-oxadiazol-5-yl)methyl]cyclopropanecarboxamide | 434 |
| 166B | 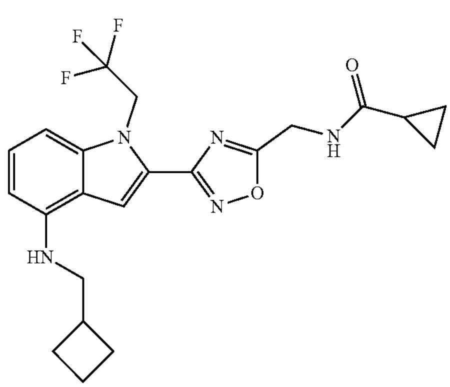 [SMILES: O=C(NCc1nc(-c2cc3c(NCC4CCC4)cccc3n2CC(F)(F)F)no1)C1CC1] | N-[(3-{4-[(cyclobutylmethyl)amino]-1-(2,2,2-trifluoroethyl)-1H-indol-2-yl}-1,2,4-oxadiazol-5-yl)methyl]cyclopropanecarboxamide | 448.2 |

TABLE 9-continued

| Compound No. | Structure | IUPAC | LC-MS (ES+, m/z) |
|---|---|---|---|
| 167B | 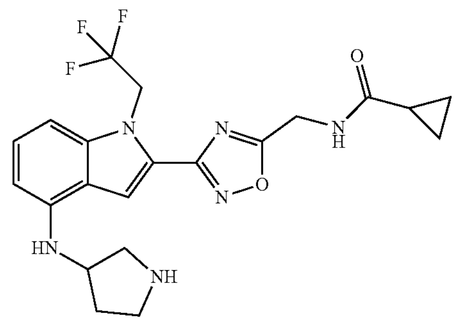 [SMILES: O=C(NCc1nc(-c2cc3c(NC4CCNC4)cccc3n2CC(F)(F)F)no1)C1CC1] | (+/−)-N-[(3-{4-[(pyrrolidin-3-yl)amino]-1-(2,2,2-trifluoroethyl)-1H-indol-2-yl}-1,2,4-oxadiazol-5-yl)methyl]cyclopropanecarboxamide | 449.2 |
| 168B | 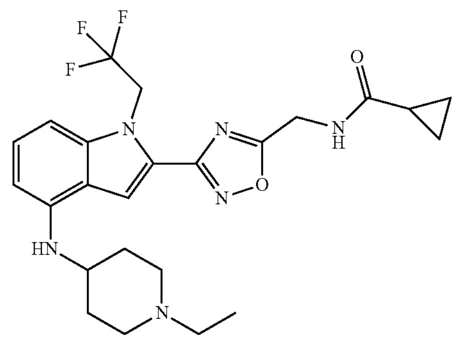 [SMILES: CCN1CCC(Nc2cccc3c2cc(-c2noc(CNC(=O)C4CC4)n2)n3CC(F)(F)F)CC1] | N-[(3-{4-[(1-ethylpiperidin-4-yl)amino]-1-(2,2,2-trifluoroethyl)-1H-indol-2-yl}-1,2,4-oxadiazol-5-yl)methyl]cyclopropanecarboxamide | 491.3 |
| 169B | 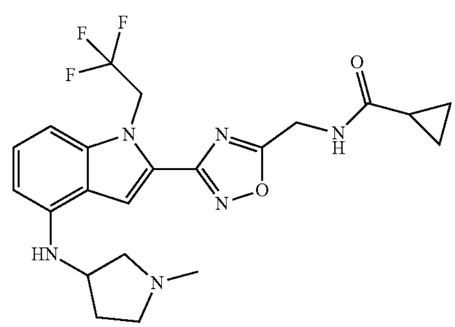 [SMILES: CN1CCC(Nc2cccc3c2cc(-c2noc(CNC(=O)C4CC4)n2)n3CC(F)(F)F)C1] | (+/−)-N-[(3-{4-[(1-methylpyrrolidin-3-yl)amino]-1-(2,2,2-trifluoroethyl)-1H-indol-2-yl}-1,2,4-oxadiazol-5-yl)methyl]cyclopropanecarboxamide | 463.2 |
| 170B | 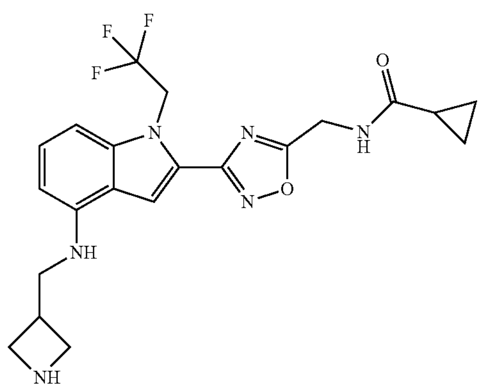 [SMILES: O=C(NCc1nc(-c2cc3c(NCC4CNC4)cccc3n2CC(F)(F)F)no1)C1CC1] | N-{[3-(4-{[(432zetidine-3-yl)methyl]amino}-1-(2,2,2-trifluoroethyl)-1H-indol-2-yl)-1,2,4-oxadiazol-5-yl]methyl}cyclopropanecarboxamide | 449.2 |

TABLE 9-continued

| Compound No. | Structure | IUPAC | LC-MS (ES+, m/z) |
|---|---|---|---|
| 171B | 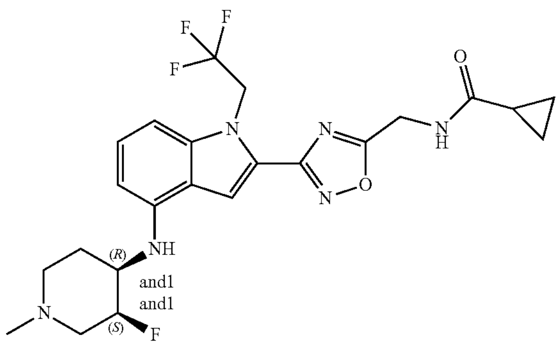 | (+/−)-N-{[3-(4-{[(3R,4S)-3-fluoro-1-methylpiperidin-4-yl]amino}-1-(2,2,2-trifluoroethyl)-1H-indol-2-yl)-1,2,4-oxadiazol-5-yl]methyl}cyclopropanecarboxamide | 495.2 |
| 172B | 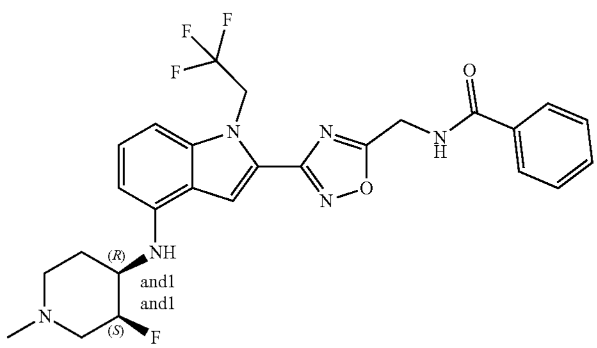 | (+/−)-N-{[3-(4-{[(3R,4S)-3-fluoro-1-methylpiperidin-4-yl]amino}-1-(2,2,2-trifluoroethyl)-1H-indol-2-yl)-1,2,4-oxadiazol-5-yl]methyl}benzamide | 531.3 |
| 173B | 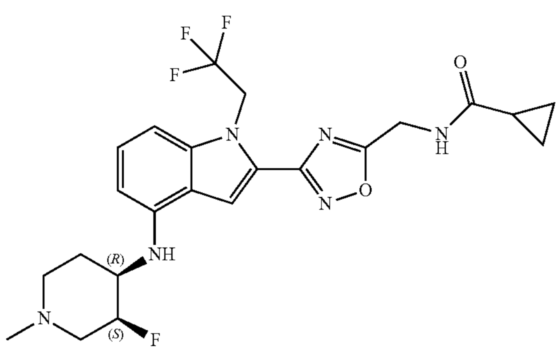 | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}cyclopropanecarboxamide | 495.2 |
| 174B | 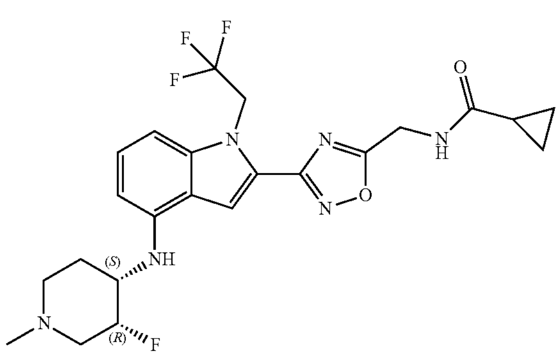 | N-{[3-(4-{[(3R,4S)-3-fluoro-1-methylpiperidin-4-yl]amino}-1-(2,2,2-trifluoroethyl)-1H-indol-2-yl)-1,2,4-oxadiazol-5-yl]methyl}cyclopropanecarboxamide | 495.2 |

TABLE 9-continued

| Compound No. | Structure | IUPAC | LC-MS (ES+, m/z) |
|---|---|---|---|
| 175B | 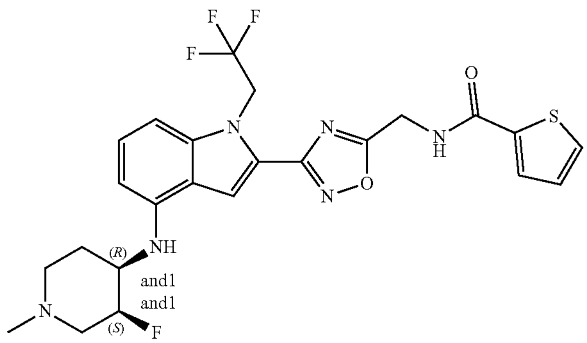 | (+/−)-N-{[3-(4-{[(3R,4S)-3-fluoro-1-methylpiperidin-4-yl]amino}-1-(2,2,2-trifluoroethyl)-1H-indol-2-yl)-1,2,4-oxadiazol-5-yl]methyl}thiophene-2-carboxamide | 537.2 |
| 176B | 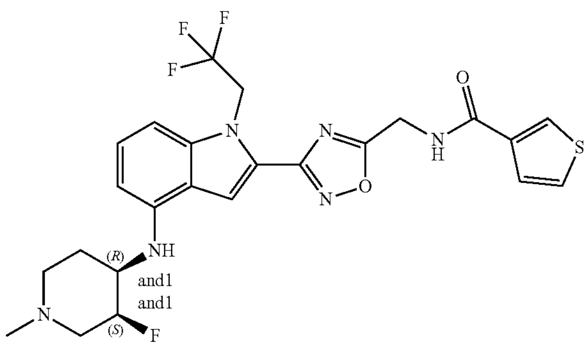 | (+/−)-N-{[3-(4-{[(3R,4S)-3-fluoro-1-methylpiperidin-4-yl]amino}-1-(2,2,2-trifluoroethyl)-1H-indol-2-yl)-1,2,4-oxadiazol-5-yl]methyl}thiophene-3-carboxamide | 537.2 |
| 177B | 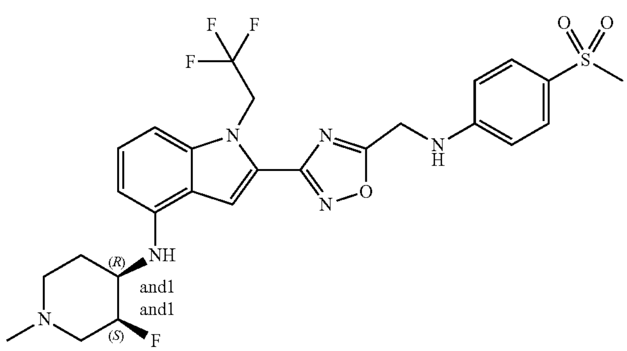 | (+/−)-N-[(3R,4S)-3-fluoro-1-methylpiperidin-4-yl]-2-(5-{[(4-methanesulfonylphenyl)amino]methyl}-1,2,4-oxadiazol-3-yl)-1-(2,2,2-trifluoroethyl)-1H-indol-4-amine | 581.2 |
| 178B | 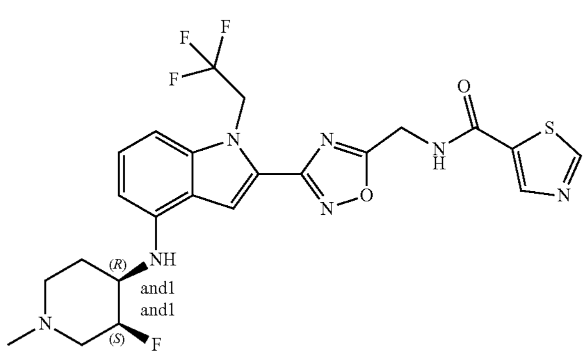 | (+/−)-N-{[3-(4-{[(3R,4S)-3-fluoro-1-methylpiperidin-4-yl]amino}-1-(2,2,2-trifluoroethyl)-1H-indol-2-yl)-1,2,4-oxadiazol-5-yl]methyl}-1,3-thiazole-5-carboxamide | 537.2 |

TABLE 9-continued

| Compound No. | Structure | IUPAC | LC-MS (ES+, m/z) |
|---|---|---|---|
| 179B | 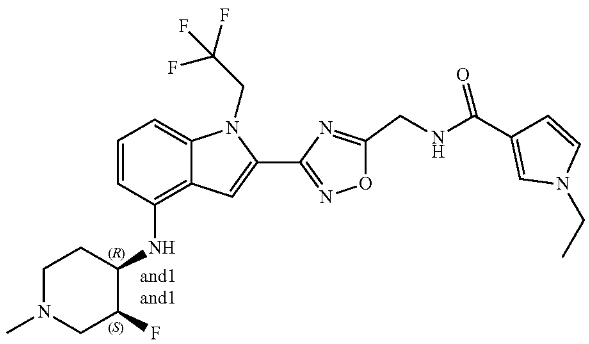 | (+/−)-1-ethyl-N-{[3-(4-{[(3R,4S)-3-fluoro-1-methylpiperidin-4-yl]amino}-1-(2,2,2-trifluoroethyl)-1H-indol-2-yl)-1,2,4-oxadiazol-5-yl]methyl}-1H-pyrrole-3-carboxamide | 548.3 |
| 180B | 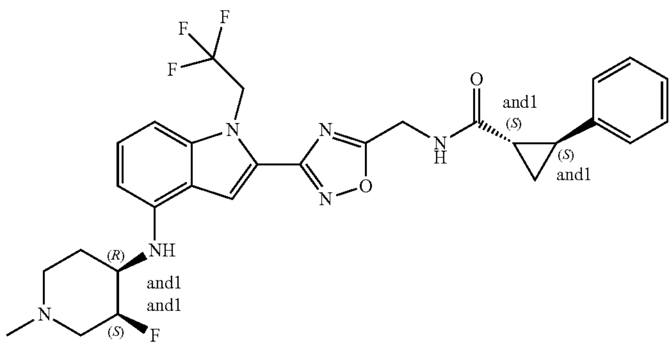 | (+/−)-(1R,2R)-N-{[3-(4-{[(3R,4S)-3-fluoro-1-methylpiperidin-4-yl]amino}-1-(2,2,2-trifluoroethyl)-1H-indol-2-yl)-1,2,4-oxadiazol-5-yl]methyl}-2-phenylcyclopropane-1-carboxamide | 571.2 |
| 181B | 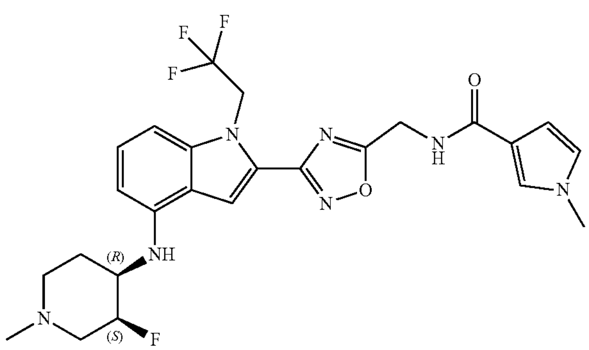 | N-{[3-(4-{[(3S,4R)-3-fluoro-1-methylpiperidin-4-yl]amino}-1-(2,2,2-trifluoroehyl)-1H-indol-2-yl)-1,2,4-oxadiazol-5-yl]methyl}-1-methyl-1H-pyrrole-3-carboxamide | 534.2 |
| 182B | 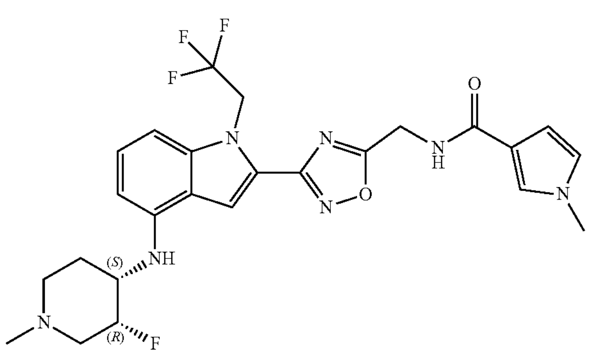 | N-{[3-(4-{[(3R,4S)-3-fluoro-1-methylpiperidin-4-yl]amino}-1-(2,2,2-trifluoroethyl)-1H-indol-2-yl)-1,2,4-oxadiazol-5-yl]methyl}-1-methyl-1H-pyrrole-3-carboxamide | 534.2 |

TABLE 9-continued

| Compound No. | Structure | IUPAC | LC-MS (ES+, m/z) |
|---|---|---|---|
| 183B | 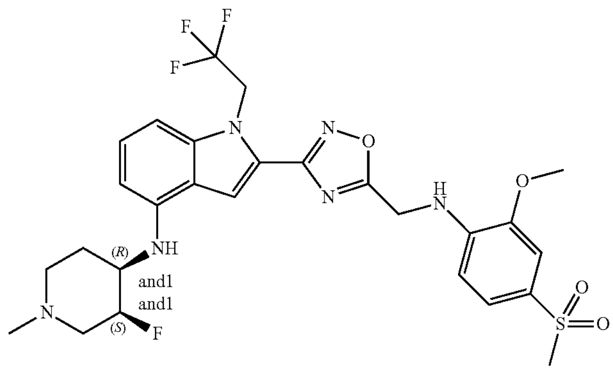 | (+/−)-N-[(3R,4S)-3-fluoro-1-methylpiperidin-4-yl]-2-(5-{[(4-methanesulfonyl-2-methoxyphenyl)amino]methyl}-1,2,4-oxadiazol-3-yl)-1-(2,2,2-trifluoroethyl)-1H-indol-4-amine | 611.2 |
| 184B | 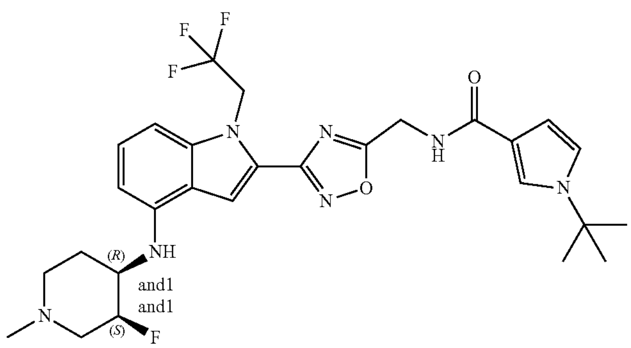 | (+/−)-tert-butyl-N-{[3-(4-{[(3R,4S)-3-fluoro-1-methylpiperidin-4-yl]amino}-1-(2,2,2-trifluoroethyl)-1H-indol-2-yl)-1,2,4-oxadiazol-5-yl]methyl}-1H-pyrrole-3-carboxamide | 576.3 |
| 185B | 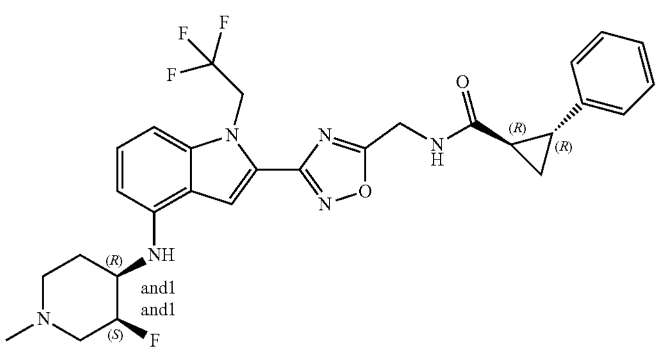 | (+/−)-(1R,2R)-N-{[3-(4-{[(3RS,4SR)-3-fluoro-1-methylpiperidin-4-yl]amino}-1-(2,2,2-trifluoroethyl)-1H-indol-2-yl)-1,2,4-oxadiazol-5-yl]methyl}-2-phenylcyclopropane-1-carboxamide | 571.2 |
| 186B | 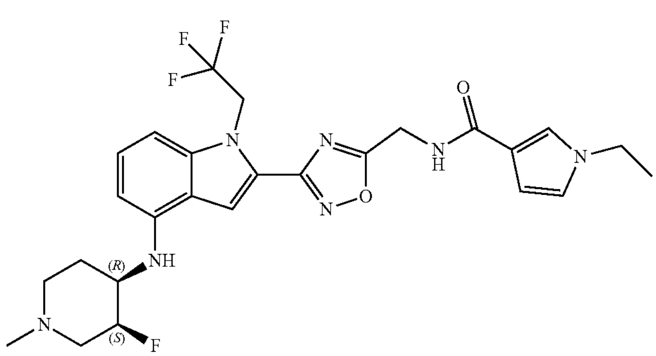 | 1-ethyl-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-pyrrole-3-carboxamide | 548.2 |

TABLE 9-continued

| Compound No. | Structure | IUPAC | LC-MS (ES+, m/z) |
|---|---|---|---|
| 187B | 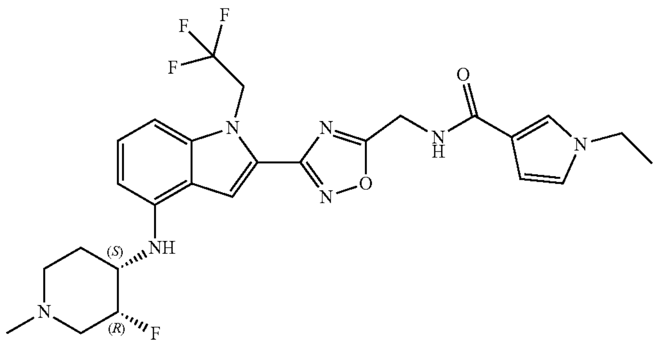 | 1-ethyl-N-{[3-(4-{[(3R,4S)-3-fluoro-1-methylpiperidin-4-yl]amino}-1-(2,2,2-trifluoroethyl)-1H-indol-2-yl)-1,2,4-oxadiazol-5-yl]methyl}-1H-pyrrole-3-carboxamide | 548.2 |
| 188B | 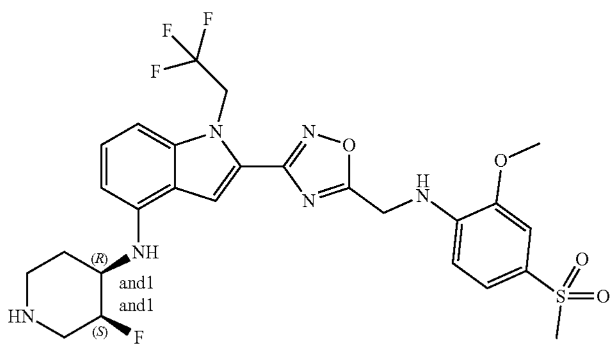 | (+/−)-N-[(3R,4S)-3-fluoropiperidin-4-yl]-2-(5-{[(4-methanesulfonyl-2-methoxyphenyl)amino]methyl}-1,2,4-oxadiazol-3-yl)-1-(2,2,2-trifluoroethyl)-1H-indol-4-amine | 597.2 |
| 189B | 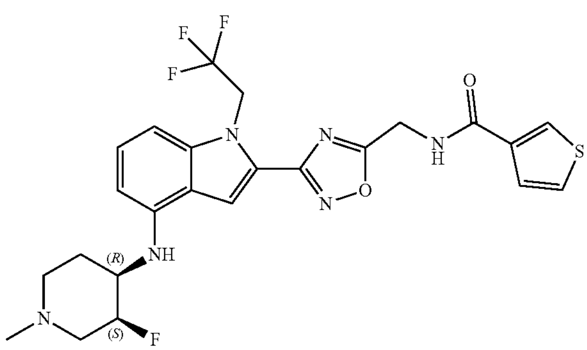 | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}thiophene-3-carboxamide | 537.2 |
| 190B | 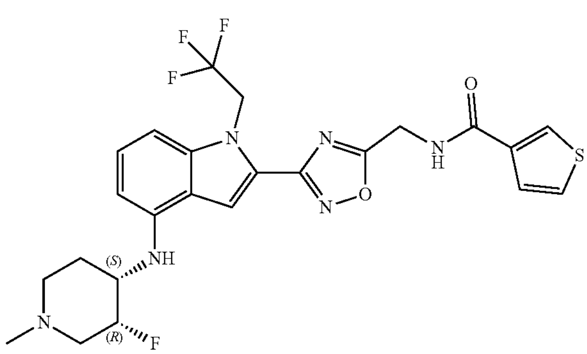 | N-{[3-(4-{[(3R,4S)-3-fluoro-1-methylpiperidin-4-yl]amino}-1-(2,2,2-trifluoroethyl)-1H-indol-2-yl)-1,2,4-oxadiazol-5-yl]methyl}thiophene-3-carboxamide | 537.1 |

TABLE 9-continued

| Compound No. | Structure | IUPAC | LC-MS (ES+, m/z) |
|---|---|---|---|
| 191B | 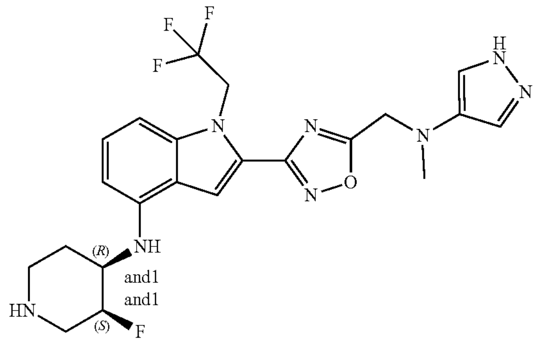 | (+/−)-N-[(3R,4S)-3-fluoropiperidin-4-yl]-2-(5-{[methyl(1H-pyrazol-4-yl)amino]methyl}-1,2,4-oxadiazol-3-yl)-1-(2,2,2-trifluoroethyl)-1H-indol-4-amine | 493.2 |
| 192B | 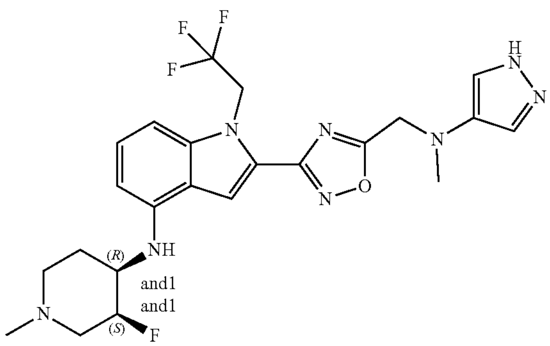 | (+/−)-N-[(3R,4S)-3-fluoro-1-methylpiperidin-4-yl]-2-(5-{[methyl(1H-pyrazol-4-yl)amino]methyl}-1,2,4-oxadiazol-3-yl)-1-(2,2,2-trifluoroethyl)-1H-indol-4-amine | 507.2 |
| 193B | 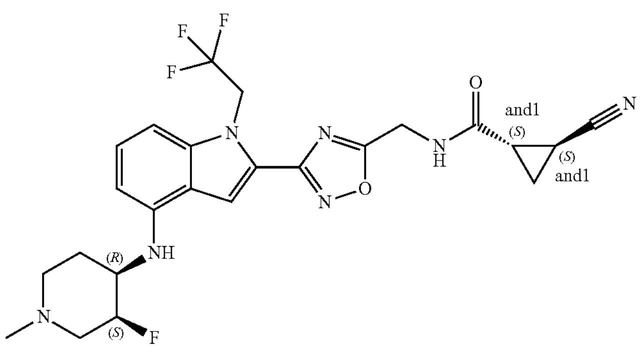 | (1RS,2RS)-2-cyano-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}cyclopropane-1-carboxamide | 519.9 |
| 194B | 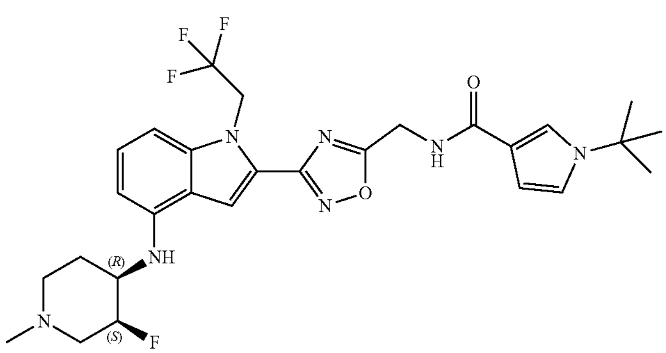 | 1-tert-butyl-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-pyrrole-3-carboxamide | 576.2 |

TABLE 9-continued

| Compound No. | Structure | IUPAC | LC-MS (ES+, m/z) |
|---|---|---|---|
| 195B | 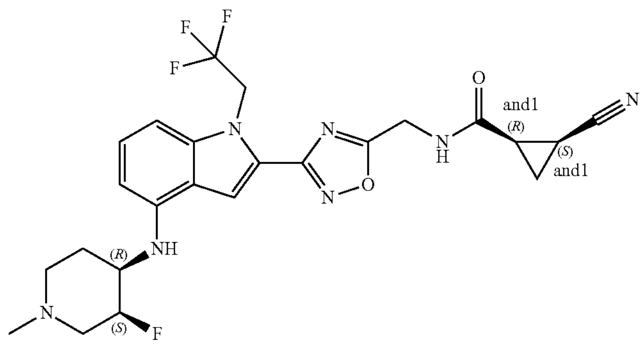 | (1RS,2SR)-2-cyano-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}cyclopropane-1-carboxamide | 519.9 |
| 196B | 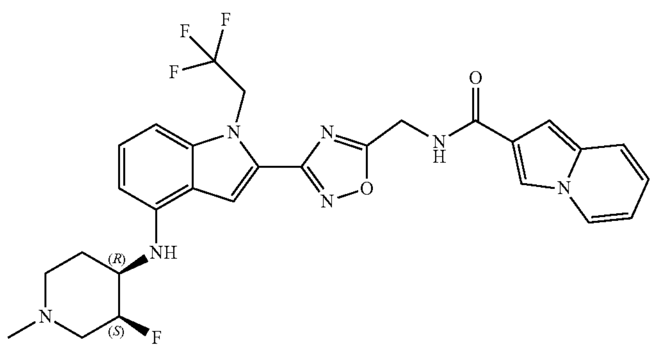 | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}indolizine-2-carboxamide | 569.9 |
| 197B | 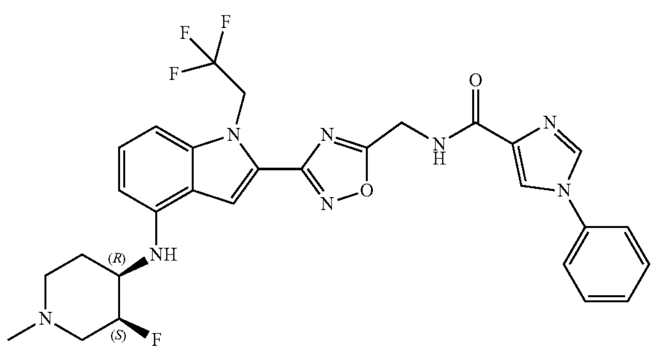 | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-phenyl-1H-imidazole-4-carboxamide | 596.9 |
| 198B | 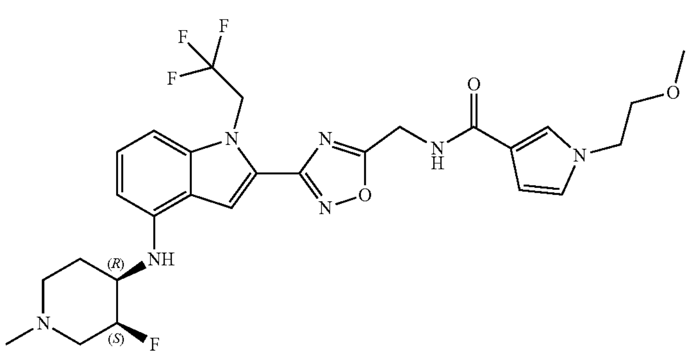 | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(2-methoxyethyl)-1H-pyrrole-3-carboxamide | 578.2 |

TABLE 9-continued

| Compound No. | Structure | IUPAC | LC-MS (ES+, m/z) |
|---|---|---|---|
| 199B | 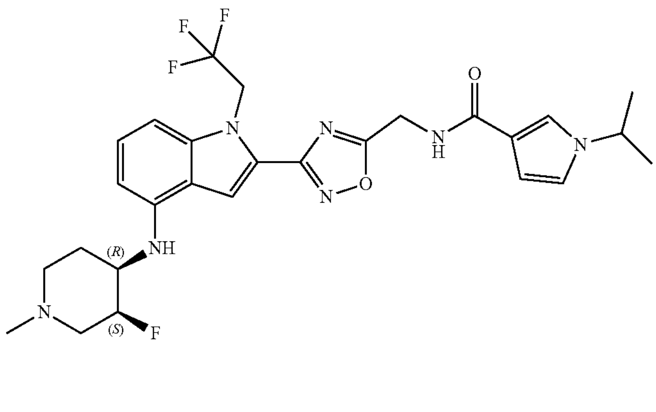 | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(propan-2-yl)-1H-pyrrole-3-carboxamide | 562.3 |
| 200B | 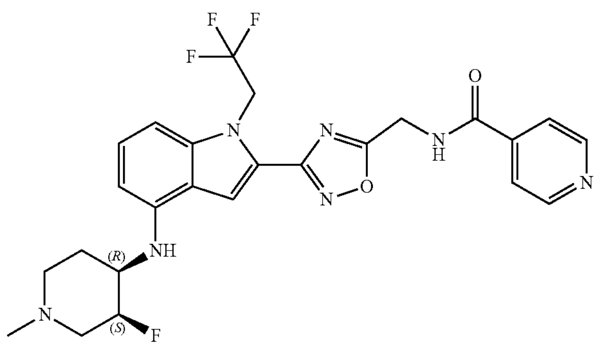 | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}pyridine-4-carboxamide | 532.2 |
| 201B | 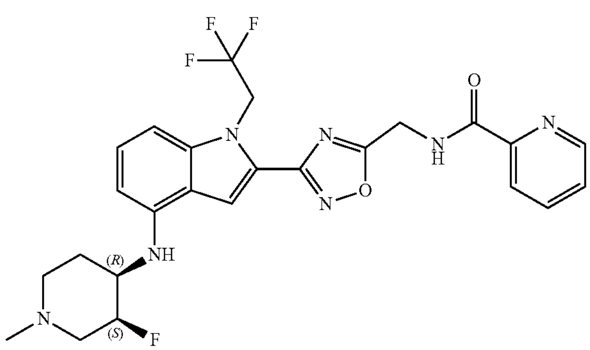 | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}pyridine-2-carboxamide | 532.3 |
| 202B | 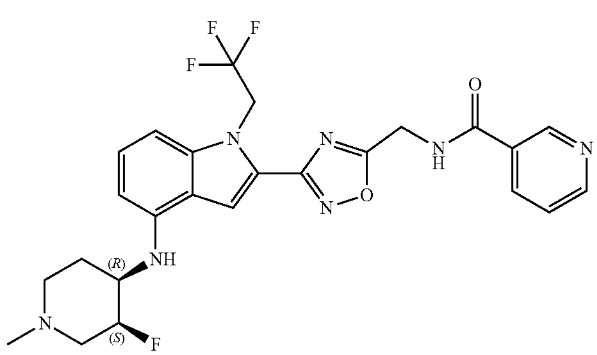 | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}pyridine-3-carboxamide | 532.2 |

TABLE 9-continued

| Compound No. | Structure | IUPAC | LC-MS (ES⁺, m/z) |
|---|---|---|---|
| 203B | 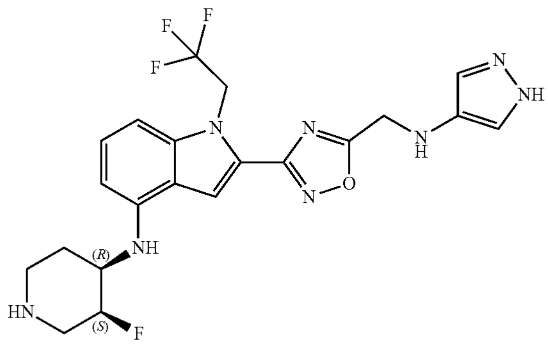 | N-[(3S,4R)-3-fluoropiperidin-4-yl]-2-(5-{[(1H-pyrazol-4-yl)amino]methyl}-1,2,4-oxadiazol-3-yl)-1-(2,2,2-trifluoroethyl)-1H-indol-4-amine | 479.1 |
| 204B | 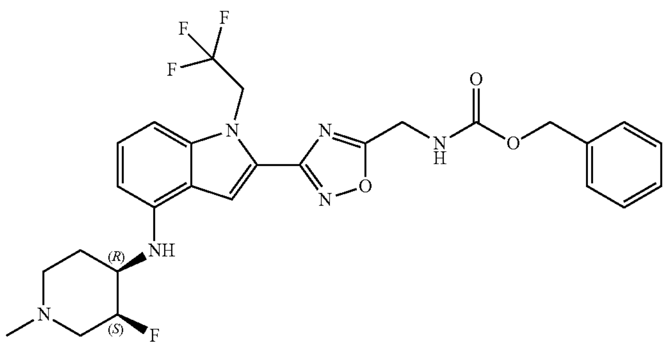 | benzyl N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}carbamate | 561.2 |
| 205B | 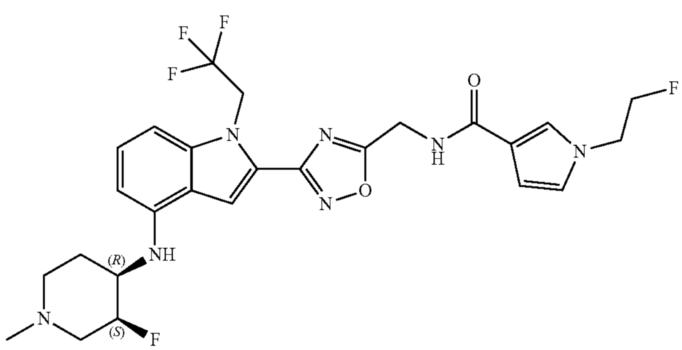 | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(2-fluoroethyl)-1H-pyrrole-3-carboxamide | 566.3 |
| 206B | 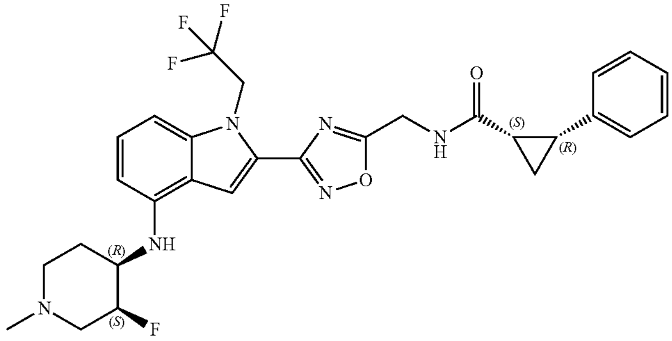 | (1S,2R)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-phenylcyclopropane-1-carboxamide | 571.3 |

TABLE 9-continued

| Compound No. | Structure | IUPAC | LC-MS (ES+, m/z) |
|---|---|---|---|
| 207B | 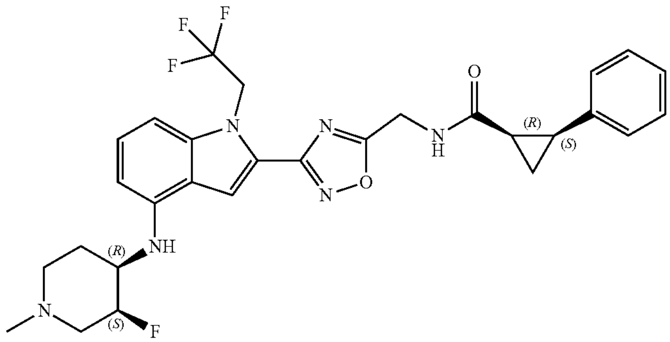 | (1R,2S)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-phenylcyclopropane-1-carboxamide | 571.3 |
| 208B | 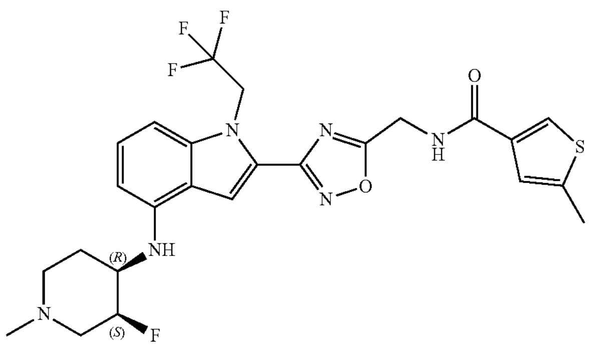 | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-5-methylthiophene-3-carboxamide | 551.2 |
| 209B | 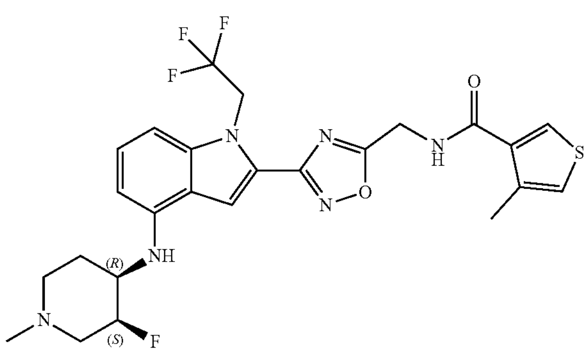 | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-4-methylthiophene-3-carboxamide | 551.1 |
| 210B | 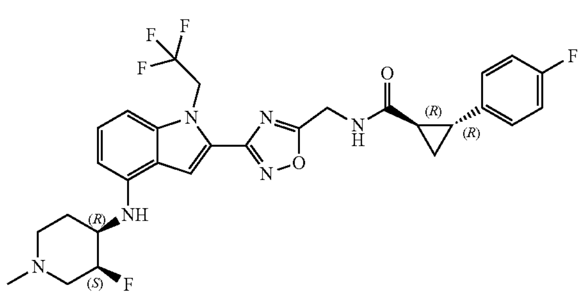 | (1R,2R)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-(4-fluorophenyl)cyclopropane-1-carboxamide | 589.3 |

TABLE 9-continued

| Compound No. | Structure | IUPAC | LC-MS (ES+, m/z) |
|---|---|---|---|
| 211B | 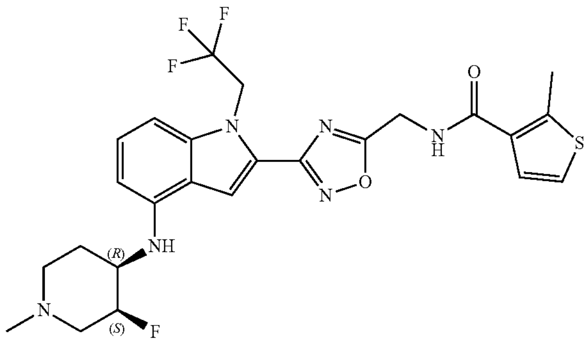 | N-{3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-methylthiophene-3-carboxamide | 551.2 |
| 212B | 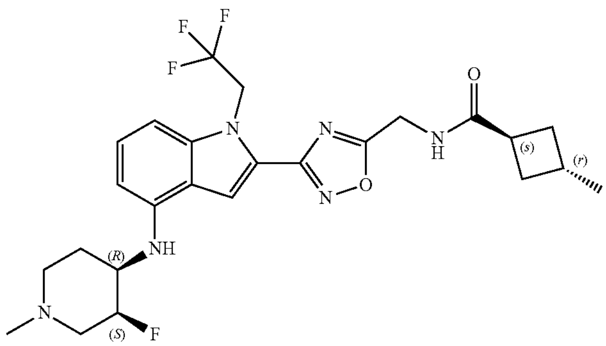 | (1s,3r)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-3-methylcyclobutane-1-carboxamide | 523.3 |
| 213B | 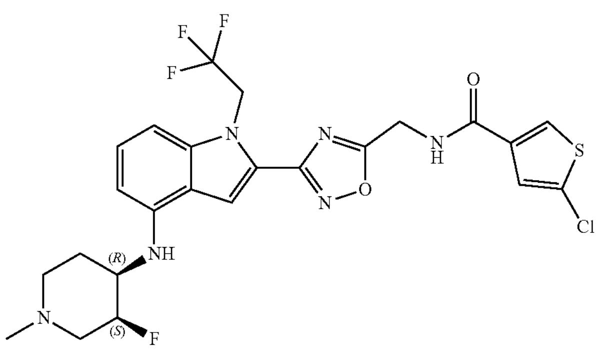 | 5-chloro-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}thiophene-3-carboxamide | 571.1 |
| 214B | 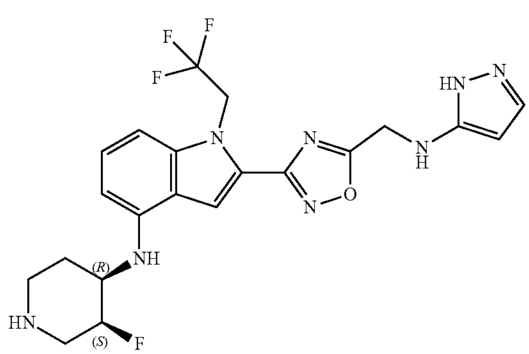 | N-[(3S,4R)-3-fluoropiperidin-4-yl]-2-(5-{[(1H-pyrazol-5-yl)amino]methyl}-1,2,4-oxadiazol-3-yl)-1-(2,2,2-trifluoroethyl)-1H-indol-4-amine | 479.1 |

TABLE 9-continued

| Compound No. | Structure | IUPAC | LC-MS (ES+, m/z) |
|---|---|---|---|
| 215B | 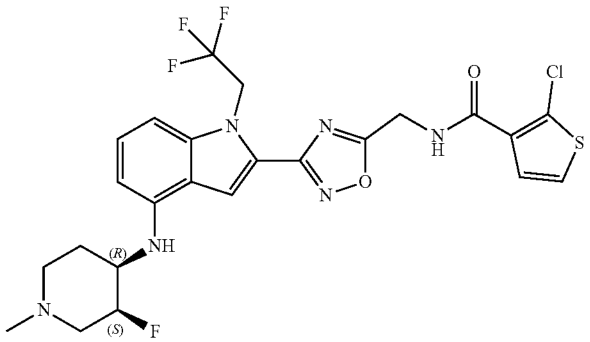 | 2-chloro-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}thiophene-3-carboxamide | 571.1 |
| 216B | 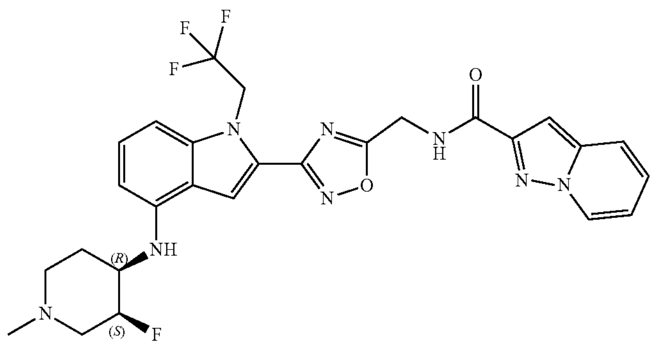 | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}pyrazolo[1,5-a]pyridine-2-carboxamide | 570.9 |
| 217B | 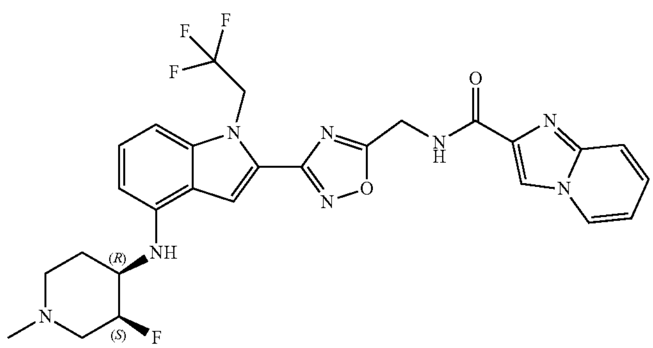 | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}imidazo[1,2-a]pyridine-2-carboxamide | 570.9 |
| 218B | 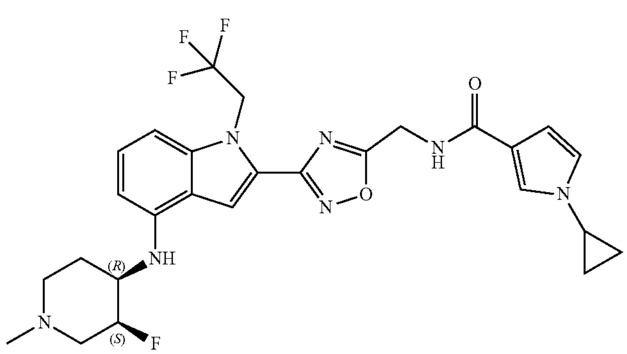 | 1-cyclopropyl-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-pyrrole-3-carboxamide | 559.9 |

TABLE 9-continued

| Compound No. | Structure | IUPAC | LC-MS (ES+, m/z) |
|---|---|---|---|
| 219B | 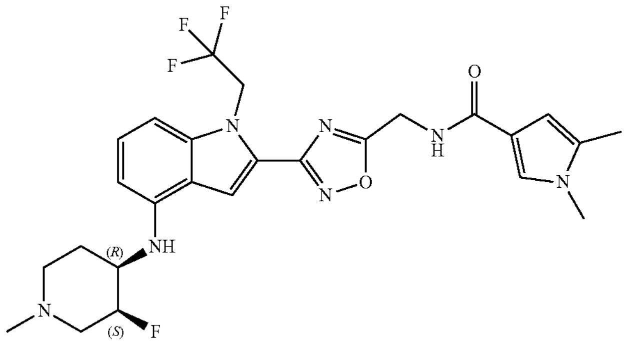 | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1,5-dimethyl-1H-pyrrole-3-carboxamide | 548 |
| 220B | 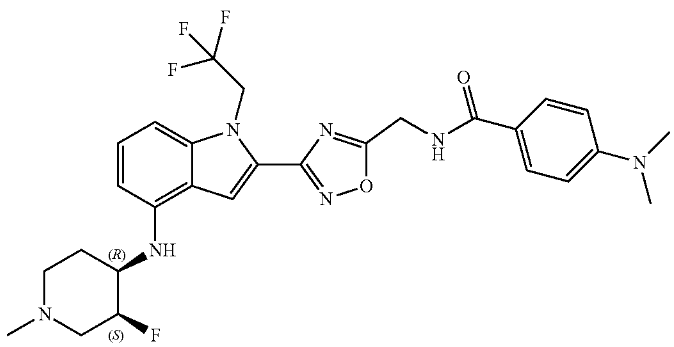 | 4-(dimethylamino)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}benzamide | 573.9 |
| 221B | 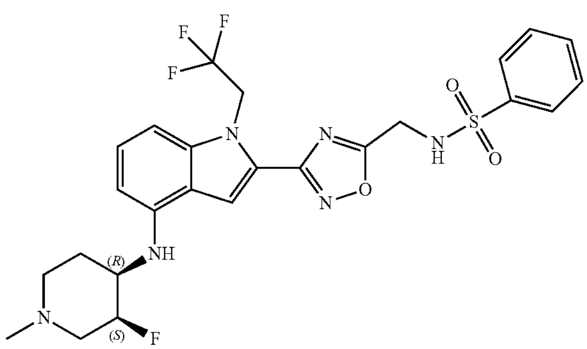 | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}benzenesulfonamide | 566.9 |
| 222B | 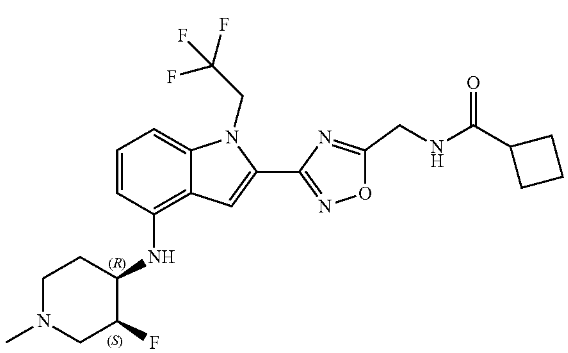 | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}cyclobutanecarboxamide | 509.2 |

TABLE 9-continued

| Compound No. | Structure | IUPAC | LC-MS (ES+, m/z) |
|---|---|---|---|
| 223B | 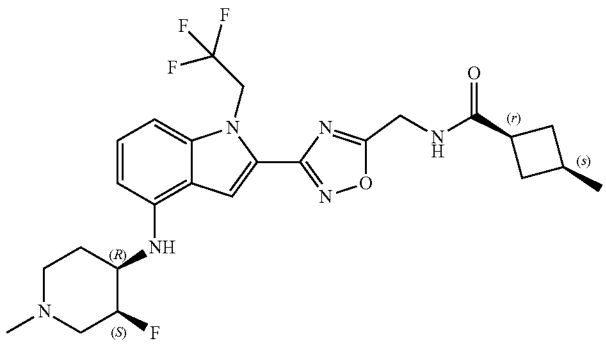 | (1r,3s)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-3-methylcyclobutane-1-carboxamide | 523.3 |
| 224B | 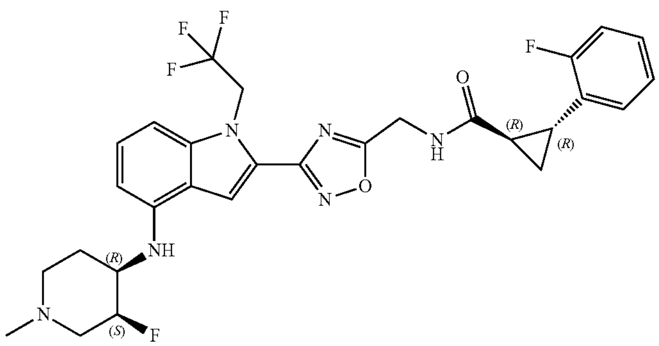 | (1R,2R)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-(2-fluorophenyl)cyclopropane-1-carboxamide | 589.1 |
| 225B | 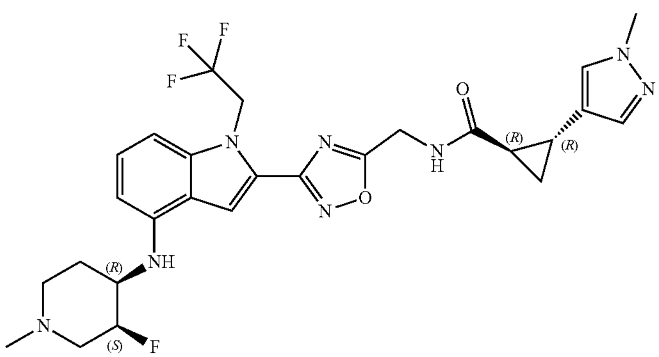 | (1R,2R)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-(1-methyl-1H-pyrazol-4-yl)cyclopropane-1-carboxamide | 575.1 |
| 226B | 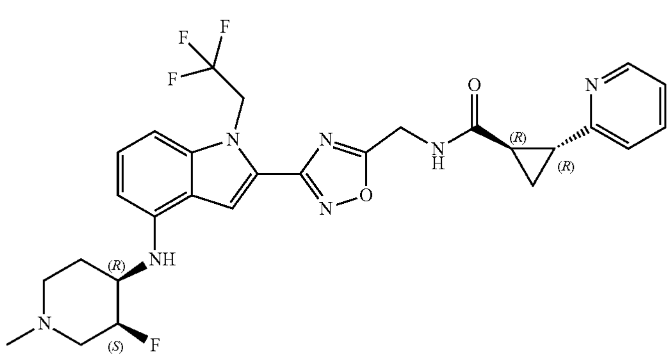 | (1R,2R)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-(pyridin-2-yl)cyclopropane-1-carboxamide | 572.1 |

TABLE 9-continued

| Compound No. | Structure | IUPAC | LC-MS (ES+, m/z) |
|---|---|---|---|
| 227B | 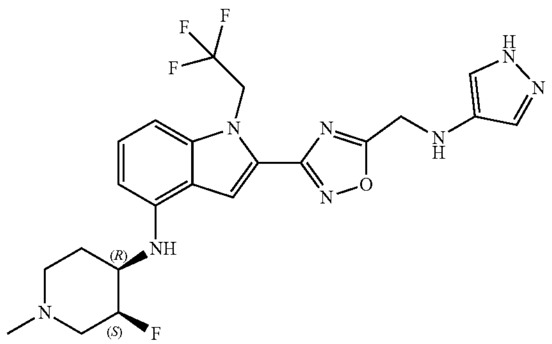 | N-[(3S,4R)-3-fluoro-1-methylpiperidin-4-yl]-2-(5-{[(1H-pyrazol-4-yl)amino]methyl}-1,2,4-oxadiazol-3-yl)-1-(2,2,2-trifluoroethyl)-1H-indol-4-amine | 493.2 |
| 228B | 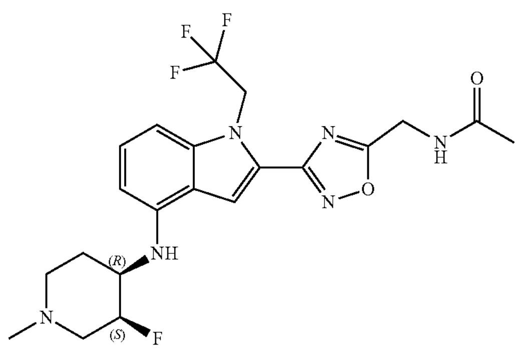 | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}acetamide | 469.2 |
| 229B | 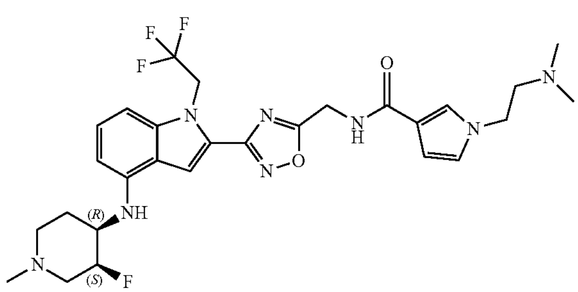 | 1-[2-(dimethylamino)ethyl]-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-pyrrole-3-carboxamide | 591.1 |
| 230B | 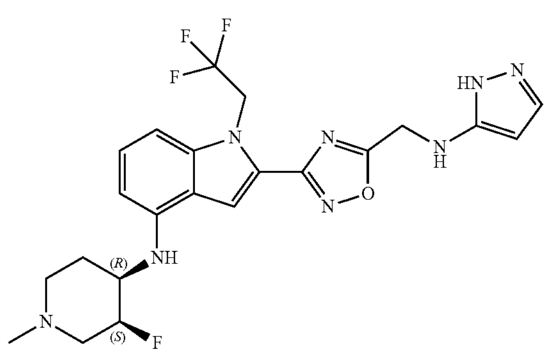 | N-[(3S,4R)-3-fluoro-1-methylpiperidin-4-yl]-2-(5-{[(1H-pyrazol-5-yl)amino]methyl}-1,2,4-oxadiazol-3-yl)-1-(2,2,2-trifluoroethyl)-1H-indol-4-amine | 493.2 |

TABLE 9-continued

| Compound No. | Structure | IUPAC | LC-MS (ES+, m/z) |
|---|---|---|---|
| 231B | 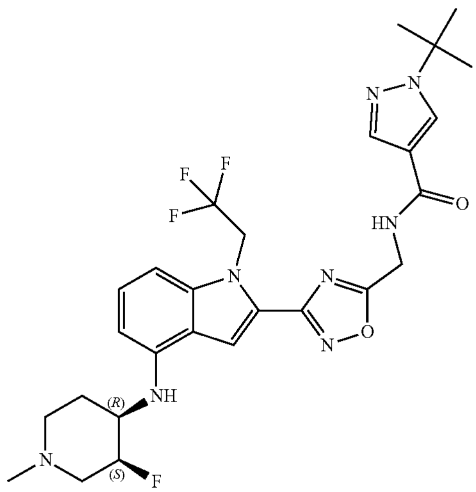 | 1-tert-butyl-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-pyrazole-4-carboxamide | 576.9 |
| 232B | 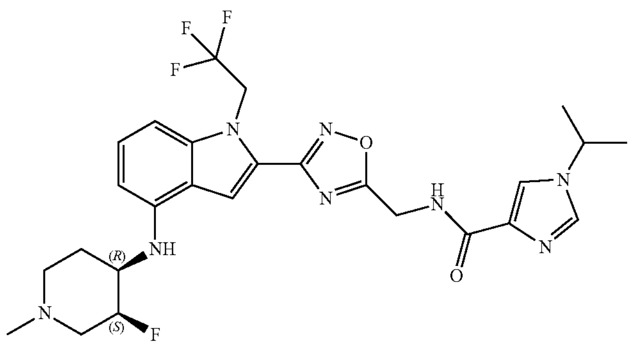 | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(propan-2-yl)-1H-imidazole-4-carboxamide | 562.9 |
| 233B | 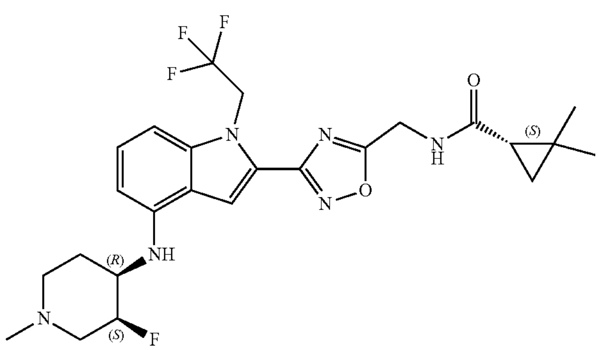 | (1S)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2,2-dimethylcyclopropane-1-carboxamide | 523.2 |
| 234B | 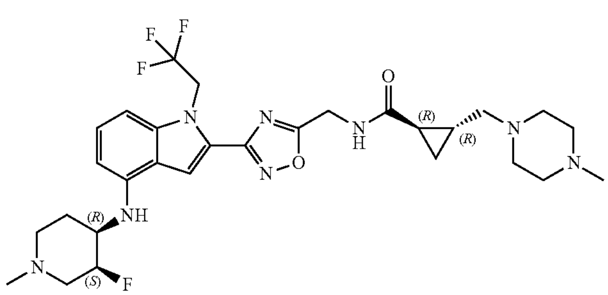 | (1R,2R)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-[(4-methylpiperazin-1-yl)methyl]cyclopropane-1-carboxamide | 607.1 |

TABLE 9-continued

| Compound No. | Structure | IUPAC | LC-MS (ES+, m/z) |
|---|---|---|---|
| 235B | 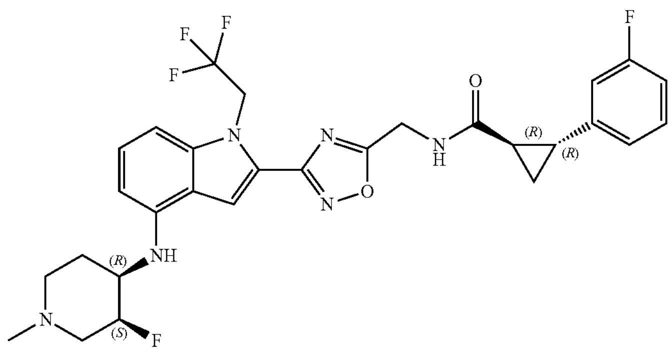 | (1R,2R)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-(3-fluorophenyl)cyclopropane-1-carboxamide | 589.1 |
| 236B | 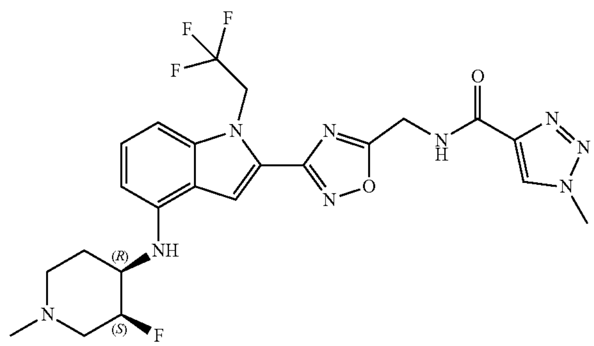 | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-methyl-1H-1,2,3-triazole-4-carboxamide | 536.1 |
| 237B | 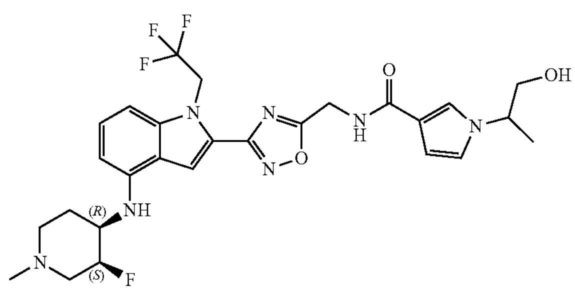 | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(1-hydroxypropan-2-yl)-1H-pyrrole-3-carboxamide | 578.1 |
| 238B | 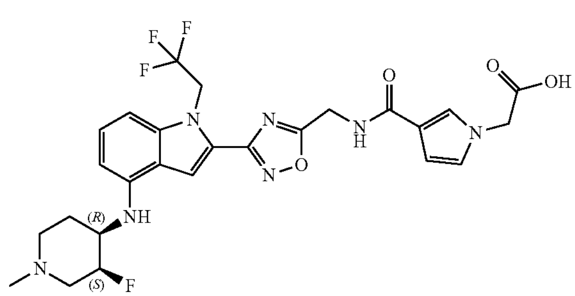 | 2-[3-({[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}carbamoyl)-1H-pyrrol-1-yl]acetic acid | 578.2 |

TABLE 9-continued

| Compound No. | Structure | IUPAC | LC-MS (ES+, m/z) |
|---|---|---|---|
| 239B | 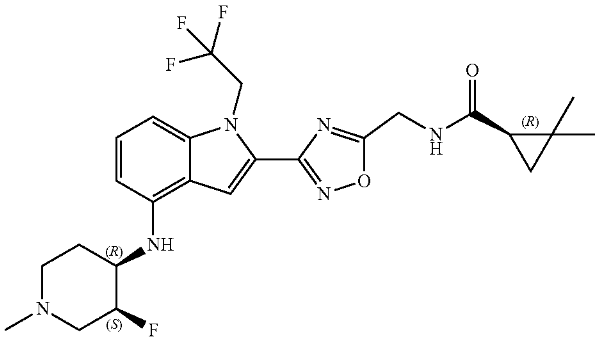 | (1R)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2,2-dimethylcyclopropane-1-carboxamide | 523.2 |
| 240B | 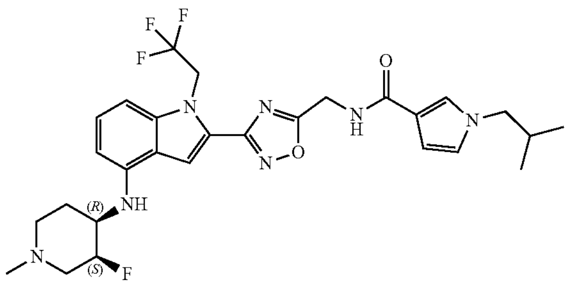 | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(2-methylpropyl)-1H-pyrrole-3-carboxamide | 576.2 |
| 241B | 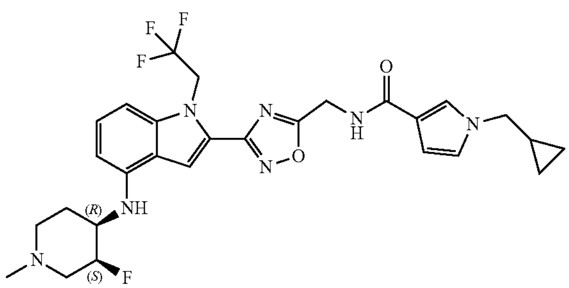 | 1-(cyclopropylmethyl)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-pyrrole-3-carboxamide | 574.1 |
| 242B | 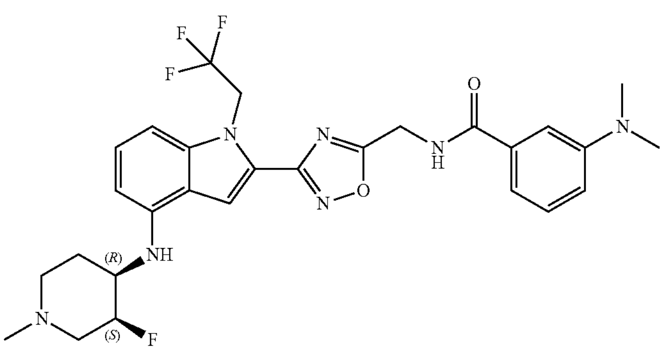 | 3-(dimethylamino)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}benzamide | 574.1 |
| 243B | 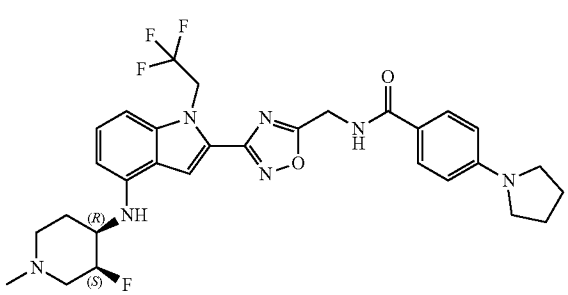 | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-4-(pyrrolidin-1-yl)benzamide | 600.2 |

TABLE 9-continued

| Compound No. | Structure | IUPAC | LC-MS (ES+, m/z) |
|---|---|---|---|
| 244B | 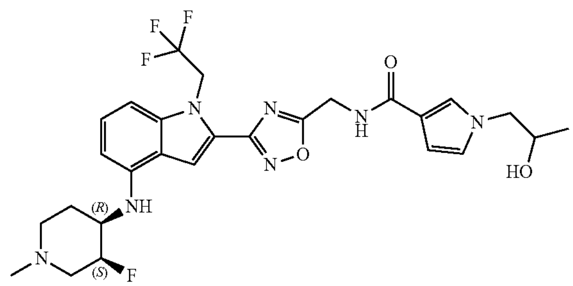 | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(2-hydroxypropyl)-1H-pyrrole-3-carboxamide | 578.1 |
| 245B | 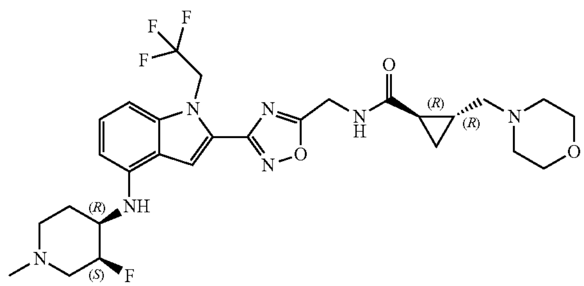 | (1R,2R)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-[(morpholin-4-yl)methyl]cyclopropane-1-carboxamide | 594.1 |
| 246B | 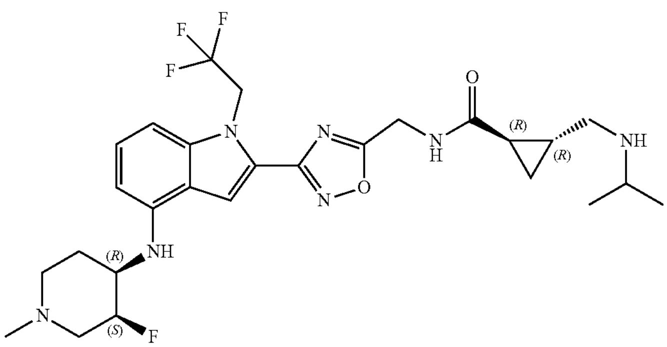 | (1R,2R)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-{[(propan-2-yl)amino]methyl}cyclopropane-1-carboxamide | 566.2 |
| 247B | 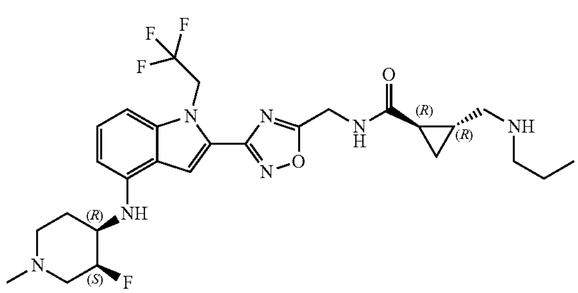 | (1R,2R)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-[(propylamino)methyl]cyclopropane-1-carboxamide | 566.2 |
| 248B | 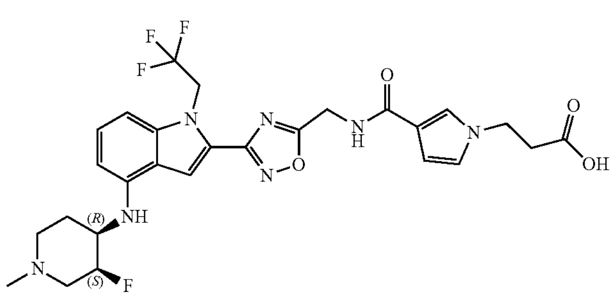 | 3-[3-({[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}carbamoyl)-1H-pyrrol-1-yl]propanoic acid | 592.1 |

TABLE 9-continued

| Compound No. | Structure | IUPAC | LC-MS (ES+, m/z) |
|---|---|---|---|
| 249B | 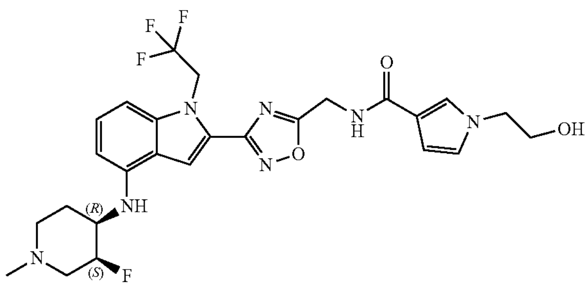 | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(2-hydroxyethyl)-1H-pyrrole-3-carboxamide | 564.1 |
| 250B | 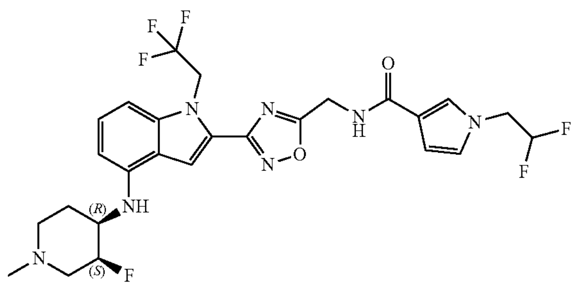 | 1-(2,2-difluoroethyl)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-pyrrole-3-carboxamide | 584.1 |
| 251B | 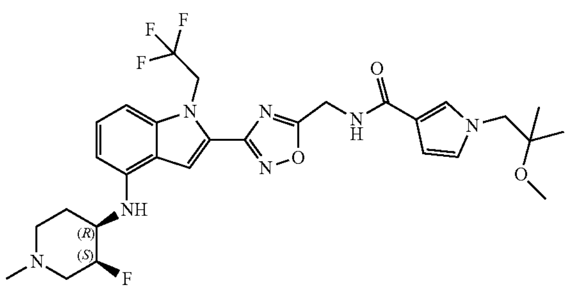 | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(2-methoxy-2-methylpropyl)-1H-pyrrole-3-carboxamide | 606.2 |
| 252B | 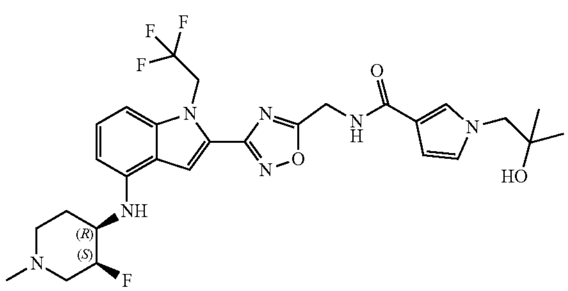 | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(2-hydroxy-2-methylpropyl)-1H-pyrrole-3-carboxamide | 592.1 |
| 253B | 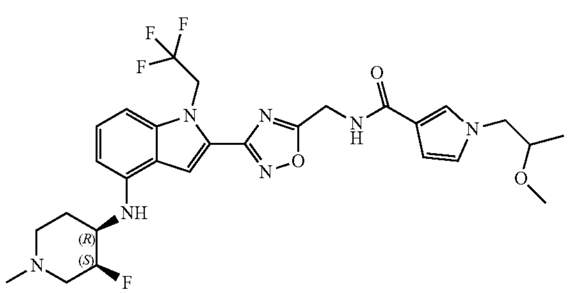 | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(2-methoxypropyl)-1H-pyrrole-3-carboxamide | 592.2 |

TABLE 9-continued

| Compound No. | Structure | IUPAC | LC-MS (ES+, m/z) |
|---|---|---|---|
| 254B | 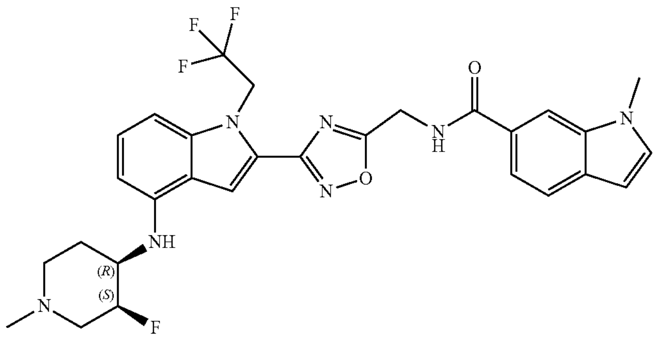 | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-methyl-1H-indole-6-carboxamide | 584.1 |
| 255B | 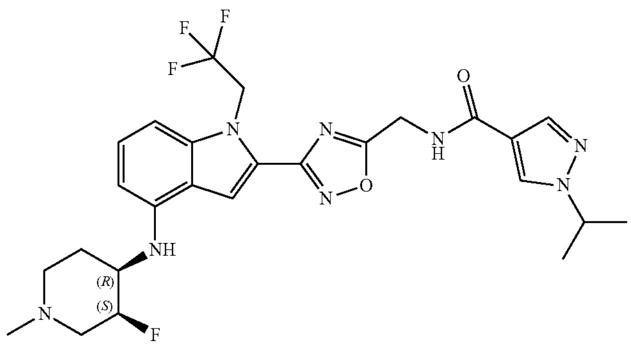 | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(propan-2-yl)-1H-pyrazole-4-carboxamide | 563.1 |
| 256B | 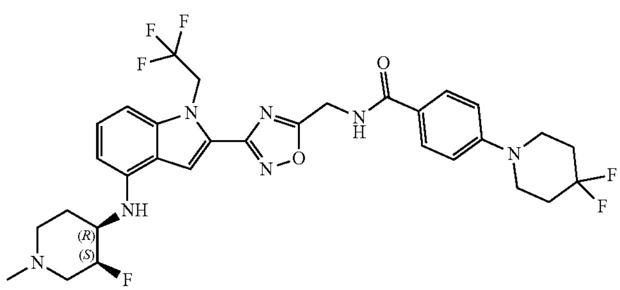 | 4-(4,4-difluoropiperidin-1-yl)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}benzamide | 650.3 |
| 257B | 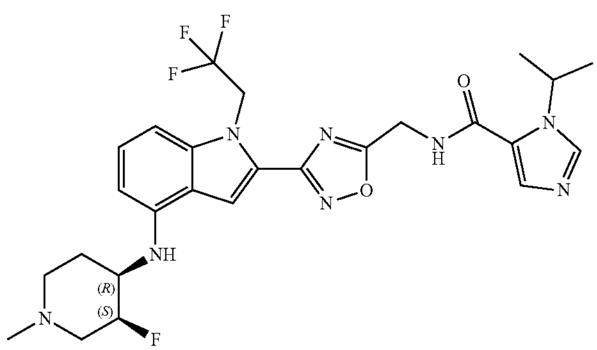 | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(propan-2-yl)-1H-imidazole-5-carboxamide | 563.3 |

TABLE 9-continued

| Compound No. | Structure | IUPAC | LC-MS (ES+, m/z) |
|---|---|---|---|
| 258B | 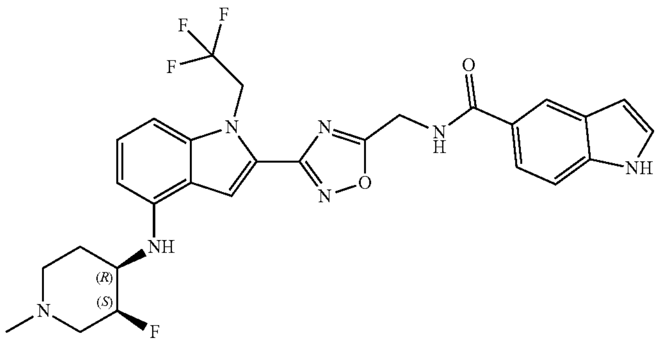 | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-indole-5-carboxamide | 570.1 |
| 259B | 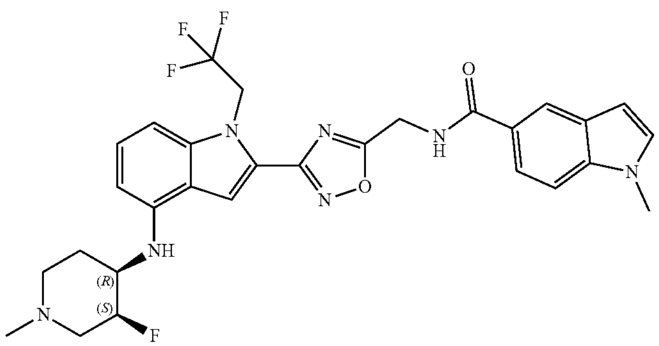 | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-methyl-1H-indole-5-carboxamide | 584.1 |
| 260B | 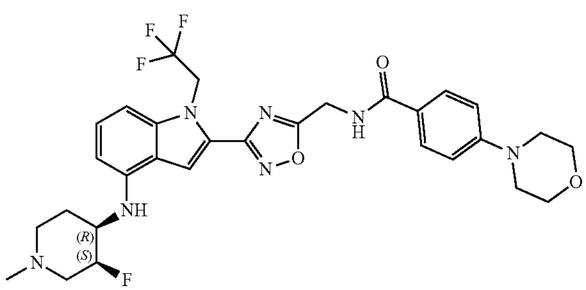 | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-4-(morpholin-4-yl)benzamide | 616.1 |
| 261B | 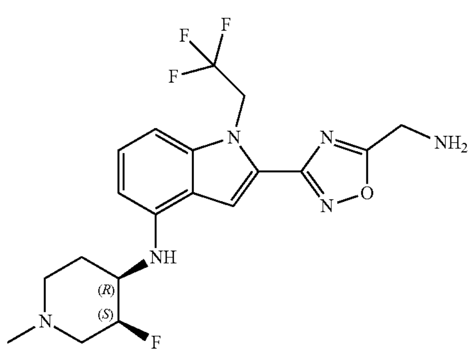 | 2-[5-(aminomethyl)-1,2,4-oxadiazol-3-yl]-N-[(3S,4R)-3-fluoro-1-methylpiperidin-4-yl]-1-(2,2,2-trifluoroethyl)-1H-indol-4-amine | 427.1 |

TABLE 9-continued

| Compound No. | Structure | IUPAC | LC-MS (ES+, m/z) |
|---|---|---|---|
| 262B | 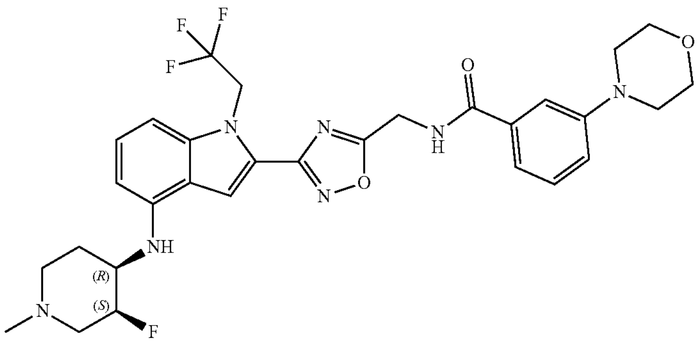 | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-3-(morpholin-4-yl)benzamide | 616.2 |
| 263B | 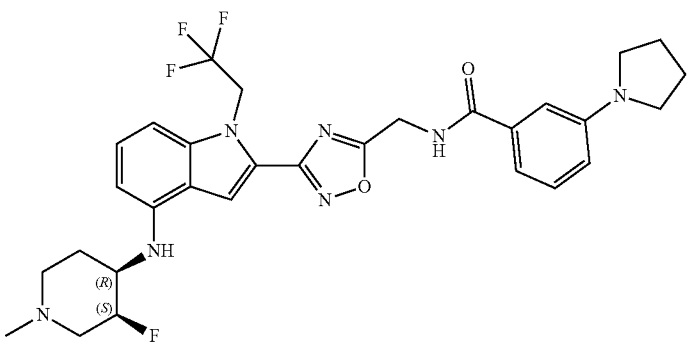 | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-3-(pyrrolidin-1-yl)benzamide | 600.3 |
| 264B | 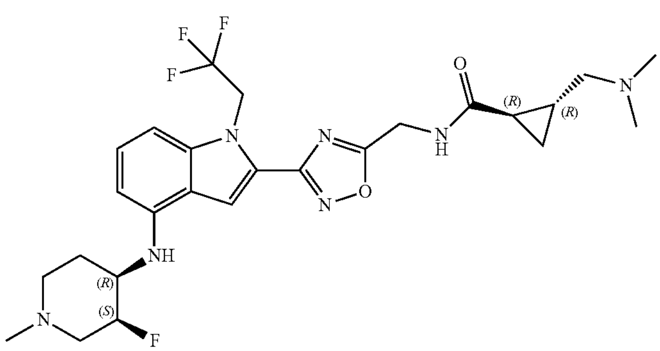 | (1R,2R)-2-[(dimethylamino)methyl]-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}cyclopropane-1-carboxamide | 552.1 |
| 265B | 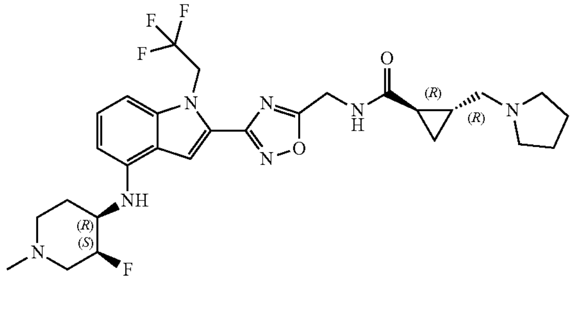 | (1R,2R)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-[(pyrrolidin-1-yl)methyl]cyclopropane-1-carboxamide | 578.1 |

TABLE 9-continued

| Compound No. | Structure | IUPAC | LC-MS (ES+, m/z) |
|---|---|---|---|
| 266B | 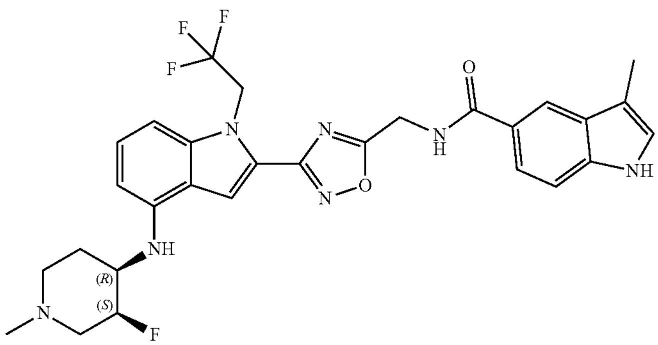 | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-3-methyl-1H-indole-5-carboxamide | 584.1 |
| 267B | 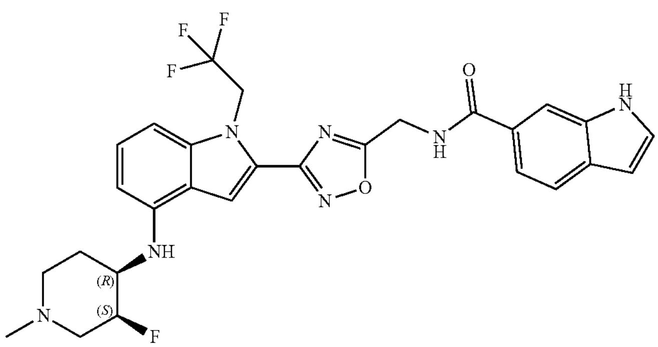 | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-indole-6-carboxamide | 570.3 |
| 268B | 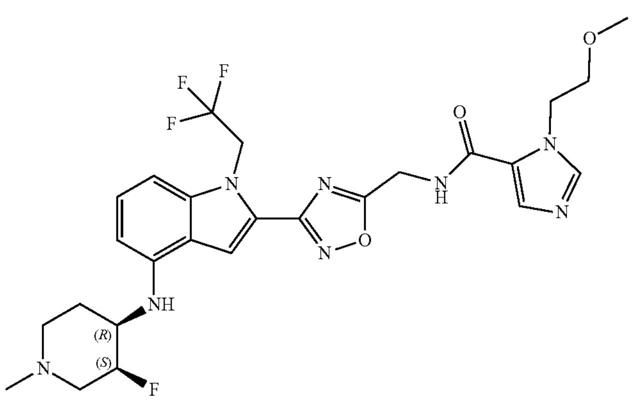 | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(2-methoxyethyl)-1H-imidazole-5-carboxamide | 579.3 |
| 269B | 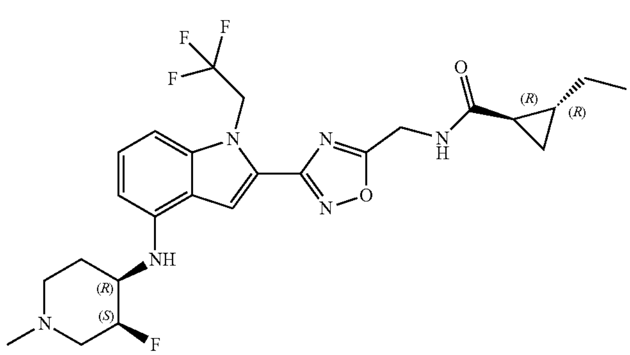 | (1R,2R)-2-ethyl-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}cyclopropane-1-carboxamide | 523.1 |

TABLE 9-continued

| Compound No. | Structure | IUPAC | LC-MS (ES+, m/z) |
|---|---|---|---|
| 270B | 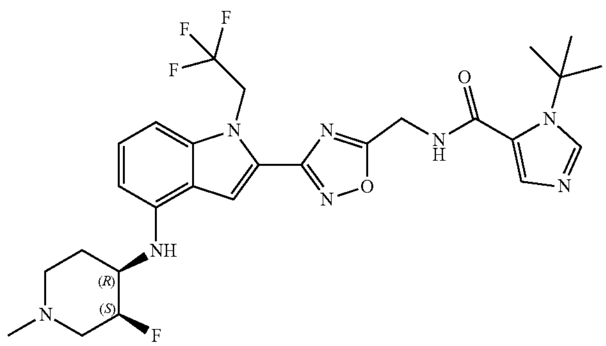 | 1-tert-butyl-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-imidazole-5-carboxamide | 577.1 |
| 271B | 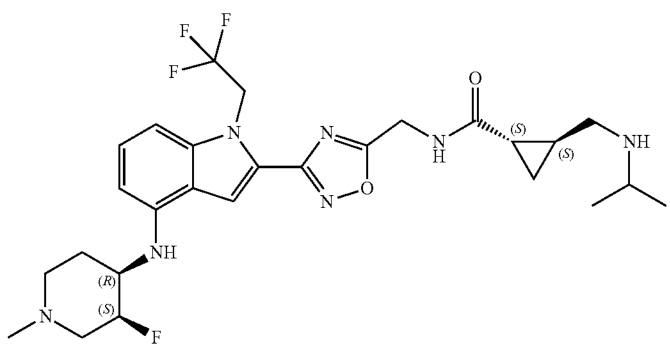 | (1S,2S)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-{[(propan-2-yl)amino]methyl}cyclopropane-1-carboxamide | 566.2 |
| 272B | 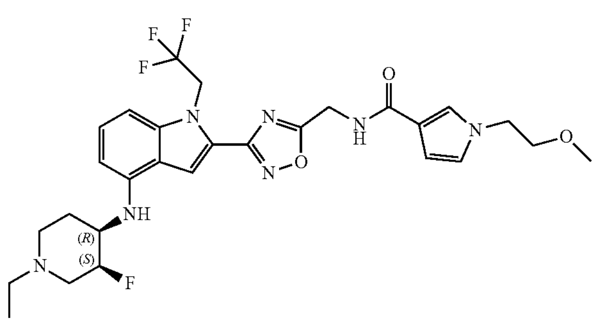 | N-{[3-(4-{[(3S,4R)-1-ethyl-3-fluoropiperidin-4-yl]amino}-1-(2,2,2-trifluoroethyl)-1H-indol-2-yl)-1,2,4-oxadiazol-5-yl]methyl}-1-(2-methoxyethyl)-1H-pyrrole-3-carboxamide | 592.2 |
| 273B | 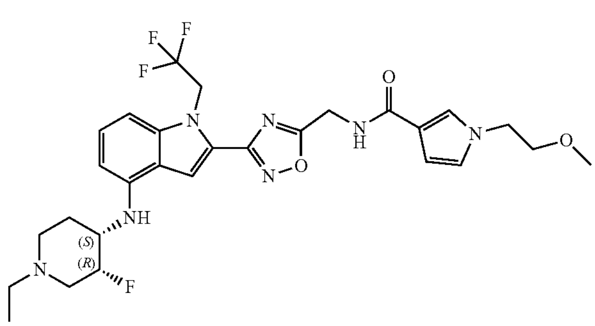 | N-{[3-(4-{[(3R,4S)-1-ethyl-3-fluoropiperidin-4-yl]amino}-1-(2,2,2-trifluoroethyl)-1H-indol-2-yl)-1,2,4-oxadiazol-5-yl]methyl}-1-(2-methoxyethyl)-1H-pyrrole-3-carboxamide | 592.1 |

TABLE 9-continued

| Compound No. | Structure | IUPAC | LC-MS (ES+, m/z) |
|---|---|---|---|
| 274B | 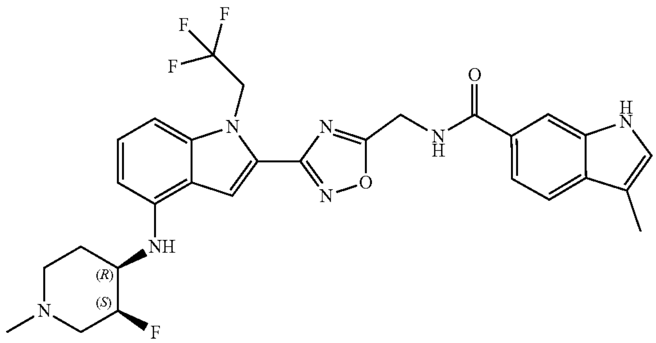 | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-3-methyl-1H-indole-6-carboxamide | 584.1 |
| 275B | 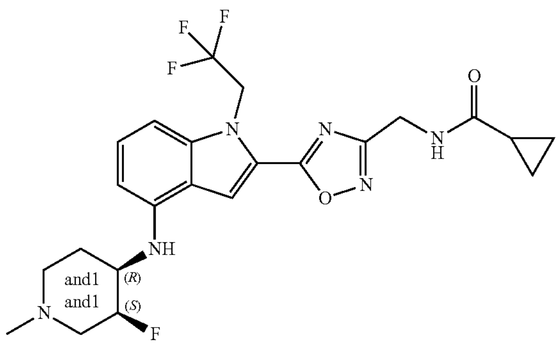 | (+/−)-N-{[5-(4-{[(3R,4S)-3-fluoro-1-methylpiperidin-4-yl]amino}-1-(2,2,2-trifluoroethyl)-1H-indol-2-yl)-1,2,4-oxadiazol-3-yl]methyl}cyclopropanecarboxamide | 495.2 |
| 276B | 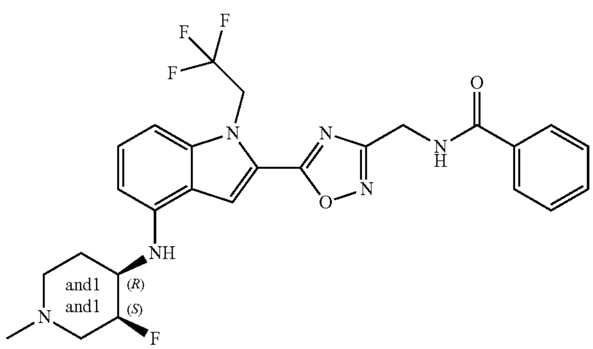 | (+/−)-N-{[5-(4-{[(3R,4S)-3-fluoro-1-methylpiperidin-4-yl]amino}-1-(2,2,2-trifluoroethyl)-1H-indol-2-yl)-1,2,4-oxadiazol-3-yl]methyl}benzamide | 531.2 |
| 277B | 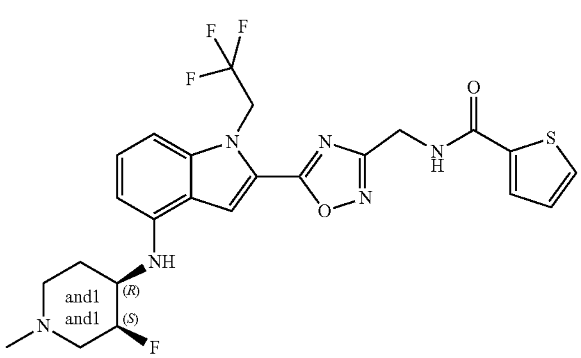 | (+/−)-N-{[5-(4-{[(3R,4S)-3-fluoro-1-methylpiperidin-4-yl]amino}-1-(2,2,2-trifluoroethyl)-1H-indol-2-yl)-1,2,4-oxadiazol-3-yl]methyl}thiophene-2-carboxamide | 537 |

TABLE 9-continued

| Compound No. | Structure | IUPAC | LC-MS (ES+, m/z) |
|---|---|---|---|
| 278B | 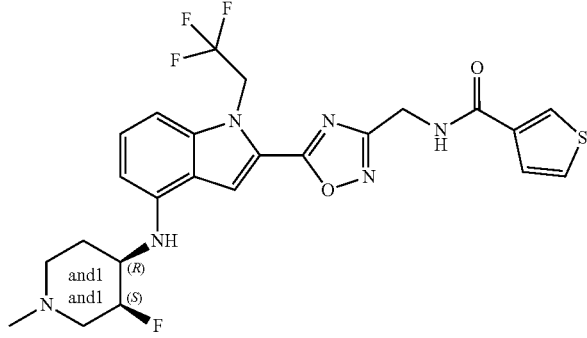 | (+/−)-N-{[5-(4-{[(3R,4S)-3-fluoro-1-methylpiperidin-4-yl]amino}-1-(2,2,2-trifluoroethyl)-1H-indol-2-yl)-1,2,4-oxadiazol-3-yl]methyl}thiophene-3-carboxamide | 537.2 |
| 279B | 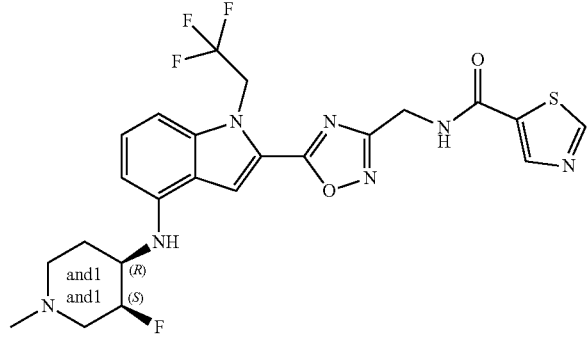 | (+/−)-N-{[5-(4-{[(3R,4S)-3-fluoro-1-methylpiperidin-4-yl]amino}-1-(2,2,2-trifluoroethyl)-1H-indol-2-yl)-1,2,4-oxadiazol-3-yl]methyl}-1,3-thiazole-5-carboxamide | 538.2 |
| 280B | 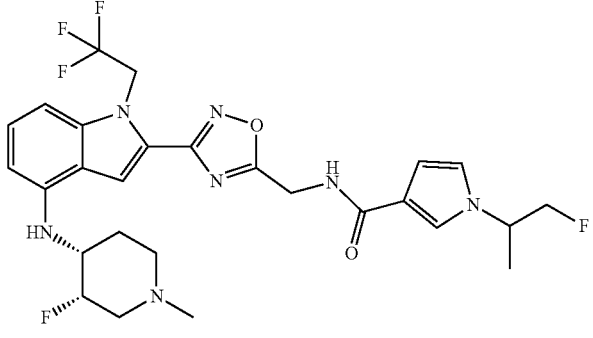 [SMILES: CC(CF)n1ccc(C(=O)NCc2nc(-c3cc4c(N[C@@H]5CCN(C)C[C@@H]5F)cccc4n3CC(F)(F)F)no2)c1] | N-((3-(4-(((3S,4R)-3-fluoro-1-methylpiperidin-4-yl)amino)-1-(2,2,2-trifluoroethyl)-1H-indol-2-yl)-1,2,4-oxadiazol-5-yl)methyl)-1-(1-fluoropropan-2-yl)-1H-pyrrole-3-carboxamide | |
| 281B | 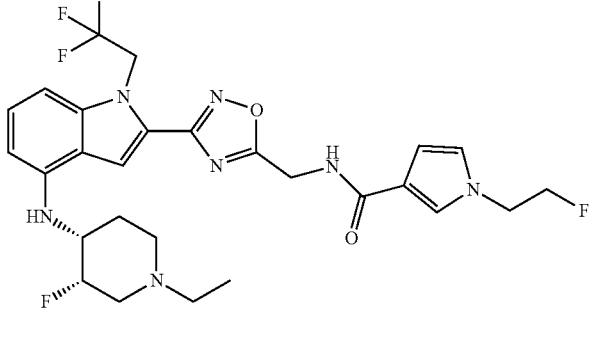 | N-((3-(4-(((3S,4R)-1-ethyl-3-fluoropiperidin-4-yl)amino)-1-(2,2,2-trifluoroethyl)-1H-indol-2-yl)-1,2,4-oxadiazol-5-yl)methyl)-1-(2-fluoroethyl)-1H-pyrrole-3-carboxamide | |

TABLE 9-continued

| Compound No. | Structure | IUPAC | LC-MS (ES+, m/z) |
|---|---|---|---|
| 282B | 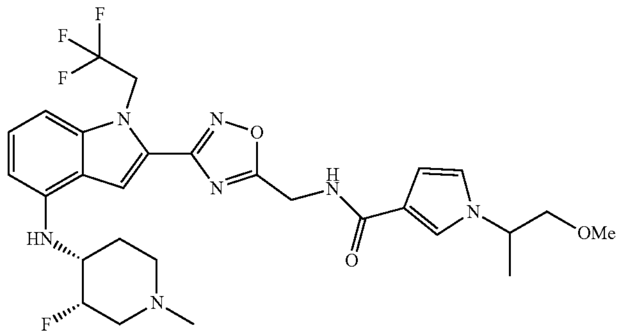 [SMILES: COCC(C)n1ccc(C(=O)NCc2nc(-c3cc4c(N[C@@H]5CCN(C)C[C@@H]5F)cccc4n3CC(F)(F)F)no2)c1] | N-((3-(4-(((3S,4R)-3-fluoro-1-methylpiperidin-4-yl)amino)-1-(2,2,2-trifluoroethyl)-1H-indol-2-yl)-1,2,4-oxadiazol-5-yl)methyl)-1-(1-methoxypropan-2-yl)-1H-pyrrole-3-carboxamide | |
| 289B | 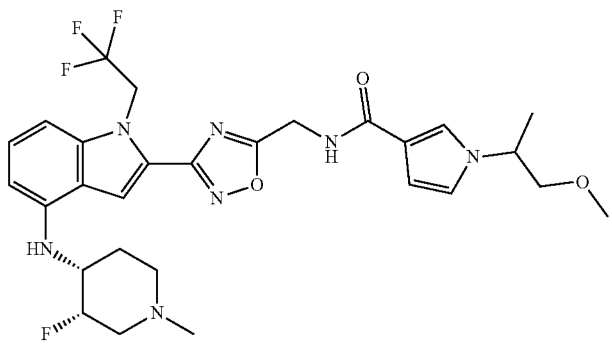 [SMILES: COCC(C)n1ccc(C(=O)NCc2nc(-c3cc4c(N[C@@H]5CCN(C)C[C@@H]5F)cccc4n3CC(F)(F)F)no2)c1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(1-methoxypropan-2-yl)-1H-pyrrole-3-carboxamide | 592.2 |
| 290B | 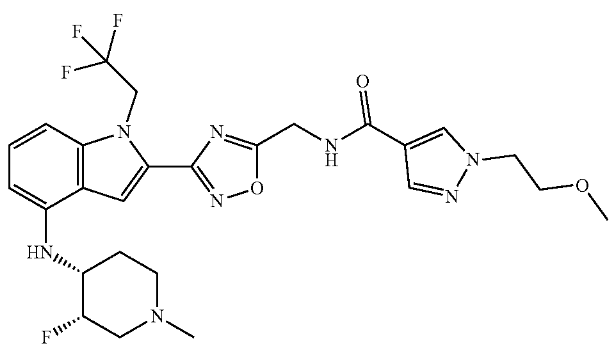 [SMILES: COCCn1cc(C(=O)NCc2nc(-c3cc4c(N[C@@H]5CCN(C)C[C@@H]5F)cccc4n3CC(F)(F)F)no2)cn1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(2-methoxyethyl)-1H-pyrazole-4-carboxamide | 579.1 |
| 291B | 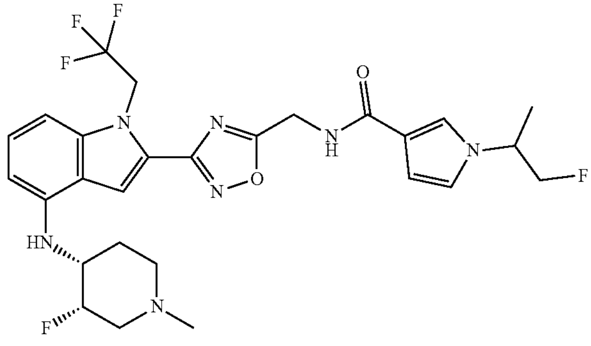 [SMILES: CC(CF)n1ccc(C(=O)NCc2nc(-c3cc4c(N[C@@H]5CCN(C)C[C@@H]5F)cccc4n3CC(F)(F)F)no2)c1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(1-fluoropropan-2-yl)-1H-pyrrole-3-carboxamide | 580.1 |

TABLE 9-continued

| Compound No. | Structure | IUPAC | LC-MS (ES+, m/z) |
|---|---|---|---|
| 292B | 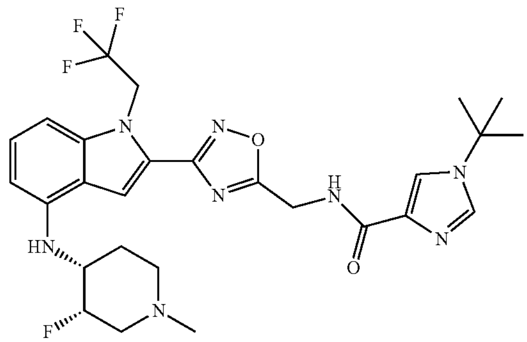 [SMILES: CN1CC[C@@H](Nc2cccc3c2cc(-c2noc(CNC(=O)c4cn(C(C)(C)C)cn4)n2)n3CC(F)(F)F)[C@@H](F)C1] | 1-tert-butyl-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-imidazole-4-carboxamide | 577.1 |
| 293B | 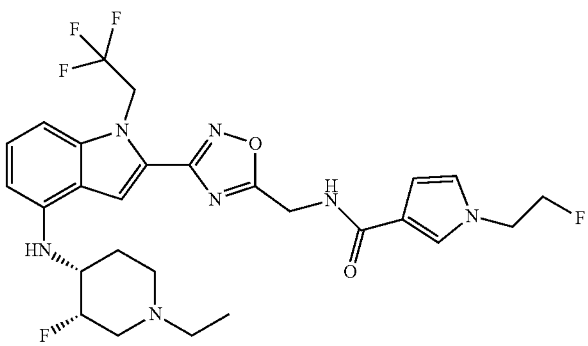 [SMILES: CCN1CC[C@@H](Nc2cccc3c2cc(-c2noc(CNC(=O)c4ccn(CCF)c4)n2)n3CC(F)(F)F)[C@@H](F)C1] | N-{[3-(4-{[(3S,4R)-1-ethyl-3-fluoropiperidin-4-yl]amino}-1-(2,2,2-trifluoroethyl)-1H-indol-2-yl)-1,2,4-oxadiazol-5-yl]methyl}-1-(2-fluoroethyl)-1H-pyrrole-3-carboxamide | 580.1 |
| 294B | 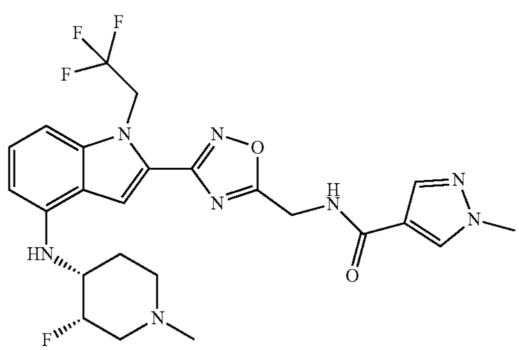 [SMILES: CN1CC[C@@H](Nc2cccc3c2cc(-c2noc(CNC(=O)c4cnn(C)c4)n2)n3CC(F)(F)F)[C@@H](F)C1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-methyl-1H-pyrazole-4-carboxamide | 535.1 |
| 295B | 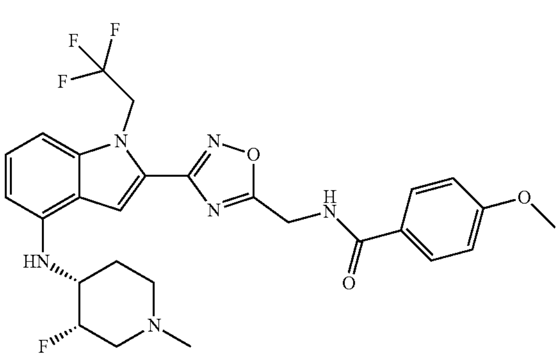 [SMILES: COc1ccc(C(=O)NCc2nc(-c3cc4c(N[C@@H]5CCN(C)C[C@@H]5F)cccc4n3CC(F)(F)F)no2)cc1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-4-methoxybenzamide | 560.9 |

TABLE 9-continued

| Compound No. | Structure | IUPAC | LC-MS (ES+, m/z) |
|---|---|---|---|
| 296B | 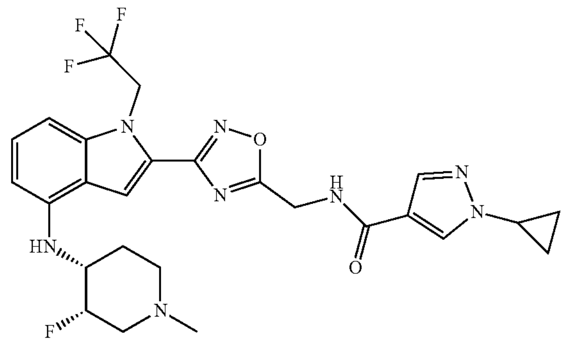 [SMILES: CN1CC[C@@H](Nc2cccc3c2cc(-c2noc(CNC(=O)c4cnn(C5CC5)c4)n2)n3CC(F)(F)F)[C@@H](F)C1] | 1-cyclopropyl-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-pyrazole-4-carboxamide | 561.1 |
| 297B | 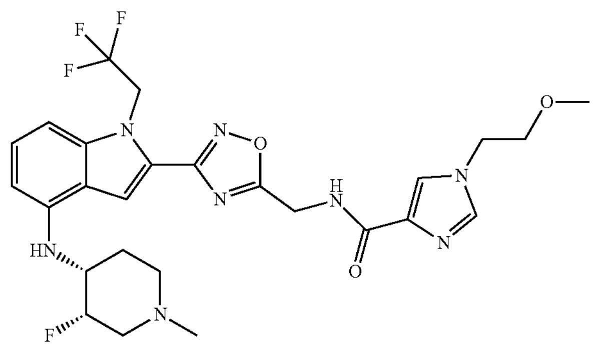 [SMILES: COCCn1cnc(C(=O)NCc2nc(-c3cc4c(N[C@@H]5CCN(C)C[C@@H]5F)cccc4n3CC(F)(F)F)no2)c1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(2-methoxyethyl)-1H-imidazole-4-carboxamide | 579.2 |
| 298B | 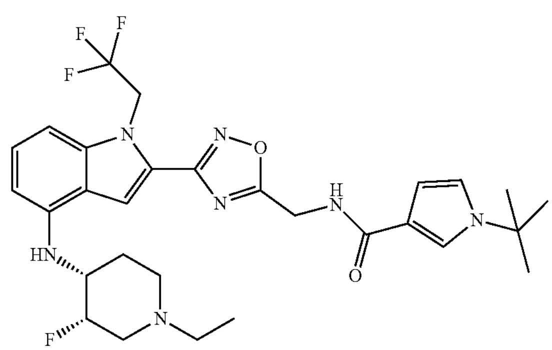 [SMILES: CCN1CC[C@@H](Nc2cccc3c2cc(-c2noc(CNC(=O)c4ccn(C(C)(C)C)c4)n2)n3CC(F)(F)F)[C@@H](F)C1] | 1-tert-butyl-N-{[3-(4-{[(3S,4R)-1-ethyl-3-fluoropiperidin-4-yl]amino}-1-(2,2,2-trifluoroethyl)-1H-indol-2-yl)-1,2,4-oxadiazol-5-yl]methyl}-1H-pyrrole-3-carboxamide | 590.1 |
| 299B | 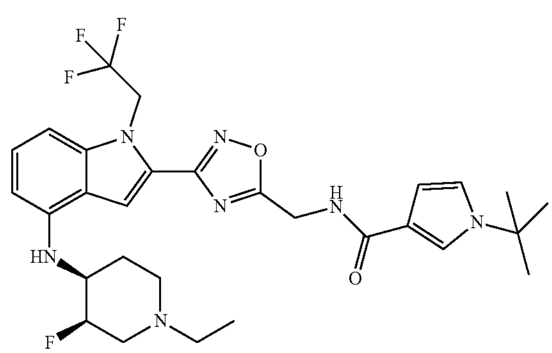 [SMILES: CCN1CC[C@H](Nc2cccc3c2cc(-c2noc(CNC(=O)c4ccn(C(C)(C)C)c4)n2)n3CC(F)(F)F)[C@H](F)C1] | 1-tert-butyl-N-{[3-(4-{[(3R,4S)-1-ethyl-3-fluoropiperidin-4-yl]amino}-1-(2,2,2-trifluoroethyl)-1H-indol-2-yl)-1,2,4-oxadiazol-5-yl]methyl}-1H-pyrrole-3-carboxamide | 590.2 |

TABLE 9-continued

| Compound No. | Structure | IUPAC | LC-MS (ES+, m/z) |
|---|---|---|---|
| 300B | 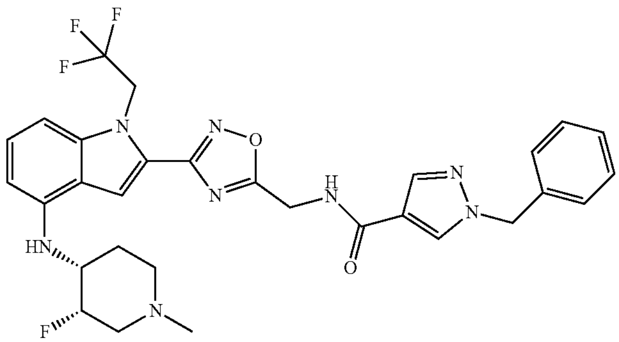 [SMILES: CN1CC[C@@H](Nc2cccc3c2cc(-c2noc(CNC(=O)c4cnn(Cc5ccccc5)c4)n2)n3CC(F)(F)F)[C@@H](F)C1] | 1-benzyl-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-pyrazole-4-carboxamide | 610.9 |
| 301B | 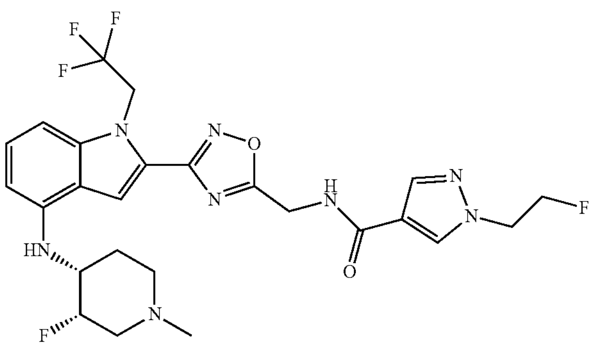 [SMILES: CN1CC[C@@H](Nc2cccc3c2cc(-c2noc(CNC(=O)c4cnn(CCF)c4)n2)n3CC(F)(F)F)[C@@H](F)C1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(2-fluoroethyl)-1H-pyrazole-4-carboxamide | 567.1 |
| 302B | 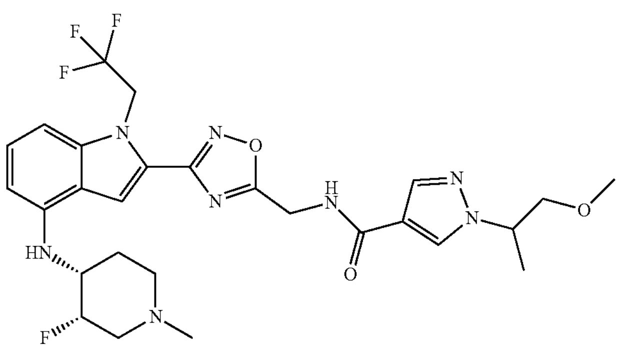 [SMILES: COCC(C)n1cc(C(=O)NCc2nc(-c3cc4c(N[C@@H]5CCN(C)C[C@@H]5F)cccc4n3CC(F)(F)F)no2)cn1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(1-methoxypropan-2-yl)-1H-pyrazole-4-carboxamide | 593.1 |
| 303B | 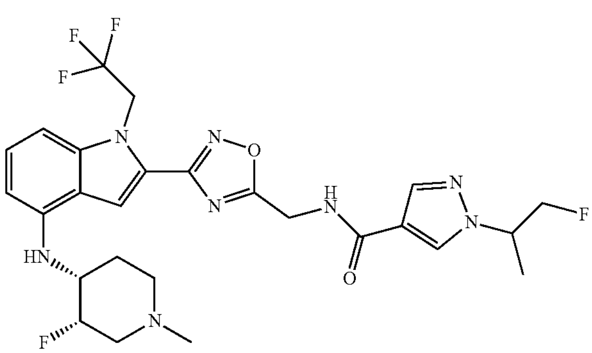 [SMILES: CC(CF)n1cc(C(=O)NCc2nc(-c3cc4c(N[C@@H]5CCN(C)C[C@@H]5F)cccc4n3CC(F)(F)F)no2)cn1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(1-fluoropropan-2-yl)-1H-pyrazole-4-carboxamide | 581.1 |

TABLE 9-continued

| Compound No. | Structure | IUPAC | LC-MS (ES+, m/z) |
|---|---|---|---|
| 304B | 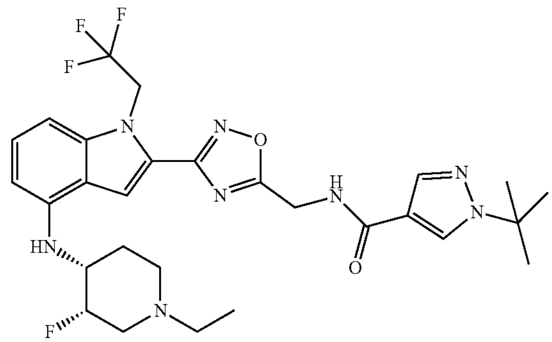 [SMILES: CCN1CC[C@@H](Nc2cccc3c2cc(-c2noc(CNC(=O)c4cnn(C(C)(C)C)c4)n2)n3CC(F)(F)F)[C@@H](F)C1] | 1-tert-butyl-N-{[3-(4-{[(3S,4R)-1-ethyl-3-fluoropiperidin-4-yl]amino}-1-(2,2,2-trifluoroethyl)-1H-indol-2-yl)-1,2,4-oxadiazol-5-yl]methyl}-1H-pyrazole-4-carboxamide | 591.1 |
| 305B | 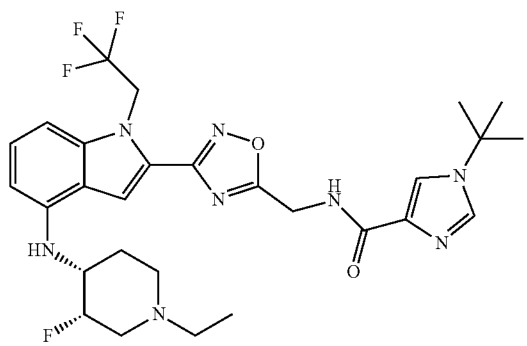 [SMILES: CCN1CC[C@@H](Nc2cccc3c2cc(-c2noc(CNC(=O)c4cn(C(C)(C)C)cn4)n2)n3CC(F)(F)F)[C@@H](F)C1] | 1-tert-butyl-N-{[3-(4-{[(3S,4R)-1-ethyl-3-fluoropiperidin-4-yl]amino}-1-(2,2,2-trifluoroethyl)-1H-indol-2-yl)-1,2,4-oxadiazol-5-yl]methyl}-1H-imidazole-4-carboxamide | 591.1 |
| 306B | 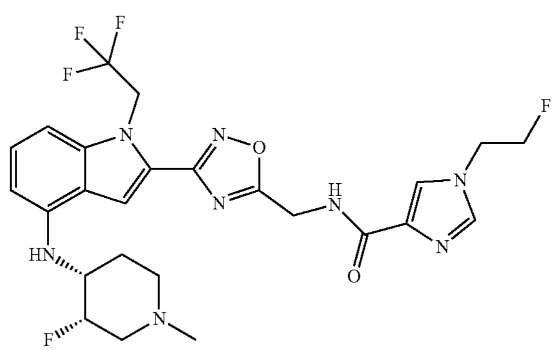 [SMILES: CN1CC[C@@H](Nc2cccc3c2cc(-c2noc(CNC(=O)c4cn(CCF)cn4)n2)n3CC(F)(F)F)[C@@H](F)C1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(2-fluoroethyl)-1H-imidazole-4-carboxamide | 567.1 |
| 307B | 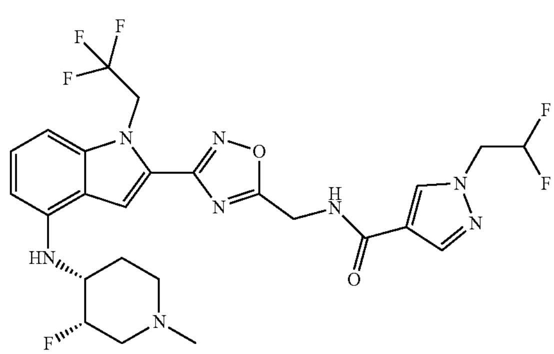 [SMILES: CN1CC[C@@H](Nc2cccc3c2cc(-c2noc(CNC(=O)c4cnn(CC(F)F)c4)n2)n3CC(F)(F)F)[C@@H](F)C1] | 1-(2,2-difluoroethyl)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-pyrazole-4-carboxamide | 585.3 |

TABLE 9-continued

| Compound No. | Structure | IUPAC | LC-MS (ES+, m/z) |
|---|---|---|---|
| 308B | 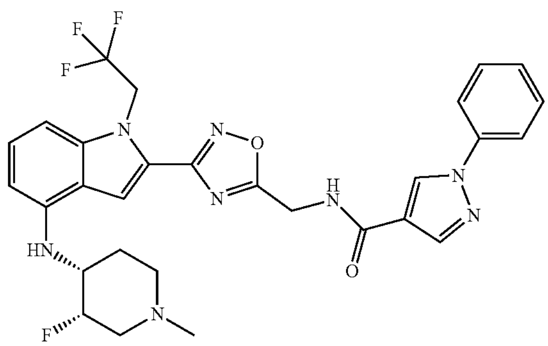 [SMILES: CN1CC[C@@H](Nc2cccc3c2cc(-c2noc(CNC(=O)c4cnn(-c5ccccc5)c4)n2)n3CC(F)(F)F)[C@@H](F)C1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-phenyl-1H-pyrazole-4-carboxamide | 597.1 |
| 309B | 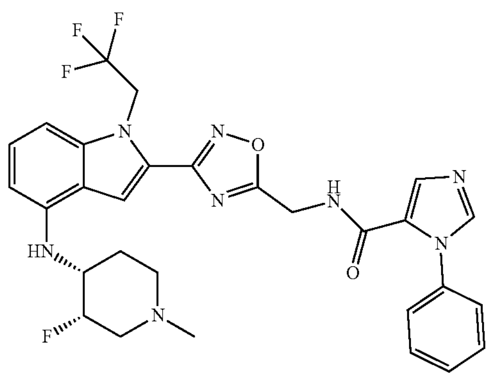 [SMILES: CN1CC[C@@H](Nc2cccc3c2cc(-c2noc(CNC(=O)c4cncn4-c4ccccc4)n2)n3CC(F)(F)F)[C@@H](F)C1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-phenyl-1H-imidazole-5-carboxamide | 597.1 |
| 310B | 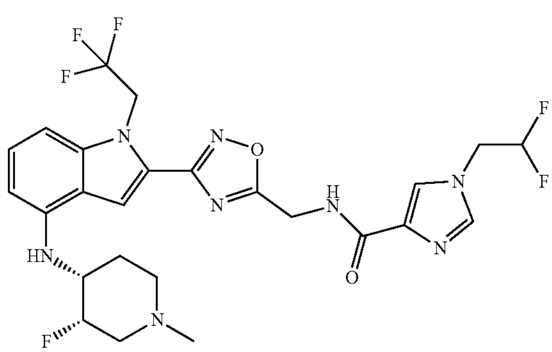 [SMILES: CN1CC[C@@H](Nc2cccc3c2cc(-c2noc(CNC(=O)c4cn(CC(F)F)cn4)n2)n3CC(F)(F)F)[C@@H](F)C1] | 1-(2,2-difluoroethyl)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-imidazole-4-carboxamide | 585.1 |
| 311B | 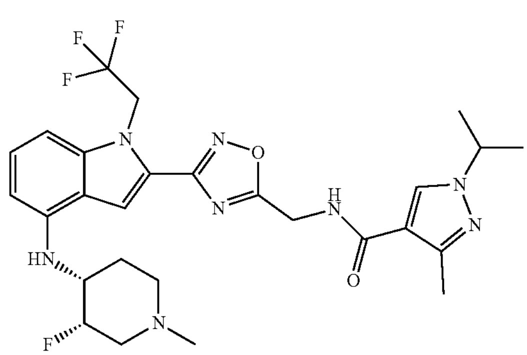 [SMILES: Cc1nn(C(C)C)cc1C(=O)NCc1nc(-c2cc3c(N[C@@H]4CCN(C)C[C@@H]4F)cccc3n2CC(F)(F)F)no1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-3-methyl-1-(propan-2-yl)-1H-pyrazole-4-carboxamide | 577.1 |

TABLE 9-continued

| Compound No. | Structure | IUPAC | LC-MS (ES+, m/z) |
|---|---|---|---|
| 312B | 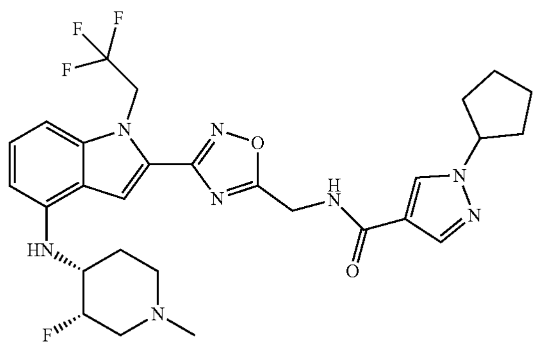 [SMILES: CN1CC[C@@H](Nc2cccc3c2cc(-c2noc(CNC(=O)c4cnn(C5CCCC5)c4)n2)n3CC(F)(F)F)[C@@H](F)C1] | 1-cyclopentyl-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-pyrazole-4-carboxamide | 589.3 |
| 313B | 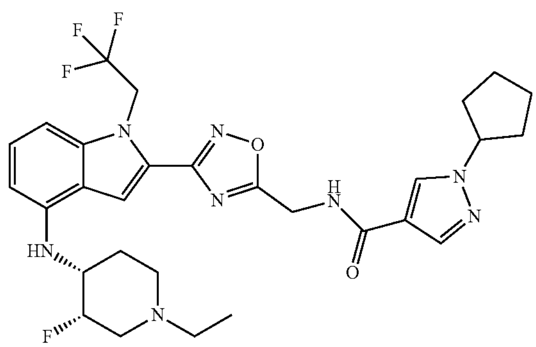 [SMILES: CCN1CC[C@@H](Nc2cccc3c2cc(-c2noc(CNC(=O)c4cnn(C5CCCC5)c4)n2)n3CC(F)(F)F)[C@@H](F)C1] | 1-cyclopentyl-N-{[3-(4-{[(3S,4R)-1-ethyl-3-fluoropiperidin-4-yl]amino}-1-(2,2,2-trifluoroethyl)-1H-indol-2-yl)-1,2,4-oxadiazol-5-yl]methyl}-1H-pyrazole-4-carboxamide | 602.64 |
| 314B | 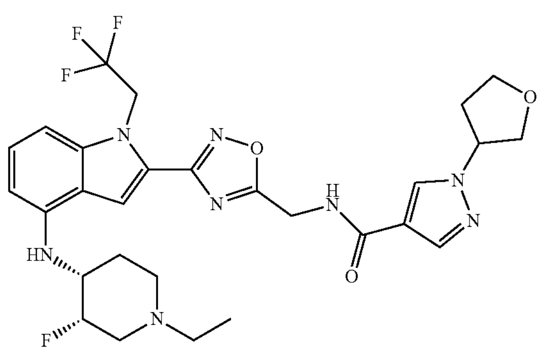 [SMILES: CCN1CC[C@@H](Nc2cccc3c2cc(-c2noc(CNC(=O)c4cnn(C5CCOC5)c4)n2)n3CC(F)(F)F)[C@@H](F)C1] | N-{[3-(4-{[(3S,4R)-1-ethyl-3-fluoropiperidin-4-yl]amino}-1-(2,2,2-trifluoroethyl)-1H-indol-2-yl)-1,2,4-oxadiazol-5-yl]methyl}-1-(oxolan-3-yl)-1H-pyrazole-4-carboxamide | 605.1 |
| 315B | 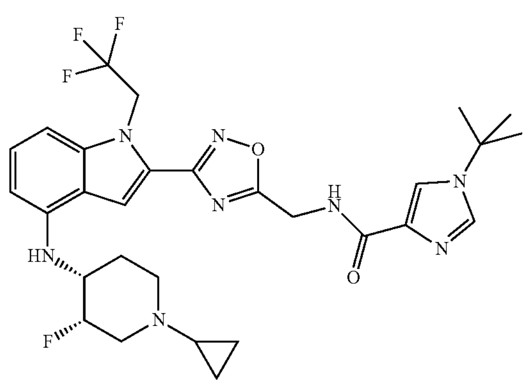 [SMILES: CC(C)(C)n1cnc(C(=O)NCc2nc(-c3cc4c(N[C@@H]5CCN(C6CC6)C[C@@H]5F)cccc4n3CC(F)(F)F)no2)c1] | 1-tert-butyl-N-{[3-(4-{[(3S,4R)-1-cyclopropyl-3-fluoropiperidin-4-yl]amino}-1-(2,2,2-trifluoroethyl)-1H-indol-2-yl)-1,2,4-oxadiazol-5-yl]methyl}-1H-pyrazole-4-carboxamide | 603.1 |

TABLE 9-continued

| Compound No. | Structure | IUPAC | LC-MS (ES+, m/z) |
|---|---|---|---|
| 316B | 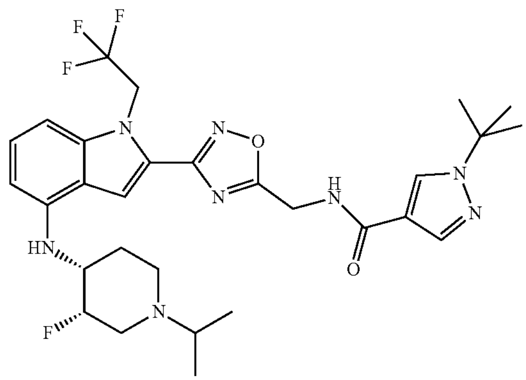 [SMILES: CC(C)N1CC[C@@H](Nc2cccc3c2cc(-c2noc(CNC(=O)c4cnn(C(C)(C)C)c4)n2)n3CC(F)(F)F)[C@@H](F)C1] | 1-tert-butyl-N-{[3-(4-{[(3S,4R)-3-fluoro-1-(propan-2-yl)piperidin-4-yl]amino}-1-(2,2,2-trifluoroethyl)-1H-indol-2-yl)-1,2,4-oxadiazol-5-yl]methyl}-1H-pyrazole-4-carboxamide | 605.1 |
| 317B | 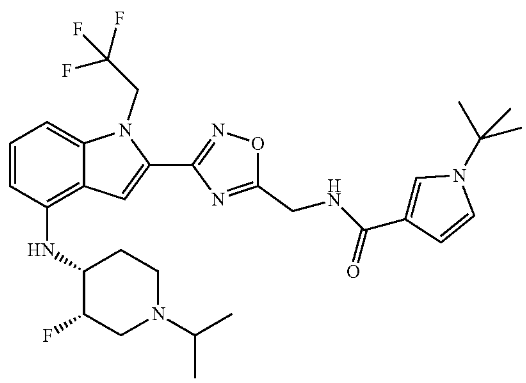 [SMILES: CC(C)N1CC[C@@H](Nc2cccc3c2cc(-c2noc(CNC(=O)c4ccn(C(C)(C)C)c4)n2)n3CC(F)(F)F)[C@@H](F)C1] | 1-tert-butyl-N-{[3-(4-{[(3S,4R)-3-fluoro-1-(propan-2-yl)piperidin-4-yl]amino}-1-(2,2,2-trifluoroethyl)-1H-indol-2-yl)-1,2,4-oxadiazol-5-yl]methyl}-1H-pyrrole-3-carboxamide | 604.2 |
| 318B | 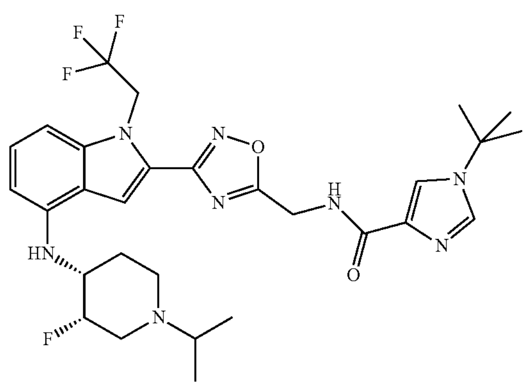 [SMILES: CC(C)N1CC[C@@H](Nc2cccc3c2cc(-c2noc(CNC(=O)c4cn(C(C)(C)C)cn4)n2)n3CC(F)(F)F)[C@@H](F)C1] | 1-tert-butyl-N-{[3-(4-{[(3S,4R)-3-fluoro-1-(propan-2-yl)piperidin-4-yl]amino}-1-(2,2,2-trifluoroethyl)-1H-indol-2-yl)-1,2,4-oxadiazol-5-yl]methyl}-1H-imidazole-4-carboxamide | 605.2 |
| 319B | 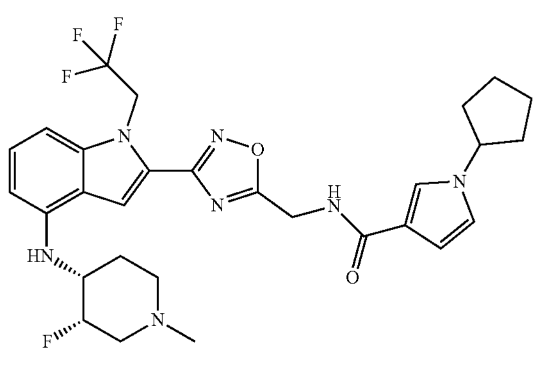 [SMILES: CN1CC[C@@H](Nc2cccc3c2cc(-c2noc(CNC(=O)c4ccn(C5CCCC5)c4)n2)n3CC(F)(F)F)[C@@H](F)C1] | 1-cyclopentyl-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-pyrrole-3-carboxamide | 588.2 |

TABLE 9-continued

| Compound No. | Structure | IUPAC | LC-MS (ES+, m/z) |
|---|---|---|---|
| 320B | 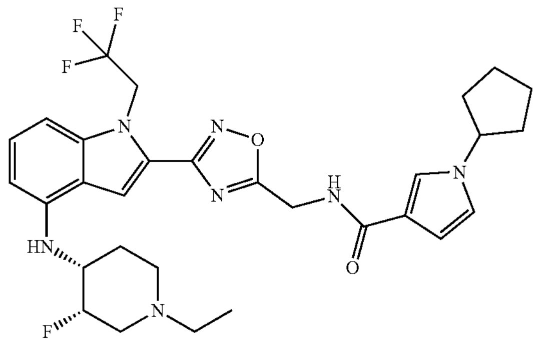 [SMILES: CCN1CC[C@@H](Nc2cccc3c2cc(-c2noc(CNC(=O)c4ccn(C5CCCC5)c4)n2)n3CC(F)(F)F)[C@@H](F)C1] | 1-cyclopentyl-N-{[3-(4-{[(3S,4R)-1-ethyl-3-fluoropiperidin-4-yl]amino}-1-(2,2,2-trifluoroethyl)-1H-indol-2-yl)-1,2,4-oxadiazol-5-yl]methyl}-1H-pyrrole-3-carboxamide | 602.2 |
| 321B | 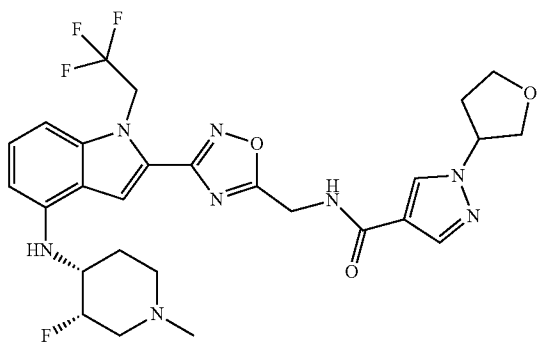 [SMILES: CN1CC[C@@H](Nc2cccc3c2cc(-c2noc(CNC(=O)c4cnn(C5CCOC5)c4)n2)n3CC(F)(F)F)[C@@H](F)C1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(oxolan-3-yl)-1H-pyrazole-4-carboxamide | 591.1 |
| 322B | 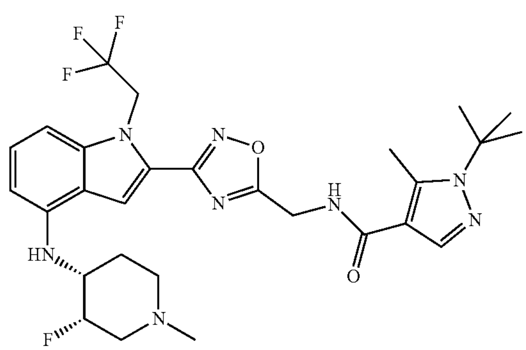 [SMILES: Cc1c(C(=O)NCc2nc(-c3cc4c(N[C@@H]5CCN(C)C[C@@H]5F)cccc4n3CC(F)(F)F)no2)cnn1C(C)(C)C] | 1-tert-butyl-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-5-methyl-1H-pyrazole-4-carboxamide | 591.1 |
| 323B | 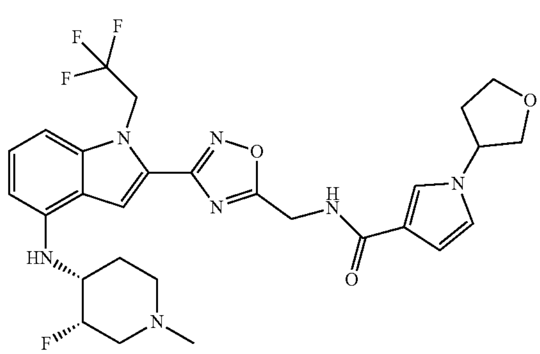 [SMILES: CN1CC[C@@H](Nc2cccc3c2cc(-c2noc(CNC(=O)c4ccn(C5CCOC5)c4)n2)n3CC(F)(F)F)[C@@H](F)C1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(oxolan-3-yl)-1H-pyrrole-3-carboxamide | 590.1 |

TABLE 9-continued

| Compound No. | Structure | IUPAC | LC-MS (ES+, m/z) |
|---|---|---|---|
| 324B | 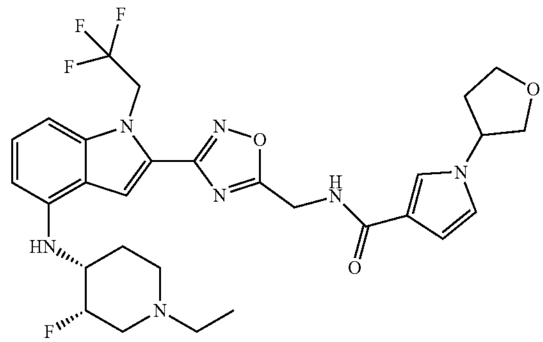 [SMILES: CCN1CC[C@@H](Nc2cccc3c2cc(-c2noc(CNC(=O)c4ccn(C5CCOC5)c4)n2)n3CC(F)(F)F)[C@@H](F)C1] | N-{[3-(4-{[(3S,4R)-1-ethyl-3-fluoropiperidin-4-yl]amino}-1-(2,2,2-trifluoroethyl)-1H-indol-2-yl)-1,2,4-oxadiazol-5-yl]methyl}-1-(oxolan-3-yl)-1H-pyrrole-3-carboxamide | 604.3 |
| 325B | 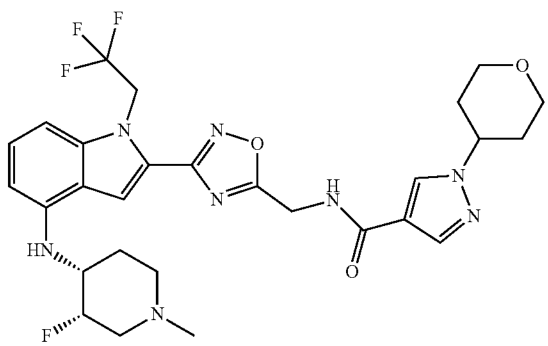 [SMILES: CN1CC[C@@H](Nc2cccc3c2cc(-c2noc(CNC(=O)c4cnn(C5CCOCC5)c4)n2)n3CC(F)(F)F)[C@@H](F)C1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(oxan-4-yl)-1H-pyrazole-4-carboxamide | 605.1 |
| 326B | 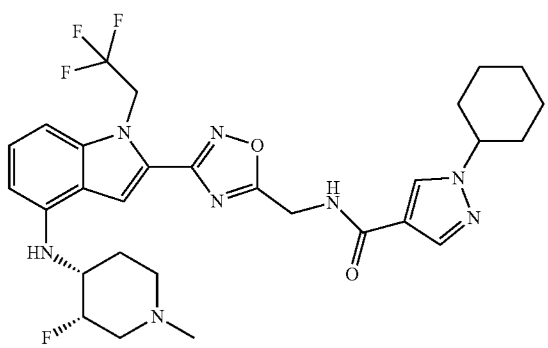 [SMILES: CN1CC[C@@H](Nc2cccc3c2cc(-c2noc(CNC(=O)c4cnn(C5CCCCC5)c4)n2)n3CC(F)(F)F)[C@@H](F)C1] | 1-cyclohexyl-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-pyrazole-4-carboxamide | 603.1 |
| 327B | 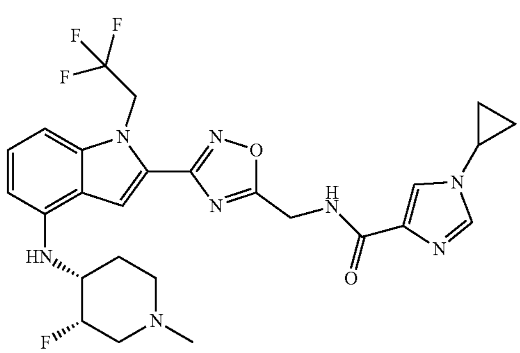 [SMILES: CN1CC[C@@H](Nc2cccc3c2cc(-c2noc(CNC(=O)c4cn(C5CC5)cn4)n2)n3CC(F)(F)F)[C@@H](F)C1] | 1-cyclopropyl-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-imidazole-4-carboxamide | 561.1 |

TABLE 9-continued

| Compound No. | Structure | IUPAC | LC-MS (ES+, m/z) |
|---|---|---|---|
| 328B | 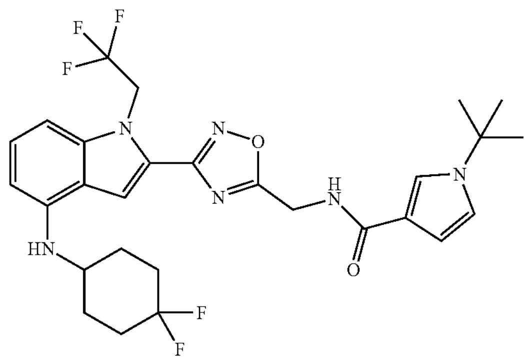 [SMILES: CC(C)(C)n1ccc(C(=O)NCc2nc(-c3cc4c(NC5CCC(F)(F)CC5)cccc4n3CC(F)(F)F)no2)c1] | 1-tert-butyl-N-[(3-{4-[(4,4-difluorocyclohexyl)amino]-1-(2,2,2-trifluoroethyl)-1H-indol-2-yl}-1,2,4-oxadiazol-5-yl)methyl]-1H-pyrrole-3-carboxamide | 579.1 |
| 329B | 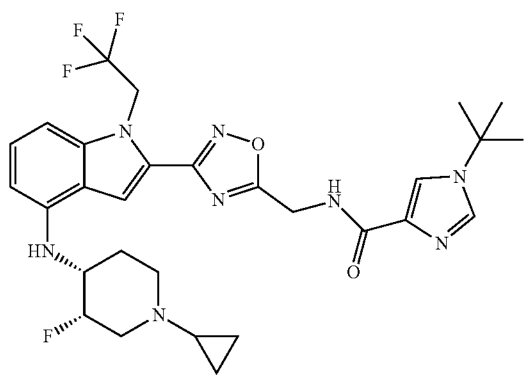 [SMILES: CC(C)(C)n1cnc(C(=O)NCc2nc(-c3cc4c(N[C@@H]5CCN(C6CC6)C[C@@H]5F)cccc4n3CC(F)(F)F)no2)c1] | 1-tert-butyl-N-{[3-(4-{[(3S,4R)-1-cyclopropyl-3-fluoropiperidin-4-yl]amino}-1-(2,2,2-trifluoroethyl)-1H-indol-2-yl)-1,2,4-oxadiazol-5-yl]methyl}-1H-imidazole-4-carboxamide | 603.4 |
| 330B | 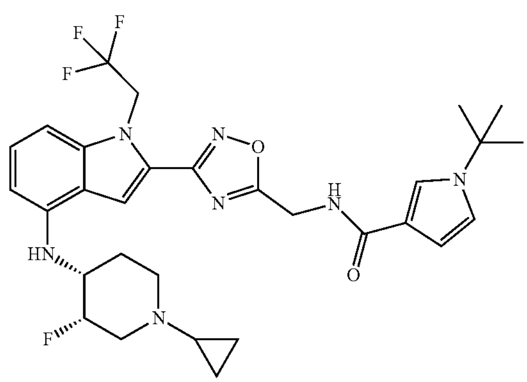 [SMILES: CC(C)(C)n1ccc(C(=O)NCc2nc(-c3cc4c(N[C@@H]5CCN(C6CC6)C[C@@H]5F)cccc4n3CC(F)(F)F)no2)c1] | 1-tert-butyl-N-{[3-(4-{[(3S,4R)-1-cyclopropyl-3-fluoropiperidin-4-yl]amino}-1-(2,2,2-trifluoroethyl)-1H-indol-2-yl)-1,2,4-oxadiazol-5-yl]methyl}-1H-pyrrole-3-carboxamide | 602.2 |
| 331B | 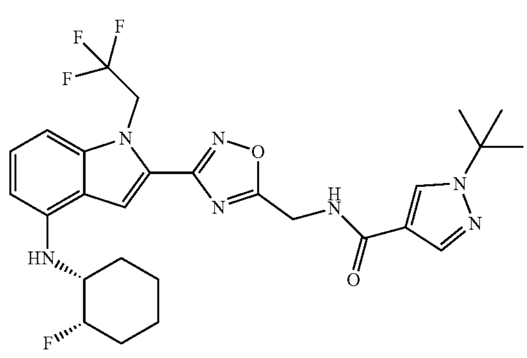 [SMILES: CC(C)(C)n1cc(C(=O)NCc2nc(-c3cc4c(N[C@@H]5CCCC[C@@H]5F)cccc4n3CC(F)(F)F)no2)cn1] | 1-tert-butyl-N-{[3-(4-{[(1R,2S)-2-fluorocyclohexyl]amino}-1-(2,2,2-trifluoroethyl)-1H-indol-2-yl)-1,2,4-oxadiazol-5-yl]methyl}-1H-pyrazole-4-carboxamide | 562.2 |

TABLE 9-continued

| Compound No. | Structure | IUPAC | LC-MS (ES+, m/z) |
|---|---|---|---|
| 332B | 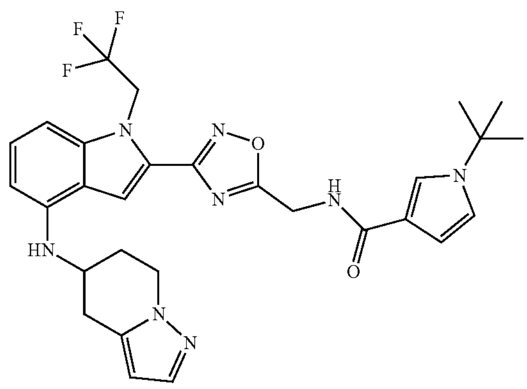 [SMILES: CC(C)(C)n1ccc(C(=O)NCc2nc(-c3cc4c(NC5CCn6nccc6C5)cccc4n3CC(F)(F)F)no2)c1] | 1-tert-butyl-N-({3-[4-({4H,5H,6H,7H-pyrazolo[1,5-a]pyridin-5-yl}amino)-1-(2,2,2-trifluoroethyl)-1H-indol-2-yl]-1,2,4-oxadiazol-5-yl}methyl)-1H-pyrrole-3-carboxamide | 581.3 |
| 333B | 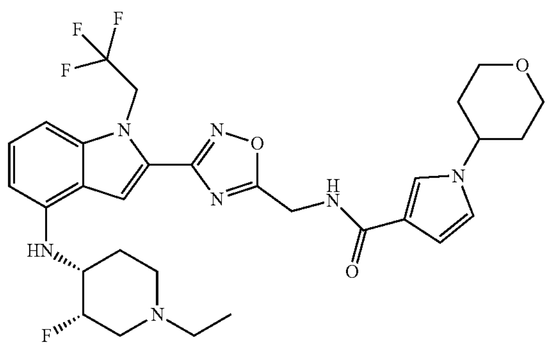 [SMILES: CCN1CC[C@@H](Nc2cccc3c2cc(-c2noc(CNC(=O)c4ccn(C5CCOCC5)c4)n2)n3CC(F)(F)F)[C@@H](F)C1] | N-{[3-(4-{[(3S,4R)-1-ethyl-3-fluoropiperidin-4-yl]amino}-1-(2,2,2-trifluoroethyl)-1H-indol-2-yl)-1,2,4-oxadiazol-5-yl]methyl}-1-(oxan-4-yl)-1H-pyrrole-3-carboxamide | 618.1 |
| 334B | 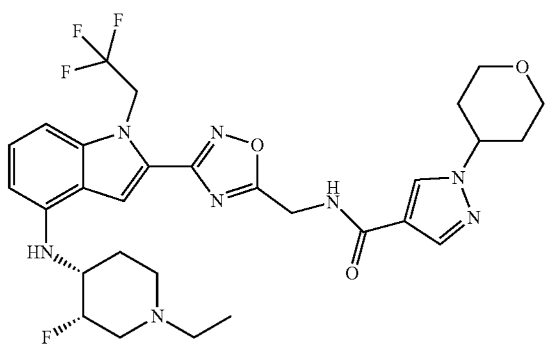 [SMILES: CCN1CC[C@@H](Nc2cccc3c2cc(-c2noc(CNC(=O)c4cnn(C5CCOCC5)c4)n2)n3CC(F)(F)F)[C@@H](F)C1] | N-{[3-(4-{[(3S,4R)-1-ethyl-3-fluoropiperidin-4-yl]amino}-1-(2,2,2-trifluoroethyl)-1H-indol-2-yl)-1,2,4-oxadiazol-5-yl]methyl}-1-(oxan-4-yl)-1H-pyrazole-4-carboxamide | 619.1 |
| 335B | 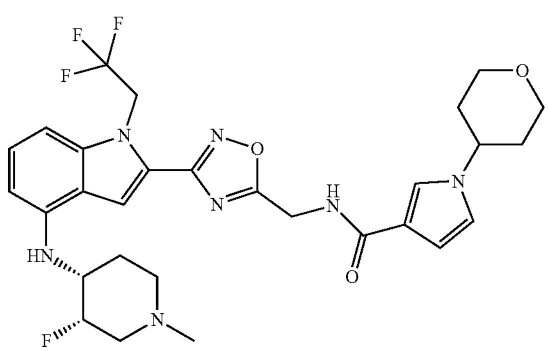 [SMILES: CN1CC[C@@H](Nc2cccc3c2cc(-c2noc(CNC(=O)c4ccn(C5CCOCC5)c4)n2)n3CC(F)(F)F)[C@@H](F)C1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(oxan-4-yl)-1H-pyrrole-3-carboxamide | 604.1 |

TABLE 9-continued

| Compound No. | Structure | IUPAC | LC-MS (ES+, m/z) |
|---|---|---|---|
| 336B | 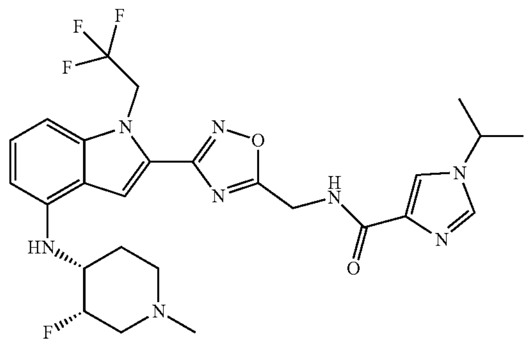 [SMILES: CC(C)n1cnc(C(=O)NCc2nc(-c3cc4c(N[C@@H]5CCN(C)C[C@@H]5F)cccc4n3CC(F)(F)F)no2)c1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(propan-2-yl)-1H-imidazole-2-carboxamide | 563.1 |
| 337B | 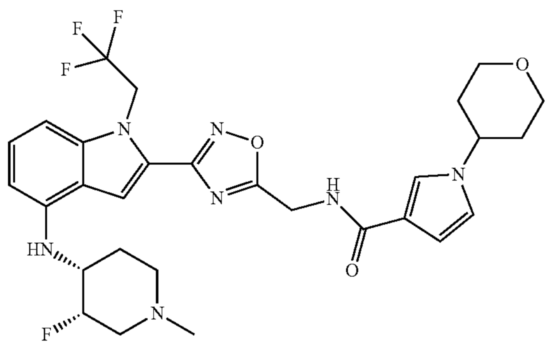 [SMILES: CN1CC[C@@H](Nc2cccc3c2cc(-c2noc(CNC(=O)c4ccn(C5CCOCC5)c4)n2)n3CC(F)(F)F)[C@@H](F)C1] | 1-tert-butyl-N-{[3-(4-{[(3S,4R)-3-fluoro-1-(2-methoxyethyl)piperidin-4-yl]amino}-1-(2,2,2-trifluoroethyl)-1H-indol-2-yl)-1,2,4-oxadiazol-5-yl]methyl}-1H-pyrrole-3-carboxamide | 620.2 |
| 338B | 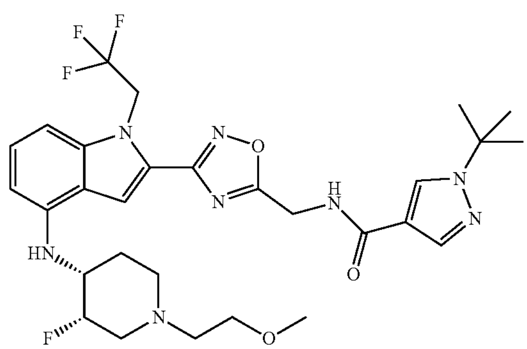 [SMILES: COCCN1CC[C@@H](Nc2cccc3c2cc(-c2noc(CNC(=O)c4cnn(C(C)(C)C)c4)n2)n3CC(F)(F)F)[C@@H](F)C1] | 1-tert-butyl-N-{[3-(4-{[(3S,4R)-3-fluoro-1-(2-methoxyethyl)piperidin-4-yl]amino}-1-(2,2,2-trifluoroethyl)-1H-indol-2-yl)-1,2,4-oxadiazol-5-yl]methyl}-1H-pyrazole-4-carboxamide | 621.3 |
| 339B | 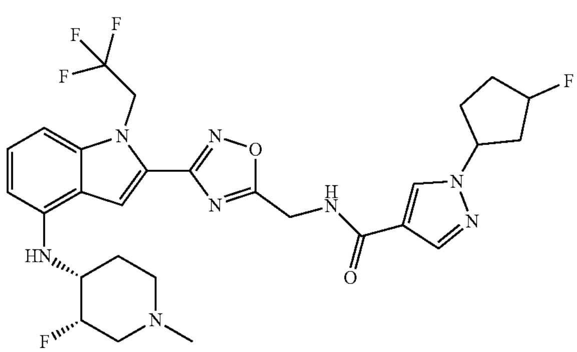 [SMILES: CN1CC[C@@H](Nc2cccc3c2cc(-c2noc(CNC(=O)c4cnn(C5CCC(F)C5)c4)n2)n3CC(F)(F)F)[C@@H](F)C1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(3-fluorocyclopentyl)-1H-pyrazole-4-carboxamide | 607.1 |

TABLE 9-continued

| Compound No. | Structure | IUPAC | LC-MS (ES+, m/z) |
|---|---|---|---|
| 340B | 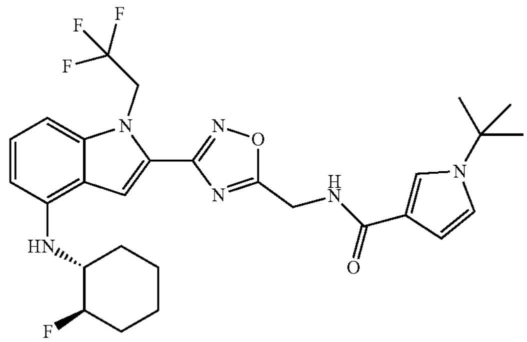 [SMILES: CC(C)(C)n1ccc(C(=O)NCc2nc(-c3cc4c(N[C@@H]5CCCC[C@H]5F)cccc4n3CC(F)(F)F)no2)c1] | 1-tert-butyl-N-{[3-(4-{[(1S,2S)-2-fluorocyclohexyl]amino}-1-(2,2,2-trifluoroethyl)-1H-indol-2-yl)-1,2,4-oxadiazol-5-yl]methyl}-1H-pyrrole-3-carboxamide | 561.1 |
| 341B | 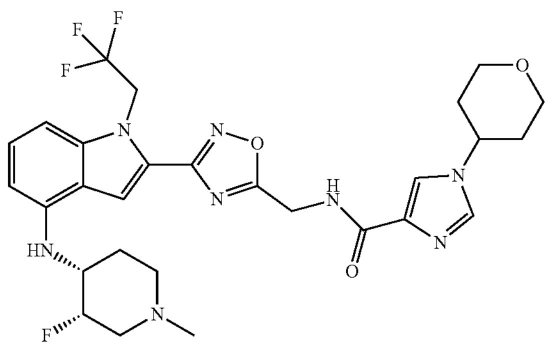 [SMILES: CN1CC[C@@H](Nc2cccc3c2cc(-c2noc(CNC(=O)c4cn(C5CCOCC5)cn4)n2)n3CC(F)(F)F)[C@@H](F)C1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(oxan-4-yl)-1H-imidazole-4-carboxamide | 604.6 |
| 342B | 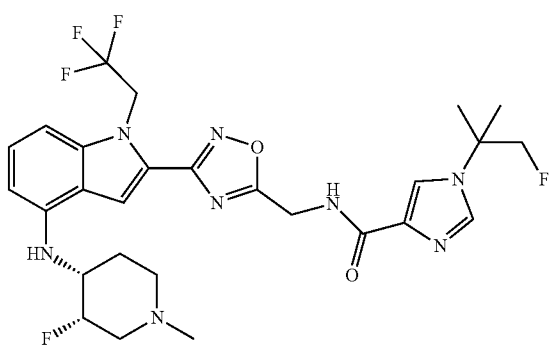 [SMILES: CN1CC[C@@H](Nc2cccc3c2cc(-c2noc(CNC(=O)c4cn(C(C)(C)CF)cn4)n2)n3CC(F)(F)F)[C@@H](F)C1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(1-fluoro-2-methylpropan-2-yl)-1H-imidazole-4-carboxamide | 595.2 |
| 343B | 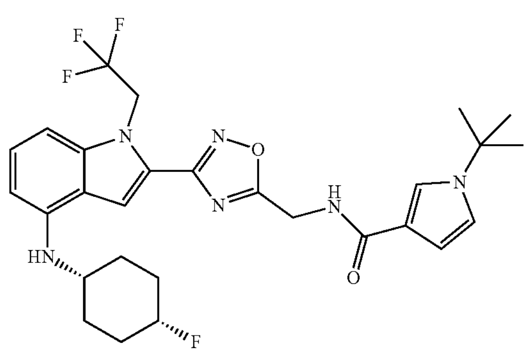 [SMILES: CC(C)(C)n1ccc(C(=O)NCc2nc(-c3cc4c(N[C@H]5CC[C@@H](F)CC5)cccc4n3CC(F)(F)F)no2)c1] | 1-tert-butyl-N-{[3-(4-{[(1s,4s)-4-fluorocyclohexyl]amino}-1-(2,2,2-trifluoroethyl)-1H-indol-2-yl)-1,2,4-oxadiazol-5-yl]methyl}-1H-pyrrole-3-carboxamide | 561.3 |

TABLE 9-continued

| Compound No. | Structure | IUPAC | LC-MS (ES+, m/z) |
|---|---|---|---|
| 344B | 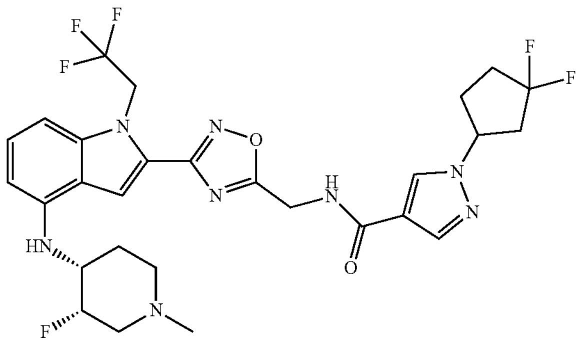 [SMILES: CN1CC[C@@H](Nc2cccc3c2cc(-c2noc(CNC(=O)c4cnn(C5CCC(F)(F)C5)c4)n2)n3CC(F)(F)F)[C@@H](F)C1] | 1-(3,3-difluorocyclopentyl)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-pyrazole-4-carboxamide | 625.1 |
| 345B | 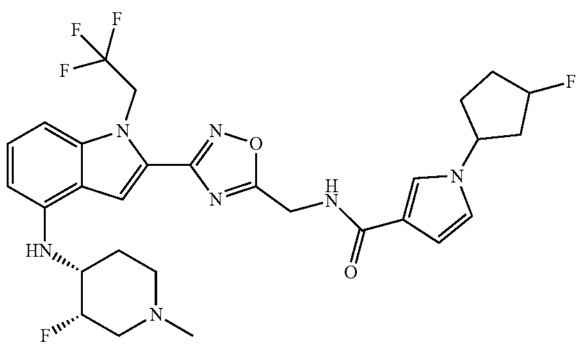 [SMILES: CN1CC[C@@H](Nc2cccc3c2cc(-c2noc(CNC(=O)c4ccn(C5CCC(F)C5)c4)n2)n3CC(F)(F)F)[C@@H](F)C1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(3-fluorocyclopentyl)-1H-pyrrole-3-carboxamide | 606.3 |
| 346B | 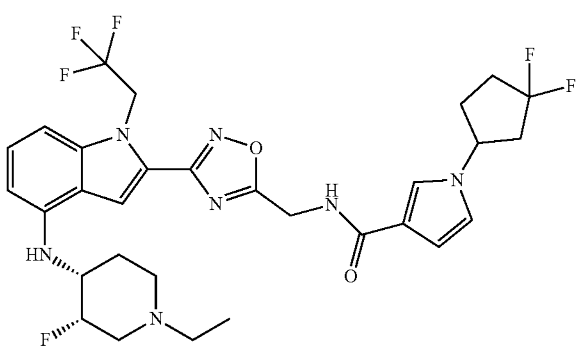 [SMILES: CCN1CC[C@@H](Nc2cccc3c2cc(-c2noc(CNC(=O)c4ccn(C5CCC(F)(F)C5)c4)n2)n3CC(F)(F)F)[C@@H](F)C1] | 1-(3,3-difluorocyclopentyl)-N-{[3-(4-{[(3S,4R)-1-ethyl-3-fluoropiperidin-4-yl]amino}-1-(2,2,2-trifluoroethyl)-1H-indol-2-yl)-1,2,4-oxadiazol-5-yl]methyl}-1H-pyrrole-3-carboxamide | 638.3 |
| 347B | 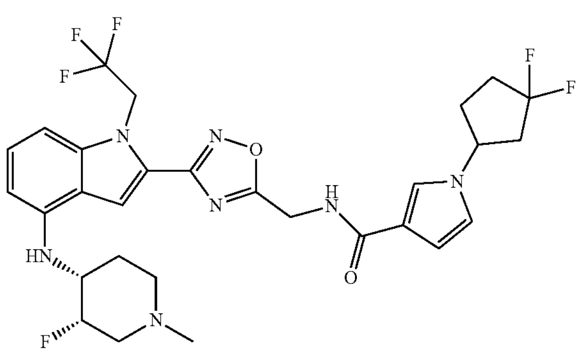 [SMILES: CN1CC[C@@H](Nc2cccc3c2cc(-c2noc(CNC(=O)c4ccn(C5CCC(F)(F)C5)c4)n2)n3CC(F)(F)F)[C@@H](F)C1] | 1-(3,3-difluorocyclopentyl)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-pyrrole-3-carboxamide | 624.3 |

TABLE 9-continued

| Compound No. | Structure | IUPAC | LC-MS (ES+, m/z) |
|---|---|---|---|
| 348B | 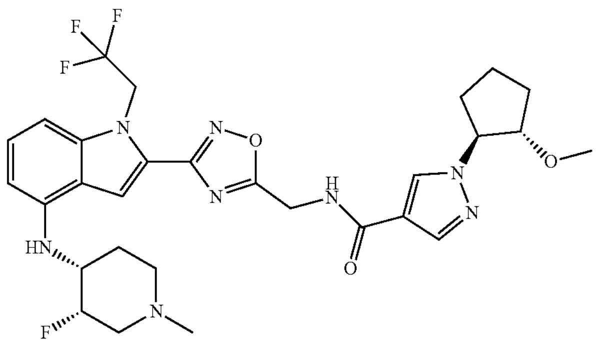 [SMILES: CO[C@H]1CCC[C@@H]1n1cc(C(=O)NCc2nc(-c3cc4c(N[C@@H]5CCN(C)C[C@@H]5F)cccc4n3CC(F)(F)F)no2)cn1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-[(1R,2R)-2-methoxycyclopentyl]-1H-pyrazole-4-carboxamide | 619.3 |
| 349B | 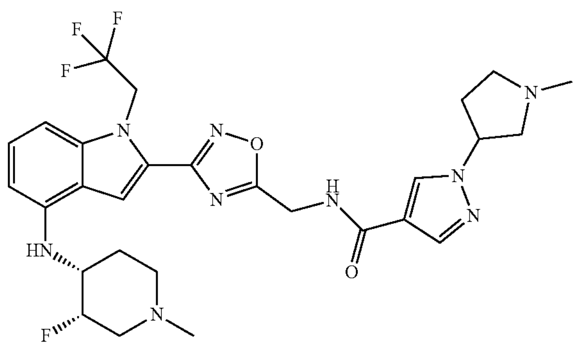 [SMILES: CN1CCC(n2cc(C(=O)NCc3nc(-c4cc5c(N[C@@H]6CCN(C)C[C@@H]6F)cccc5n4CC(F)(F)F)no3)cn2)C1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(1-methylpyrrolidin-3-yl)-1H-pyrazole-4-carboxamide | 604.1 |
| 350B | 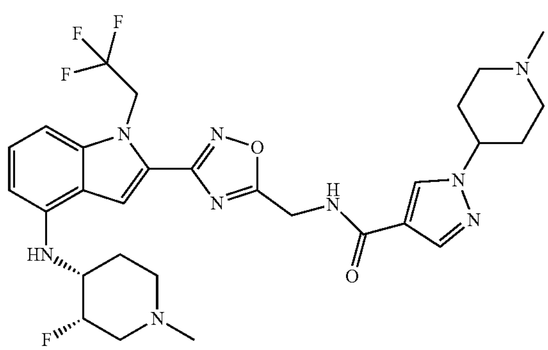 [SMILES: CN1CCC(n2cc(C(=O)NCc3nc(-c4cc5c(N[C@@H]6CCN(C)C[C@@H]6F)cccc5n4CC(F)(F)F)no3)cn2)CC1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(1-methylpiperidin-4-yl)-1H-pyrazole-4-carboxamide | 618.3 |
| 351B | 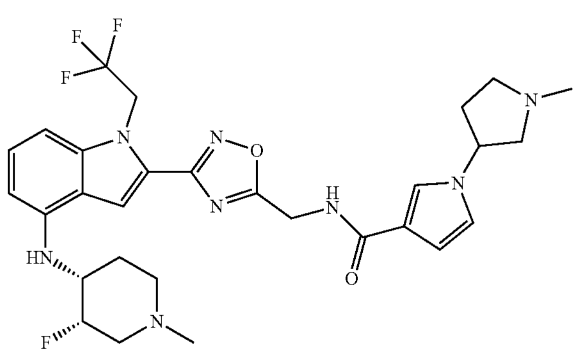 [SMILES: CN1CCC(n2ccc(C(=O)NCc3nc(-c4cc5c(N[C@@H]6CCN(C)C[C@@H]6F)cccc5n4CC(F)(F)F)no3)c2)C1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(1-methylpyrrolidin-3-yl)-1H-pyrrole-3-carboxamide | 603.4 |

TABLE 9-continued

| Compound No. | Structure | IUPAC | LC-MS (ES+, m/z) |
|---|---|---|---|
| 352B | 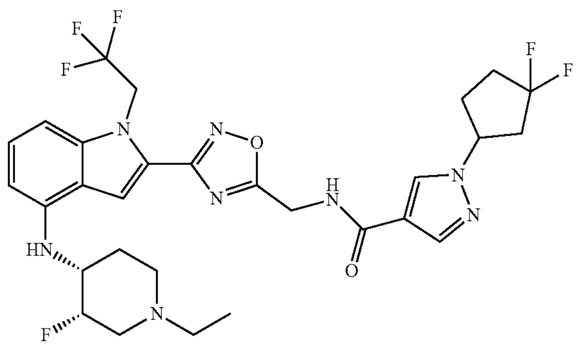 [SMILES: CCN1CC[C@@H](Nc2cccc3c2cc(-c2noc(CNC(=O)c4cnn(C5CCC(F)(F)C5)c4)n2)n3CC(F)(F)F)[C@@H](F)C1] | 1-(3,3-difluorocyclopentyl)-N-{[3-(4-{[(3S,4R)-1-ethyl-3-fluoropiperidin-4-yl]amino}-1-(2,2,2-trifluoroethyl)-1H-indol-2-yl)-1,2,4-oxadiazol-5-yl]methyl}-1H-pyrazole-4-carboxamide | 639.1 |
| 353B | 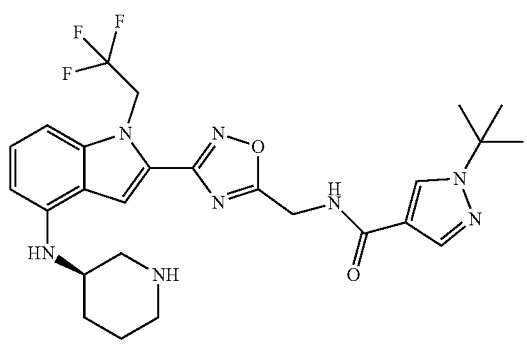 [SMILES: CC(C)(C)n1cc(C(=O)NCc2nc(-c3cc4c(N[C@@H]5CCCNC5)cccc4n3CC(F)(F)F)no2)cn1] | 1-tert-butyl-N-{[3-(4-{[(3S)-piperidin-3-yl]amino}-1-(2,2,2-trifluoroethyl)-1H-indol-2-yl)-1,2,4-oxadiazol-5-yl]methyl}-1H-pyrazole-4-carboxamide | 545.2 |
| 354B | 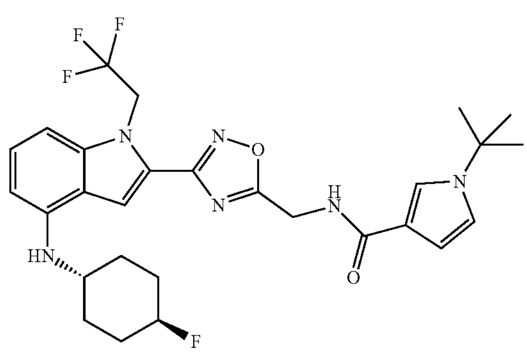 [SMILES: CC(C)(C)n1ccc(C(=O)NCc2nc(-c3cc4c(N[C@H]5CC[C@H](F)CC5)cccc4n3CC(F)(F)F)no2)c1] | 1-tert-butyl-N-{[3-(4-{[(1r,4r)-4-fluorocyclohexyl]amino}-1-(2,2,2-trifluoroethyl)-1H-indol-2-yl)-1,2,4-oxadiazol-5-yl]methyl}-1H-pyrrole-3-carboxamide | 561.3 |
| 355B | 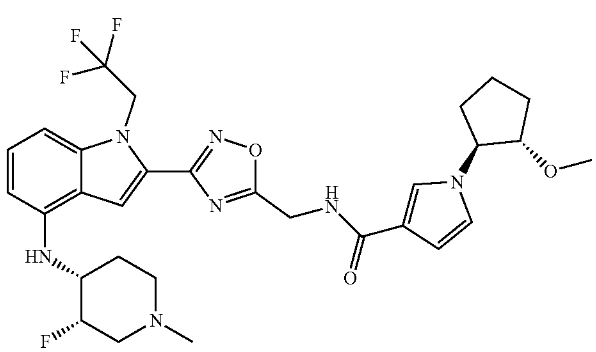 [SMILES: CO[C@H]1CCC[C@@H]1n1ccc(C(=O)NCc2nc(-c3cc4c(N[C@@H]5CCN(C)C[C@@H]5F)cccc4n3CC(F)(F)F)no2)c1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-[(1R,2R)-2-methoxycyclopentyl]-1H-pyrrole-3-carboxamide | 618.3 |

TABLE 9-continued

| Compound No. | Structure | IUPAC | LC-MS (ES+, m/z) |
|---|---|---|---|
| 356B | 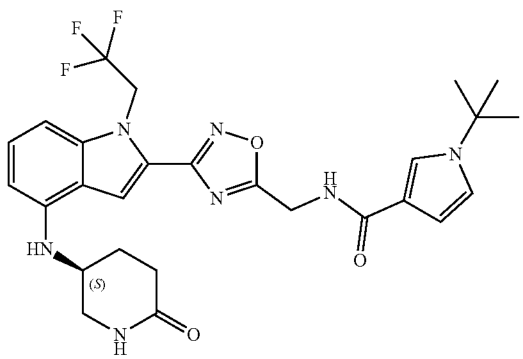 | 1-tert-butyl-N-{[3-(4-{[(3S)-6-oxopiperidin-3-yl]amino}-1-(2,2,2-trifluoroethyl)-1H-indol-2-yl)-1,2,4-oxadiazol-5-yl]methyl}-1H-pyrrole-3-carboxamide | 558.2 |
| 357B | 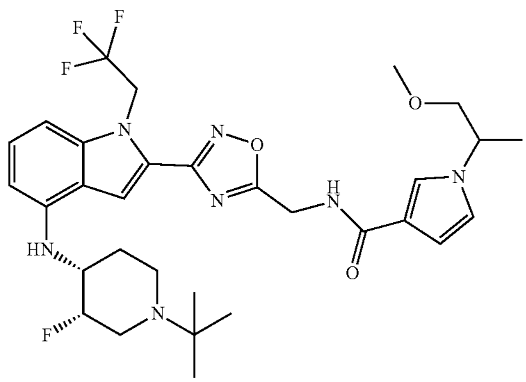 [SMILES: COCC(C)n1ccc(C(=O)NCc2nc(-c3cc4c(N[C@@H]5CCN(C(C)(C)C)C[C@@H]5F)cccc4n3CC(F)(F)F)no2)c1] | rac-N-{[3-(4-{[(3R,4S)-1-tert-butyl-3-fluoropiperidin-4-yl]amino}-1-(2,2,2-trifluoroethyl)-1H-indol-2-yl)-1,2,4-oxadiazol-5-yl]methyl}-1-(1-methoxypropan-2-yl)-1H-pyrrole-3-carboxamide | 634.4 |
| 358B | 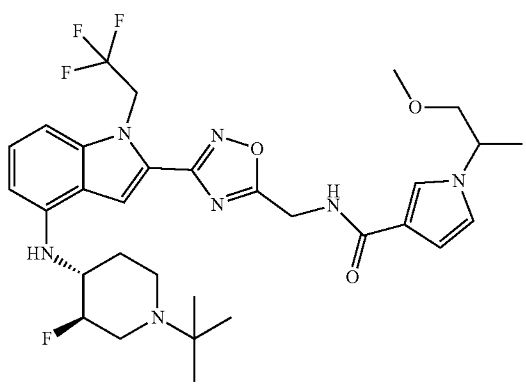 [SMILES: COCC(C)n1ccc(C(=O)NCc2nc(-c3cc4c(N[C@@H]5CCN(C(C)(C)C)C[C@H]5F)cccc4n3CC(F)(F)F)no2)c1] | rac-N-{[3-(4-{[(3R,4R)-1-tert-butyl-3-fluoropiperidin-4-yl]amino}-1-(2,2,2-trifluoroethyl)-1H-indol-2-yl)-1,2,4-oxadiazol-5-yl]methyl}-1-(1-methoxypropan-2-yl)-1H-pyrrole-3-carboxamide | 634.4 |
| 359B | 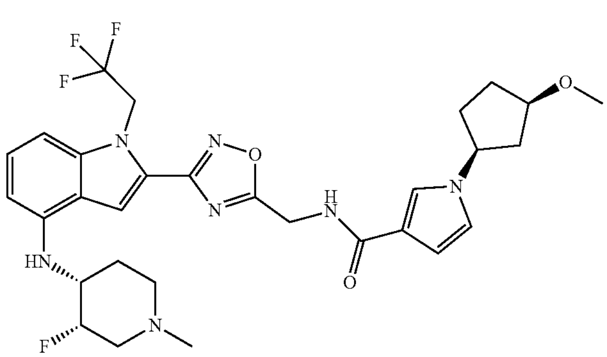 [SMILES: CO[C@@H]1CC[C@H](n2ccc(C(=O)NCc3nc(-c4cc5c(N[C@@H]6CCN(C)C[C@@H]6F)cccc5n4CC(F)(F)F)no3)c2)C1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-[(1R,3S)-3-methoxycyclopentyl]-1H-pyrrole-3-carboxamide | 618.3 |

TABLE 9-continued

| Compound No. | Structure | IUPAC | LC-MS (ES+, m/z) |
|---|---|---|---|
| 360B | 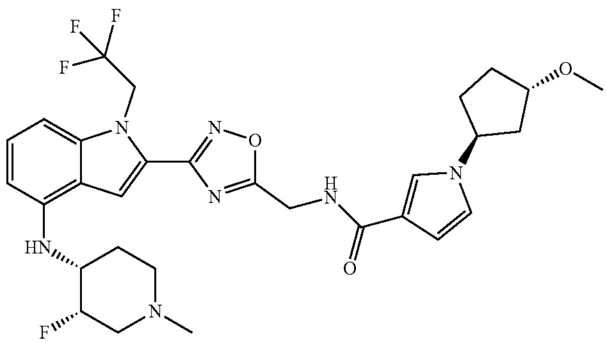 [SMILES: CO[C@H]1CC[C@H](n2ccc(C(=O)NCc3nc(-c4cc5c(N[C@@H]6CCN(C)C[C@@H]6F)cccc5n4CC(F)(F)F)no3)c2)C1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-[(1R,3R)-3-methoxycyclopentyl]-1H-pyrrole-3-carboxamide | 618.3 |
| 361B | 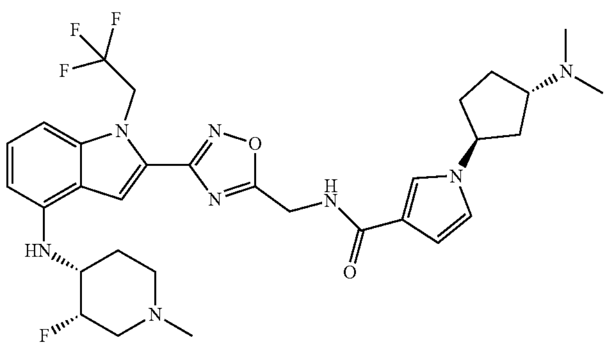 [SMILES: CN1CC[C@@H](Nc2cccc3c2cc(-c2noc(CNC(=O)c4ccn([C@H]5CC[C@H](N(C)C)C5)c4)n2)n3CC(F)(F)F)[C@@H](F)C1] | 1-[(1R,3R)-3-(dimethylamino)cyclopentyl]-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-pyrrole-3-carboxamide | 631.4 |
| 362B | 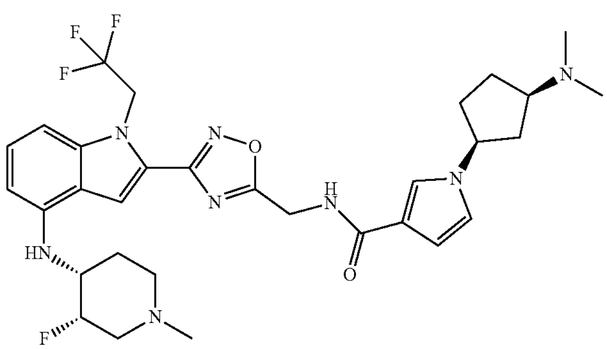 [SMILES: CN1CC[C@@H](Nc2cccc3c2cc(-c2noc(CNC(=O)c4ccn([C@H]5CC[C@@H](N(C)C)C5)c4)n2)n3CC(F)(F)F)[C@@H](F)C1] | 1-[(1R,3S)-3-(dimethylamino)cyclopentyl]-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-pyrrole-3-carboxamide | 631.3 |
| 363B | 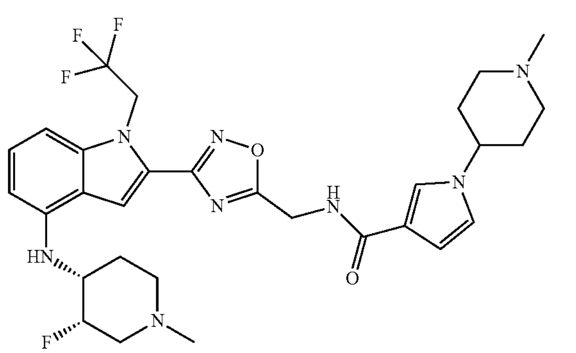 [SMILES: CN1CCC(n2ccc(C(=O)NCc3nc(-c4cc5c(N[C@@H]6CCN(C)C[C@@H]6F)cccc5n4CC(F)(F)F)no3)c2)CC1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(1-methylpiperidin-4-yl)-1H-pyrrole-3-carboxamide | 617.3 |

TABLE 9-continued

| Compound No. | Structure | IUPAC | LC-MS (ES+, m/z) |
|---|---|---|---|
| 364B | 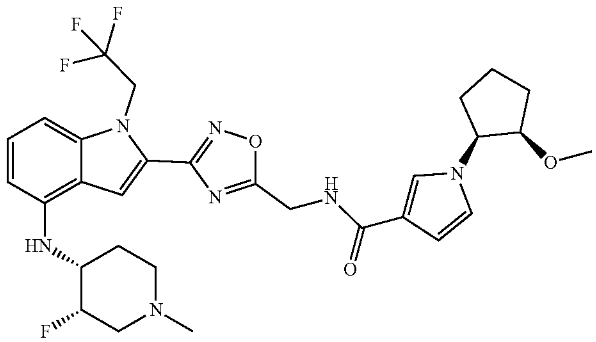 [SMILES: CO[C@@H]1CCC[C@@H]1n1ccc(C(=O)NCc2nc(-c3cc4c(N[C@@H]5CCN(C)C[C@@H]5F)cccc4n3CC(F)(F)F)no2)c1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-[(1R,2S)-2-methoxycyclopentyl]-1H-pyrrole-3-carboxamide | 618.4 |
| 365B | 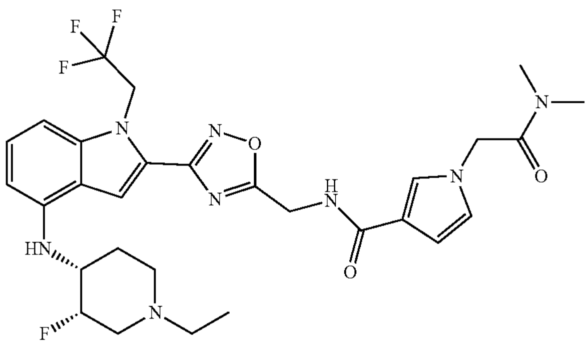 [SMILES: CCN1CC[C@@H](Nc2cccc3c2cc(-c2noc(CNC(=O)c4ccn(CC(=O)N(C)C)c4)n2)n3CC(F)(F)F)[C@@H](F)C1] | 1-[(dimethylcarbamoyl)methyl]-N-{[3-(4-{[(3S,4R)-1-ethyl-3-fluoropiperidin-4-yl]amino}-1-(2,2,2-trifluoroethyl)-1H-indol-2-yl)-1,2,4-oxadiazol-5-yl]methyl}-1H-pyrrole-3-carboxamide | 619.3 |
| 366B | 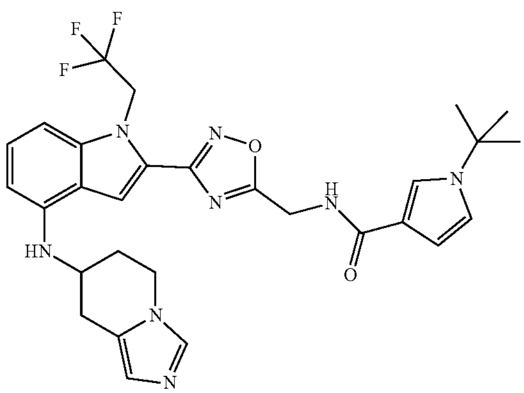 [SMILES: CC(C)(C)n1ccc(C(=O)NCc2nc(-c3cc4c(NC5CCn6cncc6C5)cccc4n3CC(F)(F)F)no2)c1] | 1-tert-butyl-N-({3-[4-({5H,6H,7H,8H-imidazo[1,2-a]pyridin-7-yl}amino)-1-(2,2,2-trifluoroethyl)-1H-indol-2-yl]-1,2,4-oxadiazol-5-yl}methyl)-1H-pyrrole-3-carboxamide | 581.3 |
| 367B | 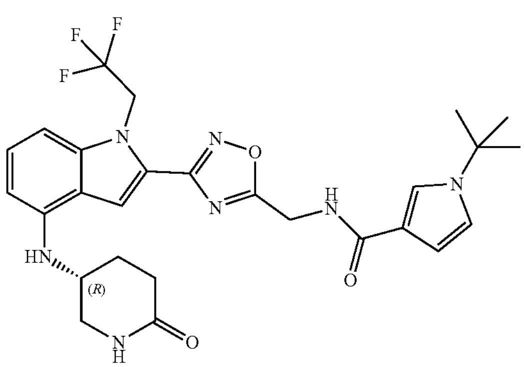 | 1-tert-butyl-N-{[3-(4-{[(3R)-6-oxopiperidin-3-yl]amino}-1-(2,2,2-trifluoroethyl)-1H-indol-2-yl)-1,2,4-oxadiazol-5-yl]methyl}-1H-pyrrole-3-carboxamide | 558.3 |

TABLE 9-continued

| Compound No. | Structure | IUPAC | LC-MS (ES+, m/z) |
|---|---|---|---|
| 368B | 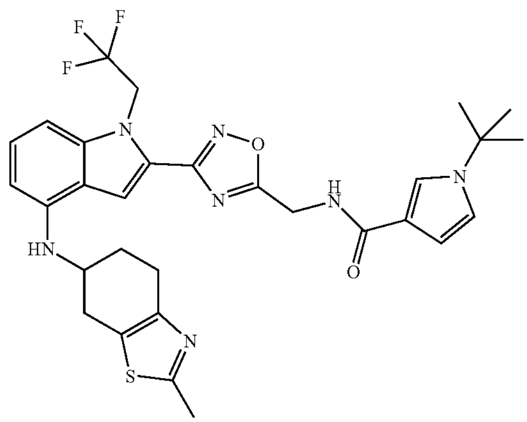 [SMILES: Cc1nc2c(s1)CC(Nc1cccc3c1cc(-c1noc(CNC(=O)c4ccn(C(C)(C)C)c4)n1)n3CC(F)(F)F)CC2] | 1-tert-butyl-N-[(3-{4-[(2-methyl-4,5,6,7-tetrahydro-1,3-benzothiazol-6-yl)amino]-1-(2,2,2-trifluoroethyl)-1H-indol-2-yl}-1,2,4-oxadiazol-5-yl)methyl]-1H-pyrrole-3-carboxamide | 612.3 |
| 369B | 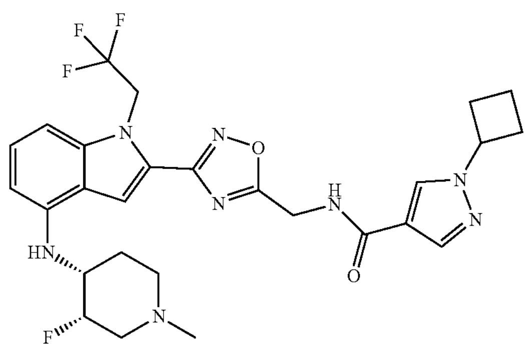 | 1-cyclobutyl-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-pyrazole-4-carboxamide | 575.3 |
| 370B | 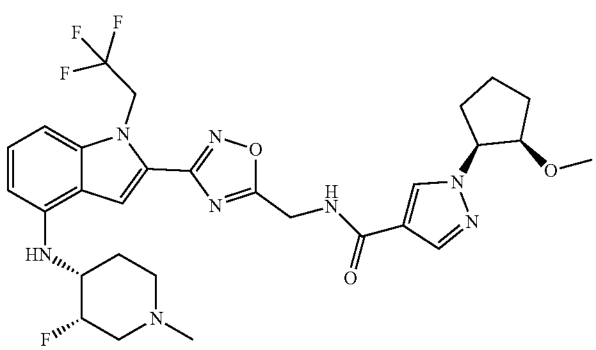 | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-[(1R,2S)-2-methoxycyclopentyl]-1H-pyrazole-4-carboxamide | 619.3 |
| 371B | 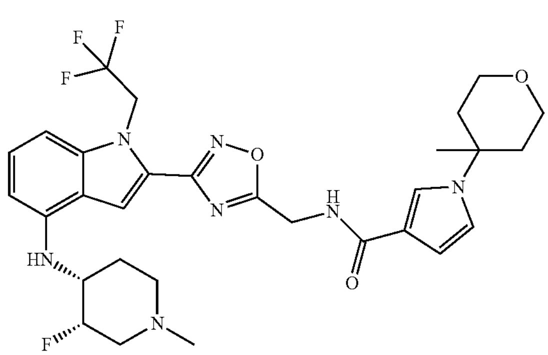 [SMILES: CN1CC[C@@H](Nc2cccc3c2cc(-c2noc(CNC(=O)c4ccn(C5(C)CCOCC5)c4)n2)n3CC(F)(F)F)[C@@H](F)C1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(4-methyloxan-4-yl)-1H-pyrrole-3-carboxamide | 618.3 |

TABLE 9-continued

| Compound No. | Structure | IUPAC | LC-MS (ES+, m/z) |
|---|---|---|---|
| 372B | 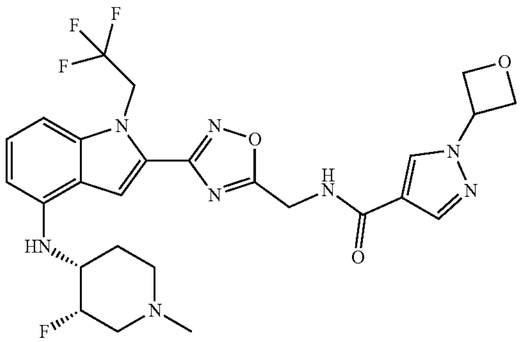 [SMILES: CN1CC[C@@H](Nc2cccc3c2cc(-c2noc(CNC(=O)c4cnn(C5COC5)c4)n2)n3CC(F)(F)F)[C@@H](F)C1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(oxetan-3-yl)-1H-pyrazole-4-carboxamide | 577.3 |
| 373B | 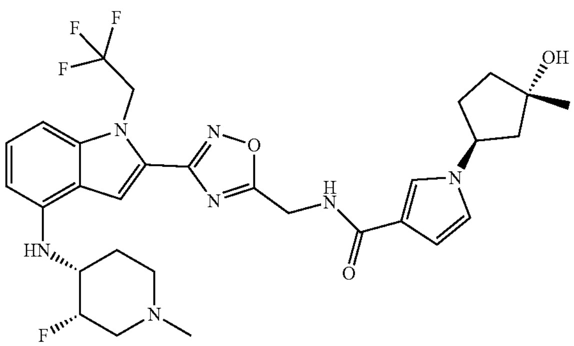 [SMILES: CN1CC[C@@H](Nc2cccc3c2cc(-c2noc(CNC(=O)c4ccn([C@H]5CC[C@](C)(O)C5)c4)n2)n3CC(F)(F)F)[C@@H](F)C1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-[(1R,3R)-3-hydroxy-3-methylcyclopentyl]-1H-pyrrole-3-carboxamide | 618.3 |
| 374B | 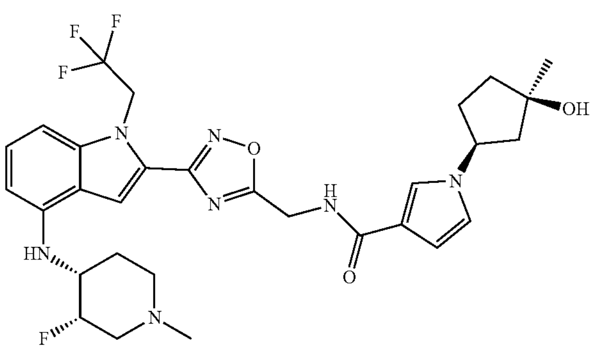 [SMILES: CN1CC[C@@H](Nc2cccc3c2cc(-c2noc(CNC(=O)c4ccn([C@H]5CC[C@@](C)(O)C5)c4)n2)n3CC(F)(F)F)[C@@H](F)C1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-[(1R,3S)-3-hydroxy-3-methylcyclopentyl]-1H-pyrrole-3-carboxamide | 618.4 |
| 375B | 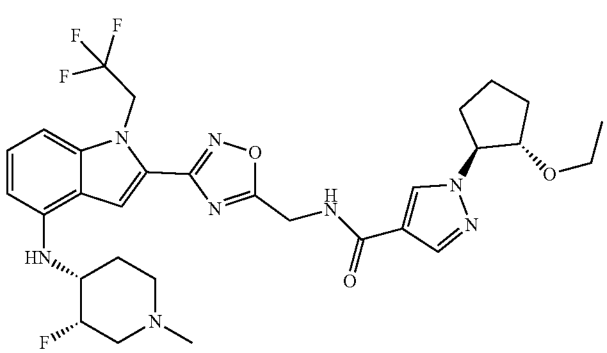 [SMILES: CCO[C@H]1CCC[C@@H]1n1cc(C(=O)NCc2nc(-c3cc4c(N[C@@H]5CCN(C)C[C@@H]5F)cccc4n3CC(F)(F)F)no2)cn1] | 1-[(1R,2R)-2-ethoxycyclopentyl]-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-pyrazole-4-carboxamide | 633.3 |

TABLE 9-continued

| Compound No. | Structure | IUPAC | LC-MS (ES+, m/z) |
|---|---|---|---|
| 376B | 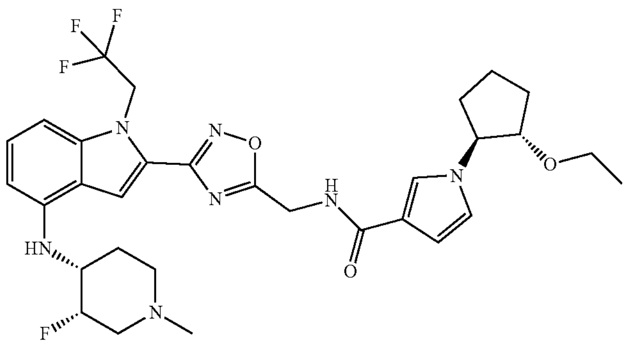 [SMILES: CCO[C@H]1CCC[C@@H]1n1ccc(C(=O)NCc2nc(-c3cc4c(N[C@@H]5CCN(C)C[C@@H]5F)cccc4n3CC(F)(F)F)no2)c1] | 1-[(1R,2R)-2-ethoxycyclopentyl]-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-pyrrole-3-carboxamide | 632.3 |
| 377B | 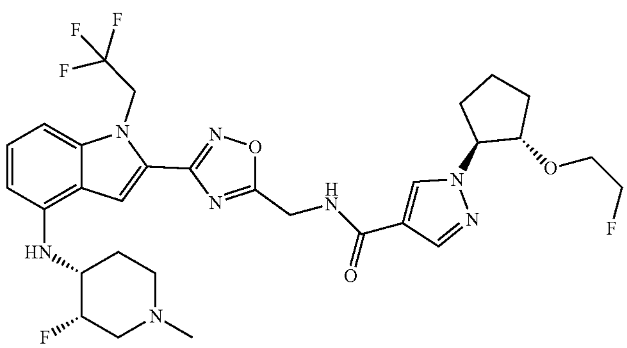 [SMILES: CN1CC[C@@H](Nc2cccc3c2cc(-c2noc(CNC(=O)c4cnn([C@H]5CCC[C@@H]5OCCF)c4)n2)n3CC(F)(F)F)[C@@H](F)C1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-[(1R,2R)-2-(2-fluoroethoxy)cyclopentyl]-1H-pyrazole-4-carboxamide | 651.3 |
| 378B | 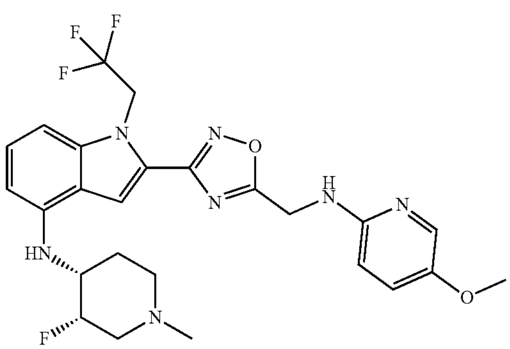 [SMILES: COc1ccc(NCc2nc(-c3cc4c(N[C@@H]5CCN(C)C[C@@H]5F)cccc4n3CC(F)(F)F)no2)nc1] | N-[(3S,4R)-3-fluoro-1-methylpiperidin-4-yl]-2-(5-{[(5-methoxypyridin-2-yl)amino]methyl}-1,2,4-oxadiazol-3-yl)-1-(2,2,2-trifluoroethyl)-1H-indol-4-amine | 534.2 |
| 379B | 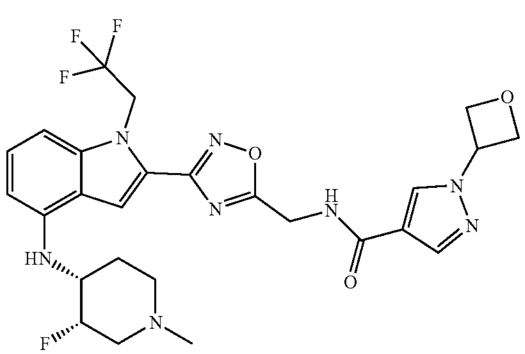 [SMILES: CN1CC[C@@H](Nc2cccc3c2cc(-c2noc(CNC(=O)c4cnn(C5COC5)c4)n2)n3CC(F)(F)F)[C@@H](F)C1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(oxetan-3-yl)-1H-pyrrole-3-carboxamide | 576.3 |

TABLE 9-continued

| Compound No. | Structure | IUPAC | LC-MS (ES+, m/z) |
|---|---|---|---|
| 380B | 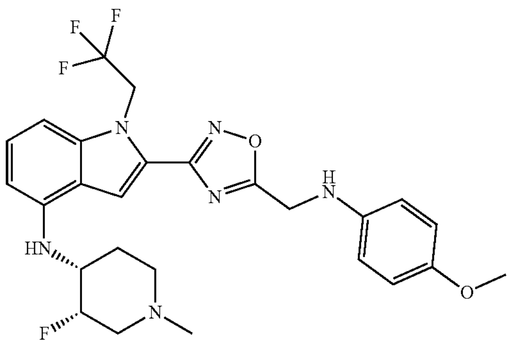 [SMILES: COc1ccc(NCc2nc(-c3cc4c(N[C@@H]5CCN(C)C[C@@H]5F)cccc4n3CC(F)(F)F)no2)cc1] | N-[(3S,4R)-3-fluoro-1-methylpiperidin-4-yl]-2-(5-{[(4-methoxyphenyl)amino]methyl}-1,2,4-oxadiazol-3-yl)-1-(2,2,2-trifluoroethyl)-1H-indol-4-amine | 533.2 |
| 381B | 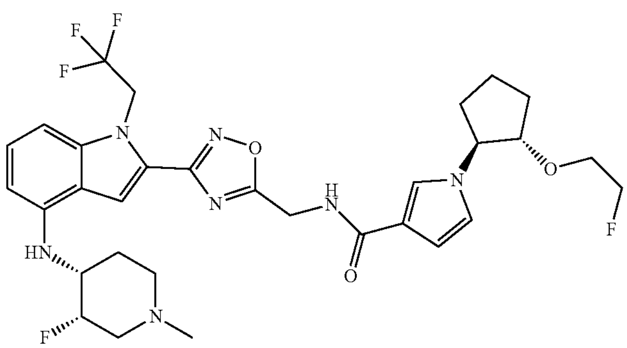 [SMILES: CN1CC[C@@H](Nc2cccc3c2cc(-c2noc(CNC(=O)c4ccn([C@H]5CCC[C@@H]5OCCF)c4)n2)n3CC(F)(F)F)[C@@H](F)C1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-[(1R,2R)-2-(2-fluoroethoxy)cyclopentyl]-1H-pyrrole-3-carboxamide | 650.3 |
| 382B | 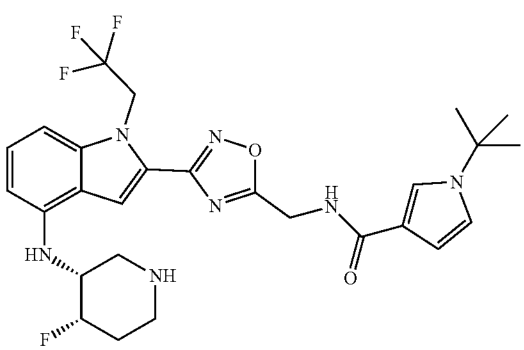 [SMILES: CC(C)(C)n1ccc(C(=O)NCc2nc(-c3cc4c(N[C@@H]5CNCC[C@@H]5F)cccc4n3CC(F)(F)F)no2)c1] | rac-1-tert-butyl-N-{[3-(4-{[(3R,4S)-4-fluoropiperidin-3-yl]amino}-1-(2,2,2-trifluoroethyl)-1H-indol-2-yl)-1,2,4-oxadiazol-5-yl]methyl}-1H-pyrrole-3-carboxamide | 562.3 |
| 383B | 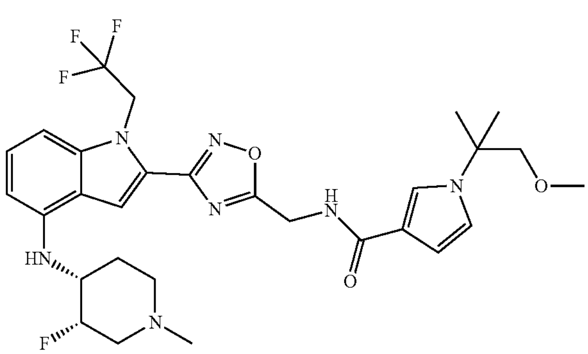 [SMILES: COCC(C)(C)n1ccc(C(=O)NCc2nc(-c3cc4c(N[C@@H]5CCN(C)C[C@@H]5F)cccc4n3CC(F)(F)F)no2)c1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(1-methoxy-2-methylpropan-2-yl)-1H-pyrrole-3-carboxamide | 606.3 |

TABLE 9-continued

| Compound No. | Structure | IUPAC | LC-MS (ES+, m/z) |
|---|---|---|---|
| 384B | 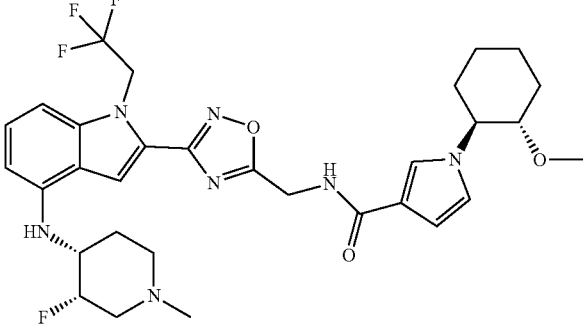 | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-[(1R,2R)-2-methoxycyclohexyl]-1H-pyrrole-3-carboxamide | 632.3 |
| 385B | 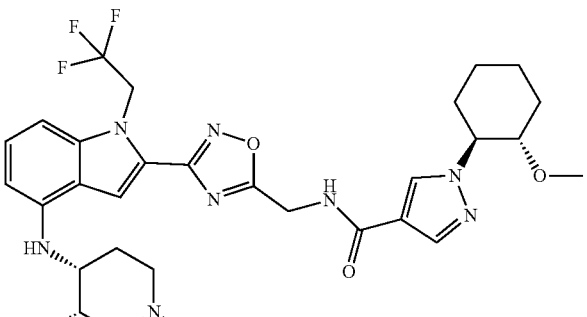 | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-[(1R,2R)-2-methoxycyclohexyl]-1H-pyrazole-4-carboxamide | 633.3 |
| 386B | 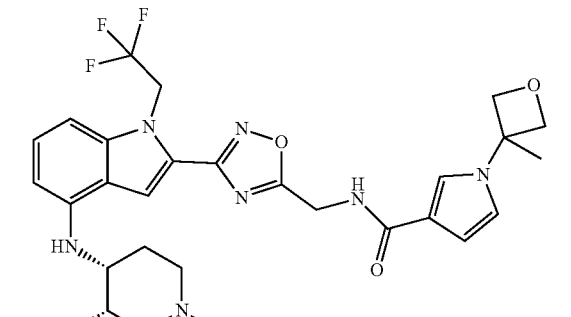 | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(3-methyloxetan-3-yl)-1H-pyrrole-3-carboxamide | 590.2 |
| 387B | 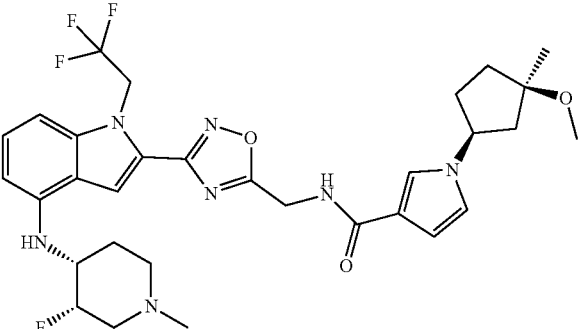 | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-[(1R,3S)-3-methoxy-3-methylcyclopentyl]-1H-pyrrole-3-carboxamide | 632.3 |

TABLE 9-continued

| Compound No. | Structure | IUPAC | LC-MS (ES+, m/z) |
|---|---|---|---|
| 388B | 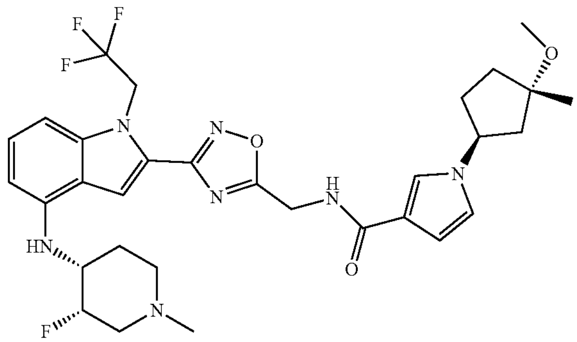 [SMILES: CO[C@@]1(C)CC[C@H](n2ccc(C(=O)NCc3nc(-c4cc5c(N[C@@H]6CCN(C)C[C@@H]6F)cccc5n4CC(F)(F)F)no3)c2)C1] | N-{3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-[(1R,3R)-3-methoxy-3-methylcyclopentyl]-1H-pyrrole-3-carboxamide | 632.3 |
| 389B | 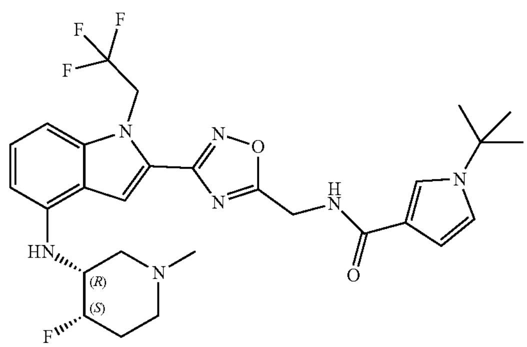 | rac-1-tert-butyl-N-{[3-(4-{[(3R,4S)-4-fluoro-1-methylpiperidin-3-yl]amino}-1-(2,2,2-trifluoroethyl)-1H-indol-2-yl)-1,2,4-oxadiazol-5-yl]methyl}-1H-pyrrole-3-carboxamide | 576.3 |
| 390B | 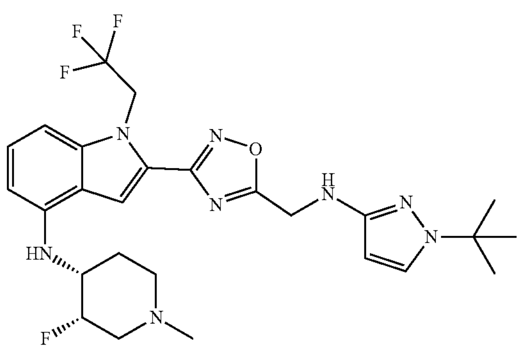 [SMILES: CN1CC[C@@H](Nc2cccc3c2cc(-c2noc(CNc4ccn(C(C)(C)C)n4)n2)n3CC(F)(F)F)[C@@H](F)C1] | 2-(5-{[(1-tert-butyl-1H-pyrazol-3-yl)amino]methyl}-1,2,4-oxadiazol-3-yl)-N-[(3S,4R)-3-fluoro-1-methylpiperidin-4-yl]-1-(2,2,2-trifluoroethyl)-1H-indol-4-amine | 549.3 |
| 391B | 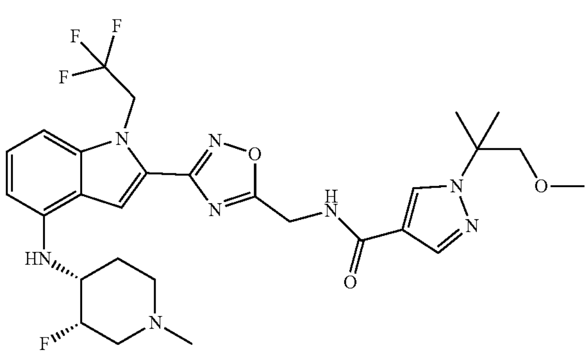 [SMILES: COCC(C)(C)n1cc(C(=O)NCc2nc(-c3cc4c(N[C@@H]5CCN(C)C[C@@H]5F)cccc4n3CC(F)(F)F)no2)cn1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(1-methoxy-2-methylpropan-2-yl)-1H-pyrazole-4-carboxamide | 607.3 |

TABLE 9-continued

| Compound No. | Structure | IUPAC | LC-MS (ES+, m/z) |
|---|---|---|---|
| 392B | 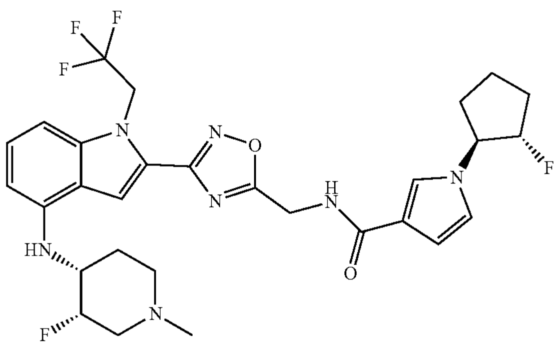 [SMILES: CN1CC[C@@H](Nc2cccc3c2cc(-c2noc(CNC(=O)c4ccn([C@H]5CCC[C@@H]5F)c4)n2)n3CC(F)(F)F)[C@@H](F)C1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-[(1R,2R)-2-fluorocyclopentyl]-1H-pyrrole-3-carboxamide | 606.3 |
| 393B | 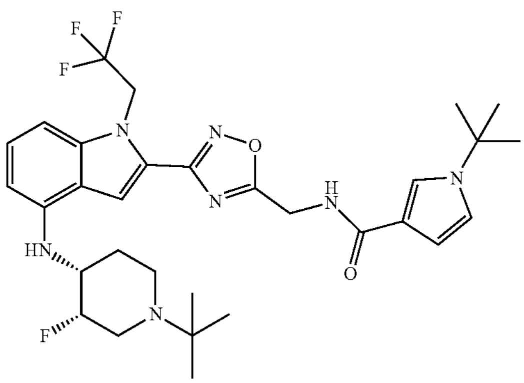 [SMILES: CC(C)(C)N1CC[C@@H](Nc2cccc3c2cc(-c2noc(CNC(=O)c4ccn(C(C)(C)C)c4)n2)n3CC(F)(F)F)[C@@H](F)C1] | 1-tert-butyl-N-{[3-(4-{[(3S,4R)-1-tert-butyl-3-fluoropiperidin-4-yl]amino}-1-(2,2,2-trifluoroethyl)-1H-indol-2-yl)-1,2,4-oxadiazol-5-yl]methyl}-1H-pyrrole-3-carboxamide | 618.3 |
| 394B | 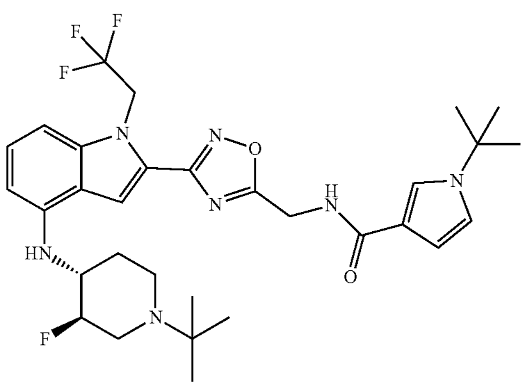 [SMILES: CC(C)(C)N1CC[C@@H](Nc2cccc3c2cc(-c2noc(CNC(=O)c4ccn(C(C)(C)C)c4)n2)n3CC(F)(F)F)[C@H](F)C1] | 1-tert-butyl-N-{[3-(4-{[(3R,4R)-1-tert-butyl-3-fluoropiperidin-4-yl]amino}-1-(2,2,2-trifluoroethyl)-1H-indol-2-yl)-1,2,4-oxadiazol-5-yl]methyl}-1H-pyrrole-3-carboxamide | 618.3 |
| 395B | 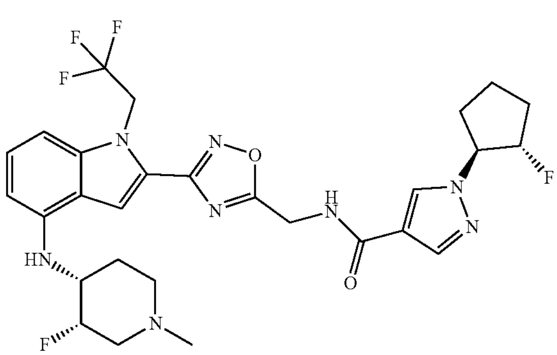 [SMILES: CN1CC[C@@H](Nc2cccc3c2cc(-c2noc(CNC(=O)c4cnn([C@H]5CCC[C@@H]5F)c4)n2)n3CC(F)(F)F)[C@@H](F)C1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-[(1R,2R)-2-fluorocyclopentyl]-1H-pyrazole-4-carboxamide | 607.3 |

TABLE 9-continued

| Compound No. | Structure | IUPAC | LC-MS (ES+, m/z) |
|---|---|---|---|
| 396B | 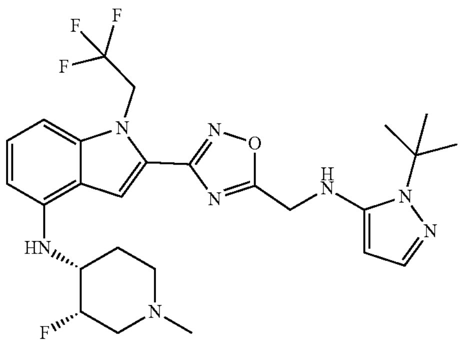 [SMILES: CN1CC[C@@H](Nc2cccc3c2cc(-c2noc(CNc4ccnn4C(C)(C)C)n2)n3CC(F)(F)F)[C@@H](F)C1] | 2-(5-{[(1-tert-butyl-1H-pyrazol-5-yl)amino]methyl}-1,2,4-oxadiazol-3-yl)-N-[(3S,4R)-3-fluoro-1-methylpiperidin-4-yl]-1-(2,2,2-trifluoroethyl)-1H-indol-4-amine | 549.3 |
| 397B | 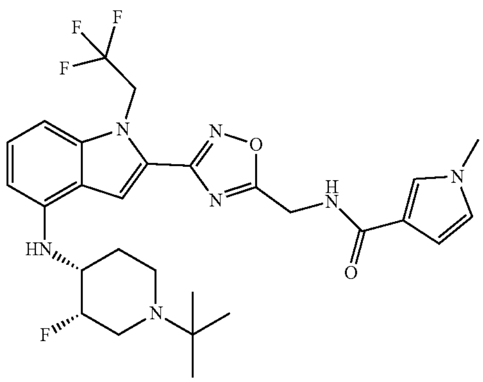 [SMILES: Cn1ccc(C(=O)NCc2nc(-c3cc4c(N[C@@H]5CCN(C(C)(C)C)C[C@@H]5F)cccc4n3CC(F)(F)F)no2)c1] | N-{[3-(4-{[(3S,4R)-1-tert-butyl-3-fluoropiperidin-4-yl]amino}-1-(2,2,2-trifluoroethyl)-1H-indol-2-yl)-1,2,4-oxadiazol-5-yl]methyl}-1-methyl-1H-pyrrole-3-carboxamide | 576.3 |
| 398B | 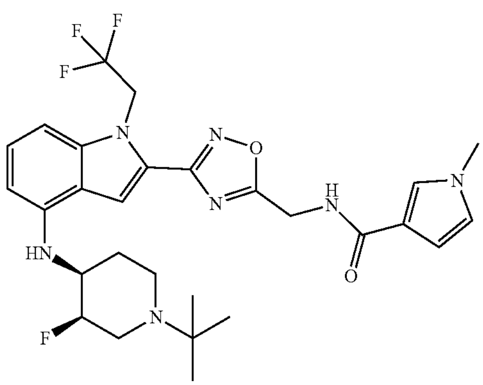 [SMILES: Cn1ccc(C(=O)NCc2nc(-c3cc4c(N[C@H]5CCN(C(C)(C)C)C[C@H]5F)cccc4n3CC(F)(F)F)no2)c1] | N-{[3-(4-{[(3R,4S)-1-tert-butyl-3-fluoropiperidin-4-yl]amino}-1-(2,2,2-trifluoroethyl)-1H-indol-2-yl)-1,2,4-oxadiazol-5-yl]methyl}-1-methyl-1H-pyrrole-3-carboxamide | 576.3 |
| 399B | 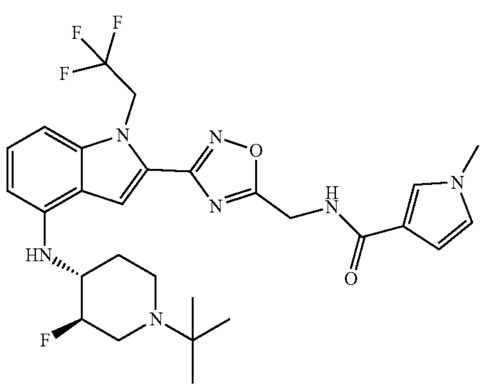 [SMILES: Cn1ccc(C(=O)NCc2nc(-c3cc4c(N[C@@H]5CCN(C(C)(C)C)C[C@H]5F)cccc4n3CC(F)(F)F)no2)c1] | N-{[3-(4-{[(3R,4R)-1-tert-butyl-3-fluoropiperidin-4-yl]amino}-1-(2,2,2-trifluoroethyl)-1H-indol-2-yl)-1,2,4-oxadiazol-5-yl]methyl}-1-methyl-1H-pyrrole-3-carboxamide | 576.3 |

TABLE 9-continued

| Compound No. | Structure | IUPAC | LC-MS (ES+, m/z) |
|---|---|---|---|
| 400B | 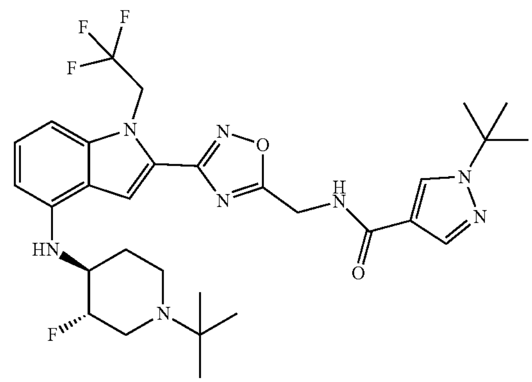 [SMILES: CC(C)(C)N1CC[C@H](Nc2cccc3c2cc(-c2noc(CNC(=O)c4cnn(C(C)(C)C)c4)n2)n3CC(F)(F)F)[C@@H](F)C1] | 1-tert-butyl-N-{[3-(4-{[(3S,4R)-1-tert-butyl-3-fluoropiperidin-4-yl]amino}-1-(2,2,2-trifluoroethyl)-1H-indol-2-yl)-1,2,4-oxadiazol-5-yl]methyl}-1H-pyrazole-4-carboxamide | 619.3 |
| 401B | 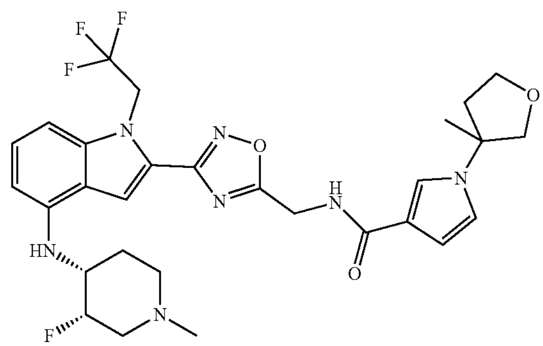 [SMILES: CN1CC[C@@H](Nc2cccc3c2cc(-c2noc(CNC(=O)c4ccn(C5(C)CCOC5)c4)n2)n3CC(F)(F)F)[C@@H](F)C1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(3-methyloxolan-3-yl)-1H-pyrrole-3-carboxamide | 604.3 |
| 402B | 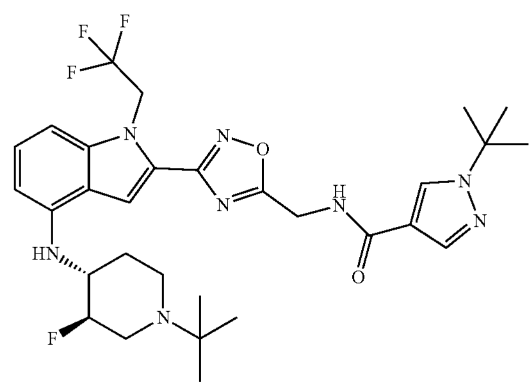 [SMILES: CC(C)(C)N1CC[C@@H](Nc2cccc3c2cc(-c2noc(CNC(=O)c4cnn(C(C)(C)C)c4)n2)n3CC(F)(F)F)[C@H](F)C1] | 1-tert-butyl-N-{[3-(4-{[(3R,4R)-1-tert-butyl-3-fluoropiperidin-4-yl]amino}-1-(2,2,2-trifluoroethyl)-1H-indol-2-yl)-1,2,4-oxadiazol-5-yl]methyl}-1H-pyrazole-4-carboxamide | 619.3 |
| 403B | 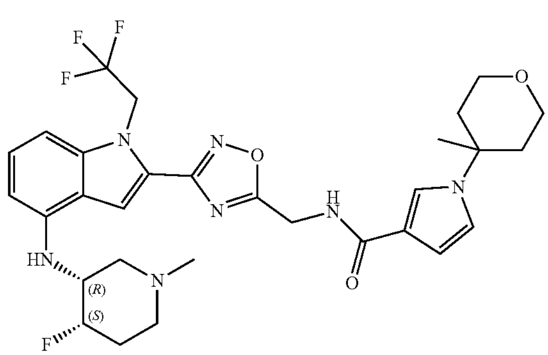 | N-{[3-(4-{[(3R,4S)-4-fluoro-1-methylpiperidin-3-yl]amino}-1-(2,2,2-trifluoroethyl)-1H-indol-2-yl)-1,2,4-oxadiazol-5-yl]methyl}-1-(4-methyloxan-4-yl)-1H-pyrrole-3-carboxamide | 618.3 |

TABLE 9-continued

| Compound No. | Structure | IUPAC | LC-MS (ES+, m/z) |
|---|---|---|---|
| 404B | 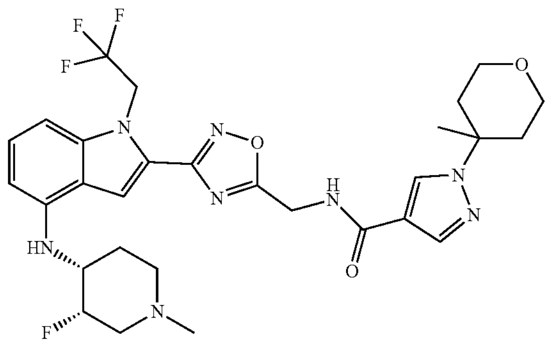 [SMILES: CN1CC[C@@H](Nc2cccc3c2cc(-c2noc(CNC(=O)c4cnn(C5(C)CCOCC5)c4)n2)n3CC(F)(F)F)[C@@H](F)C1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(4-methyloxan-4-yl)-1H-pyrazole-4-carboxamide | 619.3 |
| 405B | 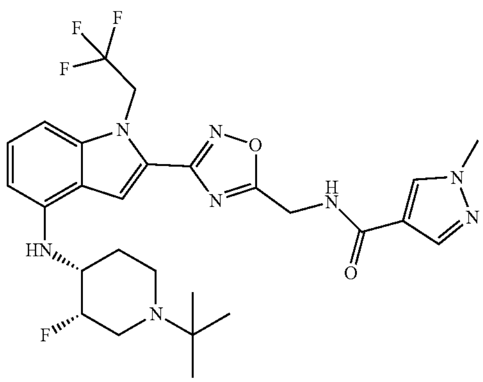 [SMILES: Cn1cc(C(=O)NCc2nc(-c3cc4c(N[C@@H]5CCN(C(C)(C)C)C[C@@H]5F)cccc4n3CC(F)(F)F)no2)cn1] | N-{[3-(4-{[(3S,4R)-1-tert-butyl-3-fluoropiperidin-4-yl]amino}-1-(2,2,2-trifluoroethyl)-1H-indol-2-yl)-1,2,4-oxadiazol-5-yl]methyl}-1-methyl-1H-pyrazole-4-carboxamide | 577.3 |
| 406B | 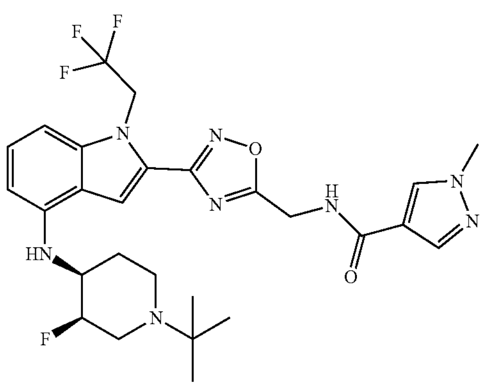 [SMILES: Cn1cc(C(=O)NCc2nc(-c3cc4c(N[C@H]5CCN(C(C)(C)C)C[C@H]5F)cccc4n3CC(F)(F)F)no2)cn1] | N-{[3-(4-{[(3R,4S)-1-tert-butyl-3-fluoropiperidin-4-yl]amino}-1-(2,2,2-trifluoroethyl)-1H-indol-2-yl)-1,2,4-oxadiazol-5-yl]methyl}-1-methyl-1H-pyrazole-4-carboxamide | 577.3 |
| 407B | 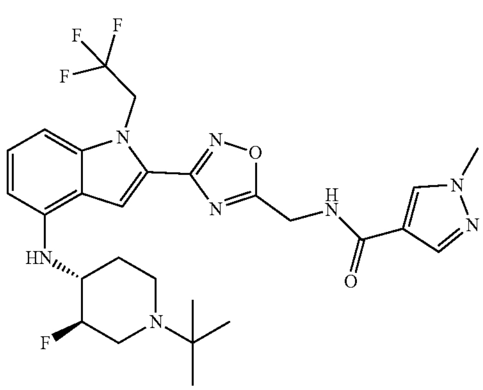 [SMILES: Cn1cc(C(=O)NCc2nc(-c3cc4c(N[C@@H]5CCN(C(C)(C)C)C[C@H]5F)cccc4n3CC(F)(F)F)no2)cn1] | Racemic N-{[3-(4-{[(3R,4R)-1-tert-butyl-3-fluoropiperidin-4-yl]amino}-1-(2,2,2-trifluoroethyl)-1H-indol-2-yl)-1,2,4-oxadiazol-5-yl]methyl}-1-methyl-1H-pyrazole-4-carboxamide | 577.3 |

TABLE 9-continued

| Compound No. | Structure | IUPAC | LC-MS (ES+, m/z) |
|---|---|---|---|
| 408B | 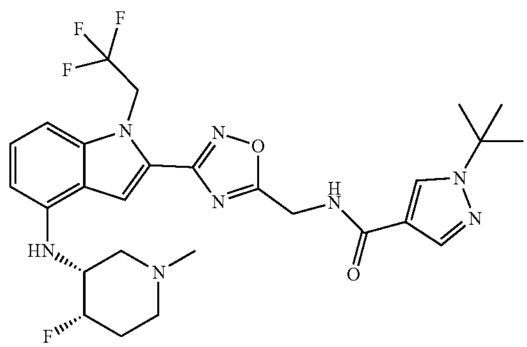 [SMILES: CN1CC[C@H](F)[C@H](Nc2cccc3c2cc(-c2noc(CNC(=O)c4cnn(C(C)(C)C)c4)n2)n3CC(F)(F)F)C1] | 1-tert-butyl-N-{[3-(4-{[(3R,4S)-4-fluoro-1-methylpiperidin-3-yl]amino}-1-(2,2,2-trifluoroethyl)-1H-indol-2-yl)-1,2,4-oxadiazol-5-yl]methyl}-1H-pyrazole-4-carboxamide | 577.3 |
| 409B | 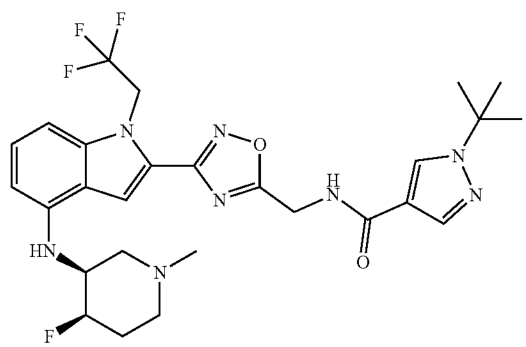 [SMILES: CN1CC[C@@H](F)[C@@H](Nc2cccc3c2cc(-c2noc(CNC(=O)c4cnn(C(C)(C)C)c4)n2)n3CC(F)(F)F)C1] | 1-tert-butyl-N-{[3-(4-{[(3S,4R)-4-fluoro-1-methylpiperidin-3-yl]amino}-1-(2,2,2-trifluoroethyl)-1H-indol-2-yl)-1,2,4-oxadiazol-5-yl]methyl}-1H-pyrazole-4-carboxamide | 577.3 |
| 410B | 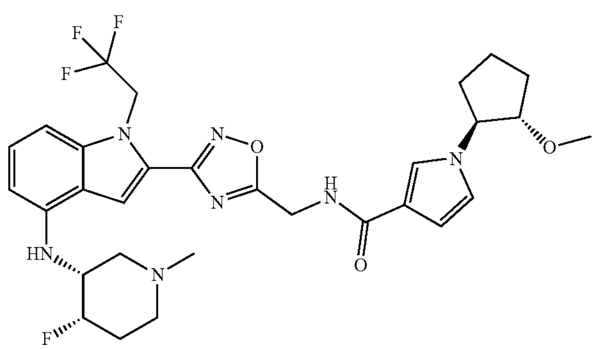 [SMILES: CO[C@H]1CCC[C@@H]1n1ccc(C(=O)NCc2nc(-c3cc4c(N[C@@H]5CN(C)CC[C@@H]5F)cccc4n3CC(F)(F)F)no2)c1] | N-{[3-(4-{[(3R,4S)-4-fluoro-1-methylpiperidin-3-yl]amino}-1-(2,2,2-trifluoroethyl)-1H-indol-2-yl)-1,2,4-oxadiazol-5-yl]methyl}-1-[(1R,2R)-2-methoxycyclopentyl]-1H-pyrrole-3-carboxamide | 618.3 |
| 411B | 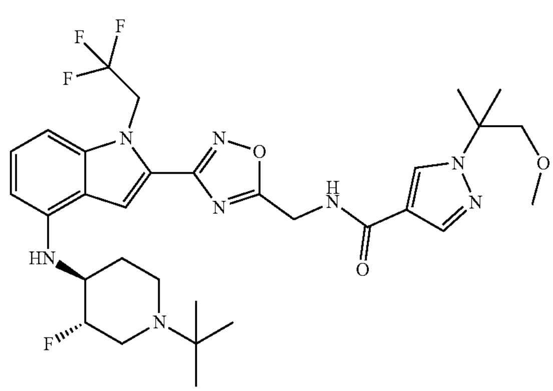 [SMILES: COCC(C)(C)n1cc(C(=O)NCc2nc(-c3cc4c(N[C@H]5CCN(C(C)(C)C)C[C@@H]5F)cccc4n3CC(F)(F)F)no2)cn1] | Racemic N-{[3-(4-{[(3R,4R)-1-tert-butyl-3-fluoropiperidin-4-yl]amino}-1-(2,2,2-trifluoroethyl)-1H-indol-2-yl)-1,2,4-oxadiazol-5-yl]methyl}-1-(1-methoxy-2-methylpropan-2-yl)-1H-pyrazole-4-carboxamide | 649.4 |

TABLE 9-continued

| Compound No. | Structure | IUPAC | LC-MS (ES+, m/z) |
|---|---|---|---|
| 412B | 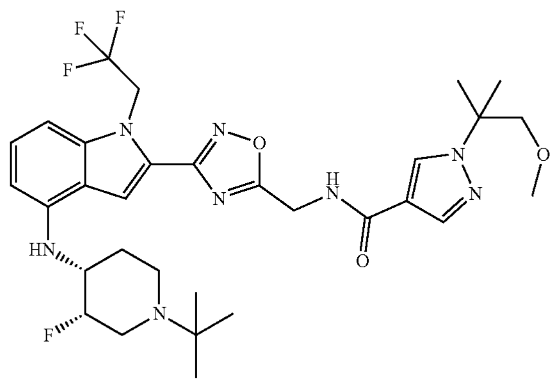 [SMILES: COCC(C)(C)n1cc(C(=O)NCc2nc(-c3cc4c(N[C@@H]5CCN(C(C)(C)C)C[C@@H]5F)cccc4n3CC(F)(F)F)no2)cn1] | N-{[3-(4-{[(3S,4R)-1-tert-butyl-3-fluoropiperidin-4-yl]amino}-1-(2,2,2-trifluoroethyl)-1H-indol-2-yl)-1,2,4-oxadiazol-5-yl]methyl}-1-(1-methoxy-2-methylpropan-2-yl)-1H-pyrazole-4-carboxamide | 649.4 |
| 413B | 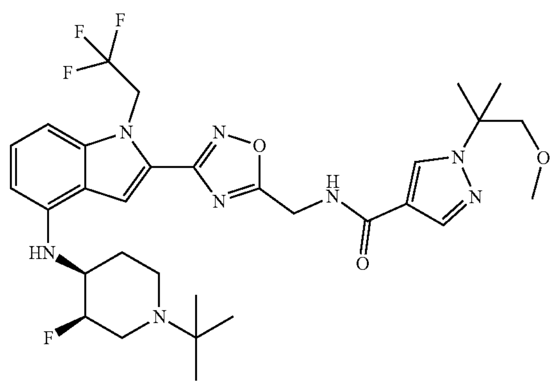 [SMILES: COCC(C)(C)n1cc(C(=O)NCc2nc(-c3cc4c(N[C@H]5CCN(C(C)(C)C)C[C@H]5F)cccc4n3CC(F)(F)F)no2)cn1] | N-{[3-(4-{[(3R,4S)-1-tert-butyl-3-fluoropiperidin-4-yl]amino}-1-(2,2,2-trifluoroethyl)-1H-indol-2-yl)-1,2,4-oxadiazol-5-yl]methyl}-1-(1-methoxy-2-methylpropan-2-yl)-1H-pyrazole-4-carboxamide | 649.4 |
| 414B | 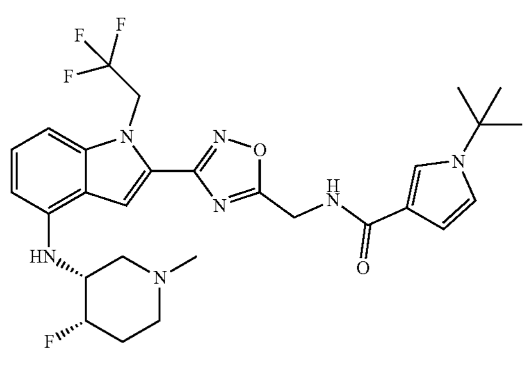 [SMILES: CN1CC[C@H](F)[C@H](Nc2cccc3c2cc(-c2noc(CNC(=O)c4ccn(C(C)(C)C)c4)n2)n3CC(F)(F)F)C1] | 1-tert-butyl-N-{[3-(4-{[(3R,4S)-4-fluoro-1-methylpiperidin-3-yl]amino}-1-(2,2,2-trifluoroethyl)-1H-indol-2-yl)-1,2,4-oxadiazol-5-yl]methyl}-1H-pyrrole-3-carboxamide | 576.3 |
| 415B | 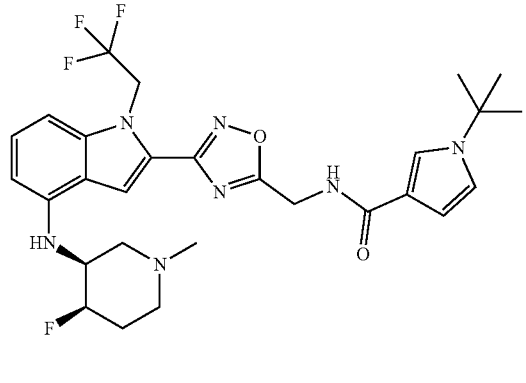 [SMILES: CN1CC[C@@H](F)[C@@H](Nc2cccc3c2cc(-c2noc(CNC(=O)c4ccn(C(C)(C)C)c4)n2)n3CC(F)(F)F)C1] | 1-tert-butyl-N-{[3-(4-{[(3S,4R)-4-fluoro-1-methylpiperidin-3-yl]amino}-1-(2,2,2-trifluoroethyl)-1H-indol-2-yl)-1,2,4-oxadiazol-5-yl]methyl}-1H-pyrazole-4-carboxamide | 576.3 |

TABLE 9-continued

| Compound No. | Structure | IUPAC | LC-MS (ES+, m/z) |
|---|---|---|---|
| 416B | 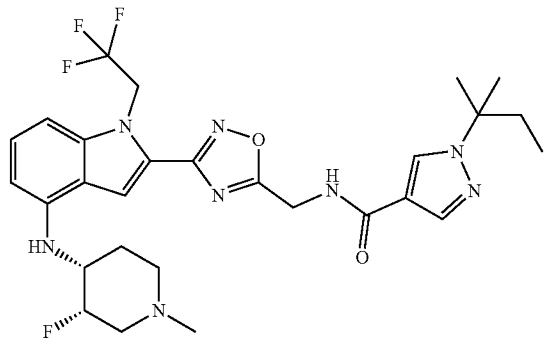 [SMILES: CCC(C)(C)n1cc(C(=O)NCc2nc(-c3cc4c(N[C@@H]5CCN(C)C[C@@H]5F)cccc4n3CC(F)(F)F)no2)cn1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(2-methylbutan-2-yl)-1H-pyrazole-4-carboxamide | 591.3 |
| 417B | 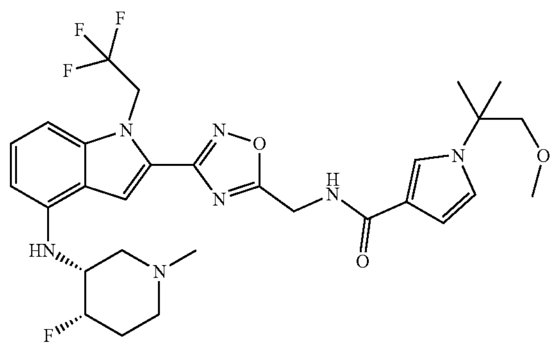 [SMILES: COCC(C)(C)n1ccc(C(=O)NCc2nc(-c3cc4c(N[C@@H]5CN(C)CC[C@@H]5F)cccc4n3CC(F)(F)F)no2)c1] | N-{[3-(4-{[(3R,4S)-4-fluoro-1-methylpiperidin-3-yl]amino}-1-(2,2,2-trifluoroethyl)-1H-indol-2-yl)-1,2,4-oxadiazol-5-yl]methyl}-1-(1-methoxy-2-methylpropan-2-yl)-1H-pyrrole-3-carboxamide | 606.3 |
| 418B | 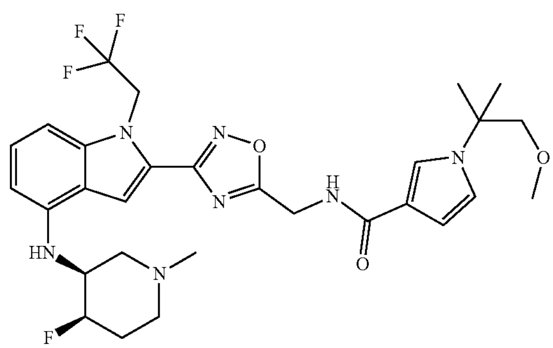 [SMILES: COCC(C)(C)n1ccc(C(=O)NCc2nc(-c3cc4c(N[C@H]5CN(C)CC[C@H]5F)cccc4n3CC(F)(F)F)no2)c1] | N-{[3-(4-{[(3S,4R)-4-fluoro-1-methylpiperidin-3-yl]amino}-1-(2,2,2-trifluoroethyl)-1H-indol-2-yl)-1,2,4-oxadiazol-5-yl]methyl}-1-(1-methoxy-2-methylpropan-2-yl)-1H-pyrrole-3-carboxamide | 606.3 |
| 419B | 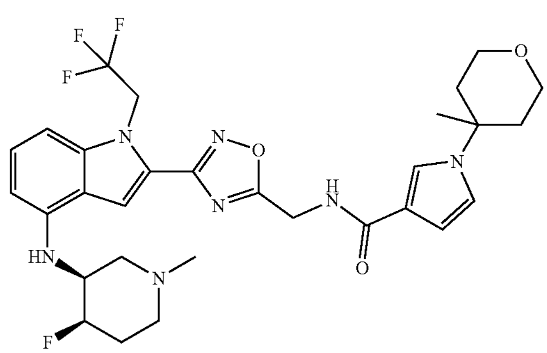 [SMILES: CN1CC[C@@H](F)[C@@H](Nc2cccc3c2cc(-c2noc(CNC(=O)c4ccn(C5(C)CCOCC5)c4)n2)n3CC(F)(F)F)C1] | N-{[3-(4-{[(3S,4R)-4-fluoro-1-methylpiperidin-3-yl]amino}-1-(2,2,2-trifluoroethyl)-1H-indol-2-yl)-1,2,4-oxadiazol-5-yl]methyl}-1-(4-methyloxan-4-yl)-1H-pyrrole-3-carboxamide | 618.3 |

TABLE 9-continued

| Compound No. | Structure | IUPAC | LC-MS (ES+, m/z) |
|---|---|---|---|
| 420B | 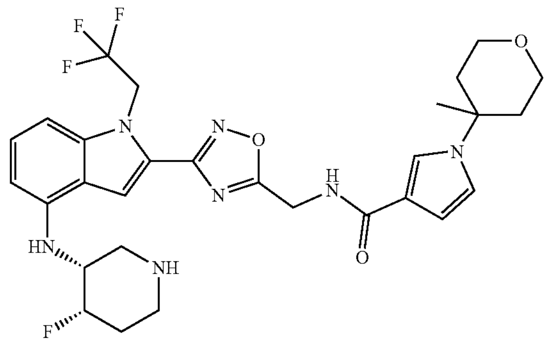 [SMILES: CC1(n2ccc(C(=O)NCc3nc(-c4cc5c(N[C@@H]6CNCC[C@@H]6F)cccc5n4CC(F)(F)F)no3)c2)CCOCC1] | N-{[3-(4-{[(3R,4S)-4-fluoropiperidin-3-yl]amino}-1-(2,2,2-trifluoroethyl)-1H-indol-2-yl)-1,2,4-oxadiazol-5-yl]methyl}-1-(4-methyloxan-4-yl)-1H-pyrrole-3-carboxamide | 604.3 |
| 421B | 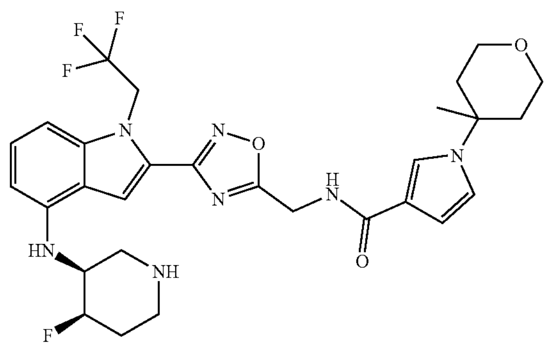 [SMILES: CC1(n2ccc(C(=O)NCc3nc(-c4cc5c(N[C@H]6CNCC[C@H]6F)cccc5n4CC(F)(F)F)no3)c2)CCOCC1] | N-{[3-(4-{[(3S,4R)-4-fluoropiperidin-3-yl]amino}-1-(2,2,2-trifluoroethyl)-1H-indol-2-yl)-1,2,4-oxadiazol-5-yl]methyl}-1-(4-methyloxan-4-yl)-1H-pyrrole-3-carboxamide | 604.3 |
| 422B | 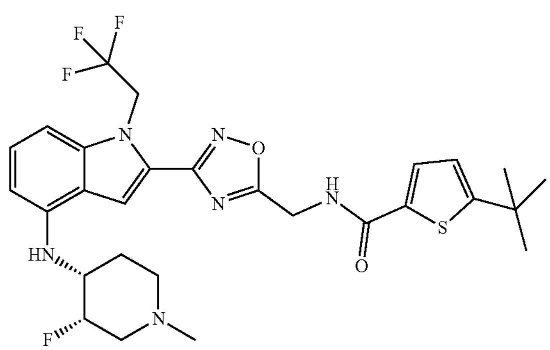 [SMILES: CN1CC[C@@H](Nc2cccc3c2cc(-c2noc(CNC(=O)c4ccc(C(C)(C)C)s4)n2)n3CC(F)(F)F)[C@@H](F)C1] | 5-tert-butyl-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}thiophene-2-carboxamide | 593.3 |
| 423B | 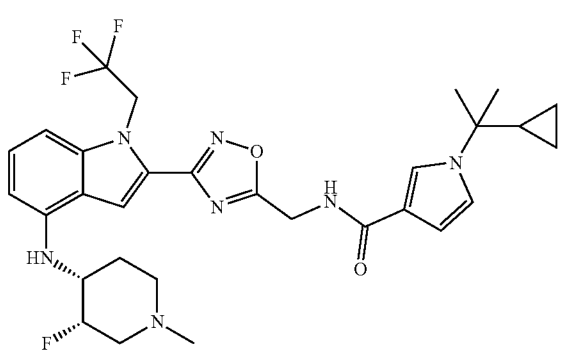 [SMILES: CN1CC[C@@H](Nc2cccc3c2cc(-c2noc(CNC(=O)c4ccn(C(C)(C)C5CC5)c4)n2)n3CC(F)(F)F)[C@@H](F)C1] | 1-(2-cyclopropylpropan-2-yl)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-pyrrole-3-carboxamide | 602.3 |

TABLE 9-continued

| Compound No. | Structure | IUPAC | LC-MS (ES+, m/z) |
| --- | --- | --- | --- |
| 424B | 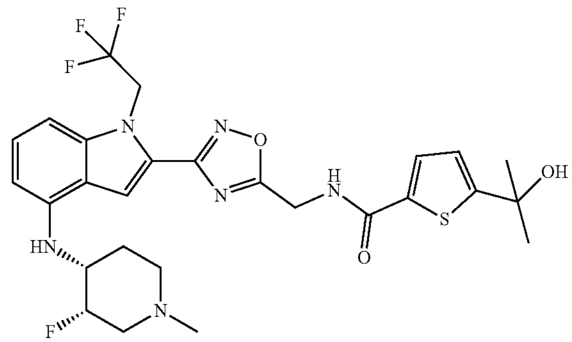 | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-5-(2-hydroxypropan-2-yl)thiophene-2-carboxamide | 595.2 |
| 425B | 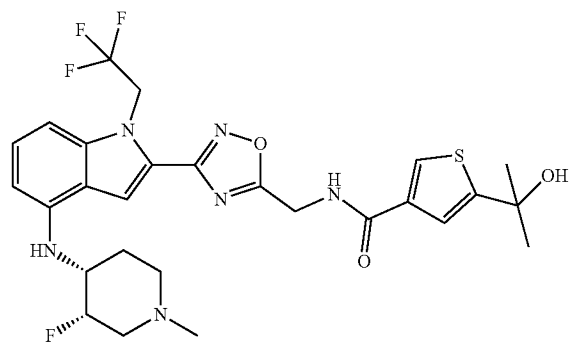 [SMILES: CN1CC[C@@H](Nc2cccc3c2cc(-c2noc(CNC(=O)c4csc(C(C)(C)O)c4)n2)n3CC(F)(F)F)[C@@H](F)C1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-5-(2-hydroxypropan-2-yl)thiophene-3-carboxamide | 595.6 |
| 426B | 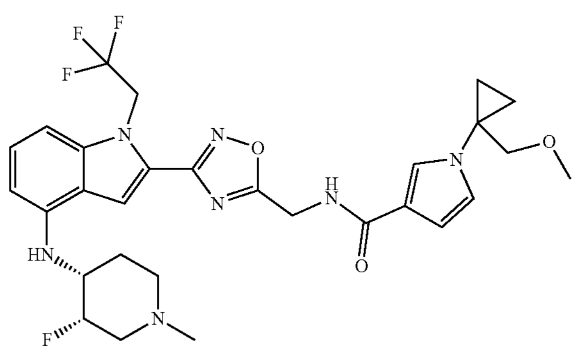 [SMILES: COCC1(n2ccc(C(=O)NCc3nc(-c4cc5c(N[C@@H]6CCN(C)C[C@@H]6F)cccc5n4CC(F)(F)F)no3)c2)CC1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-[1-(methoxymethyl)cyclopropyl]-1H-pyrrole-3-carboxamide | 604.4 |
| 427B | 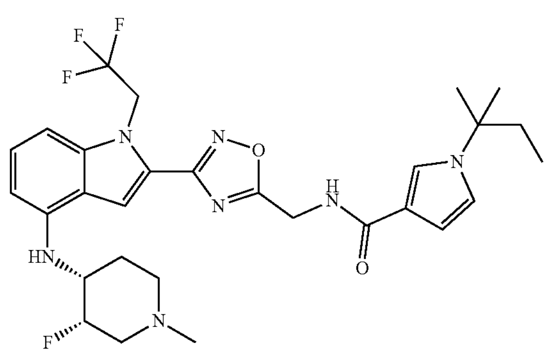 [SMILES: CCC(C)(C)n1ccc(C(=O)NCc2nc(-c3cc4c(N[C@@H]5CCN(C)C[C@@H]5F)cccc4n3CC(F)(F)F)no2)c1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(2-methylbutan-2-yl)-1H-pyrrole-3-carboxamide | 590.3 |

TABLE 9-continued

| Compound No. | Structure | IUPAC | LC-MS (ES+, m/z) |
|---|---|---|---|
| 428B | 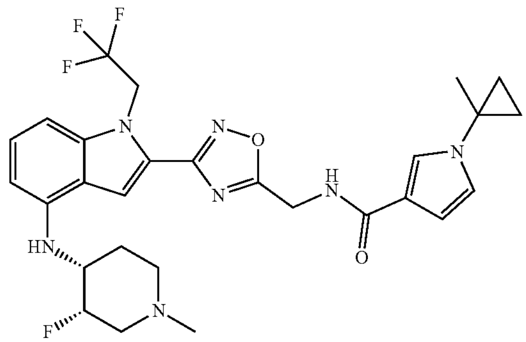 [SMILES: CN1CC[C@@H](Nc2cccc3c2cc(-c2noc(CNC(=O)c4ccn(C5(C)CC5)c4)n2)n3CC(F)(F)F)[C@@H](F)C1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(1-methylcyclopropyl)-1H-pyrrole-3-carboxamide | 574.3 |
| 429B | 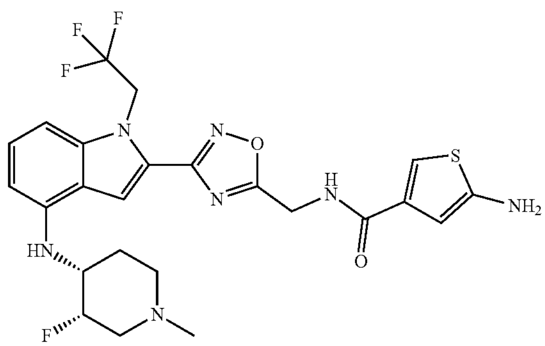 [SMILES: CN1CC[C@@H](Nc2cccc3c2cc(-c2noc(CNC(=O)c4csc(N)c4)n2)n3CC(F)(F)F)[C@@H](F)C1] | 5-amino-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}thiophene-3-carboxamide | 552.2 |
| 430B | 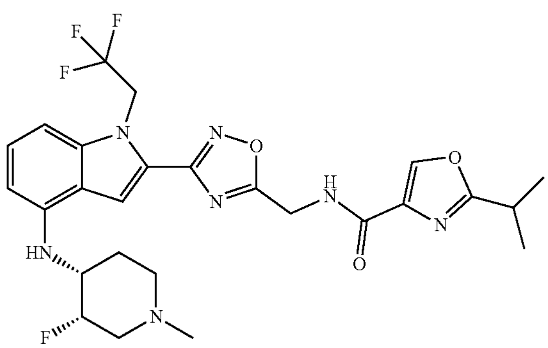 [SMILES: CC(C)c1nc(C(=O)NCc2nc(-c3cc4c(N[C@@H]5CCN(C)C[C@@H]5F)cccc4n3CC(F)(F)F)no2)co1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-(propan-2-yl)-1,3-oxazole-4-carboxamide | 564.3 |
| 431B | 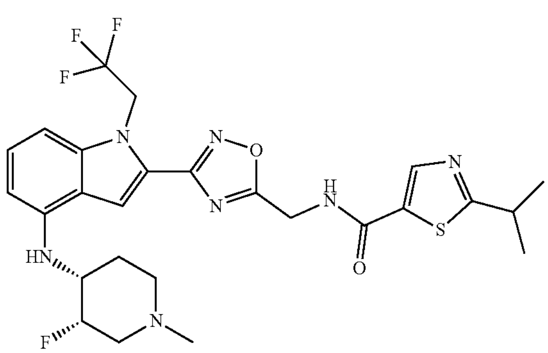 [SMILES: CC(C)c1ncc(C(=O)NCc2nc(-c3cc4c(N[C@@H]5CCN(C)C[C@@H]5F)cccc4n3CC(F)(F)F)no2)s1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-(propan-2-yl)-1,3-thiazole-5-carboxamide | 580.3 |

TABLE 9-continued

| Compound No. | Structure | IUPAC | LC-MS (ES+, m/z) |
|---|---|---|---|
| 432B | 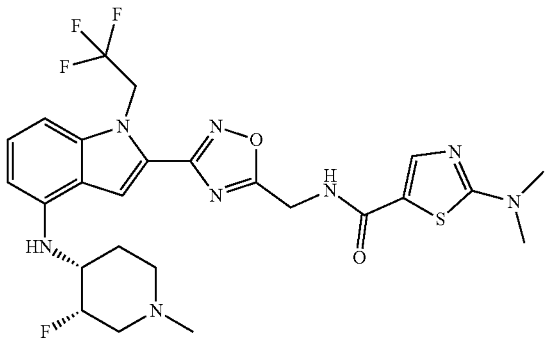 [SMILES: CN1CC[C@@H](Nc2cccc3c2cc(-c2noc(CNC(=O)c4cnc(N(C)C)s4)n2)n3CC(F)(F)F)[C@@H](F)C1] | 2-(dimethylamino)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1,3-thiazole-5-carboxamide | 581.3 |
| 433B | 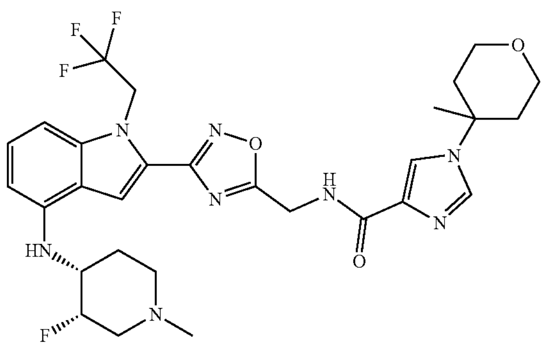 [SMILES: CN1CC[C@@H](Nc2cccc3c2cc(-c2noc(CNC(=O)c4cn(C5(C)CCOCC5)cn4)n2)n3CC(F)(F)F)[C@@H](F)C1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(4-methyloxan-4-yl)-1H-imidazole-4-carboxamide | 619.3 |
| 434B | 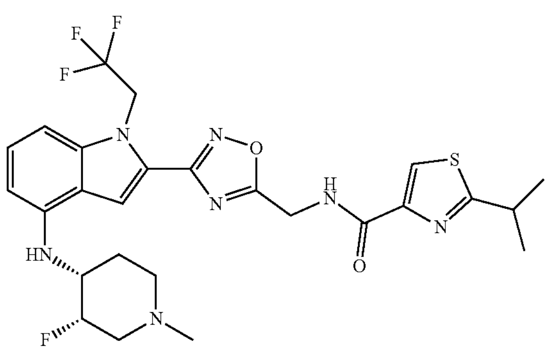 | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-(propan-2-yl)-1,3-thiazole-4-carboxamide | 580.3 |
| 435B | 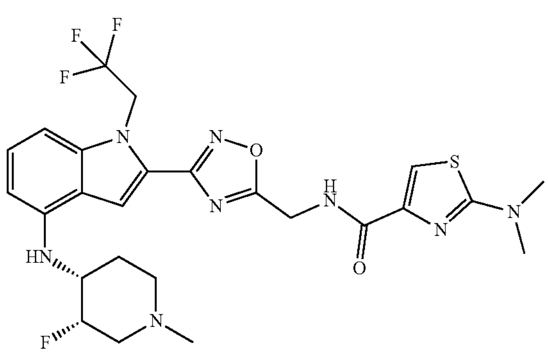 [SMILES: CN1CC[C@@H](Nc2cccc3c2cc(-c2noc(CNC(=O)c4csc(N(C)C)n4)n2)n3CC(F)(F)F)[C@@H](F)C1] | 2-(dimethylamino)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1,3-thiazole-4-carboxamide | 581.3 |

TABLE 9-continued

| Compound No. | Structure | IUPAC | LC-MS (ES+, m/z) |
|---|---|---|---|
| 436B | 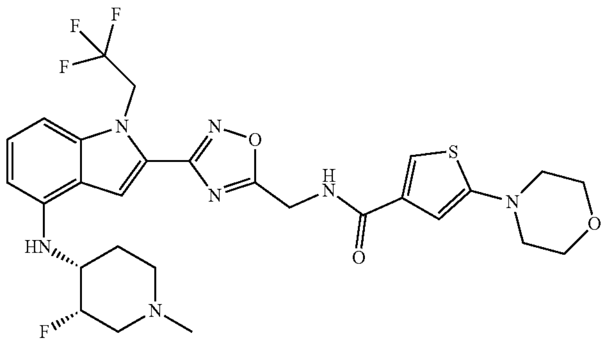 [SMILES: CN1CC[C@@H](Nc2cccc3c2cc(-c2noc(CNC(=O)c4csc(N5CCOCC5)c4)n2)n3CC(F)(F)F)[C@@H](F)C1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-5-(morpholin-4-yl)thiophene-3-carboxamide | 622.2 |
| 437B | 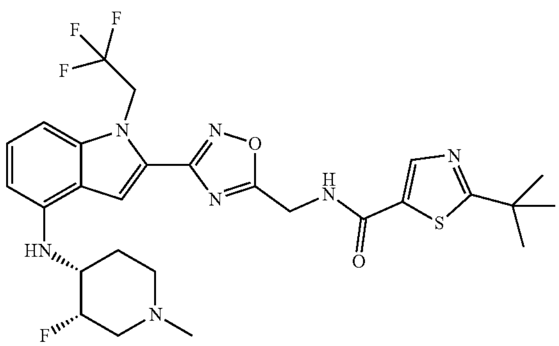 [SMILES: CN1CC[C@@H](Nc2cccc3c2cc(-c2noc(CNC(=O)c4cnc(C(C)(C)C)s4)n2)n3CC(F)(F)F)[C@@H](F)C1] | 2-tert-butyl-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1,3-thiazole-5-carboxamide | 594.3 |
| 438B | 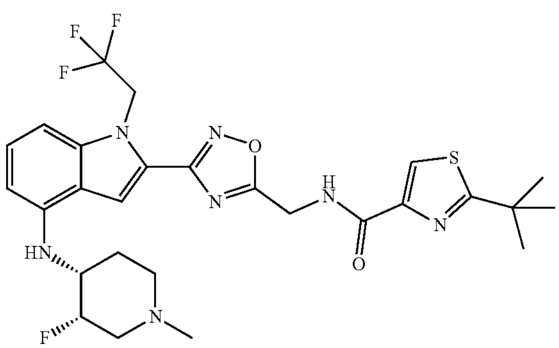 [SMILES: CN1CC[C@@H](Nc2cccc3c2cc(-c2noc(CNC(=O)c4csc(C(C)(C)C)n4)n2)n3CC(F)(F)F)[C@@H](F)C1] | 2-tert-butyl-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1,3-thiazole-4-carboxamide | 594.2 |
| 439B | 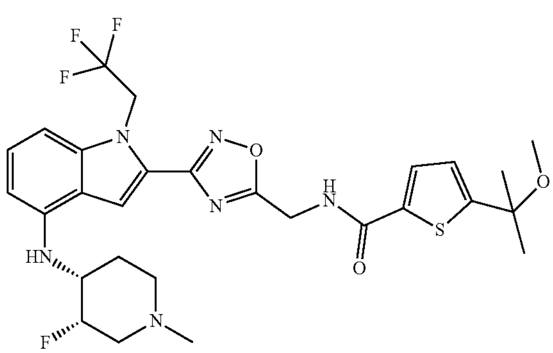 [SMILES: COC(C)(C)c1ccc(C(=O)NCc2nc(-c3cc4c(N[C@@H]5CCN(C)C[C@@H]5F)cccc4n3CC(F)(F)F)no2)s1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-5-(2-methoxypropan-2-yl)thiophene-2-carboxamide | 609.3 |

TABLE 9-continued

| Compound No. | Structure | IUPAC | LC-MS (ES+, m/z) |
|---|---|---|---|
| 440B | 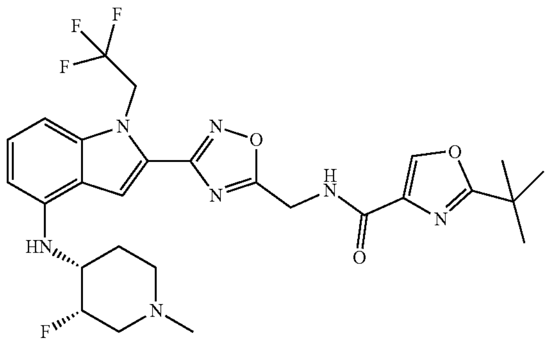 [SMILES: CN1CC[C@@H](Nc2cccc3c2cc(-c2noc(CNC(=O)c4coc(C(C)(C)C)n4)n2)n3CC(F)(F)F)[C@@H](F)C1] | 2-tert-butyl-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1,3-oxazole-4-carboxamide | 578.3 |
| 441B | 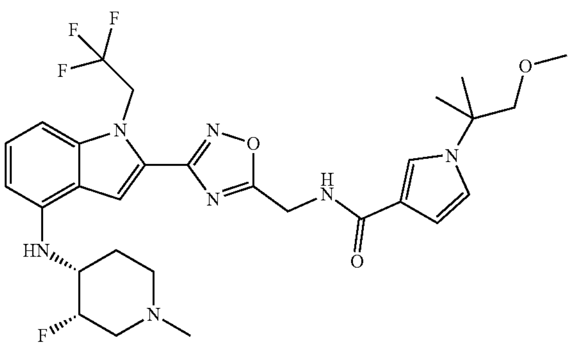 [SMILES: COCC(C)(C)n1ccc(C(=O)NCc2nc(-c3cc4c(N[C@@H]5CCN(C)C[C@@H]5F)cccc4n3CC(F)(F)F)no2)c1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(1-hydroxy-2-methylpropan-2-yl)-1H-pyrrole-3-carboxamide | 592.3 |
| 442B | 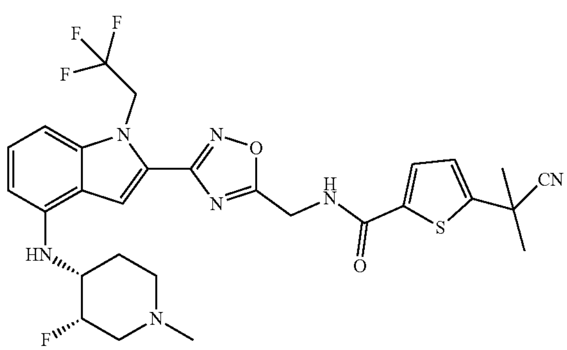 [SMILES: CN1CC[C@@H](Nc2cccc3c2cc(-c2noc(CNC(=O)c4ccc(C(C)(C)C#N)s4)n2)n3CC(F)(F)F)[C@@H](F)C1] | 5-(1-cyano-1-methylethyl)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}thiophene-2-carboxamide | 604.3 |
| 443B | 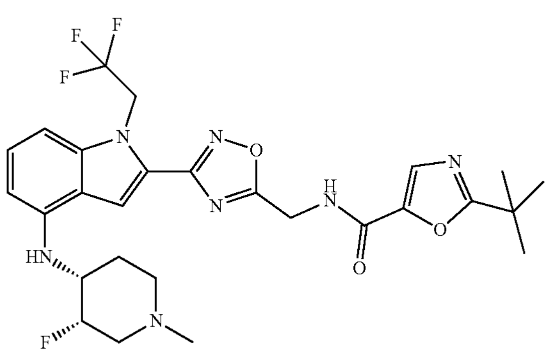 [SMILES: CN1CC[C@@H](Nc2cccc3c2cc(-c2noc(CNC(=O)c4cnc(C(C)(C)C)o4)n2)n3CC(F)(F)F)[C@@H](F)C1] | 2-tert-butyl-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1,3-oxazole-5-carboxamide | 578.3 |

TABLE 9-continued

| Compound No. | Structure | IUPAC | LC-MS (ES+, m/z) |
|---|---|---|---|
| 444B | 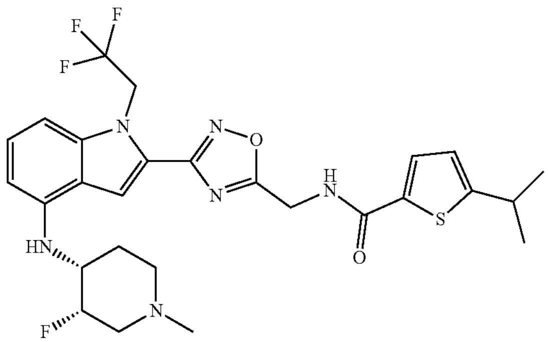 [SMILES: CC(C)c1ccc(C(=O)NCc2nc(-c3cc4c(N[C@@H]5CCN(C)C[C@@H]5F)cccc4n3CC(F)(F)F)no2)s1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-5-(propan-2-yl)thiophene-2-carboxamide | 579.2 |
| 445B | 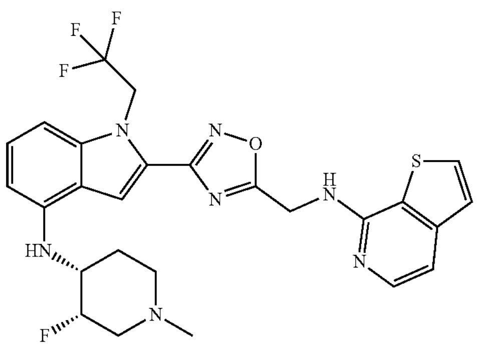 [SMILES: CN1CC[C@@H](Nc2cccc3c2cc(-c2noc(CNc4nccc5ccsc45)n2)n3CC(F)(F)F)[C@@H](F)C1] | N-[(3S,4R)-3-fluoro-1-methylpiperidin-4-yl]-2-{5-[({thieno[2,3-c]pyridin-7-yl}amino)methyl]-1,2,4-oxadiazol-3-yl}-1-(2,2,2-trifluoroethyl)-1H-indol-4-amine | 560.2 |
| 446B | 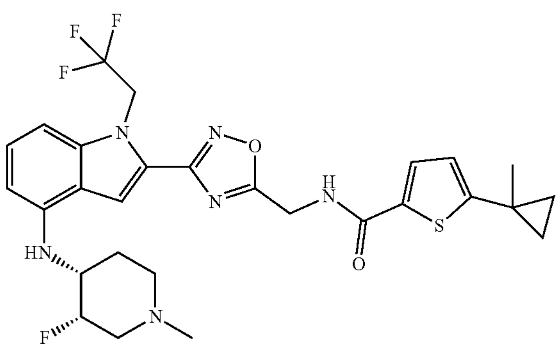 [SMILES: CN1CC[C@@H](Nc2cccc3c2cc(-c2noc(CNC(=O)c4ccc(C5(C)CC5)s4)n2)n3CC(F)(F)F)[C@@H](F)C1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-5-(1-methylcyclopropyl)thiophene-2-carboxamide | 591.3 |
| 447B | 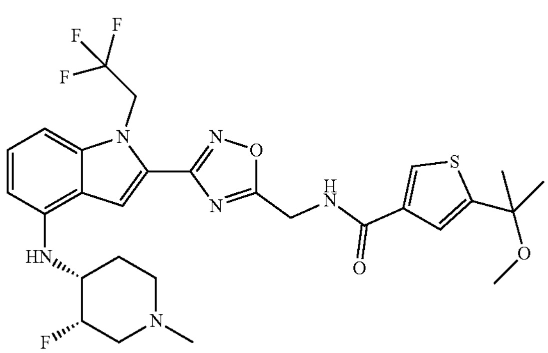 [SMILES: COC(C)(C)c1cc(C(=O)NCc2nc(-c3cc4c(N[C@@H]5CCN(C)C[C@@H]5F)cccc4n3CC(F)(F)F)no2)cs1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-5-(2-methoxypropan-2-yl)thiophene-3-carboxamide | 609.3 |

TABLE 9-continued

| Compound No. | Structure | IUPAC | LC-MS (ES+, m/z) |
|---|---|---|---|
| 448B | 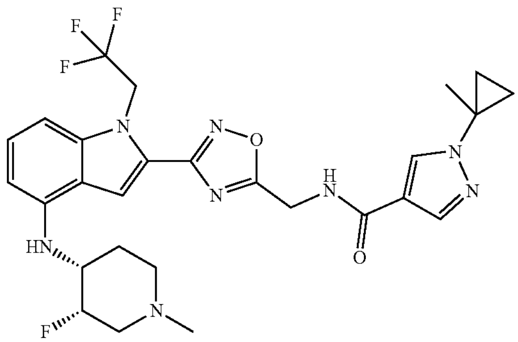 [SMILES: CN1CC[C@@H](Nc2cccc3c2cc(-c2noc(CNC(=O)c4cnn(C5(C)CC5)c4)n2)n3CC(F)(F)F)[C@@H](F)C1] | N-{3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(1-methylcyclopropyl)-1H-pyrazole-4-carboxamide | 575.3 |
| 449B | 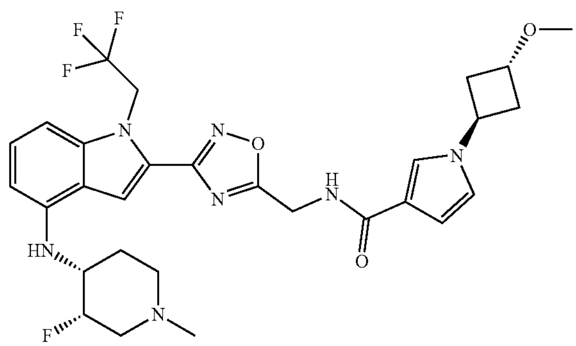 [SMILES: CO[C@H]1C[C@H](n2ccc(C(=O)NCc3nc(-c4cc5c(N[C@@H]6CCN(C)C[C@@H]6F)cccc5n4CC(F)(F)F)no3)c2)C1] | N-{3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-[(1r,3r)-3-methoxycyclobutyl]-1H-pyrrole-3-carboxamide | 604.3 |
| 450B | 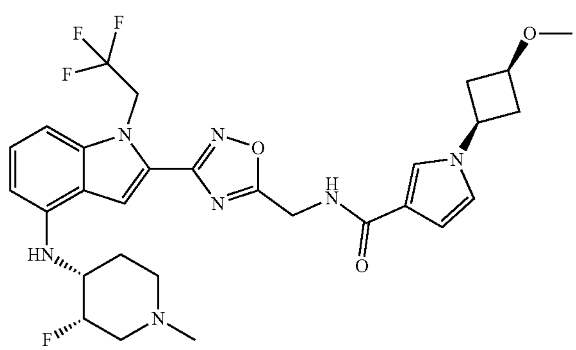 [SMILES: CO[C@H]1C[C@@H](n2ccc(C(=O)NCc3nc(-c4cc5c(N[C@@H]6CCN(C)C[C@@H]6F)cccc5n4CC(F)(F)F)no3)c2)C1] | N-{3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-[(1s,3s)-3-methoxycyclobutyl]-1H-pyrrole-3-carboxamide | 604.3 |
| 451B | 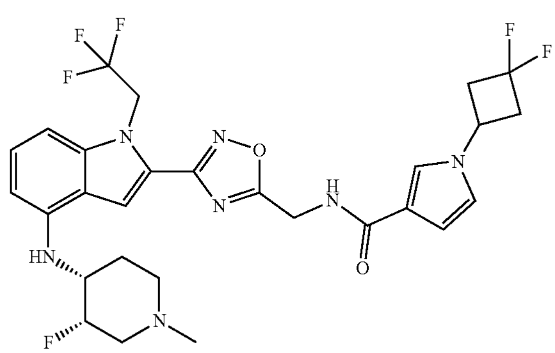 [SMILES: CN1CC[C@@H](Nc2cccc3c2cc(-c2noc(CNC(=O)c4ccn(C5CC(F)(F)C5)c4)n2)n3CC(F)(F)F)[C@@H](F)C1] | 1-(3,3-difluorocyclobutyl)-N-{3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-pyrrole-3-carboxamide | 610.3 |

TABLE 9-continued

| Compound No. | Structure | IUPAC | LC-MS (ES+, m/z) |
|---|---|---|---|
| 452B | 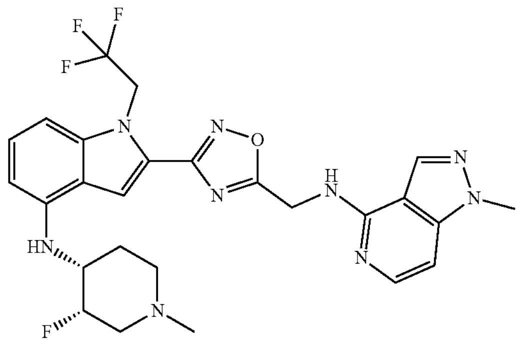 [SMILES: CN1CC[C@@H](Nc2cccc3c2cc(-c2noc(CNc4nccc5c4cnn5C)n2)n3CC(F)(F)F)[C@@H](F)C1] | N-[(3S,4R)-3-fluoro-1-methylpiperidin-4-yl]-2-{5-[({1-methyl-1H-pyrazolo[4,3-c]pyridin-4-yl}amino)methyl]-1,2,4-oxadiazol-3-yl}-1-(2,2,2-trifluoroethyl)-1H-indol-4-amine | 558.3 |
| 453B | 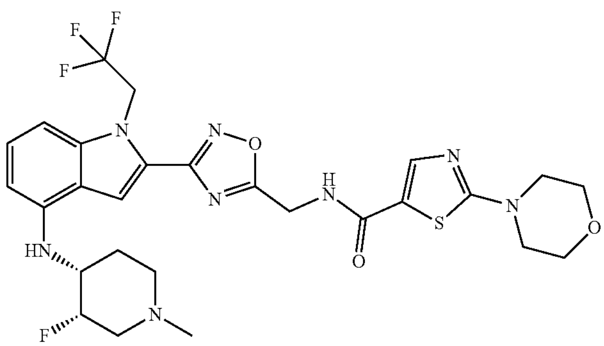 [SMILES: CN1CC[C@@H](Nc2cccc3c2cc(-c2noc(CNC(=O)c4cnc(N5CCOCC5)s4)n2)n3CC(F)(F)F)[C@@H](F)C1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-(morpholin-4-yl)-1,3-thiazole-5-carboxamide | 623.3 |
| 454B | 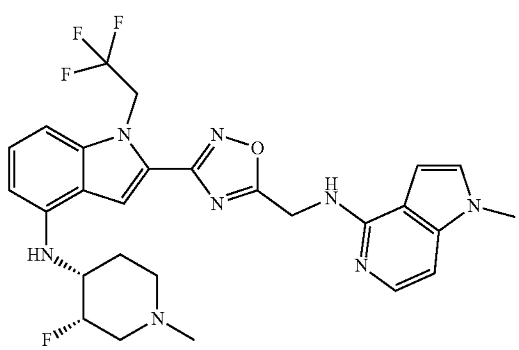 [SMILES: CN1CC[C@@H](Nc2cccc3c2cc(-c2noc(CNc4nccc5c4ccn5C)n2)n3CC(F)(F)F)[C@@H](F)C1] | N-[(3S,4R)-3-fluoro-1-methylpiperidin-4-yl]-2-{5-[({1-methyl-1H-pyrrolo[3,2-c]pyridin-4-yl}amino)methyl]-1,2,4-oxadiazol-3-yl}-1-(2,2,2-trifluoroethyl)-1H-indol-4-amine | 557.3 |
| 455B | 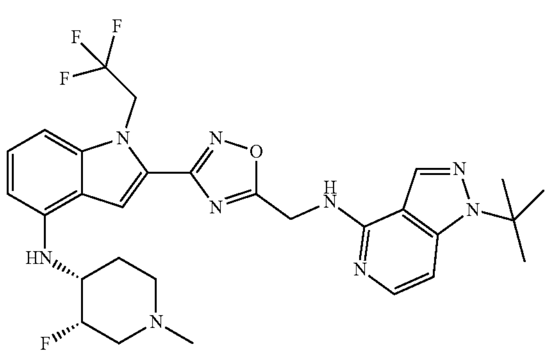 [SMILES: CN1CC[C@@H](Nc2cccc3c2cc(-c2noc(CNc4nccc5c4cnn5C(C)(C)C)n2)n3CC(F)(F)F)[C@@H](F)C1] | 2-{5-[({1-tert-butyl-1H-pyrazolo[4,3-c]pyridin-4-yl}amino)methyl]-1,2,4-oxadiazol-3-yl}-N-[(3S,4R)-3-fluoro-1-methylpiperidin-4-yl]-1-(2,2,2-trifluoroethyl)-1H-indol-4-amine | 603.3 |

TABLE 9-continued

| Compound No. | Structure | IUPAC | LC-MS (ES+, m/z) |
|---|---|---|---|
| 456B | 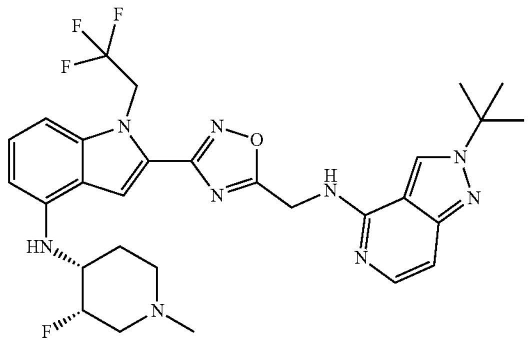 [SMILES: CN1CC[C@@H](Nc2cccc3c2cc(-c2noc(CNc4nccc5nn(C(C)(C)C)cc45)n2)n3CC(F)(F)F)[C@@H](F)C1] | 2-{5-[({2-tert-butyl-2H-pyrazolo[4,3-c]pyridin-4-yl}amino)methyl]-1,2,4-oxadiazol-3-yl}-N-[(3S,4R)-3-fluoro-1-methylpiperidin-4-yl]-1-(2,2,2-trifluoroethyl)-1H-indol-4-amine | 603.3 |
| 457B | 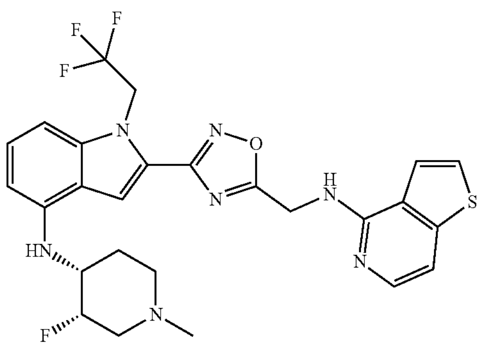 [SMILES: CN1CC[C@@H](Nc2cccc3c2cc(-c2noc(CNc4nccc5sccc45)n2)n3CC(F)(F)F)[C@@H](F)C1] | N-[(3S,4R)-3-fluoro-1-methylpiperidin-4-yl]-2-{5-[({thieno[3,2-c]pyridin-4-yl}amino)methyl]-1,2,4-oxadiazol-3-yl}-1-(2,2,2-trifluoroethyl)-1H-indol-4-amine | 560.2 |
| 458B | 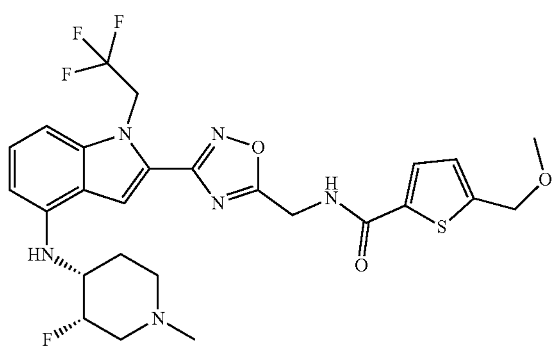 [SMILES: COCc1ccc(C(=O)NCc2nc(-c3cc4c(N[C@@H]5CCN(C)C[C@@H]5F)cccc4n3CC(F)(F)F)no2)s1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-5-(methoxymethyl)thiophene-2-carboxamide | 581.3 |
| 459B | 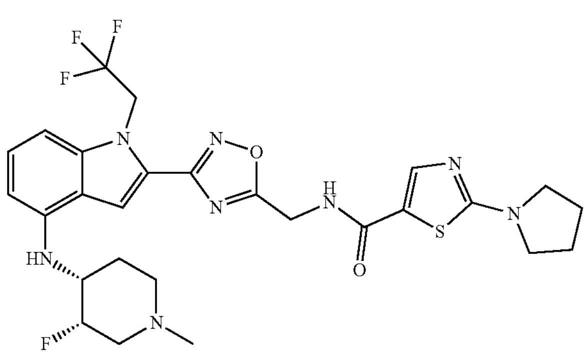 [SMILES: CN1CC[C@@H](Nc2cccc3c2cc(-c2noc(CNC(=O)c4cnc(N5CCCC5)s4)n2)n3CC(F)(F)F)[C@@H](F)C1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-(pyrrolidin-1-yl)-1,3-thiazole-5-carboxamide | 607.3 |

TABLE 9-continued

| Compound No. | Structure | IUPAC | LC-MS (ES+, m/z) |
|---|---|---|---|
| 460B | 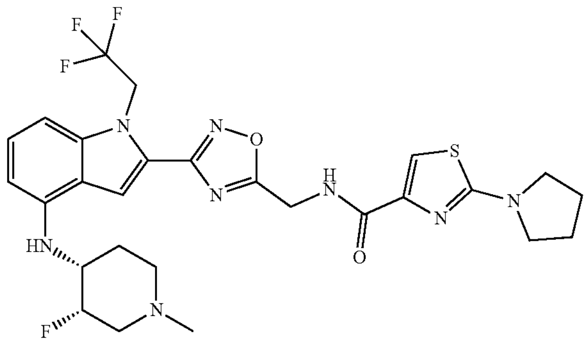 [SMILES: CN1CC[C@@H](Nc2cccc3c2cc(-c2noc(CNC(=O)c4csc(N5CCCC5)n4)n2)n3CC(F)(F)F)[C@@H](F)C1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-(pyrrolidin-1-yl)-1,3-thiazole-4-carboxamide | 607.3 |
| 461B | 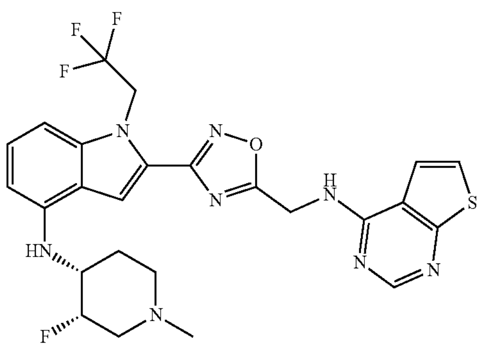 [SMILES: CN1CC[C@@H](Nc2cccc3c2cc(-c2noc(CNc4ncnc5sccc45)n2)n3CC(F)(F)F)[C@@H](F)C1] | N-[(3S,4R)-3-fluoro-1-methylpiperidin-4-yl]-2-{5-[({thieno[2,3-d]pyrimidin-4-yl}amino)methyl]-1,2,4-oxadiazol-3-yl}-1-(2,2,2-trifluoroethyl)-1H-indol-4-amine | 561.2 |
| 462B | 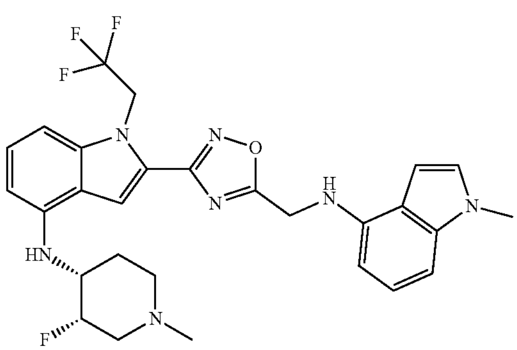 [SMILES: CN1CC[C@@H](Nc2cccc3c2cc(-c2noc(CNc4cccc5c4ccn5C)n2)n3CC(F)(F)F)[C@@H](F)C1] | N-[(3S,4R)-3-fluoro-1-methylpiperidin-4-yl]-2-(5-{[(1-methyl-1H-indol-4-yl)amino]methyl}-1,2,4-oxadiazol-3-yl)-1-(2,2,2-trifluoroethyl)-1H-indol-4-amine | 556.2 |
| 463B | 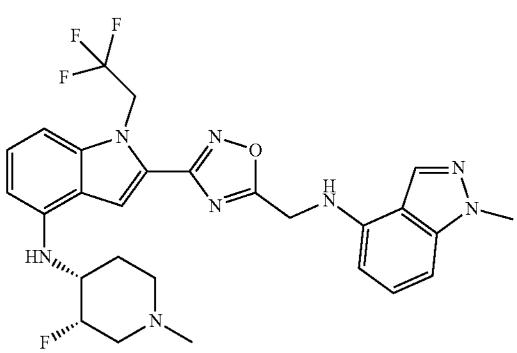 [SMILES: CN1CC[C@@H](Nc2cccc3c2cc(-c2noc(CNc4cccc5c4cnn5C)n2)n3CC(F)(F)F)[C@@H](F)C1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-methyl-1H-indazol-4-amine | 557.3 |

TABLE 9-continued

| Compound No. | Structure | IUPAC | LC-MS (ES+, m/z) |
|---|---|---|---|
| 464B | 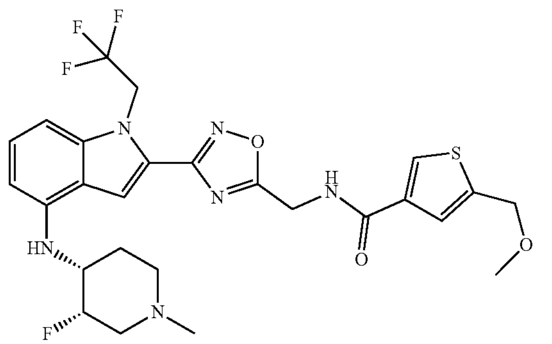 [SMILES: COCc1cc(C(=O)NCc2nc(-c3cc4c(N[C@@H]5CCN(C)C[C@@H]5F)cccc4n3CC(F)(F)F)no2)cs1] | N-{3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-5-(methoxymethyl)thiophene-3-carboxamide | 581.2 |
| 465B | 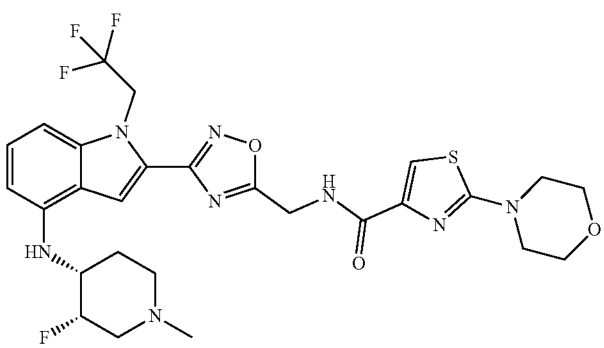 [SMILES: CN1CC[C@@H](Nc2cccc3c2cc(-c2noc(CNC(=O)c4csc(N5CCOCC5)n4)n2)n3CC(F)(F)F)[C@@H](F)C1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-(morpholin-4-yl)-1,3-thiazole-4-carboxamide | 623.1 |
| 466B | 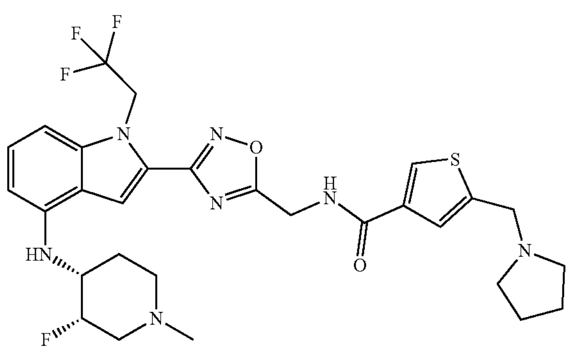 [SMILES: CN1CC[C@@H](Nc2cccc3c2cc(-c2noc(CNC(=O)c4csc(CN5CCCC5)c4)n2)n3CC(F)(F)F)[C@@H](F)C1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-5-[(pyrrolidin-1-yl)methyl]thiophene-3-carboxamide | 620.3 |
| 467B | 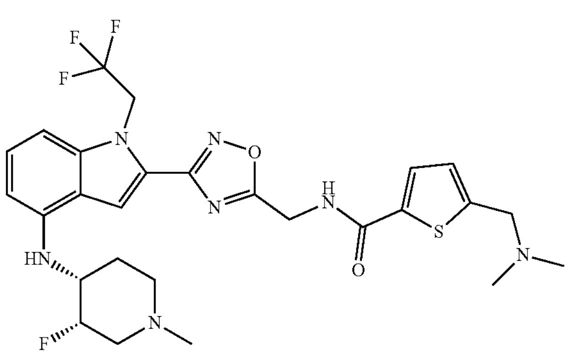 [SMILES: CN(C)Cc1ccc(C(=O)NCc2nc(-c3cc4c(N[C@@H]5CCN(C)C[C@@H]5F)cccc4n3CC(F)(F)F)no2)s1] | 5-[(dimethylamino)methyl]-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}thiophene-2-carboxamide | 594.3 |

TABLE 9-continued

| Compound No. | Structure | IUPAC | LC-MS (ES+, m/z) |
| --- | --- | --- | --- |
| 468B | 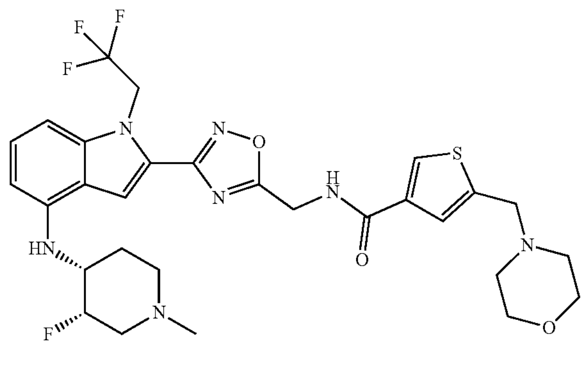 [SMILES: CN1CC[C@@H](Nc2cccc3c2cc(-c2noc(CNC(=O)c4csc(CN5CCOCC5)c4)n2)n3CC(F)(F)F)[C@@H](F)C1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-5-[(morpholin-4-yl)methyl]thiophene-3-carboxamide | 636.3 |
| 469B | 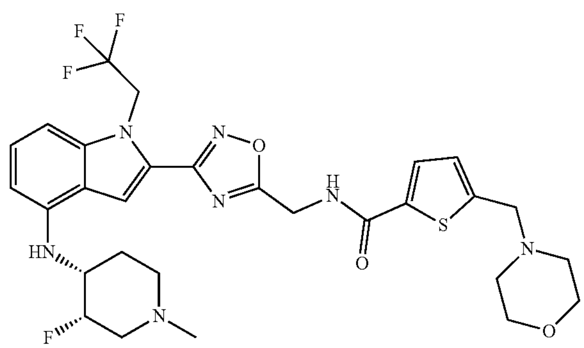 [SMILES: CN1CC[C@@H](Nc2cccc3c2cc(-c2noc(CNC(=O)c4ccc(CN5CCOCC5)s4)n2)n3CC(F)(F)F)[C@@H](F)C1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-5-[(morpholin-4-yl)methyl]thiophene-2-carboxamide | 636.3 |
| 470B | 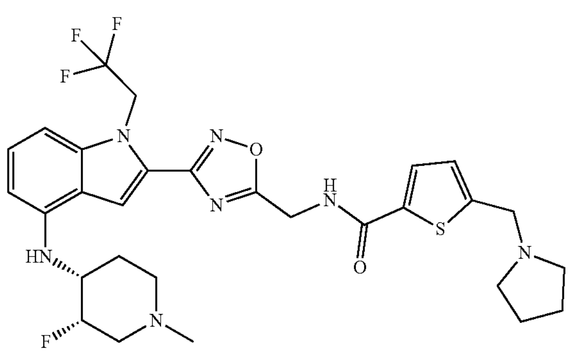 [SMILES: CN1CC[C@@H](Nc2cccc3c2cc(-c2noc(CNC(=O)c4ccc(CN5CCCC5)s4)n2)n3CC(F)(F)F)[C@@H](F)C1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-5-[(pyrrolidin-1-yl)methyl]thiophene-2-carboxamide | 620.3 |
| 471B | 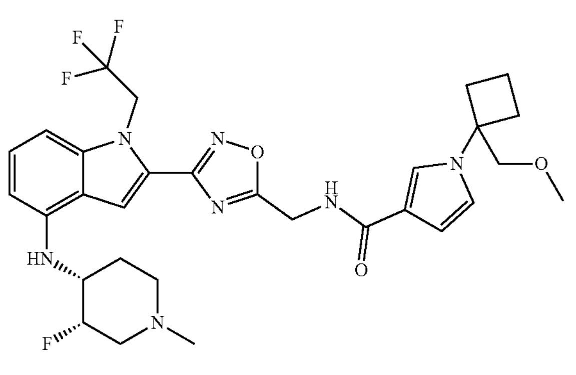 [SMILES: COCC1(n2ccc(C(=O)NCc3nc(-c4cc5c(N[C@@H]6CCN(C)C[C@@H]6F)cccc5n4CC(F)(F)F)no3)c2)CCC1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-[1-(methoxymethyl)cyclobutyl]-1H-pyrrole-3-carboxamide | 618.3 |

TABLE 9-continued

| Compound No. | Structure | IUPAC | LC-MS (ES+, m/z) |
|---|---|---|---|
| 472B | 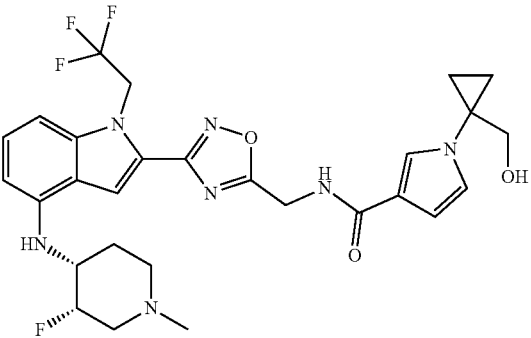 [SMILES: CN1CC[C@@H](Nc2cccc3c2cc(-c2noc(CNC(=O)c4ccn(C5(CO)CC5)c4)n2)n3CC(F)(F)F)[C@@H](F)C1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-[1-(hydroxymethyl)cyclopropyl]-1H-pyrrole-3-carboxamide | 590.3 |
| 473B | 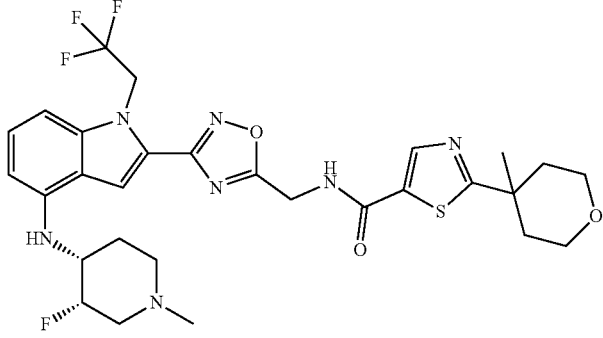 [SMILES: CN1CC[C@@H](Nc2cccc3c2cc(-c2noc(CNC(=O)c4cnc(C5(C)CCOCC5)s4)n2)n3CC(F)(F)F)[C@@H](F)C1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-(4-methyloxan-4-yl)-1,3-thiazole-5-carboxamide | 636.3 |
| 474B | 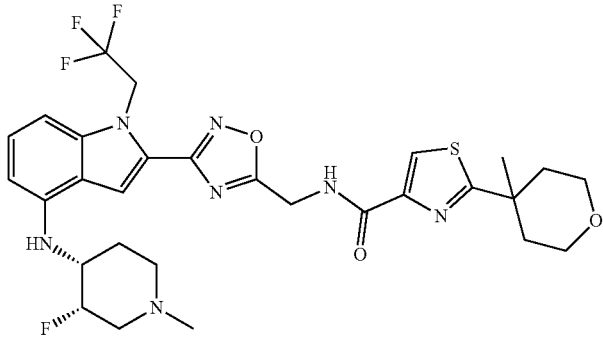 [SMILES: CN1CC[C@@H](Nc2cccc3c2cc(-c2noc(CNC(=O)c4csc(C5(C)CCOCC5)n4)n2)n3CC(F)(F)F)[C@@H](F)C1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-(4-methyloxan-4-yl)-1,3-thiazole-4-carboxamide | 636.3 |
| 475B | 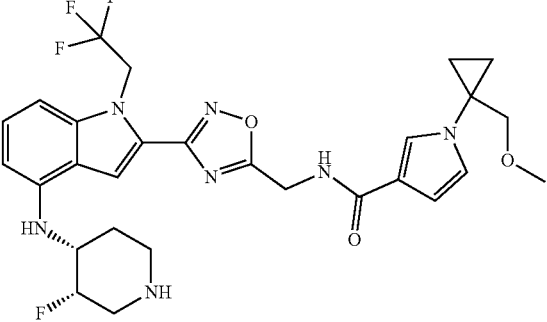 | N-{[3-(4-{[(3S,4R)-3-fluoropiperidin-4-yl]amino}-1-(2,2,2-trifluoroethyl)-1H-indol-2-yl)-1,2,4-oxadiazol-5-yl]methyl}-1-[1-(methoxymethyl)cyclopropyl]-1H-pyrrole-3-carboxamide | 590.2 |

TABLE 9-continued

| Compound No. | Structure | IUPAC | LC-MS (ES+, m/z) |
|---|---|---|---|
| 476B | 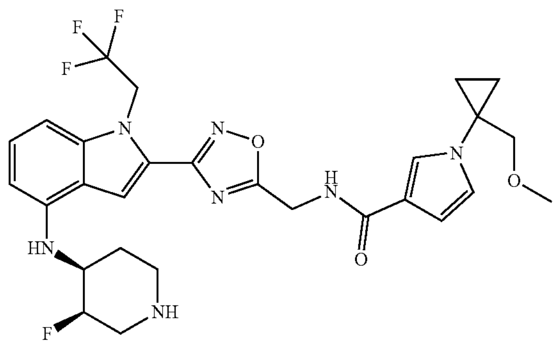 [SMILES: COCC1(n2ccc(C(=O)NCc3nc(-c4cc5c(N[C@H]6CCNC[C@H]6F)cccc5n4CC(F)(F)F)no3)c2)CC1] | N-{[3-(4-{[(3R,4S)-3-fluoropiperidin-4-yl]amino}-1-(2,2,2-trifluoroethyl)-1H-indol-2-yl)-1,2,4-oxadiazol-5-yl]methyl}-1-[1-(methoxymethyl)cyclopropyl]-1H-pyrrole-3-carboxamide | 590.3 |
| 477B | 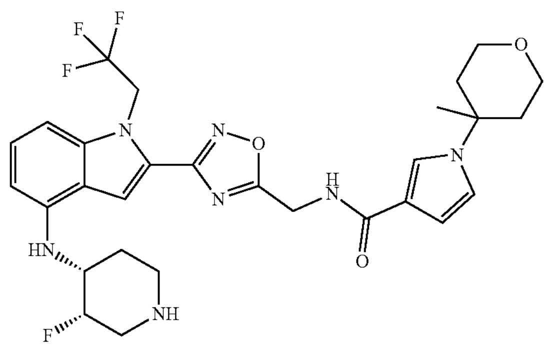 [SMILES: CC1(n2ccc(C(=O)NCc3nc(-c4cc5c(N[C@@H]6CCNC[C@@H]6F)cccc5n4CC(F)(F)F)no3)c2)CCOCC1] | N-{[3-(4-{[(3S,4R)-3-fluoropiperidin-4-yl]amino}-1-(2,2,2-trifluoroethyl)-1H-indol-2-yl)-1,2,4-oxadiazol-5-yl]methyl}-1-(4-methyloxan-4-yl)-1H-pyrrole-3-carboxamide | 604.4 |
| 478B | 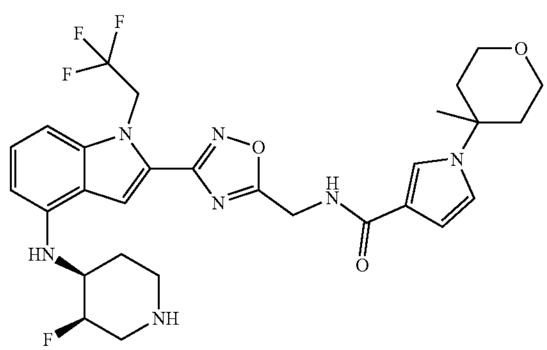 [SMILES: CC1(n2ccc(C(=O)NCc3nc(-c4cc5c(N[C@H]6CCNC[C@H]6F)cccc5n4CC(F)(F)F)no3)c2)CCOCC1] | N-{[3-(4-{[(3R,4S)-3-fluoropiperidin-4-yl]amino}-1-(2,2,2-trifluoroethyl)-1H-indol-2-yl)-1,2,4-oxadiazol-5-yl]methyl}-1-(4-methyloxan-4-yl)-1H-pyrrole-3-carboxamide | 604.2 |
| 479B | 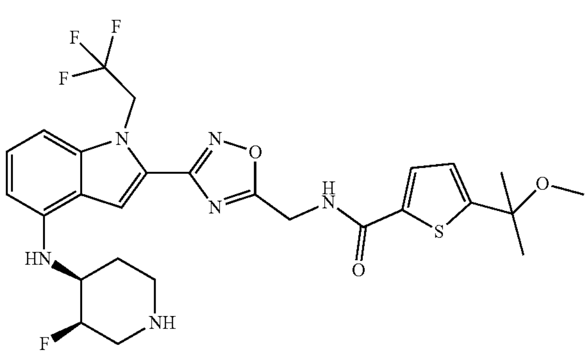 [SMILES: COC(C)(C)c1ccc(C(=O)NCc2nc(-c3cc4c(N[C@H]5CCNC[C@H]5F)cccc4n3CC(F)(F)F)no2)s1] | N-{[3-(4-{[(3R,4S)-3-fluoropiperidin-4-yl]amino}-1-(2,2,2-trifluoroethyl)-1H-indol-2-yl)-1,2,4-oxadiazol-5-yl]methyl}-5-(2-methoxypropan-2-yl)thiophene-2-carboxamide | 595.2 |

TABLE 9-continued

| Compound No. | Structure | IUPAC | LC-MS (ES+, m/z) |
|---|---|---|---|
| 480B | 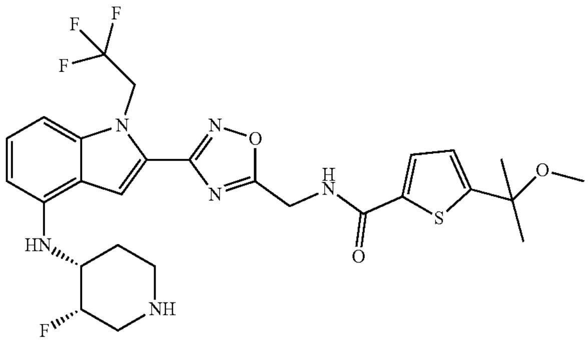 [SMILES: COC(C)(C)c1ccc(C(=O)NCc2nc(-c3cc4c(N[C@@H]5CCNC[C@@H]5F)cccc4n3CC(F)(F)F)no2)s1] | N-{[3-(4-{[(3S,4R)-3-fluoropiperidin-4-yl]amino}-1-(2,2,2-trifluoroethyl)-1H-indol-2-yl)-1,2,4-oxadiazol-5-yl]methyl}-5-(2-methoxypropan-2-yl)thiophene-2-carboxamide | 595.2 |
| 481B | 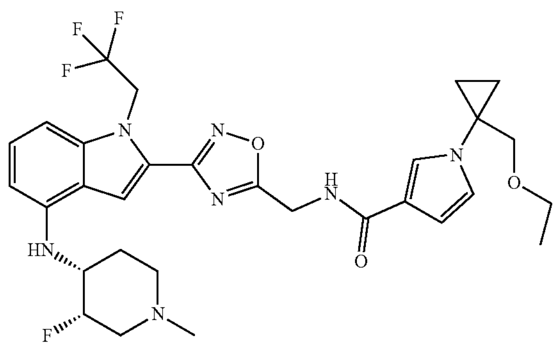 [SMILES: CCOCC1(n2ccc(C(=O)NCc3nc(-c4cc5c(N[C@@H]6CCN(C)C[C@@H]6F)cccc5n4CC(F)(F)F)no3)c2)CC1] | 1-[1-(ethoxymethyl)cyclopropyl]-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-pyrrole-3-carboxamide | 618.3 |
| 482B | 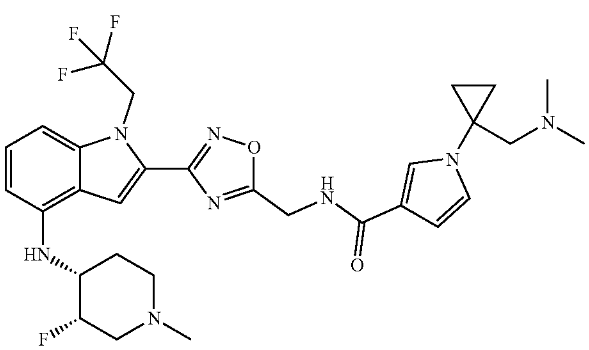 [SMILES: CN(C)CC1(n2ccc(C(=O)NCc3nc(-c4cc5c(N[C@@H]6CCN(C)C[C@@H]6F)cccc5n4CC(F)(F)F)no3)c2)CC1] | 1-{1-[(dimethylamino)methyl]cyclopropyl}-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-pyrrole-3-carboxamide | 617.4 |
| 483B | 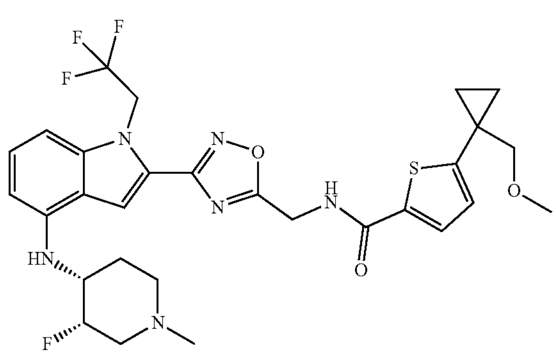 [SMILES: COCC1(c2ccc(C(=O)NCc3nc(-c4cc5c(N[C@@H]6CCN(C)C[C@@H]6F)cccc5n4CC(F)(F)F)no3)s2)CC1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-5-[1-(methoxymethyl)cyclopropyl]thiophene-2-carboxamide | 621.2 |

TABLE 9-continued

| Compound No. | Structure | IUPAC | LC-MS (ES+, m/z) |
|---|---|---|---|
| 484B | 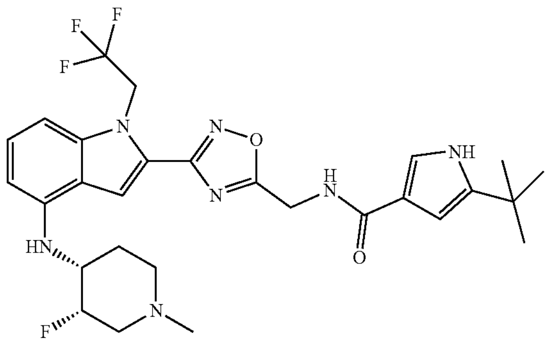 [SMILES: CN1CC[C@@H](Nc2cccc3c2cc(-c2noc(CNC(=O)c4c[nH]c(C(C)(C)C)c4)n2)n3CC(F)(F)F)[C@@H](F)C1] | 5-tert-butyl-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-pyrrole-3-carboxamide | 576.3 |
| 485B | 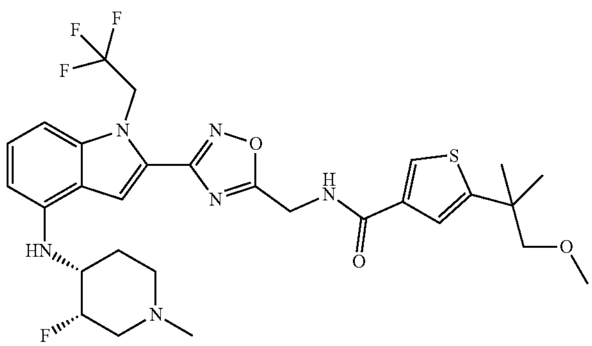 [SMILES: COCC(C)(C)c1cc(C(=O)NCc2nc(-c3cc4c(N[C@@H]5CCN(C)C[C@@H]5F)cccc4n3CC(F)(F)F)no2)cs1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-5-(1-methoxy-2-methylpropan-2-yl)thiophene-3-carboxamide | 623.2 |
| 486B | 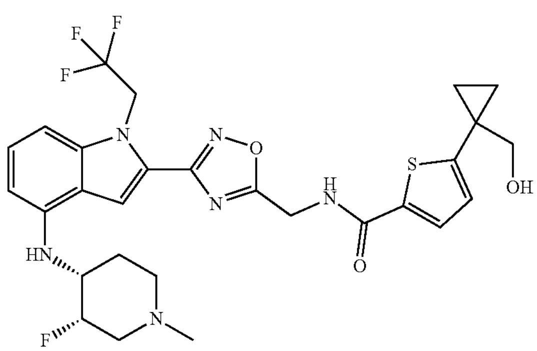 [SMILES: CN1CC[C@@H](Nc2cccc3c2cc(-c2noc(CNC(=O)c4ccc(C5(CO)CC5)s4)n2)n3CC(F)(F)F)[C@@H](F)C1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-5-[1-(hydroxymethyl)cyclopropyl]thiophene-2-carboxamide | 607.1 |
| 487B | 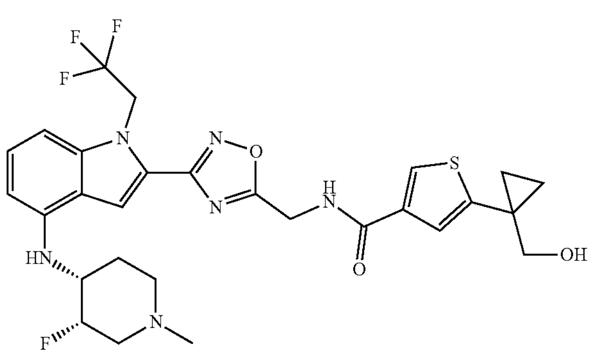 [SMILES: CN1CC[C@@H](Nc2cccc3c2cc(-c2noc(CNC(=O)c4csc(C5(CO)CC5)c4)n2)n3CC(F)(F)F)[C@@H](F)C1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-5-[1-(hydroxymethyl)cyclopropyl]thiophene-3-carboxamide | 607.1 |

TABLE 9-continued

| Compound No. | Structure | IUPAC | LC-MS (ES+, m/z) |
|---|---|---|---|
| 488B | 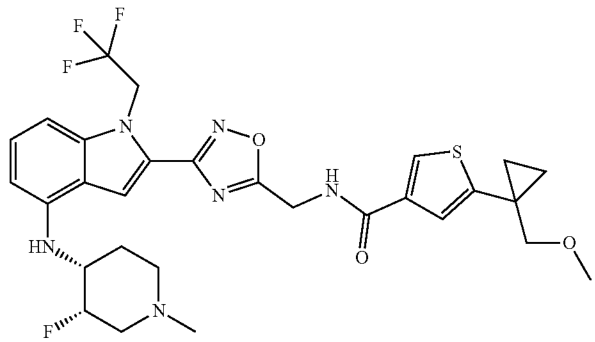 [SMILES: COCC1(c2cc(C(=O)NCc3nc(-c4cc5c(N[C@@H]6CCN(C)C[C@@H]6F)cccc5n4CC(F)(F)F)no3)cs2)CC1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-5-[1-(methoxymethyl)cyclopropyl]thiophene-3-carboxamide | 621.1 |
| 489B | 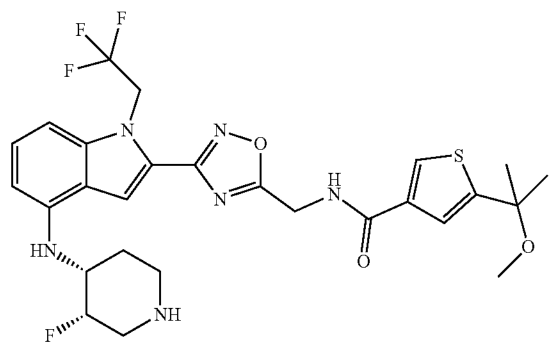 [SMILES: COC(C)(C)c1cc(C(=O)NCc2nc(-c3cc4c(N[C@@H]5CCNC[C@@H]5F)cccc4n3CC(F)(F)F)no2)cs1] | N-{[3-(4-{[(3S,4R)-3-fluoropiperidin-4-yl]amino}-1-(2,2,2-trifluoroethyl)-1H-indol-2-yl)-1,2,4-oxadiazol-5-yl]methyl}-5-(2-methoxypropan-2-yl)thiophene-3-carboxamide | 595.3 |
| 490B | 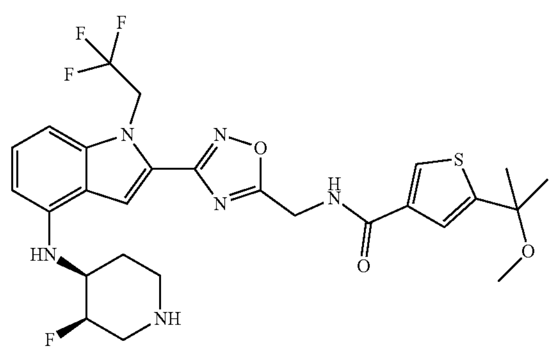 [SMILES: COC(C)(C)c1cc(C(=O)NCc2nc(-c3cc4c(N[C@H]5CCNC[C@H]5F)cccc4n3CC(F)(F)F)no2)cs1] | N-{[3-(4-{[(3R,4S)-3-fluoropiperidin-4-yl]amino}-1-(2,2,2-trifluoroethyl)-1H-indol-2-yl)-1,2,4-oxadiazol-5-yl]methyl}-5-(2-methoxypropan-2-yl)thiophene-3-carboxamide | 595.2 |
| 491B | 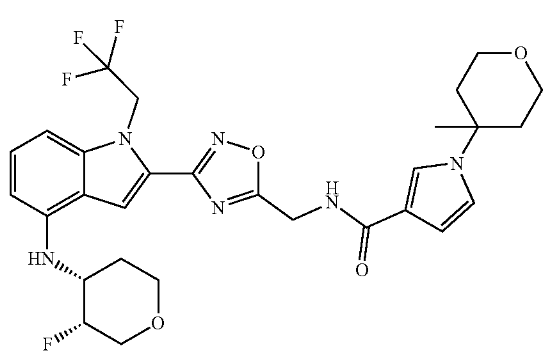 [SMILES: CC1(n2ccc(C(=O)NCc3nc(-c4cc5c(N[C@@H]6CCOC[C@@H]6F)cccc5n4CC(F)(F)F)no3)c2)CCOCC1] | N-{[3-(4-{[(3S,4S)-3-fluorooxan-4-yl]amino}-1-(2,2,2-trifluoroethyl)-1H-indol-2-yl)-1,2,4-oxadiazol-5-yl]methyl}-1-(4-methyloxan-4-yl)-1H-pyrrole-3-carboxamide | 605.3 |

TABLE 9-continued

| Compound No. | Structure | IUPAC | LC-MS (ES+, m/z) |
|---|---|---|---|
| 492B | 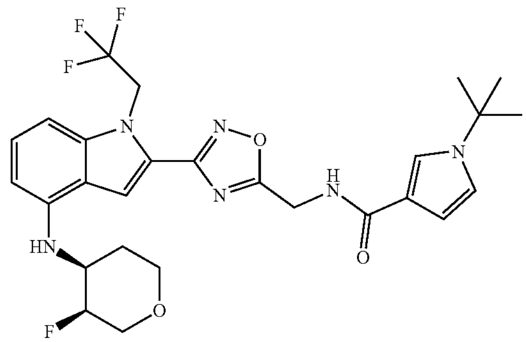 | 1-tert-butyl-N-{[3-(4-{[(3S,4S)-3-fluorooxan-4-yl]amino}-1-(2,2,2-trifluoroethyl)-1H-indol-2-yl)-1,2,4-oxadiazol-5-yl]methyl}-1H-pyrrole-3-carboxamide | 563.2 |
| 493B | 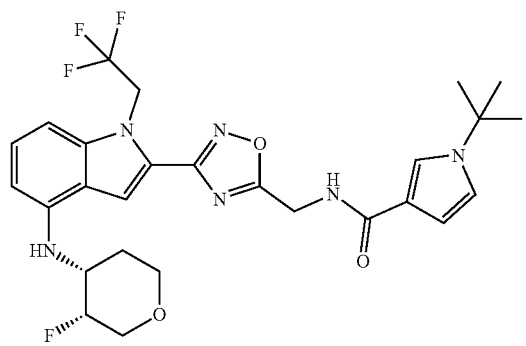 | 1-tert-butyl-N-{[3-(4-{[(3R,4R)-3-fluorooxan-4-yl]amino}-1-(2,2,2-trifluoroethyl)-1H-indol-2-yl)-1,2,4-oxadiazol-5-yl]methyl}-1H-pyrrole-3-carboxamide | 563.3 |
| 494B | 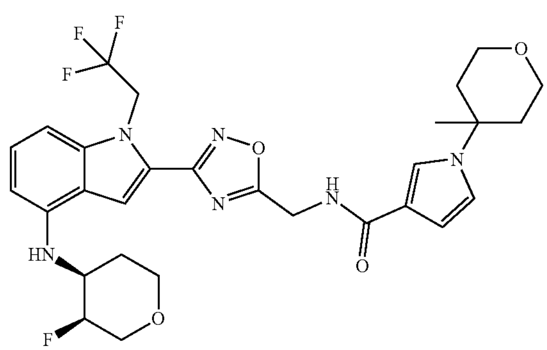 [SMILES: CC1(n2ccc(C(=O)NCc3nc(-c4cc5c(N[C@H]6CCOC[C@H]6F)cccc5n4CC(F)(F)F)no3)c2)CCOCC1] | N-{[3-(4-{[(3R,4R)-3-fluorooxan-4-yl]amino}-1-(2,2,2-trifluoroethyl)-1H-indol-2-yl)-1,2,4-oxadiazol-5-yl]methyl}-1-(4-methyloxan-4-yl)-1H-pyrrole-3-carboxamide | 605.2 |
| 495B | 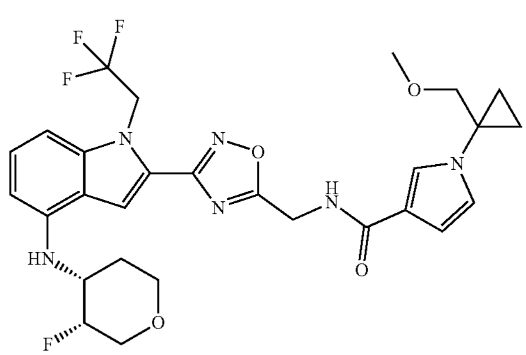 [SMILES: COCC1(n2ccc(C(=O)NCc3nc(-c4cc5c(N[C@@H]6CCOC[C@@H]6F)cccc5n4CC(F)(F)F)no3)c2)CC1] | N-{[3-(4-{[(3R,4R)-3-fluorooxan-4-yl]amino}-1-(2,2,2-trifluoroethyl)-1H-indol-2-yl)-1,2,4-oxadiazol-5-yl]methyl}-1-[1-(methoxymethyl)cyclopropyl]-1H-pyrrole-3-carboxamide | 591.2 |

TABLE 9-continued

| Compound No. | Structure | IUPAC | LC-MS (ES+, m/z) |
|---|---|---|---|
| 496B | 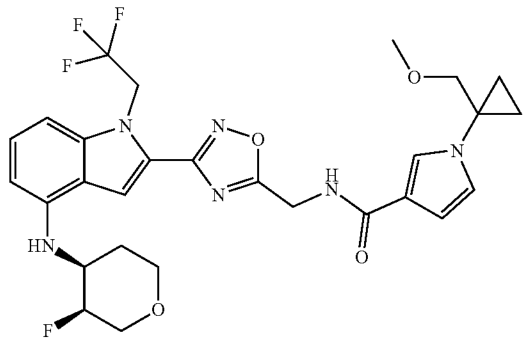 [SMILES: COCC1(n2ccc(C(=O)NCc3nc(-c4cc5c(N[C@H]6CCOC[C@H]6F)cccc5n4CC(F)(F)F)no3)c2)CC1] | N-{[3-(4-{[(3S,4S)-3-fluorooxan-4-yl]amino}-1-(2,2,2-trifluoroethyl)-1H-indol-2-yl)-1,2,4-oxadiazol-5-yl]methyl}-1-[1-(methoxymethyl)cyclopropyl]-1H-pyrrole-3-carboxamide | 591.3 |
| 497B | 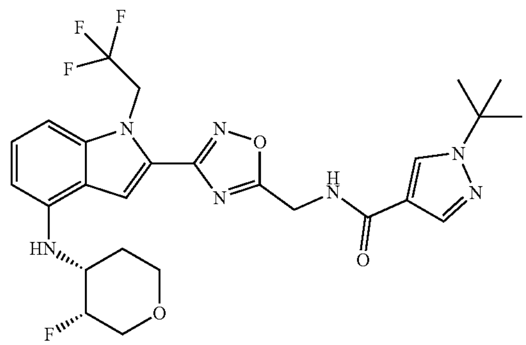 [SMILES: CC(C)(C)n1cc(C(=O)NCc2nc(-c3cc4c(N[C@@H]5CCOC[C@@H]5F)cccc4n3CC(F)(F)F)no2)cn1] | 1-tert-butyl-N-{[3-(4-{[(3R,4R)-3-fluorooxan-4-yl]amino}-1-(2,2,2-trifluoroethyl)-1H-indol-2-yl)-1,2,4-oxadiazol-5-yl]methyl}-1H-pyrazole-4-carboxamide | 564.1 |
| 498B | 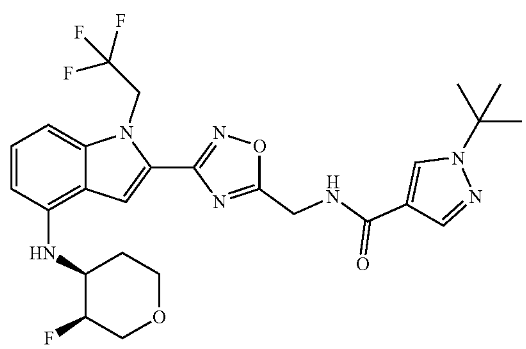 [SMILES: CC(C)(C)n1cc(C(=O)NCc2nc(-c3cc4c(N[C@H]5CCOC[C@H]5F)cccc4n3CC(F)(F)F)no2)cn1] | 1-tert-butyl-N-{[3-(4-{[(3S,4S)-3-fluorooxan-4-yl]amino}-1-(2,2,2-trifluoroethyl)-1H-indol-2-yl)-1,2,4-oxadiazol-5-yl]methyl}-1H-pyrazole-4-carboxamide | 564.3 |
| 499B | 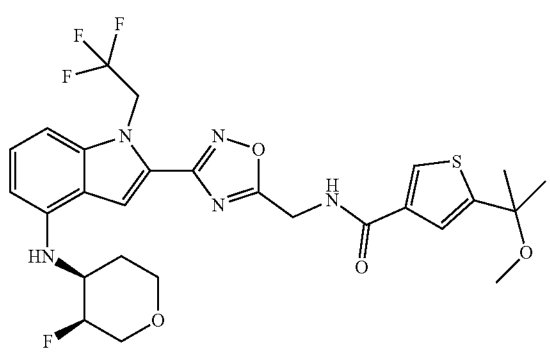 [SMILES: COC(C)(C)c1cc(C(=O)NCc2nc(-c3cc4c(N[C@H]5CCOC[C@H]5F)cccc4n3CC(F)(F)F)no2)cs1] | N-{[3-(4-{[(3S,4S)-3-fluorooxan-4-yl]amino}-1-(2,2,2-trifluoroethyl)-1H-indol-2-yl)-1,2,4-oxadiazol-5-yl]methyl}-5-(2-methoxypropan-2-yl)thiophene-3-carboxamide | 564.2 (M − OMe)+ |

TABLE 9-continued

| Compound No. | Structure | IUPAC | LC-MS (ES+, m/z) |
|---|---|---|---|
| 500B | 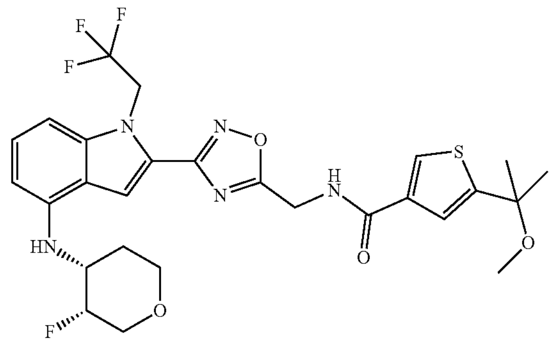 [SMILES: COC(C)(C)c1cc(C(=O)NCc2nc(-c3cc4c(N[C@@H]5CCOC[C@@H]5F)cccc4n3CC(F)(F)F)no2)cs1] | N-{[3-(4-{[(3R,4R)-3-fluorooxan-4-yl]amino}-1-(2,2,2-trifluoroethyl)-1H-indol-2-yl)-1,2,4-oxadiazol-5-yl]methyl}-5-(2-methoxypropan-2-yl)thiophene-3-carboxamide | 564.2 (M − OMe)+ |
| 501B | 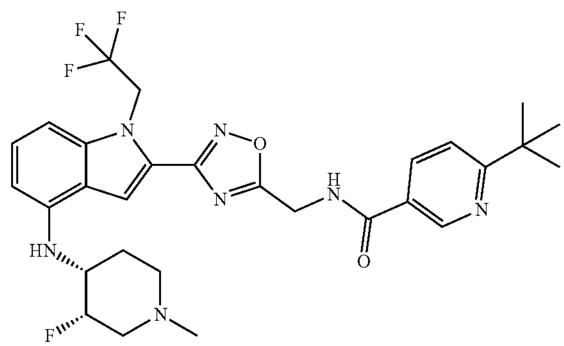 [SMILES: CN1CC[C@@H](Nc2cccc3c2cc(-c2noc(CNC(=O)c4ccc(C(C)(C)C)nc4)n2)n3CC(F)(F)F)[C@@H](F)C1] | 6-tert-butyl-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}pyridine-3-carboxamide | 588.1 |
| 502B | 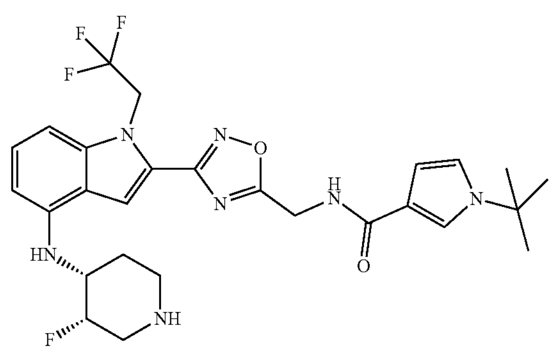 [SMILES: CC(C)(C)n1ccc(C(=O)NCc2nc(-c3cc4c(N[C@@H]5CCNC[C@@H]5F)cccc4n3CC(F)(F)F)no2)c1] | 1-tert-butyl-N-{[3-(4-{[(3S,4R)-3-fluoropiperidin-4-yl]amino}-1-(2,2,2-trifluoroethyl)-1H-indol-2-yl)-1,2,4-oxadiazol-5-yl]methyl}-1H-pyrrole-3-carboxamide | 562.4 |
| 503B | 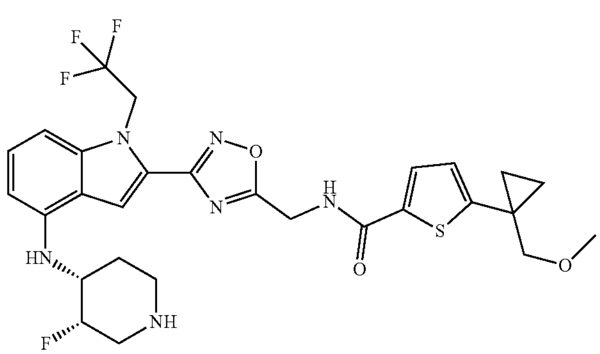 [SMILES: COCC1(c2ccc(C(=O)NCc3nc(-c4cc5c(N[C@@H]6CCNC[C@@H]6F)cccc5n4CC(F)(F)F)no3)s2)CC1] | N-{[3-(4-{[(3S,4R)-3-fluoropiperidin-4-yl]amino}-1-(2,2,2-trifluoroethyl)-1H-indol-2-yl)-1,2,4-oxadiazol-5-yl]methyl}-5-[1-(methoxymethyl)cyclopropyl]thiophene-2-carboxamide | 607.0 |

TABLE 9-continued

| Compound No. | Structure | IUPAC | LC-MS (ES+, m/z) |
|---|---|---|---|
| 504B | 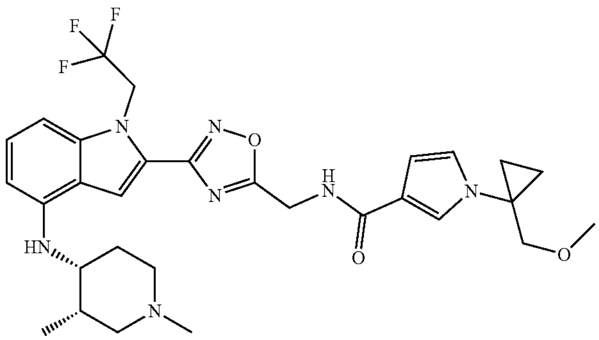 [SMILES: COCC1(n2ccc(C(=O)NCc3nc(-c4cc5c(N[C@@H]6CCN(C)C[C@@H]6C)cccc5n4CC(F)(F)F)no3)c2)CC1] | N-{[3-(4-{[(3S,4R)-1,3-dimethylpiperidin-4-yl]amino}-1-(2,2,2-trifluoroethyl)-1H-indol-2-yl)-1,2,4-oxadiazol-5-yl]methyl}-1-[1-(methoxymethyl)cyclopropyl]-1H-pyrrole-3-carboxamide | 600.2 |
| 505B | 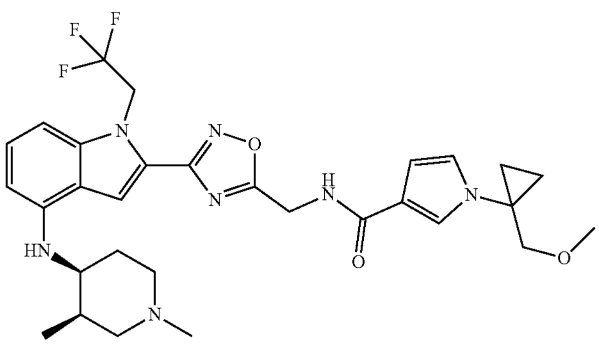 [SMILES: COCC1(n2ccc(C(=O)NCc3nc(-c4cc5c(N[C@H]6CCN(C)C[C@H]6C)cccc5n4CC(F)(F)F)no3)c2)CC1] | N-{[3-(4-{[(3R,4S)-1,3-dimethylpiperidin-4-yl]amino}-1-(2,2,2-trifluoroethyl)-1H-indol-2-yl)-1,2,4-oxadiazol-5-yl]methyl}-1-[1-(methoxymethyl)cyclopropyl]-1H-pyrrole-3-carboxamide | 600.3 |
| 506B | 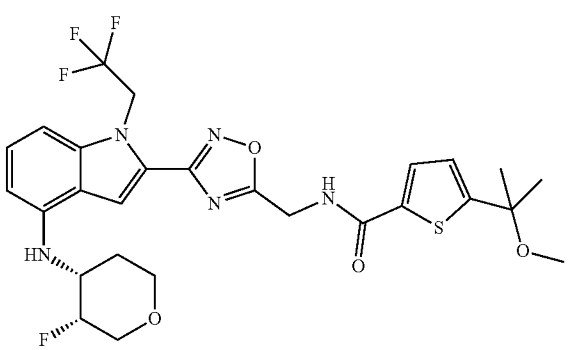 [SMILES: COC(C)(C)c1ccc(C(=O)NCc2nc(-c3cc4c(N[C@@H]5CCOC[C@@H]5F)cccc4n3CC(F)(F)F)no2)s1] | N-{[3-(4-{[(3R,4R)-3-fluorooxan-4-yl]amino}-1-(2,2,2-trifluoroethyl)-1H-indol-2-yl)-1,2,4-oxadiazol-5-yl]methyl}-5-(2-methoxypropan-2-yl)thiophene-2-carboxamide | 564.2 |
| 507B | 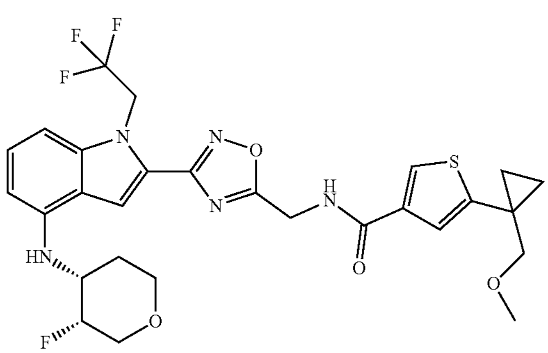 [SMILES: COCC1(c2cc(C(=O)NCc3nc(-c4cc5c(N[C@@H]6CCOC[C@@H]6F)cccc5n4CC(F)(F)F)no3)cs2)CC1] | N-{[3-(4-{[(3R,4R)-3-fluorooxan-4-yl]amino}-1-(2,2,2-trifluoroethyl)-1H-indol-2-yl)-1,2,4-oxadiazol-5-yl]methyl}-5-[1-(methoxymethyl)cyclopropyl]thiophene-3-carboxamide | 608.3 |

TABLE 9-continued

| Compound No. | Structure | IUPAC | LC-MS (ES+, m/z) |
|---|---|---|---|
| 508B | 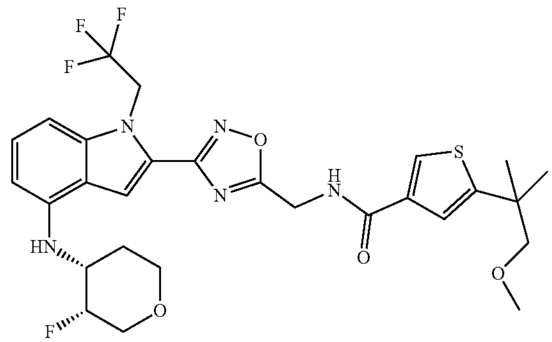 [SMILES: COCC(C)(C)c1cc(C(=O)NCc2nc(-c3cc4c(N[C@@H]5CCOC[C@@H]5F)cccc4n3CC(F)(F)F)no2)cs1] | N-{[3-(4-{[(3R,4R)-3-fluorooxan-4-yl]amino}-1-(2,2,2-trifluoroethyl)-1H-indol-2-yl)-1,2,4-oxadiazol-5-yl]methyl}-5-(1-methoxy-2-methylpropan-2-yl)thiophene-3-carboxamide | 610.1 |
| 509B | 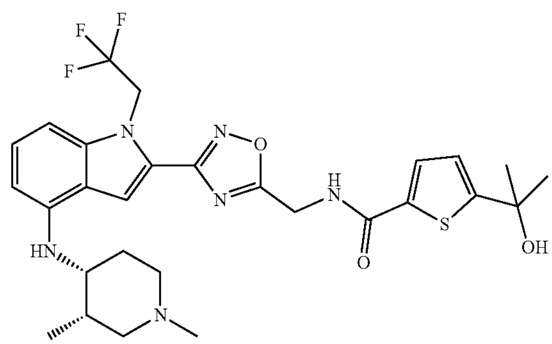 [SMILES: C[C@H]1CN(C)CC[C@H]1Nc1cccc2c1cc(-c1noc(CNC(=O)c3ccc(C(C)(C)O)s3)n1)n2CC(F)(F)F] | N-{[3-(4-{[(3S,4R)-1,3-dimethylpiperidin-4-yl]amino}-1-(2,2,2-trifluoroethyl)-1H-indol-2-yl)-1,2,4-oxadiazol-5-yl]methyl}-5-(2-hydroxypropan-2-yl)thiophene-2-carboxamide | 591.1 |
| 510B | 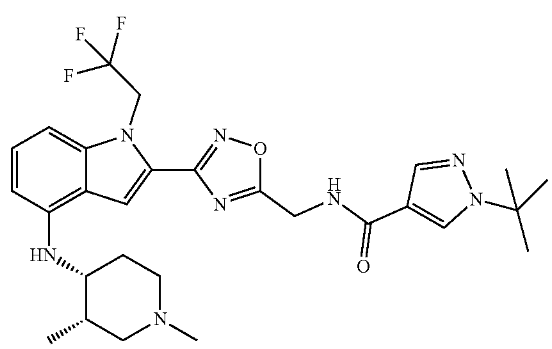 [SMILES: C[C@H]1CN(C)CC[C@H]1Nc1cccc2c1cc(-c1noc(CNC(=O)c3cnn(C(C)(C)C)c3)n1)n2CC(F)(F)F] | 1-tert-butyl-N-{[3-(4-{[(3S,4R)-1,3-dimethylpiperidin-4-yl]amino}-1-(2,2,2-trifluoroethyl)-1H-indol-2-yl)-1,2,4-oxadiazol-5-yl]methyl}-1H-pyrazole-4-carboxamide | 573.3 |
| 511B | 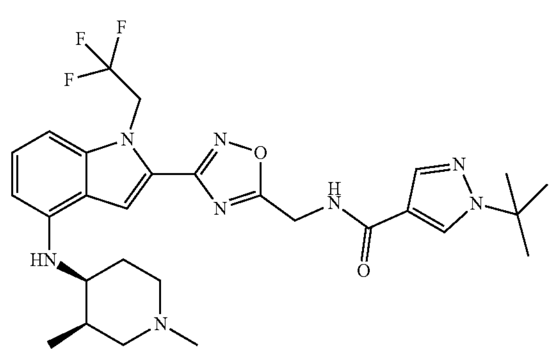 [SMILES: C[C@@H]1CN(C)CC[C@@H]1Nc1cccc2c1cc(-c1noc(CNC(=O)c3cnn(C(C)(C)C)c3)n1)n2CC(F)(F)F] | 1-tert-butyl-N-{[3-(4-{[(3R,4S)-1,3-dimethylpiperidin-4-yl]amino}-1-(2,2,2-trifluoroethyl)-1H-indol-2-yl)-1,2,4-oxadiazol-5-yl]methyl}-1H-pyrazole-4-carboxamide | 573.2 |

TABLE 9-continued

| Compound No. | Structure | IUPAC | LC-MS (ES+, m/z) |
|---|---|---|---|
| 512B | 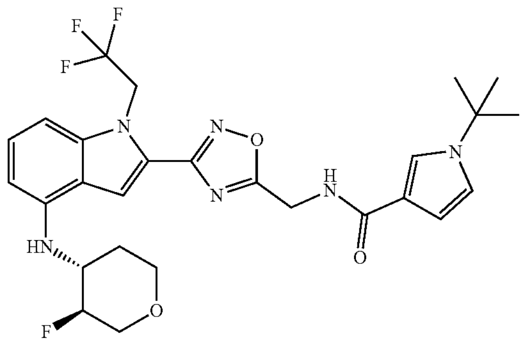 [SMILES: CC(C)(C)n1ccc(C(=O)NCc2nc(-c3cc4c(N[C@@H]5CCOC[C@H]5F)cccc4n3CC(F)(F)F)no2)c1] | 1-tert-butyl-N-{[3-(4-{[(3S,4R)-3-fluorooxan-4-yl]amino}-1-(2,2,2-trifluoroethyl)-1H-indol-2-yl)-1,2,4-oxadiazol-5-yl]methyl}-1H-pyrrole-3-carboxamide | 563.3 |
| 513B | 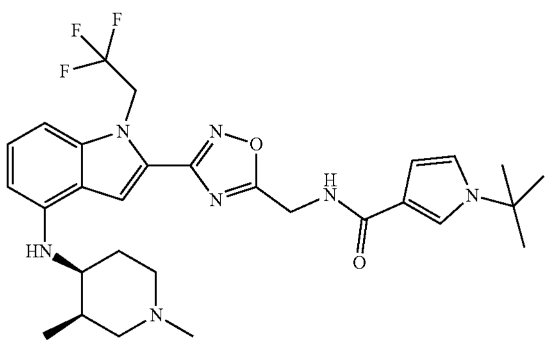 [SMILES: C[C@@H]1CN(C)CC[C@@H]1Nc1cccc2c1cc(-c1noc(CNC(=O)c3ccn(C(C)(C)C)c3)n1)n2CC(F)(F)F] | 1-tert-butyl-N-{[3-(4-{[(3R,4S)-1,3-dimethylpiperidin-4-yl]amino}-1-(2,2,2-trifluoroethyl)-1H-indol-2-yl)-1,2,4-oxadiazol-5-yl]methyl}-1H-pyrrole-3-carboxamide | 572.3 |
| 514B | 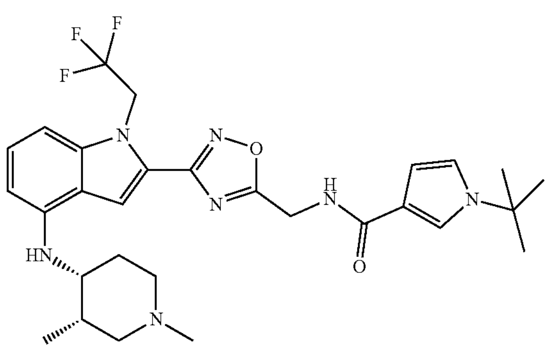 [SMILES: C[C@H]1CN(C)CC[C@H]1Nc1cccc2c1cc(-c1noc(CNC(=O)c3ccn(C(C)(C)C)c3)n1)n2CC(F)(F)F] | 1-tert-butyl-N-{[3-(4-{[(3S,4R)-1,3-dimethylpiperidin-4-yl]amino}-1-(2,2,2-trifluoroethyl)-1H-indol-2-yl)-1,2,4-oxadiazol-5-yl]methyl}-1H-pyrrole-3-carboxamide | 572.4 |
| 515B | 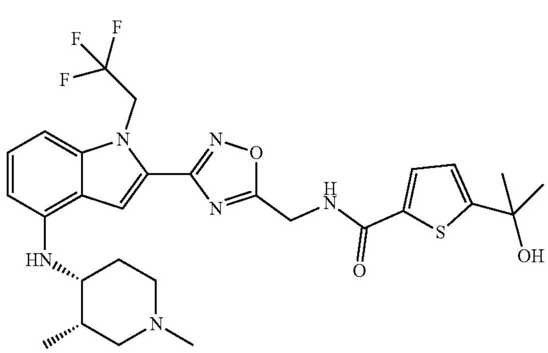 [SMILES: C[C@H]1CN(C)CC[C@H]1Nc1cccc2c1cc(-c1noc(CNC(=O)c3ccc(C(C)(C)O)s3)n1)n2CC(F)(F)F] | N-{[3-(4-{[(3R,4S)-1,3-dimethylpiperidin-4-yl]amino}-1-(2,2,2-trifluoroethyl)-1H-indol-2-yl)-1,2,4-oxadiazol-5-yl]methyl}-5-(2-hydroxypropan-2-yl)thiophene-2-carboxamide | |

TABLE 9-continued

| Compound No. | Structure | IUPAC | LC-MS (ES+, m/z) |
|---|---|---|---|
| 516B | 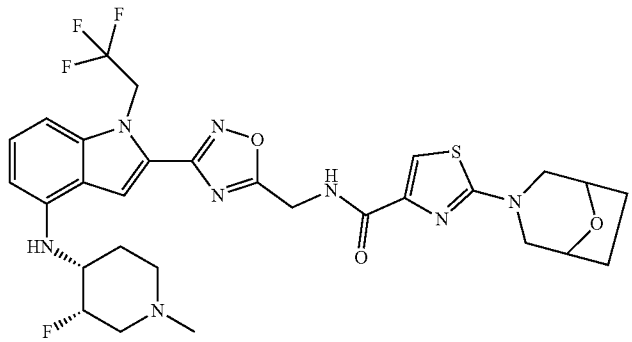 [SMILES: CN1CC[C@@H](Nc2cccc3c2cc(-c2noc(CNC(=O)c4csc(N5CC6CCC(C5)O6)n4)n2)n3CC(F)(F)F)[C@@H](F)C1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-{8-oxa-3-azabicyclo[3.2.1]octan-3-yl}-1,3-thiazole-4-carboxamide | 640.1 |
| 517B | 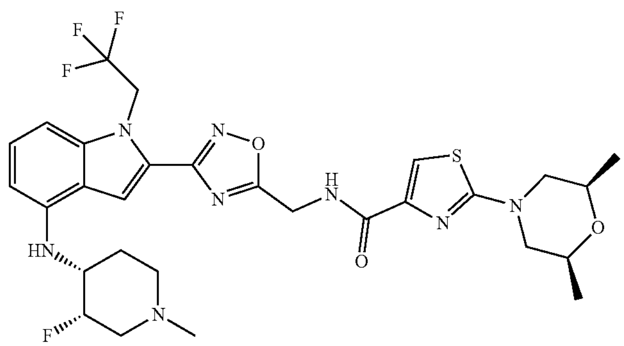 [SMILES: C[C@@H]1CN(c2nc(C(=O)NCc3nc(-c4cc5c(N[C@@H]6CCN(C)C[C@@H]6F)cccc5n4CC(F)(F)F)no3)cs2)C[C@H](C)O1] | 2-[(2S,6S)-2,6-dimethylmorpholin-4-yl]-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1,3-thiazole-4-carboxamide | 651.0 |
| 518B | 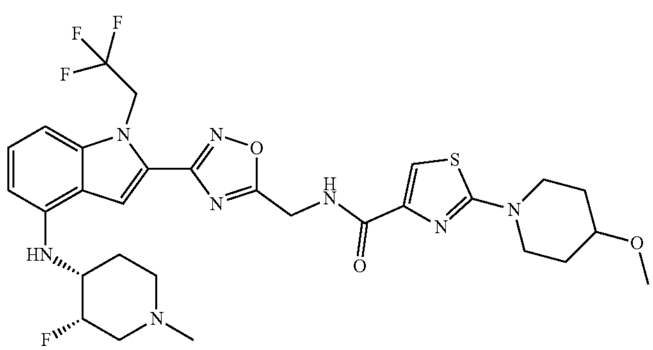 [SMILES: COC1CCN(c2nc(C(=O)NCc3nc(-c4cc5c(N[C@@H]6CCN(C)C[C@@H]6F)cccc5n4CC(F)(F)F)no3)cs2)CC1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-(4-methoxypiperidin-1-yl)-1,3-thiazole-4-carboxamide | 650.3 |
| 519B | 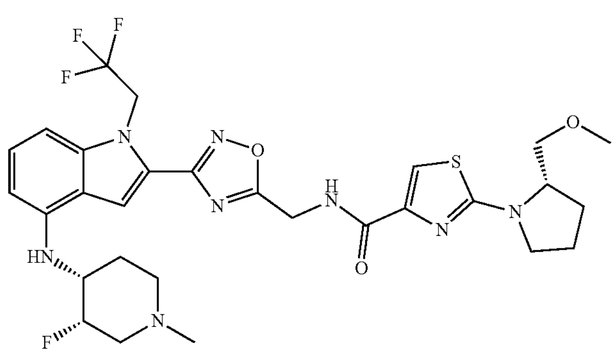 [SMILES: COC[C@@H]1CCCN1c1nc(C(=O)NCc2nc(-c3cc4c(N[C@@H]5CCN(C)C[C@@H]5F)cccc4n3CC(F)(F)F)no2)cs1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-[(2S)-2-(methoxymethyl)pyrrolidin-1-yl]-1,3-thiazole-4-carboxamide | 651.1 |

TABLE 9-continued

| Compound No. | Structure | IUPAC | LC-MS (ES+, m/z) |
|---|---|---|---|
| 520B | 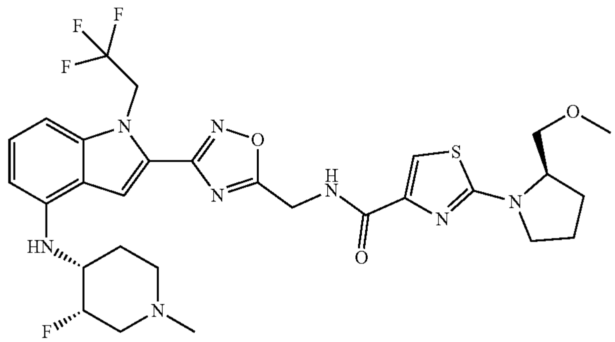 [SMILES: COC[C@H]1CCCN1c1nc(C(=O)NCc2nc(-c3cc4c(N[C@@H]5CCN(C)C[C@@H]5F)cccc4n3CC(F)(F)F)no2)cs1] | N-{3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-[(2R)-2-(methoxymethyl)pyrrolidin-1-yl]-1,3-thiazole-4-carboxamide | 651.1 |
| 521B | 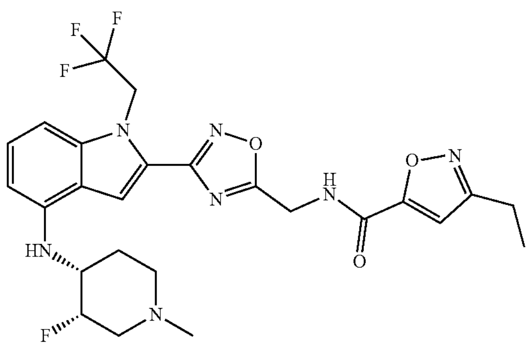 [SMILES: CCc1cc(C(=O)NCc2nc(-c3cc4c(N[C@@H]5CCN(C)C[C@@H]5F)cccc4n3CC(F)(F)F)no2)on1] | 3-ethyl-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1,2-oxazole-5-carboxamide | 550.1 |
| 522B | 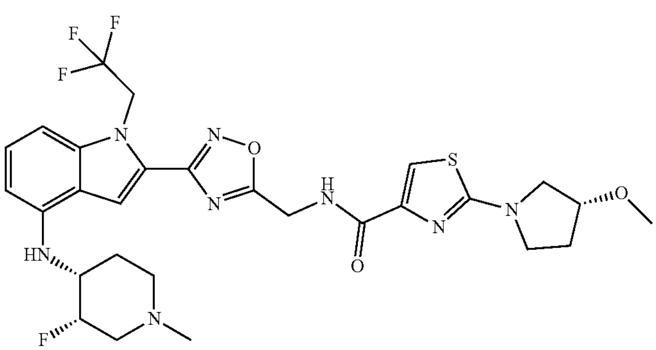 [SMILES: CO[C@@H]1CCN(c2nc(C(=O)NCc3nc(-c4cc5c(N[C@@H]6CCN(C)C[C@@H]6F)cccc5n4CC(F)(F)F)no3)cs2)C1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-[(3R)-3-methoxypyrrolidin-1-yl]-1,3-thiazole-4-carboxamide | 637.2 |
| 523B | 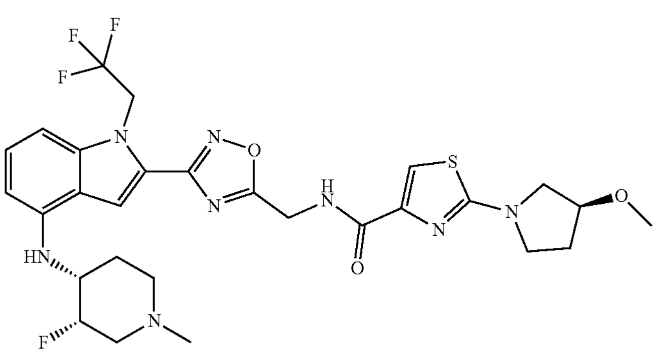 [SMILES: CO[C@H]1CCN(c2nc(C(=O)NCc3nc(-c4cc5c(N[C@@H]6CCN(C)C[C@@H]6F)cccc5n4CC(F)(F)F)no3)cs2)C1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-[(3S)-3-methoxypyrrolidin-1-yl]-1,3-thiazole-4-carboxamide | 637.2 |

TABLE 9-continued

| Compound No. | Structure | IUPAC | LC-MS (ES+, m/z) |
|---|---|---|---|
| 524B | 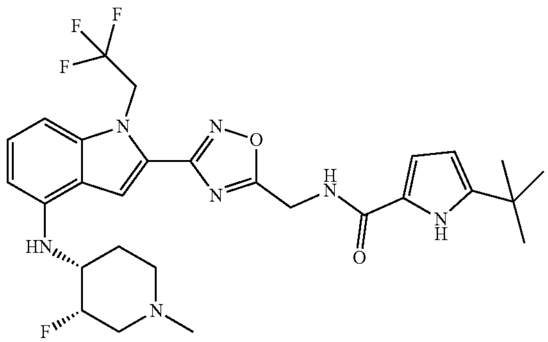 [SMILES: CN1CC[C@@H](Nc2cccc3c2cc(-c2noc(CNC(=O)c4ccc(C(C)(C)C)[nH]4)n2)n3CC(F)(F)F)[C@@H](F)C1] | 5-tert-butyl-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-pyrrole-2-carboxamide | 576.1 |
| 525B | 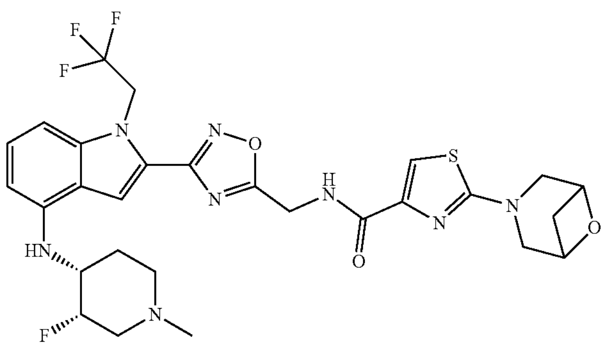 [SMILES: CN1CC[C@@H](Nc2cccc3c2cc(-c2noc(CNC(=O)c4csc(N5CC6CC(C5)O6)n4)n2)n3CC(F)(F)F)[C@@H](F)C1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-{6-oxa-3-azabicyclo[3.1.1]heptan-3-yl}-1,3-thiazole-4-carboxamide | 635.1 |
| 526B | 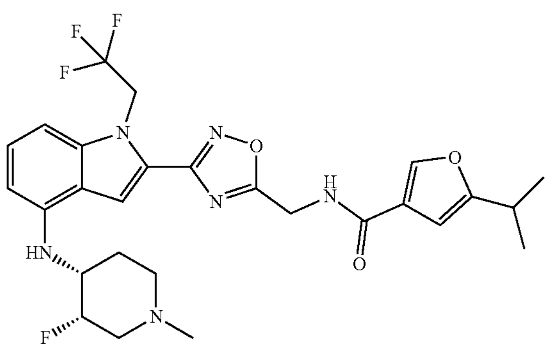 [SMILES: CC(C)c1cc(C(=O)NCc2nc(-c3cc4c(N[C@@H]5CCN(C)C[C@@H]5F)cccc4n3CC(F)(F)F)no2)co1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-5-(propan-2-yl)furan-3-carboxamide | 563.2 |
| 527B | 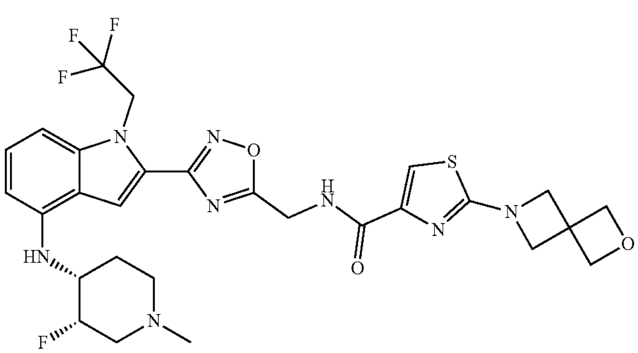 [SMILES: CN1CC[C@@H](Nc2cccc3c2cc(-c2noc(CNC(=O)c4csc(N5CC6(COC6)C5)n4)n2)n3CC(F)(F)F)[C@@H](F)C1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-{2-oxa-6-azaspiro[3.3]heptan-6-yl}-1,3-thiazole-4-carboxamide | 635.2 |

TABLE 9-continued

| Compound No. | Structure | IUPAC | LC-MS (ES+, m/z) |
|---|---|---|---|
| 528B | 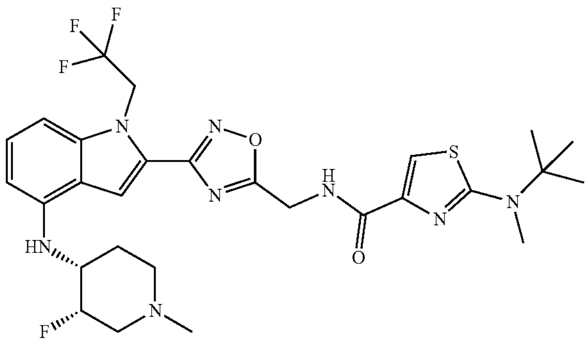 [SMILES: CN1CC[C@@H](Nc2cccc3c2cc(-c2noc(CNC(=O)c4csc(N(C)C(C)(C)C)n4)n2)n3CC(F)(F)F)[C@@H](F)C1] | 2-[tert-butyl(methyl)amino]-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1,3-thiazole-4-carboxamide | 623.2. |
| 529B | 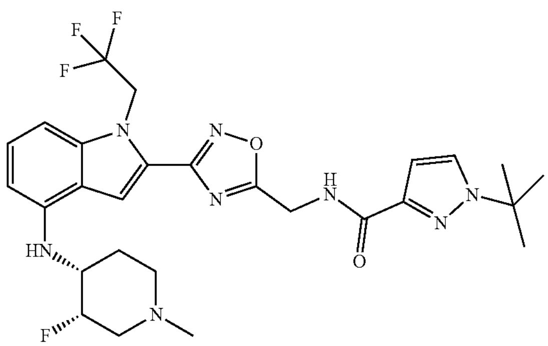 [SMILES: CN1CC[C@@H](Nc2cccc3c2cc(-c2noc(CNC(=O)c4ccn(C(C)(C)C)n4)n2)n3CC(F)(F)F)[C@@H](F)C1] | 1-tert-butyl-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-pyrazole-3-carboxamide | |
| 530B | 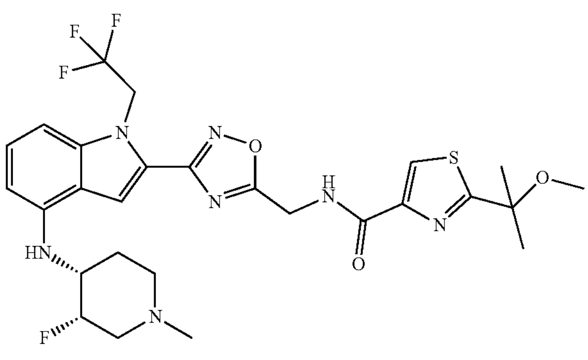 [SMILES: COC(C)(C)c1nc(C(=O)NCc2nc(-c3cc4c(N[C@@H]5CCN(C)C[C@@H]5F)cccc4n3CC(F)(F)F)no2)cs1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-(2-methoxypropan-2-yl)-1,3-thiazole-4-carboxamide | 610.3 |
| 531B | 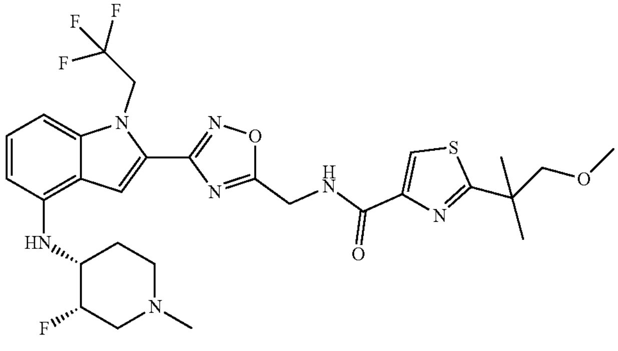 [SMILES: COCC(C)(C)c1nc(C(=O)NCc2nc(-c3cc4c(N[C@@H]5CCN(C)C[C@@H]5F)cccc4n3CC(F)(F)F)no2)cs1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-(1-methoxy-2-methylpropan-2-yl)-1,3-thiazole-4-carboxamide | 624.2 |

TABLE 9-continued

| Compound No. | Structure | IUPAC | LC-MS (ES+, m/z) |
|---|---|---|---|
| 532B | 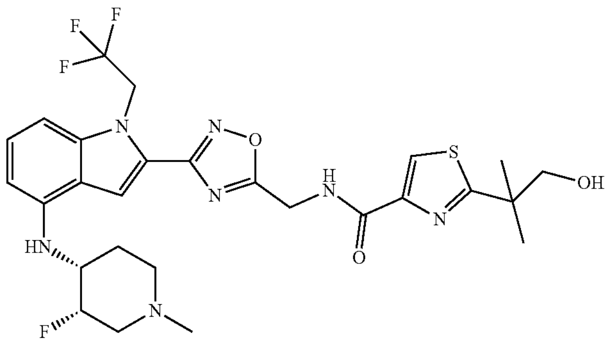 [SMILES: CN1CC[C@@H](Nc2cccc3c2cc(-c2noc(CNC(=O)c4csc(C(C)(C)CO)n4)n2)n3CC(F)(F)F)[C@@H](F)C1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-(1-hydroxy-2-methylpropan-2-yl)-1,3-thiazole-4-carboxamide | 610.1 |
| 533B | 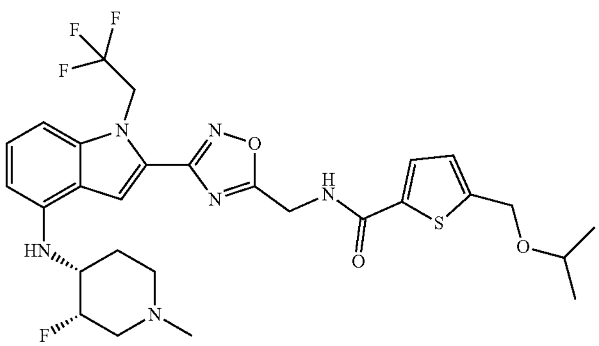 [SMILES: CC(C)OCc1ccc(C(=O)NCc2nc(-c3cc4c(N[C@@H]5CCN(C)C[C@@H]5F)cccc4n3CC(F)(F)F)no2)s1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-5-[(propan-2-yloxy)methyl]thiophene-2-carboxamide | n/a |
| 534B | 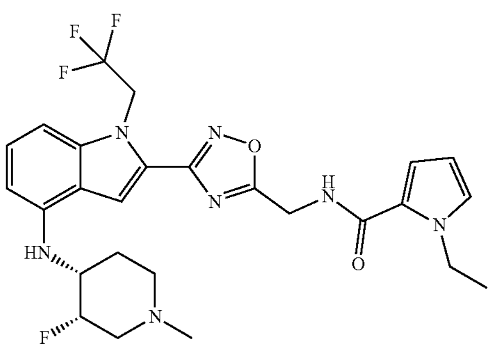 [SMILES: CCn1cccc1C(=O)NCc1nc(-c2cc3c(N[C@@H]4CCN(C)C[C@@H]4F)cccc3n2CC(F)(F)F)no1] | 1-ethyl-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1H-pyrrole-2-carboxamide | 548.2 |
| 535B | 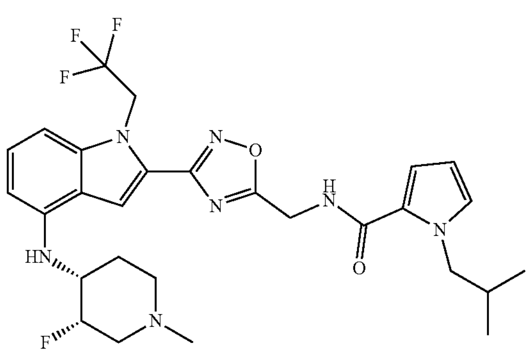 [SMILES: CC(C)Cn1cccc1C(=O)NCc1nc(-c2cc3c(N[C@@H]4CCN(C)C[C@@H]4F)cccc3n2CC(F)(F)F)no1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(2-methylpropyl)-1H-pyrrole-2-carboxamide | 576.2 |

TABLE 9-continued

| Compound No. | Structure | IUPAC | LC-MS (ES+, m/z) |
|---|---|---|---|
| 536B | 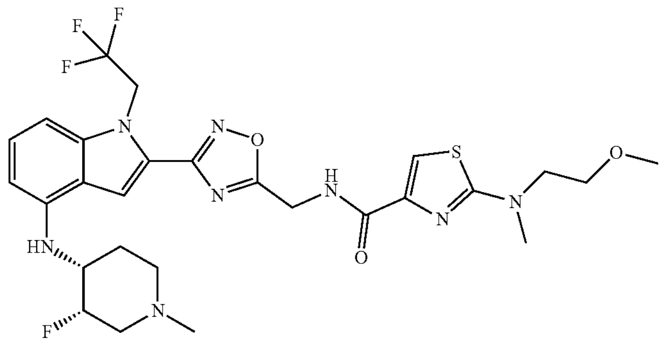 [SMILES: COCCN(C)c1nc(C(=O)NCc2nc(-c3cc4c(N[C@@H]5CCN(C)C[C@@H]5F)cccc4n3CC(F)(F)F)no2)cs1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-[(2-methoxyethyl)(methyl)amino]-1,3-thiazole-4-carboxamide | 625.1 |
| 537B | 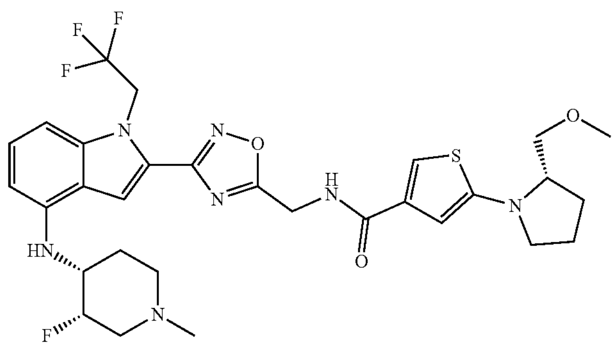 [SMILES: COC[C@@H]1CCCN1c1cc(C(=O)NCc2nc(-c3cc4c(N[C@@H]5CCN(C)C[C@@H]5F)cccc4n3CC(F)(F)F)no2)cs1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-5-[(2S)-2-(methoxymethyl)pyrrolidin-1-yl]thiophene-3-carboxamide | 650.1 |
| 538B | 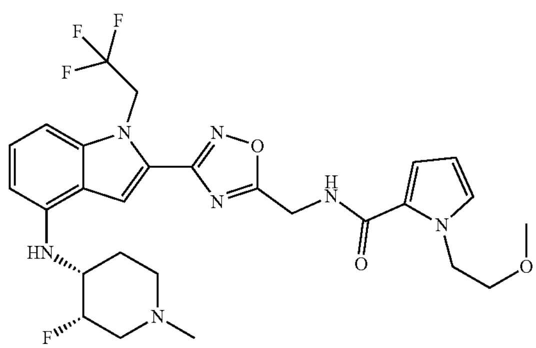 [SMILES: COCCn1cccc1C(=O)NCc1nc(-c2cc3c(N[C@@H]4CCN(C)C[C@@H]4F)cccc3n2CC(F)(F)F)no1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(2-methoxyethyl)-1H-pyrrole-2-carboxamide | 578.2 |
| 539B | 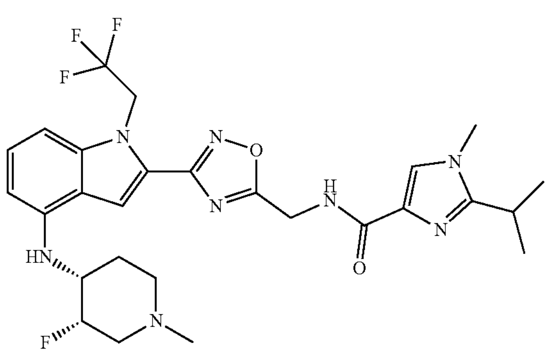 [SMILES: CC(C)c1nc(C(=O)NCc2nc(-c3cc4c(N[C@@H]5CCN(C)C[C@@H]5F)cccc4n3CC(F)(F)F)no2)cn1C] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-methyl-2-(propan-2-yl)-1H-imidazole-4-carboxamide | 577.2 |

TABLE 9-continued

| Compound No. | Structure | IUPAC | LC-MS (ES+, m/z) |
|---|---|---|---|
| 540B | 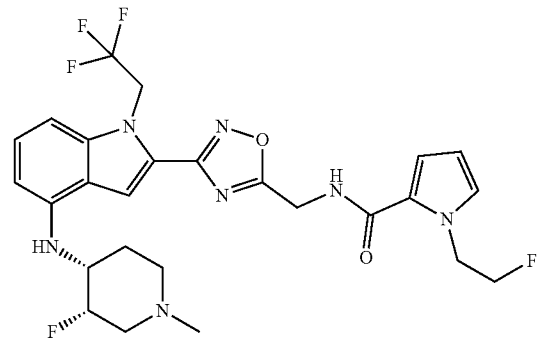 [SMILES: CN1CC[C@@H](Nc2cccc3c2cc(-c2noc(CNC(=O)c4cccn4CCF)n2)n3CC(F)(F)F)[C@@H](F)C1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(2-fluoroethyl)-1H-pyrrole-2-carboxamide | 566.1 |
| 541B | 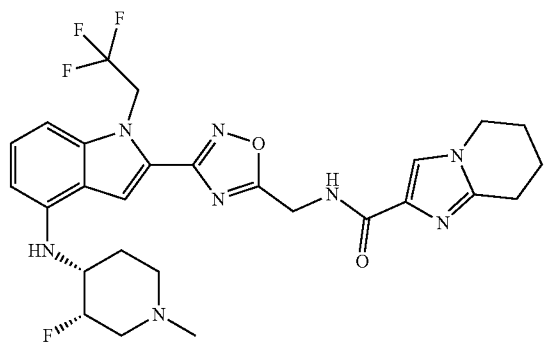 [SMILES: CN1CC[C@@H](Nc2cccc3c2cc(-c2noc(CNC(=O)c4cn5c(n4)CCCC5)n2)n3CC(F)(F)F)[C@@H](F)C1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-5H,6H,7H,8H-imidazo[1,2-a]pyridine-2-carboxamide | 574.9 |
| 542B | 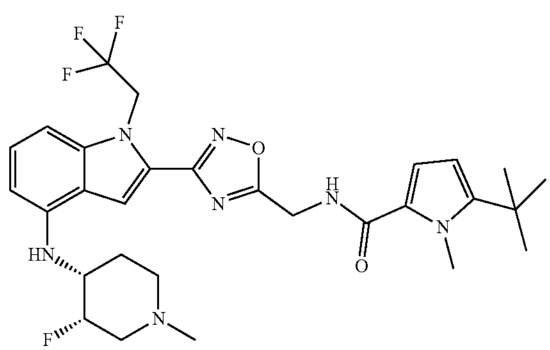 [SMILES: CN1CC[C@@H](Nc2cccc3c2cc(-c2noc(CNC(=O)c4ccc(C(C)(C)C)n4C)n2)n3CC(F)(F)F)[C@@H](F)C1] | 5-tert-butyl-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-methyl-1H-pyrrole-2-carboxamide | 590.2 |
| 543B | 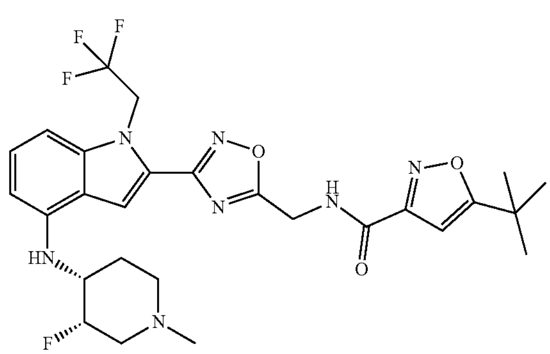 [SMILES: CN1CC[C@@H](Nc2cccc3c2cc(-c2noc(CNC(=O)c4cc(C(C)(C)C)on4)n2)n3CC(F)(F)F)[C@@H](F)C1] | 5-tert-butyl-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1,2-oxazole-3-carboxamide | 578.1 |

TABLE 9-continued

| Compound No. | Structure | IUPAC | LC-MS (ES+, m/z) |
|---|---|---|---|
| 544B | 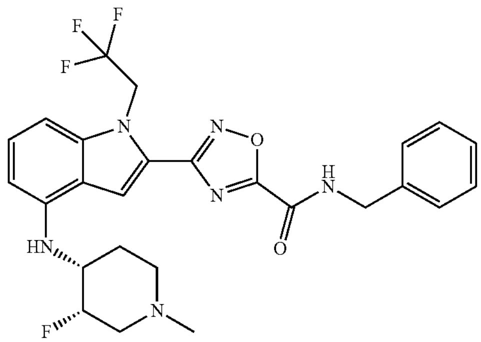 [SMILES: CN1CC[C@@H](Nc2cccc3c2cc(-c2noc(C(=O)NCc4ccccc4)n2)n3CC(F)(F)F)[C@@H](F)C1] | N-benzyl-3-(4-{[(3S,4R)-3-fluoro-1-methylpiperidin-4-yl]amino}-1-(2,2,2-trifluoroethyl)-1H-indol-2-yl)-1,2,4-oxadiazole-5-carboxamide | 531.1 |
| 545B | 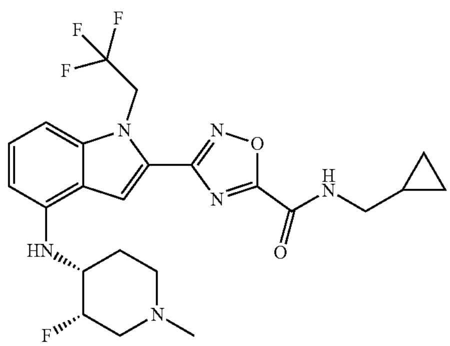 [SMILES: CN1CC[C@@H](Nc2cccc3c2cc(-c2noc(C(=O)NCC4CC4)n2)n3CC(F)(F)F)[C@@H](F)C1] | N-(cyclopropylmethyl)-3-(4-{[(3S,4R)-3-fluoro-1-methylpiperidin-4-yl]amino}-1-(2,2,2-trifluoroethyl)-1H-indol-2-yl)-1,2,4-oxadiazole-5-carboxamide | 495.1 |
| 546B | 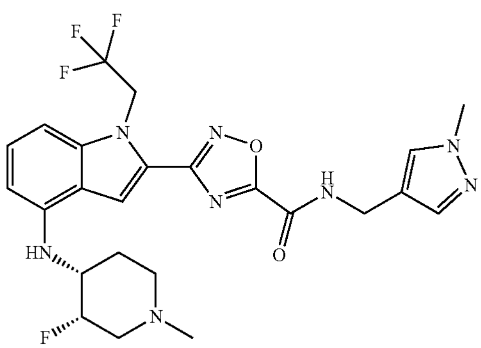 [SMILES: CN1CC[C@@H](Nc2cccc3c2cc(-c2noc(C(=O)NCc4cnn(C)c4)n2)n3CC(F)(F)F)[C@@H](F)C1] | 3-(4-{[(3S,4R)-3-fluoro-1-methylpiperidin-4-yl]amino}-1-(2,2,2-trifluoroethyl)-1H-indol-2-yl)-N-[(1-methyl-1H-pyrazol-4-yl)methyl]-1,2,4-oxadiazole-5-carboxamide | 535.1 |
| 547B | 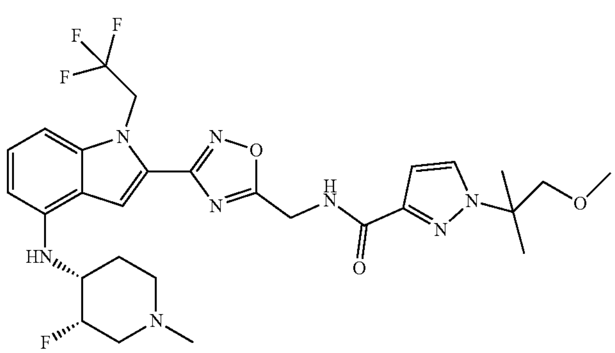 [SMILES: COCC(C)(C)n1ccc(C(=O)NCc2nc(-c3cc4c(N[C@@H]5CCN(C)C[C@@H]5F)cccc4n3CC(F)(F)F)no2)n1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(1-methoxy-2-methylpropan-2-yl)-1H-pyrazole-3-carboxamide | 607.2 |

TABLE 9-continued

| Compound No. | Structure | IUPAC | LC-MS (ES+, m/z) |
|---|---|---|---|
| 548B | 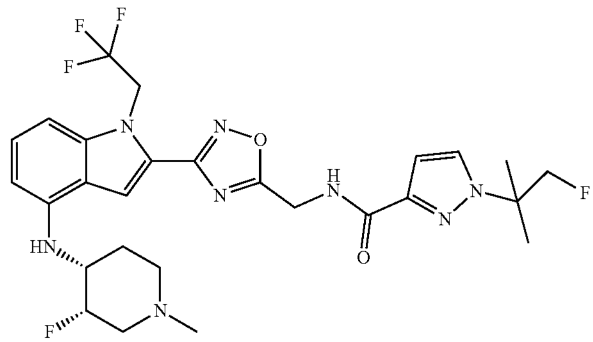 [SMILES: CN1CC[C@@H](Nc2cccc3c2cc(-c2noc(CNC(=O)c4ccn(C(C)(C)CF)n4)n2)n3CC(F)(F)F)[C@@H](F)C1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(1-fluoro-2-methylpropan-2-yl)-1H-pyrazole-3-carboxamide | 595.2 |
| 549B | 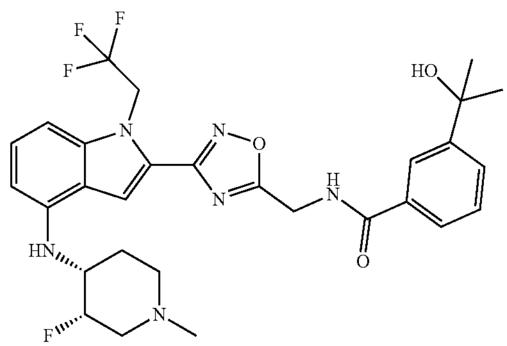 [SMILES: CN1CC[C@@H](Nc2cccc3c2cc(-c2noc(CNC(=O)c4cccc(C(C)(C)O)c4)n2)n3CC(F)(F)F)[C@@H](F)C1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-3-(2-hydroxypropan-2-yl)benzamide | 589.1 |
| 550B | 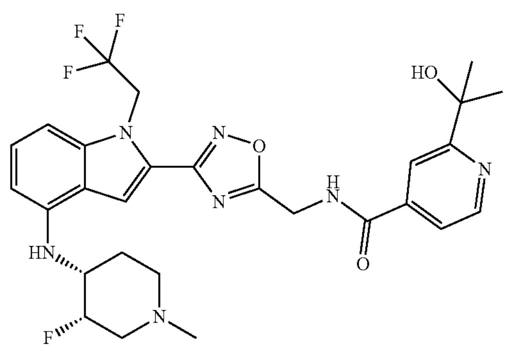 [SMILES: CN1CC[C@@H](Nc2cccc3c2cc(-c2noc(CNC(=O)c4ccnc(C(C)(C)O)c4)n2)n3CC(F)(F)F)[C@@H](F)C1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-(2-hydroxypropan-2-yl)pyridine-4-carboxamide | 590.2 |
| 551B | 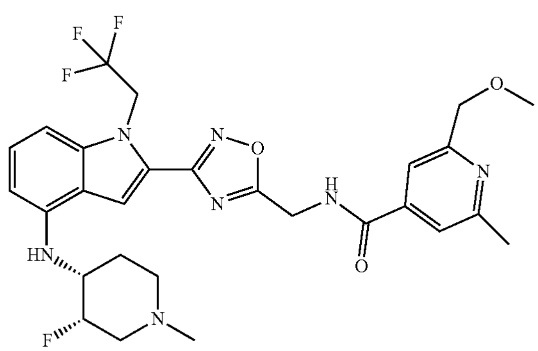 [SMILES: COCc1cc(C(=O)NCc2nc(-c3cc4c(N[C@@H]5CCN(C)C[C@@H]5F)cccc4n3CC(F)(F)F)no2)cc(C)n1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-2-(methoxymethyl)-6-methylpyridine-4-carboxamide | 590.4 |

TABLE 9-continued

| Compound No. | Structure | IUPAC | LC-MS (ES+, m/z) |
|---|---|---|---|
| 552B | 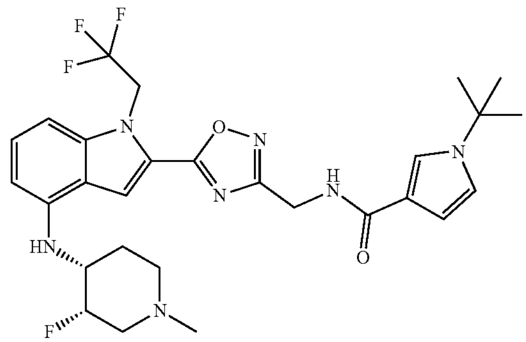 [SMILES: CN1CC[C@@H](Nc2cccc3c2cc(-c2nc(CNC(=O)c4ccn(C(C)(C)C)c4)no2)n3CC(F)(F)F)[C@@H](F)C1] | 1-tert-butyl-N-{[5-(4-{[(3S,4R)-3-fluoro-1-methylpiperidin-4-yl]amino}-1-(2,2,2-trifluoroethyl)-1H-indol-2-yl)-1,2,4-oxadiazol-3-yl]methyl}-1H-pyrrole-3-carboxamide | 576.4 |
| 553B | 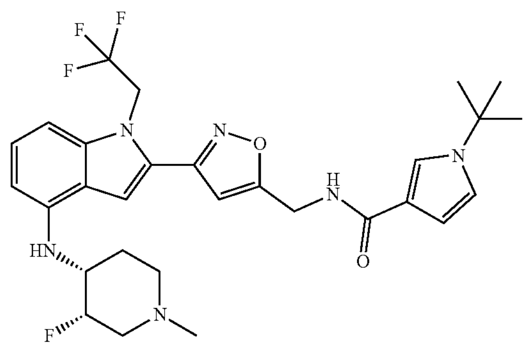 [SMILES: CN1CC[C@@H](Nc2cccc3c2cc(-c2cc(CNC(=O)c4ccn(C(C)(C)C)c4)on2)n3CC(F)(F)F)[C@@H](F)C1] | 1-tert-butyl-N-{[3-(4-{[(3S,4R)-3-fluoro-1-methylpiperidin-4-yl]amino}-1-(2,2,2-trifluoroethyl)-1H-indol-2-yl)-1,2-oxazol-5-yl]methyl}-1H-pyrrole-3-carboxamide | 575.2 |
| 554B | 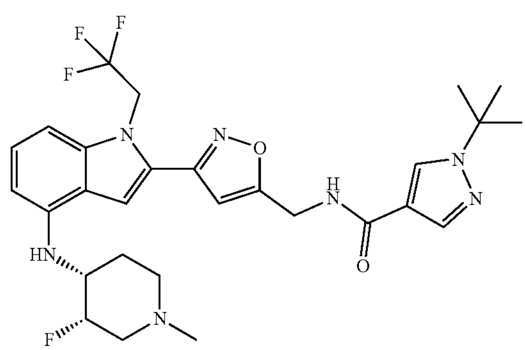 [SMILES: CN1CC[C@@H](Nc2cccc3c2cc(-c2cc(CNC(=O)c4cnn(C(C)(C)C)c4)on2)n3CC(F)(F)F)[C@@H](F)C1] | 1-tert-butyl-N-{[3-(4-{[(3S,4R)-3-fluoro-1-methylpiperidin-4-yl]amino}-1-(2,2,2-trifluoroethyl)-1H-indol-2-yl)-1,2-oxazol-5-yl]methyl}-1H-pyrazole-4-carboxamide | 576.2 |
| 555B | 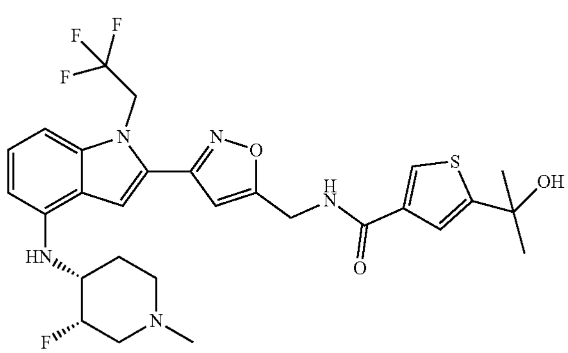 [SMILES: CN1CC[C@@H](Nc2cccc3c2cc(-c2cc(CNC(=O)c4csc(C(C)(C)O)c4)on2)n3CC(F)(F)F)[C@@H](F)C1] | N-{[3-(4-{[(3S,4R)-3-fluoro-1-methylpiperidin-4-yl]amino}-1-(2,2,2-trifluoroethyl)-1H-indol-2-yl)-1,2-oxazol-5-yl]methyl}-5-(2-hydroxypropan-2-yl)thiophene-3-carboxamide | 594.1 |

TABLE 9-continued

| Compound No. | Structure | IUPAC | LC-MS (ES+, m/z) |
|---|---|---|---|
| 556B | 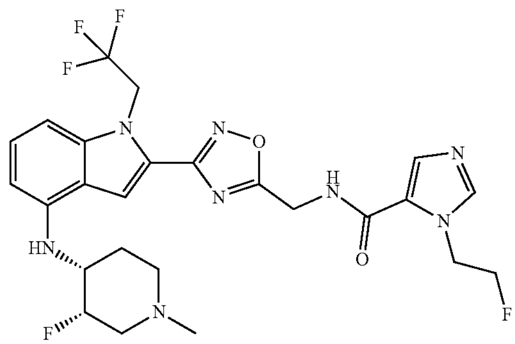 [SMILES: CN1CC[C@@H](Nc2cccc3c2cc(-c2noc(CNC(=O)c4cncn4CCF)n2)n3CC(F)(F)F)[C@@H](F)C1] | N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}-1-(2-fluoroethyl)-1H-imidazole-5-carboxamide | 567.1 |
| 557B | 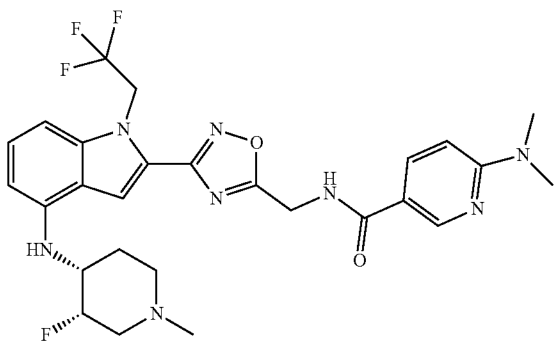 [SMILES: CN1CC[C@@H](Nc2cccc3c2cc(-c2noc(CNC(=O)c4ccc(N(C)C)nc4)n2)n3CC(F)(F)F)[C@@H](F)C1] | 6-(dimethylamino)-N-{[3-(4-{[(3S,4R)-3-fluoro-1-methylpiperidin-4-yl]amino}-1-(2,2,2-trifluoroethyl)-1H-indol-2-yl)-1,2,4-oxadiazol-5-yl]methyl}pyridine-3-carboxamide | 575.2 |
| 558B | 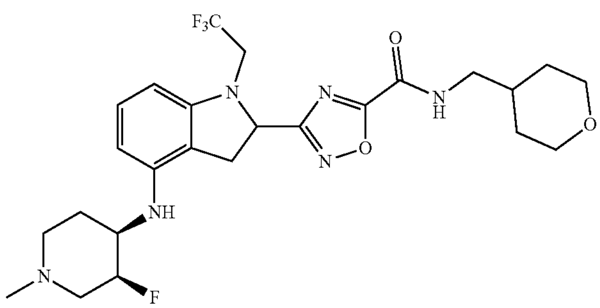 [SMILES: CN1CC[C@@H](Nc2cccc3c2CC(c2noc(C(=O)NCC4CCOCC4)n2)N3CC(F)(F)F)[C@@H](F)C1] | 3-(4-{[(3S,4R)-3-fluoro-1-methylpiperidin-4-yl]amino}-1-(2,2,2-trifluoroethyl)-1H-indol-2-yl)-N-[(oxan-4-yl)methyl]-1,2,4-oxadiazole-5-carboxamide | 539.1 |

Example 300: In Vitro DNA Binding Activity Assay

DNA binding activity of the compounds was measured using a TR-FRET (Time-Resolved Fluorescence Resonance Energy Transfer) assay in which recombinant His-tag Y220C p53 DBD protein binds to biotin-labeled consensus DNA. Binding of recombinant His-tag Y220C p53 DBD protein and biotin-labeled consensus DNA was registered by the FRET (fluorescence resonance energy transfer) between allophycocyanin (APC) conjugated anti-His tag antibody and Europium-(Eu) conjugated Streptavidin.

The compounds of TABLES 1-9 (2 mM stock in dimethylsulfoxide) were diluted 3-fold in series in dimethylsulfoxide. 1.2 µL of a compound solution was added to each well of 384-well polypropylene black plates (NUNC). Thirty µL per well of 181 nM recombinant His-tag Y220C p53 DBD protein (amino acids #~94-312; SEQ ID NO: 1) and 6.1 nM of APC conjugated anti-His tag antibody (Columbia Biosciences) in ice-cold Assay Buffer 1 (50 mM Tris-HCl, pH 7.4, 75 mM KCl, 0.75 mM DTT and 0.2 mg/ml BSA) were added. As a background control, 30 µL of Assay Buffer 1 containing 6.1 nM of APC anti-His antibody (No Y220C protein) was also added into a second set of serially diluted compound plates. The samples were spun by centrifuge at 1,200 rpm (Eppendorf 5810R Plate centrifuge) for 1 minute and incubated at room temperature (20° C.) for 15 min. The samples were then further incubated at either 27° C. or 29° C. for 60 min. Five microliters per well of 311 nM biotin labeled consensus DNA (a DNA duplex with 5' to 3' sequence of ATTAGGCATGTCTAGGCATGTCTAGG (SEQ ID NO. 2) and biotin attached to the 3' end of the complementary DNA) and 4.9 nM Europium (Eu) conjugated Streptavidin (Eu-SA, Perkin Elmer) in Assay Buffer 2 (50 mM Tris-HCl, pH 7.4, 75 mM KCl and 0.2 mg/mL BSA) were added to the wells. The samples were spun by centrifuge at 1,200 rpm for 1 min and incubated at room temperature (20° C.) for 20 min. Assay signals were monitored by reading excitation at 340 nm, and emission fluorescence at 615 nm and 665 nm on an Envision® reader. Normalized TR-FRET (time-resolved fluorescence resonance energy transfer) assay signal (Rn) was calculated by the formula:

$$Rn = [(A - Ba - C \times (D - Bd))/(D - Bd)] \times (D - Bd)$$

Wherein:

A is the fluorescence intensity of the sample at 665 nm;

D is the fluorescence intensity of the sample at 615 nm;

Ba and Bd are plate backgrounds at 665 nm and 615 nm, respectively; and

Dc is the fluorescence intensity of 0.67 nM Eu-SA in the assay buffer at 615 nm.

The cross-talk factor (C) was determined by the following formula:

$$C=(Ac-Ba)/(Dc-Bd)$$

wherein Ac is the fluorescence intensity of 0.67 nM Europium (Eu) conjugated Streptavidin in the assay buffer at 665 nm. $SC_{150}$ (substrate concentration to increase DNA binding by 1.5-fold) values were calculated using Prism (GraphPad) or XLfit software (IDBS).

TABLE 10 shows the $SC_{150}$ (μM) values of the compounds shown in TABLE 1.

TABLE 10

| Compound No. | $SC_{150}$ (μM) |
| --- | --- |
| 1A | ++++ |
| 2A | +++ |
| 3A | +++ |
| 4A | +++ |
| 5A | ++++ |
| 6A | ++ |
| 7A | ++ |
| 8A | + |
| 9A | +++ |
| 10A | ++++ |
| 11A | ++++ |
| 12A | ++++ |
| 13A | +++ |
| 14A | ++++ |
| 15A | +++ |
| 16A | ++ |
| 17A | ++ |
| 18A | + |
| 19A | + |
| 20A | ++++ |
| 21A | ++ |
| 22A | ++ |
| 24A | +++ |
| 25A | +++ |
| 26A | ++ |
| 27A | ++ |
| 28A | + |
| 29A | + |
| 30A | + |
| 31A | + |
| 32A | ++ |
| 33A | ++ |
| 34A | ++++ |
| 35A | +++ |
| 36A | ++ |
| 38A | +++ |
| 40A | ++++ |
| 41A | ++ |
| 42A | ++++ |
| 43A | + |
| 44A | + |
| 45A | + |
| 46A | + |
| 47A | +++ |
| 48A | +++ |
| 49A | ++ |
| 51A | ++++ |

+ = 0 μM ≤ $SC_{150}$ < 2 μM
++ = 2 μM ≤ $SC_{150}$ < 5 μM
+++ = 5 μM ≤ $SC_{150}$ < 10 μM
++++ = 10 μM ≤ $SC_{150}$ < 35 μM

TABLE 11 shows the $SC_{150}$ (μM) values of the compounds shown in TABLES 2-9.

TABLE 11

| Compound No. | Y220C $SC_{150}$ (μM) |
| --- | --- |
| 14B | **** |
| 15B | **** |
| 16B | **** |
| 18B | **** |
| 20B | **** |
| 21B | **** |
| 22B | ** |
| 23B | **** |
| 24B | ** |
| 25B | ** |
| 26B | ** |
| 27B | ** |
| 28B | * |
| 29B | ** |
| 30B | * |
| 31B | ** |
| 32B | ** |
| 33B | ** |
| 34B | * |
| 35B | * |
| 36B | ** |
| 37B | ** |
| 38B | * |
| 39B | * |
| 40B | *** |
| 41B | ** |
| 42B | ** |
| 43B | **** |
| 44B | * |
| 45B | * |
| 46B | * |
| 47B | * |
| 48B | * |
| 49B | ** |
| 50B | ** |
| 51B | * |
| 52B | * |
| 53B | * |
| 54B | ** |
| 55B | ** |
| 56B | ** |
| 57B | ** |
| 58B | ** |
| 59B | ** |
| 60B | ** |
| 61B | * |
| 62B | * |
| 63B | * |
| 64B | * |
| 65B | ** |
| 66B | * |
| 68B | ** |
| 69B | * |
| 70B | * |
| 71B | ** |
| 72B | * |
| 73B | * |
| 74B | ** |
| 75B | * |
| 76B | * |
| 77B | * |
| 78B | * |
| 79B | * |
| 80B | **** |
| 81B | ** |
| 82B | ** |
| 89B | **** |
| 90B | **** |
| 91B | * |
| 92B | ** |
| 93B | *** |
| 94B | * |
| 95B | * |

TABLE 11-continued

| Compound No. | Y220C SC$_{150}$ (μM) |
|---|---|
| 96B | **** |
| 98B | * |
| 99B | * |
| 100B | ** |
| 101B | * |
| 102B | ** |
| 103B | * |
| 108B | ** |
| 110B | *** |
| 111B | ** |
| 112B | *** |
| 114B | ** |
| 115B | ** |
| 116B | *** |
| 117B | ** |
| 118B | ** |
| 119B | ** |
| 120B | ** |
| 121B | **** |
| 122B | ** |
| 123B | ** |
| 136B | * |
| 137B | ** |
| 138B | ** |
| 139B | ** |
| 140B | ** |
| 141B | ** |
| 142B | * |
| 143B | * |
| 144B | * |
| 145B | * |
| 146B | * |
| 147B | * |
| 148B | * |
| 149B | * |
| 150B | * |
| 151B | * |
| 152B | * |
| 153B | * |
| 154B | * |
| 155B | * |
| 156B | * |
| 157B | * |
| 158B | * |
| 159B | * |
| 160B | ** |
| 161B | * |
| 162B | * |
| 163B | * |
| 164B | * |
| 165B | ** |
| 166B | ** |
| 167B | * |
| 168B | * |
| 169B | * |
| 170B | * |
| 171B | * |
| 172B | * |
| 173B | * |
| 174B | * |
| 175B | * |
| 176B | * |
| 177B | * |
| 178B | * |
| 179B | * |
| 180B | * |
| 181B | * |
| 182B | * |
| 183B | * |
| 184B | * |
| 185B | * |
| 186B | * |
| 187B | * |
| 188B | * |
| 189B | * |
| 190B | * |
| 191B | ** |
| 192B | * |
| 193B | * |
| 194B | * |
| 195B | * |
| 196B | * |
| 197B | * |
| 198B | * |
| 199B | * |
| 200B | * |
| 201B | * |
| 202B | * |
| 203B | * |
| 205B | * |
| 206B | * |
| 207B | ** |
| 208B | * |
| 209B | * |
| 210B | * |
| 211B | * |
| 212B | * |
| 213B | * |
| 214B | * |
| 215B | * |
| 216B | * |
| 217B | * |
| 218B | * |
| 219B | * |
| 220B | * |
| 221B | ** |
| 222B | * |
| 223B | * |
| 224B | * |
| 225B | * |
| 226B | * |
| 227B | * |
| 228B | * |
| 229B | * |
| 230B | * |
| 231B | * |
| 232B | * |
| 233B | * |
| 234B | * |
| 235B | * |
| 236B | * |
| 237B | * |
| 238B | * |
| 239B | * |
| 240B | * |
| 241B | * |
| 242B | * |
| 243B | * |
| 244B | * |
| 245B | * |
| 246B | * |
| 247B | * |
| 248B | * |
| 249B | * |
| 250B | * |
| 251B | * |
| 252B | * |
| 253B | * |
| 254B | * |
| 255B | * |
| 256B | * |
| 257B | * |
| 258B | * |
| 259B | * |
| 260B | * |
| 262B | * |
| 263B | * |
| 264B | * |
| 265B | * |
| 266B | * |
| 267B | * |
| 268B | * |
| 269B | * |
| 270B | * |

TABLE 11-continued

| Compound No. | Y220C SC$_{150}$ (μM) |
|---|---|
| 272B | * |
| 272B | * |
| 273B | * |
| 274B | * |
| 275B | * |
| 276B | * |
| 277B | * |
| 278B | * |
| 279B | * |
| 283B | ** |
| 284B | ** |
| 285B | ** |
| 286B | * |
| 287B | * |
| 288B | * |
| 289B | * |
| 290B | * |
| 292B | * |
| 293B | * |
| 294B | * |
| 295B | * |
| 296B | * |
| 297B | * |
| 298B | * |
| 299B | * |
| 300B | * |
| 301B | * |
| 302B | * |
| 303B | * |
| 304B | * |
| 305B | * |
| 306B | * |
| 307B | * |
| 308B | * |
| 309B | * |
| 310B | * |
| 311B | * |
| 312B | * |
| 313B | * |
| 314B | * |
| 315B | * |
| 316B | * |
| 317B | * |
| 318B | * |
| 319B | * |
| 320B | * |
| 321B | * |
| 322B | * |
| 323B | * |
| 324B | * |
| 325B | * |
| 326B | * |
| 327B | * |
| 328B | * |
| 329B | * |
| 330B | * |
| 331B | * |
| 332B | * |
| 333B | * |
| 334B | * |
| 335B | * |
| 336B | * |
| 337B | * |
| 338B | * |
| 339B | * |
| 340B | ** |
| 341B | * |
| 342B | * |
| 343B | * |
| 344B | * |
| 345B | * |
| 346B | * |
| 347B | * |
| 348B | * |
| 349B | * |
| 350B | * |
| 351B | * |

TABLE 11-continued

| Compound No. | Y220C SC$_{150}$ (μM) |
|---|---|
| 352B | * |
| 353B | * |
| 354B | * |
| 355B | * |
| 356B | * |
| 357B | * |
| 358B | * |
| 359B | * |
| 360B | * |
| 361B | * |
| 362B | * |
| 363B | * |
| 364B | * |
| 365B | * |
| 366B | * |
| 367B | * |
| 368B | *** |
| 369B | * |
| 370B | * |
| 371B | * |
| 372B | * |
| 373B | * |
| 374B | * |
| 375B | * |
| 376B | * |
| 377B | * |
| 378B | * |
| 379B | * |
| 380B | * |
| 381B | * |
| 382B | * |
| 383B | * |
| 384B | * |
| 385B | * |
| 386B | * |
| 387B | * |
| 388B | * |
| 389B | * |
| 390B | * |
| 391B | * |
| 392B | * |
| 393B | * |
| 394B | * |
| 395B | * |
| 396B | ** |
| 397B | * |
| 398B | * |
| 399B | * |
| 400B | * |
| 401B | * |
| 402B | * |
| 403B | * |
| 404B | * |
| 405B | * |
| 406B | * |
| 407B | * |
| 408B | * |
| 409B | * |
| 410B | * |
| 411B | * |
| 412B | * |
| 413B | * |
| 414B | * |
| 415B | * |
| 416B | * |
| 417B | * |
| 418B | * |
| 419B | * |
| 420B | * |
| 421B | * |
| 422B | * |
| 423B | * |
| 424B | * |
| 425B | * |
| 426B | * |
| 427B | * |
| 428B | * |

TABLE 11-continued

| Compound No. | Y220C SC$_{150}$ (μM) |
|---|---|
| 429B | * |
| 430B | * |
| 431B | * |
| 432B | * |
| 433B | * |
| 434B | * |
| 435B | * |
| 436B | * |
| 437B | * |
| 438B | * |
| 439B | * |
| 440B | * |
| 441B | * |
| 442B | * |
| 443B | * |
| 444B | * |
| 445B | * |
| 446B | * |
| 447B | * |
| 448B | * |
| 449B | * |
| 451B | * |
| 452B | * |
| 453B | * |
| 454B | * |
| 455B | * |
| 456B | * |
| 457B | * |
| 458B | * |
| 459B | * |
| 460B | * |
| 462B | * |
| 463B | * |
| 464B | * |
| 465B | * |
| 466B | * |
| 471B | * |
| 472B | * |
| 473B | * |
| 474B | * |
| 475B | * |
| 476B | * |
| 477B | * |
| 478B | * |
| 479B | * |
| 480B | * |
| 481B | * |
| 482B | * |
| 483B | * |
| 484B | * |
| 485B | * |
| 486B | * |
| 487B | * |
| 488B | * |
| 489B | * |
| 490B | * |
| 491B | * |
| 492B | * |
| 493B | * |
| 494B | * |
| 495B | * |
| 496B | * |
| 497B | * |
| 498B | * |
| 499B | * |
| 500B | * |
| 501B | * |
| 502B | * |
| 503B | * |
| 504B | * |
| 505B | * |
| 506B | * |
| 507B | * |
| 508B | * |
| 509B | * |
| 510B | * |
| 511B | * |
| 512B | * |
| 513B | * |
| 514B | * |
| 515B | * |
| 516B | * |
| 517B | * |
| 518B | * |
| 519B | * |
| 520B | * |
| 521B | * |
| 522B | * |
| 523B | * |
| 524B | * |
| 525B | ** |
| 526B | * |
| 527B | * |
| 528B | * |
| 529B | * |
| 530B | * |
| 531B | * |
| 532B | * |
| 534B | * |
| 535B | * |
| 536B | * |
| 537B | * |
| 538B | * |
| 539B | * |
| 540B | * |
| 541B | * |
| 542B | * |
| 543B | * |
| 544B | ** |
| 545B | ** |
| 546B | ** |
| 547B | * |
| 548B | * |
| 549B | * |
| 550B | * |
| 551B | * |
| 552B | * |
| 553B | * |
| 554B | * |
| 555B | * |
| 556B | * |
| 557B | * |
| 558B | * |

\* = 0 μM ≤ SC$_{150}$ < 0.1 μM
\*\* = 0.1 μM ≤ SC$_{150}$ < 0.5 μM
\*\*\* = 0.5 μM ≤ SC$_{150}$ < 1 μM
\*\*\*\* = 1 μM ≤ SC$_{150}$ < 10 μM

Embodiments

The following non-limiting embodiments provide illustrative examples of the invention, but do not limit the scope of the invention.

Embodiment 1. A compound of the formula:

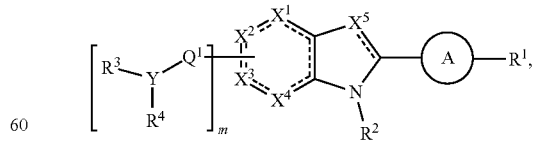

wherein:
each ====== is independently a single bond or a double bond;
$X^1$ is $CR^5$, $CR^5R^6$, N, $NR^5$, O, S, C=O, C=S, or a carbon atom connected to $Q^1$;

$X^2$ is $CR^7$, $CR^7R^8$, N, $NR^7$, O, S, C=O, C=S, or a carbon atom connected to $Q^1$;

$X^3$ is $CR^9$, $CR^9R^{10}$, N. $NR^9$, O, S, C=O, C=S, or a carbon atom connected to $Q^1$;

$X^4$ is $CR^{11}$, $CR^{11}R^{12}$, N, $NR^{11}$, O, S, C=O, C=S, or a carbon atom connected to $Q^1$;

$X^5$ is $CR^{13}$, N, or $NR^{13}$;

wherein at least one of $X^1$, $X^2$, $X^3$, and $X^4$ is a carbon atom connected to $Q^1$;

A is a substituted or unsubstituted ring;

$Q^1$ is C=O, C=S, C=$CR^{14}R^{15}$, C=$NR^{14}$, alkylene, alkenylene, or alkynylene, each of which is independently substituted or unsubstituted, or a bond;

m is 1, 2, 3, or 4;

Y is N, O, or absent;

$R^1$ is —C(O)$R^{16}$, —C(O)O$R^{16}$, —C(O)N$R^{16}R^{17}$, —O$R^{16}$, —S$R^{16}$, —N$R^{16}R^{17}$, —$NR^{16C}$(O)$R^{16}$, —OC(O)$R^{16}$, —Si$R^{16}R^{17}R^{18}$, alkyl, alkenyl, alkynyl, alkoxy, aryl, heteroaryl, heterocyclyl, or halo, each of which is independently substituted or unsubstituted, or hydrogen;

each $R^3$ and $R^4$ is independently —C(O)$R^9$, —C(O)O$R^{19}$, —C(O)N$R^{19}R^{20}$, —SO$R^{19}$, —SO$_2$$R^{19}$, alkyl, alkenyl, alkynyl, aryl, heteroaryl, or heterocyclyl, each of which is independently substituted or unsubstituted, or hydrogen, or $R^3$ and $R^4$ together with the nitrogen atom to which $R^3$ and $R^4$ are bound form a ring, wherein the ring is substituted or unsubstituted, or $R^3$ is absent;

each $R^2$, $R^5$, $R^6$, $R^7$, $R^8$, $R^9$, $R^{10}$, $R^{11}$, $R^{12}$, $R^{13}$, $R^{14}$, $R^{15}$, $R^{16}$, $R^{17}$, and $R^{18}$ is independently —C(O)$R^{21}$, —C(O)O$R^{21}$, —C(O)N$R^{21}R^{22}$, —O$R^{21}$, —S$R^{21}$, —N$R^{21}R^{22}$, —$NR^{21}$C(O)$R^{22}$, —OC(O)$R^{21}$, alkyl, alkenyl, alkynyl, aryl, heteroaryl, or heterocyclyl, each of which is independently substituted or unsubstituted, or hydrogen or halogen;

each $R^{19}$ and $R^{20}$ is independently —C(O)$R^{23}$, —C(O)O$R^{21}$, —C(O)N$R^{23}R^{24}$, —O$R^{23}$, —S$R^{23}$, —N$R^{23}R^{24}$, —$NR^{23}$C(O)$R^{24}$, —OC(O)$R^{23}$, alkyl, alkenyl, alkynyl, aryl, heteroaryl, or heterocyclyl, each of which is independently substituted or unsubstituted, or hydrogen or halogen;

each $R^{21}$ and $R^{22}$ is independently alkyl, alkenyl, alkynyl, aryl, heteroaryl, or heterocyclyl, each of which is independently substituted or unsubstituted, or hydrogen; and each $R^{23}$ and $R^{24}$ is independently alkyl, alkenyl, alkynyl, aryl, heteroaryl, or heterocyclyl, each of which is independently substituted or unsubstituted, or hydrogen, or a pharmaceutically-acceptable salt thereof.

Embodiment 2. The compound of embodiment 1, wherein A is substituted or unsubstituted aryl, heteroaryl, heterocyclyl, cycloalkylene.

Embodiment 3. The compound of embodiment 1 or 2, wherein A is substituted aryl.

Embodiment 4. The compound of embodiment 1 or 2, wherein A is substituted phenyl.

Embodiment 5. The compound of any one of embodiments 1, 2, or 4, wherein A is phenyl substituted with alkyl, cycloalkyl, alkoxy, an amine group, a carboxyl group, a carboxylic acid group, a carbamide group, or an amide group, each of which is substituted or unsubstituted; cyano, halo-, or hydrogen.

Embodiment 6. The compound of embodiment 1 or 2, wherein A is substituted heteroaryl.

Embodiment 7. The compound of any one of embodiments 1, 2, or 6, wherein A is an unsubstituted or substituted aromatic 5-membered, 6-membered, 7-membered, or 8-membered monocyclic ring system comprising 1, 2, or 3 heteroatoms as ring members, wherein each heteroatom is independently selected from 0. N, or S.

Embodiment 8. The compound of any one of embodiments 1, 2, 6, or 7, wherein A is pyridinyl, pyrimidinyl. thiadiazolyl, thiazolyl, pyrazolyl, thiophenyl, or oxadiazolyl, each of which is independently substituted or unsubstituted.

Embodiment 9. The compound of any one of embodiments 1, 2, or 6-8, wherein A is 1,3,5-thiadiazol-2-yl.

Embodiment 10. The compound of any one of embodiments 1, 2, or 6-8, wherein A is 1,3,4-oxadiazol-2-yl or 1,2,4-oxadiazol-2-yl.

Embodiment 11. The compound of any one of embodiments 1, 2, or 6-8, wherein A is pyridinyl.

Embodiment 12. The compound of any one of embodiments 1, 2, or 6-8, wherein A is an unsubstituted or substituted aromatic 8-membered, 9-membered, 10-membered, 11-membered, or 12-membered bicyclic ring system comprising 1, 2, 3, 4, 5, or 6 heteroatoms, wherein each heteroatom is independently selected from O, N, or S.

Embodiment 13. The compound of any one of embodiments 1-12, wherein m is 1.

Embodiment 14. The compound of any one of embodiments 1-13, wherein $Q^1$ is alkylene, alkenylene, or alkynylene, each of which is independently substituted or unsubstituted, or a bond.

Embodiment 15. The compound of any one of embodiments 1-14, wherein $Q^1$ is a bond.

Embodiment 16. The compound of any one of embodiments 1-15, wherein Y is N.

Embodiment 17. The compound of any one of embodiments 1-16, wherein $R^2$ is hydrogen.

Embodiment 18. The compound of any one of embodiments 1-16, wherein $R^2$ is substituted or unsubstituted alkyl.

Embodiment 19. The compound of any one of embodiments 1-16 or 18, wherein $R^2$ is trifluoroethyl.

Embodiment 20. The compound of any one of embodiments 1-16 or 18, wherein $R^2$ is cycloalkyl.

Embodiment 21. The compound of any one of embodiments 1-20, wherein $R^1$ is —C(O)$R^{16}$, —C(O)O$R^{16}$, —C(O)N$R^{16}R^{17}$, —O$R^{16}$, —N$R^{16}R^{17}$, —$NR^{16}$C(O)$R^{16}$, —OC(O)$R^{16}$, alkyl, alkoxy, aryl, heteroaryl, or heterocyclyl, each of which is independently substituted or unsubstituted; cyano, halo, or halogen.

Embodiment 22. The compound of any one of embodiments 1-21, wherein $R^1$ is —N$R^{16}R^{17}$.

Embodiment 23. The compound of any one of embodiments 1-21, wherein $R^1$ is substituted alkyl.

Embodiment 24. The compound of any one of embodiments 1-23, wherein each $R^3$ and $R^4$ is independently aryl, heteroaryl, or heterocyclyl, each of which is independently substituted or unsubstituted; or hydrogen.

Embodiment 25. The compound of any one of embodiments 1-24, wherein $R^3$ is hydrogen, and $R^4$ is heterocyclyl substituted at least with halo-.

Embodiment 26. The compound of any one of embodiments 1-25, wherein $R^4$ is heterocyclyl substituted with fluoro-.

Embodiment 27. The compound of any one of embodiments 1-25, wherein $R^4$ is heterocyclyl substituted with chloro-.

Embodiment 28. The compound of any one of embodiments 1-27, wherein $R^{13}$ is alkyl, alkenyl, hydrogen, or halogen.

Embodiment 29. The compound of any one of embodiments 1-28, wherein $R^{13}$ is hydrogen.

Embodiment 30. The compound of any one of embodiments 1-13, 15-27, or 29, wherein the compound has the formula:

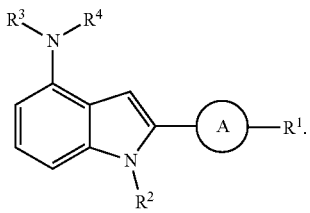

Embodiment 31. The compound of any one of embodiments 1-13, 15-19, 21-27, 29, or 30, wherein the compound has the formula:

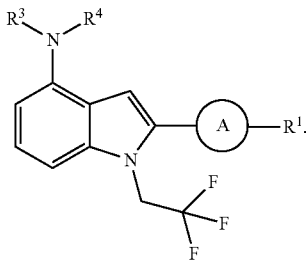

Embodiment 32. The compound of any one of embodiments 1-13, 15-27, or 29, wherein the compound has the formula:

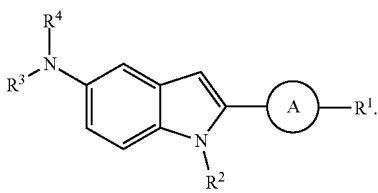

Embodiment 33. The compound of any one of embodiments 1-13, 15-19, 21-27, or 29, wherein the compound has the formula:

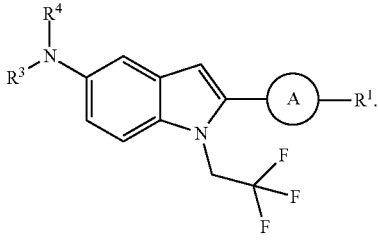

Embodiment 34. A compound of the formula:

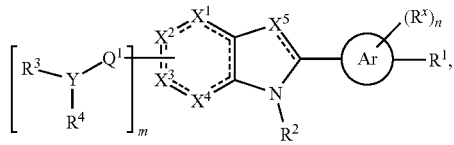

wherein:
each ------- is independently a single bond or a double bond;
$X^1$ is $CR^5$, $CR^5R^6$, N, $NR^5$, O, S, C=O, C=S, or a carbon atom connected to $Q^1$;
$X^2$ is $CR^7$, $CR^7R^8$, N, $NR^7$, O, S, C=O, C=S, or a carbon atom connected to $Q^1$;
$X^3$ is $CR^9$, $CR^9R^{10}$, N, $NR^9$, O, S, C=O, C=S, or a carbon atom connected to $Q^1$;
$X^4$ is $CR^{11}$, $CR^{11}R^{12}$, N, $NR^{11}$, O, S, C=O, C=S, or a carbon atom connected to $Q^1$;
$X^5$ is $CR^{13}$, N, or $NR^{13}$;
wherein at least one of $X^1$, $X^2$, $X^3$, and $X^4$ is a carbon atom connected to $Q^1$;
Ar is unsubstituted or substituted aryl;
$Q^1$ is C=O, C=S, C=$CR^{14}R^{15}$, C=$NR^{14}$, alkylene, alkenylene, or alkynylene, each of which is independently substituted or unsubstituted, or a bond;
m is 1, 2, 3, or 4;
n is 0, 1, 2, 3, or 4;
Y is N, O, or absent;
each $R^x$ and $R^1$ is independently $C(O)R^{16}$, —$C(O)OR^{16}$, —$C(O)NR^{16}R^{17}$, —$OR^{16}$, —$SR^{16}$, —$NR^{16}R^{17}$, —$NR^{16}C(O)R^{16}$, —$OC(O)R^{16}$, —$SiR^{16}R^7R^8$, alkyl, alkenyl, alkynyl, alkoxy, aryl, heteroaryl, or heterocyclyl, each of which is independently substituted or unsubstituted; cyano, halo, or hydrogen; or $R^1$ and $R^x$ together with Ar form a fused ring;
each $R^3$ and $R^4$ is independently —$C(O)R^{19}$, —$C(O)OR^{19}$, —$C(O)NR^{19}R^{20}$, —$SOR^{19}$, —$SO_2R^{19}$, alkyl, alkenyl, alkynyl, aryl, heteroaryl, or heterocyclyl, each of which is independently substituted or unsubstituted, or hydrogen, or $R^3$ and $R^4$ together with the nitrogen atom to which $R^3$ and $R^4$ are bound form a ring, wherein the ring is substituted or unsubstituted, or $R^3$ is absent;
each $R^2$, $R^5$, $R^6$, $R^7$, $R^8$, $R^9$, $R^{10}$, $R^{11}$, $R^{12}$, $R^{13}$, $R^{14}$, $R^{15}$, $R^{16}R^{17}$, and $R^{18}$ is independently —$C(O)R^{21}$, —$C(O)OR^{21}$, —$C(O)NR^{21}R^{22}$, —$OR^{21}$, —$SR^{21}$, —$NR^{21}R^{22}$, —$NR^{21}C(O)R^{22}$, —$OC(O)R^{21}$, alkyl, alkenyl, alkynyl, aryl, heteroaryl, or heterocyclyl, each of which is independently substituted or unsubstituted, or hydrogen or halogen;
each $R^{19}$ and $R^{20}$ is —$C(O)R^{23}$, —$C(O)OR^{23}$, —$C(O)NR^{23}R^{24}$, —$OR^{23}$, —$SR^{23}$, —$NR^{23}R^{24}$. —$NR^{23}C(O)R^{24}$, —$OC(O)R^{23}$, alkyl, alkenyl, alkynyl, aryl, heteroaryl, or heterocyclyl, each of which is independently substituted or unsubstituted, or hydrogen or halogen;
each $R^{21}$ and $R^{22}$ is independently alkyl, alkenyl, alkynyl, aryl, heteroaryl, or heterocyclyl, each of which is independently substituted or unsubstituted, or hydrogen; and
each $R^{23}$ and $R^{24}$ is independently alkyl, alkenyl, alkynyl, aryl, heteroaryl, or heterocyclyl, each of which is independently substituted or unsubstituted, or hydrogen,
or a pharmaceutically-acceptable salt thereof.

Embodiment 35. The compound of embodiment 34, wherein Ar is substituted or unsubstituted phenyl.

Embodiment 36. The compound of embodiment 34 or 35, wherein m is 1.

Embodiment 37. The compound of any one of embodiments 34-36, wherein $Q^1$ is alkylene, alkenylene, or alkynylene, each of which is independently substituted or unsubstituted, or a bond.

Embodiment 38. The compound of any one of embodiments 34-37, wherein $Q^1$ is a bond.

Embodiment 39. The compound of any one of embodiments 34-38, wherein Y is N.

Embodiment 40. The compound of any one of embodiments 34-39, wherein $R^1$ is —C(O)$R^{16}$, —C(O)O$R^{16}$, —C(O)N$R^{16}R^{17}$, —O$R^{16}$, —N$R^{16}R^{17}$, —N$R^{16}$C(O)$R^{16}$, —OC(O)$R^{16}$, alkyl, alkoxy, aryl, heteroaryl, or heterocyclyl, each of which is independently substituted or unsubstituted; cyano, halo, or halogen.

Embodiment 41. The compound of any one of embodiments 34-40, wherein each $R^3$ and $R^4$ is independently aryl, heteroaryl, or heterocyclyl, each of which is independently substituted or unsubstituted; or hydrogen.

Embodiment 42. The compound of any one of embodiments 34-41, wherein $R^3$ is hydrogen, and $R^4$ is aryl, heteroaryl, or heterocyclyl substituted at least with halo-.

Embodiment 43. The compound of any one of embodiments 34-42, wherein $R^4$ is heterocyclyl substituted with halo-.

Embodiment 44. The compound of any one of embodiments 34-43, wherein $R^4$ is heterocyclyl substituted with fluoro-.

Embodiment 45. The compound of embodiment 34-43, wherein $R^4$ is heterocyclyl substituted with chloro-.

Embodiment 46. The compound of any one of embodiments 34-45, wherein the compound is of the formula:

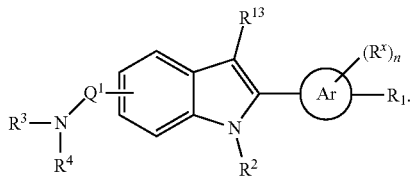

Embodiment 47. The compound of embodiment 46, wherein $Q^1$ is alkylene, alkenylene, or alkynylene, each of which is independently substituted or unsubstituted, or a bond.

Embodiment 48. The compound of embodiment 46 or 47, wherein $Q^1$ is a bond.

Embodiment 49. The compound of any one of embodiments 46-48, wherein $R^2$ is substituted alkyl.

Embodiment 50. The compound of any one of embodiments 46-49, wherein $R^2$ is trifluoroethyl.

Embodiment 51. The compound of any one of embodiments 46-50, wherein $R^1$ is —C(O)$R^{16}$, —C(O)O$R^{16}$, —C(O)N$R^{16}R^{17}$, —O$R^{16}$, —N$R^6R^{17}$, —N$R^{16}$C(O)$R^{16}$, —OC(O)$R^{16}$, alkyl, alkoxy, aryl, heteroaryl, or heterocyclyl, each of which is independently substituted or unsubstituted; cyano, halo, or halogen.

Embodiment 52. The compound of any one of embodiments 46-51, wherein $R^1$ is —N$R^{16}R^{17}$.

Embodiment 53. The compound of any one of embodiments 46-51, wherein $R^1$ is substituted alkyl.

Embodiment 54. The compound of any one of embodiments 46-53, wherein each $R^3$ and $R^4$ is independently aryl, heteroaryl, or heterocyclyl, each of which is independently substituted or unsubstituted; or hydrogen.

Embodiment 55. The compound of any one of embodiments 46-54, wherein $R^3$ is hydrogen, and $R^4$ is substituted heterocyclyl.

Embodiment 56. The compound of any one of embodiments 46-55, wherein $R^4$ is heterocyclyl substituted with halo-.

Embodiment 57. The compound of any one of embodiments 46-56, wherein $R^4$ is heterocyclyl substituted with fluoro-.

Embodiment 58. The compound of any one of embodiments 46-56, wherein $R^4$ is heterocyclyl substituted with chloro-.

Embodiment 59. The compound of any one of embodiments 46-58, wherein the compound is of the formula:

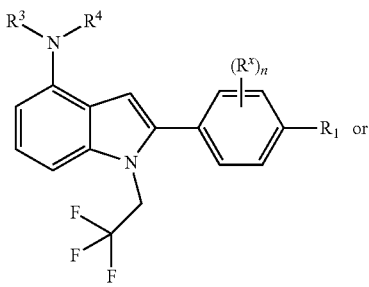

or

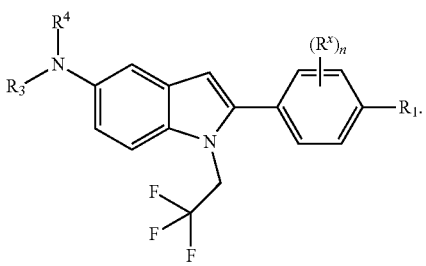

Embodiment 60. The compound of embodiment 59, wherein $R^1$ is —C(O)$R^{16}$, —C(O)O$R^{16}$, —C(O)N$R^{16}R^{17}$, —O$R^{16}$, —N$R^{16}R^{17}$, —N$R^{16}$C(O)$R^{16}$, —OC(O)$R^{16}$, alkyl, alkoxy, aryl, heteroaryl, or heterocyclyl, each of which is independently substituted or unsubstituted; cyano, halo, or halogen.

Embodiment 61. The compound of embodiment 59 or 60, wherein $R^1$ is N$R^{16}R^{17}$.

Embodiment 62. The compound of any one of embodiments 59-61, wherein $R^1$ is —C(O)$R^{16}$, —C(O)O$R^{16}$ or —C(O)N$R^{16}R^{17}$.

Embodiment 63. The compound of any one of embodiments 59-62, wherein $R^1$ is substituted alkyl.

Embodiment 64. The compound of any one of embodiments 59-63, wherein n is 0

Embodiment 65. The compound of any one of embodiments 59-63, wherein n is 1.

Embodiment 66. The compound of any one of embodiments 59, 60, or 62-64, wherein the compound is of the formula:

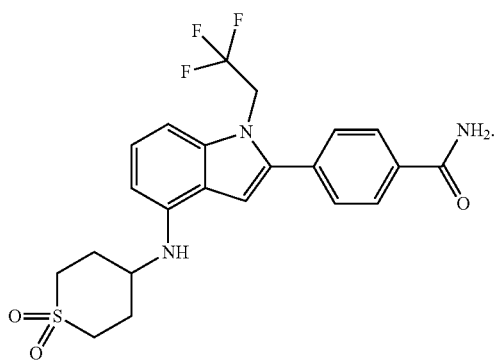 [SMILES: NC(=O)c1ccc(-c2cc3c(NC4CCS(=O)(=O)CC4)cccc3n2CC(F)(F)F)cc1]

Embodiment 67. The compound of embodiment 59, wherein the compound is of the formula:

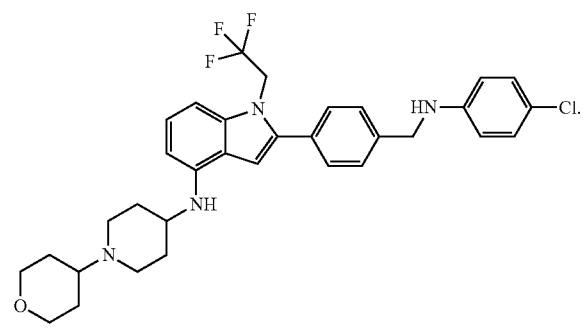 [SMILES: FC(F)(F)Cn1c(-c2ccc(CNc3ccc(Cl)cc3)cc2)cc2c(NC3CCN(C4CCOCC4)CC3)cccc21]

Embodiment 68. The compound of embodiment 59, wherein the compound is of the formula:

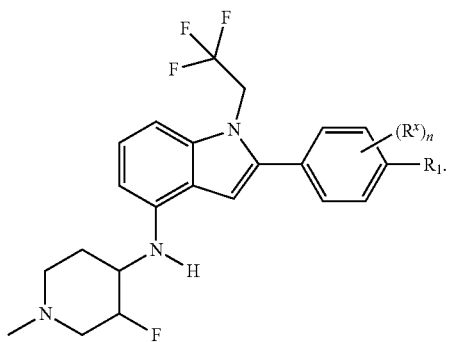

Embodiment 69. The compound of embodiment 68, wherein the compound is of the formula:

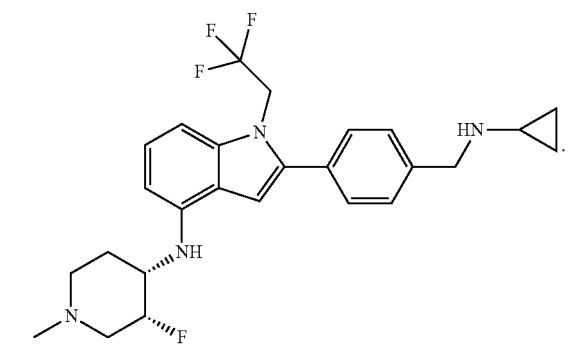 [SMILES: CN1CC[C@H](Nc2cccc3c2cc(-c2ccc(CNC4CC4)cc2)n3CC(F)(F)F)[C@H](F)C1]

Embodiment 70. The compound of embodiment 68, wherein the compound is of the formula:

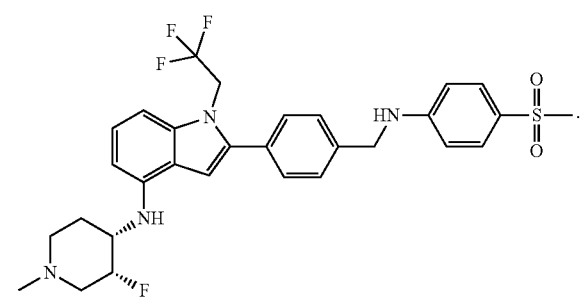

Embodiment 71. The compound of embodiment 68, wherein the compound is of the formula:

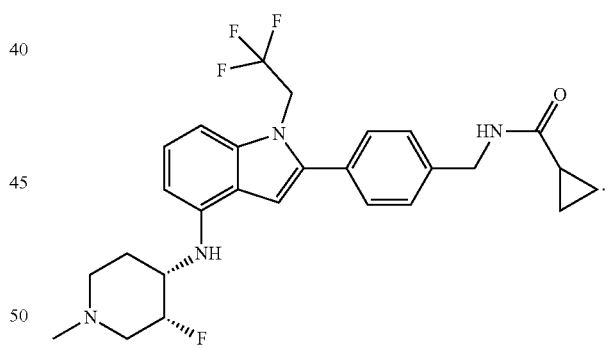

Embodiment 72. A compound of the formula:

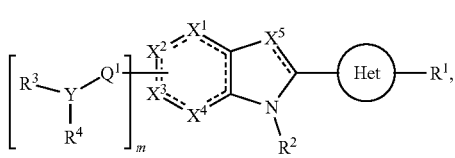

wherein:
each ===== is independently a single bond or a double bond;
$X^1$ is $CR^5$, $CR^5R^6$, N, $NR^5$, O, S, C=O, C=S, or a carbon atom connected to $Q^1$;

$X^2$ is $CR^7$, $CR^7R^8$, N, $NR^7$, O, S, C=O, C=S, or a carbon atom connected to $Q^1$;

$X^3$ is $CR^9$, $CR^9R^{10}$, N, $NR^9$, O, S, C=O, C=S, or a carbon atom connected to $Q^1$;

$X^4$ is $CR^1$, $CR^{11}R^{12}$, N, $NR^{11}$, O, S, C=O, C=S, or a carbon atom connected to $Q^1$;

$X^5$ is $CR^{13}$, N, or $NR^{11}$;

wherein at least one of $X^1$, $X^2$, $X^3$, and $X^4$ is a carbon atom connected to $Q^1$;

Het is substituted or unsubstituted heteroaryl;

$Q^1$ is C=O, C=S, C=$CR^{14}R^{15}$, C=$NR^{14}$, alkylene, alkenylene, or alkynylene, each of which is independently substituted or unsubstituted, or a bond;

m is 1, 2, 3, or 4;

Y is N, O, or absent;

$R^1$ is —C(O)$R^{16}$, —C(O)O$R^{16}$, —C(O)N$R^{16}R^{17}$, —O$R^{16}$, —S$R^{16}$, —N$R^{16}R^{17}$, —N$R^{16}$C(O)$R^{16}$, —OC(O)$R^{16}$, —Si$R^{16}R^{17}R^{18}$, alkyl, alkenyl, alkynyl, alkoxy, aryl, heteroaryl, heterocyclyl, or halo, each of which is independently substituted or unsubstituted, or hydrogen;

each $R^3$ and $R^4$ is independently —C(O)$R^{19}$, —C(O)O$R^{19}$, —C(O)N$R^{19}R^{20}$, —SO$R^{19}$, —SO$_2R^{19}$, alkyl, alkenyl, alkynyl, aryl, heteroaryl, or heterocyclyl, each of which is independently substituted or unsubstituted, or hydrogen, or $R^3$ and $R^4$ together with the nitrogen atom to which $R^3$ and $R^4$ are bound form a ring, wherein the ring is substituted or unsubstituted, or $R^3$ is absent;

each $R^2$, R, $R^6$, $R^7$, RR, $R^9$, $R^{10}$, $R^{11}$, $R^{12}$, $R^{13}$, $R^{14}$, $R^{15}$, $R^{16}$, $R^{17}$, and $R^{18}$ is independently —C(O)$R^{21}$, —C(O)O$R^{21}$, —C(O)N$R^{21}R^{22}$, —O$R^{21}$, —S$R^{21}$, —N$R^{21}R^{21}R^2$, —N$R^{21}$C(O)$R^{22}$, —OC(O)$R^{21}$, alkyl, alkenyl, alkynyl, aryl, heteroaryl, or heterocyclyl, each of which is independently substituted or unsubstituted, or hydrogen or halogen;

each $R^{19}$ and $R^{20}$ is —C(O)$R^{23}$, —C(O)O$R^{23}$, —C(O)N$R^{23}R^{24}$, —O$R^2$, —S$R^2$, —N$R^{21}R^{24}$, —N$R^{23}$C(O)$R^{24}$, —OC(O)$R^{23}$, alkyl, alkenyl, alkynyl, aryl, heteroaryl, or heterocyclyl, each of which is independently substituted or unsubstituted, or hydrogen or halogen;

each $R^{21}$ and $R^{22}$ is independently alkyl, alkenyl, alkynyl, aryl, heteroaryl, or heterocyclyl, each of which is independently substituted or unsubstituted, or hydrogen; and each $R^2$ and $R^{24}$ is independently alkyl, alkenyl, alkynyl, aryl, heteroaryl, or heterocyclyl, each of which is independently substituted or unsubstituted, or hydrogen, or a pharmaceutically-acceptable salt thereof.

Embodiment 73. The compound of embodiment 72, wherein Het is an aromatic 5-membered or 6-membered monocyclic ring.

Embodiment 74. The compound of embodiment 72 or 73, wherein Het is an aromatic 5-membered ring.

Embodiment 75. The compound of any one of embodiments 72-74, wherein Het is thiazolyl, thiadiazolyl, pyrazolyl, thiophenyl, or oxadiazolyl.

Embodiment 76. The compound of embodiment 72 or 73, wherein Het is an aromatic 6-membered ring.

Embodiment 77. The compound of any one of embodiments 72, 73, or 76, wherein Het is pyridinyl or pyrimidinyl.

Embodiment 78. The compound of any one of embodiments 72-77, wherein $R^1$ is alkyl, alkylene, alkoxy, —N$R^{21}R^{22}$, or aryl, each of which is independently substituted or unsubstituted; halo or hydrogen.

Embodiment 79. The compound of any one of embodiments 72-78, wherein $R^1$ is —N$R^{21}R^{22}$.

Embodiment 80. The compound of any one of embodiments 72-78, wherein $R^1$ is substituted alkyl.

Embodiment 81. The compound of any one of embodiments 72-80, wherein $Q^1$ is alkylene, alkenylene, alkynylene, or a bond.

Embodiment 82. The compound of any one of embodiments 72-81, wherein $Q^1$ is a bond.

Embodiment 83. The compound of any one of embodiments 72-82, wherein Y is N.

Embodiment 84. The compound of any one of embodiments 72-83, wherein m is 1.

Embodiment 85. The compound of any one of embodiments 72-84, wherein each $R^3$ and $R^4$ is independently —C(O)$R^{19}$, —C(O)O$R^{19}$, alkyl, alkenyl, alkynyl, aryl, heteroaryl, or heterocyclyl, each of which is independently substituted or unsubstituted; or hydrogen.

Embodiment 86. The compound of any one of embodiments 72-85, wherein $R^3$ is hydrogen, and $R^4$ is —C(O)$R^{19}$, —C(O)O$R^{19}$, —C(O)N$R^{19}R^{20}$, —SO$R^{19}$, —SO$_2R^{19}$, alkyl, alkenyl, alkynyl, aryl, heteroaryl, or heterocyclyl, each of which is independently substituted or unsubstituted.

Embodiment 87. The compound of any one of embodiments 72-86, wherein $R^4$ is substituted or unsubstituted heterocyclyl.

Embodiment 88. The compound of any one of embodiments 72-87, wherein $R^4$ is heterocyclyl substituted at least with halo-.

Embodiment 89. The compound of any one of embodiments 72-88, wherein $R^4$ is heterocyclyl substituted with at least fluoro-.

Embodiment 90. The compound of any one of embodiments 72-88, wherein $R^4$ is heterocyclyl substituted with at least chloro-.

Embodiment 91. The compound of any one of embodiments 72-90, wherein the compound is of the formula:

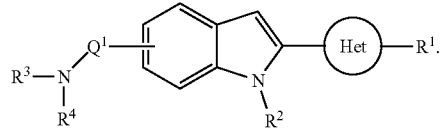

Embodiment 92. The compound of embodiment 91, wherein $Q^1$ is a bond.

Embodiment 93. The compound of embodiment 91 or 92, wherein $R^2$ is hydrogen or alkyl.

Embodiment 94. The compound of any one of embodiments 91-93, wherein $R^2$ is substituted alkyl.

Embodiment 95. The compound of any one of embodiments 91-94, wherein $R^2$ is trifluoroethyl.

Embodiment 96. The compound of any one of embodiments 91-95, wherein $R^3$ is H, and $R^4$ is —C(O)$R^9$, —C(O)O$R^{19}$, —C(O)N$R^{19}R^{20}$, —SO$R^{19}$, —SO$_2R^{19}$, alkyl, alkenyl, alkynyl, aryl, heteroaryl, or heterocyclyl, each of which is independently substituted or unsubstituted.

Embodiment 97. The compound of any one of embodiments 91-96, wherein $R^4$ is substituted heterocyclyl.

Embodiment 98. The compound of any one of embodiments 91-97, wherein $R^4$ is heterocyclyl substituted with halo-.

Embodiment 99. The compound of any one of embodiments 91-98, wherein $R^4$ is heterocyclyl substituted with fluoro-.

Embodiment 100. The compound of any one of embodiments 91-98, wherein $R^1$ is heterocyclyl substituted with chloro-.

Embodiment 101. The compound of any one of embodiments 91-100, wherein the compound is of the formula:

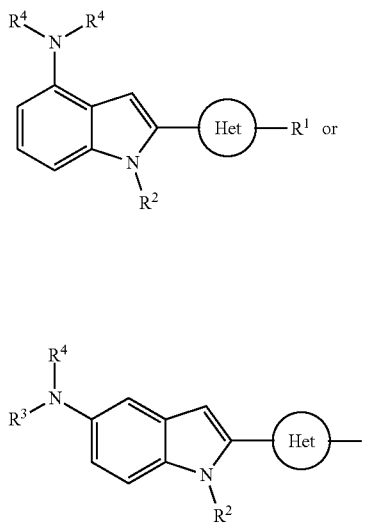

Embodiment 102. The compound of embodiment 101, wherein Het is an aromatic 5-membered ring.

Embodiment 103. The compound of embodiment 101 or 102, wherein Het is thiazolyl, thiadiazolyl, pyrazolyl, thiophenyl, or oxadiazolyl.

Embodiment 104. The compound of embodiment 101, wherein Het is an aromatic 6-membered ring.

Embodiment 105. The compound of embodiment 101 or 104, wherein Het is pyridinyl or pyrimidinyl.

Embodiment 106. The compound of any one of embodiments 101-105, wherein $Q^1$ is alkylene, alkenylene, alkynylene, or a bond.

Embodiment 107. The compound of any one of embodiments 101-106, wherein $Q^1$ is a bond.

Embodiment 108. The compound of any one of embodiments 101-107, wherein $R^1$ is alkyl, alkylene, alkoxy, —$NR^{21}R^{22}$, or aryl, each of which is independently substituted or unsubstituted; halo or hydrogen.

Embodiment 109. The compound of any one of embodiments 101-108, wherein $R^1$ is substituted alkyl or —$NR^{21}R^{22}$.

Embodiment 110. The compound of any one of embodiments 101-109, wherein $R^2$ is substituted alkyl.

Embodiment 111. The compound of any one of embodiments 101-110, wherein $R^2$ is trifluoroethyl.

Embodiment 112. The compound of any one of embodiments 101-111, wherein $R^3$ is H, and $R^4$ is —$C(O)R^{19}$, —$C(O)OR^{19}$, —$C(O)NR^{19}R^{20}$, —$SOR^{19}$, —$SO_2R^{19}$, alkyl, alkenyl, alkynyl, aryl, heteroaryl, or heterocyclyl, each of which is independently substituted or unsubstituted; or hydrogen.

Embodiment 113. The compound of any one of embodiments 101-112, wherein $R^3$ is hydrogen, and $R^4$ is substituted or unsubstituted heterocyclyl.

Embodiment 114. The compound of any one of embodiments 101-113, wherein $R^4$ is heterocyclyl substituted with halo-.

Embodiment 115. The compound of any one of embodiments 101-114, wherein $R^4$ is heterocyclyl substituted with fluoro-.

Embodiment 116. The compound of any one of embodiments 101-114, wherein $R^4$ is heterocyclyl substituted with chloro-.

Embodiment 117. The compound of embodiment 72, wherein the compound has the formula:

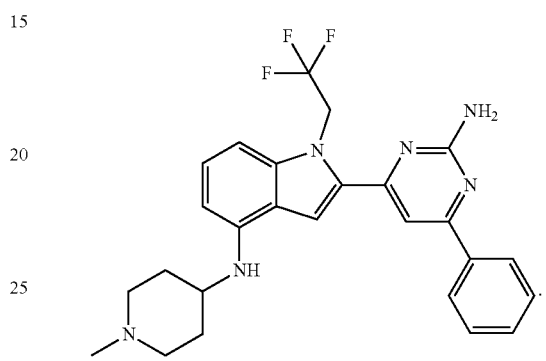

Embodiment 118. The compound of embodiment 72, wherein the compound has the formula:

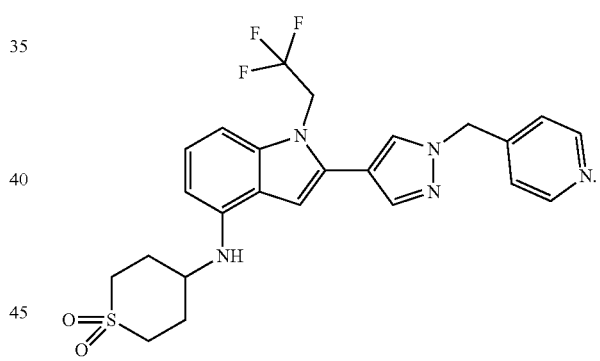

Embodiment 119. The compound of embodiment 72, wherein the compound has the formula:

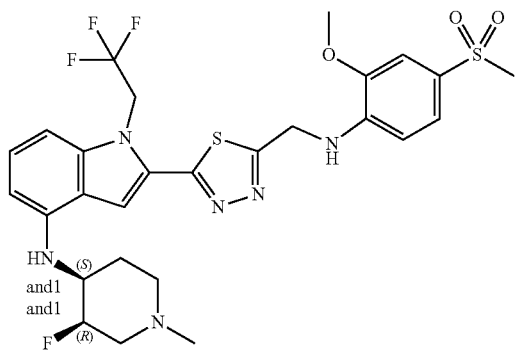

Embodiment 120. The compound of embodiment 72, wherein the compound has the formula:

Embodiment 121. The compound of embodiment 72n wherein the compound has the formula:

Embodiment 122. A method of inducing apoptosis in a cell, the method comprising contacting the cell with a therapeutically-effective amount of a compound of any one of embodiments 1-121 that binds a p53 mutant, wherein the compound increases the ability of the p53 mutant to bind DNA, wherein the cell expresses the p53 mutant.

Embodiment 123. The method of embodiment 122, wherein the p53 mutant has a mutation at amino acid 220.

Embodiment 124. The method of embodiment 122 or 123, wherein the p53 mutant is p53 Y220C.

Embodiment 125. The method of any one of embodiments 122-124, wherein the compound induces a conformational change in the p53 mutant.

Embodiment 126. The method of any one of embodiments 122-125, wherein the compound selectively binds the p53 mutant as compared to wild type p53.

Embodiment 127. The method of any one of embodiments 122-126, wherein the therapeutically-effective amount is from about 50 mg to about 3000 mg.

Embodiment 128. A method of treating a cancer, the method comprising administering to a subject in need thereof a therapeutically-effective amount of a compound of any one of embodiments 1-121.

Embodiment 129. The method of embodiment 128, wherein the therapeutically-effective amount is from about 20 mg to about 2000 mg.

Embodiment 130. The method of embodiment 128 or 129, wherein the cancer is ovarian cancer.

Embodiment 131. The method of embodiment 128 or 129, wherein the cancer is breast cancer.

Embodiment 132. The method of embodiment 128 or 129, wherein the condition is lung cancer.

Embodiment 133. The method of any one of embodiments 128-132, wherein the administration is oral.

Embodiment 134. The method of any one of embodiments 128-132, wherein the administration is intravenous.

Embodiment 135. The method of any one of embodiments 128-132, wherein the administration is subcutaneous.

Embodiment 136. The method of any one of embodiments 128-132, wherein the administration is topical.

Embodiment 137. The method of any one of embodiments 128-136, wherein the subject is human.

Embodiment 138. The method of any one of embodiments 128-137, wherein the compound increases the stability of a biologically-active conformation of the p53 mutant relative to the stability of the biologically-active conformation of the p53 mutant in absence of the compound.

Embodiment 139. A compound comprising:
  an indole group, wherein the indole group comprises:
    a) a haloalkyl group at a 1-position of the indole group;
    b) a first substituent at a 2-position of the indole group, wherein the first substituent is a cyclic group; and
    c) a second substituent, wherein the second substituent is substituted with at least halo-;
  or a pharmaceutically-acceptable salt thereof.

Embodiment 140. The compound of embodiment 139, wherein the cyclic group is aryl, heteroaryl, or heterocyclyl, each of which is substituted or unsubstituted.

Embodiment 141. The compound of embodiment 139 or 140, wherein the cyclic group is unsubstituted aryl.

Embodiment 142. The compound of embodiment 139 or 140, wherein the cyclic group is substituted aryl.

Embodiment 143. The compound of any one of embodiments 139, 140, or 142, wherein the cyclic group is substituted phenyl.

Embodiment 144. The compound of embodiment 139 or 140, wherein the cyclic group is substituted or unsubstituted heteroaryl.

Embodiment 145. The compound of embodiment 139, 140 or 144, wherein the heteroaryl is an aromatic 5-membered or 6-membered monocyclic ring.

Embodiment 146. The compound of any one of embodiments 139, 140, 144, or 145, wherein the heteroaryl is thiazolyl, thiadiazolyl, pyrazolyl, thiophenyl, or oxadiazolyl.

Embodiment 147. The compound of any one of embodiments 139, 140, 144, or 145, wherein the heteroaryl is pyridinyl or pyrimidinyl.

Embodiment 148. The compound of any one of embodiments 139-147, wherein the second substituent is at a 4-position of the indole group.

Embodiment 149. The compound of any one of embodiments 139-148, wherein the second substituent is a second cyclic group that is substituted or unsubstituted.

Embodiment 150. The compound of any one of embodiments 139-149, wherein the second cyclic group is heterocyclyl.

Embodiment 151. The compound of any one of embodiments 139-150, wherein the heterocyclyl is piperidinyl.

Embodiment 152. The compound of any one of embodiments 139-150, wherein the heterocyclyl is tetrahydropyranyl.

Embodiment 153. The compound of any one of embodiments 139-152, wherein the heterocyclyl is substituted with fluoro-.

Embodiment 154. The compound of any one of embodiments 139-152, wherein the heterocyclyl is substituted with chloro-.

Embodiment 155. The compound of any one of embodiments 139-154, wherein the haloalkyl group is trifluoroethyl.

Embodiment 156. A compound comprising an indole group, wherein the indole group comprises:
a) a substituted or unsubstituted non-cyclic group at a 3-position of the indole group; and
b) a substituted or unsubstituted cyclic group at a 2-position of the indole group, wherein the compound increases a stability of a biologically-active conformation of a p53 mutant relative to a stability of a biologically-active conformation of the p53 mutant in an absence of the compound, or a pharmaceutically-acceptable salt thereof.

Embodiment 157. The compound of embodiment 156, wherein the non-cyclic group is hydrogen.

Embodiment 158. The compound of embodiment 156, wherein the non-cyclic group is halo-.

Embodiment 159. The compound of any one of embodiments 156-158, wherein the cyclic group is aryl, heteroaryl, heterocyclyl, or cycloalkylene, each of which is substituted or unsubstituted.

Embodiment 160. The compound of any one of embodiments 156-159, wherein the cyclic group is aryl or heteroaryl, each of which is substituted or unsubstituted.

Embodiment 161. The compound of any one of embodiments 156-160, wherein the cyclic group is substituted aryl.

Embodiment 162. The compound of any one of embodiments 156-161, wherein the cyclic group is substituted phenyl.

Embodiment 163. The compound of any one of embodiments 156-162, wherein the cyclic group is phenyl substituted with alkyl, cycloalkyl, alkoxy, an amine group, a carboxyl group, a carboxylic acid group, a carbamide group, or an amide group, each of which is substituted or unsubstituted; cyano, halo-, or hydrogen.

Embodiment 164. The compound of any one of embodiments 156-160 wherein the cyclic group is substituted heteroaryl.

Embodiment 165. The compound of any one of embodiments 156-160 or 164, wherein the cyclic group is an aromatic 5-membered, 6-membered, 7-membered, or 8-membered monocyclic ring system comprising 1, 2, or 3 heteroatoms as ring members, wherein each heteroatom is independently selected from O, N, or S.

Embodiment 166. The compound of any one of embodiments 156-160, 164, or 165, wherein the cyclic group is pyridinyl, pyrimidinyl, thiadiazolyl, thiazolyl, pyrazolyl, thiophenyl, or oxadiazolyl.

Embodiment 167. The compound of any one of embodiments 156-160 or 164-166, wherein the cyclic group is 1,3,5-thiadiazol-2-yl.

Embodiment 168. The compound of any one of embodiments 156-160 or 164-166, wherein the cyclic group is 1,3,4-oxadiazol-2-yl or 1,2,4-oxadiazol-2-yl.

Embodiment 169. The compound of any one of embodiments 156-160 or 164-166, wherein the cyclic group is pyridinyl.

Embodiment 170. The compound of any one of embodiments 156-160 or 164-166, wherein the indole group further comprises a substituent at a 4-position of the indole group.

Embodiment 171. The compound of embodiment 170, wherein the substituent is an amino group that is substituted or unsubstituted.

Embodiment 172. The compound of embodiment 171, wherein the amino group is substituted with a second cyclic group.

Embodiment 173. The compound of embodiment 172, wherein the second cyclic group is a heterocyclyl group substituted with at least halo-.

Embodiment 174. The compound of embodiment 172, wherein the heterocyclyl group is substituted with at least fluoro-.

Embodiment 175. The compound of embodiment 172, wherein the heterocyclyl group is substituted with at least chloro-.

Embodiment 176. The compound of embodiment 174, wherein the heterocyclyl group is piperidinyl.

Embodiment 177. The compound of embodiment 174, wherein the heterocyclyl group is tetrahydropyranyl.

What is claimed is:

1. A compound of the formula:

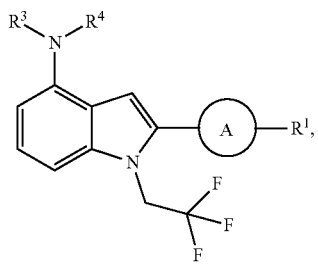

wherein:

A is a substituted or unsubstituted ring;

$R^1$ is alkyl, alkenyl, alkynyl, alkoxy, aryl, heteroaryl, heterocyclyl, or halo, each of which is independently substituted or unsubstituted; or —C(O)$R^{16}$, —C(O)O$R^{16}$, —C(O)N$R^{16}R^{17}$, —O$R^{16}$, —S$R^{16}$, —N$R^{16}R^{17}$, —N$R^{16}$C(O)$R^{16}$, —OC(O)$R^{16}$, —Si$R^{16}R^{17}R^{18}$, or hydrogen;

each $R^3$ and $R^4$ is independently alkyl, alkenyl, alkynyl, aryl, heteroaryl, or heterocyclyl, each of which is independently substituted or unsubstituted; or —C(O)$R^{19}$, —C(O)O$R^{19}$, —C(O)N$R^{19}R^{20}$, —SO$R^{19}$, —SO2$R^{19}$, or hydrogen, or $R^3$ and $R^4$ together with the nitrogen atom to which $R^3$ and $R^4$ are bound form a ring, wherein the ring is substituted or unsubstituted;

each $R^{16}$, $R^{17}$, and $R^{18}$ is independently alkyl, alkenyl, alkynyl, aryl, heteroaryl, or heterocyclyl, each of which is independently substituted or unsubstituted; or —C(O)$R^{21}$, —C(O)O$R^{21}$, —C(O)N$R^{21}R^{22}$, —O$R^{21}$, —S$R^{21}$, —N$R^{21}R^{22}$, —N$R^{21}$C(O)$R^{22}$, —OC(O)$R^{21}$, hydrogen, or halogen;

each $R^{19}$ and $R^{20}$ is independently alkyl, alkenyl, alkynyl, aryl, heteroaryl, or heterocyclyl, each of which is independently substituted or unsubstituted; or —C(O)$R^{23}$, —C(O)O$R^{23}$, —C(O)N$R^{23}R^{24}$, —O$R^{23}$, —S$R^{23}$, —N$R^{23}R^{24}$, —N$R^{23}$C(O)$R^{24}$, —OC(O)$R^{23}$, hydrogen, or halogen;

each $R^{21}$ and $R^{22}$ is independently alkyl, alkenyl, alkynyl, aryl, heteroaryl, or heterocyclyl, each of which is independently substituted or unsubstituted, or hydrogen; and each $R^{23}$ and $R^{24}$ is independently alkyl, alkenyl, alkynyl, aryl, heteroaryl, or heterocyclyl, each of which is independently substituted or unsubstituted, or hydrogen, or a pharmaceutically-acceptable salt thereof.

2. The compound of claim 1, wherein A is substituted or unsubstituted aryl, heteroaryl, heterocyclyl, or cycloalkylene.

3. The compound of claim 1, wherein A is substituted aryl.

4. The compound of claim 3, wherein A is substituted phenyl.

5. The compound of claim 4, wherein A is phenyl substituted with: alkyl, cycloalkyl, alkoxy, an amine group, a carboxyl group, a carboxylic acid group, a carbamide group, or an amide group, each of which is substituted or unsubstituted, or cyano or halo.

6. The compound of claim 1, wherein A is substituted heteroaryl.

7. The compound of claim 1, wherein A is an unsubstituted or substituted aromatic 5-membered, 6-membered, 7-membered, or 8-membered monocyclic ring system comprising 1, 2, or 3 heteroatoms as ring members, wherein each heteroatom is independently selected from O, N, and S.

8. The compound of claim 7, wherein A is pyridinyl, pyrimidinyl, thiadiazolyl, thiazolyl, pyrazolyl, thiophenyl, or oxadiazolyl, each of which is independently substituted or unsubstituted.

9. The compound of claim 8, wherein A is 1,3,5-thiadiazol-2-yl.

10. The compound of claim 8, wherein the compound is of the formula:

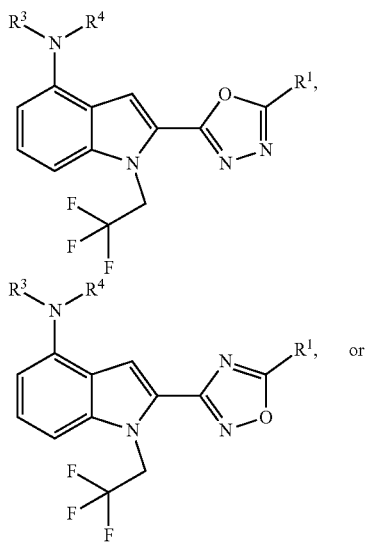

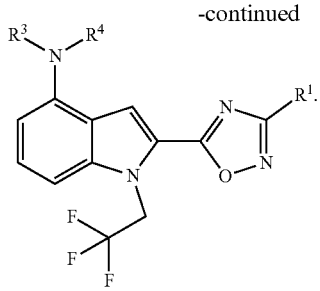

11. The compound of claim 8, wherein A is pyridinyl.

12. The compound of claim 1, wherein A is an unsubstituted or substituted aromatic 8-membered, 9-membered, 10-membered, 11-membered, or 12-membered bicyclic ring system comprising 1, 2, 3, 4, 5, or 6 heteroatoms, wherein each heteroatom is independently selected from O, N, and S.

13. The compound of claim 1, wherein $R^1$ is alkyl, alkoxy, aryl, heteroaryl, or heterocyclyl, each of which is independently substituted or unsubstituted; or —$C(O)R^{16}$, —$C(O)OR^{16}$, —$C(O)NR^{16}R^{17}$, —$OR^{16}$, —$NR^{16}R^{17}$, —$NR^{16}C(O)R^{16}$, —$OC(O)R^{16}$, or halogen.

14. The compound of claim 13, wherein $R^1$ is —$NR^{16}R^{17}$.

15. The compound of claim 13, wherein $R^1$ is substituted alkyl.

16. The compound of claim 1, wherein each $R^3$ and $R^4$ is independently aryl, heteroaryl, or heterocyclyl, each of which is independently substituted or unsubstituted; or hydrogen.

17. The compound of claim 16, wherein $R^3$ is hydrogen, and $R^4$ is heterocyclyl substituted at least with halo-.

18. The compound of claim 17, wherein $R^4$ is heterocyclyl substituted with fluoro-.

19. The compound of claim 17, wherein $R^4$ is heterocyclyl substituted with chloro-.

20. The compound of claim 13, wherein $R^1$ is alkyl substituted with $NR^{16}R^{17}$.

21. The compound of claim 13, wherein $R^1$ is methyl substituted with $NR^{16}R^{17}$, wherein $R^{16}$ is hydrogen, and $R^{17}$ is $C(O)R^{21}$, wherein $R^{21}$ is heteroaryl that is substituted or unsubstituted.

* * * * *

UNITED STATES PATENT AND TRADEMARK OFFICE
CERTIFICATE OF CORRECTION

| | | |
|---|---|---|
| PATENT NO. | : 11,807,644 B2 | Page 1 of 1 |
| APPLICATION NO. | : 17/317423 | |
| DATED | : November 7, 2023 | |
| INVENTOR(S) | : Vu et al. | |

It is certified that error appears in the above-identified patent and that said Letters Patent is hereby corrected as shown below:

In the Claims

Claim 1; Column 889; Line 67:
Delete: "–S02R$^{19}$"
And replace with: -- –SO$_2$R$^{19}$--

Signed and Sealed this
Sixteenth Day of January, 2024

*Katherine Kelly Vidal*

Katherine Kelly Vidal
*Director of the United States Patent and Trademark Office*

SEQUENCE LISTING

```
<160> NUMBER OF SEQ ID NOS: 2

<210> SEQ ID NO 1
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Ser Ser Ser Val Pro Ser Gln Lys Thr Tyr Gln Gly Ser Tyr Gly Phe
1               5                   10                  15

Arg Leu Gly Phe Leu His Ser Gly Thr Ala Lys Ser Val Thr Cys Thr
            20                  25                  30

Tyr Ser Pro Ala Leu Asn Lys Met Phe Cys Gln Leu Ala Lys Thr Cys
        35                  40                  45

Pro Val Gln Leu Trp Val Asp Ser Thr Pro Pro Gly Thr Arg Val
    50                  55                  60

Arg Ala Met Ala Ile Tyr Lys Gln Ser Gln His Met Thr Glu Val Val
```

```
                65                  70                  75                  80
Arg Arg Cys Pro His His Glu Arg Cys Ser Asp Ser Asp Gly Leu Ala
            85                  90                  95
Pro Pro Gln His Leu Ile Arg Val Glu Gly Asn Leu Arg Val Glu Tyr
            100                 105                 110
Leu Asp Asp Arg Asn Thr Phe Arg His Ser Val Val Val Pro Cys Glu
            115                 120                 125
Pro Pro Glu Val Gly Ser Asp Cys Thr Thr Ile His Tyr Asn Tyr Met
            130                 135                 140
Cys Asn Ser Ser Cys Met Gly Gly Met Asn Arg Arg Pro Ile Leu Thr
145                 150                 155                 160
Ile Ile Thr Leu Glu Asp Ser Ser Gly Asn Leu Leu Gly Arg Asn Ser
                165                 170                 175
Phe Glu Val His Val Cys Ala Cys Pro Gly Arg Asp Arg Arg Thr Glu
                180                 185                 190
Glu Glu Asn Leu Arg Lys Lys Gly Glu Pro His His Glu Leu Pro Pro
                195                 200                 205
Gly Ser Thr Lys Arg Ala Leu Ser Asn Asn Thr
            210                 215

<210> SEQ ID NO 2
<211> LENGTH: 26
<212> TYPE: DNA
<213> ORGANISM: Artificial Sequence
<220> FEATURE:
<223> OTHER INFORMATION: Description of Artificial Sequence: Synthetic
      oligonucleotide

<400> SEQUENCE: 2
attaggcatg tctaggcatg tctagg                                              26
```